US008975398B2

(12) United States Patent
Hansen et al.

(10) Patent No.: US 8,975,398 B2
(45) Date of Patent: Mar. 10, 2015

(54) NAMPT INHIBITORS

(71) Applicant: AbbVie Inc., North Chicago, IL (US)

(72) Inventors: Todd M. Hansen, Grayslake, IL (US);
Kenton Longenecker, Grayslake, IL (US); Howard R. Heyman, Deerfield, IL (US); Michael L. Curtin, Pleasant Prairie, WI (US); Richard F. Clark, Gurnee, IL (US); Bryan Sorensen, Antioch, IL (US); Zhiqin Ji, Libertyville, IL (US); Kevin Woller, Antioch, IL (US); George Doherty, Libertyville, IL (US); Robin Frey, Libertyville, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 13/891,357

(22) Filed: May 10, 2013

(65) Prior Publication Data

US 2013/0303510 A1 Nov. 14, 2013

Related U.S. Application Data

(60) Provisional application No. 61/779,756, filed on Mar. 13, 2013, provisional application No. 61/719,013, filed on Oct. 26, 2012, provisional application No. 61/645,692, filed on May 11, 2012.

(51) Int. Cl.
| C07D 401/00 | (2006.01) |
| C07D 405/14 | (2006.01) |
| A61K 31/4545 | (2006.01) |
| A61K 31/496 | (2006.01) |
| A61K 31/501 | (2006.01) |
| A61K 31/5377 | (2006.01) |
| C07D 409/14 | (2006.01) |
| C07D 417/14 | (2006.01) |
| A61K 31/506 | (2006.01) |
| C07D 401/14 | (2006.01) |
| C07D 401/04 | (2006.01) |
| C07D 403/04 | (2006.01) |
| C07D 403/14 | (2006.01) |

(52) U.S. Cl.
CPC .......... *C07D 405/14* (2013.01); *A61K 31/4545* (2013.01); *A61K 31/496* (2013.01); *A61K 31/501* (2013.01); *A61K 31/5377* (2013.01); *C07D 409/14* (2013.01); *C07D 417/14* (2013.01); *A61K 31/506* (2013.01); *C07D 401/14* (2013.01); *C07D 401/04* (2013.01); *C07D 403/04* (2013.01); *C07D 403/14* (2013.01)
USPC ........................................................ 544/238

(58) Field of Classification Search
USPC ........................................................ 544/238
See application file for complete search history.

(56) References Cited

U.S. PATENT DOCUMENTS

| 7,511,013 | B2 | 3/2009 | Molino et al. |
| 7,514,068 | B2 | 4/2009 | Tung |
| 7,521,421 | B2 | 4/2009 | Naicker et al. |
| 7,528,131 | B2 | 5/2009 | Persichetti et al. |
| 7,531,685 | B2 | 5/2009 | Czarnik |
| 7,534,814 | B2 | 5/2009 | Ascher et al. |
| 7,538,189 | B2 | 5/2009 | Naicker et al. |
| 2006/0241109 | A1* | 10/2006 | Little et al. ................. 514/230.5 |
| 2007/0244088 | A1 | 10/2007 | Brickmann et al. |
| 2009/0082471 | A1 | 3/2009 | Czarnik |
| 2009/0088416 | A1 | 4/2009 | Czarnik |
| 2009/0093422 | A1 | 4/2009 | Tung et al. |
| 2009/0105147 | A1 | 4/2009 | Masse |
| 2009/0105307 | A1 | 4/2009 | Galley et al. |
| 2009/0105338 | A1 | 4/2009 | Czarnik |
| 2009/0111840 | A1 | 4/2009 | Herold et al. |
| 2009/0118238 | A1 | 5/2009 | Czarnik |
| 2009/0131363 | A1 | 5/2009 | Harbeson |
| 2009/0131485 | A1 | 5/2009 | Liu et al. |
| 2009/0137457 | A1 | 5/2009 | Harbeson |

FOREIGN PATENT DOCUMENTS

| EP | 1700856 | A1 | 9/2006 |
| WO | 9422835 | A2 | 10/1994 |
| WO | 9507271 | A1 | 3/1995 |
| WO | 9610022 | A1 | 4/1996 |
| WO | 9710223 | A1 | 3/1997 |
| WO | 9748397 | A1 | 12/1997 |
| WO | 9748696 | A1 | 12/1997 |
| WO | 9900121 | A1 | 1/1999 |
| WO | 9900128 | A1 | 1/1999 |
| WO | 0185714 | A1 | 11/2001 |
| WO | 0206234 | A1 | 1/2002 |
| WO | 03014083 | A1 | 2/2003 |
| WO | 03074500 | A2 | 9/2003 |
| WO | 03076395 | A1 | 9/2003 |

(Continued)

OTHER PUBLICATIONS

Adya R., et al., "Nuclear Factor-kappaB Induction by Visfatin in Human Vascular Endothelial Cells: Its Role in MMP-2/9 Production and Activation," Diabetes Care, 2008, vol. 31 (4), pp. 758-760.
Beylot, M. et al., "In Vivo Studies of Intrahepatic Metabolic Pathways," Diabetes Metabolism, 1997, vol. 23 (3), pp. 251-257.
Blagojevic, N. et al., "Role of heavy water in Boron Neutron Capture Therapy," Topics in Dosimetry & Treatment Planning for Neutron Capture Therapy, 1994, pp. 125-134.
Blake, M. I. et al., "Studies With Deuterated Drugs," Journal of Pharmaceutical Sciences, 1975, vol. 64 (3), pp. 367-391.
Brickner, S.J. et al., "Synthesis and Antibacterial Activity of U-100592 and U-100766, Two Oxazolidinone Antibacterial Agents for the Potential Treatment of Multidrug-Resistant Gram-Positive Bacterial Infections," Journal of Medicinal Chemistry, 1996, vol. 39 (3), pp. 673-679.

(Continued)

*Primary Examiner* — James O Wilson
*Assistant Examiner* — Oluwafemi Masha
(74) *Attorney, Agent, or Firm* — Glen J. Gesicki

(57) ABSTRACT

Disclosed are compounds which inhibit the activity of NAMPT, compositions containing the compounds and methods of treating diseases during which NAMPT is expressed.

13 Claims, No Drawings

(56) References Cited

FOREIGN PATENT DOCUMENTS

| | | |
|---|---|---|
| WO | 03080054 A1 | 10/2003 |
| WO | 2005016915 A1 | 2/2005 |
| WO | 2005030704 A1 | 4/2005 |
| WO | 2005068468 A2 | 7/2005 |
| WO | 2005099353 A2 | 10/2005 |
| WO | 2006008754 A1 | 1/2006 |
| WO | 2006058338 A2 | 6/2006 |
| WO | 2006092608 A1 | 9/2006 |
| WO | 2007108750 A1 | 9/2007 |
| WO | 2008025857 A2 | 3/2008 |
| WO | 2008033562 A2 | 3/2008 |
| WO | 2009058338 A1 | 5/2009 |
| WO | 2009107850 A2 | 9/2009 |
| WO | 2009109610 A1 | 9/2009 |
| WO | 2009153197 A1 | 12/2009 |
| WO | 2010075200 A1 | 7/2010 |
| WO | 2011025799 A1 | 3/2011 |
| WO | 2012031199 A1 | 3/2012 |

OTHER PUBLICATIONS

Bruzzone S., et al., "Catastrophic NAD+ Depletion in Activated T Lymphocytes through Nampt Inhibition Reduces Demyelination and Disability in EAE," PLoS One, 2009, vol. 4 (11), pp. e7897.

Busso N., et al., "Pharmacological Inhibition of Nicotinamide Phosphoribosyltransferase/visfatin Enzymatic Activity Identifies a New Inflammatory Pathway Linked to NAD," PLoS One, 2008, vol. 3 (5), pp. e2267.

CAS Registry No. 1280844-01-0, Sep. 23, 2012.

CAS Registry No. 1280859-71-3, Sep. 23, 2013

CAS Registry No. 1280947-87-6, Sep. 23, 2013

CAS Registry No. 1311584-20-9, Sep. 23, 2013

CAS Registry No. 1311874-71-1, Sep. 23, 2013

Czajka, D. M. et al., "Effect of Deuterium Oxide on the Reproductive Potential of Mice," Annals of the New York Academy of Sciences, 1960, vol. 84, pp. 770-779.

Czajka, D. M. et al., "Physiological Effects of Deuterium on Dogs," American Journal of Physiology, 1961, vol. 201 (2), pp. 357-362.

Foster, A. B. et al., "Deuterium Isotope Effects in the Metabolism of Drugs and Xenobiotics: Implications for Drug Design," Advances in Drug Research, 1985, vol. 14, pp. 2-36.

Galli M., et al., "The Nicotinamide Phosphoribosyltransferase: A Molecular Link Between Metabolism, Inflammation, and Cancer," Cancer Research, 2010, vol. 70 (1), pp. 8-11.

Garten A., "Nampt: Linking NAD Biology, Metabolism and Cancer," Trends in Endocrinology and Metabolism, 2009, vol. 20 (3), pp. 130-138.

Hansen C.M., et al., "Cyanoguanidine CHS 828 Induces Programmed Cell Death with Apoptotic Features in Human Breast Cancer Cells in Vitro," Anticancer Research, 2000, vol. 20 (6B), pp. 4211-4220.

International Search Report and Written Opinion for Application No. PCT/US2013/040481, mailed on Jul. 4, 2013, 11 pages.

Kato, S. et al., "Synthesis of Deuterated Mosapride Citrate," Journal of Labelled Compounds and Radiopharmaceuticals, 1995, vol. 36 (10), pp. 927-932.

Kim S.R., et al., "Visfatin Promotes Angiogenesis by Activation of Extracellular Signal-regulated Kinase 1/2," Biochemical and Biophysical Research Communications, 2007, vol. 357 (1), pp. 150-156.

Kushner, et al., "Pharmacological uses and perspectives of heavy water and deuterated compounds," Canadian Journal of Physiology and Pharmacology, 1999, vol. 77 (2), pp. 79-88.

Lizondo, J. et al., "Linezolid: Oxazolidinone antibacterial," Drugs of the Future, 1996, vol. 21 (11), pp. 1116-1123.

Mallesham, B. et al., "Highly Efficient CuI-Catalyzed Coupling of Aryl Bromides With Oxazolidinones Using Buchwald's Protocol: A Short Route to Linezolid and Toloxatone," Organic Letters, 2003, vol. 5 (7), pp. 963-965.

Olesen U.H., et al., "A Preclinical Study on the Rescue of Normal Tissue by Nicotinic Acid in High-dose Treatment with APO866, a Specific Nicotinamide Phosphoribosyltransferase Inhibitor," Molecular Cancer Therapeutics, 2010, vol. 9 (6), pp. 1609-1617.

Thomson, J.F., "Physiological Effects of D2O in Mammals," Annals of the New York Academy of Sciences, 1960, vol. 84, pp. 736-744.

Van Beijnum J.R., et al., "Target Validation for Genomics Using Peptide-specific Phage Antibodies: A Study of Five Gene Products Overexpressed in Colorectal Cancer," International Journal of Cancer, 2002, vol. 101 (2), pp. 118-127.

Ziegler M., "New Functions of a Long-known Molecule. Emerging Roles of NAD in Cellular Signaling," European Journal of Biochemistry, 2000, vol. 267 (6), pp. 1550-1564.

\* cited by examiner

NAMPT INHIBITORS

This application claims priority to U.S. Provisional Application Ser. No. 61/645,692, filed May 11, 2012, U.S. Provisional Application Ser. No. 61/719,013, filed Oct. 26, 2012, and U.S. Provisional Application Ser. No. 61/779,756, filed Mar. 13, 2013, which are incorporated by reference in their entirety.

FIELD OF THE INVENTION

This invention pertains to compounds which inhibit the activity of NAMPT, compositions containing the compounds, and methods of treating diseases during which NAMPT is expressed.

BACKGROUND OF THE INVENTION

NAD+ (nicotinamide adenine dinucleotide) is a coenzyme that plays a critical role in many physiologically essential processes (Ziegkel, M. *Eur. J. Biochem.* 267, 1550-1564, 2000). NAD is necessary for several signaling pathways including among others poly ADP-ribosylation in DNA repair, mono-ADP-ribosylation in both the immune system and G-protein-coupled signaling, and NAD is also required by sirtuins for their deacetylase activity (Garten, A. et al *Trends in Endocrinology and Metabolism,* 20, 130-138, 2008).

NAMPT (also known as pre-B-cell-colony-enhancing factor (PBEF) and visfatin) is an enzyme that catalyzes the phosphoribosylation of nicotinamide and is the rate-limiting enzyme in one of two pathways that salvage NAD.

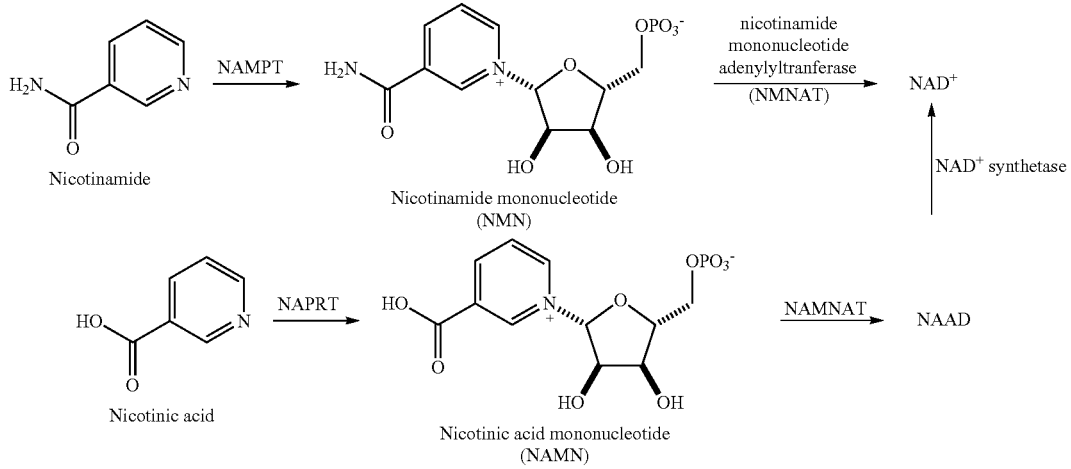

Increasing evidence suggests that NAMPT inhibitors have potential as anticancer agents. Cancer cells have a higher basal turnover of NAD and also display higher energy requirements compared with normal cells. Additionally, increased NAMPT expression has been reported in colorectal cancer (Van Beijnum, J. R. et al *Int. J. Cancer* 101, 118-127, 2002) and NAMPT is involved in angiogenesis (Kim, S. R. et al. *Biochem. Biophys. Res. Commun.* 357, 150-156, 2007). Small-molecule inhibitors of NAMPT have been shown to cause depletion of intracellular NAD+ levels and ultimately induce tumor cell death (Hansen, C M et al. *Anticancer Res.* 20, 42111-4220, 2000) as well as inhibit tumor growth in xenograft models (Olese, U. H. et al. *Mol Cancer Ther.* 9, 1609-1617, 2010).

NAMPT inhibitors also have potential as therapeutic agents in inflammatory and metabolic disorders (Galli, M. et al *Cancer Res.* 70, 8-11, 2010). For example, NAMPT is the predominant enzyme in T and B lymphocytes. Selective inhibition of NAMPT leads to NAD+ depletion in lymphocytes blocking the expansion that accompanies autoimmune disease progression whereas cell types expressing the other NAD+ generating pathways might be spared. A small molecule NAMPT inhibitor (FK866) has been shown to selectively block proliferation and induce apoptosis of activated T cells and was efficacious in animal models of arthritis (collagen-induced arthritis) (Busso, N. et al. *Plos One* 3, e2267, 2008). FK866 ameliorated the manifestations of experimental autoimmune encephalomyelitis (EAE), a model of T-cell mediated autoimmune disorders. (Bruzzone, S et al. *Plos One* 4, e7897, 2009). NaMPT activity increases NF-kB transcriptional activity in human vascular endothelial cell, resulting in MMP-2 and MMP-9 activation, suggesting a role for NAMPT inhibitors in the prevention of inflammatory mediated complications of obesity and type 2 diabetes (Adya, R. et. Al. *Diabetes Care,* 31, 758-760, 2008).

SUMMARY OF THE INVENTION

One embodiment of this invention, therefore, pertains to compounds or pharmaceutically acceptable salts thereof, which are useful as inhibitors of NAMPT, the compounds having Formula (IC)

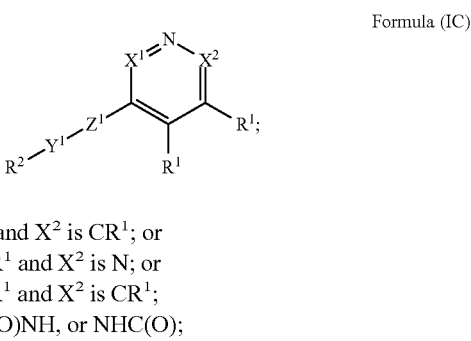

Formula (IC)

$X^1$ is N and $X^2$ is $CR^1$; or
$X^1$ is $CR^1$ and $X^2$ is N; or
$X^1$ is $CR^1$ and $X^2$ is $CR^1$;
$Y^1$ is C(O)NH, or NHC(O);

$Z^1$ is

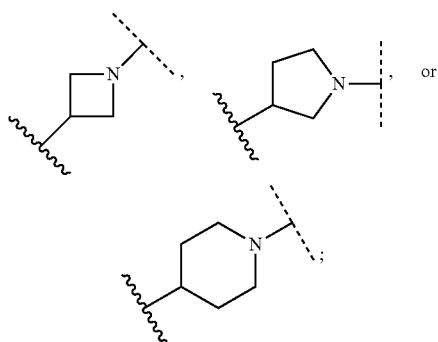, or wherein ⌇ indicates the point of attachment to $Y^1$ and ⌇ indicates the point of attachment to the nitrogen containing heteroaryl;

$R^1$, at each occurrence, is independently selected from the group consisting of hydrogen, alkyl, alkenyl, alkynyl, haloalkyl, hydroxyalkyl, alkoxy, OH, $NH_2$, CN, $NO_2$, F, Cl, Br and I;

$R^2$ is independently selected from the group consisting of $C_4$-$C_6$-alkyl, $C_4$-$C_6$-alkenyl, $C_4$-$C_6$-alkynyl, aryl, and 5-6 membered heteroaryl; wherein each $R^2 C_4$-$C_6$-alkyl, $C_4$-$C_6$-alkenyl, and $C_4$-$C_6$-alkynyl is substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(N)NH_2$, $C(N)NHR^3$, $C(N)N(R^3)_2$, CNOH, $CNOCH_3$, OH, (O), CN, $N_3$, $NO_2$, F, Cl, Br and I; wherein each $R^2$ aryl and 5-6 membered heteroaryl is optionally substituted with one or more substituents independently selected from the group consisting of $R^4$, $OR^4$, $SR^4$, $S(O)R^4$, $SO_2R^4$, $C(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, and I;

$R^3$, at each occurrence, is independently selected from the group consisting of alkyl, alkenyl, alkynyl, aryl, cycloalkyl, cycloalkenyl, and heterocyclyl; wherein each $R^3$ alkyl, alkenyl, and alkynyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, CNOH, $CNOCH_3$, OH, (O), CN, $N_3$, $NO_2$, F, Cl, Br and I; wherein each $R^3$ aryl, cycloalkyl, cycloalkenyl, and heterocyclyl is optionally substituted with one or more substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $C(N)NH_2$, $C(N)NHR^6$, $C(N)N(R^6)_2$, CNOH, $CNOCH_3$, OH, CN, $N_3$, $NO_2$, F, Cl, Br and I;

$R^4$, at each occurrence, is independently selected from the group consisting of alkyl, alkenyl, alkynyl, aryl, heterocyclyl, cycloalkyl, and cycloalkenyl; wherein each $R^4$ alkyl, alkenyl, and alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, CNOH, $CNOCH_3$, OH, (O), CN, $N_3$, $NO_2$, F, Cl, Br and I;

$R^5$, at each occurrence, is independently selected from the group consisting of alkyl, alkenyl, alkynyl, aryl, heterocyclyl, cycloalkyl, and cycloalkenyl; wherein each $R^5$ alkyl, alkenyl, and alkynyl is optionally substituted with one or more substituents independently selected from the group consisting of $R^8$, $OR^8$, $SR^8$, $S(O)R^8$, $SO_2R^8$, $NHR^8$, $N(R^8)_2$, $C(O)R^8$, $C(O)NH_2$, $C(O)NHR^8$, $C(O)N(R^8)_2$, $NHC(O)R^8$, $NR^8C(O)R^8$, $NHSO_2R^8$, $NHC(O)OR^8$, $SO_2NH_2$, $SO_2NHR^8$, $SO_2N(R^8)_2$, $NHC(O)NH_2$, $NHC(O)NHR^8$, OH, (O), C(O)OH, $N_3$, CN, $NH_2$, F, Cl, Br and I;

$R^6$, at each occurrence, is independently selected from the group consisting of alkyl, alkenyl, alkynyl, aryl, heterocyclyl, cycloalkyl, and cycloalkenyl; wherein each $R^6$ alkyl, alkenyl, and alkynyl is optionally substituted with one or more substituents independently selected from the group consisting of $R^9$, $OR^9$, $SR^9$, $S(O)R^9$, $SO_2R^9$, $NHR^9$, $N(R^9)_2$, $C(O)R^9$, $C(O)NH_2$, $C(O)NHR^9$, $C(O)N(R^9)_2$, $NHC(O)R^9$, $NR^9C(O)R^9$, $NHSO_2R^9$, $NHC(O)OR^9$, $SO_2NH_2$, $SO_2NHR^9$, $SO_2N(R^9)_2$, $NHC(O)NH_2$, $NHC(O)NHR^9$, OH, (O), C(O)OH, $N_3$, CN, $NH_2$, $CF_3$, $CF_2CF_3$, F, Cl, Br and I;

$R^7$, at each occurrence, is independently selected from the group consisting of alkyl, alkenyl, alkynyl, aryl, heterocyclyl, cycloalkyl, and cycloalkenyl;

$R^8$, at each occurrence, is independently selected from the group consisting of alkyl, alkenyl, alkynyl, aryl, heterocyclyl, cycloalkyl, and cycloalkenyl;

$R^9$, at each occurrence, is independently selected from the group consisting of alkyl, alkenyl, alkynyl, aryl, heterocyclyl, cycloalkyl, and cycloalkenyl;

wherein the cyclic moieties represented by $R^4$, $R^5$, $R^6$, $R^7$, $R^8$, and $R^9$ are independently optionally substituted with one or more substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $C(O)C(O)R^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{16}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, CNOH, $CNOCH_3$, OH, CN, $N_3$, $NO_2$, F, Cl, Br and I;

$R^{10}$, at each occurrence, is independently selected from the group consisting of alkyl, alkenyl, alkynyl, aryl, heterocyclyl, cycloalkyl, and cycloalkenyl; wherein each $R^{10}$ alkyl, alkenyl, and alkynyl is optionally substituted with one or more substituents independently selected from the group consisting of $R^{11}$, $OR^{11}$, $SR^{11}$, $S(O)R^{11}$, $SO_2R^{11}$, $C(O)R^{11}$, $CO(O)R^{11}$, $OC(O)R^{11}$, $OC(O)OR^{11}$, $NH_2$, $NHR^{11}$, $N(R^{11})_2$, $NHC(O)R^{11}$, $NR^{11}C(O)R^{11}$, $NHS(O)_2R^{11}$, $NR^{11}S(O)_2R^{11}$, $NHC(O)OR^{11}$, $NR^{11}C(O)OR^{11}$, $NHC(O)NH_2$, $NHC(O)NHR^{11}$, $NHC(O)N(R^{11})_2$, $NR^{11}C(O)NHR^{11}$, $NR^{11}C(O)N(R^{11})_2$, $C(O)NH_2$, $C(O)NHR^{11}$, $C(O)N(R^{11})_2$, $C(O)NHOH$, $C(O)NHOR^{11}$, $C(O)NHSO_2R^{11}$, $C(O)NR^{11}SO_2R^{11}$, $SO_2NH_2$, $SO_2NHR^{11}$, $SO_2N(R^{11})_2$, $C(O)H$, $C(O)OH$, $C(N)NH_2$, $C(N)NHR^{11}$, $C(N)N(R^{11})_2$, CNOH, $CNOCH_3$, OH, (O), CN, $N_3$, $NO_2$, F, Cl, Br and I; wherein each $R^{10}$ aryl, heterocyclyl, cycloalkyl, and cycloalkenyl is optionally substituted with one or more substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, $C(N)NH_2$, $C(N)NHR^{12}$, $C(N)N(R^{12})_2$, CNOH, $CNOCH_3$, OH, CN, $N_3$, $NO_2$, $CF_3$, $OCF_3$, F, Cl, Br and I;

$R^{11}$, at each occurrence, is independently selected from the group consisting of alkyl, alkenyl, alkynyl, aryl, heterocyclyl, cycloalkyl, and cycloalkenyl; wherein each $R^{11}$ alkyl, alkenyl, and alkynyl is optionally substituted with alkoxy or aryl; wherein each $R^{11}$ aryl, heterocyclyl, cycloalkyl, and cycloalkenyl is optionally substituted with one or more substituents independently selected from the group consisting of $R^{13}$, $OR^{13}$, $C(O)OR^{13}$, $OCF_3$, $CF_3$, F, Cl, Br and I;

$R^{12}$, at each occurrence, is independently selected from the group consisting of alkyl, alkenyl, alkynyl, aryl, heterocyclyl, cycloalkyl, and cycloalkenyl; and $R^{13}$, at each occurrence, is independently selected from the group consisting of alkyl, haloalkyl, alkenyl, alkynyl, aryl, heterocyclyl, cycloalkyl, and cycloalkenyl;

with the proviso that when $X^1$ is $CR^1$ and $X^2$ is $CR^1$; $R^1$ is hydrogen; $Y^1$ is NHC(O); $Z^1$ is

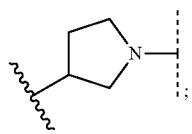

and $R^2$ is pyrrolyl; the $R^2$ pyrrolyl is not substituted with two alkyl groups. In another embodiment of Formula (IC), $Z^1$ is

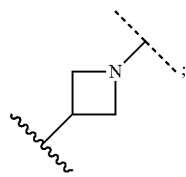

wherein ⁓ indicates the point of attachment to $Y^1$ and ⟍ indicates the point of attachment to the nitrogen containing heteroaryl. In another embodiment of Formula (IC), $Z^1$ is

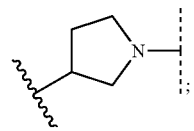

wherein ⁓ indicates the point of attachment to $Y^1$ and ⟍ indicates the point of attachment to the nitrogen containing heteroaryl. In another embodiment of Formula (IC), $Z^1$ is

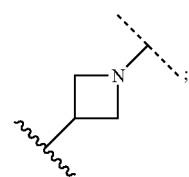

wherein ⁓ indicates the point of attachment to $Y^1$ and ⟍ indicates the point of attachment to the nitrogen containing heteroaryl; and $Y^1$ is C(O)NH. In another embodiment of Formula (IC), $Z^1$ is

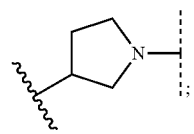

wherein ⁓ indicates the point of attachment to $Y^1$ and ⟍ indicates the point of attachment to the nitrogen containing heteroaryl; and $Y^1$ is C(O)NH. In another embodiment of Formula (IC), $Z^1$ is

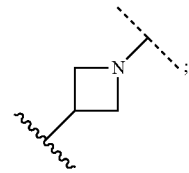

wherein ⁓ indicates the point of attachment to $Y^1$ and ⟍ indicates the point of attachment to the nitrogen containing heteroaryl; $Y^1$ is C(O)NH; and $X^1$ is N and $X^2$ is $CR^1$. In another embodiment of Formula (IC), $Z^1$ is

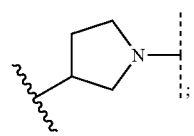

wherein ⁓ indicates the point of attachment to $Y^1$ and ⟍ indicates the point of attachment to the nitrogen containing heteroaryl; $Y^1$ is C(O)NH; $X^1$ is N and $X^2$ is $CR^1$. In another embodiment of Formula (IC), $Z^1$ is

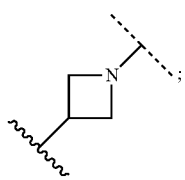

wherein ∿ indicates the point of attachment to $Y^1$ and ＼ indicates the point of attachment to the nitrogen containing heteroaryl; $Y^1$ is C(O)NH; $X^1$ is N and $X^2$ is $CR^1$; wherein $R^2$ is phenyl; wherein each $R^2$ phenyl is substituted with one substituent independently selected from the group consisting of $R^4$, $OR^4$, and $SO_2R^4$. In another embodiment of Formula (IC), $Z^1$ is

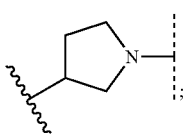

wherein ∿ indicates the point of attachment to $Y^1$ and ＼ indicates the point of attachment to the nitrogen containing heteroaryl; $Y^1$ is C(O)NH; $X^1$ is N and $X^2$ is $CR^1$; wherein $R^2$ is phenyl; wherein each $R^2$ phenyl is substituted with one substituent independently selected from the group consisting of $R^4$, $OR^4$, and $SO_2R^4$. In another embodiment of Formula (IC), $Z^1$ is

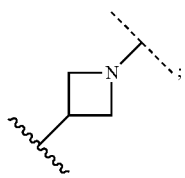

wherein ∿ indicates the point of attachment to $Y^1$ and ＼ indicates the point of attachment to the nitrogen containing heteroaryl; $Y^1$ is C(O)NH; $X^1$ is N and $X^2$ is $CR^1$; wherein $R^2$ is phenyl; wherein each $R^2$ phenyl is substituted with one substituent independently selected from the group consisting of $R^4$, $OR^4$, and $SO_2R^4$; and $R^1$, at each occurrence, is hydrogen. In another embodiment of Formula (IC), $Z^1$ is

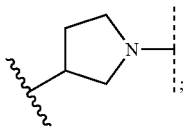

wherein ∿ indicates the point of attachment to $Y^1$ and ＼ indicates the point of attachment to the nitrogen containing heteroaryl; $Y^1$ is C(O)NH; $X^1$ is N and $X^2$ is $CR^1$; wherein $R^2$ is phenyl; wherein each $R^2$ phenyl is substituted with one substituent independently selected from the group consisting of $R^4$, $OR^4$, and $SO_2R^4$; and $R^1$, at each occurrence, is hydrogen. In another embodiment of Formula (IC), $Z^1$ is

wherein ∿ indicates the point of attachment to $Y^1$ and ＼ indicates the point of attachment to the nitrogen containing heteroaryl; $Y^1$ is C(O)NH; $X^1$ is N and $X^2$ is $CR^1$; wherein $R^2$ is phenyl; wherein each $R^2$ phenyl is substituted with one substituent independently selected from the group consisting of $R^4$, $OR^4$, and $SO_2R^4$; $R^1$, at each occurrence, is hydrogen; and $R^4$, at each occurrence, is heterocyclyl. In another embodiment of Formula (IC), $Z^1$ is wherein ∿ indicates the point of attachment to $Y^1$ and ＼ indicates the point of attachment to the nitrogen containing heteroaryl; $Y^1$ is C(O)NH; $X^1$ is N and $X^2$ is $CR^1$; wherein $R^2$ is phenyl; wherein each $R^2$ phenyl is substituted with one substituent independently selected from the group consisting of $R^4$, $OR^4$, and $SO_2R^4$; and $R^1$, at each occurrence, is hydrogen; and $R^4$, at each occurrence, is heterocyclyl.

Still another embodiment pertains to compounds, which are 1-(pyridin-3-yl)-N-(4-{[1-(tetrahydro-2H-pyran-4-ylacetyl) piperidin-4-yl]oxy}phenyl)azetidine-3-carboxamide;

1-(2-cyanopyridin-3-yl)-N-{4-[1-(2-hydroxy-2-methylpropanoyl)piperidin-4-yl]phenyl}azetidine-3-carboxamide;

N-(4-{[1-(tetrahydro-2H-pyran-4-ylacetyl)piperidin-4-yl] oxy}phenyl)-1-[2-(trifluoromethyl)pyridin-3-yl]azetidine-3-carboxamide;

1-(2-methylpyridin-3-yl)-N-(4-{[1-(tetrahydro-2H-pyran-4-ylacetyl)piperidin-4-yl]oxy}phenyl)azetidine-3-carboxamide;

1-(4-methylpyridin-3-yl)-N-(4-{[1-(tetrahydro-2H-pyran-4-ylacetyl)piperidin-4-yl]oxy}phenyl)azetidine-3-carboxamide;

1-(4-fluoropyridin-3-yl)-N-(4-{[1-(tetrahydro-2H-pyran-4-ylacetyl)piperidin-4-yl]oxy}phenyl)azetidine-3-carboxamide;

N-(4-{[1-(tetrahydro-2H-pyran-4-ylacetyl)piperidin-4-yl] oxy}phenyl)-1-[4-(trifluoromethyl)pyridin-3-yl]azetidine-3-carboxamide;

tert-butyl 4-[4-({[(3S)-1-(pyridin-3-yl)pyrrolidin-3-yl] carbonyl}amino)phenoxy]piperidine-1-carboxylate;

tert-butyl 4-[4-({[(3R)-1-(pyridin-3-yl)pyrrolidin-3-yl] carbonyl}amino)phenoxy]piperidine-1-carboxylate;

1-(pyridin-3-yl)-N-(4-{1-[(2S)-tetrahydrofuran-2-ylcarbonyl]piperidin-4-yl}phenyl)azetidine-3-carboxamide;

(3S)-1-(pyridin-3-yl)-N-(4-{[1-(tetrahydro-2H-pyran-4-ylacetyl)piperidin-4-yl]oxy}phenyl)pyrrolidine-3-carboxamide;

(3S)—N-(4-{[1-(2-methylpropanoyl)piperidin-4-yl] oxy}phenyl)-1-(pyridin-3-yl)pyrrolidine-3-carboxamide;

(3S)-1-(pyridin-3-yl)-N-[4-({1-[(2S)-tetrahydro furan-2-ylcarbonyl]piperidin-4-yl}oxy)phenyl]pyrrolidine-3-carboxamide;

(3S)-1-(pyridin-3-yl)-N-[4-({1-[(2R)-tetrahydrofuran-2-yl-carbonyl]piperidin-4-yl}oxy)phenyl]pyrrolidine-3-carboxamide;
(3S)-1-(pyridin-3-yl)-N-(4-{[1-(tetrahydrofuran-3-ylcarbonyl)piperidin-4-yl]oxy}phenyl)pyrrolidine-3-carboxamide;
(3S)—N-(4-{[1-(cyclopropylacetyl)piperidin-4-yl]oxy}phenyl)-1-(pyridin-3-yl)pyrrolidine-3-carboxamide;
(3S)—N-(4-{[1-(2-hydroxy-2-methylpropanoyl)piperidin-4-yl]oxy}phenyl)-1-(pyridin-3-yl)pyrrolidine-3-carboxamide;
(3S)-1-(pyridin-3-yl)-N-(4-{[1-(3,3,3-trifluoropropanoyl)piperidin-4-yl]oxy}phenyl)pyrrolidine-3-carboxamide;
(3S)—N-[4-({1-[(2S)-2-methylbutanoyl]piperidin-4-yl}oxy)phenyl]-1-(pyridin-3-yl)pyrrolidine-3-carboxamide;
N-{4-[1-(2-hydroxy-2-methylpropanoyl)piperidin-4-yl]phenyl}-1-(pyridin-3-yl)azetidine-3-carboxamide;
N-[1-(pyridin-3-yl)azetidin-3-yl]-4-{[1-(tetrahydro-2H-pyran-4-ylacetyl)piperidin-4-yl]oxy}benzamide;
N-(4-{1-[(2S)-2-methylbutanoyl]piperidin-4-yl}phenyl)-1-(pyridin-3-yl)azetidine-3-carboxamide;
4-({1-[(2S)-2-methylbutanoyl]piperidin-4-yl}oxy)-N-[1-(pyridin-3-yl)azetidin-3-yl]benzamide;
4-{[1-(2-hydroxy-2-methylpropanoyl)piperidin-4-yl]oxy}-N-[1-(pyridin-3-yl)azetidin-3-yl]benzamide;
1-(pyridin-3-yl)-N-{4-[1-(tetrahydro-2H-pyran-4-ylacetyl)piperidin-4-yl]phenyl}azetidine-3-carboxamide;
N-[4-(1-benzoylpiperidin-4-yl)phenyl]-1-(pyridin-3-yl)azetidine-3-carboxamide;
tert-butyl 4-(4-{[(3S)-1-(pyridin-3-yl)pyrrolidin-3-yl]carbamoyl}phenoxy)piperidine-1-carboxylate;
tert-butyl 4-(4-{[(3R)-1-(pyridin-3-yl)pyrrolidin-3-yl]carbamoyl}phenoxy)piperidine-1-carboxylate;
N-{4-[1-(2-methylpropanoyl)piperidin-4-yl]phenyl}-1-(2-methylpyridin-3-yl)azetidine-3-carboxamide;
N-{4-[1-(2-methylpropanoyl)piperidin-4-yl]phenyl}-1-(pyridin-3-yl)azetidine-3-carboxamide;
N-(4-{[1-(2-hydroxy-2-methylpropanoyl)piperidin-4-yl]oxy}phenyl)-1-(pyridin-3-yl)azetidine-3-carboxamide;
N-[4-({1-[(2S)-2-methylbutanoyl]piperidin-4-yl}oxy)phenyl]-1-(pyridin-3-yl)azetidine-3-carboxamide;
1-(pyridin-3-yl)-N-[4-({1-[(2S)-tetrahydro furan-2-ylcarbonyl]piperidin-4-yl}oxy)phenyl]azetidine-3-carboxamide;
N-{4-[(1-pentanoylpiperidin-4-yl)oxy]phenyl}-1-(pyridin-3-yl)azetidine-3-carboxamide;
N-[4-({1-[(2-methylcyclopropyl)carbonyl]piperidin-4-yl}oxy)phenyl]-1-(pyridin-3-yl)azetidine-3-carboxamide;
N-[4-({1-[(1S,4R)-bicyclo[2.2.1]hept-2-ylacetyl]piperidin-4-yl}oxy)phenyl]-1-(pyridin-3-yl)azetidine-3-carboxamide;
N-(4-{[1-(4-methylpentanoyl)piperidin-4-yl]oxy}phenyl)-1-(pyridin-3-yl)azetidine-3-carboxamide;
N-(4-{[1-(3-methylpentanoyl)piperidin-4-yl]oxy}phenyl)-1-(pyridin-3-yl)azetidine-3-carboxamide;
N-(4-{[1-(3-ethoxypropanoyl)piperidin-4-yl]oxy}phenyl)-1-(pyridin-3-yl)azetidine-3-carboxamide;
N-(4-{[1-(2,2-dimethylbutanoyl)piperidin-4-yl]oxy}phenyl)-1-(pyridin-3-yl)azetidine-3-carboxamide;
N-(4-{[1-(3,3-dimethylbutanoyl)piperidin-4-yl]oxy}phenyl)-1-(pyridin-3-yl)azetidine-3-carboxamide;
N-(4-{[1-(2,2-dimethylpropanoyl)piperidin-4-yl]oxy}phenyl)-1-(pyridin-3-yl)azetidine-3-carboxamide;
N-{4-[(1-butanoylpiperidin-4-yl)oxy]phenyl}-1-(pyridin-3-yl)azetidine-3-carboxamide;
N-(4-{[1-(ethoxyacetyl)piperidin-4-yl]oxy}phenyl)-1-(pyridin-3-yl)azetidine-3-carboxamide;
N-(4-{[1-(3-methylbutanoyl)piperidin-4-yl]oxy}phenyl)-1-(pyridin-3-yl)azetidine-3-carboxamide;
N-(4-{[1-(2-methylpropanoyl)piperidin-4-yl]oxy}phenyl)-1-(pyridin-3-yl)azetidine-3-carboxamide;
N-(4-{[1-(N-acetyl-L-leucyl)piperidin-4-yl]oxy}phenyl)-1-(pyridin-3-yl)azetidine-3-carboxamide;
N-[4-({1-[(2-methoxyethoxy)acetyl]piperidin-4-yl}oxy)phenyl]-1-(pyridin-3-yl)azetidine-3-carboxamide;
N-(4-{[1-(cyclohexylcarbonyl)piperidin-4-yl]oxy}phenyl)-1-(pyridin-3-yl)azetidine-3-carboxamide;
N-(4-{[1-(cyclohexylacetyl)piperidin-4-yl]oxy}phenyl)-1-(pyridin-3-yl)azetidine-3-carboxamide;
1-(pyridin-3-yl)-N-(4-{[1-(4,4,4-trifluorobutanoyl)piperidin-4-yl]oxy}phenyl)azetidine-3-carboxamide;
N-(4-{[1-(cyclopentylcarbonyl)piperidin-4-yl]oxy}phenyl)-1-(pyridin-3-yl)azetidine-3-carboxamide;
N-[4-({1-[(1-methylcyclohexyl)carbonyl]piperidin-4-yl}oxy)phenyl]-1-(pyridin-3-yl)azetidine-3-carboxamide;
N-(4-{[1-(furan-3-ylcarbonyl)piperidin-4-yl]oxy}phenyl)-1-(pyridin-3-yl)azetidine-3-carboxamide;
1-(pyridin-3-yl)-N-(4-{[1-(3,3,3-trifluoropropanoyl)piperidin-4-yl]oxy}phenyl)azetidine-3-carboxamide;
N-{4-[(1-acetylpiperidin-4-yl)oxy]phenyl}-1-(pyridin-3-yl)azetidine-3-carboxamide;
N-(4-{[1-(methoxyacetyl)piperidin-4-yl]oxy}phenyl)-1-(pyridin-3-yl)azetidine-3-carboxamide;
1-(pyridin-3-yl)-N-(4-{[1-(thiophen-3-ylcarbonyl)piperidin-4-yl]oxy}phenyl)azetidine-3-carboxamide;
N-[4-({1-[(3-methylthiophen-2-yl)carbonyl]piperidin-4-yl}oxy)phenyl]-1-(pyridin-3-yl)azetidine-3-carboxamide;
N-(4-{[1-(morpholin-4-ylacetyl)piperidin-4-yl]oxy}phenyl)-1-(pyridin-3-yl)azetidine-3-carboxamide;
1-(pyridin-3-yl)-N-(4-{[1-(thiophen-2-ylcarbonyl)piperidin-4-yl]oxy}phenyl)azetidine-3-carboxamide;
N-[4-({1-[(5-methylthiophen-2-yl)carbonyl]piperidin-4-yl}oxy)phenyl]-1-(pyridin-3-yl)azetidine-3-carboxamide;
N-(4-{[1-(furan-2-ylcarbonyl)piperidin-4-yl]oxy}phenyl)-1-(pyridin-3-yl)azetidine-3-carboxamide;
N-[4-({1-[(1-methyl-1H-pyrrol-2-yl)carbonyl]piperidin-4-yl}oxy)phenyl]-1-(pyridin-3-yl)azetidine-3-carboxamide;
N-{4-[(1-propanoylpiperidin-4-yl)oxy]phenyl}-1-(pyridin-3-yl)azetidine-3-carboxamide;
N-[4-({1-[(1-methylcyclopropyl)carbonyl]piperidin-4-yl}oxy)phenyl]-1-(pyridin-3-yl)azetidine-3-carboxamide;
N-(4-{[1-(N,N-dimethyl-beta-alanyl)piperidin-4-yl]oxy}phenyl)-1-(pyridin-3-yl)azetidine-3-carboxamide;
1-(pyridin-3-yl)-N-(4-{[1-(1,3-thiazol-2-ylcarbonyl)piperidin-4-yl]oxy}phenyl)azetidine-3-carboxamide;
N-(4-{[1-(cyclopentylacetyl)piperidin-4-yl]oxy}phenyl)-1-(pyridin-3-yl)azetidine-3-carboxamide;
N-(4-{[1-(2,3-dimethylbutanoyl)piperidin-4-yl]oxy}phenyl)-1-(pyridin-3-yl)azetidine-3-carboxamide;
N-{4-[1-(2-hydroxy-2-methylpropanoyl)piperidin-4-yl]phenyl}-1-(2-methylpyridin-3-yl)azetidine-3-carboxamide;
N-{4-[1-(2-hydroxy-2-methylpropanoyl)piperidin-4-yl]phenyl}-1-(4-methylpyridin-3-yl)azetidine-3-carboxamide;
N-{4-[1-(2-hydroxy-2-methylpropanoyl)piperidin-4-yl]phenyl}-1-(2-methoxypyridin-3-yl)azetidine-3-carboxamide;
N-(4-{[1-(cyclopropylmethyl)piperidin-4-yl]oxy}phenyl)-1-(pyridin-3-yl)azetidine-3-carboxamide;
N-(4-{[1-(2-methylpentyl)piperidin-4-yl]oxy}phenyl)-1-(pyridin-3-yl)azetidine-3-carboxamide;
N-(4-{[1-(2-methylpropyl)piperidin-4-yl]oxy}phenyl)-1-(pyridin-3-yl)azetidine-3-carboxamide;

N-(4-{[1-(3-methylbutyl)piperidin-4-yl]oxy}phenyl)-1-(pyridin-3-yl)azetidine-3-carboxamide;
N-(4-{[1-(2-ethylbutyl)piperidin-4-yl]oxy}phenyl)-1-(pyridin-3-yl)azetidine-3-carboxamide;
N-(4-{[1-(2,2-dimethylpropyl)piperidin-4-yl]oxy}phenyl)-1-(pyridin-3-yl)azetidine-3-carboxamide;
N-(4-{[1-(2-methylbutyl)piperidin-4-yl]oxy}phenyl)-1-(pyridin-3-yl)azetidine-3-carboxamide;
N-{4-[(1-propylpiperidin-4-yl)oxy]phenyl}-1-(pyridin-3-yl)azetidine-3-carboxamide;
N-(4-{[1-(2-cyclopropylethyl)piperidin-4-yl]oxy}phenyl)-1-(pyridin-3-yl)azetidine-3-carboxamide;
1-(pyridin-3-yl)-N-(4-{[1-(tetrahydrofuran-3-ylmethyl)piperidin-4-yl]oxy}phenyl)azetidine-3-carboxamide;
N-(4-{[1-(2,2-dimethylbutyl)piperidin-4-yl]oxy}phenyl)-1-(pyridin-3-yl)azetidine-3-carboxamide;
N-{4-[1-(2-hydroxy-2-methylpropanoyl)piperidin-4-yl]phenyl}-1-(pyridazin-4-yl)azetidine-3-carboxamide;
N-{4-[1-(cyclohexylmethyl)piperidin-4-yl]phenyl}-1-(pyridin-3-yl)azetidine-3-carboxamide;
N-{4-[1-(3,3-dimethylbutyl)piperidin-4-yl]phenyl}-1-(pyridin-3-yl)azetidine-3-carboxamide;
N-{4-[1-(cyclopentylmethyl)piperidin-4-yl]phenyl}-1-(pyridin-3-yl)azetidine-3-carboxamide;
N-{4-[1-(2,2-dimethylbutyl)piperidin-4-yl]phenyl}-1-(pyridin-3-yl)azetidine-3-carboxamide;
N-{4-[1-(2-methylpentyl)piperidin-4-yl]phenyl}-1-(pyridin-3-yl)azetidine-3-carboxamide;
N-[4-(1-butylpiperidin-4-yl)phenyl]-1-(pyridin-3-yl)azetidine-3-carboxamide;
N-{4-[1-(2-ethylbutyl)piperidin-4-yl]phenyl}-1-(pyridin-3-yl)azetidine-3-carboxamide;
N-{4-[1-(3-methylbutyl)piperidin-4-yl]phenyl}-1-(pyridin-3-yl)azetidine-3-carboxamide;
N-{4-[1-(2-methylpropyl)piperidin-4-yl]phenyl}-1-(pyridin-3-yl)azetidine-3-carboxamide;
N-[4-(1-propylpiperidin-4-yl)phenyl]-1-(pyridin-3-yl)azetidine-3-carboxamide;
N-{4-[1-(2-hydroxy-2-methylpropanoyl)piperidin-4-yl]phenyl}-1-(4-methoxypyridin-3-yl)azetidine-3-carboxamide;
1-(4-cyanopyridin-3-yl)-N-{4-[1-(2-hydroxy-2-methylpropanoyl)piperidin-4-yl]phenyl}azetidine-3-carboxamide;
N-[4-(1-pentanoylpiperidin-4-yl)phenyl]-1-(pyridin-3-yl)azetidine-3-carboxamide;
N-{4-[1-(3-methylpentanoyl)piperidin-4-yl]phenyl}-1-(pyridin-3-yl)azetidine-3-carboxamide;
N-(4-{1-[(1S,4R)-bicyclo[2.2.1]hept-2-ylacetyl]piperidin-4-yl}phenyl)-1-(pyridin-3-yl)azetidine-3-carboxamide;
N-{4-[1-(cyclopentylacetyl)piperidin-4-yl]phenyl}-1-(pyridin-3-yl)azetidine-3-carboxamide;
N-(4-{1-[(2-methylcyclopropyl)carbonyl]piperidin-4-yl}phenyl)-1-(pyridin-3-yl)azetidine-3-carboxamide;
N-{4-[1-(morpholin-4-ylacetyl)piperidin-4-yl]phenyl}-1-(pyridin-3-yl)azetidine-3-carboxamide;
N-{4-[1-(furan-3-ylcarbonyl)piperidin-4-yl]phenyl}-1-(pyridin-3-yl)azetidine-3-carboxamide;
1-(pyridin-3-yl)-N-{4-[1-(pyrrolidin-1-ylacetyl)piperidin-4-yl]phenyl}azetidine-3-carboxamide;
N-{4-[1-(5-oxo-D-prolyl)piperidin-4-yl]phenyl}-1-(pyridin-3-yl)azetidine-3-carboxamide;
N-{4-[1-(N,N-dimethyl-beta-alanyl)piperidin-4-yl]phenyl}-1-(pyridin-3-yl)azetidine-3-carboxamide;
1-(pyridin-3-yl)-N-{4-[1-(1,3-thiazol-2-ylcarbonyl)piperidin-4-yl]phenyl}azetidine-3-carboxamide;
1-(pyridin-3-yl)-N-{4-[1-(thiophen-3-ylcarbonyl)piperidin-4-yl]phenyl}azetidine-3-carboxamide;
N-(4-{1-[(1-methylcyclopropyl)carbonyl]piperidin-4-yl}phenyl)-1-(pyridin-3-yl)azetidine-3-carboxamide;
N-(4-{1-[(3-methylthiophen-2-yl)carbonyl]piperidin-4-yl}phenyl)-1-(pyridin-3-yl)azetidine-3-carboxamide;
1-(pyridin-3-yl)-N-{4-[1-(4,4,4-trifluorobutanoyl)piperidin-4-yl]phenyl}azetidine-3-carboxamide;
N-(4-{1-[(4-methylpiperazin-1-yl)acetyl]piperidin-4-yl}phenyl)-1-(pyridin-3-yl)azetidine-3-carboxamide;
N-{4-[1-(5-oxo-L-prolyl)piperidin-4-yl]phenyl}-1-(pyridin-3-yl)azetidine-3-carboxamide;
N-{4-[1-(3-ethoxypropanoyl)piperidin-4-yl]phenyl}-1-(pyridin-3-yl)azetidine-3-carboxamide;
N-{4-[1-(4-methylpentanoyl)piperidin-4-yl]phenyl}-1-(pyridin-3-yl)azetidine-3-carboxamide;
N-(4-{1-[(1-methylcyclohexyl)carbonyl]piperidin-4-yl}phenyl)-1-(pyridin-3-yl)azetidine-3-carboxamide;
N-[4-(1-acetylpiperidin-4-yl)phenyl]-1-(pyridin-3-yl)azetidine-3-carboxamide;
N-{4-[1-(cyclohexylacetyl)piperidin-4-yl]phenyl}-1-(pyridin-3-yl)azetidine-3-carboxamide;
N-{4-[1-(N-acetyl-L-leucyl)piperidin-4-yl]phenyl}-1-(pyridin-3-yl)azetidine-3-carboxamide;
N-[4-(1-propanoylpiperidin-4-yl)phenyl]-1-(pyridin-3-yl)azetidine-3-carboxamide;
1-(pyridin-3-yl)-N-{4-[1-(3,3,3-trifluoropropanoyl)piperidin-4-yl]phenyl}azetidine-3-carboxamide;
N-(4-{1-[(2-methoxyethoxy)acetyl]piperidin-4-yl}phenyl)-1-(pyridin-3-yl)azetidine-3-carboxamide;
N-(4-{1-[3-(morpholin-4-yl)propanoyl]piperidin-4-yl}phenyl)-1-(pyridin-3-yl)azetidine-3-carboxamide;
N-{4-[1-(2,2-dimethylpropanoyl)piperidin-4-yl]phenyl}-1-(pyridin-3-yl)azetidine-3-carboxamide;
N-(4-{1-[(5-methylthiophen-2-yl)carbonyl]piperidin-4-yl}phenyl)-1-(pyridin-3-yl)azetidine-3-carboxamide;
1-(pyridin-3-yl)-N-{4-[1-(thiophen-2-ylcarbonyl)piperidin-4-yl]phenyl}azetidine-3-carboxamide;
N-(4-{1-[(1-methyl-1H-pyrrol-2-yl)carbonyl]piperidin-4-yl}phenyl)-1-(pyridin-3-yl)azetidine-3-carboxamide;
N-{4-[1-(furan-2-ylcarbonyl)piperidin-4-yl]phenyl}-1-(pyridin-3-yl)azetidine-3-carboxamide;
N-(4-{1-[3-(piperidin-1-yl)propanoyl]piperidin-4-yl}phenyl)-1-(pyridin-3-yl)azetidine-3-carboxamide;
N-{4-[1-(ethoxyacetyl)piperidin-4-yl]phenyl}-1-(pyridin-3-yl)azetidine-3-carboxamide;
N-{4-[1-(3,3-dimethylbutanoyl)piperidin-4-yl]phenyl}-1-(pyridin-3-yl)azetidine-3-carboxamide;
N-{4-[1-(2,2-dimethylbutanoyl)piperidin-4-yl]phenyl}-1-(pyridin-3-yl)azetidine-3-carboxamide;
N-[4-(1-butanoylpiperidin-4-yl)phenyl]-1-(pyridin-3-yl)azetidine-3-carboxamide;
N-{4-[1-(methoxyacetyl)piperidin-4-yl]phenyl}-1-(pyridin-3-yl)azetidine-3-carboxamide;
N-{4-[1-(cyclohexylcarbonyl)piperidin-4-yl]phenyl}-1-(pyridin-3-yl)azetidine-3-carboxamide;
N-{4-[1-(3-methylbutanoyl)piperidin-4-yl]phenyl}-1-(pyridin-3-yl)azetidine-3-carboxamide;
N-{4-[1-(cyclopentylcarbonyl)piperidin-4-yl]phenyl}-1-(pyridin-3-yl)azetidine-3-carboxamide;
N-{4-[1-(2,3-dimethylbutanoyl)piperidin-4-yl]phenyl}-1-(pyridin-3-yl)azetidine-3-carboxamide;
N-{4-[1-(3,3-dimethylbutanoyl)piperidin-4-yl]phenyl}-1-(pyridazin-4-yl)azetidine-3-carboxamide;
(3S)—N-{4-[1-(2-hydroxy-2-methylpropanoyl)piperidin-4-yl]phenyl}-1-(pyridazin-4-yl)pyrrolidine-3-carboxamide;
(3S)—N-{4-[1-(cyclopentylacetyl)piperidin-4-yl]phenyl}-1-(pyridazin-4-yl)pyrrolidine-3-carboxamide;

N-(4-{1-[(2S)-2-methylbutanoyl]piperidin-4-yl}phenyl)-1-(pyridazin-4-yl)azetidine-3-carboxamide;
N-{4-[1-(cyclopentylacetyl)piperidin-4-yl]phenyl}-1-(pyridazin-4-yl)azetidine-3-carboxamide;
1-(pyridazin-4-yl)-N-{4-[1-(tetrahydro-2H-pyran-4-ylacetyl)piperidin-4-yl]phenyl}azetidine-3-carboxamide;
1-(pyridazin-4-yl)-N-{4-[1-(tetrahydro-2H-pyran-4-ylcarbonyl)piperidin-4-yl]phenyl}azetidine-3-carboxamide;
N-{4-[1-(2-methylpropanoyl)piperidin-4-yl]phenyl}-1-(pyridazin-3-yl)azetidine-3-carboxamide;
N-{4-[1-(2-methylpropyl)-1H-pyrazol-4-yl]phenyl}-1-(pyridazin-4-yl)azetidine-3-carboxamide;
N-[4-(1-benzoylpiperidin-4-yl)phenyl]-1-(2-methylpyridin-3-yl)azetidine-3-carboxamide;
N-{4-[1-(2-fluorobenzoyl)piperidin-4-yl]phenyl}-1-(2-methylpyridin-3-yl)azetidine-3-carboxamide;
N-{4-[1-(2-chlorobenzoyl)piperidin-4-yl]phenyl}-1-(2-methylpyridin-3-yl)azetidine-3-carboxamide;
N-{4-[1-(3-fluorobenzoyl)piperidin-4-yl]phenyl}-1-(2-methylpyridin-3-yl)azetidine-3-carboxamide;
N-{4-[1-(3-chlorobenzoyl)piperidin-4-yl]phenyl}-1-(2-methylpyridin-3-yl)azetidine-3-carboxamide;
N-{4-[1-(3,5-dichlorobenzoyl)piperidin-4-yl]phenyl}-1-(2-methylpyridin-3-yl)azetidine-3-carboxamide;
N-{4-[1-(4-fluorobenzoyl)piperidin-4-yl]phenyl}-1-(2-methylpyridin-3-yl)azetidine-3-carboxamide;
N-{4-[1-(4-chlorobenzoyl)piperidin-4-yl]phenyl}-1-(2-methylpyridin-3-yl)azetidine-3-carboxamide;
1-(2-methylpyridin-3-yl)-N-(4-{1-[4-(trifluoromethyl)benzoyl]piperidin-4-yl}phenyl)azetidine-3-carboxamide;
1-(2-methylpyridin-3-yl)-N-{4-[1-(pyridazin-3-ylcarbonyl)piperidin-4-yl]phenyl}azetidine-3-carboxamide;
1-(2-methylpyridin-3-yl)-N-[4-(1-pentanoylpiperidin-4-yl)phenyl]azetidine-3-carboxamide;
N-{4-[1-(3-methylpentanoyl)piperidin-4-yl]phenyl}-1-(2-methylpyridin-3-yl)azetidine-3-carboxamide;
N-(4-{1-[(1S,4R)-bicyclo[2.2.1]hept-2-ylacetyl]piperidin-4-yl}phenyl)-1-(2-methylpyridin-3-yl)azetidine-3-carboxamide;
N-{4-[1-(cyclopentylacetyl)piperidin-4-yl]phenyl}-1-(2-methylpyridin-3-yl)azetidine-3-carboxamide;
N-(4-{1-[(2-methylcyclopropyl)carbonyl]piperidin-4-yl}phenyl)-1-(2-methylpyridin-3-yl)azetidine-3-carboxamide;
1-(2-methylpyridin-3-yl)-N-{4-[1-(morpholin-4-ylacetyl)piperidin-4-yl]phenyl}azetidine-3-carboxamide;
N-{4-[1-(furan-3-ylcarbonyl)piperidin-4-yl]phenyl}-1-(2-methylpyridin-3-yl)azetidine-3-carboxamide;
1-(2-methylpyridin-3-yl)-N-{4-[1-(pyrrolidin-1-ylacetyl)piperidin-4-yl]phenyl}azetidine-3-carboxamide;
1-(2-methylpyridin-3-yl)-N-{4-[1-(5-oxo-D-prolyl)piperidin-4-yl]phenyl}azetidine-3-carboxamide;
N-{4-[1-(N,N-dimethyl-beta-alanyl)piperidin-4-yl]phenyl}-1-(2-methylpyridin-3-yl)azetidine-3-carboxamide;
1-(2-methylpyridin-3-yl)-N-{4-[1-(thiophen-3-ylcarbonyl)piperidin-4-yl]phenyl}azetidine-3-carboxamide;
N-(4-{1-[(1-methylcyclopropyl)carbonyl]piperidin-4-yl}phenyl)-1-(2-methylpyridin-3-yl)azetidine-3-carboxamide;
1-(2-methylpyridin-3-yl)-N-(4-{1-[(3-methylthiophen-2-yl)carbonyl]piperidin-4-yl}phenyl)azetidine-3-carboxamide;
1-(2-methylpyridin-3-yl)-N-{4-[1-(4,4,4-trifluorobutanoyl)piperidin-4-yl]phenyl}azetidine-3-carboxamide;
N-(4-{1-[(4-methylpiperazin-1-yl)acetyl]piperidin-4-yl}phenyl)-1-(2-methylpyridin-3-yl)azetidine-3-carboxamide;
1-(2-methylpyridin-3-yl)-N-{4-[1-(5-oxo-L-prolyl)piperidin-4-yl]phenyl}azetidine-3-carboxamide;
N-{4-[1-(3-ethoxypropanoyl)piperidin-4-yl]phenyl}-1-(2-methylpyridin-3-yl)azetidine-3-carboxamide;
N-{4-[1-(4-methylpentanoyl)piperidin-4-yl]phenyl}-1-(2-methylpyridin-3-yl)azetidine-3-carboxamide;
N-(4-{1-[(1-methylcyclohexyl)carbonyl]piperidin-4-yl}phenyl)-1-(2-methylpyridin-3-yl)azetidine-3-carboxamide;
N-[4-(1-acetylpiperidin-4-yl)phenyl]-1-(2-methylpyridin-3-yl)azetidine-3-carboxamide;
N-{4-[1-(cyclohexylacetyl)piperidin-4-yl]phenyl}-1-(2-methylpyridin-3-yl)azetidine-3-carboxamide;
N-{4-[1-(N-acetyl-L-leucyl)piperidin-4-yl]phenyl}-1-(2-methylpyridin-3-yl)azetidine-3-carboxamide;
1-(2-methylpyridin-3-yl)-N-[4-(1-propanoylpiperidin-4-yl)phenyl]azetidine-3-carboxamide;
1-(2-methylpyridin-3-yl)-N-{4-[1-(3,3,3-trifluoropropanoyl)piperidin-4-yl]phenyl}azetidine-3-carboxamide;
N-(4-{1-[(2-methoxyethoxy)acetyl]piperidin-4-yl}phenyl)-1-(2-methylpyridin-3-yl)azetidine-3-carboxamide;
1-(2-methylpyridin-3-yl)-N-(4-{1-[3-(morpholin-4-yl)propanoyl]piperidin-4-yl}phenyl)azetidine-3-carboxamide;
N-{4-[1-(2,2-dimethylpropanoyl)piperidin-4-yl]phenyl}-1-(2-methylpyridin-3-yl)azetidine-3-carboxamide;
1-(2-methylpyridin-3-yl)-N-(4-{1-[(5-methylthiophen-2-yl)carbonyl]piperidin-4-yl}phenyl)azetidine-3-carboxamide;
1-(2-methylpyridin-3-yl)-N-{4-[1-(thiophen-2-ylcarbonyl)piperidin-4-yl]phenyl}azetidine-3-carboxamide;
1-(2-methylpyridin-3-yl)-N-(4-{1-[(1-methyl-1H-pyrrol-2-yl)carbonyl]piperidin-4-yl}phenyl)azetidine-3-carboxamide;
N-{4-[1-(furan-2-ylcarbonyl)piperidin-4-yl]phenyl}-1-(2-methylpyridin-3-yl)azetidine-3-carboxamide;
1-(2-methylpyridin-3-yl)-N-(4-{1-[3-(piperidin-1-yl)propanoyl]piperidin-4-yl}phenyl)azetidine-3-carboxamide;
N-{4-[1-(ethoxyacetyl)piperidin-4-yl]phenyl}-1-(2-methylpyridin-3-yl)azetidine-3-carboxamide;
N-{4-[1-(3,3-dimethylbutanoyl)piperidin-4-yl]phenyl}-1-(2-methylpyridin-3-yl)azetidine-3-carboxamide;
N-{4-[1-(2,2-dimethylbutanoyl)piperidin-4-yl]phenyl}-1-(2-methylpyridin-3-yl)azetidine-3-carboxamide;
N-[4-(1-butanoylpiperidin-4-yl)phenyl]-1-(2-methylpyridin-3-yl)azetidine-3-carboxamide;
N-{4-[1-(methoxyacetyl)piperidin-4-yl]phenyl}-1-(2-methylpyridin-3-yl)azetidine-3-carboxamide;
N-{4-[1-(cyclohexylcarbonyl)piperidin-4-yl]phenyl}-1-(2-methylpyridin-3-yl)azetidine-3-carboxamide;
N-{4-[1-(3-methylbutanoyl)piperidin-4-yl]phenyl}-1-(2-methylpyridin-3-yl)azetidine-3-carboxamide;
N-{4-[1-(2,3-dimethylbutanoyl)piperidin-4-yl]phenyl}-1-(2-methylpyridin-3-yl)azetidine-3-carboxamide;
N-(4-{[1-(4-fluorobenzoyl)azetidin-3-yl]oxy}phenyl)-1-(pyridazin-4-yl)azetidine-3-carboxamide;
N-(4-{[1-(2,4-difluorobenzoyl)azetidin-3-yl]oxy}phenyl)-1-(pyridazin-4-yl)azetidine-3-carboxamide;
N-[4-({1-[difluoro(phenyl)acetyl]azetidin-3-yl}oxy)phenyl]-1-(pyridazin-4-yl)azetidine-3-carboxamide;
N-[4-({1-[(4,4-difluoro cyclohexyl)carbonyl]azetidin-3-yl}oxy)phenyl]-1-(pyridazin-4-yl)azetidine-3-carboxamide;
N-[4-({1-[(4-fluorophenyl)acetyl]azetidin-3-yl}oxy)phenyl]-1-(pyridazin-4-yl)azetidine-3-carboxamide;
(3S)—N-{4-[1-(cyclopentylacetyl)piperidin-4-yl]phenyl}-1-(pyridin-3-yl)pyrrolidine-3-carboxamide;

1-(pyridazin-4-yl)-N-[4-({1-[4-(trifluoromethyl)benzoyl]
  azetidin-3-yl}oxy)phenyl]azetidine-3-carboxamide;
N-{4-[(1-benzoylazetidin-3-yl)oxy]phenyl}-1-(pyridazin-4-
  yl)azetidine-3-carboxamide;
N-(4-{[1-(2-hydroxy-2-methylpropanoyl)azetidin-3-yl]
  oxy}phenyl)-1-(pyridazin-4-yl)azetidine-3-carboxamide;
1-(pyridazin-4-yl)-N-(4-{[1-(tetrahydrofuran-3-ylcarbonyl)
  azetidin-3-yl]oxy}phenyl)azetidine-3-carboxamide;
N-(4-{[1-(furan-3-ylcarbonyl)azetidin-3-yl]oxy}phenyl)-1-
  (pyridazin-4-yl)azetidine-3-carboxamide;
N-{4-[(1-pentanoylazetidin-3-yl)oxy]phenyl}-1-(pyridazin-
  4-yl)azetidine-3-carboxamide;
N-(4-{[1-(2-chlorobenzoyl)piperidin-4-yl]oxy}phenyl)-1-
  (pyridazin-3-yl)azetidine-3-carboxamide;
N-[4-({1-[(2S)-2-methylbutanoyl]piperidin-4-yl}oxy)phe-
  nyl]-1-(pyridazin-3-yl)azetidine-3-carboxamide;
1-(pyridazin-3-yl)-N-(4-{[1-(1,3-thiazol-2-ylcarbonyl)pip-
  eridin-4-yl]oxy}phenyl)azetidine-3-carboxamide;
1-(pyridazin-3-yl)-N-(4-{[1-(tetrahydro-2H-pyran-4-ylcar-
  bonyl)piperidin-4-yl]oxy}phenyl)azetidine-3-carboxam-
  ide;
N-[4-({1-[difluoro(phenyl)acetyl]piperidin-4-yl}oxy)phe-
  nyl]-1-(pyridazin-3-yl)azetidine-3-carboxamide;
N-[4-({1-[(4,4-difluorocyclohexyl)carbonyl]piperidin-4-
  yl}oxy)phenyl]-1-(pyridazin-3-yl)azetidine-3-carboxam-
  ide;
N-(4-{[1-(2-methyl-2-phenylpropanoyl)piperidin-4-yl]
  oxy}phenyl)-1-(pyridazin-3-yl)azetidine-3-carboxamide;
1-(pyridazin-3-yl)-N-(4-{[1-(1,3-thiazol-4-ylcarbonyl)pip-
  eridin-4-yl]oxy}phenyl)azetidine-3-carboxamide;
N-[4-({1-[(5-methylthiophen-2-yl)carbonyl]piperidin-4-
  yl}oxy)phenyl]-1-(pyridazin-3-yl)azetidine-3-carboxam-
  ide;
1-(pyridazin-3-yl)-N-{4-[(1-{[4-(trifluoromethyl)phenyl]
  acetyl}piperidin-4-yl)oxy]phenyl}azetidine-3-carboxam-
  ide;
1-(pyridazin-3-yl)-N-(4-{[1-(tetrahydrofuran-2-ylcarbonyl)
  piperidin-4-yl]oxy}phenyl)azetidine-3-carboxamide;
1-(pyridazin-3-yl)-N-[4-({1-[3-(trifluoromethyl)benzoyl]pi-
  peridin-4-yl}oxy)phenyl]azetidine-3-carboxamide;
1-(pyridazin-3-yl)-N-(4-{[1-(thiophen-3-ylcarbonyl)piperi-
  din-4-yl]oxy}phenyl)azetidine-3-carboxamide;
1-(pyridazin-3-yl)-N-[4-({1-[3-(trifluoromethoxy)benzoyl]
  piperidin-4-yl}oxy)phenyl]azetidine-3-carboxamide;
N-(4-{[1-(3-methylbutanoyl)piperidin-4-yl]oxy}phenyl)-1-
  (pyridazin-3-yl)azetidine-3-carboxamide;
1-(pyridazin-3-yl)-N-(4-{[1-(tetrahydrofuran-3-ylcarbonyl)
  piperidin-4-yl]oxy}phenyl)azetidine-3-carboxamide;
N-[4-({1-[(3-fluorophenyl)acetyl]piperidin-4-yl}oxy)phe-
  nyl]-1-(pyridazin-3-yl)azetidine-3-carboxamide;
N-(4-{[1-(2-fluorobenzoyl)piperidin-4-yl]oxy}phenyl)-1-
  (pyridazin-3-yl)azetidine-3-carboxamide;
N-(4-{[1-(2,4-difluorobenzoyl)piperidin-4-yl]oxy}phenyl)-
  1-(pyridazin-3-yl)azetidine-3-carboxamide;
N-(4-{[1-(4-fluorobenzoyl)piperidin-4-yl]oxy}phenyl)-1-
  (pyridazin-3-yl)azetidine-3-carboxamide;
N-(4-{[1-(3-fluorobenzoyl)piperidin-4-yl]oxy}phenyl)-1-
  (pyridazin-3-yl)azetidine-3-carboxamide;
N-[4-({1-[(4-fluorophenyl)acetyl]piperidin-4-yl}oxy)phe-
  nyl]-1-(pyridazin-3-yl)azetidine-3-carboxamide;
N-(4-{[1-(cyclopropylacetyl)piperidin-4-yl]oxy}phenyl)-1-
  (pyridazin-3-yl)azetidine-3-carboxamide;
N-(4-{[1-(3,4-difluorobenzoyl)piperidin-4-yl]oxy}phenyl)-
  1-(pyridazin-3-yl)azetidine-3-carboxamide;
1-(pyridazin-3-yl)-N-[4-({1-[4-(trifluoromethoxy)benzoyl]
  piperidin-4-yl}oxy)phenyl]azetidine-3-carboxamide;

N-[4-({1-[(2,4-difluorophenyl)acetyl]piperidin-4-yl}oxy)
  phenyl]-1-(pyridazin-3-yl)azetidine-3-carboxamide;
1-(pyridazin-3-yl)-N-[4-({1-[4-(trifluoromethyl)benzoyl]pi-
  peridin-4-yl}oxy)phenyl]azetidine-3-carboxamide;
1-(pyridazin-3-yl)-N-{4-[(1-{[4-(trifluoromethoxy)phenyl]
  acetyl}piperidin-4-yl)oxy]phenyl}azetidine-3-carboxam-
  ide;
N-[4-({1-[(3,5-difluorophenyl)acetyl]piperidin-4-yl}oxy)
  phenyl]-1-(pyridazin-3-yl)azetidine-3-carboxamide;
1-(pyridazin-3-yl)-N-{4-[(1-{[3-(trifluoromethyl)phenyl]
  acetyl}piperidin-4-yl)oxy]phenyl}azetidine-3-carboxam-
  ide;
N-(4-{[1-(2,2-dimethylpropanoyl)piperidin-4-yl]
  oxy}phenyl)-1-(pyridazin-3-yl)azetidine-3-carboxamide;
1-(pyridazin-3-yl)-N-(4-{[1-(pyridin-2-ylcarbonyl)piperi-
  din-4-yl]oxy}phenyl)azetidine-3-carboxamide;
N-(4-{[1-(3,5-difluorobenzoyl)piperidin-4-yl]oxy}phenyl)-
  1-(pyridazin-3-yl)azetidine-3-carboxamide;
N-{4-[(1-acetylpiperidin-4-yl)oxy]phenyl}-1-(pyridazin-3-
  yl)azetidine-3-carboxamide;
N-(4-{[1-(4-chlorobenzoyl)piperidin-4-yl]oxy}phenyl)-1-
  (pyridazin-3-yl)azetidine-3-carboxamide;
N-(4-{[1-(methoxyacetyl)piperidin-4-yl]oxy}phenyl)-1-
  (pyridazin-3-yl)azetidine-3-carboxamide;
N-[4-({1-[(2-fluorophenyl)acetyl]piperidin-4-yl}oxy)phe-
  nyl]-1-(pyridazin-3-yl)azetidine-3-carboxamide;
N-(4-{[1-(2,2-dimethylbutanoyl)piperidin-4-yl]
  oxy}phenyl)-1-(pyridazin-3-yl)azetidine-3-carboxamide;
1-(pyridazin-3-yl)-N-(4-{[1-(thiophen-2-ylcarbonyl)piperi-
  din-4-yl]oxy}phenyl)azetidine-3-carboxamide;
N-(4-{[1-(3-chlorobenzoyl)piperidin-4-yl]oxy}phenyl)-1-
  (pyridazin-3-yl)azetidine-3-carboxamide;
N-(4-{[1-(cyclopropylcarbonyl)piperidin-4-yl]
  oxy}phenyl)-1-(pyridazin-3-yl)azetidine-3-carboxamide;
1-(pyridazin-3-yl)-N-(4-{[1-(3,3,3-trifluoropropanoyl)pip-
  eridin-4-yl]oxy}phenyl)azetidine-3-carboxamide;
N-(4-{[1-(2-methylpropanoyl)piperidin-4-yl]oxy}phenyl)-
  1-(pyridazin-3-yl)azetidine-3-carboxamide;
N-(4-{[1-(3,3-dimethylbutanoyl)azetidin-3-yl]oxy}phenyl)-
  1-(pyridazin-4-yl)azetidine-3-carboxamide;
N-(4-{[1-(cyclohexylcarbonyl)azetidin-3-yl]oxy}phenyl)-1-
  (pyridazin-4-yl)azetidine-3-carboxamide;
1-(pyridazin-4-yl)-N-(4-{[1-(tetrahydro-2H-pyran-4-
  ylacetyl)azetidin-3-yl]oxy}phenyl)azetidine-3-carboxa-
  mide;
N-[4-({1-[(2-methylcyclopropyl)carbonyl]azetidin-3-
  yl}oxy)phenyl]-1-(pyridazin-4-yl)azetidine-3-carboxam-
  ide;
1-(pyridazin-4-yl)-N-(4-{[1-(3,3,3-trifluoropropanoyl)azeti-
  din-3-yl]oxy}phenyl)azetidine-3-carboxamide;
N-(4-{[1-(cyclopentylcarbonyl)azetidin-3-yl]oxy}phenyl)-
  1-(pyridazin-4-yl)azetidine-3-carboxamide;
N-(4-{[1-(3,3-dimethylbutanoyl)piperidin-4-yl]
  oxy}phenyl)-1-(pyridazin-4-yl)azetidine-3-carboxamide;
N-(4-{[1-(cyclobutylcarbonyl)azetidin-3-yl]oxy}phenyl)-1-
  (pyridazin-4-yl)azetidine-3-carboxamide;
1-(pyridazin-4-yl)-N-(4-{[1-(tetrahydrofuran-2-ylcarbonyl)
  azetidin-3-yl]oxy}phenyl)azetidine-3-carboxamide;
N-(4-{[1-(4-methylpentanoyl)azetidin-3-yl]oxy}phenyl)-1-
  (pyridazin-4-yl)azetidine-3-carboxamide;
N-(4-{[1-(2-methylpropanoyl)azetidin-3-yl]oxy}phenyl)-1-
  (pyridazin-4-yl)azetidine-3-carboxamide;
N-[4-({1-[(2S)-2-methylbutanoyl]azetidin-3-yl}oxy)phe-
  nyl]-1-(pyridazin-4-yl)azetidine-3-carboxamide;
N-(4-{[1-(3-methylbutanoyl)piperidin-4-yl]oxy}phenyl)-1-
  (pyridazin-4-yl)azetidine-3-carboxamide;

N-(4-{[1-(methoxyacetyl)piperidin-4-yl]oxy}phenyl)-1-(pyridazin-4-yl)azetidine-3-carboxamide;
1-(pyridazin-4-yl)-N-(4-{[1-(3,3,3-trifluoropropanoyl)piperidin-4-yl]oxy}phenyl)azetidine-3-carboxamide;
N-[4-({1-[difluoro(phenyl)acetyl]piperidin-4-yl}oxy)phenyl]-1-(pyridazin-4-yl)azetidine-3-carboxamide;
N-[4-({1-[(4,4-difluorocyclohexyl)carbonyl]piperidin-4-yl}oxy)phenyl]-1-(pyridazin-4-yl)azetidine-3-carboxamide;
N-(4-{[1-(4-fluorobenzoyl)piperidin-4-yl]oxy}phenyl)-1-(pyridazin-4-yl)azetidine-3-carboxamide;
1-(pyridazin-4-yl)-N-(4-{[1-(1,3-thiazol-4-ylcarbonyl)piperidin-4-yl]oxy}phenyl)azetidine-3-carboxamide;
1-(pyridazin-4-yl)-N-{4-[(1-{[4-(trifluoromethyl)phenyl]acetyl}piperidin-4-yl)oxy]phenyl}azetidine-3-carboxamide;
N-(4-{[1-(3,4-difluorobenzoyl)piperidin-4-yl]oxy}phenyl)-1-(pyridazin-4-yl)azetidine-3-carboxamide;
1-(pyridazin-4-yl)-N-{4-[(1-{[4-(trifluoromethoxy)phenyl]acetyl}piperidin-4-yl)oxy]phenyl}azetidine-3-carboxamide;
N-[4-({1-[(4-fluorophenyl)acetyl]piperidin-4-yl}oxy)phenyl]-1-(pyridazin-4-yl)azetidine-3-carboxamide;
N-[4-({1-[(2,4-difluorophenyl)acetyl]piperidin-4-yl}oxy)phenyl]-1-(pyridazin-4-yl)azetidine-3-carboxamide;
1-(pyridazin-4-yl)-N-(4-{[1-(thiophen-3-ylcarbonyl)piperidin-4-yl]oxy}phenyl)azetidine-3-carboxamide;
N-(4-{[1-(2-chlorobenzoyl)piperidin-4-yl]oxy}phenyl)-1-(pyridazin-4-yl)azetidine-3-carboxamide;
N-(4-{[1-(2,2-dimethylpropanoyl)piperidin-4-yl]oxy}phenyl)-1-(pyridazin-4-yl)azetidine-3-carboxamide;
N-(4-{[1-(2-methyl-2-phenylpropanoyl)piperidin-4-yl]oxy}phenyl)-1-(pyridazin-4-yl)azetidine-3-carboxamide;
N-{4-[(1-acetylpiperidin-4-yl)oxy]phenyl}-1-(pyridazin-4-yl)azetidine-3-carboxamide;
1-(pyridazin-4-yl)-N-(4-{[1-(1,3-thiazol-2-ylcarbonyl)piperidin-4-yl]oxy}phenyl)azetidine-3-carboxamide;
N-(4-{[1-(2,4-difluorobenzoyl)piperidin-4-yl]oxy}phenyl)-1-(pyridazin-4-yl)azetidine-3-carboxamide;
1-(pyridazin-4-yl)-N-[4-({1-[3-(trifluoromethyl)benzoyl]piperidin-4-yl}oxy)phenyl]azetidine-3-carboxamide;
N-(4-{[1-(3-fluorobenzoyl)piperidin-4-yl]oxy}phenyl)-1-(pyridazin-4-yl)azetidine-3-carboxamide;
1-(pyridazin-4-yl)-N-[4-({1-[4-(trifluoromethyl)benzoyl]piperidin-4-yl}oxy)phenyl]azetidine-3-carboxamide;
N-[4-({1-[(3-fluorophenyl)acetyl]piperidin-4-yl}oxy)phenyl]-1-(pyridazin-4-yl)azetidine-3-carboxamide;
N-(4-{[1-(2-fluorobenzoyl)piperidin-4-yl]oxy}phenyl)-1-(pyridazin-4-yl)azetidine-3-carboxamide;
1-(pyridazin-4-yl)-N-[4-({1-[4-(trifluoromethoxy)benzoyl]piperidin-4-yl}oxy)phenyl]azetidine-3-carboxamide;
N-[4-({1-[(3,5-difluorophenyl)acetyl]piperidin-4-yl}oxy)phenyl]-1-(pyridazin-4-yl)azetidine-3-carboxamide;
1-(pyridazin-4-yl)-N-[4-({1-[3-(trifluoromethoxy)benzoyl]piperidin-4-yl}oxy)phenyl]azetidine-3-carboxamide;
N-(4-{[1-(cyclopropylacetyl)piperidin-4-yl]oxy}phenyl)-1-(pyridazin-4-yl)azetidine-3-carboxamide;
N-(4-{[1-(2-methylpropanoyl)piperidin-4-yl]oxy}phenyl)-1-(pyridazin-4-yl)azetidine-3-carboxamide;
N-(4-{[1-(3-chlorobenzoyl)piperidin-4-yl]oxy}phenyl)-1-(pyridazin-4-yl)azetidine-3-carboxamide;
1-(pyridazin-4-yl)-N-(4-{[1-(pyridin-2-ylcarbonyl)piperidin-4-yl]oxy}phenyl)azetidine-3-carboxamide;
N-(4-{[1-(4-chlorobenzoyl)piperidin-4-yl]oxy}phenyl)-1-(pyridazin-4-yl)azetidine-3-carboxamide;
1-(pyridazin-4-yl)-N-(4-{[1-(tetrahydrofuran-3-ylcarbonyl)piperidin-4-yl]oxy}phenyl)azetidine-3-carboxamide;
N-(4-{[1-(3,5-difluorobenzoyl)piperidin-4-yl]oxy}phenyl)-1-(pyridazin-4-yl)azetidine-3-carboxamide;
N-(4-{[1-(2,2-dimethylbutanoyl)piperidin-4-yl]oxy}phenyl)-1-(pyridazin-4-yl)azetidine-3-carboxamide;
N-(4-{[1-(cyclopropylcarbonyl)piperidin-4-yl]oxy}phenyl)-1-(pyridazin-4-yl)azetidine-3-carboxamide;
1-(pyridazin-4-yl)-N-(4-{[1-(tetrahydrofuran-2-ylcarbonyl)piperidin-4-yl]oxy}phenyl)azetidine-3-carboxamide;
1-(pyridazin-4-yl)-N-(4-{[1-(thiophen-2-ylcarbonyl)piperidin-4-yl]oxy}phenyl)azetidine-3-carboxamide;
N-[4-({1-[(5-methylthiophen-2-yl)carbonyl]piperidin-4-yl}oxy)phenyl]-1-(pyridazin-4-yl)azetidine-3-carboxamide;
1-(pyridazin-4-yl)-N-{4-[(1-{[3-(trifluoromethyl)phenyl]acetyl}piperidin-4-yl)oxy]phenyl}azetidine-3-carboxamide;
1-(pyridazin-4-yl)-N-(4-{[1-(tetrahydro-2H-pyran-4-ylcarbonyl)piperidin-4-yl]oxy}phenyl)azetidine-3-carboxamide;
N-[4-({1-[(2S)-2-methylbutanoyl]piperidin-4-yl}oxy)phenyl]-1-(pyridazin-4-yl)azetidine-3-carboxamide;
N-[4-({1-[(2-fluorophenyl)acetyl]piperidin-4-yl}oxy)phenyl]-1-(pyridazin-4-yl)azetidine-3-carboxamide;
5-[1-(2-methylpropyl)-1H-pyrazol-4-yl]-N-[1-(pyridazin-3-yl)azetidin-3-yl]furan-2-carboxamide;
(3S)—N-{4-[1-(2-methylpropanoyl)piperidin-4-yl]phenyl}-1-(pyridazin-3-yl)pyrrolidine-3-carboxamide;
(3S)—N-[4-(1-benzoylpiperidin-4-yl)phenyl]-1-(pyridazin-3-yl)pyrrolidine-3-carboxamide;
(3S)-1-(pyridazin-3-yl)-N-{4-[1-(tetrahydro-2H-pyran-4-ylacetyl)piperidin-4-yl]phenyl}pyrrolidine-3-carboxamide;
(3S)—N-{4-[1-(2,2-dimethylpropanoyl)piperidin-4-yl]phenyl}-1-(pyridazin-3-yl)pyrrolidine-3-carboxamide;
tert-butyl 4-(4-{[1-(pyridazin-3-yl)azetidin-3-yl]carbamoyl}phenyl)piperidine-1-carboxylate;
5-[1-(2-methylpropyl)-1H-pyrazol-4-yl]-N-[1-(pyridazin-3-yl)azetidin-3-yl]thiophene-2-carboxamide;
N-[4-(1-acetylpiperidin-4-yl)phenyl]-1-(pyridazin-3-yl)azetidine-3-carboxamide;
N-[4-(1-butanoylpiperidin-4-yl)phenyl]-1-(pyridazin-3-yl)azetidine-3-carboxamide;
N-[4-(1-pentanoylpiperidin-4-yl)phenyl]-1-(pyridazin-3-yl)azetidine-3-carboxamide;
N-{4-[1-(2-methylbutanoyl)piperidin-4-yl]phenyl}-1-(pyridazin-3-yl)azetidine-3-carboxamide;
N-{4-[1-(3-methylbutanoyl)piperidin-4-yl]phenyl}-1-(pyridazin-3-yl)azetidine-3-carboxamide;
N-[4-(1-hexanoylpiperidin-4-yl)phenyl]-1-(pyridazin-3-yl)azetidine-3-carboxamide;
N-{4-[1-(2-methylpentanoyl)piperidin-4-yl]phenyl}-1-(pyridazin-3-yl)azetidine-3-carboxamide;
N-{4-[1-(3-methylpentanoyl)piperidin-4-yl]phenyl}-1-(pyridazin-3-yl)azetidine-3-carboxamide;
N-{4-[1-(4-methylpentanoyl)piperidin-4-yl]phenyl}-1-(pyridazin-3-yl)azetidine-3-carboxamide;
N-{4-[1-(2,2-dimethylbutanoyl)piperidin-4-yl]phenyl}-1-(pyridazin-3-yl)azetidine-3-carboxamide;
N-{4-[1-(2,3-dimethylbutanoyl)piperidin-4-yl]phenyl}-1-(pyridazin-3-yl)azetidine-3-carboxamide;
N-{4-[1-(3,3-dimethylbutanoyl)piperidin-4-yl]phenyl}-1-(pyridazin-3-yl)azetidine-3-carboxamide;
N-{4-[1-(2-ethylbutanoyl)piperidin-4-yl]phenyl}-1-(pyridazin-3-yl)azetidine-3-carboxamide;
N-[4-(1-heptanoylpiperidin-4-yl)phenyl]-1-(pyridazin-3-yl)azetidine-3-carboxamide;

N-{4-[1-(but-3-enoyl)piperidin-4-yl]phenyl}-1-(pyridazin-3-yl)azetidine-3-carboxamide;
N-{4-[1-(pent-4-enoyl)piperidin-4-yl]phenyl}-1-(pyridazin-3-yl)azetidine-3-carboxamide;
1-(pyridazin-3-yl)-N-{4-[1-(3,3,3-trifluoropropanoyl)piperidin-4-yl]phenyl}azetidine-3-carboxamide;
N-{4-[1-(methoxyacetyl)piperidin-4-yl]phenyl}-1-(pyridazin-3-yl)azetidine-3-carboxamide;
N-(4-{1-[(methylsulfanyl)acetyl]piperidin-4-yl}phenyl)-1-(pyridazin-3-yl)azetidine-3-carboxamide;
N-(4-{1-[(2-methoxyethoxy)acetyl]piperidin-4-yl}phenyl)-1-(pyridazin-3-yl)azetidine-3-carboxamide;
N-{4-[1-(3-nitropropanoyl)piperidin-4-yl]phenyl}-1-(pyridazin-3-yl)azetidine-3-carboxamide;
N-(4-{1-[3-(methylsulfanyl)propanoyl]piperidin-4-yl}phenyl)-1-(pyridazin-3-yl)azetidine-3-carboxamide;
N-{4-[1-(pent-4-ynoyl)piperidin-4-yl]phenyl}-1-(pyridazin-3-yl)azetidine-3-carboxamide;
N-{4-[1-(cyclohexylcarbonyl)piperidin-4-yl]phenyl}-1-(pyridazin-3-yl)azetidine-3-carboxamide;
N-{4-[1-(cyclohexylacetyl)piperidin-4-yl]phenyl}-1-(pyridazin-3-yl)azetidine-3-carboxamide;
N-{4-[1-(3-methylbenzoyl)piperidin-4-yl]phenyl}-1-(pyridazin-3-yl)azetidine-3-carboxamide;
N-{4-[1-(2-hydroxybenzoyl)piperidin-4-yl]phenyl}-1-(pyridazin-3-yl)azetidine-3-carboxamide;
N-{4-[1-(3-hydroxybenzoyl)piperidin-4-yl]phenyl}-1-(pyridazin-3-yl)azetidine-3-carboxamide;
N-{4-[1-(4-hydroxybenzoyl)piperidin-4-yl]phenyl}-1-(pyridazin-3-yl)azetidine-3-carboxamide;
N-{4-[1-(2-methoxybenzoyl)piperidin-4-yl]phenyl}-1-(pyridazin-3-yl)azetidine-3-carboxamide;
N-{4-[1-(3-methoxybenzoyl)piperidin-4-yl]phenyl}-1-(pyridazin-3-yl)azetidine-3-carboxamide;
N-{4-[1-(4-methoxybenzoyl)piperidin-4-yl]phenyl}-1-(pyridazin-3-yl)azetidine-3-carboxamide;
N-{4-[1-(3-fluorobenzoyl)piperidin-4-yl]phenyl}-1-(pyridazin-3-yl)azetidine-3-carboxamide;
N-{4-[1-(4-fluorobenzoyl)piperidin-4-yl]phenyl}-1-(pyridazin-3-yl)azetidine-3-carboxamide;
N-{4-[1-(2-chlorobenzoyl)piperidin-4-yl]phenyl}-1-(pyridazin-3-yl)azetidine-3-carboxamide;
N-{4-[1-(3-chlorobenzoyl)piperidin-4-yl]phenyl}-1-(pyridazin-3-yl)azetidine-3-carboxamide;
N-{4-[1-(3-cyanobenzoyl)piperidin-4-yl]phenyl}-1-(pyridazin-3-yl)azetidine-3-carboxamide;
N-{4-[1-(4-cyanobenzoyl)piperidin-4-yl]phenyl}-1-(pyridazin-3-yl)azetidine-3-carboxamide;
1-(pyridazin-3-yl)-N-(4-{1-[3-(trifluoromethyl)benzoyl]piperidin-4-yl}phenyl)azetidine-3-carboxamide;
1-(pyridazin-3-yl)-N-(4-{1-[4-(trifluoromethyl)benzoyl]piperidin-4-yl}phenyl)azetidine-3-carboxamide;
1-(pyridazin-3-yl)-N-(4-{1-[3-(trifluoromethoxy)benzoyl]piperidin-4-yl}phenyl)azetidine-3-carboxamide;
N-{4-[1-(2,3-dimethylbenzoyl)piperidin-4-yl]phenyl}-1-(pyridazin-3-yl)azetidine-3-carboxamide;
N-{4-[1-(2,4-dimethylbenzoyl)piperidin-4-yl]phenyl}-1-(pyridazin-3-yl)azetidine-3-carboxamide;
N-{4-[1-(2,5-dimethylbenzoyl)piperidin-4-yl]phenyl}-1-(pyridazin-3-yl)azetidine-3-carboxamide;
N-{4-[1-(3,4-dimethylbenzoyl)piperidin-4-yl]phenyl}-1-(pyridazin-3-yl)azetidine-3-carboxamide;
N-{4-[1-(3,5-dimethylbenzoyl)piperidin-4-yl]phenyl}-1-(pyridazin-3-yl)azetidine-3-carboxamide;
N-{4-[1-(2,4-dichlorobenzoyl)piperidin-4-yl]phenyl}-1-(pyridazin-3-yl)azetidine-3-carboxamide;
N-{4-[1-(2,5-dichlorobenzoyl)piperidin-4-yl]phenyl}-1-(pyridazin-3-yl)azetidine-3-carboxamide;
N-{4-[1-(3,4-dichlorobenzoyl)piperidin-4-yl]phenyl}-1-(pyridazin-3-yl)azetidine-3-carboxamide;
N-{4-[1-(3,5-dichlorobenzoyl)piperidin-4-yl]phenyl}-1-(pyridazin-3-yl)azetidine-3-carboxamide;
N-(4-{1-[(2-fluorophenyl)acetyl]piperidin-4-yl}phenyl)-1-(pyridazin-3-yl)azetidine-3-carboxamide;
N-(4-{1-[(3-fluorophenyl)acetyl]piperidin-4-yl}phenyl)-1-(pyridazin-3-yl)azetidine-3-carboxamide;
N-(4-{1-[(4-fluorophenyl)acetyl]piperidin-4-yl}phenyl)-1-(pyridazin-3-yl)azetidine-3-carboxamide;
N-(4-{1-[(2-chlorophenyl)acetyl]piperidin-4-yl}phenyl)-1-(pyridazin-3-yl)azetidine-3-carboxamide;
N-(4-{1-[(4-chlorophenyl)acetyl]piperidin-4-yl}phenyl)-1-(pyridazin-3-yl)azetidine-3-carboxamide;
1-(pyridazin-3-yl)-N-[4-(1-{[4-(trifluoromethyl)phenyl]acetyl}piperidin-4-yl)phenyl]azetidine-3-carboxamide;
N-(4-{1-[(3,5-dimethylphenyl)acetyl]piperidin-4-yl}phenyl)-1-(pyridazin-3-yl)azetidine-3-carboxamide;
N-(4-{1-[(2,5-difluorophenyl)acetyl]piperidin-4-yl}phenyl)-1-(pyridazin-3-yl)azetidine-3-carboxamide;
N-(4-{1-[(3,4-dichlorophenyl)acetyl]piperidin-4-yl}phenyl)-1-(pyridazin-3-yl)azetidine-3-carboxamide;
N-{4-[1-(furan-3-ylcarbonyl)piperidin-4-yl]phenyl}-1-(pyridazin-3-yl)azetidine-3-carboxamide;
1-(pyridazin-3-yl)-N-{4-[1-(thiophen-2-ylcarbonyl)piperidin-4-yl]phenyl}azetidine-3-carboxamide;
N-(4-{1-[(5-methylthiophen-2-yl)carbonyl]piperidin-4-yl}phenyl)-1-(pyridazin-3-yl)azetidine-3-carboxamide;
N-(4-{1-[(5-methylpyrazin-2-yl)carbonyl]piperidin-4-yl}phenyl)-1-(pyridazin-3-yl)azetidine-3-carboxamide;
N-(4-{1-[(1-methylcyclopropyl)carbonyl]piperidin-4-yl}phenyl)-1-(pyridazin-3-yl)azetidine-3-carboxamide;
N-{4-[1-(3-ethoxypropanoyl)piperidin-4-yl]phenyl}-1-(pyridazin-3-yl)azetidine-3-carboxamide;
N-(4-{1-[(1-phenylcyclopropyl)carbonyl]piperidin-4-yl}phenyl)-1-(pyridazin-3-yl)azetidine-3-carboxamide;
1-(pyridazin-3-yl)-N-(4-{1-[(pyrimidin-2-ylsulfanyl)acetyl]piperidin-4-yl}phenyl)azetidine-3-carboxamide;
N-(4-{1-[(1-acetylpiperidin-4-yl)carbonyl]piperidin-4-yl}phenyl)-1-(pyridazin-3-yl)azetidine-3-carboxamide;
N-(4-{1-[(3,5-difluorophenyl)acetyl]piperidin-4-yl}phenyl)-1-(pyridazin-3-yl)azetidine-3-carboxamide;
N-{4-[1-(N-acetyl-L-leucyl)piperidin-4-yl]phenyl}-1-(pyridazin-3-yl)azetidine-3-carboxamide;
N-{4-[1-(diphenylacetyl)piperidin-4-yl]phenyl}-1-(pyridazin-3-yl)azetidine-3-carboxamide;
N-{4-[1-(3-fluoro-2-methylbenzoyl)piperidin-4-yl]phenyl}-1-(pyridazin-3-yl)azetidine-3-carboxamide;
N-{4-[1-(5-fluoro-2-methylbenzoyl)piperidin-4-yl]phenyl}-1-(pyridazin-3-yl)azetidine-3-carboxamide;
N-{4-[1-(3-fluoro-4-methylbenzoyl)piperidin-4-yl]phenyl}-1-(pyridazin-3-yl)azetidine-3-carboxamide;
N-{4-[1-(2,3-difluorobenzoyl)piperidin-4-yl]phenyl}-1-(pyridazin-3-yl)azetidine-3-carboxamide;
N-{4-[1-(2,4-difluorobenzoyl)piperidin-4-yl]phenyl}-1-(pyridazin-3-yl)azetidine-3-carboxamide;
N-(4-{1-[4-(propan-2-yl)benzoyl]piperidin-4-yl}phenyl)-1-(pyridazin-3-yl)azetidine-3-carboxamide;
N-{4-[1-(4-tert-butylbenzoyl)piperidin-4-yl]phenyl}-1-(pyridazin-3-yl)azetidine-3-carboxamide;
N-(4-{1-[2-fluoro-5-(trifluoromethyl)benzoyl]piperidin-4-yl}phenyl)-1-(pyridazin-3-yl)azetidine-3-carboxamide;
N-(4-{1-[2-chloro-5-(trifluoromethyl)benzoyl]piperidin-4-yl}phenyl)-1-(pyridazin-3-yl)azetidine-3-carboxamide;

N-(4-{[(3R)-1-(4-fluorobenzoyl)pyrrolidin-3-yl]oxy}phenyl)-1-(pyridazin-4-yl)azetidine-3-carboxamide;
N-{4-[1-(cyclopentylacetyl)piperidin-4-yl]phenyl}-1-(pyridazin-3-yl)azetidine-3-carboxamide;
N-(4-{1-[(4-methylphenoxy)acetyl]piperidin-4-yl}phenyl)-1-(pyridazin-3-yl)azetidine-3-carboxamide;
N-(4-{1-[(2S)-2-phenylbutanoyl]piperidin-4-yl}phenyl)-1-(pyridazin-3-yl)azetidine-3-carboxamide;
N-{4-[1-(3,5-difluorobenzoyl)piperidin-4-yl]phenyl}-1-(pyridazin-3-yl)azetidine-3-carboxamide;
N-{4-[1-(4-chlorobenzoyl)piperidin-4-yl]phenyl}-1-(pyridazin-3-yl)azetidine-3-carboxamide;
N-{4-[1-(2,2-dimethylpropanoyl)piperidin-4-yl]phenyl}-1-(pyridazin-3-yl)azetidine-3-carboxamide;
1-(pyridazin-3-yl)-N-[4-(1-{[3-(trifluoromethyl)phenyl]acetyl}piperidin-4-yl)phenyl]azetidine-3-carboxamide;
N-(4-{1-[(3-chlorophenyl)acetyl]piperidin-4-yl}phenyl)-1-(pyridazin-3-yl)azetidine-3-carboxamide;
N-(4-{1-[(2,4-dichlorophenyl)acetyl]piperidin-4-yl}phenyl)-1-(pyridazin-3-yl)azetidine-3-carboxamide;
N-{4-[1-(naphthalen-1-ylcarbonyl)piperidin-4-yl]phenyl}-1-(pyridazin-3-yl)azetidine-3-carboxamide;
N-(4-{1-[(2R)-2-methoxy-2-phenylacetyl]piperidin-4-yl}phenyl)-1-(pyridazin-3-yl)azetidine-3-carboxamide;
N-(4-{1-[N-(furan-2-ylcarbonyl)glycyl]piperidin-4-yl}phenyl)-1-(pyridazin-3-yl)azetidine-3-carboxamide;
N-(4-{1-[(benzyloxy)acetyl]piperidin-4-yl}phenyl)-1-(pyridazin-3-yl)azetidine-3-carboxamide;
N-{4-[1-(naphthalen-1-ylacetyl)piperidin-4-yl]phenyl}-1-(pyridazin-3-yl)azetidine-3-carboxamide;
N-{4-[1-(cyclopropylcarbonyl)piperidin-4-yl]phenyl}-1-(pyridazin-3-yl)azetidine-3-carboxamide;
1-(pyridazin-3-yl)-N-{4-[1-(tetrahydrofuran-2-ylcarbonyl)piperidin-4-yl]phenyl}azetidine-3-carboxamide;
N-{4-[1-(N-benzoylglycyl)piperidin-4-yl]phenyl}-1-(pyridazin-3-yl)azetidine-3-carboxamide;
1-(pyridazin-3-yl)-N-{4-[1-(tetrahydrofuran-3-ylcarbonyl)piperidin-4-yl]phenyl}azetidine-3-carboxamide;
1-(pyridazin-3-yl)-N-(4-{1-[4-(thiophen-2-yl)butanoyl]piperidin-4-yl}phenyl)azetidine-3-carboxamide;
N-{4-[1-(2,5-difluorobenzoyl)piperidin-4-yl]phenyl}-1-(pyridazin-3-yl)azetidine-3-carboxamide;
N-{4-[1-(cyclobutylcarbonyl)piperidin-4-yl]phenyl}-1-(pyridazin-3-yl)azetidine-3-carboxamide;
N-[4-(1-{N[(4-methylphenyl)sulfonyl]glycyl}piperidin-4-yl)phenyl]-1-(pyridazin-3-yl)azetidine-3-carboxamide;
N-(4-{1-[(2,3-difluorophenyl)acetyl]piperidin-4-yl}phenyl)-1-(pyridazin-3-yl)azetidine-3-carboxamide;
N-(4-{1-[(2S)-2-methoxy-2-phenylacetyl]piperidin-4-yl}phenyl)-1-(pyridazin-3-yl)azetidine-3-carboxamide;
N-{4-[1-(naphthalen-2-ylacetyl)piperidin-4-yl]phenyl}-1-(pyridazin-3-yl)azetidine-3-carboxamide;
N-{4-[1-(3-phenylpropanoyl)piperidin-4-yl]phenyl}-1-(pyridazin-3-yl)azetidine-3-carboxamide;
N-(4-{1-[(2,6-dichlorophenyl)acetyl]piperidin-4-yl}phenyl)-1-(pyridazin-3-yl)azetidine-3-carboxamide;
N-(4-{1-[3-(phenylsulfonyl)propanoyl]piperidin-4-yl}phenyl)-1-(pyridazin-3-yl)azetidine-3-carboxamide;
1-(pyridazin-3-yl)-N-{4-[1-(thiophen-3-ylcarbonyl)piperidin-4-yl]phenyl}azetidine-3-carboxamide;
N-(4-{1-[(2,5-dimethylfuran-3-yl)carbonyl]piperidin-4-yl}phenyl)-1-(pyridazin-3-yl)azetidine-3-carboxamide;
N-{4-[1-(cyclopropylacetyl)piperidin-4-yl]phenyl}-1-(pyridazin-3-yl)azetidine-3-carboxamide;
N-{4-[1-(2-fluorobenzoyl)piperidin-4-yl]phenyl}-1-(pyridazin-3-yl)azetidine-3-carboxamide;
N-{4-[1-(2-methylbenzoyl)piperidin-4-yl]phenyl}-1-(pyridazin-3-yl)azetidine-3-carboxamide;
1-(pyridazin-3-yl)-N-{4-[1-(1,3-thiazol-4-ylcarbonyl)piperidin-4-yl]phenyl}azetidine-3-carboxamide;
1-(pyridazin-3-yl)-N-{4-[1-(1,3-thiazol-5-ylcarbonyl)piperidin-4-yl]phenyl}azetidine-3-carboxamide;
N-{4-[1-(ethoxyacetyl)piperidin-4-yl]phenyl}-1-(pyridazin-3-yl)azetidine-3-carboxamide;
1-(pyridazin-3-yl)-N-{4-[1-(4,4,4-trifluorobutanoyl)piperidin-4-yl]phenyl}azetidine-3-carboxamide;
N-(4-{1-[(6-methylpyridin-3-yl)carbonyl]piperidin-4-yl}phenyl)-1-(pyridazin-3-yl)azetidine-3-carboxamide;
N-[4-(1-benzoylpiperidin-4-yl)phenyl]-1-(pyridazin-3-yl)azetidine-3-carboxamide;
N-{4-[1-(furan-2-ylcarbonyl)piperidin-4-yl]phenyl}-1-(pyridazin-3-yl)azetidine-3-carboxamide;
N-(4-{1-[(1-methylcyclohexyl)carbonyl]piperidin-4-yl}phenyl)-1-(pyridazin-3-yl)azetidine-3-carboxamide;
N-{4-[1-(2-oxopropanoyl)piperidin-4-yl]phenyl}-1-(pyridazin-3-yl)azetidine-3-carboxamide;
N-{4-[1-(cyclopentylcarbonyl)piperidin-4-yl]phenyl}-1-(pyridazin-3-yl)azetidine-3-carboxamide;
N-[4-(1-propanoylpiperidin-4-yl)phenyl]-1-(pyridazin-3-yl)azetidine-3-carboxamide;
N-{4-[1-(4-methylbenzoyl)piperidin-4-yl]phenyl}-1-(pyridazin-3-yl)azetidine-3-carboxamide;
N-(4-{[(3R)-1-(2-chlorobenzoyl)pyrrolidin-3-yl]oxy}phenyl)-1-(pyridazin-4-yl)azetidine-3-carboxamide;
1-(pyridazin-4-yl)-N-(4-{[(3R)-1-(1,3-thiazol-2-ylcarbonyl)pyrrolidin-3-yl]oxy}phenyl)azetidine-3-carboxamide;
N-(4-{[(3R)-1-(cyclopropylacetyl)pyrrolidin-3-yl]oxy}phenyl)-1-(pyridazin-4-yl)azetidine-3-carboxamide;
N-[4-({(3R)-1-[(2S)-2-methylbutanoyl]pyrrolidin-3-yl}oxy)phenyl]-1-(pyridazin-4-yl)azetidine-3-carboxamide;
1-(pyridazin-4-yl)-N-(4-{[(3R)-1-(tetrahydro-2H-pyran-4-ylcarbonyl)pyrrolidin-3-yl]oxy}phenyl)azetidine-3-carboxamide;
1-(pyridazin-4-yl)-N-(4-{[(3R)-1-{[4-(trifluoromethoxy)phenyl]acetyl}pyrrolidin-3-yl]oxy}phenyl)azetidine-3-carboxamide;
1-(pyridazin-4-yl)-N-(4-{[(3R)-1-(thiophen-3-ylcarbonyl)pyrrolidin-3-yl]oxy}phenyl)azetidine-3-carboxamide;
N-[4-({(3R)-1-[(4-fluorophenyl)acetyl]pyrrolidin-3-yl}oxy)phenyl]-1-(pyridazin-4-yl)azetidine-3-carboxamide;
N-[4-({(3R)-1-[(3,5-difluorophenyl)acetyl]pyrrolidin-3-yl}oxy)phenyl]-1-(pyridazin-4-yl)azetidine-3-carboxamide;
N-(4-{[(3R)-1-(3,4-difluorobenzoyl)pyrrolidin-3-yl]oxy}phenyl)-1-(pyridazin-4-yl)azetidine-3-carboxamide;
N-[4-({(3R)-1-[(3-fluorophenyl)acetyl]pyrrolidin-3-yl}oxy)phenyl]-1-(pyridazin-4-yl)azetidine-3-carboxamide;
1-(pyridazin-4-yl)-N-[4-({(3R)-1-[3-(trifluoromethyl)benzoyl]pyrrolidin-3-yl}oxy)phenyl]azetidine-3-carboxamide;
N-[4-({(3R)-1-[(2,4-difluorophenyl)acetyl]pyrrolidin-3-yl}oxy)phenyl]-1-(pyridazin-4-yl)azetidine-3-carboxamide;
1-(pyridazin-4-yl)-N-(4-{[(3R)-1-{[4-(trifluoromethyl)phenyl]acetyl}pyrrolidin-3-yl]oxy}phenyl)azetidine-3-carboxamide;
1-(pyridazin-4-yl)-N-(4-{[(3R)-1-(1,3-thiazol-4-ylcarbonyl)pyrrolidin-3-yl]oxy}phenyl)azetidine-3-carboxamide;
1-(pyridazin-4-yl)-N-(4-{[3R]-1-(tetrahydrofuran-2-ylcarbonyl)pyrrolidin-3-yl]oxy}phenyl)azetidine-3-carboxamide;

N-[4-({(3R)-1-[(5-methylthiophen-2-yl)carbonyl]pyrrolidin-3-yl}oxy)phenyl]-1-(pyridazin-4-yl)azetidine-3-carboxamide;
N-[4-({(3R)-1-[(2-fluorophenyl)acetyl]pyrrolidin-3-yl}oxy)phenyl]-1-(pyridazin-4-yl)azetidine-3-carboxamide;
N-(4-{[(3R)-1-(cyclopropylcarbonyl)pyrrolidin-3-yl]oxy}phenyl)-1-(pyridazin-4-yl)azetidine-3-carboxamide;
1-(pyridazin-4-yl)-N-(4-{[(3R)-1-(tetrahydrofuran-3-ylcarbonyl)pyrrolidin-3-yl]oxy}phenyl)azetidine-3-carboxamide;
1-(pyridazin-4-yl)-N-[4-({(3R)-1-[3-(trifluoromethoxy)benzoyl]pyrrolidin-3-yl}oxy)phenyl]azetidine-3-carboxamide;
1-(pyridazin-4-yl)-N-(4-{[(3R)-1-(pyridin-2-ylcarbonyl)pyrrolidin-3-yl]oxy}phenyl)azetidine-3-carboxamide;
N-(4-{[(3R)-1-(3-chlorobenzoyl)pyrrolidin-3-yl]oxy}phenyl)-1-(pyridazin-4-yl)azetidine-3-carboxamide;
N-(4-{[(3R)-1-(4-chlorobenzoyl)pyrrolidin-3-yl]oxy}phenyl)-1-(pyridazin-4-yl)azetidine-3-carboxamide;
N-(4-{[(3R)-1-(2-methyl-2-phenylpropanoyl)pyrrolidin-3-yl]oxy}phenyl)-1-(pyridazin-4-yl)azetidine-3-carboxamide;
N-(4-{[(3R)-1-(2,4-difluorobenzoyl)pyrrolidin-3-yl]oxy}phenyl)-1-(pyridazin-4-yl)azetidine-3-carboxamide;
N-(4-{[(3R)-1-(methoxyacetyl)pyrrolidin-3-yl]oxy}phenyl)-1-(pyridazin-4-yl)azetidine-3-carboxamide;
1-(pyridazin-4-yl)-N-(4-{[(3R)-1-(thiophen-2-ylcarbonyl)pyrrolidin-3-yl]oxy}phenyl)azetidine-3-carboxamide;
1-(pyridazin-4-yl)-N-(4-{[(3R)-1-{[3-(trifluoromethyl)phenyl]acetyl}pyrrolidin-3-yl]oxy}phenyl)azetidine-3-carboxamide;
N-(4-{[(3R)-1-(2-methylpropanoyl)pyrrolidin-3-yl]oxy}phenyl)-1-(pyridazin-4-yl)azetidine-3-carboxamide;
N-(4-{[(3R)-1-(2-fluorobenzoyl)pyrrolidin-3-yl]oxy}phenyl)-1-(pyridazin-4-yl)azetidine-3-carboxamide;
N-(4-{[(3R)-1-(2,2-dimethylbutanoyl)pyrrolidin-3-yl]oxy}phenyl)-1-(pyridazin-4-yl)azetidine-3-carboxamide;
N-(4-{[(3R)-1-(3,5-difluorobenzoyl)pyrrolidin-3-yl]oxy}phenyl)-1-(pyridazin-4-yl)azetidine-3-carboxamide;
1-(pyridazin-4-yl)-N-[4-({(3R)-1-[4-(trifluoromethyl)benzoyl]pyrrolidin-3-yl}oxy)phenyl]azetidine-3-carboxamide;
N-(4-{[(3R)-1-(3-fluorobenzoyl)pyrrolidin-3-yl]oxy}phenyl)-1-(pyridazin-4-yl)azetidine-3-carboxamide;
1-(pyridazin-4-yl)-N-[4-({(3R)-1-[4-(trifluoromethoxy)benzoyl]pyrrolidin-3-yl}oxy)phenyl]azetidine-3-carboxamide;
N-(4-{[(3R)-1-(3-methylbutanoyl)pyrrolidin-3-yl]oxy}phenyl)-1-(pyridazin-4-yl)azetidine-3-carboxamide;
1-(pyridazin-4-yl)-N-(4-{[(3R)-1-(3,3,3-trifluoropropanoyl)pyrrolidin-3-yl]oxy}phenyl)azetidine-3-carboxamide;
N-[4-({(3R)-1-[difluoro(phenyl)acetyl]pyrrolidin-3-yl}oxy)phenyl]-1-(pyridazin-4-yl)azetidine-3-carboxamide;
N-(4-{[(3R)-1-(2,2-dimethylpropanoyl)pyrrolidin-3-yl]oxy}phenyl)-1-(pyridazin-4-yl)azetidine-3-carboxamide;
N-[4-({(3R)-1-[(4,4-difluorocyclohexyl)carbonyl]pyrrolidin-3-yl}oxy)phenyl]-1-(pyridazin-4-yl)azetidine-3-carboxamide;
N-(4-{[(3R)-1-(2-chlorobenzoyl)pyrrolidin-3-yl]oxy}phenyl)-1-(pyridazin-3-yl)azetidine-3-carboxamide;
1-(pyridazin-3-yl)-N-(4-{[(3R)-1-(1,3-thiazol-2-ylcarbonyl)pyrrolidin-3-yl]oxy}phenyl)azetidine-3-carboxamide;
N-(4-{[(3R)-1-(cyclopropylacetyl)pyrrolidin-3-yl]oxy}phenyl)-1-(pyridazin-3-yl)azetidine-3-carboxamide;
N-[4-({(3R)-1-[(2S)-2-methylbutanoyl]pyrrolidin-3-yl}oxy)phenyl]-1-(pyridazin-3-yl)azetidine-3-carboxamide;
1-(pyridazin-3-yl)-N-(4-{[(3R)-1-(tetrahydro-2H-pyran-4-ylcarbonyl)pyrrolidin-3-yl]oxy}phenyl)azetidine-3-carboxamide;
1-(pyridazin-3-yl)-N-(4-{[(3R)-1-{[4-(trifluoromethoxy)phenyl]acetyl}pyrrolidin-3-yl]oxy}phenyl)azetidine-3-carboxamide;
N-(4-{[(3R)-1-(4-fluorobenzoyl)pyrrolidin-3-yl]oxy}phenyl)-1-(pyridazin-3-yl)azetidine-3-carboxamide;
1-(pyridazin-3-yl)-N-(4-{[(3R)-1-(thiophen-3-ylcarbonyl)pyrrolidin-3-yl]oxy}phenyl)azetidine-3-carboxamide;
N-[4-({(3R)-1-[(4-fluorophenyl)acetyl]pyrrolidin-3-yl}oxy)phenyl]-1-(pyridazin-3-yl)azetidine-3-carboxamide;
N-[4-({(3R)-1-[(3,5-difluorophenyl)acetyl]pyrrolidin-3-yl}oxy)phenyl]-1-(pyridazin-3-yl)azetidine-3-carboxamide;
N-(4-{[(3R)-1-(3,4-difluorobenzoyl)pyrrolidin-3-yl]oxy}phenyl)-1-(pyridazin-3-yl)azetidine-3-carboxamide;
N-[4-({(3R)-1-[(3-fluorophenyl)acetyl]pyrrolidin-3-yl}oxy)phenyl]-1-(pyridazin-3-yl)azetidine-3-carboxamide;
1-(pyridazin-3-yl)-N-[4-({(3R)-1-[3-(trifluoromethyl)benzoyl]pyrrolidin-3-yl}oxy)phenyl]azetidine-3-carboxamide;
N-[4-({(3R)-1-[(2,4-difluorophenyl)acetyl]pyrrolidin-3-yl}oxy)phenyl]-1-(pyridazin-3-yl)azetidine-3-carboxamide;
1-(pyridazin-3-yl)-N-(4-{[(3R)-1-{[4-(trifluoromethyl)phenyl]acetyl}pyrrolidin-3-yl]oxy}phenyl)azetidine-3-carboxamide;
1-(pyridazin-3-yl)-N-(4-{[(3R)-1-(1,3-thiazol-4-ylcarbonyl)pyrrolidin-3-yl]oxy}phenyl)azetidine-3-carboxamide;
1-(pyridazin-3-yl)-N-(4-{[(3R)-1-(tetrahydrofuran-2-ylcarbonyl)pyrrolidin-3-yl]oxy}phenyl)azetidine-3-carboxamide;
N-[4-({(3R)-1-[(5-methylthiophen-2-yl)carbonyl]pyrrolidin-3-yl}oxy)phenyl]-1-(pyridazin-3-yl)azetidine-3-carboxamide;
N-[4-({(3R)-1-[(2-fluorophenyl)acetyl]pyrrolidin-3-yl}oxy)phenyl]-1-(pyridazin-3-yl)azetidine-3-carboxamide;
N-(4-{[(3R)-1-(cyclopropylcarbonyl)pyrrolidin-3-yl]oxy}phenyl)-1-(pyridazin-3-yl)azetidine-3-carboxamide;
1-(pyridazin-3-yl)-N-(4-{[(3R)-1-(tetrahydrofuran-3-ylcarbonyl)pyrrolidin-3-yl]oxy}phenyl)azetidine-3-carboxamide;
1-(pyridazin-3-yl)-N-[4-({(3R)-1-[3-(trifluoromethoxy)benzoyl]pyrrolidin-3-yl}oxy)phenyl]azetidine-3-carboxamide;
1-(pyridazin-3-yl)-N-(4-{[(3R)-1-(pyridin-2-ylcarbonyl)pyrrolidin-3-yl]oxy}phenyl)azetidine-3-carboxamide;
N-(4-{[(3R)-1-(3-chlorobenzoyl)pyrrolidin-3-yl]oxy}phenyl)-1-(pyridazin-3-yl)azetidine-3-carboxamide;
N-(4-{[(3R)-1-(4-chlorobenzoyl)pyrrolidin-3-yl]oxy}phenyl)-1-(pyridazin-3-yl)azetidine-3-carboxamide;
N-(4-{[(3R)-1-(2-methyl-2-phenylpropanoyl)pyrrolidin-3-yl]oxy}phenyl)-1-(pyridazin-3-yl)azetidine-3-carboxamide;
N-(4-{[(3R)-1-(2,4-difluorobenzoyl)pyrrolidin-3-yl]oxy}phenyl)-1-(pyridazin-3-yl)azetidine-3-carboxamide;
N-(4-{[(3R)-1-(methoxyacetyl)pyrrolidin-3-yl]oxy}phenyl)-1-(pyridazin-3-yl)azetidine-3-carboxamide;
1-(pyridazin-3-yl)-N-(4-{[(3R)-1-(thiophen-2-ylcarbonyl)pyrrolidin-3-yl]oxy}phenyl)azetidine-3-carboxamide;
1-(pyridazin-3-yl)-N-(4-{[(3R)-1-{[3-(trifluoromethyl)phenyl]acetyl}pyrrolidin-3-yl]oxy}phenyl)azetidine-3-carboxamide;
N-(4-{[(3R)-1-(2-methylpropanoyl)pyrrolidin-3-yl]oxy}phenyl)-1-(pyridazin-3-yl)azetidine-3-carboxamide;

N-(4-{[(3R)-1-(2-fluorobenzoyl)pyrrolidin-3-yl]oxy}phenyl)-1-(pyridazin-3-yl)azetidine-3-carboxamide;

N-(4-{[(3R)-1-(2,2-dimethylbutanoyl)pyrrolidin-3-yl]oxy}phenyl)-1-(pyridazin-3-yl)azetidine-3-carboxamide;

N-(4-{[(3R)-1-(3,5-difluorobenzoyl)pyrrolidin-3-yl]oxy}phenyl)-1-(pyridazin-3-yl)azetidine-3-carboxamide;

1-(pyridazin-3-yl)-N-[4-({(3R)-1-[4-(trifluoromethyl)benzoyl]pyrrolidin-3-yl}oxy)phenyl]azetidine-3-carboxamide;

N-(4-{[(3R)-1-(3-fluorobenzoyl)pyrrolidin-3-yl]oxy}phenyl)-1-(pyridazin-3-yl)azetidine-3-carboxamide;

1-(pyridazin-3-yl)-N-[4-({(3R)-1-[4-(trifluoromethoxy)benzoyl]pyrrolidin-3-yl}oxy)phenyl]azetidine-3-carboxamide;

N-(4-{[(3R)-1-(3-methylbutanoyl)pyrrolidin-3-yl]oxy}phenyl)-1-(pyridazin-3-yl)azetidine-3-carboxamide;

1-(pyridazin-3-yl)-N-(4-{[(3R)-1-(3,3,3-trifluoropropanoyl)pyrrolidin-3-yl]oxy}phenyl)azetidine-3-carboxamide;

N-[4-({(3R)-1-[difluoro(phenyl)acetyl]pyrrolidin-3-yl}oxy)phenyl]-1-(pyridazin-3-yl)azetidine-3-carboxamide;

N-(4-{[(3R)-1-(2,2-dimethylpropanoyl)pyrrolidin-3-yl]oxy}phenyl)-1-(pyridazin-3-yl)azetidine-3-carboxamide;

N-[4-({(3R)-1-[(4,4-difluorocyclohexyl)carbonyl]pyrrolidin-3-yl}oxy)phenyl]-1-(pyridazin-3-yl)azetidine-3-carboxamide;

N-{4-[1-(2-chlorobenzoyl)piperidin-4-yl]phenyl}-1-(pyridazin-4-yl)azetidine-3-carboxamide;

1-(pyridazin-4-yl)-N-{4-[1-(1,3-thiazol-2-ylcarbonyl)piperidin-4-yl]phenyl}azetidine-3-carboxamide;

N-{4-[1-(cyclopropylacetyl)piperidin-4-yl]phenyl}-1-(pyridazin-4-yl)azetidine-3-carboxamide;

N-{4-[1-(2-methylpropanoyl)piperidin-4-yl]phenyl}-1-(pyridazin-4-yl)azetidine-3-carboxamide;

N-{4-[1-(4-fluorobenzoyl)piperidin-4-yl]phenyl}-1-(pyridazin-4-yl)azetidine-3-carboxamide;

1-(pyridazin-4-yl)-N-{4-[1-(thiophen-3-ylcarbonyl)piperidin-4-yl]phenyl}azetidine-3-carboxamide;

N-(4-{1-[(4-fluorophenyl)acetyl]piperidin-4-yl}phenyl)-1-(pyridazin-4-yl)azetidine-3-carboxamide;

N-(4-{1-[(3,5-difluorophenyl)acetyl]piperidin-4-yl}phenyl)-1-(pyridazin-4-yl)azetidine-3-carboxamide;

N-{4-[1-(3,4-difluorobenzoyl)piperidin-4-yl]phenyl}-1-(pyridazin-4-yl)azetidine-3-carboxamide;

N-(4-{1-[(3-fluorophenyl)acetyl]piperidin-4-yl}phenyl)-1-(pyridazin-4-yl)azetidine-3-carboxamide;

1-(pyridazin-4-yl)-N-(4-{1-[3-(trifluoromethyl)benzoyl]piperidin-4-yl}phenyl)azetidine-3-carboxamide;

N-(4-{1-[(2,4-difluorophenyl)acetyl]piperidin-4-yl}phenyl)-1-(pyridazin-4-yl)azetidine-3-carboxamide;

1-(pyridazin-4-yl)-N-{4-[1-(1,3-thiazol-4-ylcarbonyl)piperidin-4-yl]phenyl}azetidine-3-carboxamide;

1-(pyridazin-4-yl)-N-{4-[1-(tetrahydrofuran-2-ylcarbonyl)piperidin-4-yl]phenyl}azetidine-3-carboxamide;

N-(4-{1-[(5-methylthiophen-2-yl)carbonyl]piperidin-4-yl}phenyl)-1-(pyridazin-4-yl)azetidine-3-carboxamide;

N-(4-{1-[(2-fluorophenyl)acetyl]piperidin-4-yl}phenyl)-1-(pyridazin-4-yl)azetidine-3-carboxamide;

N-{4-[1-(cyclopropylcarbonyl)piperidin-4-yl]phenyl}-1-(pyridazin-4-yl)azetidine-3-carboxamide;

1-(pyridazin-4-yl)-N-{4-[1-(tetrahydrofuran-3-ylcarbonyl)piperidin-4-yl]phenyl}azetidine-3-carboxamide;

1-(pyridazin-4-yl)-N-{4-[1-(pyridin-2-ylcarbonyl)piperidin-4-yl]phenyl}azetidine-3-carboxamide;

N-{4-[1-(3-chlorobenzoyl)piperidin-4-yl]phenyl}-1-(pyridazin-4-yl)azetidine-3-carboxamide;

N-{4-[1-(4-chlorobenzoyl)piperidin-4-yl]phenyl}-1-(pyridazin-4-yl)azetidine-3-carboxamide;

N-{4-[1-(2-methyl-2-phenylpropanoyl)piperidin-4-yl]phenyl}-1-(pyridazin-4-yl)azetidine-3-carboxamide;

N-{4-[1-(2,4-difluorobenzoyl)piperidin-4-yl]phenyl}-1-(pyridazin-4-yl)azetidine-3-carboxamide;

N-{4-[1-(methoxyacetyl)piperidin-4-yl]phenyl}-1-(pyridazin-4-yl)azetidine-3-carboxamide;

1-(pyridazin-4-yl)-N-{4-[1-(thiophen-2-ylcarbonyl)piperidin-4-yl]phenyl}azetidine-3-carboxamide;

1-(pyridazin-4-yl)-N-[4-(1-{[3-(trifluoromethyl)phenyl]acetyl}piperidin-4-yl)phenyl]azetidine-3-carboxamide;

N-{4-[1-(2-fluorobenzoyl)piperidin-4-yl]phenyl}-1-(pyridazin-4-yl)azetidine-3-carboxamide;

N-{4-[1-(3,5-difluorobenzoyl)piperidin-4-yl]phenyl}-1-(pyridazin-4-yl)azetidine-3-carboxamide;

1-(pyridazin-4-yl)-N-(4-{1-[4-(trifluoromethyl)benzoyl]piperidin-4-yl}phenyl)azetidine-3-carboxamide;

N-{4-[1-(3-fluorobenzoyl)piperidin-4-yl]phenyl}-1-(pyridazin-4-yl)azetidine-3-carboxamide;

1-(pyridazin-4-yl)-N-(4-{1-[4-(trifluoromethoxy)benzoyl]piperidin-4-yl}phenyl)azetidine-3-carboxamide;

N-{4-[1-(3-methylbutanoyl)piperidin-4-yl]phenyl}-1-(pyridazin-4-yl)azetidine-3-carboxamide;

1-(pyridazin-4-yl)-N-{4-[1-(3,3,3-trifluoropropanoyl)piperidin-4-yl]phenyl}azetidine-3-carboxamide;

N-(4-{1-[difluoro(phenyl)acetyl]piperidin-4-yl}phenyl)-1-(pyridazin-4-yl)azetidine-3-carboxamide;

N-{4-[1-(2,2-dimethylpropanoyl)piperidin-4-yl]phenyl}-1-(pyridazin-4-yl)azetidine-3-carboxamide;

N-(4-{1-[(4,4-difluorocyclohexyl)carbonyl]piperidin-4-yl}phenyl)-1-(pyridazin-4-yl)azetidine-3-carboxamide;

1-(pyridazin-4-yl)-N-[4-(1-{[4-(trifluoromethoxy)phenyl]acetyl}piperidin-4-yl)phenyl]azetidine-3-carboxamide;

1-(pyridazin-4-yl)-N-(4-{1-[3-(trifluoromethoxy)benzoyl]piperidin-4-yl}phenyl)azetidine-3-carboxamide;

1-(pyridazin-4-yl)-N-[4-(1-{[4-(trifluoromethyl)phenyl]acetyl}piperidin-4-yl)phenyl]azetidine-3-carboxamide;

N-(4-{[1-(3-chlorobenzoyl)piperidin-4-yl]sulfonyl}phenyl)-1-(pyridazin-3-yl)azetidine-3-carboxamide;

N-(4-{[1-(4-tert-butylbenzoyl)piperidin-4-yl]sulfonyl}phenyl)-1-(pyridazin-3-yl)azetidine-3-carboxamide;

N-(4-{[1-(4-methoxybenzoyl)piperidin-4-yl]sulfonyl}phenyl)-1-(pyridazin-3-yl)azetidine-3-carboxamide;

N-(4-{[1-(4-methylbenzoyl)piperidin-4-yl]sulfonyl}phenyl)-1-(pyridazin-3-yl)azetidine-3-carboxamide;

N-(4-{[1-(cyclohexylcarbonyl)piperidin-4-yl]sulfonyl}phenyl)-1-(pyridazin-3-yl)azetidine-3-carboxamide;

N-(4-{[1-(cyclopropylacetyl)piperidin-4-yl]sulfonyl}phenyl)-1-(pyridazin-3-yl)azetidine-3-carboxamide;

N-(4-{[1-(2-methoxybenzoyl)piperidin-4-yl]sulfonyl}phenyl)-1-(pyridazin-3-yl)azetidine-3-carboxamide;

N-[4-({1-[(2S)-2-phenylbutanoyl]piperidin-4-yl}sulfonyl)phenyl]-1-(pyridazin-3-yl)azetidine-3-carboxamide;

N-[4-({1-[4-(propan-2-yl)benzoyl]piperidin-4-yl}sulfonyl)phenyl]-1-(pyridazin-3-yl)azetidine-3-carboxamide;

N-(4-{[1-(4-chlorobenzoyl)piperidin-4-yl]sulfonyl}phenyl)-1-(pyridazin-3-yl)azetidine-3-carboxamide;

N-{4-[(1-benzoylpiperidin-4-yl)sulfonyl]phenyl}-1-(pyridazin-3-yl)azetidine-3-carboxamide;

1-(pyridazin-3-yl)-N-(4-{[1-(4,4,4-trifluorobutanoyl)piperidin-4-yl]sulfonyl}phenyl)azetidine-3-carboxamide;

N-(4-{[1-(2,5-difluorobenzoyl)piperidin-4-yl]sulfonyl}phenyl)-1-(pyridazin-3-yl)azetidine-3-carboxamide;

N-(4-{[1-(2-fluorobenzoyl)piperidin-4-yl]sulfonyl}phenyl)-1-(pyridazin-3-yl)azetidine-3-carboxamide;

N-(4-{[1-(2-methylbenzoyl)piperidin-4-yl]sulfonyl}phenyl)-1-(pyridazin-3-yl)azetidine-3-carboxamide;

N-[4-({1-[(4-fluorophenyl)acetyl]piperidin-4-yl}sulfonyl)phenyl]-1-(pyridazin-3-yl)azetidine-3-carboxamide;

N-(4-{[1-(3-methylbenzoyl)piperidin-4-yl]sulfonyl}phenyl)-1-(pyridazin-3-yl)azetidine-3-carboxamide;

N-(4-{[1-(2,3-dimethylbenzoyl)piperidin-4-yl]sulfonyl}phenyl)-1-(pyridazin-3-yl)azetidine-3-carboxamide;

N-[4-({1-[(3-fluorophenyl)acetyl]piperidin-4-yl}sulfonyl)phenyl]-1-(pyridazin-3-yl)azetidine-3-carboxamide;

N-(4-{[1-(3-fluorobenzoyl)piperidin-4-yl]sulfonyl}phenyl)-1-(pyridazin-3-yl)azetidine-3-carboxamide;

1-(pyridazin-3-yl)-N-[4-({1-[3-(trifluoromethyl)benzoyl]piperidin-4-yl}sulfonyl)phenyl]azetidine-3-carboxamide;

N-[4-({1-[(3,5-difluorophenyl)acetyl]piperidin-4-yl}sulfonyl)phenyl]-1-(pyridazin-3-yl)azetidine-3-carboxamide;

N-(4-{[1-(2,4-difluorobenzoyl)piperidin-4-yl]sulfonyl}phenyl)-1-(pyridazin-3-yl)azetidine-3-carboxamide;

1-(pyridazin-3-yl)-N-[4-({1-[4-(trifluoromethyl)benzoyl]piperidin-4-yl}sulfonyl)phenyl]azetidine-3-carboxamide;

N-(4-{[1-(4-fluorobenzoyl)piperidin-4-yl]sulfonyl}phenyl)-1-(pyridazin-3-yl)azetidine-3-carboxamide;

N-(4-{[1-(2,3-difluorobenzoyl)piperidin-4-yl]sulfonyl}phenyl)-1-(pyridazin-3-yl)azetidine-3-carboxamide;

N-(4-{[1-(2,4-dichlorobenzoyl)piperidin-4-yl]sulfonyl}phenyl)-1-(pyridazin-3-yl)azetidine-3-carboxamide;

N-(4-{[1-(naphthalen-1-ylcarbonyl)piperidin-4-yl]sulfonyl}phenyl)-1-(pyridazin-3-yl)azetidine-3-carboxamide;

N-(4-{[1-(cyclopropylcarbonyl)piperidin-4-yl]sulfonyl}phenyl)-1-(pyridazin-3-yl)azetidine-3-carboxamide;

N-(4-{[1-(3,5-difluorobenzoyl)piperidin-4-yl]sulfonyl}phenyl)-1-(pyridazin-3-yl)azetidine-3-carboxamide;

N-(4-{[1-(2,2-dimethylpropanoyl)piperidin-4-yl]sulfonyl}phenyl)-1-(pyridazin-3-yl)azetidine-3-carboxamide;

N-(4-{[1-(3,3-dimethylbutanoyl)piperidin-4-yl]sulfonyl}phenyl)-1-(pyridazin-3-yl)azetidine-3-carboxamide;

N-(4-{[1-(3-methoxybenzoyl)piperidin-4-yl]sulfonyl}phenyl)-1-(pyridazin-3-yl)azetidine-3-carboxamide;

N-(4-{[1-(3-methylbutanoyl)piperidin-4-yl]sulfonyl}phenyl)-1-(pyridazin-3-yl)azetidine-3-carboxamide;

N-(4-{[1-(2-methylpropanoyl)piperidin-4-yl]sulfonyl}phenyl)-1-(pyridazin-3-yl)azetidine-3-carboxamide;

N-(4-{[1-(cyclopentylcarbonyl)piperidin-4-yl]sulfonyl}phenyl)-1-(pyridazin-3-yl)azetidine-3-carboxamide;

N-(4-{[1-(phenylacetyl)piperidin-4-yl]sulfonyl}phenyl)-1-(pyridazin-3-yl)azetidine-3-carboxamide;

N-[4-({1-[(1-phenylcyclopropyl)carbonyl]piperidin-4-yl}sulfonyl)phenyl]-1-(pyridazin-3-yl)azetidine-3-carboxamide;

N-{4-[1-(2-methylalanyl)piperidin-4-yl]phenyl}-1-(pyridin-3-yl)azetidine-3-carboxamide;

5-[1-(2-methylpropyl)-1H-pyrazol-4-yl]-N-[(3R)-1-(pyridin-3-yl)pyrrolidin-3-yl]thiophene-2-carboxamide;

5-[1-(2-methylpropyl)-1H-pyrazol-4-yl]-N-[(3R)-1-(pyridazin-4-yl)pyrrolidin-3-yl]thiophene-2-carboxamide;

5-[1-(2-methylpropyl)-1H-pyrazol-4-yl]-N-[(3R)-1-(pyridazin-3-yl)pyrrolidin-3-yl]thiophene-2-carboxamide;

5-[1-(2-methylpropyl)-1H-pyrazol-4-yl]-N-[(3S)-1-(pyridazin-3-yl)pyrrolidin-3-yl]thiophene-2-carboxamide;

5-[1-(2-methylpropyl)-1H-pyrazol-4-yl]-N-[(3S)-1-(pyridazin-4-yl)pyrrolidin-3-yl]thiophene-2-carboxamide;

5-[1-(2-methylpropyl)-1H-pyrazol-4-yl]-N-[(3S)-1-(pyridin-3-yl)pyrrolidin-3-yl]thiophene-2-carboxamide;

tert-butyl 4-(2-methyl-1-oxo-1-{4-[4-({[1-(pyridin-3-yl)azetidin-3-yl]carbonyl}amino)phenyl]piperidin-1-yl}propan-2-yl)piperazine-1-carboxylate;

N-(4-{1-[2-methyl-2-(piperazin-1-yl)propanoyl]piperidin-4-yl}phenyl)-1-(pyridin-3-yl)azetidine-3-carboxamide;

N-(4-{[1-(2-chlorobenzoyl)piperidin-4-yl]sulfonyl}phenyl)-1-(pyridazin-3-yl)azetidine-3-carboxamide;

N-(4-{[1-(4-methylpentanoyl)piperidin-4-yl]sulfonyl}phenyl)-1-(pyridazin-3-yl)azetidine-3-carboxamide;

N-[4-({1-[(2-fluorophenyl)acetyl]piperidin-4-yl}sulfonyl)phenyl]-1-(pyridazin-3-yl)azetidine-3-carboxamide;

N-(4-{[1-(2-methylpropanoyl)piperidin-4-yl]sulfonyl}phenyl)-1-(pyridazin-4-yl)azetidine-3-carboxamide;

N-{4-[(1-benzoylpiperidin-4-yl)sulfonyl]phenyl}-1-(pyridazin-4-yl)azetidine-3-carboxamide;

N-(4-{[1-(4-fluorobenzoyl)piperidin-4-yl]sulfonyl}phenyl)-1-(pyridazin-4-yl)azetidine-3-carboxamide;

N-(4-{[1-(cyclopentylcarbonyl)piperidin-4-yl]sulfonyl}phenyl)-1-(pyridazin-4-yl)azetidine-3-carboxamide;

N-[(3R)-1-(5,6-dichloropyridazin-4-yl)pyrrolidin-3-yl]-5-[1-(2-methylpropyl)-1H-pyrazol-4-yl]thiophene-2-carboxamide;

N-[(3R)-1-(6-chloropyridazin-3-yl)pyrrolidin-3-yl]-5-[1-(2-methylpropyl)-1H-pyrazol-4-yl]thiophene-2-carboxamide;

N-[(3S)-1-(5,6-dichloropyridazin-4-yl)pyrrolidin-3-yl]-5-[1-(2-methylpropyl)-1H-pyrazol-4-yl]thiophene-2-carboxamide;

N-[(3S)-1-(6-chloropyridazin-3-yl)pyrrolidin-3-yl]-5-[1-(2-methylpropyl)-1H-pyrazol-4-yl]thiophene-2-carboxamide;

N-[(3R)-1-(5,6-dichloropyridazin-4-yl)pyrrolidin-3-yl]-5-[1-(2-methylpropyl)-1H-pyrazol-4-yl]thiophene-3-carboxamide;

5-[1-(2-methylpropyl)-1H-pyrazol-4-yl]-N-[(3R)-1-(pyridazin-3-yl)pyrrolidin-3-yl]thiophene-3-carboxamide;

5-[1-(2-methylpropyl)-1H-pyrazol-4-yl]-N-[(3R)-1-(pyridazin-4-yl)pyrrolidin-3-yl]thiophene-3-carboxamide;

N-{4-[1-(2,2-dimethylpropanoyl)piperidin-4-yl]phenyl}-1-(pyridazin-3-yl)piperidine-4-carboxamide;

N-[4-(1-benzoylpiperidin-4-yl)phenyl]-1-(pyridazin-3-yl)piperidine-4-carboxamide;

N-{4-[1-(2-fluorobenzoyl)piperidin-4-yl]phenyl}-1-(pyridazin-3-yl)piperidine-4-carboxamide;

1-(pyridazin-3-yl)-N-{4-[1-(4,4,4-trifluorobutanoyl)piperidin-4-yl]phenyl}piperidine-4-carboxamide;
N-[(3S)-1-(6-chloropyridazin-3-yl)pyrrolidin-3-yl]-5-[1-(2-methylpropyl)-1H-pyrazol-4-yl]thiophene-3-carboxamide;
(3S)-1-(pyridazin-3-yl)-N-{4-[1-(1,3-thiazol-5-ylcarbonyl)piperidin-4-yl]phenyl}pyrrolidine-3-carboxamide;
(3S)—N-{4-[1-(4-methylbenzoyl)piperidin-4-yl]phenyl}-1-(pyridazin-3-yl)pyrrolidine-3-carboxamide;
(3S)—N-(4-{1-[(2S)-2-phenylbutanoyl]piperidin-4-yl}phenyl)-1-(pyridazin-3-yl)pyrrolidine-3-carboxamide;
(3S)—N-(4-{1-[(2S)-2-methoxy-2-phenylacetyl]piperidin-4-yl}phenyl)-1-(pyridazin-3-yl)pyrrolidine-3-carboxamide;
(3S)—N-(4-{1-[(2R)-2-methoxy-2-phenylacetyl]piperidin-4-yl}phenyl)-1-(pyridazin-3-yl)pyrrolidine-3-carboxamide;
(3S)—N-{4-[1-(ethoxyacetyl)piperidin-4-yl]phenyl}-1-(pyridazin-3-yl)pyrrolidine-3-carboxamide;
(3S)—N-(4-{1-[(4-methylphenoxy)acetyl]piperidin-4-yl}phenyl)-1-(pyridazin-3-yl)pyrrolidine-3-carboxamide;
(3S)—N-{4-[1-(2-fluorobenzoyl)piperidin-4-yl]phenyl}-1-(pyridazin-3-yl)pyrrolidine-3-carboxamide;
(3S)-1-(pyridazin-3-yl)-N-{4-[1-(tetrahydrofuran-3-ylcarbonyl)piperidin-4-yl]phenyl}pyrrolidine-3-carboxamide;
(3S)—N-{4-[1-(naphthalen-1-ylcarbonyl)piperidin-4-yl]phenyl}-1-(pyridazin-3-yl)pyrrolidine-3-carboxamide;
(3S)—N-(4-{1-[(2,6-dichlorophenyl)acetyl]piperidin-4-yl}phenyl)-1-(pyridazin-3-yl)pyrrolidine-3-carboxamide;
(3S)—N-{4-[1-(naphthalen-1-ylacetyl)piperidin-4-yl]phenyl}-1-(pyridazin-3-yl)pyrrolidine-3-carboxamide;
(3S)-1-(pyridazin-3-yl)-N-(4-{1-[4-(thiophen-2-yl)butanoyl]piperidin-4-yl}phenyl)pyrrolidine-3-carboxamide;
(3S)—N-{4-[1-(cyclopropylacetyl)piperidin-4-yl]phenyl}-1-(pyridazin-3-yl)pyrrolidine-3-carboxamide;
(3S)—N-{4-[1-(cyclopentylacetyl)piperidin-4-yl]phenyl}-1-(pyridazin-3-yl)pyrrolidine-3-carboxamide;
(3S)—N-{4-[1-(2,5-difluorobenzoyl)piperidin-4-yl]phenyl}-1-(pyridazin-3-yl)pyrrolidine-3-carboxamide;
(3S)—N-{4-[1-(naphthalen-2-ylacetyl)piperidin-4-yl]phenyl}-1-(pyridazin-3-yl)pyrrolidine-3-carboxamide;
(3S)—N-(4-{1-[3-(phenylsulfonyl)propanoyl]piperidin-4-yl}phenyl)-1-(pyridazin-3-yl)pyrrolidine-3-carboxamide;
(3S)-1-(pyridazin-3-yl)-N-[4-(1-{[3-(trifluoromethyl)phenyl]acetyl}piperidin-4-yl)phenyl]pyrrolidine-3-carboxamide;
(3S)—N-{4-[1-(furan-2-ylcarbonyl)piperidin-4-yl]phenyl}-1-(pyridazin-3-yl)pyrrolidine-3-carboxamide;
(3S)—N-{4-[1-(N-benzoylglycyl)piperidin-4-yl]phenyl}-1-(pyridazin-3-yl)pyrrolidine-3-carboxamide;
(3S)—N-(4-{1-[(2,4-dichlorophenyl)acetyl]piperidin-4-yl}phenyl)-1-(pyridazin-3-yl)pyrrolidine-3-carboxamide;
(3S)—N-{4-[1-(2-methylbenzoyl)piperidin-4-yl]phenyl}-1-(pyridazin-3-yl)pyrrolidine-3-carboxamide;
(3S)-1-(pyridazin-3-yl)-N-{4-[1-(4,4,4-trifluorobutanoyl)piperidin-4-yl]phenyl}pyrrolidine-3-carboxamide;
(3S)—N-(4-{1-[(1-methylcyclohexyl)carbonyl]piperidin-4-yl}phenyl)-1-(pyridazin-3-yl)pyrrolidine-3-carboxamide;
(3S)-1-(pyridazin-3-yl)-N-{4-[1-(thiophen-3-ylcarbonyl)piperidin-4-yl]phenyl}pyrrolidine-3-carboxamide;
(3S)—N-(4-{1-[(6-methylpyridin-3-yl)carbonyl]piperidin-4-yl}phenyl)-1-(pyridazin-3-yl)pyrrolidine-3-carboxamide;
(3S)—N-(4-{1-[(3-chlorophenyl)acetyl]piperidin-4-yl}phenyl)-1-(pyridazin-3-yl)pyrrolidine-3-carboxamide;
(3S)—N-[4-(1-propanoylpiperidin-4-yl)phenyl]-1-(pyridazin-3-yl)pyrrolidine-3-carboxamide;
(3S)—N-{4-[1-(3,5-difluorobenzoyl)piperidin-4-yl]phenyl}-1-(pyridazin-3-yl)pyrrolidine-3-carboxamide;
(3S)—N-{4-[1-(cyclopentylcarbonyl)piperidin-4-yl]phenyl}-1-(pyridazin-3-yl)pyrrolidine-3-carboxamide;
(3S)-1-(pyridazin-3-yl)-N-{4-[1-(tetrahydrofuran-2-ylcarbonyl)piperidin-4-yl]phenyl}pyrrolidine-3-carboxamide;
(3S)—N-{4-[1-(cyclopropylcarbonyl)piperidin-4-yl]phenyl}-1-(pyridazin-3-yl)pyrrolidine-3-carboxamide;
(3S)—N-{4-[1-(4-chlorobenzoyl)piperidin-4-yl]phenyl}-1-(pyridazin-3-yl)pyrrolidine-3-carboxamide;
5-[1-(2-methylpropyl)-1H-pyrazol-4-yl]-N-[(3S)-1-(pyridazin-3-yl)pyrrolidin-3-yl]thiophene-3-carboxamide;
N-[4-(1-benzoylpiperidin-4-yl)phenyl]-1-(6-fluoro-5-methylpyridin-3-yl)azetidine-3-carboxamide;
N-[4-(1-benzoylpiperidin-4-yl)phenyl]-1-(5-fluoropyridin-3-yl)azetidine-3-carboxamide;
N-[4-(1-benzoylpiperidin-4-yl)phenyl]-1-(6-methylpyridin-3-yl)azetidine-3-carboxamide;
N-[4-(1-benzoylpiperidin-4-yl)phenyl]-1-(2-fluoro-6-methylpyridin-3-yl)azetidine-3-carboxamide;
(3S)—N-{4-[1-(2-chlorobenzoyl)piperidin-4-yl]phenyl}-1-(pyridazin-3-yl)pyrrolidine-3-carboxamide;
(3S)—N-{4-[1-(2-methylpentanoyl)piperidin-4-yl]phenyl}-1-(pyridazin-3-yl)pyrrolidine-3-carboxamide;
(3S)—N-{4-[1-(4-methylpentanoyl)piperidin-4-yl]phenyl}-1-(pyridazin-3-yl)pyrrolidine-3-carboxamide;
(3S)—N-{4-[1-(2,4-dimethylbenzoyl)piperidin-4-yl]phenyl}-1-(pyridazin-3-yl)pyrrolidine-3-carboxamide;
(3S)—N-[4-(1-heptanoylpiperidin-4-yl)phenyl]-1-(pyridazin-3-yl)pyrrolidine-3-carboxamide;
(3S)—N-{4-[1-(2,4-dichlorobenzoyl)piperidin-4-yl]phenyl}-1-(pyridazin-3-yl)pyrrolidine-3-carboxamide;
(3S)—N-(4-{1-[(4-fluorophenyl)acetyl]piperidin-4-yl}phenyl)-1-(pyridazin-3-yl)pyrrolidine-3-carboxamide;
(3S)—N-{4-[1-(2,3-difluorobenzoyl)piperidin-4-yl]phenyl}-1-(pyridazin-3-yl)pyrrolidine-3-carboxamide;
(3S)—N-{4-[1-(3-methylbenzoyl)piperidin-4-yl]phenyl}-1-(pyridazin-3-yl)pyrrolidine-3-carboxamide;
(3S)—N-[4-(1-hexanoylpiperidin-4-yl)phenyl]-1-(pyridazin-3-yl)pyrrolidine-3-carboxamide;
(3S)—N-(4-{1-[(3-methylthiophen-2-yl)carbonyl]piperidin-4-yl}phenyl)-1-(pyridazin-3-yl)pyrrolidine-3-carboxamide;
(3S)—N-{4-[1-(2,3-dimethylbutanoyl)piperidin-4-yl]phenyl}-1-(pyridazin-3-yl)pyrrolidine-3-carboxamide;
(3S)—N-[4-(1-butanoylpiperidin-4-yl)phenyl]-1-(pyridazin-3-yl)pyrrolidine-3-carboxamide;
(3S)—N-{4-[1-(3-methylpentanoyl)piperidin-4-yl]phenyl}-1-(pyridazin-3-yl)pyrrolidine-3-carboxamide;
(3S)—N-(4-{1-[(3,5-dimethylphenyl)acetyl]piperidin-4-yl}phenyl)-1-(pyridazin-3-yl)pyrrolidine-3-carboxamide;
(3S)—N-{4-[1-(3,5-dichlorobenzoyl)piperidin-4-yl]phenyl}-1-(pyridazin-3-yl)pyrrolidine-3-carboxamide;
(3S)—N-{4-[1-(3-fluoro-2-methylbenzoyl)piperidin-4-yl]phenyl}-1-(pyridazin-3-yl)pyrrolidine-3-carboxamide;
(3S)—N-(4-{1-[(4-chlorophenyl)acetyl]piperidin-4-yl}phenyl)-1-(pyridazin-3-yl)pyrrolidine-3-carboxamide;
(3S)—N-{4-[1-(furan-3-ylcarbonyl)piperidin-4-yl]phenyl}-1-(pyridazin-3-yl)pyrrolidine-3-carboxamide;
(3S)—N-{4-[1-(3,4-dimethylbenzoyl)piperidin-4-yl]phenyl}-1-(pyridazin-3-yl)pyrrolidine-3-carboxamide;
(3S)—N-{4-[1-(4-fluorobenzoyl)piperidin-4-yl]phenyl}-1-(pyridazin-3-yl)pyrrolidine-3-carboxamide;
(3S)—N-(4-{1-[2-chloro-5-(trifluoromethyl)benzoyl]piperidin-4-yl}phenyl)-1-(pyridazin-3-yl)pyrrolidine-3-carboxamide;

(3S)—N-[4-(1-acetylpiperidin-4-yl)phenyl]-1-(pyridazin-3-yl)pyrrolidine-3-carboxamide;
(3S)—N-{4-[1-(2,4-difluorobenzoyl)piperidin-4-yl]phenyl}-1-(pyridazin-3-yl)pyrrolidine-3-carboxamide;
(3S)—N-{4-[1-(3,5-dimethylbenzoyl)piperidin-4-yl]phenyl}-1-(pyridazin-3-yl)pyrrolidine-3-carboxamide;
(3S)—N-{4-[1-(3-ethoxypropanoyl)piperidin-4-yl]phenyl}-1-(pyridazin-3-yl)pyrrolidine-3-carboxamide;
(3S)—N-{4-[1-(2,5-dichlorobenzoyl)piperidin-4-yl]phenyl}-1-(pyridazin-3-yl)pyrrolidine-3-carboxamide;
(3S)—N-{4-[1-(2,5-dimethylbenzoyl)piperidin-4-yl]phenyl}-1-(pyridazin-3-yl)pyrrolidine-3-carboxamide;
(3S)—N-{4-[1-(5-fluoro-2-methylbenzoyl)piperidin-4-yl]phenyl}-1-(pyridazin-3-yl)pyrrolidine-3-carboxamide;
(3S)—N-{4-[1-(diphenylacetyl)piperidin-4-yl]phenyl}-1-(pyridazin-3-yl)pyrrolidine-3-carboxamide;
(3S)-1-(pyridazin-3-yl)-N-(4-{1-[4-(trifluoromethyl)benzoyl]piperidin-4-yl}phenyl)pyrrolidine-3-carboxamide;
(3S)—N-{4-[1-(pent-4-enoyl)piperidin-4-yl]phenyl}-1-(pyridazin-3-yl)pyrrolidine-3-carboxamide;
(3S)-1-(pyridazin-3-yl)-N-(4-{1-[3-(trifluoromethoxy)benzoyl]piperidin-4-yl}phenyl)pyrrolidine-3-carboxamide;
(3S)—N-(4-{1-[(1-phenylcyclopropyl)carbonyl]piperidin-4-yl}phenyl)-1-(pyridazin-3-yl)pyrrolidine-3-carboxamide;
(3S)—N-(4-{1-[2-fluoro-5-(trifluoromethyl)benzoyl]piperidin-4-yl}phenyl)-1-(pyridazin-3-yl)pyrrolidine-3-carboxamide;
(3S)—N-{4-[1-(cyclohexylacetyl)piperidin-4-yl]phenyl}-1-(pyridazin-3-yl)pyrrolidine-3-carboxamide;
(3S)—N-{4-[1-(4-methoxybenzoyl)piperidin-4-yl]phenyl}-1-(pyridazin-3-yl)pyrrolidine-3-carboxamide;
(3S)—N-{4-[1-(2-methylbutanoyl)piperidin-4-yl]phenyl}-1-(pyridazin-3-yl)pyrrolidine-3-carboxamide;
(3S)—N-{4-[1-(2-ethylbutanoyl)piperidin-4-yl]phenyl}-1-(pyridazin-3-yl)pyrrolidine-3-carboxamide;
(3S)—N-{4-[1-(4-tert-butylbenzoyl)piperidin-4-yl]phenyl}-1-(pyridazin-3-yl)pyrrolidine-3-carboxamide;
(3S)—N-{4-[1-(3-chlorobenzoyl)piperidin-4-yl]phenyl}-1-(pyridazin-3-yl)pyrrolidine-3-carboxamide;
(3S)—N-(4-{1-[(2-fluorophenyl)acetyl]piperidin-4-yl}phenyl)-1-(pyridazin-3-yl)pyrrolidine-3-carboxamide;
(3S)-1-(pyridazin-3-yl)-N-(4-{1-[3-(trifluoromethyl)benzoyl]piperidin-4-yl}phenyl)pyrrolidine-3-carboxamide;
(3S)—N-(4-{1-[(1-methylcyclopropyl)carbonyl]piperidin-4-yl}phenyl)-1-(pyridazin-3-yl)pyrrolidine-3-carboxamide;
(3S)—N-{4-[1-(pent-4-ynoyl)piperidin-4-yl]phenyl}-1-(pyridazin-3-yl)pyrrolidine-3-carboxamide;
(3S)—N-(4-{1-[(3-fluorophenyl)acetyl]piperidin-4-yl}phenyl)-1-(pyridazin-3-yl)pyrrolidine-3-carboxamide;
(3S)—N-(4-{1-[3-(methylsulfanyl)propanoyl]piperidin-4-yl}phenyl)-1-(pyridazin-3-yl)pyrrolidine-3-carboxamide;
(3S)—N-(4-{1-[(1-acetylpiperidin-4-yl)carbonyl]piperidin-4-yl}phenyl)-1-(pyridazin-3-yl)pyrrolidine-3-carboxamide;
(3S)—N-{4-[1-(but-3-enoyl)piperidin-4-yl]phenyl}-1-(pyridazin-3-yl)pyrrolidine-3-carboxamide;
(3S)—N-{4-[1-(2,2-dimethylbutanoyl)piperidin-4-yl]phenyl}-1-(pyridazin-3-yl)pyrrolidine-3-carboxamide;
(3S)—N-{4-[1-(3-fluoro-4-methylbenzoyl)piperidin-4-yl]phenyl}-1-(pyridazin-3-yl)pyrrolidine-3-carboxamide;
(3S)—N-{4-[1-(3-methoxybenzoyl)piperidin-4-yl]phenyl}-1-(pyridazin-3-yl)pyrrolidine-3-carboxamide;
(3S)—N-(4-{1-[(2-chlorophenyl)acetyl]piperidin-4-yl}phenyl)-1-(pyridazin-3-yl)pyrrolidine-3-carboxamide;
(3S)—N-(4-{1-[(2-methoxyethoxy)acetyl]piperidin-4-yl}phenyl)-1-(pyridazin-3-yl)pyrrolidine-3-carboxamide;
(3S)—N-{4-[1-(3,3-dimethylbutanoyl)piperidin-4-yl]phenyl}-1-(pyridazin-3-yl)pyrrolidine-3-carboxamide;
(3S)—N-{4-[1-(N-acetyl-L-leucyl)piperidin-4-yl]phenyl}-1-(pyridazin-3-yl)pyrrolidine-3-carboxamide;
(3S)—N-{4-[1-(3-fluorobenzoyl)piperidin-4-yl]phenyl}-1-(pyridazin-3-yl)pyrrolidine-3-carboxamide;
(3S)—N-{4-[1-(4-cyanobenzoyl)piperidin-4-yl]phenyl}-1-(pyridazin-3-yl)pyrrolidine-3-carboxamide;
(3S)—N-{4-[1-(2-methoxybenzoyl)piperidin-4-yl]phenyl}-1-(pyridazin-3-yl)pyrrolidine-3-carboxamide;
(3S)—N-{4-[1-(2,3-dimethylbenzoyl)piperidin-4-yl]phenyl}-1-(pyridazin-3-yl)pyrrolidine-3-carboxamide;
(3S)—N-(4-{1-[4-(propan-2-yl)benzoyl]piperidin-4-yl}phenyl)-1-(pyridazin-3-yl)pyrrolidine-3-carboxamide;
(3S)—N-{4-[1-(cyclohexylcarbonyl)piperidin-4-yl]phenyl}-1-(pyridazin-3-yl)pyrrolidine-3-carboxamide;
(3S)-1-(pyridazin-3-yl)-N-{4-[1-(thiophen-2-ylcarbonyl)piperidin-4-yl]phenyl}pyrrolidine-3-carboxamide;
(3S)—N-{4-[1-(4-hydroxybenzoyl)piperidin-4-yl]phenyl}-1-(pyridazin-3-yl)pyrrolidine-3-carboxamide;
(3S)—N-{4-[1-(3-cyanobenzoyl)piperidin-4-yl]phenyl}-1-(pyridazin-3-yl)pyrrolidine-3-carboxamide;
(3S)-1-(pyridazin-3-yl)-N-{4-[1-(3,3,3-trifluoropropanoyl)piperidin-4-yl]phenyl}pyrrolidine-3-carboxamide;
(3S)—N-{4-[1-(methoxyacetyl)piperidin-4-yl]phenyl}-1-(pyridazin-3-yl)pyrrolidine-3-carboxamide;
(3S)—N-{4-[1-(3-methylbutanoyl)piperidin-4-yl]phenyl}-1-(pyridazin-3-yl)pyrrolidine-3-carboxamide;
N-[4-(1-benzoylpiperidin-4-yl)phenyl]-1-(2-cyanopyridin-3-yl)azetidine-3-carboxamide;
N-[4-(1-benzoylpiperidin-4-yl)phenyl]-1-(4-cyanopyridin-3-yl)azetidine-3-carboxamide;
N-[4-(1-benzoylpiperidin-4-yl)phenyl]-1-(6-fluoro-4-methylpyridin-3-yl)azetidine-3-carboxamide;
N-[4-(1-benzoylpiperidin-4-yl)phenyl]-1-(5-cyanopyridin-3-yl)azetidine-3-carboxamide;
N-[4-(1-benzoylpiperidin-4-yl)phenyl]-1-(5-methylpyridin-3-yl)azetidine-3-carboxamide;
2-[1-(2-methylpropyl)-1H-pyrazol-4-yl]-N-[(3S)-1-(pyridazin-3-yl)pyrrolidin-3-yl]-1,3-thiazole-5-carboxamide;
(3S)—N-[4-(1-benzoylpiperidin-4-yl)phenyl]-1-(2-methylpyridin-3-yl)pyrrolidine-3-carboxamide;
(3S)—N-{4-[1-(2-fluorobenzoyl)piperidin-4-yl]phenyl}-1-(2-methylpyridin-3-yl)pyrrolidine-3-carboxamide;
(3S)-1-(2-methylpyridin-3-yl)-N-{4-[1-(4,4,4-trifluorobutanoyl)piperidin-4-yl]phenyl}pyrrolidine-3-carboxamide;
N-[(3S)-1-(6-chloropyridazin-3-yl)pyrrolidin-3-yl]-5-[1-(2-methylpropyl)-1H-pyrazol-4-yl]furan-2-carboxamide;
5-[1-(2-methylpropyl)-1H-pyrazol-4-yl]-N-[(3S)-1-(pyridazin-3-yl)pyrrolidin-3-yl]furan-2-carboxamide;
N-(4-{1-[(4-methyltetrahydro-2H-pyran-4-yl)methyl]-1H-pyrazol-4-yl}phenyl)-1-(pyridazin-3-yl)azetidine-3-carboxamide;
N-[(3S)-1-(6-chloropyridazin-3-yl)pyrrolidin-3-yl]-4-[1-(2-methylpropanoyl)piperidin-4-yl]benzamide;
N-(4-{1-[2-(piperazin-1-yl)ethyl]-1H-pyrazol-4-yl}phenyl)-1-(pyridazin-3-yl)azetidine-3-carboxamide;
N-{4-[1-(2,2-dimethylpropyl)-1H-pyrazol-4-yl]phenyl}-1-(pyridazin-3-yl)azetidine-3-carboxamide;
4-[1-(2-methylpropanoyl)piperidin-4-yl]-N-[(3S)-1-(pyridazin-3-yl)pyrrolidin-3-yl]benzamide;
N-{4-[1-(2-hydroxy-2-methylpropyl)-1H-pyrazol-4-yl]phenyl}-1-(pyridazin-3-yl)azetidine-3-carboxamide;

5-[1-(3-fluorobenzoyl)piperidin-4-yl]-N-[(3S)-1-(pyridazin-3-yl)pyrrolidin-3-yl]thiophene-2-carboxamide;

5-[1-(4-fluorobenzoyl)piperidin-4-yl]-N-[(3S)-1-(pyridazin-3-yl)pyrrolidin-3-yl]thiophene-2-carboxamide;

(3S)—N-(4-{1-[(4-methyltetrahydro-2H-pyran-4-yl)methyl]-1H-pyrazol-4-yl}phenyl)-1-(pyridazin-3-yl)pyrrolidine-3-carboxamide;

(3S)—N-{4-[1-(2-hydroxy-2-methylpropyl)-1H-pyrazol-4-yl]phenyl}-1-(pyridazin-3-yl)pyrrolidine-3-carboxamide;

N-[(3S)-1-(pyridazin-3-yl)pyrrolidin-3-yl]-5-[1-(tetrahydro-2H-pyran-4-ylcarbonyl)piperidin-4-yl]thiophene-2-carboxamide;

(3S)—N-{4-[1-(2,2-dimethylpropyl)-1H-pyrazol-4-yl]phenyl}-1-(pyridazin-3-yl)pyrrolidine-3-carboxamide;

5-[1-(2-methylpropanoyl)piperidin-4-yl]-N-[(3S)-1-(pyridazin-3-yl)pyrrolidin-3-yl]thiophene-2-carboxamide;

5-[1-(2,4-difluorobenzoyl)piperidin-4-yl]-N-[(3S)-1-(pyridazin-3-yl)pyrrolidin-3-yl]thiophene-2-carboxamide;

5-{1-[(2-methylcyclopropyl)carbonyl]piperidin-4-yl}-N-[(3S)-1-(pyridazin-3-yl)pyrrolidin-3-yl]thiophene-2-carboxamide;

5-[1-(2-fluorobenzoyl)piperidin-4-yl]-N-[(3S)-1-(pyridazin-3-yl)pyrrolidin-3-yl]thiophene-2-carboxamide;

5-(1-benzoylpiperidin-4-yl)-N-[(3S)-1-(pyridazin-3-yl)pyrrolidin-3-yl]thiophene-2-carboxamide;

N-[(3S)-1-(pyridazin-3-yl)pyrrolidin-3-yl]-5-[1-(tetrahydrofuran-3-ylcarbonyl)piperidin-4-yl]thiophene-2-carboxamide;

N-[(3S)-1-(pyridazin-3-yl)pyrrolidin-3-yl]-5-{1-[(2R)-tetrahydrofuran-2-ylcarbonyl]piperidin-4-yl}thiophene-2-carboxamide;

5-{1-[(1-methylpiperidin-4-yl)acetyl]piperidin-4-yl}-N-[(3S)-1-(pyridazin-3-yl)pyrrolidin-3-yl]thiophene-2-carboxamide;

N-[(3S)-1-(pyridazin-3-yl)pyrrolidin-3-yl]-5-[1-(1,3-thiazol-4-ylcarbonyl)piperidin-4-yl]thiophene-2-carboxamide;

(3S)—N-{4-[1-(2-methylpropyl)-1H-pyrazol-4-yl]phenyl}-1-(pyridazin-3-yl)pyrrolidine-3-carboxamide;

(3S)—N-{4-[1-(propan-2-yl)-1H-pyrazol-4-yl]phenyl}-1-(pyridazin-3-yl)pyrrolidine-3-carboxamide;

(3S)—N-{4-[1-(cyclopropylmethyl)-1H-pyrazol-4-yl]phenyl}-1-(pyridazin-3-yl)pyrrolidine-3-carboxamide;

(3S)-1-(pyridazin-3-yl)-N-{4-[1-(tetrahydro-2H-pyran-2-ylmethyl)-1H-pyrazol-4-yl]phenyl}pyrrolidine-3-carboxamide;

(3S)—N-[4-(1-tert-butyl-1H-pyrazol-4-yl)phenyl]-1-(pyridazin-3-yl)pyrrolidine-3-carboxamide;

(3S)—N-(4-{[(3R)-1-benzoylpyrrolidin-3-yl]oxy}phenyl)-1-(pyridazin-3-yl)pyrrolidine-3-carboxamide;

(3S)—N-(4-{[(3R)-1-(2-fluorobenzoyl)pyrrolidin-3-yl]oxy}phenyl)-1-(pyridazin-3-yl)pyrrolidine-3-carboxamide;

(3S)—N-(4-{[(3R)-1-(3-fluorobenzoyl)pyrrolidin-3-yl]oxy}phenyl)-1-(pyridazin-3-yl)pyrrolidine-3-carboxamide;

(3S)—N-(4-{[(3R)-1-(4-fluorobenzoyl)pyrrolidin-3-yl]oxy}phenyl)-1-(pyridazin-3-yl)pyrrolidine-3-carboxamide;

(3S)—N-(4-{[(3R)-1-(3,5-difluorobenzoyl)pyrrolidin-3-yl]oxy}phenyl)-1-(pyridazin-3-yl)pyrrolidine-3-carboxamide;

(3S)—N-(4-{[(3R)-1-(2-methylbenzoyl)pyrrolidin-3-yl]oxy}phenyl)-1-(pyridazin-3-yl)pyrrolidine-3-carboxamide;

(3S)—N-(4-{[(3R)-1-(2,2-dimethylpropanoyl)pyrrolidin-3-yl]oxy}phenyl)-1-(pyridazin-3-yl)pyrrolidine-3-carboxamide;

(3S)—N-[4-({(3R)-1-[(4,4-difluorocyclohexyl)carbonyl]pyrrolidin-3-yl}oxy)phenyl]-1-(pyridazin-3-yl)pyrrolidine-3-carboxamide;

(3S)-1-(pyridazin-3-yl)-N-(4-{[(3R)-1-(4,4,4-trifluorobutanoyl)pyrrolidin-3-yl]oxy}phenyl)pyrrolidine-3-carboxamide;

(3S)—N-(4-{[(3R)-1-(2,4-difluorobenzoyl)pyrrolidin-3-yl]oxy}phenyl)-1-(pyridazin-3-yl)pyrrolidine-3-carboxamide;

N-[4-(5-propyl-1,2,4-oxadiazol-3-yl)phenyl]-1-(pyridazin-3-yl)azetidine-3-carboxamide;

(3S)—N-{4-[1-(2-fluorobenzoyl)azetidin-3-yl]phenyl}-1-(pyridazin-3-yl)pyrrolidine-3-carboxamide;

(3S)—N-{4-[1-(3-fluorobenzoyl)azetidin-3-yl]phenyl}-1-(pyridazin-3-yl)pyrrolidine-3-carboxamide;

(3S)—N-{4-[1-(4-fluorobenzoyl)azetidin-3-yl]phenyl}-1-(pyridazin-3-yl)pyrrolidine-3-carboxamide;

(3S)—N-[4-(1-benzoylazetidin-3-yl)phenyl]-1-(pyridazin-3-yl)pyrrolidine-3-carboxamide;

(3S)—N-{4-[1-(2,2-dimethylpropanoyl)azetidin-3-yl]phenyl}-1-(pyridazin-3-yl)pyrrolidine-3-carboxamide;

(3S)—N-{4-[1-(3,5-difluorobenzoyl)azetidin-3-yl]phenyl}-1-(pyridazin-3-yl)pyrrolidine-3-carboxamide;

(3S)—N-{4-[1-(2-methylbenzoyl)azetidin-3-yl]phenyl}-1-(pyridazin-3-yl)pyrrolidine-3-carboxamide;

(3S)—N-{4-[1-(2,4-difluorobenzoyl)azetidin-3-yl]phenyl}-1-(pyridazin-3-yl)pyrrolidine-3-carboxamide;

(3R)—N-[4-(1-benzoylpiperidin-4-yl)phenyl]-1-(pyridazin-3-yl)pyrrolidine-3-carboxamide;

(3R)—N-{4-[1-(2-fluorobenzoyl)piperidin-4-yl]phenyl}-1-(pyridazin-3-yl)pyrrolidine-3-carboxamide;

(3R)—N-{4-[1-(2,2-dimethylpropanoyl)piperidin-4-yl]phenyl}-1-(pyridazin-3-yl)pyrrolidine-3-carboxamide;

(3S)—N-(4-{[1-(cyclohexylcarbonyl)piperidin-4-yl]oxy}phenyl)-1-(pyridazin-3-yl)pyrrolidine-3-carboxamide;

(3S)—N-(4-{[1-(2-fluorobenzoyl)piperidin-4-yl]oxy}phenyl)-1-(pyridazin-3-yl)pyrrolidine-3-carboxamide;

(3S)—N-(4-{[1-(3-fluorobenzoyl)piperidin-4-yl]oxy}phenyl)-1-(pyridazin-3-yl)pyrrolidine-3-carboxamide;

(3S)—N-{4-[(1-benzoylpiperidin-4-yl)oxy]phenyl}-1-(pyridazin-3-yl)pyrrolidine-3-carboxamide;

(3S)—N-(4-{[1-(4-fluorobenzoyl)piperidin-4-yl]oxy}phenyl)-1-(pyridazin-3-yl)pyrrolidine-3-carboxamide;

(3S)—N-(4-{[1-(2,2-dimethylpropanoyl)piperidin-4-yl]oxy}phenyl)-1-(pyridazin-3-yl)pyrrolidine-3-carboxamide;

(3S)—N-[4-({1-[(2-methylcyclopropyl)carbonyl]piperidin-4-yl}oxy)phenyl]-1-(pyridazin-3-yl)pyrrolidine-3-carboxamide;

N-{4-[5-(2,2-dimethylpropyl)-1,3,4-oxadiazol-2-yl]phenyl}-1-(pyridazin-3-yl)azetidine-3-carboxamide;

N-{4-[1-(2,2-dimethylpropyl)-1H-imidazol-4-yl]phenyl}-1-(pyridazin-3-yl)azetidine-3-carboxamide;

N-[4-(3-cyclopropyl-1-methyl-1H-pyrazol-5-yl)phenyl]-1-(pyridazin-3-yl)azetidine-3-carboxamide;

N-{4-[5-(2,2-dimethylpropyl)-1,2,4-oxadiazol-3-yl]phenyl}-1-(pyridazin-3-yl)azetidine-3-carboxamide;

N-{4-[3-cyclopropyl-1-(2-methoxyethyl)-1H-pyrazol-5-yl]phenyl}-1-(pyridazin-3-yl)azetidine-3-carboxamide;

tert-butyl 4-(5-{[1-(pyridazin-3-yl)azetidin-3-yl]carbamoyl}thiophen-2-yl)piperidine-1-carboxylate;
tert-butyl 4-fluoro-4-[4-({[1-(pyridazin-3-yl)azetidin-3-yl]carbonyl}amino)phenyl]piperidine-1-carboxylate;
5-(1-benzoylpiperidin-4-yl)-N-[1-(pyridazin-3-yl)azetidin-3-yl]thiophene-2-carboxamide;
5-[1-(2-fluorobenzoyl)piperidin-4-yl]-N-[1-(pyridazin-3-yl)azetidin-3-yl]thiophene-2-carboxamide;
5-[1-(2-methylbenzoyl)piperidin-4-yl]-N-[1-(pyridazin-3-yl)azetidin-3-yl]thiophene-2-carboxamide;
5-[1-(2,4-difluorobenzoyl)piperidin-4-yl]-N-[1-(pyridazin-3-yl)azetidin-3-yl]thiophene-2-carboxamide;
5-[1-(3-fluorobenzoyl)piperidin-4-yl]-N-[1-(pyridazin-3-yl)azetidin-3-yl]thiophene-2-carboxamide;
5-[1-(4-fluorobenzoyl)piperidin-4-yl]-N-[1-(pyridazin-3-yl)azetidin-3-yl]thiophene-2-carboxamide;
5-[1-(3,5-difluorobenzoyl)piperidin-4-yl]-N-[1-(pyridazin-3-yl)azetidin-3-yl]thiophene-2-carboxamide;
N-{4-[3-cyclopropyl-1-(2-hydroxyethyl)-1H-pyrazol-5-yl]phenyl}-1-(pyridazin-3-yl)azetidine-3-carboxamide;
N-[4-(1-benzoylpiperidin-4-yl)phenyl]-1-(6-fluoropyridazin-3-yl)azetidine-3-carboxamide;
N-{4-[1-(2-fluorobenzoyl)piperidin-4-yl]phenyl}-1-(6-fluoropyridazin-3-yl)azetidine-3-carboxamide;
N-{4-[1-(2,2-dimethylpropanoyl)piperidin-4-yl]phenyl}-1-(6-fluoropyridazin-3-yl)azetidine-3-carboxamide;
1-(6-fluoropyridazin-3-yl)-N-{4-[1-(2-methylpropanoyl)piperidin-4-yl]phenyl}azetidine-3-carboxamide;
N-{4-[1-(2-ethylbutanoyl)piperidin-4-yl]phenyl}-1-(6-fluoropyridazin-3-yl)azetidine-3-carboxamide;
N-{4-[1-(4-fluorobenzoyl)piperidin-4-yl]phenyl}-1-(6-fluoropyridazin-3-yl)azetidine-3-carboxamide;
(3S)—N-(4-{[(3S)-1-benzoylpyrrolidin-3-yl]oxy}phenyl)-1-(pyridazin-3-yl)pyrrolidine-3-carboxamide;
(3S)—N-(4-{[(3S)-1-(2-fluorobenzoyl)pyrrolidin-3-yl]oxy}phenyl)-1-(pyridazin-3-yl)pyrrolidine-3-carboxamide;
(3S)—N-(4-{[(3S)-1-(3,5-difluorobenzoyl)pyrrolidin-3-yl]oxy}phenyl)-1-(pyridazin-3-yl)pyrrolidine-3-carboxamide;
(3S)—N-(4-{[(3S)-1-(2,2-dimethylpropanoyl)pyrrolidin-3-yl]oxy}phenyl)-1-(pyridazin-3-yl)pyrrolidine-3-carboxamide;
N-{2-fluoro-4-[1-(2-fluorobenzoyl)piperidin-4-yl]phenyl}-1-(pyridazin-3-yl)azetidine-3-carboxamide;
N-[4-(1-benzoylpiperidin-4-yl)-2-fluorophenyl]-1-(pyridazin-3-yl)azetidine-3-carboxamide;
N-{2-fluoro-4-[1-(3-fluorobenzoyl)piperidin-4-yl]phenyl}-1-(pyridazin-3-yl)azetidine-3-carboxamide;
N-{2-fluoro-4-[1-(2-methylbenzoyl)piperidin-4-yl]phenyl}-1-(pyridazin-3-yl)azetidine-3-carboxamide;
N-{2-fluoro-4-[1-(4-fluorobenzoyl)piperidin-4-yl]phenyl}-1-(pyridazin-3-yl)azetidine-3-carboxamide;
N-{4-[1-(2,4-difluorobenzoyl)piperidin-4-yl]-2-fluorophenyl}-1-(pyridazin-3-yl)azetidine-3-carboxamide;
N-{4-[1-(3,5-difluorobenzoyl)piperidin-4-yl]-2-fluorophenyl}-1-(pyridazin-3-yl)azetidine-3-carboxamide;
N-{4-[1-(3,3-dimethylbutanoyl)piperidin-4-yl]-2-fluorophenyl}-1-(pyridazin-3-yl)azetidine-3-carboxamide;
(3S)—N-(4-{[1-(2-fluorobenzoyl)piperidin-4-yl]oxy}phenyl)-1-(6-methylpyridazin-3-yl)pyrrolidine-3-carboxamide;
(3S)—N-{4-[(1-benzoylpiperidin-4-yl)oxy]phenyl}-1-(6-methylpyridazin-3-yl)pyrrolidine-3-carboxamide;
(3S)—N-(4-{[1-(2,2-dimethylpropanoyl)piperidin-4-yl]oxy}phenyl)-1-(6-methylpyridazin-3-yl)pyrrolidine-3-carboxamide;
(3S)—N-(4-{[1-(cyclohexylcarbonyl)piperidin-4-yl]oxy}phenyl)-1-(6-methylpyridazin-3-yl)pyrrolidine-3-carboxamide;
N-{4-[8-(2-methylpropanoyl)-8-azabicyclo[3.2.1]oct-3-yl]phenyl}-1-(pyridazin-3-yl)azetidine-3-carboxamide;
1-(pyridazin-3-yl)-N-{4-[8-(4,4,4-trifluorobutanoyl)-8-azabicyclo[3.2.1]oct-3-yl]phenyl}azetidine-3-carboxamide;
N-[4-(8-benzoyl-8-azabicyclo[3.2.1]oct-3-yl)phenyl]-1-(pyridazin-3-yl)azetidine-3-carboxamide;
N-{4-[8-(2-fluorobenzoyl)-8-azabicyclo[3.2.1]oct-3-yl]phenyl}-1-(pyridazin-3-yl)azetidine-3-carboxamide;
N-{4-[8-(2,2-dimethylpropanoyl)-8-azabicyclo[3.2.1]oct-3-yl]phenyl}-1-(pyridazin-3-yl)azetidine-3-carboxamide;
N-(4-{8-[(1-methylcyclopropyl)carbonyl]-8-azabicyclo[3.2.1]oct-3-yl}phenyl)-1-(pyridazin-3-yl)azetidine-3-carboxamide;
N-{4-[1-(2-methoxyethyl)-3-(2-methylpropyl)-1H-pyrazol-5-yl]phenyl}-1-(pyridazin-3-yl)azetidine-3-carboxamide;
5-[1-(2,2-dimethylpropanoyl)piperidin-4-yl]-N-[1-(pyridazin-3-yl)azetidin-3-yl]thiophene-2-carboxamide;
5-{1-[(1-methylcyclopropyl)carbonyl]piperidin-4-yl}-N-[1-(pyridazin-3-yl)azetidin-3-yl]thiophene-2-carboxamide;
N-[1-(pyridazin-3-yl)azetidin-3-yl]-5-[1-(3,3,3-trifluoropropanoyl)piperidin-4-yl]thiophene-2-carboxamide;
5-[1-(2,2-dimethylbutanoyl)piperidin-4-yl]-N-[1-(pyridazin-3-yl)azetidin-3-yl]thiophene-2-carboxamide;
N-{4-[1-(2-fluorobenzoyl)piperidin-4-yl]phenyl}-1-(6-methylpyridazin-3-yl)azetidine-3-carboxamide;
N-{4-[1-(2,2-dimethylpropanoyl)piperidin-4-yl]phenyl}-1-(6-methylpyridazin-3-yl)azetidine-3-carboxamide;
benzyl 4-[4-({[1-(6-chloropyridazin-3-yl)azetidin-3-yl]carbonyl}amino)phenyl]-4-fluoropiperidine-1-carboxylate;
benzyl 4-[4-({[1-(6-chloropyridazin-3-yl)azetidin-3-yl]carbonyl}amino)phenyl]-4-hydroxypiperidine-1-carboxylate;
N-[1-(pyridazin-3-yl)azetidin-3-yl]-5-[1-(4,4,4-trifluorobutanoyl)piperidin-4-yl]thiophene-2-carboxamide;
5-[1-(cyclopropylcarbonyl)piperidin-4-yl]-N-[1-(pyridazin-3-yl)azetidin-3-yl]thiophene-2-carboxamide;
N-{4-[4-fluoro-1-(2-fluorobenzoyl)piperidin-4-yl]phenyl}-1-(pyridazin-3-yl)azetidine-3-carboxamide;
N-{2-fluoro-4-[1-(2-methylpropanoyl)piperidin-4-yl]phenyl}-1-(pyridazin-3-yl)azetidine-3-carboxamide;
N-{4-[1-(2,2-dimethylpropanoyl)piperidin-4-yl]-2-fluorophenyl}-1-(pyridazin-3-yl)azetidine-3-carboxamide;
N-{4-[1-(cyclopropylcarbonyl)piperidin-4-yl]-2-fluorophenyl}-1-(pyridazin-3-yl)azetidine-3-carboxamide;
N-(2-fluoro-4-{1-[(1-methylcyclopropyl)carbonyl]piperidin-4-yl}phenyl)-1-(pyridazin-3-yl)azetidine-3-carboxamide;
N-{4-[1-(cyclopropylacetyl)piperidin-4-yl]-2-fluorophenyl}-1-(pyridazin-3-yl)azetidine-3-carboxamide;
N-[4-(1-benzoyl-4-fluoropiperidin-4-yl)phenyl]-1-(pyridazin-3-yl)azetidine-3-carboxamide;
N-{4-[1-(2,2-dimethylpropanoyl)-4-fluoropiperidin-4-yl]phenyl}-1-(pyridazin-3-yl)azetidine-3-carboxamide;
N-{4-[3-tert-butyl-1-(2-methoxyethyl)-1H-pyrazol-5-yl]phenyl}-1-(pyridazin-3-yl)azetidine-3-carboxamide;
N-[4-(1-butyl-3-tert-butyl-1H-pyrazol-5-yl)phenyl]-1-(pyridazin-3-yl)azetidine-3-carboxamide;
N-{4-[3-tert-butyl-1-(tetrahydro-2H-pyran-4-ylmethyl)-1H-pyrazol-5-yl]phenyl}-1-(pyridazin-3-yl)azetidine-3-carboxamide;
N-{2-fluoro-4-[1-(2-fluorobenzoyl)piperidin-4-yl]phenyl}-1-(pyridazin-4-yl)azetidine-3-carboxamide;

N-[4-(1-benzoylpiperidin-4-yl)-2-fluorophenyl]-1-(pyridazin-4-yl)azetidine-3-carboxamide;
N-{4-[1-(2,2-dimethylpropanoyl)piperidin-4-yl]-2-fluorophenyl}-1-(pyridazin-4-yl)azetidine-3-carboxamide;
N-{4-[1-(3,3-dimethylbutanoyl)piperidin-4-yl]-2-fluorophenyl}-1-(pyridazin-4-yl)azetidine-3-carboxamide;
N-{2-fluoro-4-[1-(4,4,4-trifluorobutanoyl)piperidin-4-yl]phenyl}-1-(pyridazin-4-yl)azetidine-3-carboxamide;
N-(4-{1-[(4-methylpiperidin-4-yl)methyl]-1H-pyrazol-4-yl}phenyl)-1-(pyridazin-3-yl)azetidine-3-carboxamide;
N-{4-[1-methyl-3-(trifluoromethyl)-1H-pyrazol-5-yl]phenyl}-1-(pyridazin-3-yl)azetidine-3-carboxamide;
1-(6-chloropyridazin-3-yl)-N-{4-[1-(2,2-dimethylpropyl)-1H-pyrazol-4-yl]phenyl}azetidine-3-carboxamide;
N-[4-(1-benzoylpiperidin-4-yl)phenyl]-1-(6-methylpyridin-3-yl)azetidine-3-carboxamide;
N-(4-{1-[(4-methylpiperidin-4-yl)methyl]-1H-pyrazol-4-yl}phenyl)-1-(pyridin-3-yl)azetidine-3-carboxamide;
N-{4-[1-(2,2-dimethylpropyl)-1H-pyrazol-4-yl]phenyl}-1-(6-methylpyridazin-3-yl)azetidine-3-carboxamide;
N-{3-fluoro-4-[1-(3-fluorobenzoyl)piperidin-4-yl]phenyl}-1-(pyridazin-3-yl)azetidine-3-carboxamide;
N-{3-fluoro-4-[1-(2-methylpropanoyl)piperidin-4-yl]phenyl}-1-(pyridazin-3-yl)azetidine-3-carboxamide;
N-{3-fluoro-4-[1-(3,3,3-trifluoropropanoyl)piperidin-4-yl]phenyl}-1-(pyridazin-3-yl)azetidine-3-carboxamide;
N-{4-[1-(3,3-dimethylbutanoyl)piperidin-4-yl]-3-fluorophenyl}-1-(pyridazin-3-yl)azetidine-3-carboxamide;
N-{3-fluoro-4-[1-(4,4,4-trifluorobutanoyl)piperidin-4-yl]phenyl}-1-(pyridazin-3-yl)azetidine-3-carboxamide;
N-[4-(1-benzoylpiperidin-4-yl)-3-fluorophenyl]-1-(pyridazin-3-yl)azetidine-3-carboxamide;
N-{3-fluoro-4-[1-(2-fluorobenzoyl)piperidin-4-yl]phenyl}-1-(pyridazin-3-yl)azetidine-3-carboxamide;
N-{4-[1-(2,2-dimethylpropanoyl)piperidin-4-yl]-3-fluorophenyl}-1-(pyridazin-3-yl)azetidine-3-carboxamide;
N-{3-fluoro-4-[1-(3-methylbutanoyl)piperidin-4-yl]phenyl}-1-(pyridazin-3-yl)azetidine-3-carboxamide;
N-{4-[1-(cyclopropylacetyl)piperidin-4-yl]-3-fluorophenyl}-1-(pyridazin-3-yl)azetidine-3-carboxamide;
N-{4-[1-(2-fluorobenzoyl)-4-hydroxypiperidin-4-yl]phenyl}-1-(pyridazin-3-yl)azetidine-3-carboxamide;
N-{4-[1-(2,2-dimethylpropanoyl)-4-hydroxypiperidin-4-yl]phenyl}-1-(pyridazin-3-yl)azetidine-3-carboxamide;
1-(6-methylpyridazin-3-yl)-N-(4-{1-[(4-methyltetrahydro-2H-pyran-4-yl)methyl]-1H-pyrazol-4-yl}phenyl)azetidine-3-carboxamide;
(3S)—N-{4-[1-(2-fluorobenzoyl)piperidin-4-yl]phenyl}-1-(6-methylpyridazin-3-yl)pyrrolidine-3-carboxamide;
(3S)—N-[4-(1-benzoylpiperidin-4-yl)phenyl]-1-(6-methylpyridazin-3-yl)pyrrolidine-3-carboxamide;
(3S)—N-{4-[1-(2,2-dimethylpropanoyl)piperidin-4-yl]phenyl}-1-(6-methylpyridazin-3-yl)pyrrolidine-3-carboxamide;
N-{4-[(1-benzoylpiperidin-4-yl)methyl]phenyl}-1-(pyridazin-3-yl)azetidine-3-carboxamide;
N-(4-{[1-(2-fluorobenzoyl)piperidin-4-yl]methyl}phenyl)-1-(pyridazin-3-yl)azetidine-3-carboxamide;
N-(4-{[1-(2,2-dimethylpropanoyl)piperidin-4-yl]methyl}phenyl)-1-(pyridazin-3-yl)azetidine-3-carboxamide;
N-(4-{[1-(3,3-dimethylbutanoyl)piperidin-4-yl]methyl}phenyl)-1-(pyridazin-3-yl)azetidine-3-carboxamide;
N-(4-{[1-(2-ethylbutanoyl)piperidin-4-yl]methyl}phenyl)-1-(pyridazin-3-yl)azetidine-3-carboxamide;
1-(pyridazin-3-yl)-N-(4-{[1-(4,4,4-trifluorobutanoyl)piperidin-4-yl]methyl}phenyl)azetidine-3-carboxamide;
N-(4-{[1-(2-methylpropanoyl)piperidin-4-yl]methyl}phenyl)-1-(pyridazin-3-yl)azetidine-3-carboxamide;
N-{4-[(1-acetylpiperidin-4-yl)methyl]phenyl}-1-(pyridazin-3-yl)azetidine-3-carboxamide;
N-[4-({1-[(2S)-2-methylbutanoyl]piperidin-4-yl}methyl)phenyl]-1-(pyridazin-3-yl)azetidine-3-carboxamide;
N-[4-({1-[(1-methylcyclopropyl)carbonyl]piperidin-4-yl}methyl)phenyl]-1-(pyridazin-3-yl)azetidine-3-carboxamide;
N-[4-(1-{[4-methyl-1-(oxetan-3-yl)piperidin-4-yl]methyl}-1H-pyrazol-4-yl)phenyl]-1-(6-methylpyridazin-3-yl)azetidine-3-carboxamide;
N-[4-(1-benzoylpiperidin-4-yl)phenyl]-1-(4-methylpyridazin-3-yl)azetidine-3-carboxamide;
5-[1-(2-fluorobenzoyl)piperidin-4-yl]-N-[(3S)-1-(pyridazin-3-yl)pyrrolidin-3-yl]furan-2-carboxamide;
N-[4-(1-benzoylpiperidin-4-yl)phenyl]-1-(3-methylpyridazin-4-yl)azetidine-3-carboxamide;
N-{4-[1-(2-fluorobenzoyl)piperidin-4-yl]phenyl}-1-(3-methylpyridazin-4-yl)azetidine-3-carboxamide;
N-(4-{1-[(2-aminopyridin-3-yl)carbonyl]piperidin-4-yl}phenyl)-1-(pyridazin-3-yl)azetidine-3-carboxamide;
1-methyl-5-[4-({[1-(pyridazin-3-yl)azetidin-3-yl]carbonyl}amino)phenyl]-1H-pyrazole-3-carboxylic acid;
ethyl 1-methyl-5-[4-({[1-(pyridazin-3-yl)azetidin-3-yl]carbonyl}amino)phenyl]-1H-pyrazole-3-carboxylate;
ethyl 1-phenyl-5-[4-({[1-(pyridazin-3-yl)azetidin-3-yl]carbonyl}amino)phenyl]-1H-pyrazole-3-carboxylate;
N-{6-[1-(2-fluorobenzoyl)piperidin-4-yl]pyridin-3-yl}-1-(pyridazin-3-yl)azetidine-3-carboxamide;
N-(4-{[(3R)-1-(3-methylbutanoyl)pyrrolidin-3-yl]oxy}phenyl)-1-(6-methylpyridazin-3-yl)azetidine-3-carboxamide;
N-(4-{[(3R)-1-(2-methylpropanoyl)pyrrolidin-3-yl]oxy}phenyl)-1-(6-methylpyridazin-3-yl)azetidine-3-carboxamide;
N-(4-{[(3R)-1-(2,4-difluorobenzoyl)pyrrolidin-3-yl]oxy}phenyl)-1-(6-methylpyridazin-3-yl)azetidine-3-carboxamide;
1-(6-methylpyridazin-3-yl)-N-(4-{[(3R)-1-(1,3-thiazol-4-ylcarbonyl)pyrrolidin-3-yl]oxy}phenyl)azetidine-3-carboxamide;
1-(pyridazin-3-yl)-N-{6-[1-(4,4,4-trifluorobutanoyl)piperidin-4-yl]pyridin-3-yl}azetidine-3-carboxamide;
N-{6-[1-(3,3-dimethylbutanoyl)piperidin-4-yl]pyridin-3-yl}-1-(pyridazin-3-yl)azetidine-3-carboxamide;
(3S)—N-[4-(1-benzoylpiperidin-4-yl)phenyl]-1-(4-methylpyridazin-3-yl)pyrrolidine-3-carboxamide;
(3S)—N-{4-[1-(2,2-dimethylpropanoyl)piperidin-4-yl]phenyl}-1-(4-methylpyridazin-3-yl)pyrrolidine-3-carboxamide;
N-{4-[1-phenyl-3-(trifluoromethyl)-1H-pyrazol-5-yl]phenyl}-1-(pyridazin-3-yl)azetidine-3-carboxamide;
N-{6-[1-(2,2-dimethylpropyl)-1H-pyrazol-4-yl]pyridin-3-yl}-1-(pyridazin-3-yl)azetidine-3-carboxamide;
tert-butyl 4-[4-({[1-(pyridazin-3-yl)azetidin-3-yl]carbonyl}amino)-1H-pyrazol-1-yl]piperidine-1-carboxylate;
N-(6-{1-[(4-methylpiperidin-4-yl)methyl]-1H-pyrazol-4-yl}pyridin-3-yl)-1-(pyridazin-3-yl)azetidine-3-carboxamide;
1-(pyridazin-3-yl)-N-(4-{[1-(1,3-thiazol-5-ylcarbonyl)piperidin-4-yl]methyl}phenyl)azetidine-3-carboxamide;

N-(4-{[1-(cyclopentylcarbonyl)piperidin-4-yl]
methyl}phenyl)-1-(pyridazin-3-yl)azetidine-3-carboxamide;
N-(4-{[1-(1H-pyrazol-4-ylcarbonyl)piperidin-4-yl]
methyl}phenyl)-1-(pyridazin-3-yl)azetidine-3-carboxamide;
N-(4-{[1-(2,2-dimethylbutanoyl)piperidin-4-yl]
methyl}phenyl)-1-(pyridazin-3-yl)azetidine-3-carboxamide;
N-[4-({1-[(2-methylcyclopropyl)carbonyl]piperidin-4-yl}methyl)phenyl]-1-(pyridazin-3-yl)azetidine-3-carboxamide;
N-[4-({1-[(methylsulfanyl)acetyl]piperidin-4-yl}methyl)phenyl]-1-(pyridazin-3-yl)azetidine-3-carboxamide;
N-[4-({1-[(1S,4R)-bicyclo[2.2.1]hept-2-ylacetyl]piperidin-4-yl}methyl)phenyl]-1-(pyridazin-3-yl)azetidine-3-carboxamide;
N-(4-{[1-(2-methylpentanoyl)piperidin-4-yl]
methyl}phenyl)-1-(pyridazin-3-yl)azetidine-3-carboxamide;
N-(4-{[1-(4-methylpentanoyl)piperidin-4-yl]
methyl}phenyl)-1-(pyridazin-3-yl)azetidine-3-carboxamide;
N-[4-({1-[3-(methylsulfanyl)propanoyl]piperidin-4-yl}methyl)phenyl]-1-(pyridazin-3-yl)azetidine-3-carboxamide;
1-(pyridazin-3-yl)-N-(4-{[1-(1,3-thiazol-4-ylcarbonyl)piperidin-4-yl]methyl}phenyl)azetidine-3-carboxamide;
N-(4-{[1-(1H-pyrazol-5-ylcarbonyl)piperidin-4-yl]
methyl}phenyl)-1-(pyridazin-3-yl)azetidine-3-carboxamide;
N-[4-({1-[(6-methylpyridin-3-yl)carbonyl]piperidin-4-yl}methyl)phenyl]-1-(pyridazin-3-yl)azetidine-3-carboxamide;
N-[4-({1-[(3-methylthiophen-2-yl)carbonyl]piperidin-4-yl}methyl)phenyl]-1-(pyridazin-3-yl)azetidine-3-carboxamide;
N-(4-{[1-(pent-4-ynoyl)piperidin-4-yl]methyl}phenyl)-1-(pyridazin-3-yl)azetidine-3-carboxamide;
1-(pyridazin-3-yl)-N-(4-{[1-(thiophen-3-ylcarbonyl)piperidin-4-yl]methyl}phenyl)azetidine-3-carboxamide;
N-(4-{[1-(methoxyacetyl)piperidin-4-yl]methyl}phenyl)-1-(pyridazin-3-yl)azetidine-3-carboxamide;
1-(pyridazin-3-yl)-N-(4-{[1-(tetrahydrofuran-2-ylcarbonyl)piperidin-4-yl]methyl}phenyl)azetidine-3-carboxamide;
N-[4-({1-[(2-methoxyethoxy)acetyl]piperidin-4-yl}methyl)phenyl]-1-(pyridazin-3-yl)azetidine-3-carboxamide;
N-(4-{[1-(ethoxyacetyl)piperidin-4-yl]methyl}phenyl)-1-(pyridazin-3-yl)azetidine-3-carboxamide;
1-(pyridazin-3-yl)-N-(4-{[1-(thiophen-2-ylcarbonyl)piperidin-4-yl]methyl}phenyl)azetidine-3-carboxamide;
N-{4-[(1-hexanoylpiperidin-4-yl)methyl]phenyl}-1-(pyridazin-3-yl)azetidine-3-carboxamide;
N-[4-({1-[(1-methyl-1H-pyrrol-2-yl)carbonyl]piperidin-4-yl}methyl)phenyl]-1-(pyridazin-3-yl)azetidine-3-carboxamide;
N-(4-{[1-(but-3-enoyl)piperidin-4-yl]methyl}phenyl)-1-(pyridazin-3-yl)azetidine-3-carboxamide;
1-(pyridazin-3-yl)-N-(4-{[1-(1,3-thiazol-2-ylcarbonyl)piperidin-4-yl]methyl}phenyl)azetidine-3-carboxamide;
N-(4-{[1-(furan-2-ylcarbonyl)piperidin-4-yl]
methyl}phenyl)-1-(pyridazin-3-yl)azetidine-3-carboxamide;
N-(4-{[1-(1,2-oxazol-5-ylcarbonyl)piperidin-4-yl]
methyl}phenyl)-1-(pyridazin-3-yl)azetidine-3-carboxamide;
1-(pyridazin-3-yl)-N-(4-{[1-(pyridin-2-ylcarbonyl)piperidin-4-yl]methyl}phenyl)azetidine-3-carboxamide;
N-(4-{[1-(furan-3-ylcarbonyl)piperidin-4-yl]
methyl}phenyl)-1-(pyridazin-3-yl)azetidine-3-carboxamide;
N-(4-{[1-(cyclopropylacetyl)piperidin-4-yl]
methyl}phenyl)-1-(pyridazin-3-yl)azetidine-3-carboxamide;
N-(4-{[1-(2-methylbutanoyl)piperidin-4-yl]
methyl}phenyl)-1-(pyridazin-3-yl)azetidine-3-carboxamide;
N-{4-[(1-propanoylpiperidin-4-yl)methyl]phenyl}-1-(pyridazin-3-yl)azetidine-3-carboxamide;
N-{4-[(1-butanoylpiperidin-4-yl)methyl]phenyl}-1-(pyridazin-3-yl)azetidine-3-carboxamide;
N-(4-{[1-(cyclobutylcarbonyl)piperidin-4-yl]
methyl}phenyl)-1-(pyridazin-3-yl)azetidine-3-carboxamide;
N-{4-[(1-pentanoylpiperidin-4-yl)methyl]phenyl}-1-(pyridazin-3-yl)azetidine-3-carboxamide;
N-(4-{[1-(cyclopentylacetyl)piperidin-4-yl]
methyl}phenyl)-1-(pyridazin-3-yl)azetidine-3-carboxamide;
N-(4-{[1-(2-methylbenzoyl)piperidin-4-yl]methyl}phenyl)-1-(pyridazin-3-yl)azetidine-3-carboxamide;
N-(4-{[1-(3-methylpentanoyl)piperidin-4-yl]
methyl}phenyl)-1-(pyridazin-3-yl)azetidine-3-carboxamide;
N-(4-{[1-(cyclohexylcarbonyl)piperidin-4-yl]
methyl}phenyl)-1-(pyridazin-3-yl)azetidine-3-carboxamide;
N-(4-{[1-(3-methylbutanoyl)piperidin-4-yl]
methyl}phenyl)-1-(pyridazin-3-yl)azetidine-3-carboxamide;
N-(4-{[1-(cyclopropylcarbonyl)piperidin-4-yl]
methyl}phenyl)-1-(pyridazin-3-yl)azetidine-3-carboxamide;
1-(pyridazin-3-yl)-N-(4-{[1-(3,3,3-trifluoropropanoyl)piperidin-4-yl]methyl}phenyl)azetidine-3-carboxamide;
N-{4-[1-(3,3-dimethylbutanoyl)piperidin-4-yl]phenyl}-1-(4-methylpyridazin-3-yl)azetidine-3-carboxamide;
N-{1-[1-(3,3-dimethylbutanoyl)piperidin-4-yl]-1H-pyrazol-4-yl}-1-(pyridazin-3-yl)azetidine-3-carboxamide;
N-{1-[1-(2-fluorobenzoyl)piperidin-4-yl]-1H-pyrazol-4-yl}-1-(pyridazin-3-yl)azetidine-3-carboxamide;
N-[4-(phenylcarbamoyl)phenyl]-1-(pyridazin-3-yl)azetidine-3-carboxamide;
N-{4[(2,2-dimethylpropyl)carbamoyl]phenyl}-1-(pyridazin-3-yl)azetidine-3-carboxamide;
N-{4-[(3-methoxy-2,2-dimethylpropyl)carbamoyl]phenyl}-1-(pyridazin-3-yl)azetidine-3-carboxamide;
N-{4[(2-cyclopropylethyl)carbamoyl]phenyl}-1-(pyridazin-3-yl)azetidine-3-carboxamide;
N-(4-{[2-(2-ethylpiperidin-1-yl)ethyl]carbamoyl}phenyl)-1-(pyridazin-3-yl)azetidine-3-carboxamide;
N-{4-[(cyclobutylmethyl)carbamoyl]phenyl}-1-(pyridazin-3-yl)azetidine-3-carboxamide;
N-{4-[(2S)-butan-2-ylcarbamoyl]phenyl}-1-(pyridazin-3-yl)azetidine-3-carboxamide;
N-[4-(butylcarbamoyl)phenyl]-1-(pyridazin-3-yl)azetidine-3-carboxamide;
N-{4-[(2,2-dimethyltetrahydro-2H-pyran-4-yl)carbamoyl]phenyl}-1-(pyridazin-3-yl)azetidine-3-carboxamide;
N-(4-{[(1S)-1-cyclopropylethyl]carbamoyl}phenyl)-1-(pyridazin-3-yl)azetidine-3-carboxamide;
N-[4-({2-[methyl(phenyl)amino]ethyl}carbamoyl)phenyl]-1-(pyridazin-3-yl)azetidine-3-carboxamide;

N-{4-[1,1'-bi(cyclopropyl)-1-ylcarbamoyl]phenyl}-1-(pyridazin-3-yl)azetidine-3-carboxamide;
1-(pyridazin-3-yl)-N-[4-(thiophen-3-ylcarbamoyl)phenyl]azetidine-3-carboxamide;
N-(4-{[(1R)-1-cyclopropylethyl]carbamoyl}phenyl)-1-(pyridazin-3-yl)azetidine-3-carboxamide;
N-{4-[(1-methylpiperidin-4-yl)carbamoyl]phenyl}-1-(pyridazin-3-yl)azetidine-3-carboxamide;
N-{4-[(2R)-butan-2-ylcarbamoyl]phenyl}-1-(pyridazin-3-yl)azetidine-3-carboxamide;
N-[4-(1-azabicyclo[2.2.2]oct-3-ylcarbamoyl)phenyl]-1-(pyridazin-3-yl)azetidine-3-carboxamide;
1-(pyridazin-3-yl)-N-{4-[(tetrahydrofuran-3-ylmethyl)carbamoyl]phenyl}azetidine-3-carboxamide;
N-{4-[(oxetan-3-ylmethyl)carbamoyl]phenyl}-1-(pyridazin-3-yl)azetidine-3-carboxamide;
N-{4-[(2-methylcyclopropyl)carbamoyl]phenyl}-1-(pyridazin-3-yl)azetidine-3-carboxamide;
N-{4-(cyclobutylcarbamoyl)phenyl]-1-(pyridazin-3-yl)azetidine-3-carboxamide;
N-{4-[(1-methylcyclopropyl)carbamoyl]phenyl}-1-(pyridazin-3-yl)azetidine-3-carboxamide;
N-{4-[(2-methoxy-2-methylpropyl)carbamoyl]phenyl}-1-(pyridazin-3-yl)azetidine-3-carboxamide;
N-{4-[(cyclopropylmethyl)carbamoyl]phenyl}-1-(pyridazin-3-yl)azetidine-3-carboxamide;
1-(pyridazin-3-yl)-N-(4-{[(2R)-tetrahydrofuran-2-ylmethyl]carbamoyl}phenyl)azetidine-3-carboxamide;
1-(pyridazin-3-yl)-N-{4[(3,3,3-trifluoropropyl)carbamoyl]phenyl}azetidine-3-carboxamide;
N-{4[(1-methylpiperidin-3-yl)carbamoyl]phenyl}-1-(pyridazin-3-yl)azetidine-3-carboxamide;
N-(4-{[(3-methyloxetan-3-yl)methyl]carbamoyl}phenyl)-1-(pyridazin-3-yl)azetidine-3-carboxamide;
1-(pyridazin-3-yl)-N-(4-{[(2S)-tetrahydrofuran-2-ylmethyl]carbamoyl}phenyl)azetidine-3-carboxamide;
1-(pyridazin-3-yl)-N-{4-[(tetrahydro-2H-pyran-4-ylmethyl)carbamoyl]phenyl}azetidine-3-carboxamide;
1-(pyridazin-3-yl)-N-[4-(tetrahydro-2H-pyran-4-ylcarbamoyl)phenyl]azetidine-3-carboxamide;
N-(4-{[(1-methylpiperidin-3-yl)methyl]carbamoyl}phenyl)-1-(pyridazin-3-yl)azetidine-3-carboxamide;
N-[4-(cyclopropylcarbamoyl)phenyl]-1-(pyridazin-3-yl)azetidine-3-carboxamide;
N-[4-(cyclopentylcarbamoyl)phenyl]-1-(pyridazin-3-yl)azetidine-3-carboxamide;
N-[4-(benzylcarbamoyl)phenyl]-1-(pyridazin-3-yl)azetidine-3-carboxamide;
N-{4-[(3-fluorophenyl)carbamoyl]phenyl}-1-(pyridazin-3-yl)azetidine-3-carboxamide;
N-[4-(propylcarbamoyl)phenyl]-1-(pyridazin-3-yl)azetidine-3-carboxamide;
N-{4-[(4-fluorophenyl)carbamoyl]phenyl}-1-(pyridazin-3-yl)azetidine-3-carboxamide;
N-{4-[(2-fluorophenyl)carbamoyl]phenyl}-1-(pyridazin-3-yl)azetidine-3-carboxamide;
N-{4-[(1-methylcyclobutyl)carbamoyl]phenyl}-1-(pyridazin-3-yl)azetidine-3-carboxamide;
N-[4-(prop-2-en-1-ylcarbamoyl)phenyl]-1-(pyridazin-3-yl)azetidine-3-carboxamide;
5-[1-(2,2-dimethylpropanoyl)piperidin-4-yl]-N-[(3S)-1-(pyridazin-3-yl)pyrrolidin-3-yl]thiophene-2-carboxamide;
5-[1-(3,3-dimethylbutanoyl)piperidin-4-yl]-N-[(3S)-1-(pyridazin-3-yl)pyrrolidin-3-yl]thiophene-2-carboxamide;
5-[1-(2,2-dimethylbutanoyl)piperidin-4-yl]-N-[(3S)-1-(pyridazin-3-yl)pyrrolidin-3-yl]thiophene-2-carboxamide;
5-{1-[(1-methylcyclopropyl)carbonyl]piperidin-4-yl}-N-[(3S)-1-(pyridazin-3-yl)pyrrolidin-3-yl]thiophene-2-carboxamide;
N-[(3S)-1-(pyridazin-3-yl)pyrrolidin-3-yl]-5-[1-(3,3,3-trifluoropropanoyl)piperidin-4-yl]thiophene-2-carboxamide;
5-[1-(cyclopropylacetyl)piperidin-4-yl]-N-[(3S)-1-(pyridazin-3-yl)pyrrolidin-3-yl]thiophene-2-carboxamide;
5-[1-(bicyclo[2.2.1]hept-2-ylacetyl)piperidin-4-yl]-N-[(3S)-1-(pyridazin-3-yl)pyrrolidin-3-yl]thiophene-2-carboxamide;
1-(pyridazin-3-yl)-N-{4-[(3S)-tetrahydrofuran-3-ylcarbamoyl]phenyl}azetidine-3-carboxamide;
N-[4-({4-[2-(dimethylamino)ethyl]phenyl}carbamoyl)phenyl]-1-(pyridazin-3-yl)azetidine-3-carboxamide;
1-(pyridazin-3-yl)-N-{4-[(3R)-tetrahydrofuran-3-ylcarbamoyl]phenyl}azetidine-3-carboxamide;
N-{4-[(2-methoxyethyl)carbamoyl]phenyl}-1-(pyridazin-3-yl)azetidine-3-carboxamide;
N-{4-[1-(3-amino-2,2-dimethylpropyl)-1H-pyrazol-4-yl]phenyl}-1-(pyridazin-3-yl)azetidine-3-carboxamide;
N-(4-{1-[2,2-dimethyl-3-(piperazin-1-yl)propyl]-1H-pyrazol-4-yl}phenyl)-1-(pyridazin-3-yl)azetidine-3-carboxamide;
N-(4-{1-[2-methyl-2-(piperazin-1-yl)propanoyl]piperidin-4-yl}phenyl)-1-(pyridazin-3-yl)azetidine-3-carboxamide;
and pharmaceutically acceptable salts thereof.

Still another embodiment pertains to compounds of Formula (1A), selected from the group consisting of N-{4-[1-(2-methylpropanoyl)piperidin-4-yl]phenyl}-1-(pyridazin-3-yl)azetidine-3-carboxamide;
(3S)—N-{4-[1-(2-methylpropanoyl)piperidin-4-yl]phenyl}-1-(pyridazin-3-yl)pyrrolidine-3-carboxamide;
(3S)—N-{4-[1-(2,2-dimethylpropanoyl)piperidin-4-yl]phenyl}-1-(pyridazin-3-yl)pyrrolidine-3-carboxamide;
N-[4-(1-acetylpiperidin-4-yl)phenyl]-1-(pyridazin-3-yl)azetidine-3-carboxamide;
N-[4-(1-butanoylpiperidin-4-yl)phenyl]-1-(pyridazin-3-yl)azetidine-3-carboxamide;
N-{4-[1-(3-methylbutanoyl)piperidin-4-yl]phenyl}-1-(pyridazin-3-yl)azetidine-3-carboxamide;
1-(pyridazin-3-yl)-N-{4-[1-(3,3,3-trifluoropropanoyl)piperidin-4-yl]phenyl}azetidine-3-carboxamide;
N-{4-[1-(methoxyacetyl)piperidin-4-yl]phenyl}-1-(pyridazin-3-yl)azetidine-3-carboxamide;
N-(4-{1-[(methylsulfanyl)acetyl]piperidin-4-yl}phenyl)-1-(pyridazin-3-yl)azetidine-3-carboxamide;
N-{4-[1-(2,2-dimethylpropanoyl)piperidin-4-yl]phenyl}-1-(pyridazin-3-yl)azetidine-3-carboxamide;
1-(pyridazin-3-yl)-N-{4-[1-(4,4,4-trifluorobutanoyl)piperidin-4-yl]phenyl}azetidine-3-carboxamide;
N-[4-(1-propanoylpiperidin-4-yl)phenyl]-1-(pyridazin-3-yl)azetidine-3-carboxamide;
(3S)—N-[4-(1-propanoylpiperidin-4-yl)phenyl]-1-(pyridazin-3-yl)pyrrolidine-3-carboxamide;
(3S)—N-[4-(1-butanoylpiperidin-4-yl)phenyl]-1-(pyridazin-3-yl)pyrrolidine-3-carboxamide;
(3S)—N-[4-(1-acetylpiperidin-4-yl)phenyl]-1-(pyridazin-3-yl)pyrrolidine-3-carboxamide;
(3S)—N-{4-[1-(2-methylbutanoyl)piperidin-4-yl]phenyl}-1-(pyridazin-3-yl)pyrrolidine-3-carboxamide;
(3S)—N-{4-[1-(2-ethylbutanoyl)piperidin-4-yl]phenyl}-1-(pyridazin-3-yl)pyrrolidine-3-carboxamide;
(3S)—N-{4-[1-(3,3-dimethylbutanoyl)piperidin-4-yl]phenyl}-1-(pyridazin-3-yl)pyrrolidine-3-carboxamide;
(3S)—N-{4-[1-(3-methylbutanoyl)piperidin-4-yl]phenyl}-1-(pyridazin-3-yl)pyrrolidine-3-carboxamide;

(3R)—N-{4-[1-(2,2-dimethylpropanoyl)piperidin-4-yl]phenyl}-1-(pyridazin-3-yl)pyrrolidine-3-carboxamide; and pharmaceutically acceptable salts thereof.

Another embodiment pertains to a composition for treating inflammatory and tissue repair disorders; particularly rheumatoid arthritis, inflammatory bowel disease, asthma and COPD (chronic obstructive pulmonary disease), osteoarthritis, osteoporosis and fibrotic diseases; dermatosis, including psoriasis, atopic dermatitis and ultra-violet induced skin damage; autoimmune diseases including systemic upus erythematosis, multiple sclerosis, psoriatic arthritis, ankylosing spondylitis, tissue and organ rejection, Alzheimer's disease, stroke, athersclerosis, restenosis, diabetes, glomerulonephritis, cancer, particularly wherein the cancer is selected from breast, prostate, lung, colon, cervix, ovary, skin, CNS, bladder, pancreas, leukemia, lymphoma or Hodgkin's disease, cachexia, inflammation associated with infection and certain viral infections, including Acquired Immune Deficiency Syndrome (AIDS), adult respiratory distress syndrome, and ataxia telengiectasia, said composition comprising an excipient and a therapeutically effective amount of a compound of Formula (IC), or pharmaceutically acceptable salts thereof.

Another embodiment pertains to a method of treating inflammatory and tissue repair disorders; particularly rheumatoid arthritis, inflammatory bowel disease, asthma and COPD (chronic obstructive pulmonary disease), osteoarthritis, osteoporosis and fibrotic diseases; dermatosis, including psoriasis, atopic dermatitis and ultra-violet induced skin damage; autoimmune diseases including systemic lupus erythematosis, multiple sclerosis, psoriatic arthritis, ankylosing spondylitis, tissue and organ rejection, Alzheimer's disease, stroke, athersclerosis, restenosis, diabetes, glomerulonephritis, cancer, particularly wherein the cancer is selected from breast, prostate, lung, colon, cervix, ovary, skin, CNS, bladder, pancreas, leukemia, lymphoma or Hodgkin's disease, cachexia, inflammation associated with infection and certain viral infections, including Acquired Immune Deficiency Syndrome (AIDS), adult respiratory distress syndrome, and ataxia telengiectasia in a patient, said method comprising administering to the patient a therapeutically effective amount of a compound of Formula (IC), or pharmaceutically acceptable salts thereof.

Another embodiment pertains to a method of treating inflammatory and tissue repair disorders; particularly rheumatoid arthritis, inflammatory bowel disease, asthma and COPD (chronic obstructive pulmonary disease), osteoarthritis, osteoporosis and fibrotic diseases; dermatosis, including psoriasis, atopic dermatitis and ultra-violet induced skin damage; autoimmune diseases including systemic lupus erythematosis, multiple sclerosis, psoriatic arthritis, ankylosing spondylitis, tissue and organ rejection, Alzheimer's disease, stroke, athersclerosis, restenosis, diabetes, glomerulonephritis, cancer, particularly wherein the cancer is selected from breast, prostate, lung, colon, cervix, ovary, skin, CNS, bladder, pancreas, leukemia, lymphoma or Hodgkin's disease, cachexia, inflammation associated with infection and certain viral infections, including Acquired Immune Deficiency Syndrome (AIDS), adult respiratory distress syndrome, and ataxia telengiectasia or spleen cancer in a patient, said method comprising administering to the patient therapeutically effective amount of the compound of Formula (IC), or pharmaceutically acceptable salts thereof; and a therapeutically effective amount of one additional therapeutic agent or more than one additional therapeutic agent.

DETAILED DESCRIPTION OF THE INVENTION

This detailed description is intended only to acquaint others skilled in the art with Applicants' invention, its principles, and its practical application so that others skilled in the art may adapt and apply the invention in its numerous forms, as they may be best suited to the requirements of a particular use. This description and its specific examples are intended for purposes of illustration only. This invention, therefore, is not limited to the embodiments described in this patent application, and may be variously modified.

Abbreviations And Definitions

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. In this application, the use of "or" means "and/or" unless stated otherwise. Furthermore, the use of the term "including", as well as other forms, such as "includes" and "included", is not limiting. With reference to the use of the words "comprise" or "comprises" or "comprising" in this patent application (including the claims), Applicants note that unless the context requires otherwise, those words are used on the basis and clear understanding that they are to be interpreted inclusively, rather than exclusively, and that Applicants intend each of those words to be so interpreted in construing this patent application, including the claims below. For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds which can be isolated in a useful degree of purity from a reaction mixture.

It is meant to be understood that proper valences are maintained for all combinations herein, that monovalent moieties having more than one atom are attached through their left ends, and that divalent moieties are drawn from left to right.

As used in the specification and the appended claims, unless specified to the contrary, the following terms have the meaning indicated:

The term "alkyl" (alone or in combination with another term(s)) means a straight- or branched-chain saturated hydrocarbyl substituent typically containing from 1 to about 10 carbon atoms; or in another embodiment, from 1 to about 8 carbon atoms; in another embodiment, from 1 to about 6 carbon atoms; and in another embodiment, from 1 to about 4 carbon atoms. Examples of such substituents include methyl, ethyl, n-propyl, isopropyl, n-butyl, isobutyl, sec-butyl, tert-butyl, pentyl, iso-amyl, and hexyl and the like.

The term "alkenyl" (alone or in combination with another term(s)) means a straight- or branched-chain hydrocarbyl substituent containing one or more double bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethenyl (vinyl), 2-propenyl, 3-propenyl, 1,4-pentadienyl, 1,4-butadienyl, 1-butenyl, 2-butenyl, and 3-butenyl and the like.

The term "alkynyl" (alone or in combination with another term(s)) means a straight- or branched-chain hydrocarbyl substituent containing one or more triple bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethynyl, 2-propynyl, 3-propynyl, 2-butynyl, and 3-butynyl and the like.

The term "carbocyclyl" (alone or in combination with another term(s)) means a saturated cyclic (i.e., "cycloalkyl"), partially saturated cyclic (i.e., "cycloalkenyl"), or completely unsaturated (i.e., "aryl") hydrocarbyl substituent containing from 3 to 14 carbon ring atoms ("ring atoms" are the atoms bound together to form the ring or rings of a cyclic substituent). A carbocyclyl may be a single-ring (monocyclic) or polycyclic ring structure.

A carbocyclyl may be a single ring structure, which typically contains from 3 to 8 ring atoms, more typically from 3 to 6 ring atoms, and even more typically 5 to 6 ring atoms. Examples of such single-ring carbocyclyls include cyclopropyl (cyclopropanyl), cyclobutyl (cyclobutanyl), cyclopentyl (cyclopentanyl), cyclopentenyl, cyclopentadienyl, cyclohexyl (cyclohexanyl), cyclohexenyl, cyclohexadienyl, and phenyl. A carbocyclyl may alternatively be polycyclic (i.e., may contain more than one ring). Examples of polycyclic carbocyclyls include bridged, fused, and spirocyclic carbocyclyls. In a spirocyclic carbocyclyl, one atom is common to two different rings. An example of a spirocyclic carbocyclyl is spiropentanyl. In a bridged carbocyclyl, the rings share at least two common non-adjacent atoms. Examples of bridged carbocyclyls include bicyclo[2.2.1]heptanyl, bicyclo[2.2.1]hept-2-enyl, and adamantanyl. In a fused-ring carbocyclyl system, two or more rings may be fused together, such that two rings share one common bond. Examples of two- or three-fused ring carbocyclyls include naphthalenyl, tetrahydronaphthalenyl (tetralinyl), indenyl, indanyl (dihydroindenyl), anthracenyl, phenanthrenyl, and decalinyl.

The term "cycloalkyl" (alone or in combination with another term(s)) means a saturated cyclic hydrocarbyl substituent containing from 3 to 14 carbon ring atoms. A cycloalkyl may be a single carbon ring, which typically contains from 3 to 8 carbon ring atoms and more typically from 3 to 6 ring atoms. Examples of single-ring cycloalkyls include cyclopropyl, cyclobutyl, cyclopentyl, and cyclohexyl. A cycloalkyl may alternatively be polycyclic or contain more than one ring. Examples of polycyclic cycloalkyls include bridged, fused, and spirocyclic carbocyclyls.

The term "aryl" (alone or in combination with another term(s)) means an aromatic carbocyclyl containing from 6 to 14 carbon ring atoms. An aryl may be monocyclic or polycyclic (i.e., may contain more than one ring). In the case of polycyclic aromatic rings, only one ring the polycyclic system is required to be unsaturated while the remaining ring(s) may be saturated, partially saturated or unsaturated. Examples of aryls include phenyl, naphthalenyl, indenyl, indanyl, and tetrahydronapthyl.

In some instances, the number of carbon atoms in a hydrocarbyl substituent (e.g., alkyl, alkenyl, alkynyl, or cycloalkyl) is indicated by the prefix "$C_x$-$C_y$—", wherein x is the minimum and y is the maximum number of carbon atoms in the substituent. Thus, for example, "$C_1$-$C_6$-alkyl" refers to an alkyl substituent containing from 1 to 6 carbon atoms. Illustrating further, $C_3$-$C_8$-cycloalkyl means a saturated hydrocarbyl ring containing from 3 to 8 carbon ring atoms.

The term "hydrogen" (alone or in combination with another term(s)) means a hydrogen radical, and may be depicted as —H.

The term "hydroxy" (alone or in combination with another term(s)) means —OH.

The term "carboxy" (alone or in combination with another term(s)) means —C(O)—OH.

The term "amino" (alone or in combination with another term(s)) means —$NH_2$.

The term "halogen" or "halo" (alone or in combination with another term(s)) means a fluorine radical (which may be depicted as —F), chlorine radical (which may be depicted as —Cl), bromine radical (which may be depicted as —Br), or iodine radical (which may be depicted as —I).

If a substituent is described as being "substituted", a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there are more than one substitution on a substituent, each non-hydrogen radical may be identical or different (unless otherwise stated).

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical. If a substituent is described as being optionally substituted with one or more non-hydrogen radicals, that substituent may be either (1) not substituted; or (2) substituted by up to the maximum number of substitutable positions on the substituent. Thus, for example, if a substituent is described as a heteroaryl optionally substituted with one or more non-hydrogen radicals, then any heteroaryl with 3 substitutable positions would be optionally substituted by one, two or three non-hydrogen radicals. To illustrate, tetrazolyl (which has only one substitutable position) would be optionally substituted with up to one non-hydrogen radical.

This patent application uses the terms "substituent" and "radical" interchangeably.

The prefix "halo" indicates that the substituent to which the prefix is attached is substituted with one or more independently selected halogen radicals. For example, haloalkyl means an alkyl substituent in which at least one hydrogen radical is replaced with a halogen radical. Examples of haloalkyls include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

The prefix "perhalo" indicates that every hydrogen radical on the substituent to which the prefix is attached is replaced with independently selected halogen radicals, i.e., each hydrogen radical on the substituent is replaced with a halogen radical. If all the halogen radicals are identical, the prefix typically will identify the halogen radical. Thus, for example, the term "perfluoro" means that every hydrogen radical on the substituent to which the prefix is attached is substituted with a fluorine radical. To illustrate, the term "perfluoroalkyl" means an alkyl substituent wherein a fluorine radical is in the place of each hydrogen radical.

The term "carbonyl" (alone or in combination with another term(s)) means —C(O)—.

The term "aminocarbonyl" (alone or in combination with another term(s)) means —C(O)—NH$_2$.

The term "oxo" (alone or in combination with another term(s)) means (=O).

The term "oxy" (alone or in combination with another term(s)) means an ether substituent, and may be depicted as —O—.

The term "alkylhydroxy" (alone or in combination with another term(s)) means -alkyl-OH.

The term "alkylamino" (alone or in combination with another term(s)) means -alkyl-NH$_2$.

The term "alkyloxy" (alone or in combination with another term(s)) means an alkylether substituent, i.e., —O-alkyl. Examples of such a substituent include methoxy (—O—CH$_3$), ethoxy, n-propoxy, isopropoxy, n-butoxy, iso-butoxy, sec-butoxy, and tert-butoxy.

The term "alkylcarbonyl" (alone or in combination with another term(s)) means —C(O)-alkyl.

The term "aminoalkylcarbonyl" (alone or in combination with another term(s)) means —C(O)-alkyl-NH$_2$.

The term "alkyloxycarbonyl" (alone or in combination with another term(s)) means —C(O)—O-alkyl.

The term "carbocyclylcarbonyl" (alone or in combination with another term(s)) means —C(O)-carbocyclyl.

Similarly, the term "heterocyclylcarbonyl" (alone or in combination with another term(s)) means —C(O)-heterocyclyl.

The term "carbocyclylalkylcarbonyl" (alone or in combination with another term(s)) means —C(O)-alkyl-carbocyclyl.

Similarly, the term "heterocyclylalkylcarbonyl" (alone or in combination with another term(s)) means —C(O)-alkyl-heterocyclyl.

The term "carbocyclyloxycarbonyl" (alone or in combination with another term(s)) means —C(O)—O-carbocyclyl.

The term "carbocyclylalkyloxycarbonyl" (alone or in combination with another term(s)) means —C(O)—O-alkyl-carbocyclyl.

The term "thio" or "thia" (alone or in combination with another term(s)) means a thiaether substituent, i.e., an ether substituent wherein a divalent sulfur atom is in the place of the ether oxygen atom. Such a substituent may be depicted as —S—. This, for example, "alkyl-thio-alkyl" means alkyl-5-alkyl (alkyl-sulfanyl-alkyl).

The term "thiol" or "sulfhydryl" (alone or in combination with another term(s)) means a sulfhydryl substituent, and may be depicted as —SH.

The term "(thiocarbonyl)" (alone or in combination with another term(s)) means a carbonyl wherein the oxygen atom has been replaced with a sulfur. Such a substituent may be depicted as —C(S)—.

The term "sulfonyl" (alone or in combination with another term(s)) means —S(O)$_2$—.

The term "aminosulfonyl" (alone or in combination with another term(s)) means —S(O)$_2$—NH$_2$.

The term "sulfinyl" or "sulfoxido" (alone or in combination with another term(s)) means —S(O)—.

The term "heterocyclyl" (alone or in combination with another term(s)) means a saturated (i.e., "heterocycloalkyl"), partially saturated (i.e., "heterocycloalkenyl"), or completely unsaturated (i.e., "heteroaryl") ring structure containing a total of 3 to 14 ring atoms. At least one of the ring atoms is a heteroatom (i.e., oxygen, nitrogen, or sulfur), with the remaining ring atoms being independently selected from the group consisting of carbon, oxygen, nitrogen, and sulfur. A heterocyclyl may be a single-ring (monocyclic) or polycyclic ring structure.

A heterocyclyl may be a single ring, which typically contains from 3 to 7 ring atoms, more typically from 3 to 6 ring atoms, and even more typically 5 to 6 ring atoms. Examples of single-ring heterocyclyls include 1,2,3,6-tetrahydropyridine, thiomorpholinyl, tetrahydropyranyl, furanyl, dihydrofuranyl, tetrahydrofuranyl, thiophenyl (thiofuranyl), dihydrothiophenyl, tetrahydrothiophenyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, oxazolidinyl, isoxazolidinyl, isoxazolyl, thiazolyl, isothiazolyl, thiazolinyl, isothiazolinyl, thiazolidinyl, isothiazolidinyl, thiodiazolyl, oxadiazolyl (including 1,2,3-oxadiazolyl, 1,2,4-oxadiazolyl, 1,2,5-oxadiazolyl (furazanyl), or 1,3,4-oxadiazolyl), oxatriazolyl (including 1,2,3,4-oxatriazolyl or 1,2,3,5-oxatriazolyl), dioxazolyl (including 1,2,3-dioxazolyl, 1,2,4-dioxazolyl, 1,3,2-dioxazolyl, or 1,3,4-dioxazolyl), oxathiazolyl, oxathiolyl, oxathiolanyl, pyranyl, dihydropyranyl, thiopyranyl, tetrahydrothiopyranyl, pyridinyl (azinyl), piperidinyl, diazinyl (including pyridazinyl (1,2-diazinyl), pyrimidinyl (1,3-diazinyl), or pyrazinyl (1,4-diazinyl)), piperazinyl, pyrrolidin-2-only, triazinyl (including 1,3,5-triazinyl, 1,2,4-triazinyl, and 1,2,3-triazinyl)), oxazinyl (including 1,2-oxazinyl, 1,3-oxazinyl, or 1,4-oxazinyl)), oxathiazinyl (including 1,2,3-oxathiazinyl, 1,2,4-oxathiazinyl, 1,2,5-oxathiazinyl, or 1,2,6-oxathiazinyl)), oxadiazinyl (including 1,2,3-oxadiazinyl, 1,2,4-oxadiazinyl, 1,4,2-oxadiazinyl, or 1,3,5-oxadiazinyl)), morpholinyl, azepinyl, oxepinyl, thiepinyl, and diazepinyl.

A heterocyclyl may alternatively be polycyclic (i.e., may contain more than one ring).

Examples of polycyclic heterocyclyls include bridged, fused, and spirocyclic heterocyclyls. In a spirocyclic heterocyclyl, one atom is common to two different rings. In a bridged heterocyclyl, the rings share at least two common non-adjacent atoms. In a fused-ring heterocyclyl, two or more rings may be fused together, such that two rings share one common bond. Examples of fused-ring heterocyclyls include hexahydro-furo[3,4-c]pyrrole, hexahydro-furo[3,4-b]pyrrole, octahydro-pyrrolo[3,4-b]pyridine, octahydro-pyrrolo[3,4-c]pyridine, (3aR,6aR)-5-methyl-octahydro-pyrrolo[3,4-b]pyrrole, (3aR,6aR)-octahydro-pyrrolo[3,4-b]pyrrole, 6-methyl-2,6-diaza-bicyclo[3.2.0]heptane, (3aS,6aR)-2-methyl-octahydro-pyrrolo[3,4-c]pyrrole, decahydro-[1,5]naphthyridine, 2,3-dihydrobenzofuranyl, 2,3,4,9-tetrahydro-1H-pyrido[3,4-b]indolyl, thieno[3,2-c]pyridinyl, furo[3,2-c]pyridinyl, phthalazin-1(2H)-onyl, isoquinolinyl, isoquinolin-1(2H)-onyl, 5,6,7,8-tetrahydrophthalazin-1(2H)-onyl, fluorophthalazin-1(2H)-onyl, (Z)-3H-benzo[d][1,2]diazepin-4(5H)-onyl, (trifluoromethyl)phthalazin-1(2H)-onyl, pyrrolo[1,2-d][1,2,4]triazin-1(2H)-onyl, 1,2,3,4-tetrahydroisoquinolinyl, 2,3-dihydrobenzo[b][1,4]dioxinyl, 5,6,7,8-tetrahydrophthalazin-1(2H)-onyl, 5,6,7,8-tetrahydro-[1,2,4]triazolo[4,3-a]pyrazinyl, 5,6,7,8-tetrahydroimidazo[1,5-a]pyrazinyl, thieno[3,2-c]pyridinyl, furo[3,2-c]pyridinyl, indolizinyl, pyranopyrrolyl, 4H-quinolizinyl, purinyl, naphthyridinyl, pyridopyridinyl (including pyrido[3,4-b]-pyridinyl, pyrido[3,2-b]-pyridinyl, or pyrido[4,3-b]-pyridinyl), and pteridinyl. Other examples of fused-ring heterocyclyls include benzo-fused heterocyclyls, such as benzimidazolyl, benzo[d][1,3]dioxolyl, indolyl, isoindolyl (isobenzazolyl, pseudoisoindolyl), indoleninyl (pseudoindolyl), isoindazolyl (benzpyrazolyl), benzazinyl (including quinolinyl (1-benzazinyl) or isoquinolinyl (2-benzazinyl)), phthalazinyl, quinoxalinyl, quinazolinyl, benzodiazinyl (including cinnolinyl (1,2-benzodiazinyl) or quinazolinyl (1,3-benzodiazinyl)), benzopyranyl (including chromanyl or isochromanyl), benzoxazinyl (including 1,3,2-benzoxazinyl, 1,4,2-benzoxazinyl, 2,3,1-benzoxazinyl, or 3,1,4-benzoxazinyl), and benzisoxazinyl (including 1,2-benzisoxazinyl or 1,4-benzisoxazinyl). Examples of spirocyclic heterocyclyls include 1,4-dioxa-8-azaspiro[4.5]decanyl.

The term "5-6 membered heteroaryl" (alone or in combination with another term(s)) means aromatic heterocyclyl containing a total of 5 to 6 ring atoms. At least one of the ring atoms is a heteroatom (i.e., oxygen, nitrogen, or sulfur), with the remaining ring atoms being independently selected from the group consisting of carbon, oxygen, nitrogen, and sulfur.

The term "heterocycloalkyl" (alone or in combination with another term(s)) means a saturated heterocyclyl.

The term "heteroaryl" (alone or in combination with another term(s)) means an aromatic heterocyclyl containing from 5 to 14 ring atoms. A heteroaryl may be a single ring or 2 or 3 fused rings. Examples of heteroaryl substituents include 6-membered ring substituents such as pyridyl, pyrazyl, pyrimidinyl, pyridazinyl, and 1,3,5-, 1,2,4- or 1,2,3-triazinyl; 5-membered ring substituents such as imidazyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 6/5-membered fused ring substituents such as benzothiofuranyl, benzisoxazolyl, benzoxazolyl, and purinyl; and 6/6-membered fused rings such as benzopyranyl, quinolinyl, isoquinolinyl, cinnolinyl, quinazolinyl, and benzoxazinyl.

A prefix attached to a multi-component substituent only applies to the first component. To illustrate, the term "alkylcycloalkyl" contains two components: alkyl and cycloalkyl. Thus, the $C_1$-$C_6$- prefix on $C_1$-$C_6$-alkylcycloalkyl means that the alkyl component of the alkylcycloalkyl contains from 1 to 6 carbon atoms; the $C_1$-$C_6$-prefix does not describe the cycloalkyl component. To illustrate further, the prefix "halo" on haloalkyloxyalkyl indicates that only the alkyloxy component of the alkyloxyalkyl substituent is substituted with one or more halogen radicals. If halogen substitution may alternatively or additionally occur on the alkyl component, the substituent would instead be described as "halogen-substituted alkyloxyalkyl" rather than "haloalkyloxyalkyl." And finally, if the halogen substitution may only occur on the alkyl component, the substituent would instead be described as "alkyloxyhaloalkyl."

The terms "treat", "treating" and "treatment" refer to a method of alleviating or abrogating a disease and/or its attendant symptoms.

The terms "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The term "therapeutically effective amount" refers to that amount of the compound being administered sufficient to prevent development of or alleviate to some extent one or more of the symptoms of the condition or disorder being treated.

The term "modulate" refers to the ability of a compound to increase or decrease the function, or activity, of a kinase. "Modulation", as used herein in its various forms, is intended to encompass antagonism, agonism, partial antagonism and/or partial agonism of the activity associated with kinase. Kinase inhibitors are compounds that, e.g., bind to, partially or totally block stimulation, decrease, prevent, delay activation, inactivate, desensitize, or down regulate signal transduction. Kinase activators are compounds that, e.g., bind to, stimulate, increase, open, activate, facilitate, enhance activation, sensitize or up regulate signal transduction.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

Isotope Enriched or Labeled Compounds

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to, $^2H$, $^3H$, $^{13}C$, $^{14}C$, $^{15}N$, $^{18}O$, $^{32}P$, $^{35}S$, $^{18}F$, $^{36}Cl$ and $^{125}I$. Compounds that contain other isotopes of these and/or other atoms are within the scope of this invention.

In another embodiment, the isotope-labeled compounds contain deuterium ($^2H$), tritium ($^3H$) or $^{14}C$ isotopes. Isotope-labeled compounds of this invention can be prepared by the general methods well known to persons having ordinary skill in the art. Such isotope-labeled compounds can be conveniently prepared by carrying out the procedures disclosed in the Examples disclosed herein and Schemes by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as $D_2SO_4$/$D_2O$. In addition to the above, relevant procedures and intermediates are disclosed, for instance, in Lizondo, J et al., *Drugs Fut*, 21(11), 1116 (1996); Brickner, S J et al., *J Med Chem*, 39(3), 673 (1996); Mallesham, B et al., *Org Lett*, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention may be used as standards to determine the effectiveness in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., J. Labelled Comp. Radiopharmaceut., 36(10): 927-932 (1995); Kushner et al., Can. J. Physiol. Pharmacol., 77, 79-88 (1999).

In addition, non-radio active isotope containing drugs, such as deuterated drugs called "heavy drugs," can be used for the treatment of diseases and conditions related to NAMPT activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci. 1960 84: 736; Czakja D M et al., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug can alter its physicochemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmacokinetic profile or efficacy relative to the non-isotopic compound.

Compounds

Suitable groups for $X^1$, $X^2$, $Y^1$, $Z^1$, $R^1$, and $R^2$ in compounds of all Formulas are independently selected. The described embodiments of the present invention may be combined. Such combination is contemplated and within the scope of the present invention. For example, it is contemplated that embodiments for any of $X^1$, $X^2$, $Y^1$, $Z^1$, $R^1$, and $R^2$ can be combined with embodiments defined for any other of $X^1$, $X^2$, $Y^1$, $Z^1$, $R^1$, and $R^2$.

Embodiments of Formula (I)

One embodiment of this invention, therefore, pertains to compounds or pharmaceutically acceptable salts thereof, which are useful as inhibitors of NAMPT, the compounds having Formula (I)

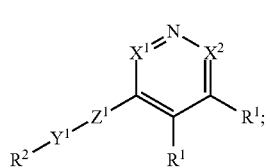

Formula (I)

wherein
$X^1$ is N and $X^2$ is $CR^1$; or
$X^1$ is $CR^1$ and $X^2$ is N; or
$X^1$ is $CR^1$ and $X^2$ is $CR^1$;
$Y^1$ is C(O)NH, or NHC(O);
$Z^1$ is

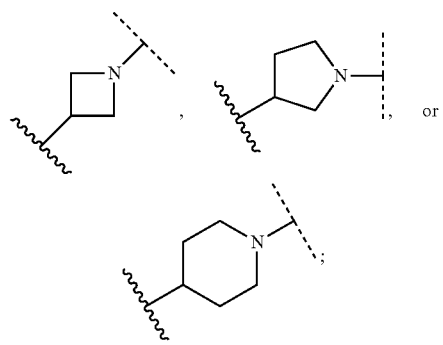

wherein $\sim$ indicates the point of attachment to $Y^1$ and $\setminus$ indicates the point of attachment to the nitrogen containing heteroaryl;

$R^1$, at each occurrence, is independently selected from the group consisting of hydrogen, alkyl, alkenyl, alkynyl, haloalkyl, hydroxyalkyl, alkoxy, OH, $NH_2$, CN, $NO_2$, F, Cl, Br and I;

$R^2$ is independently selected from the group consisting of $C_4$-$C_6$-alkyl, $C_4$-$C_6$-alkenyl, $C_4$-$C_6$-alkynyl, aryl, and 5-6 membered heteroaryl; wherein each $R^2C_4$-$C_6$-alkyl, $C_4$-$C_6$-alkenyl, and $C_4$-$C_6$-alkynyl is substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(N)NH_2$, $C(N)NHR^3$, $C(N)N(R^3)_2$, $CNOH$, $CNOCH_3$, OH, (O), CN, $N_3$, $NO_2$, F, Cl, Br and I; wherein each $R^2$ aryl and 5-6 membered heteroaryl is optionally substituted with one or more substituents independently selected from the group consisting of $R^4$, $OR^4$, $SR^4$, $S(O)R^4$, $SO_2R^4$, $C(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, $CNOH$, $CNOCH_3$, OH, CN, $N_3$, $NO_2$, F, Cl, and I;

$R^3$, at each occurrence, is independently selected from the group consisting of alkyl, alkenyl, alkynyl, aryl, cycloalkyl, cycloalkenyl, and heterocyclyl; wherein each $R^3$ alkyl, alkenyl, and alkynyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, CNOH, CNOCH₃, OH, (O), CN, N₃, NO₂, F, Cl, Br and I; wherein each R³ aryl, cycloalkyl, cycloalkenyl, and heterocyclyl is optionally substituted with one or more substituents independently selected from the group consisting of R⁶, OR⁶, SR⁶, S(O)R⁶, SO₂R⁶, C(O)R⁶, CO(O)R⁶, OC(O)R⁶, OC(O)OR⁶, NH₂, NHR⁶, N(R⁶)₂, NHC(O)R⁶, NR⁶C(O)R⁶, NHS(O)₂R⁶, NR⁶S(O)₂R⁶, NHC(O)OR⁶, NR⁶C(O)OR⁶, NHC(O)NH₂, NHC(O)NHR⁶, NHC(O)N(R⁶)₂, NR⁶C(O)NHR⁶, NR⁶C(O)N(R⁶)₂, C(O)NH₂, C(O)NHR⁶, C(O)N(R⁶)₂, C(O)NHOH, C(O)NHOR⁶, C(O)NHSO₂R⁶, C(O)NR⁶SO₂R⁶, SO₂NH₂, SO₂NHR⁶, SO₂N(R⁶)₂, C(O)H, C(O)OH, C(N)NH₂, C(N)NHR⁶, C(N)N(R⁶)₂, CNOH, CNOCH₃, OH, CN, N₃, NO₂, F, Cl, Br and I;

R⁴, at each occurrence, is independently selected from the group consisting of alkyl, alkenyl, alkynyl, aryl, heterocyclyl, cycloalkyl, and cycloalkenyl; wherein each R⁴ alkyl, alkenyl, and alkynyl is optionally substituted with one or more substituents independently selected from the group consisting of R⁷, OR⁷, SR⁷, S(O)R⁷, SO₂R⁷, C(O)R⁷, CO(O)R⁷, OC(O)R⁷, OC(O)OR⁷, NH₂, NHR⁷, N(R⁷)₂, NHC(O)R⁷, NR⁷C(O)R⁷, NHS(O)₂R⁷, NR⁷S(O)₂R⁷, NHC(O)OR⁷, NR⁷C(O)OR⁷, NHC(O)NH₂, NHC(O)NHR⁷, NHC(O)N(R⁷)₂, NR⁷C(O)NHR⁷, NR⁷C(O)N(R⁷)₂, C(O)NH₂, C(O)NHR⁷, C(O)N(R⁷)₂, C(O)NHOH, C(O)NHOR⁷, C(O)NHSO₂R⁷, C(O)NR⁷SO₂R⁷, SO₂NH₂, SO₂NHR⁷, SO₂N(R⁷)₂, C(O)H, C(O)OH, C(N)NH₂, C(N)NHR⁷, C(N)N(R⁷)₂, CNOH, CNOCH₃, OH, (O), CN, N₃, NO₂, F, Cl, Br and I;

R⁵, at each occurrence, is independently selected from the group consisting of alkyl, alkenyl, alkynyl, aryl, heterocyclyl, cycloalkyl, and cycloalkenyl; wherein each R⁵ alkyl, alkenyl, and alkynyl is optionally substituted with one or more substituents independently selected from the group consisting of R⁸, OR⁸, SR⁸, S(O)R⁸, SO₂R⁸, NHR⁸, N(R⁸)₂, C(O)R⁸, C(O)NH₂, C(O)NHR⁸, C(O)N(R⁸)₂, NHC(O)R⁸, NR⁸C(O)R⁸, NHSO₂R⁸, NHC(O)OR⁸, SO₂NH₂, SO₂NHR⁸, SO₂N(R⁸)₂, NHC(O)NH₂, NHC(O)NHR⁸, OH, (O), C(O)OH, N₃, CN, NH₂, F, Cl, Br and I;

R⁶, at each occurrence, is independently selected from the group consisting of alkyl, alkenyl, alkynyl, aryl, heterocyclyl, cycloalkyl, and cycloalkenyl; wherein each R⁶ alkyl, alkenyl, and alkynyl is optionally substituted with one or more substituents independently selected from the group consisting of R⁹, OR⁹, SR⁹, S(O)R⁹, SO₂R⁹, NHR⁹, N(R⁹)₂, C(O)R⁹, C(O)NH₂, C(O)NHR⁹, C(O)N(R⁹)₂, NHC(O)R⁹, NR⁹C(O)R⁹, NHSO₂R⁹, NHC(O)OR⁹, SO₂NH₂, SO₂NHR⁹, SO₂N(R⁹)₂, NHC(O)NH₂, NHC(O)NHR⁹, OH, (O), C(O)OH, N₃, CN, NH₂, CF₃, CF₂CF₃, F, Cl, Br and I;

R⁷, at each occurrence, is independently selected from the group consisting of alkyl, alkenyl, alkynyl, aryl, heterocyclyl, cycloalkyl, and cycloalkenyl;

R⁸, at each occurrence, is independently selected from the group consisting of alkyl, alkenyl, alkynyl, aryl, heterocyclyl, cycloalkyl, and cycloalkenyl;

R⁹, at each occurrence, is independently selected from the group consisting of alkyl, alkenyl, alkynyl, aryl, heterocyclyl, cycloalkyl, and cycloalkenyl;

wherein the cyclic moieties represented by R⁴, R⁵, R⁶, R⁷, R⁸, and R⁹ are independently optionally substituted with one or more substituents independently selected from the group consisting of R¹⁰, OR¹⁰, SR¹⁰, S(O)R¹⁰, SO₂R¹⁰, C(O)R¹⁰, CO(O)R¹⁰, OC(O)R¹⁰, OC(O)OR¹⁰, C(O)C(O)R¹⁰, NH₂, NHR¹⁰, N(R¹⁰)₂, NHC(O)R¹⁰, NR¹⁰C(O)R¹⁰, NHS(O)₂R¹⁰, NR¹⁰S(O)₂R¹⁰, NHC(O)OR¹⁰, NR¹⁰C(O)OR¹⁰, NHC(O)NH₂, NHC(O)NHR¹⁰, NHC(O)N(R¹⁰)₂, NR¹⁰C(O)NHR¹⁰, NR¹⁰C(O)N(R¹⁰)₂, C(O)NH₂, C(O)NHR¹⁰, C(O)N(R¹⁰)₂, C(O)NHOH, C(O)NHOR¹⁰, C(O)NHSO₂R¹⁰, C(O)NR¹⁰SO₂R¹⁰, SO₂NH₂, SO₂NHR¹⁰, SO₂N(R¹⁰)₂, C(O)H, C(O)OH, C(N)NH₂, C(N)NHR¹⁰, C(N)N(R¹⁰)₂, CNOH, CNOCH₃, OH, CN, N₃, NO₂, F, Cl, Br and I;

R¹⁰, at each occurrence, is independently selected from the group consisting of alkyl, alkenyl, alkynyl, aryl, heterocyclyl, cycloalkyl, and cycloalkenyl; wherein each R¹⁰ alkyl, alkenyl, and alkynyl is optionally substituted with one or more substituents independently selected from the group consisting of R¹¹, OR¹¹, SR¹¹, S(O)R¹¹, SO₂R¹¹, C(O)R¹¹, CO(O)R¹¹, OC(O)R¹¹, OC(O)OR¹¹, NH₂, NHR¹¹, N(R¹¹)₂, NHC(O)R¹¹, NR¹¹C(O)R¹¹, NHS(O)₂R¹¹, NR¹¹S(O)₂R¹¹, NHC(O)OR¹¹, NR¹¹C(O)OR¹¹, NHC(O)NH₂, NHC(O)NHR¹¹, NHC(O)N(R¹¹)₂, NR¹¹C(O)NHR¹¹, NR¹¹C(O)N(R¹¹)₂, C(O)NH₂, C(O)NHR¹¹, C(O)N(R¹¹)₂, C(O)NHOH, C(O)NHOR¹¹, C(O)NHSO₂R¹¹, C(O)NR¹¹SO₂R¹¹, SO₂NH₂, SO₂NHR¹¹, SO₂N(R¹¹)₂, C(O)H, C(O)OH, C(N)NH₂, C(N)NHR¹¹, C(N)N(R¹¹)₂, CNOH, CNOCH₃, OH, (O), CN, N₃, NO₂, F, Cl, Br and I; wherein each R¹⁰ aryl, heterocyclyl, cycloalkyl, and cycloalkenyl is optionally substituted with one or more substituents independently selected from the group consisting of R¹², OR¹², SR¹², S(O)R¹², SO₂R¹², C(O)R¹², CO(O)R¹², OC(O)R¹², OC(O)OR¹², NH₂, NHR¹², N(R¹²)₂, NHC(O)R¹², NR¹²C(O)R¹², NHS(O)₂R¹², NR¹²S(O)₂R¹², NHC(O)OR¹², NR¹²C(O)OR¹², NHC(O)NH₂, NHC(O)NHR¹², NHC(O)N(R¹²)₂, NR¹²C(O)NHR¹², NR¹²C(O)N(R¹²)₂, C(O)NH₂, C(O)NHR¹², C(O)N(R¹²)₂, C(O)NHOH, C(O)NHOR¹², C(O)NHSO₂R¹², C(O)NR¹²SO₂R¹², SO₂NH₂, SO₂NHR¹², SO₂N(R¹²)₂, C(O)H, C(O)OH, C(N)NH₂, C(N)NHR¹², C(N)N(R¹²)₂, CNOH, CNOCH₃, OH, CN, N₃, NO₂, CF₃, OCF₃, F, Cl, Br and I;

R¹¹, at each occurrence, is independently selected from the group consisting of alkyl, alkenyl, alkynyl, aryl, heterocyclyl, cycloalkyl, and cycloalkenyl; wherein each R¹¹ alkyl, alkenyl, and alkynyl is optionally substituted with alkoxy or aryl; wherein each R¹¹ aryl, heterocyclyl, cycloalkyl, and cycloalkenyl is optionally substituted with one or more substituents independently selected from the group consisting of R¹³, OR¹³, C(O)OR¹³, OCF₃, CF₃, F, Cl, Br and I;

R¹², at each occurrence, is independently selected from the group consisting of alkyl, alkenyl, alkynyl, aryl, heterocyclyl, cycloalkyl, and cycloalkenyl; and R¹³, at each occurrence, is independently selected from the group consisting of alkyl, alkyl, alkenyl, alkynyl, aryl, heterocyclyl, cycloalkyl, and cycloalkenyl;

with the proviso that
when X¹ is CR¹ and X² is CR¹; R¹ is hydrogen; Y¹ is NHC(O); Z¹ is

and R² is pyrrolyl; the R² pyrrolyl is not substituted with two alkyl groups.

In one embodiment of Formula (I), X¹ is N and X² is CR¹; or X¹ is CR¹ and X² is N; or X¹ is CR¹ and X² is CR¹. In another embodiment of Formula (I), X¹ is N and X² is CR¹. In another embodiment of Formula (I), X¹ is CR¹ and X² is N. In another embodiment of Formula (I), X¹ is CR¹ and X² is CR¹.

In one embodiment of Formula (I), R¹, at each occurrence, is independently selected from the group consisting of hydrogen, alkyl, alkenyl, alkynyl, haloalkyl, hydroxyalkyl, alkoxy, OH, NH₂, CN, NO₂, F, Cl, Br and I. In another embodiment of Formula (I), R¹, at each occurrence, is independently selected from the group consisting of hydrogen, alkyl, haloalkyl, alkoxy, CN, F, Cl, Br and I. In another embodiment of Formula (I), $R^1$, at each occurrence, is independently selected from the group consisting of hydrogen, alkyl, haloalkyl, alkoxy, CN, and F. In another embodiment of Formula (I), $R^1$, at each occurrence, is hydrogen.

In one embodiment of Formula (I), $X^1$ is $CR^1$ and $X^2$ is $CR^1$; and $R^1$, at each occurrence, is independently selected from the group consisting of hydrogen, alkyl, alkenyl, alkynyl, haloalkyl, hydroxyalkyl, alkoxy, OH, $NH_2$, CN, $NO_2$, F, Cl, Br and I. In another embodiment of Formula (I), $X^1$ is $CR^1$ and $X^2$ is $CR^1$; and $R^1$, at each occurrence, is independently selected from the group consisting of hydrogen, alkyl, haloalkyl, alkoxy, CN, F, Cl, Br and I. In another embodiment of Formula (I), $X^1$ is $CR^1$ and $X^2$ is $CR^1$; and $R^1$, at each occurrence, is independently selected from the group consisting of hydrogen, alkyl, haloalkyl, alkoxy, CN, and F. In another embodiment of Formula (I), $X^1$ is $CR^1$ and $X^2$ is $CR^1$; and $R^1$, at each occurrence, is hydrogen.

In one embodiment of Formula (I), $Y^1$ is C(O)NH, or NHC(O). In another embodiment of Formula (I), $Y^1$ is C(O)NH. In another embodiment of Formula (I), $Y^1$ is NHC(O).

In one embodiment of Formula (I), $Z^1$ is

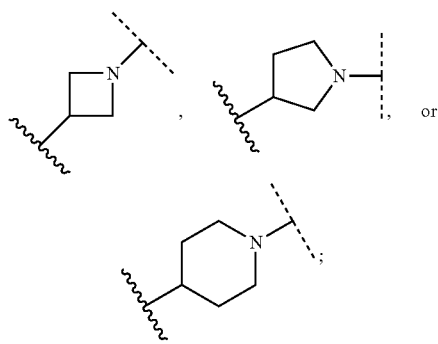

wherein ⌇ indicates the point of attachment to $Y^1$ and ⌇ indicates the point of attachment to the nitrogen containing heteroaryl. In another embodiment of Formula (I), $Z^1$ is

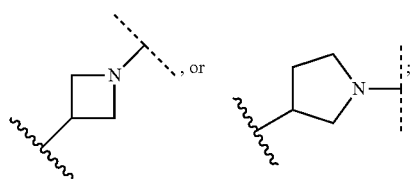

wherein ⌇ indicates the point of attachment to $Y^1$ and ⌇ indicates the point of attachment to the nitrogen containing heteroaryl. In another embodiment of Formula (I), $Z^1$ is

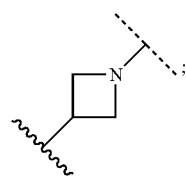

wherein ⌇ indicates the point of attachment to $Y^1$ and ⌇ indicates the point of attachment to the nitrogen containing heteroaryl. In another embodiment of Formula (I), $Z^1$ is

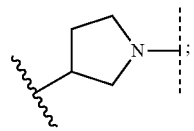

wherein ⌇ indicates the point of attachment to $Y^1$ and ⌇ indicates the point of attachment to the nitrogen containing heteroaryl.

In one embodiment of Formula (I), $R^2$ is independently selected from the group consisting of $C_4$-$C_6$-alkyl, $C_4$-$C_6$-alkenyl, $C_4$-$C_6$-alkynyl, aryl, and 5-6 membered heteroaryl; wherein each $R^2$ $C_4$-$C_6$-alkyl, $C_4$-$C_6$-alkenyl, and $C_4$-$C_6$-alkynyl is substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(N)NH_2$, $C(N)NHR^3$, $C(N)N(R^3)_2$, CNOH, $CNOCH_3$, OH, (O), CN, $N_3$, $NO_2$, F, Cl, Br and I; wherein each $R^2$ aryl and 5-6 membered heteroaryl is optionally substituted with one or more substituents independently selected from the group consisting of $R^4$, $OR^4$, $SR^4$, $S(O)R^4$, $SO_2R^4$, $C(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, and I. In another embodiment of Formula (I), $R^2$ is aryl; wherein each $R^2$ aryl is optionally substituted with one or more substituents independently selected from the group consisting of $R^4$, $OR^4$, $SO_2R^4$, F, Cl, and I. In another embodiment of Formula (I), $R^2$ is aryl; wherein each $R^2$ aryl is optionally substituted with one or more substituents independently selected from the group consisting of $R^4$, $OR^4$, and $SO_2R^4$. In another embodiment of Formula (I), $R^2$ is phenyl; wherein each $R^2$ phenyl is optionally substituted with one or more substituents independently selected from the group consisting of $R^4$, $OR^4$, and $SO_2R^4$.

In another embodiment of Formula (I), $R^2$ is 5-6 membered heteroaryl; wherein each $R^2$ 5-6 membered heteroaryl is optionally substituted with one or more substituents independently selected from the group consisting of $R^4$, $OR^4$, $SO_2R^4$, F, Cl, and I. In another embodiment of Formula (I), $R^2$ is 5-6 membered heteroaryl; wherein each $R^2$ 5-6 membered heteroaryl is optionally substituted with one or more substituents independently selected from the group consisting of $R^4$, $OR^4$, and $SO_2R^4$. In another embodiment of Formula (I), $R^2$ is furanyl or thiophenyl; wherein each $R^2$ furanyl and thiophenyl is optionally substituted with one or more substituents independently selected from the group consisting of $R^4$, $OR^4$, and $SO_2R^4$.

In one embodiment of Formula (I), $R^4$, at each occurrence, is independently selected from the group consisting of alkyl, alkenyl, alkynyl, aryl, heterocyclyl, cycloalkyl, and cycloalkenyl; wherein each $R^4$ alkyl, alkenyl, and alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, NHR⁷, N(R⁷)₂, NHC(O)R⁷, NR⁷C(O)R⁷, NHS(O)₂R⁷, NR⁷S(O)₂R⁷, NHC(O)OR⁷, NR⁷C(O)OR⁷, NHC(O)NH₂, NHC(O)NHR⁷, NHC(O)N(R⁷)₂, NR⁷C(O)NHR⁷, NR⁷C(O)N(R⁷)₂, C(O)NH₂, C(O)NHR⁷, C(O)N(R⁷)₂, C(O)NHOH, C(O)NHOR⁷, C(O)NHSO₂R⁷, C(O)NR⁷SO₂R⁷, SO₂NH₂, SO₂NHR⁷, SO₂N(R⁷)₂, C(O)H, C(O)OH, C(N)NH₂, C(N)NHR⁷, C(N)N(R⁷)₂, CNOH, CNOCH₃, OH, (O), CN, N₃, NO₂, F, Cl, Br and I. In another embodiment of Formula (I), R⁴, at each occurrence, is heterocyclyl.

In one embodiment of Formula (I), each R⁴ heterocyclyl is optionally substituted with one or more substituents independently selected from the group consisting of R¹⁰, OR¹⁰, SR¹⁰, S(O)R¹⁰, SO₂R¹⁰, C(O)R¹⁰, CO(O)R¹⁰, OC(O)R¹⁰, OC(O)OR¹⁰, NH₂, NHR¹⁰, N(R¹⁰)₂, NHC(O)R¹⁰, NR¹⁰C(O)R¹⁰, NHS(O)₂R¹⁰, NR¹⁰S(O)₂R¹⁰, NHC(O)OR¹⁰, NR¹⁰C(O)OR¹⁰, NHC(O)NH₂, NHC(O)NHR¹⁰, NHC(O)N(R¹⁰)₂, NR¹⁰C(O)NHR¹⁰, NR¹⁰C(O)N(R¹⁰)₂, C(O)NH₂, C(O)NHR¹⁰, C(O)N(R¹⁰)₂, C(O)NHOH, C(O)NHOR¹⁰, C(O)NHSO₂R¹⁰, C(O)NR¹⁰SO₂R¹⁰, SO₂NH₂, SO₂NHR¹⁰, SO₂N(R¹⁰)₂, C(O)H, C(O)OH, C(N)NH₂, C(N)NHR¹⁰, C(N)N(R¹⁰)₂, CNOH, CNOCH₃, OH, CN, N₃, NO₂, F, Cl, Br and I; R¹⁰, at each occurrence, is independently selected from the group consisting of alkyl, alkenyl, alkynyl, aryl, heterocyclyl, cycloalkyl, and cycloalkenyl; wherein each R¹⁰ alkyl, alkenyl, and alkynyl is optionally substituted with one or more substituents independently selected from the group consisting of R¹¹, OR¹¹, SR¹¹, S(O)R¹¹, SO₂R¹¹, C(O)R¹¹, CO(O)R¹¹, OC(O)R¹¹, OC(O)OR¹¹, NH₂, NHR¹¹, N(R¹¹)₂, NHC(O)R¹¹, NR¹¹C(O)R¹¹, NHS(O)₂R¹¹, NR¹¹S(O)₂R¹¹, NHC(O)OR¹¹, NR¹¹C(O)OR¹¹, NHC(O)NH₂, NHC(O)NHR¹¹, NHC(O)N(R¹¹)₂, NR¹¹C(O)NHR¹¹, NR¹¹C(O)N(R¹¹)₂, C(O)NH₂, C(O)NHR¹¹, C(O)N(R¹¹)₂, C(O)NHOH, C(O)NHOR¹¹, C(O)NHSO₂R¹¹, C(O)NR¹¹SO₂R¹¹, SO₂NH₂, SO₂NHR¹¹, SO₂N(R¹¹)₂, C(O)H, C(O)OH, C(N)NH₂, C(N)NHR¹¹, C(N)N(R¹¹)₂, CNOH, CNOCH₃, OH, (O), CN, N₃, NO₂, F, Cl, Br and I; wherein each R¹⁰ aryl, heterocyclyl, cycloalkyl, and cycloalkenyl is optionally substituted with one or more substituents independently selected from the group consisting of R¹², OR¹², SR¹², S(O)R¹², SO₂R¹², C(O)R¹², CO(O)R¹², OC(O)R¹², OC(O)OR¹², NH₂, NHR¹², N(R¹²)₂, NHC(O)R¹², NR¹²C(O)R¹², NHS(O)₂R¹², NR¹²S(O)₂R¹², NHC(O)OR¹², NR¹²C(O)OR¹², NHC(O)NH₂, NHC(O)NHR¹², NHC(O)N(R¹²)₂, NR¹²C(O)NHR¹², NR¹²C(O)N(R¹²)₂, C(O)NH₂, C(O)NHR¹², C(O)N(R¹²)₂, C(O)NHOH, C(O)NHOR¹², C(O)NHSO₂R¹², C(O)NR¹²SO₂R¹², SO₂NH₂, SO₂NHR¹², SO₂N(R¹²)₂, C(O)H, C(O)OH, C(N)NH₂, C(N)NHR¹², C(N)N(R¹²)₂, CNOH, CNOCH₃, OH, CN, N₃, NO₂, F, Cl, Br and I; R¹¹, at each occurrence, is independently selected from the group consisting of alkyl, alkenyl, alkynyl, aryl, heterocyclyl, cycloalkyl, and cycloalkenyl; wherein each R¹¹ alkyl, alkenyl, and alkynyl is optionally substituted with alkoxy; wherein each R¹¹ aryl, heterocyclyl, cycloalkyl, and cycloalkenyl is optionally substituted with alkyl or alkoxy; and R¹², at each occurrence, is independently selected alkyl. In another embodiment of Formula (I), each R⁴ heterocyclyl is optionally substituted with one or more substituents independently selected from the group consisting of R¹⁰, C(O)R¹⁰, CO(O)R¹⁰, C(O)C(O)R¹⁰, F, Cl, Br and I; R¹⁰, at each occurrence, is independently selected from the group consisting of alkyl, alkenyl, alkynyl, aryl, heterocyclyl, and cycloalkyl; wherein each R¹⁰ alkyl, alkenyl, and alkynyl, are optionally substituted with one or more substituents independently selected from the group consisting of R¹¹, OR¹¹, SR¹¹, SO₂R¹¹, NH₂, N(R¹¹)₂, NHC(O)R¹¹, NHS(O)₂R¹¹, OH, NO₂, and F; wherein each R¹⁰ aryl, heterocyclyl and cycloalkyl is optionally substituted with one or more substituents independently selected from the group consisting of R¹², OR¹², C(O)R¹², OH, CN, CF₃, OCF₃, F, and Cl; R¹¹, at each occurrence, is independently selected from the group consisting of alkyl, aryl, heterocyclyl, and cycloalkyl; wherein each R¹¹ alkyl is optionally substituted with alkoxy or aryl; wherein each R¹¹ aryl, and heterocyclyl is optionally substituted with one or more substituents independently selected from the group consisting of R¹³, C(O)OR¹³, OCF₃, CF₃, F, and Cl; R¹², at each occurrence, is independently selected from the group consisting of alkyl and aryl; and R¹³, at each occurrence, is independently selected from the group consisting of alkyl, and heterocyclyl.

One embodiment of this invention pertains to compounds or pharmaceutically acceptable salts thereof, which are useful as inhibitors of NAMPT, the compounds having Formula (I)

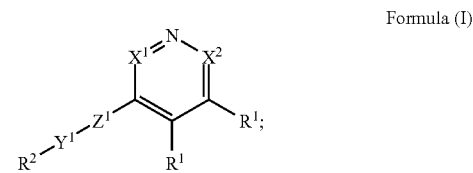

Formula (I)

wherein
X¹ is N and X² is CR¹; or
X¹ is CR¹ and X² is N; or
X¹ is CR¹ and X² is CR¹;
Y¹ is C(O)NH, or NHC(O);
Z¹ is

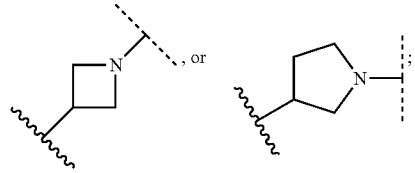

wherein ⁓ indicates the point of attachment to Y¹ and ⟍ indicates the point of attachment to the nitrogen containing heteroaryl;
R¹, at each occurrence, is independently selected from the group consisting of hydrogen, alkyl, haloalkyl, alkoxy, CN, and F;
R² is aryl or 5-6 membered heteroaryl wherein each R² aryl and 5-6 membered heteroaryl is optionally substituted with one or more substituents independently selected from the group consisting of R⁴, SO₂R⁴, and OR⁴;
R⁴, at each occurrence, is heterocyclyl;
wherein the cyclic moiety represented by R⁴ is independently optionally substituted with one or more substituents independently selected from the group consisting of R¹⁰, C(O)R¹⁰, C(O)C(O)R¹⁰, and CO(O)R¹⁰;
R¹⁰, at each occurrence, is independently selected from the group consisting of alkyl, alkenyl, alkynyl, aryl, heterocyclyl, and cycloalkyl; wherein each R¹⁰ alkyl is optionally substituted with one or more substituents independently selected from the group consisting of R¹¹, OR¹¹, SR¹¹, SO₂R¹¹, NH₂, N(R¹¹)₂, NHC(O)R¹¹, NHS(O)₂R¹¹, OH, NO₂, and F; wherein each R¹⁰ aryl, heterocyclyl and cycloalkyl is optionally substituted with one or more R¹², OR¹², C(O)R¹², OH, CN, CF₃, OCF₃, F, and Cl;
R¹¹, at each occurrence, is independently selected from the group consisting of alkyl, aryl, heterocyclyl, and cycloalkyl; wherein each R¹¹ alkyl is optionally substituted with alkoxy or aryl; wherein each $R^{11}$ aryl, and heterocyclyl is optionally substituted with one or more substituents independently selected from the group consisting of $R^{13}$, $C(O)OR^{13}$, $OCF_3$, $CF_3$, F, and Cl;

$R^{12}$, at each occurrence, is independently selected from the group consisting of alkyl, and aryl; and $R^{13}$, at each occurrence, is independently selected from the group consisting of alkyl, and heterocyclyl.

Still another embodiment pertains to compounds having Formula (I), which includes Examples 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, and pharmaceutically acceptable salts thereof.

Embodiments of Formula (II)

In another aspect, the present invention provides compounds of Formula (II)

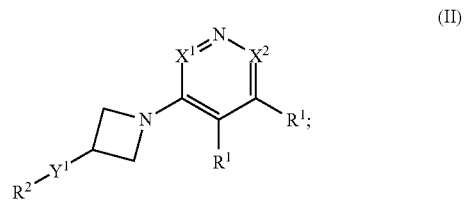

(II)

and pharmaceutically acceptable salts thereof; wherein $X^1$, $X^2$, $Y^1$, $R^1$, and $R^2$ are as described herein for Formula (I).

One embodiment of this invention pertains to compounds of Formula (II) and pharmaceutically acceptable salts thereof;
wherein
$X^1$ is N and $X^2$ is $CR^1$; or
$X^1$ is $CR^1$ and $X^2$ is N; or
$X^1$ is $CR^1$ and $X^2$ is $CR^1$;
$Y^1$ is C(O)NH, or NHC(O);
$R^1$, at each occurrence, is independently selected from the group consisting of hydrogen, alkyl, alkenyl, alkynyl, haloalkyl, hydroxyalkyl, alkoxy, OH, $NH_2$, CN, $NO_2$, F, Cl, Br and I;
$R^2$ is independently selected from the group consisting of $C_4$-$C_6$-alkyl, $C_4$-$C_6$-alkenyl, $C_4$-$C_6$-alkynyl, aryl, and 5-6 membered heteroaryl; wherein each $R^2C_4$-$C_6$-alkyl, $C_4$-$C_6$-alkenyl, and $C_4$-$C_6$-alkynyl is substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(N)NH_2$, $C(N)NHR^3$, $C(N)N(R^3)_2$, CNOH, $CNOCH_3$, OH, (O), CN, $N_3$, $NO_2$, F, Cl, Br and I;
wherein each $R^2$ aryl and 5-6 membered heteroaryl is optionally substituted with one or more substituents independently selected from the group consisting of $R^4$, $OR^4$, $SR^4$, $S(O)R^4$, $SO_2R^4$, $C(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, and I;
$R^3$, at each occurrence, is independently selected from the group consisting of alkyl, alkenyl, alkynyl, aryl, cycloalkyl, cycloalkenyl, and heterocyclyl; wherein each $R^3$ alkyl, alkenyl, and alkynyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, CNOH, $CNOCH_3$, OH, (O), CN, $N_3$, $NO_2$, F, Cl, Br and I;
wherein each $R^3$ aryl, cycloalkyl, cycloalkenyl, and heterocyclyl is optionally substituted with one or more substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $C(N)NH_2$, $C(N)NHR^6$, $C(N)N(R^6)_2$, $CNOH$, $CNOCH_3$, $OH$, $CN$, $N_3$, $NO_2$, F, Cl, Br and I;

$R^4$, at each occurrence, is independently selected from the group consisting of alkyl, alkenyl, alkynyl, aryl, heterocyclyl, cycloalkyl, and cycloalkenyl; wherein each $R^4$ alkyl, alkenyl, and alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, $CNOH$, $CNOCH_3$, $OH$, (O), $CN$, $N_3$, $NO_2$, F, Cl, Br and I;

$R^5$, at each occurrence, is independently selected from the group consisting of alkyl, alkenyl, alkynyl, aryl, heterocyclyl, cycloalkyl, and cycloalkenyl; wherein each $R^5$ alkyl, alkenyl, and alkynyl is optionally substituted with one or more substituents independently selected from the group consisting of $R^8$, $OR^8$, $SR^8$, $S(O)R^8$, $SO_2R^8$, $NHR^8$, $N(R^8)_2$, $C(O)R^8$, $C(O)NH_2$, $C(O)NHR^8$, $C(O)N(R^8)_2$, $NHC(O)R^8$, $NR^8C(O)R^8$, $NHSO_2R^8$, $NHC(O)OR^8$, $SO_2NH_2$, $SO_2NHR^8$, $SO_2N(R^8)_2$, $NHC(O)NH_2$, $NHC(O)NHR^8$, $OH$, (O), $C(O)OH$, $N_3$, $CN$, $NH_2$, F, Cl, Br and I;

$R^6$, at each occurrence, is independently selected from the group consisting of alkyl, alkenyl, alkynyl, aryl, heterocyclyl, cycloalkyl, and cycloalkenyl; wherein each $R^6$ alkyl, alkenyl, and alkynyl is optionally substituted with one or more substituents independently selected from the group consisting of $R^9$, $OR^9$, $SR^9$, $S(O)R^9$, $SO_2R^9$, $NHR^9$, $N(R^9)_2$, $C(O)R^9$, $C(O)NH_2$, $C(O)NHR^9$, $C(O)N(R^9)_2$, $NHC(O)R^9$, $NR^9C(O)R^9$, $NHSO_2R^9$, $NHC(O)OR^9$, $SO_2NH_2$, $SO_2NHR^9$, $SO_2N(R^9)_2$, $NHC(O)NH_2$, $NHC(O)NHR^9$, $OH$, (O), $C(O)OH$, $N_3$, $CN$, $NH_2$, $CF_3$, $CF_2CF_3$, F, Cl, Br and I;

$R^7$, at each occurrence, is independently selected from the group consisting of alkyl, alkenyl, alkynyl, aryl, heterocyclyl, cycloalkyl, and cycloalkenyl;

$R^8$, at each occurrence, is independently selected from the group consisting of alkyl, alkenyl, alkynyl, aryl, heterocyclyl, cycloalkyl, and cycloalkenyl;

$R^9$, at each occurrence, is independently selected from the group consisting of alkyl, alkenyl, alkynyl, aryl, heterocyclyl, cycloalkyl, and cycloalkenyl;

wherein the cyclic moieties represented by $R^4$, $R^5$, $R^6$, $R^7$, $R^8$, and $R^9$ are independently optionally substituted with one or more substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $C(O)C(O)R^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, $CNOH$, $CNOCH_3$, $OH$, $CN$, $N_3$, $NO_2$, F, Cl, Br and I;

$R^{10}$, at each occurrence, is independently selected from the group consisting of alkyl, alkenyl, alkynyl, aryl, heterocyclyl, cycloalkyl, and cycloalkenyl; wherein each $R^{10}$ alkyl, alkenyl, and alkynyl is optionally substituted with one or more substituents independently selected from the group consisting of $R^{11}$, $OR^{11}$, $SR^{11}$, $S(O)R^{11}$, $SO_2R^{11}$, $C(O)R^{11}$, $CO(O)R^{11}$, $OC(O)R^{11}$, $OC(O)OR^{11}$, $NH_2$, $NHR^{11}$, $N(R^{11})_2$, $NHC(O)R^{11}$, $NR^{11}C(O)R^{11}$, $NHS(O)_2R^{11}$, $NR^{11}S(O)_2R^{11}$, $NHC(O)OR^{11}$, $NR^{11}C(O)OR^{11}$, $NHC(O)NH_2$, $NHC(O)NHR^{11}$, $NHC(O)N(R^{11})_2$, $NR^{11}C(O)NHR^{11}$, $NR^{11}C(O)N(R^{11})_2$, $C(O)NH_2$, $C(O)NHR^{11}$, $C(O)N(R^{11})_2$, $C(O)NHOH$, $C(O)NHOR^{11}$, $C(O)NHSO_2R^{11}$, $C(O)NR^{11}SO_2R^{11}$, $SO_2NH_2$, $SO_2NHR^{11}$, $SO_2N(R^{11})_2$, $C(O)H$, $C(O)OH$, $C(N)NH_2$, $C(N)NHR^{11}$, $C(N)N(R^{11})_2$, $CNOH$, $CNOCH_3$, $OH$, (O), $CN$, $N_3$, $NO_2$, F, Cl, Br and I; wherein each $R^{10}$ aryl, heterocyclyl, cycloalkyl, and cycloalkenyl is optionally substituted with one or more substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, $C(N)NH_2$, $C(N)NHR^{12}$, $C(N)N(R^{12})_2$, $CNOH$, $CNOCH_3$, $OH$, $CN$, $N_3$, $NO_2$, $CF_3$, $OCF_3$, F, Cl, Br and I;

$R^{11}$, at each occurrence, is independently selected from the group consisting of alkyl, alkenyl, alkynyl, aryl, heterocyclyl, cycloalkyl, and cycloalkenyl; wherein each $R^{11}$ alkyl, alkenyl, and alkynyl is optionally substituted with alkoxy or aryl; wherein each $R^{11}$ aryl, heterocyclyl, cycloalkyl, and cycloalkenyl is optionally substituted with one or more substituents independently selected from the group consisting of $R^{13}$, $OR^{13}$, $C(O)OR^{13}$, $OCF_3$, $CF_3$, F, Cl, Br and I;

$R^{12}$, at each occurrence, is independently selected from the group consisting of alkyl, alkenyl, alkynyl, aryl, heterocyclyl, cycloalkyl, and cycloalkenyl; and $R^{13}$, at each occurrence, is independently selected from the group consisting of alkyl, alkyl, alkenyl, alkynyl, aryl, heterocyclyl, cycloalkyl, and cycloalkenyl.

In one embodiment of Formula (II), $X^1$ is N and $X^2$ is $CR^1$; or $X^1$ is $CR^1$ and $X^2$ is N; or $X^1$ is $CR^1$ and $X^2$ is $CR^1$. In another embodiment of Formula (II), $X^1$ is N and $X^2$ is $CR^1$.

In another embodiment of Formula (II), $X^1$ is $CR^1$ and $X^2$ is N. In another embodiment of Formula (II), $X^1$ is $CR^1$ and $X^2$ is $CR^1$.

In one embodiment of Formula (II), $R^1$, at each occurrence, is independently selected from the group consisting of hydrogen, alkyl, alkenyl, alkynyl, haloalkyl, hydroxyalkyl, alkoxy, OH, $NH_2$, CN, $NO_2$, F, Cl, Br and I. In another embodiment of Formula (II), $R^1$, at each occurrence, is independently selected from the group consisting of hydrogen, alkyl, haloalkyl, alkoxy, CN, F, Cl, Br and I. In another embodiment of Formula (II), $R^1$, at each occurrence, is independently selected from the group consisting of hydrogen, alkyl, haloalkyl, alkoxy, CN, and F. In another embodiment of Formula (II), $R^1$, at each occurrence, is hydrogen.

In one embodiment of Formula (II), $X^1$ is $CR^1$ and $X^2$ is $CR^1$; and $R^1$, at each occurrence, is independently selected from the group consisting of hydrogen, alkyl, alkenyl, alkynyl, haloalkyl, hydroxyalkyl, alkoxy, OH, $NH_2$, CN, $NO_2$, F, Cl, Br and I. In another embodiment of Formula (II), $X^1$ is $CR^1$ and $X^2$ is $CR^1$; and $R^1$, at each occurrence, is independently selected from the group consisting of hydrogen, alkyl, haloalkyl, alkoxy, CN, F, Cl, Br and I. In another embodiment of Formula (II), $X^1$ is $CR^1$ and $X^2$ is $CR^1$; and $R^1$, at each occurrence, is independently selected from the group consisting of hydrogen, alkyl, haloalkyl, alkoxy, CN, and F. In another embodiment of Formula (II), $X^1$ is $CR^1$ and $X^2$ is $CR^1$; and $R^1$, at each occurrence, is hydrogen.

In one embodiment of Formula (II), $Y^1$ is C(O)NH, or NHC(O). In another embodiment of Formula (II), $Y^1$ is C(O)NH. In another embodiment of Formula (II), $Y^1$ is NHC(O).

In one embodiment of Formula (II), $R^2$ is independently selected from the group consisting of $C_4$-$C_6$-alkyl, $C_4$-$C_6$-alkenyl, $C_4$-$C_6$-alkynyl, aryl, and 5-6 membered heteroaryl; wherein each $R^2$ $C_4$-$C_6$-alkyl, $C_4$-$C_6$-alkenyl, and $C_4$-$C_6$-alkynyl is substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(N)NH_2$, $C(N)NHR^3$, $C(N)N(R^3)_2$, $CNOH$, $CNOCH_3$, $OH$, $(O)$, $CN$, $N_3$, $NO_2$, $F$, $Cl$, $Br$ and $I$; wherein each $R^2$ aryl and 5-6 membered heteroaryl is optionally substituted with one or more substituents independently selected from the group consisting of $R^4$, $OR^4$, $SR^4$, $S(O)R^4$, $SO_2R^4$, $C(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, $CNOH$, $CNOCH_3$, $OH$, $CN$, $N_3$, $NO_2$, $F$, $Cl$, and $I$. In another embodiment of Formula (II), $R^2$ is aryl; wherein each $R^2$ aryl is optionally substituted with one or more substituents independently selected from the group consisting of $R^4$, $OR^4$, $SO_2R^4$, $F$, $Cl$, and $I$. In another embodiment of Formula (II), $R^2$ is aryl; wherein each $R^2$ aryl is optionally substituted with one or more substituents independently selected from the group consisting of $R^4$, $OR^4$, and $SO_2R^4$. In another embodiment of Formula (II), $R^2$ is phenyl; wherein each $R^2$ phenyl is optionally substituted with one or more substituents independently selected from the group consisting of $R^4$, $OR^4$, and $SO_2R^4$.

In another embodiment of Formula (II), $R^2$ is 5-6 membered heteroaryl; wherein each $R^2$ 5-6 membered heteroaryl is optionally substituted with one or more substituents independently selected from the group consisting of $R^4$, $OR^4$, $SO_2R^4$, $F$, $Cl$, and $I$. In another embodiment of Formula (II), $R^2$ is 5-6 membered heteroaryl; wherein each $R^2$ 5-6 membered heteroaryl is optionally substituted with one or more substituents independently selected from the group consisting of $R^4$, $OR^4$, and $SO_2R^4$. In another embodiment of Formula (II), $R^2$ is furanyl or thiophenyl; wherein each $R^2$ furanyl and thiophenyl is optionally substituted with one or more substituents independently selected from the group consisting of $R^4$, $OR^4$, and $SO_2R^4$.

In one embodiment of Formula (II), $R^4$, at each occurrence, is independently selected from the group consisting of alkyl, alkenyl, alkynyl, aryl, heterocyclyl, cycloalkyl, and cycloalkenyl; wherein each $R^4$ alkyl, alkenyl, and alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, $CNOH$, $CNOCH_3$, $OH$, $(O)$, $CN$, $N_3$, $NO_2$, $F$, $Cl$, $Br$ and $I$. In another embodiment of Formula (II), $R^4$, at each occurrence, is heterocyclyl.

In one embodiment of Formula (II), each $R^4$ heterocyclyl is optionally substituted with one or more substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, $CNOH$, $CNOCH_3$, $OH$, $CN$, $N_3$, $NO_2$, $F$, $Cl$, $Br$ and $I$; $R^{10}$, at each occurrence, is independently selected from the group consisting of alkyl, alkenyl, alkynyl, aryl, heterocyclyl, cycloalkyl, and cycloalkenyl; wherein each $R^{10}$ alkyl, alkenyl, and alkynyl is optionally substituted with one or more substituents independently selected from the group consisting of $R^{11}$, $OR^{11}$, $SR^{11}$, $S(O)R^{11}$, $SO_2R^{11}$, $C(O)R^{11}$, $CO(O)R^{11}$, $OC(O)R^{11}$, $OC(O)OR^{11}$, $NH_2$, $NHR^{11}$, $N(R^{11})_2$, $NHC(O)R^{11}$, $NR^{11}C(O)R^{11}$, $NHS(O)_2R^{11}$, $NR^{11}S(O)_2R^{11}$, $NHC(O)OR^{11}$, $NR^{11}C(O)OR^{11}$, $NHC(O)NH_2$, $NHC(O)NHR^{11}$, $NHC(O)N(R^{11})_2$, $NR^{11}C(O)NHR^{11}$, $NR^{11}C(O)N(R^{11})_2$, $C(O)NH_2$, $C(O)NHR^{11}$, $C(O)N(R^{11})_2$, $C(O)NHOH$, $C(O)NHOR^{11}$, $C(O)NHSO_2R^{11}$, $C(O)NR^{11}SO_2R^{11}$, $SO_2NH_2$, $SO_2NHR^{11}$, $SO_2N(R^{11})_2$, $C(O)H$, $C(O)OH$, $C(N)NH_2$, $C(N)NHR^{11}$, $C(N)N(R^{11})_2$, $CNOH$, $CNOCH_3$, $OH$, $(O)$, $CN$, $N_3$, $NO_2$, $F$, $Cl$, $Br$ and $I$; wherein each $R^{10}$ aryl, heterocyclyl, cycloalkyl, and cycloalkenyl is optionally substituted with one or more substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, $C(N)NH_2$, $C(N)NHR^{12}$, $C(N)N(R^{12})_2$, $CNOH$, $CNOCH_3$, $OH$, $CN$, $N_3$, $NO_2$, $F$, $Cl$, $Br$ and $I$; $R^{11}$, at each occurrence, is independently selected from the group consisting of alkyl, alkenyl, alkynyl, aryl, heterocyclyl, cycloalkyl, and cycloalkenyl; wherein each $R^{11}$ alkyl, alkenyl, and alkynyl is optionally substituted with alkoxy; wherein each $R^{11}$ aryl, heterocyclyl, cycloalkyl, and cycloalkenyl is optionally substituted with alkyl or alkoxy; and $R^{12}$, at each occurrence, is independently selected alkyl. In another embodiment of Formula (II), each $R^4$ heterocyclyl is optionally substituted with one or more substituents independently selected from the group consisting of $R^{10}$, $C(O)R^{10}$, $CO(O)R^{10}$, $C(O)C(O)R^{10}$, $F$, $Cl$, $Br$ and $I$; $R^{10}$, at each occurrence, is independently selected from the group consisting of alkyl, alkenyl, alkynyl, aryl, heterocyclyl, and cycloalkyl; wherein each $R^{10}$ alkyl, alkenyl, and alkynyl, are optionally substituted with one or more substituents independently selected from the group consisting of $R^{11}$, $PR^{11}$, $SR^{11}$, $SO_2R^{11}$, $NH_2$, $N(R^{11})_2$, $NHC(O)R^{11}$, $NHS(O)_2R^{11}$, $OH$, $NO_2$, and $F$; wherein each $R^{10}$ aryl, heterocyclyl and cycloalkyl is optionally substituted with one or more substituents independently selected from the group consisting of $R^{12}$, $OR^{12}$, $C(O)R^{12}$, $OH$, $CN$, $CF_3$, $OCF_3$, $F$, and $Cl$; $R^{11}$, at each occurrence, is independently selected from the group consisting of alkyl, aryl, heterocyclyl, and cycloalkyl; wherein each $R^{11}$ alkyl is optionally substituted with alkoxy or aryl; wherein each $R^{11}$ aryl, and heterocyclyl is optionally substituted with one or more substituents independently selected from the group consisting of $R^{13}$, C(O)$OR^{13}$, $OCF_3$, $CF_3$, F, and Cl; $R^{12}$, at each occurrence, is independently selected from the group consisting of alkyl and aryl; and $R^{13}$, at each occurrence, is independently selected from the group consisting of alkyl, and heterocyclyl.

One embodiment of this invention pertains to compounds or pharmaceutically acceptable salts thereof, which are useful as inhibitors of NAMPT, the compounds having Formula (II)

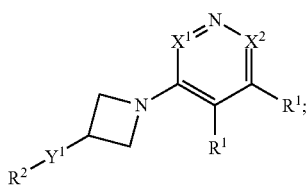

Formula (II)

wherein
$X^1$ is N and $X^2$ is $CR^1$; or
$X^1$ is $CR^1$ and $X^2$ is N; or
$X^1$ is $CR^1$ and $X^2$ is $CR^1$;
$Y^1$ is C(O)NH, or NHC(O);
$R^1$, at each occurrence, is independently selected from the group consisting of hydrogen, alkyl, haloalkyl, alkoxy, CN, and F;
$R^2$ is aryl or 5-6 membered heteroaryl wherein each $R^2$ aryl and 5-6 membered heteroaryl is optionally substituted with one or more substituents independently selected from the group consisting of $R^4$, $SO_2R^4$, and $OR^4$;
$R^4$, at each occurrence, is heterocyclyl;
wherein the cyclic moiety represented by $R^4$ is independently optionally substituted with one or more substituents independently selected from the group consisting of $R^{10}$, $C(O)R^{10}$, $C(O)C(O)R^{10}$, and $CO(O)R^{10}$;
$R^{10}$, at each occurrence, is independently selected from the group consisting of alkyl, alkenyl, alkynyl, aryl, heterocyclyl, and cycloalkyl; wherein each $R^{10}$ alkyl is optionally substituted with one or more substituents independently selected from the group consisting of $R^{11}$, $OR^{11}$, $SR^{11}$, $SO_2R^{11}$, $NH_2$, $N(R^{11})_2$, $NHC(O)R^{11}$, $NHS(O)_2R^{11}$, OH, $NO_2$, and F; wherein each $R^{10}$ aryl, heterocyclyl and cycloalkyl is optionally substituted with one or more $R^{12}$, $OR^{12}$, $C(O)R^{12}$, OH, CN, $CF_3$, $OCF_3$, F, and Cl;
$R^{11}$, at each occurrence, is independently selected from the group consisting of alkyl, aryl, heterocyclyl, and cycloalkyl; wherein each $R^{11}$ alkyl is optionally substituted with alkoxy or aryl; wherein each $R^{11}$ aryl, and heterocyclyl is optionally substituted with one or more substituents independently selected from the group consisting of $R^{13}$, $C(O)OR^{13}$, $OCF_3$, $CF_3$, F, and Cl;
$R^{12}$, at each occurrence, is independently selected from the group consisting of alkyl, and aryl; and
$R^{13}$, at each occurrence, is independently selected from the group consisting of alkyl, and heterocyclyl.

Still another embodiment pertains to compounds having Formula (II), which includes Examples 1, 2, 3, 4, 5, 6, 7, 10, 20, 21, 22, 23, 24, 25, 26, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 609, 610, 611, 612, 613, and pharmaceutically acceptable salts thereof.

Embodiments of Formula (III)

In another aspect, the present invention provides compounds of Formula (III)

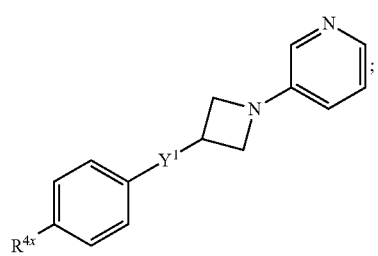

(III)

and pharmaceutically acceptable salts thereof; wherein $Y^1$ is as described in Formula (I) herein and $R^{4x}$ is as described herein for substituents on $R^2$ when $R^2$ is aryl in Formula (I).

One embodiment of this invention pertains to compounds of Formula (III) or pharmaceutically acceptable salts thereof;
wherein
$Y^1$ is C(O)NH, or NHC(O);
$R^{4x}$ is independently selected from the group consisting of $R^4$, $OR^4$, $SR^4$, $S(O)R^4$, $SO_2R^4$, $C(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, NHC (O)NHR$^4$, NHC(O)N(R$^4$)$_2$, NR$^4$C(O)NHR$^4$, NR$^4$C(O)N(R$^4$)$_2$, C(O)NH$_2$, C(O)NHR$^4$, C(O)N(R$^4$)$_2$, C(O)NHOH, C(O)NHOR$^4$, C(O)NHSO$_2$R$^4$, C(O)NR$^4$SO$_2$R$^4$, SO$_2$NH$_2$, SO$_2$NHR$^4$, SO$_2$N(R$^4$)$_2$, C(O)H, C(O)OH, C(N)NH$_2$, C(N)NHR$^4$, C(N)N(R$^4$)$_2$, CNOH, CNOCH$_3$, OH, CN, N$_3$, NO$_2$, F, Cl, and I;

R$^4$, at each occurrence, is independently selected from the group consisting of alkyl, alkenyl, alkynyl, aryl, heterocyclyl, cycloalkyl, and cycloalkenyl; wherein each R$^4$ alkyl, alkenyl, and alkynyl is optionally substituted with one or more substituents independently selected from the group consisting of R$^7$, OR$^7$, SR$^7$, S(O)R$^7$, SO$_2$R$^7$, C(O)R$^7$, CO(O)R$^7$, OC(O)R$^7$, OC(O)OR$^7$, NH$_2$, NHR$^7$, N(R$^7$)$_2$, NHC(O)R$^7$, NR$^7$C(O)R$^7$, NHS(O)$_2$R$^7$, NR$^7$S(O)$_2$R$^7$, NHC(O)OR$^7$, NR$^7$C(O)OR$^7$, NHC(O)NH$_2$, NHC(O)NHR$^7$, NHC(O)N(R$^7$)$_2$, NR$^7$C(O)NHR$^7$, NR$^7$C(O)N(R$^7$)$_2$, C(O)NH$_2$, C(O)NHR$^7$, C(O)N(R$^7$)$_2$, C(O)NHOH, C(O)NHOR$^7$, C(O)NHSO$_2$R$^7$, C(O)NR$^7$SO$_2$R$^7$, SO$_2$NH$_2$, SO$_2$NHR$^7$, SO$_2$N(R$^7$)$_2$, C(O)H, C(O)OH, C(N)NH$_2$, C(N)NHR$^7$, C(N)N(R$^7$)$_2$, CNOH, CNOCH$_3$, OH, (O), CN, N$_3$, NO$_2$, F, Cl, Br and I;

R$^7$, at each occurrence, is independently selected from the group consisting of alkyl, alkenyl, alkynyl, aryl, heterocyclyl, cycloalkyl, and cycloalkenyl;

wherein the cyclic moieties represented by R$^4$ and R$^7$ are independently optionally substituted with one or more substituents independently selected from the group consisting of R$^{10}$, OR$^{10}$, SR$^{10}$, S(O)R$^{10}$, SO$_2$R$^{10}$, C(O)R$^{10}$, CO(O)R$^{10}$, OC(O)R$^{10}$, OC(O)OR$^{10}$, C(O)C(O)R$^{10}$, NH$_2$, NHR$^{10}$, N(R$^{10}$)$_2$, NHC(O)R$^{10}$, NR$^{10}$C(O)R$^{10}$, NHS(O)$_2$R$^{10}$, NR$^{10}$S(O)$_2$R$^{10}$, NHC(O)OR$^{10}$, NR$^{10}$C(O)OR$^{10}$, NHC(O)NH$_2$, NHC(O)NHR$^{10}$, NHC(O)N(R$^{10}$)$_2$, NR$^{10}$C(O)NHR$^{10}$, NR$^{10}$C(O)N(R$^{10}$)$_2$, C(O)NH$_2$, C(O)NHR$^{10}$, C(O)N(R$^{10}$)$_2$, C(O)NHOH, C(O)NHOR$^{10}$, C(O)NHSO$_2$R$^{10}$, C(O)NR$^{10}$SO$_2$R$^{10}$, SO$_2$NH$_2$, SO$_2$NHR$^{10}$, SO$_2$N(R$^{10}$)$_2$, C(O)H, C(O)OH, C(N)NH$_2$, C(N)NHR$^{10}$, C(N)N(R$^{10}$)$_2$, CNOH, CNOCH$_3$, OH, CN, N$_3$, NO$_2$, F, Cl, Br and I;

R$^{10}$, at each occurrence, is independently selected from the group consisting of alkyl, alkenyl, alkynyl, aryl, heterocyclyl, cycloalkyl, and cycloalkenyl; wherein each R$^{10}$ alkyl, alkenyl, and alkynyl is optionally substituted with one or more substituents independently selected from the group consisting of R$^{11}$, OR$^{11}$, SR$^{11}$, S(O)R$^{11}$, SO$_2$R$^{11}$, C(O)R$^{11}$, CO(O)R$^{11}$, OC(O)R$^{11}$, OC(O)OR$^{11}$, NH$_2$, NHR$^{11}$, N(R$^{11}$)$_2$, NHC(O)R$^{11}$, NR$^{11}$C(O)R$^{11}$, NHS(O)$_2$R$^{11}$, NR$^{11}$S(O)$_2$R$^{11}$, NHC(O)OR$^{11}$, NR$^{11}$C(O)OR$^{11}$, NHC(O)NH$_2$, NHC(O)NHR$^{11}$, NHC(O)N(R$^{11}$)$_2$, NR$^{11}$C(O)NHR$^{11}$, NR$^{11}$C(O)N(R$^{11}$)$_2$, C(O)NH$_2$, C(O)NHR$^{11}$, C(O)N(R$^{11}$)$_2$, C(O)NHOH, C(O)NHOR$^{11}$, C(O)NHSO$_2$R$^{11}$, C(O)NR$^{11}$SO$_2$R$^{11}$, SO$_2$NH$_2$, SO$_2$NHR$^{11}$, SO$_2$N(R$^{11}$)$_2$, C(O)H, C(O)OH, C(N)NH$_2$, C(N)NHR$^{11}$, C(N)N(R$^{11}$)$_2$, CNOH, CNOCH$_3$, OH, (O), CN, N$_3$, NO$_2$, F, Cl, Br and I; wherein each R$^{10}$ aryl, heterocyclyl, cycloalkyl, and cycloalkenyl is optionally substituted with one or more substituents independently selected from the group consisting of R$^{12}$, OR$^{12}$, SR$^{12}$, S(O)R$^{12}$, SO$_2$R$^{12}$, C(O)R$^{12}$, CO(O)R$^{12}$, OC(O)R$^{12}$, OC(O)OR$^{12}$, NH$_2$, NHR$^{12}$, N(R$^{12}$)$_2$, NHC(O)R$^{12}$, NR$^{12}$C(O)R$^{12}$, NHS(O)$_2$R$^{12}$, NR$^{12}$S(O)$_2$R$^{12}$, NHC(O)OR$^{12}$, NR$^{12}$C(O)OR$^{12}$, NHC(O)NH$_2$, NHC(O)NHR$^{12}$, NHC(O)N(R$^{12}$)$_2$, NR$^{12}$C(O)NHR$^{12}$, NR$^{12}$C(O)N(R$^{12}$)$_2$, C(O)NH$_2$, C(O)NHR$^{12}$, C(O)N(R$^{12}$)$_2$, C(O)NHOH, C(O)NHOR$^{12}$, C(O)NHSO$_2$R$^{12}$, C(O)NR$^{12}$SO$_2$R$^{12}$, SO$_2$NH$_2$, SO$_2$NHR$^{12}$, SO$_2$N(R$^{12}$)$_2$, C(O)H, C(O)OH, C(N)NH$_2$, C(N)NHR$^{12}$, C(N)N(R$^{12}$)$_2$, CNOH, CNOCH$_3$, OH, CN, N$_3$, NO$_2$, CF$_3$, OCF$_3$, F, Cl, Br and I;

R$^{11}$, at each occurrence, is independently selected from the group consisting of alkyl, alkenyl, alkynyl, aryl, heterocyclyl, cycloalkyl, and cycloalkenyl; wherein each R$^{11}$ alkyl, alkenyl, and alkynyl is optionally substituted with alkoxy or aryl; wherein each R$^{11}$ aryl, heterocyclyl, cycloalkyl, and cycloalkenyl is optionally substituted with one or more substituents independently selected from the group consisting of R$^{13}$, OR$^{13}$, C(O)OR$^{13}$, OCF$_3$, CF$_3$, F, Cl, Br and I;

R$^{12}$, at each occurrence, is independently selected from the group consisting of alkyl, alkenyl, alkynyl, aryl, heterocyclyl, cycloalkyl, and cycloalkenyl; and R$^{13}$, at each occurrence, is independently selected from the group consisting of alkyl, alkyl, alkenyl, alkynyl, aryl, heterocyclyl, cycloalkyl, and cycloalkenyl.

In one embodiment of Formula (III), Y$^1$ is C(O)NH, or NHC(O). In another embodiment of Formula (III), Y$^1$ is C(O)NH. In another embodiment of Formula (III), Y$^1$ is NHC(O).

In one embodiment of Formula (III), R$^{4x}$ is selected from the group consisting of R$^4$, OR$^4$, SR$^4$, S(O)R$^4$, SO$_2$R$^4$, C(O)R$^4$, OC(O)OR$^4$, NH$_2$, NHR$^4$, N(R$^4$)$_2$, NHC(O)R$^4$, NR$^4$C(O)R$^4$, NHS(O)$_2$R$^4$, NR$^4$S(O)$_2$R$^4$, NHC(O)OR$^4$, NR$^4$C(O)OR$^4$, NHC(O)NH$_2$, NHC(O)NHR$^4$, NHC(O)N(R$^4$)$_2$, NR$^4$C(O)NHR$^4$, NR$^4$C(O)N(R$^4$)$_2$, C(O)NH$_2$, C(O)NHR$^4$, C(O)N(R$^4$)$_2$, C(O)NHOH, C(O)NHOR$^4$, C(O)NHSO$_2$R$^4$, C(O)NR$^4$SO$_2$R$^4$, SO$_2$NH$_2$, SO$_2$NHR$^4$, SO$_2$N(R$^4$)$_2$, C(O)H, C(O)OH, C(N)NH$_2$, C(N)NHR$^4$, C(N)N(R$^4$)$_2$, CNOH, CNOCH$_3$, OH, CN, N$_3$, NO$_2$, F, Cl, and I. In another embodiment of Formula (III), R$^{4x}$ is selected from the group consisting of R$^4$, OR$^4$, SO$_2$R$^4$, F, Cl, and I. In another embodiment of Formula (III), R$^{4x}$ is selected from the group consisting of R$^4$, SO$_2$R$^4$, and OR$^4$.

In one embodiment of Formula (III), R$^4$, at each occurrence, is independently selected from the group consisting of alkyl, alkenyl, alkynyl, aryl, heterocyclyl, cycloalkyl, and cycloalkenyl; wherein each R$^4$ alkyl, alkenyl, and alkynyl is optionally substituted with one or more substituents independently selected from the group consisting of R$^7$, OR$^7$, SR$^7$, S(O)R$^7$, SO$_2$R$^7$, C(O)R$^7$, CO(O)R$^7$, OC(O)R$^7$, OC(O)OR$^7$, NH$_2$, NHR$^7$, N(R$^7$)$_2$, NHC(O)R$^7$, NR$^7$C(O)R$^7$, NHS(O)$_2$R$^7$, NR$^7$S(O)$_2$R$^7$, NHC(O)OR$^7$, NR$^7$C(O)OR$^7$, NHC(O)NH$_2$, NHC(O)NHR$^7$, NHC(O)N(R$^7$)$_2$, NR$^7$C(O)NHR$^7$, NR$^7$C(O)N(R$^7$)$_2$, C(O)NH$_2$, C(O)NHR$^7$, C(O)N(R$^7$)$_2$, C(O)NHOH, C(O)NHOR$^7$, C(O)NHSO$_2$R$^7$, C(O)NR$^7$SO$_2$R$^7$, SO$_2$NH$_2$, SO$_2$NHR$^7$, SO$_2$N(R$^7$)$_2$, C(O)H, C(O)OH, C(N)NH$_2$, C(N)NHR$^7$, C(N)N(R$^7$)$_2$, CNOH, CNOCH$_3$, OH, (O), CN, N$_3$, NO$_2$, F, Cl, Br and I. In another embodiment of Formula (III), R$^4$, at each occurrence, is heterocyclyl.

In one embodiment of Formula (III), each R$^4$ heterocyclyl is optionally substituted with one or more substituents independently selected from the group consisting of R$^{10}$, OR$^{10}$, SR$^{10}$, S(O)R$^{10}$, SO$_2$R$^{10}$, C(O)R$^{10}$, CO(O)R$^{10}$, OC(O)R$^{10}$, OC(O)OR$^{10}$, NH$_2$, NHR$^{10}$, N(R$^{10}$)$_2$, NHC(O)R$^{10}$, NR$^{10}$C(O)R$^{10}$, NHS(O)$_2$R$^{10}$, NR$^{10}$S(O)$_2$R$^{10}$, NHC(O)OR$^{10}$, NR$^{10}$C(O)OR$^{10}$, NHC(O)NH$_2$, NHC(O)NHR$^{10}$, NHC(O)N(R$^{10}$)$_2$, NR$^{10}$C(O)NHR$^{10}$, NR$^{10}$C(O)N(R$^{10}$)$_2$, C(O)NH$_2$, C(O)NHR$^{10}$, C(O)N(R$^{10}$)$_2$, C(O)NHOH, C(O)NHOR$^{10}$, C(O)NHSO$_2$R$^{10}$, C(O)NR$^{10}$SO$_2$R$^{10}$, SO$_2$NH$_2$, SO$_2$NHR$^{10}$, SO$_2$N(R$^{10}$)$_2$, C(O)H, C(O)OH, C(N)NH$_2$, C(N)NHR$^{10}$, C(N)N(R$^{10}$)$_2$, CNOH, CNOCH$_3$, OH, CN, N$_3$, NO$_2$, F, Cl, Br and I; R$^{10}$, at each occurrence, is independently selected from the group consisting of alkyl, alkenyl, alkynyl, aryl, heterocyclyl, cycloalkyl, and cycloalkenyl; wherein each R$^{10}$ alkyl, alkenyl, and alkynyl is optionally substituted with one or more substituents independently selected from the group consisting of R$^{11}$, OR$^{11}$, SR$^{11}$, S(O)R$^{11}$, SO$_2$R$^{11}$, C(O)R$^{11}$, CO(O)R$^{11}$, OC(O)R$^{11}$, OC(O)OR$^{11}$, NH$_2$, NHR$^{11}$, N(R$^{11}$)$_2$, NHC(O)R$^{11}$, NR$^{11}$C(O)R$^{11}$, NHS(O)$_2$R$^{11}$, NR$^{11}$S(O)$_2$R$^{11}$, NHC(O)OR$^{11}$, NR$^{11}$C(O)OR$^{11}$, NHC(O)NH$_2$, NHC(O)NHR$^{11}$, NHC(O)N(R$^{11}$)$_2$, NR$^{11}$C(O)NHR$^{11}$, NR$^{11}$C(O)N(R$^{11}$)$_2$, C(O)NH$_2$, C(O)NHR$^{11}$, C(O)N(R$^{11}$)$_2$, C(O)NHOH, C(O)NHOR$^{11}$, C(O)NHSO$_2$R$^{11}$, C(O)NR$^{11}$SO$_2$R$^{11}$, $SO_2NH_2$, $SO_2NHR^{11}$, $SO_2N(R^{11})_2$, C(O)H, C(O)OH, C(N)$NH_2$, $C(N)NHR^{11}$, $C(N)N(R^{11})_2$, CNOH, $CNOCH_3$, OH, (O), CN, $N_3$, $NO_2$, F, Cl, Br and I; wherein each $R^{10}$ aryl, heterocyclyl, cycloalkyl, and cycloalkenyl is optionally substituted with one or more substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, C(O)NHOH, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, C(O)H, C(O)OH, $C(N)NH_2$, $C(N)NHR^{12}$, $C(N)N(R^{12})_2$, CNOH, $CNOCH_3$, OH, CN, $N_3$, $NO_2$, F, Cl, Br and I; $R^{11}$, at each occurrence, is independently selected from the group consisting of alkyl, alkenyl, alkynyl, aryl, heterocyclyl, cycloalkyl, and cycloalkenyl; wherein each $R^{11}$ alkyl, alkenyl, and alkynyl is optionally substituted with alkoxy; wherein each $R^{11}$ aryl, heterocyclyl, cycloalkyl, and cycloalkenyl is optionally substituted with alkyl or alkoxy; and $R^{12}$, at each occurrence, is independently selected alkyl. In another embodiment of Formula (III), each $R^4$ heterocyclyl is optionally substituted with one or more substituents independently selected from the group consisting of $R^{10}$, C(O)$R^{10}$, CO(O)$R^{10}$, C(O)C(O)$R^{10}$, F, Cl, Br and I; $R^{10}$, at each occurrence, is independently selected from the group consisting of alkyl, alkenyl, alkynyl, aryl, heterocyclyl, and cycloalkyl; wherein each $R^{10}$ alkyl, alkenyl, and alkynyl, are optionally substituted with one or more substituents independently selected from the group consisting of $R^{11}$, $OR^{11}$, $SR^{11}$, $SO_2R^{11}$, $NH_2$, $N(R^{11})_2$, $NHC(O)R^{11}$, $NHS(O)_2R^{11}$, OH, $NO_2$, and F; wherein each $R^{10}$ aryl, heterocyclyl and cycloalkyl is optionally substituted with one or more substituents independently selected from the group consisting of $R^{12}$, $OR^{12}$, $C(O)R^{12}$, OH, CN, $CF_3$, $OCF_3$, F, and Cl; $R^{11}$, at each occurrence, is independently selected from the group consisting of alkyl, aryl, heterocyclyl, and cycloalkyl; wherein each $R^{11}$ alkyl is optionally substituted with alkoxy or aryl; wherein each $R^{11}$ aryl, and heterocyclyl is optionally substituted with one or more substituents independently selected from the group consisting of $R^{13}$, $C(O)OR^{13}$, $OCF_3$, $CF_3$, F, and Cl; $R^{12}$, at each occurrence, is independently selected from the group consisting of alkyl and aryl; and $R^{13}$, at each occurrence, is independently selected from the group consisting of alkyl, and heterocyclyl.

One embodiment of this invention pertains to compounds or pharmaceutically acceptable salts thereof, which are useful as inhibitors of NAMPT, the compounds having Formula (III)

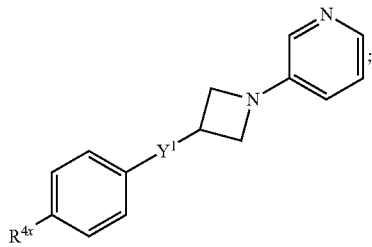

Formula (III)

wherein
$Y^1$ is C(O)NH, or NHC(O);
$R^{4x}$ is independently selected from the group consisting of $R^4$, $SO_2R^4$, and $OR^4$;
$R^4$, at each occurrence, is heterocyclyl;

wherein the cyclic moiety represented by $R^4$ is independently optionally substituted with one or more substituents independently selected from the group consisting of $R^{10}$, $C(O)R^{10}$, $C(O)C(O)R^{10}$, and $CO(O)R^{10}$;

$R^{10}$, at each occurrence, is independently selected from the group consisting of alkyl, alkenyl, alkynyl, aryl, heterocyclyl, and cycloalkyl; wherein each $R^{10}$ alkyl is optionally substituted with one or more substituents independently selected from the group consisting of $R^{11}$, $OR^{11}$, $SR^{11}$, $SO_2R^{11}$, $NH_2$, $N(R^{11})_2$, $NHC(O)R^{11}$, $NHS(O)_2R^{11}$, OH, $NO_2$, and F; wherein each $R^{10}$ aryl, heterocyclyl and cycloalkyl is optionally substituted with one or more $R^{12}$, $OR^{12}$, $C(O)R^{12}$, OH, CN, $CF_3$, $OCF_3$, F, and Cl;

$R^{11}$, at each occurrence, is independently selected from the group consisting of alkyl, aryl, heterocyclyl, and cycloalkyl; wherein each $R^{11}$ alkyl is optionally substituted with alkoxy or aryl; wherein each $R^{11}$ aryl, and heterocyclyl is optionally substituted with one or more substituents independently selected from the group consisting of $R^{13}$, $C(O)OR^{13}$, $OCF_3$, $CF_3$, F, and Cl;

$R^{12}$, at each occurrence, is independently selected from the group consisting of alkyl, and aryl; and $R^{13}$, at each occurrence, is independently selected from the group consisting of alkyl, and heterocyclyl.

Still another embodiment pertains to compounds having Formula (III), which includes Examples 1, 2, 3, 4, 5, 6, 7, 10, 20, 21, 22, 23, 24, 25, 26, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 602, 609, 610, and pharmaceutically acceptable salts thereof.

Embodiments of Formula (IV)

In another aspect, the present invention provides compounds of Formula (IV)

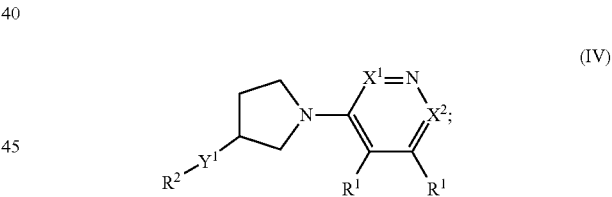

(IV)

and pharmaceutically acceptable salts thereof; wherein $X^1$, $X^2$, $Y^1$, $R^1$, and $R^2$ are as described herein for Formula (I).

One embodiment of this invention pertains to compounds of Formula (IV) and pharmaceutically acceptable salts thereof;

wherein
$X^1$ is N and $X^2$ is $CR^1$; or
$X^1$ is $CR^1$ and $X^2$ is N; or
$X^1$ is $CR^1$ and $X^2$ is $CR^1$;
$Y^1$ is C(O)NH, or NHC(O);

$R^1$, at each occurrence, is independently selected from the group consisting of hydrogen, alkyl, alkenyl, alkynyl, haloalkyl, hydroxyalkyl, alkoxy, OH, $NH_2$, CN, $NO_2$, F, Cl, Br and I;

$R^2$ is independently selected from the group consisting of $C_4$-$C_6$-alkyl, $C_4$-$C_6$-alkenyl, $C_4$-$C_6$-alkynyl, aryl, and 5-6 membered heteroaryl; wherein each $R^2C_4$-$C_6$-alkyl, $C_4$-$C_6$-alkenyl, and $C_4$-$C_6$-alkynyl is substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(N)NH_2$, $C(N)NHR^3$, $C(N)N(R^3)_2$, CNOH, $CNOCH_3$, OH, (O), CN, $N_3$, $NO_2$, F, Cl, Br and I; wherein each $R^2$ aryl and 5-6 membered heteroaryl is optionally substituted with one or more substituents independently selected from the group consisting of $R^4$, $OR^4$, $SR^4$, $S(O)R^4$, $SO_2R^4$, $C(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, and I;

$R^3$, at each occurrence, is independently selected from the group consisting of alkyl, alkenyl, alkynyl, aryl, cycloalkyl, cycloalkenyl, and heterocyclyl; wherein each $R^3$ alkyl, alkenyl, and alkynyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, CNOH, $CNOCH_3$, OH, (O), CN, $N_3$, $NO_2$, F, Cl, Br and I; wherein each $R^3$ aryl, cycloalkyl, cycloalkenyl, and heterocyclyl is optionally substituted with one or more substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $C(N)NH_2$, $C(N)NHR^6$, $C(N)N(R^6)_2$, CNOH, $CNOCH_3$, OH, CN, $N_3$, $NO_2$, F, Cl, Br and I;

$R^4$, at each occurrence, is independently selected from the group consisting of alkyl, alkenyl, alkynyl, aryl, heterocyclyl, cycloalkyl, and cycloalkenyl; wherein each $R^4$ alkyl, alkenyl, and alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, CNOH, $CNOCH_3$, OH, (O), CN, $N_3$, $NO_2$, F, Cl, Br and I;

$R^5$, at each occurrence, is independently selected from the group consisting of alkyl, alkenyl, alkynyl, aryl, heterocyclyl, cycloalkyl, and cycloalkenyl; wherein each $R^5$ alkyl, alkenyl, and alkynyl is optionally substituted with one or more substituents independently selected from the group consisting of $R^8$, $OR^8$, $SR^8$, $S(O)R^8$, $SO_2R^8$, $NHR^8$, $N(R^8)_2$, $C(O)R^8$, $C(O)NH_2$, $C(O)NHR^8$, $C(O)N(R^8)_2$, $NHC(O)R^8$, $NR^8C(O)R^8$, $NHSO_2R^8$, $NHC(O)OR^8$, $SO_2NH_2$, $SO_2NHR^8$, $SO_2N(R^8)_2$, $NHC(O)NH_2$, $NHC(O)NHR^8$, OH, (O), C(O)OH, $N_3$, CN, $NH_2$, F, Cl, Br and I;

$R^6$, at each occurrence, is independently selected from the group consisting of alkyl, alkenyl, alkynyl, aryl, heterocyclyl, cycloalkyl, and cycloalkenyl; wherein each $R^6$ alkyl, alkenyl, and alkynyl is optionally substituted with one or more substituents independently selected from the group consisting of $R^9$, $OR^9$, $SR^9$, $S(O)R^9$, $SO_2R^9$, $NHR^9$, $N(R^9)_2$, $C(O)R^9$, $C(O)NH_2$, $C(O)NHR^9$, $C(O)N(R^9)_2$, $NHC(O)R^9$, $NR^9C(O)R^9$, $NHSO_2R^9$, $NHC(O)OR^9$, $SO_2NH_2$, $SO_2NHR^9$, $SO_2N(R^9)_2$, $NHC(O)NH_2$, $NHC(O)NHR^9$, OH, (O), C(O)OH, $N_3$, CN, $NH_2$, $CF_3$, $CF_2CF_3$, F, Cl, Br and I;

$R^7$, at each occurrence, is independently selected from the group consisting of alkyl, alkenyl, alkynyl, aryl, heterocyclyl, cycloalkyl, and cycloalkenyl;

$R^8$, at each occurrence, is independently selected from the group consisting of alkyl, alkenyl, alkynyl, aryl, heterocyclyl, cycloalkyl, and cycloalkenyl;

$R^9$, at each occurrence, is independently selected from the group consisting of alkyl, alkenyl, alkynyl, aryl, heterocyclyl, cycloalkyl, and cycloalkenyl;

wherein the cyclic moieties represented by $R^4$, $R^5$, $R^6$, $R^7$, $R^8$, and $R^9$ are independently optionally substituted with one or more substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $C(O)C(O)R^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, CNOH, $CNOCH_3$, OH, CN, $N_3$, $NO_2$, F, Cl, Br and I;

$R^{10}$, at each occurrence, is independently selected from the group consisting of alkyl, alkenyl, alkynyl, aryl, heterocyclyl, cycloalkyl, and cycloalkenyl; wherein each $R^{10}$ alkyl, alkenyl, and alkynyl is optionally substituted with one or more substituents independently selected from the group consisting of $R^{11}$, $OR^{11}$, $SR^{11}$, $S(O)R^{11}$, $SO_2R^{11}$, $C(O)R^{11}$, $CO(O)R^{11}$, $OC(O)R^{11}$, $OC(O)OR^{11}$, $NH_2$, $NHR^{11}$, $N(R^{11})_2$, $NHC(O)R^{11}$, $NR^{11}C(O)R^{11}$, $NHS(O)_2R^{11}$, $NR^{11}S(O)_2R^{11}$, $NHC(O)OR^{11}$, $NR^{11}C(O)OR^{11}$, $NHC(O)NH_2$, $NHC(O)NHR^{11}$, $NHC(O)N(R^{11})_2$, $NR^{11}C(O)NHR^{11}$, $NR^{11}C(O)N(R^{11})_2$, $C(O)NH_2$, $C(O)NHR^{11}$, $C(O)N(R^{11})_2$, $C(O)NHOH$, $C(O)NHOR^{11}$, $C(O)NHSO_2R^{11}$, $C(O)NR^{11}SO_2R^{11}$, $SO_2NH_2$, $SO_2NHR^{11}$, $SO_2N(R^{11})_2$, $C(O)H$, $C(O)OH$, $C(N)NH_2$, $C(N)NHR^{11}$, $C(N)N(R^{11})_2$, CNOH, $CNOCH_3$, OH, (O), CN, $N_3$, $NO_2$, F, Cl, Br and I; wherein each $R^{10}$ aryl, heterocyclyl, cycloalkyl, and cycloalkenyl is optionally substituted with one or more substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, $C(N)NH_2$, $C(N)NHR^{12}$, $C(N)N(R^{12})_2$, CNOH, $CNOCH_3$, OH, CN, $N_3$, $NO_2$, $CF_3$, $OCF_3$, F, Cl, Br and I;

$R^{11}$, at each occurrence, is independently selected from the group consisting of alkyl, alkenyl, alkynyl, aryl, heterocyclyl, cycloalkyl, and cycloalkenyl; wherein each $R^{11}$ alkyl, alkenyl, and alkynyl is optionally substituted with alkoxy or aryl; wherein each $R^{11}$ aryl, heterocyclyl, cycloalkyl, and cycloalkenyl is optionally substituted with one or more substituents independently selected from the group consisting of $R^{13}$, $OR^{13}$, $C(O)OR^{13}$, $OCF_3$, $CF_3$, F, Cl, Br and I;

$R^{12}$, at each occurrence, is independently selected from the group consisting of alkyl, alkenyl, alkynyl, aryl, heterocyclyl, cycloalkyl, and cycloalkenyl; and $R^{13}$, at each occurrence, is independently selected from the group consisting of alkyl, alkyl, alkenyl, alkynyl, aryl, heterocyclyl, cycloalkyl, and cycloalkenyl.

In one embodiment of Formula (IV), $X^1$ is N and $X^2$ is $CR^1$; or $X^1$ is $CR^1$ and $X^2$ is N; or $X^1$ is $CR^1$ and $X^2$ is $CR^1$. In another embodiment of Formula (IV), $X^1$ is N and $X^2$ is $CR^1$. In another embodiment of Formula (IV), $X^1$ is $CR^1$ and $X^2$ is N. In another embodiment of Formula (IV), $X^1$ is $CR^1$ and $X^2$ is $CR^1$.

In one embodiment of Formula (IV), $R^1$, at each occurrence, is independently selected from the group consisting of hydrogen, alkyl, alkenyl, alkynyl, haloalkyl, hydroxyalkyl, alkoxy, OH, $NH_2$, CN, $NO_2$, F, Cl, Br and I. In another embodiment of Formula (IV), $R^1$, at each occurrence, is independently selected from the group consisting of hydrogen, alkyl, haloalkyl, alkoxy, CN, F, Cl, Br and I. In another embodiment of Formula (IV), $R^1$, at each occurrence, is independently selected from the group consisting of hydrogen, alkyl, haloalkyl, alkoxy, CN, and F. In another embodiment of Formula (IV), $R^1$, at each occurrence, is hydrogen.

In one embodiment of Formula (IV), $X^1$ is $CR^1$ and $X^2$ is $CR^1$; and $R^1$, at each occurrence, is independently selected from the group consisting of hydrogen, alkyl, alkenyl, alkynyl, haloalkyl, hydroxyalkyl, alkoxy, OH, $NH_2$, CN, $NO_2$, F, Cl, Br and I. In another embodiment of Formula (IV), $X^1$ is $CR^1$ and $X^2$ is $CR^1$; and $R^1$, at each occurrence, is independently selected from the group consisting of hydrogen, alkyl, haloalkyl, alkoxy, CN, F, Cl, Br and I. In another embodiment of Formula (IV), $X^1$ is $CR^1$ and $X^2$ is $CR^1$; and $R^1$, at each occurrence, is independently selected from the group consisting of hydrogen, alkyl, haloalkyl, alkoxy, CN, and F. In another embodiment of Formula (IV), $X^1$ is $CR^1$ and $X^2$ is $CR^1$; and $R^1$, at each occurrence, is hydrogen.

In one embodiment of Formula (IV), $Y^1$ is C(O)NH, or NHC(O). In another embodiment of Formula (IV), $Y^1$ is C(O)NH. In another embodiment of Formula (IV), $Y^1$ is NHC(O).

In one embodiment of Formula (IV), $R^2$ is independently selected from the group consisting of $C_4$-$C_6$-alkyl, $C_4$-$C_6$-alkenyl, $C_4$-$C_6$-alkynyl, aryl, and 5-6 membered heteroaryl; wherein each $R^2 C_4$-$C_6$-alkyl, $C_4$-$C_6$-alkenyl, and $C_4$-$C_6$-alkynyl is substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, C(O)H, C(O)OH, $C(N)NH_2$, $C(N)NHR^3$, $C(N)N(R^3)_2$, CNOH, $CNOCH_3$, OH, (O), CN, $N_3$, $NO_2$, F, Cl, Br and I; wherein each $R^2$ aryl and 5-6 membered heteroaryl is optionally substituted with one or more substituents independently selected from the group consisting of $R^4$, $OR^4$, $SR^4$, $S(O)R^4$, $SO_2R^4$, $C(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, C(O)H, C(O)OH, $C(N)NH_2$, $C(N)NHR^4$, $C(N)N(R^4)_2$, CNOH, $CNOCH_3$, OH, CN, $N_3$, $NO_2$, F, Cl, and I. In another embodiment of Formula (IV), $R^2$ is aryl; wherein each $R^2$ aryl is optionally substituted with one or more substituents independently selected from the group consisting of $R^4$, $OR^4$, $SO_2R^4$, F, Cl, and I. In another embodiment of Formula (IV), $R^2$ is aryl; wherein each $R^2$ aryl is optionally substituted with one or more substituents independently selected from the group consisting of $R^4$, $OR^4$, and $SO_2R^4$. In another embodiment of Formula (IV), $R^2$ is phenyl; wherein each $R^2$ phenyl is optionally substituted with one or more substituents independently selected from the group consisting of $R^4$, $OR^4$, and $SO_2R^4$.

In another embodiment of Formula (IV), $R^2$ is 5-6 membered heteroaryl; wherein each $R^2$ 5-6 membered heteroaryl is optionally substituted with one or more substituents independently selected from the group consisting of $R^4$, $OR^4$, $SO_2R^4$, F, Cl, and I. In another embodiment of Formula (IV), $R^2$ is 5-6 membered heteroaryl; wherein each $R^2$ 5-6 membered heteroaryl is optionally substituted with one or more substituents independently selected from the group consisting of $R^4$, $OR^4$, and $SO_2R^4$. In another embodiment of Formula (IV), $R^2$ is furanyl or thiophenyl; wherein each $R^2$ furanyl and thiophenyl is optionally substituted with one or more substituents independently selected from the group consisting of $R^4$, $OR^4$, and $SO_2R^4$.

In one embodiment of Formula (IV), $R^4$, at each occurrence, is independently selected from the group consisting of alkyl, alkenyl, alkynyl, aryl, heterocyclyl, cycloalkyl, and cycloalkenyl; wherein each $R^4$ alkyl, alkenyl, and alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, C(O)NHOH, $C(O)NHOR^7$, $C(O)NHSO_2R^7$, $C(O)NR^7SO_2R^7$, $SO_2NH_2$, $SO_2NHR^7$, $SO_2N(R^7)_2$, C(O)H, C(O)OH, $C(N)NH_2$, $C(N)NHR^7$, $C(N)N(R^7)_2$, CNOH, $CNOCH_3$, OH, (O), CN, $N_3$, $NO_2$, F, Cl, Br and I. In another embodiment of Formula (IV), $R^4$, at each occurrence, is heterocyclyl.

In one embodiment of Formula (IV), each $R^4$ heterocyclyl is optionally substituted with one or more substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, C(O)NHOH, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, C(O)H, C(O)OH, $C(N)NH_2$, $C(N)NHR^{10}$, $C(N)N(R^{10})_2$, CNOH, $CNOCH_3$, OH, CN, $N_3$, $NO_2$, F, Cl, Br and I; $R^{10}$, at each occurrence, is independently selected from the group consisting of alkyl, alkenyl, alkynyl, aryl, heterocyclyl, cycloalkyl, and cycloalkenyl; wherein each $R^{10}$ alkyl, alkenyl, and alkynyl is optionally substituted with one or more substituents independently selected from the group consisting of $R^{11}$, $OR^{11}$, $SR^{11}$, $S(O)R^{11}$, $SO_2R^{11}$, $C(O)R^{11}$, $CO(O)R^{11}$, $OC(O)R^{11}$, $OC(O)OR^{11}$, $NH_2$, $NHR^{11}$, $N(R^{11})_2$, $NHC(O)R^{11}$, $NR^{11}C(O)R^{11}$, $NHS(O)_2R^{11}$, $NR^{11}S(O)_2R^{11}$, $NHC(O)OR^{11}$, $NR^{11}C(O)OR^{11}$, $NHC(O)NH_2$, $NHC(O)NHR^{11}$, $NHC(O)N(R^{11})_2$, $NR^{11}C(O)NHR^{11}$, $NR^{11}C(O)N(R^{11})_2$, $C(O)NH_2$, $C(O)NHR^{11}$, $C(O)N(R^{11})_2$, C(O)NHOH, $C(O)NHOR^{11}$, $C(O)NHSO_2R^{11}$, $C(O)NR^{11}SO_2R^{11}$, $SO_2NH_2$, $SO_2NHR^{11}$, $SO_2N(R^{11})_2$, C(O)H, C(O)OH, $C(N)NH_2$, $C(N)NHR^{11}$, $C(N)N(R^{11})_2$, CNOH, $CNOCH_3$, OH, (O), CN, $N_3$, $NO_2$, F, Cl, Br and I; wherein each $R^{10}$ aryl, heterocyclyl, cycloalkyl, and cycloalkenyl is optionally substituted with one or more substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, $C(N)NH_2$, $C(N)NHR^{12}$, $C(N)N(R^{12})_2$, CNOH, $CNOCH_3$, OH, CN, $N_3$, $NO_2$, F, Cl, Br and I; $R^{11}$, at each occurrence, is independently selected from the group consisting of alkyl, alkenyl, alkynyl, aryl, heterocyclyl, cycloalkyl, and cycloalkenyl; wherein each $R^{11}$ alkyl, alkenyl, and alkynyl is optionally substituted with alkoxy; wherein each $R^{11}$ aryl, heterocyclyl, cycloalkyl, and cycloalkenyl is optionally substituted with alkyl or alkoxy; and $R^{12}$, at each occurrence, is independently selected alkyl. In another embodiment of Formula (IV), each $R^4$ heterocyclyl is optionally substituted with one or more substituents independently selected from the group consisting of $R^{10}$, $C(O)R^{10}$, $CO(O)R^{10}$, $C(O)C(O)R^{10}$, F, Cl, Br and I; $R^{10}$, at each occurrence, is independently selected from the group consisting of alkyl, alkenyl, alkynyl, aryl, heterocyclyl, and cycloalkyl; wherein each $R^{10}$ alkyl, alkenyl, and alkynyl, are optionally substituted with one or more substituents independently selected from the group consisting of $R^{11}$, $OR^{11}$, $SR^{11}$, $SO_2R^{11}$, $NH_2$, $N(R^{11})_2$, $NHC(O)R^{11}$, $NHS(O)_2R^{11}$, OH, $NO_2$, and F; wherein each $R^{10}$ aryl, heterocyclyl and cycloalkyl is optionally substituted with one or more substituents independently selected from the group consisting of $R^{12}$, $OR^{12}$, $C(O)R^{12}$, OH, CN, $CF_3$, $OCF_3$, F, and Cl; $R^{11}$, at each occurrence, is independently selected from the group consisting of alkyl, aryl, heterocyclyl, and cycloalkyl; wherein each $R^{11}$ alkyl is optionally substituted with alkoxy or aryl; wherein each $R^{11}$ aryl, and heterocyclyl is optionally substituted with one or more substituents independently selected from the group consisting of $R^{13}$, $C(O)OR^{13}$, $OCF_3$, $CF_3$, F, and Cl; $R^{12}$, at each occurrence, is independently selected from the group consisting of alkyl and aryl; and $R^{13}$, at each occurrence, is independently selected from the group consisting of alkyl, and heterocyclyl.

One embodiment of this invention pertains to compounds or pharmaceutically acceptable salts thereof, which are useful as inhibitors of NAMPT, the compounds having Formula (IV)

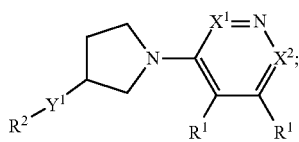

Formula (IV)

wherein
$X^1$ is N and $X^2$ is $CR^1$; or
$X^1$ is $CR^1$ and $X^2$ is N; or
$X^1$ is $CR^1$ and $X^2$ is $CR^1$;
$Y^1$ is C(O)NH, or NHC(O);
$R^1$, at each occurrence, is independently selected from the group consisting of hydrogen, alkyl, haloalkyl, alkoxy, CN, and F;
$R^2$ is aryl or 5-6 membered heteroaryl wherein each $R^2$ aryl and 5-6 membered heteroaryl is optionally substituted with one or more substituents independently selected from the group consisting of $R^4$, $SO_2R^4$, and $OR^4$;
$R^4$, at each occurrence, is heterocyclyl;
wherein the cyclic moiety represented by $R^4$ is independently optionally substituted with one or more substituents independently selected from the group consisting of $R^{10}$, $C(O)R^{10}$, $C(O)C(O)R^{10}$, and $CO(O)R^{10}$;
$R^{10}$, at each occurrence, is independently selected from the group consisting of alkyl, alkenyl, alkynyl, aryl, heterocyclyl, and cycloalkyl; wherein each $R^{10}$ alkyl is optionally substituted with one or more substituents independently selected from the group consisting of $R^{11}$, $OR^{11}$, $SR^{11}$, $SO_2R^{11}$, $NH_2$, $N(R^{11})_2$, $NHC(O)R^{11}$, $NHS(O)_2R^{11}$, OH, $NO_2$, and F; wherein each $R^{10}$ aryl, heterocyclyl and cycloalkyl is optionally substituted with one or more $R^{12}$, $OR^{12}$, $C(O)R^{12}$, OH, CN, $CF_3$, $OCF_3$, F, and Cl;
$R^{11}$, at each occurrence, is independently selected from the group consisting of alkyl, aryl, heterocyclyl, and cycloalkyl; wherein each $R^{11}$ alkyl is optionally substituted with alkoxy or aryl; wherein each $R^{11}$ aryl, and heterocyclyl is optionally substituted with one or more substituents independently selected from the group consisting of $R^{13}$, $C(O)OR^{13}$, $OCF_3$, $CF_3$, F, and Cl;
$R^{12}$, at each occurrence, is independently selected from the group consisting of alkyl, and aryl; and
$R^{13}$, at each occurrence, is independently selected from the group consisting of alkyl, and heterocyclyl;
with the proviso that
when $X^1$ is $CR^1$ and $X^2$ is $CR^1$; $R^1$ is hydrogen; $Y^1$ is NHC(O); and $R^2$ is pyrrolyl; the $R^2$ pyrrolyl is not substituted with two alkyl groups.

Still another embodiment pertains to compounds having Formula (IV), which includes Examples 8, 9, 11, 12, 13, 14, 15, 16, 17, 18, 19, 27, 28, 141, 142, 204, 310, 311, 312, 313, and pharmaceutically acceptable salts thereof.

Embodiments of Formula (IA)

One embodiment of this invention, therefore, pertains to compounds or pharmaceutically acceptable salts thereof, which are useful as inhibitors of NAMPT, the compounds having Formula (IA)

Formula (IA)

wherein
$X^1$ is N and $X^2$ is $CR^1$; or
$X^1$ is $CR^1$ and $X^2$ is N; or
$X^1$ is $CR^1$ and $X^2$ is $CR^1$;
$Y^1$ is C(O)NH, or NHC(O);
$Z^1$ is

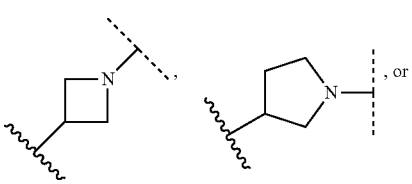

, or

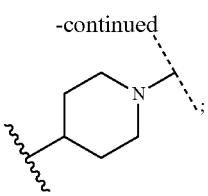

wherein ⌇ indicates the point of attachment to $Y^1$ and ⌇ indicates the point of attachment to the nitrogen containing heteroaryl;

$R^1$, at each occurrence, is independently selected from the group consisting of hydrogen, alkyl, alkenyl, alkynyl, haloalkyl, hydroxyalkyl, alkoxy, OH, $NH_2$, CN, $NO_2$, F, Cl, Br and I;

$R^2$ is independently selected from the group consisting of $C_4$-$C_6$-alkyl, $C_4$-$C_6$-alkenyl, $C_4$-$C_6$-alkynyl, aryl, and 5-6 membered heteroaryl; wherein each $R^2 C_4$-$C_6$-alkyl, $C_4$-$C_6$-alkenyl, and $C_4$-$C_6$-alkynyl is substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(N)NH_2$, $C(N)NHR^3$, $C(N)N(R^3)_2$, CNOH, $CNOCH_3$, OH, (O), CN, $N_3$, $NO_2$, F, Cl, Br and I; wherein each $R^2$ aryl and 5-6 membered heteroaryl is optionally substituted with one or more substituents independently selected from the group consisting of $R^4$, $OR^4$, $SR^4$, $S(O)R^4$, $SO_2R^4$, $C(O)R^4$, $OC(O)R^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, and I;

$R^3$, at each occurrence, is independently selected from the group consisting of alkyl, alkenyl, alkynyl, aryl, cycloalkyl, cycloalkenyl, and heterocyclyl; wherein each $R^3$ alkyl, alkenyl, and alkynyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, CNOH, $CNOCH_3$, OH, (O), CN, $N_3$, $NO_2$, F, Cl, Br and I; wherein each $R^3$ aryl, cycloalkyl, cycloalkenyl, and heterocyclyl is optionally substituted with one or more substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $C(N)NH_2$, $C(N)NHR^6$, $C(N)N(R^6)_2$, CNOH, $CNOCH_3$, OH, CN, $N_3$, $NO_2$, F, Cl, Br and I;

$R^4$, at each occurrence, is independently selected from the group consisting of alkyl, alkenyl, alkynyl, aryl, heterocyclyl, cycloalkyl, and cycloalkenyl; wherein each $R^4$ alkyl, alkenyl, and alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, CNOH, $CNOCH_3$, OH, (O), CN, $N_3$, $NO_2$, F, Cl, Br and I;

$R^5$, at each occurrence, is independently selected from the group consisting of alkyl, alkenyl, alkynyl, aryl, heterocyclyl, cycloalkyl, and cycloalkenyl; wherein each $R^5$ alkyl, alkenyl, and alkynyl is optionally substituted with one or more substituents independently selected from the group consisting of $R^8$, $OR^8$, $SR^8$, $S(O)R^8$, $SO_2R^8$, $NHR^8$, $N(R^8)_2$, $C(O)R^8$, $C(O)NH_2$, $C(O)NHR^8$, $C(O)N(R^8)_2$, $NHC(O)R^8$, $NR^8C(O)R^8$, $NHSO_2R^8$, $NHC(O)OR^8$, $SO_2NH_2$, $SO_2NHR^8$, $SO_2N(R^8)_2$, $NHC(O)NH_2$, $NHC(O)NHR^8$, OH, (O), $C(O)OH$, $N_3$, CN, $NH_2$, F, Cl, Br and I;

$R^6$, at each occurrence, is independently selected from the group consisting of alkyl, alkenyl, alkynyl, aryl, heterocyclyl, cycloalkyl, and cycloalkenyl; wherein each $R^6$ alkyl, alkenyl, and alkynyl is optionally substituted with one or more substituents independently selected from the group consisting of $R^9$, $OR^9$, $SR^9$, $S(O)R^9$, $SO_2R^9$, $NHR^9$, $N(R^9)_2$, $C(O)R^9$, $C(O)NH_2$, $C(O)NHR^9$, $C(O)N(R^9)_2$, $NHC(O)R^9$, $NR^9C(O)R^9$, $NHSO_2R^9$, $NHC(O)OR^9$, $SO_2NH_2$, $SO_2NHR^9$, $SO_2N(R^9)_2$, $NHC(O)NH_2$, $NHC(O)NHR^9$, OH, (O), $C(O)OH$, $N_3$, CN, $NH_2$, $CF_3$, $CF_2CF_3$, F, Cl, Br and I;

$R^7$, at each occurrence, is independently selected from the group consisting of alkyl, alkenyl, alkynyl, aryl, heterocyclyl, cycloalkyl, and cycloalkenyl;

$R^8$, at each occurrence, is independently selected from the group consisting of alkyl, alkenyl, alkynyl, aryl, heterocyclyl, cycloalkyl, and cycloalkenyl;

$R^9$, at each occurrence, is independently selected from the group consisting of alkyl, alkenyl, alkynyl, aryl, heterocyclyl, cycloalkyl, and cycloalkenyl;

wherein the cyclic moieties represented by $R^4$, $R^5$, $R^6$, $R^7$, $R^8$, and $R^9$ are independently optionally substituted with one or more substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $C(O)C(O)R^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, CNOH, $CNOCH_3$, OH, CN, $N_3$, $NO_2$, F, Cl, Br and I;

$R^{10}$, at each occurrence, is independently selected from the group consisting of alkyl, alkenyl, alkynyl, aryl, heterocyclyl, cycloalkyl, and cycloalkenyl; wherein each $R^{10}$ alkyl, alkenyl, and alkynyl is optionally substituted with one or more substituents independently selected from the group consisting of $R^{11}$, $OR^{11}$, $SR^{11}$, $S(O)R^{11}$, $SO_2R^{11}$, $C(O)R^{11}$, $CO(O)R^{11}$, $OC(O)R^{11}$, $OC(O)OR^{11}$, $NH_2$, $NHR^{11}$, $N(R^{11})_2$, $NHC(O)R^{11}$, $NR^{11}C(O)R^{11}$, $NHS(O)_2R^{11}$, $NR^{11}S(O)_2R^{11}$, $NHC(O)OR^{11}$, $NR^{11}C(O)OR^{11}$, $NHC(O)NH_2$, $NHC(O)NHR^{11}$, $NHC(O)N(R^{11})_2$, $NR^{11}C(O)NHR^{11}$, $NR^{11}C(O)N(R^{11})_2$, $C(O)NH_2$, $C(O)NHR^{11}$, $C(O)N(R^{11})_2$, $C(O)NHOH$, $C(O)N$-

HOR$^{11}$, C(O)NHSO$_2$R$^{11}$, C(O)NR$^{11}$SO$_2$R$^{11}$, SO$_2$NH$_2$, SO$_2$NHR$^{11}$, SO$_2$N(R$^{11}$)$_2$, C(O)H, C(O)OH, C(N)NH$_2$, C(N)NHR$^{11}$, C(N)N(R$^{11}$)$_2$, CNOH, CNOCH$_3$, OH, (O), CN, N$_3$, NO$_2$, F, Cl, Br and I; wherein each R$^{10}$ aryl, heterocyclyl, cycloalkyl, and cycloalkenyl is optionally substituted with one or more substituents independently selected from the group consisting of R$^{12}$, OR$^{12}$, SR$^{12}$, S(O)R$^{12}$, SO$_2$R$^{12}$, C(O)R$^{12}$, CO(O)R$^{12}$, OC(O)R$^{12}$, OC(O)OR$^{12}$, NH$_2$, NHR$^{12}$, N(R$^{12}$)$_2$, NHC(O)R$^{12}$, NR$^{12}$C(O)R$^{12}$, NHS(O)$_2$R$^{12}$, NR$^{12}$S(O)$_2$R$^{12}$, NHC(O)OR$^{12}$, NR$^{12}$C(O)OR$^{12}$, NHC(O)NH$_2$, NHC(O)NHR$^{12}$, NHC(O)N(R$^{12}$)$_2$, NR$^{12}$C(O)NHR$^{12}$, NR$^{12}$C(O)N(R$^{12}$)$_2$, C(O)NH$_2$, C(O)NHR$^{12}$, C(O)N(R$^{12}$)$_2$, C(O)NHOH, C(O)NHOR$^{12}$, C(O)NHSO$_2$R$^{12}$, C(O)NR$^{12}$SO$_2$R$^{12}$, SO$_2$NH$_2$, SO$_2$NHR$^{12}$, SO$_2$N(R$^{12}$)$_2$, C(O)H, C(O)OH, C(N)NH$_2$, C(N)NHR$^{12}$, C(N)N(R$^{12}$)$_2$, CNOH, CNOCH$_3$, OH, CN, N$_3$, NO$_2$, CF$_3$, OCF$_3$, F, Cl, Br and I;

R$^{11}$, at each occurrence, is independently selected from the group consisting of alkyl, alkenyl, alkynyl, aryl, heterocyclyl, cycloalkyl, and cycloalkenyl; wherein each R$^{11}$ alkyl, alkenyl, and alkynyl is optionally substituted with alkoxy or aryl; wherein each R$^{11}$ aryl, heterocyclyl, cycloalkyl, and cycloalkenyl is optionally substituted with one or more substituents independently selected from the group consisting of R$^{13}$, OR$^{13}$, C(O)OR$^{13}$, OCF$_3$, CF$_3$, F, Cl, Br and I;

R$^{12}$, at each occurrence, is independently selected from the group consisting of alkyl, alkenyl, alkynyl, aryl, heterocyclyl, cycloalkyl, and cycloalkenyl; and R$^{13}$, at each occurrence, is independently selected from the group consisting of alkyl, haloalkyl, alkenyl, alkynyl, aryl, heterocyclyl, cycloalkyl, and cycloalkenyl;

with the proviso that when X$^1$ is CR$^1$ and X$^2$ is CR$^1$; R$^1$ is hydrogen; Y$^1$ is NHC(O); Z$^1$ is

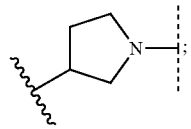

and R$^2$ is pyrrolyl; the R$^2$ pyrrolyl is not substituted with two alkyl groups.

In one embodiment of Formula (IA), X$^1$ is N and X$^2$ is CR$^1$; or X$^1$ is CR$^1$ and X$^2$ is N; or X$^1$ is CR$^1$ and X$^2$ is CR$^1$. In another embodiment of Formula (IA), X$^1$ is N and X$^2$ is CR$^1$. In another embodiment of Formula (IA), X$^1$ is CR$^1$ and X$^2$ is N. In another embodiment of Formula (IA), X$^1$ is CR$^1$ and X$^2$ is CR$^1$.

In one embodiment of Formula (IA), R$^1$, at each occurrence, is independently selected from the group consisting of hydrogen, alkyl, alkenyl, alkynyl, haloalkyl, hydroxyalkyl, alkoxy, OH, NH$_2$, CN, NO$_2$, F, Cl, Br and I. In another embodiment of Formula (IA), R$^1$, at each occurrence, is independently selected from the group consisting of hydrogen, alkyl, haloalkyl, alkoxy, CN, F, Cl, Br and I. In another embodiment of Formula (IA), R$^1$, at each occurrence, is independently selected from the group consisting of hydrogen, alkyl, haloalkyl, alkoxy, CN, F, and Cl. In another embodiment of Formula (IA), R$^1$, at each occurrence, is hydrogen.

In one embodiment of Formula (IA), X$^1$ is CR$^1$ and X$^2$ is CR$^1$; and R$^1$, at each occurrence, is independently selected from the group consisting of hydrogen, alkyl, alkenyl, alkynyl, haloalkyl, hydroxyalkyl, alkoxy, OH, NH$_2$, CN, NO$_2$, F, Cl, Br and I. In another embodiment of Formula (IA), X$^1$ is CR$^1$ and X$^2$ is CR$^1$; and R$^1$, at each occurrence, is independently selected from the group consisting of hydrogen, alkyl, haloalkyl, alkoxy, CN, F, Cl, Br and I. In another embodiment of Formula (IA), X$^1$ is CR$^1$ and X$^2$ is CR$^1$; and R$^1$, at each occurrence, is independently selected from the group consisting of hydrogen, alkyl, haloalkyl, alkoxy, CN, F, and Cl. In another embodiment of Formula (IA), X$^1$ is CR$^1$ and X$^2$ is CR$^1$; and R$^1$, at each occurrence, is hydrogen.

In one embodiment of Formula (IA), Y$^1$ is C(O)NH, or NHC(O). In another embodiment of Formula (IA), Y$^1$ is C(O)NH. In another embodiment of Formula (IA), Y$^1$ is NHC(O).

In one embodiment of Formula (IA), Z$^1$ is

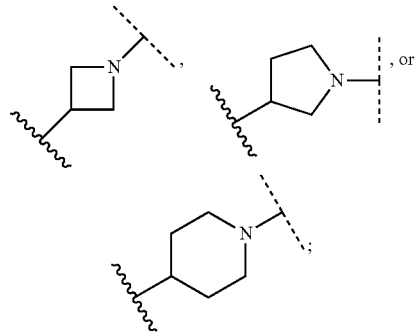

wherein ⁓ indicates the point of attachment to Y$^1$ and ⬉ indicates the point of attachment to the nitrogen containing heteroaryl. In another embodiment of Formula (IA), Z$^1$ is

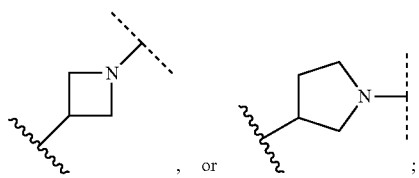

wherein ⁓ indicates the point of attachment to Y$^1$ and ⬉ indicates the point of attachment to the nitrogen containing heteroaryl. In another embodiment of Formula (IA), Z$^1$ is

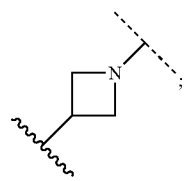

wherein ⁓ indicates the point of attachment to Y$^1$ and ⬉ indicates the point of attachment to the nitrogen containing heteroaryl. In another embodiment of Formula (IA), Z$^1$ is

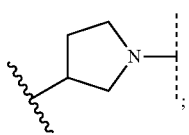

wherein ⁓ indicates the point of attachment to Y$^1$ and ⬉ indicates the point of attachment to the nitrogen containing heteroaryl. In another embodiment of Formula (IA), Z$^1$ is

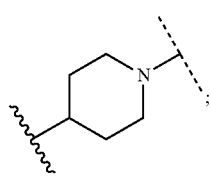

wherein ∼ indicates the point of attachment to $Y^1$ and ∖ indicates the point of attachment to the nitrogen containing heteroaryl.

In one embodiment of Formula (IA), $R^2$ is independently selected from the group consisting of $C_4$-$C_6$-alkyl, $C_4$-$C_6$-alkenyl, $C_4$-$C_6$-alkynyl, aryl, and 5-6 membered heteroaryl; wherein each $R^2C_4$-$C_6$-alkyl, $C_4$-$C_6$-alkenyl, and $C_4$-$C_6$-alkynyl is substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(N)NH_2$, $C(N)NHR^3$, $C(N)N(R^3)_2$, $CNOH$, $CNOCH_3$, $OH$, $(O)$, $CN$, $N_3$, $NO_2$, F, Cl, Br and I; wherein each $R^2$ aryl and 5-6 membered heteroaryl is optionally substituted with one or more substituents independently selected from the group consisting of $R^4$, $OR^4$, $SR^4$, $S(O)R^4$, $SO_2R^4$, $C(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, $CNOH$, $CNOCH_3$, $OH$, $CN$, $N_3$, $NO_2$, F, Cl, and I. In another embodiment of Formula (IA), $R^2$ is aryl; wherein each $R^2$ aryl is optionally substituted with one or more substituents independently selected from the group consisting of $R^4$, $OR^4$, $SO_2R^4$, F, Cl, and I. In another embodiment of Formula (IA), $R^2$ is aryl; wherein each $R^2$ aryl is optionally substituted with one or more substituents independently selected from the group consisting of $R^4$, $OR^4$, $SO_2R^4$, and F. In another embodiment of Formula (IA), $R^2$ is phenyl; wherein each $R^2$ phenyl is optionally substituted with one or more substituents independently selected from the group consisting of $R^4$, $OR^4$, $SO_2R^4$, and F. In another embodiment of Formula (IA), $R^2$ is phenyl; wherein each $R^2$ phenyl is substituted with one substituent independently selected from the group consisting of $R^4$, $OR^4$, and $SO_2R^4$.

In another embodiment of Formula (IA), $R^2$ is 5-6 membered heteroaryl; wherein each $R^2$ 5-6 membered heteroaryl is optionally substituted with one or more substituents independently selected from the group consisting of $R^4$, $OR^4$, $SO_2R^4$, F, Cl, and I. In another embodiment of Formula (IA), $R^2$ is 5-6 membered heteroaryl; wherein each $R^2$ 5-6 membered heteroaryl is optionally substituted with one or more substituents independently selected from the group consisting of $R^4$, $OR^4$, $SO_2R^4$, and F. In another embodiment of Formula (IA), $R^2$ is furanyl or thiophenyl; wherein each $R^2$ furanyl and thiophenyl is optionally substituted with one or more substituents independently selected from the group consisting of $R^4$, $OR^4$, $SO_2R^4$, and F.

In one embodiment of Formula (IA), $R^4$, at each occurrence, is independently selected from the group consisting of alkyl, alkenyl, alkynyl, aryl, heterocyclyl, cycloalkyl, and cycloalkenyl; wherein each $R^4$ alkyl, alkenyl, and alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, $CNOH$, $CNOCH_3$, $OH$, $(O)$, $CN$, $N_3$, $NO_2$, F, Cl, Br and I. In another embodiment of Formula (IA), $R^4$, at each occurrence, is alkyl or heterocyclyl.

In one embodiment of Formula (IA), each $R^4$ alkyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, $CNOH$, $CNOCH_3$, $OH$, $(O)$, $CN$, $N_3$, $NO_2$, F, Cl, Br and I. In another embodiment of Formula (IA), each $R^4$ alkyl is optionally substituted with one $R^7$.

In one embodiment of Formula (IA), $R^7$, at each occurrence, is independently selected from the group consisting of alkyl, alkenyl, alkynyl, aryl, heterocyclyl, cycloalkyl, and cycloalkenyl. In another embodiment of Formula (IA), $R^7$, at each occurrence, is heterocyclyl.

In one embodiment of Formula (IA), each $R^4$ and $R^7$ heterocyclyl is independently optionally substituted with one or more substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, $CNOH$, $CNOCH_3$, $OH$, $CN$, $N_3$, $NO_2$, F, Cl, Br and I; $R^{10}$, at each occurrence, is independently selected from the group consisting of alkyl, alkenyl, alkynyl, aryl, heterocyclyl, cycloalkyl, and cycloalkenyl; wherein each $R^{10}$ alkyl, alkenyl, and alkynyl is optionally substituted with one or more substituents independently selected from the group consisting of $R^{11}$, $OR^{11}$, $SR^{11}$, $S(O)R^{11}$, $SO_2R^{11}$, $C(O)R^{11}$, $CO(O)R^{11}$, $OC(O)R^{11}$, $OC(O)OR^{11}$, $NH_2$, $NHR^{11}$, $N(R^{11})_2$, $NHC(O)R^{11}$, $NR^{11}C(O)R^{11}$, $NHS(O)_2R^{11}$, $NR^{11}S(O)_2R^{11}$, $NHC(O)OR^{11}$, $NR^{11}C(O)OR^{11}$, $NHC(O)NH_2$, $NHC(O)NHR^{11}$, $NHC(O)N(R^{11})_2$, $NR^{11}C(O)NHR^{11}$, $NR^{11}C(O)N(R^{11})_2$, $C(O)NH_2$, $C(O)NHR^{11}$, $C(O)N(R^{11})_2$, $C(O)NHOH$, $C(O)NHOR^{11}$, $C(O)NHSO_2R^{11}$, $C(O)NR^{11}SO_2R^{11}$, $SO_2NH_2$, $SO_2NHR^{11}$, $SO_2N(R^{11})_2$, $C(O)H$, $C(O)OH$, $C(N)NH_2$, $C(N)NHR^{11}$, $C(N)N(R^{11})_2$, $CNOH$, $CNOCH_3$, $OH$, $(O)$, $CN$, $N_3$, $NO_2$, F, Cl, Br and I; wherein each $R^{10}$ aryl, heterocyclyl, cycloalkyl, and cycloalkenyl is optionally substituted with one or more substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, $C(N)NH_2$, $C(N)NHR^{12}$, $C(N)N(R^{12})_2$, $CNOH$, $CNOCH_3$, $OH$, $CN$, $N_3$, $NO_2$, F, Cl, Br and I; $R^{11}$, at each occurrence, is independently selected from the group consisting of alkyl, alkenyl, alkynyl, aryl, heterocyclyl, cycloalkyl, and cycloalkenyl; wherein each $R^{11}$ alkyl, alkenyl, and alkynyl is optionally substituted with alkoxy or aryl; wherein each $R^{11}$ aryl, heterocyclyl, cycloalkyl, and cycloalkenyl is optionally substituted with one or more substituents independently selected from the group consisting of $R^{13}$, $OR^{13}$, $C(O)OR^{13}$, $OCF_3$, $CF_3$, F, Cl, Br and I; $R^{12}$, at each occurrence, is independently selected from the group consisting of alkyl, alkenyl, alkynyl, aryl, heterocyclyl, cycloalkyl, and cycloalkenyl; and $R^{13}$, at each occurrence, is independently selected from the group consisting of alkyl, haloalkyl, alkenyl, alkynyl, aryl, heterocyclyl, cycloalkyl, and cycloalkenyl.

In another embodiment of Formula (IA), each $R^4$ and $R^7$ heterocyclyl is independently optionally substituted with one or more substituents independently selected from the group consisting of $R^{10}$, $C(O)R^{10}$, $CO(O)R^{10}$, $C(O)C(O)R^{10}$, OH, F, Cl, Br and I; $R^{10}$, at each occurrence, is independently selected from the group consisting of alkyl, alkenyl, alkynyl, aryl, heterocyclyl, and cycloalkyl; wherein each $R^{10}$ alkyl, alkenyl, and alkynyl, are optionally substituted with one or more substituents independently selected from the group consisting of $R^{11}$, $OR^{11}$, $SR^{11}$, $SO_2R^{11}$, $NH_2$, $N(R^{11})_2$, $NHC(O)R^{11}$, $NHS(O)_2R^{11}$, OH, $NO_2$, and F; wherein each $R^{10}$ aryl, heterocyclyl and cycloalkyl is optionally substituted with one or more substituents independently selected from the group consisting of $R^{12}$, $OR^{12}$, $C(O)R^{12}$, OH, CN, $CF_3$, $OCF_3$, F, and Cl; $R^{11}$, at each occurrence, is independently selected from the group consisting of alkyl, aryl, heterocyclyl, and cycloalkyl; wherein each $R^{11}$ alkyl is optionally substituted with alkoxy or aryl; wherein each $R^{11}$ aryl and heterocyclyl is optionally substituted with one or more substituents independently selected from the group consisting of $R^{13}$, $CF_3$, F, and Cl; $R^{12}$, at each occurrence, is independently selected from the group consisting of alkyl and aryl; and $R^{13}$, at each occurrence, is independently selected from the group consisting of alkyl and haloalkyl.

One embodiment of this invention pertains to compounds or pharmaceutically acceptable salts thereof, which are useful as inhibitors of NAMPT, the compounds having Formula (IA)

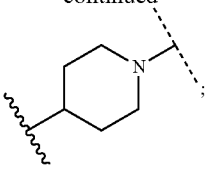

Formula (IA)

wherein
$X^1$ is N and $X^2$ is $CR^1$; or
$X^1$ is $CR^1$ and $X^2$ is N; or
$X^1$ is $CR^1$ and $X^2$ is $CR^1$;
$Y^1$ is C(O)NH, or NHC(O);
$Z^1$ is

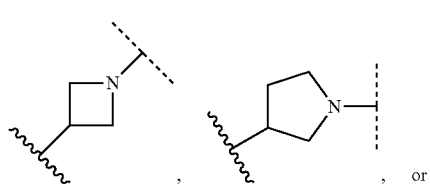

, or

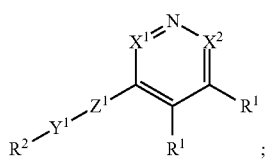

;

wherein ⁓ indicates the point of attachment to $Y^1$ and ⧵ indicates the point of attachment to the nitrogen containing heteroaryl;

$R^1$, at each occurrence, is independently selected from the group consisting of hydrogen, alkyl, haloalkyl, alkoxy, CN, Cl, and F;

$R^2$ is aryl or 5-6 membered heteroaryl wherein each $R^2$ aryl and 5-6 membered heteroaryl is optionally substituted with one or more substituents independently selected from the group consisting of $R^4$, $SO_2R^4$, $OR^4$, and F;

$R^4$, at each occurrence, is alkyl or heterocyclyl; wherein each $R^4$ alkyl is optionally substituted with $R^7$;

$R^7$, at each occurrence, is independently heterocyclyl;

wherein the cyclic moieties represented by $R^4$ and $R^7$ are independently optionally substituted with one or more substituents independently selected from the group consisting of $R^{10}$, $C(O)R^{10}$, $C(O)C(O)R^{10}$, $CO(O)R^{10}$, OH and F;

$R^{10}$, at each occurrence, is independently selected from the group consisting of alkyl, alkenyl, alkynyl, aryl, heterocyclyl, and cycloalkyl; wherein each $R^{10}$ alkyl is optionally substituted with one or more substituents independently selected from the group consisting of $R^{11}$, $OR^{11}$, $SR^{11}$, $SO_2R^{11}$, $NH_2$, $N(R^{11})_2$, $NHC(O)R^{11}$, $NHS(O)_2R^{11}$, OH, $NO_2$, and F; wherein each $R^{10}$ aryl, heterocyclyl and cycloalkyl is optionally substituted with one or more $R^{12}$, $OR^{12}$, $C(O)R^{12}$, OH, CN, $CF_3$, $OCF_3$, F, and Cl;

$R^{11}$, at each occurrence, is independently selected from the group consisting of alkyl, aryl, heterocyclyl, and cycloalkyl; wherein each $R^{11}$ alkyl is optionally substituted with alkoxy or aryl; wherein each $R^{11}$ aryl, and heterocyclyl is optionally substituted with one or more substituents independently selected from the group consisting of $R^{13}$, $C(O)OR^{13}$, $OCF_3$, $CF_3$, F, and Cl;

$R^{12}$, at each occurrence, is independently selected from the group consisting of alkyl, and aryl; and $R^{13}$, at each occurrence, is independently selected from the group consisting of alkyl, haloalkyl, and heterocyclyl;

with the proviso that
when $X^1$ is $CR^1$ and $X^2$ is $CR^1$; $R^1$ is hydrogen; $Y^1$ is NHC(O); $Z^1$ is

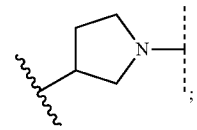

;

and $R^2$ is pyrrolyl; the $R^2$ pyrrolyl is not substituted with two alkyl groups.

Still another embodiment pertains to compounds having Formula (IA), which includes Examples 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, and pharmaceutically acceptable salts thereof.

Still another embodiment pertains to compounds of Formula (IA), selected from the group consisting of Examples 147, 310, 313, 316, 317, 320, 332, 333, 334, 402, 433, 440, 658, 681, 691, 706, 707, 723, 736, 795, and pharmaceutically acceptable salts thereof.

Embodiments of Formula (IIA)

In another aspect, the present invention provides compounds of Formula (IIA)

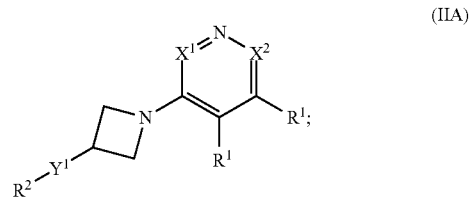

(IIA)

and pharmaceutically acceptable salts thereof; wherein $X^1$, $X^2$, $Y^1$, $R^1$, and $R^2$ are as described herein for Formula (IA).

One embodiment of this invention pertains to compounds of Formula (IIA) and pharmaceutically acceptable salts thereof;

wherein $X^1$ is N and $X^2$ is $CR^1$; or
$X^1$ is $CR^1$ and $X^2$ is N; or
$X^1$ is $CR^1$ and $X^2$ is $CR^1$;
$Y^1$ is C(O)NH, or NHC(O);
$R^1$, at each occurrence, is independently selected from the group consisting of hydrogen, alkyl, alkenyl, alkynyl, haloalkyl, hydroxyalkyl, alkoxy, OH, $NH_2$, CN, $NO_2$, F, Cl, Br and I;

$R^2$ is independently selected from the group consisting of $C_4$-$C_6$-alkyl, $C_4$-$C_6$-alkenyl, $C_4$-$C_6$-alkynyl, aryl, and 5-6 membered heteroaryl; wherein each $R^2C_4$-$C_6$-alkyl, $C_4$-$C_6$-alkenyl, and $C_4$-$C_6$-alkynyl is substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, C(O)H, C(O)OH, C(N)NH_2, C(N)NHR^3, C(N)N(R^3)_2$, CNOH, $CNOCH_3$, OH, (O), CN, $N_3$, $NO_2$, F, Cl, Br and I;
wherein each $R^2$ aryl and 5-6 membered heteroaryl is optionally substituted with one or more substituents independently selected from the group consisting of $R^4$, $OR^4$, $SR^4$, $S(O)R^4$, $SO_2R^4$, $C(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, C(O)H, C(O)OH, C(N)NH_2, C(N)NHR^4, C(N)N(R^4)_2$, CNOH, $CNOCH_3$, OH, CN, $N_3$, $NO_2$, F, Cl, and I;

$R^3$, at each occurrence, is independently selected from the group consisting of alkyl, alkenyl, alkynyl, aryl, cycloalkyl, cycloalkenyl, and heterocyclyl; wherein each $R^3$ alkyl, alkenyl, and alkynyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, C(O)

NHSO$_2$R$^5$, C(O)NR$^5$SO$_2$R$^5$, SO$_2$NH$_2$, SO$_2$NHR$^5$, SO$_2$N(R$^5$)$_2$, C(O)H, C(O)OH, C(N)NH$_2$, C(N)NHR$^5$, C(N)N(R$^5$)$_2$, CNOH, CNOCH$_3$, OH, (O), CN, N$_3$, NO$_2$, F, Cl, Br and I; wherein each R$^3$ aryl, cycloalkyl, cycloalkenyl, and heterocyclyl is optionally substituted with one or more substituents independently selected from the group consisting of R$^6$, OR$^6$, SR$^6$, S(O)R$^6$, SO$_2$R$^6$, C(O)R$^6$, CO(O)R$^6$, OC(O)R$^6$, OC(O)OR$^6$, NH$_2$, NHR$^6$, N(R$^6$)$_2$, NHC(O)R$^6$, NR$^6$C(O)R$^6$, NHS(O)$_2$R$^6$, NR$^6$S(O)$_2$R$^6$, NHC(O)OR$^6$, NR$^6$C(O)OR$^6$, NHC(O)NH$_2$, NHC(O)NHR$^6$, NHC(O)N(R$^6$)$_2$, NR$^6$C(O)NHR$^6$, NR$^6$C(O)N(R$^6$)$_2$, C(O)NH$_2$, C(O)NHR$^6$, C(O)N(R$^6$)$_2$, C(O)NHOH, C(O)NHOR$^6$, C(O)NHSO$_2$R$^6$, C(O)NR$^6$SO$_2$R$^6$, SO$_2$NH$_2$, SO$_2$NHR$^6$, SO$_2$N(R$^6$)$_2$, C(O)H, C(O)OH, C(N)NH$_2$, C(N)NHR$^6$, C(N)N(R$^6$)$_2$, CNOH, CNOCH$_3$, OH, CN, N$_3$, NO$_2$, F, Cl, Br and I;

R$^4$, at each occurrence, is independently selected from the group consisting of alkyl, alkenyl, alkynyl, aryl, heterocyclyl, cycloalkyl, and cycloalkenyl; wherein each R$^4$ alkyl, alkenyl, and alkynyl is optionally substituted with one or more substituents independently selected from the group consisting of R$^7$, OR$^7$, SR$^7$, S(O)R$^7$, SO$_2$R$^7$, C(O)R$^7$, CO(O)R$^7$, OC(O)R$^7$, OC(O)OR$^7$, NH$_2$, NHR$^7$, N(R$^7$)$_2$, NHC(O)R$^7$, NR$^7$C(O)R$^7$, NHS(O)$_2$R$^7$, NR$^7$S(O)$_2$R$^7$, NHC(O)OR$^7$, NR$^7$C(O)OR$^7$, NHC(O)NH$_2$, NHC(O)NHR$^7$, NHC(O)N(R$^7$)$_2$, NR$^7$C(O)NHR$^7$, NR$^7$C(O)N(R$^7$)$_2$, C(O)NH$_2$, C(O)NHR$^7$, C(O)N(R$^7$)$_2$, C(O)NHOH, C(O)NHOR$^7$, C(O)NHSO$_2$R$^7$, C(O)NR$^7$SO$_2$R$^7$, SO$_2$NH$_2$, SO$_2$NHR$^7$, SO$_2$N(R$^7$)$_2$, C(O)H, C(O)OH, C(N)NH$_2$, C(N)NHR$^7$, C(N)N(R$^7$)$_2$, CNOH, CNOCH$_3$, OH, (O), CN, N$_3$, NO$_2$, F, Cl, Br and I;

R$^5$, at each occurrence, is independently selected from the group consisting of alkyl, alkenyl, alkynyl, aryl, heterocyclyl, cycloalkyl, and cycloalkenyl; wherein each R$^5$ alkyl, alkenyl, and alkynyl is optionally substituted with one or more substituents independently selected from the group consisting of R$^8$, OR$^8$, SR$^8$, S(O)R$^8$, SO$_2$R$^8$, NHR$^8$, N(R$^8$)$_2$, C(O)R$^8$, C(O)NH$_2$, C(O)NHR$^8$, C(O)N(R$^8$)$_2$, NHC(O)R$^8$, NR$^8$C(O)R$^8$, NHSO$_2$R$^8$, NHC(O)OR$^8$, SO$_2$NH$_2$, SO$_2$NHR$^8$, SO$_2$N(R$^8$)$_2$, NHC(O)NH$_2$, NHC(O)NHR$^8$, OH, (O), C(O)OH, N$_3$, CN, NH$_2$, F, Cl, Br and I;

R$^6$, at each occurrence, is independently selected from the group consisting of alkyl, alkenyl, alkynyl, aryl, heterocyclyl, cycloalkyl, and cycloalkenyl; wherein each R$^6$ alkyl, alkenyl, and alkynyl is optionally substituted with one or more substituents independently selected from the group consisting of R$^9$, OR$^9$, SR$^9$, S(O)R$^9$, SO$_2$R$^9$, NHR$^9$, N(R$^9$)$_2$, C(O)R$^9$, C(O)NH$_2$, C(O)NHR$^9$, C(O)N(R$^9$)$_2$, NHC(O)R$^9$, NR$^9$C(O)R$^9$, NHSO$_2$R$^9$, NHC(O)OR$^9$, SO$_2$NH$_2$, SO$_2$NHR$^9$, SO$_2$N(R$^9$)$_2$, NHC(O)NH$_2$, NHC(O)NHR$^9$, OH, (O), C(O)OH, N$_3$, CN, NH$_2$, CF$_3$, CF$_2$CF$_3$, F, Cl, Br and I;

R$^7$, at each occurrence, is independently selected from the group consisting of alkyl, alkenyl, alkynyl, aryl, heterocyclyl, cycloalkyl, and cycloalkenyl;

R$^8$, at each occurrence, is independently selected from the group consisting of alkyl, alkenyl, alkynyl, aryl, heterocyclyl, cycloalkyl, and cycloalkenyl;

R$^9$, at each occurrence, is independently selected from the group consisting of alkyl, alkenyl, alkynyl, aryl, heterocyclyl, cycloalkyl, and cycloalkenyl;

wherein the cyclic moieties represented by R$^4$, R$^5$, R$^6$, R$^7$, R$^8$, and R$^9$ are independently optionally substituted with one or more substituents independently selected from the group consisting of R$^{10}$, OR$^{10}$, Se, S(O)R$^{10}$, SO$_2$R$^{10}$, C(O)R$^{10}$, CO(O)R$^{10}$, OC(O)R$^{10}$, OC(O)OR$^{10}$, C(O)C(O)R$^{10}$, NH$_2$, NHR$^{10}$, N(R$^{10}$)$_2$, NHC(O)R$^{10}$, NR$^{10}$C(O)R$^{10}$, NHS(O)$_2$R$^{10}$, NR$^{10}$S(O)$_2$R$^{10}$, NHC(O)OR$^{10}$, NR$^{10}$C(O)OR$^{10}$, NHC(O)NH$_2$, NHC(O)NHR$^{10}$, NHC(O)N(R$^{10}$)$_2$, NR$^{10}$C(O)NHR$^{10}$, NR$^{10}$C(O)N(R$^{10}$)$_2$, C(O)NH$_2$, C(O)NHR$^{10}$, C(O)N(R$^{10}$)$_2$, C(O)NHOH, C(O)NHOR$^{10}$, C(O)NHSO$_2$R$^{10}$, C(O)NR$^{16}$SO$_2$R$^{10}$, SO$_2$NH$_2$, SO$_2$NHR$^{10}$, SO$_2$N(R$^{10}$)$_2$, C(O)H, C(O)OH, C(N)NH$_2$, C(N)NHR$^{10}$, C(N)N(R$^{10}$)$_2$, CNOH, CNOCH$_3$, OH, CN, N$_3$, NO$_2$, F, Cl, Br and I;

R$^{10}$, at each occurrence, is independently selected from the group consisting of alkyl, alkenyl, alkynyl, aryl, heterocyclyl, cycloalkyl, and cycloalkenyl; wherein each R$^{10}$ alkyl, alkenyl, and alkynyl is optionally substituted with one or more substituents independently selected from the group consisting of R$^{11}$, OR$^{11}$, SR$^{11}$, S(O)R$^{11}$, SO$_2$R$^{11}$, C(O)R$^{11}$, CO(O)R$^{11}$, OC(O)R$^{11}$, OC(O)OR$^{11}$, NH$_2$, NHR$^{11}$, N(R$^{11}$)$_2$, NHC(O)R$^{11}$, NR$^{11}$C(O)R$^{11}$, NHS(O)$_2$R$^{11}$, NR$^{11}$S(O)$_2$R$^{11}$, NHC(O)OR$^{11}$, NR$^{11}$C(O)OR$^{11}$, NHC(O)NH$_2$, NHC(O)NHR$^{11}$, NHC(O)N(R$^{11}$)$_2$, NR$^{11}$C(O)NHR$^{11}$, NR$^{11}$C(O)N(R$^{11}$)$_2$, C(O)NH$_2$, C(O)NHR$^{11}$, C(O)N(R$^{11}$)$_2$, C(O)NHOH, C(O)NHOR$^{11}$, C(O)NHSO$_2$R$^{11}$, C(O)NR$^{11}$SO$_2$R$^{11}$, SO$_2$NH$_2$, SO$_2$NHR$^{11}$, SO$_2$N(R$^{11}$)$_2$, C(O)H, C(O)OH, C(N)NH$_2$, C(N)NHR$^{11}$, C(N)N(R$^{11}$)$_2$, CNOH, CNOCH$_3$, OH, (O), CN, N$_3$, NO$_2$, F, Cl, Br and I; wherein each R$^{10}$ aryl, heterocyclyl, cycloalkyl, and cycloalkenyl is optionally substituted with one or more substituents independently selected from the group consisting of R$^{12}$, OR$^{12}$, SR$^{12}$, S(O)R$^{12}$, SO$_2$R$^{12}$, C(O)R$^{12}$, CO(O)R$^{12}$, OC(O)R$^{12}$, OC(O)OR$^{12}$, NH$_2$, NHR$^{12}$, N(R$^{12}$)$_2$, NHC(O)R$^{12}$, NR$^{12}$C(O)R$^{12}$, NHS(O)$_2$R$^{12}$, NR$^{12}$S(O)$_2$R$^{12}$, NHC(O)OR$^{12}$, NR$^{12}$C(O)OR$^{12}$, NHC(O)NH$_2$, NHC(O)NHR$^{12}$, NHC(O)N(R$^{12}$)$_2$, NR$^{12}$C(O)NHR$^{12}$, NR$^{12}$C(O)N(R$^{12}$)$_2$, C(O)NH$_2$, C(O)NHR$^{12}$, C(O)N(R$^{12}$)$_2$, C(O)NHOH, C(O)NHOR$^{12}$, C(O)NHSO$_2$R$^{12}$, C(O)NR$^{12}$SO$_2$R$^{12}$, SO$_2$NH$_2$, SO$_2$NHR$^{12}$, SO$_2$N(R$^{12}$)$_2$, C(O)H, C(O)OH, C(N)NH$_2$, C(N)NHR$^{12}$, C(N)N(R$^{12}$)$_2$, CNOH, CNOCH$_3$, OH, CN, N$_3$, NO$_2$, CF$_3$, OCF$_3$, F, Cl, Br and I;

R$^{11}$, at each occurrence, is independently selected from the group consisting of alkyl, alkenyl, alkynyl, aryl, heterocyclyl, cycloalkyl, and cycloalkenyl; wherein each R$^{11}$ alkyl, alkenyl, and alkynyl is optionally substituted with alkoxy or aryl; wherein each R$^{11}$ aryl, heterocyclyl, cycloalkyl, and cycloalkenyl is optionally substituted with one or more substituents independently selected from the group consisting of R$^{13}$, OR$^{13}$, C(O)OR$^{13}$, OCF$_3$, CF$_3$, F, Cl, Br and I;

R$^{12}$, at each occurrence, is independently selected from the group consisting of alkyl, alkenyl, alkynyl, aryl, heterocyclyl, cycloalkyl, and cycloalkenyl; and R$^{13}$, at each occurrence, is independently selected from the group consisting of alkyl, haloalkyl, alkenyl, alkynyl, aryl, heterocyclyl, cycloalkyl, and cycloalkenyl.

In one embodiment of Formula (IIA), X$^1$ is N and X$^2$ is CR$^1$; or X$^1$ is CR$^1$ and X$^2$ is N; or X$^1$ is CR$^1$ and X$^2$ is CR$^1$. In another embodiment of Formula (IIA), X$^1$ is N and X$^2$ is CR$^1$. In another embodiment of Formula (IIA), X$^1$ is CR$^1$ and X$^2$ is N. In another embodiment of Formula (IIA), X$^1$ is CR$^1$ and X$^2$ is CR$^1$.

In one embodiment of Formula (IIA), Y$^1$ is C(O)NH, or NHC(O). In another embodiment of Formula (IIA), Y$^1$ is C(O)NH. In another embodiment of Formula (IIA), Y$^1$ is NHC(O).

In one embodiment of Formula (IIA), X$^1$ is CR$^1$ and X$^2$ is CR$^1$; and R$^1$, at each occurrence, is independently selected from the group consisting of hydrogen, alkyl, alkenyl, alkynyl, haloalkyl, hydroxyalkyl, alkoxy, OH, NH$_2$, CN, NO$_2$, F, Cl, Br and I. In another embodiment of Formula (IIA), X$^1$ is CR$^1$ and X$^2$ is CR$^1$; and R$^1$, at each occurrence, is independently selected from the group consisting of hydrogen, alkyl, haloalkyl, alkoxy, CN, F, Cl, Br and I. In another embodiment of Formula (IIA), X$^1$ is CR$^1$ and X$^2$ is CR$^1$; and R$^1$, at each occurrence, is independently selected from the group consisting of hydrogen, alkyl, haloalkyl, alkoxy, CN, F, and Cl. In another embodiment of Formula (IIA), $X^1$ is $CR^1$ and $X^2$ is $CR^1$; and $R^1$, at each occurrence, is hydrogen.

In another aspect, the present invention provides compounds of Formula (IIB),

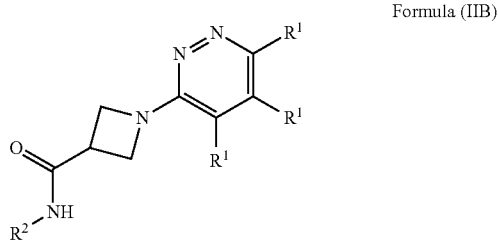

Formula (IIB)

and pharmaceutically acceptable salts thereof; wherein $R^1$ and $R^2$ are as described herein for Formula (IA).

In one embodiment of Formula (IIA) and (IIB), $R^1$, at each occurrence, is independently selected from the group consisting of hydrogen, alkyl, alkenyl, alkynyl, haloalkyl, hydroxyalkyl, alkoxy, OH, $NH_2$, CN, $NO_2$, F, Cl, Br and I. In another embodiment of Formula (IIA) and (IIB), $R^1$, at each occurrence, is independently selected from the group consisting of hydrogen, alkyl, haloalkyl, alkoxy, CN, F, Cl, Br and I. In another embodiment of Formula (IIA) and (IIB), $R^1$, at each occurrence, is independently selected from the group consisting of hydrogen, alkyl, haloalkyl, alkoxy, CN, F, and Cl. In another embodiment of Formula (IIA) and (IIB), $R^1$, at each occurrence, is hydrogen.

In one embodiment of Formula (IIA) and (IIB), $R^2$ is independently selected from the group consisting of $C_4$-$C_6$-alkyl, $C_4$-$C_6$-alkenyl, $C_4$-$C_6$-alkynyl, aryl, and 5-6 membered heteroaryl; wherein each $R^2 C_4$-$C_6$-alkyl, $C_4$-$C_6$-alkenyl, and $C_4$-$C_6$-alkynyl is substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(N)NH_2$, $C(N)NHR^3$, $C(N)N(R^3)_2$, CNOH, $CNOCH_3$, OH, (O), CN, $N_3$, $NO_2$, F, Cl, Br and I; wherein each $R^2$ aryl and 5-6 membered heteroaryl is optionally substituted with one or more substituents independently selected from the group consisting of $R^4$, $OR^4$, $SR^4$, $S(O)R^4$, $SO_2R^4$, $C(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, and I. In another embodiment of Formula (IIA) and (IIB), $R^2$ is aryl; wherein each $R^2$ aryl is optionally substituted with one or more substituents independently selected from the group consisting of $R^4$, $OR^4$, $SO_2R^4$, F, Cl, and I. In another embodiment of Formula (IIA) and (IIB), $R^2$ is aryl; wherein each $R^2$ aryl is optionally substituted with one or more substituents independently selected from the group consisting of $R^4$, $OR^4$, $SO_2R^4$, and F. In another embodiment of Formula (IIA) and (IIB), $R^2$ is phenyl; wherein each $R^2$ phenyl is optionally substituted with one or more substituents independently selected from the group consisting of $R^4$, $OR^4$, $SO_2R^4$, and F. In another embodiment of Formula (IIA) and (IIB), $R^2$ is phenyl; wherein each $R^2$ phenyl is substituted with one substituent independently selected from the group consisting of $R^4$, $OR^4$, and $SO_2R^4$.

In another embodiment of Formula (IIA) and (IIB), $R^2$ is 5-6 membered heteroaryl; wherein each $R^2$ 5-6 membered heteroaryl is optionally substituted with one or more substituents independently selected from the group consisting of $R^4$, $OR^4$, $SO_2R^4$, F, Cl, and I. In another embodiment of Formula (IIA) and (IIB), $R^2$ is 5-6 membered heteroaryl; wherein each $R^2$ 5-6 membered heteroaryl is optionally substituted with one or more substituents independently selected from the group consisting of $R^4$, $OR^4$, $SO_2R^4$, and F. In another embodiment of Formula (IIA) and (IIB), $R^2$ is furanyl or thiophenyl; wherein each $R^2$ furanyl and thiophenyl is optionally substituted with one or more substituents independently selected from the group consisting of $R^4$, $OR^4$, $SO_2R^4$, and F.

In one embodiment of Formula (IIA) and (IIB), $R^4$, at each occurrence, is independently selected from the group consisting of alkyl, alkenyl, alkynyl, aryl, heterocyclyl, cycloalkyl, and cycloalkenyl; wherein each $R^4$ alkyl, alkenyl, and alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, CNOH, $CNOCH_3$, OH, (O), CN, $N_3$, $NO_2$, F, Cl, Br and I. In another embodiment of Formula (IIA) and (IIB), $R^4$, at each occurrence, is alkyl or heterocyclyl.

In one embodiment of Formula (IIA) and (IIB), each $R^4$ alkyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, CNOH, $CNOCH_3$, OH, (O), CN, $N_3$, $NO_2$, F, Cl, Br and I. In another embodiment of Formula (I), each $R^4$ alkyl is optionally substituted with one $R^7$.

In one embodiment of Formula (IIA) and (IIB), $R^7$, at each occurrence, is independently selected from the group consisting of alkyl, alkenyl, alkynyl, aryl, heterocyclyl, cycloalkyl, and cycloalkenyl. In another embodiment of Formula (IIA) and (IIB), $R^7$, at each occurrence, is heterocyclyl.

In one embodiment of Formula (IIA) and (IIB), each $R^4$ and $R^7$ heterocyclyl is independently optionally substituted with one or more substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, CNOH, $CNOCH_3$, OH, CN, $N_3$, $NO_2$, F, Cl, Br and I; $R^{10}$, at each occurrence, is independently selected from the group consisting of alkyl, alkenyl, alkynyl, aryl, heterocyclyl, cycloalkyl, and cycloalkenyl; wherein each $R^{10}$ alkyl, alkenyl, and alkynyl is optionally substituted with one or more substituents independently selected from the group consisting of $R^{11}$, $OR^{11}$, $SR^{11}$, $S(O)R^{11}$, $SO_2R^{11}$, $C(O)R^{11}$, $CO(O)R^{11}$, $OC(O)R^{11}$, $OC(O)OR^{11}$, $NH_2$, $NHR^{11}$, $N(R^{11})_2$, $NHC(O)R^{11}$, $NR^{11}C(O)R^{11}$, $NHS(O)_2R^{11}$, $NR^{11}S(O)_2R^{11}$, $NHC(O)OR^{11}$, $NR^{11}C(O)OR^{11}$, $NHC(O)NH_2$, $NHC(O)NHR^{11}$, $NHC(O)N(R^{11})_2$, $NR^{11}C(O)NHR^{11}$, $NR^{11}C(O)N(R^{11})_2$, $C(O)NH_2$, $C(O)NHR^{11}$, $C(O)N(R^{11})_2$, $C(O)NHOH$, $C(O)NHOR^{11}$, $C(O)NHSO_2R^{11}$, $C(O)NR^{11}SO_2R^{11}$, $SO_2NH_2$, $SO_2NHR^{11}$, $SO_2N(R^{11})_2$, $C(O)H$, $C(O)OH$, $C(N)NH_2$, $C(N)NHR^{11}$, $C(N)N(R^{11})_2$, $CNOH$, $CNOCH_3$, $OH$, $(O)$, $CN$, $N_3$, $NO_2$, $F$, $Cl$, $Br$ and $I$; wherein each $R^{10}$ aryl, heterocyclyl, cycloalkyl, and cycloalkenyl is optionally substituted with one or more substituents independently selected from the group consisting of $R^{12}$, $OR^{12}$, $SR^{12}$, $S(O)R^{12}$, $so_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, $C(N)NH_2$, $C(N)NHR^{12}$, $C(N)N(R^{12})_2$, $CNOH$, $CNOCH_3$, $OH$, $CN$, $N_3$, $NO_2$, $F$, $Cl$, $Br$ and $I$; $R^{11}$, at each occurrence, is independently selected from the group consisting of alkyl, alkenyl, alkynyl, aryl, heterocyclyl, cycloalkyl, and cycloalkenyl; wherein each $R^{11}$ alkyl, alkenyl, and alkynyl is optionally substituted with alkoxy or aryl; wherein each $R^{11}$ aryl, heterocyclyl, cycloalkyl, and cycloalkenyl is optionally substituted with one or more substituents independently selected from the group consisting of $R^{13}$, $OR^{13}$, $C(O)OR^{13}$, $OCF_3$, $CF_3$, $F$, $Cl$, $Br$ and $I$; $R^{12}$, at each occurrence, is independently selected from the group consisting of alkyl, alkenyl, alkynyl, aryl, heterocyclyl, cycloalkyl, and cycloalkenyl; and $R^{13}$, at each occurrence, is independently selected from the group consisting of alkyl, haloalkyl, alkenyl, alkynyl, aryl, heterocyclyl, cycloalkyl, and cycloalkenyl.

In another embodiment of Formula (IIA) and (IIB), each $R^4$ and $R^7$ heterocyclyl is independently optionally substituted with one or more substituents independently selected from the group consisting of $R^{10}$, $C(O)R^{10}$, $CO(O)R^{10}$, $C(O)C(O)R^{10}$, $OH$, $F$, $Cl$, $Br$ and $I$; $R^{10}$, at each occurrence, is independently selected from the group consisting of alkyl, alkenyl, alkynyl, aryl, heterocyclyl, and cycloalkyl; wherein each $R^{10}$ alkyl, alkenyl, and alkynyl, are optionally substituted with one or more substituents independently selected from the group consisting of $R^{11}$, $OR^{11}$, $SR^{11}$, $SO_2R^{11}$, $NH_2$, $N(R^{11})_2$, $NHC(O)R^{11}$, $NHS(O)_2R^{11}$, $OH$, $NO_2$, and $F$; wherein each $R^{10}$ aryl, heterocyclyl and cycloalkyl is optionally substituted with one or more substituents independently selected from the group consisting of $R^{12}$, $OR^{12}$, $C(O)R^{12}$, $OH$, $CN$, $CF_3$, $OCF_3$, $F$, and $Cl$; $R^{11}$, at each occurrence, is independently selected from the group consisting of alkyl, aryl, heterocyclyl, and cycloalkyl; wherein each $R^{11}$ alkyl is optionally substituted with alkoxy or aryl; wherein each $R^{11}$ aryl and heterocyclyl is optionally substituted with one or more substituents independently selected from the group consisting of $R^{13}$, $CF_3$, $F$, and $Cl$; $R^{12}$, at each occurrence, is independently selected from the group consisting of alkyl and aryl; and $R^{13}$, at each occurrence, is independently selected from the group consisting of alkyl and haloalkyl.

One embodiment of this invention pertains to compounds or pharmaceutically acceptable salts thereof, which are useful as inhibitors of NAMPT, the compounds having Formula (IIA)

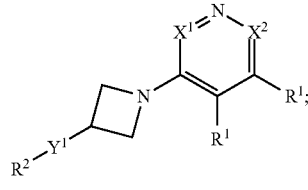

Formula (IIA)

wherein $X^1$ is N and $X^2$ is $CR^1$; or
$X^1$ is $CR^1$ and $X^2$ is N; or
$X^1$ is $CR^1$ and $X^2$ is $CR^1$;
$Y^1$ is C(O)NH, or NHC(O);
$R^1$, at each occurrence, is independently selected from the group consisting of hydrogen, alkyl, haloalkyl, alkoxy, CN, Cl, and F;
$R^2$ is aryl or 5-6 membered heteroaryl wherein each $R^2$ aryl and 5-6 membered heteroaryl is optionally substituted with one or more substituents independently selected from the group consisting of $R^4$, $SO_2R^4$, $OR^4$, and F;
$R^4$, at each occurrence, is alkyl or heterocyclyl; wherein each $R^4$ alkyl is optionally substituted with $R^7$;
$R^7$, at each occurrence, is independently heterocyclyl;
wherein the cyclic moieties represented by $R^4$ and $R^7$ are independently optionally substituted with one or more substituents independently selected from the group consisting of $R^{10}$, $C(O)R^{10}$, $C(O)C(O)R^{10}$, $CO(O)R^{10}$, $OH$ and $F$;
$R^{10}$, at each occurrence, is independently selected from the group consisting of alkyl, alkenyl, alkynyl, aryl, heterocyclyl, and cycloalkyl; wherein each $R^{10}$ alkyl is optionally substituted with one or more substituents independently selected from the group consisting of $R^{11}$, $OR^{11}$, $SR^{11}$, $SO_2R^{11}$, $NH_2$, $N(R^{11})_2$, $NHC(O)R^{11}$, $NHS(O)_2R^{11}$, $OH$, $NO_2$, and $F$; wherein each $R^{10}$ aryl, heterocyclyl and cycloalkyl is optionally substituted with one or more $R^{12}$, $OR^{12}$, $C(O)R^{12}$, $OH$, $CN$, $CF_3$, $OCF_3$, $F$, and $Cl$;
$R^{11}$, at each occurrence, is independently selected from the group consisting of alkyl, aryl, heterocyclyl, and cycloalkyl; wherein each $R^{11}$ alkyl is optionally substituted with alkoxy or aryl; wherein each $R^{11}$ aryl, and heterocyclyl is optionally substituted with one or more substituents independently selected from the group consisting of $R^{13}$, $C(O)OR^{13}$, $OCF_3$, $CF_3$, F, and Cl;
$R^{12}$, at each occurrence, is independently selected from the group consisting of alkyl, and aryl; and
$R^{13}$, at each occurrence, is independently selected from the group consisting of alkyl, haloalkyl, and heterocyclyl.

Still another embodiment pertains to compounds having Formula (IIA), which includes Examples 1, 2, 3, 4, 5, 6, 7, 10, 20, 21, 22, 23, 24, 25, 26, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 609, 610, 611, 612, 613, 614, 615, 616, 617, 665, 666, 667, 668, 737, 738, 739, 740, 741, 748, 750, 751, 753, 784, 803, 804, 805, 806, 807, 809, 817, 818, 819, 820, 821, 822, 823, 828, 829, 830, 831, 832, 833, 834, 835, 840, 841, 842, 843, 844, 845, 846, 851, 852, 853, 854, 857, 858, 859, 860, 861, 862, 863, 864, 865, 866, 867, 868, 869, 870, 871, 872, and pharmaceutically acceptable salts thereof Embodiments of Formula (IIIA)

In another aspect, the present invention provides compounds of Formula (IIIA)

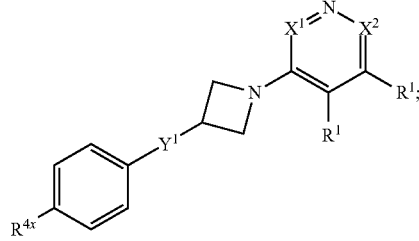

(IIIA)

and pharmaceutically acceptable salts thereof; wherein $X^1$, $X^2$, $R^1$, and $Y^1$ are as described in Formula (IA) herein and $R^{4x}$ is as described herein for substituents on $R^2$ when $R^2$ is aryl in Formula (IA).

One embodiment of this invention pertains to compounds of Formula (IIIA) or pharmaceutically acceptable salts thereof;
wherein
$X^1$ is N and $X^2$ is $CR^1$; or
$X^1$ is $CR^1$ and $X^2$ is N; or
$X^1$ is $CR^1$ and $X^2$ is $CR^1$;
$Y^1$ is C(O)NH, or NHC(O);

$R^1$, at each occurrence, is independently selected from the group consisting of hydrogen, alkyl, alkenyl, alkynyl, haloalkyl, hydroxyalkyl, alkoxy, OH, $NH_2$, CN, $NO_2$, F, Cl, Br and I;

$R^{4x}$ is independently selected from the group consisting of $R^4$, $OR^4$, $SR^4$, $S(O)R^4$, $SO_2R^4$, $C(O)R^4$, $OC(O)R^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, and I;

$R^4$, at each occurrence, is independently selected from the group consisting of alkyl, alkenyl, alkynyl, aryl, heterocyclyl, cycloalkyl, and cycloalkenyl; wherein each $R^4$ alkyl, alkenyl, and alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, CNOH, $CNOCH_3$, OH, (O), CN, $N_3$, $NO_2$, F, Cl, Br and I;

$R^7$, at each occurrence, is independently selected from the group consisting of alkyl, alkenyl, alkynyl, aryl, heterocyclyl, cycloalkyl, and cycloalkenyl;

wherein the cyclic moieties represented by $R^4$ and $R^7$, are independently optionally substituted with one or more substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $C(O)C(O)R^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, CNOH, $CNOCH_3$, OH, CN, $N_3$, $NO_2$, F, Cl, Br and I;

$R^{10}$, at each occurrence, is independently selected from the group consisting of alkyl, alkenyl, alkynyl, aryl, heterocyclyl, cycloalkyl, and cycloalkenyl; wherein each $R^{10}$ alkyl, alkenyl, and alkynyl is optionally substituted with one or more substituents independently selected from the group consisting of $R^{11}$, $OR^{11}$, $SR^{11}$, $S(O)R^{11}$, $SO_2R^{11}$, $C(O)R^{11}$, $CO(O)R^{11}$, $OC(O)R^{11}$, $OC(O)OR^{11}$, $NH_2$, $NHR^{11}$, $N(R^{11})_2$, $NHC(O)R^{11}$, $NR^{11}C(O)R^{11}$, $NHS(O)_2R^{11}$, $NR^{11}S(O)_2R^{11}$, $NHC(O)OR^{11}$, $NR^{11}C(O)OR^{11}$, $NHC(O)NH_2$, $NHC(O)NHR^{11}$, $NHC(O)N(R^{11})_2$, $NR^{11}C(O)NHR^{11}$, $NR^{11}C(O)N(R^{11})_2$, $C(O)NH_2$, $C(O)NHR^{11}$, $C(O)N(R^{11})_2$, $C(O)NHOH$, $C(O)NHOR^{11}$, $C(O)NHSO_2R^{11}$, $C(O)NR^{11}SO_2R^{11}$, $SO_2NH_2$, $SO_2NHR^{11}$, $SO_2N(R^{11})_2$, $C(O)H$, $C(O)OH$, $C(N)NH_2$, $C(N)NHR^{11}$, $C(N)N(R^{11})_2$, CNOH, $CNOCH_3$, OH, (O), CN, $N_3$, $NO_2$, F, Cl, Br and I; wherein each $R^{10}$ aryl, heterocyclyl, cycloalkyl, and cycloalkenyl is optionally substituted with one or more substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, C(O)NHOH, C(O)NHOR$^{12}$, C(O)NHSO$_2$R$^{12}$, C(O)NR$^{12}$SO$_2$R$^{12}$, SO$_2$NH$_2$, SO$_2$NHR$^{12}$, SO$_2$N(R$^{12}$)$_2$, C(O)H, C(O)OH, C(N)NH$_2$, C(N)NHR$^{12}$, C(N)N(R$^{12}$)$_2$, CNOH, CNOCH$_3$, OH, CN, N$_3$, NO$_2$, CF$_3$, OCF$_3$, F, Cl, Br and I;

R$^{11}$, at each occurrence, is independently selected from the group consisting of alkyl, alkenyl, alkynyl, aryl, heterocyclyl, cycloalkyl, and cycloalkenyl; wherein each R$^{11}$ alkyl, alkenyl, and alkynyl is optionally substituted with alkoxy or aryl; wherein each R$^{11}$ aryl, heterocyclyl, cycloalkyl, and cycloalkenyl is optionally substituted with one or more substituents independently selected from the group consisting of R$^{13}$, OR$^{13}$, C(O)OR$^{13}$, OCF$_3$, CF$_3$, F, Cl, Br and I;

R$^{12}$, at each occurrence, is independently selected from the group consisting of alkyl, alkenyl, alkynyl, aryl, heterocyclyl, cycloalkyl, and cycloalkenyl; and R$^{13}$, at each occurrence, is independently selected from the group consisting of alkyl, haloalkyl, alkenyl, alkynyl, aryl, heterocyclyl, cycloalkyl, and cycloalkenyl.

In one embodiment of Formula (IIIA), $X^1$ is N and $X^2$ is CR$^1$; or $X^1$ is CR$^1$ and $X^2$ is N; or $X^1$ is CR$^1$ and $X^2$ is CR$^1$. In another embodiment of Formula (IIIA), $X^1$ is N and $X^2$ is CR$^1$. In another embodiment of Formula (IIIA), $X^1$ is CR$^1$ and $X^2$ is N. In another embodiment of Formula (IIIA), $X^1$ is CR$^1$ and $X^2$ is CR$^1$.

In one embodiment of Formula (IIIA), $Y^1$ is C(O)NH, or NHC(O). In another embodiment of Formula (IIIA), $Y^1$ is C(O)NH. In another embodiment of Formula (IIIA), $Y^1$ is NHC(O).

In one embodiment of Formula (IIIA), $X^1$ is CR$^1$ and $X^2$ is CR$^1$; and R$^1$, at each occurrence, is independently selected from the group consisting of hydrogen, alkyl, alkenyl, alkynyl, haloalkyl, hydroxyalkyl, alkoxy, OH, NH$_2$, CN, NO$_2$, F, Cl, Br and I. In another embodiment of Formula (IIIA), $X^1$ is CR$^1$ and $X^2$ is CR$^1$; and R$^1$, at each occurrence, is independently selected from the group consisting of hydrogen, alkyl, haloalkyl, alkoxy, CN, F, Cl, Br and I. In another embodiment of Formula (IIIA), $X^1$ is CR$^1$ and $X^2$ is CR$^1$; and R$^1$, at each occurrence, is independently selected from the group consisting of hydrogen, alkyl, haloalkyl, alkoxy, CN, F, and Cl. In another embodiment of Formula (IIIA), $X^1$ is CR$^1$ and $X^2$ is CR$^1$; and R$^1$, at each occurrence, is hydrogen.

In another aspect, the present invention provides compounds of Formula (IIIB),

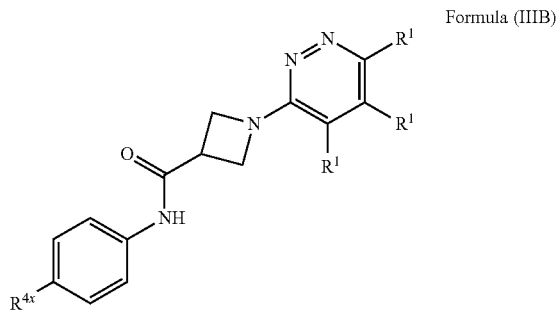

Formula (IIIB)

and pharmaceutically acceptable salts thereof; wherein R$^1$ is described herein for Formula (IA) and R$^{4x}$ is as described herein for substituents on R$^2$ when R$^2$ is aryl in Formula (IA).

In one embodiment of Formula (IIIA) and (IIIB), R$^1$, at each occurrence, is independently selected from the group consisting of hydrogen, alkyl, alkenyl, alkynyl, haloalkyl, hydroxyalkyl, alkoxy, OH, NH$_2$, CN, NO$_2$, F, Cl, Br and I. In another embodiment of Formula (IIIA) and (IIIB), R$^1$, at each occurrence, is independently selected from the group consisting of hydrogen, alkyl, haloalkyl, alkoxy, CN, F, Cl, Br and I. In another embodiment of Formula (IIIA) and (IIIB), R$^1$, at each occurrence, is independently selected from the group consisting of hydrogen, alkyl, haloalkyl, alkoxy, CN, F, and Cl. In another embodiment of Formula (IIIA) and (IIIB), R$^1$, at each occurrence, is hydrogen.

In one embodiment of Formula (IIIA) and (IIIB), R$^{4x}$ is independently selected from the group consisting of R$^4$, OR$^4$, SR$^4$, S(O)R$^4$, SO$_2$R$^4$, C(O)R$^4$, OC(O)OR$^4$, NH$_2$, NHR$^4$, N(R$^4$)$_2$, NHC(O)R$^4$, NR$^4$C(O)R$^4$, NHS(O)$_2$R$^4$, NR$^4$S(O)$_2$R$^4$, NHC(O)OR$^4$, NR$^4$C(O)OR$^4$, NHC(O)NH$_2$, NHC(O)NHR$^4$, NHC(O)N(R$^4$)$_2$, NR$^4$C(O)NHR$^4$, NR$^4$C(O)N(R$^4$)$_2$, C(O)NH$_2$, C(O)NHR$^4$, C(O)N(R$^4$)$_2$, C(O)NHOH, C(O)NHOR$^4$, C(O)NHSO$_2$R$^4$, C(O)NR$^4$SO$_2$R$^4$, SO$_2$NH$_2$, SO$_2$NHR$^4$, SO$_2$N(R$^4$)$_2$, C(O)H, C(O)OH, C(N)NH$_2$, C(N)NHR$^4$, C(N)N(R$^4$)$_2$, CNOH, CNOCH$_3$, OH, CN, N$_3$, NO$_2$, F, Cl, and I. In another embodiment of Formula (IIIA) and (IIIB), R$^{4x}$ is independently selected from the group consisting of R$^4$, OR$^4$, SO$_2$R$^4$, F, Cl, and I. In another embodiment of Formula (IIIA) and (IIIB), R$^{4x}$ is independently selected from the group consisting of R$^4$, OR$^4$, SO$_2$R$^4$, and F.

In one embodiment of Formula (IIIA) and (IIIB), R$^4$, at each occurrence, is independently selected from the group consisting of alkyl, alkenyl, alkynyl, aryl, heterocyclyl, cycloalkyl, and cycloalkenyl; wherein each R$^4$ alkyl, alkenyl, and alkynyl is optionally substituted with one or more substituents independently selected from the group consisting of R$^7$, OR$^7$, SR$^7$, S(O)R$^7$, SO$_2$R$^7$, C(O)R$^7$, CO(O)R$^7$, OC(O)R$^7$, OC(O)OR$^7$, NH$_2$, NHR$^7$, N(R$^7$)$_2$, NHC(O)R$^7$, NR$^7$C(O)R$^7$, NHS(O)$_2$R$^7$, NR$^7$S(O)$_2$R$^7$, NHC(O)OR$^7$, NR$^7$C(O)OR$^7$, NHC(O)NH$_2$, NHC(O)NHR$^7$, NHC(O)N(R$^7$)$_2$, NR$^7$C(O)NHR$^7$, NR$^7$C(O)N(R$^7$)$_2$, C(O)NH$_2$, C(O)NHR$^7$, C(O)N(R$^7$)$_2$, C(O)NHOH, C(O)NHOR$^7$, C(O)NHSO$_2$R$^7$, C(O)NR$^7$SO$_2$R$^7$, SO$_2$NH$_2$, SO$_2$NHR$^7$, SO$_2$N(R$^7$)$_2$, C(O)H, C(O)OH, C(N)NH$_2$, C(N)NHR$^7$, C(N)N(R$^7$)$_2$, CNOH, CNOCH$_3$, OH, (O), CN, N$_3$, NO$_2$, F, Cl, Br and I. In another embodiment of Formula (IIIA) and (IIIB), R$^4$, at each occurrence, is alkyl or heterocyclyl.

In one embodiment of Formula (IIIA) and (IIIB), each R$^4$ alkyl is optionally substituted with one or more substituents independently selected from the group consisting of R$^7$, OR$^7$, SR$^7$, S(O)R$^7$, SO$_2$R$^7$, C(O)R$^7$, CO(O)R$^7$, OC(O)R$^7$, OC(O)OR$^7$, NH$_2$, NHR$^7$, N(R$^7$)$_2$, NHC(O)R$^7$, NR$^7$C(O)R$^7$, NHS(O)$_2$R$^7$, NR$^7$S(O)$_2$R$^7$, NHC(O)OR$^7$, NR$^7$C(O)OR$^7$, NHC(O)NH$_2$, NHC(O)NHR$^7$, NHC(O)N(R$^7$)$_2$, NR$^7$C(O)NHR$^7$, NR$^7$C(O)N(R$^7$)$_2$, C(O)NH$_2$, C(O)NHR$^7$, C(O)N(R$^7$)$_2$, C(O)NHOH, C(O)NHOR$^7$, C(O)NHSO$_2$R$^7$, C(O)NR$^7$SO$_2$R$^7$, SO$_2$NH$_2$, SO$_2$NHR$^7$, SO$_2$N(R$^7$)$_2$, C(O)H, C(O)OH, C(N)NH$_2$, C(N)NHR$^7$, C(N)N(R$^7$)$_2$, CNOH, CNOCH$_3$, OH, (O), CN, N$_3$, NO$_2$, F, Cl, Br and I. In another embodiment of Formula (IIIA) and (IIIB), each R$^4$ alkyl is optionally substituted with one R$^7$.

In one embodiment of Formula (IIIA) and (IIIB), R$^7$, at each occurrence, is independently selected from the group consisting of alkyl, alkenyl, alkynyl, aryl, heterocyclyl, cycloalkyl, and cycloalkenyl. In another embodiment of Formula (IIIA) and (IIIB), R$^7$, at each occurrence, is heterocyclyl.

In one embodiment of Formula (IIIA) and (IIIB), each R$^4$ and R$^7$ heterocyclyl is independently optionally substituted with one or more substituents independently selected from the group consisting of R$^{10}$, OR$^{10}$, SR$^{10}$, S(O)R$^{10}$, SO$_2$R$^{10}$, C(O)R$^{10}$, CO(O)R$^{10}$, OC(O)R$^{10}$, OC(O)OR$^{10}$, NH$_2$, NHR$^{10}$, N(R$^{10}$)$_2$, NHC(O)R$^{10}$, NR$^{10}$C(O)R$^{10}$, NHS(O)$_2$R$^{10}$, NR$^{10}$S(O)$_2$R$^{10}$, NHC(O)OR$^{10}$, NR$^{10}$C(O)OR$^{10}$, NHC(O)NH$_2$, NHC(O)NHR$^{10}$, NHC(O)N(R$^{10}$)$_2$, NR$^{10}$C(O)NHR$^{10}$, NR$^{10}$C(O)N(R$^{10}$)$_2$, C(O)NH$_2$, C(O)NHR$^{10}$, C(O)N(R$^{10}$)$_2$, C(O)NHOH, C(O)NHOR$^{10}$, C(O)NHSO$_2$R$^{10}$, C(O)NR$^{10}$SO$_2$R$^{10}$, SO$_2$NH$_2$, SO$_2$NHR$^{10}$, SO$_2$N(R$^{10}$)$_2$, C(O)H, C(O)OH, C(N)NH$_2$, C(N)NHR$^{10}$, C(N)N(R$^{10}$)$_2$, CNOH, CNOCH$_3$, OH, CN, N$_3$, NO$_2$, F, Cl, Br and I; R$^{10}$, at each occurrence, is independently selected from the group consisting of alkyl, alkenyl, alkynyl, aryl, heterocyclyl, cycloalkyl, and cycloalkenyl; wherein each R$^{10}$ alkyl, alkenyl, and alkynyl is optionally substituted with one or more substituents independently selected from the group consisting of R$^{11}$, OR$^{11}$, SR$^{11}$, S(O)R$^{11}$, SO$_2$R$^{11}$, C(O)R$^{11}$, CO(O)R$^{11}$, OC(O)R$^{11}$, OC(O)OR$^{11}$, NH$_2$, NHR$^{11}$, N(R$^{11}$)$_2$, NHC(O)R$^{11}$, NR$^{11}$C(O)R$^{11}$, NHS(O)$_2$R$^{11}$, NR$^{11}$S(O)$_2$R$^{11}$, NHC(O)OR$^{11}$, NR$^{11}$C(O)OR$^{11}$, NHC(O)NH$_2$, NHC(O)NHR$^{11}$, NHC(O)N(R$^{11}$)$_2$, NR$^{11}$C(O)NHR$^{11}$, NR$^{11}$C(O)N(R$^{11}$)$_2$, C(O)NH$_2$, C(O)NHR$^{11}$, C(O)N(R$^{11}$)$_2$, C(O)NHOH, C(O)NHOR$^{11}$, C(O)NHSO$_2$R$^{11}$, C(O)NR$^{11}$SO$_2$R$^{11}$, SO$_2$NH$_2$, SO$_2$NHR$^{11}$, SO$_2$N(R$^{11}$)$_2$, C(O)H, C(O)OH, C(N)NH$_2$, C(N)NHR$^{11}$, C(N)N(R$^{11}$)$_2$, CNOH, CNOCH$_3$, OH, (O), CN, N$_3$, NO$_2$, F, Cl, Br and I; wherein each R$^{10}$ aryl, heterocyclyl, cycloalkyl, and cycloalkenyl is optionally substituted with one or more substituents independently selected from the group consisting of R$^{12}$, OR$^{12}$, SR$^{12}$, S(O)R$^{12}$, SO$_2$R$^{12}$, C(O)R$^{12}$, CO(O)R$^{12}$, OC(O)R$^{12}$, OC(O)OR$^{12}$, NH$_2$, NHR$^{12}$, N(R$^{12}$)$_2$, NHC(O)R$^{12}$, NR$^{12}$C(O)R$^{12}$, NHS(O)$_2$R$^{12}$, NR$^{12}$S(O)$_2$R$^{12}$, NHC(O)OR$^{12}$, NR$^{12}$C(O)OR$^{12}$, NHC(O)NH$_2$, NHC(O)NHR$^{12}$, NHC(O)N(R$^{12}$)$_2$, NR$^{12}$C(O)NHR$^{12}$, NR$^{12}$C(O)N(R$^{12}$)$_2$, C(O)NH$_2$, C(O)NHR$^{12}$, C(O)N(R$^{12}$)$_2$, C(O)NHOH, C(O)NHOR$^{12}$, C(O)NHSO$_2$R$^{12}$, C(O)NR$^{12}$SO$_2$R$^{12}$, SO$_2$NH$_2$, SO$_2$NHR$^{12}$, SO$_2$N(R$^{12}$)$_2$, C(O)H, C(O)OH, C(N)NH$_2$, C(N)NHR$^{12}$, C(N)N(R$^{12}$)$_2$, CNOH, CNOCH$_3$, OH, CN, N$_3$, NO$_2$, F, Cl, Br and I; R$^{11}$, at each occurrence, is independently selected from the group consisting of alkyl, alkenyl, alkynyl, aryl, heterocyclyl, cycloalkyl, and cycloalkenyl; wherein each R$^{11}$ alkyl, alkenyl, and alkynyl is optionally substituted with alkoxy or aryl; wherein each R$^{11}$ aryl, heterocyclyl, cycloalkyl, and cycloalkenyl is optionally substituted with one or more substituents independently selected from the group consisting of R$^{13}$, OR$^{13}$, C(O)OR$^{13}$, OCF$_3$, CF$_3$, F, Cl, Br and I; R$^{12}$, at each occurrence, is independently selected from the group consisting of alkyl, alkenyl, alkynyl, aryl, heterocyclyl, cycloalkyl, and cycloalkenyl; and R$^{13}$, at each occurrence, is independently selected from the group consisting of alkyl, haloalkyl, alkenyl, alkynyl, aryl, heterocyclyl, cycloalkyl, and cycloalkenyl.

In another embodiment of Formula (IIIA) and (IIIB), each R$^4$ and R$^7$ heterocyclyl is independently optionally substituted with one or more substituents independently selected from the group consisting of R$^{10}$, C(O)R$^{10}$, CO(O)R$^{10}$, C(O)C(O)R$^{10}$, OH, F, Cl, Br and I; R$^{10}$, at each occurrence, is independently selected from the group consisting of alkyl, alkenyl, alkynyl, aryl, heterocyclyl, and cycloalkyl; wherein each R$^{10}$ alkyl, alkenyl, and alkynyl, are optionally substituted with one or more substituents independently selected from the group consisting of R$^{11}$, OR$^{11}$, SR$^{11}$, SO$_2$R$^{11}$, NH$_2$, N(R$^{11}$)$_2$, NHC(O)R$^{11}$, NHS(O)$_2$R$^{11}$, OH, NO$_2$, and F; wherein each R$^{10}$ aryl, heterocyclyl and cycloalkyl is optionally substituted with one or more substituents independently selected from the group consisting of R$^{12}$, OR$^{12}$, C(O)R$^{12}$, OH, CN, CF$_3$, OCF$_3$, F, and Cl; R$^{11}$, at each occurrence, is independently selected from the group consisting of alkyl, aryl, heterocyclyl, and cycloalkyl; wherein each R$^{11}$ alkyl is optionally substituted with alkoxy or aryl; wherein each R$^{11}$ aryl and heterocyclyl is optionally substituted with one or more substituents independently selected from the group consisting of R$^{13}$, CF$_3$, F, and Cl; R$^{12}$, at each occurrence, is independently selected from the group consisting of alkyl and aryl; and R$^{13}$, at each occurrence, is independently selected from the group consisting of alkyl and haloalkyl.

One embodiment of this invention pertains to compounds or pharmaceutically acceptable salts thereof, which are useful as inhibitors of NAMPT, the compounds having Formula (IIIA)

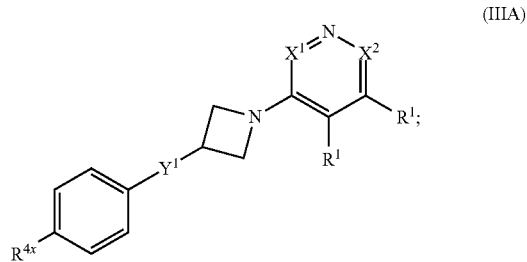

(IIIA)

wherein
X$^1$ is N and X$^2$ is CR$^1$; or
X$^1$ is CR$^1$ and X$^2$ is N; or
X$^1$ is CR$^1$ and X$^2$ is CR$^1$;
Y$^1$ is C(O)NH, or NHC(O);
R$^1$, at each occurrence, is independently selected from the group consisting of hydrogen, alkyl, haloalkyl, alkoxy, CN, Cl, and F;
R$^{4x}$ is independently selected from the group consisting of R$^4$, SO$_2$R$^4$, OR$^4$, and F;
R$^4$, at each occurrence, is alkyl or heterocyclyl; wherein each R$^4$ alkyl is optionally substituted with R$^7$;
R$^7$, at each occurrence, is independently heterocyclyl;
wherein the cyclic moieties represented by R$^4$ and R$^7$ are independently optionally substituted with one or more substituents independently selected from the group consisting of R$^{10}$, C(O)R$^{10}$, C(O)C(O)R$^{10}$, CO(O)R$^{10}$, OH and F;
R$^{10}$, at each occurrence, is independently selected from the group consisting of alkyl, alkenyl, alkynyl, aryl, heterocyclyl, and cycloalkyl; wherein each R$^{10}$ alkyl is optionally substituted with one or more substituents independently selected from the group consisting of R$^{11}$, OR$^{11}$, SR$^{11}$, SO$_2$R$^{11}$, NH$_2$, N(R$^{11}$)$_2$, NHC(O)R$^{11}$, NHS(O)$_2$R$^{11}$, OH, NO$_2$, and F; wherein each R$^{10}$ aryl, heterocyclyl and cycloalkyl is optionally substituted with one or more R$^{12}$, OR$^{12}$, C(O)R$^{12}$, OH, CN, CF$_3$, OCF$_3$, F, and Cl;
R$^{11}$, at each occurrence, is independently selected from the group consisting of alkyl, aryl, heterocyclyl, and cycloalkyl; wherein each R$^{11}$ alkyl is optionally substituted with alkoxy or aryl; wherein each R$^{11}$ aryl, and heterocyclyl is optionally substituted with one or more substituents independently selected from the group consisting of R$^{13}$, C(O)OR$^{13}$, OCF$_3$, CF$_3$, F, and Cl;
R$^{12}$, at each occurrence, is independently selected from the group consisting of alkyl, and aryl; and
R$^{13}$, at each occurrence, is independently selected from the group consisting of alkyl, haloalkyl, and heterocyclyl.

Still another embodiment pertains to compounds having Formula (IIIA), which includes Examples 1, 2, 3, 4, 5, 6, 7, 10, 20, 22, 25, 26, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 609, 610, 611, 612, 613, 614, 615, 616, 617, 665, 666, 667, 668, 737, 738, 739, 740, 741, 748, 750, 751, 753, 784, 803, 804, 805, 806, 807, 809, 817, 818, 819, 820, 821, 822, 823, 840, 841, 842, 843, 844, 845, 846, 851, 852, 853, 854, 857, 863, 864, 865, 866, 867, and pharmaceutically acceptable salts thereof.

Embodiments of Formula (IVA)

In another aspect, the present invention provides compounds of Formula (IVA)

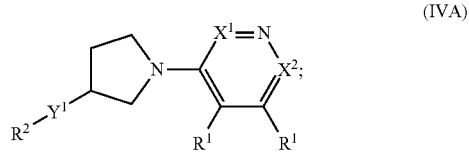

(IVA)

and pharmaceutically acceptable salts thereof; wherein each $X^1, X^2, Y^1, R^1$, and $R^2$ are as described herein for Formula (I).

One embodiment of this invention pertains to compounds of Formula (IVA) and pharmaceutically acceptable salts thereof;
wherein
$X^1$ is N and $X^2$ is $CR^1$; or
$X^1$ is $CR^1$ and $X^2$ is N; or
$X^1$ is $CR^1$ and $X^2$ is $CR^1$;
$Y^1$ is C(O)NH, or NHC(O);

$R^1$, at each occurrence, is independently selected from the group consisting of hydrogen, alkyl, alkenyl, alkynyl, haloalkyl, hydroxyalkyl, alkoxy, OH, $NH_2$, CN, $NO_2$, F, Cl, Br and I;

$R^2$ is independently selected from the group consisting of $C_4$-$C_6$-alkyl, $C_4$-$C_6$-alkenyl, $C_4$-$C_6$-alkynyl, aryl, and 5-6 membered heteroaryl; wherein each $R^2C_4$-$C_6$-alkyl, $C_4$-$C_6$-alkenyl, and $C_4$-$C_6$-alkynyl is substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(N)NH_2$, $C(N)NHR^3$, $C(N)N(R^3)_2$, CNOH, $CNOCH_3$, OH, (O), CN, $N_3$, $NO_2$, F, Cl, Br and I; wherein each $R^2$ aryl and 5-6 membered heteroaryl is optionally substituted with one or more substituents independently selected from the group consisting of $R^4$, $OR^4$, $SR^4$, $S(O)R^4$, $SO_2R^4$, $C(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, and I;

$R^3$, at each occurrence, is independently selected from the group consisting of alkyl, alkenyl, alkynyl, aryl, cycloalkyl, cycloalkenyl, and heterocyclyl; wherein each $R^3$ alkyl, alkenyl, and alkynyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, CNOH, $CNOCH_3$, OH, (O), CN, $N_3$, $NO_2$, F, Cl, Br and I; wherein each $R^3$ aryl, cycloalkyl, cycloalkenyl, and heterocyclyl is optionally substituted with one or more substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $C(N)NH_2$, $C(N)NHR^6$, $C(N)N(R^6)_2$, CNOH, $CNOCH_3$, OH, CN, $N_3$, $NO_2$, F, Cl, Br and I;

$R^4$, at each occurrence, is independently selected from the group consisting of alkyl, alkenyl, alkynyl, aryl, heterocyclyl, cycloalkyl, and cycloalkenyl; wherein each $R^4$ alkyl, alkenyl, and alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, C(O)OH, C(N)NH$_2$, C(N)NHR$^7$, C(N)N(R$^7$)$_2$, CNOH, CNOCH$_3$, OH, (O), CN, N$_3$, NO$_2$, F, Cl, Br and I;

R$^5$, at each occurrence, is independently selected from the group consisting of alkyl, alkenyl, alkynyl, aryl, heterocyclyl, cycloalkyl, and cycloalkenyl; wherein each R$^5$ alkyl, alkenyl, and alkynyl is optionally substituted with one or more substituents independently selected from the group consisting of R$^8$, OR$^8$, SR$^8$, S(O)R$^8$, SO$_2$R$^8$, NHR$^8$, N(R$^8$)$_2$, C(O)R$^8$, C(O)NH$_2$, C(O)NHR$^8$, C(O)N(R$^8$)$_2$, NHC(O)R$^8$, NR$^8$C(O)R$^8$, NHSO$_2$R$^8$, NHC(O)OR$^8$, SO$_2$NH$_2$, SO$_2$NHR$^8$, SO$_2$N(R$^8$)$_2$, NHC(O)NH$_2$, NHC(O)NHR$^8$, OH, (O), C(O)OH, N$_3$, CN, NH$_2$, F, Cl, Br and I;

R$^6$, at each occurrence, is independently selected from the group consisting of alkyl, alkenyl, alkynyl, aryl, heterocyclyl, cycloalkyl, and cycloalkenyl; wherein each R$^6$ alkyl, alkenyl, and alkynyl is optionally substituted with one or more substituents independently selected from the group consisting of R$^9$, OR$^9$, SR$^9$, S(O)R$^9$, SO$_2$R$^9$, NHR$^9$, N(R$^9$)$_2$, C(O)R$^9$, C(O)NH$_2$, C(O)NHR$^9$, C(O)N(R$^9$)$_2$, NHC(O)R$^9$, NR$^9$C(O)R$^9$, NHSO$_2$R$^9$, NHC(O)OR$^9$, SO$_2$NH$_2$, SO$_2$NHR$^9$, SO$_2$N(R$^9$)$_2$, NHC(O)NH$_2$, NHC(O)NHR$^9$, OH, (O), C(O)OH, N$_3$, CN, NH$_2$, CF$_3$, CF$_2$CF$_3$, F, Cl, Br and I;

R$^7$, at each occurrence, is independently selected from the group consisting of alkyl, alkenyl, alkynyl, aryl, heterocyclyl, cycloalkyl, and cycloalkenyl;

R$^8$, at each occurrence, is independently selected from the group consisting of alkyl, alkenyl, alkynyl, aryl, heterocyclyl, cycloalkyl, and cycloalkenyl;

R$^9$, at each occurrence, is independently selected from the group consisting of alkyl, alkenyl, alkynyl, aryl, heterocyclyl, cycloalkyl, and cycloalkenyl;

wherein the cyclic moieties represented by R$^4$, R$^5$, R$^6$, R$^7$, R$^8$, and R$^9$ are independently optionally substituted with one or more substituents independently selected from the group consisting of R$^{10}$, OR$^{10}$, SR$^{10}$, S(O)R$^{10}$, SO$_2$R$^{10}$, C(O)R$^{10}$, CO(O)R$^{10}$, OC(O)R$^{10}$, OC(O)OR$^{10}$, C(O)C(O)R$^{10}$, NH$_2$, NHR$^{10}$, N(R$^{10}$)$_2$, NHC(O)R$^{10}$, NR$^{10}$C(O)R$^{10}$, NHS(O)$_2$R$^{10}$, NR$^{10}$S(O)$_2$R$^{10}$, NHC(O)OR$^{10}$, NR$^{10}$C(O)OR$^{10}$, NHC(O)NH$_2$, NHC(O)NHR$^{10}$, NHC(O)N(R$^{10}$)$_2$, NR$^{10}$C(O)NHR$^{10}$, NR$^{10}$C(O)N(R$^{10}$)$_2$, C(O)NH$_2$, C(O)NHR$^{10}$, C(O)N(R$^{10}$)$_2$, C(O)NHOH, C(O)NHOR$^{10}$, C(O)NHSO$_2$R$^{10}$, C(O)NR$^{10}$SO$_2$R$^{10}$, SO$_2$NH$_2$, SO$_2$NHR$^{10}$, SO$_2$N(R$^{10}$)$_2$, C(O)H, C(O)OH, C(N)NH$_2$, C(N)NHR$^{10}$, C(N)N(R$^{10}$)$_2$, CNOH, CNOCH$_3$, OH, CN, N$_3$, NO$_2$, F, Cl, Br and I;

R$^{10}$, at each occurrence, is independently selected from the group consisting of alkyl, alkenyl, alkynyl, aryl, heterocyclyl, cycloalkyl, and cycloalkenyl; wherein each R$^{10}$ alkyl, alkenyl, and alkynyl is optionally substituted with one or more substituents independently selected from the group consisting of R$^{11}$, OR$^{11}$, SR$^{11}$, S(O)R$^{11}$, SO$_2$R$^{11}$, C(O)R$^{11}$, CO(O)R$^{11}$, OC(O)R$^{11}$, OC(O)OR$^{11}$, NH$_2$, NHR$^{11}$, N(R$^{11}$)$_2$, NHC(O)R$^{11}$, NR$^{11}$C(O)R$^{11}$, NHS(O)$_2$R$^{11}$, NR$^{11}$S(O)$_2$R$^{11}$, NHC(O)OR$^{11}$, NR$^{11}$C(O)OR$^{11}$, NHC(O)NH$_2$, NHC(O)NHR$^{11}$, NHC(O)N(R$^{11}$)$_2$, NR$^{11}$C(O)NHR$^{11}$, NR$^{11}$C(O)N(R$^{11}$)$_2$, C(O)NH$_2$, C(O)NHR$^{11}$, C(O)N(R$^{11}$)$_2$, C(O)NHOH, C(O)NHOR$^{11}$, C(O)NHSO$_2$R$^{11}$, C(O)NR$^{11}$SO$_2$R$^{11}$, SO$_2$NH$_2$, SO$_2$NHR$^{11}$, SO$_2$N(R$^{11}$)$_2$, C(O)H, C(O)OH, C(N)NH$_2$, C(N)NHR$^{11}$, C(N)N(R$^{11}$)$_2$, CNOH, CNOCH$_3$, OH, (O), CN, N$_3$, NO$_2$, F, Cl, Br and I; wherein each R$^{10}$ aryl, heterocyclyl, cycloalkyl, and cycloalkenyl is optionally substituted with one or more substituents independently selected from the group consisting of R$^{12}$, OR$^{12}$, SR$^{12}$, S(O)R$^{12}$, SO$_2$R$^{12}$, C(O)R$^{12}$, CO(O)R$^{12}$, OC(O)R$^{12}$, OC(O)OR$^{12}$, NH$_2$, NHR$^{12}$, N(R$^{12}$)$_2$, NHC(O)R$^{12}$, NR$^{12}$C(O)R$^{12}$, NHS(O)$_2$R$^{12}$, NR$^{12}$S(O)$_2$R$^{12}$, NHC(O)OR$^{12}$, NR$^{12}$C(O)OR$^{12}$, NHC(O)NH$_2$, NHC(O)NHR$^{12}$, NHC(O)N(R$^{12}$)$_2$, NR$^{12}$C(O)NHR$^{12}$, NR$^{12}$C(O)N(R$^{12}$)$_2$, C(O)NH$_2$, C(O)NHR$^{12}$, C(O)N(R$^{12}$)$_2$, C(O)NHOH, C(O)NHOR$^{12}$, C(O)NHSO$_2$R$^{12}$, C(O)NR$^{12}$SO$_2$R$^{12}$, SO$_2$NH$_2$, SO$_2$NHR$^{12}$, SO$_2$N(R$^{12}$)$_2$, C(O)H, C(O)OH, C(N)NH$_2$, C(N)NHR$^{12}$, C(N)N(R$^{12}$)$_2$, CNOH, CNOCH$_3$, OH, CN, N$_3$, NO$_2$, CF$_3$, OCF$_3$, F, Cl, Br and I;

R$^{11}$, at each occurrence, is independently selected from the group consisting of alkyl, alkenyl, alkynyl, aryl, heterocyclyl, cycloalkyl, and cycloalkenyl; wherein each R$^{11}$ alkyl, alkenyl, and alkynyl is optionally substituted with alkoxy or aryl; wherein each R$^{11}$ aryl, heterocyclyl, cycloalkyl, and cycloalkenyl is optionally substituted with one or more substituents independently selected from the group consisting of R$^{13}$, OR$^{13}$, C(O)OR$^{13}$, OCF$_3$, CF$_3$, F, Cl, Br and I;

R$^{12}$, at each occurrence, is independently selected from the group consisting of alkyl, alkenyl, alkynyl, aryl, heterocyclyl, cycloalkyl, and cycloalkenyl; and R$^{13}$, at each occurrence, is independently selected from the group consisting of alkyl, haloalkyl, alkenyl, alkynyl, aryl, heterocyclyl, cycloalkyl, and cycloalkenyl;

with the proviso that when X$^1$ is CR$^1$ and X$^2$ is CR$^1$; R$^1$ is hydrogen; Y$^1$ is NHC(O); and R$^2$ is pyrrolyl; the R$^2$ pyrrolyl is not substituted with two alkyl groups.

In one embodiment of Formula (IVA), X$^1$ is N and X$^2$ is CR$^1$; or X$^1$ is CR$^1$ and X$^2$ is N; or X$^1$ is CR$^1$ and X$^2$ is CR$^1$. In another embodiment of Formula (IVA), X$^1$ is N and X$^2$ is CR$^1$. In another embodiment of Formula (IVA), X$^1$ is CR$^1$ and X$^2$ is N. In another embodiment of Formula (IVA), X$^1$ is CR$^1$ and X$^2$ is CR$^1$.

In one embodiment of Formula (IVA), Y$^1$ is C(O)NH, or NHC(O). In another embodiment of Formula (IVA), Y$^1$ is C(O)NH. In another embodiment of Formula (IVA), Y$^1$ is NHC(O).

In one embodiment of Formula (IVA), X$^1$ is CR$^1$ and X$^2$ is CR$^1$; and R$^1$, at each occurrence, is independently selected from the group consisting of hydrogen, alkyl, alkenyl, alkynyl, haloalkyl, hydroxyalkyl, alkoxy, OH, NH$_2$, CN, NO$_2$, F, Cl, Br and I. In another embodiment of Formula (IVA), X$^1$ is CR$^1$ and X$^2$ is CR$^1$; and R$^1$, at each occurrence, is independently selected from the group consisting of hydrogen, alkyl, haloalkyl, alkoxy, CN, F, Cl, Br and I. In another embodiment of Formula (IVA), X$^1$ is CR$^1$ and X$^2$ is CR$^1$; and R$^1$, at each occurrence, is independently selected from the group consisting of hydrogen, alkyl, haloalkyl, alkoxy, CN, F, and Cl. In another embodiment of Formula (IVA), X$^1$ is CR$^1$ and X$^2$ is CR$^1$; and R$^1$, at each occurrence, is hydrogen.

In another aspect, the present invention provides compounds of Formula (IVB),

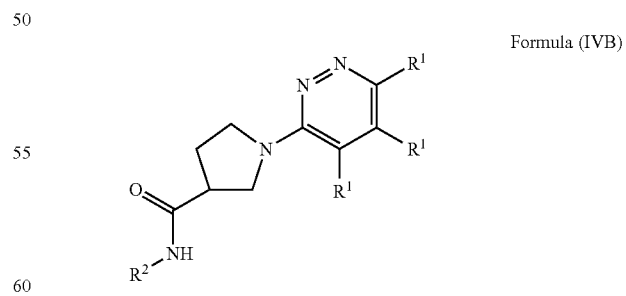

Formula (IVB)

and pharmaceutically acceptable salts thereof; wherein R$^1$ and R$^2$ are as described herein for Formula (IA).

In one embodiment of Formula (IVA) and (IVB), R$^1$, at each occurrence, is independently selected from the group consisting of hydrogen, alkyl, alkenyl, alkynyl, haloalkyl, hydroxyalkyl, alkoxy, OH, NH$_2$, CN, NO$_2$, F, Cl, Br and I. In another embodiment of Formula (IVA) and (IVB), $R^1$, at each occurrence, is independently selected from the group consisting of hydrogen, alkyl, haloalkyl, alkoxy, CN, F, Cl, Br and I. In another embodiment of Formula (IVA) and (IVB), $R^1$, at each occurrence, is independently selected from the group consisting of hydrogen, alkyl, haloalkyl, alkoxy, CN, F, and Cl. In another embodiment of Formula (IVA) and (IVB), $R^1$, at each occurrence, is hydrogen.

In one embodiment of Formula (IVA) and (IVB), $R^2$ is independently selected from the group consisting of $C_4$-$C_6$-alkyl, $C_4$-$C_6$-alkenyl, $C_4$-$C_6$-alkynyl, aryl, and 5-6 membered heteroaryl; wherein each $R^2$ $C_4$-$C_6$-alkyl, $C_4$-$C_6$-alkenyl, and $C_4$-$C_6$-alkynyl is substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(N)NH_2$, $C(N)NHR^3$, $C(N)N(R^3)_2$, $CNOH$, $CNOCH_3$, $OH$, $(O)$, $CN$, $N_3$, $NO_2$, F, Cl, Br and I; wherein each $R^2$ aryl and 5-6 membered heteroaryl is optionally substituted with one or more substituents independently selected from the group consisting of $R^4$, $OR^4$, $SR^4$, $S(O)R^4$, $SO_2R^4$, $C(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, $CNOH$, $CNOCH_3$, $OH$, $CN$, $N_3$, $NO_2$, F, Cl, and I. In another embodiment of Formula (IVA) and (IVB), $R^2$ is aryl; wherein each $R^2$ aryl is optionally substituted with one or more substituents independently selected from the group consisting of $R^4$, $OR^4$, $SO_2R^4$, F, Cl, and I. In another embodiment of Formula (IVA) and (IVB), $R^2$ is aryl; wherein each $R^2$ aryl is optionally substituted with one or more substituents independently selected from the group consisting of $R^4$, $OR^4$, $SO_2R^4$, and F. In another embodiment of Formula (IVA) and (IVB), $R^2$ is phenyl; wherein each $R^2$ phenyl is optionally substituted with one or more substituents independently selected from the group consisting of $R^4$, $OR^4$, $SO_2R^4$, and F. In another embodiment of Formula (IVA) and (IVB), $R^2$ is phenyl; wherein each $R^2$ phenyl is substituted with one substituent independently selected from the group consisting of $R^4$, $OR^4$, and $SO_2R^4$.

In another embodiment of Formula (IVA) and (IVB), $R^2$ is 5-6 membered heteroaryl; wherein each $R^2$ 5-6 membered heteroaryl is optionally substituted with one or more substituents independently selected from the group consisting of $R^4$, $OR^4$, $SO_2R^4$, F, Cl, and I. In another embodiment of Formula (IVA) and (IVB), $R^2$ is 5-6 membered heteroaryl; wherein each $R^2$ 5-6 membered heteroaryl is optionally substituted with one or more substituents independently selected from the group consisting of $R^4$, $OR^4$, $SO_2R^4$, and F. In another embodiment of Formula (IVA) and (IVB), $R^2$ is furanyl or thiophenyl; wherein each $R^2$ furanyl and thiophenyl is optionally substituted with one or more substituents independently selected from the group consisting of $R^4$, $OR^4$, $SO_2R^4$, and F.

In one embodiment of Formula (IVA) and (IVB), $R^4$, at each occurrence, is independently selected from the group consisting of alkyl, alkenyl, alkynyl, aryl, heterocyclyl, cycloalkyl, and cycloalkenyl; wherein each $R^4$ alkyl, alkenyl, and alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)R^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, $CNOH$, $CNOCH_3$, $OH$, $(O)$, $CN$, $N_3$, $NO_2$, F, Cl, Br and I. In another embodiment of Formula (IVA) and (IVB), $R^4$, at each occurrence, is alkyl or heterocyclyl.

In one embodiment of Formula (IVA) and (IVB), each $R^4$ alkyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, $CNOH$, $CNOCH_3$, $OH$, $(O)$, $CN$, $N_3$, $NO_2$, F, Cl, Br and I. In another embodiment of Formula (IVA) and (IVB), each $R^4$ alkyl is optionally substituted with one $R^7$.

In one embodiment of Formula (IVA) and (IVB), $R^7$, at each occurrence, is independently selected from the group consisting of alkyl, alkenyl, alkynyl, aryl, heterocyclyl, cycloalkyl, and cycloalkenyl. In another embodiment of Formula (IVA) and (IVB), $R^7$, at each occurrence, is heterocyclyl.

In one embodiment of Formula (IVA) and (IVB), each $R^4$ and $R^7$ heterocyclyl is independently optionally substituted with one or more substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, $CNOH$, $CNOCH_3$, $OH$, $CN$, $N_3$, $NO_2$, F, Cl, Br and I; $R^{10}$, at each occurrence, is independently selected from the group consisting of alkyl, alkenyl, alkynyl, aryl, heterocyclyl, cycloalkyl, and cycloalkenyl; wherein each $R^{10}$ alkyl, alkenyl, and alkynyl is optionally substituted with one or more substituents independently selected from the group consisting of $R^{11}$, $OR^{11}$, $SR^{11}$, $S(O)R^{11}$, $SO_2R^{11}$, $C(O)R^{11}$, $CO(O)R^{11}$, $OC(O)R^{11}$, $OC(O)OR^{11}$, $NH_2$, $NHR^{11}$, $N(R^{11})_2$, $NHC(O)R^{11}$, $NR^{11}C(O)R^{11}$, $NHS(O)_2R^{11}$, $NR^{11}S(O)_2R^{11}$, $NHC(O)OR^{11}$, $NR^{11}C(O)OR^{11}$, $NHC(O)NH_2$, $NHC(O)NHR^{11}$, $NHC(O)N(R^{11})_2$, $NR^{11}C(O)NHR^{11}$, $NR^{11}C(O)N(R^{11})_2$, $C(O)NH_2$, $C(O)NHR^{11}$, $C(O)NHOH$, $C(O)NHOR^{11}$, $C(O)NHSO_2R^{11}$, $C(O)NR^{11}SO_2R^{11}$, $SO_2NH_2$, $SO_2NHR^{11}$, $SO_2N(R^{11})_2$, $C(O)H$, $C(O)OH$, $C(N)NH_2$, $C(N)NHR^{11}$, $C(N)N(R^{11})_2$, $CNOH$, $CNOCH_3$, $OH$, $(O)$, $CN$, $N_3$, $NO_2$, F, Cl, Br and I; wherein each $R^{10}$ aryl, heterocyclyl, cycloalkyl, and cycloalkenyl is optionally substituted with one or more substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)$ $NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, $C(N)NH_2$, $C(N)NHR^{12}$, $C(N)N(R^{12})_2$, CNOH, $CNOCH_3$, OH, CN, $N_3$, $NO_2$, F, Cl, Br and I; $R^{11}$, at each occurrence, is independently selected from the group consisting of alkyl, alkenyl, alkynyl, aryl, heterocyclyl, cycloalkyl, and cycloalkenyl; wherein each $R^{11}$ alkyl, alkenyl, and alkynyl is optionally substituted with alkoxy or aryl; wherein each $R^{11}$ aryl, heterocyclyl, cycloalkyl, and cycloalkenyl is optionally substituted with one or more substituents independently selected from the group consisting of $R^{13}$, $OR^{13}$, $C(O)OR^{13}$, $OCF_3$, $CF_3$, F, Cl, Br and I; $R^{12}$, at each occurrence, is independently selected from the group consisting of alkyl, alkenyl, alkynyl, aryl, heterocyclyl, cycloalkyl, and cycloalkenyl; and $R^{13}$, at each occurrence, is independently selected from the group consisting of alkyl, haloalkyl, alkenyl, alkynyl, aryl, heterocyclyl, cycloalkyl, and cycloalkenyl.

In another embodiment of Formula (IVA) and (IVB), each $R^4$ and $R^7$ heterocyclyl is independently optionally substituted with one or more substituents independently selected from the group consisting of $R^{10}$, $C(O)R^{10}$, $CO(O)R^{10}$, $C(O)C(O)R^{10}$, OH, F, Cl, Br and I; $R^{10}$, at each occurrence, is independently selected from the group consisting of alkyl, alkenyl, alkynyl, aryl, heterocyclyl, and cycloalkyl; wherein each $R^{10}$ alkyl, alkenyl, and alkynyl, are optionally substituted with one or more substituents independently selected from the group consisting of $R^{11}$, $OR^{11}$, $SR^{11}$, $SO_2R^{11}$, $NH_2$, $N(R^{11})_2$, $NHC(O)R^{11}$, $NHS(O)_2R^{11}$, OH, $NO_2$, and F; wherein each $R^{10}$ aryl, heterocyclyl and cycloalkyl is optionally substituted with one or more substituents independently selected from the group consisting of $R^{12}$, $OR^{12}$, $C(O)R^{12}$, OH, CN, $CF_3$, $OCF_3$, F, and Cl; $R^{11}$, at each occurrence, is independently selected from the group consisting of alkyl, aryl, heterocyclyl, and cycloalkyl; wherein each $R^{11}$ alkyl is optionally substituted with alkoxy or aryl; wherein each $R^{11}$ aryl and heterocyclyl is optionally substituted with one or more substituents independently selected from the group consisting of $R^{13}$, $CF_3$, F, and Cl; $R^{12}$, at each occurrence, is independently selected from the group consisting of alkyl and aryl; and $R^{13}$, at each occurrence, is independently selected from the group consisting of alkyl and haloalkyl.

One embodiment of this invention pertains to compounds or pharmaceutically acceptable salts thereof, which are useful as inhibitors of NAMPT, the compounds having Formula (IVA)

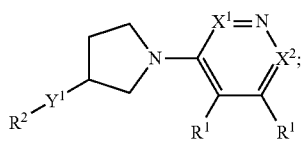

(IVA)

wherein
$X^1$ is N and $X^2$ is $CR^1$; or
$X^1$ is $CR^1$ and $X^2$ is N; or
$X^1$ is $CR^1$ and $X^2$ is $CR^1$;
$Y^1$ is C(O)NH, or NHC(O);
$R^1$, at each occurrence, is independently selected from the group consisting of hydrogen, alkyl, haloalkyl, alkoxy, CN, Cl, and F;
$R^2$ is aryl or 5-6 membered heteroaryl wherein each $R^2$ aryl and 5-6 membered heteroaryl is optionally substituted with one or more substituents independently selected from the group consisting of $R^4$, $SO_2R^4$, $OR^4$, and F;

$R^4$, at each occurrence, is alkyl or heterocyclyl; wherein each $R^4$ alkyl is optionally substituted with $R^7$;
$R^7$, at each occurrence, is independently heterocyclyl;
wherein the cyclic moieties represented by $R^4$ and $R^7$ are independently optionally substituted with one or more substituents independently selected from the group consisting of $R^{10}$, $C(O)R^{10}$, $C(O)O(O)R^{10}$, $CO(O)R^{10}$, OH and F;
$R^{10}$, at each occurrence, is independently selected from the group consisting of alkyl, alkenyl, alkynyl, aryl, heterocyclyl, and cycloalkyl; wherein each $R^{10}$ alkyl is optionally substituted with one or more substituents independently selected from the group consisting of $R^{11}$, $OR^{11}$, $SR^{11}$, $SO_2R^{11}$, $NH_2$, $N(R^{11})_2$, $NHC(O)R^{11}$, $NHS(O)_2R^{11}$, OH, $NO_2$, and F; wherein each $R^{10}$ aryl, heterocyclyl and cycloalkyl is optionally substituted with one or more $R^{12}$, $OR^{12}$, $C(O)R^{12}$, OH, CN, $CF_3$, $OCF_3$, F, and Cl;
$R^{11}$, at each occurrence, is independently selected from the group consisting of alkyl, aryl, heterocyclyl, and cycloalkyl; wherein each $R^{11}$ alkyl is optionally substituted with alkoxy or aryl; wherein each $R^{11}$ aryl, and heterocyclyl is optionally substituted with one or more substituents independently selected from the group consisting of $R^{13}$, $C(O)OR^{13}$, $OCF_3$, $CF_3$, F, and Cl;
$R^{12}$, at each occurrence, is independently selected from the group consisting of alkyl, and aryl; and
$R^{13}$, at each occurrence, is independently selected from the group consisting of alkyl, haloalkyl, and heterocyclyl;
with the proviso that
when $X^1$ is $CR^1$ and $X^2$ is $CR^1$; $R^1$ is hydrogen; $Y^1$ is NHC(O); and $R^2$ is pyrrolyl; the $R^2$ pyrrolyl is not substituted with two alkyl groups.

Still another embodiment pertains to compounds having Formula (IVA), which includes Examples 8, 9, 11, 12, 13, 14, 15, 16, 17, 18, 19, 27, 28, 141, 142, 204, 310, 311, 312, 313, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, and pharmaceutically acceptable salts thereof.

Embodiments of Formula (VA)

In another aspect, the present invention provides compounds of Formula (VA)

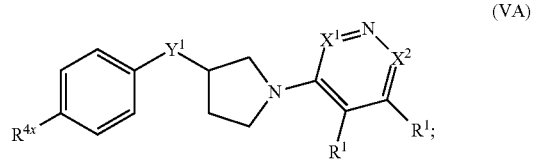

(VA)

and pharmaceutically acceptable salts thereof; wherein $X^1$, $X^2$, $R^1$, and $Y^1$ are as described in Formula (IA) herein and $R^{4x}$ is as described herein for substituents on $R^2$ when $R^2$ is aryl in Formula (IA).

One embodiment of this invention pertains to compounds of Formula (VA) or pharmaceutically acceptable salts thereof;
wherein
$X^1$ is N and $X^2$ is $CR^1$; or
$X^1$ is $CR^1$ and $X^2$ is N; or
$X^1$ is $CR^1$ and $X^2$ is $CR^1$;
$Y^1$ is C(O)NH, or NHC(O);
$R^1$, at each occurrence, is independently selected from the group consisting of hydrogen, alkyl, alkenyl, alkynyl, haloalkyl, hydroxyalkyl, alkoxy, OH, $NH_2$, CN, $NO_2$, F, Cl, Br and I;
$R^{4x}$ is independently selected from the group consisting of $R^4$, $OR^4$, $SR^4$, $S(O)R^4$, $SO_2R^4$, $C(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, C(O)H, C(O)OH, $C(N)NH_2$, $C(N)NHR^4$, $C(N)N(R^4)_2$, CNOH, $CNOCH_3$, OH, CN, $N_3$, $NO_2$, F, Cl, and I;
$R^4$, at each occurrence, is independently selected from the group consisting of alkyl, alkenyl, alkynyl, aryl, heterocyclyl, cycloalkyl, and cycloalkenyl; wherein each $R^4$ alkyl, alkenyl, and alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, C(O)H, C(O)OH, $C(N)NH_2$, $C(N)NHR^7$, $C(N)N(R^7)_2$, CNOH, $CNOCH_3$, OH, (O), CN, $N_3$, $NO_2$, F, Cl, Br and I;
$R^7$, at each occurrence, is independently selected from the group consisting of alkyl, alkenyl, alkynyl, aryl, heterocyclyl, cycloalkyl, and cycloalkenyl;
wherein the cyclic moieties represented by $R^4$, and $R^7$, are independently optionally substituted with one or more substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $C(O)C(O)R^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, C(O)H, C(O)OH, $C(N)NH_2$, $C(N)NHR^{10}$, $C(N)N(R^{10})_2$, CNOH, $CNOCH_3$, OH, CN, $N_3$, $NO_2$, F, Cl, Br and I;
$R^{10}$, at each occurrence, is independently selected from the group consisting of alkyl, alkenyl, alkynyl, aryl, heterocyclyl, cycloalkyl, and cycloalkenyl; wherein each $R^{10}$ alkyl, alkenyl, and alkynyl is optionally substituted with one or more substituents independently selected from the group consisting of $R^{11}$, $OR^{11}$, $SR^{11}$, $S(O)R^{11}$, $SO_2R^{11}$, $C(O)R^{11}$, $CO(O)R^{11}$, $OC(O)R^{11}$, $OC(O)OR^{11}$, $NH_2$, $NHR^{11}$, $N(R^{11})_2$, $NHC(O)R^{11}$, $NR^{11}C(O)R^{11}$, $NHS(O)_2R^{11}$, $NR^{11}S(O)_2R^{11}$, $NHC(O)OR^{11}$, $NR^{11}C(O)OR^{11}$, $NHC(O)NH_2$, $NHC(O)NHR^{11}$, $NHC(O)N(R^{11})_2$, $NR^{11}C(O)NHR^{11}$, $NR^{11}C(O)N(R^{11})_2$, $C(O)NH_2$, $C(O)NHR^{11}$, $C(O)N(R^{11})_2$, $C(O)NHOH$, $C(O)N$-$HOR^{11}$, $C(O)NHSO_2R^{11}$, $C(O)NR^{11}SO_2R^{11}$, $SO_2NH_2$, $SO_2NHR^{11}$, $SO_2N(R^{11})_2$, C(O)H, C(O)OH, $C(N)NH_2$, $C(N)NHR^{11}$, $C(N)N(R^{11})_2$, CNOH, $CNOCH_3$, OH, (O), CN, $N_3$, $NO_2$, F, Cl, Br and I; wherein each $R^{10}$ aryl, heterocyclyl, cycloalkyl, and cycloalkenyl is optionally substituted with one or more substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, C(O)H, C(O)OH, $C(N)NH_2$, $C(N)NHR^{12}$, $C(N)N(R^{12})_2$, CNOH, $CNOCH_3$, OH, CN, $N_3$, $NO_2$, $CF_3$, $OCF_3$, F, Cl, Br and I;
$R^{11}$, at each occurrence, is independently selected from the group consisting of alkyl, alkenyl, alkynyl, aryl, heterocyclyl, cycloalkyl, and cycloalkenyl; wherein each $R^{11}$ alkyl, alkenyl, and alkynyl is optionally substituted with alkoxy or aryl; wherein each $R^{11}$ aryl, heterocyclyl, cycloalkyl, and cycloalkenyl is optionally substituted with one or more substituents independently selected from the group consisting of $R^{13}$, $OR^{13}$, $C(O)OR^{13}$, $OCF_3$, $CF_3$, F, Cl, Br and I;
$R^{12}$, at each occurrence, is independently selected from the group consisting of alkyl, alkenyl, alkynyl, aryl, heterocyclyl, cycloalkyl, and cycloalkenyl; and
$R^{13}$, at each occurrence, is independently selected from the group consisting of alkyl, haloalkyl, alkenyl, alkynyl, aryl, heterocyclyl, cycloalkyl, and cycloalkenyl.

In one embodiment of Formula (VA), $X^1$ is N and $X^2$ is $CR^1$; or $X^1$ is $CR^1$ and $X^2$ is N; or $X^1$ is $CR^1$ and $X^2$ is $CR^1$. In another embodiment of Formula (VA), $X^1$ is N and $X^2$ is $CR^1$. In another embodiment of Formula (VA), $X^1$ is $CR^1$ and $X^2$ is N. In another embodiment of Formula (VA), $X^1$ is $CR^1$ and $X^2$ is $CR^1$.

In one embodiment of Formula (VA), $Y^1$ is C(O)NH, or NHC(O). In another embodiment of Formula (VA), $Y^1$ is C(O)NH. In another embodiment of Formula (VA), $Y^1$ is NHC(O).

In one embodiment of Formula (VA), $X^1$ is $CR^1$ and $X^2$ is $CR^1$; and $R^1$, at each occurrence, is independently selected from the group consisting of hydrogen, alkyl, alkenyl, alkynyl, haloalkyl, hydroxyalkyl, alkoxy, OH, $NH_2$, CN, $NO_2$, F, Cl, Br and I. In another embodiment of Formula (VA), $X^1$ is $CR^1$ and $X^2$ is $CR^1$; and $R^1$, at each occurrence, is independently selected from the group consisting of hydrogen, alkyl, haloalkyl, alkoxy, CN, F, Cl, Br and I. In another embodiment of Formula (VA), $X^1$ is $CR^1$ and $X^2$ is $CR^1$; and $R^1$, at each occurrence, is independently selected from the group consisting of hydrogen, alkyl, haloalkyl, alkoxy, CN, F, and Cl. In another embodiment of Formula (VA), $X^1$ is $CR^1$ and $X^2$ is $CR^1$; and $R^1$, at each occurrence, is hydrogen.

In another aspect, the present invention provides compounds of Formula (VB),

Formula (VB)

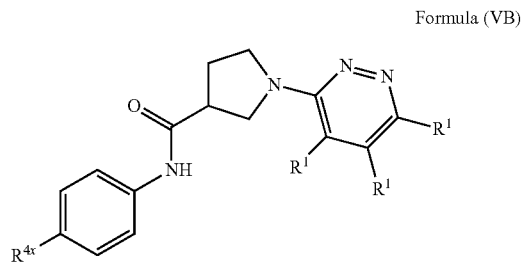

and pharmaceutically acceptable salts thereof; wherein $R^1$ is described herein for Formula (IA) and $R^{4x}$ is as described herein for substituents on $R^2$ when $R^2$ is aryl in Formula (IA).

In one embodiment of Formula (VA) and (VB), $R^1$, at each occurrence, is independently selected from the group consisting of hydrogen, alkyl, alkenyl, alkynyl, haloalkyl, hydroxyalkyl, alkoxy, OH, $NH_2$, CN, $NO_2$, F, Cl, Br and I. In another embodiment of Formula (VA) and (VB), $R^1$, at each occurrence, is independently selected from the group consisting of hydrogen, alkyl, haloalkyl, alkoxy, CN, F, Cl, Br and I. In another embodiment of Formula (VA) and (VB), $R^1$, at each occurrence, is independently selected from the group consisting of hydrogen, alkyl, haloalkyl, alkoxy, CN, F, and Cl. In another embodiment of Formula (VA) and (VB), $R^1$, at each occurrence, is hydrogen.

In one embodiment of Formula (VA) and (VB), $R^{4X}$ is independently selected from the group consisting of $R^4$, $OR^4$, $SR^4$, $S(O)R^4$, $SO_2R^4$, $C(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, and I. In another embodiment of Formula (VA) and (VB), $R^{4X}$ is independently selected from the group consisting of $R^4$, $OR^4$, $SO_2R^4$, F, Cl, and I. In another embodiment of Formula (VA) and (VB), $R^{4X}$ is independently selected from the group consisting of $R^4$, $OR^4$, $SO_2R^4$, and F.

In one embodiment of Formula (VA) and (VB), $R^4$, at each occurrence, is independently selected from the group consisting of alkyl, alkenyl, alkynyl, aryl, heterocyclyl, cycloalkyl, and cycloalkenyl; wherein each $R^4$ alkyl, alkenyl, and alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, CNOH, $CNOCH_3$, OH, (O), CN, $N_3$, $NO_2$, F, Cl, Br and I. In another embodiment of Formula (VA) and (VB), $R^4$, at each occurrence, is alkyl or heterocyclyl.

In one embodiment of Formula (VA) and (VB), each $R^4$ alkyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, CNOH, $CNOCH_3$, OH, (O), CN, $N_3$, $NO_2$, F, Cl, Br and I. In another embodiment of Formula (I), each $R^4$ alkyl is optionally substituted with one $R^7$.

In one embodiment of Formula (VA) and (VB), $R^7$, at each occurrence, is independently selected from the group consisting of alkyl, alkenyl, alkynyl, aryl, heterocyclyl, cycloalkyl, and cycloalkenyl. In another embodiment of Formula (VA) and (VB), $R^7$, at each occurrence, is heterocyclyl.

In one embodiment of Formula (VA) and (VB), each $R^4$ and $R^7$ heterocyclyl is independently optionally substituted with one or more substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, CNOH, $CNOCH_3$, OH, CN, $N_3$, $NO_2$, F, Cl, Br and I; $R^{10}$, at each occurrence, is independently selected from the group consisting of alkyl, alkenyl, alkynyl, aryl, heterocyclyl, cycloalkyl, and cycloalkenyl; wherein each $R^{10}$ alkyl, alkenyl, and alkynyl is optionally substituted with one or more substituents independently selected from the group consisting of $R^{11}$, $OR^{11}$, $SR^{11}$, $S(O)R^{11}$, $SO_2R^{11}$, $C(O)R^{11}$, $CO(O)R^{11}$, $OC(O)R^{11}$, $OC(O)OR^{11}$, $NH_2$, $NHR^{11}$, $N(R^{11})_2$, $NHC(O)R^{11}$, $NR^{11}C(O)R^{11}$, $NHS(O)_2R^{11}$, $NR^{11}S(O)_2R^{11}$, $NHC(O)OR^{11}$, $NR^{11}C(O)OR^{11}$, $NHC(O)NH_2$, $NHC(O)NHR^{11}$, $NHC(O)N(R^{11})_2$, $NR^{11}C(O)NHR^{11}$, $NR^{11}C(O)N(R^{11})_2$, $C(O)NH_2$, $C(O)NHR^{11}$, $C(O)N(R^{11})_2$, $C(O)NHOH$, $C(O)NHOR^{11}$, $C(O)NHSO_2R^{11}$, $C(O)NR^{11}SO_2R^{11}$, $SO_2NH_2$, $SO_2NHR^{11}$, $SO_2N(R^{11})_2$, $C(O)H$, $C(O)OH$, $C(N)NH_2$, $C(N)NHR^{11}$, $C(N)N(R^{11})_2$, CNOH, $CNOCH_3$, OH, (O), CN, $N_3$, $NO_2$, F, Cl, Br and I; wherein each $R^{10}$ aryl, heterocyclyl, cycloalkyl, and cycloalkenyl is optionally substituted with one or more substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, $C(N)NH_2$, $C(N)NHR^{12}$, $C(N)N(R^{12})_2$, CNOH, $CNOCH_3$, OH, CN, $N_3$, $NO_2$, F, Cl, Br and I; $R^{11}$, at each occurrence, is independently selected from the group consisting of alkyl, alkenyl, alkynyl, aryl, heterocyclyl, cycloalkyl, and cycloalkenyl; wherein each $R^{11}$ alkyl, alkenyl, and alkynyl is optionally substituted with alkoxy or aryl; wherein each $R^{11}$ aryl, heterocyclyl, cycloalkyl, and cycloalkenyl is optionally substituted with one or more substituents independently selected from the group consisting of $R^{13}$, $OR^{13}$, $C(O)OR^{13}$, $OCF_3$, $CF_3$, F, Cl, Br and I; $R^{12}$, at each occurrence, is independently selected from the group consisting of alkyl, alkenyl, alkynyl, aryl, heterocyclyl, cycloalkyl, and cycloalkenyl; and $R^{13}$, at each occurrence, is independently selected from the group consisting of alkyl, haloalkyl, alkenyl, alkynyl, aryl, heterocyclyl, cycloalkyl, and cycloalkenyl.

In another embodiment of Formula (VA) and (VB), each $R^4$ and $R^7$ heterocyclyl is independently optionally substituted with one or more substituents independently selected from the group consisting of $R^{10}$, $C(O)R^{10}$, $CO(O)R^{10}$, $C(O)C(O)R^{10}$, OH, F, Cl, Br and I; $R^{10}$, at each occurrence, is independently selected from the group consisting of alkyl, alkenyl, alkynyl, aryl, heterocyclyl, and cycloalkyl; wherein each $R^{10}$ alkyl, alkenyl, and alkynyl, are optionally substituted with one or more substituents independently selected from the group consisting of $R^{11}$, $OR^{11}$, $SR^{11}$, $SO_2R^{11}$, $NH_2$, $N(R^{11})_2$, $NHC(O)R^{11}$, $NHS(O)_2R^{11}$, OH, $NO_2$, and F; wherein each $R^{10}$ aryl, heterocyclyl and cycloalkyl is optionally substituted with one or more substituents independently selected from the group consisting of $R^{12}$, $OR^{12}$, $C(O)R^{12}$, OH, CN, $CF_3$, OCF$_3$, F, and Cl; R$^{11}$, at each occurrence, is independently selected from the group consisting of alkyl, aryl, heterocyclyl, and cycloalkyl; wherein each R$^{11}$ alkyl is optionally substituted with alkoxy or aryl; wherein each R$^{11}$ aryl and heterocyclyl is optionally substituted with one or more substituents independently selected from the group consisting of R$^{13}$, CF$_3$, F, and Cl; R$^{12}$, at each occurrence, is independently selected from the group consisting of alkyl and aryl; and R$^{13}$, at each occurrence, is independently selected from the group consisting of alkyl and haloalkyl.

One embodiment of this invention pertains to compounds or pharmaceutically acceptable salts thereof, which are useful as inhibitors of NAMPT, the compounds having Formula (VA)

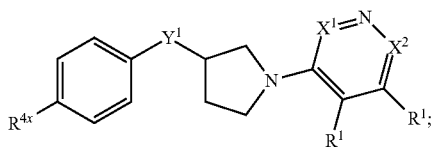

(VA)

wherein
X$^1$ is N and X$^2$ is CR$^1$; or
X$^1$ is CR$^1$ and X$^2$ is N; or
X$^1$ is CR$^1$ and X$^2$ is CR$^1$;
Y$^1$ is C(O)NH, or NHC(O);
R$^1$, at each occurrence, is independently selected from the group consisting of hydrogen, alkyl, haloalkyl, alkoxy, CN, Cl, and F;
R$^{4x}$ is independently selected from the group consisting of R$^4$, SO$_2$R$^4$, OR$^7$, and F;
R$^4$, at each occurrence, is alkyl or heterocyclyl; wherein each R$^4$ alkyl is optionally substituted with R$^7$;
R$^7$, at each occurrence, is independently heterocyclyl;
wherein the cyclic moieties represented by R$^4$ and R$^7$ are independently optionally substituted with one or more substituents independently selected from the group consisting of R$^{10}$, C(O)R$^{10}$, C(O)C(O)R$^{10}$, CO(O)R$^{10}$, OH and F;
R$^{10}$, at each occurrence, is independently selected from the group consisting of alkyl, alkenyl, alkynyl, aryl, heterocyclyl, and cycloalkyl; wherein each R$^{10}$ alkyl is optionally substituted with one or more substituents independently selected from the group consisting of R$^{11}$, OR$^{11}$, SR$^{11}$, SO$_2$R$^{11}$, NH$_2$, N(R$^{1f}$)$_2$, NHC(O)R$^{11}$, NHS(O)$_2$R$^{11}$, OH, NO$_2$, and F; wherein each R$^{10}$ aryl, heterocyclyl and cycloalkyl is optionally substituted with one or more R$^{12}$, OR$^{12}$, C(O)R$^{12}$, OH, CN, CF$_3$, OCF$_3$, F, and Cl;
R$^{11}$, at each occurrence, is independently selected from the group consisting of alkyl, aryl, heterocyclyl, and cycloalkyl; wherein each R$^{11}$ alkyl is optionally substituted with alkoxy or aryl; wherein each R$^{11}$ aryl, and heterocyclyl is optionally substituted with one or more substituents independently selected from the group consisting of R$^{13}$, C(O)OR$^{13}$, OCF$_3$, CF$_3$, F, and Cl;
R$^{12}$, at each occurrence, is independently selected from the group consisting of alkyl, and aryl; and
R$^{13}$, at each occurrence, is independently selected from the group consisting of alkyl, haloalkyl, and heterocyclyl.

Still another embodiment pertains to compounds having Formula (VA), which includes Examples 8, 9, 11, 12, 13, 14, 15, 16, 17, 18, 19, 27, 28, 141, 142, 204, 310, 311, 312, 313, 614, 615, 616, 617, 625, 626, 627, 628, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 743, 744, 745, 748, 749, 750, 751, 752, 753, 756, 757, 759, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, and pharmaceutically acceptable salts thereof.

Embodiments of Formula (IC)

One embodiment of this invention, therefore, pertains to compounds or pharmaceutically acceptable salts thereof, which are useful as inhibitors of NAMPT, the compounds having Formula (IC)

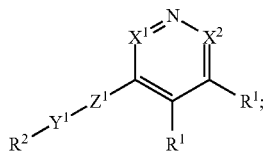

Formula (IC)

wherein
X$^1$ is N and X$^2$ is CR$^1$; or
X$^1$ is CR$^1$ and X$^2$ is N; or
X$^1$ is CR$^1$ and X$^2$ is CR$^1$;
Y$^1$ is C(O)NH, or NHC(O);
Z$^1$ is

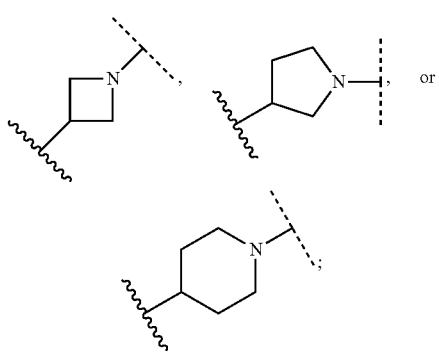

wherein ⁓ indicates the point of attachment to Y$^1$ and ⋰ indicates the point of attachment to the nitrogen containing heteroaryl;
R$^1$, at each occurrence, is independently selected from the group consisting of hydrogen, alkyl, alkenyl, alkynyl, haloalkyl, hydroxyalkyl, alkoxy, OH, NH$_2$, CN, NO$_2$, F, Cl, Br and I;
R$^2$ is independently selected from the group consisting of C$_4$-C$_6$-alkyl, C$_4$-C$_6$-alkenyl, C$_4$-C$_6$-alkynyl, aryl, and 5-6 membered heteroaryl; wherein each R$^2$C$_4$-C$_6$-alkyl, C$_4$-C$_6$-alkenyl, and C$_4$-C$_6$-alkynyl is substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(N)NH_2$, $C(N)NHR^3$, $C(N)N(R^3)_2$, CNOH, $CNOCH_3$, OH, (O), CN, $N_3$, $NO_2$, F, Cl, Br and I; wherein each $R^2$ aryl and 5-6 membered heteroaryl is optionally substituted with one or more substituents independently selected from the group consisting of $R^4$, $OR^4$, $SR^4$, $S(O)R^4$, $SO_2R^4$, $C(O)R^4$, $OC(O)R^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, and I;

$R^3$, at each occurrence, is independently selected from the group consisting of alkyl, alkenyl, alkynyl, aryl, cycloalkyl, cycloalkenyl, and heterocyclyl; wherein each $R^3$ alkyl, alkenyl, and alkynyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, CNOH, $CNOCH_3$, OH, (O), CN, $N_3$, $NO_2$, F, Cl, Br and I; wherein each $R^3$ aryl, cycloalkyl, cycloalkenyl, and heterocyclyl is optionally substituted with one or more substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $C(N)NH_2$, $C(N)NHR^6$, $C(N)N(R^6)_2$, CNOH, $CNOCH_3$, OH, CN, $N_3$, $NO_2$, F, Cl, Br and I;

$R^4$, at each occurrence, is independently selected from the group consisting of alkyl, alkenyl, alkynyl, aryl, heterocyclyl, cycloalkyl, and cycloalkenyl; wherein each $R^4$ alkyl, alkenyl, and alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, CNOH, $CNOCH_3$, OH, (O), CN, $N_3$, $NO_2$, F, Cl, Br and I;

$R^5$, at each occurrence, is independently selected from the group consisting of alkyl, alkenyl, alkynyl, aryl, heterocyclyl, cycloalkyl, and cycloalkenyl; wherein each $R^5$ alkyl, alkenyl, and alkynyl is optionally substituted with one or more substituents independently selected from the group consisting of $R^8$, $OR^8$, $SR^8$, $S(O)R^8$, $SO_2R^8$, $NHR^8$, $N(R^8)_2$, $C(O)R^8$, $C(O)NH_2$, $C(O)NHR^8$, $C(O)N(R^8)_2$, $NHC(O)R^8$, $NR^8C(O)R^8$, $NHSO_2R^8$, $NHC(O)OR^8$, $SO_2NH_2$, $SO_2NHR^8$, $SO_2N(R^8)_2$, $NHC(O)NH_2$, $NHC(O)NHR^8$, OH, (O), $C(O)OH$, $N_3$, CN, $NH_2$, F, Cl, Br and I;

$R^6$, at each occurrence, is independently selected from the group consisting of alkyl, alkenyl, alkynyl, aryl, heterocyclyl, cycloalkyl, and cycloalkenyl; wherein each $R^6$ alkyl, alkenyl, and alkynyl is optionally substituted with one or more substituents independently selected from the group consisting of $R^9$, $OR^9$, $SR^9$, $S(O)R^9$, $SO_2R^9$, $NHR^9$, $N(R^9)_2$, $C(O)R^9$, $C(O)NH_2$, $C(O)NHR^9$, $C(O)N(R^9)_2$, $NHC(O)R^9$, $NR^9C(O)R^9$, $NHSO_2R^9$, $NHC(O)OR^9$, $SO_2NH_2$, $SO_2NHR^9$, $SO_2N(R^9)_2$, $NHC(O)NH_2$, $NHC(O)NHR^9$, OH, (O), $C(O)OH$, $N_3$, CN, $NH_2$, $CF_3$, $CF_2CF_3$, F, Cl, Br and I;

$R^7$, at each occurrence, is independently selected from the group consisting of alkyl, alkenyl, alkynyl, aryl, heterocyclyl, cycloalkyl, and cycloalkenyl;

$R^8$, at each occurrence, is independently selected from the group consisting of alkyl, alkenyl, alkynyl, aryl, heterocyclyl, cycloalkyl, and cycloalkenyl;

$R^9$, at each occurrence, is independently selected from the group consisting of alkyl, alkenyl, alkynyl, aryl, heterocyclyl, cycloalkyl, and cycloalkenyl;

wherein the cyclic moieties represented by $R^4$, $R^5$, $R^6$, $R^7$, $R^8$, and $R^9$ are independently optionally substituted with one or more substituents independently selected from the group consisting of $R^{10}$, $OR^{10}$, Se, $S(O)R^{10}$, $SO_2R^{10}$, $C(O)R^{10}$, $CO(O)R^{10}$, $OC(O)R^{10}$, $OC(O)OR^{10}$, $C(O)C(O)R^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{16}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, CNOH, $CNOCH_3$, OH, CN, $N_3$, $NO_2$, F, Cl, Br and I;

$R^{10}$, at each occurrence, is independently selected from the group consisting of alkyl, alkenyl, alkynyl, aryl, heterocyclyl, cycloalkyl, and cycloalkenyl; wherein each $R^{10}$ alkyl, alkenyl, and alkynyl is optionally substituted with one or more substituents independently selected from the group consisting of $R^{11}$, $OR^{11}$, $SR^{11}$, $S(O)R^{11}$, $SO_2R^{11}$, $C(O)R^{11}$, $CO(O)R^{11}$, $OC(O)R^{11}$, $OC(O)OR^{11}$, $NH_2$, $NHR^{11}$, $N(R^{11})_2$, $NHC(O)R^{11}$, $NR^{11}C(O)R^{11}$, $NHS(O)_2R^{11}$, $NR^{11}S(O)_2R^{11}$, $NHC(O)OR^{11}$, $NR^{11}C(O)OR^{11}$, $NHC(O)NH_2$, $NHC(O)NHR^{11}$, $NHC(O)N(R^{11})_2$, $NR^{11}C(O)NHR^{11}$, $NR^{11}C(O)N(R^{11})_2$, $C(O)NH_2$, $C(O)NHR^{11}$, $C(O)N(R^{11})_2$, $C(O)NHOH$, $C(O)NHOR^{11}$, $C(O)NHSO_2R^{11}$, $C(O)NR^{11}SO_2R^{11}$, $SO_2NH_2$, $SO_2NHR^{11}$, $SO_2N(R^{11})_2$, $C(O)H$, $C(O)OH$, $C(N)NH_2$, $C(N)NHR^{11}$, $C(N)N(R^{11})_2$, CNOH, $CNOCH_3$, OH, (O), CN, $N_3$, $NO_2$, F, Cl, Br and I; wherein each $R^{10}$ aryl, heterocyclyl, cycloalkyl, and cycloalkenyl is optionally substituted with one or more substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, $C(N)NH_2$, $C(N)NHR^{12}$, $C(N)N(R^{12})_2$, CNOH, $CNOCH_3$, OH, CN, $N_3$, $NO_2$, $CF_3$, $OCF_3$, F, Cl, Br and I;

$R^{11}$, at each occurrence, is independently selected from the group consisting of alkyl, alkenyl, alkynyl, aryl, heterocyclyl, cycloalkyl, and cycloalkenyl; wherein each $R^{11}$ alkyl, alkenyl, and alkynyl is optionally substituted with alkoxy or aryl; wherein each $R^{11}$ aryl, heterocyclyl, cycloalkyl, and cycloalkenyl is optionally substituted with one or more substituents independently selected from the group consisting of $R^{13}$, $OR^{13}$, $C(O)OR^{13}$, $OCF_3$, $CF_3$, F, Cl, Br and I;

$R^{12}$, at each occurrence, is independently selected from the group consisting of alkyl, alkenyl, alkynyl, aryl, heterocyclyl, cycloalkyl, and cycloalkenyl; and $R^{13}$, at each occurrence, is independently selected from the group consisting of alkyl, haloalkyl, alkenyl, alkynyl, aryl, heterocyclyl, cycloalkyl, and cycloalkenyl;

with the proviso that when $X^1$ is $CR^1$ and $X^2$ is $CR^1$; $R^1$ is hydrogen; $Y^1$ is NHC(O); $Z^1$ is

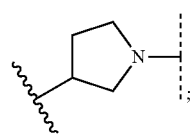

and $R^2$ is pyrrolyl; the $R^2$ pyrrolyl is not substituted with two alkyl groups.

In one embodiment of Formula (IC), $X^1$ is N and $X^2$ is $CR^1$; or $X^1$ is $CR^1$ and $X^2$ is N; or $X^1$ is $CR^1$ and $X^2$ is $CR^1$. In another embodiment of Formula (IC), $X^1$ is N and $X^2$ is $CR^1$.

In another embodiment of Formula (IC), $X^1$ is $CR^1$ and $X^2$ is N. In another embodiment of Formula (IC), $X^1$ is $CR^1$ and $X^2$ is $CR^1$.

In one embodiment of Formula (IC), $R^1$, at each occurrence, is independently selected from the group consisting of hydrogen, alkyl, alkenyl, alkynyl, haloalkyl, hydroxyalkyl, alkoxy, OH, $NH_2$, CN, $NO_2$, F, Cl, Br and I. In another embodiment of Formula (IC), $R^1$, at each occurrence, is independently selected from the group consisting of hydrogen, alkyl, haloalkyl, alkoxy, CN, F, Cl, Br and I. In another embodiment of Formula (IC), $R^1$, at each occurrence, is independently selected from the group consisting of hydrogen, alkyl, haloalkyl, alkoxy, CN, F, and Cl. In another embodiment of Formula (IC), $R^1$, at each occurrence, is hydrogen.

In one embodiment of Formula (IC), $X^1$ is $CR^1$ and $X^2$ is $CR^1$; and $R^1$, at each occurrence, is independently selected from the group consisting of hydrogen, alkyl, alkenyl, alkynyl, haloalkyl, hydroxyalkyl, alkoxy, OH, $NH_2$, CN, $NO_2$, F, Cl, Br and I. In another embodiment of Formula (IC), $X^1$ is $CR^1$ and $X^2$ is $CR^1$; and $R^1$, at each occurrence, is independently selected from the group consisting of hydrogen, alkyl, haloalkyl, alkoxy, CN, F, Cl, Br and I. In another embodiment of Formula (IC), $X^1$ is $CR^1$ and $X^2$ is $CR^1$; and $R^1$, at each occurrence, is independently selected from the group consisting of hydrogen, alkyl, haloalkyl, alkoxy, CN, F, and Cl. In another embodiment of Formula (IC), $X^1$ is $CR^1$ and $X^2$ is $CR^1$; and $R^1$, at each occurrence, is hydrogen.

In one embodiment of Formula (IC), $Y^1$ is C(O)NH, or NHC(O). In another embodiment of Formula (IC), $Y^1$ is C(O)NH. In another embodiment of Formula (IC), $Y^1$ is NHC(O).

In one embodiment of Formula (IC), $Z^1$ is

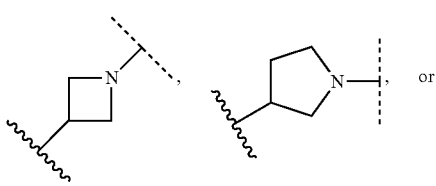

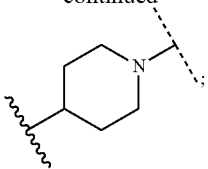

wherein ⌇ indicates the point of attachment to $Y^1$ and ⌇ indicates the point of attachment to the nitrogen containing heteroaryl. In another embodiment of Formula (IC), $Z^1$ is

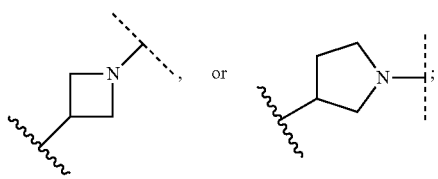

wherein ⌇ indicates the point of attachment to $Y^1$ and ⌇ indicates the point of attachment to the nitrogen containing heteroaryl. In another embodiment of Formula (IC), $Z^1$ is

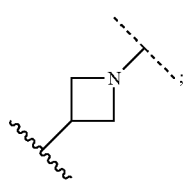

wherein ⌇ indicates the point of attachment to $Y^1$ and ⌇ indicates the point of attachment to the nitrogen containing heteroaryl. In another embodiment of Formula (IC), $Z^1$ is

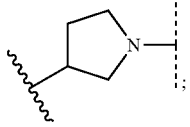

wherein ⌇ indicates the point of attachment to $Y^1$ and ⌇ indicates the point of attachment to the nitrogen containing heteroaryl. In another embodiment of Formula (IC), $Z^1$ is

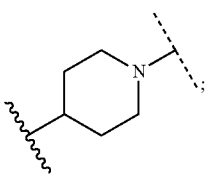

wherein ⌇ indicates the point of attachment to $Y^1$ and ⌇ indicates the point of attachment to the nitrogen containing heteroaryl.

In one embodiment of Formula (IC), $R^2$ is independently selected from the group consisting of $C_4$-$C_6$-alkyl, $C_4$-$C_6$-alkenyl, $C_4$-$C_6$-alkynyl, aryl, and 5-6 membered heteroaryl; wherein each $R^2C_4$-$C_6$-alkyl, $C_4$-$C_6$-alkenyl, and $C_4$-$C_6$-alkynyl is substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(N)NH_2$, $C(N)NHR^3$, $C(N)N(R^3)_2$, $CNOH$, $CNOCH_3$, $OH$, $(O)$, $CN$, $N_3$, $NO_2$, F, Cl, Br and I; wherein each $R^2$ aryl and 5-6 membered heteroaryl is optionally substituted with one or more substituents independently selected from the group consisting of $R^4$, $OR^4$, $SR^4$, $S(O)R^4$, $SO_2R^4$, $C(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, $CNOH$, $CNOCH_3$, $OH$, $CN$, $N_3$, $NO_2$, F, Cl, and I. In another embodiment of Formula (IC), $R^2$ is aryl; wherein each $R^2$ aryl is optionally substituted with one or more substituents independently selected from the group consisting of $R^4$, $OR^4$, $SO_2R^4$, $C(O)NHR^4$, F, Cl, and I. In another embodiment of Formula (IC), $R^2$ is aryl; wherein each $R^2$ aryl is optionally substituted with one or more substituents independently selected from the group consisting of $R^4$, $OR^4$, $SO_2R^4$, $C(O)NHR^4$, and F. In another embodiment of Formula (IC), $R^2$ is phenyl; wherein each $R^2$ phenyl is optionally substituted with one or more substituents independently selected from the group consisting of $R^4$, $OR^4$, $SO_2R^4$, $C(O)NHR^4$, and F. In another embodiment of Formula (IC), $R^2$ is phenyl; wherein each $R^2$ phenyl is substituted with one substituent independently selected from the group consisting of $R^4$, $OR^4$, and $SO_2R^4$.

In another embodiment of Formula (IC), $R^2$ is 5-6 membered heteroaryl; wherein each $R^2$ 5-6 membered heteroaryl is optionally substituted with one or more substituents independently selected from the group consisting of $R^4$, $OR^4$, $SO_2R^4$, $C(O)NHR^4$, F, Cl, and I. In another embodiment of Formula (IC), $R^2$ is 5-6 membered heteroaryl; wherein each $R^2$ 5-6 membered heteroaryl is optionally substituted with one or more substituents independently selected from the group consisting of $R^4$, $OR^4$, $SO_2R^4$, $C(O)NHR^4$, and F. In another embodiment of Formula (IC), $R^2$ is pyridinyl, furanyl, thiophenyl, pyrazole, or thiazolyl; wherein each $R^2$ pyridinyl, furanyl, thiophenyl, pyrazole, and thiazolyl is optionally substituted with one or more substituents independently selected from the group consisting of $R^4$, $OR^4$, $SO_2R^4$, $C(O)NHR^4$, and F.

In one embodiment of Formula (IC), $R^4$, at each occurrence, is independently selected from the group consisting of alkyl, alkenyl, alkynyl, aryl, heterocyclyl, cycloalkyl, and cycloalkenyl; wherein each $R^4$ alkyl, alkenyl, and alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, $CNOH$, $CNOCH_3$, $OH$, $(O)$, $CN$, $N_3$, $NO_2$, F, Cl, Br and I. In another embodiment of Formula (IC), $R^4$, at each occurrence, is independently selected from the group consisting of alkyl, alkenyl, alkynyl, aryl, heterocyclyl, and cycloalkyl.

In one embodiment of Formula (IC), each $R^4$ alkyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, $CNOH$, $CNOCH_3$, $OH$, $(O)$, $CN$, $N_3$, $NO_2$, F, Cl, Br and I. In another embodiment of Formula (IC), each $R^4$ alkyl is optionally substituted with one or more substituents independently selected from the group consisting of $R^7$, $OR^7$, $N(R^7)_2$, F, Cl, Br and I.

In one embodiment of Formula (IC), $R^7$, at each occurrence, is independently selected from the group consisting of alkyl, alkenyl, alkynyl, aryl, heterocyclyl, cycloalkyl, and cycloalkenyl. In another embodiment of Formula (IC), $R^7$, at each occurrence, is independently selected from the group consisting of alkyl, aryl, heterocyclyl, and cycloalkyl.

In one embodiment of Formula (IC), each $R^4$ and $R^7$ cyclic moiety is independently optionally substituted with one or more substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, $CNOH$, $CNOCH_3$, $OH$, $CN$, $N_3$, $NO_2$, F, Cl, Br and I; $R^{10}$, at each occurrence, is independently selected from the group consisting of alkyl, alkenyl, alkynyl, aryl, heterocyclyl, cycloalkyl, and cycloalkenyl; wherein each $R^{10}$ alkyl, alkenyl, and alkynyl is optionally substituted with one or more substituents independently selected from the group consisting of $R^{11}$, $OR^{11}$, $SR^{11}$, $S(O)R^{11}$, $SO_2R^{11}$, $C(O)R^{11}$, $CO(O)R^{11}$, $OC(O)R^{11}$, $OC(O)OR^{11}$, $NH_2$, $NHR^{11}$, $N(R^{11})_2$, $NHC(O)R^{11}$, $NR^{11}C(O)R^{11}$, $NHS(O)_2R^{11}$, $NR^{11}S(O)_2R^{11}$, $NHC(O)OR^{11}$, $NR^{11}C(O)OR^{11}$, $NHC(O)NH_2$, $NHC(O)NHR^{11}$, $NHC(O)N(R^{11})_2$, $NR^{11}C(O)NHR^{11}$, $NR^{11}C(O)N(R^{11})_2$, $C(O)NH_2$, $C(O)NHR^{11}$, $C(O)N(R^{11})_2$, $C(O)NHOH$, $C(O)NHOR^{11}$, $C(O)NHSO_2R^{11}$, $C(O)NR^{11}SO_2R^{11}$, $SO_2NH_2$, $SO_2NHR^{11}$, $SO_2N(R^{11})_2$, $C(O)H$, $C(O)OH$, $C(N)NH_2$, $C(N)NHR^{11}$, $C(N)N(R^{11})_2$, $CNOH$, $CNOCH_3$, $OH$, $(O)$, $CN$, $N_3$, $NO_2$, F, Cl, Br and I; wherein each $R^{10}$ aryl, heterocyclyl, cycloalkyl, and cycloalkenyl is optionally substituted with one or more substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, $C(N)NH_2$, $C(N)NHR^{12}$, $C(N)N(R^{12})_2$, $CNOH$, $CNOCH_3$, $OH$, $CN$, $N_3$, $NO_2$, F, Cl, Br and I; $R^{11}$, at each occurrence, is independently selected from the group consisting of alkyl, alkenyl, alkynyl, aryl, heterocyclyl, cycloalkyl, and cycloalkenyl; wherein each $R^{11}$ alkyl, alkenyl, and alkynyl is optionally substituted with alkoxy or aryl; wherein each $R^{11}$ aryl, heterocyclyl, cycloalkyl, and cycloalkenyl is optionally substituted with one or more substituents independently selected from the group consisting of $R^{13}$, $OR^{13}$, $C(O)OR^{13}$, $OCF_3$, $CF_3$, F, Cl, Br and I; $R^{12}$, at each occurrence, is independently selected from the group consisting of alkyl, alkenyl, alkynyl, aryl, heterocyclyl, cycloalkyl, and cycloalkenyl; and $R^{13}$, at each occurrence, is independently selected from the group consisting of alkyl, haloalkyl, alkenyl, alkynyl, aryl, heterocyclyl, cycloalkyl, and cycloalkenyl.

In another embodiment of Formula (IC), each $R^4$ and $R^7$ cyclic moiety is independently optionally substituted with one or more substituents independently selected from the group consisting of $R^{10}$, $C(O)R^{10}$, $CO(O)R^{10}$, $C(O)C(O)R^{10}$, $CO(O)H$, OH, F, Cl, Br and I; $R^{10}$, at each occurrence, is independently selected from the group consisting of alkyl, alkenyl, alkynyl, aryl, heterocyclyl, and cycloalkyl; wherein each $R^{10}$ alkyl, alkenyl, and alkynyl, are optionally substituted with one or more substituents independently selected from the group consisting of $R^{11}$, $OR^{11}$, $SR^{11}$, $SO_2R^{11}$, $NH_2$, $N(R^{11})_2$, $NHC(O)R^{11}$, $NHS(O)_2R^{11}$, OH, $NO_2$, and F; wherein each $R^{10}$ aryl, heterocyclyl and cycloalkyl is optionally substituted with one or more substituents independently selected from the group consisting of $R^{12}$, $OR^{12}$, $C(O)R^{12}$, $NH_2$, OH, CN, $CF_3$, $OCF_3$, F, and Cl; $R^{11}$, at each occurrence, is independently selected from the group consisting of alkyl, aryl, heterocyclyl, and cycloalkyl; wherein each $R^{11}$ alkyl is optionally substituted with alkoxy or aryl; wherein each $R^{11}$ aryl and heterocyclyl is optionally substituted with one or more substituents independently selected from the group consisting of $R^{13}$, $CF_3$, F, and Cl; $R^{12}$, at each occurrence, is independently selected from the group consisting of alkyl and aryl; and $R^{13}$, at each occurrence, is independently selected from the group consisting of alkyl, haloalkyl, and cycloalkyl.

One embodiment of this invention pertains to compounds or pharmaceutically acceptable salts thereof, which are useful as inhibitors of NAMPT, the compounds having Formula (IC)

Formula (IC)

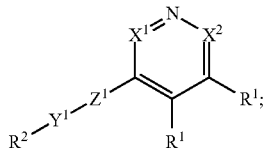

wherein $X^1$ is N and $X^2$ is $CR^1$; or $X^1$ is $CR^1$ and $X^2$ is N; or $X^1$ is $CR^1$ and $X^2$ is $CR^1$;

$Y^1$ is C(O)NH, or NHC(O);

$Z^1$ is

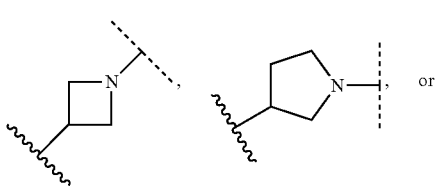

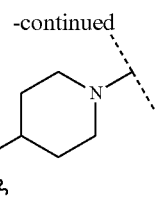

wherein ⌇ indicates the point of attachment to $Y^1$ and ⌇ indicates the point of attachment to the nitrogen containing heteroaryl;

$R^1$, at each occurrence, is independently selected from the group consisting of hydrogen, alkyl, haloalkyl, alkoxy, CN, Cl, and F;

$R^2$ is aryl or 5-6 membered heteroaryl wherein each $R^2$ aryl and 5-6 membered heteroaryl is optionally substituted with one or more substituents independently selected from the group consisting of $R^4$, $SO_2R^4$, $OR^4$, $C(O)NHR^4$, and F;

$R^4$, at each occurrence, is independently selected from the group consisting of alkyl, alkenyl, aryl, heterocyclyl, and cycloalkyl; wherein each $R^4$ alkyl is optionally substituted with one or more substituents independently selected from the group consisting of $R^7$, $OR^7$, $N(R^7)_2$, and F;

$R^7$, at each occurrence, is independently selected from the group consisting of alkyl, aryl, heterocyclyl, and cycloalkyl;

wherein the cyclic moieties represented by $R^4$ and $R^7$ are independently optionally substituted with one or more substituents independently selected from the group consisting of $R^{10}$, $C(O)R^{10}$, $C(O)C(O)R^{10}$, $CO(O)R^{110}$, $C(O)OH$, OH and F;

$R^{10}$, at each occurrence, is independently selected from the group consisting of alkyl, alkenyl, alkynyl, aryl, heterocyclyl, and cycloalkyl; wherein each $R^{10}$ alkyl is optionally substituted with one or more substituents independently selected from the group consisting of $R^{11}$, $OR^{11}$, $SR^{11}$, $SO_2R^{11}$, $NH_2$, $N(R^{11})_2$, $NHC(O)R^{11}$, $NHS(O)_2R^{11}$, OH, $NO_2$, and F; wherein each $R^{10}$ aryl, heterocyclyl and cycloalkyl is optionally substituted with one or more $R^{12}$, $OR^{12}$, $C(O)R^{12}$, $NH_2$, OH, CN, $CF_3$, $OCF_3$, F, and Cl;

$R^{11}$, at each occurrence, is independently selected from the group consisting of alkyl, aryl, heterocyclyl, and cycloalkyl; wherein each $R^{11}$ alkyl is optionally substituted with alkoxy or aryl; wherein each $R^{11}$ aryl, and heterocyclyl is optionally substituted with one or more substituents independently selected from the group consisting of $R^{13}$, $C(O)OR^{13}$, $OCF_3$, $CF_3$, F, and Cl;

$R^{12}$, at each occurrence, is independently selected from the group consisting of alkyl, and aryl; and $R^{13}$, at each occurrence, is independently selected from the group consisting of alkyl, haloalkyl, cycloalkyl, and heterocyclyl;

with the proviso that when $X^1$ is $CR^1$ and $X^2$ is $CR^1$; $R^1$ is hydrogen; $Y^1$ is NHC(O); $Z^1$ is

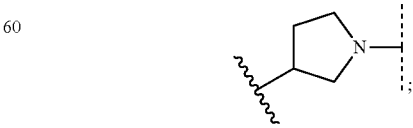

and $R^2$ is pyrrolyl; the $R^2$ pyrrolyl is not substituted with two alkyl groups.

Still another embodiment pertains to compounds having Formula (IC), which include 1-(pyridin-3-yl)-N-(4-{[1-(tetrahydro-2H-pyran-4-ylacetyl) piperidin-4-yl]oxy}phenyl)azetidine-3-carboxamide;
1-(2-cyanopyridin-3-yl)-N-{4-[1-(2-hydroxy-2-methylpropanoyl)piperidin-4-yl]phenyl}azetidine-3-carboxamide;
N-(4-{[1-(tetrahydro-2H-pyran-4-ylacetyl)piperidin-4-yl]oxy}phenyl)-1-[2-(trifluoromethyl)pyridin-3-yl]azetidine-3-carboxamide;
1-(2-methylpyridin-3-yl)-N-(4-{[1-(tetrahydro-2H-pyran-4-ylacetyl)piperidin-4-yl]oxy}phenyl)azetidine-3-carboxamide;
1-(4-methylpyridin-3-yl)-N-(4-{[1-(tetrahydro-2H-pyran-4-ylacetyl)piperidin-4-yl]oxy}phenyl)azetidine-3-carboxamide;
1-(4-fluoropyridin-3-yl)-N-(4-{[1-(tetrahydro-2H-pyran-4-ylacetyl)piperidin-4-yl]oxy}phenyl)azetidine-3-carboxamide;
N-(4-{[1-(tetrahydro-2H-pyran-4-ylacetyl)piperidin-4-yl]oxy}phenyl)-1-[4-(trifluoromethyl)pyridin-3-yl]azetidine-3-carboxamide;
tert-butyl 4-[4-({[(3S)-1-(pyridin-3-yl)pyrrolidin-3-yl]carbonyl}amino)phenoxy]piperidine-1-carboxylate;
tert-butyl 4-[4-({[(3R)-1-(pyridin-3-yl)pyrrolidin-3-yl]carbonyl}amino)phenoxy]piperidine-1-carboxylate;
1-(pyridin-3-yl)-N-(4-{1-[(2S)-tetrahydro furan-2-ylcarbonyl]piperidin-4-yl}phenyl)azetidine-3-carboxamide;
(3S)-1-(pyridin-3-yl)-N-(4-{[1-(tetrahydro-2H-pyran-4-ylacetyl)piperidin-4-yl]oxy}phenyl)pyrrolidine-3-carboxamide;
(3S)—N-(4-{[1-(2-methylpropanoyl)piperidin-4-yl]oxy}phenyl)-1-(pyridin-3-yl)pyrrolidine-3-carboxamide;
(3S)-1-(pyridin-3-yl)-N-[4-({1-[(2S)-tetrahydrofuran-2-ylcarbonyl]piperidin-4-yl}oxy)phenyl]pyrrolidine-3-carboxamide;
(3S)-1-(pyridin-3-yl)-N-[4-({1-[(2R)-tetrahydrofuran-2-ylcarbonyl]piperidin-4-yl}oxy)phenyl]pyrrolidine-3-carboxamide;
(3S)-1-(pyridin-3-yl)-N-(4-{[1-(tetrahydro furan-3-ylcarbonyl)piperidin-4-yl]oxy}phenyl)pyrrolidine-3-carboxamide;
(3S)—N-(4-{[1-(cyclopropylacetyl)piperidin-4-yl]oxy}phenyl)-1-(pyridin-3-yl)pyrrolidine-3-carboxamide;
(3S)—N-(4-{[1-(2-hydroxy-2-methylpropanoyl)piperidin-4-yl]oxy}phenyl)-1-(pyridin-3-yl)pyrrolidine-3-carboxamide;
(3S)-1-(pyridin-3-yl)-N-(4-{[1-(3,3,3-trifluoropropanoyl)piperidin-4-yl]oxy}phenyl)pyrrolidine-3-carboxamide;
(3S)—N-[4-({1-[(2S)-2-methylbutanoyl]piperidin-4-yl}oxy)phenyl]-1-(pyridin-3-yl)pyrrolidine-3-carboxamide;
N-{4-[1-(2-hydroxy-2-methylpropanoyl)piperidin-4-yl]phenyl}-1-(pyridin-3-yl)azetidine-3-carboxamide;
N-[1-(pyridin-3-yl)azetidin-3-yl]-4-{[1-(tetrahydro-2H-pyran-4-ylacetyl)piperidin-4-yl]oxy}benzamide;
N-(4-{1-[(2S)-2-methylbutanoyl]piperidin-4-yl}phenyl)-1-(pyridin-3-yl)azetidine-3-carboxamide;
4-({1-[(2S)-2-methylbutanoyl]piperidin-4-yl}oxy)-N-[1-(pyridin-3-yl)azetidin-3-yl]benzamide;
4-{[1-(2-hydroxy-2-methylpropanoyl)piperidin-4-yl]oxy}-N-[1-(pyridin-3-yl)azetidin-3-yl]benzamide;
1-(pyridin-3-yl)-N-{4-[1-(tetrahydro-2H-pyran-4-ylacetyl)piperidin-4-yl]phenyl}azetidine-3-carboxamide;
N-[4-(1-benzoylpiperidin-4-yl)phenyl]-1-(pyridin-3-yl)azetidine-3-carboxamide;
tert-butyl 4-(4-{[(3S)-1-(pyridin-3-yl)pyrrolidin-3-yl]carbamoyl}phenoxy)piperidine-1-carboxylate;
tert-butyl 4-(4-{[(3R)-1-(pyridin-3-yl)pyrrolidin-3-yl]carbamoyl}phenoxy)piperidine-1-carboxylate;
N-{4-[1-(2-methylpropanoyl)piperidin-4-yl]phenyl}-1-(2-methylpyridin-3-yl)azetidine-3-carboxamide;
N-{4-[1-(2-methylpropanoyl)piperidin-4-yl]phenyl}-1-(pyridin-3-yl)azetidine-3-carboxamide;
N-(4-{[1-(2-hydroxy-2-methylpropanoyl)piperidin-4-yl]oxy}phenyl)-1-(pyridin-3-yl)azetidine-3-carboxamide;
N-[4-({1-[(2S)-2-methylbutanoyl]piperidin-4-yl}oxy)phenyl]-1-(pyridin-3-yl)azetidine-3-carboxamide;
1-(pyridin-3-yl)-N-[4-({1-[(2S)-tetrahydro furan-2-ylcarbonyl]piperidin-4-yl}oxy)phenyl]azetidine-3-carboxamide;
N-{4-[(1-pentanoylpiperidin-4-yl)oxy]phenyl}-1-(pyridin-3-yl)azetidine-3-carboxamide;
N-[4-({1-[(2-methylcyclopropyl)carbonyl]piperidin-4-yl}oxy)phenyl]-1-(pyridin-3-yl)azetidine-3-carboxamide;
N-[4-({1-[(1S,4R)-bicyclo[2.2.1]hept-2-ylacetyl]piperidin-4-yl}oxy)phenyl]-1-(pyridin-3-yl)azetidine-3-carboxamide;
N-(4-{[1-(4-methylpentanoyl)piperidin-4-yl]oxy}phenyl)-1-(pyridin-3-yl)azetidine-3-carboxamide;
N-(4-{[1-(3-methylpentanoyl)piperidin-4-yl]oxy}phenyl)-1-(pyridin-3-yl)azetidine-3-carboxamide;
N-(4-{[1-(3-ethoxypropanoyl)piperidin-4-yl]oxy}phenyl)-1-(pyridin-3-yl)azetidine-3-carboxamide;
N-(4-{[1-(2,2-dimethylbutanoyl)piperidin-4-yl]oxy}phenyl)-1-(pyridin-3-yl)azetidine-3-carboxamide;
N-(4-{[1-(3,3-dimethylbutanoyl)piperidin-4-yl]oxy}phenyl)-1-(pyridin-3-yl)azetidine-3-carboxamide;
N-(4-{[1-(2,2-dimethylpropanoyl)piperidin-4-yl]oxy}phenyl)-1-(pyridin-3-yl)azetidine-3-carboxamide;
N-{4-[(1-butanoylpiperidin-4-yl)oxy]phenyl}-1-(pyridin-3-yl)azetidine-3-carboxamide;
N-(4-{[1-(ethoxyacetyl)piperidin-4-yl]oxy}phenyl)-1-(pyridin-3-yl)azetidine-3-carboxamide;
N-(4-{[1-(3-methylbutanoyl)piperidin-4-yl]oxy}phenyl)-1-(pyridin-3-yl)azetidine-3-carboxamide;
N-(4-{[1-(2-methylpropanoyl)piperidin-4-yl]oxy}phenyl)-1-(pyridin-3-yl)azetidine-3-carboxamide;
N-(4-{[1-(N-acetyl-L-leucyl)piperidin-4-yl]oxy}phenyl)-1-(pyridin-3-yl)azetidine-3-carboxamide;
N-[4-({1-[(2-methoxyethoxy)acetyl]piperidin-4-yl}oxy)phenyl]-1-(pyridin-3-yl)azetidine-3-carboxamide;
N-(4-{[1-(cyclohexylcarbonyl)piperidin-4-yl]oxy}phenyl)-1-(pyridin-3-yl)azetidine-3-carboxamide;
N-(4-{[1-(cyclohexylacetyl)piperidin-4-yl]oxy}phenyl)-1-(pyridin-3-yl)azetidine-3-carboxamide;
1-(pyridin-3-yl)-N-(4-{[1-(4,4,4-trifluorobutanoyl)piperidin-4-yl]oxy}phenyl)azetidine-3-carboxamide;
N-(4-{[1-(cyclopentylcarbonyl)piperidin-4-yl]oxy}phenyl)-1-(pyridin-3-yl)azetidine-3-carboxamide;
N-[4-({1-[(1-methylcyclohexyl)carbonyl]piperidin-4-yl}oxy)phenyl]-1-(pyridin-3-yl)azetidine-3-carboxamide;
N-(4-{[1-(furan-3-ylcarbonyl)piperidin-4-yl]oxy}phenyl)-1-(pyridin-3-yl)azetidine-3-carboxamide;
1-(pyridin-3-yl)-N-(4-{[1-(3,3,3-trifluoropropanoyl)piperidin-4-yl]oxy}phenyl)azetidine-3-carboxamide;
N-{4-[(1-acetylpiperidin-4-yl)oxy]phenyl}-1-(pyridin-3-yl) azetidine-3-carboxamide;
N-(4-{[1-(methoxyacetyl)piperidin-4-yl]oxy}phenyl)-1-(pyridin-3-yl)azetidine-3-carboxamide;
1-(pyridin-3-yl)-N-(4-{[1-(thiophen-3-ylcarbonyl)piperidin-4-yl]oxy}phenyl)azetidine-3-carboxamide;
N-[4-({1-[(3-methylthiophen-2-yl)carbonyl]piperidin-4-yl}oxy)phenyl]-1-(pyridin-3-yl)azetidine-3-carboxamide;
N-(4-{[1-(morpholin-4-ylacetyl)piperidin-4-yl]oxy}phenyl)-1-(pyridin-3-yl)azetidine-3-carboxamide;

1-(pyridin-3-yl)-N-(4-{[1-(thiophen-2-ylcarbonyl)piperidin-4-yl]oxy}phenyl)azetidine-3-carboxamide;
N-[4-({1-[(5-methylthiophen-2-yl)carbonyl]piperidin-4-yl}oxy)phenyl]-1-(pyridin-3-yl)azetidine-3-carboxamide;
N-(4-{[1-(furan-2-ylcarbonyl)piperidin-4-yl]oxy}phenyl)-1-(pyridin-3-yl)azetidine-3-carboxamide;
N-[4-({1-[(1-methyl-1H-pyrrol-2-yl)carbonyl]piperidin-4-yl}oxy)phenyl]-1-(pyridin-3-yl)azetidine-3-carboxamide;
N-{4-[(1-propanoylpiperidin-4-yl)oxy]phenyl}-1-(pyridin-3-yl)azetidine-3-carboxamide;
N-[4-({1-[(1-methylcyclopropyl)carbonyl]piperidin-4-yl}oxy)phenyl]-1-(pyridin-3-yl)azetidine-3-carboxamide;
N-(4-{[1-(N,N-dimethyl-beta-alanyl)piperidin-4-yl]oxy}phenyl)-1-(pyridin-3-yl)azetidine-3-carboxamide;
1-(pyridin-3-yl)-N-(4-{[1-(1,3-thiazol-2-ylcarbonyl)piperidin-4-yl]oxy}phenyl)azetidine-3-carboxamide;
N-(4-{[1-(cyclopentylacetyl)piperidin-4-yl]oxy}phenyl)-1-(pyridin-3-yl)azetidine-3-carboxamide;
N-(4-{[1-(2,3-dimethylbutanoyl)piperidin-4-yl]oxy}phenyl)-1-(pyridin-3-yl)azetidine-3-carboxamide;
N-{4-[1-(2-hydroxy-2-methylpropanoyl)piperidin-4-yl]phenyl}-1-(2-methylpyridin-3-yl)azetidine-3-carboxamide;
N-{4-[1-(2-hydroxy-2-methylpropanoyl)piperidin-4-yl]phenyl}-1-(4-methylpyridin-3-yl)azetidine-3-carboxamide;
N-{4-[1-(2-hydroxy-2-methylpropanoyl)piperidin-4-yl]phenyl}-1-(2-methoxypyridin-3-yl)azetidine-3-carboxamide;
N-(4-{[1-(cyclopropylmethyl)piperidin-4-yl]oxy}phenyl)-1-(pyridin-3-yl)azetidine-3-carboxamide;
N-(4-{[1-(2-methylpentyl)piperidin-4-yl]oxy}phenyl)-1-(pyridin-3-yl)azetidine-3-carboxamide;
N-(4-{[1-(2-methylpropyl)piperidin-4-yl]oxy}phenyl)-1-(pyridin-3-yl)azetidine-3-carboxamide;
N-(4-{[1-(3-methylbutyl)piperidin-4-yl]oxy}phenyl)-1-(pyridin-3-yl)azetidine-3-carboxamide;
N-(4-{[1-(2-ethylbutyl)piperidin-4-yl]oxy}phenyl)-1-(pyridin-3-yl)azetidine-3-carboxamide;
N-(4-{[1-(2,2-dimethylpropyl)piperidin-4-yl]oxy}phenyl)-1-(pyridin-3-yl)azetidine-3-carboxamide;
N-(4-{[1-(2-methylbutyl)piperidin-4-yl]oxy}phenyl)-1-(pyridin-3-yl)azetidine-3-carboxamide;
N-{4-[(1-propylpiperidin-4-yl)oxy]phenyl}-1-(pyridin-3-yl)azetidine-3-carboxamide;
N-(4-{[1-(2-cyclopropylethyl)piperidin-4-yl]oxy}phenyl)-1-(pyridin-3-yl)azetidine-3-carboxamide;
1-(pyridin-3-yl)-N-(4-{[1-(tetrahydrofuran-3-ylmethyl)piperidin-4-yl]oxy}phenyl)azetidine-3-carboxamide;
N-(4-{[1-(2,2-dimethylbutyl)piperidin-4-yl]oxy}phenyl)-1-(pyridin-3-yl)azetidine-3-carboxamide;
N-{4-[1-(2-hydroxy-2-methylpropanoyl)piperidin-4-yl]phenyl}-1-(pyridazin-4-yl)azetidine-3-carboxamide;
N-{4-[1-(cyclohexylmethyl)piperidin-4-yl]phenyl}-1-(pyridin-3-yl)azetidine-3-carboxamide;
N-{4-[1-(3,3-dimethylbutyl)piperidin-4-yl]phenyl}-1-(pyridin-3-yl)azetidine-3-carboxamide;
N-{4-[1-(cyclopentylmethyl)piperidin-4-yl]phenyl}-1-(pyridin-3-yl)azetidine-3-carboxamide;
N-{4-[1-(2,2-dimethylbutyl)piperidin-4-yl]phenyl}-1-(pyridin-3-yl)azetidine-3-carboxamide;
N-{4-[1-(2-methylpentyl)piperidin-4-yl]phenyl}-1-(pyridin-3-yl)azetidine-3-carboxamide;
N-[4-(1-butylpiperidin-4-yl)phenyl]-1-(pyridin-3-yl)azetidine-3-carboxamide;
N-{4-[1-(2-ethylbutyl)piperidin-4-yl]phenyl}-1-(pyridin-3-yl)azetidine-3-carboxamide;
N-{4-[1-(3-methylbutyl)piperidin-4-yl]phenyl}-1-(pyridin-3-yl)azetidine-3-carboxamide;
N-{4-[1-(2-methylpropyl)piperidin-4-yl]phenyl}-1-(pyridin-3-yl)azetidine-3-carboxamide;
N-[4-(1-propylpiperidin-4-yl)phenyl]-1-(pyridin-3-yl)azetidine-3-carboxamide;
N-{4-[1-(2-hydroxy-2-methylpropanoyl)piperidin-4-yl]phenyl}-1-(4-methoxypyridin-3-yl)azetidine-3-carboxamide;
1-(4-cyanopyridin-3-yl)-N-{4-[1-(2-hydroxy-2-methylpropanoyl)piperidin-4-yl]phenyl}azetidine-3-carboxamide;
N-[4-(1-pentanoylpiperidin-4-yl)phenyl]-1-(pyridin-3-yl)azetidine-3-carboxamide;
N-{4-[1-(3-methylpentanoyl)piperidin-4-yl]phenyl}-1-(pyridin-3-yl)azetidine-3-carboxamide;
N-(4-{1-[(1S,4R)-bicyclo[2.2.1]hept-2-ylacetyl]piperidin-4-yl}phenyl)-1-(pyridin-3-yl)azetidine-3-carboxamide;
N-{4-[1-(cyclopentylacetyl)piperidin-4-yl]phenyl}-1-(pyridin-3-yl)azetidine-3-carboxamide;
N-(4-{1-[(2-methylcyclopropyl)carbonyl]piperidin-4-yl}phenyl)-1-(pyridin-3-yl)azetidine-3-carboxamide;
N-{4-[1-(morpholin-4-ylacetyl)piperidin-4-yl]phenyl}-1-(pyridin-3-yl)azetidine-3-carboxamide;
N-{4-[1-(furan-3-ylcarbonyl)piperidin-4-yl]phenyl}-1-(pyridin-3-yl)azetidine-3-carboxamide;
1-(pyridin-3-yl)-N-{4-[1-(pyrrolidin-1-ylacetyl)piperidin-4-yl]phenyl}azetidine-3-carboxamide;
N-{4-[1-(5-oxo-D-prolyl)piperidin-4-yl]phenyl}-1-(pyridin-3-yl)azetidine-3-carboxamide;
N-{4-[1-(N,N-dimethyl-beta-alanyl)piperidin-4-yl]phenyl}-1-(pyridin-3-yl)azetidine-3-carboxamide;
1-(pyridin-3-yl)-N-{4-[1-(1,3-thiazol-2-ylcarbonyl)piperidin-4-yl]phenyl}azetidine-3-carboxamide;
1-(pyridin-3-yl)-N-{4-[1-(thiophen-3-ylcarbonyl)piperidin-4-yl]phenyl}azetidine-3-carboxamide;
N-(4-{1-[(1-methylcyclopropyl)carbonyl]piperidin-4-yl}phenyl)-1-(pyridin-3-yl)azetidine-3-carboxamide;
N-(4-{1-[(3-methylthiophen-2-yl)carbonyl]piperidin-4-yl}phenyl)-1-(pyridin-3-yl)azetidine-3-carboxamide;
1-(pyridin-3-yl)-N-{4-[1-(4,4,4-trifluorobutanoyl)piperidin-4-yl]phenyl}azetidine-3-carboxamide;
N-(4-{1-[(4-methylpiperazin-1-yl)acetyl]piperidin-4-yl}phenyl)-1-(pyridin-3-yl)azetidine-3-carboxamide;
N-{4-[1-(5-oxo-L-prolyl)piperidin-4-yl]phenyl}-1-(pyridin-3-yl)azetidine-3-carboxamide;
N-{4-[1-(3-ethoxypropanoyl)piperidin-4-yl]phenyl}-1-(pyridin-3-yl)azetidine-3-carboxamide;
N-{4-[1-(4-methylpentanoyl)piperidin-4-yl]phenyl}-1-(pyridin-3-yl)azetidine-3-carboxamide;
N-(4-{1-[(1-methylcyclohexyl)carbonyl]piperidin-4-yl}phenyl)-1-(pyridin-3-yl)azetidine-3-carboxamide;
N-[4-(1-acetylpiperidin-4-yl)phenyl]-1-(pyridin-3-yl)azetidine-3-carboxamide;
N-{4-[1-(cyclohexylacetyl)piperidin-4-yl]phenyl}-1-(pyridin-3-yl)azetidine-3-carboxamide;
N-{4-[1-(N-acetyl-L-leucyl)piperidin-4-yl]phenyl}-1-(pyridin-3-yl)azetidine-3-carboxamide;
N-[4-(1-propanoylpiperidin-4-yl)phenyl]-1-(pyridin-3-yl)azetidine-3-carboxamide;
1-(pyridin-3-yl)-N-{4-[1-(3,3,3-trifluoropropanoyl)piperidin-4-yl]phenyl}azetidine-3-carboxamide;
N-(4-{1-[(2-methoxyethoxy)acetyl]piperidin-4-yl}phenyl)-1-(pyridin-3-yl)azetidine-3-carboxamide;
N-(4-{1-[3-(morpholin-4-yl)propanoyl]piperidin-4-yl}phenyl)-1-(pyridin-3-yl)azetidine-3-carboxamide;
N-{4-[1-(2,2-dimethylpropanoyl)piperidin-4-yl]phenyl}-1-(pyridin-3-yl)azetidine-3-carboxamide;

N-(4-{1-[(5-methylthiophen-2-yl)carbonyl]piperidin-4-yl}phenyl)-1-(pyridin-3-yl)azetidine-3-carboxamide;
1-(pyridin-3-yl)-N-{4-[1-(thiophen-2-ylcarbonyl)piperidin-4-yl]phenyl}azetidine-3-carboxamide;
N-(4-{1-[(1-methyl-1H-pyrrol-2-yl)carbonyl]piperidin-4-yl}phenyl)-1-(pyridin-3-yl)azetidine-3-carboxamide;
N-{4-[1-(furan-2-ylcarbonyl)piperidin-4-yl]phenyl}-1-(pyridin-3-yl)azetidine-3-carboxamide;
N-(4-{1-[3-(piperidin-1-yl)propanoyl]piperidin-4-yl}phenyl)-1-(pyridin-3-yl)azetidine-3-carboxamide;
N-{4-[1-(ethoxyacetyl)piperidin-4-yl]phenyl}-1-(pyridin-3-yl)azetidine-3-carboxamide;
N-{4-[1-(3,3-dimethylbutanoyl)piperidin-4-yl]phenyl}-1-(pyridin-3-yl)azetidine-3-carboxamide;
N-{4-[1-(2,2-dimethylbutanoyl)piperidin-4-yl]phenyl}-1-(pyridin-3-yl)azetidine-3-carboxamide;
N-[4-(1-butanoylpiperidin-4-yl)phenyl]-1-(pyridin-3-yl)azetidine-3-carboxamide;
N-{4-[1-(methoxyacetyl)piperidin-4-yl]phenyl}-1-(pyridin-3-yl)azetidine-3-carboxamide;
N-{4-[1-(cyclohexylcarbonyl)piperidin-4-yl]phenyl}-1-(pyridin-3-yl)azetidine-3-carboxamide;
N-{4-[1-(3-methylbutanoyl)piperidin-4-yl]phenyl}-1-(pyridin-3-yl)azetidine-3-carboxamide;
N-{4-[1-(cyclopentylcarbonyl)piperidin-4-yl]phenyl}-1-(pyridin-3-yl)azetidine-3-carboxamide;
N-{4-[1-(2,3-dimethylbutanoyl)piperidin-4-yl]phenyl}-1-(pyridin-3-yl)azetidine-3-carboxamide;
N-{4-[1-(3,3-dimethylbutanoyl)piperidin-4-yl]phenyl}-1-(pyridazin-4-yl)azetidine-3-carboxamide;
(3S)—N-{4-[1-(2-hydroxy-2-methylpropanoyl)piperidin-4-yl]phenyl}-1-(pyridazin-4-yl)pyrrolidine-3-carboxamide;
(3S)—N-{4-[1-(cyclopentylacetyl)piperidin-4-yl]phenyl}-1-(pyridazin-4-yl)pyrrolidine-3-carboxamide;
N-(4-{1-[(2S)-2-methylbutanoyl]piperidin-4-yl}phenyl)-1-(pyridazin-4-yl)azetidine-3-carboxamide;
N-{4-[1-(cyclopentylacetyl)piperidin-4-yl]phenyl}-1-(pyridazin-4-yl)azetidine-3-carboxamide;
1-(pyridazin-4-yl)-N-{4-[1-(tetrahydro-2H-pyran-4-ylacetyl)piperidin-4-yl]phenyl}azetidine-3-carboxamide;
1-(pyridazin-4-yl)-N-{4-[1-(tetrahydro-2H-pyran-4-ylcarbonyl)piperidin-4-yl]phenyl}azetidine-3-carboxamide;
N-{4-[1-(2-methylpropanoyl)piperidin-4-yl]phenyl}-1-(pyridazin-3-yl)azetidine-3-carboxamide;
N-{4-[1-(2-methylpropyl)-1H-pyrazol-4-yl]phenyl}-1-(pyridazin-4-yl)azetidine-3-carboxamide;
N-[4-(1-benzoylpiperidin-4-yl)phenyl]-1-(2-methylpyridin-3-yl)azetidine-3-carboxamide;
N-{4-[1-(2-fluorobenzoyl)piperidin-4-yl]phenyl}-1-(2-methylpyridin-3-yl)azetidine-3-carboxamide;
N-{4-[1-(2-chlorobenzoyl)piperidin-4-yl]phenyl}-1-(2-methylpyridin-3-yl)azetidine-3-carboxamide;
N-{4-[1-(3-fluorobenzoyl)piperidin-4-yl]phenyl}-1-(2-methylpyridin-3-yl)azetidine-3-carboxamide;
N-{4-[1-(3-chlorobenzoyl)piperidin-4-yl]phenyl}-1-(2-methylpyridin-3-yl)azetidine-3-carboxamide;
N-{4-[1-(3,5-dichlorobenzoyl)piperidin-4-yl]phenyl}-1-(2-methylpyridin-3-yl)azetidine-3-carboxamide;
N-{4-[1-(4-fluorobenzoyl)piperidin-4-yl]phenyl}-1-(2-methylpyridin-3-yl)azetidine-3-carboxamide;
N-{4-[1-(4-chlorobenzoyl)piperidin-4-yl]phenyl}-1-(2-methylpyridin-3-yl)azetidine-3-carboxamide;
1-(2-methylpyridin-3-yl)-N-(4-{1-[4-(trifluoromethyl)benzoyl]piperidin-4-yl}phenyl)azetidine-3-carboxamide;
1-(2-methylpyridin-3-yl)-N-{4-[1-(pyridazin-3-ylcarbonyl)piperidin-4-yl]phenyl}azetidine-3-carboxamide;
1-(2-methylpyridin-3-yl)-N-[4-(1-pentanoylpiperidin-4-yl)phenyl]azetidine-3-carboxamide;
N-{4-[1-(3-methylpentanoyl)piperidin-4-yl]phenyl}-1-(2-methylpyridin-3-yl)azetidine-3-carboxamide;
N-(4-{1-[(1S,4R)-bicyclo[2.2.1]hept-2-ylacetyl]piperidin-4-yl}phenyl)-1-(2-methylpyridin-3-yl)azetidine-3-carboxamide;
N-{4-[1-(cyclopentylacetyl)piperidin-4-yl]phenyl}-1-(2-methylpyridin-3-yl)azetidine-3-carboxamide;
N-(4-{1-[(2-methylcyclopropyl)carbonyl]piperidin-4-yl}phenyl)-1-(2-methylpyridin-3-yl)azetidine-3-carboxamide;
1-(2-methylpyridin-3-yl)-N-{4-[1-(morpholin-4-ylacetyl)piperidin-4-yl]phenyl}azetidine-3-carboxamide;
N-{4-[1-(furan-3-ylcarbonyl)piperidin-4-yl]phenyl}-1-(2-methylpyridin-3-yl)azetidine-3-carboxamide;
1-(2-methylpyridin-3-yl)-N-{4-[1-(pyrrolidin-1-ylacetyl)piperidin-4-yl]phenyl}azetidine-3-carboxamide;
1-(2-methylpyridin-3-yl)-N-{4-[1-(5-oxo-D-prolyl)piperidin-4-yl]phenyl}azetidine-3-carboxamide;
N-{4-[1-(N,N-dimethyl-beta-alanyl)piperidin-4-yl]phenyl}-1-(2-methylpyridin-3-yl)azetidine-3-carboxamide;
1-(2-methylpyridin-3-yl)-N-{4-[1-(thiophen-3-ylcarbonyl)piperidin-4-yl]phenyl}azetidine-3-carboxamide;
N-(4-{1-[(1-methylcyclopropyl)carbonyl]piperidin-4-yl}phenyl)-1-(2-methylpyridin-3-yl)azetidine-3-carboxamide;
1-(2-methylpyridin-3-yl)-N-(4-{1-[(3-methylthiophen-2-yl)carbonyl]piperidin-4-yl}phenyl)azetidine-3-carboxamide;
1-(2-methylpyridin-3-yl)-N-{4-[1-(4,4,4-trifluorobutanoyl)piperidin-4-yl]phenyl}azetidine-3-carboxamide;
N-(4-{1-[(4-methylpiperazin-1-yl)acetyl]piperidin-4-yl}phenyl)-1-(2-methylpyridin-3-yl)azetidine-3-carboxamide;
1-(2-methylpyridin-3-yl)-N-{4-[1-(5-oxo-L-prolyl)piperidin-4-yl]phenyl}azetidine-3-carboxamide;
N-{4-[1-(3-ethoxypropanoyl)piperidin-4-yl]phenyl}-1-(2-methylpyridin-3-yl)azetidine-3-carboxamide;
N-{4-[1-(4-methylpentanoyl)piperidin-4-yl]phenyl}-1-(2-methylpyridin-3-yl)azetidine-3-carboxamide;
N-(4-{1-[(1-methylcyclohexyl)carbonyl]piperidin-4-yl}phenyl)-1-(2-methylpyridin-3-yl)azetidine-3-carboxamide;
N-[4-(1-acetylpiperidin-4-yl)phenyl]-1-(2-methylpyridin-3-yl)azetidine-3-carboxamide;
N-{4-[1-(cyclohexylacetyl)piperidin-4-yl]phenyl}-1-(2-methylpyridin-3-yl)azetidine-3-carboxamide;
N-{4-[1-(N-acetyl-L-leucyl)piperidin-4-yl]phenyl}-1-(2-methylpyridin-3-yl)azetidine-3-carboxamide;
1-(2-methylpyridin-3-yl)-N-[4-(1-propanoylpiperidin-4-yl)phenyl]azetidine-3-carboxamide;
1-(2-methylpyridin-3-yl)-N-{4-[1-(3,3,3-trifluoropropanoyl)piperidin-4-yl]phenyl}azetidine-3-carboxamide;
N-(4-{1-[(2-methoxyethoxy)acetyl]piperidin-4-yl}phenyl)-1-(2-methylpyridin-3-yl)azetidine-3-carboxamide;
1-(2-methylpyridin-3-yl)-N-(4-{1-[3-(morpholin-4-yl)propanoyl]piperidin-4-yl}phenyl)azetidine-3-carboxamide;
N-{4-[1-(2,2-dimethylpropanoyl)piperidin-4-yl]phenyl}-1-(2-methylpyridin-3-yl)azetidine-3-carboxamide;
1-(2-methylpyridin-3-yl)-N-(4-{1-[(5-methylthiophen-2-yl)carbonyl]piperidin-4-yl}phenyl)azetidine-3-carboxamide;
1-(2-methylpyridin-3-yl)-N-{4-[1-(thiophen-2-ylcarbonyl)piperidin-4-yl]phenyl}azetidine-3-carboxamide;

1-(2-methylpyridin-3-yl)-N-(4-{1-[(1-methyl-1H-pyrrol-2-yl)carbonyl]piperidin-4-yl}phenyl)azetidine-3-carboxamide;

N-{4-[1-(furan-2-ylcarbonyl)piperidin-4-yl]phenyl}-1-(2-methylpyridin-3-yl)azetidine-3-carboxamide;

1-(2-methylpyridin-3-yl)-N-(4-{1-[3-(piperidin-1-yl)propanoyl]piperidin-4-yl}phenyl)azetidine-3-carboxamide;

N-{4-[1-(ethoxyacetyl)piperidin-4-yl]phenyl}-1-(2-methylpyridin-3-yl)azetidine-3-carboxamide;

N-{4-[1-(3,3-dimethylbutanoyl)piperidin-4-yl]phenyl}-1-(2-methylpyridin-3-yl)azetidine-3-carboxamide;

N-{4-[1-(2,2-dimethylbutanoyl)piperidin-4-yl]phenyl}-1-(2-methylpyridin-3-yl)azetidine-3-carboxamide;

N-[4-(1-butanoylpiperidin-4-yl)phenyl]-1-(2-methylpyridin-3-yl)azetidine-3-carboxamide;

N-{4-[1-(methoxyacetyl)piperidin-4-yl]phenyl}-1-(2-methylpyridin-3-yl)azetidine-3-carboxamide;

N-{4-[1-(cyclohexylcarbonyl)piperidin-4-yl]phenyl}-1-(2-methylpyridin-3-yl)azetidine-3-carboxamide;

N-{4-[1-(3-methylbutanoyl)piperidin-4-yl]phenyl}-1-(2-methylpyridin-3-yl)azetidine-3-carboxamide;

N-{4-[1-(2,3-dimethylbutanoyl)piperidin-4-yl]phenyl}-1-(2-methylpyridin-3-yl)azetidine-3-carboxamide;

N-(4-{[1-(4-fluorobenzoyl)azetidin-3-yl]oxy}phenyl)-1-(pyridazin-4-yl)azetidine-3-carboxamide;

N-(4-{[1-(2,4-difluorobenzoyl)azetidin-3-yl]oxy}phenyl)-1-(pyridazin-4-yl)azetidine-3-carboxamide;

N-[4-({1-[difluoro(phenyl)acetyl]azetidin-3-yl}oxy)phenyl]-1-(pyridazin-4-yl)azetidine-3-carboxamide;

N-[4-({1-[(4,4-difluoro cyclohexyl)carbonyl]azetidin-3-yl}oxy)phenyl]-1-(pyridazin-4-yl)azetidine-3-carboxamide;

N-[4-({1-[(4-fluorophenyl)acetyl]azetidin-3-yl}oxy)phenyl]-1-(pyridazin-4-yl)azetidine-3-carboxamide;

(3S)—N-{4-[1-(cyclopentylacetyl)piperidin-4-yl]phenyl}-1-(pyridin-3-yl)pyrrolidine-3-carboxamide;

1-(pyridazin-4-yl)-N-[4-({1-[4-(trifluoromethyl)benzoyl]azetidin-3-yl}oxy)phenyl]azetidine-3-carboxamide;

N-{4-[(1-benzoylazetidin-3-yl)oxy]phenyl}-1-(pyridazin-4-yl)azetidine-3-carboxamide;

N-(4-{[1-(2-hydroxy-2-methylpropanoyl)azetidin-3-yl]oxy}phenyl)-1-(pyridazin-4-yl)azetidine-3-carboxamide;

1-(pyridazin-4-yl)-N-(4-{[1-(tetrahydrofuran-3-ylcarbonyl)azetidin-3-yl]oxy}phenyl)azetidine-3-carboxamide;

N-(4-{[1-(furan-3-ylcarbonyl)azetidin-3-yl]oxy}phenyl)-1-(pyridazin-4-yl)azetidine-3-carboxamide;

N-{4-[(1-pentanoylazetidin-3-yl)oxy]phenyl}-1-(pyridazin-4-yl)azetidine-3-carboxamide;

N-(4-{[1-(2-chlorobenzoyl)piperidin-4-yl]oxy}phenyl)-1-(pyridazin-3-yl)azetidine-3-carboxamide;

N-[4-({1-[(2S)-2-methylbutanoyl]piperidin-4-yl}oxy)phenyl]-1-(pyridazin-3-yl)azetidine-3-carboxamide;

1-(pyridazin-3-yl)-N-(4-{[1-(1,3-thiazol-2-ylcarbonyl)piperidin-4-yl]oxy}phenyl)azetidine-3-carboxamide;

1-(pyridazin-3-yl)-N-(4-{[1-(tetrahydro-2H-pyran-4-ylcarbonyl)piperidin-4-yl]oxy}phenyl)azetidine-3-carboxamide;

N-[4-({1-[difluoro(phenyl)acetyl]piperidin-4-yl}oxy)phenyl]-1-(pyridazin-3-yl)azetidine-3-carboxamide;

N-[4-({1-[(4,4-difluorocyclohexyl)carbonyl]piperidin-4-yl}oxy)phenyl]-1-(pyridazin-3-yl)azetidine-3-carboxamide;

N-(4-{[1-(2-methyl-2-phenylpropanoyl)piperidin-4-yl]oxy}phenyl)-1-(pyridazin-3-yl)azetidine-3-carboxamide;

1-(pyridazin-3-yl)-N-(4-{[1-(1,3-thiazol-4-ylcarbonyl)piperidin-4-yl]oxy}phenyl)azetidine-3-carboxamide;

N-[4-({1-[(5-methylthiophen-2-yl)carbonyl]piperidin-4-yl}oxy)phenyl]-1-(pyridazin-3-yl)azetidine-3-carboxamide;

1-(pyridazin-3-yl)-N-{4-[(1-{[4-(trifluoromethyl)phenyl]acetyl}piperidin-4-yl)oxy]phenyl}azetidine-3-carboxamide;

1-(pyridazin-3-yl)-N-(4-{[1-(tetrahydrofuran-2-ylcarbonyl)piperidin-4-yl]oxy}phenyl)azetidine-3-carboxamide;

1-(pyridazin-3-yl)-N-[4-({1-[3-(trifluoromethyl)benzoyl]piperidin-4-yl}oxy)phenyl]azetidine-3-carboxamide;

1-(pyridazin-3-yl)-N-(4-{[1-(thiophen-3-ylcarbonyl)piperidin-4-yl]oxy}phenyl)azetidine-3-carboxamide;

1-(pyridazin-3-yl)-N-[4-({1-[3-(trifluoromethoxy)benzoyl]piperidin-4-yl}oxy)phenyl]azetidine-3-carboxamide;

N-(4-{[1-(3-methylbutanoyl)piperidin-4-yl]oxy}phenyl)-1-(pyridazin-3-yl)azetidine-3-carboxamide;

1-(pyridazin-3-yl)-N-(4-{[1-(tetrahydrofuran-3-ylcarbonyl)piperidin-4-yl]oxy}phenyl)azetidine-3-carboxamide;

N-[4-({1-[(3-fluorophenyl)acetyl]piperidin-4-yl}oxy)phenyl]-1-(pyridazin-3-yl)azetidine-3-carboxamide;

N-(4-{[1-(2-fluorobenzoyl)piperidin-4-yl]oxy}phenyl)-1-(pyridazin-3-yl)azetidine-3-carboxamide;

N-(4-{[1-(2,4-difluorobenzoyl)piperidin-4-yl]oxy}phenyl)-1-(pyridazin-3-yl)azetidine-3-carboxamide;

N-(4-{[1-(4-fluorobenzoyl)piperidin-4-yl]oxy}phenyl)-1-(pyridazin-3-yl)azetidine-3-carboxamide;

N-(4-{[1-(3-fluorobenzoyl)piperidin-4-yl]oxy}phenyl)-1-(pyridazin-3-yl)azetidine-3-carboxamide;

N-[4-({1-[(4-fluorophenyl)acetyl]piperidin-4-yl}oxy)phenyl]-1-(pyridazin-3-yl)azetidine-3-carboxamide;

N-(4-{[1-(cyclopropylacetyl)piperidin-4-yl]oxy}phenyl)-1-(pyridazin-3-yl)azetidine-3-carboxamide;

N-(4-{[1-(3,4-difluorobenzoyl)piperidin-4-yl]oxy}phenyl)-1-(pyridazin-3-yl)azetidine-3-carboxamide;

1-(pyridazin-3-yl)-N-[4-({1-[4-(trifluoromethoxy)benzoyl]piperidin-4-yl}oxy)phenyl]azetidine-3-carboxamide;

N-[4-({1-[(2,4-difluorophenyl)acetyl]piperidin-4-yl}oxy)phenyl]-1-(pyridazin-3-yl)azetidine-3-carboxamide;

1-(pyridazin-3-yl)-N-[4-({1-[4-(trifluoromethyl)benzoyl]piperidin-4-yl}oxy)phenyl]azetidine-3-carboxamide;

1-(pyridazin-3-yl)-N-{4-[(1-{[4-(trifluoromethoxy)phenyl]acetyl}piperidin-4-yl)oxy]phenyl}azetidine-3-carboxamide;

N-[4-({1-[(3,5-difluorophenyl)acetyl]piperidin-4-yl}oxy)phenyl]-1-(pyridazin-3-yl)azetidine-3-carboxamide;

1-(pyridazin-3-yl)-N-{4-[(1-{[3-(trifluoromethyl)phenyl]acetyl}piperidin-4-yl)oxy]phenyl}azetidine-3-carboxamide;

N-(4-{[1-(2,2-dimethylpropanoyl)piperidin-4-yl]oxy}phenyl)-1-(pyridazin-3-yl)azetidine-3-carboxamide;

1-(pyridazin-3-yl)-N-(4-{[1-(pyridin-2-ylcarbonyl)piperidin-4-yl]oxy}phenyl)azetidine-3-carboxamide;

N-(4-{[1-(3,5-difluorobenzoyl)piperidin-4-yl]oxy}phenyl)-1-(pyridazin-3-yl)azetidine-3-carboxamide;

N-{4-[(1-acetylpiperidin-4-yl)oxy]phenyl}-1-(pyridazin-3-yl)azetidine-3-carboxamide;

N-(4-{[1-(4-chlorobenzoyl)piperidin-4-yl]oxy}phenyl)-1-(pyridazin-3-yl)azetidine-3-carboxamide;

N-(4-{[1-(methoxyacetyl)piperidin-4-yl]oxy}phenyl)-1-(pyridazin-3-yl)azetidine-3-carboxamide;

N-[4-({1-[(2-fluorophenyl)acetyl]piperidin-4-yl}oxy)phenyl]-1-(pyridazin-3-yl)azetidine-3-carboxamide;

N-(4-{[1-(2,2-dimethylbutanoyl)piperidin-4-yl]oxy}phenyl)-1-(pyridazin-3-yl)azetidine-3-carboxamide;

1-(pyridazin-3-yl)-N-(4-{[1-(thiophen-2-ylcarbonyl)piperidin-4-yl]oxy}phenyl)azetidine-3-carboxamide;

N-(4-{[1-(3-chlorobenzoyl)piperidin-4-yl]oxy}phenyl)-1-(pyridazin-3-yl)azetidine-3-carboxamide;
N-(4-{[1-(cyclopropylcarbonyl)piperidin-4-yl]oxy}phenyl)-1-(pyridazin-3-yl)azetidine-3-carboxamide;
1-(pyridazin-3-yl)-N-(4-{[1-(3,3,3-trifluoropropanoyl)piperidin-4-yl]oxy}phenyl)azetidine-3-carboxamide;
N-(4-{[1-(2-methylpropanoyl)piperidin-4-yl]oxy}phenyl)-1-(pyridazin-3-yl)azetidine-3-carboxamide;
N-(4-{[1-(3,3-dimethylbutanoyl)azetidin-3-yl]oxy}phenyl)-1-(pyridazin-4-yl)azetidine-3-carboxamide;
N-(4-{[1-(cyclohexylcarbonyl)azetidin-3-yl]oxy}phenyl)-1-(pyridazin-4-yl)azetidine-3-carboxamide;
1-(pyridazin-4-yl)-N-(4-{[1-(tetrahydro-2H-pyran-4-ylacetyl)azetidin-3-yl]oxy}phenyl)azetidine-3-carboxamide;
N-[4-({1-[(2-methylcyclopropyl)carbonyl]azetidin-3-yl}oxy)phenyl]-1-(pyridazin-4-yl)azetidine-3-carboxamide;
1-(pyridazin-4-yl)-N-(4-{[1-(3,3,3-trifluoropropanoyl)azetidin-3-yl]oxy}phenyl)azetidine-3-carboxamide;
N-(4-{[1-(cyclopentylcarbonyl)azetidin-3-yl]oxy}phenyl)-1-(pyridazin-4-yl)azetidine-3-carboxamide;
N-(4-{[1-(3,3-dimethylbutanoyl)piperidin-4-yl]oxy}phenyl)-1-(pyridazin-4-yl)azetidine-3-carboxamide;
N-(4-{[1-(cyclobutylcarbonyl)azetidin-3-yl]oxy}phenyl)-1-(pyridazin-4-yl)azetidine-3-carboxamide;
1-(pyridazin-4-yl)-N-(4-{[1-(tetrahydrofuran-2-ylcarbonyl)azetidin-3-yl]oxy}phenyl)azetidine-3-carboxamide;
N-(4-{[1-(4-methylpentanoyl)azetidin-3-yl]oxy}phenyl)-1-(pyridazin-4-yl)azetidine-3-carboxamide;
N-(4-{[1-(2-methylpropanoyl)azetidin-3-yl]oxy}phenyl)-1-(pyridazin-4-yl)azetidine-3-carboxamide;
N-[4-({1-[(2S)-2-methylbutanoyl]azetidin-3-yl}oxy)phenyl]-1-(pyridazin-4-yl)azetidine-3-carboxamide;
N-(4-{[1-(3-methylbutanoyl)piperidin-4-yl]oxy}phenyl)-1-(pyridazin-4-yl)azetidine-3-carboxamide;
N-(4-{[1-(methoxyacetyl)piperidin-4-yl]oxy}phenyl)-1-(pyridazin-4-yl)azetidine-3-carboxamide;
1-(pyridazin-4-yl)-N-(4-{[1-(3,3,3-trifluoropropanoyl)piperidin-4-yl]oxy}phenyl)azetidine-3-carboxamide;
N-[4-({1-[difluoro(phenyl)acetyl]piperidin-4-yl}oxy)phenyl]-1-(pyridazin-4-yl)azetidine-3-carboxamide;
N-[4-({1-[(4,4-difluorocyclohexyl)carbonyl]piperidin-4-yl}oxy)phenyl]-1-(pyridazin-4-yl)azetidine-3-carboxamide;
N-(4-{[1-(4-fluorobenzoyl)piperidin-4-yl]oxy}phenyl)-1-(pyridazin-4-yl)azetidine-3-carboxamide;
1-(pyridazin-4-yl)-N-(4-{[1-(1,3-thiazol-4-ylcarbonyl)piperidin-4-yl]oxy}phenyl)azetidine-3-carboxamide;
1-(pyridazin-4-yl)-N-{4-[(1-{[4-(trifluoromethyl)phenyl]acetyl}piperidin-4-yl)oxy]phenyl}azetidine-3-carboxamide;
N-(4-{[1-(3,4-difluorobenzoyl)piperidin-4-yl]oxy}phenyl)-1-(pyridazin-4-yl)azetidine-3-carboxamide;
1-(pyridazin-4-yl)-N-{4-[(1-{[4-(trifluoromethoxy)phenyl]acetyl}piperidin-4-yl)oxy]phenyl}azetidine-3-carboxamide;
N-[4-({1-[(4-fluorophenyl)acetyl]piperidin-4-yl}oxy)phenyl]-1-(pyridazin-4-yl)azetidine-3-carboxamide;
N-[4-({1-[(2,4-difluorophenyl)acetyl]piperidin-4-yl}oxy)phenyl]-1-(pyridazin-4-yl)azetidine-3-carboxamide;
1-(pyridazin-4-yl)-N-(4-{[1-(thiophen-3-ylcarbonyl)piperidin-4-yl]oxy}phenyl)azetidine-3-carboxamide;
N-(4-{[1-(2-chlorobenzoyl)piperidin-4-yl]oxy}phenyl)-1-(pyridazin-4-yl)azetidine-3-carboxamide;
N-(4-{[1-(2,2-dimethylpropanoyl)piperidin-4-yl]oxy}phenyl)-1-(pyridazin-4-yl)azetidine-3-carboxamide;
N-(4-{[1-(2-methyl-2-phenylpropanoyl)piperidin-4-yl]oxy}phenyl)-1-(pyridazin-4-yl)azetidine-3-carboxamide;
N-{4-[(1-acetylpiperidin-4-yl)oxy]phenyl}-1-(pyridazin-4-yl)azetidine-3-carboxamide;
1-(pyridazin-4-yl)-N-(4-{[1-(1,3-thiazol-2-ylcarbonyl)piperidin-4-yl]oxy}phenyl)azetidine-3-carboxamide;
N-(4-{[1-(2,4-difluorobenzoyl)piperidin-4-yl]oxy}phenyl)-1-(pyridazin-4-yl)azetidine-3-carboxamide;
1-(pyridazin-4-yl)-N-[4-({1-[3-(trifluoromethyl)benzoyl]piperidin-4-yl}oxy)phenyl]azetidine-3-carboxamide;
N-(4-{[1-(3-fluorobenzoyl)piperidin-4-yl]oxy}phenyl)-1-(pyridazin-4-yl)azetidine-3-carboxamide;
1-(pyridazin-4-yl)-N-[4-({1-[4-(trifluoromethyl)benzoyl]piperidin-4-yl}oxy)phenyl]azetidine-3-carboxamide;
N-[4-({1-[(3-fluorophenyl)acetyl]piperidin-4-yl}oxy)phenyl]-1-(pyridazin-4-yl)azetidine-3-carboxamide;
N-(4-{[1-(2-fluorobenzoyl)piperidin-4-yl]oxy}phenyl)-1-(pyridazin-4-yl)azetidine-3-carboxamide;
1-(pyridazin-4-yl)-N-[4-({1-[4-(trifluoromethoxy)benzoyl]piperidin-4-yl}oxy)phenyl]azetidine-3-carboxamide;
N-[4-({1-[(3,5-difluorophenyl)acetyl]piperidin-4-yl}oxy)phenyl]-1-(pyridazin-4-yl)azetidine-3-carboxamide;
1-(pyridazin-4-yl)-N-[4-({1-[3-(trifluoromethoxy)benzoyl]piperidin-4-yl}oxy)phenyl]azetidine-3-carboxamide;
N-(4-{[1-(cyclopropylacetyl)piperidin-4-yl]oxy}phenyl)-1-(pyridazin-4-yl)azetidine-3-carboxamide;
N-(4-{[1-(2-methylpropanoyl)piperidin-4-yl]oxy}phenyl)-1-(pyridazin-4-yl)azetidine-3-carboxamide;
N-(4-{[1-(3-chlorobenzoyl)piperidin-4-yl]oxy}phenyl)-1-(pyridazin-4-yl)azetidine-3-carboxamide;
1-(pyridazin-4-yl)-N-(4-{[1-(pyridin-2-ylcarbonyl)piperidin-4-yl]oxy}phenyl)azetidine-3-carboxamide;
N-(4-{[1-(4-chlorobenzoyl)piperidin-4-yl]oxy}phenyl)-1-(pyridazin-4-yl)azetidine-3-carboxamide;
1-(pyridazin-4-yl)-N-(4-{[1-(tetrahydrofuran-3-ylcarbonyl)piperidin-4-yl]oxy}phenyl)azetidine-3-carboxamide;
N-(4-{[1-(3,5-difluorobenzoyl)piperidin-4-yl]oxy}phenyl)-1-(pyridazin-4-yl)azetidine-3-carboxamide;
N-(4-{[1-(2,2-dimethylbutanoyl)piperidin-4-yl]oxy}phenyl)-1-(pyridazin-4-yl)azetidine-3-carboxamide;
N-(4-{[1-(cyclopropylcarbonyl)piperidin-4-yl]oxy}phenyl)-1-(pyridazin-4-yl)azetidine-3-carboxamide;
1-(pyridazin-4-yl)-N-(4-{[1-(tetrahydrofuran-2-ylcarbonyl)piperidin-4-yl]oxy}phenyl)azetidine-3-carboxamide;
1-(pyridazin-4-yl)-N-(4-{[1-(thiophen-2-ylcarbonyl)piperidin-4-yl]oxy}phenyl)azetidine-3-carboxamide;
N-[4-({1-[(5-methylthiophen-2-yl)carbonyl]piperidin-4-yl}oxy)phenyl]-1-(pyridazin-4-yl)azetidine-3-carboxamide;
1-(pyridazin-4-yl)-N-{4-[(1-{[3-(trifluoromethyl)phenyl]acetyl}piperidin-4-yl)oxy]phenyl}azetidine-3-carboxamide;
1-(pyridazin-4-yl)-N-(4-{[1-(tetrahydro-2H-pyran-4-ylcarbonyl)piperidin-4-yl]oxy}phenyl)azetidine-3-carboxamide;
N-[4-({1-[(2S)-2-methylbutanoyl]piperidin-4-yl}oxy)phenyl]-1-(pyridazin-4-yl)azetidine-3-carboxamide;
N-[4-({1-[(2-fluorophenyl)acetyl]piperidin-4-yl}oxy)phenyl]-1-(pyridazin-4-yl)azetidine-3-carboxamide;
5-[1-(2-methylpropyl)-1H-pyrazol-4-yl]-N-[1-(pyridazin-3-yl)azetidin-3-yl]furan-2-carboxamide;
(3S)—N-{4-[1-(2-methylpropanoyl)piperidin-4-yl]phenyl}-1-(pyridazin-3-yl)pyrrolidine-3-carboxamide;
(3S)—N-[4-(1-benzoylpiperidin-4-yl)phenyl]-1-(pyridazin-3-yl)pyrrolidine-3-carboxamide;

(3S)-1-(pyridazin-3-yl)-N-{4-[1-(tetrahydro-2H-pyran-4-ylacetyl)piperidin-4-yl]phenyl}pyrrolidine-3-carboxamide;
(3S)—N-{4-[1-(2,2-dimethylpropanoyl)piperidin-4-yl]phenyl}-1-(pyridazin-3-yl)pyrrolidine-3-carboxamide;
tert-butyl 4-(4-{[1-(pyridazin-3-yl)azetidin-3-yl]carbamoyl}phenyl)piperidine-1-carboxylate;
5-[1-(2-methylpropyl)-1H-pyrazol-4-yl]-N-[1-(pyridazin-3-yl)azetidin-3-yl]thiophene-2-carboxamide;
N-[4-(1-acetylpiperidin-4-yl)phenyl]-1-(pyridazin-3-yl)azetidine-3-carboxamide;
N-[4-(1-butanoylpiperidin-4-yl)phenyl]-1-(pyridazin-3-yl)azetidine-3-carboxamide;
N-[4-(1-pentanoylpiperidin-4-yl)phenyl]-1-(pyridazin-3-yl)azetidine-3-carboxamide;
N-{4-[1-(2-methylbutanoyl)piperidin-4-yl]phenyl}-1-(pyridazin-3-yl)azetidine-3-carboxamide;
N-{4-[1-(3-methylbutanoyl)piperidin-4-yl]phenyl}-1-(pyridazin-3-yl)azetidine-3-carboxamide;
N-[4-(1-hexanoylpiperidin-4-yl)phenyl]-1-(pyridazin-3-yl)azetidine-3-carboxamide;
N-{4-[1-(2-methylpentanoyl)piperidin-4-yl]phenyl}-1-(pyridazin-3-yl)azetidine-3-carboxamide;
N-{4-[1-(3-methylpentanoyl)piperidin-4-yl]phenyl}-1-(pyridazin-3-yl)azetidine-3-carboxamide;
N-{4-[1-(4-methylpentanoyl)piperidin-4-yl]phenyl}-1-(pyridazin-3-yl)azetidine-3-carboxamide;
N-{4-[1-(2,2-dimethylbutanoyl)piperidin-4-yl]phenyl}-1-(pyridazin-3-yl)azetidine-3-carboxamide;
N-{4-[1-(2,3-dimethylbutanoyl)piperidin-4-yl]phenyl}-1-(pyridazin-3-yl)azetidine-3-carboxamide;
N-{4-[1-(3,3-dimethylbutanoyl)piperidin-4-yl]phenyl}-1-(pyridazin-3-yl)azetidine-3-carboxamide;
N-{4-[1-(2-ethylbutanoyl)piperidin-4-yl]phenyl}-1-(pyridazin-3-yl)azetidine-3-carboxamide;
N-[4-(1-heptanoylpiperidin-4-yl)phenyl]-1-(pyridazin-3-yl)azetidine-3-carboxamide;
N-{4-[1-(but-3-enoyl)piperidin-4-yl]phenyl}-1-(pyridazin-3-yl)azetidine-3-carboxamide;
N-{4-[1-(pent-4-enoyl)piperidin-4-yl]phenyl}-1-(pyridazin-3-yl)azetidine-3-carboxamide;
1-(pyridazin-3-yl)-N-{4-[1-(3,3,3-trifluoropropanoyl)piperidin-4-yl]phenyl}azetidine-3-carboxamide;
N-{4-[1-(methoxyacetyl)piperidin-4-yl]phenyl}-1-(pyridazin-3-yl)azetidine-3-carboxamide;
N-(4-{1-[(methylsulfanyl)acetyl]piperidin-4-yl}phenyl)-1-(pyridazin-3-yl)azetidine-3-carboxamide;
N-(4-{1-[(2-methoxyethoxy)acetyl]piperidin-4-yl}phenyl)-1-(pyridazin-3-yl)azetidine-3-carboxamide;
N-{4-[1-(3-nitropropanoyl)piperidin-4-yl]phenyl}-1-(pyridazin-3-yl)azetidine-3-carboxamide;
N-(4-{1-[3-(methylsulfanyl)propanoyl]piperidin-4-yl}phenyl)-1-(pyridazin-3-yl)azetidine-3-carboxamide;
N-{4-[1-(pent-4-ynoyl)piperidin-4-yl]phenyl}-1-(pyridazin-3-yl)azetidine-3-carboxamide;
N-{4-[1-(cyclohexylcarbonyl)piperidin-4-yl]phenyl}-1-(pyridazin-3-yl)azetidine-3-carboxamide;
N-{4-[1-(cyclohexylacetyl)piperidin-4-yl]phenyl}-1-(pyridazin-3-yl)azetidine-3-carboxamide;
N-{4-[1-(3-methylbenzoyl)piperidin-4-yl]phenyl}-1-(pyridazin-3-yl)azetidine-3-carboxamide;
N-{4-[1-(2-hydroxybenzoyl)piperidin-4-yl]phenyl}-1-(pyridazin-3-yl)azetidine-3-carboxamide;
N-{4-[1-(3-hydroxybenzoyl)piperidin-4-yl]phenyl}-1-(pyridazin-3-yl)azetidine-3-carboxamide;
N-{4-[1-(4-hydroxybenzoyl)piperidin-4-yl]phenyl}-1-(pyridazin-3-yl)azetidine-3-carboxamide;
N-{4-[1-(2-methoxybenzoyl)piperidin-4-yl]phenyl}-1-(pyridazin-3-yl)azetidine-3-carboxamide;
N-{4-[1-(3-methoxybenzoyl)piperidin-4-yl]phenyl}-1-(pyridazin-3-yl)azetidine-3-carboxamide;
N-{4-[1-(4-methoxybenzoyl)piperidin-4-yl]phenyl}-1-(pyridazin-3-yl)azetidine-3-carboxamide;
N-{4-[1-(3-fluorobenzoyl)piperidin-4-yl]phenyl}-1-(pyridazin-3-yl)azetidine-3-carboxamide;
N-{4-[1-(4-fluorobenzoyl)piperidin-4-yl]phenyl}-1-(pyridazin-3-yl)azetidine-3-carboxamide;
N-{4-[1-(2-chlorobenzoyl)piperidin-4-yl]phenyl}-1-(pyridazin-3-yl)azetidine-3-carboxamide;
N-{4-[1-(3-chlorobenzoyl)piperidin-4-yl]phenyl}-1-(pyridazin-3-yl)azetidine-3-carboxamide;
N-{4-[1-(3-cyanobenzoyl)piperidin-4-yl]phenyl}-1-(pyridazin-3-yl)azetidine-3-carboxamide;
N-{4-[1-(4-cyanobenzoyl)piperidin-4-yl]phenyl}-1-(pyridazin-3-yl)azetidine-3-carboxamide;
1-(pyridazin-3-yl)-N-(4-{1-[3-(trifluoromethyl)benzoyl]piperidin-4-yl}phenyl)azetidine-3-carboxamide;
1-(pyridazin-3-yl)-N-(4-{1-[4-(trifluoromethyl)benzoyl]piperidin-4-yl}phenyl)azetidine-3-carboxamide;
1-(pyridazin-3-yl)-N-(4-{1-[3-(trifluoromethoxy)benzoyl]piperidin-4-yl}phenyl)azetidine-3-carboxamide;
N-{4-[1-(2,3-dimethylbenzoyl)piperidin-4-yl]phenyl}-1-(pyridazin-3-yl)azetidine-3-carboxamide;
N-{4-[1-(2,4-dimethylbenzoyl)piperidin-4-yl]phenyl}-1-(pyridazin-3-yl)azetidine-3-carboxamide;
N-{4-[1-(2,5-dimethylbenzoyl)piperidin-4-yl]phenyl}-1-(pyridazin-3-yl)azetidine-3-carboxamide;
N-{4-[1-(3,4-dimethylbenzoyl)piperidin-4-yl]phenyl}-1-(pyridazin-3-yl)azetidine-3-carboxamide;
N-{4-[1-(3,5-dimethylbenzoyl)piperidin-4-yl]phenyl}-1-(pyridazin-3-yl)azetidine-3-carboxamide;
N-{4-[1-(2,4-dichlorobenzoyl)piperidin-4-yl]phenyl}-1-(pyridazin-3-yl)azetidine-3-carboxamide;
N-{4-[1-(2,5-dichlorobenzoyl)piperidin-4-yl]phenyl}-1-(pyridazin-3-yl)azetidine-3-carboxamide;
N-{4-[1-(3,4-dichlorobenzoyl)piperidin-4-yl]phenyl}-1-(pyridazin-3-yl)azetidine-3-carboxamide;
N-{4-[1-(3,5-dichlorobenzoyl)piperidin-4-yl]phenyl}-1-(pyridazin-3-yl)azetidine-3-carboxamide;
N-(4-{1-[(2-fluorophenyl)acetyl]piperidin-4-yl}phenyl)-1-(pyridazin-3-yl)azetidine-3-carboxamide;
N-(4-{1-[(3-fluorophenyl)acetyl]piperidin-4-yl}phenyl)-1-(pyridazin-3-yl)azetidine-3-carboxamide;
N-(4-{1-[(4-fluorophenyl)acetyl]piperidin-4-yl}phenyl)-1-(pyridazin-3-yl)azetidine-3-carboxamide;
N-(4-{1-[(2-chlorophenyl)acetyl]piperidin-4-yl}phenyl)-1-(pyridazin-3-yl)azetidine-3-carboxamide;
N-(4-{1-[(4-chlorophenyl)acetyl]piperidin-4-yl}phenyl)-1-(pyridazin-3-yl)azetidine-3-carboxamide;
1-(pyridazin-3-yl)-N-[4-(1-{[4-(trifluoromethyl)phenyl]acetyl}piperidin-4-yl)phenyl]azetidine-3-carboxamide;
N-(4-{1-[(3,5-dimethylphenyl)acetyl]piperidin-4-yl}phenyl)-1-(pyridazin-3-yl)azetidine-3-carboxamide;
N-(4-{1-[(2,5-difluorophenyl)acetyl]piperidin-4-yl}phenyl)-1-(pyridazin-3-yl)azetidine-3-carboxamide;
N-(4-{1-[(3,4-dichlorophenyl)acetyl]piperidin-4-yl}phenyl)-1-(pyridazin-3-yl)azetidine-3-carboxamide;
N-{4-[1-(furan-3-ylcarbonyl)piperidin-4-yl]phenyl}-1-(pyridazin-3-yl)azetidine-3-carboxamide;
1-(pyridazin-3-yl)-N-{4-[1-(thiophen-2-ylcarbonyl)piperidin-4-yl]phenyl}azetidine-3-carboxamide;
N-(4-{1-[(5-methylthiophen-2-yl)carbonyl]piperidin-4-yl}phenyl)-1-(pyridazin-3-yl)azetidine-3-carboxamide;

N-(4-{1-[(5-methylpyrazin-2-yl)carbonyl]piperidin-4-yl}phenyl)-1-(pyridazin-3-yl)azetidine-3-carboxamide;
N-(4-{1-[(1-methylcyclopropyl)carbonyl]piperidin-4-yl}phenyl)-1-(pyridazin-3-yl)azetidine-3-carboxamide;
N-{4-[1-(3-ethoxypropanoyl)piperidin-4-yl]phenyl}-1-(pyridazin-3-yl)azetidine-3-carboxamide;
N-(4-{1-[(1-phenylcyclopropyl)carbonyl]piperidin-4-yl}phenyl)-1-(pyridazin-3-yl)azetidine-3-carboxamide;
1-(pyridazin-3-yl)-N-(4-{1-[(pyrimidin-2-ylsulfanyl)acetyl]piperidin-4-yl}phenyl)azetidine-3-carboxamide;
N-(4-{1-[(1-acetylpiperidin-4-yl)carbonyl]piperidin-4-yl}phenyl)-1-(pyridazin-3-yl)azetidine-3-carboxamide;
N-(4-{1-[(3,5-difluorophenyl)acetyl]piperidin-4-yl}phenyl)-1-(pyridazin-3-yl)azetidine-3-carboxamide;
N-{4-[1-(N-acetyl-L-leucyl)piperidin-4-yl]phenyl}-1-(pyridazin-3-yl)azetidine-3-carboxamide;
N-{4-[1-(diphenylacetyl)piperidin-4-yl]phenyl}-1-(pyridazin-3-yl)azetidine-3-carboxamide;
N-{4-[1-(3-fluoro-2-methylbenzoyl)piperidin-4-yl]phenyl}-1-(pyridazin-3-yl)azetidine-3-carboxamide;
N-{4-[1-(5-fluoro-2-methylbenzoyl)piperidin-4-yl]phenyl}-1-(pyridazin-3-yl)azetidine-3-carboxamide;
N-{4-[1-(3-fluoro-4-methylbenzoyl)piperidin-4-yl]phenyl}-1-(pyridazin-3-yl)azetidine-3-carboxamide;
N-{4-[1-(2,3-difluorobenzoyl)piperidin-4-yl]phenyl}-1-(pyridazin-3-yl)azetidine-3-carboxamide;
N-{4-[1-(2,4-difluorobenzoyl)piperidin-4-yl]phenyl}-1-(pyridazin-3-yl)azetidine-3-carboxamide;
N-(4-{1-[4-(propan-2-yl)benzoyl]piperidin-4-yl}phenyl)-1-(pyridazin-3-yl)azetidine-3-carboxamide;
N-{4-[1-(4-tert-butylbenzoyl)piperidin-4-yl]phenyl}-1-(pyridazin-3-yl)azetidine-3-carboxamide;
N-(4-{1-[2-fluoro-5-(trifluoromethyl)benzoyl]piperidin-4-yl}phenyl)-1-(pyridazin-3-yl)azetidine-3-carboxamide;
N-(4-{1-[2-chloro-5-(trifluoromethyl)benzoyl]piperidin-4-yl}phenyl)-1-(pyridazin-3-yl)azetidine-3-carboxamide;
N-(4-{[(3R)-1-(4-fluorobenzoyl)pyrrolidin-3-yl]oxy}phenyl)-1-(pyridazin-4-yl)azetidine-3-carboxamide;
N-{4-[1-(cyclopentylacetyl)piperidin-4-yl]phenyl}-1-(pyridazin-3-yl)azetidine-3-carboxamide;
N-(4-{1-[(4-methylphenoxy)acetyl]piperidin-4-yl}phenyl)-1-(pyridazin-3-yl)azetidine-3-carboxamide;
N-(4-{1-[(2S)-2-phenylbutanoyl]piperidin-4-yl}phenyl)-1-(pyridazin-3-yl)azetidine-3-carboxamide;
N-{4-[1-(3,5-difluorobenzoyl)piperidin-4-yl]phenyl}-1-(pyridazin-3-yl)azetidine-3-carboxamide;
N-{4-[1-(4-chlorobenzoyl)piperidin-4-yl]phenyl}-1-(pyridazin-3-yl)azetidine-3-carboxamide;
N-{4-[1-(2,2-dimethylpropanoyl)piperidin-4-yl]phenyl}-1-(pyridazin-3-yl)azetidine-3-carboxamide;
1-(pyridazin-3-yl)-N-[4-(1-{[3-(trifluoromethyl)phenyl]acetyl}piperidin-4-yl)phenyl]azetidine-3-carboxamide;
N-(4-{1-[(3-chlorophenyl)acetyl]piperidin-4-yl}phenyl)-1-(pyridazin-3-yl)azetidine-3-carboxamide;
N-(4-{1-[(2,4-dichlorophenyl)acetyl]piperidin-4-yl}phenyl)-1-(pyridazin-3-yl)azetidine-3-carboxamide;
N-{4-[1-(naphthalen-1-ylcarbonyl)piperidin-4-yl]phenyl}-1-(pyridazin-3-yl)azetidine-3-carboxamide;
N-(4-{1-[(2R)-2-methoxy-2-phenylacetyl]piperidin-4-yl}phenyl)-1-(pyridazin-3-yl)azetidine-3-carboxamide;
N-(4-{1-[N-(furan-2-ylcarbonyl)glycyl]piperidin-4-yl}phenyl)-1-(pyridazin-3-yl)azetidine-3-carboxamide;
N-(4-{1-[(benzyloxy)acetyl]piperidin-4-yl}phenyl)-1-(pyridazin-3-yl)azetidine-3-carboxamide;
N-{4-[1-(naphthalen-1-ylacetyl)piperidin-4-yl]phenyl}-1-(pyridazin-3-yl)azetidine-3-carboxamide;
N-{4-[1-(cyclopropylcarbonyl)piperidin-4-yl]phenyl}-1-(pyridazin-3-yl)azetidine-3-carboxamide;
1-(pyridazin-3-yl)-N-{4-[1-(tetrahydrofuran-2-ylcarbonyl)piperidin-4-yl]phenyl}azetidine-3-carboxamide;
N-{4-[1-(N-benzoylglycyl)piperidin-4-yl]phenyl}-1-(pyridazin-3-yl)azetidine-3-carboxamide;
1-(pyridazin-3-yl)-N-{4-[1-(tetrahydrofuran-3-ylcarbonyl)piperidin-4-yl]phenyl}azetidine-3-carboxamide;
1-(pyridazin-3-yl)-N-(4-{1-[4-(thiophen-2-yl)butanoyl]piperidin-4-yl}phenyl)azetidine-3-carboxamide;
N-{4-[1-(2,5-difluorobenzoyl)piperidin-4-yl]phenyl}-1-(pyridazin-3-yl)azetidine-3-carboxamide;
N-{4-[1-(cyclobutylcarbonyl)piperidin-4-yl]phenyl}-1-(pyridazin-3-yl)azetidine-3-carboxamide;
N-[4-(1-{N[(4-methylphenyl)sulfonyl]glycyl}piperidin-4-yl)phenyl]-1-(pyridazin-3-yl)azetidine-3-carboxamide;
N-(4-{1-[(2,3-difluorophenyl)acetyl]piperidin-4-yl}phenyl)-1-(pyridazin-3-yl)azetidine-3-carboxamide;
N-(4-{1-[(2S)-2-methoxy-2-phenylacetyl]piperidin-4-yl}phenyl)-1-(pyridazin-3-yl)azetidine-3-carboxamide;
N-{4-[1-(naphthalen-2-ylacetyl)piperidin-4-yl]phenyl}-1-(pyridazin-3-yl)azetidine-3-carboxamide;
N-{4-[1-(3-phenylpropanoyl)piperidin-4-yl]phenyl}-1-(pyridazin-3-yl)azetidine-3-carboxamide;
N-(4-{1-[(2,6-dichlorophenyl)acetyl]piperidin-4-yl}phenyl)-1-(pyridazin-3-yl)azetidine-3-carboxamide;
N-(4-{1-[3-(phenylsulfonyl)propanoyl]piperidin-4-yl}phenyl)-1-(pyridazin-3-yl)azetidine-3-carboxamide;
1-(pyridazin-3-yl)-N-{4-[1-(thiophen-3-ylcarbonyl)piperidin-4-yl]phenyl}azetidine-3-carboxamide;
N-(4-{1-[(2,5-dimethylfuran-3-yl)carbonyl]piperidin-4-yl}phenyl)-1-(pyridazin-3-yl)azetidine-3-carboxamide;
N-{4-[1-(cyclopropylacetyl)piperidin-4-yl]phenyl}-1-(pyridazin-3-yl)azetidine-3-carboxamide;
N-{4-[1-(2-fluorobenzoyl)piperidin-4-yl]phenyl}-1-(pyridazin-3-yl)azetidine-3-carboxamide;
N-{4-[1-(2-methylbenzoyl)piperidin-4-yl]phenyl}-1-(pyridazin-3-yl)azetidine-3-carboxamide;
1-(pyridazin-3-yl)-N-{4-[1-(1,3-thiazol-4-ylcarbonyl)piperidin-4-yl]phenyl}azetidine-3-carboxamide;
1-(pyridazin-3-yl)-N-{4-[1-(1,3-thiazol-5-ylcarbonyl)piperidin-4-yl]phenyl}azetidine-3-carboxamide;
N-{4-[1-(ethoxyacetyl)piperidin-4-yl]phenyl}-1-(pyridazin-3-yl)azetidine-3-carboxamide;
1-(pyridazin-3-yl)-N-{4-[1-(4,4,4-trifluorobutanoyl)piperidin-4-yl]phenyl}azetidine-3-carboxamide;
N-(4-{1-[(6-methylpyridin-3-yl)carbonyl]piperidin-4-yl}phenyl)-1-(pyridazin-3-yl)azetidine-3-carboxamide;
N-[4-(1-benzoylpiperidin-4-yl)phenyl]-1-(pyridazin-3-yl)azetidine-3-carboxamide;
N-{4-[1-(furan-2-ylcarbonyl)piperidin-4-yl]phenyl}-1-(pyridazin-3-yl)azetidine-3-carboxamide;
N-(4-{1-[(1-methylcyclohexyl)carbonyl]piperidin-4-yl}phenyl)-1-(pyridazin-3-yl)azetidine-3-carboxamide;
N-{4-[1-(2-oxopropanoyl)piperidin-4-yl]phenyl}-1-(pyridazin-3-yl)azetidine-3-carboxamide;
N-{4-[1-(cyclopentylcarbonyl)piperidin-4-yl]phenyl}-1-(pyridazin-3-yl)azetidine-3-carboxamide;
N-[4-(1-propanoylpiperidin-4-yl)phenyl]-1-(pyridazin-3-yl)azetidine-3-carboxamide;
N-{4-[1-(4-methylbenzoyl)piperidin-4-yl]phenyl}-1-(pyridazin-3-yl)azetidine-3-carboxamide;
N-(4-{[(3R)-1-(2-chlorobenzoyl)pyrrolidin-3-yl]oxy}phenyl)-1-(pyridazin-4-yl)azetidine-3-carboxamide;
1-(pyridazin-4-yl)-N-(4-{[(3R)-1-(1,3-thiazol-2-ylcarbonyl)pyrrolidin-3-yl]oxy}phenyl)azetidine-3-carboxamide;

N-(4-{[(3R)-1-(cyclopropylacetyl)pyrrolidin-3-yl]oxy}phenyl)-1-(pyridazin-4-yl)azetidine-3-carboxamide;
N-[4-({(3R)-1-[(2S)-2-methylbutanoyl]pyrrolidin-3-yl}oxy)phenyl]-1-(pyridazin-4-yl)azetidine-3-carboxamide;
1-(pyridazin-4-yl)-N-(4-{[(3R)-1-(tetrahydro-2H-pyran-4-ylcarbonyl)pyrrolidin-3-yl]oxy}phenyl)azetidine-3-carboxamide;
1-(pyridazin-4-yl)-N-(4-{[(3R)-1-{[4-(trifluoromethoxy)phenyl]acetyl}pyrrolidin-3-yl]oxy}phenyl)azetidine-3-carboxamide;
1-(pyridazin-4-yl)-N-(4-{[(3R)-1-(thiophen-3-ylcarbonyl)pyrrolidin-3-yl]oxy}phenyl)azetidine-3-carboxamide;
N-[4-({(3R)-1-[(4-fluorophenyl)acetyl]pyrrolidin-3-yl}oxy)phenyl]-1-(pyridazin-4-yl)azetidine-3-carboxamide;
N-[4-({(3R)-1-[(3,5-difluorophenyl)acetyl]pyrrolidin-3-yl}oxy)phenyl]-1-(pyridazin-4-yl)azetidine-3-carboxamide;
N-(4-{[(3R)-1-(3,4-difluorobenzoyl)pyrrolidin-3-yl]oxy}phenyl)-1-(pyridazin-4-yl)azetidine-3-carboxamide;
N-[4-({(3R)-1-[(3-fluorophenyl)acetyl]pyrrolidin-3-yl}oxy)phenyl]-1-(pyridazin-4-yl)azetidine-3-carboxamide;
1-(pyridazin-4-yl)-N-[4-({(3R)-1-[3-(trifluoromethyl)benzoyl]pyrrolidin-3-yl}oxy)phenyl]azetidine-3-carboxamide;
N-[4-({(3R)-1-[(2,4-difluorophenyl)acetyl]pyrrolidin-3-yl}oxy)phenyl]-1-(pyridazin-4-yl)azetidine-3-carboxamide;
1-(pyridazin-4-yl)-N-(4-{[(3R)-1-{[4-(trifluoromethyl)phenyl]acetyl}pyrrolidin-3-yl]oxy}phenyl)azetidine-3-carboxamide;
1-(pyridazin-4-yl)-N-(4-{[(3R)-1-(1,3-thiazol-4-ylcarbonyl)pyrrolidin-3-yl]oxy}phenyl)azetidine-3-carboxamide;
1-(pyridazin-4-yl)-N-(4-{[(3R)-1-(tetrahydrofuran-2-ylcarbonyl)pyrrolidin-3-yl]oxy}phenyl)azetidine-3-carboxamide;
N-[4-({(3R)-1-[(5-methylthiophen-2-yl)carbonyl]pyrrolidin-3-yl}oxy)phenyl]-1-(pyridazin-4-yl)azetidine-3-carboxamide;
N-[4-({(3R)-1-[(2-fluorophenyl)acetyl]pyrrolidin-3-yl}oxy)phenyl]-1-(pyridazin-4-yl)azetidine-3-carboxamide;
N-(4-{[(3R)-1-(cyclopropylcarbonyl)pyrrolidin-3-yl]oxy}phenyl)-1-(pyridazin-4-yl)azetidine-3-carboxamide;
1-(pyridazin-4-yl)-N-(4-{[(3R)-1-(tetrahydrofuran-3-ylcarbonyl)pyrrolidin-3-yl]oxy}phenyl)azetidine-3-carboxamide;
1-(pyridazin-4-yl)-N-[4-({(3R)-1-[3-(trifluoromethoxy)benzoyl]pyrrolidin-3-yl}oxy)phenyl]azetidine-3-carboxamide;
1-(pyridazin-4-yl)-N-(4-{[(3R)-1-(pyridin-2-ylcarbonyl)pyrrolidin-3-yl]oxy}phenyl)azetidine-3-carboxamide;
N-(4-{[(3R)-1-(3-chlorobenzoyl)pyrrolidin-3-yl]oxy}phenyl)-1-(pyridazin-4-yl)azetidine-3-carboxamide;
N-(4-{[(3R)-1-(4-chlorobenzoyl)pyrrolidin-3-yl]oxy}phenyl)-1-(pyridazin-4-yl)azetidine-3-carboxamide;
N-(4-{[(3R)-1-(2-methyl-2-phenylpropanoyl)pyrrolidin-3-yl]oxy}phenyl)-1-(pyridazin-4-yl)azetidine-3-carboxamide;
N-(4-{[(3R)-1-(2,4-difluorobenzoyl)pyrrolidin-3-yl]oxy}phenyl)-1-(pyridazin-4-yl)azetidine-3-carboxamide;
N-(4-{[(3R)-1-(methoxyacetyl)pyrrolidin-3-yl]oxy}phenyl)-1-(pyridazin-4-yl)azetidine-3-carboxamide;
1-(pyridazin-4-yl)-N-(4-{[(3R)-1-(thiophen-2-ylcarbonyl)pyrrolidin-3-yl]oxy}phenyl)azetidine-3-carboxamide;
1-(pyridazin-4-yl)-N-(4-{[(3R)-1-{[3-(trifluoromethyl)phenyl]acetyl}pyrrolidin-3-yl]oxy}phenyl)azetidine-3-carboxamide;
N-(4-{[(3R)-1-(2-methylpropanoyl)pyrrolidin-3-yl]oxy}phenyl)-1-(pyridazin-4-yl)azetidine-3-carboxamide;
N-(4-{[(3R)-1-(2-fluorobenzoyl)pyrrolidin-3-yl]oxy}phenyl)-1-(pyridazin-4-yl)azetidine-3-carboxamide;
N-(4-{[(3R)-1-(2,2-dimethylbutanoyl)pyrrolidin-3-yl]oxy}phenyl)-1-(pyridazin-4-yl)azetidine-3-carboxamide;
N-(4-{[(3R)-1-(3,5-difluorobenzoyl)pyrrolidin-3-yl]oxy}phenyl)-1-(pyridazin-4-yl)azetidine-3-carboxamide;
1-(pyridazin-4-yl)-N-[4-({(3R)-1-[4-(trifluoromethyl)benzoyl]pyrrolidin-3-yl}oxy)phenyl]azetidine-3-carboxamide;
N-(4-{[(3R)-1-(3-fluorobenzoyl)pyrrolidin-3-yl]oxy}phenyl)-1-(pyridazin-4-yl)azetidine-3-carboxamide;
1-(pyridazin-4-yl)-N-[4-({(3R)-1-[4-(trifluoromethoxy)benzoyl]pyrrolidin-3-yl}oxy)phenyl]azetidine-3-carboxamide;
N-(4-{[(3R)-1-(3-methylbutanoyl)pyrrolidin-3-yl]oxy}phenyl)-1-(pyridazin-4-yl)azetidine-3-carboxamide;
1-(pyridazin-4-yl)-N-(4-{[(3R)-1-(3,3,3-trifluoropropanoyl)pyrrolidin-3-yl]oxy}phenyl)azetidine-3-carboxamide;
N-[4-({(3R)-1-[difluoro(phenyl)acetyl]pyrrolidin-3-yl}oxy)phenyl]-1-(pyridazin-4-yl)azetidine-3-carboxamide;
N-(4-{[(3R)-1-(2,2-dimethylpropanoyl)pyrrolidin-3-yl]oxy}phenyl)-1-(pyridazin-4-yl)azetidine-3-carboxamide;
N-[4-({(3R)-1-[(4,4-difluorocyclohexyl)carbonyl]pyrrolidin-3-yl}oxy)phenyl]-1-(pyridazin-4-yl)azetidine-3-carboxamide;
N-(4-{[(3R)-1-(2-chlorobenzoyl)pyrrolidin-3-yl]oxy}phenyl)-1-(pyridazin-4-yl)azetidine-3-carboxamide;
1-(pyridazin-3-yl)-N-(4-{[(3R)-1-(1,3-thiazol-2-ylcarbonyl)pyrrolidin-3-yl]oxy}phenyl)azetidine-3-carboxamide;
N-(4-{[(3R)-1-(cyclopropylacetyl)pyrrolidin-3-yl]oxy}phenyl)-1-(pyridazin-3-yl)azetidine-3-carboxamide;
N-[4-({(3R)-1-[(2S)-2-methylbutanoyl]pyrrolidin-3-yl}oxy)phenyl]-1-(pyridazin-3-yl)azetidine-3-carboxamide;
1-(pyridazin-3-yl)-N-(4-{[(3R)-1-(tetrahydro-2H-pyran-4-ylcarbonyl)pyrrolidin-3-yl]oxy}phenyl)azetidine-3-carboxamide;
1-(pyridazin-3-yl)-N-(4-{[(3R)-1-{[4-(trifluoromethoxy)phenyl]acetyl}pyrrolidin-3-yl]oxy}phenyl)azetidine-3-carboxamide;
N-(4-{[(3R)-1-(4-fluorobenzoyl)pyrrolidin-3-yl]oxy}phenyl)-1-(pyridazin-3-yl)azetidine-3-carboxamide;
1-(pyridazin-3-yl)-N-(4-{[(3R)-1-(thiophen-3-ylcarbonyl)pyrrolidin-3-yl]oxy}phenyl)azetidine-3-carboxamide;
N-[4-({(3R)-1-[(4-fluorophenyl)acetyl]pyrrolidin-3-yl}oxy)phenyl]-1-(pyridazin-3-yl)azetidine-3-carboxamide;
N-[4-({(3R)-1-[(3,5-difluorophenyl)acetyl]pyrrolidin-3-yl}oxy)phenyl]-1-(pyridazin-3-yl)azetidine-3-carboxamide;
N-(4-{[(3R)-1-(3,4-difluorobenzoyl)pyrrolidin-3-yl]oxy}phenyl)-1-(pyridazin-3-yl)azetidine-3-carboxamide;
N-[4-({(3R)-1-[(3-fluorophenyl)acetyl]pyrrolidin-3-yl}oxy)phenyl]-1-(pyridazin-3-yl)azetidine-3-carboxamide;
1-(pyridazin-3-yl)-N-[4-({(3R)-1-[3-(trifluoromethyl)benzoyl]pyrrolidin-3-yl}oxy)phenyl]azetidine-3-carboxamide;
N-[4-({(3R)-1-[(2,4-difluorophenyl)acetyl]pyrrolidin-3-yl}oxy)phenyl]-1-(pyridazin-3-yl)azetidine-3-carboxamide;
1-(pyridazin-3-yl)-N-(4-{[(3R)-1-{[4-(trifluoromethyl)phenyl]acetyl}pyrrolidin-3-yl]oxy}phenyl)azetidine-3-carboxamide;
1-(pyridazin-3-yl)-N-(4-{[(3R)-1-(1,3-thiazol-4-ylcarbonyl)pyrrolidin-3-yl]oxy}phenyl)azetidine-3-carboxamide;

1-(pyridazin-3-yl)-N-(4-{[(3R)-1-(tetrahydrofuran-2-ylcarbonyl)pyrrolidin-3-yl]oxy}phenyl)azetidine-3-carboxamide;
N-[4-({(3R)-1-[(5-methylthiophen-2-yl)carbonyl]pyrrolidin-3-yl}oxy)phenyl]-1-(pyridazin-3-yl)azetidine-3-carboxamide;
N-[4-({(3R)-1-[(2-fluorophenyl)acetyl]pyrrolidin-3-yl}oxy)phenyl]-1-(pyridazin-3-yl)azetidine-3-carboxamide;
N-(4-{[(3R)-1-(cyclopropylcarbonyl)pyrrolidin-3-yl]oxy}phenyl)-1-(pyridazin-3-yl)azetidine-3-carboxamide;
1-(pyridazin-3-yl)-N-(4-{[(3R)-1-(tetrahydrofuran-3-ylcarbonyl)pyrrolidin-3-yl]oxy}phenyl)azetidine-3-carboxamide;
1-(pyridazin-3-yl)-N-[4-({(3R)-1-[3-(trifluoromethoxy)benzoyl]pyrrolidin-3-yl}oxy)phenyl]azetidine-3-carboxamide;
1-(pyridazin-3-yl)-N-(4-{[(3R)-1-(pyridin-2-ylcarbonyl)pyrrolidin-3-yl]oxy}phenyl)azetidine-3-carboxamide;
N-(4-{[(3R)-1-(3-chlorobenzoyl)pyrrolidin-3-yl]oxy}phenyl)-1-(pyridazin-3-yl)azetidine-3-carboxamide;
N-(4-{[(3R)-1-(4-chlorobenzoyl)pyrrolidin-3-yl]oxy}phenyl)-1-(pyridazin-3-yl)azetidine-3-carboxamide;
N-(4-{[(3R)-1-(2-methyl-2-phenylpropanoyl)pyrrolidin-3-yl]oxy}phenyl)-1-(pyridazin-3-yl)azetidine-3-carboxamide;
N-(4-{[(3R)-1-(2,4-difluorobenzoyl)pyrrolidin-3-yl]oxy}phenyl)-1-(pyridazin-3-yl)azetidine-3-carboxamide;
N-(4-{[(3R)-1-(methoxyacetyl)pyrrolidin-3-yl]oxy}phenyl)-1-(pyridazin-3-yl)azetidine-3-carboxamide;
1-(pyridazin-3-yl)-N-(4-{[(3R)-1-(thiophen-2-ylcarbonyl)pyrrolidin-3-yl]oxy}phenyl)azetidine-3-carboxamide;
1-(pyridazin-3-yl)-N-(4-{[(3R)-1-{[3-(trifluoromethyl)phenyl]acetyl}pyrrolidin-3-yl]oxy}phenyl)azetidine-3-carboxamide;
N-(4-{[(3R)-1-(2-methylpropanoyl)pyrrolidin-3-yl]oxy}phenyl)-1-(pyridazin-3-yl)azetidine-3-carboxamide;
N-(4-{[(3R)-1-(2-fluorobenzoyl)pyrrolidin-3-yl]oxy}phenyl)-1-(pyridazin-3-yl)azetidine-3-carboxamide;
N-(4-{[(3R)-1-(2,2-dimethylbutanoyl)pyrrolidin-3-yl]oxy}phenyl)-1-(pyridazin-3-yl)azetidine-3-carboxamide;
N-(4-{[(3R)-1-(3,5-difluorobenzoyl)pyrrolidin-3-yl]oxy}phenyl)-1-(pyridazin-3-yl)azetidine-3-carboxamide;
1-(pyridazin-3-yl)-N-[4-({(3R)-1-[4-(trifluoromethyl)benzoyl]pyrrolidin-3-yl}oxy)phenyl]azetidine-3-carboxamide;
N-(4-{[(3R)-1-(3-fluorobenzoyl)pyrrolidin-3-yl]oxy}phenyl)-1-(pyridazin-3-yl)azetidine-3-carboxamide;
1-(pyridazin-3-yl)-N-[4-({(3R)-1-[4-(trifluoromethoxy)benzoyl]pyrrolidin-3-yl}oxy)phenyl]azetidine-3-carboxamide;
N-(4-{[(3R)-1-(3-methylbutanoyl)pyrrolidin-3-yl]oxy}phenyl)-1-(pyridazin-3-yl)azetidine-3-carboxamide;
1-(pyridazin-3-yl)-N-(4-{[(3R)-1-(3,3,3-trifluoropropanoyl)pyrrolidin-3-yl]oxy}phenyl)azetidine-3-carboxamide;
N-[4-({(3R)-1-[difluoro(phenyl)acetyl]pyrrolidin-3-yl}oxy)phenyl]-1-(pyridazin-3-yl)azetidine-3-carboxamide;
N-(4-{[(3R)-1-(2,2-dimethylpropanoyl)pyrrolidin-3-yl]oxy}phenyl)-1-(pyridazin-3-yl)azetidine-3-carboxamide;
N-[4-({(3R)-1-[(4,4-difluorocyclohexyl)carbonyl]pyrrolidin-3-yl}oxy)phenyl]-1-(pyridazin-3-yl)azetidine-3-carboxamide;
N-{4-[1-(2-chlorobenzoyl)piperidin-4-yl]phenyl}-1-(pyridazin-4-yl)azetidine-3-carboxamide;
1-(pyridazin-4-yl)-N-{4-[1-(1,3-thiazol-2-ylcarbonyl)piperidin-4-yl]phenyl}azetidine-3-carboxamide;
N-{4-[1-(cyclopropylacetyl)piperidin-4-yl]phenyl}-1-(pyridazin-4-yl)azetidine-3-carboxamide;
N-{4-[1-(2-methylpropanoyl)piperidin-4-yl]phenyl}-1-(pyridazin-4-yl)azetidine-3-carboxamide;
N-{4-[1-(4-fluorobenzoyl)piperidin-4-yl]phenyl}-1-(pyridazin-4-yl)azetidine-3-carboxamide;
1-(pyridazin-4-yl)-N-{4-[1-(thiophen-3-ylcarbonyl)piperidin-4-yl]phenyl}azetidine-3-carboxamide;
N-(4-{1-[(4-fluorophenyl)acetyl]piperidin-4-yl}phenyl)-1-(pyridazin-4-yl)azetidine-3-carboxamide;
N-(4-{1-[(3,5-difluorophenyl)acetyl]piperidin-4-yl}phenyl)-1-(pyridazin-4-yl)azetidine-3-carboxamide;
N-{4-[1-(3,4-difluorobenzoyl)piperidin-4-yl]phenyl}-1-(pyridazin-4-yl)azetidine-3-carboxamide;
N-(4-{1-[(3-fluorophenyl)acetyl]piperidin-4-yl}phenyl)-1-(pyridazin-4-yl)azetidine-3-carboxamide;
1-(pyridazin-4-yl)-N-(4-{1-[3-(trifluoromethyl)benzoyl]piperidin-4-yl}phenyl)azetidine-3-carboxamide;
N-(4-{1-[(2,4-difluorophenyl)acetyl]piperidin-4-yl}phenyl)-1-(pyridazin-4-yl)azetidine-3-carboxamide;
1-(pyridazin-4-yl)-N-{4-[1-(1,3-thiazol-4-ylcarbonyl)piperidin-4-yl]phenyl}azetidine-3-carboxamide;
1-(pyridazin-4-yl)-N-{4-[1-(tetrahydrofuran-2-ylcarbonyl)piperidin-4-yl]phenyl}azetidine-3-carboxamide;
N-(4-{1-[(5-methylthiophen-2-yl)carbonyl]piperidin-4-yl}phenyl)-1-(pyridazin-4-yl)azetidine-3-carboxamide;
N-(4-{1-[(2-fluorophenyl)acetyl]piperidin-4-yl}phenyl)-1-(pyridazin-4-yl)azetidine-3-carboxamide;
N-{4-[1-(cyclopropylcarbonyl)piperidin-4-yl]phenyl}-1-(pyridazin-4-yl)azetidine-3-carboxamide;
1-(pyridazin-4-yl)-N-{4-[1-(tetrahydrofuran-3-ylcarbonyl)piperidin-4-yl]phenyl}azetidine-3-carboxamide;
1-(pyridazin-4-yl)-N-{4-[1-(pyridin-2-ylcarbonyl)piperidin-4-yl]phenyl}azetidine-3-carboxamide;
N-{4-[1-(3-chlorobenzoyl)piperidin-4-yl]phenyl}-1-(pyridazin-4-yl)azetidine-3-carboxamide;
N-{4-[1-(4-chlorobenzoyl)piperidin-4-yl]phenyl}-1-(pyridazin-4-yl)azetidine-3-carboxamide;
N-{4-[1-(2-methyl-2-phenylpropanoyl)piperidin-4-yl]phenyl}-1-(pyridazin-4-yl)azetidine-3-carboxamide;
N-{4-[1-(2,4-difluorobenzoyl)piperidin-4-yl]phenyl}-1-(pyridazin-4-yl)azetidine-3-carboxamide;
N-{4-[1-(methoxyacetyl)piperidin-4-yl]phenyl}-1-(pyridazin-4-yl)azetidine-3-carboxamide;
1-(pyridazin-4-yl)-N-{4-[1-(thiophen-2-ylcarbonyl)piperidin-4-yl]phenyl}azetidine-3-carboxamide;
1-(pyridazin-4-yl)-N-[4-(1-{[3-(trifluoromethyl)phenyl]acetyl}piperidin-4-yl)phenyl]azetidine-3-carboxamide;
N-{4-[1-(2-fluorobenzoyl)piperidin-4-yl]phenyl}-1-(pyridazin-4-yl)azetidine-3-carboxamide;
N-{4-[1-(3,5-difluorobenzoyl)piperidin-4-yl]phenyl}-1-(pyridazin-4-yl)azetidine-3-carboxamide;
1-(pyridazin-4-yl)-N-(4-{1-[4-(trifluoromethyl)benzoyl]piperidin-4-yl}phenyl)azetidine-3-carboxamide;
N-{4-[1-(3-fluorobenzoyl)piperidin-4-yl]phenyl}-1-(pyridazin-4-yl)azetidine-3-carboxamide;
1-(pyridazin-4-yl)-N-(4-{1-[4-(trifluoromethoxy)benzoyl]piperidin-4-yl}phenyl)azetidine-3-carboxamide;
N-{4-[1-(3-methylbutanoyl)piperidin-4-yl]phenyl}-1-(pyridazin-4-yl)azetidine-3-carboxamide;
1-(pyridazin-4-yl)-N-{4-[1-(3,3,3-trifluoropropanoyl)piperidin-4-yl]phenyl}azetidine-3-carboxamide;
N-(4-{1-[difluoro(phenyl)acetyl]piperidin-4-yl}phenyl)-1-(pyridazin-4-yl)azetidine-3-carboxamide;
N-{4-[1-(2,2-dimethylpropanoyl)piperidin-4-yl]phenyl}-1-(pyridazin-4-yl)azetidine-3-carboxamide;
N-(4-{1-[(4,4-difluorocyclohexyl)carbonyl]piperidin-4-yl}phenyl)-1-(pyridazin-4-yl)azetidine-3-carboxamide;

1-(pyridazin-4-yl)-N-[4-(1-{[4-(trifluoromethoxy)phenyl]acetyl}piperidin-4-yl)phenyl]azetidine-3-carboxamide;
1-(pyridazin-4-yl)-N-(4-{1-[3-(trifluoromethoxy)benzoyl]piperidin-4-yl}phenyl)azetidine-3-carboxamide;
1-(pyridazin-4-yl)-N-[4-(1-{[4-(trifluoromethyl)phenyl]acetyl}piperidin-4-yl)phenyl]azetidine-3-carboxamide;
N-(4-{[1-(3-chlorobenzoyl)piperidin-4-yl]sulfonyl}phenyl)-1-(pyridazin-3-yl)azetidine-3-carboxamide;
N-(4-{[1-(4-tert-butylbenzoyl)piperidin-4-yl]sulfonyl}phenyl)-1-(pyridazin-3-yl)azetidine-3-carboxamide;
N-(4-{[1-(4-methoxybenzoyl)piperidin-4-yl]sulfonyl}phenyl)-1-(pyridazin-3-yl)azetidine-3-carboxamide;
N-(4-{[1-(4-methylbenzoyl)piperidin-4-yl]sulfonyl}phenyl)-1-(pyridazin-3-yl)azetidine-3-carboxamide;
N-(4-{[1-(cyclohexylcarbonyl)piperidin-4-yl]sulfonyl}phenyl)-1-(pyridazin-3-yl)azetidine-3-carboxamide;
N-(4-{[1-(cyclopropylacetyl)piperidin-4-yl]sulfonyl}phenyl)-1-(pyridazin-3-yl)azetidine-3-carboxamide;
N-(4-{[1-(2-methoxybenzoyl)piperidin-4-yl]sulfonyl}phenyl)-1-(pyridazin-3-yl)azetidine-3-carboxamide;
N-[4-({1-[(2S)-2-phenylbutanoyl]piperidin-4-yl}sulfonyl)phenyl]-1-(pyridazin-3-yl)azetidine-3-carboxamide;
N-(4-({1-[4-(propan-2-yl)benzoyl]piperidin-4-yl}sulfonyl)phenyl]-1-(pyridazin-3-yl)azetidine-3-carboxamide;
N-(4-{[1-(4-chlorobenzoyl)piperidin-4-yl]sulfonyl}phenyl)-1-(pyridazin-3-yl)azetidine-3-carboxamide;
N-{4-[(1-benzoylpiperidin-4-yl)sulfonyl]phenyl}-1-(pyridazin-3-yl)azetidine-3-carboxamide;
1-(pyridazin-3-yl)-N-(4-{[1-(4,4,4-trifluorobutanoyl)piperidin-4-yl]sulfonyl}phenyl)azetidine-3-carboxamide;
N-(4-{[1-(2,5-difluorobenzoyl)piperidin-4-yl]sulfonyl}phenyl)-1-(pyridazin-3-yl)azetidine-3-carboxamide;
N-(4-{[1-(2-fluorobenzoyl)piperidin-4-yl]sulfonyl}phenyl)-1-(pyridazin-3-yl)azetidine-3-carboxamide;
N-(4-{[1-(2-methylbenzoyl)piperidin-4-yl]sulfonyl}phenyl)-1-(pyridazin-3-yl)azetidine-3-carboxamide;
N-[4-({1-[(4-fluorophenyl)acetyl]piperidin-4-yl}sulfonyl)phenyl]-1-(pyridazin-3-yl)azetidine-3-carboxamide;
N-(4-{[1-(3-methylbenzoyl)piperidin-4-yl]sulfonyl}phenyl)-1-(pyridazin-3-yl)azetidine-3-carboxamide;
N-(4-{[1-(2,3-dimethylbenzoyl)piperidin-4-yl]sulfonyl}phenyl)-1-(pyridazin-3-yl)azetidine-3-carboxamide;
N-[4-({1-[(3-fluorophenyl)acetyl]piperidin-4-yl}sulfonyl)phenyl]-1-(pyridazin-3-yl)azetidine-3-carboxamide;
N-(4-{[1-(3-fluorobenzoyl)piperidin-4-yl]sulfonyl}phenyl)-1-(pyridazin-3-yl)azetidine-3-carboxamide;
1-(pyridazin-3-yl)-N-[4-({1-[3-(trifluoromethyl)benzoyl]piperidin-4-yl}sulfonyl)phenyl]azetidine-3-carboxamide;
N-[4-({1-[(3,5-difluorophenyl)acetyl]piperidin-4-yl}sulfonyl)phenyl]-1-(pyridazin-3-yl)azetidine-3-carboxamide;
N-(4-{[1-(2,4-difluorobenzoyl)piperidin-4-yl]sulfonyl}phenyl)-1-(pyridazin-3-yl)azetidine-3-carboxamide;
1-(pyridazin-3-yl)-N-[4-({1-[4-(trifluoromethyl)benzoyl]piperidin-4-yl}sulfonyl)phenyl]azetidine-3-carboxamide;
N-(4-{[1-(4-fluorobenzoyl)piperidin-4-yl]sulfonyl}phenyl)-1-(pyridazin-3-yl)azetidine-3-carboxamide;
N-(4-{[1-(2,3-difluorobenzoyl)piperidin-4-yl]sulfonyl}phenyl)-1-(pyridazin-3-yl)azetidine-3-carboxamide;
N-(4-{[1-(2,4-dichlorobenzoyl)piperidin-4-yl]sulfonyl}phenyl)-1-(pyridazin-3-yl)azetidine-3-carboxamide;
N-(4-{[1-(naphthalen-1-ylcarbonyl)piperidin-4-yl]sulfonyl}phenyl)-1-(pyridazin-3-yl)azetidine-3-carboxamide;
N-(4-{[1-(cyclopropylcarbonyl)piperidin-4-yl]sulfonyl}phenyl)-1-(pyridazin-3-yl)azetidine-3-carboxamide;
N-(4-{[1-(3,5-difluorobenzoyl)piperidin-4-yl]sulfonyl}phenyl)-1-(pyridazin-3-yl)azetidine-3-carboxamide;
N-(4-{[1-(2,2-dimethylpropanoyl)piperidin-4-yl]sulfonyl}phenyl)-1-(pyridazin-3-yl)azetidine-3-carboxamide;
N-(4-{[1-(3,3-dimethylbutanoyl)piperidin-4-yl]sulfonyl}phenyl)-1-(pyridazin-3-yl)azetidine-3-carboxamide;
N-(4-{[1-(3-methoxybenzoyl)piperidin-4-yl]sulfonyl}phenyl)-1-(pyridazin-3-yl)azetidine-3-carboxamide;
N-(4-{[1-(3-methylbutanoyl)piperidin-4-yl]sulfonyl}phenyl)-1-(pyridazin-3-yl)azetidine-3-carboxamide;
N-(4-{[1-(2-methylpropanoyl)piperidin-4-yl]sulfonyl}phenyl)-1-(pyridazin-3-yl)azetidine-3-carboxamide;
N-(4-{[1-(cyclopentylcarbonyl)piperidin-4-yl]sulfonyl}phenyl)-1-(pyridazin-3-yl)azetidine-3-carboxamide;
N-(4-{[1-(phenylacetyl)piperidin-4-yl]sulfonyl}phenyl)-1-(pyridazin-3-yl)azetidine-3-carboxamide;
N-[4-({1-[(1-phenylcyclopropyl)carbonyl]piperidin-4-yl}sulfonyl)phenyl]-1-(pyridazin-3-yl)azetidine-3-carboxamide;
N-{4-[1-(2-methylalanyl)piperidin-4-yl]phenyl}-1-(pyridin-3-yl)azetidine-3-carboxamide;
5-[1-(2-methylpropyl)-1H-pyrazol-4-yl]-N-[(3R)-1-(pyridin-4-yl)pyrrolidin-3-yl]thiophene-2-carboxamide;
5-[1-(2-methylpropyl)-1H-pyrazol-4-yl]-N-[(3R)-1-(pyridazin-4-yl)pyrrolidin-3-yl]thiophene-2-carboxamide;
5-[1-(2-methylpropyl)-1H-pyrazol-4-yl]-N-[(3R)-1-(pyridazin-3-yl)pyrrolidin-3-yl]thiophene-2-carboxamide;
5-[1-(2-methylpropyl)-1H-pyrazol-4-yl]-N-[(3S)-1-(pyridazin-3-yl)pyrrolidin-3-yl]thiophene-2-carboxamide;
5-[1-(2-methylpropyl)-1H-pyrazol-4-yl]-N-[(3S)-1-(pyridazin-4-yl)pyrrolidin-3-yl]thiophene-2-carboxamide;
5-[1-(2-methylpropyl)-1H-pyrazol-4-yl]-N-[(3S)-1-(pyridin-3-yl)pyrrolidin-3-yl]thiophene-2-carboxamide;
tert-butyl 4-(2-methyl-1-oxo-1-{4-[4-({[1-(pyridin-3-yl)azetidin-3-yl]carbonyl}amino)phenyl]piperidin-1-yl}propan-2-yl)piperazine-1-carboxylate;
N-(4-{1-[2-methyl-2-(piperazin-1-yl)propanoyl]piperidin-4-yl}phenyl)-1-(pyridin-3-yl)azetidine-3-carboxamide;
N-(4-{[1-(2-chlorobenzoyl)piperidin-4-yl]sulfonyl}phenyl)-1-(pyridazin-3-yl)azetidine-3-carboxamide;
N-(4-{[1-(4-methylpentanoyl)piperidin-4-yl]sulfonyl}phenyl)-1-(pyridazin-3-yl)azetidine-3-carboxamide;

N-[4-({1-[(2-fluorophenyl)acetyl]piperidin-4-yl}sulfonyl)phenyl]-1-(pyridazin-3-yl)azetidine-3-carboxamide;
N-(4-{[1-(2-methylpropanoyl)piperidin-4-yl]sulfonyl}phenyl)-1-(pyridazin-4-yl)azetidine-3-carboxamide;
N-{4-[(1-benzoylpiperidin-4-yl)sulfonyl]phenyl}-1-(pyridazin-4-yl)azetidine-3-carboxamide;
N-(4-{[1-(4-fluorobenzoyl)piperidin-4-yl]sulfonyl}phenyl)-1-(pyridazin-4-yl)azetidine-3-carboxamide;
N-(4-{[1-(cyclopentylcarbonyl)piperidin-4-yl]sulfonyl}phenyl)-1-(pyridazin-4-yl)azetidine-3-carboxamide;
N-[(3R)-1-(5,6-dichloropyridazin-4-yl)pyrrolidin-3-yl]-5-[1-(2-methylpropyl)-1H-pyrazol-4-yl]thiophene-2-carboxamide;
N-[(3R)-1-(6-chloropyridazin-3-yl)pyrrolidin-3-yl]-5-[1-(2-methylpropyl)-1H-pyrazol-4-yl]thiophene-2-carboxamide;
N-[(3S)-1-(5,6-dichloropyridazin-4-yl)pyrrolidin-3-yl]-5-[1-(2-methylpropyl)-1H-pyrazol-4-yl]thiophene-2-carboxamide;
N-[(3S)-1-(6-chloropyridazin-3-yl)pyrrolidin-3-yl]-5-[1-(2-methylpropyl)-1H-pyrazol-4-yl]thiophene-2-carboxamide;
N-[(3R)-1-(5,6-dichloropyridazin-4-yl)pyrrolidin-3-yl]-5-[1-(2-methylpropyl)-1H-pyrazol-4-yl]thiophene-3-carboxamide;
5-[1-(2-methylpropyl)-1H-pyrazol-4-yl]-N-[(3R)-1-(pyridazin-4-yl)pyrrolidin-3-yl]thiophene-3-carboxamide;
5-[1-(2-methylpropyl)-1H-pyrazol-4-yl]-N-[(3R)-1-(pyridazin-4-yl)pyrrolidin-3-yl]thiophene-3-carboxamide;
N-{4-[1-(2,2-dimethylpropanoyl)piperidin-4-yl]phenyl}-1-(pyridazin-3-yl)piperidine-4-carboxamide;
N-[4-(1-benzoylpiperidin-4-yl)phenyl]-1-(pyridazin-3-yl)piperidine-4-carboxamide;
N-{4-[1-(2-fluorobenzoyl)piperidin-4-yl]phenyl}-1-(pyridazin-3-yl)piperidine-4-carboxamide;
1-(pyridazin-3-yl)-N-{4-[1-(4,4,4-trifluorobutanoyl)piperidin-4-yl]phenyl}piperidine-4-carboxamide;
N-[(3S)-1-(6-chloropyridazin-3-yl)pyrrolidin-3-yl]-5-[1-(2-methylpropyl)-1H-pyrazol-4-yl]thiophene-3-carboxamide;
(3S)-1-(pyridazin-3-yl)-N-{4-[1-(1,3-thiazol-5-ylcarbonyl)piperidin-4-yl]phenyl}pyrrolidine-3-carboxamide;
(3S)—N-{4-[1-(4-methylbenzoyl)piperidin-4-yl]phenyl}-1-(pyridazin-3-yl)pyrrolidine-3-carboxamide;
(3S)—N-(4-{1-[(2S)-2-phenylbutanoyl]piperidin-4-yl}phenyl)-1-(pyridazin-3-yl)pyrrolidine-3-carboxamide;
(3S)—N-(4-{1-[(2S)-2-methoxy-2-phenylacetyl]piperidin-4-yl}phenyl)-1-(pyridazin-3-yl)pyrrolidine-3-carboxamide;
(3S)—N-(4-{1-[(2R)-2-methoxy-2-phenylacetyl]piperidin-4-yl}phenyl)-1-(pyridazin-3-yl)pyrrolidine-3-carboxamide;
(3S)—N-{4-[1-(ethoxyacetyl)piperidin-4-yl]phenyl}-1-(pyridazin-3-yl)pyrrolidine-3-carboxamide;
(3S)—N-(4-{1-[(4-methylphenoxy)acetyl]piperidin-4-yl}phenyl)-1-(pyridazin-3-yl)pyrrolidine-3-carboxamide;
(3S)—N-{4-[1-(2-fluorobenzoyl)piperidin-4-yl]phenyl}-1-(pyridazin-3-yl)pyrrolidine-3-carboxamide;
(3S)-1-(pyridazin-3-yl)-N-{4-[1-(tetrahydrofuran-3-ylcarbonyl)piperidin-4-yl]phenyl}pyrrolidine-3-carboxamide;
(3S)—N-{4-[1-(naphthalen-1-ylcarbonyl)piperidin-4-yl]phenyl}-1-(pyridazin-3-yl)pyrrolidine-3-carboxamide;
(3S)—N-(4-{1-[(2,6-dichlorophenyl)acetyl]piperidin-4-yl}phenyl)-1-(pyridazin-3-yl)pyrrolidine-3-carboxamide;
(3S)—N-{4-[1-(naphthalen-1-ylacetyl)piperidin-4-yl]phenyl}-1-(pyridazin-3-yl)pyrrolidine-3-carboxamide;
(3S)-1-(pyridazin-3-yl)-N-(4-{1-[4-(thiophen-2-yl)butanoyl]piperidin-4-yl}phenyl)pyrrolidine-3-carboxamide;
(3S)—N-{4-[1-(cyclopropylacetyl)piperidin-4-yl]phenyl}-1-(pyridazin-3-yl)pyrrolidine-3-carboxamide;
(3S)—N-{4-[1-(cyclopentylacetyl)piperidin-4-yl]phenyl}-1-(pyridazin-3-yl)pyrrolidine-3-carboxamide;
(3S)—N-{4-[1-(2,5-difluorobenzoyl)piperidin-4-yl]phenyl}-1-(pyridazin-3-yl)pyrrolidine-3-carboxamide;
(3S)—N-{4-[1-(naphthalen-2-ylacetyl)piperidin-4-yl]phenyl}-1-(pyridazin-3-yl)pyrrolidine-3-carboxamide;
(3S)—N-(4-{1-[3-(phenylsulfonyl)propanoyl]piperidin-4-yl}phenyl)-1-(pyridazin-3-yl)pyrrolidine-3-carboxamide;
(3S)-1-(pyridazin-3-yl)-N-[4-(1-{[3-(trifluoromethyl)phenyl]acetyl}piperidin-4-yl)phenyl]pyrrolidine-3-carboxamide;
(3S)—N-{4-[1-(furan-2-ylcarbonyl)piperidin-4-yl]phenyl}-1-(pyridazin-3-yl)pyrrolidine-3-carboxamide;
(3S)—N-{4-[1-(N-benzoylglycyl)piperidin-4-yl]phenyl}-1-(pyridazin-3-yl)pyrrolidine-3-carboxamide;
(3S)—N-(4-{1-[(2,4-dichlorophenyl)acetyl]piperidin-4-yl}phenyl)-1-(pyridazin-3-yl)pyrrolidine-3-carboxamide;
(3S)—N-{4-[1-(2-methylbenzoyl)piperidin-4-yl]phenyl}-1-(pyridazin-3-yl)pyrrolidine-3-carboxamide;
(3S)-1-(pyridazin-3-yl)-N-{4-[1-(4,4,4-trifluorobutanoyl)piperidin-4-yl]phenyl}pyrrolidine-3-carboxamide;
(3S)—N-(4-{1-[(1-methylcyclohexyl)carbonyl]piperidin-4-yl}phenyl)-1-(pyridazin-3-yl)pyrrolidine-3-carboxamide;
(3S)-1-(pyridazin-3-yl)-N-{4-[1-(thiophen-3-ylcarbonyl)piperidin-4-yl]phenyl}pyrrolidine-3-carboxamide;
(3S)—N-(4-{1-[(6-methylpyridin-3-yl)carbonyl]piperidin-4-yl}phenyl)-1-(pyridazin-3-yl)pyrrolidine-3-carboxamide;
(3S)—N-(4-{1-[(3-chlorophenyl)acetyl]piperidin-4-yl}phenyl)-1-(pyridazin-3-yl)pyrrolidine-3-carboxamide;
(3S)—N-[4-(1-propanoylpiperidin-4-yl)phenyl]-1-(pyridazin-3-yl)pyrrolidine-3-carboxamide;
(3S)—N-{4-[1-(3,5-difluorobenzoyl)piperidin-4-yl]phenyl}-1-(pyridazin-3-yl)pyrrolidine-3-carboxamide;
(3S)—N-{4-[1-(cyclopentylcarbonyl)piperidin-4-yl]phenyl}-1-(pyridazin-3-yl)pyrrolidine-3-carboxamide;
(3S)-1-(pyridazin-3-yl)-N-{4-[1-(tetrahydrofuran-2-ylcarbonyl)piperidin-4-yl]phenyl}pyrrolidine-3-carboxamide;
(3S)—N-{4-[1-(cyclopropylcarbonyl)piperidin-4-yl]phenyl}-1-(pyridazin-3-yl)pyrrolidine-3-carboxamide;
(3S)—N-{4-[1-(4-chlorobenzoyl)piperidin-4-yl]phenyl}-1-(pyridazin-3-yl)pyrrolidine-3-carboxamide;
5-[1-(2-methylpropyl)-1H-pyrazol-4-yl]-N-[(3S)-1-(pyridazin-3-yl)pyrrolidin-3-yl]thiophene-3-carboxamide;
N-[4-(1-benzoylpiperidin-4-yl)phenyl]-1-(6-fluoro-5-methylpyridin-3-yl)azetidine-3-carboxamide;
N-[4-(1-benzoylpiperidin-4-yl)phenyl]-1-(5-fluoropyridin-3-yl)azetidine-3-carboxamide;
N-[4-(1-benzoylpiperidin-4-yl)phenyl]-1-(6-methylpyridin-3-yl)azetidine-3-carboxamide;
N-[4-(1-benzoylpiperidin-4-yl)phenyl]-1-(2-fluoro-6-methylpyridin-3-yl)azetidine-3-carboxamide;
(3S)—N-{4-[1-(2-chlorobenzoyl)piperidin-4-yl]phenyl}-1-(pyridazin-3-yl)pyrrolidine-3-carboxamide;
(3S)—N-{4-[1-(2-methylpentanoyl)piperidin-4-yl]phenyl}-1-(pyridazin-3-yl)pyrrolidine-3-carboxamide;
(3S)—N-{4-[1-(4-methylpentanoyl)piperidin-4-yl]phenyl}-1-(pyridazin-3-yl)pyrrolidine-3-carboxamide;
(3S)—N-{4-[1-(2,4-dimethylbenzoyl)piperidin-4-yl]phenyl}-1-(pyridazin-3-yl)pyrrolidine-3-carboxamide;

(3S)—N-[4-(1-heptanoylpiperidin-4-yl)phenyl]-1-(pyridazin-3-yl)pyrrolidine-3-carboxamide;
(3S)—N-{4-[1-(2,4-dichlorobenzoyl)piperidin-4-yl]phenyl}-1-(pyridazin-3-yl)pyrrolidine-3-carboxamide;
(3S)—N-(4-{1-[(4-fluorophenyl)acetyl]piperidin-4-yl}phenyl)-1-(pyridazin-3-yl)pyrrolidine-3-carboxamide;
(3S)—N-{4-[1-(2,3-difluorobenzoyl)piperidin-4-yl]phenyl}-1-(pyridazin-3-yl)pyrrolidine-3-carboxamide;
(3S)—N-{4-[1-(3-methylbenzoyl)piperidin-4-yl]phenyl}-1-(pyridazin-3-yl)pyrrolidine-3-carboxamide;
(3S)—N-[4-(1-hexanoylpiperidin-4-yl)phenyl]-1-(pyridazin-3-yl)pyrrolidine-3-carboxamide;
(3S)—N-(4-{1-[(3-methylthiophen-2-yl)carbonyl]piperidin-4-yl}phenyl)-1-(pyridazin-3-yl)pyrrolidine-3-carboxamide;
(3S)—N-{4-[1-(2,3-dimethylbutanoyl)piperidin-4-yl]phenyl}-1-(pyridazin-3-yl)pyrrolidine-3-carboxamide;
(3S)—N-[4-(1-butanoylpiperidin-4-yl)phenyl]-1-(pyridazin-3-yl)pyrrolidine-3-carboxamide;
(3S)—N-{4-[1-(3-methylpentanoyl)piperidin-4-yl]phenyl}-1-(pyridazin-3-yl)pyrrolidine-3-carboxamide;
(3S)—N-(4-{1-[(3,5-dimethylphenyl)acetyl]piperidin-4-yl}phenyl)-1-(pyridazin-3-yl)pyrrolidine-3-carboxamide;
(3S)—N-{4-[1-(3,5-dichlorobenzoyl)piperidin-4-yl]phenyl}-1-(pyridazin-3-yl)pyrrolidine-3-carboxamide;
(3S)—N-{4-[1-(3-fluoro-2-methylbenzoyl)piperidin-4-yl]phenyl}-1-(pyridazin-3-yl)pyrrolidine-3-carboxamide;
(3S)—N-(4-{1-[(4-chlorophenyl)acetyl]piperidin-4-yl}phenyl)-1-(pyridazin-3-yl)pyrrolidine-3-carboxamide;
(3S)—N-{4-[1-(furan-3-ylcarbonyl)piperidin-4-yl]phenyl}-1-(pyridazin-3-yl)pyrrolidine-3-carboxamide;
(3S)—N-{4-[1-(3,4-dimethylbenzoyl)piperidin-4-yl]phenyl}-1-(pyridazin-3-yl)pyrrolidine-3-carboxamide;
(3S)—N-{4-[1-(4-fluorobenzoyl)piperidin-4-yl]phenyl}-1-(pyridazin-3-yl)pyrrolidine-3-carboxamide;
(3S)—N-(4-{1-[2-chloro-5-(trifluoromethyl)benzoyl]piperidin-4-yl}phenyl)-1-(pyridazin-3-yl)pyrrolidine-3-carboxamide;
(3S)—N-[4-(1-acetylpiperidin-4-yl)phenyl]-1-(pyridazin-3-yl)pyrrolidine-3-carboxamide;
(3S)—N-{4-[1-(2,4-difluorobenzoyl)piperidin-4-yl]phenyl}-1-(pyridazin-3-yl)pyrrolidine-3-carboxamide;
(3S)—N-{4-[1-(3,5-dimethylbenzoyl)piperidin-4-yl]phenyl}-1-(pyridazin-3-yl)pyrrolidine-3-carboxamide;
(3S)—N-{4-[1-(3-ethoxypropanoyl)piperidin-4-yl]phenyl}-1-(pyridazin-3-yl)pyrrolidine-3-carboxamide;
(3S)—N-{4-[1-(2,5-dichlorobenzoyl)piperidin-4-yl]phenyl}-1-(pyridazin-3-yl)pyrrolidine-3-carboxamide;
(3S)—N-{4-[1-(2,5-dimethylbenzoyl)piperidin-4-yl]phenyl}-1-(pyridazin-3-yl)pyrrolidine-3-carboxamide;
(3S)—N-{4-[1-(5-fluoro-2-methylbenzoyl)piperidin-4-yl]phenyl}-1-(pyridazin-3-yl)pyrrolidine-3-carboxamide;
(3S)—N-{4-[1-(diphenylacetyl)piperidin-4-yl]phenyl}-1-(pyridazin-3-yl)pyrrolidine-3-carboxamide;
(3S)-1-(pyridazin-3-yl)-N-(4-{1-[4-(trifluoromethyl)benzoyl]piperidin-4-yl}phenyl)pyrrolidine-3-carboxamide;
(3S)—N-{4-[1-(pent-4-enoyl)piperidin-4-yl]phenyl}-1-(pyridazin-3-yl)pyrrolidine-3-carboxamide;
(3S)-1-(pyridazin-3-yl)-N-(4-{1-[3-(trifluoromethoxy)benzoyl]piperidin-4-yl}phenyl)pyrrolidine-3-carboxamide;
(3S)—N-(4-{1-[(1-phenylcyclopropyl)carbonyl]piperidin-4-yl}phenyl)-1-(pyridazin-3-yl)pyrrolidine-3-carboxamide;
(3S)—N-(4-{1-[2-fluoro-5-(trifluoromethyl)benzoyl]piperidin-4-yl}phenyl)-1-(pyridazin-3-yl)pyrrolidine-3-carboxamide;
(3S)—N-{4-[1-(cyclohexylacetyl)piperidin-4-yl]phenyl}-1-(pyridazin-3-yl)pyrrolidine-3-carboxamide;
(3S)—N-{4-[1-(4-methoxybenzoyl)piperidin-4-yl]phenyl}-1-(pyridazin-3-yl)pyrrolidine-3-carboxamide;
(3S)—N-{4-[1-(2-methylbutanoyl)piperidin-4-yl]phenyl}-1-(pyridazin-3-yl)pyrrolidine-3-carboxamide;
(3S)—N-{4-[1-(2-ethylbutanoyl)piperidin-4-yl]phenyl}-1-(pyridazin-3-yl)pyrrolidine-3-carboxamide;
(3S)—N-{4-[1-(4-tert-butylbenzoyl)piperidin-4-yl]phenyl}-1-(pyridazin-3-yl)pyrrolidine-3-carboxamide;
(3S)—N-{4-[1-(3-chlorobenzoyl)piperidin-4-yl]phenyl}-1-(pyridazin-3-yl)pyrrolidine-3-carboxamide;
(3S)—N-(4-{1-[(2-fluorophenyl)acetyl]piperidin-4-yl}phenyl)-1-(pyridazin-3-yl)pyrrolidine-3-carboxamide;
(3S)-1-(pyridazin-3-yl)-N-(4-{1-[3-(trifluoromethyl)benzoyl]piperidin-4-yl}phenyl)pyrrolidine-3-carboxamide;
(3S)—N-(4-{1-[(1-methylcyclopropyl)carbonyl]piperidin-4-yl}phenyl)-1-(pyridazin-3-yl)pyrrolidine-3-carboxamide;
(3S)—N-{4-[1-(pent-4-ynoyl)piperidin-4-yl]phenyl}-1-(pyridazin-3-yl)pyrrolidine-3-carboxamide;
(3S)—N-(4-{1-[(3-fluorophenyl)acetyl]piperidin-4-yl}phenyl)-1-(pyridazin-3-yl)pyrrolidine-3-carboxamide;
(3S)—N-(4-{1-[3-(methylsulfanyl)propanoyl]piperidin-4-yl}phenyl)-1-(pyridazin-3-yl)pyrrolidine-3-carboxamide;
(3S)—N-(4-{1-[(1-acetylpiperidin-4-yl)carbonyl]piperidin-4-yl}phenyl)-1-(pyridazin-3-yl)pyrrolidine-3-carboxamide;
(3S)—N-{4-[1-(but-3-enoyl)piperidin-4-yl]phenyl}-1-(pyridazin-3-yl)pyrrolidine-3-carboxamide;
(3S)—N-{4-[1-(2,2-dimethylbutanoyl)piperidin-4-yl]phenyl}-1-(pyridazin-3-yl)pyrrolidine-3-carboxamide;
(3S)—N-{4-[1-(3-fluoro-4-methylbenzoyl)piperidin-4-yl]phenyl}-1-(pyridazin-3-yl)pyrrolidine-3-carboxamide;
(3S)—N-{4-[1-(3-methoxybenzoyl)piperidin-4-yl]phenyl}-1-(pyridazin-3-yl)pyrrolidine-3-carboxamide;
(3S)—N-(4-{1-[(2-chlorophenyl)acetyl]piperidin-4-yl}phenyl)-1-(pyridazin-3-yl)pyrrolidine-3-carboxamide;
(3S)—N-(4-{1-[(2-methoxyethoxy)acetyl]piperidin-4-yl}phenyl)-1-(pyridazin-3-yl)pyrrolidine-3-carboxamide;
(3S)—N-{4-[1-(3,3-dimethylbutanoyl)piperidin-4-yl]phenyl}-1-(pyridazin-3-yl)pyrrolidine-3-carboxamide;
(3S)—N-{4-[1-(N-acetyl-L-leucyl)piperidin-4-yl]phenyl}-1-(pyridazin-3-yl)pyrrolidine-3-carboxamide;
(3S)—N-{4-[1-(3-fluorobenzoyl)piperidin-4-yl]phenyl}-1-(pyridazin-3-yl)pyrrolidine-3-carboxamide;
(3S)—N-{4-[1-(4-cyanobenzoyl)piperidin-4-yl]phenyl}-1-(pyridazin-3-yl)pyrrolidine-3-carboxamide;
(3S)—N-{4-[1-(2-methoxybenzoyl)piperidin-4-yl]phenyl}-1-(pyridazin-3-yl)pyrrolidine-3-carboxamide;
(3S)—N-{4-[1-(2,3-dimethylbenzoyl)piperidin-4-yl]phenyl}-1-(pyridazin-3-yl)pyrrolidine-3-carboxamide;
(3S)—N-(4-{1-[4-(propan-2-yl)benzoyl]piperidin-4-yl}phenyl)-1-(pyridazin-3-yl)pyrrolidine-3-carboxamide;
(3S)—N-{4-[1-(cyclohexylcarbonyl)piperidin-4-yl]phenyl}-1-(pyridazin-3-yl)pyrrolidine-3-carboxamide;
(3S)-1-(pyridazin-3-yl)-N-{4-[1-(thiophen-2-ylcarbonyl)piperidin-4-yl]phenyl}pyrrolidine-3-carboxamide;
(3S)—N-{4-[1-(4-hydroxybenzoyl)piperidin-4-yl]phenyl}-1-(pyridazin-3-yl)pyrrolidine-3-carboxamide;
(3S)—N-{4-[1-(3-cyanobenzoyl)piperidin-4-yl]phenyl}-1-(pyridazin-3-yl)pyrrolidine-3-carboxamide;
(3S)-1-(pyridazin-3-yl)-N-{4-[1-(3,3,3-trifluoropropanoyl)piperidin-4-yl]phenyl}pyrrolidine-3-carboxamide;
(3S)—N-{4-[1-(methoxyacetyl)piperidin-4-yl]phenyl}-1-(pyridazin-3-yl)pyrrolidine-3-carboxamide;

(3S)—N-{4-[1-(3-methylbutanoyl)piperidin-4-yl]phenyl}-1-(pyridazin-3-yl)pyrrolidine-3-carboxamide;
N-[4-(1-benzoylpiperidin-4-yl)phenyl]-1-(2-cyanopyridin-3-yl)azetidine-3-carboxamide;
N-[4-(1-benzoylpiperidin-4-yl)phenyl]-1-(4-cyanopyridin-3-yl)azetidine-3-carboxamide;
N-[4-(1-benzoylpiperidin-4-yl)phenyl]-1-(6-fluoro-4-methylpyridin-3-yl)azetidine-3-carboxamide;
N-[4-(1-benzoylpiperidin-4-yl)phenyl]-1-(5-cyanopyridin-3-yl)azetidine-3-carboxamide;
N-[4-(1-benzoylpiperidin-4-yl)phenyl]-1-(5-methylpyridin-3-yl)azetidine-3-carboxamide;
2-[1-(2-methylpropyl)-1H-pyrazol-4-yl]-N-[(3S)-1-(pyridazin-3-yl)pyrrolidin-3-yl]-1,3-thiazole-5-carboxamide;
(3S)—N-[4-(1-benzoylpiperidin-4-yl)phenyl]-1-(2-methylpyridin-3-yl)pyrrolidine-3-carboxamide;
(3S)—N-{4-[1-(2-fluorobenzoyl)piperidin-4-yl]phenyl}-1-(2-methylpyridin-3-yl)pyrrolidine-3-carboxamide;
(3S)-1-(2-methylpyridin-3-yl)-N-{4-[1-(4,4,4-trifluorobutanoyl)piperidin-4-yl]phenyl}pyrrolidine-3-carboxamide;
N-[(3S)-1-(6-chloropyridazin-3-yl)pyrrolidin-3-yl]-5-[1-(2-methylpropyl)-1H-pyrazol-4-yl]furan-2-carboxamide;
5-[1-(2-methylpropyl)-1H-pyrazol-4-yl]-N-[(3S)-1-(pyridazin-3-yl)pyrrolidin-3-yl]furan-2-carboxamide;
N-(4-{1-[(4-methyltetrahydro-2H-pyran-4-yl)methyl]-1H-pyrazol-4-yl}phenyl)-1-(pyridazin-3-yl)azetidine-3-carboxamide;
N-[(3S)-1-(6-chloropyridazin-3-yl)pyrrolidin-3-yl]-4-[1-(2-methylpropanoyl)piperidin-4-yl]benzamide;
N-(4-{1-[2-(piperazin-1-yl)ethyl]-1H-pyrazol-4-yl}phenyl)-1-(pyridazin-3-yl)azetidine-3-carboxamide;
N-{4-[1-(2,2-dimethylpropyl)-1H-pyrazol-4-yl]phenyl}-1-(pyridazin-3-yl)azetidine-3-carboxamide;
4-[1-(2-methylpropanoyl)piperidin-4-yl]-N-[(3S)-1-(pyridazin-3-yl)pyrrolidin-3-yl]benzamide;
N-{4-[1-(2-hydroxy-2-methylpropyl)-1H-pyrazol-4-yl]phenyl}-1-(pyridazin-3-yl)azetidine-3-carboxamide;
5-[1-(3-fluorobenzoyl)piperidin-4-yl]-N-[(3S)-1-(pyridazin-3-yl)pyrrolidin-3-yl]thiophene-2-carboxamide;
5-[1-(4-fluorobenzoyl)piperidin-4-yl]-N-[(3S)-1-(pyridazin-3-yl)pyrrolidin-3-yl]thiophene-2-carboxamide;
(3S)—N-(4-{1-[(4-methyltetrahydro-2H-pyran-4-yl)methyl]-1H-pyrazol-4-yl}phenyl)-1-(pyridazin-3-yl)pyrrolidine-3-carboxamide;
(3S)—N-{4-[1-(2-hydroxy-2-methylpropyl)-1H-pyrazol-4-yl]phenyl}-1-(pyridazin-3-yl)pyrrolidine-3-carboxamide;
N-[(3S)-1-(pyridazin-3-yl)pyrrolidin-3-yl]-5-[1-(tetrahydro-2H-pyran-4-ylcarbonyl)piperidin-4-yl]thiophene-2-carboxamide;
(3S)—N-{4-[1-(2,2-dimethylpropyl)-1H-pyrazol-4-yl]phenyl}-1-(pyridazin-3-yl)pyrrolidine-3-carboxamide;
5-[1-(2-methylpropanoyl)piperidin-4-yl]-N-[(3S)-1-(pyridazin-3-yl)pyrrolidin-3-yl]thiophene-2-carboxamide;
5-[1-(2,4-difluorobenzoyl)piperidin-4-yl]-N-[(3S)-1-(pyridazin-3-yl)pyrrolidin-3-yl]thiophene-2-carboxamide;
5-{1-[(2-methylcyclopropyl)carbonyl]piperidin-4-yl}-N-[(3S)-1-(pyridazin-3-yl)pyrrolidin-3-yl]thiophene-2-carboxamide;
5-[1-(2-fluorobenzoyl)piperidin-4-yl]-N-[(3S)-1-(pyridazin-3-yl)pyrrolidin-3-yl]thiophene-2-carboxamide;
5-(1-benzoylpiperidin-4-yl)-N-[(3S)-1-(pyridazin-3-yl)pyrrolidin-3-yl]thiophene-2-carboxamide;
N-[(3S)-1-(pyridazin-3-yl)pyrrolidin-3-yl]-5-[1-(tetrahydrofuran-3-ylcarbonyl)piperidin-4-yl]thiophene-2-carboxamide;
N-[(3S)-1-(pyridazin-3-yl)pyrrolidin-3-yl]-5-{1-[(2R)-tetrahydrofuran-2-ylcarbonyl]piperidin-4-yl}thiophene-2-carboxamide;
5-{1-[(1-methylpiperidin-4-yl)acetyl]piperidin-4-yl}-N-[(3S)-1-(pyridazin-3-yl)pyrrolidin-3-yl]thiophene-2-carboxamide;
N-[(3S)-1-(pyridazin-3-yl)pyrrolidin-3-yl]-5-[1-(1,3-thiazol-4-ylcarbonyl)piperidin-4-yl]thiophene-2-carboxamide;
(3S)—N-{4-[1-(2-methylpropyl)-1H-pyrazol-4-yl]phenyl}-1-(pyridazin-3-yl)pyrrolidine-3-carboxamide;
(3S)—N-{4-[1-(propan-2-yl)-1H-pyrazol-4-yl]phenyl}-1-(pyridazin-3-yl)pyrrolidine-3-carboxamide;
(3S)—N-{4-[1-(cyclopropylmethyl)-1H-pyrazol-4-yl]phenyl}-1-(pyridazin-3-yl)pyrrolidine-3-carboxamide;
(3S)-1-(pyridazin-3-yl)-N-{4-[1-(tetrahydro-2H-pyran-2-ylmethyl)-1H-pyrazol-4-yl]phenyl}pyrrolidine-3-carboxamide;
(3S)—N-[4-(1-tert-butyl-1H-pyrazol-4-yl)phenyl]-1-(pyridazin-3-yl)pyrrolidine-3-carboxamide;
(3S)—N-(4-{[(3R)-1-benzoylpyrrolidin-3-yl]oxy}phenyl)-1-(pyridazin-3-yl)pyrrolidine-3-carboxamide;
(3S)—N-(4-{[(3R)-1-(2-fluorobenzoyl)pyrrolidin-3-yl]oxy}phenyl)-1-(pyridazin-3-yl)pyrrolidine-3-carboxamide;
(3S)—N-(4-{[(3R)-1-(3-fluorobenzoyl)pyrrolidin-3-yl]oxy}phenyl)-1-(pyridazin-3-yl)pyrrolidine-3-carboxamide;
(3S)—N-(4-{[(3R)-1-(4-fluorobenzoyl)pyrrolidin-3-yl]oxy}phenyl)-1-(pyridazin-3-yl)pyrrolidine-3-carboxamide;
(3S)—N-(4-{[(3R)-1-(3,5-difluorobenzoyl)pyrrolidin-3-yl]oxy}phenyl)-1-(pyridazin-3-yl)pyrrolidine-3-carboxamide;
(3S)—N-(4-{[(3R)-1-(2-methylbenzoyl)pyrrolidin-3-yl]oxy}phenyl)-1-(pyridazin-3-yl)pyrrolidine-3-carboxamide;
(3S)—N-(4-{[(3R)-1-(2,2-dimethylpropanoyl)pyrrolidin-3-yl]oxy}phenyl)-1-(pyridazin-3-yl)pyrrolidine-3-carboxamide;
(3S)—N-[4-({(3R)-1-[(4,4-difluorocyclohexyl)carbonyl]pyrrolidin-3-yl}oxy)phenyl]-1-(pyridazin-3-yl)pyrrolidine-3-carboxamide;
(3S)-1-(pyridazin-3-yl)-N-(4-{[(3R)-1-(4,4,4-trifluorobutanoyl)pyrrolidin-3-yl]oxy}phenyl)pyrrolidine-3-carboxamide;
(3S)—N-(4-{[(3R)-1-(2,4-difluorobenzoyl)pyrrolidin-3-yl]oxy}phenyl)-1-(pyridazin-3-yl)pyrrolidine-3-carboxamide;
N-[4-(5-propyl-1,2,4-oxadiazol-3-yl)phenyl]-1-(pyridazin-3-yl)azetidine-3-carboxamide;
(3S)—N-{4-[1-(2-fluorobenzoyl)azetidin-3-yl]phenyl}-1-(pyridazin-3-yl)pyrrolidine-3-carboxamide;
(3S)—N-{4-[1-(3-fluorobenzoyl)azetidin-3-yl]phenyl}-1-(pyridazin-3-yl)pyrrolidine-3-carboxamide;
(3S)—N-{4-[1-(4-fluorobenzoyl)azetidin-3-yl]phenyl}-1-(pyridazin-3-yl)pyrrolidine-3-carboxamide;
(3S)—N-[4-(1-benzoylazetidin-3-yl)phenyl]-1-(pyridazin-3-yl)pyrrolidine-3-carboxamide;
(3S)—N-{4-[1-(2,2-dimethylpropanoyl)azetidin-3-yl]phenyl}-1-(pyridazin-3-yl)pyrrolidine-3-carboxamide;
(3S)—N-{4-[1-(3,5-difluorobenzoyl)azetidin-3-yl]phenyl}-1-(pyridazin-3-yl)pyrrolidine-3-carboxamide;
(3S)—N-{4-[1-(2-methylbenzoyl)azetidin-3-yl]phenyl}-1-(pyridazin-3-yl)pyrrolidine-3-carboxamide;
(3S)—N-{4-[1-(2,4-difluorobenzoyl)azetidin-3-yl]phenyl}-1-(pyridazin-3-yl)pyrrolidine-3-carboxamide;

(3R)—N-[4-(1-benzoylpiperidin-4-yl)phenyl]-1-(pyridazin-3-yl)pyrrolidine-3-carboxamide;
(3R)—N-{4-[1-(2-fluorobenzoyl)piperidin-4-yl]phenyl}-1-(pyridazin-3-yl)pyrrolidine-3-carboxamide;
(3R)—N-{4-[1-(2,2-dimethylpropanoyl)piperidin-4-yl]phenyl}-1-(pyridazin-3-yl)pyrrolidine-3-carboxamide;
(3S)—N-(4-{[1-(cyclohexylcarbonyl)piperidin-4-yl]oxy}phnyl)-1-(pyridazin-3-yl)pyrrolidine-3-carboxamide;
(3S)—N-(4-{[1-(2-fluorobenzoyl)piperidin-4-yl]oxy}phenyl)-1-(pyridazin-3-yl)pyrrolidine-3-carboxamide;
(3S)—N-(4-{[1-(3-fluorobenzoyl)piperidin-4-yl]oxy}phenyl)-1-(pyridazin-3-yl)pyrrolidine-3-carboxamide;
(3S)—N-{4-[(1-benzoylpiperidin-4-yl)oxy]phenyl}-1-(pyridazin-3-yl)pyrrolidine-3-carboxamide;
(3S)—N-(4-{[1-(4-fluorobenzoyl)piperidin-4-yl]oxy}phenyl)-1-(pyridazin-3-yl)pyrrolidine-3-carboxamide;
(3S)—N-(4-{[1-(2,2-dimethylpropanoyl)piperidin-4-yl]oxy}phenyl)-1-(pyridazin-3-yl)pyrrolidine-3-carboxamide;
(3S)—N-[4-({1-[(2-methylcyclopropyl)carbonyl]piperidin-4-yl}oxy)phenyl]-1-(pyridazin-3-yl)pyrrolidine-3-carboxamide;
N-{4-[5-(2,2-dimethylpropyl)-1,3,4-oxadiazol-2-yl]phenyl}-1-(pyridazin-3-yl)azetidine-3-carboxamide;
N-{4-[1-(2,2-dimethylpropyl)-1H-imidazol-4-yl]phenyl}-1-(pyridazin-3-yl)azetidine-3-carboxamide;
N-[4-(3-cyclopropyl-1-methyl-1H-pyrazol-5-yl)phenyl]-1-(pyridazin-3-yl)azetidine-3-carboxamide;
N-{4-[5-(2,2-dimethylpropyl)-1,2,4-oxadiazol-3-yl]phenyl}-1-(pyridazin-3-yl)azetidine-3-carboxamide;
N-{4-[3-cyclopropyl-1-(2-methoxyethyl)-1H-pyrazol-5-yl]phenyl}-1-(pyridazin-3-yl)azetidine-3-carboxamide;
tert-butyl 4-(5-{[1-(pyridazin-3-yl)azetidin-3-yl]carbamoyl}thiophen-2-yl)piperidine-1-carboxylate;
tert-butyl 4-fluoro-4-[4-({[1-(pyridazin-3-yl)azetidin-3-yl]carbonyl}amino)phenyl]piperidine-1-carboxylate;
5-(1-benzoylpiperidin-4-yl)-N-[1-(pyridazin-3-yl)azetidin-3-yl]thiophene-2-carboxamide;
5-[1-(2-fluorobenzoyl)piperidin-4-yl]-N-[1-(pyridazin-3-yl)azetidin-3-yl]thiophene-2-carboxamide;
5-[1-(2-methylbenzoyl)piperidin-4-yl]-N-[1-(pyridazin-3-yl)azetidin-3-yl]thiophene-2-carboxamide;
5-[1-(2,4-difluorobenzoyl)piperidin-4-yl]-N-[1-(pyridazin-3-yl)azetidin-3-yl]thiophene-2-carboxamide;
5-[1-(3-fluorobenzoyl)piperidin-4-yl]-N-[1-(pyridazin-3-yl)azetidin-3-yl]thiophene-2-carboxamide;
5-[1-(4-fluorobenzoyl)piperidin-4-yl]-N-[1-(pyridazin-3-yl)azetidin-3-yl]thiophene-2-carboxamide;
5-[1-(3,5-difluorobenzoyl)piperidin-4-yl]-N-[1-(pyridazin-3-yl)azetidin-3-yl]thiophene-2-carboxamide;
N-{4-[3-cyclopropyl-1-(2-hydroxyethyl)-1H-pyrazol-5-yl]phenyl}-1-(pyridazin-3-yl)azetidine-3-carboxamide;
N-[4-(1-benzoylpiperidin-4-yl)phenyl]-1-(6-fluoropyridazin-3-yl)azetidine-3-carboxamide;
N-{4-[1-(2-fluorobenzoyl)piperidin-4-yl]phenyl}-1-(6-fluoropyridazin-3-yl)azetidine-3-carboxamide;
N-{4-[1-(2,2-dimethylpropanoyl)piperidin-4-yl]phenyl}-1-(6-fluoropyridazin-3-yl)azetidine-3-carboxamide;
1-(6-fluoropyridazin-3-yl)-N-{4-[1-(2-methylpropanoyl)piperidin-4-yl]phenyl}azetidine-3-carboxamide;
N-{4-[1-(2-ethylbutanoyl)piperidin-4-yl]phenyl}-1-(6-fluoropyridazin-3-yl)azetidine-3-carboxamide;
N-{4-[1-(4-fluorobenzoyl)piperidin-4-yl]phenyl}-1-(6-fluoropyridazin-3-yl)azetidine-3-carboxamide;
(3S)—N-(4-{[(3S)-1-benzoylpyrrolidin-3-yl]oxy}phenyl)-1-(pyridazin-3-yl)pyrrolidine-3-carboxamide;
(3S)—N-(4-{[(3S)-1-(2-fluorobenzoyl)pyrrolidin-3-yl]oxy}phenyl)-1-(pyridazin-3-yl)pyrrolidine-3-carboxamide;
(3S)—N-(4-{[(3S)-1-(3,5-difluorobenzoyl)pyrrolidin-3-yl]oxy}phenyl)-1-(pyridazin-3-yl)pyrrolidine-3-carboxamide;
(3S)—N-(4-{[(3S)-1-(2,2-dimethylpropanoyl)pyrrolidin-3-yl]oxy}phenyl)-1-(pyridazin-3-yl)pyrrolidine-3-carboxamide;
N-{2-fluoro-4-[1-(2-fluorobenzoyl)piperidin-4-yl]phenyl}-1-(pyridazin-3-yl)azetidine-3-carboxamide;
N-[4-(1-benzoylpiperidin-4-yl)-2-fluorophenyl]-1-(pyridazin-3-yl)azetidine-3-carboxamide;
N-{2-fluoro-4-[1-(3-fluorobenzoyl)piperidin-4-yl]phenyl}-1-(pyridazin-3-yl)azetidine-3-carboxamide;
N-{2-fluoro-4-[1-(2-methylbenzoyl)piperidin-4-yl]phenyl}-1-(pyridazin-3-yl)azetidine-3-carboxamide;
N-{2-fluoro-4-[1-(4-fluorobenzoyl)piperidin-4-yl]phenyl}-1-(pyridazin-3-yl)azetidine-3-carboxamide;
N-{4-[1-(2,4-difluorobenzoyl)piperidin-4-yl]-2-fluorophenyl}-1-(pyridazin-3-yl)azetidine-3-carboxamide;
N-{4-[1-(3,5-difluorobenzoyl)piperidin-4-yl]-2-fluorophenyl}-1-(pyridazin-3-yl)azetidine-3-carboxamide;
N-{4-[1-(3,3-dimethylbutanoyl)piperidin-4-yl]-2-fluorophenyl}-1-(pyridazin-3-yl)azetidine-3-carboxamide;
(3S)—N-(4-{[1-(2-fluorobenzoyl)piperidin-4-yl]oxy}phenyl)-1-(6-methylpyridazin-3-yl)pyrrolidine-3-carboxamide;
(3S)—N-{4-[(1-benzoylpiperidin-4-yl)oxy]phenyl}-1-(6-methylpyridazin-3-yl)pyrrolidine-3-carboxamide;
(3S)—N-(4-{[1-(2,2-dimethylpropanoyl)piperidin-4-yl]oxy}phenyl)-1-(6-methylpyridazin-3-yl)pyrrolidine-3-carboxamide;
(3S)—N-(4-{[1-(cyclohexylcarbonyl)piperidin-4-yl]oxy}phenyl)-1-(6-methylpyridazin-3-yl)pyrrolidine-3-carboxamide;
N-{4-[8-(2-methylpropanoyl)-8-azabicyclo[3.2.1]oct-3-yl]phenyl}-1-(pyridazin-3-yl)azetidine-3-carboxamide;
1-(pyridazin-3-yl)-N-{4-[8-(4,4,4-trifluorobutanoyl)-8-azabicyclo[3.2.1]oct-3-yl]phenyl}azetidine-3-carboxamide;
N-[4-(8-benzoyl-8-azabicyclo[3.2.1]oct-3-yl)phenyl]-1-(pyridazin-3-yl)azetidine-3-carboxamide;
N-{4-[8-(2-fluorobenzoyl)-8-azabicyclo[3.2.1]oct-3-yl]phenyl}-1-(pyridazin-3-yl)azetidine-3-carboxamide;
N-{4-[8-(2,2-dimethylpropanoyl)-8-azabicyclo[3.2.1]oct-3-yl]phenyl}-1-(pyridazin-3-yl)azetidine-3-carboxamide;
N-(4-{8-[(1-methylcyclopropyl)carbonyl]-8-azabicyclo[3.2.1]oct-3-yl}phenyl)-1-(pyridazin-3-yl)azetidine-3-carboxamide;
N-{4-[1-(2-methoxyethyl)-3-(2-methylpropyl)-1H-pyrazol-5-yl]phenyl}-1-(pyridazin-3-yl)azetidine-3-carboxamide;
5-[1-(2,2-dimethylpropanoyl)piperidin-4-yl]-N-[1-(pyridazin-3-yl)azetidin-3-yl]thiophene-2-carboxamide;
5-{1-[(1-methylcyclopropyl)carbonyl]piperidin-4-yl}-N-[1-(pyridazin-3-yl)azetidin-3-yl]thiophene-2-carboxamide;
N-[1-(pyridazin-3-yl)azetidin-3-yl]-5-[1-(3,3,3-trifluoropropanoyl)piperidin-4-yl]thiophene-2-carboxamide;
5-[1-(2,2-dimethylbutanoyl)piperidin-4-yl]-N-[1-(pyridazin-3-yl)azetidin-3-yl]thiophene-2-carboxamide;
N-{4-[1-(2-fluorobenzoyl)piperidin-4-yl]phenyl}-1-(6-methylpyridazin-3-yl)azetidine-3-carboxamide;

N-{4-[1-(2,2-dimethylpropanoyl)piperidin-4-yl]phenyl}-1-(6-methylpyridazin-3-yl)azetidine-3-carboxamide;
benzyl 4-[4-({[1-(6-chloropyridazin-3-yl)azetidin-3-yl]carbonyl}amino)phenyl]-4-fluoropiperidine-1-carboxylate;
benzyl 4-[4-({[1-(6-chloropyridazin-3-yl)azetidin-3-yl]carbonyl}amino)phenyl]-4-hydroxypiperidine-1-carboxylate;
N-[1-(pyridazin-3-yl)azetidin-3-yl]-5-[1-(4,4,4-trifluorobutanoyl)piperidin-4-yl]thiophene-2-carboxamide;
5-[1-(cyclopropylcarbonyl)piperidin-4-yl]-N-[1-(pyridazin-3-yl)azetidin-3-yl]thiophene-2-carboxamide;
N-{4-[4-fluoro-1-(2-fluorobenzoyl)piperidin-4-yl]phenyl}-1-(pyridazin-3-yl)azetidine-3-carboxamide;
N-{2-fluoro-4-[1-(2-methylpropanoyl)piperidin-4-yl]phenyl}-1-(pyridazin-3-yl)azetidine-3-carboxamide;
N-{4-[1-(2,2-dimethylpropanoyl)piperidin-4-yl]-2-fluorophenyl}-1-(pyridazin-3-yl)azetidine-3-carboxamide;
N-{4-[1-(cyclopropylcarbonyl)piperidin-4-yl]-2-fluorophenyl}-1-(pyridazin-3-yl)azetidine-3-carboxamide;
N-(2-fluoro-4-{1-[(1-methylcyclopropyl)carbonyl]piperidin-4-yl}phenyl)-1-(pyridazin-3-yl)azetidine-3-carboxamide;
N-{4-[1-(cyclopropylacetyl)piperidin-4-yl]-2-fluorophenyl}-1-(pyridazin-3-yl)azetidine-3-carboxamide;
N-[4-(1-benzoyl-4-fluoropiperidin-4-yl)phenyl]-1-(pyridazin-3-yl)azetidine-3-carboxamide;
N-{4-[1-(2,2-dimethylpropanoyl)-4-fluoropiperidin-4-yl]phenyl}-1-(pyridazin-3-yl)azetidine-3-carboxamide;
N-{4-[3-tert-butyl-1-(2-methoxyethyl)-1H-pyrazol-5-yl]phenyl}-1-(pyridazin-3-yl)azetidine-3-carboxamide;
N-[4-(1-butyl-3-tert-butyl-1H-pyrazol-5-yl)phenyl]-1-(pyridazin-3-yl)azetidine-3-carboxamide;
N-{4-[3-tert-butyl-1-(tetrahydro-2H-pyran-4-ylmethyl)-1H-pyrazol-5-yl]phenyl}-1-(pyridazin-3-yl)azetidine-3-carboxamide;
N-{2-fluoro-4-[1-(2-fluorobenzoyl)piperidin-4-yl]phenyl}-1-(pyridazin-4-yl)azetidine-3-carboxamide;
N-[4-(1-benzoylpiperidin-4-yl)-2-fluorophenyl]-1-(pyridazin-4-yl)azetidine-3-carboxamide;
N-{4-[1-(2,2-dimethylpropanoyl)piperidin-4-yl]-2-fluorophenyl}-1-(pyridazin-4-yl)azetidine-3-carboxamide;
N-{4-[1-(3,3-dimethylbutanoyl)piperidin-4-yl]-2-fluorophenyl}-1-(pyridazin-4-yl)azetidine-3-carboxamide;
N-{2-fluoro-4-[1-(4,4,4-trifluorobutanoyl)piperidin-4-yl]phenyl}-1-(pyridazin-4-yl)azetidine-3-carboxamide;
N-(4-{1-[(4-methylpiperidin-4-yl)methyl]-1H-pyrazol-4-yl}phenyl)-1-(pyridazin-4-yl)azetidine-3-carboxamide;
N-{4-[1-methyl-3-(trifluoromethyl)-1H-pyrazol-5-yl]phenyl}-1-(pyridazin-3-yl)azetidine-3-carboxamide;
1-(6-chloropyridazin-3-yl)-N-{4-[1-(2,2-dimethylpropyl)-1H-pyrazol-4-yl]phenyl}azetidine-3-carboxamide;
N-[4-(1-benzoylpiperidin-4-yl)phenyl]-1-(6-methylpyridin-3-yl)azetidine-3-carboxamide;
N-(4-{1-[(4-methylpiperidin-4-yl)methyl]-1H-pyrazol-4-yl}phenyl)-1-(pyridin-3-yl)azetidine-3-carboxamide;
N-{4-[1-(2,2-dimethylpropyl)-1H-pyrazol-4-yl]phenyl}-1-(6-methylpyridazin-3-yl)azetidine-3-carboxamide;
N-{3-fluoro-4-[1-(3-fluorobenzoyl)piperidin-4-yl]phenyl}-1-(pyridazin-3-yl)azetidine-3-carboxamide;
N-{3-fluoro-4-[1-(3-methylpropanoyl)piperidin-4-yl]phenyl}-1-(pyridazin-3-yl)azetidine-3-carboxamide;
N-{3-fluoro-4-[1-(3,3,3-trifluoropropanoyl)piperidin-4-yl]phenyl}-1-(pyridazin-3-yl)azetidine-3-carboxamide;
N-{4-[1-(3,3-dimethylbutanoyl)piperidin-4-yl]-3-fluorophenyl}-1-(pyridazin-3-yl)azetidine-3-carboxamide;
N-{3-fluoro-4-[1-(4,4,4-trifluorobutanoyl)piperidin-4-yl]phenyl}-1-(pyridazin-3-yl)azetidine-3-carboxamide;
N-[4-(1-benzoylpiperidin-4-yl)-3-fluorophenyl]-1-(pyridazin-3-yl)azetidine-3-carboxamide;
N-{3-fluoro-4-[1-(2-fluorobenzoyl)piperidin-4-yl]phenyl}-1-(pyridazin-3-yl)azetidine-3-carboxamide;
N-{4-[1-(2,2-dimethylpropanoyl)piperidin-4-yl]-3-fluorophenyl}-1-(pyridazin-3-yl)azetidine-3-carboxamide;
N-{3-fluoro-4-[1-(3-methylbutanoyl)piperidin-4-yl]phenyl}-1-(pyridazin-3-yl)azetidine-3-carboxamide;
N-{4-[1-(cyclopropylacetyl)piperidin-4-yl]-3-fluorophenyl}-1-(pyridazin-3-yl)azetidine-3-carboxamide;
N-{4-[1-(2-fluorobenzoyl)-4-hydroxypiperidin-4-yl]phenyl}-1-(pyridazin-3-yl)azetidine-3-carboxamide;
N-{4-[1-(2,2-dimethylpropanoyl)-4-hydroxypiperidin-4-yl]phenyl}-1-(pyridazin-3-yl)azetidine-3-carboxamide;
1-(6-methylpyridazin-3-yl)-N-(4-{1-[(4-methyltetrahydro-2H-pyran-4-yl)methyl]-1H-pyrazol-4-yl}phenyl)azetidine-3-carboxamide;
(3S)—N-{4-[1-(2-fluorobenzoyl)piperidin-4-yl]phenyl}-1-(6-methylpyridazin-3-yl)pyrrolidine-3-carboxamide;
(3S)—N-[4-(1-benzoylpiperidin-4-yl)phenyl]-1-(6-methylpyridazin-3-yl)pyrrolidine-3-carboxamide;
(3S)—N-{4-[1-(2,2-dimethylpropanoyl)piperidin-4-yl]phenyl}-1-(6-methylpyridazin-3-yl)pyrrolidine-3-carboxamide;
N-{4-[(1-benzoylpiperidin-4-yl)methyl]phenyl}-1-(pyridazin-3-yl)azetidine-3-carboxamide;
N-(4-{[1-(2-fluorobenzoyl)piperidin-4-yl]methyl}phenyl)-1-(pyridazin-3-yl)azetidine-3-carboxamide;
N-(4-{[1-(2,2-dimethylpropanoyl)piperidin-4-yl]methyl}phenyl)-1-(pyridazin-3-yl)azetidine-3-carboxamide;
N-(4-{[1-(3,3-dimethylbutanoyl)piperidin-4-yl]methyl}phenyl)-1-(pyridazin-3-yl)azetidine-3-carboxamide;
N-(4-{[1-(2-ethylbutanoyl)piperidin-4-yl]methyl}phenyl)-1-(pyridazin-3-yl)azetidine-3-carboxamide;
1-(pyridazin-3-yl)-N-(4-{[1-(4,4,4-trifluorobutanoyl)piperidin-4-yl]methyl}phenyl)azetidine-3-carboxamide;
N-(4-{[1-(2-methylpropanoyl)piperidin-4-yl]methyl}phenyl)-1-(pyridazin-3-yl)azetidine-3-carboxamide;
N-{4-[(1-acetylpiperidin-4-yl)methyl]phenyl}-1-(pyridazin-3-yl)azetidine-3-carboxamide;
N-[4-({1-[(2S)-2-methylbutanoyl]piperidin-4-yl}methyl)phenyl]-1-(pyridazin-3-yl)azetidine-3-carboxamide;
N-[4-({1-[(1-methylcyclopropyl)carbonyl]piperidin-4-yl}methyl)phenyl]-1-(pyridazin-3-yl)azetidine-3-carboxamide;
N-[4-(1-{[4-methyl-1-(oxetan-3-yl)piperidin-4-yl]methyl}-1H-pyrazol-4-yl)phenyl]-1-(6-methylpyridazin-3-yl)azetidine-3-carboxamide;
N-[4-(1-benzoylpiperidin-4-yl)phenyl]-1-(4-methylpyridazin-3-yl)azetidine-3-carboxamide;
5-[1-(2-fluorobenzoyl)piperidin-4-yl]-N-[(3S)-1-(pyridazin-3-yl)pyrrolidin-3-yl]furan-2-carboxamide;
N-[4-(1-benzoylpiperidin-4-yl)phenyl]-1-(3-methylpyridazin-4-yl)azetidine-3-carboxamide;
N-{4-[1-(2-fluorobenzoyl)piperidin-4-yl]phenyl}-1-(3-methylpyridazin-4-yl)azetidine-3-carboxamide;
N-(4-{1-[(2-aminopyridin-3-yl)carbonyl]piperidin-4-yl}phenyl)-1-(pyridazin-3-yl)azetidine-3-carboxamide;
1-methyl-5-[4-({[1-(pyridazin-3-yl)azetidin-3-yl]carbonyl}amino)phenyl]-1H-pyrazole-3-carboxylic acid;
ethyl 1-methyl-5-[4-({[1-(pyridazin-3-yl)azetidin-3-yl]carbonyl}amino)phenyl]-1H-pyrazole-3-carboxylate;

ethyl 1-phenyl-5-[4-({[1-(pyridazin-3-yl)azetidin-3-yl]carbonyl}amino)phenyl]-1H-pyrazole-3-carboxylate;
N-{6-[1-(2-fluorobenzoyl)piperidin-4-yl]pyridin-3-yl}-1-(pyridazin-3-yl)azetidine-3-carboxamide;
N-(4-{[(3R)-1-(3-methylbutanoyl)pyrrolidin-3-yl]oxy}phenyl)-1-(6-methylpyridin-3-yl)azetidine-3-carboxamide;
N-(4-{[(3R)-1-(2-methylpropanoyl)pyrrolidin-3-yl]oxy}phenyl)-1-(6-methylpyridin-3-yl)azetidine-3-carboxamide;
N-(4-{[(3R)-1-(2,4-difluorobenzoyl)pyrrolidin-3-yl]oxy}phenyl)-1-(6-methylpyridin-3-yl)azetidine-3-carboxamide;
1-(6-methylpyridin-3-yl)-N-(4-{[(3R)-1-(1,3-thiazol-4-ylcarbonyl)pyrrolidin-3-yl]oxy}phenyl)azetidine-3-carboxamide;
1-(pyridazin-3-yl)-N-{6-[1-(4,4,4-trifluorobutanoyl)piperidin-4-yl]pyridin-3-yl}azetidine-3-carboxamide;
N-{6-[1-(3,3-dimethylbutanoyl)piperidin-4-yl]pyridin-3-yl}-1-(pyridazin-3-yl)azetidine-3-carboxamide;
(3S)—N-[4-(1-benzoylpiperidin-4-yl)phenyl]-1-(4-methylpyridin-3-yl)pyrrolidine-3-carboxamide;
(3S)—N-{4-[1-(2,2-dimethylpropanoyl)piperidin-4-yl]phenyl}-1-(4-methylpyridin-3-yl)pyrrolidine-3-carboxamide;
N-{4-[1-phenyl-3-(trifluoromethyl)-1H-pyrazol-5-yl]phenyl}-1-(pyridazin-3-yl)azetidine-3-carboxamide;
N-{6-[1-(2,2-dimethylpropyl)-1H-pyrazol-4-yl]pyridin-3-yl}-1-(pyridazin-3-yl)azetidine-3-carboxamide;
tert-butyl 4-[4-({[1-(pyridazin-3-yl)azetidin-3-yl]carbonyl}amino)-1H-pyrazol-1-yl]piperidine-1-carboxylate;
N-(6-{1-[(4-methylpiperidin-4-yl)methyl]-1H-pyrazol-4-yl}pyridin-3-yl)-1-(pyridazin-3-yl)azetidine-3-carboxamide;
1-(pyridazin-3-yl)-N-(4-{[1-(1,3-thiazol-5-ylcarbonyl)piperidin-4-yl]methyl}phenyl)azetidine-3-carboxamide;
N-(4-{[1-(cyclopentylcarbonyl)piperidin-4-yl]methyl}phenyl)-1-(pyridazin-3-yl)azetidine-3-carboxamide;
N-(4-{[1-(1H-pyrazol-4-ylcarbonyl)piperidin-4-yl]methyl}phenyl)-1-(pyridazin-3-yl)azetidine-3-carboxamide;
N-(4-{[1-(2,2-dimethylbutanoyl)piperidin-4-yl]methyl}phenyl)-1-(pyridazin-3-yl)azetidine-3-carboxamide;
N-[4-({1-[(2-methylcyclopropyl)carbonyl]piperidin-4-yl}methyl)phenyl]-1-(pyridazin-3-yl)azetidine-3-carboxamide;
N-[4-({1-[(methylsulfanyl)acetyl]piperidin-4-yl}methyl)phenyl]-1-(pyridazin-3-yl)azetidine-3-carboxamide;
N-[4-({1-[(1S,4R)-bicyclo[2.2.1]hept-2-ylacetyl]piperidin-4-yl}methyl)phenyl]-1-(pyridazin-3-yl)azetidine-3-carboxamide;
N-(4-{[1-(2-methylpentanoyl)piperidin-4-yl]methyl}phenyl)-1-(pyridazin-3-yl)azetidine-3-carboxamide;
N-(4-{[1-(4-methylpentanoyl)piperidin-4-yl]methyl}phenyl)-1-(pyridazin-3-yl)azetidine-3-carboxamide;
N-[4-({1-[3-(methylsulfanyl)propanoyl]piperidin-4-yl}methyl)phenyl]-1-(pyridazin-3-yl)azetidine-3-carboxamide;
1-(pyridazin-3-yl)-N-(4-{[1-(1,3-thiazol-4-ylcarbonyl)piperidin-4-yl]methyl}phenyl)azetidine-3-carboxamide;
N-(4-{[1-(1H-pyrazol-5-ylcarbonyl)piperidin-4-yl]methyl}phenyl)-1-(pyridazin-3-yl)azetidine-3-carboxamide;
N-[4-({1-[(6-methylpyridin-3-yl)carbonyl]piperidin-4-yl}methyl)phenyl]-1-(pyridazin-3-yl)azetidine-3-carboxamide;
N-[4-({1-[(3-methylthiophen-2-yl)carbonyl]piperidin-4-yl}methyl)phenyl]-1-(pyridazin-3-yl)azetidine-3-carboxamide;
N-(4-{[1-(pent-4-ynoyl)piperidin-4-yl]methyl}phenyl)-1-(pyridazin-3-yl)azetidine-3-carboxamide;
1-(pyridazin-3-yl)-N-(4-{[1-(thiophen-3-ylcarbonyl)piperidin-4-yl]methyl}phenyl)azetidine-3-carboxamide;
N-(4-{[1-(methoxyacetyl)piperidin-4-yl]methyl}phenyl)-1-(pyridazin-3-yl)azetidine-3-carboxamide;
1-(pyridazin-3-yl)-N-(4-{[1-(tetrahydrofuran-2-ylcarbonyl)piperidin-4-yl]methyl}phenyl)azetidine-3-carboxamide;
N-[4-({1-[(2-methoxyethoxy)acetyl]piperidin-4-yl}methyl)phenyl]-1-(pyridazin-3-yl)azetidine-3-carboxamide;
N-(4-{[1-(ethoxyacetyl)piperidin-4-yl]methyl}phenyl)-1-(pyridazin-3-yl)azetidine-3-carboxamide;
1-(pyridazin-3-yl)-N-(4-{[1-(thiophen-2-ylcarbonyl)piperidin-4-yl]methyl}phenyl)azetidine-3-carboxamide;
N-{4-[(1-hexanoylpiperidin-4-yl)methyl]phenyl}-1-(pyridazin-3-yl)azetidine-3-carboxamide;
N-[4-({1-[(1-methyl-1H-pyrrol-2-yl)carbonyl]piperidin-4-yl}methyl)phenyl]-1-(pyridazin-3-yl)azetidine-3-carboxamide;
N-(4-{[1-(but-3-enoyl)piperidin-4-yl]methyl}phenyl)-1-(pyridazin-3-yl)azetidine-3-carboxamide;
1-(pyridazin-3-yl)-N-(4-{[1-(1,3-thiazol-2-ylcarbonyl)piperidin-4-yl]methyl}phenyl)azetidine-3-carboxamide;
N-(4-{[1-(furan-2-ylcarbonyl)piperidin-4-yl]methyl}phenyl)-1-(pyridazin-3-yl)azetidine-3-carboxamide;
N-(4-{[1-(1,2-oxazol-5-ylcarbonyl)piperidin-4-yl]methyl}phenyl)-1-(pyridazin-3-yl)azetidine-3-carboxamide;
1-(pyridazin-3-yl)-N-(4-{[1-(pyridin-2-ylcarbonyl)piperidin-4-yl]methyl}phenyl)azetidine-3-carboxamide;
N-(4-{[1-(furan-3-ylcarbonyl)piperidin-4-yl]methyl}phenyl)-1-(pyridazin-3-yl)azetidine-3-carboxamide;
N-(4-{[1-(cyclopropylacetyl)piperidin-4-yl]methyl}phenyl)-1-(pyridazin-3-yl)azetidine-3-carboxamide;
N-(4-{[1-(2-methylbutanoyl)piperidin-4-yl]methyl}phenyl)-1-(pyridazin-3-yl)azetidine-3-carboxamide;
N-{4-[(1-propanoylpiperidin-4-yl)methyl]phenyl}-1-(pyridazin-3-yl)azetidine-3-carboxamide;
N-{4-[(1-butanoylpiperidin-4-yl)methyl]phenyl}-1-(pyridazin-3-yl)azetidine-3-carboxamide;
N-(4-{[1-(cyclobutylcarbonyl)piperidin-4-yl]methyl}phenyl)-1-(pyridazin-3-yl)azetidine-3-carboxamide;
N-{4-[(1-pentanoylpiperidin-4-yl)methyl]phenyl}-1-(pyridazin-3-yl)azetidine-3-carboxamide;
N-(4-{[1-(cyclopentylacetyl)piperidin-4-yl]methyl}phenyl)-1-(pyridazin-3-yl)azetidine-3-carboxamide;
N-(4-{[1-(2-methylbenzoyl)piperidin-4-yl]methyl}phenyl)-1-(pyridazin-3-yl)azetidine-3-carboxamide;
N-(4-{[1-(3-methylpentanoyl)piperidin-4-yl]methyl}phenyl)-1-(pyridazin-3-yl)azetidine-3-carboxamide;

N-(4-{[1-(cyclohexylcarbonyl)piperidin-4-yl]methyl}phenyl)-1-(pyridazin-3-yl)azetidine-3-carboxamide;
N-(4-{[1-(3-methylbutanoyl)piperidin-4-yl]methyl}phenyl)-1-(pyridazin-3-yl)azetidine-3-carboxamide;
N-(4-{[1-(cyclopropylcarbonyl)piperidin-4-yl]methyl}phenyl)-1-(pyridazin-3-yl)azetidine-3-carboxamide;
1-(pyridazin-3-yl)-N-(4-{[1-(3,3,3-trifluoropropanoyl)piperidin-4-yl]methyl}phenyl)azetidine-3-carboxamide;
N-{4-[1-(3,3-dimethylbutanoyl)piperidin-4-yl]phenyl}-1-(4-methylpyridazin-3-yl)azetidine-3-carboxamide;
N-{1-[1-(3,3-dimethylbutanoyl)piperidin-4-yl]-1H-pyrazol-4-yl}-1-(pyridazin-3-yl)azetidine-3-carboxamide;
N-{1-[1-(2-fluorobenzoyl)piperidin-4-yl]-1H-pyrazol-4-yl}-1-(pyridazin-3-yl)azetidine-3-carboxamide;
N-[4-(phenylcarbamoyl)phenyl]-1-(pyridazin-3-yl)azetidine-3-carboxamide;
N-{4[(2,2-dimethylpropyl)carbamoyl]phenyl}-1-(pyridazin-3-yl)azetidine-3-carboxamide;
N-{4-[(3-methoxy-2,2-dimethylpropyl)carbamoyl]phenyl}-1-(pyridazin-3-yl)azetidine-3-carboxamide;
N-{4[(2-cyclopropylethyl)carbamoyl]phenyl}-1-(pyridazin-3-yl)azetidine-3-carboxamide;
N-(4-{[2-(2-ethylpiperidin-1-yl)ethyl]carbamoyl}phenyl)-1-(pyridazin-3-yl)azetidine-3-carboxamide;
N-{4-[(cyclobutylmethyl)carbamoyl]phenyl}-1-(pyridazin-3-yl)azetidine-3-carboxamide;
N-{4-[(2S)-butan-2-ylcarbamoyl]phenyl}-1-(pyridazin-3-yl)azetidine-3-carboxamide;
N-[4-(butylcarbamoyl)phenyl]-1-(pyridazin-3-yl)azetidine-3-carboxamide;
N-{4-[(2,2-dimethyltetrahydro-2H-pyran-4-yl)carbamoyl]phenyl}-1-(pyridazin-3-yl)azetidine-3-carboxamide;
N-(4-{[(1S)-1-cyclopropylethyl]carbamoyl}phenyl)-1-(pyridazin-3-yl)azetidine-3-carboxamide;
N-(4-({2-[methyl(phenyl)amino]ethyl}carbamoyl)phenyl]-1-(pyridazin-3-yl)azetidine-3-carboxamide;
N-{4-[1,1'-bi(cyclopropyl)-1-ylcarbamoyl]phenyl}-1-(pyridazin-3-yl)azetidine-3-carboxamide;
1-(pyridazin-3-yl)-N-{4-[(thiophen-3-ylcarbamoyl)phenyl]azetidine-3-carboxamide;
N-(4-{[(1R)-1-cyclopropylethyl]carbamoyl}phenyl)-1-(pyridazin-3-yl)azetidine-3-carboxamide;
N-{4-[(1-methylpiperidin-4-yl)carbamoyl]phenyl}-1-(pyridazin-3-yl)azetidine-3-carboxamide;
N-{4[(2R)-butan-2-ylcarbamoyl]phenyl}-1-(pyridazin-3-yl)azetidine-3-carboxamide;
N-[4-(1-azabicyclo[2.2.2]oct-3-ylcarbamoyl)phenyl]-1-(pyridazin-3-yl)azetidine-3-carboxamide;
1-(pyridazin-3-yl)-N-{4-[(tetrahydrofuran-3-ylmethyl)carbamoyl]phenyl}azetidine-3-carboxamide;
N-{4-[(oxetan-3-ylmethyl)carbamoyl]phenyl}-1-(pyridazin-3-yl)azetidine-3-carboxamide;
N-{4-[(2-methylcyclopropyl)carbamoyl]phenyl}-1-(pyridazin-3-yl)azetidine-3-carboxamide;
N-[4-(cyclobutylcarbamoyl)phenyl]-1-(pyridazin-3-yl)azetidine-3-carboxamide;
N-{4-[(1-methylcyclopropyl)carbamoyl]phenyl}-1-(pyridazin-3-yl)azetidine-3-carboxamide;
N-{4-[(2-methoxy-2-methylpropyl)carbamoyl]phenyl}-1-(pyridazin-3-yl)azetidine-3-carboxamide;
N-{4-[(cyclopropylmethyl)carbamoyl]phenyl}-1-(pyridazin-3-yl)azetidine-3-carboxamide;
1-(pyridazin-3-yl)-N-(4-{[(2R)-tetrahydrofuran-2-ylmethyl]carbamoyl}phenyl)azetidine-3-carboxamide;
1-(pyridazin-3-yl)-N-{4[(3,3,3-trifluoropropyl)carbamoyl]phenyl}azetidine-3-carboxamide;
N-{4[(1-methylpiperidin-3-yl)carbamoyl]phenyl}-1-(pyridazin-3-yl)azetidine-3-carboxamide;
N-(4-{[(3-methyloxetan-3-yl)methyl]carbamoyl}phenyl)-1-(pyridazin-3-yl)azetidine-3-carboxamide;
1-(pyridazin-3-yl)-N-(4-{[(2S)-tetrahydrofuran-2-ylmethyl]carbamoyl}phenyl)azetidine-3-carboxamide;
1-(pyridazin-3-yl)-N-{4-[(tetrahydro-2H-pyran-4-ylmethyl)carbamoyl]phenyl}azetidine-3-carboxamide;
1-(pyridazin-3-yl)-N-[4-(tetrahydro-2H-pyran-4-ylcarbamoyl)phenyl]azetidine-3-carboxamide;
N-(4-{[(1-methylpiperidin-3-yl)methyl]carbamoyl}phenyl)-1-(pyridazin-3-yl)azetidine-3-carboxamide;
N-[4-(cyclopropylcarbamoyl)phenyl]-1-(pyridazin-3-yl)azetidine-3-carboxamide;
N-[4-(cyclopentylcarbamoyl)phenyl]-1-(pyridazin-3-yl)azetidine-3-carboxamide;
N-[4-(benzylcarbamoyl)phenyl]-1-(pyridazin-3-yl)azetidine-3-carboxamide;
N-{4-[(3-fluorophenyl)carbamoyl]phenyl}-1-(pyridazin-3-yl)azetidine-3-carboxamide;
N-[4-(propylcarbamoyl)phenyl]-1-(pyridazin-3-yl)azetidine-3-carboxamide;
N-{4-[(4-fluorophenyl)carbamoyl]phenyl}-1-(pyridazin-3-yl)azetidine-3-carboxamide;
N-{4-[(2-fluorophenyl)carbamoyl]phenyl}-1-(pyridazin-3-yl)azetidine-3-carboxamide;
N-{4-[(1-methylcyclobutyl)carbamoyl]phenyl}-1-(pyridazin-3-yl)azetidine-3-carboxamide;
N-[4-(prop-2-en-1-ylcarbamoyl)phenyl]-1-(pyridazin-3-yl)azetidine-3-carboxamide;
5-[1-(2,2-dimethylpropanoyl)piperidin-4-yl]-N-[(3S)-1-(pyridazin-3-yl)pyrrolidin-3-yl]thiophene-2-carboxamide;
5-[1-(3,3-dimethylbutanoyl)piperidin-4-yl]-N-[(3S)-1-(pyridazin-3-yl)pyrrolidin-3-yl]thiophene-2-carboxamide;
5-[1-(2,2-dimethylbutanoyl)piperidin-4-yl]-N-[(3S)-1-(pyridazin-3-yl)pyrrolidin-3-yl]thiophene-2-carboxamide;
5-{1-[(1-methylcyclopropyl)carbonyl]piperidin-4-yl}-N-[(3S)-1-(pyridazin-3-yl)pyrrolidin-3-yl]thiophene-2-carboxamide;
N-[(3S)-1-(pyridazin-3-yl)pyrrolidin-3-yl]-5-[1-(3,3,3-trifluoropropanoyl)piperidin-4-yl]thiophene-2-carboxamide;
5-[1-(cyclopropylacetyl)piperidin-4-yl]-N-[(3S)-1-(pyridazin-3-yl)pyrrolidin-3-yl]thiophene-2-carboxamide;
5-[1-(bicyclo[2.2.1]hept-2-ylacetyl)piperidin-4-yl]-N-[(3S)-1-(pyridazin-3-yl)pyrrolidin-3-yl]thiophene-2-carboxamide;
1-(pyridazin-3-yl)-N-{4-[(3S)-tetrahydrofuran-3-ylcarbamoyl]phenyl}azetidine-3-carboxamide;
N-[4-({4-[2-(dimethylamino)ethyl]phenyl}carbamoyl)phenyl]-1-(pyridazin-3-yl)azetidine-3-carboxamide;
1-(pyridazin-3-yl)-N-{4-[(3R)-tetrahydrofuran-3-ylcarbamoyl]phenyl}azetidine-3-carboxamide;
N-{4-[(2-methoxyethyl)carbamoyl]phenyl}-1-(pyridazin-3-yl)azetidine-3-carboxamide;
N-{4-[1-(3-amino-2,2-dimethylpropyl)-1H-pyrazol-4-yl]phenyl}-1-(pyridazin-3-yl)azetidine-3-carboxamide;
N-(4-{1-[2,2-dimethyl-3-(piperazin-1-yl)propyl]-1H-pyrazol-4-yl}phenyl)-1-(pyridazin-3-yl)azetidine-3-carboxamide;
N-(4-{1-[2-methyl-2-(piperazin-1-yl)propanoyl]piperidin-4-yl}phenyl)-1-(pyridazin-3-yl)azetidine-3-carboxamide;
and pharmaceutically acceptable salts thereof.

Still another embodiment pertains to compounds of Formula (IA), selected from the group consisting of
N-{4-[1-(2-methylpropanoyl)piperidin-4-yl]phenyl}-1-(pyridazin-3-yl)azetidine-3-carboxamide;
(3S)—N-{4-[1-(2-methylpropanoyl)piperidin-4-yl]phenyl}-1-(pyridazin-3-yl)pyrrolidine-3-carboxamide;
(3S)—N-{4-[1-(2,2-dimethylpropanoyl)piperidin-4-yl]phenyl}-1-(pyridazin-3-yl)pyrrolidine-3-carboxamide;
N-[4-(1-acetylpiperidin-4-yl)phenyl]-1-(pyridazin-3-yl)azetidine-3-carboxamide;
N-[4-(1-butanoylpiperidin-4-yl)phenyl]-1-(pyridazin-3-yl)azetidine-3-carboxamide;
N-{4-[1-(3-methylbutanoyl)piperidin-4-yl]phenyl}-1-(pyridazin-3-yl)azetidine-3-carboxamide;
1-(pyridazin-3-yl)-N-{4-[1-(3,3,3-trifluoropropanoyl)piperidin-4-yl]phenyl}azetidine-3-carboxamide;
N-{4-[1-(methoxyacetyl)piperidin-4-yl]phenyl}-1-(pyridazin-3-yl)azetidine-3-carboxamide;
N-(4-{1-[(methylsulfanyl)acetyl]piperidin-4-yl}phenyl)-1-(pyridazin-3-yl)azetidine-3-carboxamide;
N-{4-[1-(2,2-dimethylpropanoyl)piperidin-4-yl]phenyl}-1-(pyridazin-3-yl)azetidine-3-carboxamide;
1-(pyridazin-3-yl)-N-{4-[1-(4,4,4-trifluorobutanoyl)piperidin-4-yl]phenyl}azetidine-3-carboxamide;
N-[4-(1-propanoylpiperidin-4-yl)phenyl]-1-(pyridazin-3-yl)azetidine-3-carboxamide;
(3S)—N-[4-(1-propanoylpiperidin-4-yl)phenyl]-1-(pyridazin-3-yl)pyrrolidine-3-carboxamide;
(3S)—N-[4-(1-butanoylpiperidin-4-yl)phenyl]-1-(pyridazin-3-yl)pyrrolidine-3-carboxamide;
(3S)—N-[4-(1-acetylpiperidin-4-yl)phenyl]-1-(pyridazin-3-yl)pyrrolidine-3-carboxamide;
(3S)—N-{4-[1-(2-methylbutanoyl)piperidin-4-yl]phenyl}-1-(pyridazin-3-yl)pyrrolidine-3-carboxamide;
(3S)—N-{4-[1-(2-ethylbutanoyl)piperidin-4-yl]phenyl}-1-(pyridazin-3-yl)pyrrolidine-3-carboxamide;
(3S)—N-{4-[1-(3,3-dimethylbutanoyl)piperidin-4-yl]phenyl}-1-(pyridazin-3-yl)pyrrolidine-3-carboxamide;
(3S)—N-{4-[1-(3-methylbutanoyl)piperidin-4-yl]phenyl}-1-(pyridazin-3-yl)pyrrolidine-3-carboxamide;
(3R)—N-{4-[1-(2,2-dimethylpropanoyl)piperidin-4-yl]phenyl}-1-(pyridazin-3-yl)pyrrolidine-3-carboxamide; and pharmaceutically acceptable salts thereof.

Embodiments of Formula (IIC)

In another aspect, the present invention provides compounds of Formula (IIC)

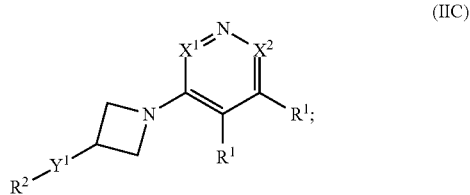

(IIC)

and pharmaceutically acceptable salts thereof; wherein $X^1$, $X^2$, $Y^1$, $R^1$, and $R^2$ are as described herein for Formula (IC).

One embodiment of this invention pertains to compounds of Formula (IIC) and pharmaceutically acceptable salts thereof;
wherein
$X^1$ is N and $X^2$ is $CR^1$; or
$X^1$ is $CR^1$ and $X^2$ is N; or
$X^1$ is $CR^1$ and $X^2$ is $CR^1$;
$Y^1$ is C(O)NH, or NHC(O);

$R^1$, at each occurrence, is independently selected from the group consisting of hydrogen, alkyl, alkenyl, alkynyl, haloalkyl, hydroxyalkyl, alkoxy, OH, $NH_2$, CN, $NO_2$, F, Cl, Br and I;

$R^2$ is independently selected from the group consisting of $C_4$-$C_6$-alkyl, $C_4$-$C_6$-alkenyl, $C_4$-$C_6$-alkynyl, aryl, and 5-6 membered heteroaryl; wherein each $R^2C_4$-$C_6$-alkyl, $C_4$-$C_6$-alkenyl, and $C_4$-$C_6$-alkynyl is substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(N)NH_2$, $C(N)NHR^3$, $C(N)N(R^3)_2$, CNOH, $CNOCH_3$, OH, (O), CN, $N_3$, $NO_2$, F, Cl, Br and I; wherein each $R^2$ aryl and 5-6 membered heteroaryl is optionally substituted with one or more substituents independently selected from the group consisting of $R^4$, $OR^4$, $SR^4$, $S(O)R^4$, $SO_2R^4$, $C(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, and I;

$R^3$, at each occurrence, is independently selected from the group consisting of alkyl, alkenyl, alkynyl, aryl, cycloalkyl, cycloalkenyl, and heterocyclyl; wherein each $R^3$ alkyl, alkenyl, and alkynyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, CNOH, $CNOCH_3$, OH, (O), CN, $N_3$, $NO_2$, F, Cl, Br and I; wherein each $R^3$ aryl, cycloalkyl, cycloalkenyl, and heterocyclyl is optionally substituted with one or more substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $C(N)NH_2$, $C(N)NHR^6$, $C(N)N(R^6)_2$, CNOH, $CNOCH_3$, OH, CN, $N_3$, $NO_2$, F, Cl, Br and I;

$R^4$, at each occurrence, is independently selected from the group consisting of alkyl, alkenyl, alkynyl, aryl, heterocyclyl, cycloalkyl, and cycloalkenyl; wherein each $R^4$ alkyl, alkenyl, and alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, C(O)OH, C(N)NH$_2$, C(N)NHR$^7$, C(N)N(R$^7$)$_2$, CNOH, CNOCH$_3$, OH, (O), CN, N$_3$, NO$_2$, F, Cl, Br and I;

R$^5$, at each occurrence, is independently selected from the group consisting of alkyl, alkenyl, alkynyl, aryl, heterocyclyl, cycloalkyl, and cycloalkenyl; wherein each R$^5$ alkyl, alkenyl, and alkynyl is optionally substituted with one or more substituents independently selected from the group consisting of R$^8$, OR$^8$, SR$^8$, S(O)R$^8$, SO$_2$R$^8$, NHR$^8$, N(R$^8$)$_2$, C(O)R$^8$, C(O)NH$_2$, C(O)NHR$^8$, C(O)N(R$^8$)$_2$, NHC(O)R$^8$, NR$^8$C(O)R$^8$, NHSO$_2$R$^8$, NHC(O)OR$^8$, SO$_2$NH$_2$, SO$_2$NHR$^8$, SO$_2$N(R$^8$)$_2$, NHC(O)NH$_2$, NHC(O)NHR$^8$, OH, (O), C(O)OH, N$_3$, CN, NH$_2$, F, Cl, Br and I;

R$^6$, at each occurrence, is independently selected from the group consisting of alkyl, alkenyl, alkynyl, aryl, heterocyclyl, cycloalkyl, and cycloalkenyl; wherein each R$^6$ alkyl, alkenyl, and alkynyl is optionally substituted with one or more substituents independently selected from the group consisting of R$^9$, OR$^9$, SR$^9$, S(O)R$^9$, SO$_2$R$^9$, NHR$^9$, N(R$^9$)$_2$, C(O)R$^9$, C(O)NH$_2$, C(O)NHR$^9$, C(O)N(R$^9$)$_2$, NHC(O)R$^9$, NR$^9$C(O)R$^9$, NHSO$_2$R$^9$, NHC(O)OR$^9$, SO$_2$NH$_2$, SO$_2$NHR$^9$, SO$_2$N(R$^9$)$_2$, NHC(O)NH$_2$, NHC(O)NHR$^9$, OH, (O), C(O)OH, N$_3$, CN, NH$_2$, CF$_3$, CF$_2$CF$_3$, F, Cl, Br and I;

R$^7$, at each occurrence, is independently selected from the group consisting of alkyl, alkenyl, alkynyl, aryl, heterocyclyl, cycloalkyl, and cycloalkenyl;

R$^8$, at each occurrence, is independently selected from the group consisting of alkyl, alkenyl, alkynyl, aryl, heterocyclyl, cycloalkyl, and cycloalkenyl;

R$^9$, at each occurrence, is independently selected from the group consisting of alkyl, alkenyl, alkynyl, aryl, heterocyclyl, cycloalkyl, and cycloalkenyl;

wherein the cyclic moieties represented by R$^4$, R$^5$, R$^6$, R$^7$, R$^8$, and R$^9$ are independently optionally substituted with one or more substituents independently selected from the group consisting of R$^{10}$, OR$^{10}$, Se, S(O)R$^{10}$, SO$_2$R$^{10}$, C(O)R$^{10}$, CO(O)R$^{10}$, OC(O)R$^{10}$, OC(O)OR$^{10}$, C(O)C(O)R$^{10}$, NH$_2$, NHR$^{10}$, N(R$^{10}$)$_2$, NHC(O)R$^{10}$, NR$^{10}$C(O)R$^{10}$, NHS(O)$_2$R$^{10}$, NR$^{10}$S(O)$_2$R$^{10}$, NHC(O)OR$^{10}$, NR$^{10}$C(O)OR$^{10}$, NHC(O)NH$_2$, NHC(O)NHR$^{10}$, NHC(O)N(R$^{10}$)$_2$, NR$^{10}$C(O)NHR$^{10}$, NR$^{10}$C(O)N(R$^{10}$)$_2$, C(O)NH$_2$, C(O)NHR$^{10}$, C(O)N(R$^{10}$)$_2$, C(O)NHOH, C(O)NHOR$^{10}$, C(O)NHSO$_2$R$^{10}$, C(O)NR$^{16}$SO$_2$R$^{16}$, SO$_2$NH$_2$, SO$_2$NHR$^{10}$, SO$_2$N(R$^{10}$)$_2$, C(O)H, C(O)OH, C(N)NH$_2$, C(N)NHR$^{10}$, C(N)N(R$^{10}$)$_2$, CNOH, CNOCH$_3$, OH, CN, N$_3$, NO$_2$, F, Cl, Br and I;

R$^{10}$, at each occurrence, is independently selected from the group consisting of alkyl, alkenyl, alkynyl, aryl, heterocyclyl, cycloalkyl, and cycloalkenyl; wherein each R$^{10}$ alkyl, alkenyl, and alkynyl is optionally substituted with one or more substituents independently selected from the group consisting of R$^{11}$, OR$^{11}$, SR$^{11}$, S(O)R$^{11}$, SO$_2$R$^{11}$, C(O)R$^{11}$, CO(O)R$^{11}$, OC(O)R$^{11}$, OC(O)OR$^{11}$, NH$_2$, NHR$^{11}$, N(R$^{11}$)$_2$, NHC(O)R$^{11}$, NR$^{11}$C(O)R$^{11}$, NHS(O)$_2$R$^{11}$, NR$^{11}$S(O)$_2$R$^{11}$, NHC(O)OR$^{11}$, NR$^{11}$C(O)OR$^{11}$, NHC(O)NH$_2$, NHC(O)NHR$^{11}$, NHC(O)N(R$^{11}$)$_2$, NR$^{11}$C(O)NHR$^{11}$, NR$^{11}$C(O)N(R$^{11}$)$_2$, C(O)NH$_2$, C(O)NHR$^{11}$, C(O)N(R$^{11}$)$_2$, C(O)NHOH, C(O)NHOR$^{11}$, C(O)NHSO$_2$R$^{11}$, C(O)NR$^{11}$SO$_2$R$^{11}$, SO$_2$NH$_2$, SO$_2$NHR$^{11}$, SO$_2$N(R$^{11}$)$_2$, C(O)H, C(O)OH, C(N)NH$_2$, C(N)NHR$^{11}$, C(N)N(R$^{11}$)$_2$, CNOH, CNOCH$_3$, OH, (O), CN, N$_3$, NO$_2$, F, Cl, Br and I; wherein each R$^{10}$ aryl, heterocyclyl, cycloalkyl, and cycloalkenyl is optionally substituted with one or more substituents independently selected from the group consisting of R$^{12}$, OR$^{12}$, SR$^{12}$, S(O)R$^{12}$, SO$_2$R$^{12}$, C(O)R$^{12}$, CO(O)R$^{12}$, OC(O)R$^{12}$, OC(O)OR$^{12}$, NH$_2$, NHR$^{12}$, N(R$^{12}$)$_2$, NHC(O)R$^{12}$, NR$^{12}$C(O)R$^{12}$, NHS(O)$_2$R$^{12}$, NR$^{12}$S(O)$_2$R$^{12}$, NHC(O)OR$^{12}$, NR$^{12}$C(O)OR$^{12}$, NHC(O)NH$_2$, NHC(O)NHR$^{12}$, NHC(O)N(R$^{12}$)$_2$, NR$^{12}$C(O)NHR$^{12}$, NR$^{12}$C(O)N(R$^{12}$)$_2$, C(O)NH$_2$, C(O)NHR$^{12}$, C(O)N(R$^{12}$)$_2$, C(O)NHOH, C(O)NHOR$^{12}$, C(O)NHSO$_2$R$^{12}$, C(O)NR$^{12}$SO$_2$R$^{12}$, SO$_2$NH$_2$, SO$_2$NHR$^{12}$, SO$_2$N(R$^{12}$)$_2$, C(O)H, C(O)OH, C(N)NH$_2$, C(N)NHR$^{12}$, C(N)N(R$^{12}$)$_2$, CNOH, CNOCH$_3$, OH, CN, N$_3$, NO$_2$, CF$_3$, OCF$_3$, F, Cl, Br and I;

R$^{11}$, at each occurrence, is independently selected from the group consisting of alkyl, alkenyl, alkynyl, aryl, heterocyclyl, cycloalkyl, and cycloalkenyl; wherein each R$^{11}$ alkyl, alkenyl, and alkynyl is optionally substituted with alkoxy or aryl; wherein each R$^{11}$ aryl, heterocyclyl, cycloalkyl, and cycloalkenyl is optionally substituted with one or more substituents independently selected from the group consisting of R$^{13}$, OR$^{13}$, C(O)OR$^{13}$, OCF$_3$, CF$_3$, F, Cl, Br and I;

R$^{12}$, at each occurrence, is independently selected from the group consisting of alkyl, alkenyl, alkynyl, aryl, heterocyclyl, cycloalkyl, and cycloalkenyl; and R$^{13}$, at each occurrence, is independently selected from the group consisting of alkyl, haloalkyl, alkenyl, alkynyl, aryl, heterocyclyl, cycloalkyl, and cycloalkenyl.

In one embodiment of Formula (IIC), X$^1$ is N and X$^2$ is CR$^1$; or X$^1$ is CR$^1$ and X$^2$ is N; or X$^1$ is CR$^1$ and X$^2$ is CR$^1$. In another embodiment of Formula (IIC), X$^1$ is N and X$^2$ is CR$^1$. In another embodiment of Formula (IIC), X$^1$ is CR$^1$ and X$^2$ is N. In another embodiment of Formula (IIC), X$^1$ is CR$^1$ and X$^2$ is CR$^1$.

In one embodiment of Formula (IIC), Y$^1$ is C(O)NH, or NHC(O). In another embodiment of Formula (IIC), Y$^1$ is C(O)NH. In another embodiment of Formula (IIC), Y$^1$ is NHC(O).

In one embodiment of Formula (IIC), X$^1$ is CR$^1$ and X$^2$ is CR$^1$; and R$^1$, at each occurrence, is independently selected from the group consisting of hydrogen, alkyl, alkenyl, alkynyl, haloalkyl, hydroxyalkyl, alkoxy, OH, NH$_2$, CN, NO$_2$, F, Cl, Br and I. In another embodiment of Formula (IIC), X$^1$ is CR$^1$ and X$^2$ is CR$^1$; and R$^1$, at each occurrence, is independently selected from the group consisting of hydrogen, alkyl, haloalkyl, alkoxy, CN, F, Cl, Br and I. In another embodiment of Formula (IIC), X$^1$ is CR$^1$ and X$^2$ is CR$^1$; and R$^1$, at each occurrence, is independently selected from the group consisting of hydrogen, alkyl, haloalkyl, alkoxy, CN, F, and Cl. In another embodiment of Formula (IIC), X$^1$ is CR$^1$ and X$^2$ is CR$^1$; and R$^1$, at each occurrence, is hydrogen.

In another aspect, the present invention provides compounds of Formula (IID),

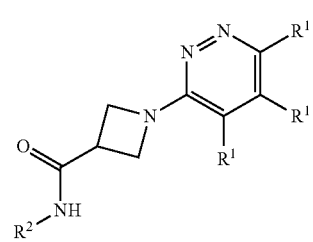

Formula (IID)

and pharmaceutically acceptable salts thereof; wherein R$^1$ and R$^2$ are as described herein for Formula (IC).

In one embodiment of Formula (IIC) and (IID), R$^1$, at each occurrence, is independently selected from the group consisting of hydrogen, alkyl, alkenyl, alkynyl, haloalkyl, hydroxyalkyl, alkoxy, OH, NH$_2$, CN, NO$_2$, F, Cl, Br and I. In another embodiment of Formula (IIC) and (IID), R$^1$, at each occurrence, is independently selected from the group consisting of hydrogen, alkyl, haloalkyl, alkoxy, CN, F, Cl, Br and I. In another embodiment of Formula (IIC) and (IID), R$^1$, at each occurrence, is independently selected from the group consisting of hydrogen, alkyl, haloalkyl, alkoxy, CN, F, and Cl. In another embodiment of Formula (IIC) and (IID), $R^1$, at each occurrence, is hydrogen.

In one embodiment of Formula (IIC) and (IID), $R^2$ is independently selected from the group consisting of $C_4$-$C_6$-alkyl, $C_4$-$C_6$-alkenyl, $C_4$-$C_6$-alkynyl, aryl, and 5-6 membered heteroaryl; wherein each $R^2 C_4$-$C_6$-alkyl, $C_4$-$C_6$-alkenyl, and $C_4$-$C_6$-alkynyl is substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(N)NH_2$, $C(N)NHR^3$, $C(N)N(R^3)_2$, CNOH, CNOCH$_3$, OH, (O), CN, $N_3$, $NO_2$, F, Cl, Br and I; wherein each $R^2$ aryl and 5-6 membered heteroaryl is optionally substituted with one or more substituents independently selected from the group consisting of $R^4$, $OR^4$, $SR^4$, $S(O)R^4$, $SO_2R^4$, $C(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, CNOCH$_3$, OH, CN, $N_3$, $NO_2$, F, Cl, and I. In another embodiment of Formula (IIC) and (IID), $R^2$ is aryl; wherein each $R^2$ aryl is optionally substituted with one or more substituents independently selected from the group consisting of $R^4$, $OR^4$, $SO_2R^4$, $C(O)NHR^4$, F, Cl, and I. In another embodiment of Formula (IIC) and (IID), $R^2$ is aryl; wherein each $R^2$ aryl is optionally substituted with one or more substituents independently selected from the group consisting of $R^4$, $OR^4$, $SO_2R^4$, $C(O)NHR^4$, and F. In another embodiment of Formula (IIC) and (IID), $R^2$ is phenyl; wherein each $R^2$ phenyl is optionally substituted with one or more substituents independently selected from the group consisting of $R^4$, $OR^4$, $SO_2R^4$, $C(O)NHR^4$, and F. In another embodiment of Formula (IIC) and (IID), $R^2$ is phenyl; wherein each $R^2$ phenyl is substituted with one substituent independently selected from the group consisting of $R^4$, $OR^4$, and $SO_2R^4$.

In another embodiment of Formula (IIC) and (IID), $R^2$ is 5-6 membered heteroaryl; wherein each $R^2$ 5-6 membered heteroaryl is optionally substituted with one or more substituents independently selected from the group consisting of $R^4$, $OR^4$, $SO_2R^4$, $C(O)NHR^4$, F, Cl, and I. In another embodiment of Formula (IIC) and (IID), $R^2$ is 5-6 membered heteroaryl; wherein each $R^2$ 5-6 membered heteroaryl is optionally substituted with one or more substituents independently selected from the group consisting of $R^4$, $OR^4$, $SO_2R^4$, $C(O)NHR^4$, and F. In another embodiment of Formula (IIC) and (IID), $R^2$ is pyridinyl, furanyl, thiophenyl, pyrazole, or thiazolyl; wherein each $R^2$ pyridinyl, furanyl, thiophenyl, pyrazole, and thiazolyl is optionally substituted with one or more substituents independently selected from the group consisting of $R^4$, $OR^4$, $SO_2R^4$, $C(O)NHR^4$, and F.

In one embodiment of Formula (IIC) and (IID), $R^4$, at each occurrence, is independently selected from the group consisting of alkyl, alkenyl, alkynyl, aryl, heterocyclyl, cycloalkyl, and cycloalkenyl; wherein each $R^4$ alkyl, alkenyl, and alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, CNOH, CNOCH$_3$, OH, (O), CN, $N_3$, $NO_2$, F, Cl, Br and I. In another embodiment of Formula (IIC) and (IID), $R^4$, at each occurrence, is independently selected from the group consisting of alkyl, alkenyl, alkynyl, aryl, heterocyclyl, and cycloalkyl.

In one embodiment of Formula (IIC) and (IID), each $R^4$ alkyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R)_2$, CNOH, CNOCH$_3$, OH, (O), CN, $N_3$, $NO_2$, F, Cl, Br and I. In another embodiment of Formula (IIC) and (IID), each $R^4$ alkyl is optionally substituted with one or more substituents independently selected from the group consisting of $R^7$, $OR^7$, $N(R^7)_2$, F, Cl, Br and I.

In one embodiment of Formula (IIC) and (IID), $R^7$, at each occurrence, is independently selected from the group consisting of alkyl, alkenyl, alkynyl, aryl, heterocyclyl, cycloalkyl, and cycloalkenyl. In another embodiment of Formula (IIC) and (IID), $R^7$, at each occurrence, is independently selected from the group consisting of alkyl, aryl, heterocyclyl, and cycloalkyl.

In one embodiment of Formula (IIC) and (IID), each $R^4$ and $R^7$ cyclic moiety is independently optionally substituted with one or more substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, CNOH, CNOCH$_3$, OH, CN, $N_3$, $NO_2$, F, Cl, Br and I; $R^{10}$, at each occurrence, is independently selected from the group consisting of alkyl, alkenyl, alkynyl, aryl, heterocyclyl, cycloalkyl, and cycloalkenyl; wherein each $R^{10}$ alkyl, alkenyl, and alkynyl is optionally substituted with one or more substituents independently selected from the group consisting of $R^{11}$, $OR^{11}$, $SR^{11}$, $S(O)R^{11}$, $SO_2R^{11}$, $C(O)R^{11}$, $CO(O)R^{11}$, $OC(O)R^{11}$, $OC(O)OR^{11}$, $NH_2$, $NHR^{11}$, $N(R^{11})_2$, $NHC(O)R^{11}$, $NR^{11}C(O)R^{11}$, $NHS(O)_2R^{11}$, $NR^{11}S(O)_2R^{11}$, $NHC(O)OR^{11}$, $NR^{11}C(O)OR^{11}$, $NHC(O)NH_2$, $NHC(O)NHR^{11}$, $NHC(O)N(R^{11})_2$, $NR^{11}C(O)NHR^{11}$, $NR^{11}C(O)N(R^{11})_2$, $C(O)NH_2$, $C(O)NHR^{11}$, $C(O)N(R^{11})_2$, $C(O)NHOH$, $C(O)NHOR^{11}$, $C(O)NHSO_2R^{11}$, $C(O)NR^{11}SO_2R^{11}$, $SO_2NH_2$, $SO_2NHR^{11}$, $SO_2N(R^{11})_2$, $C(O)H$, $C(O)OH$, $C(N)NH_2$, $C(N)NHR^{11}$, $C(N)N(R^{11})_2$, CNOH, CNOCH$_3$, OH, (O), CN, $N_3$, $NO_2$, F, Cl, Br and I; wherein each $R^{10}$ aryl, heterocyclyl, cycloalkyl, and cycloalkenyl is optionally substituted with one or more substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, C(O)NH₂, C(O)NHR¹², C(O)N(R¹²)₂, C(O)NHOH, C(O)N-HOR¹², C(O)NHSO₂R¹², C(O)NR¹²SO₂R¹², SO₂NH₂, SO₂NHR¹², SO₂N(R¹²)₂, C(O)H, C(O)OH, C(N)NH₂, C(N)NHR¹², C(N)N(R¹²)₂, CNOH, CNOCH₃, OH, CN, N₃, NO₂, F, Cl, Br and I; R¹¹, at each occurrence, is independently selected from the group consisting of alkyl, alkenyl, alkynyl, aryl, heterocyclyl, cycloalkyl, and cycloalkenyl; wherein each R¹¹ alkyl, alkenyl, and alkynyl is optionally substituted with alkoxy or aryl; wherein each R¹¹ aryl, heterocyclyl, cycloalkyl, and cycloalkenyl is optionally substituted with one or more substituents independently selected from the group consisting of R¹³, OR¹³, C(O)OR¹³, OCF₃, CF₃, F, Cl, Br and I; R¹², at each occurrence, is independently selected from the group consisting of alkyl, alkenyl, alkynyl, aryl, heterocyclyl, cycloalkyl, and cycloalkenyl; and R¹³, at each occurrence, is independently selected from the group consisting of alkyl, haloalkyl, alkenyl, alkynyl, aryl, heterocyclyl, cycloalkyl, and cycloalkenyl.

In another embodiment of Formula (IIC) and (IID), each R⁴ and R⁷ cyclic moiety is independently optionally substituted with one or more substituents independently selected from the group consisting of R¹⁰, C(O)R¹⁰, CO(O)R¹⁰, C(O)C(O)R¹⁰, CO(O)H, OH, F, Cl, Br and I; R¹⁰, at each occurrence, is independently selected from the group consisting of alkyl, alkenyl, alkynyl, aryl, heterocyclyl, and cycloalkyl; wherein each R¹⁰ alkyl, alkenyl, and alkynyl, are optionally substituted with one or more substituents independently selected from the group consisting of R¹¹, OR¹¹, SR¹¹, SO₂R¹¹, NH₂, N(R¹¹)₂, NHC(O)R¹¹, NHS(O)₂R¹¹, OH, NO₂, and F; wherein each R¹⁰ aryl, heterocyclyl and cycloalkyl is optionally substituted with one or more substituents independently selected from the group consisting of R¹², OR¹², C(O)R¹², NH₂, OH, CN, CF₃, OCF₃, F, and Cl; R¹¹, at each occurrence, is independently selected from the group consisting of alkyl, aryl, heterocyclyl, and cycloalkyl; wherein each R¹¹ alkyl is optionally substituted with alkoxy or aryl; wherein each R¹¹ aryl and heterocyclyl is optionally substituted with one or more substituents independently selected from the group consisting of R¹³, CF₃, F, and Cl; R¹², at each occurrence, is independently selected from the group consisting of alkyl and aryl; and R¹³, at each occurrence, is independently selected from the group consisting of alkyl, haloalkyl, and cycloalkyl.

One embodiment of this invention pertains to compounds or pharmaceutically acceptable salts thereof, which are useful as inhibitors of NAMPT, the compounds having Formula (IIC)

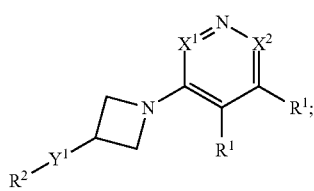

Formula (IIC)

wherein
X¹ is N and X² is CR¹; or
X¹ is CR¹ and X² is N; or
X¹ is CR¹ and X² is CR¹;
Y¹ is C(O)NH, or NHC(O);
R¹, at each occurrence, is independently selected from the group consisting of hydrogen, alkyl, haloalkyl, alkoxy, CN, Cl, and F;

R² is aryl or 5-6 membered heteroaryl wherein each R² aryl and 5-6 membered heteroaryl is optionally substituted with one or more substituents independently selected from the group consisting of R⁴, SO₂R⁴, OR⁴, C(O)NHR⁴, and F;

R⁴, at each occurrence, is independently selected from the group consisting of alkyl, alkenyl, aryl, heterocyclyl, and cycloalkyl; wherein each R⁴ alkyl is optionally substituted with one or more substituents independently selected from the group consisting of R⁷, OR⁷, N(R⁷)₂, and F;

R⁷, at each occurrence, is independently selected from the group consisting of alkyl, aryl, heterocyclyl, and cycloalkyl;

wherein the cyclic moieties represented by R⁴ and R⁷ are independently optionally substituted with one or more substituents independently selected from the group consisting of R¹⁰, C(O)R¹⁰, C(O)C(O)R¹⁰, CO(O)R¹⁰, C(O)OH, OH and F;

R¹⁰, at each occurrence, is independently selected from the group consisting of alkyl, alkenyl, alkynyl, aryl, heterocyclyl, and cycloalkyl; wherein each R¹⁰ alkyl is optionally substituted with one or more substituents independently selected from the group consisting of R¹¹, OR¹¹, SR¹¹, SO₂R¹¹, NH₂, N(R¹¹)₂, NHC(O)R¹¹, NH S(O)₂R¹¹, OH, NO₂, and F; wherein each R¹⁰ aryl, heterocyclyl and cycloalkyl is optionally substituted with one or more R¹², OR¹², C(O)R¹², NH₂, OH, CN, CF₃, OCF₃, F, and Cl;

R¹¹, at each occurrence, is independently selected from the group consisting of alkyl, aryl, heterocyclyl, and cycloalkyl; wherein each R¹¹ alkyl is optionally substituted with alkoxy or aryl; wherein each R¹¹ aryl, and heterocyclyl is optionally substituted with one or more substituents independently selected from the group consisting of R¹³, C(O)OR¹³, OCF₃, CF₃, F, and Cl;

R¹², at each occurrence, is independently selected from the group consisting of alkyl, and aryl; and R¹³, at each occurrence, is independently selected from the group consisting of alkyl, haloalkyl, cycloalkyl, and heterocyclyl.

Still another embodiment pertains to compounds having Formula (IIC), which includes 1-(pyridin-3-yl)-N-(4-{[1-(tetrahydro-2H-pyran-4-ylacetyl)piperidin-4-yl]oxy}phenyl)azetidine-3-carboxamide;

1-(2-cyanopyridin-3-yl)-N-{4-[1-(2-hydroxy-2-methylpropanoyl)piperidin-4-yl]phenyl}azetidine-3-carboxamide;

N-(4-{[1-(tetrahydro-2H-pyran-4-ylacetyl)piperidin-4-yl]oxy}phenyl)-1-[2-(trifluoromethyl)pyridin-3-yl]azetidine-3-carboxamide;

1-(2-methylpyridin-3-yl)-N-(4-{[1-(tetrahydro-2H-pyran-4-ylacetyl)piperidin-4-yl]oxy}phenyl)azetidine-3-carboxamide;

1-(4-methylpyridin-3-yl)-N-(4-{[1-(tetrahydro-2H-pyran-4-ylacetyl)piperidin-4-yl]oxy}phenyl)azetidine-3-carboxamide;

1-(4-fluoropyridin-3-yl)-N-(4-{[1-(tetrahydro-2H-pyran-4-ylacetyl)piperidin-4-yl]oxy}phenyl)azetidine-3-carboxamide;

N-(4-{[1-(tetrahydro-2H-pyran-4-ylacetyl)piperidin-4-yl]oxy}phenyl)-1-[4-(trifluoromethyl)pyridin-3-yl]azetidine-3-carboxamide;

1-(pyridin-3-yl)-N-(4-{1-[(2S)-tetrahydro furan-2-ylcarbonyl]piperidin-4-yl}phenyl)azetidine-3-carboxamide;

N-{4-[1-(2-hydroxy-2-methylpropanoyl)piperidin-4-yl]phenyl}-1-(pyridin-3-yl)azetidine-3-carboxamide;

N-[1-(pyridin-3-yl)azetidin-3-yl]-4-{[1-(tetrahydro-2H-pyran-4-ylacetyl)piperidin-4-yl]oxy}benzamide;

N-(4-{1-[(2S)-2-methylbutanoyl]piperidin-4-yl}phenyl)-1-(pyridin-3-yl)azetidine-3-carboxamide;

4-({1-[(2S)-2-methylbutanoyl]piperidin-4-yl}oxy)-N-[1-(pyridin-3-yl)azetidin-3-yl]benzamide;
4-{[1-(2-hydroxy-2-methylpropanoyl)piperidin-4-yl]oxy}-N-[1-(pyridin-3-yl)azetidin-3-yl]benzamide;
1-(pyridin-3-yl)-N-{4-[1-(tetrahydro-2H-pyran-4-ylacetyl)piperidin-4-yl]phenyl}azetidine-3-carboxamide;
N-[4-(1-benzoylpiperidin-4-yl)phenyl]-1-(pyridin-3-yl)azetidine-3-carboxamide;
N-{4-[1-(2-methylpropanoyl)piperidin-4-yl]phenyl}-1-(2-methylpyridin-3-yl)azetidine-3-carboxamide;
N-{4-[1-(2-methylpropanoyl)piperidin-4-yl]phenyl}-1-(pyridin-3-yl)azetidine-3-carboxamide;
N-(4-{[1-(2-hydroxy-2-methylpropanoyl)piperidin-4-yl]oxy}phenyl)-1-(pyridin-3-yl)azetidine-3-carboxamide;
N-[4-({1-[(2S)-2-methylbutanoyl]piperidin-4-yl}oxy)phenyl]-1-(pyridin-3-yl)azetidine-3-carboxamide;
1-(pyridin-3-yl)-N-[4-({1-[(2S)-tetrahydro furan-2-ylcarbonyl]piperidin-4-yl}oxy)phenyl]azetidine-3-carboxamide;
N-{4-[(1-pentanoylpiperidin-4-yl)oxy]phenyl}-1-(pyridin-3-yl)azetidine-3-carboxamide;
N-[4-({1-[(2-methylcyclopropyl)carbonyl]piperidin-4-yl}oxy)phenyl]-1-(pyridin-3-yl)azetidine-3-carboxamide;
N-[4-({1-[(1S,4R)-bicyclo[2.2.1]hept-2-ylacetyl]piperidin-4-yl}oxy)phenyl]-1-(pyridin-3-yl)azetidine-3-carboxamide;
N-(4-{[1-(4-methylpentanoyl)piperidin-4-yl]oxy}phenyl)-1-(pyridin-3-yl)azetidine-3-carboxamide;
N-(4-{[1-(3-methylpentanoyl)piperidin-4-yl]oxy}phenyl)-1-(pyridin-3-yl)azetidine-3-carboxamide;
N-(4-{[1-(3-ethoxypropanoyl)piperidin-4-yl]oxy}phenyl)-1-(pyridin-3-yl)azetidine-3-carboxamide;
N-(4-{[1-(2,2-dimethylbutanoyl)piperidin-4-yl]oxy}phenyl)-1-(pyridin-3-yl)azetidine-3-carboxamide;
N-(4-{[1-(3,3-dimethylbutanoyl)piperidin-4-yl]oxy}phenyl)-1-(pyridin-3-yl)azetidine-3-carboxamide;
N-(4-{[1-(2,2-dimethylpropanoyl)piperidin-4-yl]oxy}phenyl)-1-(pyridin-3-yl)azetidine-3-carboxamide;
N-{4-[(1-butanoylpiperidin-4-yl)oxy]phenyl}-1-(pyridin-3-yl)azetidine-3-carboxamide;
N-(4-{[1-(ethoxyacetyl)piperidin-4-yl]oxy}phenyl)-1-(pyridin-3-yl)azetidine-3-carboxamide;
N-(4-{[1-(3-methylbutanoyl)piperidin-4-yl]oxy}phenyl)-1-(pyridin-3-yl)azetidine-3-carboxamide;
N-(4-{[1-(2-methylpropanoyl)piperidin-4-yl]oxy}phenyl)-1-(pyridin-3-yl)azetidine-3-carboxamide;
N-(4-{[1-(N-acetyl-L-leucyl)piperidin-4-yl]oxy}phenyl)-1-(pyridin-3-yl)azetidine-3-carboxamide;
N-[4-({1-[(2-methoxyethoxy)acetyl]piperidin-4-yl}oxy)phenyl]-1-(pyridin-3-yl)azetidine-3-carboxamide;
N-(4-{[1-(cyclohexylcarbonyl)piperidin-4-yl]oxy}phenyl)-1-(pyridin-3-yl)azetidine-3-carboxamide;
N-(4-{[1-(cyclohexylacetyl)piperidin-4-yl]oxy}phenyl)-1-(pyridin-3-yl)azetidine-3-carboxamide;
1-(pyridin-3-yl)-N-(4-{[1-(4,4,4-trifluorobutanoyl)piperidin-4-yl]oxy}phenyl)azetidine-3-carboxamide;
N-(4-{[1-(cyclopentylcarbonyl)piperidin-4-yl]oxy}phenyl)-1-(pyridin-3-yl)azetidine-3-carboxamide;
N-[4-({1-[(1-methylcyclohexyl)carbonyl]piperidin-4-yl}oxy)phenyl]-1-(pyridin-3-yl)azetidine-3-carboxamide;
N-(4-{[1-(furan-3-ylcarbonyl)piperidin-4-yl]oxy}phenyl)-1-(pyridin-3-yl)azetidine-3-carboxamide;
1-(pyridin-3-yl)-N-(4-{[1-(3,3,3-trifluoropropanoyl)piperidin-4-yl]oxy}phenyl)azetidine-3-carboxamide;
N-{4-[(1-acetylpiperidin-4-yl)oxy]phenyl}-1-(pyridin-3-yl)azetidine-3-carboxamide;
N-(4-{[1-(methoxyacetyl)piperidin-4-yl]oxy}phenyl)-1-(pyridin-3-yl)azetidine-3-carboxamide;
1-(pyridin-3-yl)-N-(4-{[1-(thiophen-3-ylcarbonyl)piperidin-4-yl]oxy}phenyl)azetidine-3-carboxamide;
N-[4-({1-[(3-methylthiophen-2-yl)carbonyl]piperidin-4-yl}oxy)phenyl]-1-(pyridin-3-yl)azetidine-3-carboxamide;
N-(4-{[1-(morpholin-4-ylacetyl)piperidin-4-yl]oxy}phenyl)-1-(pyridin-3-yl)azetidine-3-carboxamide;
1-(pyridin-3-yl)-N-(4-{[1-(thiophen-2-ylcarbonyl)piperidin-4-yl]oxy}phenyl)azetidine-3-carboxamide;
N-[4-({1-[(5-methylthiophen-2-yl)carbonyl]piperidin-4-yl}oxy)phenyl]-1-(pyridin-3-yl)azetidine-3-carboxamide;
N-(4-{[1-(furan-2-ylcarbonyl)piperidin-4-yl]oxy}phenyl)-1-(pyridin-3-yl)azetidine-3-carboxamide;
N-[4-({1-[(1-methyl-1H-pyrrol-2-yl)carbonyl]piperidin-4-yl}oxy)phenyl]-1-(pyridin-3-yl)azetidine-3-carboxamide;
N-{4-[(1-propanoylpiperidin-4-yl)oxy]phenyl}-1-(pyridin-3-yl)azetidine-3-carboxamide;
N-[4-({1-[(1-methylcyclopropyl)carbonyl]piperidin-4-yl}oxy)phenyl]-1-(pyridin-3-yl)azetidine-3-carboxamide;
N-(4-{[1-(N,N-dimethyl-beta-alanyl)piperidin-4-yl]oxy}phenyl)-1-(pyridin-3-yl)azetidine-3-carboxamide;
1-(pyridin-3-yl)-N-(4-{[1-(1,3-thiazol-2-ylcarbonyl)piperidin-4-yl]oxy}phenyl)azetidine-3-carboxamide;
N-(4-{[1-(cyclopentylacetyl)piperidin-4-yl]oxy}phenyl)-1-(pyridin-3-yl)azetidine-3-carboxamide;
N-(4-{[1-(2,3-dimethylbutanoyl)piperidin-4-yl]oxy}phenyl)-1-(pyridin-3-yl)azetidine-3-carboxamide;
N-{4-[1-(2-hydroxy-2-methylpropanoyl)piperidin-4-yl]phenyl}-1-(2-methylpyridin-3-yl)azetidine-3-carboxamide;
N-{4-[1-(2-hydroxy-2-methylpropanoyl)piperidin-4-yl]phenyl}-1-(4-methylpyridin-3-yl)azetidine-3-carboxamide;
N-{4-[1-(2-hydroxy-2-methylpropanoyl)piperidin-4-yl]phenyl}-1-(2-methoxypyridin-3-yl)azetidine-3-carboxamide;
N-(4-{[1-(cyclopropylmethyl)piperidin-4-yl]oxy}phenyl)-1-(pyridin-3-yl)azetidine-3-carboxamide;
N-(4-{[1-(2-methylpentyl)piperidin-4-yl]oxy}phenyl)-1-(pyridin-3-yl)azetidine-3-carboxamide;
N-(4-{[1-(2-methylpropyl)piperidin-4-yl]oxy}phenyl)-1-(pyridin-3-yl)azetidine-3-carboxamide;
N-(4-{[1-(3-methylbutyl)piperidin-4-yl]oxy}phenyl)-1-(pyridin-3-yl)azetidine-3-carboxamide;
N-(4-{[1-(2-ethylbutyl)piperidin-4-yl]oxy}phenyl)-1-(pyridin-3-yl)azetidine-3-carboxamide;
N-(4-{[1-(2,2-dimethylpropyl)piperidin-4-yl]oxy}phenyl)-1-(pyridin-3-yl)azetidine-3-carboxamide;
N-(4-{[1-(2-methylbutyl)piperidin-4-yl]oxy}phenyl)-1-(pyridin-3-yl)azetidine-3-carboxamide;
N-{4-[(1-propylpiperidin-4-yl)oxy]phenyl}-1-(pyridin-3-yl)azetidine-3-carboxamide;
N-(4-{[1-(2-cyclopropylethyl)piperidin-4-yl]oxy}phenyl)-1-(pyridin-3-yl)azetidine-3-carboxamide;
1-(pyridin-3-yl)-N-(4-{[1-(tetrahydrofuran-3-ylmethyl)piperidin-4-yl]oxy}phenyl)azetidine-3-carboxamide;
N-(4-{[1-(2,2-dimethylbutyl)piperidin-4-yl]oxy}phenyl)-1-(pyridin-3-yl)azetidine-3-carboxamide;
N-{4-[1-(2-hydroxy-2-methylpropanoyl)piperidin-4-yl]phenyl}-1-(pyridazin-4-yl)azetidine-3-carboxamide;
N-{4-[1-(cyclohexylmethyl)piperidin-4-yl]phenyl}-1-(pyridin-3-yl)azetidine-3-carboxamide;
N-{4-[1-(3,3-dimethylbutyl)piperidin-4-yl]phenyl}-1-(pyridin-3-yl)azetidine-3-carboxamide;
N-{4-[1-(cyclopentylmethyl)piperidin-4-yl]phenyl}-1-(pyridin-3-yl)azetidine-3-carboxamide;
N-{4-[1-(2,2-dimethylbutyl)piperidin-4-yl]phenyl}-1-(pyridin-3-yl)azetidine-3-carboxamide;

N-{4-[1-(2-methylpentyl)piperidin-4-yl]phenyl}-1-(pyridin-3-yl)azetidine-3-carboxamide;
N-[4-(1-butylpiperidin-4-yl)phenyl]-1-(pyridin-3-yl)azetidine-3-carboxamide;
N-{4-[1-(2-ethylbutyl)piperidin-4-yl]phenyl}-1-(pyridin-3-yl)azetidine-3-carboxamide;
N-{4-[1-(3-methylbutyl)piperidin-4-yl]phenyl}-1-(pyridin-3-yl)azetidine-3-carboxamide;
N-{4-[1-(2-methylpropyl)piperidin-4-yl]phenyl}-1-(pyridin-3-yl)azetidine-3-carboxamide;
N-[4-(1-propylpiperidin-4-yl)phenyl]-1-(pyridin-3-yl)azetidine-3-carboxamide;
N-{4-[1-(2-hydroxy-2-methylpropanoyl)piperidin-4-yl]phenyl}-1-(4-methoxypyridin-3-yl)azetidine-3-carboxamide;
1-(4-cyanopyridin-3-yl)-N-{4-[1-(2-hydroxy-2-methylpropanoyl)piperidin-4-yl]phenyl}azetidine-3-carboxamide;
N-[4-(1-pentanoylpiperidin-4-yl)phenyl]-1-(pyridin-3-yl)azetidine-3-carboxamide;
N-{4-[1-(3-methylpentanoyl)piperidin-4-yl]phenyl}-1-(pyridin-3-yl)azetidine-3-carboxamide;
N-(4-{1-[(1S,4R)-bicyclo[2.2.1]hept-2-ylacetyl]piperidin-4-yl}phenyl)-1-(pyridin-3-yl)azetidine-3-carboxamide;
N-{4-[1-(cyclopentylacetyl)piperidin-4-yl]phenyl}-1-(pyridin-3-yl)azetidine-3-carboxamide;
N-(4-{1-[(2-methylcyclopropyl)carbonyl]piperidin-4-yl}phenyl)-1-(pyridin-3-yl)azetidine-3-carboxamide;
N-{4-[1-(morpholin-4-ylacetyl)piperidin-4-yl]phenyl}-1-(pyridin-3-yl)azetidine-3-carboxamide;
N-{4-[1-(furan-3-ylcarbonyl)piperidin-4-yl]phenyl}-1-(pyridin-3-yl)azetidine-3-carboxamide;
1-(pyridin-3-yl)-N-{4-[1-(pyrrolidin-1-ylacetyl)piperidin-4-yl]phenyl}azetidine-3-carboxamide;
N-{4-[1-(5-oxo-D-prolyl)piperidin-4-yl]phenyl}-1-(pyridin-3-yl)azetidine-3-carboxamide;
N-{4-[1-(N,N-dimethyl-beta-alanyl)piperidin-4-yl]phenyl}-1-(pyridin-3-yl)azetidine-3-carboxamide;
1-(pyridin-3-yl)-N-{4-[1-(1,3-thiazol-2-ylcarbonyl)piperidin-4-yl]phenyl}azetidine-3-carboxamide;
1-(pyridin-3-yl)-N-{4-[1-(thiophen-3-ylcarbonyl)piperidin-4-yl]phenyl}azetidine-3-carboxamide;
N-(4-{1-[(1-methylcyclopropyl)carbonyl]piperidin-4-yl}phenyl)-1-(pyridin-3-yl)azetidine-3-carboxamide;
N-(4-{1-[(3-methylthiophen-2-yl)carbonyl]piperidin-4-yl}phenyl)-1-(pyridin-3-yl)azetidine-3-carboxamide;
1-(pyridin-3-yl)-N-{4-[1-(4,4,4-trifluorobutanoyl)piperidin-4-yl]phenyl}azetidine-3-carboxamide;
N-(4-{1-[(4-methylpiperazin-1-yl)acetyl]piperidin-4-yl}phenyl)-1-(pyridin-3-yl)azetidine-3-carboxamide;
N-{4-[1-(5-oxo-L-prolyl)piperidin-4-yl]phenyl}-1-(pyridin-3-yl)azetidine-3-carboxamide;
N-{4-[1-(3-ethoxypropanoyl)piperidin-4-yl]phenyl}-1-(pyridin-3-yl)azetidine-3-carboxamide;
N-{4-[1-(4-methylpentanoyl)piperidin-4-yl]phenyl}-1-(pyridin-3-yl)azetidine-3-carboxamide;
N-(4-{1-[(1-methylcyclohexyl)carbonyl]piperidin-4-yl}phenyl)-1-(pyridin-3-yl)azetidine-3-carboxamide;
N-[4-(1-acetylpiperidin-4-yl)phenyl]-1-(pyridin-3-yl)azetidine-3-carboxamide;
N-{4-[1-(cyclohexylacetyl)piperidin-4-yl]phenyl}-1-(pyridin-3-yl)azetidine-3-carboxamide;
N-{4-[1-(N-acetyl-L-leucyl)piperidin-4-yl]phenyl}-1-(pyridin-3-yl)azetidine-3-carboxamide;
N-[4-(1-propanoylpiperidin-4-yl)phenyl]-1-(pyridin-3-yl)azetidine-3-carboxamide;
1-(pyridin-3-yl)-N-{4-[1-(3,3,3-trifluoropropanoyl)piperidin-4-yl]phenyl}azetidine-3-carboxamide;
N-(4-{1-[(2-methoxyethoxy)acetyl]piperidin-4-yl}phenyl)-1-(pyridin-3-yl)azetidine-3-carboxamide;
N-(4-{1-[3-(morpholin-4-yl)propanoyl]piperidin-4-yl}phenyl)-1-(pyridin-3-yl)azetidine-3-carboxamide;
N-{4-[1-(2,2-dimethylpropanoyl)piperidin-4-yl]phenyl}-1-(pyridin-3-yl)azetidine-3-carboxamide;
N-(4-{1-[(5-methylthiophen-2-yl)carbonyl]piperidin-4-yl}phenyl)-1-(pyridin-3-yl)azetidine-3-carboxamide;
1-(pyridin-3-yl)-N-{4-[1-(thiophen-2-ylcarbonyl)piperidin-4-yl]phenyl}azetidine-3-carboxamide;
N-(4-{1-[(1-methyl-1H-pyrrol-2-yl)carbonyl]piperidin-4-yl}phenyl)-1-(pyridin-3-yl)azetidine-3-carboxamide;
N-{4-[1-(furan-2-ylcarbonyl)piperidin-4-yl]phenyl}-1-(pyridin-3-yl)azetidine-3-carboxamide;
N-(4-{1-[3-(piperidin-1-yl)propanoyl]piperidin-4-yl}phenyl)-1-(pyridin-3-yl)azetidine-3-carboxamide;
N-{4-[1-(ethoxyacetyl)piperidin-4-yl]phenyl}-1-(pyridin-3-yl)azetidine-3-carboxamide;
N-{4-[1-(3,3-dimethylbutanoyl)piperidin-4-yl]phenyl}-1-(pyridin-3-yl)azetidine-3-carboxamide;
N-{4-[1-(2,2-dimethylbutanoyl)piperidin-4-yl]phenyl}-1-(pyridin-3-yl)azetidine-3-carboxamide;
N-[4-(1-butanoylpiperidin-4-yl)phenyl]-1-(pyridin-3-yl)azetidine-3-carboxamide;
N-{4-[1-(methoxyacetyl)piperidin-4-yl]phenyl}-1-(pyridin-3-yl)azetidine-3-carboxamide;
N-{4-[1-(cyclohexylcarbonyl)piperidin-4-yl]phenyl}-1-(pyridin-3-yl)azetidine-3-carboxamide;
N-{4-[1-(3-methylbutanoyl)piperidin-4-yl]phenyl}-1-(pyridin-3-yl)azetidine-3-carboxamide;
N-{4-[1-(cyclopentylcarbonyl)piperidin-4-yl]phenyl}-1-(pyridin-3-yl)azetidine-3-carboxamide;
N-{4-[1-(2,3-dimethylbutanoyl)piperidin-4-yl]phenyl}-1-(pyridin-3-yl)azetidine-3-carboxamide;
N-{4-[1-(3,3-dimethylbutanoyl)piperidin-4-yl]phenyl}-1-(pyridazin-4-yl)azetidine-3-carboxamide;
N-(4-{1-[(2S)-2-methylbutanoyl]piperidin-4-yl}phenyl)-1-(pyridazin-4-yl)azetidine-3-carboxamide;
N-{4-[1-(cyclopentylacetyl)piperidin-4-yl]phenyl}-1-(pyridazin-4-yl)azetidine-3-carboxamide;
1-(pyridazin-4-yl)-N-{4-[1-(tetrahydro-2H-pyran-4-ylacetyl)piperidin-4-yl]phenyl}azetidine-3-carboxamide;
1-(pyridazin-4-yl)-N-{4-[1-(tetrahydro-2H-pyran-4-ylcarbonyl)piperidin-4-yl]phenyl}azetidine-3-carboxamide;
N-{4-[1-(2-methylpropanoyl)piperidin-4-yl]phenyl}-1-(pyridazin-3-yl)azetidine-3-carboxamide;
N-{4-[1-(2-methylpropyl)-1H-pyrazol-4-yl]phenyl}-1-(pyridazin-4-yl)azetidine-3-carboxamide;
N-[4-(1-benzoylpiperidin-4-yl)phenyl]-1-(2-methylpyridin-3-yl)azetidine-3-carboxamide;
N-{4-[1-(2-fluorobenzoyl)piperidin-4-yl]phenyl}-1-(2-methylpyridin-3-yl)azetidine-3-carboxamide;
N-{4-[1-(2-chlorobenzoyl)piperidin-4-yl]phenyl}-1-(2-methylpyridin-3-yl)azetidine-3-carboxamide;
N-{4-[1-(3-fluorobenzoyl)piperidin-4-yl]phenyl}-1-(2-methylpyridin-3-yl)azetidine-3-carboxamide;
N-{4-[1-(3-chlorobenzoyl)piperidin-4-yl]phenyl}-1-(2-methylpyridin-3-yl)azetidine-3-carboxamide;
N-{4-[1-(3,5-dichlorobenzoyl)piperidin-4-yl]phenyl}-1-(2-methylpyridin-3-yl)azetidine-3-carboxamide;
N-{4-[1-(4-fluorobenzoyl)piperidin-4-yl]phenyl}-1-(2-methylpyridin-3-yl)azetidine-3-carboxamide;
N-{4-[1-(4-chlorobenzoyl)piperidin-4-yl]phenyl}-1-(2-methylpyridin-3-yl)azetidine-3-carboxamide;
1-(2-methylpyridin-3-yl)-N-(4-{1-[4-(trifluoromethyl)benzoyl]piperidin-4-yl}phenyl)azetidine-3-carboxamide;

1-(2-methylpyridin-3-yl)-N-{4-[1-(pyridazin-3-ylcarbonyl)piperidin-4-yl]phenyl}azetidine-3-carboxamide;

1-(2-methylpyridin-3-yl)-N-[4-(1-pentanoylpiperidin-4-yl)phenyl]azetidine-3-carboxamide;

N-{4-[1-(3-methylpentanoyl)piperidin-4-yl]phenyl}-1-(2-methylpyridin-3-yl)azetidine-3-carboxamide;

N-(4-{1-[(1S,4R)-bicyclo[2.2.1]hept-2-ylacetyl]piperidin-4-yl}phenyl)-1-(2-methylpyridin-3-yl)azetidine-3-carboxamide;

N-{4-[1-(cyclopentylacetyl)piperidin-4-yl]phenyl}-1-(2-methylpyridin-3-yl)azetidine-3-carboxamide;

N-(4-{1-[(2-methylcyclopropyl)carbonyl]piperidin-4-yl}phenyl)-1-(2-methylpyridin-3-yl)azetidine-3-carboxamide;

1-(2-methylpyridin-3-yl)-N-{4-[1-(morpholin-4-ylacetyl)piperidin-4-yl]phenyl}azetidine-3-carboxamide;

N-{4-[1-(furan-3-ylcarbonyl)piperidin-4-yl]phenyl}-1-(2-methylpyridin-3-yl)azetidine-3-carboxamide;

1-(2-methylpyridin-3-yl)-N-{4-[1-(pyrrolidin-1-ylacetyl)piperidin-4-yl]phenyl}azetidine-3-carboxamide;

1-(2-methylpyridin-3-yl)-N-{4-[1-(5-oxo-D-prolyl)piperidin-4-yl]phenyl}azetidine-3-carboxamide;

N-{4-[1-(N,N-dimethyl-beta-alanyl)piperidin-4-yl]phenyl}-1-(2-methylpyridin-3-yl)azetidine-3-carboxamide;

1-(2-methylpyridin-3-yl)-N-{4-[1-(thiophen-3-ylcarbonyl)piperidin-4-yl]phenyl}azetidine-3-carboxamide;

N-(4-{1-[(1-methylcyclopropyl)carbonyl]piperidin-4-yl}phenyl)-1-(2-methylpyridin-3-yl)azetidine-3-carboxamide;

1-(2-methylpyridin-3-yl)-N-(4-{1-[(3-methylthiophen-2-yl)carbonyl]piperidin-4-yl}phenyl)azetidine-3-carboxamide;

1-(2-methylpyridin-3-yl)-N-{4-[1-(4,4,4-trifluorobutanoyl)piperidin-4-yl]phenyl}azetidine-3-carboxamide;

N-(4-{1-[(4-methylpiperazin-1-yl)acetyl]piperidin-4-yl}phenyl)-1-(2-methylpyridin-3-yl)azetidine-3-carboxamide;

1-(2-methylpyridin-3-yl)-N-{4-[1-(5-oxo-L-prolyl)piperidin-4-yl]phenyl}azetidine-3-carboxamide;

N-{4-[1-(3-ethoxypropanoyl)piperidin-4-yl]phenyl}-1-(2-methylpyridin-3-yl)azetidine-3-carboxamide;

N-{4-[1-(4-methylpentanoyl)piperidin-4-yl]phenyl}-1-(2-methylpyridin-3-yl)azetidine-3-carboxamide;

N-(4-{1-[(1-methylcyclohexyl)carbonyl]piperidin-4-yl}phenyl)-1-(2-methylpyridin-3-yl)azetidine-3-carboxamide;

N-[4-(1-acetylpiperidin-4-yl)phenyl]-1-(2-methylpyridin-3-yl)azetidine-3-carboxamide;

N-{4-[1-(cyclohexylacetyl)piperidin-4-yl]phenyl}-1-(2-methylpyridin-3-yl)azetidine-3-carboxamide;

N-{4-[1-(N-acetyl-L-leucyl)piperidin-4-yl]phenyl}-1-(2-methylpyridin-3-yl)azetidine-3-carboxamide;

1-(2-methylpyridin-3-yl)-N-[4-(1-propanoylpiperidin-4-yl)phenyl]azetidine-3-carboxamide;

1-(2-methylpyridin-3-yl)-N-{4-[1-(3,3,3-trifluoropropanoyl)piperidin-4-yl]phenyl}azetidine-3-carboxamide;

N-(4-{1-[(2-methoxyethoxy)acetyl]piperidin-4-yl}phenyl)-1-(2-methylpyridin-3-yl)azetidine-3-carboxamide;

1-(2-methylpyridin-3-yl)-N-(4-{1-[3-(morpholin-4-yl)propanoyl]piperidin-4-yl}phenyl)azetidine-3-carboxamide;

N-{4-[1-(2,2-dimethylpropanoyl)piperidin-4-yl]phenyl}-1-(2-methylpyridin-3-yl)azetidine-3-carboxamide;

1-(2-methylpyridin-3-yl)-N-(4-{1-[(5-methylthiophen-2-yl)carbonyl]piperidin-4-yl}phenyl)azetidine-3-carboxamide;

1-(2-methylpyridin-3-yl)-N-{4-[1-(thiophen-2-ylcarbonyl)piperidin-4-yl]phenyl}azetidine-3-carboxamide;

1-(2-methylpyridin-3-yl)-N-(4-{1-[(1-methyl-1H-pyrrol-2-yl)carbonyl]piperidin-4-yl}phenyl)azetidine-3-carboxamide;

N-{4-[1-(furan-2-ylcarbonyl)piperidin-4-yl]phenyl}-1-(2-methylpyridin-3-yl)azetidine-3-carboxamide;

1-(2-methylpyridin-3-yl)-N-(4-{1-[3-(piperidin-1-yl)propanoyl]piperidin-4-yl}phenyl)azetidine-3-carboxamide;

N-{4-[1-(ethoxyacetyl)piperidin-4-yl]phenyl}-1-(2-methylpyridin-3-yl)azetidine-3-carboxamide;

N-{4-[1-(3,3-dimethylbutanoyl)piperidin-4-yl]phenyl}-1-(2-methylpyridin-3-yl)azetidine-3-carboxamide;

N-{4-[1-(2,2-dimethylbutanoyl)piperidin-4-yl]phenyl}-1-(2-methylpyridin-3-yl)azetidine-3-carboxamide;

N-[4-(1-butanoylpiperidin-4-yl)phenyl]-1-(2-methylpyridin-3-yl)azetidine-3-carboxamide;

N-{4-[1-(methoxyacetyl)piperidin-4-yl]phenyl}-1-(2-methylpyridin-3-yl)azetidine-3-carboxamide;

N-{4-[1-(cyclohexylcarbonyl)piperidin-4-yl]phenyl}-1-(2-methylpyridin-3-yl)azetidine-3-carboxamide;

N-{4-[1-(3-methylbutanoyl)piperidin-4-yl]phenyl}-1-(2-methylpyridin-3-yl)azetidine-3-carboxamide;

N-{4-[1-(2,3-dimethylbutanoyl)piperidin-4-yl]phenyl}-1-(2-methylpyridin-3-yl)azetidine-3-carboxamide;

N-(4-{[1-(4-fluorobenzoyl)azetidin-3-yl]oxy}phenyl)-1-(pyridazin-4-yl)azetidine-3-carboxamide;

N-(4-{[1-(2,4-difluorobenzoyl)azetidin-3-yl]oxy}phenyl)-1-(pyridazin-4-yl)azetidine-3-carboxamide;

N-[4-({1-[difluoro(phenyl)acetyl]azetidin-3-yl}oxy)phenyl]-1-(pyridazin-4-yl)azetidine-3-carboxamide;

N-[4-({1-[(4,4-difluoro cyclohexyl)carbonyl]azetidin-3-yl}oxy)phenyl]-1-(pyridazin-4-yl)azetidine-3-carboxamide;

N-[4-({1-[(4-fluorophenyl)acetyl]azetidin-3-yl}oxy)phenyl]-1-(pyridazin-4-yl)azetidine-3-carboxamide;

1-(pyridazin-4-yl)-N-[4-({1-[4-(trifluoromethyl)benzoyl]azetidin-3-yl}oxy)phenyl]azetidine-3-carboxamide;

N-{4-[(1-benzoylazetidin-3-yl)oxy]phenyl}-1-(pyridazin-4-yl)azetidine-3-carboxamide;

N-(4-{[1-(2-hydroxy-2-methylpropanoyl)azetidin-3-yl]oxy}phenyl)-1-(pyridazin-4-yl)azetidine-3-carboxamide;

1-(pyridazin-4-yl)-N-(4-{[1-(tetrahydrofuran-3-ylcarbonyl)azetidin-3-yl]oxy}phenyl)azetidine-3-carboxamide;

N-(4-{[1-(furan-3-ylcarbonyl)azetidin-3-yl]oxy}phenyl)-1-(pyridazin-4-yl)azetidine-3-carboxamide;

N-{4-[(1-pentanoylazetidin-3-yl)oxy]phenyl}-1-(pyridazin-4-yl)azetidine-3-carboxamide;

N-(4-{[1-(2-chlorobenzoyl)piperidin-4-yl]oxy}phenyl)-1-(pyridazin-3-yl)azetidine-3-carboxamide;

N-[4-({1-[(2S)-2-methylbutanoyl]piperidin-4-yl}oxy)phenyl]-1-(pyridazin-3-yl)azetidine-3-carboxamide;

1-(pyridazin-3-yl)-N-(4-{[1-(1,3-thiazol-2-ylcarbonyl)piperidin-4-yl]oxy}phenyl)azetidine-3-carboxamide;

1-(pyridazin-3-yl)-N-(4-{[1-(tetrahydro-2H-pyran-4-ylcarbonyl)piperidin-4-yl]oxy}phenyl)azetidine-3-carboxamide;

N-[4-({1-[difluoro(phenyl)acetyl]piperidin-4-yl}oxy)phenyl]-1-(pyridazin-3-yl)azetidine-3-carboxamide;

N-[4-({1-[(4,4-difluorocyclohexyl)carbonyl]piperidin-4-yl}oxy)phenyl]-1-(pyridazin-3-yl)azetidine-3-carboxamide;

N-(4-{[1-(2-methyl-2-phenylpropanoyl)piperidin-4-yl]oxy}phenyl)-1-(pyridazin-3-yl)azetidine-3-carboxamide;

1-(pyridazin-3-yl)-N-(4-{[1-(1,3-thiazol-4-ylcarbonyl)piperidin-4-yl]oxy}phenyl)azetidine-3-carboxamide;

N-[4-({1-[(5-methylthiophen-2-yl)carbonyl]piperidin-4-yl}oxy)phenyl]-1-(pyridazin-3-yl)azetidine-3-carboxamide;

1-(pyridazin-3-yl)-N-{4-[(1-{[4-(trifluoromethyl)phenyl]acetyl}piperidin-4-yl)oxy]phenyl}azetidine-3-carboxamide;
1-(pyridazin-3-yl)-N-(4-{[1-(tetrahydrofuran-2-ylcarbonyl)piperidin-4-yl]oxy}phenyl)azetidine-3-carboxamide;
1-(pyridazin-3-yl)-N-[4-({1-[3-(trifluoromethyl)benzoyl]piperidin-4-yl}oxy)phenyl]azetidine-3-carboxamide;
1-(pyridazin-3-yl)-N-(4-{[1-(thiophen-3-ylcarbonyl)piperidin-4-yl]oxy}phenyl)azetidine-3-carboxamide;
1-(pyridazin-3-yl)-N-[4-({1-[3-(trifluoromethoxy)benzoyl]piperidin-4-yl}oxy)phenyl]azetidine-3-carboxamide;
N-(4-{[1-(3-methylbutanoyl)piperidin-4-yl]oxy}phenyl)-1-(pyridazin-3-yl)azetidine-3-carboxamide;
1-(pyridazin-3-yl)-N-(4-{[1-(tetrahydrofuran-3-ylcarbonyl)piperidin-4-yl]oxy}phenyl)azetidine-3-carboxamide;
N-[4-({1-[(3-fluorophenyl)acetyl]piperidin-4-yl}oxy)phenyl]-1-(pyridazin-3-yl)azetidine-3-carboxamide;
N-(4-{[1-(2-fluorobenzoyl)piperidin-4-yl]oxy}phenyl)-1-(pyridazin-3-yl)azetidine-3-carboxamide;
N-(4-{[1-(2,4-difluorobenzoyl)piperidin-4-yl]oxy}phenyl)-1-(pyridazin-3-yl)azetidine-3-carboxamide;
N-(4-{[1-(4-fluorobenzoyl)piperidin-4-yl]oxy}phenyl)-1-(pyridazin-3-yl)azetidine-3-carboxamide;
N-(4-{[1-(3-fluorobenzoyl)piperidin-4-yl]oxy}phenyl)-1-(pyridazin-3-yl)azetidine-3-carboxamide;
N-[4-({1-[(4-fluorophenyl)acetyl]piperidin-4-yl}oxy)phenyl]-1-(pyridazin-3-yl)azetidine-3-carboxamide;
N-(4-{[1-(cyclopropylacetyl)piperidin-4-yl]oxy}phenyl)-1-(pyridazin-3-yl)azetidine-3-carboxamide;
N-(4-{[1-(3,4-difluorobenzoyl)piperidin-4-yl]oxy}phenyl)-1-(pyridazin-3-yl)azetidine-3-carboxamide;
1-(pyridazin-3-yl)-N-[4-({1-[4-(trifluoromethoxy)benzoyl]piperidin-4-yl}oxy)phenyl]azetidine-3-carboxamide;
N-[4-({1-[(2,4-difluorophenyl)acetyl]piperidin-4-yl}oxy)phenyl]-1-(pyridazin-3-yl)azetidine-3-carboxamide;
1-(pyridazin-3-yl)-N-[4-({1-[4-(trifluoromethyl)benzoyl]piperidin-4-yl}oxy)phenyl]azetidine-3-carboxamide;
1-(pyridazin-3-yl)-N-{4-[(1-{[4-(trifluoromethoxy)phenyl]acetyl}piperidin-4-yl)oxy]phenyl}azetidine-3-carboxamide;
N-[4-({1-[(3,5-difluorophenyl)acetyl]piperidin-4-yl}oxy)phenyl]-1-(pyridazin-3-yl)azetidine-3-carboxamide;
1-(pyridazin-3-yl)-N-{4-[(1-{[3-(trifluoromethyl)phenyl]acetyl}piperidin-4-yl)oxy]phenyl}azetidine-3-carboxamide;
N-(4-{[1-(2,2-dimethylpropanoyl)piperidin-4-yl]oxy}phenyl)-1-(pyridazin-3-yl)azetidine-3-carboxamide;
1-(pyridazin-3-yl)-N-(4-{[1-(pyridin-2-ylcarbonyl)piperidin-4-yl]oxy}phenyl)azetidine-3-carboxamide;
N-(4-{[1-(3,5-difluorobenzoyl)piperidin-4-yl]oxy}phenyl)-1-(pyridazin-3-yl)azetidine-3-carboxamide;
N-{4-[(1-acetylpiperidin-4-yl)oxy]phenyl}-1-(pyridazin-3-yl)azetidine-3-carboxamide;
N-(4-{[1-(4-chlorobenzoyl)piperidin-4-yl]oxy}phenyl)-1-(pyridazin-3-yl)azetidine-3-carboxamide;
N-(4-{[1-(methoxyacetyl)piperidin-4-yl]oxy}phenyl)-1-(pyridazin-3-yl)azetidine-3-carboxamide;
N-[4-({1-[(2-fluorophenyl)acetyl]piperidin-4-yl}oxy)phenyl]-1-(pyridazin-3-yl)azetidine-3-carboxamide;
N-(4-{[1-(2,2-dimethylbutanoyl)piperidin-4-yl]oxy}phenyl)-1-(pyridazin-3-yl)azetidine-3-carboxamide;
1-(pyridazin-3-yl)-N-(4-{[1-(thiophen-2-ylcarbonyl)piperidin-4-yl]oxy}phenyl)azetidine-3-carboxamide;
N-(4-{[1-(3-chlorobenzoyl)piperidin-4-yl]oxy}phenyl)-1-(pyridazin-3-yl)azetidine-3-carboxamide;
N-(4-{[1-(cyclopropylcarbonyl)piperidin-4-yl]oxy}phenyl)-1-(pyridazin-3-yl)azetidine-3-carboxamide;
1-(pyridazin-3-yl)-N-(4-{[1-(3,3,3-trifluoropropanoyl)piperidin-4-yl]oxy}phenyl)azetidine-3-carboxamide;
N-(4-{[1-(2-methylpropanoyl)piperidin-4-yl]oxy}phenyl)-1-(pyridazin-3-yl)azetidine-3-carboxamide;
N-(4-{[1-(3,3-dimethylbutanoyl)azetidin-3-yl]oxy}phenyl)-1-(pyridazin-4-yl)azetidine-3-carboxamide;
N-(4-{[1-(cyclohexylcarbonyl)azetidin-3-yl]oxy}phenyl)-1-(pyridazin-4-yl)azetidine-3-carboxamide;
1-(pyridazin-4-yl)-N-(4-{[1-(tetrahydro-2H-pyran-4-ylacetyl)azetidin-3-yl]oxy}phenyl)azetidine-3-carboxamide;
N-[4-({1-[(2-methylcyclopropyl)carbonyl]azetidin-3-yl}oxy)phenyl]-1-(pyridazin-4-yl)azetidine-3-carboxamide;
1-(pyridazin-4-yl)-N-(4-{[1-(3,3,3-trifluoropropanoyl)azetidin-3-yl]oxy}phenyl)azetidine-3-carboxamide;
N-(4-{[1-(cyclopentylcarbonyl)azetidin-3-yl]oxy}phenyl)-1-(pyridazin-4-yl)azetidine-3-carboxamide;
N-(4-{[1-(3,3-dimethylbutanoyl)piperidin-4-yl]oxy}phenyl)-1-(pyridazin-4-yl)azetidine-3-carboxamide;
N-(4-{[1-(cyclobutylcarbonyl)azetidin-3-yl]oxy}phenyl)-1-(pyridazin-4-yl)azetidine-3-carboxamide;
1-(pyridazin-4-yl)-N-(4-{[1-(tetrahydrofuran-2-ylcarbonyl)azetidin-3-yl]oxy}phenyl)azetidine-3-carboxamide;
N-(4-{[1-(4-methylpentanoyl)azetidin-3-yl]oxy}phenyl)-1-(pyridazin-4-yl)azetidine-3-carboxamide;
N-(4-{[1-(2-methylpropanoyl)azetidin-3-yl]oxy}phenyl)-1-(pyridazin-4-yl)azetidine-3-carboxamide;
N-[4-({1-[(2S)-2-methylbutanoyl]azetidin-3-yl}oxy)phenyl]-1-(pyridazin-4-yl)azetidine-3-carboxamide;
N-(4-{[1-(3-methylbutanoyl)piperidin-4-yl]oxy}phenyl)-1-(pyridazin-4-yl)azetidine-3-carboxamide;
N-(4-{[1-(methoxyacetyl)piperidin-4-yl]oxy}phenyl)-1-(pyridazin-4-yl)azetidine-3-carboxamide;
1-(pyridazin-4-yl)-N-(4-{[1-(3,3,3-trifluoropropanoyl)piperidin-4-yl]oxy}phenyl)azetidine-3-carboxamide;
N-[4-({1-[difluoro(phenyl)acetyl]piperidin-4-yl}oxy)phenyl]-1-(pyridazin-4-yl)azetidine-3-carboxamide;
N-[4-({1-[(4,4-difluorocyclohexyl)carbonyl]piperidin-4-yl}oxy)phenyl]-1-(pyridazin-4-yl)azetidine-3-carboxamide;
N-(4-{[1-(4-fluorobenzoyl)piperidin-4-yl]oxy}phenyl)-1-(pyridazin-4-yl)azetidine-3-carboxamide;
1-(pyridazin-4-yl)-N-(4-{[1-(1,3-thiazol-4-ylcarbonyl)piperidin-4-yl]oxy}phenyl)azetidine-3-carboxamide;
1-(pyridazin-4-yl)-N-{4-[(1-{[4-(trifluoromethyl)phenyl]acetyl}piperidin-4-yl)oxy]phenyl}azetidine-3-carboxamide;
N-(4-{[1-(3,4-difluorobenzoyl)piperidin-4-yl]oxy}phenyl)-1-(pyridazin-4-yl)azetidine-3-carboxamide;
1-(pyridazin-4-yl)-N-{4-[(1-{[4-(trifluoromethoxy)phenyl]acetyl}piperidin-4-yl)oxy]phenyl}azetidine-3-carboxamide;
N-[4-({1-[(4-fluorophenyl)acetyl]piperidin-4-yl}oxy)phenyl]-1-(pyridazin-4-yl)azetidine-3-carboxamide;
N-[4-({1-[(2,4-difluorophenyl)acetyl]piperidin-4-yl}oxy)phenyl]-1-(pyridazin-4-yl)azetidine-3-carboxamide;
1-(pyridazin-4-yl)-N-(4-{[1-(thiophen-3-ylcarbonyl)piperidin-4-yl]oxy}phenyl)azetidine-3-carboxamide;
N-(4-{[1-(2-chlorobenzoyl)piperidin-4-yl]oxy}phenyl)-1-(pyridazin-4-yl)azetidine-3-carboxamide;
N-(4-{[1-(2,2-dimethylpropanoyl)piperidin-4-yl]oxy}phenyl)-1-(pyridazin-4-yl)azetidine-3-carboxamide;
N-(4-{[1-(2-methyl-2-phenylpropanoyl)piperidin-4-yl]oxy}phenyl)-1-(pyridazin-4-yl)azetidine-3-carboxamide;
N-{4-[(1-acetylpiperidin-4-yl)oxy]phenyl}-1-(pyridazin-4-yl)azetidine-3-carboxamide;

1-(pyridazin-4-yl)-N-(4-{[1-(1,3-thiazol-2-ylcarbonyl)piperidin-4-yl]oxy}phenyl)azetidine-3-carboxamide;
N-(4-{[1-(2,4-difluorobenzoyl)piperidin-4-yl]oxy}phenyl)-1-(pyridazin-4-yl)azetidine-3-carboxamide;
1-(pyridazin-4-yl)-N-[4-({1-[3-(trifluoromethyl)benzoyl]piperidin-4-yl}oxy)phenyl]azetidine-3-carboxamide;
N-(4-{[1-(3-fluorobenzoyl)piperidin-4-yl]oxy}phenyl)-1-(pyridazin-4-yl)azetidine-3-carboxamide;
1-(pyridazin-4-yl)-N-[4-({1-[4-(trifluoromethyl)benzoyl]piperidin-4-yl}oxy)phenyl]azetidine-3-carboxamide;
N-[4-({1-[(3-fluorophenyl)acetyl]piperidin-4-yl}oxy)phenyl]-1-(pyridazin-4-yl)azetidine-3-carboxamide;
N-(4-{[1-(2-fluorobenzoyl)piperidin-4-yl]oxy}phenyl)-1-(pyridazin-4-yl)azetidine-3-carboxamide;
1-(pyridazin-4-yl)-N-[4-({1-[4-(trifluoromethoxy)benzoyl]piperidin-4-yl}oxy)phenyl]azetidine-3-carboxamide;
N-(4-({1-[(3,5-difluorophenyl)acetyl]piperidin-4-yl}oxy)phenyl]-1-(pyridazin-4-yl)azetidine-3-carboxamide;
1-(pyridazin-4-yl)-N-[4-({1-[3-(trifluoromethoxy)benzoyl]piperidin-4-yl}oxy)phenyl]azetidine-3-carboxamide;
N-(4-{[1-(cyclopropylacetyl)piperidin-4-yl]oxy}phenyl)-1-(pyridazin-4-yl)azetidine-3-carboxamide;
N-(4-{[1-(2-methylpropanoyl)piperidin-4-yl]oxy}phenyl)-1-(pyridazin-4-yl)azetidine-3-carboxamide;
N-(4-{[1-(3-chlorobenzoyl)piperidin-4-yl]oxy}phenyl)-1-(pyridazin-4-yl)azetidine-3-carboxamide;
1-(pyridazin-4-yl)-N-(4-{[1-(pyridin-2-ylcarbonyl)piperidin-4-yl]oxy}phenyl)azetidine-3-carboxamide;
N-(4-{[1-(4-chlorobenzoyl)piperidin-4-yl]oxy}phenyl)-1-(pyridazin-4-yl)azetidine-3-carboxamide;
1-(pyridazin-4-yl)-N-(4-{[1-(tetrahydrofuran-3-ylcarbonyl)piperidin-4-yl]oxy}phenyl)azetidine-3-carboxamide;
N-(4-{[1-(3,5-difluorobenzoyl)piperidin-4-yl]oxy}phenyl)-1-(pyridazin-4-yl)azetidine-3-carboxamide;
N-(4-{[1-(2,2-dimethylbutanoyl)piperidin-4-yl]oxy}phenyl)-1-(pyridazin-4-yl)azetidine-3-carboxamide;
N-(4-{[1-(cyclopropylcarbonyl)piperidin-4-yl]oxy}phenyl)-1-(pyridazin-4-yl)azetidine-3-carboxamide;
1-(pyridazin-4-yl)-N-(4-{[1-(tetrahydrofuran-2-ylcarbonyl)piperidin-4-yl]oxy}phenyl)azetidine-3-carboxamide;
1-(pyridazin-4-yl)-N-(4-{[1-(thiophen-2-ylcarbonyl)piperidin-4-yl]oxy}phenyl)azetidine-3-carboxamide;
N-[4-({1-[(5-methylthiophen-2-yl)carbonyl]piperidin-4-yl}oxy)phenyl]-1-(pyridazin-4-yl)azetidine-3-carboxamide;
1-(pyridazin-4-yl)-N-{4-[(1-{[3-(trifluoromethyl)phenyl]acetyl}piperidin-4-yl)oxy]phenyl}azetidine-3-carboxamide;
1-(pyridazin-4-yl)-N-(4-{[1-(tetrahydro-2H-pyran-4-ylcarbonyl)piperidin-4-yl]oxy}phenyl)azetidine-3-carboxamide;
N-[4-({1-[(2S)-2-methylbutanoyl]piperidin-4-yl}oxy)phenyl]-1-(pyridazin-4-yl)azetidine-3-carboxamide;
N-[4-({1-[(2-fluorophenyl)acetyl]piperidin-4-yl}oxy)phenyl]-1-(pyridazin-4-yl)azetidine-3-carboxamide;
5-[1-(2-methylpropyl)-1H-pyrazol-4-yl]-N-[1-(pyridazin-3-yl)azetidin-3-yl]furan-2-carboxamide;
tert-butyl 4-(4-{[1-(pyridazin-3-yl)azetidin-3-yl]carbamoyl}phenyl)piperidine-1-carboxylate;
5-[1-(2-methylpropyl)-1H-pyrazol-4-yl]-N-[1-(pyridazin-3-yl)azetidin-3-yl]thiophene-2-carboxamide;
N-[4-(1-acetylpiperidin-4-yl)phenyl]-1-(pyridazin-3-yl)azetidine-3-carboxamide;
N-[4-(1-butanoylpiperidin-4-yl)phenyl]-1-(pyridazin-3-yl)azetidine-3-carboxamide;
N-[4-(1-pentanoylpiperidin-4-yl)phenyl]-1-(pyridazin-3-yl)azetidine-3-carboxamide;
N-{4-[1-(2-methylbutanoyl)piperidin-4-yl]phenyl}-1-(pyridazin-3-yl)azetidine-3-carboxamide;
N-{4-[1-(3-methylbutanoyl)piperidin-4-yl]phenyl}-1-(pyridazin-3-yl)azetidine-3-carboxamide;
N-[4-(1-hexanoylpiperidin-4-yl)phenyl]-1-(pyridazin-3-yl)azetidine-3-carboxamide;
N-{4-[1-(2-methylpentanoyl)piperidin-4-yl]phenyl}-1-(pyridazin-3-yl)azetidine-3-carboxamide;
N-{4-[1-(3-methylpentanoyl)piperidin-4-yl]phenyl}-1-(pyridazin-3-yl)azetidine-3-carboxamide;
N-{4-[1-(4-methylpentanoyl)piperidin-4-yl]phenyl}-1-(pyridazin-3-yl)azetidine-3-carboxamide;
N-{4-[1-(2,2-dimethylbutanoyl)piperidin-4-yl]phenyl}-1-(pyridazin-3-yl)azetidine-3-carboxamide;
N-{4-[1-(2,3-dimethylbutanoyl)piperidin-4-yl]phenyl}-1-(pyridazin-3-yl)azetidine-3-carboxamide;
N-{4-[1-(3,3-dimethylbutanoyl)piperidin-4-yl]phenyl}-1-(pyridazin-3-yl)azetidine-3-carboxamide;
N-{4-[1-(2-ethylbutanoyl)piperidin-4-yl]phenyl}-1-(pyridazin-3-yl)azetidine-3-carboxamide;
N-[4-(1-heptanoylpiperidin-4-yl)phenyl]-1-(pyridazin-3-yl)azetidine-3-carboxamide;
N-{4-[1-(but-3-enoyl)piperidin-4-yl]phenyl}-1-(pyridazin-3-yl)azetidine-3-carboxamide;
N-{4-[1-(pent-4-enoyl)piperidin-4-yl]phenyl}-1-(pyridazin-3-yl)azetidine-3-carboxamide;
1-(pyridazin-3-yl)-N-{4-[1-(3,3,3-trifluoropropanoyl)piperidin-4-yl]phenyl}azetidine-3-carboxamide;
N-{4-[1-(methoxyacetyl)piperidin-4-yl]phenyl}-1-(pyridazin-3-yl)azetidine-3-carboxamide;
N-(4-{1-[(methylsulfanyl)acetyl]piperidin-4-yl}phenyl)-1-(pyridazin-3-yl)azetidine-3-carboxamide;
N-(4-{1-[(2-methoxyethoxy)acetyl]piperidin-4-yl}phenyl)-1-(pyridazin-3-yl)azetidine-3-carboxamide;
N-{4-[1-(3-nitropropanoyl)piperidin-4-yl]phenyl}-1-(pyridazin-3-yl)azetidine-3-carboxamide;
N-(4-{1-[3-(methylsulfanyl)propanoyl]piperidin-4-yl}phenyl)-1-(pyridazin-3-yl)azetidine-3-carboxamide;
N-{4-[1-(pent-4-ynoyl)piperidin-4-yl]phenyl}-1-(pyridazin-3-yl)azetidine-3-carboxamide;
N-{4-[1-(cyclohexylcarbonyl)piperidin-4-yl]phenyl}-1-(pyridazin-3-yl)azetidine-3-carboxamide;
N-{4-[1-(cyclohexylacetyl)piperidin-4-yl]phenyl}-1-(pyridazin-3-yl)azetidine-3-carboxamide;
N-{4-[1-(3-methylbenzoyl)piperidin-4-yl]phenyl}-1-(pyridazin-3-yl)azetidine-3-carboxamide;
N-{4-[1-(2-hydroxybenzoyl)piperidin-4-yl]phenyl}-1-(pyridazin-3-yl)azetidine-3-carboxamide;
N-{4-[1-(3-hydroxybenzoyl)piperidin-4-yl]phenyl}-1-(pyridazin-3-yl)azetidine-3-carboxamide;
N-{4-[1-(4-hydroxybenzoyl)piperidin-4-yl]phenyl}-1-(pyridazin-3-yl)azetidine-3-carboxamide;
N-{4-[1-(2-methoxybenzoyl)piperidin-4-yl]phenyl}-1-(pyridazin-3-yl)azetidine-3-carboxamide;
N-{4-[1-(3-methoxybenzoyl)piperidin-4-yl]phenyl}-1-(pyridazin-3-yl)azetidine-3-carboxamide;
N-{4-[1-(4-methoxybenzoyl)piperidin-4-yl]phenyl}-1-(pyridazin-3-yl)azetidine-3-carboxamide;
N-{4-[1-(3-fluorobenzoyl)piperidin-4-yl]phenyl}-1-(pyridazin-3-yl)azetidine-3-carboxamide;
N-{4-[1-(4-fluorobenzoyl)piperidin-4-yl]phenyl}-1-(pyridazin-3-yl)azetidine-3-carboxamide;
N-{4-[1-(2-chlorobenzoyl)piperidin-4-yl]phenyl}-1-(pyridazin-3-yl)azetidine-3-carboxamide;
N-{4-[1-(3-chlorobenzoyl)piperidin-4-yl]phenyl}-1-(pyridazin-3-yl)azetidine-3-carboxamide;

N-{4-[1-(3-cyanobenzoyl)piperidin-4-yl]phenyl}-1-(pyridazin-3-yl)azetidine-3-carboxamide;
N-{4-[1-(4-cyanobenzoyl)piperidin-4-yl]phenyl}-1-(pyridazin-3-yl)azetidine-3-carboxamide;
1-(pyridazin-3-yl)-N-(4-{1-[3-(trifluoromethyl)benzoyl]piperidin-4-yl}phenyl)azetidine-3-carboxamide;
1-(pyridazin-3-yl)-N-(4-{1-[4-(trifluoromethyl)benzoyl]piperidin-4-yl}phenyl)azetidine-3-carboxamide;
1-(pyridazin-3-yl)-N-(4-{1-[3-(trifluoromethoxy)benzoyl]piperidin-4-yl}phenyl)azetidine-3-carboxamide;
N-{4-[1-(2,3-dimethylbenzoyl)piperidin-4-yl]phenyl}-1-(pyridazin-3-yl)azetidine-3-carboxamide;
N-{4-[1-(2,4-dimethylbenzoyl)piperidin-4-yl]phenyl}-1-(pyridazin-3-yl)azetidine-3-carboxamide;
N-{4-[1-(2,5-dimethylbenzoyl)piperidin-4-yl]phenyl}-1-(pyridazin-3-yl)azetidine-3-carboxamide;
N-{4-[1-(3,4-dimethylbenzoyl)piperidin-4-yl]phenyl}-1-(pyridazin-3-yl)azetidine-3-carboxamide;
N-{4-[1-(3,5-dimethylbenzoyl)piperidin-4-yl]phenyl}-1-(pyridazin-3-yl)azetidine-3-carboxamide;
N-{4-[1-(2,4-dichlorobenzoyl)piperidin-4-yl]phenyl}-1-(pyridazin-3-yl)azetidine-3-carboxamide;
N-{4-[1-(2,5-dichlorobenzoyl)piperidin-4-yl]phenyl}-1-(pyridazin-3-yl)azetidine-3-carboxamide;
N-{4-[1-(3,4-dichlorobenzoyl)piperidin-4-yl]phenyl}-1-(pyridazin-3-yl)azetidine-3-carboxamide;
N-{4-[1-(3,5-dichlorobenzoyl)piperidin-4-yl]phenyl}-1-(pyridazin-3-yl)azetidine-3-carboxamide;
N-(4-{1-[(2-fluorophenyl)acetyl]piperidin-4-yl}phenyl)-1-(pyridazin-3-yl)azetidine-3-carboxamide;
N-(4-{1-[(3-fluorophenyl)acetyl]piperidin-4-yl}phenyl)-1-(pyridazin-3-yl)azetidine-3-carboxamide;
N-(4-{1-[(4-fluorophenyl)acetyl]piperidin-4-yl}phenyl)-1-(pyridazin-3-yl)azetidine-3-carboxamide;
N-(4-{1-[(2-chlorophenyl)acetyl]piperidin-4-yl}phenyl)-1-(pyridazin-3-yl)azetidine-3-carboxamide;
N-(4-{1-[(4-chlorophenyl)acetyl]piperidin-4-yl}phenyl)-1-(pyridazin-3-yl)azetidine-3-carboxamide;
1-(pyridazin-3-yl)-N-[4-(1-{[4-(trifluoromethyl)phenyl]acetyl}piperidin-4-yl)phenyl]azetidine-3-carboxamide;
N-(4-{1-[(3,5-dimethylphenyl)acetyl]piperidin-4-yl}phenyl)-1-(pyridazin-3-yl)azetidine-3-carboxamide;
N-(4-{1-[(2,5-difluorophenyl)acetyl]piperidin-4-yl}phenyl)-1-(pyridazin-3-yl)azetidine-3-carboxamide;
N-(4-{1-[(3,4-dichlorophenyl)acetyl]piperidin-4-yl}phenyl)-1-(pyridazin-3-yl)azetidine-3-carboxamide;
N-{4-[1-(furan-3-ylcarbonyl)piperidin-4-yl]phenyl}-1-(pyridazin-3-yl)azetidine-3-carboxamide;
1-(pyridazin-3-yl)-N-{4-[1-(thiophen-2-ylcarbonyl)piperidin-4-yl]phenyl}azetidine-3-carboxamide;
N-(4-{1-[(5-methylthiophen-2-yl)carbonyl]piperidin-4-yl}phenyl)-1-(pyridazin-3-yl)azetidine-3-carboxamide;
N-(4-{1-[(5-methylpyrazin-2-yl)carbonyl]piperidin-4-yl}phenyl)-1-(pyridazin-3-yl)azetidine-3-carboxamide;
N-(4-{1-[(1-methylcyclopropyl)carbonyl]piperidin-4-yl}phenyl)-1-(pyridazin-3-yl)azetidine-3-carboxamide;
N-{4-[1-(3-ethoxypropanoyl)piperidin-4-yl]phenyl}-1-(pyridazin-3-yl)azetidine-3-carboxamide;
N-(4-{1-[(1-phenylcyclopropyl)carbonyl]piperidin-4-yl}phenyl)-1-(pyridazin-3-yl)azetidine-3-carboxamide;
1-(pyridazin-3-yl)-N-(4-{1-[(pyrimidin-2-ylsulfanyl)acetyl]piperidin-4-yl}phenyl)azetidine-3-carboxamide;
N-(4-{1-[(1-acetylpiperidin-4-yl)carbonyl]piperidin-4-yl}phenyl)-1-(pyridazin-3-yl)azetidine-3-carboxamide;
N-(4-{1-[(3,5-difluorophenyl)acetyl]piperidin-4-yl}phenyl)-1-(pyridazin-3-yl)azetidine-3-carboxamide;
N-{4-[1-(N-acetyl-L-leucyl)piperidin-4-yl]phenyl}-1-(pyridazin-3-yl)azetidine-3-carboxamide;
N-{4-[1-(diphenylacetyl)piperidin-4-yl]phenyl}-1-(pyridazin-3-yl)azetidine-3-carboxamide;
N-{4-[1-(3-fluoro-2-methylbenzoyl)piperidin-4-yl]phenyl}-1-(pyridazin-3-yl)azetidine-3-carboxamide;
N-{4-[1-(5-fluoro-2-methylbenzoyl)piperidin-4-yl]phenyl}-1-(pyridazin-3-yl)azetidine-3-carboxamide;
N-{4-[1-(3-fluoro-4-methylbenzoyl)piperidin-4-yl]phenyl}-1-(pyridazin-3-yl)azetidine-3-carboxamide;
N-{4-[1-(2,3-difluorobenzoyl)piperidin-4-yl]phenyl}-1-(pyridazin-3-yl)azetidine-3-carboxamide;
N-{4-[1-(2,4-difluorobenzoyl)piperidin-4-yl]phenyl}-1-(pyridazin-3-yl)azetidine-3-carboxamide;
N-(4-{1-[4-(propan-2-yl)benzoyl]piperidin-4-yl}phenyl)-1-(pyridazin-3-yl)azetidine-3-carboxamide;
N-{4-[1-(4-tert-butylbenzoyl)piperidin-4-yl]phenyl}-1-(pyridazin-3-yl)azetidine-3-carboxamide;
N-(4-{1-[2-fluoro-5-(trifluoromethyl)benzoyl]piperidin-4-yl}phenyl)-1-(pyridazin-3-yl)azetidine-3-carboxamide;
N-(4-{1-[2-chloro-5-(trifluoromethyl)benzoyl]piperidin-4-yl}phenyl)-1-(pyridazin-3-yl)azetidine-3-carboxamide;
N-(4-{[(3R)-1-(4-fluorobenzoyl)pyrrolidin-3-yl]oxy}phenyl)-1-(pyridazin-4-yl)azetidine-3-carboxamide;
N-{4-[1-(cyclopentylacetyl)piperidin-4-yl]phenyl}-1-(pyridazin-3-yl)azetidine-3-carboxamide;
N-(4-{1-[(4-methylphenoxy)acetyl]piperidin-4-yl}phenyl)-1-(pyridazin-3-yl)azetidine-3-carboxamide;
N-(4-{1-[(2S)-2-phenylbutanoyl]piperidin-4-yl}phenyl)-1-(pyridazin-3-yl)azetidine-3-carboxamide;
N-{4-[1-(3,5-difluorobenzoyl)piperidin-4-yl]phenyl}-1-(pyridazin-3-yl)azetidine-3-carboxamide;
N-{4-[1-(4-chlorobenzoyl)piperidin-4-yl]phenyl}-1-(pyridazin-3-yl)azetidine-3-carboxamide;
N-{4-[1-(2,2-dimethylpropanoyl)piperidin-4-yl]phenyl}-1-(pyridazin-3-yl)azetidine-3-carboxamide;
1-(pyridazin-3-yl)-N-[4-(1-{[3-(trifluoromethyl)phenyl]acetyl}piperidin-4-yl)phenyl]azetidine-3-carboxamide;
N-(4-{1-[(3-chlorophenyl)acetyl]piperidin-4-yl}phenyl)-1-(pyridazin-3-yl)azetidine-3-carboxamide;
N-(4-{1-[(2,4-dichlorophenyl)acetyl]piperidin-4-yl}phenyl)-1-(pyridazin-3-yl)azetidine-3-carboxamide;
N-{4-[1-(naphthalen-1-ylcarbonyl)piperidin-4-yl]phenyl}-1-(pyridazin-3-yl)azetidine-3-carboxamide;
N-(4-{1-[(2R)-2-methoxy-2-phenylacetyl]piperidin-4-yl}phenyl)-1-(pyridazin-3-yl)azetidine-3-carboxamide;
N-(4-{1-[N-(furan-2-ylcarbonyl)glycyl]piperidin-4-yl}phenyl)-1-(pyridazin-3-yl)azetidine-3-carboxamide;
N-(4-{1-[(benzyloxy)acetyl]piperidin-4-yl}phenyl)-1-(pyridazin-3-yl)azetidine-3-carboxamide;
N-{4-[1-(naphthalen-1-ylacetyl)piperidin-4-yl]phenyl}-1-(pyridazin-3-yl)azetidine-3-carboxamide;
N-{4-[1-(cyclopropylcarbonyl)piperidin-4-yl]phenyl}-1-(pyridazin-3-yl)azetidine-3-carboxamide;
1-(pyridazin-3-yl)-N-{4-[1-(tetrahydrofuran-2-ylcarbonyl)piperidin-4-yl]phenyl}azetidine-3-carboxamide;
N-{4-[1-(N-benzoylglycyl)piperidin-4-yl]phenyl}-1-(pyridazin-3-yl)azetidine-3-carboxamide;
1-(pyridazin-3-yl)-N-{4-[1-(tetrahydrofuran-3-ylcarbonyl)piperidin-4-yl]phenyl}azetidine-3-carboxamide;
1-(pyridazin-3-yl)-N-(4-{1-[4-(thiophen-2-yl)butanoyl]piperidin-4-yl}phenyl)azetidine-3-carboxamide;
N-{4-[1-(2,5-difluorobenzoyl)piperidin-4-yl]phenyl}-1-(pyridazin-3-yl)azetidine-3-carboxamide;
N-{4-[1-(cyclobutylcarbonyl)piperidin-4-yl]phenyl}-1-(pyridazin-3-yl)azetidine-3-carboxamide;

N-[4-(1-{N-[(4-methylphenyl)sulfonyl]glycyl}piperidin-4-yl)phenyl]-1-(pyridazin-3-yl)azetidine-3-carboxamide;
N-(4-{1-[(2,3-difluorophenyl)acetyl]piperidin-4-yl}phenyl)-1-(pyridazin-3-yl)azetidine-3-carboxamide;
N-(4-{1-[(2S)-2-methoxy-2-phenylacetyl]piperidin-4-yl}phenyl)-1-(pyridazin-3-yl)azetidine-3-carboxamide;
N-{4-[1-(naphthalen-2-ylacetyl)piperidin-4-yl]phenyl}-1-(pyridazin-3-yl)azetidine-3-carboxamide;
N-{4-[1-(3-phenylpropanoyl)piperidin-4-yl]phenyl}-1-(pyridazin-3-yl)azetidine-3-carboxamide;
N-(4-{1-[(2,6-dichlorophenyl)acetyl]piperidin-4-yl}phenyl)-1-(pyridazin-3-yl)azetidine-3-carboxamide;
N-(4-{1-[3-(phenylsulfonyl)propanoyl]piperidin-4-yl}phenyl)-1-(pyridazin-3-yl)azetidine-3-carboxamide;
1-(pyridazin-3-yl)-N-{4-[1-(thiophen-3-ylcarbonyl)piperidin-4-yl]phenyl}azetidine-3-carboxamide;
N-(4-{1-[(2,5-dimethylfuran-3-yl)carbonyl]piperidin-4-yl}phenyl)-1-(pyridazin-3-yl)azetidine-3-carboxamide;
N-{4-[1-(cyclopropylacetyl)piperidin-4-yl]phenyl}-1-(pyridazin-3-yl)azetidine-3-carboxamide;
N-{4-[1-(2-fluorobenzoyl)piperidin-4-yl]phenyl}-1-(pyridazin-3-yl)azetidine-3-carboxamide;
N-{4-[1-(2-methylbenzoyl)piperidin-4-yl]phenyl}-1-(pyridazin-3-yl)azetidine-3-carboxamide;
1-(pyridazin-3-yl)-N-{4-[1-(1,3-thiazol-4-ylcarbonyl)piperidin-4-yl]phenyl}azetidine-3-carboxamide;
1-(pyridazin-3-yl)-N-{4-[1-(1,3-thiazol-5-ylcarbonyl)piperidin-4-yl]phenyl}azetidine-3-carboxamide;
N-{4-[1-(ethoxyacetyl)piperidin-4-yl]phenyl}-1-(pyridazin-3-yl)azetidine-3-carboxamide;
1-(pyridazin-3-yl)-N-{4-[1-(4,4,4-trifluorobutanoyl)piperidin-4-yl]phenyl}azetidine-3-carboxamide;
N-(4-{1-[(6-methylpyridin-3-yl)carbonyl]piperidin-4-yl}phenyl)-1-(pyridazin-3-yl)azetidine-3-carboxamide;
N-[4-(1-benzoylpiperidin-4-yl)phenyl]-1-(pyridazin-3-yl)azetidine-3-carboxamide;
N-{4-[1-(furan-2-ylcarbonyl)piperidin-4-yl]phenyl}-1-(pyridazin-3-yl)azetidine-3-carboxamide;
N-(4-{1-[(1-methylcyclohexyl)carbonyl]piperidin-4-yl}phenyl)-1-(pyridazin-3-yl)azetidine-3-carboxamide;
N-{4-[1-(2-oxopropanoyl)piperidin-4-yl]phenyl}-1-(pyridazin-3-yl)azetidine-3-carboxamide;
N-{4-[1-(cyclopentylcarbonyl)piperidin-4-yl]phenyl}-1-(pyridazin-3-yl)azetidine-3-carboxamide;
N-[4-(1-propanoylpiperidin-4-yl)phenyl]-1-(pyridazin-3-yl)azetidine-3-carboxamide;
N-{4-[1-(4-methylbenzoyl)piperidin-4-yl]phenyl}-1-(pyridazin-3-yl)azetidine-3-carboxamide;
N-(4-{[(3R)-1-(2-chlorobenzoyl)pyrrolidin-3-yl]oxy}phenyl)-1-(pyridazin-4-yl)azetidine-3-carboxamide;
1-(pyridazin-4-yl)-N-(4-{[(3R)-1-(1,3-thiazol-2-ylcarbonyl)pyrrolidin-3-yl]oxy}phenyl)azetidine-3-carboxamide;
N-(4-{[(3R)-1-(cyclopropylacetyl)pyrrolidin-3-yl]oxy}phenyl)-1-(pyridazin-4-yl)azetidine-3-carboxamide;
N-[4-({(3R)-1-[(2S)-2-methylbutanoyl]pyrrolidin-3-yl}oxy)phenyl]-1-(pyridazin-4-yl)azetidine-3-carboxamide;
1-(pyridazin-4-yl)-N-(4-{[(3R)-1-(tetrahydro-2H-pyran-4-ylcarbonyl)pyrrolidin-3-yl]oxy}phenyl)azetidine-3-carboxamide;
1-(pyridazin-4-yl)-N-(4-{[(3R)-1-{[4-(trifluoromethoxy)phenyl]acetyl}pyrrolidin-3-yl]oxy}phenyl)azetidine-3-carboxamide;
1-(pyridazin-4-yl)-N-(4-{[(3R)-1-(thiophen-3-ylcarbonyl)pyrrolidin-3-yl]oxy}phenyl)azetidine-3-carboxamide;
N-[4-({(3R)-1-[(4-fluorophenyl)acetyl]pyrrolidin-3-yl}oxy)phenyl]-1-(pyridazin-4-yl)azetidine-3-carboxamide;
N-[4-({(3R)-1-[(3,5-difluorophenyl)acetyl]pyrrolidin-3-yl}oxy)phenyl]-1-(pyridazin-4-yl)azetidine-3-carboxamide;
N-(4-{[(3R)-1-(3,4-difluorobenzoyl)pyrrolidin-3-yl]oxy}phenyl)-1-(pyridazin-4-yl)azetidine-3-carboxamide;
N-[4-({(3R)-1-[(3-fluorophenyl)acetyl]pyrrolidin-3-yl}oxy)phenyl]-1-(pyridazin-4-yl)azetidine-3-carboxamide;
1-(pyridazin-4-yl)-N-[4-({(3R)-1-[3-(trifluoromethyl)benzoyl]pyrrolidin-3-yl}oxy)phenyl]azetidine-3-carboxamide;
N-[4-({(3R)-1-[(2,4-difluorophenyl)acetyl]pyrrolidin-3-yl}oxy)phenyl]-1-(pyridazin-4-yl)azetidine-3-carboxamide;
1-(pyridazin-4-yl)-N-(4-{[(3R)-1-{[4-(trifluoromethyl)phenyl]acetyl}pyrrolidin-3-yl]oxy}phenyl)azetidine-3-carboxamide;
1-(pyridazin-4-yl)-N-(4-{[(3R)-1-(1,3-thiazol-4-ylcarbonyl)pyrrolidin-3-yl]oxy}phenyl)azetidine-3-carboxamide;
1-(pyridazin-4-yl)-N-(4-{[(3R)-1-(tetrahydrofuran-2-ylcarbonyl)pyrrolidin-3-yl]oxy}phenyl)azetidine-3-carboxamide;
N-[4-({(3R)-1-[(5-methylthiophen-2-yl)carbonyl]pyrrolidin-3-yl}oxy)phenyl]-1-(pyridazin-4-yl)azetidine-3-carboxamide;
N-[4-({(3R)-1-[(2-fluorophenyl)acetyl]pyrrolidin-3-yl}oxy)phenyl]-1-(pyridazin-4-yl)azetidine-3-carboxamide;
N-(4-{[(3R)-1-(cyclopropylcarbonyl)pyrrolidin-3-yl]oxy}phenyl)-1-(pyridazin-4-yl)azetidine-3-carboxamide;
1-(pyridazin-4-yl)-N-(4-{[(3R)-1-(tetrahydrofuran-3-ylcarbonyl)pyrrolidin-3-yl]oxy}phenyl)azetidine-3-carboxamide;
1-(pyridazin-4-yl)-N-[4-({(3R)-1-[3-(trifluoromethoxy)benzoyl]pyrrolidin-3-yl}oxy)phenyl]azetidine-3-carboxamide;
1-(pyridazin-4-yl)-N-(4-{[(3R)-1-(pyridin-2-ylcarbonyl)pyrrolidin-3-yl]oxy}phenyl)azetidine-3-carboxamide;
N-(4-{[(3R)-1-(3-chlorobenzoyl)pyrrolidin-3-yl]oxy}phenyl)-1-(pyridazin-4-yl)azetidine-3-carboxamide;
N-(4-{[(3R)-1-(4-chlorobenzoyl)pyrrolidin-3-yl]oxy}phenyl)-1-(pyridazin-4-yl)azetidine-3-carboxamide;
N-(4-{[(3R)-1-(2-methyl-2-phenylpropanoyl)pyrrolidin-3-yl]oxy}phenyl)-1-(pyridazin-4-yl)azetidine-3-carboxamide;
N-(4-{[(3R)-1-(2,4-difluorobenzoyl)pyrrolidin-3-yl]oxy}phenyl)-1-(pyridazin-4-yl)azetidine-3-carboxamide;
N-(4-{[(3R)-1-(methoxyacetyl)pyrrolidin-3-yl]oxy}phenyl)-1-(pyridazin-4-yl)azetidine-3-carboxamide;
1-(pyridazin-4-yl)-N-(4-{[(3R)-1-(thiophen-2-ylcarbonyl)pyrrolidin-3-yl]oxy}phenyl)azetidine-3-carboxamide;
1-(pyridazin-4-yl)-N-(4-{[(3R)-1-{[3-(trifluoromethyl)phenyl]acetyl}pyrrolidin-3-yl]oxy}phenyl)azetidine-3-carboxamide;
N-(4-{[(3R)-1-(2-methylpropanoyl)pyrrolidin-3-yl]oxy}phenyl)-1-(pyridazin-4-yl)azetidine-3-carboxamide;
N-(4-{[(3R)-1-(2-fluorobenzoyl)pyrrolidin-3-yl]oxy}phenyl)-1-(pyridazin-4-yl)azetidine-3-carboxamide;
N-(4-{[(3R)-1-(2,2-dimethylbutanoyl)pyrrolidin-3-yl]oxy}phenyl)-1-(pyridazin-4-yl)azetidine-3-carboxamide;
N-(4-{[(3R)-1-(3,5-difluorobenzoyl)pyrrolidin-3-yl]oxy}phenyl)-1-(pyridazin-4-yl)azetidine-3-carboxamide;
1-(pyridazin-4-yl)-N-[4-({(3R)-1-[4-(trifluoromethyl)benzoyl]pyrrolidin-3-yl}oxy)phenyl]azetidine-3-carboxamide;
N-(4-{[(3R)-1-(3-fluorobenzoyl)pyrrolidin-3-yl]oxy}phenyl)-1-(pyridazin-4-yl)azetidine-3-carboxamide;

1-(pyridazin-4-yl)-N-[4-({(3R)-1-[4-(trifluoromethoxy)benzoyl]pyrrolidin-3-yl}oxy)phenyl]azetidine-3-carboxamide;
N-(4-{[(3R)-1-(3-methylbutanoyl)pyrrolidin-3-yl]oxy}phenyl)-1-(pyridazin-4-yl)azetidine-3-carboxamide;
1-(pyridazin-4-yl)-N-(4-{[(3R)-1-(3,3,3-trifluoropropanoyl)pyrrolidin-3-yl]oxy}phenyl)azetidine-3-carboxamide;
N-[4-({(3R)-1-[difluoro(phenyl)acetyl]pyrrolidin-3-yl}oxy)phenyl]-1-(pyridazin-4-yl)azetidine-3-carboxamide;
N-(4-{[(3R)-1-(2,2-dimethylpropanoyl)pyrrolidin-3-yl]oxy}phenyl)-1-(pyridazin-4-yl)azetidine-3-carboxamide;
N-[4-({(3R)-1-[(4,4-difluorocyclohexyl)carbonyl]pyrrolidin-3-yl}oxy)phenyl]-1-(pyridazin-4-yl)azetidine-3-carboxamide;
N-(4-{[(3R)-1-(2-chlorobenzoyl)pyrrolidin-3-yl]oxy}phenyl)-1-(pyridazin-3-yl)azetidine-3-carboxamide;
1-(pyridazin-3-yl)-N-(4-{[(3R)-1-(1,3-thiazol-2-ylcarbonyl)pyrrolidin-3-yl]oxy}phenyl)azetidine-3-carboxamide;
N-(4-{[(3R)-1-(cyclopropylacetyl)pyrrolidin-3-yl]oxy}phenyl)-1-(pyridazin-3-yl)azetidine-3-carboxamide;
N-[4-({(3R)-1-[(2S)-2-methylbutanoyl]pyrrolidin-3-yl}oxy)phenyl]-1-(pyridazin-3-yl)azetidine-3-carboxamide;
1-(pyridazin-3-yl)-N-(4-{[(3R)-1-(tetrahydro-2H-pyran-4-ylcarbonyl)pyrrolidin-3-yl]oxy}phenyl)azetidine-3-carboxamide;
1-(pyridazin-3-yl)-N-(4-{[(3R)-1-{[4-(trifluoromethoxy)phenyl]acetyl}pyrrolidin-3-yl]oxy}phenyl)azetidine-3-carboxamide;
N-(4-{[(3R)-1-(4-fluorobenzoyl)pyrrolidin-3-yl]oxy}phenyl)-1-(pyridazin-3-yl)azetidine-3-carboxamide;
1-(pyridazin-3-yl)-N-(4-{[(3R)-1-(thiophen-3-ylcarbonyl)pyrrolidin-3-yl]oxy}phenyl)azetidine-3-carboxamide;
N-[4-({(3R)-1-[(4-fluorophenyl)acetyl]pyrrolidin-3-yl}oxy)phenyl]-1-(pyridazin-3-yl)azetidine-3-carboxamide;
N-[4-({(3R)-1-[(3,5-difluorophenyl)acetyl]pyrrolidin-3-yl}oxy)phenyl]-1-(pyridazin-3-yl)azetidine-3-carboxamide;
N-(4-{[(3R)-1-(3,4-difluorobenzoyl)pyrrolidin-3-yl]oxy}phenyl)-1-(pyridazin-3-yl)azetidine-3-carboxamide;
N-[4-({(3R)-1-[(3-fluorophenyl)acetyl]pyrrolidin-3-yl}oxy)phenyl]-1-(pyridazin-3-yl)azetidine-3-carboxamide;
1-(pyridazin-3-yl)-N-[4-({(3R)-1-[3-(trifluoromethyl)benzoyl]pyrrolidin-3-yl}oxy)phenyl]azetidine-3-carboxamide;
N-[4-({(3R)-1-[(2,4-difluorophenyl)acetyl]pyrrolidin-3-yl}oxy)phenyl]-1-(pyridazin-3-yl)azetidine-3-carboxamide;
1-(pyridazin-3-yl)-N-(4-{[(3R)-1-{[4-(trifluoromethyl)phenyl]acetyl}pyrrolidin-3-yl]oxy}phenyl)azetidine-3-carboxamide;
1-(pyridazin-3-yl)-N-(4-{[(3R)-1-(1,3-thiazol-4-ylcarbonyl)pyrrolidin-3-yl]oxy}phenyl)azetidine-3-carboxamide;
1-(pyridazin-3-yl)-N-(4-{[(3R)-1-(tetrahydrofuran-2-ylcarbonyl)pyrrolidin-3-yl]oxy}phenyl)azetidine-3-carboxamide;
N-[4-({(3R)-1-[(5-methylthiophen-2-yl)carbonyl]pyrrolidin-3-yl}oxy)phenyl]-1-(pyridazin-3-yl)azetidine-3-carboxamide;
N-[4-({(3R)-1-[(2-fluorophenyl)acetyl]pyrrolidin-3-yl}oxy)phenyl]-1-(pyridazin-3-yl)azetidine-3-carboxamide;
N-(4-{[(3R)-1-(cyclopropylcarbonyl)pyrrolidin-3-yl]oxy}phenyl)-1-(pyridazin-3-yl)azetidine-3-carboxamide;
1-(pyridazin-3-yl)-N-(4-{[(3R)-1-(tetrahydrofuran-3-ylcarbonyl)pyrrolidin-3-yl]oxy}phenyl)azetidine-3-carboxamide;
1-(pyridazin-3-yl)-N-[4-({(3R)-1-[3-(trifluoromethoxy)benzoyl]pyrrolidin-3-yl}oxy)phenyl]azetidine-3-carboxamide;
1-(pyridazin-3-yl)-N-(4-{[(3R)-1-(pyridin-2-ylcarbonyl)pyrrolidin-3-yl]oxy}phenyl)azetidine-3-carboxamide;
N-(4-{[(3R)-1-(3-chlorobenzoyl)pyrrolidin-3-yl]oxy}phenyl)-1-(pyridazin-3-yl)azetidine-3-carboxamide;
N-(4-{[(3R)-1-(4-chlorobenzoyl)pyrrolidin-3-yl]oxy}phenyl)-1-(pyridazin-3-yl)azetidine-3-carboxamide;
N-(4-{[(3R)-1-(2-methyl-2-phenylpropanoyl)pyrrolidin-3-yl]oxy}phenyl)-1-(pyridazin-3-yl)azetidine-3-carboxamide;
N-(4-{[(3R)-1-(2,4-difluorobenzoyl)pyrrolidin-3-yl]oxy}phenyl)-1-(pyridazin-3-yl)azetidine-3-carboxamide;
N-(4-{[(3R)-1-(methoxyacetyl)pyrrolidin-3-yl]oxy}phenyl)-1-(pyridazin-3-yl)azetidine-3-carboxamide;
1-(pyridazin-3-yl)-N-(4-{[(3R)-1-(thiophen-2-ylcarbonyl)pyrrolidin-3-yl]oxy}phenyl)azetidine-3-carboxamide;
1-(pyridazin-3-yl)-N-(4-{[(3R)-1-{[3-(trifluoromethyl)phenyl]acetyl}pyrrolidin-3-yl]oxy}phenyl)azetidine-3-carboxamide;
N-(4-{[(3R)-1-(2-methylpropanoyl)pyrrolidin-3-yl]oxy}phenyl)-1-(pyridazin-3-yl)azetidine-3-carboxamide;
N-(4-{[(3R)-1-(2-fluorobenzoyl)pyrrolidin-3-yl]oxy}phenyl)-1-(pyridazin-3-yl)azetidine-3-carboxamide;
N-(4-{[(3R)-1-(2,2-dimethylbutanoyl)pyrrolidin-3-yl]oxy}phenyl)-1-(pyridazin-3-yl)azetidine-3-carboxamide;
N-(4-{[(3R)-1-(3,5-difluorobenzoyl)pyrrolidin-3-yl]oxy}phenyl)-1-(pyridazin-3-yl)azetidine-3-carboxamide;
1-(pyridazin-3-yl)-N-[4-({(3R)-1-[4-(trifluoromethyl)benzoyl]pyrrolidin-3-yl}oxy)phenyl]azetidine-3-carboxamide;
N-(4-{[(3R)-1-(3-fluorobenzoyl)pyrrolidin-3-yl]oxy}phenyl)-1-(pyridazin-3-yl)azetidine-3-carboxamide;
1-(pyridazin-3-yl)-N-[4-({(3R)-1-[4-(trifluoromethoxy)benzoyl]pyrrolidin-3-yl}oxy)phenyl]azetidine-3-carboxamide;
N-(4-{[(3R)-1-(3-methylbutanoyl)pyrrolidin-3-yl]oxy}phenyl)-1-(pyridazin-3-yl)azetidine-3-carboxamide;
1-(pyridazin-3-yl)-N-(4-{[(3R)-1-(3,3,3-trifluoropropanoyl)pyrrolidin-3-yl]oxy}phenyl)azetidine-3-carboxamide;
N-[4-({(3R)-1-[difluoro(phenyl)acetyl]pyrrolidin-3-yl}oxy)phenyl]-1-(pyridazin-3-yl)azetidine-3-carboxamide;
N-(4-{[(3R)-1-(2,2-dimethylpropanoyl)pyrrolidin-3-yl]oxy}phenyl)-1-(pyridazin-3-yl)azetidine-3-carboxamide;
N-[4-({(3R)-1-[(4,4-difluorocyclohexyl)carbonyl]pyrrolidin-3-yl}oxy)phenyl]-1-(pyridazin-3-yl)azetidine-3-carboxamide;
N-{4-[1-(2-chlorobenzoyl)piperidin-4-yl]phenyl}-1-(pyridazin-4-yl)azetidine-3-carboxamide;
1-(pyridazin-4-yl)-N-{4-[1-(1,3-thiazol-2-ylcarbonyl)piperidin-4-yl]phenyl}azetidine-3-carboxamide;
N-{4-[1-(cyclopropylacetyl)piperidin-4-yl]phenyl}-1-(pyridazin-4-yl)azetidine-3-carboxamide;
N-{4-[1-(2-methylpropanoyl)piperidin-4-yl]phenyl}-1-(pyridazin-4-yl)azetidine-3-carboxamide;
N-{4-[1-(4-fluorobenzoyl)piperidin-4-yl]phenyl}-1-(pyridazin-4-yl)azetidine-3-carboxamide;
1-(pyridazin-4-yl)-N-{4-[1-(thiophen-3-ylcarbonyl)piperidin-4-yl]phenyl}azetidine-3-carboxamide;
N-(4-{1-[(4-fluorophenyl)acetyl]piperidin-4-yl}phenyl)-1-(pyridazin-4-yl)azetidine-3-carboxamide;
N-(4-{1-[(3,5-difluorophenyl)acetyl]piperidin-4-yl}phenyl)-1-(pyridazin-4-yl)azetidine-3-carboxamide;
N-{4-[1-(3,4-difluorobenzoyl)piperidin-4-yl]phenyl}-1-(pyridazin-4-yl)azetidine-3-carboxamide;

N-(4-{1-[(3-fluorophenyl)acetyl]piperidin-4-yl}phenyl)-1-(pyridazin-4-yl)azetidine-3-carboxamide;

1-(pyridazin-4-yl)-N-(4-{1-[3-(trifluoromethyl)benzoyl]piperidin-4-yl}phenyl)azetidine-3-carboxamide;

N-(4-{1-[(2,4-difluorophenyl)acetyl]piperidin-4-yl}phenyl)-1-(pyridazin-4-yl)azetidine-3-carboxamide;

1-(pyridazin-4-yl)-N-{4-[1-(1,3-thiazol-4-ylcarbonyl)piperidin-4-yl]phenyl}azetidine-3-carboxamide;

1-(pyridazin-4-yl)-N-{4-[1-(tetrahydrofuran-2-ylcarbonyl)piperidin-4-yl]phenyl}azetidine-3-carboxamide;

N-(4-{1-[(5-methylthiophen-2-yl)carbonyl]piperidin-4-yl}phenyl)-1-(pyridazin-4-yl)azetidine-3-carboxamide;

N-(4-{1-[(2-fluorophenyl)acetyl]piperidin-4-yl}phenyl)-1-(pyridazin-4-yl)azetidine-3-carboxamide;

N-{4-[1-(cyclopropylcarbonyl)piperidin-4-yl]phenyl}-1-(pyridazin-4-yl)azetidine-3-carboxamide;

1-(pyridazin-4-yl)-N-{4-[1-(tetrahydrofuran-3-ylcarbonyl)piperidin-4-yl]phenyl}azetidine-3-carboxamide;

1-(pyridazin-4-yl)-N-{4-[1-(pyridin-2-ylcarbonyl)piperidin-4-yl]phenyl}azetidine-3-carboxamide;

N-{4-[1-(3-chlorobenzoyl)piperidin-4-yl]phenyl}-1-(pyridazin-4-yl)azetidine-3-carboxamide;

N-{4-[1-(4-chlorobenzoyl)piperidin-4-yl]phenyl}-1-(pyridazin-4-yl)azetidine-3-carboxamide;

N-{4-[1-(2-methyl-2-phenylpropanoyl)piperidin-4-yl]phenyl}-1-(pyridazin-4-yl)azetidine-3-carboxamide;

N-{4-[1-(2,4-difluorobenzoyl)piperidin-4-yl]phenyl}-1-(pyridazin-4-yl)azetidine-3-carboxamide;

N-{4-[1-(methoxyacetyl)piperidin-4-yl]phenyl}-1-(pyridazin-4-yl)azetidine-3-carboxamide;

1-(pyridazin-4-yl)-N-{4-[1-(thiophen-2-ylcarbonyl)piperidin-4-yl]phenyl}azetidine-3-carboxamide;

1-(pyridazin-4-yl)-N-[4-(1-{[3-(trifluoromethyl)phenyl]acetyl}piperidin-4-yl)phenyl]azetidine-3-carboxamide;

N-{4-[1-(2-fluorobenzoyl)piperidin-4-yl]phenyl}-1-(pyridazin-4-yl)azetidine-3-carboxamide;

N-{4-[1-(3,5-difluorobenzoyl)piperidin-4-yl]phenyl}-1-(pyridazin-4-yl)azetidine-3-carboxamide;

1-(pyridazin-4-yl)-N-(4-{1-[4-(trifluoromethyl)benzoyl]piperidin-4-yl}phenyl)azetidine-3-carboxamide;

N-{4-[1-(3-fluorobenzoyl)piperidin-4-yl]phenyl}-1-(pyridazin-4-yl)azetidine-3-carboxamide;

1-(pyridazin-4-yl)-N-(4-{1-[4-(trifluoromethoxy)benzoyl]piperidin-4-yl}phenyl)azetidine-3-carboxamide;

N-{4-[1-(3-methylbutanoyl)piperidin-4-yl]phenyl}-1-(pyridazin-4-yl)azetidine-3-carboxamide;

1-(pyridazin-4-yl)-N-{4-[1-(3,3,3-trifluoropropanoyl)piperidin-4-yl]phenyl}azetidine-3-carboxamide;

N-(4-{1-[difluoro(phenyl)acetyl]piperidin-4-yl}phenyl)-1-(pyridazin-4-yl)azetidine-3-carboxamide;

N-{4-[1-(2,2-dimethylpropanoyl)piperidin-4-yl]phenyl}-1-(pyridazin-4-yl)azetidine-3-carboxamide;

N-(4-{1-[(4,4-difluorocyclohexyl)carbonyl]piperidin-4-yl}phenyl)-1-(pyridazin-4-yl)azetidine-3-carboxamide;

1-(pyridazin-4-yl)-N-[4-(1-{[4-(trifluoromethoxy)phenyl]acetyl}piperidin-4-yl)phenyl]azetidine-3-carboxamide;

1-(pyridazin-4-yl)-N-(4-{1-[3-(trifluoromethoxy)benzoyl]piperidin-4-yl}phenyl)azetidine-3-carboxamide;

1-(pyridazin-4-yl)-N-[4-(1-{[4-(trifluoromethyl)phenyl]acetyl}piperidin-4-yl)phenyl]azetidine-3-carboxamide;

N-(4-{[1-(3-chlorobenzoyl)piperidin-4-yl]sulfonyl}phenyl)-1-(pyridazin-3-yl)azetidine-3-carboxamide;

N-(4-{[1-(4-tert-butylbenzoyl)piperidin-4-yl]sulfonyl}phenyl)-1-(pyridazin-3-yl)azetidine-3-carboxamide;

N-(4-{[1-(4-methoxybenzoyl)piperidin-4-yl]sulfonyl}phenyl)-1-(pyridazin-3-yl)azetidine-3-carboxamide;

N-(4-{[1-(4-methylbenzoyl)piperidin-4-yl]sulfonyl}phenyl)-1-(pyridazin-3-yl)azetidine-3-carboxamide;

N-(4-{[1-(cyclohexylcarbonyl)piperidin-4-yl]sulfonyl}phenyl)-1-(pyridazin-3-yl)azetidine-3-carboxamide;

N-(4-{[1-(cyclopropylacetyl)piperidin-4-yl]sulfonyl}phenyl)-1-(pyridazin-3-yl)azetidine-3-carboxamide;

N-(4-{[1-(2-methoxybenzoyl)piperidin-4-yl]sulfonyl}phenyl)-1-(pyridazin-3-yl)azetidine-3-carboxamide;

N-[4-({1-[(2S)-2-phenylbutanoyl]piperidin-4-yl}sulfonyl)phenyl]-1-(pyridazin-3-yl)azetidine-3-carboxamide;

N-[4-({1-[4-(propan-2-yl)benzoyl]piperidin-4-yl}sulfonyl)phenyl]-1-(pyridazin-3-yl)azetidine-3-carboxamide;

N-(4-{[1-(4-chlorobenzoyl)piperidin-4-yl]sulfonyl}phenyl)-1-(pyridazin-3-yl)azetidine-3-carboxamide;

N-{4-[(1-benzoylpiperidin-4-yl)sulfonyl]phenyl}-1-(pyridazin-3-yl)azetidine-3-carboxamide;

1-(pyridazin-3-yl)-N-(4-{[1-(4,4,4-trifluorobutanoyl)piperidin-4-yl]sulfonyl}phenyl)azetidine-3-carboxamide;

N-(4-{[1-(2,5-difluorobenzoyl)piperidin-4-yl]sulfonyl}phenyl)-1-(pyridazin-3-yl)azetidine-3-carboxamide;

N-(4-{[1-(2-fluorobenzoyl)piperidin-4-yl]sulfonyl}phenyl)-1-(pyridazin-3-yl)azetidine-3-carboxamide;

N-(4-{[1-(2-methylbenzoyl)piperidin-4-yl]sulfonyl}phenyl)-1-(pyridazin-3-yl)azetidine-3-carboxamide;

N-[4-({1-[(4-fluorophenyl)acetyl]piperidin-4-yl}sulfonyl)phenyl]-1-(pyridazin-3-yl)azetidine-3-carboxamide;

N-(4-{[1-(3-methylbenzoyl)piperidin-4-yl]sulfonyl}phenyl)-1-(pyridazin-3-yl)azetidine-3-carboxamide;

N-(4-{[1-(2,3-dimethylbenzoyl)piperidin-4-yl]sulfonyl}phenyl)-1-(pyridazin-3-yl)azetidine-3-carboxamide;

N-[4-({1-[(3-fluorophenyl)acetyl]piperidin-4-yl}sulfonyl)phenyl]-1-(pyridazin-3-yl)azetidine-3-carboxamide;

N-(4-{[1-(3-fluorobenzoyl)piperidin-4-yl]sulfonyl}phenyl)-1-(pyridazin-3-yl)azetidine-3-carboxamide;

1-(pyridazin-3-yl)-N-[4-({1-[3-(trifluoromethyl)benzoyl]piperidin-4-yl}sulfonyl)phenyl]azetidine-3-carboxamide;

N-[4-({1-[(3,5-difluorophenyl)acetyl]piperidin-4-yl}sulfonyl)phenyl]-1-(pyridazin-3-yl)azetidine-3-carboxamide;

N-(4-{[1-(2,4-difluorobenzoyl)piperidin-4-yl]sulfonyl}phenyl)-1-(pyridazin-3-yl)azetidine-3-carboxamide;

1-(pyridazin-3-yl)-N-[4-({1-[4-(trifluoromethyl)benzoyl]piperidin-4-yl}sulfonyl)phenyl]azetidine-3-carboxamide;

N-(4-{[1-(4-fluorobenzoyl)piperidin-4-yl]sulfonyl}phenyl)-1-(pyridazin-3-yl)azetidine-3-carboxamide;

N-(4-{[1-(2,3-difluorobenzoyl)piperidin-4-yl]sulfonyl}phenyl)-1-(pyridazin-3-yl)azetidine-3-carboxamide;

N-(4-{[1-(2,4-dichlorobenzoyl)piperidin-4-yl]sulfonyl}phenyl)-1-(pyridazin-3-yl)azetidine-3-carboxamide;

N-(4-{[1-(naphthalen-1-ylcarbonyl)piperidin-4-yl]sulfonyl}phenyl)-1-(pyridazin-3-yl)azetidine-3-carboxamide;

N-(4-{[1-(cyclopropylcarbonyl)piperidin-4-yl]
  sulfonyl}phenyl)-1-(pyridazin-3-yl)azetidine-3-carboxa-
  mide;
N-(4-{[1-(3,5-difluorobenzoyl)piperidin-4-yl]
  sulfonyl}phenyl)-1-(pyridazin-3-yl)azetidine-3-carboxa-
  mide;
N-(4-{[1-(2,2-dimethylpropanoyl)piperidin-4-yl]
  sulfonyl}phenyl)-1-(pyridazin-3-yl)azetidine-3-carboxa-
  mide;
N-(4-{[1-(3,3-dimethylbutanoyl)piperidin-4-yl]
  sulfonyl}phenyl)-1-(pyridazin-3-yl)azetidine-3-carboxa-
  mide;
N-(4-{[1-(3-methoxybenzoyl)piperidin-4-yl]
  sulfonyl}phenyl)-1-(pyridazin-3-yl)azetidine-3-carboxa-
  mide;
N-(4-{[1-(3-methylbutanoyl)piperidin-4-yl]
  sulfonyl}phenyl)-1-(pyridazin-3-yl)azetidine-3-carboxa-
  mide;
N-(4-{[1-(2-methylpropanoyl)piperidin-4-yl]
  sulfonyl}phenyl)-1-(pyridazin-3-yl)azetidine-3-carboxa-
  mide;
N-(4-{[1-(cyclopentylcarbonyl)piperidin-4-yl]
  sulfonyl}phenyl)-1-(pyridazin-3-yl)azetidine-3-carboxa-
  mide;
N-(4-{[1-(phenylacetyl)piperidin-4-yl]sulfonyl}phenyl)-1-
  (pyridazin-3-yl)azetidine-3-carboxamide;
N-[4-({1-[(1-phenylcyclopropyl)carbonyl]piperidin-4-
  yl}sulfonyl)phenyl]-1-(pyridazin-3-yl)azetidine-3-car-
  boxamide;
N-{4-[1-(2-methylalanyl)piperidin-4-yl]phenyl}-1-(pyri-
  din-3-yl)azetidine-3-carboxamide;
tert-butyl 4-(2-methyl-1-oxo-1-{4-[4-({[1-(pyridin-3-yl)
  azetidin-3-yl]carbonyl}amino)phenyl]piperidin-1-
  yl}propan-2-yl)piperazine-1-carboxylate;
N-(4-{1-[2-methyl-2-(piperazin-1-yl)propanoyl]piperidin-
  4-yl}phenyl)-1-(pyridin-3-yl)azetidine-3-carboxamide;
N-(4-{[1-(2-chlorobenzoyl)piperidin-4-yl]
  sulfonyl}phenyl)-1-(pyridazin-3-yl)azetidine-3-carboxa-
  mide;
N-(4-{[1-(4-methylpentanoyl)piperidin-4-yl]
  sulfonyl}phenyl)-1-(pyridazin-3-yl)azetidine-3-carboxa-
  mide;
N-[4-({1-[(2-fluorophenyl)acetyl]piperidin-4-yl}sulfonyl)
  phenyl]-1-(pyridazin-3-yl)azetidine-3-carboxamide;
N-(4-{[1-(2-methylpropanoyl)piperidin-4-yl]
  sulfonyl}phenyl)-1-(pyridazin-3-yl)azetidine-3-carboxa-
  mide;
N-{4-[(1-benzoylpiperidin-4-yl)sulfonyl]phenyl}-1-(py-
  ridazin-4-yl)azetidine-3-carboxamide;
N-(4-{[1-(4-fluorobenzoyl)piperidin-4-yl]sulfonyl}phenyl)-
  1-(pyridazin-4-yl)azetidine-3-carboxamide;
N-(4-{[1-(cyclopentylcarbonyl)piperidin-4-yl]
  sulfonyl}phenyl)-1-(pyridazin-4-yl)azetidine-3-carboxa-
  mide;
N-[4-(1-benzoylpiperidin-4-yl)phenyl]-1-(6-fluoro-5-meth-
  ylpyridin-3-yl)azetidine-3-carboxamide;
N-[4-(1-benzoylpiperidin-4-yl)phenyl]-1-(5-fluoropyridin-
  3-yl)azetidine-3-carboxamide;
N-[4-(1-benzoylpiperidin-4-yl)phenyl]-1-(6-methylpy-
  ridazin-3-yl)azetidine-3-carboxamide;
N-[4-(1-benzoylpiperidin-4-yl)phenyl]-1-(2-fluoro-6-meth-
  ylpyridin-3-yl)azetidine-3-carboxamide;
N-[4-(1-benzoylpiperidin-4-yl)phenyl]-1-(2-cyanopyridin-
  3-yl)azetidine-3-carboxamide;
N-[4-(1-benzoylpiperidin-4-yl)phenyl]-1-(4-cyanopyridin-
  3-yl)azetidine-3-carboxamide;
N-[4-(1-benzoylpiperidin-4-yl)phenyl]-1-(6-fluoro-4-meth-
  ylpyridin-3-yl)azetidine-3-carboxamide;
N-[4-(1-benzoylpiperidin-4-yl)phenyl]-1-(5-cyanopyridin-
  3-yl)azetidine-3-carboxamide;
N-[4-(1-benzoylpiperidin-4-yl)phenyl]-1-(5-methylpyridin-
  3-yl)azetidine-3-carboxamide;
N-(4-{1-[(4-methyltetrahydro-2H-pyran-4-yl)methyl]-1H-
  pyrazol-4-yl}phenyl)-1-(pyridazin-3-yl)azetidine-3-car-
  boxamide;
N-(4-{1-[2-(piperazin-1-yl)ethyl]-1H-pyrazol-4-
  yl}phenyl)-1-(pyridazin-3-yl)azetidine-3-carboxamide;
N-{4-[1-(2,2-dimethylpropyl)-1H-pyrazol-4-yl]phenyl}-1-
  (pyridazin-3-yl)azetidine-3-carboxamide;
N-{4-[1-(2-hydroxy-2-methylpropyl)-1H-pyrazol-4-yl]phe-
  nyl}-1-(pyridazin-3-yl)azetidine-3-carboxamide;
N-[4-(5-propyl-1,2,4-oxadiazol-3-yl)phenyl]-1-(pyridazin-
  3-yl)azetidine-3-carboxamide;
N-{4-[5-(2,2-dimethylpropyl)-1,3,4-oxadiazol-2-yl]phe-
  nyl}-1-(pyridazin-3-yl)azetidine-3-carboxamide;
N-{4-[1-(2,2-dimethylpropyl)-1H-imidazol-4-yl]phenyl}-1-
  (pyridazin-3-yl)azetidine-3-carboxamide;
N-[4-(3-cyclopropyl-1-methyl-1H-pyrazol-5-yl)phenyl]-1-
  (pyridazin-3-yl)azetidine-3-carboxamide;
N-{4-[5-(2,2-dimethylpropyl)-1,2,4-oxadiazol-3-yl]phe-
  nyl}-1-(pyridazin-3-yl)azetidine-3-carboxamide;
N-{4-[3-cyclopropyl-1-(2-methoxyethyl)-1H-pyrazol-5-yl]
  phenyl}-1-(pyridazin-3-yl)azetidine-3-carboxamide;
tert-butyl 4-fluoro-4-[4-({[1-(pyridazin-3-yl)azetidin-3-yl]
  carbonyl}amino)phenyl]piperidine-1-carboxylate;
N-{4-[3-cyclopropyl-1-(2-hydroxyethyl)-1H-pyrazol-5-yl]
  phenyl}-1-(pyridazin-3-yl)azetidine-3-carboxamide;
N-[4-(1-benzoylpiperidin-4-yl)phenyl]-1-(6-fluoropy-
  ridazin-3-yl)azetidine-3-carboxamide;
N-{4-[1-(2-fluorobenzoyl)piperidin-4-yl]phenyl}-1-(6-fluo-
  ropyridazin-3-yl)azetidine-3-carboxamide;
N-{4-[1-(2,2-dimethylpropanoyl)piperidin-4-yl]phenyl}-1-
  (6-fluoropyridazin-3-yl)azetidine-3-carboxamide;
1-(6-fluoropyridazin-3-yl)-N-{4-[1-(2-methylpropanoyl)pi-
  peridin-4-yl]phenyl}azetidine-3-carboxamide;
N-{4-[1-(2-ethylbutanoyl)piperidin-4-yl]phenyl}-1-(6-fluo-
  ropyridazin-3-yl)azetidine-3-carboxamide;
N-{4-[1-(4-fluorobenzoyl)piperidin-4-yl]phenyl}-1-(6-fluo-
  ropyridazin-3-yl)azetidine-3-carboxamide;
N-{2-fluoro-4-[1-(2-fluorobenzoyl)piperidin-4-yl]phenyl}-
  1-(pyridazin-3-yl)azetidine-3-carboxamide;
N-[4-(1-benzoylpiperidin-4-yl)-2-fluorophenyl]-1-(py-
  ridazin-3-yl)azetidine-3-carboxamide;
N-{2-fluoro-4-[1-(3-fluorobenzoyl)piperidin-4-yl]phenyl}-
  1-(pyridazin-3-yl)azetidine-3-carboxamide;
N-{2-fluoro-4-[1-(2-methylbenzoyl)piperidin-4-yl]phenyl}-
  1-(pyridazin-3-yl)azetidine-3-carboxamide;
N-{2-fluoro-4-[1-(4-fluorobenzoyl)piperidin-4-yl]phenyl}-
  1-(pyridazin-3-yl)azetidine-3-carboxamide;
N-{4-[1-(2,4-difluorobenzoyl)piperidin-4-yl]-2-fluorophe-
  nyl}-1-(pyridazin-3-yl)azetidine-3-carboxamide;
N-{4-[1-(3,5-difluorobenzoyl)piperidin-4-yl]-2-fluorophe-
  nyl}-1-(pyridazin-3-yl)azetidine-3-carboxamide;
N-{4-[1-(3,3-dimethylbutanoyl)piperidin-4-yl]-2-fluo-
  rophenyl}-1-(pyridazin-3-yl)azetidine-3-carboxamide;
N-{4-[8-(2-methylpropanoyl)-8-azabicyclo[3.2.1]oct-3-yl]
  phenyl}-1-(pyridazin-3-yl)azetidine-3-carboxamide;
1-(pyridazin-3-yl)-N-{4-[8-(4,4,4-trifluorobutanoyl)-8-
  azabicyclo[3.2.1]oct-3-yl]phenyl}azetidine-3-carboxam-
  ide;
N-[4-(8-benzoyl-8-azabicyclo[3.2.1]oct-3-yl)phenyl]-1-(py-
  ridazin-3-yl)azetidine-3-carboxamide;

N-{4-[8-(2-fluorobenzoyl)-8-azabicyclo[3.2.1]oct-3-yl]phenyl}-1-(pyridazin-3-yl)azetidine-3-carboxamide;
N-{4-[8-(2,2-dimethylpropanoyl)-8-azabicyclo[3.2.1]oct-3-yl]phenyl}-1-(pyridazin-3-yl)azetidine-3-carboxamide;
N-(4-{8-[(1-methylcyclopropyl)carbonyl]-8-azabicyclo[3.2.1]oct-3-yl}phenyl)-1-(pyridazin-3-yl)azetidine-3-carboxamide;
N-{4-[1-(2-methoxyethyl)-3-(2-methylpropyl)-1H-pyrazol-5-yl]phenyl}-1-(pyridazin-3-yl)azetidine-3-carboxamide;
N-{4-[1-(2-fluorobenzoyl)piperidin-4-yl]phenyl}-1-(6-methylpyridazin-3-yl)azetidine-3-carboxamide;
N-{4-[1-(2,2-dimethylpropanoyl)piperidin-4-yl]phenyl}-1-(6-methylpyridazin-3-yl)azetidine-3-carboxamide;
benzyl 4-[4-({[1-(6-chloropyridazin-3-yl)azetidin-3-yl]carbonyl}amino)phenyl]-4-fluoropiperidine-1-carboxylate;
benzyl 4-[4-({[1-(6-chloropyridazin-3-yl)azetidin-3-yl]carbonyl}amino)phenyl]-4-hydroxypiperidine-1-carboxylate;
N-{4-[4-fluoro-1-(2-fluorobenzoyl)piperidin-4-yl]phenyl}-1-(pyridazin-3-yl)azetidine-3-carboxamide;
N-{2-fluoro-4-[1-(2-methylpropanoyl)piperidin-4-yl]phenyl}-1-(pyridazin-3-yl)azetidine-3-carboxamide;
N-{4-[1-(2,2-dimethylpropanoyl)piperidin-4-yl]-2-fluorophenyl}-1-(pyridazin-3-yl)azetidine-3-carboxamide;
N-{4-[1-(cyclopropylcarbonyl)piperidin-4-yl]-2-fluorophenyl}-1-(pyridazin-3-yl)azetidine-3-carboxamide;
N-(2-fluoro-4-{1-[(1-methylcyclopropyl)carbonyl]piperidin-4-yl}phenyl)-1-(pyridazin-3-yl)azetidine-3-carboxamide;
N-{4-[1-(cyclopropylacetyl)piperidin-4-yl]-2-fluorophenyl}-1-(pyridazin-3-yl)azetidine-3-carboxamide;
N-[4-(1-benzoyl-4-fluoropiperidin-4-yl)phenyl]-1-(pyridazin-3-yl)azetidine-3-carboxamide;
N-{4-[1-(2,2-dimethylpropanoyl)-4-fluoropiperidin-4-yl]phenyl}-1-(pyridazin-3-yl)azetidine-3-carboxamide;
N-{4-[3-tert-butyl-1-(2-methoxyethyl)-1H-pyrazol-5-yl]phenyl}-1-(pyridazin-3-yl)azetidine-3-carboxamide;
N-{4-(1-butyl-3-tert-butyl-1H-pyrazol-5-yl)phenyl]-1-(pyridazin-3-yl)azetidine-3-carboxamide;
N-{4-[3-tert-butyl-1-(tetrahydro-2H-pyran-4-ylmethyl)-1H-pyrazol-5-yl]phenyl}-1-(pyridazin-3-yl)azetidine-3-carboxamide;
N-{2-fluoro-4-[1-(2-fluorobenzoyl)piperidin-4-yl]phenyl}-1-(pyridazin-4-yl)azetidine-3-carboxamide;
N-[4-(1-benzoylpiperidin-4-yl)-2-fluorophenyl]-1-(pyridazin-4-yl)azetidine-3-carboxamide;
N-{4-[1-(2,2-dimethylpropanoyl)piperidin-4-yl]-2-fluorophenyl}-1-(pyridazin-4-yl)azetidine-3-carboxamide;
N-{4-[1-(3,3-dimethylbutanoyl)piperidin-4-yl]-2-fluorophenyl}-1-(pyridazin-4-yl)azetidine-3-carboxamide;
N-{2-fluoro-4-[1-(4,4,4-trifluorobutanoyl)piperidin-4-yl]phenyl}-1-(pyridazin-4-yl)azetidine-3-carboxamide;
N-(4-{1-[(4-methylpiperidin-4-yl)methyl]-1H-pyrazol-4-yl}phenyl)-1-(pyridazin-3-yl)azetidine-3-carboxamide;
N-{4-[1-methyl-3-(trifluoromethyl)-1H-pyrazol-5-yl]phenyl}-1-(pyridazin-3-yl)azetidine-3-carboxamide;
1-(6-chloropyridazin-3-yl)-N-{4-[1-(2,2-dimethylpropyl)-1H-pyrazol-4-yl]phenyl}azetidine-3-carboxamide;
N-[4-(1-benzoylpiperidin-4-yl)phenyl]-1-(6-methylpyridin-3-yl)azetidine-3-carboxamide;
N-(4-{1-[(4-methylpiperidin-4-yl)methyl]-1H-pyrazol-4-yl}phenyl)-1-(pyridin-3-yl)azetidine-3-carboxamide;
N-{4-[1-(2,2-dimethylpropyl)-1H-pyrazol-4-yl]phenyl}-1-(6-methylpyridazin-3-yl)azetidine-3-carboxamide;
N-{3-fluoro-4-[1-(3-fluorobenzoyl)piperidin-4-yl]phenyl}-1-(pyridazin-3-yl)azetidine-3-carboxamide;
N-{3-fluoro-4-[1-(2-methylpropanoyl)piperidin-4-yl]phenyl}-1-(pyridazin-3-yl)azetidine-3-carboxamide;
N-{3-fluoro-4-[1-(3,3,3-trifluoropropanoyl)piperidin-4-yl]phenyl}-1-(pyridazin-3-yl)azetidine-3-carboxamide;
N-{4-[1-(3,3-dimethylbutanoyl)piperidin-4-yl]-3-fluorophenyl}-1-(pyridazin-3-yl)azetidine-3-carboxamide;
N-{3-fluoro-4-[1-(4,4,4-trifluorobutanoyl)piperidin-4-yl]phenyl}-1-(pyridazin-3-yl)azetidine-3-carboxamide;
N-[4-(1-benzoylpiperidin-4-yl)-3-fluorophenyl]-1-(pyridazin-3-yl)azetidine-3-carboxamide;
N-{3-fluoro-4-[1-(2-fluorobenzoyl)piperidin-4-yl]phenyl}-1-(pyridazin-3-yl)azetidine-3-carboxamide;
N-{4-[1-(2,2-dimethylpropanoyl)piperidin-4-yl]-3-fluorophenyl}-1-(pyridazin-3-yl)azetidine-3-carboxamide;
N-{3-fluoro-4-[1-(3-methylbutanoyl)piperidin-4-yl]phenyl}-1-(pyridazin-3-yl)azetidine-3-carboxamide;
N-{4-[1-(cyclopropylacetyl)piperidin-4-yl]-3-fluorophenyl}-1-(pyridazin-3-yl)azetidine-3-carboxamide;
N-{4-[1-(2-fluorobenzoyl)-4-hydroxypiperidin-4-yl]phenyl}-1-(pyridazin-3-yl)azetidine-3-carboxamide;
N-{4-[1-(2,2-dimethylpropanoyl)-4-hydroxypiperidin-4-yl]phenyl}-1-(pyridazin-3-yl)azetidine-3-carboxamide;
1-(6-methylpyridazin-3-yl)-N-(4-{1-[(4-methyltetrahydro-2H-pyran-4-yl)methyl]-1H-pyrazol-4-yl}phenyl)azetidine-3-carboxamide;
N-{4-[(1-benzoylpiperidin-4-yl)methyl]phenyl}-1-(pyridazin-3-yl)azetidine-3-carboxamide;
N-(4-{[1-(2-fluorobenzoyl)piperidin-4-yl]methyl}phenyl)-1-(pyridazin-3-yl)azetidine-3-carboxamide;
N-(4-{[1-(2,2-dimethylpropanoyl)piperidin-4-yl]methyl}phenyl)-1-(pyridazin-3-yl)azetidine-3-carboxamide;
N-(4-{[1-(3,3-dimethylbutanoyl)piperidin-4-yl]methyl}phenyl)-1-(pyridazin-3-yl)azetidine-3-carboxamide;
N-(4-{[1-(2-ethylbutanoyl)piperidin-4-yl]methyl}phenyl)-1-(pyridazin-3-yl)azetidine-3-carboxamide;
1-(pyridazin-3-yl)-N-(4-{[1-(4,4,4-trifluorobutanoyl)piperidin-4-yl]methyl}phenyl)azetidine-3-carboxamide;
N-(4-{[1-(2-methylpropanoyl)piperidin-4-yl]methyl}phenyl)-1-(pyridazin-3-yl)azetidine-3-carboxamide;
N-{4-[(1-acetylpiperidin-4-yl)methyl]phenyl}-1-(pyridazin-3-yl)azetidine-3-carboxamide;
N-[4-({1-[(2S)-2-methylbutanoyl]piperidin-4-yl}methyl)phenyl]-1-(pyridazin-3-yl)azetidine-3-carboxamide;
N-[4-({1-[(1-methylcyclopropyl)carbonyl]piperidin-4-yl}methyl)phenyl]-1-(pyridazin-3-yl)azetidine-3-carboxamide;
N-[4-(1-{[4-methyl-1-(oxetan-3-yl)piperidin-4-yl]methyl}-1H-pyrazol-4-yl)phenyl]-1-(6-methylpyridazin-3-yl)azetidine-3-carboxamide;
N-[4-(1-benzoylpiperidin-4-yl)phenyl]-1-(4-methylpyridazin-3-yl)azetidine-3-carboxamide;
N-[4-(1-benzoylpiperidin-4-yl)phenyl]-1-(3-methylpyridazin-4-yl)azetidine-3-carboxamide;
N-{4-[1-(2-fluorobenzoyl)piperidin-4-yl]phenyl}-1-(3-methylpyridazin-4-yl)azetidine-3-carboxamide;
N-(4-{1-[(2-aminopyridin-3-yl)carbonyl]piperidin-4-yl}phenyl)-1-(pyridazin-3-yl)azetidine-3-carboxamide;
1-methyl-5-[4-({[1-(pyridazin-3-yl)azetidin-3-yl]carbonyl}amino)phenyl]-1H-pyrazole-3-carboxylic acid;
ethyl 1-methyl-5-[4-({[1-(pyridazin-3-yl)azetidin-3-yl]carbonyl}amino)phenyl]-1H-pyrazole-3-carboxylate;
ethyl 1-phenyl-5-[4-({[1-(pyridazin-3-yl)azetidin-3-yl]carbonyl}amino)phenyl]-1H-pyrazole-3-carboxylate;

N-{6-[1-(2-fluorobenzoyl)piperidin-4-yl]pyridin-3-yl}-1-(pyridazin-3-yl)azetidine-3-carboxamide;
N-(4-{[(3R)-1-(3-methylbutanoyl)pyrrolidin-3-yl]oxy}phenyl)-1-(6-methylpyridazin-3-yl)azetidine-3-carboxamide;
N-(4-{[(3R)-1-(2-methylpropanoyl)pyrrolidin-3-yl]oxy}phenyl)-1-(6-methylpyridazin-3-yl)azetidine-3-carboxamide;
N-(4-{[(3R)-1-(2,4-difluorobenzoyl)pyrrolidin-3-yl]oxy}phenyl)-1-(6-methylpyridazin-3-yl)azetidine-3-carboxamide;
1-(6-methylpyridazin-3-yl)-N-(4-{[(3R)-1-(1,3-thiazol-4-ylcarbonyl)pyrrolidin-3-yl]oxy}phenyl)azetidine-3-carboxamide;
1-(pyridazin-3-yl)-N-{6-[1-(4,4,4-trifluorobutanoyl)piperidin-4-yl]pyridin-3-yl}azetidine-3-carboxamide;
N-{6-[1-(3,3-dimethylbutanoyl)piperidin-4-yl]pyridin-3-yl}-1-(pyridazin-3-yl)azetidine-3-carboxamide;
N-{4-[1-phenyl-3-(trifluoromethyl)-1H-pyrazol-5-yl]phenyl}-1-(pyridazin-3-yl)azetidine-3-carboxamide;
N-{6-[1-(2,2-dimethylpropyl)-1H-pyrazol-4-yl]pyridin-3-yl}-1-(pyridazin-3-yl)azetidine-3-carboxamide;
tert-butyl 4-[4-({[1-(pyridazin-3-yl)azetidin-3-yl]carbonyl}amino)-1H-pyrazol-1-yl]piperidine-1-carboxylate;
N-(6-{1-[(4-methylpiperidin-4-yl)methyl]-1H-pyrazol-4-yl}pyridin-3-yl)-1-(pyridazin-3-yl)azetidine-3-carboxamide;
1-(pyridazin-3-yl)-N-(4-{[1-(1,3-thiazol-5-ylcarbonyl)piperidin-4-yl]methyl}phenyl)azetidine-3-carboxamide;
N-(4-{[1-(cyclopentylcarbonyl)piperidin-4-yl]methyl}phenyl)-1-(pyridazin-3-yl)azetidine-3-carboxamide;
N-(4-{[1-(1H-pyrazol-4-ylcarbonyl)piperidin-4-yl]methyl}phenyl)-1-(pyridazin-3-yl)azetidine-3-carboxamide;
N-(4-{[1-(2,2-dimethylbutanoyl)piperidin-4-yl]methyl}phenyl)-1-(pyridazin-3-yl)azetidine-3-carboxamide;
N-[4-({1-[(2-methylcyclopropyl)carbonyl]piperidin-4-yl}methyl)phenyl]-1-(pyridazin-3-yl)azetidine-3-carboxamide;
N-[4-({1-[(methylsulfanyl)acetyl]piperidin-4-yl}methyl)phenyl]-1-(pyridazin-3-yl)azetidine-3-carboxamide;
N-[4-({1-[(1S,4R)-bicyclo[2.2.1]hept-2-ylacetyl]piperidin-4-yl}methyl)phenyl]-1-(pyridazin-3-yl)azetidine-3-carboxamide;
N-(4-{[1-(2-methylpentanoyl)piperidin-4-yl]methyl}phenyl)-1-(pyridazin-3-yl)azetidine-3-carboxamide;
N-(4-{[1-(4-methylpentanoyl)piperidin-4-yl]methyl}phenyl)-1-(pyridazin-3-yl)azetidine-3-carboxamide;
N-[4-({1-[3-(methylsulfanyl)propanoyl]piperidin-4-yl}methyl)phenyl]-1-(pyridazin-3-yl)azetidine-3-carboxamide;
1-(pyridazin-3-yl)-N-(4-{[1-(1,3-thiazol-4-ylcarbonyl)piperidin-4-yl]methyl}phenyl)azetidine-3-carboxamide;
N-(4-{[1-(1H-pyrazol-5-ylcarbonyl)piperidin-4-yl]methyl}phenyl)-1-(pyridazin-3-yl)azetidine-3-carboxamide;
N-[4-({1-[(6-methylpyridin-3-yl)carbonyl]piperidin-4-yl}methyl)phenyl]-1-(pyridazin-3-yl)azetidine-3-carboxamide;
N-[4-({1-[(3-methylthiophen-2-yl)carbonyl]piperidin-4-yl}methyl)phenyl]-1-(pyridazin-3-yl)azetidine-3-carboxamide;
N-(4-{[1-(pent-4-ynoyl)piperidin-4-yl]methyl}phenyl)-1-(pyridazin-3-yl)azetidine-3-carboxamide;
1-(pyridazin-3-yl)-N-(4-{[1-(thiophen-3-ylcarbonyl)piperidin-4-yl]methyl}phenyl)azetidine-3-carboxamide;
N-(4-{[1-(methoxyacetyl)piperidin-4-yl]methyl}phenyl)-1-(pyridazin-3-yl)azetidine-3-carboxamide;
1-(pyridazin-3-yl)-N-(4-{[1-(tetrahydrofuran-2-ylcarbonyl)piperidin-4-yl]methyl}phenyl)azetidine-3-carboxamide;
N-[4-({1-[(2-methoxyethoxy)acetyl]piperidin-4-yl}methyl)phenyl]-1-(pyridazin-3-yl)azetidine-3-carboxamide;
N-(4-{[1-(ethoxyacetyl)piperidin-4-yl]methyl}phenyl)-1-(pyridazin-3-yl)azetidine-3-carboxamide;
1-(pyridazin-3-yl)-N-(4-{[1-(thiophen-2-ylcarbonyl)piperidin-4-yl]methyl}phenyl)azetidine-3-carboxamide;
N-{4-[(1-hexanoylpiperidin-4-yl)methyl]phenyl}-1-(pyridazin-3-yl)azetidine-3-carboxamide;
N-[4-({1-[(1-methyl-1H-pyrrol-2-yl)carbonyl]piperidin-4-yl}methyl)phenyl]-1-(pyridazin-3-yl)azetidine-3-carboxamide;
N-(4-{[1-(but-3-enoyl)piperidin-4-yl]methyl}phenyl)-1-(pyridazin-3-yl)azetidine-3-carboxamide;
1-(pyridazin-3-yl)-N-(4-{[1-(1,3-thiazol-2-ylcarbonyl)piperidin-4-yl]methyl}phenyl)azetidine-3-carboxamide;
N-(4-{[1-(furan-2-ylcarbonyl)piperidin-4-yl]methyl}phenyl)-1-(pyridazin-3-yl)azetidine-3-carboxamide;
N-(4-{[1-(1,2-oxazol-5-ylcarbonyl)piperidin-4-yl]methyl}phenyl)-1-(pyridazin-3-yl)azetidine-3-carboxamide;
1-(pyridazin-3-yl)-N-(4-{[1-(pyridin-2-ylcarbonyl)piperidin-4-yl]methyl}phenyl)azetidine-3-carboxamide;
N-(4-{[1-(furan-3-ylcarbonyl)piperidin-4-yl]methyl}phenyl)-1-(pyridazin-3-yl)azetidine-3-carboxamide;
N-(4-{[1-(cyclopropylacetyl)piperidin-4-yl]methyl}phenyl)-1-(pyridazin-3-yl)azetidine-3-carboxamide;
N-(4-{[1-(2-methylbutanoyl)piperidin-4-yl]methyl}phenyl)-1-(pyridazin-3-yl)azetidine-3-carboxamide;
N-{4-[(1-propanoylpiperidin-4-yl)methyl]phenyl}-1-(pyridazin-3-yl)azetidine-3-carboxamide;
N-{4-[(1-butanoylpiperidin-4-yl)methyl]phenyl}-1-(pyridazin-3-yl)azetidine-3-carboxamide;
N-(4-{[1-(cyclobutylcarbonyl)piperidin-4-yl]methyl}phenyl)-1-(pyridazin-3-yl)azetidine-3-carboxamide;
N-{4-[(1-pentanoylpiperidin-4-yl)methyl]phenyl}-1-(pyridazin-3-yl)azetidine-3-carboxamide;
N-(4-{[1-(cyclopentylacetyl)piperidin-4-yl]methyl}phenyl)-1-(pyridazin-3-yl)azetidine-3-carboxamide;
N-(4-{[1-(2-methylbenzoyl)piperidin-4-yl]methyl}phenyl)-1-(pyridazin-3-yl)azetidine-3-carboxamide;
N-(4-{[1-(3-methylpentanoyl)piperidin-4-yl]methyl}phenyl)-1-(pyridazin-3-yl)azetidine-3-carboxamide;
N-(4-{[1-(cyclohexylcarbonyl)piperidin-4-yl]methyl}phenyl)-1-(pyridazin-3-yl)azetidine-3-carboxamide;
N-(4-{[1-(3-methylbutanoyl)piperidin-4-yl]methyl}phenyl)-1-(pyridazin-3-yl)azetidine-3-carboxamide;
N-(4-{[1-(cyclopropylcarbonyl)piperidin-4-yl]methyl}phenyl)-1-(pyridazin-3-yl)azetidine-3-carboxamide;

1-(pyridazin-3-yl)-N-(4-{[1-(3,3,3-trifluoropropanoyl)piperidin-4-yl]methyl}phenyl)azetidine-3-carboxamide;
N-{4-[1-(3,3-dimethylbutanoyl)piperidin-4-yl]phenyl}-1-(4-methylpyridazin-3-yl)azetidine-3-carboxamide;
N-{1-[1-(3,3-dimethylbutanoyl)piperidin-4-yl]-1H-pyrazol-4-yl}-1-(pyridazin-3-yl)azetidine-3-carboxamide;
N-{1-[1-(2-fluorobenzoyl)piperidin-4-yl]-1H-pyrazol-4-yl}-1-(pyridazin-3-yl)azetidine-3-carboxamide;
N-[4-(phenylcarbamoyl)phenyl]-1-(pyridazin-3-yl)azetidine-3-carboxamide;
N-{4[(2,2-dimethylpropyl)carbamoyl]phenyl}-1-(pyridazin-3-yl)azetidine-3-carboxamide;
N-{4-[(3-methoxy-2,2-dimethylpropyl)carbamoyl]phenyl}-1-(pyridazin-3-yl)azetidine-3-carboxamide;
N-{4[(2-cyclopropylethyl)carbamoyl]phenyl}-1-(pyridazin-3-yl)azetidine-3-carboxamide;
N-(4-{[2-(2-ethylpiperidin-1-yl)ethyl]carbamoyl}phenyl)-1-(pyridazin-3-yl)azetidine-3-carboxamide;
N-{4-[(cyclobutylmethyl)carbamoyl]phenyl}-1-(pyridazin-3-yl)azetidine-3-carboxamide;
N-{4-[(2S)-butan-2-ylcarbamoyl]phenyl}-1-(pyridazin-3-yl)azetidine-3-carboxamide;
N-[4-(butylcarbamoyl)phenyl]-1-(pyridazin-3-yl)azetidine-3-carboxamide;
N-{4-[(2,2-dimethyltetrahydro-2H-pyran-4-yl)carbamoyl]phenyl}-1-(pyridazin-3-yl)azetidine-3-carboxamide;
N-(4-{[(1S)-1-cyclopropylethyl]carbamoyl}phenyl)-1-(pyridazin-3-yl)azetidine-3-carboxamide;
N-[4-({2-[methyl(phenyl)amino]ethyl}carbamoyl)phenyl]-1-(pyridazin-3-yl)azetidine-3-carboxamide;
N-{4-[1,1'-bi(cyclopropyl)-1-ylcarbamoyl]phenyl}-1-(pyridazin-3-yl)azetidine-3-carboxamide;
1-(pyridazin-3-yl)-N-[4-(thiophen-3-ylcarbamoyl)phenyl]azetidine-3-carboxamide;
N-(4-{[(1R)-1-cyclopropylethyl]carbamoyl}phenyl)-1-(pyridazin-3-yl)azetidine-3-carboxamide;
N-{4-[(1-methylpiperidin-4-yl)carbamoyl]phenyl}-1-(pyridazin-3-yl)azetidine-3-carboxamide;
N-{4[(2R)-butan-2-ylcarbamoyl]phenyl}-1-(pyridazin-3-yl)azetidine-3-carboxamide;
N-[4-(1-azabicyclo[2.2.2]oct-3-ylcarbamoyl)phenyl]-1-(pyridazin-3-yl)azetidine-3-carboxamide;
1-(pyridazin-3-yl)-N-{4-[(tetrahydrofuran-3-ylmethyl)carbamoyl]phenyl}azetidine-3-carboxamide;
N-{4-[(oxetan-3-ylmethyl)carbamoyl]phenyl}-1-(pyridazin-3-yl)azetidine-3-carboxamide;
N-{4-[(2-methylcyclopropyl)carbamoyl]phenyl}-1-(pyridazin-3-yl)azetidine-3-carboxamide;
N-[4-(cyclobutylcarbamoyl)phenyl]-1-(pyridazin-3-yl)azetidine-3-carboxamide;
N-{4-[(1-methylcyclopropyl)carbamoyl]phenyl}-1-(pyridazin-3-yl)azetidine-3-carboxamide;
N-{4-[(2-methoxy-2-methylpropyl)carbamoyl]phenyl}-1-(pyridazin-3-yl)azetidine-3-carboxamide;
N-{4-[(cyclopropylmethyl)carbamoyl]phenyl}-1-(pyridazin-3-yl)azetidine-3-carboxamide;
1-(pyridazin-3-yl)-N-(4-{[(2R)-tetrahydro furan-2-ylmethyl]carbamoyl}phenyl)azetidine-3-carboxamide;
1-(pyridazin-3-yl)-N-{4[(3,3,3-trifluoropropyl)carbamoyl]phenyl}azetidine-3-carboxamide;
N-{4[(1-methylpiperidin-3-yl)carbamoyl]phenyl}-1-(pyridazin-3-yl)azetidine-3-carboxamide;
N-(4-{[(3-methyloxetan-3-yl)methyl]carbamoyl}phenyl)-1-(pyridazin-3-yl)azetidine-3-carboxamide;
1-(pyridazin-3-yl)-N-(4-{[(2S)-tetrahydrofuran-2-ylmethyl]carbamoyl}phenyl)azetidine-3-carboxamide;
1-(pyridazin-3-yl)-N-{4-[(tetrahydro-2H-pyran-4-ylmethyl)carbamoyl]phenyl}azetidine-3-carboxamide;
1-(pyridazin-3-yl)-N-[4-(tetrahydro-2H-pyran-4-ylcarbamoyl)phenyl]azetidine-3-carboxamide;
N-(4-{[(1-methylpiperidin-3-yl)methyl]carbamoyl}phenyl)-1-(pyridazin-3-yl)azetidine-3-carboxamide;
N-[4-(cyclopropylcarbamoyl)phenyl]-1-(pyridazin-3-yl)azetidine-3-carboxamide;
N-[4-(cyclopentylcarbamoyl)phenyl]-1-(pyridazin-3-yl)azetidine-3-carboxamide;
N-[4-(benzylcarbamoyl)phenyl]-1-(pyridazin-3-yl)azetidine-3-carboxamide;
N-{4-[(3-fluorophenyl)carbamoyl]phenyl}-1-(pyridazin-3-yl)azetidine-3-carboxamide;
N-[4-(propylcarbamoyl)phenyl]-1-(pyridazin-3-yl)azetidine-3-carboxamide;
N-{4-[(4-fluorophenyl)carbamoyl]phenyl}-1-(pyridazin-3-yl)azetidine-3-carboxamide;
N-{4-[(2-fluorophenyl)carbamoyl]phenyl}-1-(pyridazin-3-yl)azetidine-3-carboxamide;
N-{4-[(1-methylcyclobutyl)carbamoyl]phenyl}-1-(pyridazin-3-yl)azetidine-3-carboxamide;
N-[4-(prop-2-en-1-ylcarbamoyl)phenyl]-1-(pyridazin-3-yl)azetidine-3-carboxamide;
1-(pyridazin-3-yl)-N-{4-[(3S)-tetrahydrofuran-3-ylcarbamoyl]phenyl}azetidine-3-carboxamide;
N-[4-({4-[2-(dimethylamino)ethyl]phenyl}carbamoyl)phenyl]-1-(pyridazin-3-yl)azetidine-3-carboxamide;
1-(pyridazin-3-yl)-N-{4-[(3R)-tetrahydrofuran-3-ylcarbamoyl]phenyl}azetidine-3-carboxamide;
N-{4-[(2-methoxyethyl)carbamoyl]phenyl}-1-(pyridazin-3-yl)azetidine-3-carboxamide;
N-{4-[1-(3-amino-2,2-dimethylpropyl)-1H-pyrazol-4-yl]phenyl}-1-(pyridazin-3-yl)azetidine-3-carboxamide;
N-(4-{1-[2,2-dimethyl-3-(piperazin-1-yl)propyl]-1H-pyrazol-4-yl}phenyl)-1-(pyridazin-3-yl)azetidine-3-carboxamide;
N-(4-{1-[2-methyl-2-(piperazin-1-yl)propanoyl]piperidin-4-yl}phenyl)-1-(pyridazin-3-yl)azetidine-3-carboxamide;
and pharmaceutically acceptable salts thereof.

Embodiments of Formula (IIIC)0

In another aspect, the present invention provides compounds of Formula (IIIC)

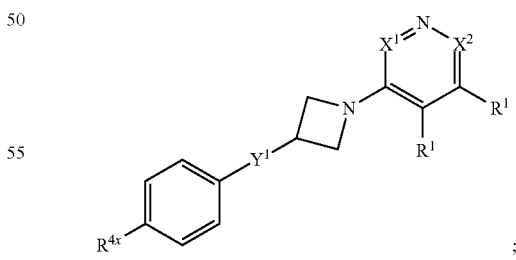

(IIIC)

and pharmaceutically acceptable salts thereof; wherein $X^1$, $X^2$, $R^1$, and $Y^1$ are as described in Formula (IC) herein and $R^{4x}$ is as described herein for substituents on $R^2$ when $R^2$ is aryl in Formula (IC).

One embodiment of this invention pertains to compounds of Formula (IIIC) or pharmaceutically acceptable salts thereof;

wherein
X$^1$ is N and X$^2$ is CR$^1$; or
X$^1$ is CR$^1$ and X$^2$ is N; or
X$^1$ is CR$^1$ and X$^2$ is CR$^1$;
Y$^1$ is C(O)NH, or NHC(O);

R$^1$, at each occurrence, is independently selected from the group consisting of hydrogen, alkyl, alkenyl, alkynyl, haloalkyl, hydroxyalkyl, alkoxy, OH, NH$_2$, CN, NO$_2$, F, Cl, Br and I;

R$^{4x}$ is independently selected from the group consisting of R$^4$, OR$^4$, SW, S(O)R$^4$, SO$_2$R$^4$, C(O)R$^4$, OC(O)OR$^4$, NH$_2$, NHR$^4$, N(R$^4$)$_2$, NHC(O)R$^4$, NR$^4$C(O)R$^4$, NHS(O)$_2$R$^4$, NR$^4$S(O)$_2$R$^4$, NHC(O)OR$^4$, NR$^4$C(O)OR$^4$, NHC(O)NH$_2$, NHC(O)NHR$^4$, NHC(O)N(R$^4$)$_2$, NR$^4$C(O)NHR$^4$, NR$^4$C(O)N(R$^4$)$_2$, C(O)NH$_2$, C(O)NHR$^4$, C(O)N(R$^4$)$_2$, C(O)NHOH, C(O)NHOR$^4$, C(O)NHSO$_2$R$^4$, C(O)NR$^4$SO$_2$R$^4$, SO$_2$NH$_2$, SO$_2$NHR$^4$, SO$_2$N(R$^4$)$_2$, C(O)H, C(O)OH, C(N)NH$_2$, C(N)NHR$^4$, C(N)N(R$^4$)$_2$, CNOH, CNOCH$_3$, OH, CN, N$_3$, NO$_2$, F, Cl, and I;

R$^4$, at each occurrence, is independently selected from the group consisting of alkyl, alkenyl, alkynyl, aryl, heterocyclyl, cycloalkyl, and cycloalkenyl; wherein each R$^4$ alkyl, alkenyl, and alkynyl is optionally substituted with one or more substituents independently selected from the group consisting of R$^7$, OR$^7$, SW, S(O)R$^7$, SO$_2$R$^7$, C(O)R$^7$, CO(O)R$^7$, OC(O)R$^7$, OC(O)OR$^7$, NH$_2$, NHR$^7$, N(R$^7$)$_2$, NHC(O)R$^7$, NR$^7$C(O)R$^7$, NHS(O)$_2$R$^7$, NR$^7$S(O)$_2$R$^7$, NHC(O)OR$^7$, NR$^7$C(O)OR$^7$, NHC(O)NH$_2$, NHC(O)NHR$^7$, NHC(O)N(R$^7$)$_2$, NR$^7$C(O)NHR$^7$, NR$^7$C(O)N(R$^7$)$_2$, C(O)NH$_2$, C(O)NHR$^7$, C(O)N(R$^7$)$_2$, C(O)NHOH, C(O)NHOR$^7$, C(O)NHSO$_2$R$^7$, C(O)NR$^7$SO$_2$R$^7$, SO$_2$NH$_2$, SO$_2$NHR$^7$, SO$_2$N(R$^7$)$_2$, C(O)H, C(O)OH, C(N)NH$_2$, C(N)NHR$^7$, C(N)N(R$^7$)$_2$, CNOH, CNOCH$_3$, OH, (O), CN, N$_3$, NO$_2$, F, Cl, Br and I;

R$^7$, at each occurrence, is independently selected from the group consisting of alkyl, alkenyl, alkynyl, aryl, heterocyclyl, cycloalkyl, and cycloalkenyl;

wherein the cyclic moieties represented by R$^4$ and R$^7$, are independently optionally substituted with one or more substituents independently selected from the group consisting of R$^{10}$, OR$^{10}$, SR$^{10}$, S(O)R$^{10}$, SO$_2$R$^{10}$, C(O)R$^{10}$, CO(O)R$^{10}$, OC(O)R$^{10}$, OC(O)OR$^{10}$, C(O)C(O)R$^{10}$, NH$_2$, NHR$^{10}$, N(R$^{10}$)$_2$, NHC(O)R$^{10}$, NR$^{10}$C(O)R$^{10}$, NHS(O)$_2$R$^{10}$, NR$^{10}$S(O)$_2$R$^{10}$, NHC(O)OR$^{10}$, NR$^{10}$C(O)OR$^{10}$, NHC(O)NH$_2$, NHC(O)NHR$^{10}$, NHC(O)N(R$^{10}$)$_2$, NR$^{10}$C(O)NHR$^{10}$, NR$^{10}$C(O)N(R$^{10}$)$_2$, C(O)NH$_2$, C(O)NHR$^{10}$, C(O)N(R$^{10}$)$_2$, C(O)NHOH, C(O)NHOR$^{10}$, C(O)NHSO$_2$R$^{10}$, C(O)NR$^{10}$SO$_2$R$^{10}$, SO$_2$NH$_2$, SO$_2$NHR$^{10}$, SO$_2$N(R$^{10}$)$_2$, C(O)H, C(O)OH, C(N)NH$_2$, C(N)NHR$^{10}$, C(N)N(R$^{10}$)$_2$, CNOH, CNOCH$_3$, OH, CN, N$_3$, NO$_2$, F, Cl, Br and I;

R$^{10}$, at each occurrence, is independently selected from the group consisting of alkyl, alkenyl, alkynyl, aryl, heterocyclyl, cycloalkyl, and cycloalkenyl; wherein each R$^{10}$ alkyl, alkenyl, and alkynyl is optionally substituted with one or more substituents independently selected from the group consisting of R$^{11}$, OR$^{11}$, SR$^{11}$, S(O)R$^{11}$, SO$_2$R$^{11}$, C(O)R$^{11}$, CO(O)R$^{11}$, OC(O)R$^{11}$, OC(O)OR$^{11}$, NH$_2$, NHR$^{11}$, N(R$^{11}$)$_2$, NHC(O)R$^{11}$, NR$^{11}$C(O)R$^{11}$, NHS(O)$_2$R$^{11}$, NR$^{11}$S(O)$_2$R$^{11}$, NHC(O)OR$^{11}$, NR$^{11}$C(O)OR$^{11}$, NHC(O)NH$_2$, NHC(O)NHR$^{11}$, NHC(O)N(R$^{11}$)$_2$, NR$^{11}$C(O)NHR$^{11}$, NR$^{11}$C(O)N(R$^{11}$)$_2$, C(O)NH$_2$, C(O)NHR$^{11}$, C(O)N(R$^{11}$)$_2$, C(O)NHOH, C(O)NHOR$^{11}$, C(O)NHSO$_2$R$^{11}$, C(O)NR$^{11}$SO$_2$R$^{11}$, SO$_2$NH$_2$, SO$_2$NHR$^{11}$, SO$_2$N(R$^{11}$)$_2$, C(O)H, C(O)OH, C(N)NH$_2$, C(N)NHR$^{11}$, C(N)N(R$^{11}$)$_2$, CNOH, CNOCH$_3$, OH, (O), CN, N$_3$, NO$_2$, F, Cl, Br and I; wherein each R$^{10}$ aryl, heterocyclyl, cycloalkyl, and cycloalkenyl is optionally substituted with one or more substituents independently selected from the group consisting of R$^{12}$, OR$^{12}$, SR$^{12}$, S(O)R$^{12}$, SO$_2$R$^{12}$, C(O)R$^{12}$, CO(O)R$^{12}$, OC(O)R$^{12}$, OC(O)OR$^{12}$, NH$_2$, NHR$^{12}$, N(R$^{12}$)$_2$, NHC(O)R$^{12}$, NR$^{12}$C(O)R$^{12}$, NHS(O)$_2$R$^{12}$, NR$^{12}$S(O)$_2$R$^{12}$, NHC(O)OR$^{12}$, NR$^{12}$C(O)OR$^{12}$, NHC(O)NH$_2$, NHC(O)NHR$^{12}$, NHC(O)N(R$^{12}$)$_2$, NR$^{12}$C(O)NHR$^{12}$, NR$^{12}$C(O)N(R$^{12}$)$_2$, C(O)NH$_2$, C(O)NHR$^{12}$, C(O)N(R$^{12}$)$_2$, C(O)NHOH, C(O)NHOR$^{12}$, C(O)NHSO$_2$R$^{12}$, C(O)NR$^{12}$SO$_2$R$^{12}$, SO$_2$NH$_2$, SO$_2$NHR$^{12}$, SO$_2$N(R$^{12}$)$_2$, C(O)H, C(O)OH, C(N)NH$_2$, C(N)NHR$^{12}$, C(N)N(R$^{12}$)$_2$, CNOH, CNOCH$_3$, OH, CN, N$_3$, NO$_2$, CF$_3$, OCF$_3$, F, Cl, Br and I;

R$^{11}$, at each occurrence, is independently selected from the group consisting of alkyl, alkenyl, alkynyl, aryl, heterocyclyl, cycloalkyl, and cycloalkenyl; wherein each R$^{11}$ alkyl, alkenyl, and alkynyl is optionally substituted with alkoxy or aryl; wherein each R$^{11}$ aryl, heterocyclyl, cycloalkyl, and cycloalkenyl is optionally substituted with one or more substituents independently selected from the group consisting of R$^{13}$, OR$^{13}$, C(O)OR$^{13}$, OCF$_3$, CF$_3$, F, Cl, Br and I;

R$^{12}$, at each occurrence, is independently selected from the group consisting of alkyl, alkenyl, alkynyl, aryl, heterocyclyl, cycloalkyl, and cycloalkenyl; and R$^{13}$, at each occurrence, is independently selected from the group consisting of alkyl, haloalkyl, alkenyl, alkynyl, aryl, heterocyclyl, cycloalkyl, and cycloalkenyl.

In one embodiment of Formula (IIIC), X$^1$ is N and X$^2$ is CR$^1$; or X$^1$ is CR$^1$ and X$^2$ is N; or X$^1$ is CR$^1$ and X$^2$ is CR$^1$. In another embodiment of Formula (IIIC), X$^1$ is N and X$^2$ is CR$^1$. In another embodiment of Formula (IIIC), X$^1$ is CR$^1$ and X$^2$ is N. In another embodiment of Formula (IIIC), X$^1$ is CR$^1$ and X$^2$ is CR$^1$.

In one embodiment of Formula (IIIC), Y$^1$ is C(O)NH, or NHC(O). In another embodiment of Formula (IIIC), Y$^1$ is C(O)NH. In another embodiment of Formula (IIIC), Y$^1$ is NHC(O).

In one embodiment of Formula (IIIC), X$^1$ is CR$^1$ and X$^2$ is CR$^1$; and R$^1$, at each occurrence, is independently selected from the group consisting of hydrogen, alkyl, alkenyl, alkynyl, haloalkyl, hydroxyalkyl, alkoxy, OH, NH$_2$, CN, NO$_2$, F, Cl, Br and I. In another embodiment of Formula (IIIC), X$^1$ is CR$^1$ and X$^2$ is CR$^1$; and R$^1$, at each occurrence, is independently selected from the group consisting of hydrogen, alkyl, haloalkyl, alkoxy, CN, F, Cl, Br and I. In another embodiment of Formula (IIIC), X$^1$ is CR$^1$ and X$^2$ is CR$^1$; and R$^1$, at each occurrence, is independently selected from the group consisting of hydrogen, alkyl, haloalkyl, alkoxy, CN, F, and Cl. In another embodiment of Formula (IIIC), X$^1$ is CR$^1$ and X$^2$ is CR$^1$; and R$^1$, at each occurrence, is hydrogen.

In another aspect, the present invention provides compounds of Formula (IIID),

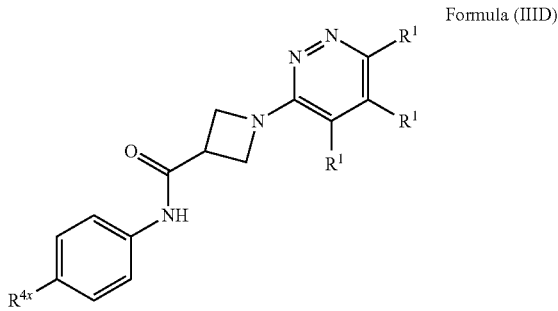

Formula (IIID)

and pharmaceutically acceptable salts thereof; wherein R$^1$ is described herein for Formula (IC) and R$^{4x}$ is as described herein for substituents on R$^2$ when R$^2$ is aryl in Formula (IC).

In one embodiment of Formula (IIIC) and (IIID), $R^1$, at each occurrence, is independently selected from the group consisting of hydrogen, alkyl, alkenyl, alkynyl, haloalkyl, hydroxyalkyl, alkoxy, OH, $NH_2$, CN, $NO_2$, F, Cl, Br and I. In another embodiment of Formula (IIIC) and (IIID), $R^1$, at each occurrence, is independently selected from the group consisting of hydrogen, alkyl, haloalkyl, alkoxy, CN, F, Cl, Br and I. In another embodiment of Formula (IIIC) and (IIID), $R^1$, at each occurrence, is independently selected from the group consisting of hydrogen, alkyl, haloalkyl, alkoxy, CN, F, and Cl. In another embodiment of Formula (IIIC) and (IIID), $R^1$, at each occurrence, is hydrogen.

In one embodiment of Formula (IIIC) and (IIID), $R^{4X}$ is independently selected from the group consisting of $R^4$, $OR^4$, $SR^4$, $S(O)R^4$, $SO_2R^4$, $C(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, and I. In another embodiment of Formula (IIIC) and (IIID), $R^{4X}$ is independently selected from the group consisting of $R^4$, $OR^4$, $SO_2R^4$, $C(O)NHR^4$, F, Cl, and I. In another embodiment of Formula (IIIC) and (IIID), $R^{4X}$ is independently selected from the group consisting of $R^4$, $OR^4$, $SO_2R^4$, $C(O)NHR^4$, and F.

In one embodiment of Formula (IIIC) and (IIID), $R^4$, at each occurrence, is independently selected from the group consisting of alkyl, alkenyl, alkynyl, aryl, heterocyclyl, cycloalkyl, and cycloalkenyl; wherein each $R^4$ alkyl, alkenyl, and alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, CNOH, $CNOCH_3$, OH, (O), CN, $N_3$, $NO_2$, F, Cl, Br and I. In another embodiment of Formula (IIIC) and (IIID), $R^4$, at each occurrence, is independently selected from the group consisting of alkyl, alkenyl, alkynyl, aryl, heterocyclyl, and cycloalkyl.

In one embodiment of Formula (IIIC) and (IIID), each $R^4$ alkyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, CNOH, $CNOCH_3$, OH, (O), CN, $N_3$, $NO_2$, F, Cl, Br and I. In another embodiment of Formula (IIIC) and (IIID), each $R^4$ alkyl is optionally substituted with one or more substituents independently selected from the group consisting of $R^7$, $OR^7$, $N(R^7)_2$, F, Cl, Br and I.

In one embodiment of Formula (IIIC) and (IIID), $R^7$, at each occurrence, is independently selected from the group consisting of alkyl, alkenyl, alkynyl, aryl, heterocyclyl, cycloalkyl, and cycloalkenyl. In another embodiment of Formula (IIIC) and (IIID), $R^7$, at each occurrence, is independently selected from the group consisting of alkyl, aryl, heterocyclyl, and cycloalkyl.

In one embodiment of Formula (IIIC) and (IIID), each $R^4$ and $R^7$ cyclic moiety is independently optionally substituted with one or more substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, CNOH, $CNOCH_3$, OH, CN, $N_3$, $NO_2$, F, Cl, Br and I; $R^{10}$, at each occurrence, is independently selected from the group consisting of alkyl, alkenyl, alkynyl, aryl, heterocyclyl, cycloalkyl, and cycloalkenyl; wherein each $R^{10}$ alkyl, alkenyl, and alkynyl is optionally substituted with one or more substituents independently selected from the group consisting of $R^{11}$, $OR^{11}$, $SR^{11}$, $S(O)R^{11}$, $SO_2R^{11}$, $C(O)R^{11}$, $CO(O)R^{11}$, $OC(O)R^{11}$, $OC(O)OR^{11}$, $NH_2$, $NHR^{11}$, $N(R^{11})_2$, $NHC(O)R^{11}$, $NR^{11}C(O)R^{11}$, $NHS(O)_2R^{11}$, $NR^{11}S(O)_2R^{11}$, $NHC(O)OR^{11}$, $NR^{11}C(O)OR^{11}$, $NHC(O)NH_2$, $NHC(O)NHR^{11}$, $NHC(O)N(R^{11})_2$, $NR^{11}C(O)NHR^{11}$, $NR^{11}C(O)N(R^{11})_2$, $C(O)NH_2$, $C(O)NHR^{11}$, $C(O)N(R^{11})_2$, $C(O)NHOH$, $C(O)NHOR^{11}$, $C(O)NHSO_2R^{11}$, $C(O)NR^{11}SO_2R^{11}$, $SO_2NH_2$, $SO_2NHR^{11}$, $SO_2N(R^{11})_2$, $C(O)H$, $C(O)OH$, $C(N)NH_2$, $C(N)NHR^{11}$, $C(N)N(R^{11})_2$, CNOH, $CNOCH_3$, OH, (O), CN, $N_3$, $NO_2$, F, Cl, Br and I; wherein each $R^{10}$ aryl, heterocyclyl, cycloalkyl, and cycloalkenyl is optionally substituted with one or more substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, $C(N)NH_2$, $C(N)NHR^{12}$, $C(N)N(R^{12})_2$, CNOH, $CNOCH_3$, OH, CN, $N_3$, $NO_2$, F, Cl, Br and I; $R^{11}$, at each occurrence, is independently selected from the group consisting of alkyl, alkenyl, alkynyl, aryl, heterocyclyl, cycloalkyl, and cycloalkenyl; wherein each $R^{11}$ alkyl, alkenyl, and alkynyl is optionally substituted with alkoxy or aryl; wherein each $R^{11}$ aryl, heterocyclyl, cycloalkyl, and cycloalkenyl is optionally substituted with one or more substituents independently selected from the group consisting of $R^{13}$, $OR^{13}$, $C(O)OR^{13}$, $OCF_3$, $CF_3$, F, Cl, Br and I; $R^{12}$, at each occurrence, is independently selected from the group consisting of alkyl, alkenyl, alkynyl, aryl, heterocyclyl, cycloalkyl, and cycloalkenyl; and $R^{13}$, at each occurrence, is independently selected from the group consisting of alkyl, haloalkyl, alkenyl, alkynyl, aryl, heterocyclyl, cycloalkyl, and cycloalkenyl.

In another embodiment of Formula (IIIC) and (IIID), each $R^4$ and $R^7$ cyclic moiety is independently optionally substituted with one or more substituents independently selected from the group consisting of $R^{10}$, $C(O)R^{10}$, $CO(O)R^{10}$, $C(O)C(O)R^{10}$, $CO(O)H$, OH, F, Cl, Br and I; $R^{10}$, at each occurrence, is independently selected from the group consisting of alkyl, alkenyl, alkynyl, aryl, heterocyclyl, and cycloalkyl; wherein each $R^{10}$ alkyl, alkenyl, and alkynyl, are optionally substituted with one or more substituents independently selected from the group consisting of $R^{11}$, $OR^{11}$, $SR^{11}$, $SO_2R^{11}$, $NH_2$, $N(R^{11})_2$, $NHC(O)R^{11}$, $NHS(O)_2R^{11}$, OH, NO₂, and F; wherein each R¹⁰ aryl, heterocyclyl and cycloalkyl is optionally substituted with one or more substituents independently selected from the group consisting of R¹², OR¹², C(O)R¹², NH₂, OH, CN, CF₃, OCF₃, F, and Cl; R¹¹, at each occurrence, is independently selected from the group consisting of alkyl, aryl, heterocyclyl, and cycloalkyl; wherein each R¹¹ alkyl is optionally substituted with alkoxy or aryl; wherein each R¹¹ aryl and heterocyclyl is optionally substituted with one or more substituents independently selected from the group consisting of R¹³, CF₃, F, and Cl; R¹², at each occurrence, is independently selected from the group consisting of alkyl and aryl; and R¹³, at each occurrence, is independently selected from the group consisting of alkyl, haloalkyl, and cycloalkyl.

One embodiment of this invention pertains to compounds or pharmaceutically acceptable salts thereof, which are useful as inhibitors of NAMPT, the compounds having Formula (IIIC)

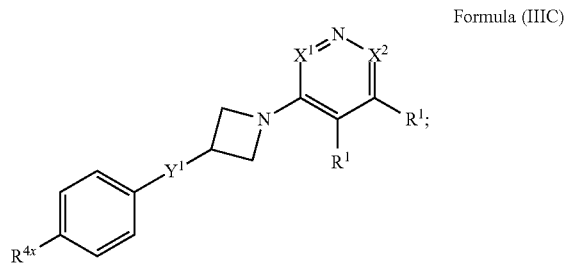

Formula (IIIC)

wherein
X¹ is N and X² is CR¹; or
X¹ is CR¹ and X² is N; or
X¹ is CR¹ and X² is CR¹;
Y¹ is C(O)NH, or NHC(O);
R¹, at each occurrence, is independently selected from the group consisting of hydrogen, alkyl, haloalkyl, alkoxy, CN, Cl, and F;
R⁴ˣ is independently selected from the group consisting of R⁴, SO₂R⁴, OR⁴, and F;
R⁴, at each occurrence, is independently selected from the group consisting of alkyl, alkenyl, aryl, heterocyclyl, and cycloalkyl; wherein each R⁴ alkyl is optionally substituted with one or more substituents independently selected from the group consisting of R⁷, OR⁷, N(R⁷)₂, and F;
R⁷, at each occurrence, is independently selected from the group consisting of alkyl, aryl, heterocyclyl, and cycloalkyl; wherein the cyclic moieties represented by R⁴ and R⁷ are independently optionally substituted with one or more substituents independently selected from the group consisting of R¹⁰, C(O)R¹⁰, C(O)C(O)R¹⁰, CO(O)R¹⁰, C(O)OH, OH and F;
R¹⁰, at each occurrence, is independently selected from the group consisting of alkyl, alkenyl, alkynyl, aryl, heterocyclyl, and cycloalkyl; wherein each R¹⁰ alkyl is optionally substituted with one or more substituents independently selected from the group consisting of R¹¹, OR¹¹, SR¹¹, SO₂R¹¹, NH₂, N(R¹¹)₂, NHC(O)R¹¹, NH S(O)₂R¹¹, OH, NO₂, and F; wherein each R¹⁰ aryl, heterocyclyl and cycloalkyl is optionally substituted with one or more R¹², OR¹², C(O)R¹², NH₂, OH, CN, CF₃, OCF₃, F, and Cl;
R¹¹, at each occurrence, is independently selected from the group consisting of alkyl, aryl, heterocyclyl, and cycloalkyl; wherein each R¹¹ alkyl is optionally substituted with alkoxy or aryl; wherein each R¹¹ aryl, and heterocyclyl is optionally substituted with one or more substituents independently selected from the group consisting of R¹³, C(O)OR¹³, OCF₃, CF₃, F, and Cl;
R¹², at each occurrence, is independently selected from the group consisting of alkyl, and aryl; and
R¹³, at each occurrence, is independently selected from the group consisting of alkyl, haloalkyl, cycloalkyl, and heterocyclyl.

Still another embodiment pertains to compounds having Formula (IIIC), which include
1-(pyridin-3-yl)-N-(4-{[1-(tetrahydro-2H-pyran-4-ylacetyl) piperidin-4-yl]oxy}phenyl)azetidine-3-carboxamide;
1-(2-cyanopyridin-3-yl)-N-{4-[1-(2-hydroxy-2-methylpropanoyl)piperidin-4-yl]phenyl}azetidine-3-carboxamide;
N-(4-{[1-(tetrahydro-2H-pyran-4-ylacetyl)piperidin-4-yl] oxy}phenyl)-1-[2-(trifluoromethyl)pyridin-3-yl]azetidine-3-carboxamide;
1-(2-methylpyridin-3-yl)-N-(4-{[1-(tetrahydro-2H-pyran-4-ylacetyl)piperidin-4-yl]oxy}phenyl)azetidine-3-carboxamide;
1-(4-methylpyridin-3-yl)-N-(4-{[1-(tetrahydro-2H-pyran-4-ylacetyl)piperidin-4-yl]oxy}phenyl)azetidine-3-carboxamide;
1-(4-fluoropyridin-3-yl)-N-(4-{[1-(tetrahydro-2H-pyran-4-ylacetyl)piperidin-4-yl]oxy}phenyl)azetidine-3-carboxamide;
N-(4-{[1-(tetrahydro-2H-pyran-4-ylacetyl)piperidin-4-yl] oxy}phenyl)-1-[4-(trifluoromethyl)pyridin-3-yl]azetidine-3-carboxamide;
1-(pyridin-3-yl)-N-(4-{1-[(2S)-tetrahydro furan-2-ylcarbonyl]piperidin-4-yl}phenyl)azetidine-3-carboxamide;
N-{4-[1-(2-hydroxy-2-methylpropanoyl)piperidin-4-yl] phenyl}-1-(pyridin-3-yl)azetidine-3-carboxamide;
N-(4-{1-[(2S)-2-methylbutanoyl]piperidin-4-yl}phenyl)-1-(pyridin-3-yl)azetidine-3-carboxamide;
1-(pyridin-3-yl)-N-{4-[1-(tetrahydro-2H-pyran-4-ylacetyl) piperidin-4-yl]phenyl}azetidine-3-carboxamide;
N-[4-(1-benzoylpiperidin-4-yl)phenyl]-1-(pyridin-3-yl)azetidine-3-carboxamide;
N-{4-[1-(2-methylpropanoyl)piperidin-4-yl]phenyl}-1-(2-methylpyridin-3-yl)azetidine-3-carboxamide;
N-{4-[1-(2-methylpropanoyl)piperidin-4-yl]phenyl}-1-(pyridin-3-yl)azetidine-3-carboxamide;
N-(4-{[1-(2-hydroxy-2-methylpropanoyl)piperidin-4-yl] oxy}phenyl)-1-(pyridin-3-yl)azetidine-3-carboxamide;
N-[4-({1-[(2S)-2-methylbutanoyl]piperidin-4-yl}oxy)phenyl]-1-(pyridin-3-yl)azetidine-3-carboxamide;
1-(pyridin-3-yl)-N-[4-({1-[(2S)-tetrahydro furan-2-ylcarbonyl]piperidin-4-yl}oxy)phenyl]azetidine-3-carboxamide;
N-{4-[(1-pentanoylpiperidin-4-yl)oxy]phenyl}-1-(pyridin-3-yl)azetidine-3-carboxamide;
N-[4-({1-[(2-methylcyclopropyl)carbonyl]piperidin-4-yl}oxy)phenyl]-1-(pyridin-3-yl)azetidine-3-carboxamide;
N-[4-({1-[(1S,4R)-bicyclo[2.2.1]hept-2-ylacetyl]piperidin-4-yl}oxy)phenyl]-1-(pyridin-3-yl)azetidine-3-carboxamide;
N-(4-{[1-(4-methylpentanoyl)piperidin-4-yl]oxy}phenyl)-1-(pyridin-3-yl)azetidine-3-carboxamide;
N-(4-{[1-(3-methylpentanoyl)piperidin-4-yl]oxy}phenyl)-1-(pyridin-3-yl)azetidine-3-carboxamide;
N-(4-{[1-(3-ethoxypropanoyl)piperidin-4-yl]oxy}phenyl)-1-(pyridin-3-yl)azetidine-3-carboxamide;
N-(4-{[1-(2,2-dimethylbutanoyl)piperidin-4-yl] oxy}phenyl)-1-(pyridin-3-yl)azetidine-3-carboxamide;
N-(4-{[1-(3,3-dimethylbutanoyl)piperidin-4-yl] oxy}phenyl)-1-(pyridin-3-yl)azetidine-3-carboxamide;

N-(4-{[1-(2,2-dimethylpropanoyl)piperidin-4-yl]oxy}phenyl)-1-(pyridin-3-yl)azetidine-3-carboxamide;
N-{4-[(1-butanoylpiperidin-4-yl)oxy]phenyl}-1-(pyridin-3-yl)azetidine-3-carboxamide;
N-(4-{[1-(ethoxyacetyl)piperidin-4-yl]oxy}phenyl)-1-(pyridin-3-yl)azetidine-3-carboxamide;
N-(4-{[1-(3-methylbutanoyl)piperidin-4-yl]oxy}phenyl)-1-(pyridin-3-yl)azetidine-3-carboxamide;
N-(4-{[1-(2-methylpropanoyl)piperidin-4-yl]oxy}phenyl)-1-(pyridin-3-yl)azetidine-3-carboxamide;
N-(4-{[1-(N-acetyl-L-leucyl)piperidin-4-yl]oxy}phenyl)-1-(pyridin-3-yl)azetidine-3-carboxamide;
N-[4-({1-[(2-methoxyethoxy)acetyl]piperidin-4-yl}oxy)phenyl]-1-(pyridin-3-yl)azetidine-3-carboxamide;
N-(4-{[1-(cyclohexylcarbonyl)piperidin-4-yl]oxy}phenyl)-1-(pyridin-3-yl)azetidine-3-carboxamide;
N-(4-{[1-(cyclohexylacetyl)piperidin-4-yl]oxy}phenyl)-1-(pyridin-3-yl)azetidine-3-carboxamide;
1-(pyridin-3-yl)-N-(4-{[1-(4,4,4-trifluorobutanoyl)piperidin-4-yl]oxy}phenyl)azetidine-3-carboxamide;
N-(4-{[1-(cyclopentylcarbonyl)piperidin-4-yl]oxy}phenyl)-1-(pyridin-3-yl)azetidine-3-carboxamide;
N-[4-({1-[(1-methylcyclohexyl)carbonyl]piperidin-4-yl}oxy)phenyl]-1-(pyridin-3-yl)azetidine-3-carboxamide;
N-(4-{[1-(furan-3-ylcarbonyl)piperidin-4-yl]oxy}phenyl)-1-(pyridin-3-yl)azetidine-3-carboxamide;
1-(pyridin-3-yl)-N-(4-{[1-(3,3,3-trifluoropropanoyl)piperidin-4-yl]oxy}phenyl)azetidine-3-carboxamide;
N-{4-[(1-acetylpiperidin-4-yl)oxy]phenyl}-1-(pyridin-3-yl)azetidine-3-carboxamide;
N-(4-{[1-(methoxyacetyl)piperidin-4-yl]oxy}phenyl)-1-(pyridin-3-yl)azetidine-3-carboxamide;
1-(pyridin-3-yl)-N-(4-{[1-(thiophen-3-ylcarbonyl)piperidin-4-yl]oxy}phenyl)azetidine-3-carboxamide;
N-[4-({1-[(3-methylthiophen-2-yl)carbonyl]piperidin-4-yl}oxy)phenyl]-1-(pyridin-3-yl)azetidine-3-carboxamide;
N-(4-{[1-(morpholin-4-ylacetyl)piperidin-4-yl]oxy}phenyl)-1-(pyridin-3-yl)azetidine-3-carboxamide;
1-(pyridin-3-yl)-N-(4-{[1-(thiophen-2-ylcarbonyl)piperidin-4-yl]oxy}phenyl)azetidine-3-carboxamide;
N-[4-({1-[(5-methylthiophen-2-yl)carbonyl]piperidin-4-yl}oxy)phenyl]-1-(pyridin-3-yl)azetidine-3-carboxamide;
N-(4-{[1-(furan-2-ylcarbonyl)piperidin-4-yl]oxy}phenyl)-1-(pyridin-3-yl)azetidine-3-carboxamide;
N-[4-({1-[(1-methyl-1H-pyrrol-2-yl)carbonyl]piperidin-4-yl}oxy)phenyl]-1-(pyridin-3-yl)azetidine-3-carboxamide;
N-{4-[(1-propanoylpiperidin-4-yl)oxy]phenyl}-1-(pyridin-3-yl)azetidine-3-carboxamide;
N-[4-({1-[(1-methylcyclopropyl)carbonyl]piperidin-4-yl}oxy)phenyl]-1-(pyridin-3-yl)azetidine-3-carboxamide;
N-(4-{[1-(N,N-dimethyl-beta-alanyl)piperidin-4-yl]oxy}phenyl)-1-(pyridin-3-yl)azetidine-3-carboxamide;
1-(pyridin-3-yl)-N-(4-{[1-(1,3-thiazol-2-ylcarbonyl)piperidin-4-yl]oxy}phenyl)azetidine-3-carboxamide;
N-(4-{[1-(cyclopentylacetyl)piperidin-4-yl]oxy}phenyl)-1-(pyridin-3-yl)azetidine-3-carboxamide;
N-(4-{[1-(2,3-dimethylbutanoyl)piperidin-4-yl]oxy}phenyl)-1-(pyridin-3-yl)azetidine-3-carboxamide;
N-{4-[1-(2-hydroxy-2-methylpropanoyl)piperidin-4-yl]phenyl}-1-(2-methylpyridin-3-yl)azetidine-3-carboxamide;
N-{4-[1-(2-hydroxy-2-methylpropanoyl)piperidin-4-yl]phenyl}-1-(4-methylpyridin-3-yl)azetidine-3-carboxamide;
N-{4-[1-(2-hydroxy-2-methylpropanoyl)piperidin-4-yl]phenyl}-1-(2-methoxypyridin-3-yl)azetidine-3-carboxamide;
N-(4-{[1-(cyclopropylmethyl)piperidin-4-yl]oxy}phenyl)-1-(pyridin-3-yl)azetidine-3-carboxamide;
N-(4-{[1-(2-methylpentyl)piperidin-4-yl]oxy}phenyl)-1-(pyridin-3-yl)azetidine-3-carboxamide;
N-(4-{[1-(2-methylpropyl)piperidin-4-yl]oxy}phenyl)-1-(pyridin-3-yl)azetidine-3-carboxamide;
N-(4-{[1-(3-methylbutyl)piperidin-4-yl]oxy}phenyl)-1-(pyridin-3-yl)azetidine-3-carboxamide;
N-(4-{[1-(2-ethylbutyl)piperidin-4-yl]oxy}phenyl)-1-(pyridin-3-yl)azetidine-3-carboxamide;
N-(4-{[1-(2,2-dimethylpropyl)piperidin-4-yl]oxy}phenyl)-1-(pyridin-3-yl)azetidine-3-carboxamide;
N-(4-{[1-(2-methylbutyl)piperidin-4-yl]oxy}phenyl)-1-(pyridin-3-yl)azetidine-3-carboxamide;
N-{4-[(1-propylpiperidin-4-yl)oxy]phenyl}-1-(pyridin-3-yl)azetidine-3-carboxamide;
N-(4-{[1-(2-cyclopropylethyl)piperidin-4-yl]oxy}phenyl)-1-(pyridin-3-yl)azetidine-3-carboxamide;
1-(pyridin-3-yl)-N-(4-{[1-(tetrahydrofuran-3-ylmethyl)piperidin-4-yl]oxy}phenyl)azetidine-3-carboxamide;
N-(4-{[1-(2,2-dimethylbutyl)piperidin-4-yl]oxy}phenyl)-1-(pyridin-3-yl)azetidine-3-carboxamide;
N-{4-[1-(2-hydroxy-2-methylpropanoyl)piperidin-4-yl]phenyl}-1-(pyridazin-4-yl)azetidine-3-carboxamide;
N-{4-[1-(cyclohexylmethyl)piperidin-4-yl]phenyl}-1-(pyridin-3-yl)azetidine-3-carboxamide;
N-{4-[1-(3,3-dimethylbutyl)piperidin-4-yl]phenyl}-1-(pyridin-3-yl)azetidine-3-carboxamide;
N-{4-[1-(cyclopentylmethyl)piperidin-4-yl]phenyl}-1-(pyridin-3-yl)azetidine-3-carboxamide;
N-{4-[1-(2,2-dimethylbutyl)piperidin-4-yl]phenyl}-1-(pyridin-3-yl)azetidine-3-carboxamide;
N-{4-[1-(2-methylpentyl)piperidin-4-yl]phenyl}-1-(pyridin-3-yl)azetidine-3-carboxamide;
N-[4-(1-butylpiperidin-4-yl)phenyl]-1-(pyridin-3-yl)azetidine-3-carboxamide;
N-{4-[1-(2-ethylbutyl)piperidin-4-yl]phenyl}-1-(pyridin-3-yl)azetidine-3-carboxamide;
N-{4-[1-(3-methylbutyl)piperidin-4-yl]phenyl}-1-(pyridin-3-yl)azetidine-3-carboxamide;
N-{4-[1-(2-methylpropyl)piperidin-4-yl]phenyl}-1-(pyridin-3-yl)azetidine-3-carboxamide;
N-[4-(1-propylpiperidin-4-yl)phenyl]-1-(pyridin-3-yl)azetidine-3-carboxamide;
N-{4-[1-(2-hydroxy-2-methylpropanoyl)piperidin-4-yl]phenyl}-1-(4-methoxypyridin-3-yl)azetidine-3-carboxamide;
1-(4-cyanopyridin-3-yl)-N-{4-[1-(2-hydroxy-2-methylpropanoyl)piperidin-4-yl]phenyl}azetidine-3-carboxamide;
N-[4-(1-pentanoylpiperidin-4-yl)phenyl]-1-(pyridin-3-yl)azetidine-3-carboxamide;
N-{4-[1-(3-methylpentanoyl)piperidin-4-yl]phenyl}-1-(pyridin-3-yl)azetidine-3-carboxamide;
N-(4-{1-[(1S,4R)-bicyclo[2.2.1]hept-2-ylacetyl]piperidin-4-yl}phenyl)-1-(pyridin-3-yl)azetidine-3-carboxamide;
N-{4-[1-(cyclopentylacetyl)piperidin-4-yl]phenyl}-1-(pyridin-3-yl)azetidine-3-carboxamide;
N-{4-[1-[(2-methylcyclopropyl)carbonyl]piperidin-4-yl]phenyl}-1-(pyridin-3-yl)azetidine-3-carboxamide;
N-{4-[1-(morpholin-4-ylacetyl)piperidin-4-yl]phenyl}-1-(pyridin-3-yl)azetidine-3-carboxamide;
N-{4-[1-(furan-3-ylcarbonyl)piperidin-4-yl]phenyl}-1-(pyridin-3-yl)azetidine-3-carboxamide;
1-(pyridin-3-yl)-N-{4-[1-(pyrrolidin-1-ylacetyl)piperidin-4-yl]phenyl}azetidine-3-carboxamide;
N-{4-[1-(5-oxo-D-prolyl)piperidin-4-yl]phenyl}-1-(pyridin-3-yl)azetidine-3-carboxamide;

N-{4-[1-(N,N-dimethyl-beta-alanyl)piperidin-4-yl]phenyl}-1-(pyridin-3-yl)azetidine-3-carboxamide;
1-(pyridin-3-yl)-N-{4-[1-(1,3-thiazol-2-ylcarbonyl)piperidin-4-yl]phenyl}azetidine-3-carboxamide;
1-(pyridin-3-yl)-N-{4-[1-(thiophen-3-ylcarbonyl)piperidin-4-yl]phenyl}azetidine-3-carboxamide;
N-(4-{1-[(1-methylcyclopropyl)carbonyl]piperidin-4-yl}phenyl)-1-(pyridin-3-yl)azetidine-3-carboxamide;
N-(4-{1-[(3-methylthiophen-2-yl)carbonyl]piperidin-4-yl}phenyl)-1-(pyridin-3-yl)azetidine-3-carboxamide;
1-(pyridin-3-yl)-N-{4-[1-(4,4,4-trifluorobutanoyl)piperidin-4-yl]phenyl}azetidine-3-carboxamide;
N-(4-{1-[(4-methylpiperazin-1-yl)acetyl]piperidin-4-yl}phenyl)-1-(pyridin-3-yl)azetidine-3-carboxamide;
N-{4-[1-(5-oxo-L-prolyl)piperidin-4-yl]phenyl}-1-(pyridin-3-yl)azetidine-3-carboxamide;
N-{4-[1-(3-ethoxypropanoyl)piperidin-4-yl]phenyl}-1-(pyridin-3-yl)azetidine-3-carboxamide;
N-{4-[1-(4-methylpentanoyl)piperidin-4-yl]phenyl}-1-(pyridin-3-yl)azetidine-3-carboxamide;
N-(4-{1-[(1-methylcyclohexyl)carbonyl]piperidin-4-yl}phenyl)-1-(pyridin-3-yl)azetidine-3-carboxamide;
N-[4-(1-acetylpiperidin-4-yl)phenyl]-1-(pyridin-3-yl)azetidine-3-carboxamide;
N-{4-[1-(cyclohexylacetyl)piperidin-4-yl]phenyl}-1-(pyridin-3-yl)azetidine-3-carboxamide;
N-{4-[1-(N-acetyl-L-leucyl)piperidin-4-yl]phenyl}-1-(pyridin-3-yl)azetidine-3-carboxamide;
N-[4-(1-propanoylpiperidin-4-yl)phenyl]-1-(pyridin-3-yl)azetidine-3-carboxamide;
1-(pyridin-3-yl)-N-{4-[1-(3,3,3-trifluoropropanoyl)piperidin-4-yl]phenyl}azetidine-3-carboxamide;
N-(4-{1-[(2-methoxyethoxy)acetyl]piperidin-4-yl}phenyl)-1-(pyridin-3-yl)azetidine-3-carboxamide;
N-(4-{1-[3-(morpholin-4-yl)propanoyl]piperidin-4-yl}phenyl)-1-(pyridin-3-yl)azetidine-3-carboxamide;
N-{4-[1-(2,2-dimethylpropanoyl)piperidin-4-yl]phenyl}-1-(pyridin-3-yl)azetidine-3-carboxamide;
N-(4-{1-[(5-methylthiophen-2-yl)carbonyl]piperidin-4-yl}phenyl)-1-(pyridin-3-yl)azetidine-3-carboxamide;
1-(pyridin-3-yl)-N-{4-[1-(thiophen-2-ylcarbonyl)piperidin-4-yl]phenyl}azetidine-3-carboxamide;
N-(4-{1-[(1-methyl-1H-pyrrol-2-yl)carbonyl]piperidin-4-yl}phenyl)-1-(pyridin-3-yl)azetidine-3-carboxamide;
N-{4-[1-(furan-2-ylcarbonyl)piperidin-4-yl]phenyl}-1-(pyridin-3-yl)azetidine-3-carboxamide;
N-(4-{1-[3-(piperidin-1-yl)propanoyl]piperidin-4-yl}phenyl)-1-(pyridin-3-yl)azetidine-3-carboxamide;
N-{4-[1-(ethoxyacetyl)piperidin-4-yl]phenyl}-1-(pyridin-3-yl)azetidine-3-carboxamide;
N-{4-[1-(3,3-dimethylbutanoyl)piperidin-4-yl]phenyl}-1-(pyridin-3-yl)azetidine-3-carboxamide;
N-{4-[1-(2,2-dimethylbutanoyl)piperidin-4-yl]phenyl}-1-(pyridin-3-yl)azetidine-3-carboxamide;
N-[4-(1-butanoylpiperidin-4-yl)phenyl]-1-(pyridin-3-yl)azetidine-3-carboxamide;
N-{4-[1-(methoxyacetyl)piperidin-4-yl]phenyl}-1-(pyridin-3-yl)azetidine-3-carboxamide;
N-{4-[1-(cyclohexylcarbonyl)piperidin-4-yl]phenyl}-1-(pyridin-3-yl)azetidine-3-carboxamide;
N-{4-[1-(3-methylbutanoyl)piperidin-4-yl]phenyl}-1-(pyridin-3-yl)azetidine-3-carboxamide;
N-{4-[1-(cyclopentylcarbonyl)piperidin-4-yl]phenyl}-1-(pyridin-3-yl)azetidine-3-carboxamide;
N-{4-[1-(2,3-dimethylbutanoyl)piperidin-4-yl]phenyl}-1-(pyridin-3-yl)azetidine-3-carboxamide;
N-{4-[1-(3,3-dimethylbutanoyl)piperidin-4-yl]phenyl}-1-(pyridazin-4-yl)azetidine-3-carboxamide;
N-(4-{1-[(2S)-2-methylbutanoyl]piperidin-4-yl}phenyl)-1-(pyridazin-4-yl)azetidine-3-carboxamide;
N-{4-[1-(cyclopentylacetyl)piperidin-4-yl]phenyl}-1-(pyridazin-4-yl)azetidine-3-carboxamide;
1-(pyridazin-4-yl)-N-{4-[1-(tetrahydro-2H-pyran-4-ylacetyl)piperidin-4-yl]phenyl}azetidine-3-carboxamide;
1-(pyridazin-4-yl)-N-{4-[1-(tetrahydro-2H-pyran-4-ylcarbonyl)piperidin-4-yl]phenyl}azetidine-3-carboxamide;
N-{4-[1-(2-methylpropanoyl)piperidin-4-yl]phenyl}-1-(pyridazin-3-yl)azetidine-3-carboxamide;
N-{4-[1-(2-methylpropyl)-1H-pyrazol-4-yl]phenyl}-1-(pyridazin-4-yl)azetidine-3-carboxamide;
N-[4-(1-benzoylpiperidin-4-yl)phenyl]-1-(2-methylpyridin-3-yl)azetidine-3-carboxamide;
N-{4-[1-(2-fluorobenzoyl)piperidin-4-yl]phenyl}-1-(2-methylpyridin-3-yl)azetidine-3-carboxamide;
N-{4-[1-(2-chlorobenzoyl)piperidin-4-yl]phenyl}-1-(2-methylpyridin-3-yl)azetidine-3-carboxamide;
N-{4-[1-(3-fluorobenzoyl)piperidin-4-yl]phenyl}-1-(2-methylpyridin-3-yl)azetidine-3-carboxamide;
N-{4-[1-(3-chlorobenzoyl)piperidin-4-yl]phenyl}-1-(2-methylpyridin-3-yl)azetidine-3-carboxamide;
N-{4-[1-(3,5-dichlorobenzoyl)piperidin-4-yl]phenyl}-1-(2-methylpyridin-3-yl)azetidine-3-carboxamide;
N-{4-[1-(4-fluorobenzoyl)piperidin-4-yl]phenyl}-1-(2-methylpyridin-3-yl)azetidine-3-carboxamide;
N-{4-[1-(4-chlorobenzoyl)piperidin-4-yl]phenyl}-1-(2-methylpyridin-3-yl)azetidine-3-carboxamide;
1-(2-methylpyridin-3-yl)-N-(4-{1-[4-(trifluoromethyl)benzoyl]piperidin-4-yl}phenyl)azetidine-3-carboxamide;
1-(2-methylpyridin-3-yl)-N-{4-[1-(pyridazin-3-ylcarbonyl)piperidin-4-yl]phenyl}azetidine-3-carboxamide;
1-(2-methylpyridin-3-yl)-N-[4-(1-pentanoylpiperidin-4-yl)phenyl]azetidine-3-carboxamide;
N-{4-[1-(3-methylpentanoyl)piperidin-4-yl]phenyl}-1-(2-methylpyridin-3-yl)azetidine-3-carboxamide;
N-(4-{1-[(1S,4R)-bicyclo[2.2.1]hept-2-ylacetyl]piperidin-4-yl}phenyl)-1-(2-methylpyridin-3-yl)azetidine-3-carboxamide;
N-{4-[1-(cyclopentylacetyl)piperidin-4-yl]phenyl}-1-(2-methylpyridin-3-yl)azetidine-3-carboxamide;
N-(4-{1-[(2-methylcyclopropyl)carbonyl]piperidin-4-yl}phenyl)-1-(2-methylpyridin-3-yl)azetidine-3-carboxamide;
1-(2-methylpyridin-3-yl)-N-{4-[1-(morpholin-4-ylacetyl)piperidin-4-yl]phenyl}azetidine-3-carboxamide;
N-{4-[1-(furan-3-ylcarbonyl)piperidin-4-yl]phenyl}-1-(2-methylpyridin-3-yl)azetidine-3-carboxamide;
1-(2-methylpyridin-3-yl)-N-{4-[1-(pyrrolidin-1-ylacetyl)piperidin-4-yl]phenyl}azetidine-3-carboxamide;
1-(2-methylpyridin-3-yl)-N-{4-[1-(5-oxo-D-prolyl)piperidin-4-yl]phenyl}azetidine-3-carboxamide;
N-{4-[1-(N,N-dimethyl-beta-alanyl)piperidin-4-yl]phenyl}-1-(2-methylpyridin-3-yl)azetidine-3-carboxamide;
1-(2-methylpyridin-3-yl)-N-{4-[1-(thiophen-3-ylcarbonyl)piperidin-4-yl]phenyl}azetidine-3-carboxamide;
N-(4-{1-[(1-methylcyclopropyl)carbonyl]piperidin-4-yl}phenyl)-1-(2-methylpyridin-3-yl)azetidine-3-carboxamide;
1-(2-methylpyridin-3-yl)-N-(4-{1-[(3-methylthiophen-2-yl)carbonyl]piperidin-4-yl}phenyl)azetidine-3-carboxamide;
1-(2-methylpyridin-3-yl)-N-{4-[1-(4,4,4-trifluorobutanoyl)piperidin-4-yl]phenyl}azetidine-3-carboxamide;

N-(4-{1-[(4-methylpiperazin-1-yl)acetyl]piperidin-4-yl}phenyl)-1-(2-methylpyridin-3-yl)azetidine-3-carboxamide;
1-(2-methylpyridin-3-yl)-N-{4-[1-(5-oxo-L-prolyl)piperidin-4-yl]phenyl}azetidine-3-carboxamide;
N-{4-[1-(3-ethoxypropanoyl)piperidin-4-yl]phenyl}-1-(2-methylpyridin-3-yl)azetidine-3-carboxamide;
N-{4-[1-(4-methylpentanoyl)piperidin-4-yl]phenyl}-1-(2-methylpyridin-3-yl)azetidine-3-carboxamide;
N-(4-{1-[(1-methylcyclohexyl)carbonyl]piperidin-4-yl}phenyl)-1-(2-methylpyridin-3-yl)azetidine-3-carboxamide;
N-[4-(1-acetylpiperidin-4-yl)phenyl]-1-(2-methylpyridin-3-yl)azetidine-3-carboxamide;
N-{4-[1-(cyclohexylacetyl)piperidin-4-yl]phenyl}-1-(2-methylpyridin-3-yl)azetidine-3-carboxamide;
N-{4-[1-(N-acetyl-L-leucyl)piperidin-4-yl]phenyl}-1-(2-methylpyridin-3-yl)azetidine-3-carboxamide;
1-(2-methylpyridin-3-yl)-N-[4-(1-propanoylpiperidin-4-yl)phenyl]azetidine-3-carboxamide;
1-(2-methylpyridin-3-yl)-N-{4-[1-(3,3,3-trifluoropropanoyl)piperidin-4-yl]phenyl}azetidine-3-carboxamide;
N-(4-{1-[(2-methoxyethoxy)acetyl]piperidin-4-yl}phenyl)-1-(2-methylpyridin-3-yl)azetidine-3-carboxamide;
1-(2-methylpyridin-3-yl)-N-(4-{1-[3-(morpholin-4-yl)propanoyl]piperidin-4-yl}phenyl)azetidine-3-carboxamide;
N-{4-[1-(2,2-dimethylpropanoyl)piperidin-4-yl]phenyl}-1-(2-methylpyridin-3-yl)azetidine-3-carboxamide;
1-(2-methylpyridin-3-yl)-N-(4-{1-[(5-methylthiophen-2-yl)carbonyl]piperidin-4-yl}phenyl)azetidine-3-carboxamide;
1-(2-methylpyridin-3-yl)-N-{4-[1-(thiophen-2-ylcarbonyl)piperidin-4-yl]phenyl}azetidine-3-carboxamide;
1-(2-methylpyridin-3-yl)-N-(4-{1-[(1-methyl-1H-pyrrol-2-yl)carbonyl]piperidin-4-yl}phenyl)azetidine-3-carboxamide;
N-{4-[1-(furan-2-ylcarbonyl)piperidin-4-yl]phenyl}-1-(2-methylpyridin-3-yl)azetidine-3-carboxamide;
1-(2-methylpyridin-3-yl)-N-(4-{1-[3-(piperidin-1-yl)propanoyl]piperidin-4-yl}phenyl)azetidine-3-carboxamide;
N-{4-[1-(ethoxyacetyl)piperidin-4-yl]phenyl}-1-(2-methylpyridin-3-yl)azetidine-3-carboxamide;
N-{4-[1-(3,3-dimethylbutanoyl)piperidin-4-yl]phenyl}-1-(2-methylpyridin-3-yl)azetidine-3-carboxamide;
N-{4-[1-(2,2-dimethylbutanoyl)piperidin-4-yl]phenyl}-1-(2-methylpyridin-3-yl)azetidine-3-carboxamide;
N-[4-(1-butanoylpiperidin-4-yl)phenyl]-1-(2-methylpyridin-3-yl)azetidine-3-carboxamide;
N-{4-[1-(methoxyacetyl)piperidin-4-yl]phenyl}-1-(2-methylpyridin-3-yl)azetidine-3-carboxamide;
N-{4-[1-(cyclohexylcarbonyl)piperidin-4-yl]phenyl}-1-(2-methylpyridin-3-yl)azetidine-3-carboxamide;
N-{4-[1-(3-methylbutanoyl)piperidin-4-yl]phenyl}-1-(2-methylpyridin-3-yl)azetidine-3-carboxamide;
N-{4-[1-(2,3-dimethylbutanoyl)piperidin-4-yl]phenyl}-1-(2-methylpyridin-3-yl)azetidine-3-carboxamide;
N-(4-{[1-(4-fluorobenzoyl)azetidin-3-yl]oxy}phenyl)-1-(pyridazin-4-yl)azetidine-3-carboxamide;
N-(4-{[1-(2,4-difluorobenzoyl)azetidin-3-yl]oxy}phenyl)-1-(pyridazin-4-yl)azetidine-3-carboxamide;
N-[4-({1-[difluoro(phenyl)acetyl]azetidin-3-yl}oxy)phenyl]-1-(pyridazin-4-yl)azetidine-3-carboxamide;
N-[4-({1-[(4,4-difluoro cyclohexyl)carbonyl]azetidin-3-yl}oxy)phenyl]-1-(pyridazin-4-yl)azetidine-3-carboxamide;
N-[4-({1-[(4-fluorophenyl)acetyl]azetidin-3-yl}oxy)phenyl]-1-(pyridazin-4-yl)azetidine-3-carboxamide;
1-(pyridazin-4-yl)-N-[4-({1-[4-(trifluoromethyl)benzoyl]azetidin-3-yl}oxy)phenyl]azetidine-3-carboxamide;
N-{4-[(1-benzoylazetidin-3-yl)oxy]phenyl}-1-(pyridazin-4-yl)azetidine-3-carboxamide;
N-(4-{[1-(2-hydroxy-2-methylpropanoyl)azetidin-3-yl]oxy}phenyl)-1-(pyridazin-4-yl)azetidine-3-carboxamide;
1-(pyridazin-4-yl)-N-(4-{[1-(tetrahydrofuran-3-ylcarbonyl)azetidin-3-yl]oxy}phenyl)azetidine-3-carboxamide;
N-(4-{[1-(furan-3-ylcarbonyl)azetidin-3-yl]oxy}phenyl)-1-(pyridazin-4-yl)azetidine-3-carboxamide;
N-{4-[(1-pentanoylazetidin-3-yl)oxy]phenyl}-1-(pyridazin-4-yl)azetidine-3-carboxamide;
N-(4-{[1-(2-chlorobenzoyl)piperidin-4-yl]oxy}phenyl)-1-(pyridazin-3-yl)azetidine-3-carboxamide;
N-[4-({1-[(2S)-2-methylbutanoyl]piperidin-4-yl}oxy)phenyl]-1-(pyridazin-3-yl)azetidine-3-carboxamide;
1-(pyridazin-3-yl)-N-(4-{[1-(1,3-thiazol-2-ylcarbonyl)piperidin-4-yl]oxy}phenyl)azetidine-3-carboxamide;
1-(pyridazin-3-yl)-N-(4-{[1-(tetrahydro-2H-pyran-4-ylcarbonyl)piperidin-4-yl]oxy}phenyl)azetidine-3-carboxamide;
N-[4-({1-[difluoro(phenyl)acetyl]piperidin-4-yl}oxy)phenyl]-1-(pyridazin-3-yl)azetidine-3-carboxamide;
N-[4-({1-[(4,4-difluorocyclohexyl)carbonyl]piperidin-4-yl}oxy)phenyl]-1-(pyridazin-3-yl)azetidine-3-carboxamide;
N-(4-{[1-(2-methyl-2-phenylpropanoyl)piperidin-4-yl]oxy}phenyl)-1-(pyridazin-3-yl)azetidine-3-carboxamide;
1-(pyridazin-3-yl)-N-(4-{[1-(1,3-thiazol-4-ylcarbonyl)piperidin-4-yl]oxy}phenyl)azetidine-3-carboxamide;
N-[4-({1-[(5-methylthiophen-2-yl)carbonyl]piperidin-4-yl}oxy)phenyl]-1-(pyridazin-3-yl)azetidine-3-carboxamide;
1-(pyridazin-3-yl)-N-{4-[(1-{[4-(trifluoromethyl)phenyl]acetyl}piperidin-4-yl)oxy]phenyl}azetidine-3-carboxamide;
1-(pyridazin-3-yl)-N-(4-{[1-(tetrahydrofuran-2-ylcarbonyl)piperidin-4-yl]oxy}phenyl)azetidine-3-carboxamide;
1-(pyridazin-3-yl)-N-[4-({1-[3-(trifluoromethyl)benzoyl]piperidin-4-yl}oxy)phenyl]azetidine-3-carboxamide;
1-(pyridazin-3-yl)-N-(4-{[1-(thiophen-3-ylcarbonyl)piperidin-4-yl]oxy}phenyl)azetidine-3-carboxamide;
1-(pyridazin-3-yl)-N-[4-({1-[3-(trifluoromethoxy)benzoyl]piperidin-4-yl}oxy)phenyl]azetidine-3-carboxamide;
N-(4-{[1-(3-methylbutanoyl)piperidin-4-yl]oxy}phenyl)-1-(pyridazin-3-yl)azetidine-3-carboxamide;
1-(pyridazin-3-yl)-N-(4-{[1-(tetrahydrofuran-3-ylcarbonyl)piperidin-4-yl]oxy}phenyl)azetidine-3-carboxamide;
N-[4-({1-[(3-fluorophenyl)acetyl]piperidin-4-yl}oxy)phenyl]-1-(pyridazin-3-yl)azetidine-3-carboxamide;
N-(4-{[1-(2-fluorobenzoyl)piperidin-4-yl]oxy}phenyl)-1-(pyridazin-3-yl)azetidine-3-carboxamide;
N-(4-{[1-(2,4-difluorobenzoyl)piperidin-4-yl]oxy}phenyl)-1-(pyridazin-3-yl)azetidine-3-carboxamide;
N-(4-{[1-(4-fluorobenzoyl)piperidin-4-yl]oxy}phenyl)-1-(pyridazin-3-yl)azetidine-3-carboxamide;
N-(4-{[1-(3-fluorobenzoyl)piperidin-4-yl]oxy}phenyl)-1-(pyridazin-3-yl)azetidine-3-carboxamide;
N-[4-({1-[(4-fluorophenyl)acetyl]piperidin-4-yl}oxy)phenyl]-1-(pyridazin-3-yl)azetidine-3-carboxamide;
N-(4-{[1-(cyclopropylacetyl)piperidin-4-yl]oxy}phenyl)-1-(pyridazin-3-yl)azetidine-3-carboxamide;
N-(4-{[1-(3,4-difluorobenzoyl)piperidin-4-yl]oxy}phenyl)-1-(pyridazin-3-yl)azetidine-3-carboxamide;
1-(pyridazin-3-yl)-N-[4-({1-[4-(trifluoromethoxy)benzoyl]piperidin-4-yl}oxy)phenyl]azetidine-3-carboxamide;

N-[4-({1-[(2,4-difluorophenyl)acetyl]piperidin-4-yl}oxy)phenyl]-1-(pyridazin-3-yl)azetidine-3-carboxamide;
1-(pyridazin-3-yl)-N-[4-({1-[4-(trifluoromethyl)benzoyl]piperidin-4-yl}oxy)phenyl]azetidine-3-carboxamide;
1-(pyridazin-3-yl)-N-{4-[(1-{[4-(trifluoromethoxy)phenyl]acetyl}piperidin-4-yl)oxy]phenyl}azetidine-3-carboxamide;
N-[4-({1-[(3,5-difluorophenyl)acetyl]piperidin-4-yl}oxy)phenyl]-1-(pyridazin-3-yl)azetidine-3-carboxamide;
1-(pyridazin-3-yl)-N-{4-[(1-{[3-(trifluoromethyl)phenyl]acetyl}piperidin-4-yl)oxy]phenyl}azetidine-3-carboxamide;
N-(4-{[1-(2,2-dimethylpropanoyl)piperidin-4-yl]oxy}phenyl)-1-(pyridazin-3-yl)azetidine-3-carboxamide;
1-(pyridazin-3-yl)-N-(4-{[1-(pyridin-2-ylcarbonyl)piperidin-4-yl]oxy}phenyl)azetidine-3-carboxamide;
N-(4-{[1-(3,5-difluorobenzoyl)piperidin-4-yl]oxy}phenyl)-1-(pyridazin-3-yl)azetidine-3-carboxamide;
N-{4-[(1-acetylpiperidin-4-yl)oxy]phenyl}-1-(pyridazin-3-yl)azetidine-3-carboxamide;
N-(4-{[1-(4-chlorobenzoyl)piperidin-4-yl]oxy}phenyl)-1-(pyridazin-3-yl)azetidine-3-carboxamide;
N-(4-{[1-(methoxyacetyl)piperidin-4-yl]oxy}phenyl)-1-(pyridazin-3-yl)azetidine-3-carboxamide;
N-[4-({1-[(2-fluorophenyl)acetyl]piperidin-4-yl}oxy)phenyl]-1-(pyridazin-3-yl)azetidine-3-carboxamide;
N-(4-{[1-(2,2-dimethylbutanoyl)piperidin-4-yl]oxy}phenyl)-1-(pyridazin-3-yl)azetidine-3-carboxamide;
1-(pyridazin-3-yl)-N-(4-{[1-(thiophen-2-ylcarbonyl)piperidin-4-yl]oxy}phenyl)azetidine-3-carboxamide;
N-(4-{[1-(3-chlorobenzoyl)piperidin-4-yl]oxy}phenyl)-1-(pyridazin-3-yl)azetidine-3-carboxamide;
N-(4-{[1-(cyclopropylcarbonyl)piperidin-4-yl]oxy}phenyl)-1-(pyridazin-3-yl)azetidine-3-carboxamide;
1-(pyridazin-3-yl)-N-(4-{[1-(3,3,3-trifluoropropanoyl)piperidin-4-yl]oxy}phenyl)azetidine-3-carboxamide;
N-(4-{[1-(2-methylpropanoyl)piperidin-4-yl]oxy}phenyl)-1-(pyridazin-3-yl)azetidine-3-carboxamide;
N-(4-{[1-(3,3-dimethylbutanoyl)azetidin-3-yl]oxy}phenyl)-1-(pyridazin-4-yl)azetidine-3-carboxamide;
N-(4-{[1-(cyclohexylcarbonyl)azetidin-3-yl]oxy}phenyl)-1-(pyridazin-4-yl)azetidine-3-carboxamide;
1-(pyridazin-4-yl)-N-(4-{[1-(tetrahydro-2H-pyran-4-ylacetyl)azetidin-3-yl]oxy}phenyl)azetidine-3-carboxamide;
N-[4-({1-[(2-methylcyclopropyl)carbonyl]azetidin-3-yl}oxy)phenyl]-1-(pyridazin-4-yl)azetidine-3-carboxamide;
1-(pyridazin-4-yl)-N-(4-{[1-(3,3,3-trifluoropropanoyl)azetidin-3-yl]oxy}phenyl)azetidine-3-carboxamide;
N-(4-{[1-(cyclopentylcarbonyl)azetidin-3-yl]oxy}phenyl)-1-(pyridazin-4-yl)azetidine-3-carboxamide;
N-(4-{[1-(3,3-dimethylbutanoyl)piperidin-4-yl]oxy}phenyl)-1-(pyridazin-4-yl)azetidine-3-carboxamide;
N-(4-{[1-(cyclobutylcarbonyl)azetidin-3-yl]oxy}phenyl)-1-(pyridazin-4-yl)azetidine-3-carboxamide;
1-(pyridazin-4-yl)-N-(4-{[1-(tetrahydrofuran-2-ylcarbonyl)azetidin-3-yl]oxy}phenyl)azetidine-3-carboxamide;
N-(4-{[1-(4-methylpentanoyl)azetidin-3-yl]oxy}phenyl)-1-(pyridazin-4-yl)azetidine-3-carboxamide;
N-(4-{[1-(2-methylpropanoyl)azetidin-3-yl]oxy}phenyl)-1-(pyridazin-4-yl)azetidine-3-carboxamide;
N-[4-({1-[(2S)-2-methylbutanoyl]azetidin-3-yl}oxy)phenyl]-1-(pyridazin-4-yl)azetidine-3-carboxamide;
N-(4-{[1-(3-methylbutanoyl)piperidin-4-yl]oxy}phenyl)-1-(pyridazin-4-yl)azetidine-3-carboxamide;
N-(4-{[1-(methoxyacetyl)piperidin-4-yl]oxy}phenyl)-1-(pyridazin-4-yl)azetidine-3-carboxamide;
1-(pyridazin-4-yl)-N-(4-{[1-(3,3,3-trifluoropropanoyl)piperidin-4-yl]oxy}phenyl)azetidine-3-carboxamide;
N-[4-({1-[difluoro(phenyl)acetyl]piperidin-4-yl}oxy)phenyl]-1-(pyridazin-4-yl)azetidine-3-carboxamide;
N-[4-({1-[(4,4-difluorocyclohexyl)carbonyl]piperidin-4-yl}oxy)phenyl]-1-(pyridazin-4-yl)azetidine-3-carboxamide;
N-(4-{[1-(4-fluorobenzoyl)piperidin-4-yl]oxy}phenyl)-1-(pyridazin-4-yl)azetidine-3-carboxamide;
1-(pyridazin-4-yl)-N-(4-{[1-(1,3-thiazol-4-ylcarbonyl)piperidin-4-yl]oxy}phenyl)azetidine-3-carboxamide;
1-(pyridazin-4-yl)-N-{4-[(1-{[4-(trifluoromethyl)phenyl]acetyl}piperidin-4-yl)oxy]phenyl}azetidine-3-carboxamide;
N-(4-{[1-(3,4-difluorobenzoyl)piperidin-4-yl]oxy}phenyl)-1-(pyridazin-4-yl)azetidine-3-carboxamide;
1-(pyridazin-4-yl)-N-{4-[(1-{[4-(trifluoromethoxy)phenyl]acetyl}piperidin-4-yl)oxy]phenyl}azetidine-3-carboxamide;
N-[4-({1-[(4-fluorophenyl)acetyl]piperidin-4-yl}oxy)phenyl]-1-(pyridazin-4-yl)azetidine-3-carboxamide;
N-[4-({1-[(2,4-difluorophenyl)acetyl]piperidin-4-yl}oxy)phenyl]-1-(pyridazin-4-yl)azetidine-3-carboxamide;
1-(pyridazin-4-yl)-N-(4-{[1-(thiophen-3-ylcarbonyl)piperidin-4-yl]oxy}phenyl)azetidine-3-carboxamide;
N-(4-{[1-(2-chlorobenzoyl)piperidin-4-yl]oxy}phenyl)-1-(pyridazin-4-yl)azetidine-3-carboxamide;
N-(4-{[1-(2,2-dimethylpropanoyl)piperidin-4-yl]oxy}phenyl)-1-(pyridazin-4-yl)azetidine-3-carboxamide;
N-(4-{[1-(2-methyl-2-phenylpropanoyl)piperidin-4-yl]oxy}phenyl)-1-(pyridazin-4-yl)azetidine-3-carboxamide;
N-{4-[(1-acetylpiperidin-4-yl)oxy]phenyl}-1-(pyridazin-4-yl)azetidine-3-carboxamide;
1-(pyridazin-4-yl)-N-(4-{[1-(1,3-thiazol-2-ylcarbonyl)piperidin-4-yl]oxy}phenyl)azetidine-3-carboxamide;
N-(4-{[1-(2,4-difluorobenzoyl)piperidin-4-yl]oxy}phenyl)-1-(pyridazin-4-yl)azetidine-3-carboxamide;
1-(pyridazin-4-yl)-N-[4-({1-[3-(trifluoromethyl)benzoyl]piperidin-4-yl}oxy)phenyl]azetidine-3-carboxamide;
N-(4-{[1-(3-fluorobenzoyl)piperidin-4-yl]oxy}phenyl)-1-(pyridazin-4-yl)azetidine-3-carboxamide;
1-(pyridazin-4-yl)-N-[4-({1-[4-(trifluoromethyl)benzoyl]piperidin-4-yl}oxy)phenyl]azetidine-3-carboxamide;
N-[4-({1-[(3-fluorophenyl)acetyl]piperidin-4-yl}oxy)phenyl]-1-(pyridazin-4-yl)azetidine-3-carboxamide;
N-(4-{[1-(2-fluorobenzoyl)piperidin-4-yl]oxy}phenyl)-1-(pyridazin-4-yl)azetidine-3-carboxamide;
1-(pyridazin-4-yl)-N-[4-({1-[4-(trifluoromethoxy)benzoyl]piperidin-4-yl}oxy)phenyl]azetidine-3-carboxamide;
N-[4-({1-[(3,5-difluorophenyl)acetyl]piperidin-4-yl}oxy)phenyl]-1-(pyridazin-4-yl)azetidine-3-carboxamide;
1-(pyridazin-4-yl)-N-[4-({1-[3-(trifluoromethoxy)benzoyl]piperidin-4-yl}oxy)phenyl]azetidine-3-carboxamide;
N-(4-{[1-(cyclopropylacetyl)piperidin-4-yl]oxy}phenyl)-1-(pyridazin-4-yl)azetidine-3-carboxamide;
N-(4-{[1-(2-methylpropanoyl)piperidin-4-yl]oxy}phenyl)-1-(pyridazin-4-yl)azetidine-3-carboxamide;
N-(4-{[1-(3-chlorobenzoyl)piperidin-4-yl]oxy}phenyl)-1-(pyridazin-4-yl)azetidine-3-carboxamide;
1-(pyridazin-4-yl)-N-(4-{[1-(pyridin-2-ylcarbonyl)piperidin-4-yl]oxy}phenyl)azetidine-3-carboxamide;
N-(4-{[1-(4-chlorobenzoyl)piperidin-4-yl]oxy}phenyl)-1-(pyridazin-4-yl)azetidine-3-carboxamide;
1-(pyridazin-4-yl)-N-(4-{[1-(tetrahydrofuran-3-ylcarbonyl)piperidin-4-yl]oxy}phenyl)azetidine-3-carboxamide;

N-(4-{[1-(3,5-difluorobenzoyl)piperidin-4-yl]oxy}phenyl)-1-(pyridazin-4-yl)azetidine-3-carboxamide;
N-(4-{[1-(2,2-dimethylbutanoyl)piperidin-4-yl]oxy}phenyl)-1-(pyridazin-4-yl)azetidine-3-carboxamide;
N-(4-{[1-(cyclopropylcarbonyl)piperidin-4-yl]oxy}phenyl)-1-(pyridazin-4-yl)azetidine-3-carboxamide;
1-(pyridazin-4-yl)-N-(4-{[1-(tetrahydrofuran-2-ylcarbonyl)piperidin-4-yl]oxy}phenyl)azetidine-3-carboxamide;
1-(pyridazin-4-yl)-N-(4-{[1-(thiophen-2-ylcarbonyl)piperidin-4-yl]oxy}phenyl)azetidine-3-carboxamide;
N-[4-({1-[(5-methylthiophen-2-yl)carbonyl]piperidin-4-yl}oxy)phenyl]-1-(pyridazin-4-yl)azetidine-3-carboxamide;
1-(pyridazin-4-yl)-N-{4-[(1-{[3-(trifluoromethyl)phenyl]acetyl}piperidin-4-yl)oxy]phenyl}azetidine-3-carboxamide;
1-(pyridazin-4-yl)-N-(4-{[1-(tetrahydro-2H-pyran-4-ylcarbonyl)piperidin-4-yl]oxy}phenyl)azetidine-3-carboxamide;
N-[4-({1-[(2S)-2-methylbutanoyl]piperidin-4-yl}oxy)phenyl]-1-(pyridazin-4-yl)azetidine-3-carboxamide;
N-[4-({1-[(2-fluorophenyl)acetyl]piperidin-4-yl}oxy)phenyl]-1-(pyridazin-4-yl)azetidine-3-carboxamide;
N-[4-(1-acetylpiperidin-4-yl)phenyl]-1-(pyridazin-3-yl)azetidine-3-carboxamide;
N-[4-(1-butanoylpiperidin-4-yl)phenyl]-1-(pyridazin-3-yl)azetidine-3-carboxamide;
N-[4-(1-pentanoylpiperidin-4-yl)phenyl]-1-(pyridazin-3-yl)azetidine-3-carboxamide;
N-{4-[1-(2-methylbutanoyl)piperidin-4-yl]phenyl}-1-(pyridazin-3-yl)azetidine-3-carboxamide;
N-{4-[1-(3-methylbutanoyl)piperidin-4-yl]phenyl}-1-(pyridazin-3-yl)azetidine-3-carboxamide;
N-[4-(1-hexanoylpiperidin-4-yl)phenyl]-1-(pyridazin-3-yl)azetidine-3-carboxamide;
N-{4-[1-(2-methylpentanoyl)piperidin-4-yl]phenyl}-1-(pyridazin-3-yl)azetidine-3-carboxamide;
N-{4-[1-(3-methylpentanoyl)piperidin-4-yl]phenyl}-1-(pyridazin-3-yl)azetidine-3-carboxamide;
N-{4-[1-(4-methylpentanoyl)piperidin-4-yl]phenyl}-1-(pyridazin-3-yl)azetidine-3-carboxamide;
N-{4-[1-(2,2-dimethylbutanoyl)piperidin-4-yl]phenyl}-1-(pyridazin-3-yl)azetidine-3-carboxamide;
N-{4-[1-(2,3-dimethylbutanoyl)piperidin-4-yl]phenyl}-1-(pyridazin-3-yl)azetidine-3-carboxamide;
N-{4-[1-(3,3-dimethylbutanoyl)piperidin-4-yl]phenyl}-1-(pyridazin-3-yl)azetidine-3-carboxamide;
N-{4-[1-(2-ethylbutanoyl)piperidin-4-yl]phenyl}-1-(pyridazin-3-yl)azetidine-3-carboxamide;
N-[4-(1-heptanoylpiperidin-4-yl)phenyl]-1-(pyridazin-3-yl)azetidine-3-carboxamide;
N-{4-[1-(but-3-enoyl)piperidin-4-yl]phenyl}-1-(pyridazin-3-yl)azetidine-3-carboxamide;
N-{4-[1-(pent-4-enoyl)piperidin-4-yl]phenyl}-1-(pyridazin-3-yl)azetidine-3-carboxamide;
1-(pyridazin-3-yl)-N-{4-[1-(3,3,3-trifluoropropanoyl)piperidin-4-yl]phenyl}azetidine-3-carboxamide;
N-{4-[1-(methoxyacetyl)piperidin-4-yl]phenyl}-1-(pyridazin-3-yl)azetidine-3-carboxamide;
N-(4-{1-[(methylsulfanyl)acetyl]piperidin-4-yl}phenyl)-1-(pyridazin-3-yl)azetidine-3-carboxamide;
N-(4-{1-[(2-methoxyethoxy)acetyl]piperidin-4-yl}phenyl)-1-(pyridazin-3-yl)azetidine-3-carboxamide;
N-{4-[1-(3-nitropropanoyl)piperidin-4-yl]phenyl}-1-(pyridazin-3-yl)azetidine-3-carboxamide;
N-(4-{1-[3-(methylsulfanyl)propanoyl]piperidin-4-yl}phenyl)-1-(pyridazin-3-yl)azetidine-3-carboxamide;
N-{4-[1-(pent-4-ynoyl)piperidin-4-yl]phenyl}-1-(pyridazin-3-yl)azetidine-3-carboxamide;
N-{4-[1-(cyclohexylcarbonyl)piperidin-4-yl]phenyl}-1-(pyridazin-3-yl)azetidine-3-carboxamide;
N-{4-[1-(cyclohexylacetyl)piperidin-4-yl]phenyl}-1-(pyridazin-3-yl)azetidine-3-carboxamide;
N-{4-[1-(3-methylbenzoyl)piperidin-4-yl]phenyl}-1-(pyridazin-3-yl)azetidine-3-carboxamide;
N-{4-[1-(2-hydroxybenzoyl)piperidin-4-yl]phenyl}-1-(pyridazin-3-yl)azetidine-3-carboxamide;
N-{4-[1-(3-hydroxybenzoyl)piperidin-4-yl]phenyl}-1-(pyridazin-3-yl)azetidine-3-carboxamide;
N-{4-[1-(4-hydroxybenzoyl)piperidin-4-yl]phenyl}-1-(pyridazin-3-yl)azetidine-3-carboxamide;
N-{4-[1-(2-methoxybenzoyl)piperidin-4-yl]phenyl}-1-(pyridazin-3-yl)azetidine-3-carboxamide;
N-{4-[1-(3-methoxybenzoyl)piperidin-4-yl]phenyl}-1-(pyridazin-3-yl)azetidine-3-carboxamide;
N-{4-[1-(4-methoxybenzoyl)piperidin-4-yl]phenyl}-1-(pyridazin-3-yl)azetidine-3-carboxamide;
N-{4-[1-(3-fluorobenzoyl)piperidin-4-yl]phenyl}-1-(pyridazin-3-yl)azetidine-3-carboxamide;
N-{4-[1-(4-fluorobenzoyl)piperidin-4-yl]phenyl}-1-(pyridazin-3-yl)azetidine-3-carboxamide;
N-{4-[1-(2-chlorobenzoyl)piperidin-4-yl]phenyl}-1-(pyridazin-3-yl)azetidine-3-carboxamide;
N-{4-[1-(3-chlorobenzoyl)piperidin-4-yl]phenyl}-1-(pyridazin-3-yl)azetidine-3-carboxamide;
N-{4-[1-(3-cyanobenzoyl)piperidin-4-yl]phenyl}-1-(pyridazin-3-yl)azetidine-3-carboxamide;
N-{4-[1-(4-cyanobenzoyl)piperidin-4-yl]phenyl}-1-(pyridazin-3-yl)azetidine-3-carboxamide;
1-(pyridazin-3-yl)-N-(4-{1-[3-(trifluoromethyl)benzoyl]piperidin-4-yl}phenyl)azetidine-3-carboxamide;
1-(pyridazin-3-yl)-N-(4-{1-[4-(trifluoromethyl)benzoyl]piperidin-4-yl}phenyl)azetidine-3-carboxamide;
1-(pyridazin-3-yl)-N-(4-{1-[3-(trifluoromethoxy)benzoyl]piperidin-4-yl}phenyl)azetidine-3-carboxamide;
N-{4-[1-(2,3-dimethylbenzoyl)piperidin-4-yl]phenyl}-1-(pyridazin-3-yl)azetidine-3-carboxamide;
N-{4-[1-(2,4-dimethylbenzoyl)piperidin-4-yl]phenyl}-1-(pyridazin-3-yl)azetidine-3-carboxamide;
N-{4-[1-(2,5-dimethylbenzoyl)piperidin-4-yl]phenyl}-1-(pyridazin-3-yl)azetidine-3-carboxamide;
N-{4-[1-(3,4-dimethylbenzoyl)piperidin-4-yl]phenyl}-1-(pyridazin-3-yl)azetidine-3-carboxamide;
N-{4-[1-(3,5-dimethylbenzoyl)piperidin-4-yl]phenyl}-1-(pyridazin-3-yl)azetidine-3-carboxamide;
N-{4-[1-(2,4-dichlorobenzoyl)piperidin-4-yl]phenyl}-1-(pyridazin-3-yl)azetidine-3-carboxamide;
N-{4-[1-(2,5-dichlorobenzoyl)piperidin-4-yl]phenyl}-1-(pyridazin-3-yl)azetidine-3-carboxamide;
N-{4-[1-(3,4-dichlorobenzoyl)piperidin-4-yl]phenyl}-1-(pyridazin-3-yl)azetidine-3-carboxamide;
N-{4-[1-(3,5-dichlorobenzoyl)piperidin-4-yl]phenyl}-1-(pyridazin-3-yl)azetidine-3-carboxamide;
N-(4-{1-[(2-fluorophenyl)acetyl]piperidin-4-yl}phenyl)-1-(pyridazin-3-yl)azetidine-3-carboxamide;
N-(4-{1-[(3-fluorophenyl)acetyl]piperidin-4-yl}phenyl)-1-(pyridazin-3-yl)azetidine-3-carboxamide;
N-(4-{1-[(4-fluorophenyl)acetyl]piperidin-4-yl}phenyl)-1-(pyridazin-3-yl)azetidine-3-carboxamide;
N-(4-{1-[(2-chlorophenyl)acetyl]piperidin-4-yl}phenyl)-1-(pyridazin-3-yl)azetidine-3-carboxamide;
N-(4-{1-[(4-chlorophenyl)acetyl]piperidin-4-yl}phenyl)-1-(pyridazin-3-yl)azetidine-3-carboxamide;

1-(pyridazin-3-yl)-N-[4-(1-{[4-(trifluoromethyl)phenyl]
acetyl}piperidin-4-yl)phenyl]azetidine-3-carboxamide;
N-(4-{1-[(3,5-dimethylphenyl)acetyl]piperidin-4-
yl}phenyl)-1-(pyridazin-3-yl)azetidine-3-carboxamide;
N-(4-{1-[(2,5-difluorophenyl)acetyl]piperidin-4-
yl}phenyl)-1-(pyridazin-3-yl)azetidine-3-carboxamide;
N-(4-{1-[(3,4-dichlorophenyl)acetyl]piperidin-4-
yl}phenyl)-1-(pyridazin-3-yl)azetidine-3-carboxamide;
N-{4-[1-(furan-3-ylcarbonyl)piperidin-4-yl]phenyl}-1-(pyridazin-3-yl)azetidine-3-carboxamide;
1-(pyridazin-3-yl)-N-{4-[1-(thiophen-2-ylcarbonyl)piperidin-4-yl]phenyl}azetidine-3-carboxamide;
N-(4-{1-[(5-methylthiophen-2-yl)carbonyl]piperidin-4-
yl}phenyl)-1-(pyridazin-3-yl)azetidine-3-carboxamide;
N-(4-{1-[(5-methylpyrazin-2-yl)carbonyl]piperidin-4-
yl}phenyl)-1-(pyridazin-3-yl)azetidine-3-carboxamide;
N-(4-{1-[(1-methylcyclopropyl)carbonyl]piperidin-4-
yl}phenyl)-1-(pyridazin-3-yl)azetidine-3-carboxamide;
N-{4-[1-(3-ethoxypropanoyl)piperidin-4-yl]phenyl}-1-(pyridazin-3-yl)azetidine-3-carboxamide;
N-(4-{1-[(1-phenylcyclopropyl)carbonyl]piperidin-4-
yl}phenyl)-1-(pyridazin-3-yl)azetidine-3-carboxamide;
1-(pyridazin-3-yl)-N-(4-{1-[(pyrimidin-2-ylsulfanyl)acetyl]
piperidin-4-yl}phenyl)azetidine-3-carboxamide;
N-(4-{1-[(1-acetylpiperidin-4-yl)carbonyl]piperidin-4-
yl}phenyl)-1-(pyridazin-3-yl)azetidine-3-carboxamide;
N-(4-{1-[(3,5-difluorophenyl)acetyl]piperidin-4-
yl}phenyl)-1-(pyridazin-3-yl)azetidine-3-carboxamide;
N-{4-[1-(N-acetyl-L-leucyl)piperidin-4-yl]phenyl}-1-(pyridazin-3-yl)azetidine-3-carboxamide;
N-{4-[1-(diphenylacetyl)piperidin-4-yl]phenyl}-1-(pyridazin-3-yl)azetidine-3-carboxamide;
N-{4-[1-(3-fluoro-2-methylbenzoyl)piperidin-4-yl]phenyl}-1-(pyridazin-3-yl)azetidine-3-carboxamide;
N-{4-[1-(5-fluoro-2-methylbenzoyl)piperidin-4-yl]phenyl}-1-(pyridazin-3-yl)azetidine-3-carboxamide;
N-{4-[1-(3-fluoro-4-methylbenzoyl)piperidin-4-yl]phenyl}-1-(pyridazin-3-yl)azetidine-3-carboxamide;
N-{4-[1-(2,3-difluorobenzoyl)piperidin-4-yl]phenyl}-1-(pyridazin-3-yl)azetidine-3-carboxamide;
N-{4-[1-(2,4-difluorobenzoyl)piperidin-4-yl]phenyl}-1-(pyridazin-3-yl)azetidine-3-carboxamide;
N-(4-{1-[4-(propan-2-yl)benzoyl]piperidin-4-yl}phenyl)-1-(pyridazin-3-yl)azetidine-3-carboxamide;
N-{4-[1-(4-tert-butylbenzoyl)piperidin-4-yl]phenyl}-1-(pyridazin-3-yl)azetidine-3-carboxamide;
N-(4-{1-[2-fluoro-5-(trifluoromethyl)benzoyl]piperidin-4-
yl}phenyl)-1-(pyridazin-3-yl)azetidine-3-carboxamide;
N-(4-{1-[2-chloro-5-(trifluoromethyl)benzoyl]piperidin-4-
yl}phenyl)-1-(pyridazin-3-yl)azetidine-3-carboxamide;
N-(4-{[(3R)-1-(4-fluorobenzoyl)pyrrolidin-3-yl]
oxy}phenyl)-1-(pyridazin-4-yl)azetidine-3-carboxamide;
N-{4-[1-(cyclopentylacetyl)piperidin-4-yl]phenyl}-1-(pyridazin-3-yl)azetidine-3-carboxamide;
N-(4-{1-[(4-methylphenoxy)acetyl]piperidin-4-yl}phenyl)-1-(pyridazin-3-yl)azetidine-3-carboxamide;
N-(4-{1-[(2S)-2-phenylbutanoyl]piperidin-4-yl}phenyl)-1-(pyridazin-3-yl)azetidine-3-carboxamide;
N-{4-[1-(3,5-difluorobenzoyl)piperidin-4-yl]phenyl}-1-(pyridazin-3-yl)azetidine-3-carboxamide;
N-{4-[1-(4-chlorobenzoyl)piperidin-4-yl]phenyl}-1-(pyridazin-3-yl)azetidine-3-carboxamide;
N-{4-[1-(2,2-dimethylpropanoyl)piperidin-4-yl]phenyl}-1-(pyridazin-3-yl)azetidine-3-carboxamide;
1-(pyridazin-3-yl)-N-[4-(1-{[3-(trifluoromethyl)phenyl]
acetyl}piperidin-4-yl)phenyl]azetidine-3-carboxamide;
N-(4-{1-[(3-chlorophenyl)acetyl]piperidin-4-yl}phenyl)-1-(pyridazin-3-yl)azetidine-3-carboxamide;
N-(4-{1-[(2,4-dichlorophenyl)acetyl]piperidin-4-
yl}phenyl)-1-(pyridazin-3-yl)azetidine-3-carboxamide;
N-{4-[1-(naphthalen-1-ylcarbonyl)piperidin-4-yl]phenyl}-
1-(pyridazin-3-yl)azetidine-3-carboxamide;
N-(4-{1-[(2R)-2-methoxy-2-phenylacetyl]piperidin-4-
yl}phenyl)-1-(pyridazin-3-yl)azetidine-3-carboxamide;
N-(4-{1-[N-(furan-2-ylcarbonyl)glycyl]piperidin-4-
yl}phenyl)-1-(pyridazin-3-yl)azetidine-3-carboxamide;
N-(4-{1-[(benzyloxy)acetyl]piperidin-4-yl}phenyl)-1-(pyridazin-3-yl)azetidine-3-carboxamide;
N-{4-[1-(naphthalen-1-ylacetyl)piperidin-4-yl]phenyl}-1-
(pyridazin-3-yl)azetidine-3-carboxamide;
N-{4-[1-(cyclopropylcarbonyl)piperidin-4-yl]phenyl}-1-
(pyridazin-3-yl)azetidine-3-carboxamide;
1-(pyridazin-3-yl)-N-{4-[1-(tetrahydrofuran-2-ylcarbonyl)
piperidin-4-yl]phenyl}azetidine-3-carboxamide;
N-{4-[1-(N-benzoylglycyl)piperidin-4-yl]phenyl}-1-(pyridazin-3-yl)azetidine-3-carboxamide;
1-(pyridazin-3-yl)-N-{4-[1-(tetrahydrofuran-3-ylcarbonyl)
piperidin-4-yl]phenyl}azetidine-3-carboxamide;
1-(pyridazin-3-yl)-N-(4-{1-[4-(thiophen-2-yl)butanoyl]piperidin-4-yl}phenyl)azetidine-3-carboxamide;
N-{4-[1-(2,5-difluorobenzoyl)piperidin-4-yl]phenyl}-1-
(pyridazin-3-yl)azetidine-3-carboxamide;
N-{4-[1-(cyclobutylcarbonyl)piperidin-4-yl]phenyl}-1-(pyridazin-3-yl)azetidine-3-carboxamide;
N-[4-(1-{N-[(4-methylphenyl)sulfonyl]glycyl}piperidin-4-
yl)phenyl]-1-(pyridazin-3-yl)azetidine-3-carboxamide;
N-(4-{1-[(2,3-difluorophenyl)acetyl]piperidin-4-
yl}phenyl)-1-(pyridazin-3-yl)azetidine-3-carboxamide;
N-(4-{1-[(2S)-2-methoxy-2-phenylacetyl]piperidin-4-
yl}phenyl)-1-(pyridazin-3-yl)azetidine-3-carboxamide;
N-{4-[1-(naphthalen-2-ylacetyl)piperidin-4-yl]phenyl}-1-
(pyridazin-3-yl)azetidine-3-carboxamide;
N-{4-[1-(3-phenylpropanoyl)piperidin-4-yl]phenyl}-1-(pyridazin-3-yl)azetidine-3-carboxamide;
N-(4-{1-[(2,6-dichlorophenyl)acetyl]piperidin-4-
yl}phenyl)-1-(pyridazin-3-yl)azetidine-3-carboxamide;
N-(4-{1-[3-(phenylsulfonyl)propanoyl]piperidin-4-
yl}phenyl)-1-(pyridazin-3-yl)azetidine-3-carboxamide;
1-(pyridazin-3-yl)-N-{4-[1-(thiophen-3-ylcarbonyl)piperidin-4-yl]phenyl}azetidine-3-carboxamide;
N-(4-{1-[(2,5-dimethylfuran-3-yl)carbonyl]piperidin-4-
yl}phenyl)-1-(pyridazin-3-yl)azetidine-3-carboxamide;
N-{4-[1-(cyclopropylacetyl)piperidin-4-yl]phenyl}-1-(pyridazin-3-yl)azetidine-3-carboxamide;
N-{4-[1-(2-fluorobenzoyl)piperidin-4-yl]phenyl}-1-(pyridazin-3-yl)azetidine-3-carboxamide;
N-{4-[1-(2-methylbenzoyl)piperidin-4-yl]phenyl}-1-(pyridazin-3-yl)azetidine-3-carboxamide;
1-(pyridazin-3-yl)-N-{4-[1-(1,3-thiazol-4-ylcarbonyl)piperidin-4-yl]phenyl}azetidine-3-carboxamide;
1-(pyridazin-3-yl)-N-{4-[1-(1,3-thiazol-5-ylcarbonyl)piperidin-4-yl]phenyl}azetidine-3-carboxamide;
N-{4-[1-(ethoxyacetyl)piperidin-4-yl]phenyl}-1-(pyridazin-3-yl)azetidine-3-carboxamide;
1-(pyridazin-3-yl)-N-{4-[1-(4,4,4-trifluorobutanoyl)piperidin-4-yl]phenyl}azetidine-3-carboxamide;
N-(4-{1-[(6-methylpyridin-3-yl)carbonyl]piperidin-4-
yl}phenyl)-1-(pyridazin-3-yl)azetidine-3-carboxamide;
N-[4-(1-benzoylpiperidin-4-yl)phenyl]-1-(pyridazin-3-yl)
azetidine-3-carboxamide;
N-{4-[1-(furan-2-ylcarbonyl)piperidin-4-yl]phenyl}-1-(pyridazin-3-yl)azetidine-3-carboxamide;

N-(4-{1-[(1-methylcyclohexyl)carbonyl]piperidin-4-yl}phenyl)-1-(pyridazin-3-yl)azetidine-3-carboxamide;
N-{4-[1-(2-oxopropanoyl)piperidin-4-yl]phenyl}-1-(pyridazin-3-yl)azetidine-3-carboxamide;
N-{4-[1-(cyclopentylcarbonyl)piperidin-4-yl]phenyl}-1-(pyridazin-3-yl)azetidine-3-carboxamide;
N-[4-(1-propanoylpiperidin-4-yl)phenyl]-1-(pyridazin-3-yl)azetidine-3-carboxamide;
N-{4-[1-(4-methylbenzoyl)piperidin-4-yl]phenyl}-1-(pyridazin-3-yl)azetidine-3-carboxamide;
N-(4-{[(3R)-1-(2-chlorobenzoyl)pyrrolidin-3-yl]oxy}phenyl)-1-(pyridazin-4-yl)azetidine-3-carboxamide;
1-(pyridazin-4-yl)-N-(4-{[(3R)-1-(1,3-thiazol-2-ylcarbonyl)pyrrolidin-3-yl]oxy}phenyl)azetidine-3-carboxamide;
N-(4-{[(3R)-1-(cyclopropylacetyl)pyrrolidin-3-yl]oxy}phenyl)-1-(pyridazin-4-yl)azetidine-3-carboxamide;
N-[4-({(3R)-1-[(2S)-2-methylbutanoyl]pyrrolidin-3-yl}oxy)phenyl]-1-(pyridazin-4-yl)azetidine-3-carboxamide;
1-(pyridazin-4-yl)-N-(4-{[(3R)-1-(tetrahydro-2H-pyran-4-ylcarbonyl)pyrrolidin-3-yl]oxy}phenyl)azetidine-3-carboxamide;
1-(pyridazin-4-yl)-N-(4-{[(3R)-1-{[4-(trifluoromethoxy)phenyl]acetyl}pyrrolidin-3-yl]oxy}phenyl)azetidine-3-carboxamide;
1-(pyridazin-4-yl)-N-(4-{[(3R)-1-(thiophen-3-ylcarbonyl)pyrrolidin-3-yl]oxy}phenyl)azetidine-3-carboxamide;
N-[4-({(3R)-1-[(4-fluorophenyl)acetyl]pyrrolidin-3-yl}oxy)phenyl]-1-(pyridazin-4-yl)azetidine-3-carboxamide;
N-[4-({(3R)-1-[(3,5-difluorophenyl)acetyl]pyrrolidin-3-yl}oxy)phenyl]-1-(pyridazin-4-yl)azetidine-3-carboxamide;
N-(4-{[(3R)-1-(3,4-difluorobenzoyl)pyrrolidin-3-yl]oxy}phenyl)-1-(pyridazin-4-yl)azetidine-3-carboxamide;
N-[4-({(3R)-1-[(3-fluorophenyl)acetyl]pyrrolidin-3-yl}oxy)phenyl]-1-(pyridazin-4-yl)azetidine-3-carboxamide;
1-(pyridazin-4-yl)-N-[4-({(3R)-1-[3-(trifluoromethyl)benzoyl]pyrrolidin-3-yl}oxy)phenyl]azetidine-3-carboxamide;
N-[4-({(3R)-1-[(2,4-difluorophenyl)acetyl]pyrrolidin-3-yl}oxy)phenyl]-1-(pyridazin-4-yl)azetidine-3-carboxamide;
1-(pyridazin-4-yl)-N-(4-{[(3R)-1-{[4-(trifluoromethyl)phenyl]acetyl}pyrrolidin-3-yl]oxy}phenyl)azetidine-3-carboxamide;
1-(pyridazin-4-yl)-N-(4-{[(3R)-1-(1,3-thiazol-4-ylcarbonyl)pyrrolidin-3-yl]oxy}phenyl)azetidine-3-carboxamide;
1-(pyridazin-4-yl)-N-(4-{[(3R)-1-(tetrahydrofuran-2-ylcarbonyl)pyrrolidin-3-yl]oxy}phenyl)azetidine-3-carboxamide;
N-[4-({(3R)-1-[(5-methylthiophen-2-yl)carbonyl]pyrrolidin-3-yl}oxy)phenyl]-1-(pyridazin-4-yl)azetidine-3-carboxamide;
N-[4-({(3R)-1-[(2-fluorophenyl)acetyl]pyrrolidin-3-yl}oxy)phenyl]-1-(pyridazin-4-yl)azetidine-3-carboxamide;
N-(4-{[(3R)-1-(cyclopropylcarbonyl)pyrrolidin-3-yl]oxy}phenyl)-1-(pyridazin-4-yl)azetidine-3-carboxamide;
1-(pyridazin-4-yl)-N-(4-{[(3R)-1-(tetrahydrofuran-3-ylcarbonyl)pyrrolidin-3-yl]oxy}phenyl)azetidine-3-carboxamide;
1-(pyridazin-4-yl)-N-[4-({(3R)-1-[3-(trifluoromethoxy)benzoyl]pyrrolidin-3-yl}oxy)phenyl]azetidine-3-carboxamide;
1-(pyridazin-4-yl)-N-(4-{[(3R)-1-(pyridin-2-ylcarbonyl)pyrrolidin-3-yl]oxy}phenyl)azetidine-3-carboxamide;
N-(4-{[(3R)-1-(3-chlorobenzoyl)pyrrolidin-3-yl]oxy}phenyl)-1-(pyridazin-4-yl)azetidine-3-carboxamide;
N-(4-{[(3R)-1-(4-chlorobenzoyl)pyrrolidin-3-yl]oxy}phenyl)-1-(pyridazin-4-yl)azetidine-3-carboxamide;
N-(4-{[(3R)-1-(2-methyl-2-phenylpropanoyl)pyrrolidin-3-yl]oxy}phenyl)-1-(pyridazin-4-yl)azetidine-3-carboxamide;
N-(4-{[(3R)-1-(2,4-difluorobenzoyl)pyrrolidin-3-yl]oxy}phenyl)-1-(pyridazin-4-yl)azetidine-3-carboxamide;
N-(4-{[(3R)-1-(methoxyacetyl)pyrrolidin-3-yl]oxy}phenyl)-1-(pyridazin-4-yl)azetidine-3-carboxamide;
1-(pyridazin-4-yl)-N-(4-{[(3R)-1-(thiophen-2-ylcarbonyl)pyrrolidin-3-yl]oxy}phenyl)azetidine-3-carboxamide;
1-(pyridazin-4-yl)-N-(4-{[(3R)-1-{[3-(trifluoromethyl)phenyl]acetyl}pyrrolidin-3-yl]oxy}phenyl)azetidine-3-carboxamide;
N-(4-{[(3R)-1-(2-methylpropanoyl)pyrrolidin-3-yl]oxy}phenyl)-1-(pyridazin-4-yl)azetidine-3-carboxamide;
N-(4-{[(3R)-1-(2-fluorobenzoyl)pyrrolidin-3-yl]oxy}phenyl)-1-(pyridazin-4-yl)azetidine-3-carboxamide;
N-(4-{[(3R)-1-(2,2-dimethylbutanoyl)pyrrolidin-3-yl]oxy}phenyl)-1-(pyridazin-4-yl)azetidine-3-carboxamide;
N-(4-{[(3R)-1-(3,5-difluorobenzoyl)pyrrolidin-3-yl]oxy}phenyl)-1-(pyridazin-4-yl)azetidine-3-carboxamide;
1-(pyridazin-4-yl)-N-[4-({(3R)-1-[4-(trifluoromethyl)benzoyl]pyrrolidin-3-yl}oxy)phenyl]azetidine-3-carboxamide;
N-(4-{[(3R)-1-(3-fluorobenzoyl)pyrrolidin-3-yl]oxy}phenyl)-1-(pyridazin-4-yl)azetidine-3-carboxamide;
1-(pyridazin-4-yl)-N-[4-({(3R)-1-[4-(trifluoromethoxy)benzoyl]pyrrolidin-3-yl}oxy)phenyl]azetidine-3-carboxamide;
N-(4-{[(3R)-1-(3-methylbutanoyl)pyrrolidin-3-yl]oxy}phenyl)-1-(pyridazin-4-yl)azetidine-3-carboxamide;
1-(pyridazin-4-yl)-N-(4-{[(3R)-1-(3,3,3-trifluoropropanoyl)pyrrolidin-3-yl]oxy}phenyl)azetidine-3-carboxamide;
N-[4-({(3R)-1-[difluoro(phenyl)acetyl]pyrrolidin-3-yl}oxy)phenyl]-1-(pyridazin-4-yl)azetidine-3-carboxamide;
N-(4-{[(3R)-1-(2,2-dimethylpropanoyl)pyrrolidin-3-yl]oxy}phenyl)-1-(pyridazin-4-yl)azetidine-3-carboxamide;
N-[4-({(3R)-1-[(4,4-difluorocyclohexyl)carbonyl]pyrrolidin-3-yl}oxy)phenyl]-1-(pyridazin-4-yl)azetidine-3-carboxamide;
N-(4-{[(3R)-1-(2-chlorobenzoyl)pyrrolidin-3-yl]oxy}phenyl)-1-(pyridazin-3-yl)azetidine-3-carboxamide;
1-(pyridazin-3-yl)-N-(4-{[(3R)-1-(1,3-thiazol-2-ylcarbonyl)pyrrolidin-3-yl]oxy}phenyl)azetidine-3-carboxamide;
N-(4-{[(3R)-1-(cyclopropylacetyl)pyrrolidin-3-yl]oxy}phenyl)-1-(pyridazin-3-yl)azetidine-3-carboxamide;
N-[4-({(3R)-1-[(2S)-2-methylbutanoyl]pyrrolidin-3-yl}oxy)phenyl]-1-(pyridazin-3-yl)azetidine-3-carboxamide;
1-(pyridazin-3-yl)-N-(4-{[(3R)-1-(tetrahydro-2H-pyran-4-ylcarbonyl)pyrrolidin-3-yl]oxy}phenyl)azetidine-3-carboxamide;
1-(pyridazin-3-yl)-N-(4-{[(3R)-1-{[4-(trifluoromethoxy)phenyl]acetyl}pyrrolidin-3-yl]oxy}phenyl)azetidine-3-carboxamide;
N-(4-{[(3R)-1-(4-fluorobenzoyl)pyrrolidin-3-yl]oxy}phenyl)-1-(pyridazin-3-yl)azetidine-3-carboxamide;
1-(pyridazin-3-yl)-N-(4-{[(3R)-1-(thiophen-3-ylcarbonyl)pyrrolidin-3-yl]oxy}phenyl)azetidine-3-carboxamide;
N-[4-({(3R)-1-[(4-fluorophenyl)acetyl]pyrrolidin-3-yl}oxy)phenyl]-1-(pyridazin-3-yl)azetidine-3-carboxamide;
N-[4-({(3R)-1-[(3,5-difluorophenyl)acetyl]pyrrolidin-3-yl}oxy)phenyl]-1-(pyridazin-3-yl)azetidine-3-carboxamide;
N-(4-{[(3R)-1-(3,4-difluorobenzoyl)pyrrolidin-3-yl]oxy}phenyl)-1-(pyridazin-3-yl)azetidine-3-carboxamide;

N-[4-({(3R)-1-[(3-fluorophenyl)acetyl]pyrrolidin-3-yl}oxy)phenyl]-1-(pyridazin-3-yl)azetidine-3-carboxamide;

1-(pyridazin-3-yl)-N-[4-({(3R)-1-[3-(trifluoromethyl)benzoyl]pyrrolidin-3-yl}oxy)phenyl]azetidine-3-carboxamide;

N-[4-({(3R)-1-[(2,4-difluorophenyl)acetyl]pyrrolidin-3-yl}oxy)phenyl]-1-(pyridazin-3-yl)azetidine-3-carboxamide;

1-(pyridazin-3-yl)-N-(4-{[(3R)-1-{[4-(trifluoromethyl)phenyl]acetyl}pyrrolidin-3-yl]oxy}phenyl)azetidine-3-carboxamide;

1-(pyridazin-3-yl)-N-(4-{[(3R)-1-(1,3-thiazol-4-ylcarbonyl)pyrrolidin-3-yl]oxy}phenyl)azetidine-3-carboxamide;

1-(pyridazin-3-yl)-N-(4-{[(3R)-1-(tetrahydrofuran-2-ylcarbonyl)pyrrolidin-3-yl]oxy}phenyl)azetidine-3-carboxamide;

N-[4-({(3R)-1-[(5-methylthiophen-2-yl)carbonyl]pyrrolidin-3-yl}oxy)phenyl]-1-(pyridazin-3-yl)azetidine-3-carboxamide;

N-[4-({(3R)-1-[(2-fluorophenyl)acetyl]pyrrolidin-3-yl}oxy)phenyl]-1-(pyridazin-3-yl)azetidine-3-carboxamide;

N-(4-{[(3R)-1-(cyclopropylcarbonyl)pyrrolidin-3-yl]oxy}phenyl)-1-(pyridazin-3-yl)azetidine-3-carboxamide;

1-(pyridazin-3-yl)-N-(4-{[(3R)-1-(tetrahydrofuran-3-ylcarbonyl)pyrrolidin-3-yl]oxy}phenyl)azetidine-3-carboxamide;

1-(pyridazin-3-yl)-N-[4-({(3R)-1-[3-(trifluoromethoxy)benzoyl]pyrrolidin-3-yl}oxy)phenyl]azetidine-3-carboxamide;

1-(pyridazin-3-yl)-N-(4-{[(3R)-1-(pyridin-2-ylcarbonyl)pyrrolidin-3-yl]oxy}phenyl)azetidine-3-carboxamide;

N-(4-{[(3R)-1-(3-chlorobenzoyl)pyrrolidin-3-yl]oxy}phenyl)-1-(pyridazin-3-yl)azetidine-3-carboxamide;

N-(4-{[(3R)-1-(4-chlorobenzoyl)pyrrolidin-3-yl]oxy}phenyl)-1-(pyridazin-3-yl)azetidine-3-carboxamide;

N-(4-{[(3R)-1-(2-methyl-2-phenylpropanoyl)pyrrolidin-3-yl]oxy}phenyl)-1-(pyridazin-3-yl)azetidine-3-carboxamide;

N-(4-{[(3R)-1-(2,4-difluorobenzoyl)pyrrolidin-3-yl]oxy}phenyl)-1-(pyridazin-3-yl)azetidine-3-carboxamide;

N-(4-{[(3R)-1-(methoxyacetyl)pyrrolidin-3-yl]oxy}phenyl)-1-(pyridazin-3-yl)azetidine-3-carboxamide;

1-(pyridazin-3-yl)-N-(4-{[(3R)-1-(thiophen-2-ylcarbonyl)pyrrolidin-3-yl]oxy}phenyl)azetidine-3-carboxamide;

1-(pyridazin-3-yl)-N-(4-{[(3R)-1-{[3-(trifluoromethyl)phenyl]acetyl}pyrrolidin-3-yl]oxy}phenyl)azetidine-3-carboxamide;

N-(4-{[(3R)-1-(2-methylpropanoyl)pyrrolidin-3-yl]oxy}phenyl)-1-(pyridazin-3-yl)azetidine-3-carboxamide;

N-(4-{[(3R)-1-(2-fluorobenzoyl)pyrrolidin-3-yl]oxy}phenyl)-1-(pyridazin-3-yl)azetidine-3-carboxamide;

N-(4-{[(3R)-1-(2,2-dimethylbutanoyl)pyrrolidin-3-yl]oxy}phenyl)-1-(pyridazin-3-yl)azetidine-3-carboxamide;

N-(4-{[(3R)-1-(3,5-difluorobenzoyl)pyrrolidin-3-yl]oxy}phenyl)-1-(pyridazin-3-yl)azetidine-3-carboxamide;

1-(pyridazin-3-yl)-N-[4-({(3R)-1-[4-(trifluoromethyl)benzoyl]pyrrolidin-3-yl}oxy)phenyl]azetidine-3-carboxamide;

N-(4-{[(3R)-1-(3-fluorobenzoyl)pyrrolidin-3-yl]oxy}phenyl)-1-(pyridazin-3-yl)azetidine-3-carboxamide;

1-(pyridazin-3-yl)-N-[4-({(3R)-1-[4-(trifluoromethoxy)benzoyl]pyrrolidin-3-yl}oxy)phenyl]azetidine-3-carboxamide;

N-(4-{[(3R)-1-(3-methylbutanoyl)pyrrolidin-3-yl]oxy}phenyl)-1-(pyridazin-3-yl)azetidine-3-carboxamide;

1-(pyridazin-3-yl)-N-(4-{[(3R)-1-(3,3,3-trifluoropropanoyl)pyrrolidin-3-yl]oxy}phenyl)azetidine-3-carboxamide;

N-[4-({(3R)-1-[difluoro(phenyl)acetyl]pyrrolidin-3-yl}oxy)phenyl]-1-(pyridazin-3-yl)azetidine-3-carboxamide;

N-(4-{[(3R)-1-(2,2-dimethylpropanoyl)pyrrolidin-3-yl]oxy}phenyl)-1-(pyridazin-3-yl)azetidine-3-carboxamide;

N-[4-({(3R)-1-[(4,4-difluorocyclohexyl)carbonyl]pyrrolidin-3-yl}oxy)phenyl]-1-(pyridazin-3-yl)azetidine-3-carboxamide;

N-{4-[1-(2-chlorobenzoyl)piperidin-4-yl]phenyl}-1-(pyridazin-4-yl)azetidine-3-carboxamide;

1-(pyridazin-4-yl)-N-{4-[1-(1,3-thiazol-2-ylcarbonyl)piperidin-4-yl]phenyl}azetidine-3-carboxamide;

N-{4-[1-(cyclopropylacetyl)piperidin-4-yl]phenyl}-1-(pyridazin-4-yl)azetidine-3-carboxamide;

N-{4-[1-(2-methylpropanoyl)piperidin-4-yl]phenyl}-1-(pyridazin-4-yl)azetidine-3-carboxamide;

N-{4-[1-(4-fluorobenzoyl)piperidin-4-yl]phenyl}-1-(pyridazin-4-yl)azetidine-3-carboxamide;

1-(pyridazin-4-yl)-N-{4-[1-(thiophen-3-ylcarbonyl)piperidin-4-yl]phenyl}azetidine-3-carboxamide;

N-(4-{1-[(4-fluorophenyl)acetyl]piperidin-4-yl}phenyl)-1-(pyridazin-4-yl)azetidine-3-carboxamide;

N-(4-{1-[(3,5-difluorophenyl)acetyl]piperidin-4-yl}phenyl)-1-(pyridazin-4-yl)azetidine-3-carboxamide;

N-{4-[1-(3,4-difluorobenzoyl)piperidin-4-yl]phenyl}-1-(pyridazin-4-yl)azetidine-3-carboxamide;

N-(4-{1-[(3-fluorophenyl)acetyl]piperidin-4-yl}phenyl)-1-(pyridazin-4-yl)azetidine-3-carboxamide;

1-(pyridazin-4-yl)-N-(4-{1-[3-(trifluoromethyl)benzoyl]piperidin-4-yl}phenyl)azetidine-3-carboxamide;

N-(4-{1-[(2,4-difluorophenyl)acetyl]piperidin-4-yl}phenyl)-1-(pyridazin-4-yl)azetidine-3-carboxamide;

1-(pyridazin-4-yl)-N-{4-[1-(1,3-thiazol-4-ylcarbonyl)piperidin-4-yl]phenyl}azetidine-3-carboxamide;

1-(pyridazin-4-yl)-N-{4-[1-(tetrahydrofuran-2-ylcarbonyl)piperidin-4-yl]phenyl}azetidine-3-carboxamide;

N-(4-{1-[(5-methylthiophen-2-yl)carbonyl]piperidin-4-yl}phenyl)-1-(pyridazin-4-yl)azetidine-3-carboxamide;

N-(4-{1-[(2-fluorophenyl)acetyl]piperidin-4-yl}phenyl)-1-(pyridazin-4-yl)azetidine-3-carboxamide;

N-{4-[1-(cyclopropylcarbonyl)piperidin-4-yl]phenyl}-1-(pyridazin-4-yl)azetidine-3-carboxamide;

1-(pyridazin-4-yl)-N-{4-[1-(tetrahydrofuran-3-ylcarbonyl)piperidin-4-yl]phenyl}azetidine-3-carboxamide;

1-(pyridazin-4-yl)-N-{4-[1-(pyridin-2-ylcarbonyl)piperidin-4-yl]phenyl}azetidine-3-carboxamide;

N-{4-[1-(3-chlorobenzoyl)piperidin-4-yl]phenyl}-1-(pyridazin-4-yl)azetidine-3-carboxamide;

N-{4-[1-(4-chlorobenzoyl)piperidin-4-yl]phenyl}-1-(pyridazin-4-yl)azetidine-3-carboxamide;

N-{4-[1-(2-methyl-2-phenylpropanoyl)piperidin-4-yl]phenyl}-1-(pyridazin-4-yl)azetidine-3-carboxamide;

N-{4-[1-(2,4-difluorobenzoyl)piperidin-4-yl]phenyl}-1-(pyridazin-4-yl)azetidine-3-carboxamide;

N-{4-[1-(methoxyacetyl)piperidin-4-yl]phenyl}-1-(pyridazin-4-yl)azetidine-3-carboxamide;

1-(pyridazin-4-yl)-N-{4-[1-(thiophen-2-ylcarbonyl)piperidin-4-yl]phenyl}azetidine-3-carboxamide;

1-(pyridazin-4-yl)-N-[4-(1-{[3-(trifluoromethyl)phenyl]acetyl}piperidin-4-yl)phenyl]azetidine-3-carboxamide;

N-{4-[1-(2-fluorobenzoyl)piperidin-4-yl]phenyl}-1-(pyridazin-4-yl)azetidine-3-carboxamide;

N-{4-[1-(3,5-difluorobenzoyl)piperidin-4-yl]phenyl}-1-(pyridazin-4-yl)azetidine-3-carboxamide;

1-(pyridazin-4-yl)-N-(4-{1-[4-(trifluoromethyl)benzoyl]piperidin-4-yl}phenyl)azetidine-3-carboxamide;

N-{4-[1-(3-fluorobenzoyl)piperidin-4-yl]phenyl}-1-(pyridazin-4-yl)azetidine-3-carboxamide;

1-(pyridazin-4-yl)-N-(4-{1-[4-(trifluoromethoxy)benzoyl]piperidin-4-yl}phenyl)azetidine-3-carboxamide;
N-{4-[1-(3-methylbutanoyl)piperidin-4-yl]phenyl}-1-(pyridazin-4-yl)azetidine-3-carboxamide;
1-(pyridazin-4-yl)-N-{4-[1-(3,3,3-trifluoropropanoyl)piperidin-4-yl]phenyl}azetidine-3-carboxamide;
N-(4-{1-[difluoro(phenyl)acetyl]piperidin-4-yl}phenyl)-1-(pyridazin-4-yl)azetidine-3-carboxamide;
N-{4-[1-(2,2-dimethylpropanoyl)piperidin-4-yl]phenyl}-1-(pyridazin-4-yl)azetidine-3-carboxamide;
N-(4-{1-[(4,4-difluorocyclohexyl)carbonyl]piperidin-4-yl}phenyl)-1-(pyridazin-4-yl)azetidine-3-carboxamide;
1-(pyridazin-4-yl)-N-[4-(1-{[4-(trifluoromethoxy)phenyl]acetyl}piperidin-4-yl)phenyl]azetidine-3-carboxamide;
1-(pyridazin-4-yl)-N-(4-{1-[3-(trifluoromethoxy)benzoyl]piperidin-4-yl}phenyl)azetidine-3-carboxamide;
1-(pyridazin-4-yl)-N-[4-(1-{[4-(trifluoromethyl)phenyl]acetyl}piperidin-4-yl)phenyl]azetidine-3-carboxamide;
N-(4-{[1-(3-chlorobenzoyl)piperidin-4-yl]sulfonyl}phenyl)-1-(pyridazin-3-yl)azetidine-3-carboxamide;
N-(4-{[1-(4-tert-butylbenzoyl)piperidin-4-yl]sulfonyl}phenyl)-1-(pyridazin-3-yl)azetidine-3-carboxamide;
N-(4-{[1-(4-methoxybenzoyl)piperidin-4-yl]sulfonyl}phenyl)-1-(pyridazin-3-yl)azetidine-3-carboxamide;
N-(4-{[1-(4-methylbenzoyl)piperidin-4-yl]sulfonyl}phenyl)-1-(pyridazin-3-yl)azetidine-3-carboxamide;
N-(4-{[1-(cyclohexylcarbonyl)piperidin-4-yl]sulfonyl}phenyl)-1-(pyridazin-3-yl)azetidine-3-carboxamide;
N-(4-{[1-(cyclopropylacetyl)piperidin-4-yl]sulfonyl}phenyl)-1-(pyridazin-3-yl)azetidine-3-carboxamide;
N-(4-{[1-(2-methoxybenzoyl)piperidin-4-yl]sulfonyl}phenyl)-1-(pyridazin-3-yl)azetidine-3-carboxamide;
N-[4-({1-[(2S)-2-phenylbutanoyl]piperidin-4-yl}sulfonyl)phenyl]-1-(pyridazin-3-yl)azetidine-3-carboxamide;
N-[4-({1-[4-(propan-2-yl)benzoyl]piperidin-4-yl}sulfonyl)phenyl]-1-(pyridazin-3-yl)azetidine-3-carboxamide;
N-(4-{[1-(4-chlorobenzoyl)piperidin-4-yl]sulfonyl}phenyl)-1-(pyridazin-3-yl)azetidine-3-carboxamide;
N-{4-[(1-benzoylpiperidin-4-yl)sulfonyl]phenyl}-1-(pyridazin-3-yl)azetidine-3-carboxamide;
1-(pyridazin-3-yl)-N-(4-{[1-(4,4,4-trifluorobutanoyl)piperidin-4-yl]sulfonyl}phenyl)azetidine-3-carboxamide;
N-(4-{[1-(2,5-difluorobenzoyl)piperidin-4-yl]sulfonyl}phenyl)-1-(pyridazin-3-yl)azetidine-3-carboxamide;
N-(4-{[1-(2-fluorobenzoyl)piperidin-4-yl]sulfonyl}phenyl)-1-(pyridazin-3-yl)azetidine-3-carboxamide;
N-(4-{[1-(2-methylbenzoyl)piperidin-4-yl]sulfonyl}phenyl)-1-(pyridazin-3-yl)azetidine-3-carboxamide;
N-[4-({1-[(4-fluorophenyl)acetyl]piperidin-4-yl}sulfonyl)phenyl]-1-(pyridazin-3-yl)azetidine-3-carboxamide;
N-(4-{[1-(3-methylbenzoyl)piperidin-4-yl]sulfonyl}phenyl)-1-(pyridazin-3-yl)azetidine-3-carboxamide;
N-(4-{[1-(2,3-dimethylbenzoyl)piperidin-4-yl]sulfonyl}phenyl)-1-(pyridazin-3-yl)azetidine-3-carboxamide;
N-[4-({1-[(3-fluorophenyl)acetyl]piperidin-4-yl}sulfonyl)phenyl]-1-(pyridazin-3-yl)azetidine-3-carboxamide;
N-(4-{[1-(3-fluorobenzoyl)piperidin-4-yl]sulfonyl}phenyl)-1-(pyridazin-3-yl)azetidine-3-carboxamide;
1-(pyridazin-3-yl)-N-[4-({1-[3-(trifluoromethyl)benzoyl]piperidin-4-yl}sulfonyl)phenyl]azetidine-3-carboxamide;
N-[4-({1-[(3,5-difluorophenyl)acetyl]piperidin-4-yl}sulfonyl)phenyl]-1-(pyridazin-3-yl)azetidine-3-carboxamide;
N-(4-{[1-(2,4-difluorobenzoyl)piperidin-4-yl]sulfonyl}phenyl)-1-(pyridazin-3-yl)azetidine-3-carboxamide;
1-(pyridazin-3-yl)-N-[4-({1-[4-(trifluoromethyl)benzoyl]piperidin-4-yl}sulfonyl)phenyl]azetidine-3-carboxamide;
N-(4-{[1-(4-fluorobenzoyl)piperidin-4-yl]sulfonyl}phenyl)-1-(pyridazin-3-yl)azetidine-3-carboxamide;
N-(4-{[1-(2,3-difluorobenzoyl)piperidin-4-yl]sulfonyl}phenyl)-1-(pyridazin-3-yl)azetidine-3-carboxamide;
N-(4-{[1-(2,4-dichlorobenzoyl)piperidin-4-yl]sulfonyl}phenyl)-1-(pyridazin-3-yl)azetidine-3-carboxamide;
N-(4-{[1-(naphthalen-1-ylcarbonyl)piperidin-4-yl]sulfonyl}phenyl)-1-(pyridazin-3-yl)azetidine-3-carboxamide;
N-(4-{[1-(cyclopropylcarbonyl)piperidin-4-yl]sulfonyl}phenyl)-1-(pyridazin-3-yl)azetidine-3-carboxamide;
N-(4-{[1-(3,5-difluorobenzoyl)piperidin-4-yl]sulfonyl}phenyl)-1-(pyridazin-3-yl)azetidine-3-carboxamide;
N-(4-{[1-(2,2-dimethylpropanoyl)piperidin-4-yl]sulfonyl}phenyl)-1-(pyridazin-3-yl)azetidine-3-carboxamide;
N-(4-{[1-(3,3-dimethylbutanoyl)piperidin-4-yl]sulfonyl}phenyl)-1-(pyridazin-3-yl)azetidine-3-carboxamide;
N-(4-{[1-(3-methoxybenzoyl)piperidin-4-yl]sulfonyl}phenyl)-1-(pyridazin-3-yl)azetidine-3-carboxamide;
N-(4-{[1-(3-methylbutanoyl)piperidin-4-yl]sulfonyl}phenyl)-1-(pyridazin-3-yl)azetidine-3-carboxamide;
N-(4-{[1-(2-methylpropanoyl)piperidin-4-yl]sulfonyl}phenyl)-1-(pyridazin-3-yl)azetidine-3-carboxamide;
N-(4-{[1-(cyclopentylcarbonyl)piperidin-4-yl]sulfonyl}phenyl)-1-(pyridazin-3-yl)azetidine-3-carboxamide;
N-(4-{[1-(phenylacetyl)piperidin-4-yl]sulfonyl}phenyl)-1-(pyridazin-3-yl)azetidine-3-carboxamide;
N-[4-({1-[(1-phenylcyclopropyl)carbonyl]piperidin-4-yl}sulfonyl)phenyl]-1-(pyridazin-3-yl)azetidine-3-carboxamide;
N-{4-[1-(2-methylalanyl)piperidin-4-yl]phenyl}-1-(pyridin-3-yl)azetidine-3-carboxamide;
tert-butyl 4-(2-methyl-1-oxo-1-{4-[4-({[1-(pyridin-3-yl)azetidin-3-yl]carbonyl}amino)phenyl]piperidin-1-yl}propan-2-yl)piperazine-1-carboxylate;
N-(4-{1-[2-methyl-2-(piperazin-1-yl)propanoyl]piperidin-4-yl}phenyl)-1-(pyridin-3-yl)azetidine-3-carboxamide;
N-(4-{[1-(2-chlorobenzoyl)piperidin-4-yl]sulfonyl}phenyl)-1-(pyridin-3-yl)azetidine-3-carboxamide;
N-(4-{[1-(4-methylpentanoyl)piperidin-4-yl]sulfonyl}phenyl)-1-(pyridazin-3-yl)azetidine-3-carboxamide;

N-[4-({1-[(2-fluorophenyl)acetyl]piperidin-4-yl}sulfonyl)phenyl]-1-(pyridazin-3-yl)azetidine-3-carboxamide;
N-(4-{[1-(2-methylpropanoyl)piperidin-4-yl]sulfonyl}phenyl)-1-(pyridazin-4-yl)azetidine-3-carboxamide;
N-{4-[(1-benzoylpiperidin-4-yl)sulfonyl]phenyl}-1-(pyridazin-4-yl)azetidine-3-carboxamide;
N-(4-{[1-(4-fluorobenzoyl)piperidin-4-yl]sulfonyl}phenyl)-1-(pyridazin-4-yl)azetidine-3-carboxamide;
N-(4-{[1-(cyclopentylcarbonyl)piperidin-4-yl]sulfonyl}phenyl)-1-(pyridazin-4-yl)azetidine-3-carboxamide;
N-[4-(1-benzoylpiperidin-4-yl)phenyl]-1-(6-fluoro-5-methylpyridin-3-yl)azetidine-3-carboxamide;
N-[4-(1-benzoylpiperidin-4-yl)phenyl]-1-(5-fluoropyridin-3-yl)azetidine-3-carboxamide;
N-[4-(1-benzoylpiperidin-4-yl)phenyl]-1-(6-methylpyridazin-3-yl)azetidine-3-carboxamide;
N-[4-(1-benzoylpiperidin-4-yl)phenyl]-1-(2-fluoro-6-methylpyridin-3-yl)azetidine-3-carboxamide;
N-[4-(1-benzoylpiperidin-4-yl)phenyl]-1-(2-cyanopyridin-3-yl)azetidine-3-carboxamide;
N-[4-(1-benzoylpiperidin-4-yl)phenyl]-1-(4-cyanopyridin-3-yl)azetidine-3-carboxamide;
N-[4-(1-benzoylpiperidin-4-yl)phenyl]-1-(6-fluoro-4-methylpyridin-3-yl)azetidine-3-carboxamide;
N-[4-(1-benzoylpiperidin-4-yl)phenyl]-1-(5-cyanopyridin-3-yl)azetidine-3-carboxamide;
N-[4-(1-benzoylpiperidin-4-yl)phenyl]-1-(5-methylpyridin-3-yl)azetidine-3-carboxamide;
N-(4-{1-[(4-methyltetrahydro-2H-pyran-4-yl)methyl]-1H-pyrazol-4-yl}phenyl)-1-(pyridazin-3-yl)azetidine-3-carboxamide;
N-(4-{1-[2-(piperazin-1-yl)ethyl]-1H-pyrazol-4-yl}phenyl)-1-(pyridazin-3-yl)azetidine-3-carboxamide;
N-{4-[1-(2,2-dimethylpropyl)-1H-pyrazol-4-yl]phenyl}-1-(pyridazin-3-yl)azetidine-3-carboxamide;
N-{4-[1-(2-hydroxy-2-methylpropyl)-1H-pyrazol-4-yl]phenyl}-1-(pyridazin-3-yl)azetidine-3-carboxamide;
N-[4-(5-propyl-1,2,4-oxadiazol-3-yl)phenyl]-1-(pyridazin-3-yl)azetidine-3-carboxamide;
N-{4-[5-(2,2-dimethylpropyl)-1,3,4-oxadiazol-2-yl]phenyl}-1-(pyridazin-3-yl)azetidine-3-carboxamide;
N-{4-[1-(2,2-dimethylpropyl)-1H-imidazol-4-yl]phenyl}-1-(pyridazin-3-yl)azetidine-3-carboxamide;
N-[4-(3-cyclopropyl-1-methyl-1H-pyrazol-5-yl)phenyl]-1-(pyridazin-3-yl)azetidine-3-carboxamide;
N-{4-[5-(2,2-dimethylpropyl)-1,2,4-oxadiazol-3-yl]phenyl}-1-(pyridazin-3-yl)azetidine-3-carboxamide;
N-{4-[3-cyclopropyl-1-(2-methoxyethyl)-1H-pyrazol-5-yl]phenyl}-1-(pyridazin-3-yl)azetidine-3-carboxamide;
tert-butyl 4-fluoro-4-[4-({[1-(pyridazin-3-yl)azetidin-3-yl]carbonyl}amino)phenyl]piperidine-1-carboxylate;
N-{4-[3-cyclopropyl-1-(2-hydroxyethyl)-1H-pyrazol-5-yl]phenyl}-1-(pyridazin-3-yl)azetidine-3-carboxamide;
N-[4-(1-benzoylpiperidin-4-yl)phenyl]-1-(6-fluoropyridazin-3-yl)azetidine-3-carboxamide;
N-{4-[1-(2-fluorobenzoyl)piperidin-4-yl]phenyl}-1-(6-fluoropyridazin-3-yl)azetidine-3-carboxamide;
N-{4-[1-(2,2-dimethylpropanoyl)piperidin-4-yl]phenyl}-1-(6-fluoropyridazin-3-yl)azetidine-3-carboxamide;
1-(6-fluoropyridazin-3-yl)-N-{4-[1-(2-methylpropanoyl)piperidin-4-yl]phenyl}azetidine-3-carboxamide;
N-{4-[1-(2-ethylbutanoyl)piperidin-4-yl]phenyl}-1-(6-fluoropyridazin-3-yl)azetidine-3-carboxamide;
N-{4-[1-(4-fluorobenzoyl)piperidin-4-yl]phenyl}-1-(6-fluoropyridazin-3-yl)azetidine-3-carboxamide;
N-{4-[8-(2-methylpropanoyl)-8-azabicyclo[3.2.1]oct-3-yl]phenyl}-1-(pyridazin-3-yl)azetidine-3-carboxamide;
1-(pyridazin-3-yl)-N-{4-[8-(4,4,4-trifluorobutanoyl)-8-azabicyclo[3.2.1]oct-3-yl]phenyl}azetidine-3-carboxamide;
N-[4-(8-benzoyl-8-azabicyclo[3.2.1]oct-3-yl)phenyl]-1-(pyridazin-3-yl)azetidine-3-carboxamide;
N-{4-[8-(2-fluorobenzoyl)-8-azabicyclo[3.2.1]oct-3-yl]phenyl}-1-(pyridazin-3-yl)azetidine-3-carboxamide;
N-{4-[8-(2,2-dimethylpropanoyl)-8-azabicyclo[3.2.1]oct-3-yl]phenyl}-1-(pyridazin-3-yl)azetidine-3-carboxamide;
N-(4-{8-[(1-methylcyclopropyl)carbonyl]-8-azabicyclo[3.2.1]oct-3-yl}phenyl)-1-(pyridazin-3-yl)azetidine-3-carboxamide;
N-{4-[1-(2-methoxyethyl)-3-(2-methylpropyl)-1H-pyrazol-5-yl]phenyl}-1-(pyridazin-3-yl)azetidine-3-carboxamide;
N-{4-[1-(2-fluorobenzoyl)piperidin-4-yl]phenyl}-1-(6-methylpyridazin-3-yl)azetidine-3-carboxamide;
N-{4-[1-(2,2-dimethylpropanoyl)piperidin-4-yl]phenyl}-1-(6-methylpyridazin-3-yl)azetidine-3-carboxamide;
benzyl 4-[4-({[1-(6-chloropyridazin-3-yl)azetidin-3-yl]carbonyl}amino)phenyl]-4-fluoropiperidine-1-carboxylate;
benzyl 4-[4-({[1-(6-chloropyridazin-3-yl)azetidin-3-yl]carbonyl}amino)phenyl]-4-hydroxypiperidine-1-carboxylate;
N-{4-[4-fluoro-1-(2-fluorobenzoyl)piperidin-4-yl]phenyl}-1-(pyridazin-3-yl)azetidine-3-carboxamide;
N-[4-(1-benzoyl-4-fluoropiperidin-4-yl)phenyl]-1-(pyridazin-3-yl)azetidine-3-carboxamide;
N-{4-[1-(2,2-dimethylpropanoyl)-4-fluoropiperidin-4-yl]phenyl}-1-(pyridazin-3-yl)azetidine-3-carboxamide;
N-{4-[3-tert-butyl-1-(2-methoxyethyl)-1H-pyrazol-5-yl]phenyl}-1-(pyridazin-3-yl)azetidine-3-carboxamide;
N-[4-(1-butyl-3-tert-butyl-1H-pyrazol-5-yl)phenyl]-1-(pyridazin-3-yl)azetidine-3-carboxamide;
N-{4-[3-tert-butyl-1-(tetrahydro-2H-pyran-4-ylmethyl)-1H-pyrazol-5-yl]phenyl}-1-(pyridazin-3-yl)azetidine-3-carboxamide;
N-(4-{1-[(4-methylpiperidin-4-yl)methyl]-1H-pyrazol-4-yl}phenyl)-1-(pyridazin-3-yl)azetidine-3-carboxamide;
N-{4-[1-methyl-3-(trifluoromethyl)-1H-pyrazol-5-yl]phenyl}-1-(pyridazin-3-yl)azetidine-3-carboxamide;
1-(6-chloropyridazin-3-yl)-N-{4-[1-(2,2-dimethylpropyl)-1H-pyrazol-4-yl]phenyl}azetidine-3-carboxamide;
N-[4-(1-benzoylpiperidin-4-yl)phenyl]-1-(6-methylpyridin-3-yl)azetidine-3-carboxamide;
N-(4-{1-[(4-methylpiperidin-4-yl)methyl]-1H-pyrazol-4-yl}phenyl)-1-(pyridin-3-yl)azetidine-3-carboxamide;
N-{4-[1-(2,2-dimethylpropyl)-1H-pyrazol-4-yl]phenyl}-1-(6-methylpyridazin-3-yl)azetidine-3-carboxamide;
N-{4-[1-(2-fluorobenzoyl)-4-hydroxypiperidin-4-yl]phenyl}-1-(pyridazin-3-yl)azetidine-3-carboxamide;
N-{4-[1-(2,2-dimethylpropanoyl)-4-hydroxypiperidin-4-yl]phenyl}-1-(pyridazin-3-yl)azetidine-3-carboxamide;
1-(6-methylpyridazin-3-yl)-N-(4-{1-[(4-methyltetrahydro-2H-pyran-4-yl)methyl]-1H-pyrazol-4-yl}phenyl)azetidine-3-carboxamide;
N-{4-[(1-benzoylpiperidin-4-yl)methyl]phenyl}-1-(pyridazin-3-yl)azetidine-3-carboxamide;
N-(4-{[1-(2-fluorobenzoyl)piperidin-4-yl]methyl}phenyl)-1-(pyridazin-3-yl)azetidine-3-carboxamide;
N-(4-{[1-(2,2-dimethylpropanoyl)piperidin-4-yl]methyl}phenyl)-1-(pyridazin-3-yl)azetidine-3-carboxamide;

N-(4-{[1-(3,3-dimethylbutanoyl)piperidin-4-yl]methyl}phenyl)-1-(pyridazin-3-yl)azetidine-3-carboxamide;
N-(4-{[1-(2-ethylbutanoyl)piperidin-4-yl]methyl}phenyl)-1-(pyridazin-3-yl)azetidine-3-carboxamide;
1-(pyridazin-3-yl)-N-(4-{[1-(4,4,4-trifluorobutanoyl)piperidin-4-yl]methyl}phenyl)azetidine-3-carboxamide;
N-(4-{[1-(2-methylpropanoyl)piperidin-4-yl]methyl}phenyl)-1-(pyridazin-3-yl)azetidine-3-carboxamide;
N-{4[(1-acetylpiperidin-4-yl)methyl]phenyl}-1-(pyridazin-3-yl)azetidine-3-carboxamide;
N-[4-({1-[(2S)-2-methylbutanoyl]piperidin-4-yl}methyl)phenyl]-1-(pyridazin-3-yl)azetidine-3-carboxamide;
N-(4-({1-[(1-methylcyclopropyl)carbonyl]piperidin-4-yl}methyl)phenyl]-1-(pyridazin-3-yl)azetidine-3-carboxamide;
N-[4-(1-{[4-methyl-1-(oxetan-3-yl)piperidin-4-yl]methyl}-1H-pyrazol-4-yl)phenyl]-1-(6-methylpyridazin-3-yl)azetidine-3-carboxamide;
N-[4-(1-benzoylpiperidin-4-yl)phenyl]-1-(4-methylpyridazin-3-yl)azetidine-3-carboxamide;
N-[4-(1-benzoylpiperidin-4-yl)phenyl]-1-(3-methylpyridazin-3-yl)azetidine-3-carboxamide;
N-{4-[1-(2-fluorobenzoyl)piperidin-4-yl]phenyl}-1-(3-methylpyridazin-4-yl)azetidine-3-carboxamide;
N-(4-{1-[(2-aminopyridin-3-yl)carbonyl]piperidin-4-yl}phenyl)-1-(pyridazin-3-yl)azetidine-3-carboxamide;
1-methyl-5-[4-({[1-(pyridazin-3-yl)azetidin-3-yl]carbonyl}amino)phenyl]-1H-pyrazole-3-carboxylic acid;
ethyl 1-methyl-5-[4-({[1-(pyridazin-3-yl)azetidin-3-yl]carbonyl}amino)phenyl]-1H-pyrazole-3-carboxylate;
ethyl 1-phenyl-5-[4-({[1-(pyridazin-3-yl)azetidin-3-yl]carbonyl}amino)phenyl]-1H-pyrazole-3-carboxylate;
N-(4-{[(3R)-1-(3-methylbutanoyl)pyrrolidin-3-yl]oxy}phenyl)-1-(6-methylpyridazin-3-yl)azetidine-3-carboxamide;
N-(4-{[(3R)-1-(2-methylpropanoyl)pyrrolidin-3-yl]oxy}phenyl)-1-(6-methylpyridazin-3-yl)azetidine-3-carboxamide;
N-(4-{[(3R)-1-(2,4-difluorobenzoyl)pyrrolidin-3-yl]oxy}phenyl)-1-(6-methylpyridazin-3-yl)azetidine-3-carboxamide;
1-(6-methylpyridazin-3-yl)-N-(4-{[(3R)-1-(1,3-thiazol-4-ylcarbonyl)pyrrolidin-3-yl]oxy}phenyl)azetidine-3-carboxamide;
N-{4-[1-phenyl-3-(trifluoromethyl)-1H-pyrazol-5-yl]phenyl}-1-(pyridazin-3-yl)azetidine-3-carboxamide;
1-(pyridazin-3-yl)-N-(4-{[1-(1,3-thiazol-5-ylcarbonyl)piperidin-4-yl]methyl}phenyl)azetidine-3-carboxamide;
N-(4-{[1-(cyclopentylcarbonyl)piperidin-4-yl]methyl}phenyl)-1-(pyridazin-3-yl)azetidine-3-carboxamide;
N-(4-{[1-(1H-pyrazol-4-ylcarbonyl)piperidin-4-yl]methyl}phenyl)-1-(pyridazin-3-yl)azetidine-3-carboxamide;
N-(4-{[1-(2,2-dimethylbutanoyl)piperidin-4-yl]methyl}phenyl)-1-(pyridazin-3-yl)azetidine-3-carboxamide;
N-[4-({1-[(2-methylcyclopropyl)carbonyl]piperidin-4-yl}methyl)phenyl]-1-(pyridazin-3-yl)azetidine-3-carboxamide;
N-[4-({1-[(methylsulfanyl)acetyl]piperidin-4-yl}methyl)phenyl]-1-(pyridazin-3-yl)azetidine-3-carboxamide;
N-[4-({1-[(1S,4R)-bicyclo[2.2.1]hept-2-ylacetyl]piperidin-4-yl}methyl)phenyl]-1-(pyridazin-3-yl)azetidine-3-carboxamide;
N-(4-{[1-(2-methylpentanoyl)piperidin-4-yl]methyl}phenyl)-1-(pyridazin-3-yl)azetidine-3-carboxamide;
N-(4-{[1-(4-methylpentanoyl)piperidin-4-yl]methyl}phenyl)-1-(pyridazin-3-yl)azetidine-3-carboxamide;
N-[4-({1-[3-(methylsulfanyl)propanoyl]piperidin-4-yl}methyl)phenyl]-1-(pyridazin-3-yl)azetidine-3-carboxamide;
1-(pyridazin-3-yl)-N-(4-{[1-(1,3-thiazol-4-ylcarbonyl)piperidin-4-yl]methyl}phenyl)azetidine-3-carboxamide;
N-(4-{[1-(1H-pyrazol-5-ylcarbonyl)piperidin-4-yl]methyl}phenyl)-1-(pyridazin-3-yl)azetidine-3-carboxamide;
N-[4-({1-[(6-methylpyridin-3-yl)carbonyl]piperidin-4-yl}methyl)phenyl]-1-(pyridazin-3-yl)azetidine-3-carboxamide;
N-[4-({1-[(3-methylthiophen-2-yl)carbonyl]piperidin-4-yl}methyl)phenyl]-1-(pyridazin-3-yl)azetidine-3-carboxamide;
N-(4-{[1-(pent-4-ynoyl)piperidin-4-yl]methyl}phenyl)-1-(pyridazin-3-yl)azetidine-3-carboxamide;
1-(pyridazin-3-yl)-N-(4-{[1-(thiophen-3-ylcarbonyl)piperidin-4-yl]methyl}phenyl)azetidine-3-carboxamide;
N-(4-{[1-(methoxyacetyl)piperidin-4-yl]methyl}phenyl)-1-(pyridazin-3-yl)azetidine-3-carboxamide;
1-(pyridazin-3-yl)-N-(4-{[1-(tetrahydrofuran-2-ylcarbonyl)piperidin-4-yl]methyl}phenyl)azetidine-3-carboxamide;
N-[4-({1-[(2-methoxyethoxy)acetyl]piperidin-4-yl}methyl)phenyl]-1-(pyridazin-3-yl)azetidine-3-carboxamide;
N-(4-{[1-(ethoxyacetyl)piperidin-4-yl]methyl}phenyl)-1-(pyridazin-3-yl)azetidine-3-carboxamide;
1-(pyridazin-3-yl)-N-(4-{[1-(thiophen-2-ylcarbonyl)piperidin-4-yl]methyl}phenyl)azetidine-3-carboxamide;
N-{4-[(1-hexanoylpiperidin-4-yl)methyl]phenyl}-1-(pyridazin-3-yl)azetidine-3-carboxamide;
N-[4-({1-[(1-methyl-1H-pyrrol-2-yl)carbonyl]piperidin-4-yl}methyl)phenyl]-1-(pyridazin-3-yl)azetidine-3-carboxamide;
N-(4-{[1-(but-3-enoyl)piperidin-4-yl]methyl}phenyl)-1-(pyridazin-3-yl)azetidine-3-carboxamide;
1-(pyridazin-3-yl)-N-(4-{[1-(1,3-thiazol-2-ylcarbonyl)piperidin-4-yl]methyl}phenyl)azetidine-3-carboxamide;
N-(4-{[1-(furan-2-ylcarbonyl)piperidin-4-yl]methyl}phenyl)-1-(pyridazin-3-yl)azetidine-3-carboxamide;
N-(4-{[1-(1,2-oxazol-5-ylcarbonyl)piperidin-4-yl]methyl}phenyl)-1-(pyridazin-3-yl)azetidine-3-carboxamide;
1-(pyridazin-3-yl)-N-(4-{[1-(pyridin-2-ylcarbonyl)piperidin-4-yl]methyl}phenyl)azetidine-3-carboxamide;
N-(4-{[1-(furan-3-ylcarbonyl)piperidin-4-yl]methyl}phenyl)-1-(pyridazin-3-yl)azetidine-3-carboxamide;
N-(4-{[1-(cyclopropylacetyl)piperidin-4-yl]methyl}phenyl)-1-(pyridazin-3-yl)azetidine-3-carboxamide;
N-(4-{[1-(2-methylbutanoyl)piperidin-4-yl]methyl}phenyl)-1-(pyridazin-3-yl)azetidine-3-carboxamide;
N-{4-[(1-propanoylpiperidin-4-yl)methyl]phenyl}-1-(pyridazin-3-yl)azetidine-3-carboxamide;
N-{4-[(1-butanoylpiperidin-4-yl)methyl]phenyl}-1-(pyridazin-3-yl)azetidine-3-carboxamide;
N-(4-{[1-(cyclobutylcarbonyl)piperidin-4-yl]methyl}phenyl)-1-(pyridazin-3-yl)azetidine-3-carboxamide;

N-{4-[(1-pentanoylpiperidin-4-yl)methyl]phenyl}-1-(pyridazin-3-yl)azetidine-3-carboxamide;
N-(4-{[1-(cyclopentylacetyl)piperidin-4-yl]methyl}phenyl)-1-(pyridazin-3-yl)azetidine-3-carboxamide;
N-(4-{[1-(2-methylbenzoyl)piperidin-4-yl]methyl}phenyl)-1-(pyridazin-3-yl)azetidine-3-carboxamide;
N-(4-{[1-(3-methylpentanoyl)piperidin-4-yl]methyl}phenyl)-1-(pyridazin-3-yl)azetidine-3-carboxamide;
N-(4-{[1-(cyclohexylcarbonyl)piperidin-4-yl]methyl}phenyl)-1-(pyridazin-3-yl)azetidine-3-carboxamide;
N-(4-{[1-(3-methylbutanoyl)piperidin-4-yl]methyl}phenyl)-1-(pyridazin-3-yl)azetidine-3-carboxamide;
N-(4-{[1-(cyclopropylcarbonyl)piperidin-4-yl]methyl}phenyl)-1-(pyridazin-3-yl)azetidine-3-carboxamide;
1-(pyridazin-3-yl)-N-(4-{[1-(3,3,3-trifluoropropanoyl)piperidin-4-yl]methyl}phenyl)azetidine-3-carboxamide;
N-{4-[1-(3,3-dimethylbutanoyl)piperidin-4-yl]phenyl}-1-(4-methylpyridazin-3-yl)azetidine-3-carboxamide;
N-[4-(phenylcarbamoyl)phenyl]-1-(pyridazin-3-yl)azetidine-3-carboxamide;
N-{4[(2,2-dimethylpropyl)carbamoyl]phenyl}-1-(pyridazin-3-yl)azetidine-3-carboxamide;
N-{4-[(3-methoxy-2,2-dimethylpropyl)carbamoyl]phenyl}-1-(pyridazin-3-yl)azetidine-3-carboxamide;
N-{4[(2-cyclopropylethyl)carbamoyl]phenyl}-1-(pyridazin-3-yl)azetidine-3-carboxamide;
N-(4-{[2-(2-ethylpiperidin-1-yl)ethyl]carbamoyl}phenyl)-1-(pyridazin-3-yl)azetidine-3-carboxamide;
N-{4-[(cyclobutylmethyl)carbamoyl]phenyl}-1-(pyridazin-3-yl)azetidine-3-carboxamide;
N-{4-[(2S)-butan-2-ylcarbamoyl]phenyl}-1-(pyridazin-3-yl)azetidine-3-carboxamide;
N-[4-(butylcarbamoyl)phenyl]-1-(pyridazin-3-yl)azetidine-3-carboxamide;
N-{4-[(2,2-dimethyltetrahydro-2H-pyran-4-yl)carbamoyl]phenyl}-1-(pyridazin-3-yl)azetidine-3-carboxamide;
N-(4-{[(1S)-1-cyclopropylethyl]carbamoyl}phenyl)-1-(pyridazin-3-yl)azetidine-3-carboxamide;
N-[4-({2-[methyl(phenyl)amino]ethyl}carbamoyl)phenyl]-1-(pyridazin-3-yl)azetidine-3-carboxamide;
N-{4-[1,1'-bi(cyclopropyl)-1-ylcarbamoyl]phenyl}-1-(pyridazin-3-yl)azetidine-3-carboxamide;
1-(pyridazin-3-yl)-N-[4-(thiophen-3-ylcarbamoyl)phenyl]azetidine-3-carboxamide;
N-(4-{[(1R)-1-cyclopropylethyl]carbamoyl}phenyl)-1-(pyridazin-3-yl)azetidine-3-carboxamide;
N-{4-[(1-methylpiperidin-4-yl)carbamoyl]phenyl}-1-(pyridazin-3-yl)azetidine-3-carboxamide;
N-{4[(2R)-butan-2-ylcarbamoyl]phenyl}-1-(pyridazin-3-yl)azetidine-3-carboxamide;
N-[4-(1-azabicyclo[2.2.2]oct-3-ylcarbamoyl)phenyl]-1-(pyridazin-3-yl)azetidine-3-carboxamide;
1-(pyridazin-3-yl)-N-{4-[(tetrahydrofuran-3-ylmethyl)carbamoyl]phenyl}azetidine-3-carboxamide;
N-{4-[(oxetan-3-ylmethyl)carbamoyl]phenyl}-1-(pyridazin-3-yl)azetidine-3-carboxamide;
N-{4-[(2-methylcyclopropyl)carbamoyl]phenyl}-1-(pyridazin-3-yl)azetidine-3-carboxamide;
N-[4-(cyclobutylcarbamoyl)phenyl]-1-(pyridazin-3-yl)azetidine-3-carboxamide;
N-{4-[(1-methylcyclopropyl)carbamoyl]phenyl}-1-(pyridazin-3-yl)azetidine-3-carboxamide;
N-{4-[(2-methoxy-2-methylpropyl)carbamoyl]phenyl}-1-(pyridazin-3-yl)azetidine-3-carboxamide;
N-{4-[(cyclopropylmethyl)carbamoyl]phenyl}-1-(pyridazin-3-yl)azetidine-3-carboxamide;
1-(pyridazin-3-yl)-N-(4-{[(2R)-tetrahydrofuran-2-ylmethyl]carbamoyl}phenyl)azetidine-3-carboxamide;
1-(pyridazin-3-yl)-N-{4[(3,3,3-trifluoropropyl)carbamoyl]phenyl}azetidine-3-carboxamide;
N-{4[(1-methylpiperidin-3-yl)carbamoyl]phenyl}-1-(pyridazin-3-yl)azetidine-3-carboxamide;
N-(4-{[(3-methyloxetan-3-yl)methyl]carbamoyl}phenyl)-1-(pyridazin-3-yl)azetidine-3-carboxamide;
1-(pyridazin-3-yl)-N-(4-{[(2S)-tetrahydrofuran-2-ylmethyl]carbamoyl}phenyl)azetidine-3-carboxamide;
1-(pyridazin-3-yl)-N-{4-[(tetrahydro-2H-pyran-4-ylmethyl)carbamoyl]phenyl}azetidine-3-carboxamide;
1-(pyridazin-3-yl)-N-[4-(tetrahydro-2H-pyran-4-ylcarbamoyl)phenyl]azetidine-3-carboxamide;
N-(4-{[(1-methylpiperidin-3-yl)methyl]carbamoyl}phenyl)-1-(pyridazin-3-yl)azetidine-3-carboxamide;
N-[4-(cyclopropylcarbamoyl)phenyl]-1-(pyridazin-3-yl)azetidine-3-carboxamide;
N-[4-(cyclopentylcarbamoyl)phenyl]-1-(pyridazin-3-yl)azetidine-3-carboxamide;
N-[4-(benzylcarbamoyl)phenyl]-1-(pyridazin-3-yl)azetidine-3-carboxamide;
N-{4-[(3-fluorophenyl)carbamoyl]phenyl}-1-(pyridazin-3-yl)azetidine-3-carboxamide;
N-[4-(propylcarbamoyl)phenyl]-1-(pyridazin-3-yl)azetidine-3-carboxamide;
N-{4-[(4-fluorophenyl)carbamoyl]phenyl}-1-(pyridazin-3-yl)azetidine-3-carboxamide;
N-{4-[(2-fluorophenyl)carbamoyl]phenyl}-1-(pyridazin-3-yl)azetidine-3-carboxamide;
N-{4-[(1-methylcyclobutyl)carbamoyl]phenyl}-1-(pyridazin-3-yl)azetidine-3-carboxamide;
N-[4-(prop-2-en-1-ylcarbamoyl)phenyl]-1-(pyridazin-3-yl)azetidine-3-carboxamide;
1-(pyridazin-3-yl)-N-{4-[(3S)-tetrahydrofuran-3-ylcarbamoyl]phenyl}azetidine-3-carboxamide;
N-[4-({4-[2-(dimethylamino)ethyl]phenyl}carbamoyl)phenyl]-1-(pyridazin-3-yl)azetidine-3-carboxamide;
1-(pyridazin-3-yl)-N-{4-[(3R)-tetrahydrofuran-3-ylcarbamoyl]phenyl}azetidine-3-carboxamide;
N-{4-[(2-methoxyethyl)carbamoyl]phenyl}-1-(pyridazin-3-yl)azetidine-3-carboxamide;
N-{4-[1-(3-amino-2,2-dimethylpropyl)-1H-pyrazol-4-yl]phenyl}-1-(pyridazin-3-yl)azetidine-3-carboxamide;
N-(4-{1-[2,2-dimethyl-3-(piperazin-1-yl)propyl]-1H-pyrazol-4-yl}phenyl)-1-(pyridazin-3-yl)azetidine-3-carboxamide;
N-(4-{1-[2-methyl-2-(piperazin-1-yl)propanoyl]piperidin-4-yl}phenyl)-1-(pyridazin-3-yl)azetidine-3-carboxamide;
and pharmaceutically acceptable salts thereof.

Embodiments of Formula (IVC)

In another aspect, the present invention provides compounds of Formula (IVC)

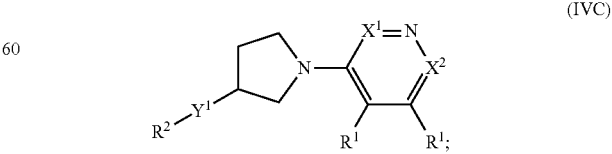

(IVC)

and pharmaceutically acceptable salts thereof; wherein each $X^1$, $X^2$, $Y^1$, $R^1$, and $R^2$ are as described herein for Formula (I).

One embodiment of this invention pertains to compounds of Formula (IVC) and pharmaceutically acceptable salts thereof;
wherein
$X^1$ is N and $X^2$ is $CR^1$; or
$X^1$ is $CR^1$ and $X^2$ is N; or
$X^1$ is $CR^1$ and $X^2$ is $CR^1$;
$Y^1$ is C(O)NH, or NHC(O);

$R^1$, at each occurrence, is independently selected from the group consisting of hydrogen, alkyl, alkenyl, alkynyl, haloalkyl, hydroxyalkyl, alkoxy, OH, $NH_2$, CN, $NO_2$, F, Cl, Br and I;

$R^2$ is independently selected from the group consisting of $C_4$-$C_6$-alkyl, $C_4$-$C_6$-alkenyl, $C_4$-$C_6$-alkynyl, aryl, and 5-6 membered heteroaryl; wherein each $R^2C_4$-$C_6$-alkyl, $C_4$-$C_6$-alkenyl, and $C_4$-$C_6$-alkynyl is substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(N)NH_2$, $C(N)NHR^3$, $C(N)N(R^3)_2$, CNOH, $CNOCH_3$, OH, (O), CN, $N_3$, $NO_2$, F, Cl, Br and I; wherein each $R^2$ aryl and 5-6 membered heteroaryl is optionally substituted with one or more substituents independently selected from the group consisting of $R^4$, $OR^4$, $SR^4$, $S(O)R^4$, $SO_2R^4$, $C(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, and I;

$R^3$, at each occurrence, is independently selected from the group consisting of alkyl, alkenyl, alkynyl, aryl, cycloalkyl, cycloalkenyl, and heterocyclyl; wherein each $R^3$ alkyl, alkenyl, and alkynyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, CNOH, $CNOCH_3$, OH, (O), CN, $N_3$, $NO_2$, F, Cl, Br and I; wherein each $R^3$ aryl, cycloalkyl, cycloalkenyl, and heterocyclyl is optionally substituted with one or more substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $C(N)NH_2$, $C(N)NHR^6$, $C(N)N(R^6)_2$, CNOH, $CNOCH_3$, OH, CN, $N_3$, $NO_2$, F, Cl, Br and I;

$R^4$, at each occurrence, is independently selected from the group consisting of alkyl, alkenyl, alkynyl, aryl, heterocyclyl, cycloalkyl, and cycloalkenyl; wherein each $R^4$ alkyl, alkenyl, and alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, CNOH, $CNOCH_3$, OH, (O), CN, $N_3$, $NO_2$, F, Cl, Br and I;

$R^5$, at each occurrence, is independently selected from the group consisting of alkyl, alkenyl, alkynyl, aryl, heterocyclyl, cycloalkyl, and cycloalkenyl; wherein each $R^5$ alkyl, alkenyl, and alkynyl is optionally substituted with one or more substituents independently selected from the group consisting of $R^8$, $OR^8$, $SR^8$, $S(O)R^8$, $SO_2R^8$, $NHR^8$, $N(R^8)_2$, $C(O)R^8$, $C(O)NH_2$, $C(O)NHR^8$, $C(O)N(R^8)_2$, $NHC(O)R^8$, $NR^8C(O)R^8$, $NHSO_2R^8$, $NHC(O)OR^8$, $SO_2NH_2$, $SO_2NHR^8$, $SO_2N(R^8)_2$, $NHC(O)NH_2$, $NHC(O)NHR^8$, OH, (O), $C(O)OH$, $N_3$, CN, $NH_2$, F, Cl, Br and I;

$R^6$, at each occurrence, is independently selected from the group consisting of alkyl, alkenyl, alkynyl, aryl, heterocyclyl, cycloalkyl, and cycloalkenyl; wherein each $R^6$ alkyl, alkenyl, and alkynyl is optionally substituted with one or more substituents independently selected from the group consisting of $R^9$, $OR^9$, $SR^9$, $S(O)R^9$, $SO_2R^9$, $NHR^9$, $N(R^9)_2$, $C(O)R^9$, $C(O)NH_2$, $C(O)NHR^9$, $C(O)N(R^9)_2$, $NHC(O)R^9$, $NR^9C(O)R^9$, $NHSO_2R^9$, $NHC(O)OR^9$, $SO_2NH_2$, $SO_2NHR^9$, $SO_2N(R^9)_2$, $NHC(O)NH_2$, $NHC(O)NHR^9$, OH, (O), $C(O)OH$, $N_3$, CN, $NH_2$, $CF_3$, $CF_2CF_3$, F, Cl, Br and I;

$R^7$, at each occurrence, is independently selected from the group consisting of alkyl, alkenyl, alkynyl, aryl, heterocyclyl, cycloalkyl, and cycloalkenyl;

$R^8$, at each occurrence, is independently selected from the group consisting of alkyl, alkenyl, alkynyl, aryl, heterocyclyl, cycloalkyl, and cycloalkenyl;

$R^9$, at each occurrence, is independently selected from the group consisting of alkyl, alkenyl, alkynyl, aryl, heterocyclyl, cycloalkyl, and cycloalkenyl;

wherein the cyclic moieties represented by $R^4$, $R^5$, $R^6$, $R^7$, $R^8$, and $R^9$ are independently optionally substituted with one or more substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $C(O)C(O)R^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, CNOH, $CNOCH_3$, OH, CN, $N_3$, $NO_2$, F, Cl, Br and I;

$R^{10}$, at each occurrence, is independently selected from the group consisting of alkyl, alkenyl, alkynyl, aryl, heterocyclyl, cycloalkyl, and cycloalkenyl; wherein each $R^{10}$ alkyl, alkenyl, and alkynyl is optionally substituted with one or more substituents independently selected from the group consisting of $R^{11}$, $OR^{11}$, $SR^{11}$, $S(O)R^{11}$, $SO_2R^{11}$, $C(O)R^{11}$, $CO(O)R^{11}$, $OC(O)R^{11}$, $OC(O)OR^{11}$, $NH_2$, $NHR^{11}$, $N(R^{11})_2$, $NHC(O)R^{11}$, $NR^{11}C(O)R^{11}$, $NHS(O)_2R^{11}$, $NR^{11}S(O)_2R^{11}$, $NHC(O)OR^{11}$, $NR^{11}C(O)OR^{11}$, $NHC(O)NH_2$, $NHC(O)NHR^{11}$, $NHC(O)N(R^{11})_2$, $NR^{11}C(O)NHR^{11}$, $NR^{11}C(O)N(R^{11})_2$, $C(O)NH_2$, $C(O)NHR^{11}$, $C(O)N(R^{11})_2$, $C(O)NHOH$, $C(O)N-HOR^{11}$, $C(O)NHSO_2R^{11}$, $C(O)NR^{11}SO_2R^{11}$, $SO_2NH_2$, $SO_2NHR^{11}$, $SO_2N(R^{11})_2$, $C(O)H$, $C(O)OH$, $C(N)NH_2$, $C(N)NHR^{11}$, $C(N)N(R^{11})_2$, CNOH, $CNOCH_3$, OH, (O), CN, $N_3$, $NO_2$, F, Cl, Br and I; wherein each $R^{10}$ aryl, heterocyclyl, cycloalkyl, and cycloalkenyl is optionally substituted with one or more substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, $C(N)NH_2$, $C(N)NHR^{12}$, $C(N)N(R^{12})_2$, $CNOH$, $CNOCH_3$, OH, CN, $N_3$, $NO_2$, $CF_3$, $OCF_3$, F, Cl, Br and I;

$R^{11}$, at each occurrence, is independently selected from the group consisting of alkyl, alkenyl, alkynyl, aryl, heterocyclyl, cycloalkyl, and cycloalkenyl; wherein each $R^{11}$ alkyl, alkenyl, and alkynyl is optionally substituted with alkoxy or aryl; wherein each $R^{11}$ aryl, heterocyclyl, cycloalkyl, and cycloalkenyl is optionally substituted with one or more substituents independently selected from the group consisting of $R^{13}$, $OR^{13}$, $C(O)OR^{13}$, $OCF_3$, $CF_3$, F, Cl, Br and I;

$R^{12}$, at each occurrence, is independently selected from the group consisting of alkyl, alkenyl, alkynyl, aryl, heterocyclyl, cycloalkyl, and cycloalkenyl; and $R^{13}$, at each occurrence, is independently selected from the group consisting of alkyl, haloalkyl, alkenyl, alkynyl, aryl, heterocyclyl, cycloalkyl, and cycloalkenyl;

with the proviso that when $X^1$ is $CR^1$ and $X^2$ is $CR^1$; $R^1$ is hydrogen; $Y^1$ is NHC(O); and $R^2$ is pyrrolyl; the $R^2$ pyrrolyl is not substituted with two alkyl groups.

In one embodiment of Formula (IVC), $X^1$ is N and $X^2$ is $CR^1$; or $X^1$ is $CR^1$ and $X^2$ is N; or $X^1$ is $CR^1$ and $X^2$ is $CR^1$. In another embodiment of Formula (IVC), $X^1$ is N and $X^2$ is $CR^1$. In another embodiment of Formula (IVC), $X^1$ is $CR^1$ and $X^2$ is N. In another embodiment of Formula (IVC), $X^1$ is $CR^1$ and $X^2$ is $CR^1$.

In one embodiment of Formula (IVC), $Y^1$ is C(O)NH, or NHC(O). In another embodiment of Formula (IVC), $Y^1$ is C(O)NH. In another embodiment of Formula (IVC), $Y^1$ is NHC(O).

In one embodiment of Formula (IVC), $X^1$ is $CR^1$ and $X^2$ is $CR^1$; and $R^1$, at each occurrence, is independently selected from the group consisting of hydrogen, alkyl, alkenyl, alkynyl, haloalkyl, hydroxyalkyl, alkoxy, OH, $NH_2$, CN, $NO_2$, F, Cl, Br and I. In another embodiment of Formula (IVC), $X^1$ is $CR^1$ and $X^2$ is $CR^1$; and $R^1$, at each occurrence, is independently selected from the group consisting of hydrogen, alkyl, haloalkyl, alkoxy, CN, F, Cl, Br and I. In another embodiment of Formula (IVC), $X^1$ is $CR^1$ and $X^2$ is $CR^1$; and $R^1$, at each occurrence, is independently selected from the group consisting of hydrogen, alkyl, haloalkyl, alkoxy, CN, F, and Cl. In another embodiment of Formula (IVC), $X^1$ is $CR^1$ and $X^2$ is $CR^1$; and $R^1$, at each occurrence, is hydrogen.

In another aspect, the present invention provides compounds of Formula (IVD),

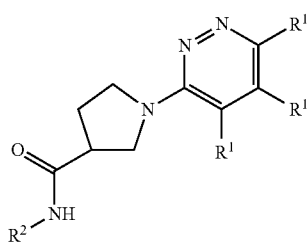

Formula (IVD)

and pharmaceutically acceptable salts thereof; wherein $R^1$ and $R^2$ are as described herein for Formula (IC).

In one embodiment of Formula (IVC) and (IVD), $R^1$, at each occurrence, is independently selected from the group consisting of hydrogen, alkyl, alkenyl, alkynyl, haloalkyl, hydroxyalkyl, alkoxy, OH, $NH_2$, CN, $NO_2$, F, Cl, Br and I. In another embodiment of Formula (IVC) and (IVD), $R^1$, at each occurrence, is independently selected from the group consisting of hydrogen, alkyl, haloalkyl, alkoxy, CN, F, Cl, Br and I. In another embodiment of Formula (IVC) and (IVD), $R^1$, at each occurrence, is independently selected from the group consisting of hydrogen, alkyl, haloalkyl, alkoxy, CN, F, and Cl. In another embodiment of Formula (IVC) and (IVD), $R^1$, at each occurrence, is hydrogen.

In one embodiment of Formula (IVC) and (IVD), $R^2$ is independently selected from the group consisting of $C_4$-$C_6$-alkyl, $C_4$-$C_6$-alkenyl, $C_4$-$C_6$-alkynyl, aryl, and 5-6 membered heteroaryl; wherein each $R^2$ $C_4$-$C_6$-alkyl, $C_4$-$C_6$-alkenyl, and $C_4$-$C_6$-alkynyl is substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(N)NH_2$, $C(N)NHR^3$, $C(N)N(R^3)_2$, $CNOH$, $CNOCH_3$, OH, (O), CN, $N_3$, $NO_2$, F, Cl, Br and I; wherein each $R^2$ aryl and 5-6 membered heteroaryl is optionally substituted with one or more substituents independently selected from the group consisting of $R^4$, $OR^4$, $SR^4$, $S(O)R^4$, $SO_2R^4$, $C(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, $CNOH$, $CNOCH_3$, OH, CN, $N_3$, $NO_2$, F, Cl, and I. In another embodiment of Formula (IVC) and (IVD), $R^2$ is aryl; wherein each $R^2$ aryl is optionally substituted with one or more substituents independently selected from the group consisting of $R^4$, $OR^4$, $SO_2R^4$, $C(O)NHR^4$, F, Cl, and I. In another embodiment of Formula (IVC) and (IVD), $R^2$ is aryl; wherein each $R^2$ aryl is optionally substituted with one or more substituents independently selected from the group consisting of $R^4$, $OR^4$, $SO_2R^4$, $C(O)NHR^4$, and F. In another embodiment of Formula (IVC) and (IVD), $R^2$ is phenyl; wherein each $R^2$ phenyl is optionally substituted with one or more substituents independently selected from the group consisting of $R^4$, $OR^4$, $SO_2R^4$, $C(O)NHR^4$, and F. In another embodiment of Formula (IVC) and (IVD), $R^2$ is phenyl; wherein each $R^2$ phenyl is substituted with one substituent independently selected from the group consisting of $R^4$, $OR^4$, and $SO_2R^4$.

In another embodiment of Formula (IVC) and (IVD), $R^2$ is 5-6 membered heteroaryl; wherein each $R^2$ 5-6 membered heteroaryl is optionally substituted with one or more substituents independently selected from the group consisting of $R^4$, $OR^4$, $SO_2R^4$, $C(O)NHR^4$, F, Cl, and I. In another embodiment of Formula (IVC) and (IVD), $R^2$ is 5-6 membered heteroaryl; wherein each $R^2$ 5-6 membered heteroaryl is optionally substituted with one or more substituents independently selected from the group consisting of $R^4$, $OR^4$, $SO_2R^4$, $C(O)NHR^4$, and F. In another embodiment of Formula (IVC) and (IVD), $R^2$ is pyridinyl, furanyl, thiophenyl, pyrazole, or thiazolyl; wherein each $R^2$ pyridinyl, furanyl, thiophenyl, pyrazole, and thiazolyl is optionally substituted with one or more substituents independently selected from the group consisting of $R^4$, $OR^4$, $SO_2R^4$, $C(O)NHR^4$, and F.

In one embodiment of Formula (IVC) and (IVD), $R^4$, at each occurrence, is independently selected from the group consisting of alkyl, alkenyl, alkynyl, aryl, heterocyclyl, cycloalkyl, and cycloalkenyl; wherein each $R^4$ alkyl, alkenyl, and alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)R^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, CNOH, $CNOCH_3$, OH, (O), CN, $N_3$, $NO_2$, F, Cl, Br and I. In another embodiment of Formula (IVC) and (IVD), $R^4$, at each occurrence, is independently selected from the group consisting of alkyl, alkenyl, alkynyl, aryl, heterocyclyl, and cycloalkyl.

In one embodiment of Formula (IVC) and (IVD), each $R^4$ alkyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)R^7$, $NH_2$, $NHR^7$, $N(R^7)_2$, $NHC(O)R^7$, $NICC(O)R^7$, $NHS(O)_2R^7$, $NR^7S(O)_2R^7$, $NHC(O)OR^7$, $NICC(O)OR^7$, $NHC(O)NH_2$, $NHC(O)NHR^7$, $NHC(O)N(R^7)_2$, $NICC(O)NHR^7$, $NICC(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, CNOH, $CNOCH_3$, OH, (O), CN, $N_3$, $NO_2$, F, Cl, Br and I. In another embodiment of Formula (IVC) and (IVD), each $R^4$ alkyl is optionally substituted with one or more substituents independently selected from the group consisting of $R^7$, $OR^7$, $N(R^7)_2$, F, Cl, Br and I.

In one embodiment of Formula (IVC) and (IVD), $R^7$, at each occurrence, is independently selected from the group consisting of alkyl, alkenyl, alkynyl, aryl, heterocyclyl, cycloalkyl, and cycloalkenyl. In another embodiment of Formula (IVC) and (IVD), $R^7$, at each occurrence, is independently selected from the group consisting of alkyl, aryl, heterocyclyl, and cycloalkyl.

In one embodiment of Formula (IVC) and (IVD), each $R^4$ and $R^7$ cyclic moiety is independently optionally substituted with one or more substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, CNOH, $CNOCH_3$, OH, CN, $N_3$, $NO_2$, F, Cl, Br and I; $R^{10}$, at each occurrence, is independently selected from the group consisting of alkyl, alkenyl, alkynyl, aryl, heterocyclyl, cycloalkyl, and cycloalkenyl; wherein each $R^{10}$ alkyl, alkenyl, and alkynyl is optionally substituted with one or more substituents independently selected from the group consisting of $R^{11}$, $OR^{11}$, $SR^{11}$, $S(O)R^{11}$, $SO_2R^{11}$, $C(O)R^{11}$, $CO(O)R^{11}$, $OC(O)R^{11}$, $OC(O)OR^{11}$, $NH_2$, $NHR^{11}$, $N(R^{11})_2$, $NHC(O)R^{11}$, $NR^{11}C(O)R^{11}$, $NHS(O)_2R^{11}$, $NR^{11}S(O)_2R^{11}$, $NHC(O)OR^{11}$, $NR^{11}C(O)OR^{11}$, $NHC(O)NH_2$, $NHC(O)NHR^{11}$, $NHC(O)N(R^{11})_2$, $NR^{11}C(O)NHR^{11}$, $NR^{11}C(O)N(R^{11})_2$, $C(O)NH_2$, $C(O)NHR^{11}$, $C(O)N(R^{11})_2$, $C(O)NHOH$, $C(O)NHOR^{11}$, $C(O)NHSO_2R^{11}$, $C(O)NR^{11}SO_2R^{11}$, $SO_2NH_2$, $SO_2NHR^{11}$, $SO_2N(R^{11})_2$, $C(O)H$, $C(O)OH$, $C(N)NH_2$, $C(N)NHR^{11}$, $C(N)N(R^{11})_2$, CNOH, $CNOCH_3$, OH, (O), CN, $N_3$, $NO_2$, F, Cl, Br and I; wherein each $R^{10}$ aryl, heterocyclyl, cycloalkyl, and cycloalkenyl is optionally substituted with one or more substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, $C(N)NH_2$, $C(N)NHR^{12}$, $C(N)N(R^{12})_2$, CNOH, $CNOCH_3$, OH, CN, $N_3$, $NO_2$, F, Cl, Br and I; $R^{11}$, at each occurrence, is independently selected from the group consisting of alkyl, alkenyl, alkynyl, aryl, heterocyclyl, cycloalkyl, and cycloalkenyl; wherein each $R^{11}$ alkyl, alkenyl, and alkynyl is optionally substituted with alkoxy or aryl; wherein each $R^{11}$ aryl, heterocyclyl, cycloalkyl, and cycloalkenyl is optionally substituted with one or more substituents independently selected from the group consisting of $R^{13}$, $OR^{13}$, $C(O)OR^{13}$, $OCF_3$, $CF_3$, F, Cl, Br and I; $R^{12}$, at each occurrence, is independently selected from the group consisting of alkyl, alkenyl, alkynyl, aryl, heterocyclyl, cycloalkyl, and cycloalkenyl; and $R^{13}$, at each occurrence, is independently selected from the group consisting of alkyl, haloalkyl, alkenyl, alkynyl, aryl, heterocyclyl, cycloalkyl, and cycloalkenyl.

In another embodiment of Formula (IVC) and (IVD), each $R^4$ and $R^7$ cyclic moiety is independently optionally substituted with one or more substituents independently selected from the group consisting of $R^{10}$, $C(O)R^{10}$, $CO(O)R^{10}$, $C(O)C(O)R^{10}$, $CO(O)H$, OH, F, Cl, Br and I; $R^{10}$, at each occurrence, is independently selected from the group consisting of alkyl, alkenyl, alkynyl, aryl, heterocyclyl, and cycloalkyl; wherein each $R^{10}$ alkyl, alkenyl, and alkynyl, are optionally substituted with one or more substituents independently selected from the group consisting of $R^{11}$, $OR^{11}$, $SR^{11}$, $SO_2R^{11}$, $NH_2$, $N(R^{11})_2$, $NHC(O)R^{11}$, $NHS(O)_2R^{11}$, OH, $NO_2$, and F; wherein each $R^{10}$ aryl, heterocyclyl and cycloalkyl is optionally substituted with one or more substituents independently selected from the group consisting of $R^{12}$, $OR^{12}$, $C(O)R^{12}$, $NH_2$, OH, CN, $CF_3$, $OCF_3$, F, and Cl; $R^{11}$, at each occurrence, is independently selected from the group consisting of alkyl, aryl, heterocyclyl, and cycloalkyl; wherein each $R^{11}$ alkyl is optionally substituted with alkoxy or aryl; wherein each $R^{11}$ aryl and heterocyclyl is optionally substituted with one or more substituents independently selected from the group consisting of $R^{13}$, $CF_3$, F, and Cl; $R^{12}$, at each occurrence, is independently selected from the group consisting of alkyl and aryl; and $R^{13}$, at each occurrence, is independently selected from the group consisting of alkyl, haloalkyl, and cycloalkyl.

One embodiment of this invention pertains to compounds or pharmaceutically acceptable salts thereof, which are useful as inhibitors of NAMPT, the compounds having Formula (IVC)

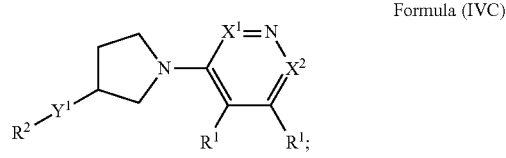

Formula (IVC)

wherein
X¹ is N and X² is CR¹; or
X¹ is CR¹ and X² is N; or
X¹ is CR¹ and X² is CR¹;
Y¹ is C(O)NH, or NHC(O);

R¹, at each occurrence, is independently selected from the group consisting of hydrogen, alkyl, haloalkyl, alkoxy, CN, Cl, and F;

R² is aryl or 5-6 membered heteroaryl wherein each R² aryl and 5-6 membered heteroaryl is optionally substituted with one or more substituents independently selected from the group consisting of R⁴, SO₂R⁴, OR⁷, C(O)NHR⁴, and F;

R⁴, at each occurrence, is independently selected from the group consisting of alkyl, lkenyl, aryl, heterocyclyl, and cycloalkyl; wherein each R⁴ alkyl is optionally substituted with one or more substituents independently selected from the group consisting of R⁷, OR⁷, N(R⁷)₂, and F;

R⁷, at each occurrence, is independently selected from the group consisting of alkyl, aryl, heterocyclyl, and cycloalkyl; wherein the cyclic moieties represented by R⁴ and R⁷ are independently optionally substituted with one or more substituents independently selected from the group consisting of R¹⁰, C(O)R¹⁰, C(O)C(O)R¹⁰, CO(O)R¹⁰, C(O)OH, OH and F;

R¹⁰, at each occurrence, is independently selected from the group consisting of alkyl, alkenyl, alkynyl, aryl, heterocyclyl, and cycloalkyl; wherein each R¹⁰ alkyl is optionally substituted with one or more substituents independently selected from the group consisting of R¹¹, OR¹¹, SR¹¹, SO₂R¹¹, NH₂, N(R¹¹)₂, NHC(O)R¹¹, NHS(O)₂R¹¹, OH, NO₂, and F; wherein each R¹⁰ aryl, heterocyclyl and cycloalkyl is optionally substituted with one or more R¹², OR¹², C(O)R¹², NH₂, OH, CN, CF₃, OCF₃, F, and Cl;

R¹¹, at each occurrence, is independently selected from the group consisting of alkyl, aryl, heterocyclyl, and cycloalkyl; wherein each R¹¹ alkyl is optionally substituted with alkoxy or aryl; wherein each R¹¹ aryl, and heterocyclyl is optionally substituted with one or more substituents independently selected from the group consisting of R¹³, C(O)OR¹³, OCF₃, CF₃, F, and Cl;

R¹², at each occurrence, is independently selected from the group consisting of alkyl, and aryl; and R¹³, at each occurrence, is independently selected from the group consisting of alkyl, haloalkyl, cycloalkyl, and heterocyclyl; with the proviso that when X¹ is CR¹ and X² is CR¹; R¹ is hydrogen; Y¹ is NHC(O); and R² is pyrrolyl; the R² pyrrolyl is not substituted with two alkyl groups.

Still another embodiment pertains to compounds having Formula (IV), which include tert-butyl 4-[4-({[(3S)-1-(pyridin-3-yl)pyrrolidin-3-yl]carbonyl}amino)phenoxy]piperidine-1-carboxylate;
tert-butyl 4-[4-({[(3R)-1-(pyridin-3-yl)pyrrolidin-3-yl]carbonyl}amino)phenoxy]piperidine-1-carboxylate;
(3S)-1-(pyridin-3-yl)-N-(4-{[1-(tetrahydro-2H-pyran-4-ylacetyl)piperidin-4-yl]oxy}phenyl)pyrrolidine-3-carboxamide;
(3S)—N-(4-{[1-(2-methylpropanoyl)piperidin-4-yl]oxy}phenyl)-1-(pyridin-3-yl)pyrrolidine-3-carboxamide;
(3S)-1-(pyridin-3-yl)-N-[4-({1-[(2S)-tetrahydro furan-2-ylcarbonyl]piperidin-4-yl}oxy)phenyl]pyrrolidine-3-carboxamide;
(3S)-1-(pyridin-3-yl)-N-[4-({1-[(2R)-tetrahydro furan-2-ylcarbonyl]piperidin-4-yl}oxy)phenyl]pyrrolidine-3-carboxamide;
(3S)-1-(pyridin-3-yl)-N-(4-{[1-(tetrahydrofuran-3-ylcarbonyl)piperidin-4-yl]oxy}phenyl)pyrrolidine-3-carboxamide;
(3S)—N-(4-{[1-(cyclopropylacetyl)piperidin-4-yl]oxy}phenyl)-1-(pyridin-3-yl)pyrrolidine-3-carboxamide;
(3S)—N-(4-{[1-(2-hydroxy-2-methylpropanoyl)piperidin-4-yl]oxy}phenyl)-1-(pyridin-3-yl)pyrrolidine-3-carboxamide;
(3S)-1-(pyridin-3-yl)-N-(4-{[1-(3,3,3-trifluoropropanoyl)piperidin-4-yl]oxy}phenyl)pyrrolidine-3-carboxamide;
(3S)—N-[4-({1-[(2S)-2-methylbutanoyl]piperidin-4-yl}oxy)phenyl]-1-(pyridin-3-yl)pyrrolidine-3-carboxamide;
tert-butyl 4-(4-{[(3S)-1-(pyridin-3-yl)pyrrolidin-3-yl]carbamoyl}phenoxy)piperidine-1-carboxylate;
tert-butyl 4-(4-{[(3R)-1-(pyridin-3-yl)pyrrolidin-3-yl]carbamoyl}phenoxy)piperidine-1-carboxylate;
(3S)—N-{4-[1-(2-hydroxy-2-methylpropanoyl)piperidin-4-yl]phenyl}-1-(pyridazin-4-yl)pyrrolidine-3-carboxamide;
(3S)—N-{4-[1-(cyclopentylacetyl)piperidin-4-yl]phenyl}-1-(pyridazin-4-yl)pyrrolidine-3-carboxamide;
(3S)—N-{4-[1-(cyclopentylacetyl)piperidin-4-yl]phenyl}-1-(pyridin-3-yl)pyrrolidine-3-carboxamide;
(3S)—N-{4-[1-(2-methylpropanoyl)piperidin-4-yl]phenyl}-1-(pyridazin-3-yl)pyrrolidine-3-carboxamide;
(3S)—N-[4-(1-benzoylpiperidin-4-yl)phenyl]-1-(pyridazin-3-yl)pyrrolidine-3-carboxamide;
(3S)-1-(pyridazin-3-yl)-N-{4-[1-(tetrahydro-2H-pyran-4-ylacetyl)piperidin-4-yl]phenyl}pyrrolidine-3-carboxamide;
(3S)—N-{4-[1-(2,2-dimethylpropanoyl)piperidin-4-yl]phenyl}-1-(pyridazin-3-yl)pyrrolidine-3-carboxamide; and pharmaceutically acceptable salts thereof.
N-(4-{[1-(2-methylpropanoyl)piperidin-4-yl]sulfonyl}phenyl)-1-(pyridazin-4-yl)azetidine-3-carboxamide;
N-{4-[(1-benzoylpiperidin-4-yl)sulfonyl]phenyl}-1-(pyridazin-4-yl)azetidine-3-carboxamide;
N-(4-{[1-(4-fluorobenzoyl)piperidin-4-yl]sulfonyl}phenyl)-1-(pyridazin-4-yl)azetidine-3-carboxamide;
N-(4-{[1-(cyclopentylcarbonyl)piperidin-4-yl]sulfonyl}phenyl)-1-(pyridazin-4-yl)azetidine-3-carboxamide;
N-[(3R)-1-(5,6-dichloropyridazin-4-yl)pyrrolidin-3-yl]-5-[1-(2-methylpropyl)-1H-pyrazol-4-yl]thiophene-2-carboxamide;
N-[(3R)-1-(6-chloropyridazin-3-yl)pyrrolidin-3-yl]-5-[1-(2-methylpropyl)-1H-pyrazol-4-yl]thiophene-2-carboxamide;
N-[(3S)-1-(5,6-dichloropyridazin-4-yl)pyrrolidin-3-yl]-5-[1-(2-methylpropyl)-1H-pyrazol-4-yl]thiophene-2-carboxamide;
N-[(3S)-1-(6-chloropyridazin-3-yl)pyrrolidin-3-yl]-5-[1-(2-methylpropyl)-1H-pyrazol-4-yl]thiophene-2-carboxamide;
N-[(3R)-1-(5,6-dichloropyridazin-4-yl)pyrrolidin-3-yl]-5-[1-(2-methylpropyl)-1H-pyrazol-4-yl]thiophene-3-carboxamide;
5-[1-(2-methylpropyl)-1H-pyrazol-4-yl]-N-[(3R)-1-(pyridazin-3-yl)pyrrolidin-3-yl]thiophene-3-carboxamide;
5-[1-(2-methylpropyl)-1H-pyrazol-4-yl]-N-[(3R)-1-(pyridazin-4-yl)pyrrolidin-3-yl]thiophene-3-carboxamide;
N-{4-[1-(2,2-dimethylpropanoyl)piperidin-4-yl]phenyl}-1-(pyridazin-3-yl)piperidine-4-carboxamide;
N-[4-(1-benzoylpiperidin-4-yl)phenyl]-1-(pyridazin-3-yl)piperidine-4-carboxamide;
N-{4-[1-(2-fluorobenzoyl)piperidi4-yl]phenyl}-1-(pyridazin-3-yl)piperidine-4-carboxamide;
1-(pyridazin-3-yl)-N-{4-[1-(4,4,4-trifluorobutanoyl)piperidin-4-yl]phenyl}piperidine-4-carboxamide;

N-[(3S)-1-(6-chloropyridazin-3-yl)pyrrolidin-3-yl]-5-[1-(2-methylpropyl)-1H-pyrazol-4-yl]thiophene-3-carboxamide;
(3S)-1-(pyridazin-3-yl)-N-{4-[1-(1,3-thiazol-5-ylcarbonyl)piperidin-4-yl]phenyl}pyrrolidine-3-carboxamide;
(3S)—N-{4-[1-(4-methylbenzoyl)piperidin-4-yl]phenyl}-1-(pyridazin-3-yl)pyrrolidine-3-carboxamide;
(3S)—N-(4-{1-[(2S)-2-phenylbutanoyl]piperidin-4-yl}phenyl)-1-(pyridazin-3-yl)pyrrolidine-3-carboxamide;
(3S)—N-(4-{1-[(2S)-2-methoxy-2-phenylacetyl]piperidin-4-yl}phenyl)-1-(pyridazin-3-yl)pyrrolidine-3-carboxamide;
(3S)—N-(4-{1-[(2R)-2-methoxy-2-phenylacetyl]piperidin-4-yl}phenyl)-1-(pyridazin-3-yl)pyrrolidine-3-carboxamide;
(3S)—N-{4-[1-(ethoxyacetyl)piperidin-4-yl]phenyl}-1-(pyridazin-3-yl)pyrrolidine-3-carboxamide;
(3S)—N-(4-{1-[(4-methylphenoxy)acetyl]piperidin-4-yl}phenyl)-1-(pyridazin-3-yl)pyrrolidine-3-carboxamide;
(3S)—N-{4-[1-(2-fluorobenzoyl)piperidin-4-yl]phenyl}-1-(pyridazin-3-yl)pyrrolidine-3-carboxamide;
(3S)-1-(pyridazin-3-yl)-N-{4-[1-(tetrahydrofuran-3-ylcarbonyl)piperidin-4-yl]phenyl}pyrrolidine-3-carboxamide;
(3S)—N-{4-[1-(naphthalen-1-ylcarbonyl)piperidin-4-yl]phenyl}-1-(pyridazin-3-yl)pyrrolidine-3-carboxamide;
(3S)—N-(4-{1-[(2,6-dichlorophenyl)acetyl]piperidin-4-yl}phenyl)-1-(pyridazin-3-yl)pyrrolidine-3-carboxamide;
(3S)—N-{4-[1-(naphthalen-1-ylacetyl)piperidin-4-yl]phenyl}-1-(pyridazin-3-yl)pyrrolidine-3-carboxamide;
(3S)-1-(pyridazin-3-yl)-N-(4-{1-[4-(thiophen-2-yl)butanoyl]piperidin-4-yl}phenyl)pyrrolidine-3-carboxamide;
(3S)—N-{4-[1-(cyclopropylacetyl)piperidin-4-yl]phenyl}-1-(pyridazin-3-yl)pyrrolidine-3-carboxamide;
(3S)—N-{4-[1-(cyclopentylacetyl)piperidin-4-yl]phenyl}-1-(pyridazin-3-yl)pyrrolidine-3-carboxamide;
(3S)—N-{4-[1-(2,5-difluorobenzoyl)piperidin-4-yl]phenyl}-1-(pyridazin-3-yl)pyrrolidine-3-carboxamide;
(3S)—N-{4-[1-(naphthalen-2-ylacetyl)piperidin-4-yl]phenyl}-1-(pyridazin-3-yl)pyrrolidine-3-carboxamide;
(3S)—N-(4-{1-[3-(phenylsulfonyl)propanoyl]piperidin-4-yl}phenyl)-1-(pyridazin-3-yl)pyrrolidine-3-carboxamide;
(3S)-1-(pyridazin-3-yl)-N-[4-(1-{[3-(trifluoromethyl)phenyl]acetyl}piperidin-4-yl)phenyl]pyrrolidine-3-carboxamide;
(3S)—N-{4-[1-(furan-2-ylcarbonyl)piperidin-4-yl]phenyl}-1-(pyridazin-3-yl)pyrrolidine-3-carboxamide;
(3S)—N-{4-[1-(N-benzoylglycyl)piperidin-4-yl]phenyl}-1-(pyridazin-3-yl)pyrrolidine-3-carboxamide;
(3S)—N-(4-{1-[(2,4-dichlorophenyl)acetyl]piperidin-4-yl}phenyl)-1-(pyridazin-3-yl)pyrrolidine-3-carboxamide;
(3S)—N-{4-[1-(2-methylbenzoyl)piperidin-4-yl]phenyl}-1-(pyridazin-3-yl)pyrrolidine-3-carboxamide;
(3S)-1-(pyridazin-3-yl)-N-{4-[1-(4,4,4-trifluorobutanoyl)piperidin-4-yl]phenyl}pyrrolidine-3-carboxamide;
(3S)—N-(4-{1-[(1-methylcyclohexyl)carbonyl]piperidin-4-yl}phenyl)-1-(pyridazin-3-yl)pyrrolidine-3-carboxamide;
(3S)-1-(pyridazin-3-yl)-N-{4-[1-(thiophen-3-ylcarbonyl)piperidin-4-yl]phenyl}pyrrolidine-3-carboxamide;
(3S)—N-(4-{1-[(6-methylpyridin-3-yl)carbonyl]piperidin-4-yl}phenyl)-1-(pyridazin-3-yl)pyrrolidine-3-carboxamide;
(3S)—N-(4-{1-[(3-chlorophenyl)acetyl]piperidin-4-yl}phenyl)-1-(pyridazin-3-yl)pyrrolidine-3-carboxamide;
(3S)—N-[4-(1-propanoylpiperidin-4-yl)phenyl]-1-(pyridazin-3-yl)pyrrolidine-3-carboxamide;
(3S)—N-{4-[1-(3,5-difluorobenzoyl)piperidin-4-yl]phenyl}-1-(pyridazin-3-yl)pyrrolidine-3-carboxamide;
(3S)—N-{4-[1-(cyclopentylcarbonyl)piperidin-4-yl]phenyl}-1-(pyridazin-3-yl)pyrrolidine-3-carboxamide;
(3S)-1-(pyridazin-3-yl)-N-{4-[1-(tetrahydrofuran-2-ylcarbonyl)piperidin-4-yl]phenyl}pyrrolidine-3-carboxamide;
(3S)—N-{4-[1-(cyclopropylcarbonyl)piperidin-4-yl]phenyl}-1-(pyridazin-3-yl)pyrrolidine-3-carboxamide;
(3S)—N-{4-[1-(4-chlorobenzoyl)piperidin-4-yl]phenyl}-1-(pyridazin-3-yl)pyrrolidine-3-carboxamide;
5-[1-(2-methylpropyl)-1H-pyrazol-4-yl]-N-[(3S)-1-(pyridazin-3-yl)pyrrolidin-3-yl]thiophene-3-carboxamide;
N-[4-(1-benzoylpiperidin-4-yl)phenyl]-1-(6-fluoro-5-methylpyridin-3-yl)azetidine-3-carboxamide;
N-[4-(1-benzoylpiperidin-4-yl)phenyl]-1-(5-fluoropyridin-3-yl)azetidine-3-carboxamide;
N-[4-(1-benzoylpiperidin-4-yl)phenyl]-1-(6-methylpyridin-3-yl)azetidine-3-carboxamide;
N-[4-(1-benzoylpiperidin-4-yl)phenyl]-1-(2-fluoro-6-methylpyridin-3-yl)azetidine-3-carboxamide;
(3S)—N-{4-[1-(2-chlorobenzoyl)piperidin-4-yl]phenyl}-1-(pyridazin-3-yl)pyrrolidine-3-carboxamide;
(3S)—N-{4-[1-(2-methylpentanoyl)piperidin-4-yl]phenyl}-1-(pyridazin-3-yl)pyrrolidine-3-carboxamide;
(3S)—N-{4-[1-(4-methylpentanoyl)piperidin-4-yl]phenyl}-1-(pyridazin-3-yl)pyrrolidine-3-carboxamide;
(3S)—N-{4-[1-(2,4-dimethylbenzoyl)piperidin-4-yl]phenyl}-1-(pyridazin-3-yl)pyrrolidine-3-carboxamide;
(3S)—N-[4-(1-heptanoylpiperidin-4-yl)phenyl]-1-(pyridazin-3-yl)pyrrolidine-3-carboxamide;
(3S)—N-{4-[1-(2,4-dichlorobenzoyl)piperidin-4-yl]phenyl}-1-(pyridazin-3-yl)pyrrolidine-3-carboxamide;
(3S)—N-(4-{1-[(4-fluorophenyl)acetyl]piperidin-4-yl}phenyl)-1-(pyridazin-3-yl)pyrrolidine-3-carboxamide;
(3S)—N-{4-[1-(2,3-difluorobenzoyl)piperidin-4-yl]phenyl}-1-(pyridazin-3-yl)pyrrolidine-3-carboxamide;
(3S)—N-{4-[1-(3-methylbenzoyl)piperidin-4-yl]phenyl}-1-(pyridazin-3-yl)pyrrolidine-3-carboxamide;
(3S)—N-[4-(1-hexanoylpiperidin-4-yl)phenyl]-1-(pyridazin-3-yl)pyrrolidine-3-carboxamide;
(3S)—N-(4-{1-[(3-methylthiophen-2-yl)carbonyl]piperidin-4-yl}phenyl)-1-(pyridazin-3-yl)pyrrolidine-3-carboxamide;
(3S)—N-{4-[1-(2,3-dimethylbutanoyl)piperidin-4-yl]phenyl}-1-(pyridazin-3-yl)pyrrolidine-3-carboxamide;
(3S)—N-[4-(1-butanoylpiperidin-4-yl)phenyl]-1-(pyridazin-3-yl)pyrrolidine-3-carboxamide;
(3S)—N-{4-[1-(3-methylpentanoyl)piperidin-4-yl]phenyl}-1-(pyridazin-3-yl)pyrrolidine-3-carboxamide;
(3S)—N-(4-{1-[(3,5-dimethylphenyl)acetyl]piperidin-4-yl}phenyl)-1-(pyridazin-3-yl)pyrrolidine-3-carboxamide;
(3S)—N-{4-[1-(3,5-dichlorobenzoyl)piperidin-4-yl]phenyl}-1-(pyridazin-3-yl)pyrrolidine-3-carboxamide;
(3S)—N-{4-[1-(3-fluoro-2-methylbenzoyl)piperidin-4-yl]phenyl}-1-(pyridazin-3-yl)pyrrolidine-3-carboxamide;
(3S)—N-(4-{1-[(4-chlorophenyl)acetyl]piperidin-4-yl}phenyl)-1-(pyridazin-3-yl)pyrrolidine-3-carboxamide;
(3S)—N-{4-[1-(furan-3-ylcarbonyl)piperidin-4-yl]phenyl}-1-(pyridazin-3-yl)pyrrolidine-3-carboxamide;
(3S)—N-{4-[1-(3,4-dimethylbenzoyl)piperidin-4-yl]phenyl}-1-(pyridazin-3-yl)pyrrolidine-3-carboxamide;
(3S)—N-{4-[1-(4-fluorobenzoyl)piperidin-4-yl]phenyl}-1-(pyridazin-3-yl)pyrrolidine-3-carboxamide;
(3S)—N-(4-{1-[2-chloro-5-(trifluoromethyl)benzoyl]piperidin-4-yl}phenyl)-1-(pyridazin-3-yl)pyrrolidine-3-carboxamide;
(3S)—N-[4-(1-acetylpiperidin-4-yl)phenyl]-1-(pyridazin-3-yl)pyrrolidine-3-carboxamide;

(3S)—N-{4-[1-(2,4-difluorobenzoyl)piperidin-4-yl]phenyl}-1-(pyridazin-3-yl)pyrrolidine-3-carboxamide;
(3S)—N-{4-[1-(3,5-dimethylbenzoyl)piperidin-4-yl]phenyl}-1-(pyridazin-3-yl)pyrrolidine-3-carboxamide;
(3S)—N-{4-[1-(3-ethoxypropanoyl)piperidin-4-yl]phenyl}-1-(pyridazin-3-yl)pyrrolidine-3-carboxamide;
(3S)—N-{4-[1-(2,5-dichlorobenzoyl)piperidin-4-yl]phenyl}-1-(pyridazin-3-yl)pyrrolidine-3-carboxamide;
(3S)—N-{4-[1-(2,5-dimethylbenzoyl)piperidin-4-yl]phenyl}-1-(pyridazin-3-yl)pyrrolidine-3-carboxamide;
(3S)—N-{4-[1-(5-fluoro-2-methylbenzoyl)piperidin-4-yl]phenyl}-1-(pyridazin-3-yl)pyrrolidine-3-carboxamide;
(3S)—N-{4-[1-(diphenylacetyl)piperidin-4-yl]phenyl}-1-(pyridazin-3-yl)pyrrolidine-3-carboxamide;
(3S)-1-(pyridazin-3-yl)-N-(4-{1-[4-(trifluoromethyl)benzoyl]piperidin-4-yl}phenyl)pyrrolidine-3-carboxamide;
(3S)—N-{4-[1-(pent-4-enoyl)piperidin-4-yl]phenyl}-1-(pyridazin-3-yl)pyrrolidine-3-carboxamide;
(3S)-1-(pyridazin-3-yl)-N-(4-{1-[3-(trifluoromethoxy)benzoyl]piperidin-4-yl}phenyl)pyrrolidine-3-carboxamide;
(3S)—N-(4-{1-[(1-phenylcyclopropyl)carbonyl]piperidin-4-yl}phenyl)-1-(pyridazin-3-yl)pyrrolidine-3-carboxamide;
(3S)—N-(4-{1-[2-fluoro-5-(trifluoromethyl)benzoyl]piperidin-4-yl}phenyl)-1-(pyridazin-3-yl)pyrrolidine-3-carboxamide;
(3S)—N-{4-[1-(cyclohexylacetyl)piperidin-4-yl]phenyl}-1-(pyridazin-3-yl)pyrrolidine-3-carboxamide;
(3S)—N-{4-[1-(4-methoxybenzoyl)piperidin-4-yl]phenyl}-1-(pyridazin-3-yl)pyrrolidine-3-carboxamide;
(3S)—N-{4-[1-(2-methylbutanoyl)piperidin-4-yl]phenyl}-1-(pyridazin-3-yl)pyrrolidine-3-carboxamide;
(3S)—N-{4-[1-(2-ethylbutanoyl)piperidin-4-yl]phenyl}-1-(pyridazin-3-yl)pyrrolidine-3-carboxamide;
(3S)—N-{4-[1-(4-tert-butylbenzoyl)piperidin-4-yl]phenyl}-1-(pyridazin-3-yl)pyrrolidine-3-carboxamide;
(3S)—N-{4-[1-(3-chlorobenzoyl)piperidin-4-yl]phenyl}-1-(pyridazin-3-yl)pyrrolidine-3-carboxamide;
(3S)—N-(4-{1-[(2-fluorophenyl)acetyl]piperidin-4-yl}phenyl)-1-(pyridazin-3-yl)pyrrolidine-3-carboxamide;
(3S)-1-(pyridazin-3-yl)-N-(4-{1-[3-(trifluoromethyl)benzoyl]piperidin-4-yl}phenyl)pyrrolidine-3-carboxamide;
(3S)—N-(4-{1-[(1-methylcyclopropyl)carbonyl]piperidin-4-yl}phenyl)-1-(pyridazin-3-yl)pyrrolidine-3-carboxamide;
(3S)—N-{4-[1-(pent-4-ynoyl)piperidin-4-yl]phenyl}-1-(pyridazin-3-yl)pyrrolidine-3-carboxamide;
(3S)—N-(4-{1-[(3-fluorophenyl)acetyl]piperidin-4-yl}phenyl)-1-(pyridazin-3-yl)pyrrolidine-3-carboxamide;
(3S)—N-(4-{1-[3-(methylsulfanyl)propanoyl]piperidin-4-yl}phenyl)-1-(pyridazin-3-yl)pyrrolidine-3-carboxamide;
(3S)—N-(4-{1-[(1-acetylpiperidin-4-yl)carbonyl]piperidin-4-yl}phenyl)-1-(pyridazin-3-yl)pyrrolidine-3-carboxamide;
(3S)—N-{4-[1-(but-3-enoyl)piperidin-4-yl]phenyl}-1-(pyridazin-3-yl)pyrrolidine-3-carboxamide;
(3S)—N-{4-[1-(2,2-dimethylbutanoyl)piperidin-4-yl]phenyl}-1-(pyridazin-3-yl)pyrrolidine-3-carboxamide;
(3S)—N-{4-[1-(3-fluoro-4-methylbenzoyl)piperidin-4-yl]phenyl}-1-(pyridazin-3-yl)pyrrolidine-3-carboxamide;
(3S)—N-{4-[1-(3-methoxybenzoyl)piperidin-4-yl]phenyl}-1-(pyridazin-3-yl)pyrrolidine-3-carboxamide;
(3S)—N-(4-{1-[(2-chlorophenyl)acetyl]piperidin-4-yl}phenyl)-1-(pyridazin-3-yl)pyrrolidine-3-carboxamide;
(3S)—N-(4-{1-[(2-methoxyethoxy)acetyl]piperidin-4-yl}phenyl)-1-(pyridazin-3-yl)pyrrolidine-3-carboxamide;
(3S)—N-{4-[1-(3,3-dimethylbutanoyl)piperidin-4-yl]phenyl}-1-(pyridazin-3-yl)pyrrolidine-3-carboxamide;
(3S)—N-{4-[1-(N-acetyl-L-leucyl)piperidin-4-yl]phenyl}-1-(pyridazin-3-yl)pyrrolidine-3-carboxamide;
(3S)—N-{4-[1-(3-fluorobenzoyl)piperidin-4-yl]phenyl}-1-(pyridazin-3-yl)pyrrolidine-3-carboxamide;
(3S)—N-{4-[1-(4-cyanobenzoyl)piperidin-4-yl]phenyl}-1-(pyridazin-3-yl)pyrrolidine-3-carboxamide;
(3S)—N-{4-[1-(2-methoxybenzoyl)piperidin-4-yl]phenyl}-1-(pyridazin-3-yl)pyrrolidine-3-carboxamide;
(3S)—N-{4-[1-(2,3-dimethylbenzoyl)piperidin-4-yl]phenyl}-1-(pyridazin-3-yl)pyrrolidine-3-carboxamide;
(3S)—N-(4-{1-[4-(propan-2-yl)benzoyl]piperidin-4-yl}phenyl)-1-(pyridazin-3-yl)pyrrolidine-3-carboxamide;
(3S)—N-{4-[1-(cyclohexylcarbonyl)piperidin-4-yl]phenyl}-1-(pyridazin-3-yl)pyrrolidine-3-carboxamide;
(3S)-1-(pyridazin-3-yl)-N-{4-[1-(thiophen-2-ylcarbonyl)piperidin-4-yl]phenyl}pyrrolidine-3-carboxamide;
(3S)—N-{4-[1-(4-hydroxybenzoyl)piperidin-4-yl]phenyl}-1-(pyridazin-3-yl)pyrrolidine-3-carboxamide;
(3S)—N-{4-[1-(3-cyanobenzoyl)piperidin-4-yl]phenyl}-1-(pyridazin-3-yl)pyrrolidine-3-carboxamide;
(3S)-1-(pyridazin-3-yl)-N-{4-[1-(3,3,3-trifluoropropanoyl)piperidin-4-yl]phenyl}pyrrolidine-3-carboxamide;
(3S)—N-{4-[1-(methoxyacetyl)piperidin-4-yl]phenyl}-1-(pyridazin-3-yl)pyrrolidine-3-carboxamide;
(3S)—N-{4-[1-(3-methylbutanoyl)piperidin-4-yl]phenyl}-1-(pyridazin-3-yl)pyrrolidine-3-carboxamide;
N-[4-(1-benzoylpiperidin-4-yl)phenyl]-1-(2-cyanopyridin-3-yl)azetidine-3-carboxamide;
N-[4-(1-benzoylpiperidin-4-yl)phenyl]-1-(4-cyanopyridin-3-yl)azetidine-3-carboxamide;
N-[4-(1-benzoylpiperidin-4-yl)phenyl]-1-(6-fluoro-4-methylpyridin-3-yl)azetidine-3-carboxamide;
N-[4-(1-benzoylpiperidin-4-yl)phenyl]-1-(5-cyanopyridin-3-yl)azetidine-3-carboxamide;
N-[4-(1-benzoylpiperidin-4-yl)phenyl]-1-(5-methylpyridin-3-yl)azetidine-3-carboxamide;
2-[1-(2-methylpropyl)-1H-pyrazol-4-yl]-N-[(3S)-1-(pyridazin-3-yl)pyrrolidin-3-yl]-1,3-thiazole-5-carboxamide;
(3S)—N-[4-(1-benzoylpiperidin-4-yl)phenyl]-1-(2-methylpyridin-3-yl)pyrrolidine-3-carboxamide;
(3S)—N-{4-[1-(2-fluorobenzoyl)piperidin-4-yl]phenyl}-1-(2-methylpyridin-3-yl)pyrrolidine-3-carboxamide;
(3S)-1-(2-methylpyridin-3-yl)-N-{4-[1-(4,4,4-trifluorobutanoyl)piperidin-4-yl]phenyl}pyrrolidine-3-carboxamide;
N-[(3S)-1-(6-chloropyridazin-3-yl)pyrrolidin-3-yl]-5-[1-(2-methylpropyl)-1H-pyrazol-4-yl]furan-2-carboxamide;
5-[1-(2-methylpropyl)-1H-pyrazol-4-yl]-N-[(3S)-1-(pyridazin-3-yl)pyrrolidin-3-yl]furan-2-carboxamide;
N-(4-{1-[(4-methyltetrahydro-2H-pyran-4-yl)methyl]-1H-pyrazol-4-yl}phenyl)-1-(pyridazin-3-yl)azetidine-3-carboxamide;
N-[(3S)-1-(6-chloropyridazin-3-yl)pyrrolidin-3-yl]-4-[1-(2-methylpropanoyl)piperidin-4-yl]benzamide;
N-(4-{1-[2-(piperazin-1-yl)ethyl]-1H-pyrazol-4-yl}phenyl)-1-(pyridazin-3-yl)azetidine-3-carboxamide;
N-{4-[1-(2,2-dimethylpropyl)-1H-pyrazol-4-yl]phenyl}-1-(pyridazin-3-yl)azetidine-3-carboxamide;
4-[1-(2-methylpropanoyl)piperidin-4-yl]-N-[(3S)-1-(pyridazin-3-yl)pyrrolidin-3-yl]benzamide;
N-{4-[1-(2-hydroxy-2-methylpropyl)-1H-pyrazol-4-yl]phenyl}-1-(pyridazin-3-yl)azetidine-3-carboxamide;
5-[1-(3-fluorobenzoyl)piperidin-4-yl]-N-[(3S)-1-(pyridazin-3-yl)pyrrolidin-3-yl]thiophene-2-carboxamide;

5-[1-(4-fluorobenzoyl)piperidin-4-yl]-N-[(3S)-1-(pyridazin-3-yl)pyrrolidin-3-yl]thiophene-2-carboxamide;
(3S)—N-(4-{1-[(4-methyltetrahydro-2H-pyran-4-yl)methyl]-1H-pyrazol-4-yl}phenyl)-1-(pyridazin-3-yl)pyrrolidine-3-carboxamide;
(3S)—N-{4-[1-(2-hydroxy-2-methylpropyl)-1H-pyrazol-4-yl]phenyl}-1-(pyridazin-3-yl)pyrrolidine-3-carboxamide;
N-[(3S)-1-(pyridazin-3-yl)pyrrolidin-3-yl]-5-[1-(tetrahydro-2H-pyran-4-ylcarbonyl)piperidin-4-yl]thiophene-2-carboxamide;
(3S)—N-{4-[1-(2,2-dimethylpropyl)-1H-pyrazol-4-yl]phenyl}-1-(pyridazin-3-yl)pyrrolidine-3-carboxamide;
5-[1-(2-methylpropanoyl)piperidin-4-yl]-N-[(3S)-1-(pyridazin-3-yl)pyrrolidin-3-yl]thiophene-2-carboxamide;
5-[1-(2,4-difluorobenzoyl)piperidin-4-yl]-N-[(3S)-1-(pyridazin-3-yl)pyrrolidin-3-yl]thiophene-2-carboxamide;
5-{1-[(2-methylcyclopropyl)carbonyl]piperidin-4-yl}-N-[(3S)-1-(pyridazin-3-yl)pyrrolidin-3-yl]thiophene-2-carboxamide;
5-[1-(2-fluorobenzoyl)piperidin-4-yl]-N-[(3S)-1-(pyridazin-3-yl)pyrrolidin-3-yl]thiophene-2-carboxamide;
5-(1-benzoylpiperidin-4-yl)-N-[(3S)-1-(pyridazin-3-yl)pyrrolidin-3-yl]thiophene-2-carboxamide;
N-[(3S)-1-(pyridazin-3-yl)pyrrolidin-3-yl]-5-[1-(tetrahydrofuran-3-ylcarbonyl)piperidin-4-yl]thiophene-2-carboxamide;
N-[(3S)-1-(pyridazin-3-yl)pyrrolidin-3-yl]-5-{1-[(2R)-tetrahydrofuran-2-ylcarbonyl]piperidin-4-yl}thiophene-2-carboxamide;
5-{1-[(1-methylpiperidin-4-yl)acetyl]piperidin-4-yl}-N-[(3S)-1-(pyridazin-3-yl)pyrrolidin-3-yl]thiophene-2-carboxamide;
N-[(3S)-1-(pyridazin-3-yl)pyrrolidin-3-yl]-5-[1-(1,3-thiazol-4-ylcarbonyl)piperidin-4-yl]thiophene-2-carboxamide;
(3S)—N-{4-[1-(2-methylpropyl)-1H-pyrazol-4-yl]phenyl}-1-(pyridazin-3-yl)pyrrolidine-3-carboxamide;
(3S)—N-{4-[1-(propan-2-yl)-1H-pyrazol-4-yl]phenyl}-1-(pyridazin-3-yl)pyrrolidine-3-carboxamide;
(3S)—N-{4-[1-(cyclopropylmethyl)-1H-pyrazol-4-yl]phenyl}-1-(pyridazin-3-yl)pyrrolidine-3-carboxamide;
(3S)-1-(pyridazin-3-yl)-N-{4-[1-(tetrahydro-2H-pyran-2-ylmethyl)-1H-pyrazol-4-yl]phenyl}pyrrolidine-3-carboxamide;
(3S)—N-[4-(1-tert-butyl-1H-pyrazol-4-yl)phenyl]-1-(pyridazin-3-yl)pyrrolidine-3-carboxamide;
(3S)—N-(4-{[(3R)-1-benzoylpyrrolidin-3-yl]oxy}phenyl)-1-(pyridazin-3-yl)pyrrolidine-3-carboxamide;
(3S)—N-(4-{[(3R)-1-(2-fluorobenzoyl)pyrrolidin-3-yl]oxy}phenyl)-1-(pyridazin-3-yl)pyrrolidine-3-carboxamide;
(3S)—N-(4-{[(3R)-1-(3-fluorobenzoyl)pyrrolidin-3-yl]oxy}phenyl)-1-(pyridazin-3-yl)pyrrolidine-3-carboxamide;
(3S)—N-(4-{[(3R)-1-(4-fluorobenzoyl)pyrrolidin-3-yl]oxy}phenyl)-1-(pyridazin-3-yl)pyrrolidine-3-carboxamide;
(3S)—N-(4-{[(3R)-1-(3,5-difluorobenzoyl)pyrrolidin-3-yl]oxy}phenyl)-1-(pyridazin-3-yl)pyrrolidine-3-carboxamide;
(3S)—N-(4-{[(3R)-1-(2-methylbenzoyl)pyrrolidin-3-yl]oxy}phenyl)-1-(pyridazin-3-yl)pyrrolidine-3-carboxamide;
(3S)—N-(4-{[(3R)-1-(2,2-dimethylpropanoyl)pyrrolidin-3-yl]oxy}phenyl)-1-(pyridazin-3-yl)pyrrolidine-3-carboxamide;
(3S)—N-[4-({(3R)-1-[(4,4-difluorocyclohexyl)carbonyl]pyrrolidin-3-yl}oxy)phenyl]-1-(pyridazin-3-yl)pyrrolidine-3-carboxamide;
(3S)-1-(pyridazin-3-yl)-N-(4-{[(3R)-1-(4,4,4-trifluorobutanoyl)pyrrolidin-3-yl]oxy}phenyl)pyrrolidine-3-carboxamide;
(3S)—N-(4-{[(3R)-1-(2,4-difluorobenzoyl)pyrrolidin-3-yl]oxy}phenyl)-1-(pyridazin-3-yl)pyrrolidine-3-carboxamide;
N-[4-(5-propyl-1,2,4-oxadiazol-3-yl)phenyl]-1-(pyridazin-3-yl)azetidine-3-carboxamide;
(3S)—N-{4-[1-(2-fluorobenzoyl)azetidin-3-yl]phenyl}-1-(pyridazin-3-yl)pyrrolidine-3-carboxamide;
(3S)—N-{4-[1-(3-fluorobenzoyl)azetidin-3-yl]phenyl}-1-(pyridazin-3-yl)pyrrolidine-3-carboxamide;
(3S)—N-{4-[1-(4-fluorobenzoyl)azetidin-3-yl]phenyl}-1-(pyridazin-3-yl)pyrrolidine-3-carboxamide;
(3S)—N-[4-(1-benzoylazetidin-3-yl)phenyl]-1-(pyridazin-3-yl)pyrrolidine-3-carboxamide;
(3S)—N-{4-[1-(2,2-dimethylpropanoyl)azetidin-3-yl]phenyl}-1-(pyridazin-3-yl)pyrrolidine-3-carboxamide;
(3S)—N-{4-[1-(3,5-difluorobenzoyl)azetidin-3-yl]phenyl}-1-(pyridazin-3-yl)pyrrolidine-3-carboxamide;
(3S)—N-{4-[1-(2-methylbenzoyl)azetidin-3-yl]phenyl}-1-(pyridazin-3-yl)pyrrolidine-3-carboxamide;
(3S)—N-{4-[1-(2,4-difluorobenzoyl)azetidin-3-yl]phenyl}-1-(pyridazin-3-yl)pyrrolidine-3-carboxamide;
(3R)—N-[4-(1-benzoylpiperidin-4-yl)phenyl]-1-(pyridazin-3-yl)pyrrolidine-3-carboxamide;
(3R)—N-{4-[1-(2-fluorobenzoyl)piperidin-4-yl]phenyl}-1-(pyridazin-3-yl)pyrrolidine-3-carboxamide;
(3R)—N-{4-[1-(2,2-dimethylpropanoyl)piperidin-4-yl]phenyl}-1-(pyridazin-3-yl)pyrrolidine-3-carboxamide;
(3S)—N-(4-{[1-(cyclohexylcarbonyl)piperidin-4-yl]oxy}phenyl)-1-(pyridazin-3-yl)pyrrolidine-3-carboxamide;
(3S)—N-(4-{[1-(2-fluorobenzoyl)piperidin-4-yl]oxy}phenyl)-1-(pyridazin-3-yl)pyrrolidine-3-carboxamide;
(3S)—N-(4-{[1-(3-fluorobenzoyl)piperidin-4-yl]oxy}phenyl)-1-(pyridazin-3-yl)pyrrolidine-3-carboxamide;
(3S)—N-{4-[(1-benzoylpiperidin-4-yl)oxy]phenyl}-1-(pyridazin-3-yl)pyrrolidine-3-carboxamide;
(3S)—N-(4-{[1-(4-fluorobenzoyl)piperidin-4-yl]oxy}phenyl)-1-(pyridazin-3-yl)pyrrolidine-3-carboxamide;
(3S)—N-(4-{[1-(2,2-dimethylpropanoyl)piperidin-4-yl]oxy}phenyl)-1-(pyridazin-3-yl)pyrrolidine-3-carboxamide;
(3S)—N-[4-({1-[(2-methylcyclopropyl)carbonyl]piperidin-4-yl}oxy)phenyl]-1-(pyridazin-3-yl)pyrrolidine-3-carboxamide;
N-{4-[5-(2,2-dimethylpropyl)-1,3,4-oxadiazol-2-yl]phenyl}-1-(pyridazin-3-yl)azetidine-3-carboxamide;
N-{4-[1-(2,2-dimethylpropyl)-1H-imidazol-4-yl]phenyl}-1-(pyridazin-3-yl)azetidine-3-carboxamide;
N-[4-(3-cyclopropyl-1-methyl-1H-pyrazol-5-yl)phenyl]-1-(pyridazin-3-yl)azetidine-3-carboxamide;
N-{4-[5-(2,2-dimethylpropyl)-1,2,4-oxadiazol-3-yl]phenyl}-1-(pyridazin-3-yl)azetidine-3-carboxamide;
N-{4-[3-cyclopropyl-1-(2-methoxyethyl)-1H-pyrazol-5-yl]phenyl}-1-(pyridazin-3-yl)azetidine-3-carboxamide;
tert-butyl 4-(5-{[1-(pyridazin-3-yl)azetidin-3-yl]carbamoyl}thiophen-2-yl)piperidine-1-carboxylate;
tert-butyl 4-fluoro-4-[4-({[1-(pyridazin-3-yl)azetidin-3-yl]carbonyl}amino)phenyl]piperidine-1-carboxylate;

5-(1-benzoylpiperidin-4-yl)-N-[1-(pyridazin-3-yl)azetidin-3-yl]thiophene-2-carboxamide;
5-[1-(2-fluorobenzoyl)piperidin-4-yl]-N-[1-(pyridazin-3-yl)azetidin-3-yl]thiophene-2-carboxamide;
5-[1-(2-methylbenzoyl)piperidin-4-yl]-N-[1-(pyridazin-3-yl)azetidin-3-yl]thiophene-2-carboxamide;
5-[1-(2,4-difluorobenzoyl)piperidin-4-yl]-N-[1-(pyridazin-3-yl)azetidin-3-yl]thiophene-2-carboxamide;
5-[1-(3-fluorobenzoyl)piperidin-4-yl]-N-[1-(pyridazin-3-yl)azetidin-3-yl]thiophene-2-carboxamide;
5-[1-(4-fluorobenzoyl)piperidin-4-yl]-N-[1-(pyridazin-3-yl)azetidin-3-yl]thiophene-2-carboxamide;
5-[1-(3,5-difluorobenzoyl)piperidin-4-yl]-N-[1-(pyridazin-3-yl)azetidin-3-yl]thiophene-2-carboxamide;
N-{4-[3-cyclopropyl-1-(2-hydroxyethyl)-1H-pyrazol-5-yl]phenyl}-1-(pyridazin-3-yl)azetidine-3-carboxamide;
N-[4-(1-benzoylpiperidin-4-yl)phenyl]-1-(6-fluoropyridazin-3-yl)azetidine-3-carboxamide;
N-{4-[1-(2-fluorobenzoyl)piperidin-4-yl]phenyl}-1-(6-fluoropyridazin-3-yl)azetidine-3-carboxamide;
N-{4-[1-(2,2-dimethylpropanoyl)piperidin-4-yl]phenyl}-1-(6-fluoropyridazin-3-yl)azetidine-3-carboxamide;
1-(6-fluoropyridazin-3-yl)-N-{4-[1-(2-methylpropanoyl)piperidin-4-yl]phenyl}azetidine-3-carboxamide;
N-{4-[1-(2-ethylbutanoyl)piperidin-4-yl]phenyl}-1-(6-fluoropyridazin-3-yl)azetidine-3-carboxamide;
N-{4-[1-(4-fluorobenzoyl)piperidin-4-yl]phenyl}-1-(6-fluoropyridazin-3-yl)azetidine-3-carboxamide;
(3S)—N-(4-{[(3S)-1-benzoylpyrrolidin-3-yl]oxy}phenyl)-1-(pyridazin-3-yl)pyrrolidine-3-carboxamide;
(3S)—N-(4-{[(3S)-1-(2-fluorobenzoyl)pyrrolidin-3-yl]oxy}phenyl)-1-(pyridazin-3-yl)pyrrolidine-3-carboxamide;
(3S)—N-(4-{[(3S)-1-(3,5-difluorobenzoyl)pyrrolidin-3-yl]oxy}phenyl)-1-(pyridazin-3-yl)pyrrolidine-3-carboxamide;
(3S)—N-(4-{[(3S)-1-(2,2-dimethylpropanoyl)pyrrolidin-3-yl]oxy}phenyl)-1-(pyridazin-3-yl)pyrrolidine-3-carboxamide;
N-{2-fluoro-4-[1-(2-fluorobenzoyl)piperidin-4-yl]phenyl}-1-(pyridazin-3-yl)azetidine-3-carboxamide;
N-[4-(1-benzoylpiperidin-4-yl)-2-fluorophenyl]-1-(pyridazin-3-yl)azetidin-3-yl)azetidine-3-carboxamide;
N-{2-fluoro-4-[1-(3-fluorobenzoyl)piperidin-4-yl]phenyl}-1-(pyridazin-3-yl)azetidine-3-carboxamide;
N-{2-fluoro-4-[1-(2-methylbenzoyl)piperidin-4-yl]phenyl}-1-(pyridazin-3-yl)azetidine-3-carboxamide;
N-{2-fluoro-4-[1-(4-fluorobenzoyl)piperidin-4-yl]phenyl}-1-(pyridazin-3-yl)azetidine-3-carboxamide;
N-{4-[1-(2,4-difluorobenzoyl)piperidin-4-yl]-2-fluorophenyl}-1-(pyridazin-3-yl)azetidine-3-carboxamide;
N-{4-[1-(3,5-difluorobenzoyl)piperidin-4-yl]-2-fluorophenyl}-1-(pyridazin-3-yl)azetidine-3-carboxamide;
N-{4-[1-(3,3-dimethylbutanoyl)piperidin-4-yl]-2-fluorophenyl}-1-(pyridazin-3-yl)azetidine-3-carboxamide;
(3S)—N-(4-{[1-(2-fluorobenzoyl)piperidin-4-yl]oxy}phenyl)-1-(6-methylpyridazin-3-yl)pyrrolidine-3-carboxamide;
(3S)—N-{4-[(1-benzoylpiperidin-4-yl)oxy]phenyl}-1-(6-methylpyridazin-3-yl)pyrrolidine-3-carboxamide;
(3S)—N-(4-{[1-(2,2-dimethylpropanoyl)piperidin-4-yl]oxy}phenyl)-1-(6-methylpyridazin-3-yl)pyrrolidine-3-carboxamide;
(3S)—N-(4-{[1-(cyclohexylcarbonyl)piperidin-4-yl]oxy}phenyl)-1-(6-methylpyridazin-3-yl)pyrrolidine-3-carboxamide;
N-{4-[8-(2-methylpropanoyl)-8-azabicyclo[3.2.1]oct-3-yl]phenyl}-1-(pyridazin-3-yl)azetidine-3-carboxamide;
1-(pyridazin-3-yl)-N-{4-[8-(4,4,4-trifluorobutanoyl)-8-azabicyclo[3.2.1]oct-3-yl]phenyl}azetidine-3-carboxamide;
N-[4-(8-benzoyl-8-azabicyclo[3.2.1]oct-3-yl)phenyl]-1-(pyridazin-3-yl)azetidine-3-carboxamide;
N-{4-[8-(2-fluorobenzoyl)-8-azabicyclo[3.2.1]oct-3-yl]phenyl}-1-(pyridazin-3-yl)azetidine-3-carboxamide;
N-{4-[8-(2,2-dimethylpropanoyl)-8-azabicyclo[3.2.1]oct-3-yl]phenyl}-1-(pyridazin-3-yl)azetidine-3-carboxamide;
N-(4-{8-[(1-methylcyclopropyl)carbonyl]-8-azabicyclo[3.2.1]oct-3-yl}phenyl)-1-(pyridazin-3-yl)azetidine-3-carboxamide;
N-{4-[1-(2-methoxyethyl)-3-(2-methylpropyl)-1H-pyrazol-5-yl]phenyl}-1-(pyridazin-3-yl)azetidine-3-carboxamide;
5-[1-(2,2-dimethylpropanoyl)piperidin-4-yl]-N-[1-(pyridazin-3-yl)azetidin-3-yl]thiophene-2-carboxamide;
5-{1-[(1-methylcyclopropyl)carbonyl]piperidin-4-yl}-N-[1-(pyridazin-3-yl)azetidin-3-yl]thiophene-2-carboxamide;
N-[1-(pyridazin-3-yl)azetidin-3-yl]-5-[1-(3,3,3-trifluoropropanoyl)piperidin-4-yl]thiophene-2-carboxamide;
5-[1-(2,2-dimethylbutanoyl)piperidin-4-yl]-N-[1-(pyridazin-3-yl)azetidin-3-yl]thiophene-2-carboxamide;
N-{4-[1-(2-fluorobenzoyl)piperidin-4-yl]phenyl}-1-(6-methylpyridazin-3-yl)azetidine-3-carboxamide;
N-{4-[1-(2,2-dimethylpropanoyl)piperidin-4-yl]phenyl}-1-(6-methylpyridazin-3-yl)azetidine-3-carboxamide;
benzyl 4-[4-({[1-(6-chloropyridazin-3-yl)azetidin-3-yl]carbonyl}amino)phenyl]-4-fluoropiperidine-1-carboxylate;
benzyl 4-[4-({[1-(6-chloropyridazin-3-yl)azetidin-3-yl]carbonyl}amino)phenyl]-4-hydroxypiperidine-1-carboxylate;
N-[1-(pyridazin-3-yl)azetidin-3-yl]-5-[1-(4,4,4-trifluorobutanoyl)piperidin-4-yl]thiophene-2-carboxamide;
5-[1-(cyclopropylcarbonyl)piperidin-4-yl]-N-[1-(pyridazin-3-yl)azetidin-3-yl]thiophene-2-carboxamide;
N-{4-[4-fluoro-1-(2-fluorobenzoyl)piperidin-4-yl]phenyl}-1-(pyridazin-3-yl)azetidine-3-carboxamide;
N-{2-fluoro-4-[1-(2-methylpropanoyl)piperidin-4-yl]phenyl}-1-(pyridazin-3-yl)azetidine-3-carboxamide;
N-{4-[1-(2,2-dimethylpropanoyl)piperidin-4-yl]-2-fluorophenyl}-1-(pyridazin-3-yl)azetidine-3-carboxamide;
N-{4-[1-(cyclopropylcarbonyl)piperidin-4-yl]-2-fluorophenyl}-1-(pyridazin-3-yl)azetidine-3-carboxamide;
N-(2-fluoro-4-{1-[(1-methylcyclopropyl)carbonyl]piperidin-4-yl}phenyl)-1-(pyridazin-3-yl)azetidine-3-carboxamide;
N-{4-[1-(cyclopropylacetyl)piperidin-4-yl]-2-fluorophenyl}-1-(pyridazin-3-yl)azetidine-3-carboxamide;
N-[4-(1-benzoyl-4-fluoropiperidin-4-yl)phenyl]-1-(pyridazin-3-yl)azetidine-3-carboxamide;
N-{4-[1-(2,2-dimethylpropanoyl)-4-fluoropiperidin-4-yl]phenyl}-1-(pyridazin-3-yl)azetidine-3-carboxamide;
N-{4-[3-tert-butyl-1-(2-methoxyethyl)-1H-pyrazol-5-yl]phenyl}-1-(pyridazin-3-yl)azetidine-3-carboxamide;
N-[4-(1-butyl-3-tert-butyl-1H-pyrazol-5-yl)phenyl]-1-(pyridazin-3-yl)azetidine-3-carboxamide;
N-{4-[3-tert-butyl-1-(tetrahydro-2H-pyran-4-ylmethyl)-1H-pyrazol-5-yl]phenyl}-1-(pyridazin-3-yl)azetidine-3-carboxamide;
N-{2-fluoro-4-[1-(2-fluorobenzoyl)piperidin-4-yl]phenyl}-1-(pyridazin-4-yl)azetidine-3-carboxamide;
N-[4-(1-benzoylpiperidin-4-yl)-2-fluorophenyl]-1-(pyridazin-4-yl)azetidine-3-carboxamide;

N-{4-[1-(2,2-dimethylpropanoyl)piperidin-4-yl]-2-fluorophenyl}-1-(pyridazin-4-yl)azetidine-3-carboxamide;
N-{4-[1-(3,3-dimethylbutanoyl)piperidin-4-yl]-2-fluorophenyl}-1-(pyridazin-4-yl)azetidine-3-carboxamide;
N-{2-fluoro-4-[1-(4,4,4-trifluorobutanoyl)piperidin-4-yl]phenyl}-1-(pyridazin-4-yl)azetidine-3-carboxamide;
(3S)—N-{4-[1-(2-fluorobenzoyl)piperidin-4-yl]phenyl}-1-(6-methylpyridazin-3-yl)pyrrolidine-3-carboxamide;
(3S)—N-[4-(1-benzoylpiperidin-4-yl)phenyl]-1-(6-methylpyridazin-3-yl)pyrrolidine-3-carboxamide;
(3S)—N-{4-[1-(2,2-dimethylpropanoyl)piperidin-4-yl]phenyl}-1-(6-methylpyridazin-3-yl)pyrrolidine-3-carboxamide;
5-[1-(2-fluorobenzoyl)piperidin-4-yl]-N-[(3S)-1-(pyridazin-3-yl)pyrrolidin-3-yl]furan-2-carboxamide;
(3S)—N-[4-(1-benzoylpiperidin-4-yl)phenyl]-1-(4-methylpyridazin-3-yl)pyrrolidine-3-carboxamide;
(3S)—N-{4-[1-(2,2-dimethylpropanoyl)piperidin-4-yl]phenyl}-1-(4-methylpyridazin-3-yl)pyrrolidine-3-carboxamide;
5-[1-(2,2-dimethylpropanoyl)piperidin-4-yl]-N-[(3S)-1-(pyridazin-3-yl)pyrrolidin-3-yl]thiophene-2-carboxamide;
5-[1-(3,3-dimethylbutanoyl)piperidin-4-yl]-N-[(3S)-1-(pyridazin-3-yl)pyrrolidin-3-yl]thiophene-2-carboxamide;
5-[1-(2,2-dimethylbutanoyl)piperidin-4-yl]-N-[(3S)-1-(pyridazin-3-yl)pyrrolidin-3-yl]thiophene-2-carboxamide;
5-{1-[(1-methylcyclopropyl)carbonyl]piperidin-4-yl}-N-[(3S)-1-(pyridazin-3-yl)pyrrolidin-3-yl]thiophene-2-carboxamide;
N-[(3S)-1-(pyridazin-3-yl)pyrrolidin-3-yl]-5-[1-(3,3,3-trifluoropropanoyl)piperidin-4-yl]thiophene-2-carboxamide;
5-[1-(cyclopropylacetyl)piperidin-4-yl]-N-[(3S)-1-(pyridazin-3-yl)pyrrolidin-3-yl]thiophene-2-carboxamide;
5-[1-(bicyclo[2.2.1]hept-2-ylacetyl)piperidin-4-yl]-N-[(3S)-1-(pyridazin-3-yl)pyrrolidin-3-yl]thiophene-2-carboxamide; and pharmaceutically acceptable salts thereof.

Embodiments of Formula (VC)

In another aspect, the present invention provides compounds of Formula (VC)

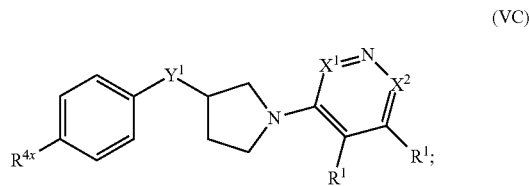

(VC)

and pharmaceutically acceptable salts thereof; wherein $X^1$, $X^2$, $R^1$, and $Y^1$ are as described in Formula (IC) herein and $R^{4x}$ is as described herein for substituents on $R^2$ when $R^2$ is aryl in Formula (IC).

One embodiment of this invention pertains to compounds of Formula (VC) or pharmaceutically acceptable salts thereof;
wherein
$X^1$ is N and $X^2$ is $CR^1$; or
$X^1$ is $CR^1$ and $X^2$ is N; or
$X^1$ is $CR^1$ and $X^2$ is $CR^1$;
$Y^1$ is C(O)NH, or NHC(O);
$R^1$, at each occurrence, is independently selected from the group consisting of hydrogen, alkyl, alkenyl, alkynyl, haloalkyl, hydroxyalkyl, alkoxy, OH, $NH_2$, CN, $NO_2$, F, Cl, Br and I;

$R^{4x}$ is independently selected from the group consisting of $R^4$, $OR^4$, $SR^4$, $S(O)R^4$, $SO_2R^4$, $C(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, and I;

$R^4$, at each occurrence, is independently selected from the group consisting of alkyl, alkenyl, alkynyl, aryl, heterocyclyl, cycloalkyl, and cycloalkenyl; wherein each $R^4$ alkyl, alkenyl, and alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, CNOH, $CNOCH_3$, OH, (O), CN, $N_3$, $NO_2$, F, Cl, Br and I;

$R^7$, at each occurrence, is independently selected from the group consisting of alkyl, alkenyl, alkynyl, aryl, heterocyclyl, cycloalkyl, and cycloalkenyl;

wherein the cyclic moieties represented by $R^4$, and $R^7$, are independently optionally substituted with one or more substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $C(O)C(O)R^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, CNOH, $CNOCH_3$, OH, CN, $N_3$, $NO_2$, F, Cl, Br and I;

$R^{10}$, at each occurrence, is independently selected from the group consisting of alkyl, alkenyl, alkynyl, aryl, heterocyclyl, cycloalkyl, and cycloalkenyl; wherein each $R^{10}$ alkyl, alkenyl, and alkynyl is optionally substituted with one or more substituents independently selected from the group consisting of $R^{11}$, $OR^{11}$, $SR^{11}$, $S(O)R^{11}$, $SO_2R^{11}$, $C(O)R^{11}$, $CO(O)R^{11}$, $OC(O)R^{11}$, $OC(O)OR^{11}$, $NH_2$, $NHR^{11}$, $N(R^{11})_2$, $NHC(O)R^{11}$, $NR^{11}C(O)R^{11}$, $NHS(O)_2R^{11}$, $NR^{11}S(O)_2R^{11}$, $NHC(O)OR^{11}$, $NR^{11}C(O)OR^{11}$, $NHC(O)NH_2$, $NHC(O)NHR^{11}$, $NHC(O)N(R^{11})_2$, $NR^{11}C(O)NHR^{11}$, $NR^{11}C(O)N(R^{11})_2$, $C(O)NH_2$, $C(O)NHR^{11}$, $C(O)N(R^{11})_2$, $C(O)NHOH$, $C(O)NHOR^{11}$, $C(O)NHSO_2R^{11}$, $C(O)NR^{11}SO_2R^{11}$, $SO_2NH_2$, $SO_2NHR^{11}$, $SO_2N(R^{11})_2$, $C(O)H$, $C(O)OH$, $C(N)NH_2$, $C(N)NHR^{11}$, $C(N)N(R^{11})_2$, CNOH, $CNOCH_3$, OH, (O), CN, $N_3$, $NO_2$, F, Cl, Br and I; wherein each $R^{10}$ aryl, heterocyclyl, cycloalkyl, and cycloalkenyl is optionally substituted with one or more substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, $C(N)NH_2$, $C(N)NHR^{12}$, $C(N)N(R^{12})_2$, CNOH, $CNOCH_3$, OH, CN, $N_3$, $NO_2$, $CF_3$, $OCF_3$, F, Cl, Br and I;

$R^{11}$, at each occurrence, is independently selected from the group consisting of alkyl, alkenyl, alkynyl, aryl, heterocyclyl, cycloalkyl, and cycloalkenyl; wherein each $R^{11}$ alkyl, alkenyl, and alkynyl is optionally substituted with alkoxy or aryl; wherein each $R^{11}$ aryl, heterocyclyl, cycloalkyl, and cycloalkenyl is optionally substituted with one or more substituents independently selected from the group consisting of $R^{13}$, $OR^{13}$, $C(O)OR^{13}$, $OCF_3$, $CF_3$, F, Cl, Br and I;

$R^{12}$, at each occurrence, is independently selected from the group consisting of alkyl, alkenyl, alkynyl, aryl, heterocyclyl, cycloalkyl, and cycloalkenyl; and $R^{13}$, at each occurrence, is independently selected from the group consisting of alkyl, haloalkyl, alkenyl, alkynyl, aryl, heterocyclyl, cycloalkyl, and cycloalkenyl.

In one embodiment of Formula (VC), $X^1$ is N and $X^2$ is $CR^1$; or $X^1$ is $CR^1$ and $X^2$ is N; or $X^1$ is $CR^1$ and $X^2$ is $CR^1$. In another embodiment of Formula (VC), $X^1$ is N and $X^2$ is $CR^1$. In another embodiment of Formula (VC), $X^1$ is $CR^1$ and $X^2$ is N. In another embodiment of Formula (VC), $X^1$ is $CR^1$ and $X^2$ is $CR^1$.

In one embodiment of Formula (VC), $Y^1$ is C(O)NH, or NHC(O). In another embodiment of Formula (VC), $Y^1$ is C(O)NH. In another embodiment of Formula (VC), $Y^1$ is NHC(O).

In one embodiment of Formula (VC), $X^1$ is $CR^1$ and $X^2$ is $CR^1$; and $R^1$, at each occurrence, is independently selected from the group consisting of hydrogen, alkyl, alkenyl, alkynyl, haloalkyl, hydroxyalkyl, alkoxy, OH, $NH_2$, CN, $NO_2$, F, Cl, Br and I. In another embodiment of Formula (VC), $X^1$ is $CR^1$ and $X^2$ is $CR^1$; and $R^1$, at each occurrence, is independently selected from the group consisting of hydrogen, alkyl, haloalkyl, alkoxy, CN, F, Cl, Br and I. In another embodiment of Formula (VC), $X^1$ is $CR^1$ and $X^2$ is $CR^1$; and $R^1$, at each occurrence, is independently selected from the group consisting of hydrogen, alkyl, haloalkyl, alkoxy, CN, F, and Cl. In another embodiment of Formula (VC), $X^1$ is $CR^1$ and $X^2$ is $CR^1$; and $R^1$, at each occurrence, is hydrogen.

In another aspect, the present invention provides compounds of Formula (VD),

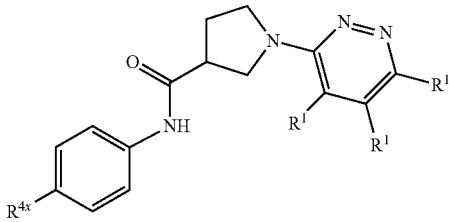

Formula (VD)

and pharmaceutically acceptable salts thereof; wherein $R^1$ is described herein for Formula (IC) and $R^{4x}$ is as described herein for substituents on $R^2$ when $R^2$ is aryl in Formula (IC).

In one embodiment of Formula (VC) and (VD), $R^1$, at each occurrence, is independently selected from the group consisting of hydrogen, alkyl, alkenyl, alkynyl, haloalkyl, hydroxyalkyl, alkoxy, OH, $NH_2$, CN, $NO_2$, F, Cl, Br and I. In another embodiment of Formula (VC) and (VD), $R^1$, at each occurrence, is independently selected from the group consisting of hydrogen, alkyl, haloalkyl, alkoxy, CN, F, Cl, Br and I. In another embodiment of Formula (VC) and (VD), $R^1$, at each occurrence, is independently selected from the group consisting of hydrogen, alkyl, haloalkyl, alkoxy, CN, F, and Cl. In another embodiment of Formula (VC) and (VD), $R^1$, at each occurrence, is hydrogen.

In one embodiment of Formula (VC) and (VD), $R^{4x}$ is independently selected from the group consisting of $R^4$, $OR^4$, $SR^4$, $S(O)R^4$, $SO_2R^4$, $C(O)R^4$, $OC(O)R^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, and I. In another embodiment of Formula (VC) and (VD), $R^{4x}$ is independently selected from the group consisting of $R^4$, $OR^4$, $SO_2R^4$, $C(O)NHR^4$, F, Cl, and I. In another embodiment of Formula (VC) and (VD), $R^{4x}$ is independently selected from the group consisting of $R^4$, $OR^4$, $SO_2R^4$, $C(O)NHR^4$, and F.

In one embodiment of Formula (VC) and (VD), $R^4$, at each occurrence, is independently selected from the group consisting of alkyl, alkenyl, alkynyl, aryl, heterocyclyl, cycloalkyl, and cycloalkenyl; wherein each $R^4$ alkyl, alkenyl, and alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, CNOH, $CNOCH_3$, OH, (O), CN, $N_3$, $NO_2$, F, Cl, Br and I. In another embodiment of Formula (VC) and (VD), $R^4$, at each occurrence, is independently selected from the group consisting of alkyl, alkenyl, alkynyl, aryl, heterocyclyl, and cycloalkyl.

In one embodiment of Formula (VC) and (VD), each $R^4$ alkyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, CNOH, $CNOCH_3$, OH, (O), CN, $N_3$, $NO_2$, F, Cl, Br and I. In another embodiment of Formula (VC) and (VD), each $R^4$ alkyl is optionally substituted with one or more substituents independently selected from the group consisting of $R^7$, $OR^7$, $N(R^7)_2$, F, Cl, Br and I.

In one embodiment of Formula (VC) and (VD), $R^7$, at each occurrence, is independently selected from the group consisting of alkyl, alkenyl, alkynyl, aryl, heterocyclyl, cycloalkyl, and cycloalkenyl. In another embodiment of Formula (VC) and (VD), $R^7$, at each occurrence, is independently selected from the group consisting of alkyl, aryl, heterocyclyl, and cycloalkyl.

In one embodiment of Formula (VC) and (VD), each $R^4$ and $R^7$ cyclic moiety is independently optionally substituted with one or more substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, C(O)OH, C(N)NH₂, C(N)NHR¹⁰, C(N)N(R¹⁰)₂, CNOH, CNOCH₃, OH, CN, N₃, NO₂, F, Cl, Br and I; R¹⁰, at each occurrence, is independently selected from the group consisting of alkyl, alkenyl, alkynyl, aryl, heterocyclyl, cycloalkyl, and cycloalkenyl; wherein each R¹⁰ alkyl, alkenyl, and alkynyl is optionally substituted with one or more substituents independently selected from the group consisting of R¹¹, OR¹¹, SR¹¹, S(O)R¹¹, SO₂R¹¹, C(O)R¹¹, CO(O)R¹¹, OC(O)R¹¹, OC(O)OR¹¹, NH₂, NHR¹¹, N(R¹¹)₂, NHC(O)R¹¹, NR¹¹C(O)R¹¹, NHS(O)₂R¹¹, NR¹¹S(O)₂R¹¹, NHC(O)OR¹¹, NR¹¹C(O)OR¹¹, NHC(O)NH₂, NHC(O)NHR¹¹, NHC(O)N(R¹¹)₂, NR¹¹C(O)NHR¹¹, NR¹¹C(O)N(R¹¹)₂, C(O)NH₂, C(O)NHR¹¹, C(O)N(R¹¹)₂, C(O)NHOH, C(O)NHOR¹¹, C(O)NHSO₂R¹¹, C(O)NR¹¹SO₂R¹¹, SO₂NH₂, SO₂NHR¹¹, SO₂N(R¹¹)₂, C(O)H, C(O)OH, C(N)NH₂, C(N)NHR¹¹, C(N)N(R¹¹)₂, CNOH, CNOCH₃, OH, (O), CN, N₃, NO₂, F, Cl, Br and I; wherein each R¹⁰ aryl, heterocyclyl, cycloalkyl, and cycloalkenyl is optionally substituted with one or more substituents independently selected from the group consisting of R¹², OR¹², SR¹², S(O)R¹², SO₂R¹², C(O)R¹², CO(O)R¹², OC(O)R¹², OC(O)OR¹², NH₂, NHR¹², N(R¹²)₂, NHC(O)R¹², NR¹²C(O)R¹², NHS(O)₂R¹², NR¹²S(O)₂R¹², NHC(O)OR¹², NR¹²C(O)OR¹², NHC(O)NH₂, NHC(O)NHR¹², NHC(O)N(R¹²)₂, NR¹²C(O)NHR¹², NR¹²C(O)N(R¹²)₂, C(O)NH₂, C(O)NHR¹², C(O)N(R¹²)₂, C(O)NHOH, C(O)NHOR¹², C(O)NHSO₂R¹², C(O)NR¹²SO₂R¹², SO₂NH₂, SO₂NHR¹², SO₂N(R¹²)₂, C(O)H, C(O)OH, C(N)NH₂, C(N)NHR¹², C(N)N(R¹²)₂, CNOH, CNOCH₃, OH, CN, N₃, NO₂, F, Cl, Br and I; R¹¹, at each occurrence, is independently selected from the group consisting of alkyl, alkenyl, alkynyl, aryl, heterocyclyl, cycloalkyl, and cycloalkenyl; wherein each R¹¹ alkyl, alkenyl, and alkynyl is optionally substituted with alkoxy or aryl; wherein each R¹¹ aryl, heterocyclyl, cycloalkyl, and cycloalkenyl is optionally substituted with one or more substituents independently selected from the group consisting of R¹³, OR¹³, C(O)OR¹³, OCF₃, CF₃, F, Cl, Br and I; R¹², at each occurrence, is independently selected from the group consisting of alkyl, alkenyl, alkynyl, aryl, heterocyclyl, cycloalkyl, and cycloalkenyl; and R¹³, at each occurrence, is independently selected from the group consisting of alkyl, haloalkyl, alkenyl, alkynyl, aryl, heterocyclyl, cycloalkyl, and cycloalkenyl.

In another embodiment of Formula (VC) and (VD), each R⁴ and R⁷ cyclic moiety is independently optionally substituted with one or more substituents independently selected from the group consisting of R¹⁰, C(O)R¹⁰, CO(O)R¹⁰, C(O)C(O)R¹⁰, CO(O)H, OH, F, Cl, Br and I; R¹⁰, at each occurrence, is independently selected from the group consisting of alkyl, alkenyl, alkynyl, aryl, heterocyclyl, and cycloalkyl; wherein each R¹⁰ alkyl, alkenyl, and alkynyl, are optionally substituted with one or more substituents independently selected from the group consisting of R¹¹, OR¹¹, SR¹¹, SO₂R¹¹, NH₂, N(R¹¹)₂, NHC(O)R¹¹, NHS(O)₂R¹¹, OH, NO₂, and F; wherein each R¹⁰ aryl, heterocyclyl and cycloalkyl is optionally substituted with one or more substituents independently selected from the group consisting of R¹², OR¹², C(O)R¹², NH₂, OH, CN, CF₃, OCF₃, F, and Cl; R¹¹, at each occurrence, is independently selected from the group consisting of alkyl, aryl, heterocyclyl, and cycloalkyl; wherein each R¹¹ alkyl is optionally substituted with alkoxy or aryl; wherein each R¹¹ aryl and heterocyclyl is optionally substituted with one or more substituents independently selected from the group consisting of R¹³, CF₃, F, and Cl; R¹², at each occurrence, is independently selected from the group consisting of alkyl and aryl; and R¹³, at each occurrence, is independently selected from the group consisting of alkyl, haloalkyl, and cycloalkyl.

One embodiment of this invention pertains to compounds or pharmaceutically acceptable salts thereof, which are useful as inhibitors of NAMPT, the compounds having Formula (VC)

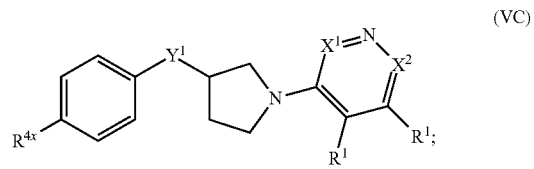

wherein
X¹ is N and X² is CR¹; or
X¹ is CR¹ and X² is N; or
X¹ is CR¹ and X² is CR¹;
Y¹ is C(O)NH, or NHC(O);
R¹, at each occurrence, is independently selected from the group consisting of hydrogen, alkyl, haloalkyl, alkoxy, CN, Cl, and F;
R⁴ˣ is independently selected from the group consisting of R⁴, SO₂R⁴, OR⁴, and F;
R⁴, at each occurrence, is independently selected from the group consisting of alkyl, alkenyl, aryl, heterocyclyl, and cycloalkyl; wherein each R⁴ alkyl is optionally substituted with one or more substituents independently selected from the group consisting of R⁷, OR⁷, N(R⁷)₂, and F;
R⁷, at each occurrence, is independently selected from the group consisting of alkyl, aryl, heterocyclyl, and cycloalkyl;
wherein the cyclic moieties represented by R⁴ and R⁷ are independently optionally substituted with one or more substituents independently selected from the group consisting of R¹⁰, C(O)R¹⁰, C(O)C(O)R¹⁰, CO(O)R¹⁰, C(O)OH, OH and F;
R¹⁰, at each occurrence, is independently selected from the group consisting of alkyl, alkenyl, alkynyl, aryl, heterocyclyl, and cycloalkyl; wherein each R¹⁰ alkyl is optionally substituted with one or more substituents independently selected from the group consisting of R¹¹, OR¹¹, SR¹¹, SO₂R¹¹, NH₂, N(R¹¹)₂, NHC(O)R¹¹, NHS(O)₂R¹¹, OH, NO₂, and F; wherein each R¹⁰ aryl, heterocyclyl and cycloalkyl is optionally substituted with one or more R¹², OR¹², C(O)R¹², NH₂, OH, CN, CF₃, OCF₃, F, and Cl;
R¹¹, at each occurrence, is independently selected from the group consisting of alkyl, aryl, heterocyclyl, and cycloalkyl; wherein each R¹¹ alkyl is optionally substituted with alkoxy or aryl; wherein each R¹¹ aryl, and heterocyclyl is optionally substituted with one or more substituents independently selected from the group consisting of R¹³, C(O)OR¹³, OCF₃, CF₃, F, and Cl;
R¹², at each occurrence, is independently selected from the group consisting of alkyl, and aryl; and
R¹³, at each occurrence, is independently selected from the group consisting of alkyl, haloalkyl, cycloalkyl, and heterocyclyl.

Still another embodiment pertains to compounds having Formula (VC), which include
tert-butyl 4-[4-({[(3S)-1-(pyridin-3-yl)pyrrolidin-3-yl]carbonyl}amino)phenoxy]piperidine-1-carboxylate;
tert-butyl 4-[4-({[(3R)-1-(pyridin-3-yl)pyrrolidin-3-yl]carbonyl}amino)phenoxy]piperidine-1-carboxylate;
(3S)-1-(pyridin-3-yl)-N-(4-{[1-(tetrahydro-2H-pyran-4-ylacetyl)piperidin-4-yl]oxy}phenyl)pyrrolidine-3-carboxamide;

(3S)—N-(4-{[1-(2-methylpropanoyl)piperidin-4-yl]oxy}phenyl)-1-(pyridin-3-yl)pyrrolidine-3-carboxamide;
(3S)-1-(pyridin-3-yl)-N-[4-({1-[(2S)-tetrahydro furan-2-ylcarbonyl]piperidin-4-yl}oxy)phenyl]pyrrolidine-3-carboxamide;
(3S)-1-(pyridin-3-yl)-N-[4-({1-[(2R)-tetrahydrofuran-2-ylcarbonyl]piperidin-4-yl}oxy)phenyl]pyrrolidine-3-carboxamide;
(3S)-1-(pyridin-3-yl)-N-(4-{[1-(tetrahydrofuran-3-ylcarbonyl)piperidin-4-yl]oxy}phenyl)pyrrolidine-3-carboxamide;
(3S)—N-(4-{[1-(cyclopropylacetyl)piperidin-4-yl]oxy}phenyl)-1-(pyridin-3-yl)pyrrolidine-3-carboxamide;
(3S)—N-(4-{[1-(2-hydroxy-2-methylpropanoyl)piperidin-4-yl]oxy}phenyl)-1-(pyridin-3-yl)pyrrolidine-3-carboxamide;
(3S)-1-(pyridin-3-yl)-N-(4-{[1-(3,3,3-trifluoropropanoyl)piperidin-4-yl]oxy}phenyl)pyrrolidine-3-carboxamide;
(3S)—N-[4-({1-[(2S)-2-methylbutanoyl]piperidin-4-yl}oxy)phenyl]-1-(pyridin-3-yl)pyrrolidine-3-carboxamide;
tert-butyl 4-(4-{[(3S)-1-(pyridin-3-yl)pyrrolidin-3-yl]carbamoyl}phenoxy)piperidine-1-carboxylate;
tert-butyl 4-(4-{[(3R)-1-(pyridin-3-yl)pyrrolidin-3-yl]carbamoyl}phenoxy)piperidine-1-carboxylate;
(3S)—N-{4-[1-(2-hydroxy-2-methylpropanoyl)piperidin-4-yl]phenyl}-1-(pyridazin-4-yl)pyrrolidine-3-carboxamide;
(3S)—N-{4-[1-(cyclopentylacetyl)piperidin-4-yl]phenyl}-1-(pyridazin-4-yl)pyrrolidine-3-carboxamide;
(3S)—N-{4-[1-(cyclopentylacetyl)piperidin-4-yl]phenyl}-1-(pyridin-3-yl)pyrrolidine-3-carboxamide;
(3S)—N-{4-[1-(2-methylpropanoyl)piperidin-4-yl]phenyl}-1-(pyridazin-3-yl)pyrrolidine-3-carboxamide;
(3S)—N-[4-(1-benzoylpiperidin-4-yl)phenyl]-1-(pyridazin-3-yl)pyrrolidine-3-carboxamide;
(3S)-1-(pyridazin-3-yl)-N-{4-[1-(tetrahydro-2H-pyran-4-ylacetyl)piperidin-4-yl]phenyl}pyrrolidine-3-carboxamide;
(3S)—N-{4-[1-(2,2-dimethylpropanoyl)piperidin-4-yl]phenyl}-1-(pyridazin-3-yl)pyrrolidine-3-carboxamide; and pharmaceutically acceptable salts thereof.
N-(4-{[1-(2-methylpropanoyl)piperidin-4-yl]sulfonyl}phenyl)-1-(pyridazin-4-yl)azetidine-3-carboxamide;
N-{4-[(1-benzoylpiperidin-4-yl)sulfonyl]phenyl}-1-(pyridazin-4-yl)azetidine-3-carboxamide;
N-(4-{[1-(4-fluorobenzoyl)piperidin-4-yl]sulfonyl}phenyl)-1-(pyridazin-4-yl)azetidine-3-carboxamide;
N-(4-{[1-(cyclopentylcarbonyl)piperidin-4-yl]sulfonyl}phenyl)-1-(pyridazin-4-yl)azetidine-3-carboxamide;
N-{4-[1-(2,2-dimethylpropanoyl)piperidin-4-yl]phenyl}-1-(pyridazin-3-yl)piperidine-4-carboxamide;
N-[4-(1-benzoylpiperidin-4-yl)phenyl]-1-(pyridazin-3-yl)piperidine-4-carboxamide;
N-{4-[1-(2-fluorobenzoyl)piperidi4-yl]phenyl}-1-(pyridazin-3-yl)piperidine-4-carboxamide;
1-(pyridazin-3-yl)-N-{4-[1-(4,4,4-trifluorobutanoyl)piperidin-4-yl]phenyl}piperidine-4-carboxamide;
(3S)-1-(pyridazin-3-yl)-N-{4-[1-(1,3-thiazol-5-ylcarbonyl)piperidin-4-yl]phenyl}pyrrolidine-3-carboxamide;
(3S)—N-{4-[1-(4-methylbenzoyl)piperidin-4-yl]phenyl}-1-(pyridazin-3-yl)pyrrolidine-3-carboxamide;
(3S)—N-(4-{1-[(2S)-2-phenylbutanoyl]piperidin-4-yl}phenyl)-1-(pyridazin-3-yl)pyrrolidine-3-carboxamide;
(3S)—N-(4-{1-[(2S)-2-methoxy-2-phenylacetyl]piperidin-4-yl}phenyl)-1-(pyridazin-3-yl)pyrrolidine-3-carboxamide;
(3S)—N-(4-{1-[(2R)-2-methoxy-2-phenylacetyl]piperidin-4-yl}phenyl)-1-(pyridazin-3-yl)pyrrolidine-3-carboxamide;
(3S)—N-{4-[1-(ethoxyacetyl)piperidin-4-yl]phenyl}-1-(pyridazin-3-yl)pyrrolidine-3-carboxamide;
(3S)—N-(4-{1-[(4-methylphenoxy)acetyl]piperidin-4-yl}phenyl)-1-(pyridazin-3-yl)pyrrolidine-3-carboxamide;
(3S)—N-{4-[1-(2-fluorobenzoyl)piperidin-4-yl]phenyl}-1-(pyridazin-3-yl)pyrrolidine-3-carboxamide;
(3S)-1-(pyridazin-3-yl)-N-{4-[1-(tetrahydrofuran-3-ylcarbonyl)piperidin-4-yl]phenyl}pyrrolidine-3-carboxamide;
(3S)—N-{4-[1-(naphthalen-1-ylcarbonyl)piperidin-4-yl]phenyl}-1-(pyridazin-3-yl)pyrrolidine-3-carboxamide;
(3S)—N-(4-{1-[(2,6-dichlorophenyl)acetyl]piperidin-4-yl}phenyl)-1-(pyridazin-3-yl)pyrrolidine-3-carboxamide;
(3S)—N-{4-[1-(naphthalen-1-ylacetyl)piperidin-4-yl]phenyl}-1-(pyridazin-3-yl)pyrrolidine-3-carboxamide;
(3S)-1-(pyridazin-3-yl)-N-(4-{1-[4-(thiophen-2-yl)butanoyl]piperidin-4-yl}phenyl)pyrrolidine-3-carboxamide;
(3S)—N-{4-[1-(cyclopropylacetyl)piperidin-4-yl]phenyl}-1-(pyridazin-3-yl)pyrrolidine-3-carboxamide;
(3S)—N-{4-[1-(cyclopentylacetyl)piperidin-4-yl]phenyl}-1-(pyridazin-3-yl)pyrrolidine-3-carboxamide;
(3S)—N-{4-[1-(2,5-difluorobenzoyl)piperidin-4-yl]phenyl}-1-(pyridazin-3-yl)pyrrolidine-3-carboxamide;
(3S)—N-{4-[1-(naphthalen-2-ylacetyl)piperidin-4-yl]phenyl}-1-(pyridazin-3-yl)pyrrolidine-3-carboxamide;
(3S)—N-(4-{1-[3-(phenylsulfonyl)propanoyl]piperidin-4-yl}phenyl)-1-(pyridazin-3-yl)pyrrolidine-3-carboxamide;
(3S)-1-(pyridazin-3-yl)-N-[4-(1-{[3-(trifluoromethyl)phenyl]acetyl}piperidin-4-yl)phenyl]pyrrolidine-3-carboxamide;
(3S)—N-{4-[1-(furan-2-ylcarbonyl)piperidin-4-yl]phenyl}-1-(pyridazin-3-yl)pyrrolidine-3-carboxamide;
(3S)—N-{4-[1-(N-benzoylglycyl)piperidin-4-yl]phenyl}-1-(pyridazin-3-yl)pyrrolidine-3-carboxamide;
(3S)—N-(4-{1-[(2,4-dichlorophenyl)acetyl]piperidin-4-yl}phenyl)-1-(pyridazin-3-yl)pyrrolidine-3-carboxamide;
(3S)—N-{4-[1-(2-methylbenzoyl)piperidin-4-yl]phenyl}-1-(pyridazin-3-yl)pyrrolidine-3-carboxamide;
(3S)-1-(pyridazin-3-yl)-N-{4-[1-(4,4,4-trifluorobutanoyl)piperidin-4-yl]phenyl}pyrrolidine-3-carboxamide;
(3S)—N-(4-{1-[(1-methylcyclohexyl)carbonyl]piperidin-4-yl}phenyl)-1-(pyridazin-3-yl)pyrrolidine-3-carboxamide;
(3S)-1-(pyridazin-3-yl)-N-{4-[1-(thiophen-3-ylcarbonyl)piperidin-4-yl]phenyl}pyrrolidine-3-carboxamide;
(3S)—N-(4-{1-[(6-methylpyridin-3-yl)carbonyl]piperidin-4-yl}phenyl)-1-(pyridazin-3-yl)pyrrolidine-3-carboxamide;
(3S)—N-(4-{1-[(3-chlorophenyl)acetyl]piperidin-4-yl}phenyl)-1-(pyridazin-3-yl)pyrrolidine-3-carboxamide;
(3S)—N-[4-(1-propanoylpiperidin-4-yl)phenyl]-1-(pyridazin-3-yl)pyrrolidine-3-carboxamide;
(3S)—N-{4-[1-(3,5-difluorobenzoyl)piperidin-4-yl]phenyl}-1-(pyridazin-3-yl)pyrrolidine-3-carboxamide;
(3S)—N-{4-[1-(cyclopentylcarbonyl)piperidin-4-yl]phenyl}-1-(pyridazin-3-yl)pyrrolidine-3-carboxamide;
(3S)-1-(pyridazin-3-yl)-N-{4-[1-(tetrahydrofuran-2-ylcarbonyl)piperidin-4-yl]phenyl}pyrrolidine-3-carboxamide;
(3S)—N-{4-[1-(cyclopropylcarbonyl)piperidin-4-yl]phenyl}-1-(pyridazin-3-yl)pyrrolidine-3-carboxamide;
(3S)—N-{4-[1-(4-chlorobenzoyl)piperidin-4-yl]phenyl}-1-(pyridazin-3-yl)pyrrolidine-3-carboxamide;

N-[4-(1-benzoylpiperidin-4-yl)phenyl]-1-(6-fluoro-5-methylpyridin-3-yl)azetidine-3-carboxamide;
N-[4-(1-benzoylpiperidin-4-yl)phenyl]-1-(5-fluoropyridin-3-yl)azetidine-3-carboxamide;
N-[4-(1-benzoylpiperidin-4-yl)phenyl]-1-(6-methylpyridazin-3-yl)azetidine-3-carboxamide;
N-[4-(1-benzoylpiperidin-4-yl)phenyl]-1-(2-fluoro-6-methylpyridin-3-yl)azetidine-3-carboxamide;
(3S)—N-{4-[1-(2-chlorobenzoyl)piperidin-4-yl]phenyl}-1-(pyridazin-3-yl)pyrrolidine-3-carboxamide;
(3S)—N-{4-[1-(2-methylpentanoyl)piperidin-4-yl]phenyl}-1-(pyridazin-3-yl)pyrrolidine-3-carboxamide;
(3S)—N-{4-[1-(4-methylpentanoyl)piperidin-4-yl]phenyl}-1-(pyridazin-3-yl)pyrrolidine-3-carboxamide;
(3S)—N-{4-[1-(2,4-dimethylbenzoyl)piperidin-4-yl]phenyl}-1-(pyridazin-3-yl)pyrrolidine-3-carboxamide;
(3S)—N-[4-(1-heptanoylpiperidin-4-yl)phenyl]-1-(pyridazin-3-yl)pyrrolidine-3-carboxamide;
(3S)—N-{4-[1-(2,4-dichlorobenzoyl)piperidin-4-yl]phenyl}-1-(pyridazin-3-yl)pyrrolidine-3-carboxamide;
(3S)—N-(4-{1-[(4-fluorophenyl)acetyl]piperidin-4-yl}phenyl)-1-(pyridazin-3-yl)pyrrolidine-3-carboxamide;
(3S)—N-{4-[1-(2,3-difluorobenzoyl)piperidin-4-yl]phenyl}-1-(pyridazin-3-yl)pyrrolidine-3-carboxamide;
(3S)—N-{4-[1-(3-methylbenzoyl)piperidin-4-yl]phenyl}-1-(pyridazin-3-yl)pyrrolidine-3-carboxamide;
(3S)—N-[4-(1-hexanoylpiperidin-4-yl)phenyl]-1-(pyridazin-3-yl)pyrrolidine-3-carboxamide;
(3S)—N-(4-{1-[(3-methylthiophen-2-yl)carbonyl]piperidin-4-yl}phenyl)-1-(pyridazin-3-yl)pyrrolidine-3-carboxamide;
(3S)—N-{4-[1-(2,3-dimethylbutanoyl)piperidin-4-yl]phenyl}-1-(pyridazin-3-yl)pyrrolidine-3-carboxamide;
(3S)—N-[4-(1-butanoylpiperidin-4-yl)phenyl]-1-(pyridazin-3-yl)pyrrolidine-3-carboxamide;
(3S)—N-{4-[1-(3-methylpentanoyl)piperidin-4-yl]phenyl}-1-(pyridazin-3-yl)pyrrolidine-3-carboxamide;
(3S)—N-(4-{1-[(3,5-dimethylphenyl)acetyl]piperidin-4-yl}phenyl)-1-(pyridazin-3-yl)pyrrolidine-3-carboxamide;
(3S)—N-{4-[1-(3,5-dichlorobenzoyl)piperidin-4-yl]phenyl}-1-(pyridazin-3-yl)pyrrolidine-3-carboxamide;
(3S)—N-{4-[1-(3-fluoro-2-methylbenzoyl)piperidin-4-yl]phenyl}-1-(pyridazin-3-yl)pyrrolidine-3-carboxamide;
(3S)—N-(4-{1-[(4-chlorophenyl)acetyl]piperidin-4-yl}phenyl)-1-(pyridazin-3-yl)pyrrolidine-3-carboxamide;
(3S)—N-{4-[1-(furan-3-ylcarbonyl)piperidin-4-yl]phenyl}-1-(pyridazin-3-yl)pyrrolidine-3-carboxamide;
(3S)—N-{4-[1-(3,4-dimethylbenzoyl)piperidin-4-yl]phenyl}-1-(pyridazin-3-yl)pyrrolidine-3-carboxamide;
(3S)—N-{4-[1-(4-fluorobenzoyl)piperidin-4-yl]phenyl}-1-(pyridazin-3-yl)pyrrolidine-3-carboxamide;
(3S)—N-(4-{1-[2-chloro-5-(trifluoromethyl)benzoyl]piperidin-4-yl}phenyl)-1-(pyridazin-3-yl)pyrrolidine-3-carboxamide;
(3S)—N-[4-(1-acetylpiperidin-4-yl)phenyl]-1-(pyridazin-3-yl)pyrrolidine-3-carboxamide;
(3S)—N-{4-[1-(2,4-difluorobenzoyl)piperidin-4-yl]phenyl}-1-(pyridazin-3-yl)pyrrolidine-3-carboxamide;
(3S)—N-{4-[1-(3,5-dimethylbenzoyl)piperidin-4-yl]phenyl}-1-(pyridazin-3-yl)pyrrolidine-3-carboxamide;
(3S)—N-{4-[1-(3-ethoxypropanoyl)piperidin-4-yl]phenyl}-1-(pyridazin-3-yl)pyrrolidine-3-carboxamide;
(3S)—N-{4-[1-(2,5-dichlorobenzoyl)piperidin-4-yl]phenyl}-1-(pyridazin-3-yl)pyrrolidine-3-carboxamide;
(3S)—N-{4-[1-(2,5-dimethylbenzoyl)piperidin-4-yl]phenyl}-1-(pyridazin-3-yl)pyrrolidine-3-carboxamide;
(3S)—N-{4-[1-(5-fluoro-2-methylbenzoyl)piperidin-4-yl]phenyl}-1-(pyridazin-3-yl)pyrrolidine-3-carboxamide;
(3S)—N-{4-[1-(diphenylacetyl)piperidin-4-yl]phenyl}-1-(pyridazin-3-yl)pyrrolidine-3-carboxamide;
(3S)-1-(pyridazin-3-yl)-N-(4-{1-[4-(trifluoromethyl)benzoyl]piperidin-4-yl}phenyl)pyrrolidine-3-carboxamide;
(3S)—N-{4-[1-(pent-4-enoyl)piperidin-4-yl]phenyl}-1-(pyridazin-3-yl)pyrrolidine-3-carboxamide;
(3S)-1-(pyridazin-3-yl)-N-(4-{1-[3-(trifluoromethoxy)benzoyl]piperidin-4-yl}phenyl)pyrrolidine-3-carboxamide;
(3S)—N-(4-{1-[(1-phenylcyclopropyl)carbonyl]piperidin-4-yl}phenyl)-1-(pyridazin-3-yl)pyrrolidine-3-carboxamide;
(3S)—N-(4-{1-[2-fluoro-5-(trifluoromethyl)benzoyl]piperidin-4-yl}phenyl)-1-(pyridazin-3-yl)pyrrolidine-3-carboxamide;
(3S)—N-{4-[1-(cyclohexylacetyl)piperidin-4-yl]phenyl}-1-(pyridazin-3-yl)pyrrolidine-3-carboxamide;
(3S)—N-{4-[1-(4-methoxybenzoyl)piperidin-4-yl]phenyl}-1-(pyridazin-3-yl)pyrrolidine-3-carboxamide;
(3S)—N-{4-[1-(2-methylbutanoyl)piperidin-4-yl]phenyl}-1-(pyridazin-3-yl)pyrrolidine-3-carboxamide;
(3S)—N-{4-[1-(2-ethylbutanoyl)piperidin-4-yl]phenyl}-1-(pyridazin-3-yl)pyrrolidine-3-carboxamide;
(3S)—N-{4-[1-(4-tert-butylbenzoyl)piperidin-4-yl]phenyl}-1-(pyridazin-3-yl)pyrrolidine-3-carboxamide;
(3S)—N-{4-[1-(3-chlorobenzoyl)piperidin-4-yl]phenyl}-1-(pyridazin-3-yl)pyrrolidine-3-carboxamide;
(3S)—N-(4-{1-[(2-fluorophenyl)acetyl]piperidin-4-yl}phenyl)-1-(pyridazin-3-yl)pyrrolidine-3-carboxamide;
(3S)-1-(pyridazin-3-yl)-N-(4-{1-[3-(trifluoromethyl)benzoyl]piperidin-4-yl}phenyl)pyrrolidine-3-carboxamide;
(3S)—N-(4-{1-[(1-methylcyclopropyl)carbonyl]piperidin-4-yl}phenyl)-1-(pyridazin-3-yl)pyrrolidine-3-carboxamide;
(3S)—N-{4-[1-(pent-4-ynoyl)piperidin-4-yl]phenyl}-1-(pyridazin-3-yl)pyrrolidine-3-carboxamide;
(3S)—N-(4-{1-[(3-fluorophenyl)acetyl]piperidin-4-yl}phenyl)-1-(pyridazin-3-yl)pyrrolidine-3-carboxamide;
(3S)—N-(4-{1-[3-(methylsulfanyl)propanoyl]piperidin-4-yl}phenyl)-1-(pyridazin-3-yl)pyrrolidine-3-carboxamide;
(3S)—N-(4-{1-[(1-acetylpiperidin-4-yl)carbonyl]piperidin-4-yl}phenyl)-1-(pyridazin-3-yl)pyrrolidine-3-carboxamide;
(3S)—N-{4-[1-(but-3-enoyl)piperidin-4-yl]phenyl}-1-(pyridazin-3-yl)pyrrolidine-3-carboxamide;
(3S)—N-{4-[1-(2,2-dimethylbutanoyl)piperidin-4-yl]phenyl}-1-(pyridazin-3-yl)pyrrolidine-3-carboxamide;
(3S)—N-{4-[1-(3-fluoro-4-methylbenzoyl)piperidin-4-yl]phenyl}-1-(pyridazin-3-yl)pyrrolidine-3-carboxamide;
(3S)—N-{4-[1-(3-methoxybenzoyl)piperidin-4-yl]phenyl}-1-(pyridazin-3-yl)pyrrolidine-3-carboxamide;
(3S)—N-(4-{1-[(2-chlorophenyl)acetyl]piperidin-4-yl}phenyl)-1-(pyridazin-3-yl)pyrrolidine-3-carboxamide;
(3S)—N-(4-{1-[(2-methoxyethoxy)acetyl]piperidin-4-yl}phenyl)-1-(pyridazin-3-yl)pyrrolidine-3-carboxamide;
(3S)—N-{4-[1-(3,3-dimethylbutanoyl)piperidin-4-yl]phenyl}-1-(pyridazin-3-yl)pyrrolidine-3-carboxamide;
(3S)—N-{4-[1-(N-acetyl-L-leucyl)piperidin-4-yl]phenyl}-1-(pyridazin-3-yl)pyrrolidine-3-carboxamide;
(3S)—N-{4-[1-(3-fluorobenzoyl)piperidin-4-yl]phenyl}-1-(pyridazin-3-yl)pyrrolidine-3-carboxamide;
(3S)—N-{4-[1-(4-cyanobenzoyl)piperidin-4-yl]phenyl}-1-(pyridazin-3-yl)pyrrolidine-3-carboxamide;
(3S)—N-{4-[1-(2-methoxybenzoyl)piperidin-4-yl]phenyl}-1-(pyridazin-3-yl)pyrrolidine-3-carboxamide;

(3S)—N-{4-[1-(2,3-dimethylbenzoyl)piperidin-4-yl]phenyl}-1-(pyridazin-3-yl)pyrrolidine-3-carboxamide;
(3S)—N-(4-{1-[4-(propan-2-yl)benzoyl]piperidin-4-yl}phenyl)-1-(pyridazin-3-yl)pyrrolidine-3-carboxamide;
(3S)—N-{4-[1-(cyclohexylcarbonyl)piperidin-4-yl]phenyl}-1-(pyridazin-3-yl)pyrrolidine-3-carboxamide;
(3S)-1-(pyridazin-3-yl)-N-{4-[1-(thiophen-2-ylcarbonyl)piperidin-4-yl]phenyl}pyrrolidine-3-carboxamide;
(3S)—N-{4-[1-(4-hydroxybenzoyl)piperidin-4-yl]phenyl}-1-(pyridazin-3-yl)pyrrolidine-3-carboxamide;
(3S)—N-{4-[1-(3-cyanobenzoyl)piperidin-4-yl]phenyl}-1-(pyridazin-3-yl)pyrrolidine-3-carboxamide;
(3S)-1-(pyridazin-3-yl)-N-{4-[1-(3,3,3-trifluoropropanoyl)piperidin-4-yl]phenyl}pyrrolidine-3-carboxamide;
(3S)—N-{4-[1-(methoxyacetyl)piperidin-4-yl]phenyl}-1-(pyridazin-3-yl)pyrrolidine-3-carboxamide;
(3S)—N-{4-[1-(3-methylbutanoyl)piperidin-4-yl]phenyl}-1-(pyridazin-3-yl)pyrrolidine-3-carboxamide;
N-[4-(1-benzoylpiperidin-4-yl)phenyl]-1-(2-cyanopyridin-3-yl)azetidine-3-carboxamide;
N-[4-(1-benzoylpiperidin-4-yl)phenyl]-1-(4-cyanopyridin-3-yl)azetidine-3-carboxamide;
N-[4-(1-benzoylpiperidin-4-yl)phenyl]-1-(6-fluoro-4-methylpyridin-3-yl)azetidine-3-carboxamide;
N-[4-(1-benzoylpiperidin-4-yl)phenyl]-1-(5-cyanopyridin-3-yl)azetidine-3-carboxamide;
N-[4-(1-benzoylpiperidin-4-yl)phenyl]-1-(5-methylpyridin-3-yl)azetidine-3-carboxamide;
(3S)—N-[4-(1-benzoylpiperidin-4-yl)phenyl]-1-(2-methylpyridin-3-yl)pyrrolidine-3-carboxamide;
(3S)—N-{4-[1-(2-fluorobenzoyl)piperidin-4-yl]phenyl}-1-(2-methylpyridin-3-yl)pyrrolidine-3-carboxamide;
(3S)-1-(2-methylpyridin-3-yl)-N-{4-[1-(4,4,4-trifluorobutanoyl)piperidin-4-yl]phenyl}pyrrolidine-3-carboxamide;
N-(4-{1-[(4-methyltetrahydro-2H-pyran-4-yl)methyl]-1H-pyrazol-4-yl}phenyl)-1-(pyridazin-3-yl)azetidine-3-carboxamide;
N-[(3S)-1-(6-chloropyridazin-3-yl)pyrrolidin-3-yl]-4-[1-(2-methylpropanoyl)piperidin-4-yl]benzamide;
N-(4-{1-[2-(piperazin-1-yl)ethyl]-1H-pyrazol-4-yl}phenyl)-1-(pyridazin-3-yl)azetidine-3-carboxamide;
N-{4-[1-(2,2-dimethylpropyl)-1H-pyrazol-4-yl]phenyl}-1-(pyridazin-3-yl)azetidine-3-carboxamide;
4-[1-(2-methylpropanoyl)piperidin-4-yl]-N-[(3S)-1-(pyridazin-3-yl)pyrrolidin-3-yl]benzamide;
N-{4-[1-(2-hydroxy-2-methylpropyl)-1H-pyrazol-4-yl]phenyl}-1-(pyridazin-3-yl)azetidine-3-carboxamide;
(3S)—N-(4-{1-[(4-methyltetrahydro-2H-pyran-4-yl)methyl]-1H-pyrazol-4-yl}phenyl)-1-(pyridazin-3-yl)pyrrolidine-3-carboxamide;
(3S)—N-{4-[1-(2-hydroxy-2-methylpropyl)-1H-pyrazol-4-yl]phenyl}-1-(pyridazin-3-yl)pyrrolidine-3-carboxamide;
(3S)—N-{4-[1-(2,2-dimethylpropyl)-1H-pyrazol-4-yl]phenyl}-1-(pyridazin-3-yl)pyrrolidine-3-carboxamide;
(3S)—N-{4-[1-(2-methylpropyl)-1H-pyrazol-4-yl]phenyl}-1-(pyridazin-3-yl)pyrrolidine-3-carboxamide;
(3S)—N-{4-[1-(propan-2-yl)-1H-pyrazol-4-yl]phenyl}-1-(pyridazin-3-yl)pyrrolidine-3-carboxamide;
(3S)—N-{4-[1-(cyclopropylmethyl)-1H-pyrazol-4-yl]phenyl}-1-(pyridazin-3-yl)pyrrolidine-3-carboxamide;
(3S)-1-(pyridazin-3-yl)-N-{4-[1-(tetrahydro-2H-pyran-2-ylmethyl)-1H-pyrazol-4-yl]phenyl}pyrrolidine-3-carboxamide;
(3S)—N-[4-(1-tert-butyl-1H-pyrazol-4-yl)phenyl]-1-(pyridazin-3-yl)pyrrolidine-3-carboxamide;
(3S)—N-(4-{[(3R)-1-benzoylpyrrolidin-3-yl]oxy}phenyl)-1-(pyridazin-3-yl)pyrrolidine-3-carboxamide;
(3S)—N-(4-{[(3R)-1-(2-fluorobenzoyl)pyrrolidin-3-yl]oxy}phenyl)-1-(pyridazin-3-yl)pyrrolidine-3-carboxamide;
(3S)—N-(4-{[(3R)-1-(3-fluorobenzoyl)pyrrolidin-3-yl]oxy}phenyl)-1-(pyridazin-3-yl)pyrrolidine-3-carboxamide;
(3S)—N-(4-{[(3R)-1-(4-fluorobenzoyl)pyrrolidin-3-yl]oxy}phenyl)-1-(pyridazin-3-yl)pyrrolidine-3-carboxamide;
(3S)—N-(4-{[(3R)-1-(3,5-difluorobenzoyl)pyrrolidin-3-yl]oxy}phenyl)-1-(pyridazin-3-yl)pyrrolidine-3-carboxamide;
(3S)—N-(4-{[(3R)-1-(2-methylbenzoyl)pyrrolidin-3-yl]oxy}phenyl)-1-(pyridazin-3-yl)pyrrolidine-3-carboxamide;
(3S)—N-(4-{[(3R)-1-(2,2-dimethylpropanoyl)pyrrolidin-3-yl]oxy}phenyl)-1-(pyridazin-3-yl)pyrrolidine-3-carboxamide;
(3S)—N-[4-({(3R)-1-[(4,4-difluorocyclohexyl)carbonyl]pyrrolidin-3-yl}oxy)phenyl]-1-(pyridazin-3-yl)pyrrolidine-3-carboxamide;
(3S)-1-(pyridazin-3-yl)-N-(4-{[(3R)-1-(4,4,4-trifluorobutanoyl)pyrrolidin-3-yl]oxy}phenyl)pyrrolidine-3-carboxamide;
(3S)—N-(4-{[(3R)-1-(2,4-difluorobenzoyl)pyrrolidin-3-yl]oxy}phenyl)-1-(pyridazin-3-yl)pyrrolidine-3-carboxamide;
N-[4-(5-propyl-1,2,4-oxadiazol-3-yl)phenyl]-1-(pyridazin-3-yl)azetidine-3-carboxamide;
(3S)—N-{4-[1-(2-fluorobenzoyl)azetidin-3-yl]phenyl}-1-(pyridazin-3-yl)pyrrolidine-3-carboxamide;
(3S)—N-{4-[1-(3-fluorobenzoyl)azetidin-3-yl]phenyl}-1-(pyridazin-3-yl)pyrrolidine-3-carboxamide;
(3S)—N-{4-[1-(4-fluorobenzoyl)azetidin-3-yl]phenyl}-1-(pyridazin-3-yl)pyrrolidine-3-carboxamide;
(3S)—N-[4-(1-benzoylazetidin-3-yl)phenyl]-1-(pyridazin-3-yl)pyrrolidine-3-carboxamide;
(3S)—N-{4-[1-(2,2-dimethylpropanoyl)azetidin-3-yl]phenyl}-1-(pyridazin-3-yl)pyrrolidine-3-carboxamide;
(3S)—N-{4-[1-(3,5-difluorobenzoyl)azetidin-3-yl]phenyl}-1-(pyridazin-3-yl)pyrrolidine-3-carboxamide;
(3S)—N-{4-[1-(2-methylbenzoyl)azetidin-3-yl]phenyl}-1-(pyridazin-3-yl)pyrrolidine-3-carboxamide;
(3S)—N-{4-[1-(2,4-difluorobenzoyl)azetidin-3-yl]phenyl}-1-(pyridazin-3-yl)pyrrolidine-3-carboxamide;
(3R)—N-[4-(1-benzoylpiperidin-4-yl)phenyl]-1-(pyridazin-3-yl)pyrrolidine-3-carboxamide;
(3R)—N-{4-[1-(2-fluorobenzoyl)piperidin-4-yl]phenyl}-1-(pyridazin-3-yl)pyrrolidine-3-carboxamide;
(3R)—N-{4-[1-(2,2-dimethylpropanoyl)piperidin-4-yl]phenyl}-1-(pyridazin-3-yl)pyrrolidine-3-carboxamide;
(3S)—N-(4-{[1-(cyclohexylcarbonyl)piperidin-4-yl]oxy}phenyl)-1-(pyridazin-3-yl)pyrrolidine-3-carboxamide;
(3S)—N-(4-{[1-(2-fluorobenzoyl)piperidin-4-yl]oxy}phenyl)-1-(pyridazin-3-yl)pyrrolidine-3-carboxamide;
(3S)—N-(4-{[1-(3-fluorobenzoyl)piperidin-4-yl]oxy}phenyl)-1-(pyridazin-3-yl)pyrrolidine-3-carboxamide;
(3S)—N-{4-[(1-benzoylpiperidin-4-yl)oxy]phenyl}-1-(pyridazin-3-yl)pyrrolidine-3-carboxamide;
(3S)—N-(4-{[1-(4-fluorobenzoyl)piperidin-4-yl]oxy}phenyl)-1-(pyridazin-3-yl)pyrrolidine-3-carboxamide;

(3S)—N-(4-{[1-(2,2-dimethylpropanoyl)piperidin-4-yl]oxy}phenyl)-1-(pyridazin-3-yl)pyrrolidine-3-carboxamide;
(3S)—N-[4-({1-[(2-methylcyclopropyl)carbonyl]piperidin-4-yl}oxy)phenyl]-1-(pyridazin-3-yl)pyrrolidine-3-carboxamide;
N-{4-[5-(2,2-dimethylpropyl)-1,3,4-oxadiazol-2-yl]phenyl}-1-(pyridazin-3-yl)azetidine-3-carboxamide;
N-{4-[1-(2,2-dimethylpropyl)-1H-imidazol-4-yl]phenyl}-1-(pyridazin-3-yl)azetidine-3-carboxamide;
N-[4-(3-cyclopropyl-1-methyl-1H-pyrazol-5-yl)phenyl]-1-(pyridazin-3-yl)azetidine-3-carboxamide;
N-{4-[5-(2,2-dimethylpropyl)-1,2,4-oxadiazol-3-yl]phenyl}-1-(pyridazin-3-yl)azetidine-3-carboxamide;
N-{4-[3-cyclopropyl-1-(2-methoxyethyl)-1H-pyrazol-5-yl]phenyl}-1-(pyridazin-3-yl)azetidine-3-carboxamide;
tert-butyl 4-(5-{[1-(pyridazin-3-yl)azetidin-3-yl]carbamoyl}thiophen-2-yl)piperidine-1-carboxylate;
tert-butyl 4-fluoro-4-[4-({[1-(pyridazin-3-yl)azetidin-3-yl]carbonyl}amino)phenyl]piperidine-1-carboxylate;
5-(1-benzoylpiperidin-4-yl)-N-[1-(pyridazin-3-yl)azetidin-3-yl]thiophene-2-carboxamide;
5-[1-(2-fluorobenzoyl)piperidin-4-yl]-N-[1-(pyridazin-3-yl)azetidin-3-yl]thiophene-2-carboxamide;
5-[1-(2-methylbenzoyl)piperidin-4-yl]-N-[1-(pyridazin-3-yl)azetidin-3-yl]thiophene-2-carboxamide;
5-[1-(2,4-difluorobenzoyl)piperidin-4-yl]-N-[1-(pyridazin-3-yl)azetidin-3-yl]thiophene-2-carboxamide;
5-[1-(3-fluorobenzoyl)piperidin-4-yl]-N-[1-(pyridazin-3-yl)azetidin-3-yl]thiophene-2-carboxamide;
5-[1-(4-fluorobenzoyl)piperidin-4-yl]-N-[1-(pyridazin-3-yl)azetidin-3-yl]thiophene-2-carboxamide;
5-[1-(3,5-difluorobenzoyl)piperidin-4-yl]-N-[1-(pyridazin-3-yl)azetidin-3-yl]thiophene-2-carboxamide;
N-{4-[3-cyclopropyl-1-(2-hydroxyethyl)-1H-pyrazol-5-yl]phenyl}-1-(pyridazin-3-yl)azetidine-3-carboxamide;
N-[4-(1-benzoylpiperidin-4-yl)phenyl]-1-(6-fluoropyridazin-3-yl)azetidine-3-carboxamide;
N-{4-[1-(2-fluorobenzoyl)piperidin-4-yl]phenyl}-1-(6-fluoropyridazin-3-yl)azetidine-3-carboxamide;
N-{4-[1-(2,2-dimethylpropanoyl)piperidin-4-yl]phenyl}-1-(6-fluoropyridazin-3-yl)azetidine-3-carboxamide;
1-(6-fluoropyridazin-3-yl)-N-{4-[1-(2-methylpropanoyl)piperidin-4-yl]phenyl}azetidine-3-carboxamide;
N-{4-[1-(2-ethylbutanoyl)piperidin-4-yl]phenyl}-1-(6-fluoropyridazin-3-yl)azetidine-3-carboxamide;
N-{4-[1-(4-fluorobenzoyl)piperidin-4-yl]phenyl}-1-(6-fluoropyridazin-3-yl)azetidine-3-carboxamide;
(3S)—N-(4-{[(3S)-1-benzoylpyrrolidin-3-yl]oxy}phenyl)-1-(pyridazin-3-yl)pyrrolidine-3-carboxamide;
(3S)—N-(4-{[(3S)-1-(2-fluorobenzoyl)pyrrolidin-3-yl]oxy}phenyl)-1-(pyridazin-3-yl)pyrrolidine-3-carboxamide;
(3S)—N-(4-{[(3S)-1-(3,5-difluorobenzoyl)pyrrolidin-3-yl]oxy}phenyl)-1-(pyridazin-3-yl)pyrrolidine-3-carboxamide;
(3S)—N-(4-{[(3S)-1-(2,2-dimethylpropanoyl)pyrrolidin-3-yl]oxy}phenyl)-1-(pyridazin-3-yl)pyrrolidine-3-carboxamide;
N-{2-fluoro-4-[1-(2-fluorobenzoyl)piperidin-4-yl]phenyl}-1-(pyridazin-3-yl)azetidine-3-carboxamide;
N-[4-(1-benzoylpiperidin-4-yl)-2-fluorophenyl]-1-(pyridazin-3-yl)azetidine-3-carboxamide;
N-{2-fluoro-4-[1-(3-fluorobenzoyl)piperidin-4-yl]phenyl}-1-(pyridazin-3-yl)azetidine-3-carboxamide;
N-{2-fluoro-4-[1-(2-methylbenzoyl)piperidin-4-yl]phenyl}-1-(pyridazin-3-yl)azetidine-3-carboxamide;
N-{2-fluoro-4-[1-(4-fluorobenzoyl)piperidin-4-yl]phenyl}-1-(pyridazin-3-yl)azetidine-3-carboxamide;
N-{4-[1-(2,4-difluorobenzoyl)piperidin-4-yl]-2-fluorophenyl}-1-(pyridazin-3-yl)azetidine-3-carboxamide;
N-{4-[1-(3,5-difluorobenzoyl)piperidin-4-yl]-2-fluorophenyl}-1-(pyridazin-3-yl)azetidine-3-carboxamide;
N-{4-[1-(3,3-dimethylbutanoyl)piperidin-4-yl]-2-fluorophenyl}-1-(pyridazin-3-yl)azetidine-3-carboxamide;
(3S)—N-(4-{[1-(2-fluorobenzoyl)piperidin-4-yl]oxy}phenyl)-1-(6-methylpyridazin-3-yl)pyrrolidine-3-carboxamide;
(3S)—N-{4-[(1-benzoylpiperidin-4-yl)oxy]phenyl}-1-(6-methylpyridazin-3-yl)pyrrolidine-3-carboxamide;
(3S)—N-(4-{[1-(2,2-dimethylpropanoyl)piperidin-4-yl]oxy}phenyl)-1-(6-methylpyridazin-3-yl)pyrrolidine-3-carboxamide;
(3S)—N-(4-{[1-(cyclohexylcarbonyl)piperidin-4-yl]oxy}phenyl)-1-(6-methylpyridazin-3-yl)pyrrolidine-3-carboxamide;
N-{4-[8-(2-methylpropanoyl)-8-azabicyclo[3.2.1]oct-3-yl]phenyl}-1-(pyridazin-3-yl)azetidine-3-carboxamide;
1-(pyridazin-3-yl)-N-{4-[8-(4,4,4-trifluorobutanoyl)-8-azabicyclo[3.2.1]oct-3-yl]phenyl}azetidine-3-carboxamide;
N-[4-(8-benzoyl-8-azabicyclo[3.2.1]oct-3-yl)phenyl]-1-(pyridazin-3-yl)azetidine-3-carboxamide;
N-{4-[8-(2-fluorobenzoyl)-8-azabicyclo[3.2.1]oct-3-yl]phenyl}-1-(pyridazin-3-yl)azetidine-3-carboxamide;
N-{4-[8-(2,2-dimethylpropanoyl)-8-azabicyclo[3.2.1]oct-3-yl]phenyl}-1-(pyridazin-3-yl)azetidine-3-carboxamide;
N-(4-{8-[(1-methylcyclopropyl)carbonyl]-8-azabicyclo[3.2.1]oct-3-yl}phenyl)-1-(pyridazin-3-yl)azetidine-3-carboxamide;
N-{4-[1-(2-methoxyethyl)-3-(2-methylpropyl)-1H-pyrazol-5-yl]phenyl}-1-(pyridazin-3-yl)azetidine-3-carboxamide;
5-[1-(2,2-dimethylpropanoyl)piperidin-4-yl]-N-[1-(pyridazin-3-yl)azetidin-3-yl]thiophene-2-carboxamide;
5-{1-[(1-methylcyclopropyl)carbonyl]piperidin-4-yl}-N-[1-(pyridazin-3-yl)azetidin-3-yl]thiophene-2-carboxamide;
N-[1-(pyridazin-3-yl)azetidin-3-yl]-5-[1-(3,3,3-trifluoropropanoyl)piperidin-4-yl]thiophene-2-carboxamide;
5-[1-(2,2-dimethylbutanoyl)piperidin-4-yl]-N-[1-(pyridazin-3-yl)azetidin-3-yl]thiophene-2-carboxamide;
N-{4-[1-(2-fluorobenzoyl)piperidin-4-yl]phenyl}-1-(6-methylpyridazin-3-yl)azetidine-3-carboxamide;
N-{4-[1-(2,2-dimethylpropanoyl)piperidin-4-yl]phenyl}-1-(6-methylpyridazin-3-yl)azetidine-3-carboxamide;
benzyl 4-[4-({[1-(6-chloropyridazin-3-yl)azetidin-3-yl]carbonyl}amino)phenyl]-4-fluoropiperidine-1-carboxylate;
benzyl 4-[4-({[1-(6-chloropyridazin-3-yl)azetidin-3-yl]carbonyl}amino)phenyl]-4-hydroxypiperidine-1-carboxylate;
N-[1-(pyridazin-3-yl)azetidin-3-yl]-5-[1-(4,4,4-trifluorobutanoyl)piperidin-4-yl]thiophene-2-carboxamide;
5-[1-(cyclopropylcarbonyl)piperidin-4-yl]-N-[1-(pyridazin-3-yl)azetidin-3-yl]thiophene-2-carboxamide;
N-{4-[4-fluoro-1-(2-fluorobenzoyl)piperidin-4-yl]phenyl}-1-(pyridazin-3-yl)azetidine-3-carboxamide;
N-{2-fluoro-4-[1-(2-methylpropanoyl)piperidin-4-yl]phenyl}-1-(pyridazin-3-yl)azetidine-3-carboxamide;
N-{4-[1-(2,2-dimethylpropanoyl)piperidin-4-yl]-2-fluorophenyl}-1-(pyridazin-3-yl)azetidine-3-carboxamide;
N-{4-[1-(cyclopropylcarbonyl)piperidin-4-yl]-2-fluorophenyl}-1-(pyridazin-3-yl)azetidine-3-carboxamide;
N-(2-fluoro-4-{1-[(1-methylcyclopropyl)carbonyl]piperidin-4-yl}phenyl)-1-(pyridazin-3-yl)azetidine-3-carboxamide;

N-{4-[1-(cyclopropylacetyl)piperidin-4-yl]-2-fluorophenyl}-1-(pyridazin-3-yl)azetidine-3-carboxamide;
N-[4-(1-benzoyl-4-fluoropiperidin-4-yl)phenyl]-1-(pyridazin-3-yl)azetidine-3-carboxamide;
N-{4-[1-(2,2-dimethylpropanoyl)-4-fluoropiperidin-4-yl]phenyl}-1-(pyridazin-3-yl)azetidine-3-carboxamide;
N-{4-[3-tert-butyl-1-(2-methoxyethyl)-1H-pyrazol-5-yl]phenyl}-1-(pyridazin-3-yl)azetidine-3-carboxamide;
N-[4-(1-butyl-3-tert-butyl-1H-pyrazol-5-yl)phenyl]-1-(pyridazin-3-yl)azetidine-3-carboxamide;
N-{4-[3-tert-butyl-1-(tetrahydro-2H-pyran-4-ylmethyl)-1H-pyrazol-5-yl]phenyl}-1-(pyridazin-3-yl)azetidine-3-carboxamide;
N-{2-fluoro-4-[1-(2-fluorobenzoyl)piperidin-4-yl]phenyl}-1-(pyridazin-4-yl)azetidine-3-carboxamide;
N-[4-(1-benzoylpiperidin-4-yl)-2-fluorophenyl]-1-(pyridazin-4-yl)azetidine-3-carboxamide;
N-{4-[1-(2,2-dimethylpropanoyl)piperidin-4-yl]-2-fluorophenyl}-1-(pyridazin-4-yl)azetidine-3-carboxamide;
N-{4-[1-(3,3-dimethylbutanoyl)piperidin-4-yl]-2-fluorophenyl}-1-(pyridazin-4-yl)azetidine-3-carboxamide;
N-{2-fluoro-4-[1-(4,4,4-trifluorobutanoyl)piperidin-4-yl]phenyl}-1-(pyridazin-4-yl)azetidine-3-carboxamide;
(3S)—N-{4-[1-(2-fluorobenzoyl)piperidin-4-yl]phenyl}-1-(6-methylpyridazin-3-yl)pyrrolidine-3-carboxamide;
(3S)—N-[4-(1-benzoylpiperidin-4-yl)phenyl]-1-(6-methylpyridazin-3-yl)pyrrolidine-3-carboxamide;
(3S)—N-{4-[1-(2,2-dimethylpropanoyl)piperidin-4-yl]phenyl}-1-(6-methylpyridazin-3-yl)pyrrolidine-3-carboxamide;
(3S)—N-[4-(1-benzoylpiperidin-4-yl)phenyl]-1-(4-methylpyridazin-3-yl)pyrrolidine-3-carboxamide;
(3S)—N-{4-[1-(2,2-dimethylpropanoyl)piperidin-4-yl]phenyl}-1-(4-methylpyridazin-3-yl)pyrrolidine-3-carboxamide; and pharmaceutically acceptable salts thereof.

Pharmaceutical Compositions, Combination Therapies, Methods of Treatment, and Administration Another embodiment comprises pharmaceutical compositions comprising a compound having Formula (I) and an excipient.

Still another embodiment comprises methods of treating cancer in a mammal comprising administering thereto a therapeutically acceptable amount of a compound having Formula (I).

Still another embodiment pertains to compositions for treating diseases during which NAMPT is expressed, said compositions comprising an excipient and a therapeutically effective amount of the compound having Formula (I).

Still another embodiment pertains to methods of treating disease in a patient during which NAMPT is expressed, said methods comprising administering to the patient a therapeutically effective amount of a compound having Formula (I).

Still another embodiment pertains to compositions for treating inflammatory and tissue repair disorders; particularly rheumatoid arthritis, inflammatory bowel disease, asthma and COPD (chronic obstructive pulmonary disease), osteoarthritis, osteoporosis and fibrotic diseases; dermatosis, including psoriasis, atopic dermatitis and ultra-violet induced skin damage; autoimmune diseases including systemic lupus erythematosis, multiple sclerosis, psoriatic arthritis, ankylosing spondylitis, tissue and organ rejection, Alzheimer's disease, stroke, athersclerosis, restenosis, diabetes, glomerulonephritis, cancer, particularly wherein the cancer is selected from breast, prostate, lung, colon, cervix, ovary, skin, CNS, bladder, pancreas, leukemia, lymphoma or Hodgkin's disease, cachexia, inflammation associated with infection and certain viral infections, including Acquired Immune Deficiency Syndrome (AIDS), adult respiratory distress syndrome, and ataxia telengiectasia, said compositions comprising an excipient and a therapeutically effective amount of the compound having Formula (I).

Still another embodiment pertains to methods of treating inflammatory and tissue repair disorders; particularly rheumatoid arthritis, inflammatory bowel disease, asthma and COPD (chronic obstructive pulmonary disease), osteoarthritis, osteoporosis and fibrotic diseases; dermatosis, including psoriasis, atopic dermatitis and ultra-violet induced skin damage; autoimmune diseases including systemic lupus erythematosis, multiple sclerosis, psoriatic arthritis, ankylosing spondylitis, tissue and organ rejection, Alzheimer's disease, stroke, athersclerosis, restenosis, diabetes, glomerulonephritis, cancer, particularly wherein the cancer is selected from breast, prostate, lung, colon, cervix, ovary, skin, CNS, bladder, pancreas, leukemia, lymphoma or Hodgkin's disease, cachexia, inflammation associated with infection and certain viral infections, including Acquired Immune Deficiency Syndrome (AIDS), adult respiratory distress syndrome, and ataxia telengiectasia in a patient, said methods comprising administering to the patient a therapeutically effective amount of a compound having Formula (I).

Still another embodiment pertains to compositions for treating diseases during which NAMPT is expressed, said compositions comprising an excipient and a therapeutically effective amount of the compound having Formula (I) and a therapeutically effective amount of one additional therapeutic agent or more than one additional therapeutic agent.

Still another embodiment pertains to methods of treating disease in a patient during which NAMPT is expressed, said methods comprising administering to the patient a therapeutically effective amount of a compound having Formula (I) and a therapeutically effective amount of one additional therapeutic agent or more than one additional therapeutic agent.

Still another embodiment pertains to compositions for treating inflammatory and tissue repair disorders; particularly rheumatoid arthritis, inflammatory bowel disease, asthma and COPD (chronic obstructive pulmonary disease), osteoarthritis, osteoporosis and fibrotic diseases; dermatosis, including psoriasis, atopic dermatitis and ultra-violet induced skin damage; autoimmune diseases including systemic lupus erythematosis, multiple sclerosis, psoriatic arthritis, ankylosing spondylitis, tissue and organ rejection, Alzheimer's disease, stroke, athersclerosis, restenosis, diabetes, glomerulonephritis, cancer, particularly wherein the cancer is selected from breast, prostate, lung, colon, cervix, ovary, skin, CNS, bladder, pancreas, leukemia, lymphoma or Hodgkin's disease, cachexia, inflammation associated with infection and certain viral infections, including Acquired Immune Deficiency Syndrome (AIDS), adult respiratory distress syndrome, and ataxia telengiectasia, said compositions comprising an excipient and a therapeutically effective amount of the compound having Formula (I) and a therapeutically effective amount of one additional therapeutic agent or more than one additional therapeutic agent.

Still another embodiment pertains to methods of treating inflammatory and tissue repair disorders; particularly rheumatoid arthritis, inflammatory bowel disease, asthma and COPD (chronic obstructive pulmonary disease), osteoarthritis, osteoporosis and fibrotic diseases; dermatosis, including psoriasis, atopic dermatitis and ultra-violet induced skin damage; autoimmune diseases including systemic lupus erythematosis, multiple sclerosis, psoriatic arthritis, ankylosing spondylitis, tissue and organ rejection, Alzheimer's disease, stroke, atherosclerosis, restenosis, diabetes, glomerulonephritis, cancer, particularly wherein the cancer is selected from breast, prostate, lung, colon, cervix, ovary, skin, CNS, bladder, pancreas, leukemia, lymphoma or Hodgkin's disease, cachexia, inflammation associated with infection and certain viral infections, including Acquired Immune Deficiency Syndrome (AIDS), adult respiratory distress syndrome, and ataxia telengiectasia in a patient, said methods comprising administering to the patient a therapeutically effective amount of the compound having Formula (I) and a therapeutically effective amount of one additional therapeutic agent or more than one additional therapeutic agent.

Metabolites of compounds having Formula (I), produced by in vitro or in vivo metabolic processes, may also have utility for treating diseases associated with NAMPT.

Certain precursor compounds which may be metabolized in vitro or in vivo to form compounds having Formula (I) may also have utility for treating diseases associated with NAMPT.

Compounds having Formula (I) may exist as acid addition salts, basic addition salts or zwitterions. Salts of the compounds are prepared during isolation or following purification of the compounds. Acid addition salts of the compounds are those derived from the reaction of the compounds with an acid. For example, the acetate, adipate, alginate, bicarbonate, citrate, aspartate, benzoate, benzenesulfonate, bisulfate, butyrate, camphorate, camphorsulfonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetic, trifluoroacetic, para-toluenesulfonate, and undecanoate salts of the compounds are contemplated as being embraced by this invention. Basic addition salts of the compounds are those derived from the reaction of the compounds with the hydroxide, carbonate or bicarbonate of cations such as lithium, sodium, potassium, calcium, and magnesium.

The compounds having Formula (I) may be administered, for example, bucally, ophthalmically, orally, osmotically, parenterally (intramuscularly, intraperitoneally intrasternally, intravenously, subcutaneously), rectally, topically, transdermally or vaginally.

Therapeutically effective amounts of compounds having Formula (I) depend on the recipient of the treatment, the disorder being treated and the severity thereof, the composition containing the compound, the time of administration, the route of administration, the duration of treatment, the compound potency, its rate of clearance and whether or not another drug is co-administered. The amount of a compound of this invention having Formula (I) used to make a composition to be administered daily to a patient in a single dose or in divided doses is from about 0.03 to about 200 mg/kg body weight. Single dose compositions contain these amounts or a combination of submultiples thereof.

Compounds having Formula (I) may be administered with or without an excipient. Excipients include, for example, encapsulating materials or additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof.

Excipients for preparation of compositions comprising a compound having Formula (I) to be administered orally in solid dosage form include, for example, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl cellulose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, and mixtures thereof. Excipients for preparation of compositions comprising a compound of this invention having Formula (I) to be administered ophthalmically or orally in liquid dosage forms include, for example, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water and mixtures thereof. Excipients for preparation of compositions comprising a compound of this invention having Formula (I) to be administered osmotically include, for example, chlorofluorohydrocarbons, ethanol, water and mixtures thereof. Excipients for preparation of compositions comprising a compound of this invention having Formula (I) to be administered parenterally include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water and mixtures thereof. Excipients for preparation of compositions comprising a compound of this invention having Formula (I) to be administered rectally or vaginally include, for example, cocoa butter, polyethylene glycol, wax and mixtures thereof.

Compounds having Formula (I) are expected to be useful when used with alkylating agents, angiogenesis inhibitors, antibodies, antimetabolites, antimitotics, antiproliferatives, antivirals, aurora kinase inhibitors, apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (PI3K) inhibitors, proteosome inhibitors, purine analogs, pyrimidine analogs, receptor tyrosine kinase inhibitors, retinoids/deltoids plant alkaloids, small inhibitory ribonucleic acids (siRNAs), topoisomerase inhibitors, ubiquitin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B.

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand.

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, trofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemeterxed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, peliterxol, pentostatin, raltitrexed, Ribavirin, triapine, trimeterxate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl) propyl)amino)-3-nitrobenzenesulfonamide) (ABT-737), N-(4-(44(2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax) and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecific antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FCl, PU-3, radicicol, SNX-2112, STA-9090 VER49009 and the like.

Inhibitors of inhibitors of apoptosis proteins include HGS1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-011-vcMMAE, PSMA-ADC, MEDI-547, SGN-19 Am SGN-35, SGN-75 and the like Activators of death receptor pathway include TRAIL, antibodies or other agents that target TRAIL or death receptors (e.g., DR4 and DR5) such as Apomab, conatumumab, ETR2-ST01, GDC0145 (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474) and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirbucin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab, CD20 antibodies types I and II and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-n1, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofiran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds having Formula (I) may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EP0906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimeterxate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (*Streptomyces staurospores*), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

Data

Determination of the utility of compounds having Formula (I) as binders to and inhibitors of NAMPT was performed using Time-Resolved Fluorescence Resonance Energy Transfer (TR-FRET) binding assays.

Time-Resolved Fluorescence Resonance Energy Transfer (TR-FRET) Binding Assay of NAMPT Test compounds were serially diluted (typically 11 half log dilutions) in neat DMSO to 50× final concentrations prior to dilution with assay buffer (50 mM HEPES (NaOH), pH 7.5, 100 mM NaCl, 10 mM $MgCl_2$, 1 mM DTT, 1% Glycerol) to 3× and 6% DMSO. Six μL were transferred to 384-well low-volume plates (Owens Corning #3673). To this, 12 μL of a 1.5× solution containing enzyme, probe and antibody were added. Final concentrations in the 18 μL, reactions were 1× assay buffer, 2% DMSO, 6.8 nM NAMPT (human, recombinant, C-terminally His-tagged), 200 nM probe (a potent nicotinamide-competitive inhibitor conjugated to Oregon Green 488) and 1 nM Tb-anti-His antibody (Invitrogen #PV5895). Reactions were equilibrated at room temperature for 3 hours prior to reading on an Envision multi-label plate reader (Perkin Elmer; Ex=337 nm, Em=520 and 495 nm). Time-resolved FRET ratios ($Em_{520}/Em_{495}$) were normalized to controls, plotted as a function of compound concentration and fit with the four-parameter logistic equation to determine IC50s.

Time-Resolved Fluorescence Resonance Energy Transfer (TR-FRET) Binding Assay of NAMPT with PRPP Compound handling and data processing were identical to the assay in the absence of substrates (above). Final concentrations were 1× assay buffer, 2% DMSO, 2 nM NAMPT, 2 nM probe, 1 nM Tb-anti-His antibody (Invitrogen #PV5895), 200 uM PRPP and 2.5 mM ATP. Reactions were equilibrated for 16 hours prior to measurement to allow for potential enzymatic modification of test compounds.

Table 1 shows the utility of compounds having Formula I to functionally inhibit NAMPT.

TABLE 1

| Example | TR-FRET Binding-IC50 (μM) | TR-FRET Binding-IC50 (with PRPP) (μM) |
|---|---|---|
| 1 | 0.120000 | 0.000386 |
| 2 | 0.022300 | 0.020000 |
| 3 | 0.357000 | 0.019200 |
| 4 | 0.424000 | 0.024000 |
| 5 | 0.107000 | 0.010200 |
| 6 | 0.544000 | 0.002340 |
| 7 | 0.104000 | 0.084700 |
| 8 | 3.360000 | 0.005300 |
| 9 | 8.620000 | 0.017200 |
| 10 | 0.034500 | 0.000518 |

TABLE 1-continued

| Example | TR-FRET Binding-IC50 (μM) | TR-FRET Binding-IC50 (with PRPP) (μM) |
|---|---|---|
| 11 | 2.370000 | 0.001930 |
| 12 | 1.410000 | 0.002050 |
| 13 | 0.858000 | 0.002880 |
| 14 | 3.840000 | 0.003080 |
| 15 | 1.660000 | 0.002490 |
| 16 | 2.480000 | 0.004130 |
| 17 | 3.510000 | 0.002360 |
| 18 | 2.740000 | 0.005320 |
| 19 | 1.170000 | 0.000554 |
| 20 | 0.006740 | 0.000296 |
| 21 | 7.380000 | 0.000507 |
| 22 | 0.011700 | 0.000169 |
| 23 | 1.950000 | 0.000610 |
| 24 | 5.880000 | 0.000861 |
| 25 | 0.028100 | 0.000598 |
| 26 | 0.005050 | 0.000761 |
| 27 | nd | 0.011200 |
| 28 | nd | 0.002510 |
| 29 | 0.079800 | 0.016700 |
| 30 | 0.015000 | 0.000267 |
| 31 | 0.135000 | 0.000693 |
| 32 | 0.010200 | 0.000284 |
| 33 | 0.109000 | 0.000342 |
| 34 | 0.071400 | 0.000886 |
| 35 | 0.091600 | 0.000866 |
| 36 | 0.040100 | 0.000882 |
| 37 | 0.068900 | 0.000983 |
| 38 | 0.046500 | 0.000900 |
| 39 | 0.104000 | 0.001050 |
| 40 | 0.042800 | 0.000490 |
| 41 | 0.069200 | 0.000780 |
| 42 | 0.226000 | 0.002390 |
| 43 | 0.086500 | 0.000803 |
| 44 | 0.138000 | 0.001010 |
| 45 | 0.087300 | 0.001080 |
| 46 | 0.093400 | 0.001020 |
| 47 | 0.080500 | 0.001780 |
| 48 | 0.112000 | 0.000861 |
| 49 | 0.066100 | 0.001020 |
| 50 | 0.063500 | 0.001100 |
| 51 | 0.109000 | 0.001170 |
| 52 | 0.051000 | 0.000696 |
| 53 | 0.025600 | 0.000689 |
| 54 | 0.072100 | 0.000806 |
| 55 | 0.168000 | 0.002220 |
| 56 | 0.360000 | 0.000812 |
| 57 | 0.180000 | 0.001070 |
| 58 | 0.059500 | 0.000683 |
| 59 | 0.027900 | 0.000606 |
| 60 | 0.150000 | 0.001010 |
| 61 | 0.033700 | 0.000675 |
| 62 | 0.041600 | 0.000666 |
| 63 | 0.052700 | 0.000514 |
| 64 | 0.055200 | 0.000927 |
| 65 | 0.121000 | 0.000704 |
| 66 | 0.056600 | 0.000535 |
| 67 | 0.452000 | 0.000497 |
| 68 | 0.080600 | 0.000569 |
| 69 | 0.068600 | 0.000918 |
| 70 | 0.035700 | 0.000742 |
| 71 | 0.041200 | 0.014600 |
| 72 | 0.006540 | 0.007340 |
| 73 | 0.224000 | 0.071100 |
| 74 | 0.911000 | 0.000666 |
| 75 | 1.340000 | 0.000719 |
| 76 | 1.920000 | 0.000440 |
| 77 | 3.010000 | 0.000832 |
| 78 | 0.265000 | 0.000632 |
| 79 | 2.690000 | 0.000824 |
| 80 | 1.600000 | 0.000686 |
| 81 | 3.720000 | 0.001130 |
| 82 | 0.955000 | 0.000526 |
| 83 | 1.210000 | 0.000503 |
| 84 | 6.070000 | 0.001810 |
| 85 | 0.032200 | 0.017000 |
| 86 | 1.260000 | 0.000833 |
| 87 | 1.390000 | 0.001270 |
| 88 | 0.574000 | 0.000640 |
| 89 | 2.000000 | 0.000647 |
| 90 | 1.410000 | 0.000902 |
| 91 | 0.992000 | 0.000868 |
| 92 | 0.784000 | 0.000548 |
| 93 | 1.220000 | 0.001250 |
| 94 | 2.270000 | 0.001030 |
| 95 | 1.360000 | 0.001020 |
| 96 | 0.115000 | 0.282000 |
| 97 | 0.036600 | 0.131000 |
| 98 | 0.013000 | 0.000209 |
| 99 | 0.013500 | 0.000169 |
| 100 | 0.030600 | 0.000497 |
| 101 | 0.016500 | 0.000486 |
| 102 | 0.008840 | 0.000210 |
| 103 | 0.056200 | 0.000493 |
| 104 | 0.001200 | 0.000193 |
| 105 | 0.296000 | 0.000244 |
| 106 | 0.160000 | 0.000221 |
| 107 | 0.163000 | 0.000169 |
| 108 | 0.003330 | 0.000176 |
| 109 | 0.005030 | 0.000398 |
| 110 | 0.006630 | 0.000169 |
| 111 | 0.002840 | 0.000199 |
| 112 | 0.040200 | 0.000362 |
| 113 | 0.060600 | 0.000254 |
| 114 | 0.083900 | 0.000247 |
| 115 | 0.048200 | 0.000178 |
| 116 | 0.026500 | 0.000204 |
| 117 | 0.006270 | 0.000355 |
| 118 | 0.014100 | 0.000169 |
| 119 | 0.006120 | 0.000169 |
| 120 | 0.011600 | 0.000294 |
| 121 | 0.009940 | 0.000169 |
| 122 | 0.007940 | 0.000169 |
| 123 | 0.065600 | 0.000282 |
| 124 | 0.123000 | 0.000278 |
| 125 | 0.015400 | 0.000518 |
| 126 | 0.014900 | 0.000359 |
| 127 | 0.003640 | 0.000391 |
| 128 | 0.008360 | 0.000610 |
| 129 | 0.004490 | 0.000367 |
| 130 | 0.288000 | 0.000535 |
| 131 | 0.069900 | 0.000474 |
| 132 | 0.008460 | 0.000441 |
| 133 | 0.012000 | 0.000626 |
| 134 | 0.016900 | 0.000361 |
| 135 | 0.033900 | 0.000293 |
| 136 | 0.020400 | 0.000635 |
| 137 | 0.017600 | 0.000459 |
| 138 | 0.021800 | 0.000445 |
| 139 | 0.012000 | 0.000473 |
| 140 | 0.011000 | 0.008870 |
| 141 | 1.240000 | 0.075200 |
| 142 | 1.560000 | 0.032800 |
| 143 | 0.017000 | 0.031100 |
| 144 | 0.014600 | 0.034400 |
| 145 | 0.040600 | 0.058100 |
| 146 | 0.065900 | 0.109000 |
| 147 | 0.034600 | 0.001470 |
| 148 | 0.042900 | 0.020100 |
| 149 | 0.020700 | 0.054300 |
| 150 | 0.006530 | 0.043800 |
| 151 | 0.017400 | 0.043600 |
| 152 | 0.087600 | 0.101000 |
| 153 | 0.266000 | 0.122000 |
| 154 | 0.524000 | 0.016100 |

TABLE 1-continued

| Example | TR-FRET Binding-IC50 (μM) | TR-FRET Binding-IC50 (with PRPP) (μM) |
|---|---|---|
| 155 | 0.294000 | 0.044000 |
| 156 | 0.396000 | 0.084300 |
| 157 | 1.070000 | 0.192000 |
| 158 | 2.900000 | 0.224000 |
| 159 | 0.137000 | 0.061200 |
| 160 | 0.074500 | 0.070800 |
| 161 | 0.128000 | 0.059700 |
| 162 | 0.144000 | 0.071000 |
| 163 | 0.166000 | 0.083100 |
| 164 | 0.987000 | 0.124000 |
| 165 | 0.035200 | 0.068300 |
| 166 | 2.270000 | 0.206000 |
| 167 | 3.740000 | 0.204000 |
| 168 | 2.940000 | 0.171000 |
| 169 | 0.033700 | 0.067900 |
| 170 | 0.091500 | 0.089800 |
| 171 | 0.019700 | 0.037900 |
| 172 | 0.286000 | 0.170000 |
| 173 | 0.524000 | 0.154000 |
| 174 | 2.100000 | 0.158000 |
| 175 | 0.664000 | 0.161000 |
| 176 | 0.165000 | 0.111000 |
| 177 | 0.060400 | 0.091300 |
| 178 | 0.247000 | 0.065200 |
| 179 | 0.099200 | 0.070700 |
| 180 | 0.304000 | 0.123000 |
| 181 | 0.284000 | 0.128000 |
| 182 | 0.140000 | 0.104000 |
| 183 | 1.040000 | 0.185000 |
| 184 | 0.625000 | 0.078900 |
| 185 | 0.081300 | 0.044100 |
| 186 | 0.098900 | 0.118000 |
| 187 | 0.010200 | 0.027300 |
| 188 | 0.020500 | 0.049900 |
| 189 | 0.006910 | 0.026900 |
| 190 | 1.910000 | 0.103000 |
| 191 | 0.743000 | 0.184000 |
| 192 | 0.047300 | 0.072300 |
| 193 | 0.040200 | 0.054000 |
| 194 | 0.122000 | 0.062600 |
| 195 | 0.305000 | 0.094100 |
| 196 | 0.083800 | 0.098500 |
| 197 | 0.126000 | 0.079800 |
| 198 | 0.084500 | 0.103000 |
| 199 | 0.033700 | 0.028000 |
| 200 | 0.033100 | 0.034400 |
| 201 | 0.012100 | 0.018200 |
| 202 | 0.117000 | 0.089500 |
| 203 | 0.034200 | 0.021100 |
| 204 | 0.380000 | 0.002760 |
| 205 | 0.025100 | 0.034000 |
| 206 | 0.023800 | 0.024100 |
| 207 | 0.141000 | 0.086700 |
| 208 | 0.117000 | 0.049600 |
| 209 | 0.061700 | 0.028900 |
| 210 | 0.031700 | 0.038300 |
| 211 | 0.031900 | 0.000801 |
| 212 | 0.070400 | 0.000787 |
| 213 | 0.104000 | 0.000678 |
| 214 | 0.165000 | 0.000841 |
| 215 | 0.068200 | 0.001140 |
| 216 | 0.228000 | 0.001410 |
| 217 | 0.043900 | 0.001510 |
| 218 | 0.265000 | 0.001640 |
| 219 | 0.105000 | 0.000480 |
| 220 | 0.267000 | 0.001010 |
| 221 | 0.164000 | 0.000576 |
| 222 | 0.215000 | 0.001030 |
| 223 | 0.150000 | 0.000959 |
| 224 | 0.151000 | 0.001390 |
| 225 | 0.158000 | 0.001070 |
| 226 | 0.242000 | 0.000896 |
| 227 | 0.065900 | 0.000696 |
| 228 | 0.054600 | 0.000911 |
| 229 | 0.048000 | 0.000584 |
| 230 | 0.158000 | 0.000843 |
| 231 | 0.174000 | 0.000831 |
| 232 | 0.141000 | 0.000563 |
| 233 | 0.113000 | 0.000614 |
| 234 | 0.185000 | 0.000730 |
| 235 | 0.283000 | 0.001410 |
| 236 | 0.130000 | 0.001110 |
| 237 | 0.240000 | 0.001270 |
| 238 | 0.207000 | 0.000554 |
| 239 | 0.112000 | 0.000833 |
| 240 | 0.192000 | 0.000925 |
| 241 | 0.131000 | 0.000811 |
| 242 | 0.278000 | 0.001170 |
| 243 | 0.269000 | 0.000970 |
| 244 | 0.449000 | 0.000916 |
| 245 | 0.101000 | 0.000707 |
| 246 | 0.178000 | 0.000676 |
| 247 | 0.086000 | 0.001020 |
| 248 | 0.082600 | 0.000817 |
| 249 | 0.059900 | 0.000600 |
| 250 | 0.107000 | 0.000641 |
| 251 | 0.230000 | 0.000880 |
| 252 | 0.238000 | 0.001100 |
| 253 | 0.134000 | 0.000639 |
| 254 | 0.033900 | 0.011200 |
| 255 | 0.047300 | 0.037800 |
| 256 | 0.091100 | 0.038400 |
| 257 | 0.064700 | 0.041900 |
| 258 | 0.108000 | 0.034800 |
| 259 | 0.032500 | 0.017700 |
| 260 | 0.075400 | 0.019000 |
| 261 | 0.062900 | 0.023700 |
| 262 | 0.130000 | 0.034300 |
| 263 | 0.031300 | 0.020200 |
| 264 | 0.052800 | 0.013400 |
| 265 | 0.029500 | 0.021800 |
| 266 | 0.120000 | 0.053200 |
| 267 | 0.274000 | 0.056500 |
| 268 | 0.119000 | 0.042100 |
| 269 | 0.037700 | 0.022300 |
| 270 | 0.074800 | 0.035700 |
| 271 | 0.078000 | 0.025200 |
| 272 | 0.165000 | 0.052400 |
| 273 | 0.128000 | 0.042100 |
| 274 | 0.152000 | 0.064500 |
| 275 | 0.231000 | 0.045100 |
| 276 | 0.134000 | 0.034900 |
| 277 | 0.062400 | 0.026700 |
| 278 | 0.075800 | 0.033400 |
| 279 | 0.020200 | 0.015500 |
| 280 | 0.123000 | 0.051900 |
| 281 | 0.020500 | 0.014900 |
| 282 | 0.383000 | 0.090000 |
| 283 | 0.072300 | 0.032200 |
| 284 | 0.062400 | 0.038200 |
| 285 | 0.149000 | 0.086200 |
| 286 | 0.127000 | 0.066400 |
| 287 | 0.125000 | 0.063200 |
| 288 | 0.044900 | 0.019500 |
| 289 | 0.041600 | 0.032100 |
| 290 | 0.099300 | 0.045700 |
| 291 | 0.045600 | 0.018200 |
| 292 | 0.099000 | 0.064700 |
| 293 | 0.078200 | 0.025300 |
| 294 | 0.112000 | 0.055100 |
| 295 | 0.077600 | 0.051000 |
| 296 | 0.149000 | 0.057100 |
| 297 | 0.104000 | 0.047000 |
| 298 | 0.192000 | 0.061100 |

TABLE 1-continued

| Example | TR-FRET Binding-IC50 (μM) | TR-FRET Binding-IC50 (with PRPP) (μM) |
|---|---|---|
| 299 | 0.154000 | 0.086900 |
| 300 | 0.064200 | 0.039100 |
| 301 | 0.143000 | 0.048300 |
| 302 | 0.150000 | 0.048300 |
| 303 | 0.030900 | 0.015500 |
| 304 | 0.055400 | 0.024200 |
| 305 | 0.109000 | 0.035000 |
| 306 | 0.112000 | 0.046300 |
| 307 | 0.037700 | 0.015900 |
| 308 | 0.036900 | 0.018400 |
| 309 | 4.150000 | 0.000293 |
| 310 | 0.456000 | 0.005370 |
| 311 | 0.030200 | 0.003960 |
| 312 | 1.130000 | 0.008940 |
| 313 | 0.217000 | 0.004130 |
| 314 | 3.860000 | 0.000572 |
| 315 | 0.469000 | 0.000641 |
| 316 | 0.104000 | 0.000924 |
| 317 | 0.043900 | 0.000991 |
| 318 | 0.037700 | 0.000716 |
| 319 | 0.024900 | 0.000747 |
| 320 | 0.026400 | 0.000611 |
| 321 | 0.038700 | 0.000864 |
| 322 | 0.028600 | 0.000843 |
| 323 | 0.025300 | 0.000885 |
| 324 | 0.047300 | 0.001040 |
| 325 | 0.014000 | 0.001080 |
| 326 | 0.018300 | 0.000626 |
| 327 | 0.012600 | 0.000655 |
| 328 | 0.012200 | 0.000614 |
| 329 | 0.024200 | 0.000616 |
| 330 | 0.031700 | 0.000887 |
| 331 | 0.024900 | 0.000830 |
| 332 | 0.021900 | 0.000699 |
| 333 | 0.050900 | 0.000631 |
| 334 | 0.018200 | 0.000578 |
| 335 | 0.210000 | 0.001020 |
| 336 | 0.077300 | 0.000494 |
| 337 | 0.050000 | 0.000522 |
| 338 | 0.027600 | 0.000520 |
| 339 | 0.017900 | 0.000663 |
| 340 | 0.017600 | 0.000722 |
| 341 | 0.035100 | 0.000727 |
| 342 | 0.013100 | 0.000698 |
| 343 | 0.006180 | 0.000728 |
| 344 | 0.037800 | 0.000569 |
| 345 | 0.009540 | 0.000392 |
| 346 | 0.030800 | 0.000457 |
| 347 | 0.066200 | 0.000940 |
| 348 | 0.015300 | 0.000628 |
| 349 | 0.059500 | 0.000738 |
| 350 | 0.004620 | 0.000642 |
| 351 | 0.037100 | 0.000765 |
| 352 | 0.095800 | 0.000615 |
| 353 | 0.088200 | 0.000472 |
| 354 | 0.082800 | 0.000837 |
| 355 | 0.115000 | 0.000986 |
| 356 | 0.067700 | 0.000878 |
| 357 | 0.017700 | 0.001140 |
| 358 | 0.015900 | 0.000815 |
| 359 | 0.021300 | 0.000869 |
| 360 | 0.022000 | 0.000782 |
| 361 | 0.037400 | 0.000988 |
| 362 | 0.015200 | 0.000832 |
| 363 | 0.010400 | 0.000798 |
| 364 | 0.036900 | 0.000334 |
| 365 | 0.050100 | 0.001050 |
| 366 | 0.035100 | 0.000681 |
| 367 | 0.033700 | 0.000735 |
| 368 | 0.064000 | 0.000635 |
| 369 | 0.018300 | 0.000479 |
| 370 | 0.030535 | 0.000555 |
| 371 | 0.056700 | 0.000438 |
| 372 | 0.016600 | 0.000633 |
| 373 | 0.022400 | 0.000576 |
| 374 | 0.023900 | 0.000973 |
| 375 | 0.006720 | 0.000679 |
| 376 | 0.003220 | 0.000468 |
| 377 | 0.016200 | 0.000632 |
| 378 | 0.077100 | 0.000632 |
| 379 | 0.015900 | 0.000432 |
| 380 | 0.109000 | 0.000883 |
| 381 | 0.015100 | 0.001130 |
| 382 | 0.065800 | 0.000657 |
| 383 | 0.103000 | 0.000859 |
| 384 | 0.028800 | 0.000497 |
| 385 | 0.055100 | 0.001240 |
| 528 | 0.026200 | 0.017300 | nd = no data

NAMPT Cell Proliferation Assay

PC3 cells were seeded in 96-well black plates (Corning #3904) at 500 cells/well in 90 μl of RPMI media containing 10% heat-inactivated FBS and incubated overnight at 37° C. and 5% $CO_2$ to allow cells to attach to wells. The following day, test compounds were serially diluted in neat DMSO to 1000× final concentrations prior to dilution with RPMI media to 10× and 1% DMSO. Ten μL of the 10× compounds were then transferred to wells containing cells to produce a dose response of 10-fold dilutions from 10 μM to $1×10^{-5}$ μM. Cells were incubated for 5 days at 37° C. and 5% $CO_2$, then cell viability was measured using Cell Titer Glo reagent (Promega #G7571). Percent inhibition values were calculated and fitted to a sigmoidal dose response curves using Assay Explorer software to determine IC50s. To assess whether inhibition of cell viability was due to NAMPT inhibition, the proliferation assay was also performed in the presence of 0.3 mM nicotinamide mononucleotide.

Table 2 shows the results of the cell proliferation assay.

TABLE 2

| Example | Cell Titer-Glo - IC50 (μM) |
|---|---|
| 1 | 0.00656 |
| 2 | >10 |
| 3 | 7.33 |
| 4 | 0.112 |
| 5 | 0.00675 |
| 6 | 0.0677 |
| 7 | 0.876 |
| 8 | 0.0708 |
| 9 | 0.739 |
| 10 | 0.00184 |
| 11 | 0.0227 |
| 12 | 0.0844 |
| 13 | 0.0791 |
| 14 | 0.0548 |
| 15 | 0.0347 |
| 16 | 0.0926 |
| 17 | 0.0937 |
| 18 | 0.148 |
| 19 | 0.0564 |

TABLE 2-continued

| Example | Cell Titer-Glo - IC50 (μM) |
|---|---|
| 20 | 0.00028 |
| 21 | 0.15 |
| 22 | 0.00125 |
| 23 | 0.0725 |
| 24 | 0.169 |
| 25 | 0.00141 |
| 26 | 0.000682 |
| 27 | >10 |
| 28 | >10 |
| 29 | 0.135 |
| 30 | 0.00197 |
| 31 | 0.0069 |
| 32 | 0.00654 |
| 33 | 0.00366 |
| 34 | 0.0068 |
| 35 | 0.00692 |
| 36 | 0.00966 |
| 37 | 0.00648 |
| 38 | 0.00639 |
| 39 | 0.00738 |
| 40 | 0.00217 |
| 41 | 0.00376 |
| 42 | 0.0646 |
| 43 | 0.00688 |
| 44 | 0.00547 |
| 45 | 0.00677 |
| 46 | 0.00301 |
| 47 | 0.00335 |
| 48 | 0.00288 |
| 49 | 0.00696 |
| 50 | 0.00895 |
| 51 | 0.00362 |
| 52 | 0.00628 |
| 53 | 0.00367 |
| 54 | 0.00331 |
| 55 | 0.0211 |
| 56 | 0.00927 |
| 57 | 0.00875 |
| 58 | 0.00648 |
| 59 | 0.00614 |
| 60 | 0.00507 |
| 61 | 0.00352 |
| 62 | 0.0142 |
| 63 | 0.00635 |
| 64 | 0.00632 |
| 65 | 0.00638 |
| 66 | 0.00581 |
| 67 | 0.386 |
| 68 | 0.00354 |
| 69 | 0.00422 |
| 70 | 0.00397 |
| 71 | 0.0729 |
| 72 | 0.00569 |
| 73 | 1.98 |
| 74 | 0.0114 |
| 75 | nd |
| 76 | 0.0191 |
| 77 | nd |
| 78 | 0.0212 |
| 79 | nd |
| 80 | 0.0255 |
| 81 | nd |
| 82 | 0.00955 |
| 83 | nd |
| 84 | 0.0389 |
| 85 | 0.0205 |
| 86 | 0.0697 |
| 87 | 0.0317 |
| 88 | 0.0663 |
| 89 | 0.0646 |
| 90 | 0.0601 |
| 91 | 0.0599 |
| 92 | 0.024 |
| 93 | 0.0584 |
| 94 | 0.0657 |
| 95 | 0.0739 |
| 96 | 7.61 |
| 97 | 0.922 |
| 98 | 0.00605 |
| 99 | 0.00572 |
| 100 | 0.00613 |
| 101 | 0.00031 |
| 102 | 0.00059 |
| 103 | 0.00144 |
| 104 | 0.00018 |
| 105 | 0.00617 |
| 106 | 0.0618 |
| 107 | 0.00688 |
| 108 | 0.00013 |
| 109 | 0.00066 |
| 110 | 0.00026 |
| 111 | 0.00064 |
| 112 | 0.00076 |
| 113 | 0.00634 |
| 114 | 0.0181 |
| 115 | 0.0004 |
| 116 | 0.00064 |
| 117 | 0.00063 |
| 118 | 0.00022 |
| 119 | 0.00019 |
| 120 | 0.00023 |
| 121 | 0.00062 |
| 122 | 0.00061 |
| 123 | 0.00103 |
| 124 | 0.00144 |
| 125 | 0.00024 |
| 126 | 0.00026 |
| 127 | 0.00014 |
| 128 | 0.00016 |
| 129 | 0.00016 |
| 130 | 0.00181 |
| 131 | 0.0003 |
| 132 | 0.00023 |
| 133 | 0.00062 |
| 134 | 0.00064 |
| 135 | 0.0003 |
| 136 | 0.00023 |
| 137 | 0.00031 |
| 138 | 0.00023 |
| 139 | 0.00018 |
| 140 | 0.00354 |
| 141 | 0.834 |
| 142 | 0.7406 |
| 143 | 0.00496 |
| 144 | 0.0184 |
| 145 | 0.0709 |
| 146 | 0.0707 |
| 147 | 0.00095 |
| 148 | 0.0761 |
| 149 | 0.058 |
| 150 | 0.0589 |
| 151 | 0.0609 |
| 152 | 0.116 |
| 153 | 0.699 |
| 154 | 0.803 |
| 155 | 0.701 |
| 156 | 0.712 |
| 157 | 0.948 |
| 158 | 1.3 |
| 159 | 0.182 |
| 160 | 0.173 |
| 161 | 0.213 |
| 162 | 0.225 |
| 163 | 0.12 |
| 164 | 0.202 |
| 165 | 0.0682 |
| 166 | 1.07 |
| 167 | 6.25 |
| 168 | 1.01 |
| 169 | 0.0654 |
| 170 | 0.0655 |
| 171 | 0.0681 |

TABLE 2-continued

| Example | Cell Titer-Glo - IC50 (μM) |
|---|---|
| 172 | 0.329 |
| 173 | 0.627 |
| 174 | 1.13 |
| 175 | 0.683 |
| 176 | 0.218 |
| 177 | 0.107 |
| 178 | 0.3 |
| 179 | 0.192 |
| 180 | 0.164 |
| 181 | 0.238 |
| 182 | 0.0879 |
| 183 | 0.346 |
| 184 | 0.604 |
| 185 | 0.0742 |
| 186 | 0.627 |
| 187 | 0.0206 |
| 188 | 0.0224 |
| 189 | 0.0146 |
| 190 | 0.694 |
| 191 | 0.677 |
| 192 | 0.0693 |
| 193 | 0.071 |
| 194 | 0.124 |
| 195 | 0.701 |
| 196 | 0.111 |
| 197 | 0.103 |
| 198 | 0.0716 |
| 199 | 0.0974 |
| 200 | 0.0719 |
| 201 | 0.0609 |
| 202 | 0.168 |
| 203 | 0.606 |
| 204 | 0.0245 |
| 205 | 0.0387 |
| 206 | 0.0674 |
| 207 | 0.671 |
| 208 | 0.593 |
| 209 | 0.0816 |
| 210 | 0.0627 |
| 211 | 0.00594 |
| 212 | 0.00579 |
| 213 | 0.00688 |
| 214 | 0.00909 |
| 215 | 0.00695 |
| 216 | 0.00599 |
| 217 | 0.00255 |
| 218 | 0.00886 |
| 219 | 0.00886 |
| 220 | 0.0132 |
| 221 | 0.00899 |
| 222 | 0.0155 |
| 223 | 0.0055 |
| 224 | 0.00752 |
| 225 | 0.00876 |
| 226 | 0.00889 |
| 227 | 0.00453 |
| 228 | 0.00597 |
| 229 | 0.00646 |
| 230 | 0.00905 |
| 231 | 0.00875 |
| 232 | 0.00874 |
| 233 | 0.00873 |
| 234 | 0.0105 |
| 235 | 0.0124 |
| 236 | 0.00925 |
| 237 | 0.0103 |
| 238 | 0.0157 |
| 239 | 0.0067 |
| 240 | 0.0103 |
| 241 | 0.00773 |
| 242 | 0.00906 |
| 243 | 0.00928 |
| 244 | 0.0104 |
| 245 | 0.00706 |
| 246 | 0.00965 |
| 247 | 0.00798 |
| 248 | 0.00658 |
| 249 | 0.00235 |
| 250 | 0.00911 |
| 251 | 0.00787 |
| 252 | 0.00951 |
| 253 | 0.00809 |
| 254 | 0.012 |
| 255 | 0.0241 |
| 256 | 0.145 |
| 257 | 0.0761 |
| 258 | 0.309 |
| 259 | 0.0726 |
| 260 | 0.0746 |
| 261 | 0.0715 |
| 262 | 0.119 |
| 263 | 0.0595 |
| 264 | 0.1 |
| 265 | 0.0701 |
| 266 | 0.083 |
| 267 | 0.622 |
| 268 | 0.0829 |
| 269 | 0.0604 |
| 270 | 0.0627 |
| 271 | 0.0515 |
| 272 | 0.0795 |
| 273 | 0.634 |
| 274 | 0.107 |
| 275 | 0.683 |
| 276 | 0.13 |
| 277 | 0.0731 |
| 278 | 0.0791 |
| 279 | 0.00972 |
| 280 | 0.0719 |
| 281 | 0.0169 |
| 282 | 0.629 |
| 283 | 0.0725 |
| 284 | 0.0666 |
| 285 | 0.0692 |
| 286 | 0.074 |
| 287 | 0.121 |
| 288 | 0.0248 |
| 289 | 0.0532 |
| 290 | 0.0807 |
| 291 | 0.0736 |
| 292 | 0.0934 |
| 293 | 0.0723 |
| 294 | 0.0832 |
| 295 | 0.0715 |
| 296 | 0.0689 |
| 297 | 0.0932 |
| 298 | 0.0979 |
| 299 | 0.0846 |
| 300 | 0.0259 |
| 301 | 0.0905 |
| 302 | 0.0824 |
| 303 | 0.0586 |
| 304 | 0.0332 |
| 305 | 0.102 |
| 306 | 0.0347 |
| 307 | 0.0208 |
| 308 | 0.0614 |
| 309 | 8.2 |
| 310 | 0.0161 |
| 311 | 0.0029 |
| 312 | 0.0217 |
| 313 | 0.00603 |
| 314 | 0.621 |
| 315 | 0.0868 |
| 316 | 0.00312 |
| 317 | 0.00183 |
| 318 | 0.00272 |
| 319 | 0.00124 |
| 320 | 0.00237 |
| 321 | 0.00321 |
| 322 | 0.00214 |
| 323 | 0.00281 |

TABLE 2-continued

| Example | Cell Titer-Glo - IC50 (μM) |
|---|---|
| 324 | 0.00708 |
| 325 | 0.00128 |
| 326 | 0.00577 |
| 327 | 0.00123 |
| 328 | 0.00159 |
| 329 | 0.00283 |
| 330 | 0.00138 |
| 331 | 0.00209 |
| 332 | 0.00099 |
| 333 | 0.00568 |
| 334 | 0.00097 |
| 335 | 0.00607 |
| 336 | 0.00826 |
| 337 | 0.00694 |
| 338 | 0.00111 |
| 339 | 0.00183 |
| 340 | 0.00242 |
| 341 | 0.00198 |
| 342 | 0.0023 |
| 343 | 0.00653 |
| 344 | 0.0089 |
| 345 | 0.00199 |
| 346 | 0.0038 |
| 347 | 0.00806 |
| 348 | 0.002 |
| 349 | 0.00728 |
| 350 | 0.00075 |
| 351 | 0.00236 |
| 352 | 0.00888 |
| 353 | 0.00715 |
| 354 | 0.00751 |
| 355 | 0.00979 |
| 356 | 0.00909 |
| 357 | 0.00147 |
| 358 | 0.00186 |
| 359 | 0.00177 |
| 360 | 0.00235 |
| 361 | 0.00277 |
| 362 | 0.00261 |
| 363 | 0.0056 |
| 364 | 0.00863 |
| 365 | 0.00784 |
| 366 | 0.00657 |
| 367 | 0.00638 |
| 368 | 0.0077 |
| 369 | 0.00214 |
| 370 | 0.00879 |
| 371 | 0.00894 |
| 372 | 0.00706 |
| 373 | 0.00595 |
| 374 | 0.00632 |
| 375 | 0.00087 |
| 376 | 0.00062 |
| 377 | 0.00213 |
| 378 | 0.00709 |
| 379 | 0.00107 |
| 380 | 0.00757 |
| 381 | 0.00187 |
| 382 | 0.00899 |
| 383 | 0.0627 |
| 384 | 0.00827 |
| 385 | 0.0232 |
| 386 | 0.00318 |
| 387 | 0.0022 |
| 388 | 0.00088 |
| 389 | 0.00717 |
| 390 | 0.0015 |
| 391 | 0.00599 |
| 392 | 0.00354 |
| 393 | 0.00372 |
| 394 | 0.00199 |
| 395 | 0.00214 |
| 396 | 0.06848 |
| 397 | 0.00335 |
| 398 | 0.00819 |
| 399 | 0.00635 |
| 400 | 0.0068 |
| 401 | 0.00854 |
| 402 | 0.00168 |
| 403 | 0.0041 |
| 404 | 0.0027 |
| 405 | 0.00675 |
| 406 | 0.00742 |
| 407 | 0.00101 |
| 408 | 0.0299 |
| 409 | 0.00672 |
| 410 | 0.00868 |
| 411 | 0.00715 |
| 412 | 0.00137 |
| 413 | 0.01 |
| 414 | 0.0074 |
| 415 | 0.00228 |
| 416 | 0.00112 |
| 417 | 0.00645 |
| 418 | 0.00826 |
| 419 | 0.00217 |
| 420 | 0.00235 |
| 421 | 0.00372 |
| 422 | 0.00112 |
| 423 | 0.00038 |
| 424 | 0.0015 |
| 425 | 0.00091 |
| 426 | 0.00207 |
| 427 | 0.00203 |
| 428 | 0.00019 |
| 429 | 0.0008 |
| 430 | 0.00142 |
| 431 | 0.00167 |
| 432 | 0.008 |
| 433 | 0.00577 |
| 434 | 0.00635 |
| 435 | 0.0003 |
| 436 | 0.00067 |
| 437 | 0.00098 |
| 438 | 0.00196 |
| 439 | 0.00336 |
| 440 | 0.0018 |
| 441 | 0.00683 |
| 442 | 0.00625 |
| 443 | 0.00565 |
| 444 | 0.078 |
| 445 | 0.0191 |
| 446 | 0.108 |
| 447 | 0.903 |
| 448 | 0.00932 |
| 449 | 0.678 |
| 450 | 0.0509 |
| 451 | 0.0868 |
| 452 | 0.0632 |
| 453 | 0.105 |
| 454 | 0.106 |
| 455 | 0.458 |
| 456 | 0.0395 |
| 457 | 0.142 |
| 458 | 0.0644 |
| 459 | 0.0369 |
| 460 | 0.223 |
| 461 | 0.646 |
| 462 | 0.214 |
| 463 | 0.0709 |
| 464 | 0.0659 |
| 465 | 0.616 |
| 466 | 0.00807 |
| 467 | 0.0156 |
| 468 | 0.73 |
| 469 | 0.00861 |
| 470 | 0.715 |
| 471 | 0.072 |
| 472 | 0.00656 |
| 473 | 0.0093 |
| 474 | 0.0685 |
| 475 | 0.594 |

TABLE 2-continued

| Example | Cell Titer-Glo - IC50 (μM) |
|---|---|
| 476 | 0.0174 |
| 477 | 0.235 |
| 478 | 0.0143 |
| 479 | 0.0689 |
| 480 | 0.00424 |
| 481 | 0.0121 |
| 482 | 0.0326 |
| 483 | 0.00214 |
| 484 | 0.00056 |
| 485 | 0.00635 |
| 486 | 0.00624 |
| 487 | 0.072 |
| 488 | 0.0642 |
| 489 | 0.00207 |
| 490 | 0.00068 |
| 491 | 0.00845 |
| 492 | 0.00373 |
| 493 | 0.00673 |
| 494 | 0.00105 |
| 495 | 0.00706 |
| 496 | 0.0063 |
| 497 | 0.0234 |
| 498 | 0.00664 |
| 499 | 0.0121 |
| 500 | 0.00102 |
| 501 | 0.00607 |
| 502 | 0.00474 |
| 503 | 0.0582 |
| 504 | 0.00775 |
| 505 | 0.00684 |
| 506 | 0.00128 |
| 507 | 0.00834 |
| 508 | 0.00079 |
| 509 | 0.00119 |
| 510 | 0.0664 |
| 511 | 0.00082 |
| 512 | 0.0155 |
| 513 | 0.0035 |
| 514 | 0.00032 |
| 515 | 0.00085 |
| 516 | 0.00226 |
| 517 | 0.00921 |
| 518 | 0.00087 |
| 519 | 0.00321 |
| 520 | 0.00047 |
| 521 | 0.00472 |
| 522 | 0.00078 |
| 523 | 0.00099 |
| 524 | 0.00573 |
| 525 | 0.00093 |
| 526 | 0.00094 |
| 527 | 0.00778 |
| 528 | 0.01923 |
| 529 | 0.00933 |
| 530 | 0.00202 |
| 531 | 0.0176 |
| 532 | 0.00724 |
| 533 | 0.0246 |
| 534 | 0.00546 |
| 535 | 0.00939 |
| 536 | 0.00614 |
| 537 | 0.0033 |
| 538 | 0.0137 |
| 539 | 0.00257 |
| 540 | 0.00391 |
| 541 | 0.0042 |
| 542 | 0.0676 |
| 543 | 0.0077 |
| 544 | 0.00717 |
| 545 | 0.0152 |
| 546 | 0.00141 |
| 547 | 0.00302 |
| 548 | 0.0649 |
| 549 | 0.00067 |
| 550 | 0.00821 |
| 551 | 0.00048 |
| 552 | 0.00332 |
| 553 | 0.0441 |
| 554 | 0.00263 |
| 555 | 0.0239 |
| 556 | 0.00598 |
| 557 | 0.0102 |
| 558 | 0.00066 |
| 559 | 0.00133 |
| 560 | 0.00585 |
| 561 | 0.0622 |
| 562 | 0.00945 |
| 563 | 0.0242 |
| 564 | 0.0792 |
| 565 | 0.0741 |
| 566 | 0.0822 |
| 567 | 0.0765 |
| 568 | 0.0482 |
| 569 | 0.207 |
| 570 | 0.631 |
| 571 | 0.118 |
| 572 | 0.0598 |
| 573 | 0.0819 |
| 574 | 0.0553 |
| 575 | 0.269 |
| 576 | 0.0848 |
| 577 | 0.093 |
| 578 | 0.0887 |
| 579 | 0.267 |
| 580 | 0.078 |
| 581 | 0.0807 |
| 582 | 0.627 |
| 583 | 0.0874 |
| 584 | 0.0872 |
| 585 | 0.283 |
| 586 | 0.107 |
| 587 | 0.0814 |
| 588 | 0.113 |
| 589 | 0.0979 |
| 590 | 0.0822 |
| 591 | 0.0936 |
| 592 | 0.62 |
| 593 | 0.0634 |
| 594 | 0.0478 |
| 595 | 0.0806 |
| 596 | 0.0846 |
| 597 | 0.117 |
| 598 | 0.208 |
| 599 | 0.0797 |
| 600 | 0.219 |
| 601 | 0.0968 |
| 602 | 0.002 |
| 603 | 0.576 |
| 604 | 8.26127 |
| 605 | 1.4 |
| 606 | 0.0867 |
| 607 | 7.65 |
| 608 | 0.712 |
| 609 | 0.00205 |
| 610 | 0.0079 |
| 611 | 0.09 |
| 612 | 0.0536 |
| 613 | 0.70691 |
| 614 | 7.66 |
| 615 | 6.15 |
| 616 | 7.29 |
| 617 | 1.87 |
| 618 | >10 |
| 619 | >10 |
| 620 | 2.83 |
| 621 | >10 |
| 622 | >10 |
| 623 | 6.17 |
| 624 | >10 |
| 625 | 1.9 |
| 626 | 5.22 |
| 627 | 0.853 |

TABLE 2-continued

| Example | Cell Titer-Glo - IC50 (μM) |
|---|---|
| 628 | >10 |
| 629 | 5.01 |
| 630 | 0.00812 |
| 631 | 0.00958 |
| 632 | 0.00881 |
| 633 | 0.00895 |
| 634 | 0.00922 |
| 635 | 0.0416 |
| 636 | 0.0828 |
| 637 | 0.00124 |
| 638 | 0.0299 |
| 639 | 0.00816 |
| 640 | 0.00292 |
| 641 | 0.0726 |
| 642 | 0.00726 |
| 643 | 0.00846 |
| 644 | 0.00823 |
| 645 | 0.0033 |
| 646 | 0.0587 |
| 647 | 0.00573 |
| 648 | 0.0268 |
| 649 | 0.00111 |
| 650 | 0.0869 |
| 651 | 0.0276 |
| 652 | 0.00614 |
| 653 | 0.00972 |
| 654 | 0.00276 |
| 655 | 0.000475 |
| 656 | 0.061 |
| 657 | 0.00844 |
| 658 | 0.0144 |
| 659 | 0.0112 |
| 660 | 0.00523 |
| 661 | 0.0216 |
| 662 | 0.0159 |
| 663 | 0.0316 |
| 664 | 1.15 |
| 665 | 7.62 |
| 666 | 0.008059 |
| 667 | 0.01248 |
| 668 | >10 |
| 669 | 0.00188 |
| 670 | 0.00853 |
| 671 | 0.00853 |
| 672 | 0.00405 |
| 673 | 0.0116 |
| 674 | 0.00572 |
| 675 | 0.0693 |
| 676 | 0.00202 |
| 677 | 0.0093 |
| 678 | 0.00609 |
| 679 | 0.0006 |
| 680 | 0.00355 |
| 681 | 0.00902 |
| 682 | 0.00273 |
| 683 | 0.00902 |
| 684 | 0.0766 |
| 685 | 0.00828 |
| 686 | 0.0649 |
| 687 | 0.00611 |
| 688 | 0.0094 |
| 689 | 0.00968 |
| 690 | 0.00314 |
| 691 | 0.03 |
| 692 | 0.00423 |
| 693 | 0.0136 |
| 694 | 0.0716 |
| 695 | 0.00616 |
| 696 | 0.00467 |
| 697 | 0.00596 |
| 698 | 0.0679 |
| 699 | 0.065 |
| 700 | 0.00876 |
| 701 | 0.0752 |
| 702 | 0.00207 |
| 703 | 0.00843 |
| 704 | 0.0053 |
| 705 | 0.0202 |
| 706 | 0.0077 |
| 707 | 0.00693 |
| 708 | 0.0142 |
| 709 | 0.0145 |
| 710 | 0.0103 |
| 711 | 0.0595 |
| 712 | 0.00679 |
| 713 | 0.00999 |
| 714 | 0.0176 |
| 715 | 0.0118 |
| 716 | 0.0692 |
| 717 | 0.0121 |
| 718 | 0.00627 |
| 719 | 0.00963 |
| 720 | 0.00857 |
| 721 | 0.00839 |
| 722 | 0.0848 |
| 723 | 0.003507 |
| 724 | 0.0809 |
| 725 | 0.00401 |
| 726 | 0.0327 |
| 727 | 0.0046 |
| 728 | 0.00697 |
| 729 | 0.0135 |
| 730 | 0.00681 |
| 731 | 0.00050 |
| 732 | 0.0299 |
| 733 | 0.0375 |
| 734 | 0.00833 |
| 735 | 0.0689 |
| 736 | 0.00809 |
| 737 | 1.86 |
| 738 | 0.853926 |
| 739 | 7.31 |
| 740 | 0.914369 |
| 741 | 0.181262 |
| 742 | 0.734 |
| 743 | 6.62 |
| 744 | 2.72 |
| 745 | >10 |
| 746 | >10 |
| 747 | 5.92 |
| 748 | 0.00258 |
| 749 | >10 |
| 750 | 0.226 |
| 751 | 0.00271 |
| 752 | 2.45 |
| 753 | 0.00892 |
| 754 | 0.0948 |
| 755 | 0.19 |
| 756 | 0.00908 |
| 757 | 0.0677 |
| 758 | 0.857 |
| 759 | 0.0062 |
| 760 | 0.253 |
| 761 | 0.0923 |
| 762 | 0.709 |
| 763 | 0.00841 |
| 764 | 0.022126 |
| 765 | 1.02 |
| 766 | 0.787 |
| 767 | 1.28 |
| 768 | 0.111 |
| 769 | 0.0186 |
| 770 | 0.138 |
| 771 | 0.0699 |
| 772 | 0.0636 |
| 773 | 0.0857 |
| 774 | 0.00252 |
| 775 | 0.00215 |
| 776 | 0.00764 |
| 777 | 0.0192 |
| 778 | 0.0197 |
| 779 | 0.00148 |

TABLE 2-continued

| Example | Cell Titer-Glo - IC50 (μM) |
|---|---|
| 780 | 0.00407 |
| 781 | 0.01 |
| 782 | 0.0669 |
| 783 | 0.00646 |
| 784 | 0.016 |
| 785 | 0.00117 |
| 786 | 0.012 |
| 787 | 0.0639 |
| 788 | 0.00759 |
| 789 | 0.0284 |
| 790 | 0.0746 |
| 791 | 0.00748 |
| 792 | 0.0088 |
| 793 | 0.329 |
| 794 | 0.196 |
| 795 | 0.773 |
| 796 | 0.0117 |
| 797 | 0.0126 |
| 798 | 0.0664 |
| 799 | 0.0255 |
| 800 | 0.06 |
| 801 | 0.024555 |
| 802 | 0.0263 |
| 803 | 0.00161 |
| 804 | 0.00792 |
| 805 | 0.065 |
| 806 | 0.00313 |
| 807 | 0.00415 |
| 808 | 0.0411 |
| 809 | 0.0024 |
| 810 | 0.0611 |
| 811 | 0.011 |
| 812 | 0.0102 |
| 813 | 0.0786 |
| 814 | 0.0819 |
| 815 | 0.185 |
| 816 | 0.188 |
| 817 | 0.0641 |
| 818 | 0.0294 |
| 819 | 0.00856 |
| 820 | 0.0754 |
| 821 | 0.165 |
| 822 | 0.0605 |
| 823 | 0.247 |
| 824 | 0.0706 |
| 825 | 0.0623 |
| 826 | 0.0983 |
| 827 | 0.0737 |
| 828 | 0.000826 |
| 829 | 0.00295 |
| 830 | 0.00796 |
| 831 | 0.00725 |
| 832 | 0.0167 |
| 833 | 0.00667 |
| 834 | 0.0144 |
| 835 | 0.00235 |
| 836 | 0.658 |
| 837 | 0.769 |
| 838 | 1.77 |
| 839 | 2 |
| 840 | 0.0028 |
| 841 | 0.00355 |
| 842 | 0.000665 |
| 843 | 0.00061 |
| 844 | 0.00252 |
| 845 | 0.00209 |
| 846 | 0.00724 |
| 847 | 0.115 |
| 848 | 0.609 |
| 849 | 0.685 |
| 850 | 0.0705 |
| 851 | 0.00275 |
| 852 | 0.0124 |
| 853 | >10 |
| 854 | >10 |
| 855 | 0.747 |
| 856 | 0.729 |
| 857 | 0.00252 |
| 858 | 0.00436 |
| 859 | 0.0027 |
| 860 | 0.01 |
| 861 | 0.00758 |
| 862 | 0.00849 |
| 863 | 0.00567 |
| 864 | 0.00529 |
| 865 | 0.00406 |
| 866 | 0.00792 |
| 867 | 0.00784 |
| 868 | 0.00229 |
| 869 | 0.00198 |
| 870 | 0.0032 |
| 871 | 0.00361 |
| 872 | 0.0236 |
| 873 | 0.675 |
| 874 | 0.0711 |
| 875 | >10 |
| 876 | 0.0292 |
| 877 | 0.02960 |
| 878 | 0.0706 |
| 879 | 0.00583 |
| 880 | 0.01540 |
| 881 | 0.00818 |
| 882 | 0.00643 |
| 883 | 0.0309 |
| 884 | 0.00275 |
| 885 | 0.00163 |
| 886 | 0.00766 |
| 887 | 0.00847 |
| 888 | 0.00976 |
| 889 | 0.00285 |
| 890 | 0.00409 |
| 891 | 0.0656 |
| 892 | 0.146 |
| 893 | 0.681 |
| 894 | 0.752 |
| 895 | 0.00215 |
| 896 | 0.00109 |
| 897 | 0.00156 |
| 898 | .000851 |
| 899 | .000401 |
| 900 | 0.00224 |
| 901 | 0.00207 |
| 902 | 0.00645 |
| 903 | .000618 |
| 904 | 0.00195 |
| 905 | 0.0133 |
| 906 | .000879 |
| 907 | 6.75 |
| 908 | 0.0925 |
| 909 | 0.067 |
| 910 | 0.00651 |
| 911 | >10 |
| 912 | 0.0642 |
| 913 | 0.0663 |
| 914 | 0.0027 |
| 915 | 0.139 |
| 916 | 0.646 |
| 917 | 0.101 |
| 918 | 0.717 |
| 919 | 0.0519 |
| 920 | 0.00543 |
| 921 | 0.0029 |
| 922 | 0.00338 |
| 923 | 0.0694 |
| 924 | 0.00117 |
| 925 | 0.0101 |
| 926 | 0.602 |
| 927 | 0.0039 |
| 928 | 0.00256 |
| 929 | 0.0271 |
| 930 | 0.0027 |
| 931 | 0.00317 |

TABLE 2-continued

| Example | Cell Titer-Glo - IC50 (μM) |
|---|---|
| 932 | 0.00582 |
| 933 | 0.00239 |
| 934 | 0.00245 |
| 935 | 0.002 |
| 936 | 0.00218 |
| 937 | 0.00262 |
| 938 | 0.00875 |
| 939 | 0.00296 |
| 940 | 0.00197 |
| 941 | 0.0021 |
| 942 | 0.00276 |
| 943 | 0.0076 |
| 944 | 0.00714 |
| 945 | 0.00451 |
| 946 | 0.00289 |
| 947 | 0.00256 |
| 948 | 0.00226 |
| 949 | 0.00595 |
| 950 | 0.00606 |
| 951 | 0.00277 |
| 952 | 0.00217 |
| 953 | 0.00334 |
| 954 | 0.00638 |
| 955 | 0.00597 |
| 956 | 0.00640 |
| 957 | 0.00193 |
| 958 | 0.00263 |
| 959 | 0.00233 |
| 960 | 0.00286 |
| 961 | 0.00557 |
| 962 | 0.0024 |
| 963 | 0.00214 |
| 964 | 0.00184 |
| 965 | 0.00260 |
| 966 | 0.00323 |
| 967 | 0.00305 |
| 968 | 0.0037 |
| 969 | .000347 |
| 970 | 0.0285 |
| 971 | 0.0708 |
| 972 | 0.667 |
| 973 | 0.00553 |
| 974 | 0.00784 |
| 975 | 0.098 |
| 976 | 0.0612 |
| 977 | 0.0124 |
| 978 | 1.07 |
| 979 | 0.072 |
| 980 | 0.0822 |
| 981 | 1.06 |
| 982 | 0.0835 |
| 983 | 0.604 |
| 984 | 0.696 |
| 985 | 0.635 |
| 986 | 7.47 |
| 987 | 0.609 |
| 988 | 1.24 |
| 989 | 0.602 |
| 990 | 6.81 |
| 991 | 0.76 |
| 992 | 1.51 |
| 993 | 0.809 |
| 994 | 0.059 |
| 995 | 0.245 |
| 996 | 0.104 |
| 997 | 0.0935 |
| 998 | 1.28 |
| 999 | 0.25 |
| 1000 | 0.077 |
| 1001 | 0.0532 |
| 1002 | 0.911 |
| 1003 | 1.07 |
| 1004 | 7.92 |
| 1005 | 0.592 |
| 1006 | 0.00536 |
| 1007 | 0.0567 |
| 1008 | 0.299 |
| 1009 | 0.0818 |
| 1010 | 0.0709 |
| 1011 | 0.113 |
| 1012 | 0.782 |
| 1013 | 0.213 |
| 1014 | 0.219 |
| 1015 | 0.0901 |
| 1016 | 0.212 |
| 1017 | 0.752 |
| 1018 | 0.716 |
| 1019 | 2.46 |
| 1020 | 7.27 |
| 1021 | 0.0477 |
| 1022 | 8.16 |
| 1023 | 0.508 |
| 1024 | nd |
| 1025 | nd | nd = no data

Compounds which inhibit NAMPT are useful for treating diseases in which activation of NF-KB is implicated. Such methods are useful in the treatment of a variety of diseases including inflammatory and tissue repair disorders; particularly rheumatoid arthritis, inflammatory bowel disease, asthma and COPD (chronic obstructive pulmonary disease), osteoarthritis, osteoporosis and fibrotic diseases; dermatosis, including psoriasis, atopic dermatitis and ultra-violet induced skin damage; autoimmune diseases including systemic lupus erythematosis, multiple sclerosis, psoriatic arthritis, ankylosing spondylitis, tissue and organ rejection, Alzheimer's disease, stroke, athersclerosis, restenosis, diabetes, glomerulonephritis, cancer, particularly wherein the cancer is selected from breast, prostate, lung, colon, cervix, ovary, skin, CNS, bladder, pancreas, leukaemia, lymphoma or Hodgkin's disease, cachexia, inflammation associated with infection and certain viral infections, including Acquired Immune Deficiency Syndrome (AIDS), adult respiratory distress syndrome, and ataxia telengiectasia.

Involvement of NAMPT in the treatment of cancer is described in WO 97/48696. Involvement of NAMPT in immuno-supression is described in WO 97/48397. Involvement of NAMPT for the treatment of diseases involving angiogenesis is described in WO 2003/80054. Involvement of NAMPT for the treatment of rheumatoid arthritis and septic shock is described in WO 2008/025857. Involvement of NAMPT for the prophylaxis and treatment of ischaemia is described in WO 2009/109610.

Cancers include, but are not limited to, hematologic and solid tumor types such as acoustic neuroma, acute leukemia, acute lymphoblastic leukemia, acute myelogenous leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer (including estrogen-receptor positive breast cancer), bronchogenic carcinoma, Burkitt's lymphoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, gastric carcinoma, germ cell testicular cancer, gestational trophobalstic disease, glioblastoma, head and neck cancer, heavy chain disease, hemangioblastoma, hepatoma, hepatocellular cancer, hormone insensitive prostate cancer, leiomyosarcoma, liposarcoma, lung cancer (including small cell lung cancer and non-small cell lung cancer), lymphangioendothelio-sarcoma, lymphangiosarcoma, lymphoblastic leukemia, lymphoma (lymphoma, including diffuse large B-cell lymphoma, follicular lymphoma, Hodgkin's lymphoma and non-Hodgkin's lymphoma), malignancies and hyperproliferative disorders of the bladder, breast, colon, lung, ovaries, pancreas, prostate, skin and uterus, lymphoid malignancies of T-cell or B-cell origin, leukemia, medullary carcinoma, medulloblastoma, melanoma, meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer (including hormone-insensitive (refractory) prostate cancer), rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), stomach cancer, squamous cell carcinoma, synovioma, sweat gland carcinoma, testicular cancer (including germ cell testicular cancer), thyroid cancer, Waldenström's macroglobulinemia, testicular tumors, uterine cancer, Wilms' tumor and the like.

Schemes and Experimentals

The following abbreviations have the meanings indicated. ADDP means 1,1'-(azodicarbonyl)dipiperidine; AD-mix-β means a mixture of $(DHQD)_2PHAL$, $K_3Fe(CN)_6$, $K_2CO_3$, and $K_2SO_4$; 9-BBN means 9-borabicyclo(3.3.1)nonane; Boc means tert-butoxycarbonyl; $(DHQD)_2PHAL$ means hydroquinidine 1,4-phthalazinediyl diethyl ether; DBU means 1,8-diazabicyclo[5.4.0]undec-7-ene; DIBAL means diisobutylaluminum hydride; DIEA means diisopropylethylamine; DMAP means N,N-dimethylaminopyridine; DMF means N,N-dimethylformamide; dmpe means 1,2-bis(dimethylphosphino)ethane; DMSO means dimethylsulfoxide; dppb means 1,4-bis(diphenylphosphino)-butane; dppe means 1,2-bis(diphenylphosphino)ethane; dppf means 1,1'-bis(diphenylphosphino)ferrocene; dppm means 1,1-bis(diphenylphosphino)methane; EDAC.HCl means 1-(3-dimethylaminopropyl)-3-ethylcarbodiimide hydrochloride; Fmoc means fluorenylmethoxycarbonyl; HATU means O-(7-azabenzotriazol-1-yl)-N,N'N'N'-tetramethyluronium hexafluorophosphate; HMPA means hexamethylphosphoramide; IPA means isopropyl alcohol; $MP-BH_3$ means macroporous triethylammonium methylpolystyrene cyanoborohydride; TEA means triethylamine; TFA means trifluoroacetic acid; THF means tetrahydrofuran; NCS means N-chlorosuccinimide; NMM means N-methylmorpholine; NMP means N-methylpyrrolidine; $PPh_3$ means triphenylphosphine.

The following schemes are presented to provide what is believed to be the most useful and readily understood description of procedures and conceptual aspects of this invention. Compounds of this invention may be made by synthetic chemical processes, examples of which are shown herein. It is meant to be understood that the order of the steps in the processes may be varied, that reagents, solvents and reaction conditions may be substituted for those specifically mentioned, and that vulnerable moieties may be protected and deprotected, as necessary.

Schemes

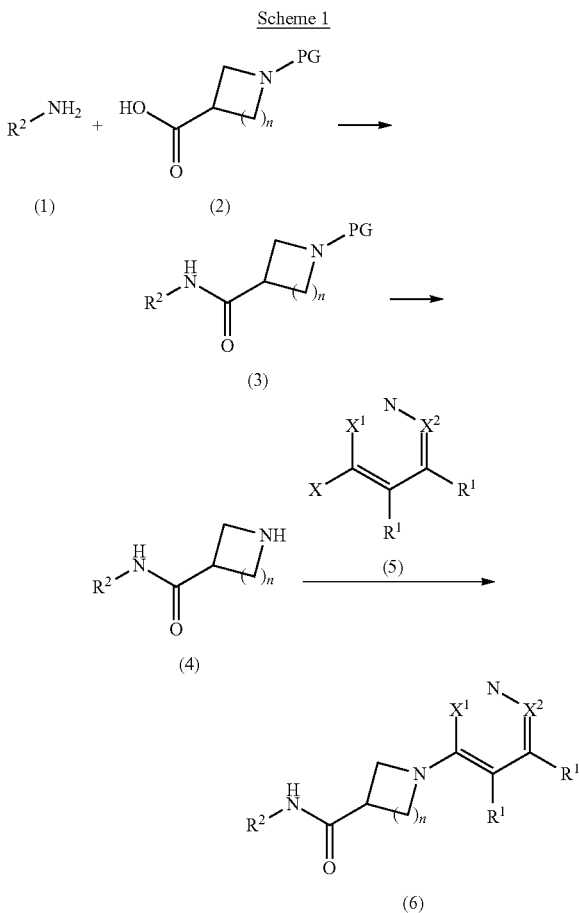

As shown in Scheme 1, compounds of formula (1), wherein $R^2$ is as described herein, can be reacted with acids of formula (2); wherein PG is a suitable protecting group and n is 1, 2, or 3, in the presence of a base such as but not limited to diisopropylethylamine, to provide compounds of formula (3). The reaction may involve the use of a carboxyl activating agent such as but not limited to N-(3-dimethylaminopropyl)-N'-ethylcarbodiimide hydrochloride, and a ester activating agent such as but not limited to 1-hydroxybenzotriazole hydrate. The reaction is typically performed at ambient temperature in a solvent such as but not limited to N,N-dimethylformamide, N,N-dimethylacetamide, or mixtures thereof. Compounds of formula (4) can be prepared from compounds of formula (3) after removal of the suitable protecting group using standard reaction conditions known to those skilled in the art and readily available in the literature. Compounds of formula (5), wherein $X^1$, $X^2$, and $R^1$ are as described herein and X is an appropriate halide, can be reacted with compounds of formula (4) to provide compounds of formula (6) which are representative of compounds of Formula (1). This C—N cross coupling reaction typically employs a base such as but not limited to cesium carbonate, a palladium catalyst such as but not limited to bis(dibenzylideneacetone)palladium(0), and a ligand such as but not limited to (9,9-dimethyl-9H-xanthene-4,5-diyl)bis(diphenylphosphine). The reaction is typically performed at an elevated temperature in a solvent such as but not limited to dioxane.

Scheme 2

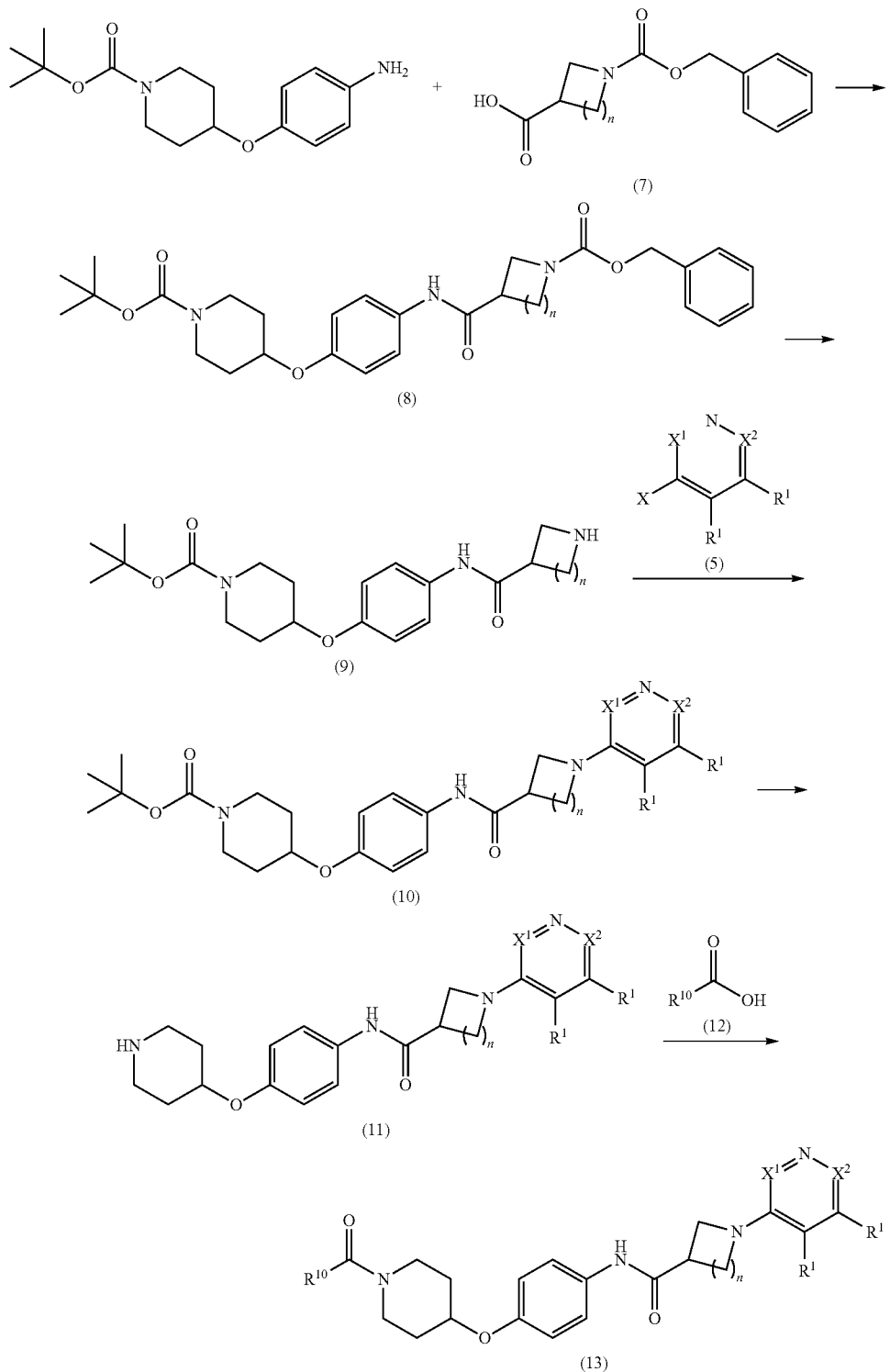

tert-Butyl 4-(4-aminophenoxy)piperidine-1-carboxylate can be reacted with acids of formula (7); wherein n is 1, 2, or 3, in the presence of a base such as but not limited to diisopropylethylamine; to provide compounds of formula (8). The reaction may involve the use of a carboxyl activating agent such as but not limited to N-(3-dimethylaminopropyl)-N'-ethylcarbodiimide hydrochloride, and a ester activating agent such as but not limited to 1-hydroxybenzotriazole hydrate. The reaction is typically performed at ambient temperature in a solvent such as but not limited to N,N-dimethylformamide, N,N-dimethylacetamide, or mixtures thereof. Compounds of formula (9) can be prepared from compounds of formula (8)

by reacting the latter with hydrogen in the presence of palladium hydroxide. The reaction is typically performed at ambient temperature in a solvent such as but not limited to tetrahydrofuran. Compounds of formula (5), wherein $X^1$, $X^2$, and $R^1$ are as described herein and X is an appropriate halide, can be reacted with compounds of formula (9) to provide compounds of formula (10). The C—N cross coupling reaction typically employs a base such as but not limited to cesium carbonate, a palladium catalyst such as but not limited to bis(dibenzylideneacetone)palladium(0), and a ligand such as but not limited to (9,9-dimethyl-9H-xanthene-4,5-diyl)bis(diphenylphosphine). The reaction is typically performed at an elevated temperature in a solvent such as but not limited to dioxane. Compounds of formula (11) can be prepared by treating compounds of formula (10) with an acid such as but not limited to trifluoroacetic acid in a solvent such as but not limited to dichloromethane. Compounds of formula (13), which are representative of compounds of Formula (I), can be prepared by reacting compounds of formula (11) with compounds of formula (12), wherein $R^{10}$ is as described herein, in the presence of a base such as but not limited to diisopropylethylamine. The reaction may involve the use of a carboxyl activating agent such as but not limited to N-(3-dimethylaminopropyl)-N'-ethylcarbodiimide hydrochloride, and a ester activating agent such as but not limited to 1-hydroxybenzotriazole hydrate. The reaction is typically performed at ambient temperature in a solvent such as but not limited to N,N-dimethylformamide, N,N-dimethylacetamide, or mixtures thereof.

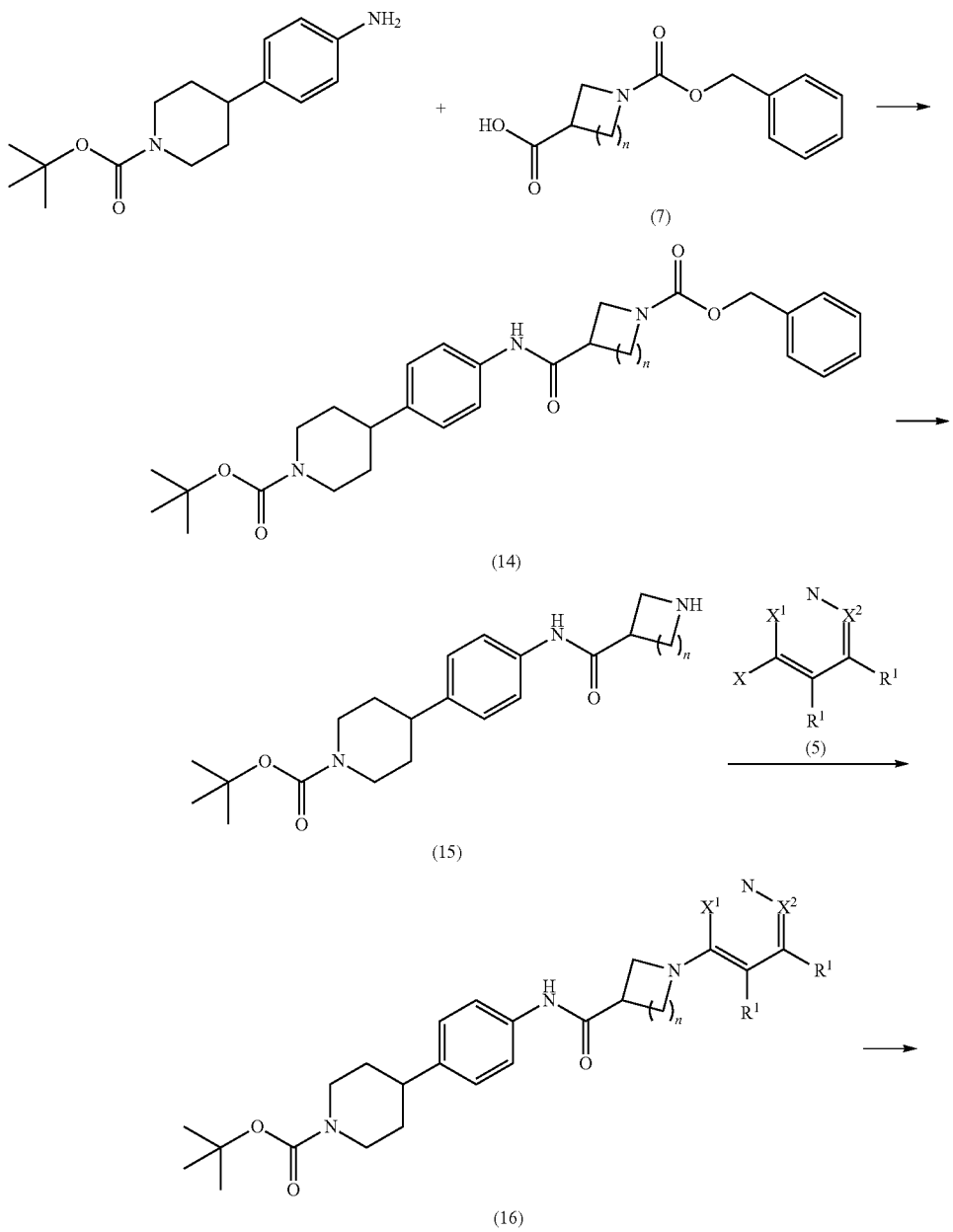

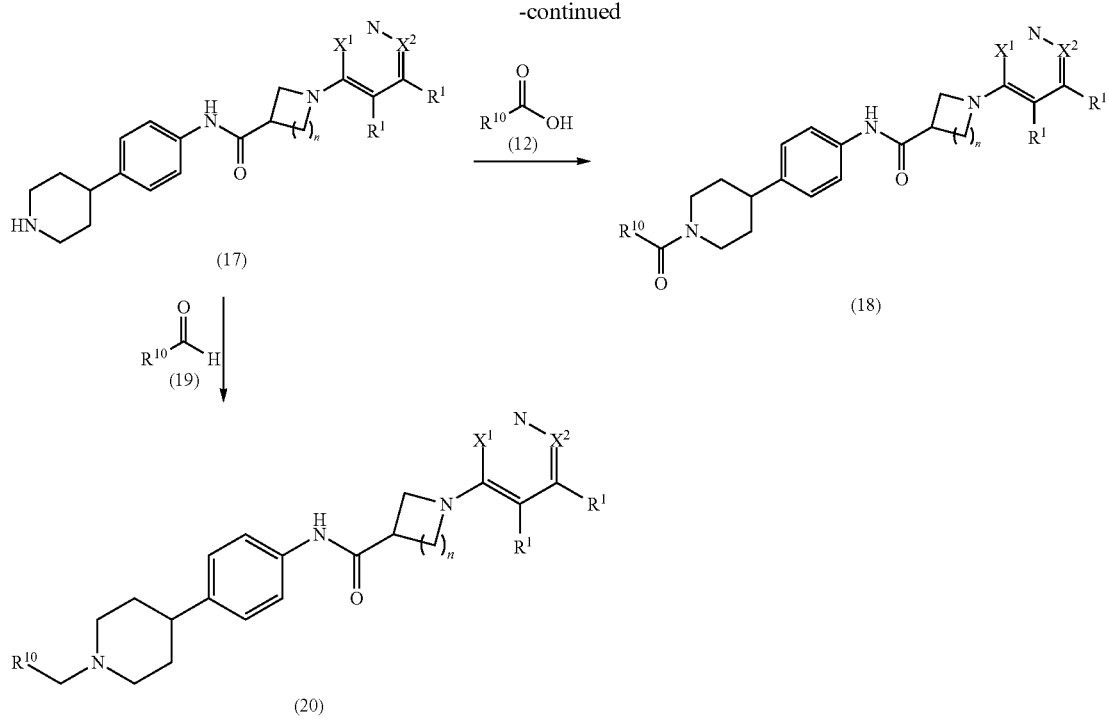

As shown in Scheme 3, tert-Butyl 4-(4-aminophenyl)piperidine-1-carboxylate can be reacted with acids of formula (7); wherein n is 1, 2, or 3, in the presence of a base such as but not limited to diisopropylethylamine; to provide compounds of formula (14). The reaction may involve the use of a carboxyl activating agent such as but not limited to N-(3-dimethylaminopropyl)-N'-ethylcarbodiimide hydrochloride, and a ester activating agent such as but not limited to 1-hydroxybenzotriazole hydrate. The reaction is typically performed at ambient temperature in a solvent such as but not limited to N,N-dimethylformamide, N,N-dimethylacetamide, or mixtures thereof. Compounds of formula (15) can be prepared from compounds of formula (14) by reacting the latter with hydrogen in the presence of palladium hydroxide. The reaction is typically performed at ambient temperature in a solvent such as but not limited to tetrahydrofuran. Compounds of formula (5), wherein $X^1$, $X^2$, and $R^1$ are as described herein and X is an appropriate halide, can be reacted with compounds of formula (15) to provide compounds of formula (16). The C—N cross coupling reaction typically employs a base such as but not limited to cesium carbonate, a palladium catalyst such as but not limited to bis(dibenzylideneacetone)palladium(0), and a ligand such as but not limited to (9,9-dimethyl-9H-xanthene-4,5-diyl)bis(diphenylphosphine). The reaction is typically performed at an elevated temperature in a solvent such as but not limited to dioxane. Compounds of formula (17) can be prepared by treating compounds of formula (16) with an acid such as but not limited to trifluoroacetic acid in a solvent such as but not limited to dichloromethane. Compounds of formula (18), which are representative of compounds of Formula (I), can be prepared by reacting compounds of formula (17) with compounds of formula (12), wherein $R^{10}$ is as described herein, in the presence of a base such as but not limited to diisopropylethylamine. The reaction may involve the use of a carboxyl activating agent such as but not limited to N-(3-dimethylaminopropyl)-N'-ethylcarbodiimide hydrochloride, and a ester activating agent such as but not limited to 1-hydroxybenzotriazole hydrate. The reaction is typically performed at ambient temperature in a solvent such as but not limited to N,N-dimethylformamide, N,N-dimethylacetamide, or mixtures thereof. Alternatively, compounds of formula (17) can be reacted with compounds of formula (19), wherein $R^{10}$ is as described herein, to provide compounds of formula (20), which are representative of compounds of Formula (I). The reaction is typically performed in the presence of a reducing agent such as but not limited to sodium triacetoxyborohydride and acetic acid in a solvent such as but not limited to methanol and may be performed at an elevated temperature.

EXAMPLES

The following examples are presented to provide what is believed to be the most useful and readily understood description of procedures and conceptual aspects of this invention. Each exemplified compound and intermediate was named using ACD/ChemSketch Version 12.5 (20 Apr. 2011) or (3 Sep. 2012), Advanced Chemistry Development Inc., Toronto, Ontario), or ChemDraw® Ver. 9.0.7 (CambridgeSoft, Cambridge, Mass.).

EXPERIMENTALS

Example 1

1-(pyridin-3-yl)-N-(4-{[1-(tetrahydro-2H-pyran-4-ylacetyl)piperidin-4-yl]oxy}phenyl)azetidine-3-carboxamide Example 1A tert-butyl 4-(4-(1-(benzyloxycarbonyl)azetidine-3-carboxamido)phenoxy)piperidine-1-carboxylate 1-(Benzyloxycarbonyl)azetidine-3-carboxylic acid (5.10 g, 21.67 mmol), 1-hydroxybenzotriazole hydrate (4.15 g, 27.1 mmol) and tert-butyl 4-(4-aminophenoxy)piperidine-1-carboxylate (5.28 g, 18.06 mmol) were suspended in dimethylformamide (25 ml) followed by addition of diisopropylethylamine (9.64 ml, 54.2 mmol) and N-(3-dimethylaminopropyl)-N'-ethylcarbodiimide hydrochloride (5.19 g, 27.1 mmol). The mixture was stirred at room temperature overnight and the solution was diluted with water. The resulting turbid mixture was extracted with ethyl acetate and then ethyl acetate/tetrahydrofuran. The organics were combined and dried over magnesium sulfate, filtered and concentrated to give a solid which was triturated with ether and filtered to give the title compound.

Example 1B tert-butyl 4-(4-(azetidine-3-carboxamido)phenoxy)piperidine-1-carboxylate tert-Butyl 4-(4-(1-(benzyloxycarbonyl)azetidine-3-carboxamido)phenoxy)piperidine-1-carboxylate (50 mg, 0.098 mmol) and tetrahydrofuran (5 ml) were added to 20% wet palladium hydroxide on carbon (10 mg, 0.071 mmol) in a 50 ml pressure bottle and the mixture was stirred for 16 hours at 30 psi and room temperature. The mixture was filtered through a nylon membrane and the filtrate was concentrated to give the title compound.

Example 1C tert-butyl 4-(4-(1-(pyridin-3-yl)azetidine-3-carboxamido)phenoxy)piperidine-1-carboxylate tert-Butyl 4-(4-(azetidine-3-carboxamido)phenoxy)piperidine-1-carboxylate (4.97 g, 13.24 mmol), cesium carbonate (10.78 g, 33.1 mmol), 3-bromopyridine (1.307 ml, 13.24 mmol), (9,9-dimethyl-9H-xanthene-4,5-diyl)bis(diphenylphosphine) (0.764 g, 1.32 mmol) and bis(dibenzylideneacetone)palladium(0) (0.606 g, 0.662 mmol) were suspended in dioxane (50 ml), bubbled with nitrogen for 30 minutes and heated at 100° C. overnight. The mixture was filtered through a celite pad with dichloromethane washes and the filtrate was concentrated. Normal phase chromatography provided the title compound.

Example 1D

N-(4-(piperidin-4-yloxy)phenyl)-1-(pyridin-3-yl)azetidine-3-carboxamide tert-Butyl 4-(4-(1-(pyridin-3-yl)azetidine-3-carboxamido)phenoxy)piperidine-1-carboxylate (3.82 g, 8.44 mmol) was dissolved in 60 ml dichloromethane, cooled to 0° C. and treated with trifluoroacetic acid (10 ml). The mixture was allowed to warm to room temperature and was stirred for 2 hours. Removal of the solvent under vacuum provided the title compound.

Example 1E 1-(pyridin-3-yl)-N-(4-{[1-(tetrahydro-2H-pyran-4-ylacetyl)piperidin-4-yl]oxy}phenyl)azetidine-3-carboxamide The title compound was prepared as described in Example 1A, substituting N-(4-(piperidin-4-yloxy)phenyl)-1-(pyridin-3-yl)azetidine-3-carboxamide for tert-butyl 4-(4-aminophenoxy)piperidine-1-carboxylate and 2-(tetrahydro-2H-pyran-4-yl)acetic acid for 1-(benzyloxycarbonyl)azetidine-3-carboxylic acid. $^1$H NMR (300 MHz, DMSO-$d_6$) δ ppm 9.95 (bs, 1H), 7.93 (d, J=4.2 Hz, 1H), 7.88-7.83 (m, 1H), 7.55-7.47 (m, 2H), 7.26-7.08 (m, 1H), 7.01-6.78 (m, 3H), 4.14-4.04 (m, 2H), 4.02-3.62 (m, 6H), 2.37-1.73 (m, 6H), 1.66-1.00 (m, 8H); MS (ESI(+)) m/e 479 (M+H)$^+$.

TABLE 1

The following Examples were prepared essentially as described in Example 1, substituting the appropriate bromopyridine in Example 1C and the appropriate carboxylic acid in Example 1E. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
| 3 | N-(4-{[1-(tetrahydro-2H-pyran-4-ylacetyl)piperidin-4-yl]oxy}phenyl)-1-[2-(trifluoromethyl)pyridin-3-yl]azetidine-3-carboxamide | $^1$H NMR (300 MHz, DMSO-$d_6$) δ ppm 9.96 (s, 1H), 8.02 (dd, J = 4.3, 1.2 Hz, 1H), 7.55-7.45 (m, 3H), 7.15 (d, J = 8.5 Hz, 1H), 6.97-6.90 (m, 2H), 4.59-4.47 (m, 1H), 4.28-4.05 (m, 4H), 3.93-3.53 (m, 6H), 2.27 (d, J = 1.3 Hz, 2H), 2.00-1.78 (m, 4H), 1.64-1.38 (m, 5H), 1.39-1.04 (m, 3H) | (ESI(+)) m/e 547 (M + H)$^+$ |
| 4 | 1-(2-methylpyridin-3-yl)-N-(4-{[1-(tetrahydro-2H-pyran-4-ylacetyl)piperidin-4-yl]oxy}phenyl)azetidine-3-carboxamide | $^1$H NMR (300 MHz, DMSO-$d_6$) δ ppm 9.92 (s, 1H), 7.88 (dd, J = 4.7, 1.4 Hz, 1H), 7.55-7.48 (m, 2H), 7.07 (dd, J = 8.0, 4.7 Hz, 1H), 6.97-6.92 (m, 1H), 6.94-6.81 (m, 2H), 4.58-4.47 (m, 1H), 4.10 (t, J = 7.7 Hz, 2H), 3.98 (t, J = 6.8 Hz, 2H), 3.93-3.50 (m, 6H), 3.29-3.14 (m, 2H), 2.35 (s, 3H), 2.26 (d, J = 6.9 Hz, 2H), 2.05-1.79 (m, 3H), 1.66-1.32 (m, 5H), 1.31-1.06 (m, 2H) | (ESI(+)) m/e 493 (M + H)$^+$ |
| 5 | 1-(4-methylpyridin-3-yl)-N-(4-{[1- | $^1$H NMR (300 MHz, DMSO-$d_6$) δ ppm 9.93 (s, 1H), 7.90 (d, J = 4.7 Hz, 1H), 7.76 (s, 1H), 7.55-7.48 (m, 2H), 7.03-6.89 (m, 3H), 4.58-4.47 (m, 1H), 4.20-3.95 (m, 4H), 3.95-3.53 (m, 5H), | (ESI(+)) m/e 493 (M + H)$^+$ |

TABLE 1-continued

The following Examples were prepared essentially as described in Example 1, substituting the appropriate bromopyridine in Example 1C and the appropriate carboxylic acid in Example 1E. Some products were purified by flash chromatography while others were purified by reverse-phase HPLC. Accordingly, some Examples were isolated as trifluoroacetic acid salts.

| Ex | Name | ¹H NMR | MS |
|---|---|---|---|
|  | (tetrahydro-2H-pyran-4-ylacetyl)piperidin-4-yl]oxy}phenyl)azetidine-3-carboxamide | 3.26-3.15 (m, 4H), 2.26 (d, J = 6.9 Hz, 2H), 2.18 (s, 3H), 2.05-1.78 (m, 3H), 1.66-1.35 (m, 4H), 1.32-1.08 (m, 2H) |  |
| 6 | 1-(4-fluoropyridin-3-yl)-N-(4-{[1-(tetrahydro-2H-pyran-4-ylacetyl)piperidin-4-yl]oxy}phenyl)azetidine-3-carboxamide | ¹H NMR (300 MHz, DMSO-d₆) δ ppm 9.93 (bs, 1H), 7.95 (t, J = 11.6 Hz, 2H), 7.55-7.47 (m, 2H), 7.16 (dd, J = 12.7, 5.2 Hz, 1H), 6.97-6.90 (m, 2H), 4.59-4.48 (m, 1H), 4.29-4.00 (m, 5H), 3.93-3.41 (m, 5H), 2.30-2.23 (m, 2H), 1.99-1.78 (m, 4H), 1.66-1.39 (m, 5H), 1.40-1.00 (m, 3H) | (ESI(+)) m/e 497 (M + H)⁺ |
| 7 | N-(4-{[1-(tetrahydro-2H-pyran-4-ylacetyl)piperidin-4-yl]oxy}phenyl)-1-[4-(trifluoromethyl)pyridin-3-yl]azetidine-3-carboxamide | ¹H NMR (300 MHz, DMSO-d₆) δ ppm 9.93 (bs, 1H), 7.95 (t, J = 11.6 Hz, 2H), 7.55-7.47 (m, 2H), 7.16 (dd, J = 12.7, 5.2 Hz, 1H), 6.97-6.90 (m, 2H), 4.59-4.48 (m, 1H), 4.29-4.00 (m, 5H), 3.93-3.41 (m, 5H), 2.30-2.23 (m, 2H), 1.99-1.78 (m, 4H), 1.66-1.39 (m, 5H), 1.40-1.00 (m, 3H) | (ESI(+)) m/e 547 (M + H)⁺ |
| 31 | N-(4-{[1-(2-hydroxy-2-methylpropanoyl)piperidin-4-yl]oxy}phenyl)-1-(pyridin-3-yl)azetidine-3-carboxamide | ¹H NMR (300 MHz, DMSO-d₆) δ ppm 9.94 (s, 1H), 7.97-7.70 (m, 2H), 7.55-7.47 (m, 2H), 7.18 (dd, J = 8.2, 4.6 Hz, 1H), 7.00-6.78 (m, 3H), 5.39 (s, 1H), 4.58-4.41 (m, 1H), 4.09 (t, J = 7.8 Hz, 2H), 3.95 (t, J = 6.7 Hz, 2H), 3.78-3.47 (m, 2H), 1.99-1.82 (m, 2H), 1.62-1.34 (m, 2H), 1.35-1.02 (m, 8H) | (ESI(+)) m/e 439 (M + H)⁺ |
| 32 | N-[4-({1-[(2S)-2-methylbutanoyl]piperidin-4-yl}oxy)phenyl]-1-(pyridin-3-yl)azetidine-3-carboxamide | ¹H NMR (300 MHz, DMSO-d₆) δ ppm 9.94 (s, 1H), 7.94 (d, J = 4.7 Hz, 1H), 7.86 (d, J = 2.8 Hz, 1H), 7.55-7.47 (m, 2H), 7.24-7.04 (m, 1H), 7.02-6.80 (m, 3H), 4.59-4.48 (m, 1H), 4.09 (t, J = 7.8 Hz, 2H), 4.03-3.62 (m, 5H), 3.38 (dd, J = 13.6, 6.6 Hz, 1H), 2.80-2.64 (m, 1H), 2.01-1.78 (m, 2H), 1.64-1.36 (m, 3H), 1.38-1.15 (m, 1H), 1.15-0.86 (m, 4H), 0.81 (t, J = 7.3 Hz, 3H) | (ESI(+)) m/e 437 (M + H)⁺ |
| 33 | 1-(pyridin-3-yl)-N-[4-({1-[(2S)-tetrahydrofuran-2-ylcarbonyl]piperidin-4-yl}oxy)phenyl]azetidine-3-carboxamide | ¹H NMR (300 MHz, DMSO-d₆) δ ppm 9.94 (s, 1H), 7.98-7.82 (m, 2H), 7.55-7.48 (m, 2H), 7.20 (dd, J = 8.3, 4.6 Hz, 1H), 7.00-6.80 (m, 3H), 4.67 (t, J = 6.5 Hz, 1H), 4.53 (s, 1H), 4.10 (t, J = 7.8 Hz, 2H), 3.96 (t, J = 6.6 Hz, 2H), 3.89-3.58 (m, 4H), 3.46-3.08 (m, 4H), 2.12-1.68 (m, 5H), 1.66-1.38 (m, 2H) | (ESI(+)) m/e 451 (M + H)⁺ |
| 34 | N-{4-[(1-pentanoylpiperidin-4-yl)oxy]phenyl}-1-(pyridin-3-yl)azetidine-3-carboxamide | ¹H NMR (500 MHz, DMSO-d₆/D₂O) δ ppm 8.12 (d, J = 5.49 Hz, 1 H) 8.04 (d, J = 2.75 Hz, 1 H) 7.80 (dd, J = 8.85, 5.49 Hz, 1 H) 7.60 (dd, J = 8.39, 2.29 Hz, 1 H) 7.51 (d, J = 9.16 Hz, 2 H) 6.96 (d, J = 8.85 Hz, 2 H) 4.51-4.59 (m, 1 H) 4.25 (t, J = 8.24 Hz, 2 H) 4.14 (dd, J = 7.93, 5.80 Hz, 2 H) 3.80-3.90 (m, 1 H) 3.73-3.79 (m, 2 H) 3.31-3.41 (m, 1 H) 3.19-3.27 (m, 1 H) 2.29-2.36 (m, 2 H) 1.83-2.00 (m, 2 H) 1.53-1.62 (m, 1 H) 1.42-1.51 (m, 3 H) 1.24-1.35 (m, 2 H) 0.87 (t, 3 H) | (ESI(+)) m/e 437 (M + H)⁺ |
| 35 | N-[4-({1-[(2-methylcyclopropyl)carbonyl]piperidin-4-yl}oxy)phenyl]-1-(pyridin-3-yl)azetidine-3-carboxamide | ¹H NMR (500 MHz, DMSO-d₆/D₂O) δ ppm 8.12 (d, J = 5.49 Hz, 1 H) 8.04 (d, J = 2.44 Hz, 1 H) 7.80 (dd, J = 8.54, 5.49 Hz, 1 H) 7.59 (dd, J = 8.70, 1.98 Hz, 1 H) 7.52 (d, J = 8.85 Hz, 2 H) 6.97 (d, J = 8.85 Hz, 2 H) 4.51-4.62 (m, 1 H) 4.25 (t, J = 8.39 Hz, 2 H) 4.14 (dd, J = 7.93, 5.80 Hz, 2 H) 3.79-4.01 (m, 2 H) 3.73-3.78 (m, 1 H) 3.46-3.54 (m, 1 H) | (ESI(+)) m/e 435 (M + H)⁺ |

TABLE 1-continued

The following Examples were prepared essentially as described in Example 1, substituting the appropriate bromopyridine in Example 1C and the appropriate carboxylic acid in Example 1E. Some products were purified by flash chromatography while others were purified by reverse-phase HPLC. Accordingly, some Examples were isolated as trifluoroacetic acid salts.

| Ex | Name | ¹H NMR | MS |
|---|---|---|---|
| | | 3.16-3.28 (m, 1 H) 1.89 (d, J = 1.53 Hz, 2 H) 1.70-1.76 (m, 1 H) 1.53 (d, J = 55.85 Hz, 2 H) 1.03-1.17 (m, 4 H) 0.89-0.97 (m, 1 H) 0.49-0.59 (m, 1 H) | |
| 36 | N-[4-({1-[(1S,4R)-bicyclo[2.2.1]hept-2-ylacetyl]piperidin-4-yl}oxy)phenyl]-1-(pyridin-3-yl)azetidine-3-carboxamide | ¹H NMR (500 MHz, DMSO-$d_6$/$D_2O$) δ ppm 8.12 (d, J = 5.19 Hz, 1 H) 8.04 (d, J = 2.75 Hz, 1 H) 7.80 (dd, J = 8.85, 5.49 Hz, 1 H) 7.60 (dd, J = 8.54, 2.14 Hz, 1 H) 7.47-7.54 (m, 2 H) 6.93-6.99 (m, 2 H) 4.49-4.58 (m, 1 H) 4.25 (t, J = 8.39 Hz, 2 H) 4.10-4.16 (m, J = 8.09, 5.95 Hz, 2 H) 3.81-3.89 (m, 1 H) 3.73-3.79 (m, 2 H) 3.18-3.39 (m, 2 H) 2.27-2.36 (m, 1 H) 2.11-2.21 (m, 2 H) 1.73-1.99 (m, 4 H) 1.38-1.60 (m, 5 H) 1.34 (d, J = 9.77 Hz, 1 H) 0.97-1.19 (m, 4 H) | (ESI(+)) m/e 489 (M + H)⁺ |
| 37 | N-(4-{[1-(4-methylpentanoyl)piperidin-4-yl]oxy}phenyl)-1-(pyridin-3-yl)azetidine-3-carboxamide | ¹H NMR (500 MHz, DMSO-$d_6$/$D_2O$) δ ppm 8.12 (d, J = 5.19 Hz, 1 H) 8.04 (d, J = 2.75 Hz, 1 H) 7.80 (dd, J = 8.70, 5.34 Hz, 1 H) 7.59 (dd, J = 8.70, 1.98 Hz, 1 H) 7.47-7.54 (m, 2 H) 6.93-6.99 (m, 2 H) 4.51-4.57 (m, 1 H) 4.25 (t, J = 8.39 Hz, 2 H) 4.10-4.16 (m, J = 8.09, 5.95 Hz, 2 H) 3.80-3.87 (m, J = 17.70 Hz, 1 H) 3.74-3.79 (m, 2 H) 3.17-3.38 (m, 2 H) 2.27-2.36 (m, J = 8.85, 6.71 Hz, 2 H) 1.83-1.99 (m, J = 22.89 Hz, 2 H) 1.32-1.62 (m, 5 H) 0.87 (d, J = 6.41 Hz, 6 H) | (ESI(+)) m/e 451 (M + H)⁺ |
| 38 | N-(4-{[1-(3-methylpentanoyl)piperidin-4-yl]oxy}phenyl)-1-(pyridin-3-yl)azetidine-3-carboxamide | ¹H NMR (500 MHz, DMSO-$d_6$/$D_2O$) δ ppm 8.12 (d, J = 5.19 Hz, 1 H) 8.05 (d, J = 2.44 Hz, 1 H) 7.80 (dd, J = 8.85, 5.49 Hz, 1 H) 7.60 (dd, J = 8.54, 2.14 Hz, 1 H) 7.49-7.53 (m, 2 H) 6.93-6.97 (m, 2 H) 4.51-4.59 (m, 1 H) 4.25 (t, J = 8.39 Hz, 2 H) 4.14 (dd, J = 8.09, 5.95 Hz, 2 H) 3.83-3.91 (m, 1 H) 3.73-3.79 (m, 2 H) 3.19-3.39 (m, 2 H) 2.27-2.34 (m, 1 H) 2.10-2.18 (m, 1 H) 1.84-1.98 (m, 2 H) 1.73-1.81 (m, 1 H) 1.42-1.59 (m, 2 H) 1.29-1.39 (m, 1 H) 1.11-1.21 (m, 1 H) 0.82-0.89 (m, 6 H) | (ESI(+)) m/e 451 (M + H)⁺ |
| 39 | N-(4-{[1-(3-ethoxypropanoyl)piperidin-4-yl]oxy}phenyl)-1-(pyridin-3-yl)azetidine-3-carboxamide | ¹H NMR (500 MHz, DMSO-$d_6$/$D_2O$) δ ppm 8.12 (d, J = 5.49 Hz, 1 H) 8.05 (d, J = 2.44 Hz, 1 H) 7.80 (dd, J = 8.54, 5.49 Hz, 1 H) 7.60 (dd, J = 8.85, 1.83 Hz, 1 H) 7.51 (d, J = 9.16 Hz, 2 H) 6.92-6.98 (m, 2 H) 4.49-4.59 (m, 1 H) 4.25 (t, J = 8.39 Hz, 2 H) 4.14 (dd, J = 7.93, 5.80 Hz, 2 H) 3.80-3.89 (m, 1 H) 3.74-3.79 (m, 2 H) 3.59 (t, J = 6.56 Hz, 2 H) 3.42 (q, J = 7.02 Hz, 2 H) 3.20-3.38 (m, 2 H) 2.55-2.63 (m, 2 H) 1.83-1.99 (m, 2 H) 1.41-1.63 (m, 2 H) 1.09 (t, J = 7.02 Hz, 3 H) | (ESI(+)) m/e 453 (M + H)⁺ |
| 40 | N-(4-{[1-(2,2-dimethylbutanoyl)piperidin-4-yl]oxy}phenyl)-1-(pyridin-3-yl)azetidine-3-carboxamide | ¹H NMR (500 MHz, DMSO-$d_6$/$D_2O$) δ ppm 8.12 (d, J = 5.49 Hz, 1 H) 8.05 (d, J = 2.75 Hz, 1 H) 7.81 (dd, J = 8.54, 5.49 Hz, 1 H) 7.60 (dd, J = 8.85, 1.83 Hz, 1 H) 7.49-7.53 (m, 2 H) 6.96 (d, J = 9.16 Hz, 2 H) 4.53-4.59 (m, 1 H) 4.25 (t, J = 8.39 Hz, 2 H) 4.12-4.18 (m, J = 7.93, 6.10 Hz, 2 H) 3.87-3.93 (m, 1 H) 3.75-3.80 (m, 2 H) 3.28-3.38 (m, 2 H) 1.89-1.97 (m, 2 H) 1.60 (q, J = 7.53 Hz, 2 H) 1.46-1.54 (m, 2 H) 1.16 (s, 6 H) 0.80 (t, J = 7.48 Hz, 3 H) | (ESI(+)) m/e 451 (M + H)⁺ |
| 41 | N-(4-{[1-(3,3-dimethylbutanoyl)piperidin-4-yl]oxy}phenyl)-1-(pyridin-3-yl)azetidine-3-carboxamide | ¹H NMR (500 MHz, DMSO-$d_6$/$D_2O$) δ ppm 8.12 (d, J = 5.49 Hz, 1 H) 8.05 (d, J = 2.44 Hz, 1 H) 7.80 (dd, J = 8.54, 5.49 Hz, 1 H) 7.60 (dd, J = 8.70, 1.98 Hz, 1 H) 7.49-7.52 (m, 2 H) 6.92-6.99 (m, 2 H) 4.47-4.58 (m, 1 H) 4.22-4.29 (m, 2 H) 4.14 (dd, J = 8.09, 5.95 Hz, 2 H) 3.85-3.92 (m, 1 H) 3.74-3.80 (m, 2 H) 3.34-3.43 (m, 1 H) 3.20-3.27 (m, 1 H) 2.26 (s, 2 H) 1.82-2.01 (m, 2 H) 1.38-1.60 (m, 2 H) 0.99 (s, 9 H) | (ESI(+)) m/e 451 (M + H)⁺ |
| 42 | N-(4-{[1-(2,2-dimethylpropanoyl)piperidin-4-yl]oxy}phenyl)-1-(pyridin-3-yl)azetidine-3-carboxamide | ¹H NMR (500 MHz, DMSO-$d_6$/$D_2O$) δ ppm 8.12 (d, J = 5.49 Hz, 1 H) 8.04 (d, J = 2.44 Hz, 1 H) 7.80 (dd, J = 8.54, 5.49 Hz, 1 H) 7.59-7.61 (m, 1 H) 7.49-7.54 (m, 2 H) 6.93-6.98 (m, 2 H) 4.51-4.61 (m, 1 H) 4.25 (t, J = 8.39 Hz, 2 H) 4.14 (dd, J = 8.09, 5.95 Hz, 2 H) 3.85-3.92 (m, 2 H) 3.73-3.79 (m, 1 H) 3.29-3.38 (m, 2 H) 1.89-1.99 (m, 2 H) 1.45-1.56 (m, 2 H) 1.20 (s, 9 H) | (ESI(+)) m/e 437 (M + H)⁺ |

TABLE 1-continued

The following Examples were prepared essentially as described in Example 1,
substituting the appropriate bromopyridine in Example 1C and the appropriate carboxylic acid
in Example 1E. Some products were purified by flash chromatography while others were
purified by reverse-phase HPLC. Accordingly, some Examples were isolated as
trifluoroacetic acid salts.

| Ex | Name | $^1$H NMR | MS |
|----|------|-----------|-----|
| 43 | N-{4-[(1-butanoylpiperidin-4-yl)oxy]phenyl}-1-(pyridin-3-yl)azetidine-3-carboxamide | $^1$H NMR (500 MHz, DMSO-$d_6$/D$_2$O) δ ppm 8.12 (d, J = 5.49 Hz, 1 H) 8.05 (d, J = 2.44 Hz, 1 H) 7.80 (dd, J = 8.54, 5.49 Hz, 1 H) 7.60 (dd, J = 8.85, 1.83 Hz, 1 H) 7.49-7.53 (m, 2 H) 6.93-6.98 (m, 2 H) 4.49-4.60 (m, 1 H) 4.25 (t, J = 8.39 Hz, 2 H) 4.14 (dd, J = 7.93, 6.10 Hz, 2 H) 3.82-3.90 (m, 1 H) 3.73-3.79 (m, 2 H) 3.20-3.37 (m, 2H) 2.31 (t, J = 7.17 Hz, 2 H) 1.82-1.98 (m, 2 H) 1.41-1.63 (m, 4 H) 0.89 (t, J = 7.32 Hz, 3 H) | (ESI(+)) m/e 423 (M + H)$^+$ |
| 44 | N-(4-{[1-(ethoxyacetyl)piperidin-4-yl]oxy}phenyl)-1-(pyridin-3-yl)azetidine-3-carboxamide | $^1$H NMR (500 MHz, DMSO-$d_6$/D$_2$O) δ ppm 8.12 (d, J = 5.49 Hz, 1 H) 8.05 (d, J = 2.44 Hz, 1 H) 7.80 (dd, J = 8.54, 5.49 Hz, 1 H) 7.60 (dd, J = 8.54, 1.83 Hz, 1 H) 7.51 (d, J = 9.16 Hz, 2 H) 6.96 (d, J = 9.16 Hz, 2 H) 4.50-4.59 (m, 1 H) 4.25 (t, J = 8.39 Hz, 2 H) 4.10-4.16 (m, 4 H) 3.80-3.87 (m, 1 H) 3.73-3.78 (m, 2 H) 3.47 (q, J = 7.02 Hz, 2 H) 3.20-3.35 (m, 2 H) 1.86-1.98 (m, J = 21.67 Hz, 2 H) 1.45-1.64 (m, 2 H) 1.13 (t, J = 7.02 Hz, 3 H) | (ESI(+)) m/e 439 (M + H)$^+$ |
| 45 | N-(4-{[1-(3-methylbutanoyl)piperidin-4-yl]oxy}phenyl)-1-(pyridin-3-yl)azetidine-3-carboxamide | $^1$H NMR (500 MHz, DMSO-$d_6$/D$_2$O) δ ppm 8.12 (d, J = 5.49 Hz, 1 H) 8.05 (d, J = 2.44 Hz, 1 H) 7.80 (dd, J = 8.85, 5.49 Hz, 1 H) 7.60 (dd, J = 8.70, 1.98 Hz, 1 H) 7.47-7.55 (m, 2 H) 6.93-6.98 (m, 2 H) 4.51-4.57 (m, 1 H) 4.25 (t, J = 8.39 Hz, 2 H) 4.14 (dd, J = 7.93, 6.10 Hz, 2 H) 3.83-3.90 (m, 1 H) 3.74-3.79 (m, 2 H) 3.19-3.37 (m, 2 H) 2.19-2.24 (m, 2 H) 1.82-2.03 (m, 3 H) 1.41-1.60 (m, 2 H) 0.90 (d, J = 6.71 Hz, 6 H) | (ESI(+)) m/e 437 (M + H)$^+$ |
| 46 | N-(4-{[1-(2-methylpropanoyl)piperidin-4-yl]oxy}phenyl)-1-(pyridin-3-yl)azetidine-3-carboxamide | $^1$H NMR (500 MHz, DMSO-$d_6$/D$_2$O) δ ppm 8.12 (d, J = 5.49 Hz, 1 H) 8.05 (d, J = 2.44 Hz, 1 H) 7.80 (dd, J = 8.54, 5.49 Hz, 1 H) 7.60 (dd, J = 8.70, 1.98 Hz, 1 H) 7.49-7.54 (m, 2 H) 6.93-6.99 (m, 2 H) 4.52-4.60 (m, 1 H) 4.25 (t, J = 8.24 Hz, 2 H) 4.14 (dd, J = 7.93, 6.10 Hz, 2 H) 3.84 (s, 1 H) 3.75-3.79 (m, 2 H) 3.18-3.42 (m, 2 H) 2.86-2.93 (m, 1 H) 1.84-1.99 (m, 2 H) 1.42-1.63 (m, 2 H) 1.00 (d, J = 6.71 Hz, 6 H) | (ESI(+)) m/e 423 (M + H)$^+$ |
| 47 | N-(4-{[1-(N-acetyl-L-leucyl)piperidin-4-yl]oxy}phenyl)-1-(pyridin-3-yl)azetidine-3-carboxamide | $^1$H NMR (500 MHz, DMSO-$d_6$/D$_2$O) δ ppm 8.12 (d, J = 5.49 Hz, 1 H) 8.05 (d, J = 2.75 Hz, 1 H) 7.81 (dd, J = 8.54, 5.49 Hz, 1 H) 7.60 (dd, J = 8.85, 1.83 Hz, 1 H) 7.52 (d, J = 8.85 Hz, 2 H) 6.95-6.99 (m, 2 H) 4.77 (dd, J = 9.00, 3.81 Hz, 1 H) 4.53-4.62 (m, 1 H) 4.25 (t, J = 8.39 Hz, 2 H) 4.12-4.17 (m, 2 H) 3.92 (d, J = 13.12 Hz, 1 H) 3.74-3.79 (m, 2 H) 3.31-3.47 (m, 2 H) 3.14-3.21 (m, 1 H) 1.92-2.01 (m, 1 H) 1.85 (s, 3 H) 1.28-1.63 (m, 5 H) 0.85-0.91 (m, 6 H) | (ESI(+)) m/e 508 (M + H)$^+$ |
| 48 | N-[4-({1-[(2-methoxyethoxy)acetyl]piperidin-4-yl}oxy)phenyl]-1-(pyridin-3-yl)azetidine-3-carboxamide | $^1$H NMR (500 MHz, DMSO-$d_6$/D$_2$O) δ ppm 8.12 (d, J = 5.19 Hz, 1 H) 8.05 (d, J = 2.44 Hz, 1 H) 7.80 (dd, J = 8.85, 5.49 Hz, 1 H) 7.60 (dd, J = 8.54, 2.14 Hz, 1 H) 7.51 (d, J = 9.16 Hz, 2 H) 6.93-6.99 (m, J = 9.61, 9.61 Hz, 2 H) 4.51-4.59 (m, 1 H) 4.25 (t, J = 8.39 Hz, 2 H) 4.09-4.18 (m, 4 H) 3.80-3.86 (m, 1 H) 3.74-3.77 (m, 1 H) 3.54-3.57 (m, 2 H) 3.47 (dd, J = 5.65, 3.51 Hz, 2 H) 3.20-3.33 (m, 6 H) 1.87-1.96 (m, 2 H) 1.45-1.66 (m, 2 H) | (ESI(+)) m/e 469 (M + H)$^+$ |
| 49 | N-(4-{[1-(cyclohexylcarbonyl)piperidin-4-yl]oxy}phenyl)-1-(pyridin-3-yl)azetidine-3-carboxamide | $^1$H NMR (500 MHz, DMSO-$d_6$/D$_2$O) δ ppm 8.12 (d, J = 5.49 Hz, 1 H) 8.05 (d, J = 2.75 Hz, 1 H) 7.80 (dd, J = 8.54, 5.49 Hz, 1 H) 7.60 (dd, J = 8.70, 1.98 Hz, 1 H) 7.51 (d, J = 8.85 Hz, 2 H) 6.94-6.97 (m, 2 H) 4.49-4.58 (m, 1 H) 4.25 (t, J = 8.24 Hz, 2 H) 4.14 (dd, J = 8.09, 5.95 Hz, 2 H) 3.84 (dd, 1 H) 3.73-3.78 (m, 2 H) 3.33-3.40 (m, J = 9.77 Hz, 1 H) 3.17-3.27 (m, 1 H) 2.58-2.63 (m, 1 H) 1.82-1.99 (m, 2 H) 1.09-1.73 (m, 12 H) | (ESI(+)) m/e 463 (M + H)$^+$ |

TABLE 1-continued

The following Examples were prepared essentially as described in Example 1, substituting the appropriate bromopyridine in Example 1C and the appropriate carboxylic acid in Example 1E. Some products were purified by flash chromatography while others were purified by reverse-phase HPLC. Accordingly, some Examples were isolated as trifluoroacetic acid salts.

| Ex | Name | ¹H NMR | MS |
|---|---|---|---|
| 50 | N-(4-{[1-(cyclohexylacetyl)piperidin-4-yl]oxy}phenyl)-1-(pyridin-3-yl)azetidine-3-carboxamide | ¹H NMR (500 MHz, DMSO-$d_6$/$D_2O$) δ ppm 8.12 (d, J = 5.49 Hz, 1 H) 8.05 (d, J = 2.44 Hz, 1 H) 7.81 (dd, J = 8.85, 5.49 Hz, 1 H) 7.60 (dd, J = 8.85, 1.83 Hz, 1 H) 7.48-7.53 (m, 2 H) 6.91-7.00 (m, 2 H) 4.51-4.57 (m, 1 H) 4.25 (t, J = 8.24 Hz, 2 H) 4.14 (dd, J = 7.93, 6.10 Hz, 2 H) 3.84 (d, J = 4.27 Hz, 1 H) 3.74-3.79 (m, 2 H) 3.31-3.38 (m, 1 H) 3.16-3.27 (m, 1 H) 2.18-2.23 (m, J = 6.56, 2.90 Hz, 2 H) 1.83-1.97 (m, 2 H) 1.41-1.71 (m, 8 H) 1.06-1.27 (m, 3 H) 0.88-0.98 (m, 2 H) | (ESI(+)) m/e 477 (M + H)⁺ |
| 51 | 1-(pyridin-3-yl)-N-(4-{[1-(4,4,4-trifluorobutanoyl)piperidin-4-yl]oxy}phenyl)azetidine-3-carboxamide | ¹H NMR (500 MHz, DMSO-$d_6$/$D_2O$) δ ppm 8.12 (d, J = 5.49 Hz, 1 H) 8.05 (d, J = 2.44 Hz, 1 H) 7.80 (dd, J = 8.85, 5.49 Hz, 1 H) 7.59 (dd, J = 8.70, 1.98 Hz, 1 H) 7.49-7.54 (m, 2 H) 6.93-6.99 (m, 2 H) 4.52-4.60 (m, 1 H) 4.25 (t, J = 8.39 Hz, 2 H) 4.14 (dd, J = 8.09, 5.95 Hz, 2 H) 3.81-3.89 (m, 1 H) 3.74-3.78 (m, 2 H) 3.25-3.39 (m, 2 H) 2.61-2.68 (m, 2 H) 2.43-2.51 (m, 2 H) 1.84-2.00 (m, 2 H) 1.44-1.65 (m, 2 H) | (ESI(+)) m/e 477 (M + H)⁺ |
| 52 | N-(4-{[1-(cyclopentylcarbonyl)piperidin-4-yl]oxy}phenyl)-1-(pyridin-3-yl)azetidine-3-carboxamide | ¹H NMR (500 MHz, DMSO-$d_6$/$D_2O$) δ ppm 8.12 (d, J = 5.49 Hz, 1 H) 8.05 (d, J = 2.75 Hz, 1 H) 7.80 (dd, J = 8.54, 5.49 Hz, 1 H) 7.60 (dd, J = 8.70, 1.98 Hz, 1 H) 7.51 (d, J = 8.85 Hz, 2 H) 6.96 (d, J = 8.85 Hz, 2 H) 4.51-4.59 (m, 1 H) 4.25 (t, J = 8.39 Hz, 2 H) 4.09-4.18 (m, 2 H) 3.81-3.90 (m, 1 H) 3.75-3.79 (m, 2 H) 3.33-3.42 (m, 1 H) 3.20-3.29 (m, 1 H) 2.96-3.02 (m, 1 H) 1.46-1.98 (m, 12 H) | (ESI(+)) m/e 449 (M + H)⁺ |
| 53 | N-[4-({1-[(1-methylcyclohexyl)carbonyl]piperidin-4-yl}oxy)phenyl]-1-(pyridin-3-yl)azetidine-3-carboxamide | ¹H NMR (500 MHz, DMSO-$d_6$/$D_2O$) δ ppm 8.12 (d, J = 5.19 Hz, 1 H) 8.04 (d, J = 2.44 Hz, 1 H) 7.79 (dd, J = 8.54, 5.49 Hz, 1 H) 7.59 (dd, J = 8.70, 1.98 Hz, 1 H) 7.49-7.53 (m, 2 H) 6.96 (d, J = 8.85 Hz, 2 H) 4.50-4.59 (m, 1 H) 4.25 (t, J = 8.39 Hz, 2 H) 4.14 (dd, J = 7.93, 6.10 Hz, 2 H) 3.90 (dd, J = 9.00, 5.95 Hz, 2 H) 3.74-3.78 (m, 1 H) 3.27-3.36 (m, 2 H) 1.85-1.99 (m, 4 H) 1.24-1.55 (m, 10 H) 1.18 (s, 3 H) | (ESI(+)) m/e 477 (M + H)⁺ |
| 54 | N-(4-{[1-(furan-3-ylcarbonyl)piperidin-4-yl]oxy}phenyl)-1-(pyridin-3-yl)azetidine-3-carboxamide | ¹H NMR (500 MHz, DMSO-$d_6$/$D_2O$) δ ppm 8.12 (d, J = 5.49 Hz, 1 H) 8.04 (d, J = 2.44 Hz, 1 H) 8.02 (s, 1 H) 7.80 (dd, J = 8.85, 5.49 Hz, 1 H) 7.71-7.73 (m, 1 H) 7.59 (dd, J = 8.70, 2.29 Hz, 1 H) 7.52 (d, J = 8.85 Hz, 2 H) 6.97 (d, J = 8.85 Hz, 2 H) 6.67 (s, 1 H) 4.56-4.62 (m, 1 H) 4.25 (t, J = 8.24 Hz, 2 H) 4.14 (dd, J = 7.93, 6.10 Hz, 2 H) 3.82-3.92 (m, 2 H) 3.73-3.77 (m, 1 H) 3.39-3.49 (m, 2 H) 1.91-2.00 (m, 2 H) 1.55-1.65 (m, 2 H) | (ESI(+)) m/e 447 (M + H)⁺ |
| 55 | 1-(pyridin-3-yl)-N-(4-{[1-(3,3,3-trifluoropropanoyl)piperidin-4-yl]oxy}phenyl)azetidine-3-carboxamide | ¹H NMR (500 MHz, DMSO-$d_6$/$D_2O$) δ ppm 8.09 (d, J = 4.58 Hz, 1 H) 8.02 (s, 1 H) 7.73 (dd, J = 8.54, 5.49 Hz, 1 H) 7.48-7.54 (m, J = 9.16 Hz, 3 H) 6.96 (d, J = 8.85 Hz, 2 H) 4.57 (s, 1 H) 4.23 (t, J = 8.24 Hz, 2 H) 4.09-4.14 (m, 2 H) 3.80-3.87 (m, 1 H) 3.72-3.78 (m, 2 H) 3.59-3.63 (m, 2 H) 3.26-3.39 (m, 2 H) 1.93 (s, 2 H) 1.51 (s, 2 H) | (ESI(+)) m/e 463 (M + H)⁺ |
| 56 | N-{4-[(1-acetylpiperidin-4-yl)oxy]phenyl}-1-(pyridin-3-yl)azetidine-3-carboxamide | ¹H NMR (500 MHz, DMSO-$d_6$/$D_2O$) δ ppm 8.12 (d, J = 5.19 Hz, 1 H) 8.05 (d, J = 2.75 Hz, 1 H) 7.81 (dd, J = 8.85, 5.49 Hz, 1 H) 7.60 (dd, J = 8.70, 1.98 Hz, 1 H) 7.49-7.53 (m, 2 H) 6.92-6.98 (m, 2 H) 4.50-4.58 (m, 1 H) 4.25 (t, J = 8.39 Hz, 2 H) 4.14 (dd, J = 7.93, 6.10 Hz, 2 H) 3.79-3.85 (m, 1 H) 3.75-3.79 (m, 2 H) 3.19-3.40 (m, 2 H) 2.02 (s, 3 H) 1.83-1.99 (m, 2 H) 1.41-1.68 (m, 2 H) | (ESI(+)) m/e 395 (M + H)⁺ |
| 57 | N-(4-{[1-(methoxyacetyl)piperidin-4-yl]oxy}phenyl)-1-(pyridin-3-yl)azetidine-3-carboxamide | ¹H NMR (500 MHz, DMSO-$d_6$/$D_2O$) δ ppm 8.12 (d, J = 5.49 Hz, 1 H) 8.05 (d, J = 2.44 Hz, 1 H) 7.80 (dd, J = 8.54, 5.49 Hz, 1 H) 7.60 (dd, J = 8.54, 2.44 Hz, 1 H) 7.51 (d, J = 9.16 Hz, 2 H) 6.96 (d, J = 9.16 Hz, 2 H) 4.51-4.59 (m, 1 H) 4.25 (t, J = 8.39 Hz, 2 H) 4.14 (dd, J = 8.09, 5.95 Hz, 2 H) 4.10 (d, J = 3.05 Hz, 2 H) 3.80-3.86 (m, 1 H) 3.74-3.77 (m, 1 H) 3.57-3.64 (m, 1 H) 3.18-3.34 (m, 5 H) 1.85-1.99 (m, 2 H) 1.44-1.64 (m, 2 H) | (ESI(+)) m/e 425 (M + H)⁺ |

TABLE 1-continued

The following Examples were prepared essentially as described in Example 1,
substituting the appropriate bromopyridine in Example 1C and the appropriate carboxylic acid
in Example 1E. Some products were purified by flash chromatography while others were
purified by reverse-phase HPLC. Accordingly, some Examples were isolated as
trifluoroacetic acid salts.

| Ex | Name | $^1$H NMR | MS |
|---|---|---|---|
| 58 | 1-(pyridin-3-yl)-N-(4-{[1-(thiophen-3-ylcarbonyl)piperidin-4-yl]oxy}phenyl)azetidine-3-carboxamide | $^1$H NMR (500 MHz, DMSO-$d_6$/$D_2O$) δ ppm 8.11 (d, J = 5.49 Hz, 1 H) 8.04 (d, J = 2.75 Hz, 1 H) 7.76-7.78 (m, 1 H) 7.59-7.61 (m, 2 H) 7.52 (d, J = 8.85 Hz, 2 H) 7.44 (d, J = 4.88 Hz, 1 H) 7.22 (d, J = 5.19 Hz, 1 H) 6.97 (d, J = 9.16 Hz, 2 H) 4.56-4.62 (m, 1 H) 4.25 (t, J = 8.39 Hz, 2 H) 4.12-4.16 (m, 2 H) 3.87-3.96 (m, 1 H) 3.72-3.79 (m, 2 H) 3.33-3.46 (m, 2 H) 1.90-2.01 (m, J = 1.83 Hz, 2 H) 1.54-1.70 (m, 2 H) | (ESI(+)) m/e 463 (M + H)$^+$ |
| 59 | N-[4-({1-[(3-methylthiophen-2-yl)carbonyl]piperidin-4-yl}oxy)phenyl]-1-(pyridin-3-yl)azetidine-3-carboxamide | $^1$H NMR (500 MHz, DMSO-$d_6$/$D_2O$) δ ppm 8.12 (d, J = 5.49 Hz, 1 H) 8.04 (d, J = 2.75 Hz, 1 H) 7.80 (dd, J = 8.54, 5.49 Hz, 1 H) 7.48-7.62 (m, 4 H) 6.93-6.99 (m, 3 H) 4.54-4.66 (m, 1 H) 4.25 (t, J = 8.39 Hz, 2 H) 4.14 (dd, J = 7.93, 6.10 Hz, 2 H) 3.72-3.85 (m, 3 H) 3.34-3.45 (m, 2 H) 2.20 (s, 3 H) 1.91-2.00 (m, J = 9.77 Hz, 2 H) 1.53-1.64 (m, 2 H) | (ESI(+)) m/e 477 (M + H)$^+$ |
| 60 | N-(4-{[1-(morpholin-4-ylacetyl)piperidin-4-yl]oxy}phenyl)-1-(pyridin-3-yl)azetidine-3-carboxamide | $^1$H NMR (500 MHz, DMSO-$d_6$/$D_2O$) δ ppm 8.13 (d, J = 5.49 Hz, 1 H) 8.05 (d, J = 2.44 Hz, 1 H) 7.80 (dd, J = 8.85, 5.49 Hz, 1 H) 7.60 (dd, J = 8.54, 2.14 Hz, 1 H) 7.53 (d, J = 8.85 Hz, 2 H) 6.97 (d, J = 9.16 Hz, 2 H) 4.54-4.64 (m, 1 H) 4.35 (s, 2 H) 4.25 (t, J = 8.39 Hz, 2 H) 4.14 (dd, J = 8.09, 5.95 Hz, 2 H) 3.76-4.04 (m, 6 H) 3.52-3.60 (m, 1 H) 3.25-3.49 (m, 4 H) 3.08-3.22 (m, 2 H) 1.89-2.08 (m, 2 H) 1.50-1.77 (m, 2 H) | (ESI(+)) m/e 480 (M + H)$^+$ |
| 61 | 1-(pyridin-3-yl)-N-(4-{[1-(thiophen-2-ylcarbonyl)piperidin-4-yl]oxy}phenyl)azetidine-3-carboxamide | $^1$H NMR (500 MHz, DMSO-$d_6$/$D_2O$) δ ppm 8.12 (d, J = 5.49 Hz, 1 H) 8.04 (d, J = 1.83 Hz, 1 H) 7.79 (dd, J = 8.85, 5.49 Hz, 1 H) 7.58 (dd, J = 8.54, 2.14 Hz, 1 H) 7.52 (d, J = 9.16 Hz, 2 H) 7.42 (d, J = 3.66 Hz, 1 H) 7.18-7.22 (m, 1 H) 7.14 (dd, J = 4.88, 3.66 Hz, 1 H) 6.99 (d, 2 H) 4.58-4.66 (m, 1 H) 4.25 (t, J = 8.24 Hz, 2 H) 4.14 (dd, J = 7.93, 6.10 Hz, 2 H) 3.89-3.96 (m, 2 H) 3.74-3.80 (m, 1 H) 3.52 (m, 2 H) 1.95-2.04 (m, 2 H) 1.59-1.70 (m, 2 H) | (ESI(+)) m/e 463 (M + H)$^+$ |
| 62 | N-[4-({1-[(5-methylthiophen-2-yl)carbonyl]piperidin-4-yl}oxy)phenyl]-1-(pyridin-3-yl)azetidine-3-carboxamide | $^1$H NMR (500 MHz, DMSO-$d_6$/$D_2O$) δ ppm 8.12 (d, J = 5.49 Hz, 1 H) 8.04 (d, J = 2.75 Hz, 1 H) 7.80 (dd, J = 8.54, 5.49 Hz, 1 H) 7.59 (dd, J = 8.24, 2.14 Hz, 1 H) 7.52 (d, J = 9.16 Hz, 2 H) 7.23 (d, J = 3.36 Hz, 1 H) 6.98 (d, J = 9.16 Hz, 2 H) 6.80-6.86 (m, 1 H) 4.56-4.65 (m, 1 H) 4.25 (t, J = 8.39 Hz, 2 H) 4.12-4.17 (m, 2 H) 3.90-3.95 (m, 2 H) 3.74-3.79 (m, 1 H) 3.45-3.55 (m, 2 H) 2.47 (s, 3 H) 1.94-2.05 (m, 2 H) 1.58-1.67 (m, 2 H) | (ESI(+)) m/e 477 (M + H)$^+$ |
| 63 | N-(4-{[1-(furan-2-ylcarbonyl)piperidin-4-yl]oxy}phenyl)-1-(pyridin-3-yl)azetidine-3-carboxamide | $^1$H NMR (500 MHz, DMSO-$d_6$/$D_2O$) δ ppm 8.12 (d, J = 5.49 Hz, 1 H) 8.05 (d, J = 2.44 Hz, 1 H) 7.78-7.83 (m, 2 H) 7.60 (dd, J = 8.39, 2.29 Hz, 1 H) 7.52 (d, J = 9.16 Hz, 2 H) 6.96-7.02 (m, 3 H) 6.63 (dd, J = 3.36, 1.83 Hz, 1 H) 4.58-4.67 (m, 1 H) 4.25 (t, J = 8.39 Hz, 2 H) 4.14 (dd, J = 7.93, 5.80 Hz, 2 H) 3.92-3.99 (m, 2 H) 3.75-3.80 (m, 1 H) 3.41-3.59 (m, 2 H) 1.95-2.04 (m, 2 H) 1.58-1.67 (m, 2 H) | (ESI(+)) m/e 447 (M + H)$^+$ |
| 64 | N-[4-({1-[(1-methyl-1H-pyrrol-2-yl)carbonyl]piperidin-4-yl}oxy)phenyl]-1-(pyridin-3-yl)azetidine-3-carboxamide | $^1$H NMR (500 MHz, DMSO-$d_6$/$D_2O$) δ ppm 8.11 (s, 1 H) 8.04 (d, J = 2.44 Hz, 1 H) 7.80 (dd, J = 8.70, 5.34 Hz, 1 H) 7.59 (dd, J = 8.85, 1.83 Hz, 1 H) 7.52 (d, J = 9.16 Hz, 2 H) 6.97 (d, J = 9.16 Hz, 2 H) 6.88 (s, 1 H) 6.33 (dd, J = 3.81, 1.68 Hz, 1 H) 6.01-6.05 (m, 1 H) 4.52-4.63 (m, 1 H) 4.25 (t, J = 8.39 Hz, 2 H) 4.11-4.17 (m, 2 H) 3.90-3.96 (m, 2 H) 3.74-3.79 (m, 1 H) 3.66 (s, 3 H) 3.41-3.50 (m, 2 H) 1.91-2.04 (m, 2 H) 1.52-1.67 (m, 2 H) | (ESI(+)) m/e 460 (M + H)$^+$ |

TABLE 1-continued

The following Examples were prepared essentially as described in Example 1, substituting the appropriate bromopyridine in Example 1C and the appropriate carboxylic acid in Example 1E. Some products were purified by flash chromatography while others were purified by reverse-phase HPLC. Accordingly, some Examples were isolated as trifluoroacetic acid salts.

| Ex | Name | 1H NMR | MS |
|---|---|---|---|
| 65 | N-{4-[(1-propanoylpiperidin-4-yl)oxy]phenyl}-1-(pyridin-3-yl)azetidine-3-carboxamide | 1H NMR (500 MHz, DMSO-$d_6$/$D_2O$) δ ppm 8.12 (d, J = 5.49 Hz, 1 H) 8.05 (d, J = 2.75 Hz, 1 H) 7.80 (dd, J = 8.85, 5.49 Hz, 1 H) 7.60 (dd, J = 8.39, 2.29 Hz, 1 H) 7.51 (d, J = 8.85 Hz, 2 H) 6.96 (d, 2 H) 4.48-4.60 (m, 1 H) 4.25 (t, J = 8.39 Hz, 2 H) 4.14 (dd, J = 7.93, 6.10 Hz, 2 H) 3.81-3.90 (m, 1 H) 3.72-3.80 (m, 2 H) 3.17-3.41 (m, 2 H) 2.34 (q, J = 7.53 Hz, 2 H) 1.82-2.01 (m, 2 H) 1.35-1.63 (m, 2 H) 1.00 (t, J = 7.48 Hz, 3 H) | (ESI(+)) m/e 409 (M + H)+ |
| 66 | N-[4-({1-[(1-methylcyclopropyl)carbonyl]piperidin-4-yl}oxy)phenyl]-1-(pyridin-3-yl)azetidine-3-carboxamide | 1H NMR (500 MHz, DMSO-$d_6$/$D_2O$) δ ppm 8.12 (d, J = 5.49 Hz, 1 H) 8.05 (d, J = 2.75 Hz, 1 H) 7.80 (dd, J = 8.85, 5.49 Hz, 1 H) 7.60 (dd, J = 8.55, 1.83 Hz, 1 H) 7.52 (d, J = 8.85 Hz, 2 H) 6.96 (d, J = 8.85 Hz, 2 H) 4.51-4.60 (m, 1 H) 4.25 (t, J = 8.39 Hz, 2 H) 4.14 (dd, J = 7.93, 5.80 Hz, 2 H) 3.82-3.92 (m, 2 H) 3.74-3.78 (m, 1 H) 3.31-3.46 (m, 2 H) 1.85-1.96 (m, 2 H) 1.47-1.58 (m, J = 7.32 Hz, 2 H) 1.23 (s, 3 H) 0.76-0.81 (m, 2 H) 0.52-0.56 (m, 2 H) | (ESI(+)) m/e 435 (M + H)+ |
| 67 | N-(4-{[1-(N,N-dimethyl-beta-alanyl)piperidin-4-yl]oxy}phenyl)-1-(pyridin-3-yl)azetidine-3-carboxamide | 1H NMR (500 MHz, DMSO-$d_6$/$D_2O$) δ ppm 8.12 (d, J = 5.19 Hz, 1 H) 8.05 (d, J = 2.75 Hz, 1 H) 7.80 (dd, J = 8.85, 5.49 Hz, 1 H) 7.60 (dd, J = 8.39, 2.29 Hz, 1 H) 7.53 (d, J = 9.16 Hz, 2 H) 6.99 (d, J = 8.85 Hz, 2 H) 4.56-4.64 (m, 1 H) 4.25 (t, J = 8.39 Hz, 2 H) 4.14 (dd, J = 7.93, 5.80 Hz, 2 H) 3.72-3.82 (m, 3 H) 3.67-3.70 (m, 2 H) 3.19-3.54 (m, J = 87.28 Hz, 4 H) 2.92 (d, J = 10.68 Hz, 6 H) 1.97-2.16 (m, 2 H) 1.66-1.85 (m, 2 H) | N/A |
| 68 | 1-(pyridin-3-yl)-N-(4-{[1-(1,3-thiazol-2-ylcarbonyl)piperidin-4-yl]oxy}phenyl)azetidine-3-carboxamide | 1H NMR (500 MHz, DMSO-$d_6$/$D_2O$) δ ppm 8.12 (d, J = 5.49 Hz, 1 H) 8.05 (d, J = 2.44 Hz, 1 H) 7.98-8.02 (m, 2 H) 7.81 (dd, J = 8.85, 5.49 Hz, 1 H) 7.60 (dd, J = 8.39, 2.29 Hz, 1 H) 7.53 (d, 2 H) 6.99 (d, 2 H) 4.55-4.69 (m, 2 H) 4.25 (t, J = 8.39 Hz, 2 H) 4.15 (dd, J = 7.93, 5.80 Hz, 2 H) 3.94-4.08 (m, J = 41.20, 9.46 Hz, 2 H) 3.74-3.79 (m, 1 H) 3.49-3.58 (m, 1 H) 1.98-2.08 (m, 2 H) 1.67 (s, 2 H) | (ESI(+)) m/e 464 (M + H)+ |
| 69 | N-(4-{[1-(cyclopentylacetyl)piperidin-4-yl]oxy}phenyl)-1-(pyridin-3-yl)azetidine-3-carboxamide | 1H NMR (500 MHz, DMSO-$d_6$/$D_2O$) δ ppm 8.12 (d, J = 5.49 Hz, 1 H) 8.05 (d, J = 2.44 Hz, 1 H) 7.77-7.82 (m, 1 H) 7.60 (dd, J = 8.70, 1.98 Hz, 1 H) 7.51 (d, J = 8.85 Hz, 2 H) 6.96 (d, J = 8.85 Hz, 2 H) 4.50-4.58 (m, 1 H) 4.25 (t, J = 8.39 Hz, 2 H) 4.11-4.15 (m, 2 H) 3.81-3.90 (m, 1 H) 3.73-3.79 (m, 2 H) 3.18-3.40 (m, 2 H) 2.35 (dd, J = 7.17, 2.59 Hz, 2 H) 2.05-2.16 (m, 1 H) 1.83-1.98 (m, 2 H) 1.68-1.77 (m, 2 H) 1.42-1.63 (m, 6 H) 1.05-1.19 (m, 2 H) | (ESI(+)) m/e 463 (M + H)+ |
| 70 | N-(4-{[1-(2,3-dimethylbutanoyl)piperidin-4-yl]oxy}phenyl)-1-(pyridin-3-yl)azetidine-3-carboxamide | 1H NMR (500 MHz, DMSO-$d_6$/$D_2O$) δ ppm 8.12 (d, J = 5.49 Hz, 1 H) 8.05 (d, J = 2.44 Hz, 1 H) 7.80 (dd, J = 8.85, 5.49 Hz, 1 H) 7.60 (dd, J = 8.70, 2.29 Hz, 1 H) 7.50-7.53 (m, 2 H) 6.96 (d, J = 9.16 Hz, 2 H) 4.50-4.61 (m, 1 H) 4.25 (t, J = 8.39 Hz, 2 H) 4.14 (dd, J = 8.09, 5.95 Hz, 2 H) 3.92-3.97 (m, 1 H) 3.74-3.87 (m, 3 H) 3.20-3.43 (m, 2 H) 2.55-2.61 (m, 1 H) 1.38-2.03 (m, 5 H) 0.95 (d, J = 6.71 Hz, 2 H) 0.81-0.88 (m, 6 H) | (ESI(+)) m/e 451 (M + H)+ |

Example 8 tert-butyl 4-[4-({[(3S)-1-(pyridin-3-yl)pyrrolidin-3-yl]carbonyl}amino)phenoxy]piperidine-1-carboxylate The title compound was prepared as described in Example 1A-C, substituting (S)-1-(benzyloxycarbonyl)pyrrolidine-3-carboxylic acid for 1-(benzyloxycarbonyl)azetidine-3-carboxylic acid in Example 1A. 1H NMR (300 MHz, DMSO-$d_6$) δ ppm 9.96 (s, 1H), 7.95 (d, J=2.9 Hz, 1H), 7.85 (dd, J=4.6, 1.3 Hz, 1H), 7.54-7.48 (m, 2H), 7.15 (dd, J=8.4, 4.6 Hz, 1H), 6.98-6.86 (m, 3H), 4.53-4.41 (m, 1H), 3.73-3.46 (m, 3H), 3.45-3.30 (m, 2H), 3.24 (dd, J=17.5, 10.0 Hz, 2H), 3.12 (dd, J=24.9, 15.2 Hz, 2H), 2.35-2.10 (m, 2H), 2.01-1.78 (m, 2H), 1.68-1.42 (m, 2H), 1.40 (s, 9H); MS (ESI(+)) m/e 467 (M+H)+.

Example 9 tert-butyl 4-[4-({[(3R)-1-(pyridin-3-yl)pyrrolidin-3-yl]carbonyl}amino)phenoxy]piperidine-1-carboxylate The title compound was prepared as described in Example 1A-C, substituting (R)-1-(benzyloxycarbonyl)pyrrolidine-3- carboxylic acid for 1-(benzyloxycarbonyl)azetidine-3-carboxylic acid in Example 1A. $^1$H NMR (300 MHz, DMSO-$d_6$) δ ppm 9.97 (s, 1H), 7.95 (d, J=2.9 Hz, 1H), 7.85 (dd, J=4.6, 1.3 Hz, 1H), 7.54-7.48 (m, 2H), 7.16 (dd, J=8.4, 4.6 Hz, 1H), 6.98-6.86 (m, 3H), 4.53-4.41 (m, 1H), 3.75-3.45 (m, 3H), 3.45-3.34 (m, 3H), 3.25 (dd, J=8.8, 6.2 Hz, 1H), 3.23-3.09 (m, 2H), 2.34-2.07 (m, 2H), 1.95-1.75 (m, 2H), 1.59-1.41 (m, 2H), 1.40 (s, 9H); MS (ESI(+)) m/e 467 (M+H)$^+$.

Example 10

1-(pyridin-3-yl)-N-(4-{1-[(2S)-tetrahydrofuran-2-ylcarbonyl]piperidin-4-yl}phenyl)azetidine-3-carboxamide

Example 10A tert-butyl 4-(4-(1-(benzyloxycarbonyl)azetidine-3-carboxamido)phenyl)piperidine-1-carboxylate The title compound was prepared as described in Example 1A, substituting tert-butyl 4-(4-aminophenyl)piperidine-1-carboxylate for tert-butyl 4-(4-aminophenoxy)piperidine-1-carboxylate.

Example 10B tert-butyl 4-(4-(azetidine-3-carboxamido)phenyl)piperidine-1-carboxylate The title compound was prepared as described in Example 1B, substituting tert-butyl 4-(4-(1-(benzyloxycarbonyl)azetidine-3-carboxamido)phenyl)piperidine-1-carboxylate for tert-butyl 4-(4-(1-(benzyloxycarbonyl)azetidine-3-carboxamido)phenoxy)piperidine-1-carboxylate.

Example 10C tert-butyl 4-(4-(1-(pyridin-3-yl)azetidine-3-carboxamido)phenyl)piperidine-1-carboxylate The title compound was prepared as described in Example 1C, substituting tert-butyl 4-(4-(azetidine-3-carboxamido)phenyl)piperidine-1-carboxylate for tert-butyl 4-(4-(azetidine-3-carboxamido)phenoxy)piperidine-1-carboxylate.

Example 10D

N-(4-(piperidin-4-yl)phenyl)-1-(pyridin-3-yl)azetidine-3-carboxamide

The title compound was prepared as described in Example 1D, substituting tert-butyl 4-(4-(1-(pyridin-3-yl)azetidine-3-carboxamido)phenyl)piperidine-1-carboxylate for tert-butyl 4-(4-(1-(pyridin-3-yl)azetidine-3-carboxamido)phenoxy)piperidine-1-carboxylate.

Example 10E 1-(pyridin-3-yl)-N-(4-{1-[(2S)-tetrahydrofuran-2-ylcarbonyl]piperidin-4-yl}phenyl)azetidine-3-carboxamide The title compound was prepared as described in Example 1A, substituting N-(4-(piperidin-4-yl)phenyl)-1-(pyridin-3-yl)azetidine-3-carboxamide for tert-butyl 4-(4-aminophenoxy)piperidine-1-carboxylate and (S)-tetrahydrofuran-2-carboxylic acid for 1-(benzyloxycarbonyl)azetidine-3-carboxylic acid. $^1$H NMR (300 MHz, DMSO-$d_6$) δ ppm 10.01 (s, 1H), 7.93 (dd, J=4.6, 1.3 Hz, 1H), 7.85 (d, J=2.8 Hz, 1H), 7.57-7.49 (m, 2H), 7.22-7.14 (m, 3H), 6.86 (ddd, J=8.2, 2.9, 1.4 Hz, 1H), 4.68 (dd, J=7.5, 5.7 Hz, 1H), 4.53-4.43 (m, 1H), 4.10 (d, J=8.0 Hz, 2H), 3.95 (d, J=13.3 Hz, 2H), 3.89-3.64 (m, 3H), 3.15-3.00 (m, 1H), 2.82-2.59 (m, 2H), 2.19-1.68 (m, 6H), 1.61-1.29 (m, 3H); MS (ESI(+)) m/e 435 (M+H)$^+$.

TABLE 2

The following Examples were prepared essentially as described in Example 10, substituting the appropriate bromopyridine in Example 10C and the appropriate carboxylic acid in Example 10E. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
| 2 | 1-(2-cyanopyridin-3-yl)-N-{4-[1-(2-hydroxy-2-methylpropanoyl)piperidin-4-yl]phenyl}azetidine-3-carboxamide | $^1$H NMR (300 MHz, DMSO-$d_6$) δ ppm 10.04 (s, 1H), 8.12-7.94 (m, 1H), 7.54 (d, J = 8.5 Hz, 2H), 7.48-7.37 (m, 1H), 7.21-7.16 (m, 2H), 7.14 (dt, J = 7.7, 1.9 Hz, 1H), 5.36 (s, 1H), 4.97-4.53 (m, 2H), 4.43-4.31 (m, 2H), 4.30-4.13 (m, 2H), 3.78-3.56 (m, 1H), 2.85-2.65 (m, 2H), 1.81-1.63 (m, 2H), 1.59-1.42 (m, 2H), 1.33 (s, 6H) | (ESI(+)) m/e 448 (M + H)$^+$ |
| 20 | N-{4-[1-(2-hydroxy-2-methylpropanoyl)piperidin-4-yl]phenyl}-1-(pyridin-3-yl)azetidine-3-carboxamide | $^1$H NMR (300 MHz, DMSO-$d_6$) δ ppm 10.01 (s, 1H), 7.93 (dd, J = 4.6, 1.3 Hz, 1H), 7.85 (d, J = 2.8 Hz, 1H), 7.57-7.49 (m, 2H), 7.26-7.09 (m, 3H), 6.86 (ddd, J = 8.2, 2.9, 1.4 Hz, 1H), 5.37 (s, 1H), 4.77 (bs, 1H), 4.09 (t, J = 7.8 Hz, 2H), 3.95 (t, J = 6.6 Hz, 2H), 3.77-3.55 (m, 1H), 3.18-2.62 (m, 2H), 1.81-1.71 (m, 2H), 1.67-1.35 (m, 2H), 1.33 (s, 6H), 1.30-1.00 (m, 1H) | (ESI(+)) m/e 423 (M + H)$^+$ |
| 22 | N-(4-{1-[(2S)-2-methylbutanoyl]piperidin-4-yl}phenyl)-1-(pyridin-3- | $^1$H NMR (300 MHz, DMSO-$d_6$) δ ppm 10.01 (s, 1H), 7.93 (dd, J = 4.6, 1.4 Hz, 1H), 7.86 (d, J = 2.8 Hz, 1H), 7.57-7.49 (m, 2H), 7.25-7.09 (m, 3H), 6.90-6.82 (m, 1H), 4.63-4.52 (m, 1H), 4.18-3.87 (m, 5H), 3.78-3.63 (m, 1H), | (ESI(+)) m/e 421 (M + H)$^+$ |

TABLE 2-continued

The following Examples were prepared essentially as described in Example 10, substituting the appropriate bromopyridine in Example 10C and the appropriate carboxylic acid in Example 10E. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
|  | yl)azetidine-3-carboxamide | 3.16-2.99 (m, 1H), 2.81-2.67 (m, 2H), 2.59 (d, J = 12.4 Hz, 1H), 1.88-1.67 (m, 2H), 1.68-1.07 (m, 4H), 1.05-0.94 (m, 3H), 0.91-0.72 (m, 3H) |  |
| 25 | 1-(pyridin-3-yl)-N-{4-[1-(tetrahydro-2H-pyran-4-ylacetyl)piperidin-4-yl]phenyl}azetidine-3-carboxamide | $^1$H NMR (300 MHz, DMSO-d$_6$) δ ppm 10.01 (s, 1H), 7.93 (dd, J = 4.6, 1.3 Hz, 1H), 7.85 (d, J = 2.8 Hz, 1H), 7.57-7.49 (m, 2H), 7.22-7.14 (m, 3H), 6.86 (ddd, J = 8.2, 2.8, 1.4 Hz, 1H), 4.60-4.49 (m, 1H), 4.09 (t, J = 7.8 Hz, 2H), 3.97 (dd, J = 16.6, 10.2 Hz, 2H), 3.88-3.62 (m, 3H), 3.14-3.00 (m, 1H), 2.77-2.65 (m, 1H), 2.57 (t, J = 11.1 Hz, 1H), 2.27 (d, J = 6.8 Hz, 2H), 1.91 (dd, J = 9.4, 5.6 Hz, 1H), 1.74 (d, J = 11.3 Hz, 3H), 1.59 (d, J = 12.9 Hz, 2H), 1.43 (dd, J = 31.3, 12.2 Hz, 3H), 1.20 (dd, J = 24.5, 12.0 Hz, 3H) | (ESI(+)) m/e 463 (M + H)$^+$ |
| 26 | N-[4-(1-benzoylpiperidin-4-yl)phenyl]-1-(pyridin-3-yl)azetidine-3-carboxamide | $^1$H NMR (300 MHz, DMSO-d$_6$) δ ppm 10.01 (s, 1H), 7.93 (dd, J = 4.7, 1.3 Hz, 1H), 7.86 (d, J = 2.7 Hz, 1H), 7.54 (d, J = 8.5 Hz, 2H), 7.48-7.36 (m, 5H), 7.27-7.11 (m, 3H), 6.86 (ddd, J = 8.3, 2.8, 1.3 Hz, 1H), 4.62 (s, 1H), 4.13-4.01 (m, 2H), 3.97 (dd, J = 12.1, 5.8 Hz, 2H), 3.71 (ddd, J = 14.3, 8.1, 6.1 Hz, 2H), 3.13 (s, 1H), 2.76 (t, J = 11.7 Hz, 2H), 1.85 (d, J = 32.6 Hz, 2H), 1.66-1.40 (m, 2H) | (ESI(+)) m/e 441 (M + H)$^+$ |
| 29 | N-{4-[1-(2-methylpropanoyl)piperidin-4-yl]phenyl}-1-(2-methylpyridin-3-yl)azetidine-3-carboxamide | $^1$H NMR (300 MHz, DMSO-d$_6$) δ ppm 10.00 (s, 1H), 7.88 (dd, J = 4.7, 1.4 Hz, 1H), 7.57-7.49 (m, 2H), 7.22-7.14 (m, 2H), 7.07 (dd, J = 8.0, 4.7 Hz, 1H), 6.85 (dd, J = 8.1, 1.4 Hz, 1H), 4.60-4.49 (m, 1H), 4.15-3.85 (m, 4H), 3.68-3.53 (m, 1H), 3.21-3.02 (m, 1H), 2.97-2.61 (m, 2H), 2.35 (s, 3H), 2.32-1.66 (m, 3H), 1.60-1.14 (m, 3H), 1.12-0.92 (m, 6H) | (ESI(+)) m/e 421 (M + H)$^+$ |
| 30 | N-{4-[1-(2-methylpropanoyl)piperidin-4-yl]phenyl}-1-(pyridin-3-yl)azetidine-3-carboxamide | $^1$H NMR (300 MHz, DMSO-d$_6$) δ ppm 10.01 (s, 1H), 8.11-7.82 (m, 2H), 7.80-7.31 (m, 2H), 7.33-7.07 (m, 2H), 6.86 (ddd, J = 8.3, 2.9, 1.4 Hz, 1H), 4.61-4.49 (m, 1H), 4.16-3.87 (m, 4H), 3.77-3.64 (m, 1H), 3.20-2.99 (m, 1H), 2.89 (p, J = 6.7 Hz, 1H), 2.80-2.61 (m, 1H), 2.64-2.47 (m, 1H), 1.89-1.60 (m, 2H), 1.61-1.30 (m, 2H), 1.08 (d, J = 6.8 Hz, 2H), 1.05-0.97 (m, 6H) | (ESI(+)) m/e 407 (M + H)$^+$ |
| 71 | N-{4-[1-(2-hydroxy-2-methylpropanoyl)piperidin-4-yl]phenyl}-1-(2-methylpyridin-3-yl)azetidine-3-carboxamide | $^1$H NMR (300 MHz, DMSO-d$_6$) δ ppm 10.00 (s, 1H), 7.88 (dd, J = 4.7, 1.4 Hz, 1H), 7.57-7.50 (m, 2H), 7.21-7.14 (m, 2H), 7.07 (dd, J = 8.0, 4.6 Hz, 1H), 6.85 (dd, J = 8.1, 1.4 Hz, 1H), 5.37 (s, 1H), 4.65 (bs, 1H), 4.10 (t, J = 7.7 Hz, 2H), 3.97 (t, J = 6.8 Hz, 2H), 3.70-3.56 (m, 1H), 3.05-2.63 (m, 2H), 2.35 (s, 3H), 1.81-1.71 (m, 2H), 1.66-1.36 (m, 3H), 1.33 (s, 6H), 1.28-1.13 (m, 1H) | (ESI(+)) m/e 437 (M + H)$^+$ |
| 72 | N-{4-[1-(2-hydroxy-2-methylpropanoyl)piperidin-4-yl]phenyl}-1-(4-methylpyridin-3-yl)azetidine-3-carboxamide | $^1$H NMR (300 MHz, DMSO-d$_6$) δ ppm 9.99 (s, 1H), 7.90 (d, J = 4.7 Hz, 1H), 7.76 (s, 1H), 7.57-7.50 (m, 2H), 7.21-7.14 (m, 2H), 7.00 (d, J = 4.7 Hz, 1H), 5.35 (s, 1H), 4.71 (bs, 2H), 4.15 (t, J = 7.7 Hz, 2H), 4.05 (t, J = 6.8 Hz, 2H), 3.72-3.58 (m, 1H), 3.22-2.63 (m, 1H), 2.18 (s, 3H), 1.82-1.72 (m, 2H), 1.62-1.36 (m, 2H), 1.33 (s, 6H), 1.20 (d, J = 18.3 Hz, 1H), 0.89-0.72 (m, 1H) | (ESI(+)) m/e 437 (M + H)$^+$ |
| 73 | N-{4-[1-(2-hydroxy-2-methylpropanoyl)piperidin-4-yl]phenyl}-1-(2-methoxypyridin-3-yl)azetidine-3-carboxamide | $^1$H NMR (300 MHz, DMSO-d$_6$) δ ppm 9.94 (s, 1H), 7.56-7.49 (m, 3H), 7.21-7.13 (m, 2H), 6.84 (dd, J = 7.5, 4.9 Hz, 1H), 6.72 (dd, J = 7.5, 1.6 Hz, 1H), 5.35 (s, 1H), 4.72 (bs, 1H), 4.07 (t, J = 7.9 Hz, 2H), 3.95 (d, J = 6.9 Hz, 2H), 3.83 (s, 3H), 3.66-3.52 (m, 1H), 2.73 (t, J = 11.9 Hz, 2H), 1.82-1.71 (m, 2H), 1.59-1.36 (m, 2H), 1.33 (s, 6H) | (ESI(+)) m/e 453 (M + H)$^+$ |
| 96 | N-{4-[1-(2-hydroxy-2-methylpropanoyl)piperidin-4-yl]phenyl}-1-(4- | $^1$H NMR (300 MHz, DMSO-d$_6$) δ ppm 9.94 (s, 1H), 7.93 (d, J = 5.3 Hz, 1H), 7.63 (s, 1H), 7.56-7.49 (m, 2H), 7.21-7.13 (m, 2H), 6.88 (d, J = 5.4 Hz, 1H), 5.35 (s, 1H), 4.71 (bs, 1H), 4.09 (t, J = 7.9 Hz, 2H), 3.96 (dd, J = 12.1, 4.8 Hz, 2H), | (ESI(+)) m/e 453 (M + H)$^+$ |

TABLE 2-continued

The following Examples were prepared essentially as described in Example 10, substituting the appropriate bromopyridine in Example 10C and the appropriate carboxylic acid in Example 10E. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
|  | methoxypyridin-3-yl)azetidine-3-carboxamide | 3.79 (s, 3H), 3.71-3.54 (m, 2H), 2.73 (t, J = 11.8 Hz, 1H), 1.76 (d, J = 11.4 Hz, 3H), 1.51 (s, 3H), 1.33 (s, 6H) |  |
| 97 | 1-(4-cyanopyridin-3-yl)-N-{4-[1-(2-hydroxy-2-methylpropanoyl)piperidin-4-yl]phenyl}azetidine-3-carboxamide | $^1$H NMR (300 MHz, DMSO-d$_6$) δ ppm 10.04 (s, 1H), 8.09 (s, 1H), 7.96 (d, J = 5.0 Hz, 1H), 7.54 (d, J = 8.6 Hz, 2H), 7.46 (dd, J = 5.1, 0.5 Hz, 1H), 7.18 (d, J = 8.6 Hz, 2H), 5.36 (s, 1H), 4.74 (s, 1H), 4.43 (t, J = 8.3 Hz, 2H), 4.31 (dd, J = 8.0, 5.8 Hz, 2H), 3.79-3.66 (m, 1H), 2.74 (dd, J = 13.8, 10.3 Hz, 2H), 1.81-1.72 (m, 3H), 1.65-1.45 (m, 3H), 1.33 (s, 6H) | (ESI(+)) m/e 448 (M + H)$^+$ |
| 98 | N-[4-(1-pentanoylpiperidin-4-yl)phenyl]-1-(pyridin-3-yl)azetidine-3-carboxamide |  | (ESI(+)) m/e 421 (M + H)$^+$ |
| 99 | N-{4-[1-(3-methylpentanoyl)piperidin-4-yl]phenyl}-1-(pyridin-3-yl)azetidine-3-carboxamide |  | (ESI(+)) m/e 435 (M + H)$^+$ |
| 100 | N-(4-{1-[(1S,4R)-bicyclo[2.2.1]hept-2-ylacetyl]piperidin-4-yl}phenyl)-1-(pyridin-3-yl)azetidine-3-carboxamide |  | (ESI(+)) m/e 473 (M + H)$^+$ |
| 101 | N-{4-[1-(cyclopentylacetyl)piperidin-4-yl]phenyl}-1-(pyridin-3-yl)azetidine-3-carboxamide |  | (ESI(+)) m/e 447 (M + H)$^+$ |
| 102 | N-(4-{1-[(2-methylcyclopropyl)carbonyl]piperidin-4-yl}phenyl)-1-(pyridin-3-yl)azetidine-3-carboxamide |  | (ESI(+)) m/e 419 (M + H)$^+$ |
| 103 | N-{4-[1-(morpholin-4-ylacetyl)piperidin-4-yl]phenyl}-1-(pyridin-3-yl)azetidine-3-carboxamide |  | (ESI(+)) m/e 464 (M + H)$^+$ |
| 104 | N-{4-[1-(furan-3-ylcarbonyl)piperidin-4-yl]phenyl}-1-(pyridin-3-yl)azetidine-3-carboxamide |  | (ESI(+)) m/e 431 (M + H)$^+$ |
| 105 | 1-(pyridin-3-yl)-N-{4-[1-(pyrrolidin-1-ylacetyl)piperidin-4-yl]phenyl}azetidine-3-carboxamide |  | (ESI(+)) m/e 474 (M + H)$^+$ |
| 106 | N-{4-[1-(5-oxo-D-prolyl)piperidin- |  | (ESI(+)) m/e 448 (M + H)$^+$ |

TABLE 2-continued

The following Examples were prepared essentially as described in Example 10, substituting the appropriate bromopyridine in Example 10C and the appropriate carboxylic acid in Example 10E. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
|  | 4-yl]phenyl}-1-(pyridin-3-yl)azetidine-3-carboxamide | | |
| 107 | N-{4-[1-(N,N-dimethyl-beta-alanyl)piperidin-4-yl]phenyl}-1-(pyridin-3-yl)azetidine-3-carboxamide | | (ESI(+)) m/e 436 (M + H)$^+$ |
| 108 | 1-(pyridin-3-yl)-N-{4-[1-(1,3-thiazol-2-ylcarbonyl)piperidin-4-yl]phenyl}azetidine-3-carboxamide | | (ESI(+)) m/e 448 (M + H)$^+$ |
| 109 | 1-(pyridin-3-yl)-N-{4-[1-(thiophen-3-ylcarbonyl)piperidin-4-yl]phenyl}azetidine-3-carboxamide | | (ESI(+)) m/e 447 (M + H)$^+$ |
| 110 | N-(4-{1-[(1-methylcyclopropyl)carbonyl]piperidin-4-yl}phenyl)-1-(pyridin-3-yl)azetidine-3-carboxamide | | (ESI(+)) m/e 419 (M + H)$^+$ |
| 111 | N-(4-{1-[(3-methylthiophen-2-yl)carbonyl]piperidin-4-yl}phenyl)-1-(pyridin-3-yl)azetidine-3-carboxamide | | (ESI(+)) m/e 461 (M + H)$^+$ |
| 112 | 1-(pyridin-3-yl)-N-{4-[1-(4,4,4-trifluorobutanoyl)piperidin-4-yl]phenyl}azetidine-3-carboxamide | | (ESI(+)) m/e 461 (M + H)$^+$ |
| 113 | N-(4-{1-[(4-methylpiperazin-1-yl)acetyl]piperidin-4-yl}phenyl)-1-(pyridin-3-yl)azetidine-3-carboxamide | | (ESI(+)) m/e 477 (M + H)$^+$ |
| 114 | N-{4-[1-(5-oxo-L-prolyl)piperidin-4-yl]phenyl}-1-(pyridin-3-yl)azetidine-3-carboxamide | | (ESI(+)) m/e 448 (M + H)$^+$ |
| 115 | N-{4-[1-(3-ethoxypropanoyl)piperidin-4-yl]phenyl}-1-(pyridin-3-yl)azetidine-3-carboxamide | | (ESI(+)) m/e 437 (M + H)$^+$ |

TABLE 2-continued

The following Examples were prepared essentially as described in Example 10, substituting the appropriate bromopyridine in Example 10C and the appropriate carboxylic acid in Example 10E. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
| 116 | N-{4-[1-(4-methylpentanoyl)piperidin-4-yl]phenyl}-1-(pyridin-3-yl)azetidine-3-carboxamide | | (ESI(+)) m/e 435 (M + H)$^+$ |
| 117 | N-(4-{1-[(1-methylcyclohexyl)carbonyl]piperidin-4-yl}phenyl)-1-(pyridin-3-yl)azetidine-3-carboxamide | | (ESI(+)) m/e 461 (M + H)$^+$ |
| 118 | N-[4-(1-acetylpiperidin-4-yl)phenyl]-1-(pyridin-3-yl)azetidine-3-carboxamide | | (ESI(+)) m/e 379 (M + H)$^+$ |
| 119 | N-{4-[1-(cyclohexylacetyl)piperidin-4-yl]phenyl}-1-(pyridin-3-yl)azetidine-3-carboxamide | | (ESI(+)) m/e 461 (M + H)$^+$ |
| 120 | N-{4-[1-(N-acetyl-L-leucyl)piperidin-4-yl]phenyl}-1-(pyridin-3-yl)azetidine-3-carboxamide | | (ESI(+)) m/e 492 (M + H)$^+$ |
| 121 | N-[4-(1-propanoylpiperidin-4-yl)phenyl]-1-(pyridin-3-yl)azetidine-3-carboxamide | | (ESI(+)) m/e 393 (M + H)$^+$ |
| 122 | 1-(pyridin-3-yl)-N-{4-[1-(3,3,3-trifluoropropanoyl)piperidin-4-yl]phenyl}azetidine-3-carboxamide | | (ESI(+)) m/e 447 (M + H)$^+$ |
| 123 | N-(4-{1-[(2-methoxyethoxy)acetyl]piperidin-4-yl}phenyl)-1-(pyridin-3-yl)azetidine-3-carboxamide | | (ESI(+)) m/e 453 (M + H)$^+$ |
| 124 | N-(4-{1-[3-(morpholin-4-yl)propanoyl]piperidin-4-yl}phenyl)-1-(pyridin-3-yl)azetidine-3-carboxamide | | (ESI(+)) m/e 478 (M + H)$^+$ |
| 125 | N-{4-[1-(2,2-dimethylpropanoyl)piperidin-4-yl]phenyl}-1-(pyridin-3-yl)azetidine-3-carboxamide | | (ESI(+)) m/e 421 (M + H)$^+$ |
| 126 | N-(4-{1-[(5-methylthiophen-2-yl)carbonyl]piperidin- | | (ESI(+)) m/e 461 (M + H)$^+$ |

TABLE 2-continued

The following Examples were prepared essentially as described in Example 10, substituting the appropriate bromopyridine in Example 10C and the appropriate carboxylic acid in Example 10E. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
| | 4-yl}phenyl)-1-(pyridin-3-yl)azetidine-3-carboxamide | | |
| 127 | 1-(pyridin-3-yl)-N-{4-[1-(thiophen-2-ylcarbonyl)piperidin-4-yl]phenyl}azetidine-3-carboxamide | | (ESI(+)) m/e 447 (M + H)$^+$ |
| 128 | N-(4-{1-[(1-methyl-1H-pyrrol-2-yl)carbonyl]piperidin-4-yl}phenyl)-1-(pyridin-3-yl)azetidine-3-carboxamide | | (ESI(+)) m/e 444 (M + H)$^+$ |
| 129 | N-{4-[1-(furan-2-ylcarbonyl)piperidin-4-yl]phenyl}-1-(pyridin-3-yl)azetidine-3-carboxamide | | (ESI(+)) m/e 431 (M + H)$^+$ |
| 130 | N-(4-{1-[3-(piperidin-1-yl)propanoyl]piperidin-4-yl}phenyl)-1-(pyridin-3-yl)azetidine-3-carboxamide | | (ESI(+)) m/e 476 (M + H)$^+$ |
| 131 | N-{4-[1-(ethoxyacetyl)piperidin-4-yl]phenyl}-1-(pyridin-3-yl)azetidine-3-carboxamide | | (ESI(+)) m/e 423 (M + H)$^+$ |
| 132 | N-{4-[1-(3,3-dimethylbutanoyl)piperidin-4-yl]phenyl}-1-(pyridin-3-yl)azetidine-3-carboxamide | | (ESI(+)) m/e 435 (M + H)$^+$ |
| 133 | N-{4-[1-(2,2-dimethylbutanoyl)piperidin-4-yl]phenyl}-1-(pyridin-3-yl)azetidine-3-carboxamide | | (ESI(+)) m/e 435 (M + H)$^+$ |
| 134 | N-[4-(1-butanoylpiperidin-4-yl)phenyl]-1-(pyridin-3-yl)azetidine-3-carboxamide | | (ESI(+)) m/e 407 (M + H)$^+$ |
| 135 | N-{4-[1-(methoxyacetyl)piperidin-4-yl]phenyl}-1-(pyridin-3-yl)azetidine-3-carboxamide | | (ESI(+)) m/e 409 (M + H)$^+$ |

TABLE 2-continued

The following Examples were prepared essentially as described in Example 10, substituting the appropriate bromopyridine in Example 10C and the appropriate carboxylic acid in Example 10E. Some products were purified by flash chromatography while others were purified by reverse-phase HPLC. Accordingly, some Examples were isolated as trifluoroacetic acid salts.

| Ex | Name | ¹H NMR | MS |
|---|---|---|---|
| 136 | N-{4-[1-(cyclohexylcarbonyl)piperidin-4-yl]phenyl}-1-(pyridin-3-yl)azetidine-3-carboxamide | | (ESI(+)) m/e 447 (M + H)⁺ |
| 137 | N-{4-[1-(3-methylbutanoyl)piperidin-4-yl]phenyl}-1-(pyridin-3-yl)azetidine-3-carboxamide | | (ESI(+)) m/e 421 (M + H)⁺ |
| 138 | N-{4-[1-(cyclopentylcarbonyl)piperidin-4-yl]phenyl}-1-(pyridin-3-yl)azetidine-3-carboxamide | | (ESI(+)) m/e 433 (M + H)⁺ |
| 139 | N-{4-[1-(2,3-dimethylbutanoyl)piperidin-4-yl]phenyl}-1-(pyridin-3-yl)azetidine-3-carboxamide | | (ESI(+)) m/e 435 (M + H)⁺ |
| 149 | N-[4-(1-benzoylpiperidin-4-yl)phenyl]-1-(2-methylpyridin-3-yl)azetidine-3-carboxamide | | (ESI(+)) m/e 455 (M + H)⁺ |
| 150 | N-{4-[1-(2-fluorobenzoyl)piperidin-4-yl]phenyl}-1-(2-methylpyridin-3-yl)azetidine-3-carboxamide | | (ESI(+)) m/e 473 (M + H)⁺ |
| 151 | N-{4-[1-(2-chlorobenzoyl)piperidin-4-yl]phenyl}-1-(2-methylpyridin-3-yl)azetidine-3-carboxamide | | (ESI(+)) m/e 489 (M + H)⁺ |
| 152 | N-{4-[1-(3-fluorobenzoyl)piperidin-4-yl]phenyl}-1-(2-methylpyridin-3-yl)azetidine-3-carboxamide | | (ESI(+)) m/e 473 (M + H)⁺ |
| 153 | N-{4-[1-(3-chlorobenzoyl)piperidin-4-yl]phenyl}-1-(2-methylpyridin-3-yl)azetidine-3-carboxamide | | (ESI(+)) m/e 489 (M + H)⁺ |
| 154 | N-{4-[1-(3,5-dichlorobenzoyl)piperidin-4-yl]phenyl}-1-(2-methylpyridin-3-yl)azetidine-3-carboxamide | | (ESI(+)) m/e 523 (M + H)⁺ |

TABLE 2-continued

The following Examples were prepared essentially as described in Example 10, substituting the appropriate bromopyridine in Example 10C and the appropriate carboxylic acid in Example 10E. Some products were purified by flash chromatography while others were purified by reverse-phase HPLC. Accordingly, some Examples were isolated as trifluoroacetic acid salts.

| Ex | Name | ¹H NMR | MS |
|---|---|---|---|
| 155 | N-{4-[1-(4-fluorobenzoyl)piperidin-4-yl]phenyl}-1-(2-methylpyridin-3-yl)azetidine-3-carboxamide | | (ESI(+)) m/e 473 (M + H)⁺ |
| 156 | N-{4-[1-(4-chlorobenzoyl)piperidin-4-yl]phenyl}-1-(2-methylpyridin-3-yl)azetidine-3-carboxamide | | (ESI(+)) m/e 489 (M + H)⁺ |
| 157 | 1-(2-methylpyridin-3-yl)-N-(4-{1-[4-(trifluoromethyl)benzoyl]piperidin-4-yl}phenyl)azetidine-3-carboxamide | | (ESI(+)) m/e 523 (M + H)⁺ |
| 158 | 1-(2-methylpyridin-3-yl)-N-{4-[1-(pyridazin-3-ylcarbonyl)piperidin-4-yl]phenyl}azetidine-3-carboxamide | | (ESI(+)) m/e 457 (M + H)⁺ |
| 159 | 1-(2-methylpyridin-3-yl)-N-[4-(1-pentanoylpiperidin-4-yl)phenyl]azetidine-3-carboxamide | | (ESI(+)) m/e 435 (M + H)⁺ |
| 160 | N-{4-[1-(3-methylpentanoyl)piperidin-4-yl]phenyl}-1-(2-methylpyridin-3-yl)azetidine-3-carboxamide | | (ESI(+)) m/e 449 (M + H)⁺ |
| 161 | N-(4-{1-[(1S,4R)-bicyclo[2.2.1]hept-2-ylacetyl]piperidin-4-yl}phenyl)-1-(2-methylpyridin-3-yl)azetidine-3-carboxamide | | (ESI(+)) m/e 487 (M + H)⁺ |
| 162 | N-{4-[1-(cyclopentylacetyl)piperidin-4-yl]phenyl}-1-(2-methylpyridin-3-yl)azetidine-3-carboxamide | | (ESI(+)) m/e 461 (M + H)⁺ |
| 163 | N-(4-{1-[(2-methylcyclopropyl)carbonyl]piperidin-4-yl}phenyl)-1-(2-methylpyridin-3-yl)azetidine-3-carboxamide | | (ESI(+)) m/e 433 (M + H)⁺ |

TABLE 2-continued

The following Examples were prepared essentially as described in Example 10, substituting the appropriate bromopyridine in Example 10C and the appropriate carboxylic acid in Example 10E. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
| 164 | 1-(2-methylpyridin-3-yl)-N-{4-[1-(morpholin-4-ylacetyl)piperidin-4-yl]phenyl}azetidine-3-carboxamide | | (ESI(+)) m/e 478 (M + H)$^+$ |
| 165 | N-{4-[1-(furan-3-ylcarbonyl)piperidin-4-yl]phenyl}-1-(2-methylpyridin-3-yl)azetidine-3-carboxamide | | (ESI(+)) m/e 445 (M + H)$^+$ |
| 166 | 1-(2-methylpyridin-3-yl)-N-{4-[1-(pyrrolidin-1-ylacetyl)piperidin-4-yl]phenyl}azetidine-3-carboxamide | | (ESI(+)) m/e 462 (M + H)$^+$ |
| 167 | 1-(2-methylpyridin-3-yl)-N-{4-[1-(5-oxo-D-prolyl)piperidin-4-yl]phenyl}azetidine-3-carboxamide | | (ESI(+)) m/e 462 (M + H)$^+$ |
| 168 | N-{4-[1-(N,N-dimethyl-beta-alanyl)piperidin-4-yl]phenyl}-1-(2-methylpyridin-3-yl)azetidine-3-carboxamide | | (ESI(+)) m/e 450 (M + H)$^+$ |
| 169 | 1-(2-methylpyridin-3-yl)-N-{4-[1-(thiophen-3-ylcarbonyl)piperidin-4-yl]phenyl}azetidine-3-carboxamide | | (ESI(+)) m/e 461 (M + H)$^+$ |
| 170 | N-(4-{1-[(1-methylcyclopropyl)carbonyl]piperidin-4-yl}phenyl)-1-(2-methylpyridin-3-yl)azetidine-3-carboxamide | | (ESI(+)) m/e 433 (M + H)$^+$ |
| 171 | 1-(2-methylpyridin-3-yl)-N-(4-{1-[(3-methylthiophen-2-yl)carbonyl]piperidin-4-yl}phenyl)azetidine-3-carboxamide | | (ESI(+)) m/e 475 (M + H)$^+$ |
| 172 | 1-(2-methylpyridin-3-yl)-N-{4-[1-(4,4,4- | | (ESI(+)) m/e 475 (M + H)$^+$ |

TABLE 2-continued

The following Examples were prepared essentially as described in Example 10, substituting the appropriate bromopyridine in Example 10C and the appropriate carboxylic acid in Example 10E. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
|  | trifluorobutanoyl)piperidin-4-yl]phenyl}azetidine-3-carboxamide | | |
| 173 | N-(4-{1-[(4-methylpiperazin-1-yl)acetyl]piperidin-4-yl}phenyl)-1-(2-methylpyridin-3-yl)azetidine-3-carboxamide | | (ESI(+)) m/e 491 (M + H)$^+$ |
| 174 | 1-(2-methylpyridin-3-yl)-N-{4-[1-(5-oxo-L-prolyl)piperidin-4-yl]phenyl}azetidine-3-carboxamide | | (ESI(+)) m/e 462 (M + H)$^+$ |
| 175 | N-{4-[1-(3-ethoxypropanoyl)piperidin-4-yl]phenyl}-1-(2-methylpyridin-3-yl)azetidine-3-carboxamide | | (ESI(+)) m/e 451 (M + H)$^+$ |
| 176 | N-{4-[1-(4-methylpentanoyl)piperidin-4-yl]phenyl}-1-(2-methylpyridin-3-yl)azetidine-3-carboxamide | | (ESI(+)) m/e 449 (M + H)$^+$ |
| 177 | N-(4-{1-[(1-methylcyclohexyl)carbonyl]piperidin-4-yl}phenyl)-1-(2-methylpyridin-3-yl)azetidine-3-carboxamide | | (ESI(+)) m/e 475 (M + H)$^+$ |
| 178 | N-[4-(1-acetylpiperidin-4-yl)phenyl]-1-(2-methylpyridin-3-yl)azetidine-3-carboxamide | | (ESI(+)) m/e 393 (M + H)$^+$ |
| 179 | N-{4-[1-(cyclohexylacetyl)piperidin-4-yl]phenyl}-1-(2-methylpyridin-3-yl)azetidine-3-carboxamide | | (ESI(+)) m/e 475 (M + H)$^+$ |
| 180 | N-{4-[1-(N-acetyl-L-leucyl)piperidin-4-yl]phenyl}-1-(2-methylpyridin-3-yl)azetidine-3-carboxamide | | (ESI(+)) m/e 506 (M + H)$^+$ |

TABLE 2-continued

The following Examples were prepared essentially as described in Example 10, substituting the appropriate bromopyridine in Example 10C and the appropriate carboxylic acid in Example 10E. Some products were purified by flash chromatography while others were purified by reverse-phase HPLC. Accordingly, some Examples were isolated as trifluoroacetic acid salts.

| Ex | Name | ¹H NMR | MS |
|---|---|---|---|
| 181 | 1-(2-methylpyridin-3-yl)-N-[4-(1-propanoylpiperidin-4-yl)phenyl]azetidine-3-carboxamide | | (ESI(+)) m/e 407 (M + H)⁺ |
| 182 | 1-(2-methylpyridin-3-yl)-N-{4-[1-(3,3,3-trifluoropropanoyl)piperidin-4-yl]phenyl}azetidine-3-carboxamide | | (ESI(+)) m/e 461 (M + H)⁺ |
| 183 | N-(4-{1-[(2-methoxyethoxy)acetyl]piperidin-4-yl}phenyl)-1-(2-methylpyridin-3-yl)azetidine-3-carboxamide | | (ESI(+)) m/e 467 (M + H)⁺ |
| 184 | 1-(2-methylpyridin-3-yl)-N-(4-{1-[3-(morpholin-4-yl)propanoyl]piperidin-4-yl}phenyl)azetidine-3-carboxamide | | (ESI(+)) m/e 492 (M + H)⁺ |
| 185 | N-{4-[1-(2,2-dimethylpropanoyl)piperidin-4-yl]phenyl}-1-(2-methylpyridin-3-yl)azetidine-3-carboxamide | | (ESI(+)) m/e 435 (M + H)⁺ |
| 186 | 1-(2-methylpyridin-3-yl)-N-(4-{1-[(5-methylthiophen-2-yl)carbonyl]piperidin-4-yl}phenyl)azetidine-3-carboxamide | | (ESI(+)) m/e 475 (M + H)⁺ |
| 187 | 1-(2-methylpyridin-3-yl)-N-{4-[1-(thiophen-2-ylcarbonyl)piperidin-4-yl]phenyl}azetidine-3-carboxamide | | (ESI(+)) m/e 461 (M + H)⁺ |
| 188 | 1-(2-methylpyridin-3-yl)-N-(4-{1-[(1-methyl-1H-pyrrol-2-yl)carbonyl]piperidin-4-yl}phenyl)azetidine-3-carboxamide | | (ESI(+)) m/e 458 (M + H)⁺ |

TABLE 2-continued

The following Examples were prepared essentially as described in Example 10, substituting the appropriate bromopyridine in Example 10C and the appropriate carboxylic acid in Example 10E. Some products were purified by flash chromatography while others were purified by reverse-phase HPLC. Accordingly, some Examples were isolated as trifluoroacetic acid salts.

| Ex | Name | ¹H NMR | MS |
|---|---|---|---|
| 189 | N-{4-[1-(furan-2-ylcarbonyl)piperidin-4-yl]phenyl}-1-(2-methylpyridin-3-yl)azetidine-3-carboxamide | | (ESI(+)) m/e 445 (M + H)⁺ |
| 190 | 1-(2-methylpyridin-3-yl)-N-(4-{1-[3-(piperidin-1-yl)propanoyl]piperidin-4-yl}phenyl)azetidine-3-carboxamide | | (ESI(+)) m/e 490 (M + H)⁺ |
| 191 | N-{4-[1-(ethoxyacetyl)piperidin-4-yl]phenyl}-1-(2-methylpyridin-3-yl)azetidine-3-carboxamide | | (ESI(+)) m/e 437 (M + H)⁺ |
| 192 | N-{4-[1-(3,3-dimethylbutanoyl)piperidin-4-yl]phenyl}-1-(2-methylpyridin-3-yl)azetidine-3-carboxamide | | (ESI(+)) m/e 449 (M + H)⁺ |
| 193 | N-{4-[1-(2,2-dimethylbutanoyl)piperidin-4-yl]phenyl}-1-(2-methylpyridin-3-yl)azetidine-3-carboxamide | | (ESI(+)) m/e 449 (M + H)⁺ |
| 194 | N-[4-(1-butanoylpiperidin-4-yl)phenyl]-1-(2-methylpyridin-3-yl)azetidine-3-carboxamide | | (ESI(+)) m/e 421 (M + H)⁺ |
| 195 | N-{4-[1-(methoxyacetyl)piperidin-4-yl]phenyl}-1-(2-methylpyridin-3-yl)azetidine-3-carboxamide | | (ESI(+)) m/e 423 (M + H)⁺ |
| 196 | N-{4-[1-(cyclohexylcarbonyl)piperidin-4-yl]phenyl}-1-(2-methylpyridin-3-yl)azetidine-3-carboxamide | | (ESI(+)) m/e 461 (M + H)⁺ |
| 197 | N-{4-[1-(3-methylbutanoyl)piperidin-4-yl]phenyl}-1-(2-methylpyridin-3-yl)azetidine-3-carboxamide | | (ESI(+)) m/e 435 (M + H)⁺ |

TABLE 2-continued

The following Examples were prepared essentially as described in Example 10, substituting the appropriate bromopyridine in Example 10C and the appropriate carboxylic acid in Example 10E. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
| 198 | N-{4-[1-(2,3-dimethylbutanoyl)piperidin-4-yl]phenyl}-1-(2-methylpyridin-3-yl)azetidine-3-carboxamide | | (ESI(+)) m/e 449 (M + H)$^+$ |

Example 11

(3S)-1-(pyridin-3-yl)-N-(4-{[1-(tetrahydro-2H-pyran-4-ylacetyl)piperidin-4-yl]oxy}phenyl)pyrrolidine-3-carboxamide The title compound was prepared as described in Example 1D-E, substituting tert-butyl 4-[4-({[(3S)-1-(pyridin-3-yl)pyrrolidin-3-yl]carbonyl} amino)phenoxy]piperidine-1-carboxylate for tert-butyl 4-(4-(1-(pyridin-3-yl)azetidine-3-carboxamido)phenoxy)piperidine-1-carboxylate in Example 1D. $^1$H NMR (300 MHz, DMSO-d$_6$) δ ppm 9.98 (s, 1H), 7.99 (d, J=2.9 Hz, 1H), 7.91 (d, J=4.8 Hz, 1H), 7.50 (s, 2H), 7.33 (dd, J=8.5, 4.8 Hz, 1H), 7.16-7.09 (m, 1H), 6.97-6.89 (m, 2H), 4.58-4.47 (m, 1H), 3.95-3.65 (m, 4H), 3.56 (d, J=8.6 Hz, 1H), 3.50-3.32 (m, 6H), 2.36-2.11 (m, 4H), 2.01-1.79 (m, 3H), 1.66-1.38 (m, 4H), 1.32-1.08 (m, 3H); MS (ESI(+)) m/e 493 (M+H)$^+$.

TABLE 3

The following Examples were prepared essentially as described in Example 1D-E, substituting tert-butyl 4-[4-({[(3S)-1-(pyridin-3-yl)pyrrolidin-3-yl]carbonyl}amino)phenoxy]piperidine-1-carboxylate for tert-butyl 4-(4-(1-(pyridin-3-yl)azetidine-3-carboxamido)phenoxy)piperidine-1-carboxylate in Example 1D and the appropriate carboxylic acid for 2-(tetrahydro-2H-pyran-4-yl)acetic acid in Example 1E. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
| 12 | (3S)-N-(4-{[1-(2-methylpropanoyl)piperidin-4-yl]oxy}phenyl)-1-(pyridin-3-yl)pyrrolidine-3-carboxamide | $^1$H NMR (300 MHz, DMSO-d$_6$) δ ppm 9.97 (s, 1H), 7.96 (d, J = 2.9 Hz, 1H), 7.86 (dd, J = 4.6, 1.3 Hz, 1H), 7.55-7.48 (m, 2H), 7.19 (dd, J = 8.4, 4.6 Hz, 1H), 6.99-6.90 (m, 3H), 4.59-4.48 (m, 1H), 4.03-3.67 (m, 3H), 3.54 (d, J = 8.6 Hz, 1H), 3.47-3.38 (m, 2H), 3.35 (d, J = 7.4 Hz, 2H), 3.28-3.18 (m, 1H), 2.95-2.82 (m, 1H), 2.38-2.03 (m, 2H), 2.00-1.80 (m, 1H), 1.64-1.37 (m, 2H), 1.00 (d, J = 6.7 Hz, 6H) | (ESI(+)) m/e 437 (M + H)$^+$ |
| 13 | (3S)-1-(pyridin-3-yl)-N-[4-({1-[(2S)-tetrahydrofuran-2-ylcarbonyl]piperidin-4-yl}oxy)phenyl]pyrrolidine-3-carboxamide | $^1$H NMR (300 MHz, DMSO-d$_6$) δ ppm 9.97 (s, 1H), 7.97 (d, J = 2.8 Hz, 1H), 7.88 (d, J = 5.1 Hz, 1H), 7.55-7.48 (m, 2H), 7.33-7.19 (m, 1H), 7.05-6.88 (m, 3H), 4.67 (t, J = 6.5 Hz, 1H), 4.57-4.50 (m, 1H), 3.94-3.67 (m, 4H), 3.55 (d, J = 8.6 Hz, 1H), 3.47-3.38 (m, 4H), 2.38-2.12 (m, 2H), 2.07-1.74 (m, 7H), 1.65-1.00 (m, 3H) | (ESI(+)) m/e 465 (M + H)$^+$ |
| 14 | (3S)-1-(pyridin-3-yl)-N-[4-({1-[(2R)-tetrahydrofuran-2-ylcarbonyl]piperidin-4-yl}oxy)phenyl]pyrrolidine-3-carboxamide | $^1$H NMR (300 MHz, DMSO-d$_6$) δ ppm 9.97 (s, 1H), 7.96 (d, J = 2.9 Hz, 1H), 7.87 (dd, J = 4.6, 1.2 Hz, 1H), 7.55-7.48 (m, 2H), 7.21 (dd, J = 8.4, 4.6 Hz, 1H), 7.02-6.93 (m, 2H), 6.92 (s, 1H), 4.67 (t, J = 6.6 Hz, 1H), 4.57-4.50 (m, 1H), 3.94-3.62 (m, 4H), 3.54 (d, J = 8.6 Hz, 1H), 3.44 (d, J = 6.7 Hz, 2H), 3.41 (d, J = 5.4 Hz, 2H), 3.23 (d, J = 7.8 Hz, 1H), 2.36-2.07 (m, 3H), 2.09-1.76 (m, 6H), 1.65-1.39 (m, 2H) | (ESI(+)) m/e 465 (M + H)$^+$ |
| 15 | (3S)-1-(pyridin-3-yl)-N-(4-{[1-(tetrahydrofuran-3-ylcarbonyl)piperidin-4-yl]oxy}phenyl)pyrrolidine-3-carboxamide | $^1$H NMR (300 MHz, DMSO-d$_6$) δ ppm 9.97 (s, 1H), 7.97 (d, J = 2.9 Hz, 1H), 7.88 (dd, J = 4.7, 1.2 Hz, 1H), 7.55-7.48 (m, 2H), 7.25 (dd, J = 8.4, 4.7 Hz, 1H), 7.02 (dd, J = 8.5, 2.8 Hz, 1H), 6.97-6.90 (m, 2H), 4.60-4.48 (m, 1H), 3.98-3.61 (m, 7H), 3.55 (d, J = 8.6 Hz, 1H), 3.45 (d, J = 6.9 Hz, 2H), 3.44-3.39 (m, 2H), 3.38-3.32 (m, 2H), 2.38-2.09 (m, 2H), 2.10-1.81 (m, 4H), 1.65-1.40 (m, 2H) | (ESI(+)) m/e 465 (M + H)$^+$ |

TABLE 3-continued

The following Examples were prepared essentially as described in Example 1D-E, substituting tert-butyl 4-[4-({[(3S)-1-(pyridin-3-yl)pyrrolidin-3-yl]carbonyl}amino)phenoxy]piperidine-1-carboxylate for tert-butyl 4-(4-(1-(pyridin-3-yl)azetidine-3-carboxamido)phenoxy)piperidine-1-carboxylate in Example 1D and the appropriate carboxylic acid for 2-(tetrahydro-2H-pyran-4-yl)acetic acid in Example 1E. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
| 16 | (3S)-N-(4-{[1-(cyclopropylacetyl)piperidin-4-yl]oxy}phenyl)-1-(pyridin-3-yl)pyrrolidine-3-carboxamide | $^1$H NMR (300 MHz, DMSO-$d_6$) δ ppm 9.96 (s, 1H), 7.99-7.93 (m, 1H), 7.85 (dd, J = 4.6, 1.3 Hz, 1H), 7.55-7.48 (m, 2H), 7.16 (dd, J = 8.4, 4.5 Hz, 1H), 6.98-6.87 (m, 3H), 4.59-4.47 (m, 1H), 3.92-3.80 (m, 1H), 3.73-3.61 (m, 1H), 3.54 (d, J = 8.6 Hz, 1H), 3.47-3.37 (m, 2H), 3.26-3.07 (m, 3H), 2.27 (d, J = 6.8 Hz, 3H), 2.23-2.12 (m, 1H), 1.97-1.79 (m, 2H), 1.62-1.32 (m, 2H), 1.04-0.83 (m, 1H), 0.49-0.36 (m, 2H), 0.19-0.07 (m, 2H) | (ESI(+)) m/e 449 (M + H)$^+$ |
| 17 | (3S)-N-(4-{[1-(2-hydroxy-2-methylpropanoyl)piperidin-4-yl]oxy}phenyl)-1-(pyridin-3-yl)pyrrolidine-3-carboxamide | $^1$H NMR (300 MHz, DMSO-$d_6$) δ ppm 9.96 (s, 1H), 7.96 (d, J = 3.1 Hz, 1H), 7.87 (d, J = 4.7 Hz, 1H), 7.57-7.39 (m, 2H), 7.21 (dd, J = 8.4, 4.6 Hz, 1H), 7.03-6.88 (m, 3H), 5.38 (s, 1H), 4.59-3.79 (m, 3H), 3.65-3.38 (m, 4H), 2.35-2.10 (m, 2H), 1.99-1.84 (m, 2H), 1.63-1.34 (m, 3H), 1.35-1.19 (m, 7H) | (ESI(+)) m/e 453 (M + H)$^+$ |
| 18 | (3S)-1-(pyridin-3-yl)-N-(4-{[1-(3,3,3-trifluoropropanoyl)piperidin-4-yl]oxy}phenyl)pyrrolidine-3-carboxamide | $^1$H NMR (300 MHz, DMSO-$d_6$) δ ppm 9.96 (s, 1H), 7.95 (d, J = 2.9 Hz, 1H), 7.85 (dd, J = 4.6, 1.3 Hz, 1H), 7.55-7.48 (m, 2H), 7.16 (dd, J = 8.4, 4.5 Hz, 1H), 6.98-6.88 (m, 3H), 4.55 (dq, J = 7.7, 3.8 Hz, 1H), 3.83 (ddd, J = 13.2, 6.8, 3.9 Hz, 1H), 3.74-3.49 (m, 5H), 3.48-3.38 (m, 2H), 2.38-2.06 (m, 3H), 2.02-1.80 (m, 2H), 1.71-1.36 (m, 3H) | (ESI(+)) m/e 477 (M + H)$^+$ |
| 19 | (3S)-N-[4-({1-[(2S)-2-methylbutanoyl]piperidin-4-yl}oxy)phenyl]-1-(pyridin-3-yl)pyrrolidine-3-carboxamide | $^1$H NMR (300 MHz, DMSO-$d_6$) δ ppm 9.96 (s, 1H), 7.95 (d, J = 2.9 Hz, 1H), 7.85 (dd, J = 4.6 Hz, 1H), 7.55-7.48 (m, 2H), 7.16 (dd, J = 8.4, 4.5 Hz, 1H), 6.98-6.88 (m, 3H), 4.60-4.48 (m, 1H), 4.03-3.69 (m, 2H), 3.54 (d, J = 8.6 Hz, 1H), 3.47-3.37 (m, 2H), 3.33 (d, J = 4.6 Hz, 1H), 3.27-3.17 (m, 1H), 2.72 (h, J = 6.7 Hz, 1H), 2.35-2.01 (m, 2H), 2.02-1.79 (m, 2H), 1.65-1.10 (m, 5H), 0.98 (d, J = 6.7 Hz, 3H), 0.81 (t, J = 7.4 Hz, 3H) | (ESI(+)) m/e 451 (M + H)$^+$ |

Example 21

N-[1-(pyridin-3-yl)azetidin-3-yl]-4-{[1-(tetrahydro-2H-pyran-4-ylacetyl)piperidin-4-yl]oxy}benzamide

Example 21A tert-butyl 4-(4-(1-(benzyloxycarbonyl)azetidin-3-ylcarbamoyl)phenoxy)piperidine-1-carboxylate The title compound was prepared as described in Example 1A, substituting benzyl 3-aminoazetidine-1-carboxylate for tert-butyl 4-(4-aminophenoxy)piperidine-1-carboxylate and 4-(1-(tert-butoxycarbonyl)piperidin-4-yloxy)benzoic acid for 1-(benzyloxycarbonyl)azetidine-3-carboxylic acid.

Example 21B benzyl 3-(4-(piperidin-4-yloxy)benzamido)azetidine-1-carboxylate The title compound was prepared as described in Example 1D, substituting tert-butyl 4-(4-(1-(benzyloxycarbonyl)azetidin-3-ylcarbamoyl)phenoxy)piperidine-1-carboxylate for tert-butyl 4-(4-(1-(pyridin-3-yl)azetidine-3-carboxamido)phenoxy)piperidine-1-carboxylate.

Example 21C benzyl 3-(4-(1-(2-(tetrahydro-2H-pyran-4-yl)acetyl)piperidin-4-yloxy)benzamido)azetidine-1-carboxylate The title compound was prepared as described in Example 1A, substituting benzyl 3-(4-(piperidin-4-yloxy)benzamido)azetidine-1-carboxylate for tert-butyl 4-(4-aminophenoxy)piperidine-1-carboxylate and 2-(tetrahydro-2H-pyran-4-yl)acetic acid for 1-(benzyloxycarbonyl)azetidine-3-carboxylic acid.

Example 21D

N-(azetidin-3-yl)-4-(1-(2-(tetrahydro-2H-pyran-4-yl)acetyl)piperidin-4-yloxy)benzamide The title compound was prepared as described in Example 1B, substituting benzyl 3-(4-(1-(2-(tetrahydro-2H-pyran-4-yl)acetyl)piperidin-4-yloxy)benzamido)azetidine-1-carboxylate for tert-butyl 4-(4-(1-(benzyloxycarbonyl)azetidine-3-carboxamido)phenoxy)piperidine-1-carboxylate.

Example 21E

N-[1-(pyridin-3-yl)azetidin-3-yl]-4-{[1-(tetrahydro-2H-pyran-4-ylacetyl)piperidin-4-yl]oxy}benzamide The title compound was prepared as described in Example 1C, substituting N-(azetidin-3-yl)-4-(1-(2-(tetrahydro-2H-pyran-4-yl)acetyl)piperidin-4-yloxy)benzamide for tert-butyl 4-(4-(azetidine-3-carboxamido)phenoxy)piperidine-1-carboxylate. $^1$H NMR (300 MHz, DMSO-$d_6$) δ ppm 8.83 (d, J=6.8 Hz, 1H), 7.93 (d, J=4.0 Hz, 1H), 7.85 (d, J=8.4 Hz, 3H), 7.27 (s, 2H), 7.26-7.11 (m, 1H), 7.05 (d, J=8.6 Hz, 2H), 6.87 (d, J=8.1 Hz, 1H), 4.86 (d, J=6.9 Hz, 1H), 4.71 (s, 1H), 4.28-4.19 (m, 2H), 3.93-3.64 (m, 6H), 2.30-2.23 (m, 2H), 2.05-1.67 (m, 3H), 1.52 (t, J=29.3 Hz, 5H), 1.32-0.81 (m, 3H); MS (ESI(+)) m/e 479 (M+H)$^+$.

Example 23

4-({1-[(2S)-2-methylbutanoyl]piperidin-4-yl}oxy)-N-[1-(pyridin-3-yl)azetidin-3-yl]benzamide The title compound was prepared as described in Example 21, substituting (S)-2-methylbutanoic acid for 2-(tetrahydro-2H-pyran-4-yl)acetic acid in Example 21C. $^1$H NMR (300 MHz, DMSO-$d_6$) δ ppm 8.84 (d, J=7.0 Hz, 1H), 7.99-7.84 (m, 3H), 7.83 (s, 1H), 7.18 (dd, J=8.2, 4.6 Hz, 1H), 7.09-7.01 (m, 2H), 6.87 (ddd, J=8.2, 2.8, 1.4 Hz, 1H), 4.94-4.64 (m, 2H), 4.24 (t, J=7.5 Hz, 2H), 3.98-3.72 (m, 4H), 2.73 (h, J=6.7 Hz, 1H), 2.04-1.83 (m, 2H), 1.67-1.20 (m, 4H), 1.06-0.87 (m, 4H), 0.87-0.77 (m, 4H); MS (ESI(+)) m/e 437 (M+H)$^+$.

Example 24

4-{[1-(2-hydroxy-2-methylpropanoyl)piperidin-4-yl]oxy}-N-[1-(pyridin-3-yl)azetidin-3-yl]benzamide The title compound was prepared as described in Example 21, substituting 2-hydroxy-2-methylpropanoic acid for 2-(tetrahydro-2H-pyran-4-yl)acetic acid in Example 21C. $^1$H NMR (500 MHz, DMSO-$d_6$) δ ppm 8.84 (d, J=7.0 Hz, 1H), 7.93 (dd, J=4.6, 1.3 Hz, 1H), 7.87-7.86 (m, 1H), 7.86 (s, 1H), 7.84 (s, 1H), 7.18 (dd, J=8.2, 4.6 Hz, 1H), 7.08-7.02 (m, 2H), 6.87 (ddd, J=8.2, 2.8, 1.4 Hz, 1H), 5.40 (s, 1H), 4.92-4.81 (m, 1H), 4.76-4.67 (m, 1H), 4.24 (t, J=7.5 Hz, 3H), 3.82 (dd, J=7.6, 5.9 Hz, 3H), 1.98-1.94 (m, 3H), 1.72-1.41 (m, 3H), 1.32 (s, 6H); MS (ESI(+)) m/e 439 (M+H)$^+$.

Example 27 tert-butyl 4-(4-{[(3S)-1-(pyridin-3-yl)pyrrolidin-3-yl]carbamoyl}phenoxy)piperidine-1-carboxylate The title compound was prepared as described in Example 21A, D and E, substituting (S)-benzyl 3-aminopyrrolidine-1-carboxylate for benzyl 3-aminoazetidine-1-carboxylate in Example 21A. $^1$H NMR (300 MHz, DMSO-$d_6$) δ ppm 8.43 (d, J=6.8 Hz, 1H), 7.94 (d, J=2.9 Hz, 1H), 7.87-7.80 (m, 3H), 7.15 (dd, J=8.4, 4.5 Hz, 1H), 7.03 (s, 1H), 7.00 (s, 1H), 6.90 (ddd, J=8.4, 3.0, 1.3 Hz, 1H), 4.71-4.55 (m, 2H), 3.73-3.53 (m, 3H), 3.44 (t, J=7.5 Hz, 1H), 3.18 (d, J=13.4 Hz, 2H), 3.17 (d, J=12.2 Hz, 2H), 2.34-2.19 (m, 1H), 2.14-1.97 (m, 1H), 1.98-1.82 (m, 2H), 1.63-1.43 (m, 2H), 1.40 (s, 9H); MS (ESI(+)) m/e 467(M+H)$^+$.

Example 28 tert-butyl 4-(4-{[(3R)-1-(pyridin-3-yl)pyrrolidin-3-yl]carbamoyl}phenoxy)piperidine-1-carboxylate The title compound was prepared as described in Example 21A, D and E, substituting (R)-benzyl 3-aminopyrrolidine-1-carboxylate for benzyl 3-aminoazetidine-1-carboxylate in Example 21A. $^1$H NMR (300 MHz, DMSO-$d_6$) δ ppm 8.44 (d, J=6.8 Hz, 1H), 7.94 (d, J=2.9 Hz, 1H), 7.88-7.79 (m, 3H), 7.15 (dd, J=8.3, 4.5 Hz, 1H), 7.06-6.98 (m, 2H), 6.90 (ddd, J=8.4, 3.0, 1.4 Hz, 1H), 4.72-4.54 (m, 2H), 3.74-3.50 (m, 3H), 3.51-3.39 (m, 1H), 3.18 (d, J=13.6 Hz, 2H), 3.16 (d, J=11.9 Hz, 1H), 2.33-2.18 (m, 1H), 2.07 (dq, J=12.9, 6.5 Hz, 1H), 2.00-1.82 (m, 2H), 1.67-1.43 (m, 2H), 1.40 (s, 9H); MS (ESI(+)) m/e 467 (M+H)$^+$.

Example 74

N-(4-{[1-(cyclopropylmethyl)piperidin-4-yl]oxy}phenyl)-1-(pyridin-3-yl)azetidine-3-carboxamide In a 20 mL vial was added N-(4-(piperidin-4-yloxy)phenyl)-1-(pyridin-3-yl)azetidine-3-carboxamide bis(2,2,2-trifluoroacetate) (67 mg, 0.12 mmol) dissolved in methanol (2.0 mL) followed by the addition of cyclopropanecarbaldehyde (10 mg, 0.14 mmol) dissolved in methanol (0.45 mL), followed by the addition of neat acetic acid (66 μL, 1.2 mmol). The mixture was shaken for 1 hour at 70° C. After that, 265 mg of MP-cyanoborohydride resin (2-3 mmol/g) was added and the resulting mixture was shaken at 70° C. overnight. The reaction mixture was filtered, checked by LC/MS and concentrated to dryness. The residues were dissolved in 1:1 DMSO/CH$_3$OH and purified by reverse phase HPLC. $^1$H NMR (500 MHz, pyridine-$d_5$/D$_2$O) δ ppm 8.20-8.25 (m, 1 H) 8.13 (d, J=2.75 Hz, 1 H) 7.98-8.03 (m, 2 H) 7.11 (dd, J=8.24, 4.58 Hz, 1 H) 7.02-7.07 (m, 2 H) 6.72-6.78 (m, 1 H) 4.58 (d, J=2.75 Hz, 1H) 4.34 (t, J=6.71 Hz, 2 H) 4.05 (t, J=7.63 Hz, 2 H) 3.80-3.92 (m, 1 H) 3.34 (s, 4 H) 2.92 (d, J=7.32 Hz, 2 H) 2.32-2.44 (m, 2 H) 2.12 (s, 2 H) 1.09-1.22 (m, 1 H) 0.51-0.58 (m, 2 H) 0.28-0.34 (m, 2 H); MS (ESI(+)) m/e 407 (M+H).

TABLE 4

The following Examples were prepared essentially as described in Example 74, substituting the appropriate aldehyde for cyclopropanecarbaldehyde. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
| 75 | N-(4-{[1-(2-methylpentyl)piperidin-4-yl]oxy}phenyl)-1-(pyridin-3-yl)azetidine-3- | $^1$H NMR (500 MHz, pyridine-$d_5$/D$_2$O Temp = 27° C.) δ ppm 8.23 (dd, J = 4.58, 1.22 Hz, 1 H) 8.13 (d, J = 2.75 Hz, 1 H) 7.97-8.03 (m, 2 H) 7.06-7.13 (m, 3 H) 6.71-6.77 (m, 1 H) 4.44 (s, 1 H) 4.34 (t, J = 6.56 Hz, 2 H) 4.00-4.08 (m, 2 H) 3.78-3.88 (m, 1 H) 2.96 (s, 2 H) 2.67 (s, 1 H) | (ESI(+)) m/e 437 (M + H)$^+$ |

TABLE 4-continued

The following Examples were prepared essentially as described in Example 74, substituting the appropriate aldehyde for cyclopropanecarbaldehyde. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
|  | carboxamide | 2.34-2.48 (m, J = 2.44 Hz, 3 H) 2.21 (s, 2 H) 1.97 (s, 2 H) 1.72-1.83 (m, 1 H) 1.15-1.45 (m, 3 H) 1.00-1.10 (m, 1 H) 0.96 (d, J = 6.71 Hz, 3 H) 0.85 (t, J = 7.17 Hz, 3 H) |  |
| 76 | N-(4-{[1-(2-methylpropyl)piperidin-4-yl]oxy}phenyl)-1-(pyridin-3-yl)azetidine-3-carboxamide | $^1$H NMR (500 MHz, pyridine-d$_5$/D$_2$O Temp = 27° C.) δ ppm 8.23 (dd, J = 4.73, 1.37 Hz, 1 H) 8.13 (d, J = 2.75 Hz, 1 H) 7.97-8.04 (m, 2 H) 7.04-7.15 (m, 3 H) 6.72-6.76 (m, 1 H) 4.40-4.47 (m, 1 H) 4.34 (t, J = 6.56 Hz, 2 H) 3.99-4.09 (m, 2 H) 3.79-3.89 (m, 1 H) 2.91-3.00 (m, 2 H) 2.61-2.82 (m, 2 H) 2.36-2.45 (m, 2 H) 2.13-2.26 (m, J = 9.46 Hz, 2 H) 1.79-2.04 (m, 3 H) 0.92 (d, J = 6.41 Hz, 6 H) | (ESI(+)) m/e 409 (M + H)$^+$ |
| 77 | N-(4-{[1-(3-methylbutyl)piperidin-4-yl]oxy}phenyl)-1-(pyridin-3-yl)azetidine-3-carboxamide | $^1$H NMR (500 MHz, pyridine-d$_5$/D$_2$O Temp = 27° C.) δ ppm 8.21-8.26 (m, 1 H) 8.14 (d, J = 3.05 Hz, 1 H) 7.98-8.03 (m, 2 H) 7.05-7.13 (m, 3 H) 6.71-6.77 (m, 1 H) 4.47-4.54 (m, 1 H) 4.34 (t, J = 6.56 Hz, 2 H) 4.00-4.07 (m, 2 H) 3.80-3.89 (m, 1 H) 3.11 (s, 2 H) 2.87-3.06 (m, 2 H) 2.77-2.86 (m, 2 H) 2.22-2.33 (m, 2 H) 2.04 (s, 2 H) 1.47-1.61 (m, 3 H) 0.82 (d, J = 6.41 Hz, 6 H) | (ESI(+)) m/e 423 (M + H)$^+$ |
| 78 | N-(4-{[1-(2-ethylbutyl)piperidin-4-yl]oxy}phenyl)-1-(pyridin-3-yl)azetidine-3-carboxamide | $^1$H NMR (500 MHz, pyridine-d$_5$/D$_2$O Temp = 27° C.) δ ppm 8.23 (dd, J = 4.58, 1.22 Hz, 1 H) 8.13 (d, J = 2.75 Hz, 1 H) 7.98-8.03 (m, 2 H) 7.06-7.13 (m, 3 H) 6.71-6.76 (m, 1 H) 4.40-4.49 (m, 1 H) 4.34 (t, J = 6.56 Hz, 2 H) 4.00-4.06 (m, 2 H) 3.78-3.88 (m, 1 H) 2.91-3.03 (m, 2 H) 2.57-2.77 (m, 2 H) 2.40-2.49 (m, J = 4.27, 2.14 Hz, 2 H) 2.14-2.28 (m, 2 H) 1.90-2.01 (m, J = 14.04 Hz, 2 H) 1.58 (s, 1 H) 1.29-1.45 (m, 4 H) 0.84 (t, J = 7.48 Hz, 6 H) | (ESI(+)) m/e 437 (M + H)$^+$ |
| 79 | N-(4-{[1-(2,2-dimethylpropyl)piperidin-4-yl]oxy}phenyl)-1-(pyridin-3-yl)azetidine-3-carboxamide | $^1$H NMR (500 MHz, pyridine-d$_5$/D$_2$O Temp = 27° C.) δ ppm 8.23 (dd, J = 4.58, 1.22 Hz, 1 H) 8.14 (d, J = 2.75 Hz, 1 H) 7.99-8.01 (m, 2 H) 7.07-7.13 (m, 3 H) 6.74 (d, J = 5.49 Hz, 1 H) 4.33 (t, J = 6.56 Hz, 2 H) 4.00-4.06 (m, 2 H) 3.80-3.86 (m, 1 H) 2.73-2.81 (m, 2 H) 2.34-2.43 (m, 2 H) 1.93-2.03 (m, 4 H) 1.76-1.88 (m, 2 H) 1.24-1.34 (m, 1 H) 0.87 (s, 9 H) | (ESI(+)) m/e 423 (M + H)$^+$ |
| 80 | N-(4-{[1-(2-methylbutyl)piperidin-4-yl]oxy}phenyl)-1-(pyridin-3-yl)azetidine-3-carboxamide | $^1$H NMR (500 MHz, pyridine-d$_5$/D$_2$O Temp = 27° C.) δ ppm 8.21-8.24 (m, 1 H) 8.13 (d, J = 2.75 Hz, 1 H) 8.00 (d, J = 9.16 Hz, 2 H) 7.07-7.14 (m, 3 H) 6.70-6.77 (m, 1 H) 4.29-4.39 (m, 3 H) 3.97-4.06 (m, 2 H) 3.77-3.86 (m, 1 H) 2.75-2.88 (m, 2 H) 2.45-2.56 (m, 4 H) 2.04-2.25 (m, 3 H) 1.85-1.97 (m, 2 H) 1.38-1.64 (m, 2 H) 0.81-0.93 (m, 6 H) | (ESI(+)) m/e 423 (M + H)$^+$ |
| 81 | N-{4-[(1-propylpiperidin-4-yl)oxy]phenyl}-1-(pyridin-3-yl)azetidine-3-carboxamide |  | (ESI(+)) m/e 395 (M + H)$^+$ |
| 82 | N-(4-{[1-(2-cyclopropylethyl)piperidin-4-yl]oxy}phenyl)-1-(pyridin-3-yl)azetidine-3-carboxamide | $^1$H NMR (500 MHz, pyridine-d$_5$/D$_2$O Temp = 27° C.) δ ppm 8.23 (dd, J = 4.58, 1.53 Hz, 1 H) 8.14 (d, J = 2.44 Hz, 1 H) 7.95-8.04 (m, 2 H) 7.05-7.14 (m, 3 H) 6.69-6.78 (m, 1 H) 4.42-4.51 (m, 1 H) 4.34 (t, J = 6.56 Hz, 2 H) 3.95-4.11 (m, 2 H) 3.79-3.89 (m, J = 8.24, 8.24 Hz, 1 H) 3.00-3.13 (m, 2 H) 2.73-2.93 (m, 3 H) 2.40-2.48 (m, 1 H) 2.15-2.30 (m, 2 H) 2.01 (s, 2 H) 1.50-1.61 (m, J = 8.54 Hz, 2 H) 0.54-0.70 (m, 1 H) 0.33-0.42 (m, 2 H) 0.06 (t, J = 4.73 Hz, 2 H) | (ESI(+)) m/e 421 (M + H)$^+$ |
| 83 | 1-(pyridin-3-yl)-N-(4-{[1-(tetrahydrofuran-3-ylmethyl)piperidin-4-yl]oxy}phenyl)azetidine-3-carboxamide | $^1$H NMR (500 MHz, pyridine-d$_5$/D$_2$O Temp = 27° C.) δ ppm 8.23 (dd, J = 4.58, 1.22 Hz, 1 H) 8.13 (d, J = 2.75 Hz, 1 H) 7.98-8.04 (m, 2 H) 7.03-7.15 (m, 3 H) 6.70-6.77 (m, 1 H) 4.44-4.53 (m, 1 H) 4.34 (t, J = 6.56 Hz, 2 H) 3.96-4.09 (m, 3 H) 3.77-3.92 (m, 2 H) 3.55-3.74 (m, 2 H) 3.03-3.19 (m, 2 H) 2.86-3.04 (m, 2 H) 2.75-2.88 (m, 2 H) 2.57-2.72 (m, 1 H) 2.19-2.34 (m, 2 H) 1.94-2.08 (m, 3 H) 1.56-1.71 (m, 1 H) | (ESI(+)) m/e 437 (M + H)$^+$ |

TABLE 4-continued

The following Examples were prepared essentially as described in Example 74, substituting the appropriate aldehyde for cyclopropanecarbaldehyde. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
| 84 | N-(4-{[1-(2,2-dimethylbutyl)piperidin-4-yl]oxy}phenyl)-1-(pyridin-3-yl)azetidine-3-carboxamide | $^1$H NMR (500 MHz, pyridine-d$_5$/D$_2$O Temp = 27° C.) δ ppm 8.23 (dd, J = 4.73, 1.37 Hz, 1 H) 8.14 (d, J = 2.44 Hz, 1 H) 7.97-8.02 (m, 2 H) 7.07-7.13 (m, 3 H) 6.71-6.76 (m, 1 H) 4.28-4.38 (m, 2 H) 4.00-4.06 (m, 2 H) 3.82 (s, 1 H) 2.72-2.82 (m, 2 H) 2.29-2.43 (m, 2 H) 1.91-2.07 (m, 4 H) 1.75-1.88 (m, 2 H) 1.19-1.29 (m, J = 7.22, 7.22, 7.22 Hz, 3 H) 0.72-0.86 (m, 9 H) | (ESI(+)) m/e 437 (M + H)$^+$ |

Example 85

N-{4-[1-(2-hydroxy-2-methylpropanoyl)piperidin-4-yl]phenyl}-1-(pyridazin-4-yl)azetidine-3-carboxamide The title compound was prepared as described in Example 10, substituting 4-bromopyridazine for 3-bromopyridine in Example 10C and 2-hydroxy-2-methylpropanoic acid for (S)-tetrahydrofuran-2-carboxylic acid in Example 10E. $^1$H NMR (300 MHz, DMSO-d$_6$) δ ppm 10.04 (s, 1H), 8.60 (d, J=6.0 Hz, 1H), 8.51 (d, J=3.0 Hz, 1H), 7.57-7.50 (m, 2H), 7.22-7.14 (m, 2H), 6.54 (dd, J=6.0, 3.0 Hz, 1H), 5.36 (s, 1H), 4.73 (bs, 2H), 4.30-3.96 (m, 4H), 3.87-3.60 (m, 1H), 2.71 (d, J=11.9 Hz, 1H), 1.82-1.72 (m, 2H), 1.67-1.42 (m, 2H), 1.35-1.31 (m, 8H); MS (ESI(+)) m/e 424 (M+H)$^+$.

TABLE 5

The following Examples were essentially prepared as described in Example 10, substituting 4-bromopyridazine for 3-bromopyridine in Example 10C and the appropriate acid for (S)-tetrahydrofuran-2-carboxylic acid in Example 10E. Some products were purified by flash chromatography while others were purified by reverse-phase HPLC. Accordingly, some Examples were isolated as trifluoroacetic acid salts.

| Ex | Name | MS |
|---|---|---|
| 140 | N-{4-[1-(3,3-dimethylbutanoyl)piperidin-4-yl]phenyl}-1-(pyridazin-4-yl)azetidine-3-carboxamide | (ESI(+)) m/e 436 (M + H)$^+$ |
| 143 | N-(4-{1-[(2S)-2-methylbutanoyl]piperidin-4-yl}phenyl)-1-(pyridazin-4-yl)azetidine-3-carboxamide | (ESI(+)) m/e 422 (M + H)$^+$ |
| 144 | N-{4-[1-(cyclopentylacetyl)piperidin-4-yl]phenyl}-1-(pyridazin-4-yl)azetidine-3-carboxamide | (ESI(+)) m/e 448 (M + H)$^+$ |
| 145 | 1-(pyridazin-4-yl)-N-{4-[1-(tetrahydro-2H-pyran-4-ylacetyl)piperidin-4-yl]phenyl}azetidine-3-carboxamide | (ESI(+)) m/e 464 (M + H)$^+$ |
| 146 | 1-(pyridazin-4-yl)-N-{4-[1-(tetrahydro-2H-pyran-4-ylcarbonyl)piperidin-4-yl]phenyl}azetidine-3-carboxamide | (ESI(+)) m/e 564 (M + H)$^+$ |
| 525 | N-{4-[1-(2-chlorobenzoyl)piperidin-4-yl]phenyl}-1-(pyridazin-4-yl)azetidine-3-carboxamide | (ESI(+)) m/e 476 (M + H)$^+$ |
| 526 | 1-(pyridazin-4-yl)-N-{4-[1-(1,3-thiazol-2-ylcarbonyl)piperidin-4-yl]phenyl}azetidine-3-carboxamide | (ESI(+)) m/e 449 (M + H)$^+$ |
| 527 | N-{4-[1-(cyclopropylacetyl)piperidin-4-yl]phenyl}-1-(pyridazin-4-yl)azetidine-3-carboxamide | (ESI(+)) m/e 420 (M + H)$^+$ |
| 528 | N-{4-[1-(2-methylpropanoyl)piperidin-4-yl]phenyl}-1-(pyridazin-4-yl)azetidine-3-carboxamide | (ESI(+)) m/e 408 (M + H)$^+$ |
| 529 | N-{4-[1-(4-fluorobenzoyl)piperidin-4-yl]phenyl}-1-(pyridazin-4-yl)azetidine-3-carboxamide | (ESI(+)) m/e 460 (M + H)$^+$ |
| 530 | 1-(pyridazin-4-yl)-N-{4-[1-(thiophen-3-ylcarbonyl)piperidin-4-yl]phenyl}azetidine-3-carboxamide | (ESI(+)) m/e 448 (M + H)$^+$ |
| 531 | N-(4-{1-[(4-fluorophenyl)acetyl]piperidin-4-yl}phenyl)-1-(pyridazin-4-yl)azetidine-3-carboxamide | (ESI(+)) m/e 474 (M + H)$^+$ |
| 532 | N-(4-{1-[(3,5-difluorophenyl)acetyl]piperidin-4-yl}phenyl)-1-(pyridazin-4-yl)azetidine-3-carboxamide | (ESI(+)) m/e 492 (M + H)$^+$ |

TABLE 5-continued

The following Examples were essentially prepared as described in Example 10, substituting 4-bromopyridazine for 3-bromopyridine in Example 10C and the appropriate acid for (S)-tetrahydrofuran-2-carboxylic acid in Example 10E. Some products were purified by flash chromatography while others were purified by reverse-phase HPLC. Accordingly, some Examples were isolated as trifluoroacetic acid salts.

| Ex  | Name | MS |
|-----|------|-----|
| 533 | N-{4-[1-(3,4-difluorobenzoyl)piperidin-4-yl]phenyl}-1-(pyridazin-4-yl)azetidine-3-carboxamide | (ESI(+)) m/e 478 (M + H)$^+$ |
| 534 | N-(4-{1-[(3-fluorophenyl)acetyl]piperidin-4-yl}phenyl)-1-(pyridazin-4-yl)azetidine-3-carboxamide | (ESI(+)) m/e 474 (M + H)$^+$ |
| 535 | 1-(pyridazin-4-yl)-N-(4-{1-[3-(trifluoromethyl)benzoyl]piperidin-4-yl}phenyl)azetidine-3-carboxamide | (ESI(+)) m/e 510 (M + H)$^+$ |
| 536 | N-(4-{1-[(2,4-difluorophenyl)acetyl]piperidin-4-yl}phenyl)-1-(pyridazin-4-yl)azetidine-3-carboxamide | (ESI(+)) m/e 492 (M + H)$^+$ |
| 537 | 1-(pyridazin-4-yl)-N-{4-[1-(1,3-thiazol-4-ylcarbonyl)piperidin-4-yl]phenyl}azetidine-3-carboxamide | (ESI(+)) m/e 449 (M + H)$^+$ |
| 538 | 1-(pyridazin-4-yl)-N-{4-[1-(tetrahydrofuran-2-ylcarbonyl)piperidin-4-yl]phenyl}azetidine-3-carboxamide | (ESI(+)) m/e 436 (M + H)$^+$ |
| 539 | N-(4-{1-[(5-methylthiophen-2-yl)carbonyl]piperidin-4-yl}phenyl)-1-(pyridazin-4-yl)azetidine-3-carboxamide | (ESI(+)) m/e 462 (M + H)$^+$ |
| 540 | N-(4-{1-[(2-fluorophenyl)acetyl]piperidin-4-yl}phenyl)-1-(pyridazin-4-yl)azetidine-3-carboxamide | (ESI(+)) m/e 474 (M + H)$^+$ |
| 541 | N-{4-[1-(cyclopropylcarbonyl)piperidin-4-yl]phenyl}-1-(pyridazin-4-yl)azetidine-3-carboxamide | (ESI(+)) m/e 406 (M + H)$^+$ |
| 542 | 1-(pyridazin-4-yl)-N-{4-[1-(tetrahydrofuran-3-ylcarbonyl)piperidin-4-yl]phenyl}azetidine-3-carboxamide | (ESI(+)) m/e 436 (M + H)$^+$ |
| 543 | 1-(pyridazin-4-yl)-N-{4-[1-(pyridin-2-ylcarbonyl)piperidin-4-yl]phenyl}azetidine-3-carboxamide | (ESI(+)) m/e 443 (M + H)$^+$ |
| 544 | N-{4-[1-(3-chlorobenzoyl)piperidin-4-yl]phenyl}-1-(pyridazin-4-yl)azetidine-3-carboxamide | (ESI(+)) m/e 476 (M + H)$^+$ |
| 545 | N-{4-[1-(4-chlorobenzoyl)piperidin-4-yl]phenyl}-1-(pyridazin-4-yl)azetidine-3-carboxamide | (ESI(+)) m/e 476 (M + H)$^+$ |
| 546 | N-{4-[1-(2-methyl-2-phenylpropanoyl)piperidin-4-yl]phenyl}-1-(pyridazin-4-yl)azetidine-3-carboxamide | (ESI(+)) m/e 484 (M + H)$^+$ |
| 547 | N-{4-[1-(2,4-difluorobenzoyl)piperidin-4-yl]phenyl}-1-(pyridazin-4-yl)azetidine-3-carboxamide | (ESI(+)) m/e 478 (M + H)$^+$ |
| 548 | N-{4-[1-(methoxyacetyl)piperidin-4-yl]phenyl}-1-(pyridazin-4-yl)azetidine-3-carboxamide | (ESI(+)) m/e 410 (M + H)$^+$ |
| 549 | 1-(pyridazin-4-yl)-N-{4-[1-(thiophen-2-ylcarbonyl)piperidin-4-yl]phenyl}azetidine-3-carboxamide | (ESI(+)) m/e 448 (M + H)$^+$ |
| 550 | 1-(pyridazin-4-yl)-N-[4-(1-{[3-(trifluoromethyl)phenyl]acetyl}piperidin-4-yl)phenyl]azetidine-3-carboxamide | (ESI(+)) m/e 524 (M + H)$^+$ |
| 551 | N-{4-[1-(2-fluorobenzoyl)piperidin-4-yl]phenyl}-1-(pyridazin-4-yl)azetidine-3-carboxamide | (ESI(+)) m/e 460 (M + H)$^+$ |
| 552 | N-{4-[1-(3,5-difluorobenzoyl)piperidin-4-yl]phenyl}-1-(pyridazin-4-yl)azetidine-3-carboxamide | (ESI(+)) m/e 478 (M + H)$^+$ |
| 553 | 1-(pyridazin-4-yl)-N-(4-{1-[4-(trifluoromethyl)benzoyl]piperidin-4-yl}phenyl)azetidine-3-carboxamide | (ESI(+)) m/e 510 (M + H)$^+$ |
| 554 | N-{4-[1-(3-fluorobenzoyl)piperidin-4-yl]phenyl}-1-(pyridazin-4-yl)azetidine-3-carboxamide | (ESI(+)) m/e 460 (M + H)$^+$ |
| 555 | 1-(pyridazin-4-yl)-N-(4-{1-[4-(trifluoromethoxy)benzoyl]piperidin-4-yl}phenyl)azetidine-3-carboxamide | (ESI(+)) m/e 526 (M + H)$^+$ |
| 556 | N-{4-[1-(3-methylbutanoyl)piperidin-4-yl]phenyl}-1-(pyridazin-4-yl)azetidine-3-carboxamide | (ESI(+)) m/e 422 (M + H)$^+$ |

TABLE 5-continued

The following Examples were essentially prepared as described in Example 10, substituting 4-bromopyridazine for 3-bromopyridine in Example 10C and the appropriate acid for (S)-tetrahydrofuran-2-carboxylic acid in Example 10E. Some products were purified by flash chromatography while others were purified by reverse-phase HPLC. Accordingly, some Examples were isolated as trifluoroacetic acid salts.

| Ex | Name | MS |
| --- | --- | --- |
| 557 | 1-(pyridazin-4-yl)-N-{4-[1-(3,3,3-trifluoropropanoyl)piperidin-4-yl]phenyl}azetidine-3-carboxamide | (ESI(+)) m/e 448 (M + H)+ |
| 558 | N-(4-{1-[difluoro(phenyl)acetyl]piperidin-4-yl}phenyl)-1-(pyridazin-4-yl)azetidine-3-carboxamide | (ESI(+)) m/e 492 (M + H)+ |
| 559 | N-{4-[1-(2,2-dimethylpropanoyl)piperidin-4-yl]phenyl}-1-(pyridazin-4-yl)azetidine-3-carboxamide | (ESI(+)) m/e 422 (M + H)+ |
| 560 | N-(4-{1-[(4,4-difluorocyclohexyl)carbonyl]piperidin-4-yl}phenyl)-1-(pyridazin-4-yl)azetidine-3-carboxamide | (ESI(+)) m/e 484 (M + H)+ |
| 561 | 1-(pyridazin-4-yl)-N-[4-(1-{[4-(trifluoromethoxy)phenyl]acetyl}piperidin-4-yl)phenyl]azetidine-3-carboxamide | (ESI(+)) m/e 540 (M + H)+ |
| 562 | 1-(pyridazin-4-yl)-N-(4-{1-[3-(trifluoromethoxy)benzoyl]piperidin-4-yl}phenyl)azetidine-3-carboxamide | (ESI(+)) m/e 526 (M + H)+ |
| 563 | 1-(pyridazin-4-yl)-N-[4-(1-{[4-(trifluoromethyl)phenyl]acetyl}piperidin-4-yl)phenyl]azetidine-3-carboxamide | (ESI(+)) m/e 524 (M + H)+ |

Example 86

N-{4-[1-(cyclohexylmethyl)piperidin-4-yl]phenyl}-1-(pyridin-3-yl)azetidine-3-carboxamide The title compound was prepared as described in Example 74, substituting N-(4-(piperidin-4-yl)phenyl)-1-(pyridin-3-yl)azetidine-3-carboxamide for N-(4-(piperidin-4-yloxy)phenyl)-1-(pyridin-3-yl)azetidine-3-carboxamide and cyclohexanecarbaldehyde for cyclopropanecarbaldehyde. $^1$H NMR (500 MHz, pyridine-$d_5$/$D_2O$) δ ppm 8.23 (dd, J=4.58, 1.22 Hz, 1 H) 8.13 (d, J=2.75 Hz, 1 H) 7.99 (d, J=8.54 Hz, 2 H) 7.31-7.36 (m, 2 H) 7.11 (dd, J=8.24, 4.27 Hz, 1 H) 6.71-6.75 (m, 1 H) 4.32 (t, J=6.56 Hz, 2 H) 3.98-4.05 (m, 2 H) 3.79-3.89 (m, 1 H) 3.62-3.71 (m, 2 H) 2.69-2.95 (m, 5 H) 2.37-2.49 (m, 2 H) 1.75-2.00 (m, 5H) 1.46-1.65 (m, 3 H) 0.90-1.24 (m, 5 H); (ESI(+)) m/e 433 (M+H).

TABLE 6

The following Examples were prepared essentially as described in Example 74, substituting N-(4-(piperidin-4-yl)phenyl)-1-(pyridin-3-yl)azetidine-3-carboxamide for N-(4-(piperidin-4-yloxy)phenyl)-1-(pyridin-3-yl)azetidine-3-carboxamide and the appropriate aldehyde for cyclopropanecarbaldehyde. Some products were purified by flash chromatography while others were purified by reverse-phase HPLC. Accordingly, some Examples were isolated as trifluoroacetic acid salts.

| Ex | Name | $^1$H NMR | MS |
| --- | --- | --- | --- |
| 87 | N-{4-[1-(3,3-dimethylbutyl)piperidin-4-yl]phenyl}-1-(pyridin-3-yl)azetidine-3-carboxamide | $^1$H NMR (500 MHz, pyridine-$d_5$/$D_2O$) δ ppm 8.23 (dd, J = 4.73, 1.37 Hz, 1 H) 8.13 (d, J = 2.75 Hz, 1 H) 7.98 (d, J = 8.54 Hz, 2 H) 7.29-7.32 (m, 2 H) 7.11 (dd, J = 7.93, 4.88 Hz, 1 H) 6.69-6.75 (m, 1 H) 4.32 (t, J = 6.71 Hz, 2 H) 3.98-4.04 (m, 2 H) 3.79-3.87 (m, 1 H) 3.68 (s, 2 H) 3.08-3.15 (m, 2 H) 2.80-2.92 (m, 2 H) 2.71-2.79 (m, 1 H) 2.34-2.46 (m, 2 H) 1.90-1.99 (m, 2 H) 1.71-1.78 (m, 2 H) 0.87 (s, 9 H) | (ESI(+)) m/e 421 (M + H)+ |
| 88 | N-{4-[1-(cyclopentylmethyl)piperidin-4-yl]phenyl}-1-(pyridin-3-yl)azetidine-3-carboxamide | $^1$H NMR (500 MHz, pyridine-$d_5$/$D_2O$) δ ppm 8.23 (dd, J = 4.88, 1.22 Hz, 1 H) 8.13 (d, J = 2.75 Hz, 1 H) 7.99 (d, J = 8.54 Hz, 2 H) 7.31-7.35 (m, 2 H) 7.11 (dd, J = 8.09, 4.73 Hz, 1 H) 6.70-6.75 (m, 1 H) 4.33 (t, J = 6.56 Hz, 2 H) 3.97-4.05 (m, 2 H) 3.77-3.85 (m, 1 H) 3.56-3.71 (m, 2 H) 2.98 (d, J = 6.71 Hz, 2 H) 2.69-2.86 (m, J = 12.21, 12.21 Hz, 3 H) 2.34-2.49 (m, 2 H) 2.19-2.31 (m, 1 H) 1.78-1.97 (m, 4 H) 1.35-1.57 (m, 4 H) 1.17-1.28 (m, 2 H) | (ESI(+)) m/e 419 (M + H)+ |

TABLE 6-continued

The following Examples were prepared essentially as described in Example 74, substituting N-(4-(piperidin-4-yl)phenyl)-1-(pyridin-3-yl)azetidine-3-carboxamide for N-(4-(piperidin-4-yloxy)phenyl)-1-(pyridin-3-yl)azetidine-3-carboxamide and the appropriate aldehyde for cyclopropanecarbaldehyde. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
| 89 | N-{4-[1-(2,2-dimethylbutyl)piperidin-4-yl]phenyl}-1-(pyridin-3-yl)azetidine-3-carboxamide | $^1$H NMR (500 MHz, pyridine-$d_5$/$D_2O$) δ ppm 8.23 (dd, J = 4.58, 1.22 Hz, 1 H) 8.14 (d, J = 2.75 Hz, 1 H) 8.02 (d, J = 8.54 Hz, 2 H) 7.32 (d, J = 8.24 Hz, 2 H) 7.11 (dd, J = 8.24, 4.58 Hz, 1 H) 6.71-6.75 (m, 1 H) 4.33 (t, J = 6.56 Hz, 2 H) 3.99-4.05 (m, 2 H) 3.79-3.86 (m, 1 H) 2.89-2.97 (m, 2 H) 2.29-2.50 (m, J = 59.51 Hz, 3 H) 2.14 (d, J = 3.97 Hz, 2 H) 1.84-1.97 (m, 2 H) 1.71-1.78 (m, 2 H) 1.30 (q, J = 7.63 Hz, 2 H) 0.88 (s, 6 H) 0.82 (t, J = 7.48 Hz, 3 H) | (ESI(+)) m/e 421 (M + H)$^+$ |
| 90 | N-{4-[1-(2-methylpentyl)piperidin-4-yl]phenyl}-1-(pyridin-3-yl)azetidine-3-carboxamide | $^1$H NMR (500 MHz, pyridine-$d_5$/$D_2O$) δ ppm 8.23 (dd, J = 4.73, 1.37 Hz, 1 H) 8.13 (d, J = 2.75 Hz, 1 H) 7.99 (d, J = 8.54 Hz, 2 H) 7.30-7.37 (m, 2 H) 7.11 (dd, J = 8.24, 4.27 Hz, 1 H) 6.69-6.77 (m, 1 H) 4.28-4.36 (m, 2 H) 3.96-4.06 (m, 2 H) 3.77-3.87 (m, 1 H) 3.53 (s, 2 H) 2.55-2.91 (m, 5 H) 2.23-2.42 (m, 2 H) 1.81-1.95 (m, J = 6.71 Hz, 3 H) 1.04-1.47 (m, 4 H) 1.03 (t, J = 6.41 Hz, 3 H) 0.85 (t, J = 7.17 Hz, 3 H) | (ESI(+)) m/e 421 (M + H)$^+$ |
| 91 | N-[4-(1-butylpiperidin-4-yl)phenyl]-1-(pyridin-3-yl)azetidine-3-carboxamide | $^1$H NMR (500 MHz, pyridine-$d_5$/$D_2O$) δ ppm 8.20-8.27 (m, 1 H) 8.13 (d, J = 3.05 Hz, 1 H) 7.99 (d, J = 8.54 Hz, 2 H) 7.30-7.35 (m, 2 H) 7.08-7.12 (m, 1 H) 6.68-6.74 (m, 1 H) 4.32 (t, J = 6.56 Hz, 2 H) 3.97-4.06 (m, 2 H) 3.78-3.86 (m, 1 H) 3.56-3.69 (m, 2 H) 2.92-3.03 (m, 2 H) 2.66-2.87 (m, 3 H) 2.29-2.45 (m, 2 H) 1.91 (d, J = 13.73 Hz, 2 H) 1.65-1.77 (m, 2 H) 1.10-1.31 (m, 2 H) 0.79 (t, J = 7.32 Hz, 3 H) | (ESI(+)) m/e 393 (M + H)$^+$ |
| 92 | N-{4-[1-(2-ethylbutyl)piperidin-4-yl]phenyl}-1-(pyridin-3-yl)azetidine-3-carboxamide | $^1$H NMR (500 MHz, pyridine-$d_5$/$D_2O$) δ ppm 8.23 (d, J = 4.58 Hz, 1 H) 8.13 (d, J = 2.75 Hz, 1 H) 7.99 (d, J = 8.54 Hz, 2 H) 7.33 (d, J = 8.54 Hz, 2 H) 7.09-7.11 (m, 1 H) 6.70-6.74 (m, 1 H) 4.32 (t, J = 6.56 Hz, 2 H) 3.97-4.05 (m, 2 H) 3.78-3.86 (m, 1 H) 3.43-3.61 (m, 2 H) 2.55-2.95 (m, 5 H) 2.22-2.43 (m, 2 H) 1.90 (d, J = 13.12 Hz, 2H) 1.67-1.78 (m, 1 H) 1.30-1.50 (m, 4 H) 0.85 (t, J = 7.48 Hz, 6 H) | (ESI(+)) m/e 421 (M + H)$^+$ |
| 93 | N-{4-[1-(3-methylbutyl)piperidin-4-yl]phenyl}-1-(pyridin-3-yl)azetidine-3-carboxamide | $^1$H NMR (500 MHz, pyridine-$d_5$/$D_2O$) δ ppm 8.19-8.26 (m, 1 H) 8.13 (d, J = 2.75 Hz, 1 H) 7.99 (d, J = 8.54 Hz, 2 H) 7.29-7.34 (m, 2 H) 7.11 (dd, J = 8.24, 4.58 Hz, 1 H) 6.67-6.76 (m, 1 H) 4.32 (t, J = 6.56 Hz, 2 H) 3.98-4.04 (m, 2 H) 3.77-3.87 (m, 1 H) 3.57-3.69 (m, 2 H) 2.95-3.05 (m, 2 H) 2.67-2.87 (m, 3 H) 2.29-2.44 (m, 2 H) 1.84-1.98 (m, 2 H) 1.60-1.71 (m, 2 H) 1.39-1.58 (m, 1 H) 0.82 (d, J = 6.71 Hz, 6 H) | (ESI(+)) m/e 407 (M + H)$^+$ |
| 94 | N-{4-[1-(2-methylpropyl)piperidin-4-yl]phenyl}-1-(pyridin-3-yl)azetidine-3-carboxamide | $^1$H NMR (500 MHz, pyridine-$d_5$/$D_2O$) δ ppm 8.21-8.27 (m, 1 H) 8.14 (d, J = 2.75 Hz, 1 H) 7.99 (d, J = 8.54 Hz, 2 H) 7.32 (d, J = 8.54 Hz, 2 H) 7.11 (dd, J = 8.09, 4.73 Hz, 1 H) 6.70-6.75 (m, 1 H) 4.33 (t, J = 6.56 Hz, 2 H) 3.97-4.04 (m, 2 H) 3.78-3.87 (m, 1 H) 3.27-3.41 (m, 2 H) 2.62 (s, 1 H) 2.38-2.52 (m, 4 H) 2.10-2.26 (m, J = 22.28 Hz, 2 H) 1.90-1.99 (m, 1 H) 1.81-1.88 (m, 2 H) 0.95 (d, J = 6.41 Hz, 6 H) | (ESI(+)) m/e 393 (M + H)$^+$ |
| 95 | N-[4-(1-propylpiperidin-4-yl)phenyl]-1-(pyridin-3-yl)azetidine-3-carboxamide | $^1$H NMR (500 MHz, pyridine-$d_5$/$D_2O$) δ ppm 8.21-8.25 (m, 1 H) 8.10-8.15 (m, 1 H) 7.98 (d, J = 8.54 Hz, 2 H) 7.31 (d, J = 8.54 Hz, 2 H) 7.11 (dd, J = 8.24, 4.58 Hz, 1 H) 6.71-6.76 (m, 1 H) 4.32 (t, J = 6.56 Hz, 2 H) 3.99-4.04 (m, 2 H) 3.77-3.89 (m, 1 H) 3.55-3.66 (m, 2 H) 2.86-2.98 (m, 2 H) 2.64-2.86 (m, 3 H) 2.30-2.46 (m, 2 H) 1.90 (d, J = 14.04 Hz, 2 H) 1.70-1.81 (m, 2 H) 0.78 (t, J = 7.32 Hz, 3 H) | (ESI(+)) m/e 379 (M + H)$^+$ |

Example 141

(3S)—N-{4-[1-(2-hydroxy-2-methylpropanoyl)piperidin-4-yl]phenyl}-1-(pyridazin-4-yl)pyrrolidine-3-carboxamide

Example 141A (S)-tert-butyl 4-(4-(1-((benzyloxy)carbonyl)pyrrolidine-3-carboxamido)phenyl)piperidine-1-carboxylate The title compound was prepared as described in Example 1A, substituting (S)-1-((benzyloxy)carbonyl)pyrrolidine-3-carboxylic acid for 1-(benzyloxycarbonyl)azetidine-3-carboxylic acid and tert-butyl 4-(4-aminophenyl)piperidine-1-carboxylate for tert-butyl 4-(4-aminophenoxy)piperidine-1-carboxylate.

Example 141B (S)-tert-butyl 4-(4-(pyrrolidine-3-carboxamido)phenyl)piperidine-1-carboxylate The title compound was prepared as described in Example 1B, substituting (S)-tert-butyl 4-(4-(1-((benzyloxy)carbonyl)pyrrolidine-3-carboxamido)phenyl)piperidine-1-carboxylate for tert-butyl 4-(4-(1-(benzyloxycarbonyl)azetidine-3-carboxamido)phenoxy)piperidine-1-carboxylate.

Example 141C (S)-tert-butyl 4-(4-(1-(pyridazin-4-yl)pyrrolidine-3-carboxamido)phenyl)piperidine-1-carboxylate The title compound was prepared as described in Example 1C, substituting (S)-tert-butyl 4-(4-(pyrrolidine-3-carboxamido)phenyl)piperidine-1-carboxylate for tert-butyl 4-(4-(azetidine-3-carboxamido)phenoxy)piperidine-1-carboxylate and 4-bromopyridazine for 3-bromopyridine.

Example 141D (S)—N-(4-(piperidin-4-yl)phenyl)-1-(pyridazin-4-yl)pyrrolidine-3-carboxamide The title compound was prepared as described in Example 1D, substituting tert-butyl 4-(4-(1-(pyridin-3-yl)azetidine-3-carboxamido)phenyl)piperidine-1-carboxylate for tert-butyl 4-(4-(1-(pyridin-3-yl)azetidine-3-carboxamido)phenoxy)piperidine-1-carboxylate.

Example 141E (3S)—N-{4-[1-(2-hydroxy-2-methylpropanoyl)piperidin-4-yl]phenyl}-1-(pyridazin-4-yl)pyrrolidine-3-carboxamide The title compound was prepared as described in Example 1A, substituting (S)—N-(4-(piperidin-4-yl)phenyl)-1-(pyridazin-4-yl)pyrrolidine-3-carboxamide for tert-butyl 4-(4-aminophenoxy)piperidine-1-carboxylate and 2-hydroxy-2-methylpropanoic acid for 1-(benzyloxycarbonyl)azetidine-3-carboxylic acid. $^1$H NMR (300 MHz, DMSO-$d_6$) δ ppm 10.07 (s, 1H), 8.68-8.61 (m, 1H), 8.61-8.50 (m, 1H), 7.52 (t, J=6.8 Hz, 2H), 7.17 (d, J=8.6 Hz, 2H), 6.62 (dd, J=6.3, 3.2 Hz, 1H), 5.35 (s, 1H), 3.73-3.34 (m, 8H), 2.73 (dd, J=13.9, 10.2 Hz, 2H), 2.40-2.06 (m, 2H), 1.76 (d, J=11.0 Hz, 2H), 1.64-1.38 (m, 2H), 1.33 (s, 6H); MS (ESI(+)) m/e 438 (M+H)$^+$.

Example 142

(3S)—N-{4-[1-(cyclopentylacetyl)piperidin-4-yl]phenyl}-1-(pyridazin-4-yl)pyrrolidine-3-carboxamide The title compound was prepared as described in Example 1A, substituting (S)—N-(4-(piperidin-4-yl)phenyl)-1-(pyridazin-4-yl)pyrrolidine-3-carboxamide for tert-butyl 4-(4-aminophenoxy)piperidine-1-carboxylate and cyclopentylacetic acid for 1-(benzyloxycarbonyl)azetidine-3-carboxylic acid. $^1$H NMR (300 MHz, DMSO-$d_6$) δ ppm 10.07 (s, 1H), 8.64 (dd, J=3.1, 0.9 Hz, 1H), 8.57 (dd, J=6.2, 0.9 Hz, 1H), 7.54 (s, 1H), 7.51 (s, 1H), 7.21-7.13 (m, 2H), 6.61 (dd, J=6.2, 3.1 Hz, 1H), 3.68-3.41 (m, 8H), 3.18-3.00 (m, 1H), 2.78-2.64 (m, 1H), 2.42-2.06 (m, 5H), 1.83-1.69 (m, 4H), 1.65-1.20 (m, 6H), 1.22-1.04 (m, 2H); MS (ESI(+)) m/e 462 (M+H)$^+$.

Example 147

N-{4-[1-(2-methylpropanoyl)piperidin-4-yl]phenyl}-1-(pyridazin-3-yl)azetidine-3-carboxamide

Example 147A tert-butyl 4-(4-(1-(6-chloropyridazin-3-yl)azetidine-3-carboxamido)phenyl)piperidine-1-carboxylate In a 50 mL round-bottomed flask was added tert-butyl 4-(4-(azetidine-3-carboxamido)phenyl)piperidine-1-carboxylate (918 mg, 2.55 mmol) and diisopropylethylamine (0.558 ml, 3.19 mmol) in ethanol (10.6 ml). 3,6-dichloropyridazine (317 mg, 2.128 mmol) was added as a solid in a single portion. The reaction was stirred overnight at 45° C.; and the reaction was cooled and concentrated. Dichloromethane and water were added and the layers were separated. The aqueous layer was extracted three times with dichloromethane and the combined organics were dried with magnesium sulfate, filtered and concentrated by rotary evaporation. The residue was purified by regular phase flash column chromatography to give the title compound.

Example 147B tert-butyl 4-(4-(1-(pyridazin-3-yl)azetidine-3-carboxamido)phenyl)piperidine-1-carboxylate To a 50 mL round-bottomed flask was added tert-butyl 4-(4-(1-(6-chloropyridazin-3-yl)azetidine-3-carboxamido)phenyl)piperidine-1-carboxylate (550 mg, 1.165 mmol) and Pd/C (93 mg, 0.087 mmol). The flask was flushed with nitrogen for 10 minutes and ethanol (11.7 ml) was added. Triethylamine (0.162 ml, 1.165 mmol) and cyclohexa-1,4-diene (654 mg, 8.16 mmol) were added and the reaction was stirred at 80° C. for 1 hour, cooled and filtered through diatomaceous earth. The filtrate was concentrated in vacuo and the residue was purified by regular phase flash column chromatography to give the title compound.

Example 147C

N-(4-(piperidin-4-yl)phenyl)-1-(pyridazin-3-yl)azetidine-3-carboxamide

The title compound was prepared as described in Example 1D, substituting tert-butyl 4-(4-(1-(pyridazin-3-yl)azetidine- 3-carboxamido)phenyl)piperidine-1-carboxylate for tert-butyl 4-(4-(1-(pyridin-3-yl)azetidine-3-carboxamido)phenoxy) piperidine-1-carboxylate.

Example 147D

N-{4-[1-(2-methylpropanoyl)piperidin-4-yl]phenyl}-1-(pyridazin-3-yl)azetidine-3-carboxamide The title compound was prepared as described in Example 1A, substituting N-(4-(piperidin-4-yl)phenyl)-1-(pyridazin-3-yl)azetidine-3-carboxamide for tert-butyl 4-(4-aminophenoxy)piperidine-1-carboxylate and 2-methylpropanoic acid for 1-(benzyloxycarbonyl)azetidine-3-carboxylic acid. $^1$H NMR (300 MHz, DMSO-$d_6$) δ ppm 10.03 (s, 1H), 8.56 (dd, J=4.5, 1.3 Hz, 1H), 7.52 (dd, J=9.2, 4.7 Hz, 2H), 7.40 (ddd, J=13.5, 7.9, 2.8 Hz, 1H), 7.18 (d, J=8.6 Hz, 2H), 6.82 (dd, J=8.9, 1.3 Hz, 1H), 4.55 (d, J=12.0 Hz, 1H), 4.32-3.90 (m, 5H), 3.83-3.54 (m, 1H), 3.10 (t, J=12.9 Hz, 1H), 2.89 (kept, J=6.7 Hz, 1H), 2.71 (ddd, J=28.5, 16.0, 11.7 Hz, 1H), 1.77 (d, J=12.3 Hz, 2H), 1.60-1.10 (m, 4H), 1.01 (t, J=6.0 Hz, 6H); MS (ESI(+)) m/e 408 (M+H)$^+$.

TABLE 7

The following Examples were prepared essentially as described in Example 1A, substituting N-(4-(piperidin-4-yl)phenyl)-1-(pyridazin-3-yl)azetidine-3-carboxamide for tert-butyl 4-(4-aminophenoxy)piperidine-1-carboxylate and the appropriate carboxylic acid for 1-(benzyloxycarbonyl)azetidine-3-carboxylic acid. Some products were purified by flash chromatography while others were purified by reverse-phase HPLC. Accordingly, some Examples were isolated as trifluoroacetic acid salts.

| Ex | Name | MS |
|---|---|---|
| 316 | N-[4-(1-acetylpiperidin-4-yl)phenyl]-1-(pyridazin-3-yl)azetidine-3-carboxamide | (ESI(+)) m/e 380 (M + H)$^+$ |
| 317 | N-[4-(1-butanoylpiperidin-4-yl)phenyl]-1-(pyridazin-3-yl)azetidine-3-carboxamide | (ESI(+)) m/e 408 (M + H)$^+$ |
| 318 | N-[4-(1-pentanoylpiperidin-4-yl)phenyl]-1-(pyridazin-3-yl)azetidine-3-carboxamide | (ESI(+)) m/e 422 (M + H)$^+$ |
| 319 | N-{4-[1-(2-methylbutanoyl)piperidin-4-yl]phenyl}-1-(pyridazin-3-yl)azetidine-3-carboxamide | (ESI(+)) m/e 422 (M + H)$^+$ |
| 320 | N-{4-[1-(3-methylbutanoyl)piperidin-4-yl]phenyl}-1-(pyridazin-3-yl)azetidine-3-carboxamide | (ESI(+)) m/e 422 (M + H)$^+$ |
| 321 | N-[4-(1-hexanoylpiperidin-4-yl)phenyl]-1-(pyridazin-3-yl)azetidine-3-carboxamide | (ESI(+)) m/e 436 (M + H)$^+$ |
| 322 | N-{4-[1-(2-methylpentanoyl)piperidin-4-yl]phenyl}-1-(pyridazin-3-yl)azetidine-3-carboxamide | (ESI(+)) m/e 436 (M + H)$^+$ |
| 323 | N-{4-[1-(3-methylpentanoyl)piperidin-4-yl]phenyl}-1-(pyridazin-3-yl)azetidine-3-carboxamide | (ESI(+)) m/e 436 (M + H)$^+$ |
| 324 | N-{4-[1-(4-methylpentanoyl)piperidin-4-yl]phenyl}-1-(pyridazin-3-yl)azetidine-3-carboxamide | (ESI(+)) m/e 436 (M + H)$^+$ |
| 325 | N-{4-[1-(2,2-dimethylbutanoyl)piperidin-4-yl]phenyl}-1-(pyridazin-3-yl)azetidine-3-carboxamide | (ESI(+)) m/e 436 (M + H)$^+$ |
| 326 | N-{4-[1-(2,3-dimethylbutanoyl)piperidin-4-yl]phenyl}-1-(pyridazin-3-yl)azetidine-3-carboxamide | (ESI(+)) m/e 436 (M + H)$^+$ |
| 327 | N-{4-[1-(3,3-dimethylbutanoyl)piperidin-4-yl]phenyl}-1-(pyridazin-3-yl)azetidine-3-carboxamide | (ESI(+)) m/e 436 (M + H)$^+$ |
| 328 | N-{4-[1-(2-ethylbutanoyl)piperidin-4-yl]phenyl}-1-(pyridazin-3-yl)azetidine-3-carboxamide | (ESI(+)) m/e 436 (M + H)$^+$ |
| 329 | N-[4-(1-heptanoylpiperidin-4-yl)phenyl]-1-(pyridazin-3-yl)azetidine-3-carboxamide | (ESI(+)) m/e 450 (M + H)$^+$ |
| 330 | N-{4-[1-(but-3-enoyl)piperidin-4-yl]phenyl}-1-(pyridazin-3-yl)azetidine-3-carboxamide | (ESI(+)) m/e 406 (M + H)$^+$ |
| 331 | N-{4-[1-(pent-4-enoyl)piperidin-4-yl]phenyl}-1-(pyridazin-3-yl)azetidine-3-carboxamide | (ESI(+)) m/e 420 (M + H)$^+$ |
| 332 | 1-(pyridazin-3-yl)-N-{4-[1-(3,3,3-trifluoropropanoyl)piperidin-4-yl]phenyl}azetidine-3-carboxamide | (ESI(+)) m/e 448 (M + H)$^+$ |
| 333 | N-{4-[1-(methoxyacetyl)piperidin-4-yl]phenyl}-1-(pyridazin-3-yl)azetidine-3-carboxamide | (ESI(+)) m/e 410 (M + H)$^+$ |

TABLE 7-continued

The following Examples were prepared essentially as described in Example 1A, substituting N-(4-(piperidin-4-yl)phenyl)-1-(pyridazin-3-yl)azetidine-3-carboxamide for tert-butyl 4-(4-aminophenoxy)piperidine-1-carboxylate and the appropriate carboxylic acid for 1-(benzyloxycarbonyl)azetidine-3-carboxylic acid. Some products were purified by flash chromatography while others were purified by reverse-phase HPLC. Accordingly, some Examples were isolated as trifluoroacetic acid salts.

| Ex | Name | MS |
|----|------|----|
| 334 | N-(4-{1-[(methylsulfanyl)acetyl]piperidin-4-yl}phenyl)-1-(pyridazin-3-yl)azetidine-3-carboxamide | (ESI(+)) m/e 426 (M + H)$^+$ |
| 335 | N-(4-{1-[(2-methoxyethoxy)acetyl]piperidin-4-yl}phenyl)-1-(pyridazin-3-yl)azetidine-3-carboxamide | (ESI(+)) m/e 454 (M + H)$^+$ |
| 336 | N-{4-[1-(3-nitropropanoyl)piperidin-4-yl]phenyl}-1-(pyridazin-3-yl)azetidine-3-carboxamide | (ESI(+)) m/e 439 (M + H)$^+$ |
| 337 | N-(4-{1-[3-(methylsulfanyl)propanoyl]piperidin-4-yl}phenyl)-1-(pyridazin-3-yl)azetidine-3-carboxamide | (ESI(+)) m/e 440 (M + H)$^+$ |
| 338 | N-{4-[1-(pent-4-ynoyl)piperidin-4-yl]phenyl}-1-(pyridazin-3-yl)azetidine-3-carboxamide | (ESI(+)) m/e 418 (M + H)$^+$ |
| 339 | N-{4-[1-(cyclohexylcarbonyl)piperidin-4-yl]phenyl}-1-(pyridazin-3-yl)azetidine-3-carboxamide | (ESI(+)) m/e 448 (M + H)$^+$ |
| 340 | N-{4-[1-(cyclohexylacetyl)piperidin-4-yl]phenyl}-1-(pyridazin-3-yl)azetidine-3-carboxamide | (ESI(+)) m/e 462 (M + H)$^+$ |
| 341 | N-{4-[1-(3-methylbenzoyl)piperidin-4-yl]phenyl}-1-(pyridazin-3-yl)azetidine-3-carboxamide | (ESI(+)) m/e 456 (M + H)$^+$ |
| 342 | N-{4-[1-(2-hydroxybenzoyl)piperidin-4-yl]phenyl}-1-(pyridazin-3-yl)azetidine-3-carboxamide | (ESI(+)) m/e 458 (M + H)$^+$ |
| 343 | N-{4-[1-(3-hydroxybenzoyl)piperidin-4-yl]phenyl}-1-(pyridazin-3-yl)azetidine-3-carboxamide | (ESI(+)) m/e 458 (M + H)$^+$ |
| 344 | N-{4-[1-(4-hydroxybenzoyl)piperidin-4-yl]phenyl}-1-(pyridazin-3-yl)azetidine-3-carboxamide | (ESI(+)) m/e 458 (M + H)$^+$ |
| 345 | N-{4-[1-(2-methoxybenzoyl)piperidin-4-yl]phenyl}-1-(pyridazin-3-yl)azetidine-3-carboxamide | (ESI(+)) m/e 472 (M + H)$^+$ |
| 346 | N-{4-[1-(3-methoxybenzoyl)piperidin-4-yl]phenyl}-1-(pyridazin-3-yl)azetidine-3-carboxamide | (ESI(+)) m/e 472 (M + H)$^+$ |
| 347 | N-{4-[1-(4-methoxybenzoyl)piperidin-4-yl]phenyl}-1-(pyridazin-3-yl)azetidine-3-carboxamide | (ESI(+)) m/e 472 (M + H)$^+$ |
| 348 | N-{4-[1-(3-fluorobenzoyl)piperidin-4-yl]phenyl}-1-(pyridazin-3-yl)azetidine-3-carboxamide | (ESI(+)) m/e 460 (M + H)$^+$ |
| 349 | N-{4-[1-(4-fluorobenzoyl)piperidin-4-yl]phenyl}-1-(pyridazin-3-yl)azetidine-3-carboxamide | (ESI(+)) m/e 460 (M + H)$^+$ |
| 350 | N-{4-[1-(2-chlorobenzoyl)piperidin-4-yl]phenyl}-1-(pyridazin-3-yl)azetidine-3-carboxamide | (ESI(+)) m/e 476 (M + H)$^+$ |
| 351 | N-{4-[1-(3-chlorobenzoyl)piperidin-4-yl]phenyl}-1-(pyridazin-3-yl)azetidine-3-carboxamide | (ESI(+)) m/e 476 (M + H)$^+$ |
| 352 | N-{4-[1-(3-cyanobenzoyl)piperidin-4-yl]phenyl}-1-(pyridazin-3-yl)azetidine-3-carboxamide | (ESI(+)) m/e 467 (M + H)$^+$ |
| 353 | N-{4-[1-(4-cyanobenzoyl)piperidin-4-yl]phenyl}-1-(pyridazin-3-yl)azetidine-3-carboxamide | (ESI(+)) m/e 467 (M + H)$^+$ |
| 354 | 1-(pyridazin-3-yl)-N-(4-{1-[3-(trifluoromethyl)benzoyl]piperidin-4-yl}phenyl)azetidine-3-carboxamide | (ESI(+)) m/e 510 (M + H)$^+$ |
| 355 | 1-(pyridazin-3-yl)-N-(4-{1-[4-(trifluoromethyl)benzoyl]piperidin-4-yl}phenyl)azetidine-3-carboxamide | (ESI(+)) m/e 510 (M + H)$^+$ |
| 356 | 1-(pyridazin-3-yl)-N-(4-{1-[3-(trifluoromethoxy)benzoyl]piperidin-4-yl}phenyl)azetidine-3-carboxamide | (ESI(+)) m/e 526 (M + H)$^+$ |

TABLE 7-continued

The following Examples were prepared essentially as described in Example 1A, substituting N-(4-(piperidin-4-yl)phenyl)-1-(pyridazin-3-yl)azetidine-3-carboxamide for tert-butyl 4-(4-aminophenoxy)piperidine-1-carboxylate and the appropriate carboxylic acid for 1-(benzyloxycarbonyl)azetidine-3-carboxylic acid. Some products were purified by flash chromatography while others were purified by reverse-phase HPLC. Accordingly, some Examples were isolated as trifluoroacetic acid salts.

| Ex | Name | MS |
|---|---|---|
| 357 | N-{4-[1-(2,3-dimethylbenzoyl)piperidin-4-yl]phenyl}-1-(pyridazin-3-yl)azetidine-3-carboxamide | (ESI(+)) m/e 470 (M + H)$^+$ |
| 358 | N-{4-[1-(2,4-dimethylbenzoyl)piperidin-4-yl]phenyl}-1-(pyridazin-3-yl)azetidine-3-carboxamide | (ESI(+)) m/e 470 (M + H)$^+$ |
| 359 | N-{4-[1-(2,5-dimethylbenzoyl)piperidin-4-yl]phenyl}-1-(pyridazin-3-yl)azetidine-3-carboxamide | (ESI(+)) m/e 470 (M + H)$^+$ |
| 360 | N-{4-[1-(3,4-dimethylbenzoyl)piperidin-4-yl]phenyl}-1-(pyridazin-3-yl)azetidine-3-carboxamide | (ESI(+)) m/e 470 (M + H)$^+$ |
| 361 | N-{4-[1-(3,5-dimethylbenzoyl)piperidin-4-yl]phenyl}-1-(pyridazin-3-yl)azetidine-3-carboxamide | (ESI(+)) m/e 470 (M + H)$^+$ |
| 362 | N-{4-[1-(2,4-dichlorobenzoyl)piperidin-4-yl]phenyl}-1-(pyridazin-3-yl)azetidine-3-carboxamide | (ESI(+)) m/e 510 (M + H)$^+$ |
| 363 | N-{4-[1-(2,5-dichlorobenzoyl)piperidin-4-yl]phenyl}-1-(pyridazin-3-yl)azetidine-3-carboxamide | (ESI(+)) m/e 510 (M + H)$^+$ |
| 364 | N-{4-[1-(3,4-dichlorobenzoyl)piperidin-4-yl]phenyl}-1-(pyridazin-3-yl)azetidine-3-carboxamide | (ESI(+)) m/e 510 (M + H)$^+$ |
| 365 | N-{4-[1-(3,5-dichlorobenzoyl)piperidin-4-yl]phenyl}-1-(pyridazin-3-yl)azetidine-3-carboxamide | (ESI(+)) m/e 510 (M + H)$^+$ |
| 366 | N-(4-{1-[(2-fluorophenyl)acetyl]piperidin-4-yl}phenyl)-1-(pyridazin-3-yl)azetidine-3-carboxamide | (ESI(+)) m/e 474 (M + H)$^+$ |
| 367 | N-(4-{1-[(3-fluorophenyl)acetyl]piperidin-4-yl}phenyl)-1-(pyridazin-3-yl)azetidine-3-carboxamide | (ESI(+)) m/e 474 (M + H)$^+$ |
| 368 | N-(4-{1-[(4-fluorophenyl)acetyl]piperidin-4-yl}phenyl)-1-(pyridazin-3-yl)azetidine-3-carboxamide | (ESI(+)) m/e 474 (M + H)$^+$ |
| 369 | N-(4-{1-[(2-chlorophenyl)acetyl]piperidin-4-yl}phenyl)-1-(pyridazin-3-yl)azetidine-3-carboxamide | (ESI(+)) m/e 490 (M + H)$^+$ |
| 370 | N-(4-{1-[(4-chlorophenyl)acetyl]piperidin-4-yl}phenyl)-1-(pyridazin-3-yl)azetidine-3-carboxamide | (ESI(+)) m/e 490 (M + H)$^+$ |
| 371 | 1-(pyridazin-3-yl)-N-[4-(1-{[4-(trifluoromethyl)phenyl]acetyl}piperidin-4-yl)phenyl]azetidine-3-carboxamide | (ESI(+)) m/e 524 (M + H)$^+$ |
| 372 | N-(4-{1-[(3,5-dimethylphenyl)acetyl]piperidin-4-yl}phenyl)-1-(pyridazin-3-yl)azetidine-3-carboxamide | (ESI(+)) m/e 484 (M + H)$^+$ |
| 373 | N-(4-{1-[(2,5-difluorophenyl)acetyl]piperidin-4-yl}phenyl)-1-(pyridazin-3-yl)azetidine-3-carboxamide | (ESI(+)) m/e 492 (M + H)$^+$ |
| 374 | N-(4-{1-[(3,4-dichlorophenyl)acetyl]piperidin-4-yl}phenyl)-1-(pyridazin-3-yl)azetidine-3-carboxamide | (ESI(+)) m/e 525 (M + H)$^+$ |
| 375 | N-{4-[1-(furan-3-ylcarbonyl)piperidin-4-yl]phenyl}-1-(pyridazin-3-yl)azetidine-3-carboxamide | (ESI(+)) m/e 432 (M + H)$^+$ |
| 376 | 1-(pyridazin-3-yl)-N-{4-[1-(thiophen-2-ylcarbonyl)piperidin-4-yl]phenyl}azetidine-3-carboxamide | (ESI(+)) m/e 448 (M + H)$^+$ |
| 377 | N-(4-{1-[(5-methylthiophen-2-yl)carbonyl]piperidin-4-yl}phenyl)-1-(pyridazin-3-yl)azetidine-3-carboxamide | (ESI(+)) m/e 462 (M + H)$^+$ |
| 378 | N-(4-{1-[(5-methylpyrazin-2-yl)carbonyl]piperidin-4-yl}phenyl)-1-(pyridazin-3-yl)azetidine-3-carboxamide | (ESI(+)) m/e 458 (M + H)$^+$ |
| 379 | N-(4-{1-[(1-methylcyclopropyl)carbonyl]piperidin-4-yl}phenyl)-1-(pyridazin-3-yl)azetidine-3-carboxamide | (ESI(+)) m/e 420 (M + H)$^+$ |

TABLE 7-continued

The following Examples were prepared essentially as described in Example 1A, substituting N-(4-(piperidin-4-yl)phenyl)-1-(pyridazin-3-yl)azetidine-3-carboxamide for tert-butyl 4-(4-aminophenoxy)piperidine-1-carboxylate and the appropriate carboxylic acid for 1-(benzyloxycarbonyl)azetidine-3-carboxylic acid. Some products were purified by flash chromatography while others were purified by reverse-phase HPLC. Accordingly, some Examples were isolated as trifluoroacetic acid salts.

| Ex | Name | MS |
|---|---|---|
| 380 | N-{4-[1-(3-ethoxypropanoyl)piperidin-4-yl]phenyl}-1-(pyridazin-3-yl)azetidine-3-carboxamide | (ESI(+)) m/e 438 (M + H)$^+$ |
| 381 | N-(4-{1-[(1-phenylcyclopropyl)carbonyl]piperidin-4-yl}phenyl)-1-(pyridazin-3-yl)azetidine-3-carboxamide | (ESI(+)) m/e 482 (M + H)$^+$ |
| 382 | 1-(pyridazin-3-yl)-N-(4-{1-[(pyrimidin-2-ylsulfanyl)acetyl]piperidin-4-yl}phenyl)azetidine-3-carboxamide | (ESI(+)) m/e 490 (M + H)$^+$ |
| 383 | N-(4-{1-[(1-acetylpiperidin-4-yl)carbonyl]piperidin-4-yl}phenyl)-1-(pyridazin-3-yl)azetidine-3-carboxamide | (ESI(+)) m/e 491 (M + H)$^+$ |
| 384 | N-(4-{1-[(3,5-difluorophenyl)acetyl]piperidin-4-yl}phenyl)-1-(pyridazin-3-yl)azetidine-3-carboxamide | (ESI(+)) m/e 492 (M + H)$^+$ |
| 385 | N-{4-[1-(N-acetyl-L-leucyl)piperidin-4-yl]phenyl}-1-(pyridazin-3-yl)azetidine-3-carboxamide | (ESI(+)) m/e 493 (M + H)$^+$ |
| 386 | N-{4-[1-(diphenylacetyl)piperidin-4-yl]phenyl}-1-(pyridazin-3-yl)azetidine-3-carboxamide | (ESI(+)) m/e 532 (M + H)$^+$ |
| 387 | N-{4-[1-(3-fluoro-2-methylbenzoyl)piperidin-4-yl]phenyl}-1-(pyridazin-3-yl)azetidine-3-carboxamide | (ESI(+)) m/e 474 (M + H)$^+$ |
| 388 | N-{4-[1-(5-fluoro-2-methylbenzoyl)piperidin-4-yl]phenyl}-1-(pyridazin-3-yl)azetidine-3-carboxamide | (ESI(+)) m/e 474 (M + H)$^+$ |
| 389 | N-{4-[1-(3-fluoro-4-methylbenzoyl)piperidin-4-yl]phenyl}-1-(pyridazin-3-yl)azetidine-3-carboxamide | (ESI(+)) m/e 474 (M + H)$^+$ |
| 390 | N-{4-[1-(2,3-difluorobenzoyl)piperidin-4-yl]phenyl}-1-(pyridazin-3-yl)azetidine-3-carboxamide | (ESI(+)) m/e 478 (M + H)$^+$ |
| 391 | N-{4-[1-(2,4-difluorobenzoyl)piperidin-4-yl]phenyl}-1-(pyridazin-3-yl)azetidine-3-carboxamide | (ESI(+)) m/e 478 (M + H)$^+$ |
| 392 | N-(4-{1-[4-(propan-2-yl)benzoyl]piperidin-4-yl}phenyl)-1-(pyridazin-3-yl)azetidine-3-carboxamide | (ESI(+)) m/e 484 (M + H)$^+$ |
| 393 | N-{4-[1-(4-tert-butylbenzoyl)piperidin-4-yl]phenyl}-1-(pyridazin-3-yl)azetidine-3-carboxamide | (ESI(+)) m/e 498 (M + H)$^+$ |
| 394 | N-(4-{1-[2-fluoro-5-(trifluoromethyl)benzoyl]piperidin-4-yl}phenyl)-1-(pyridazin-3-yl)azetidine-3-carboxamide | (ESI(+)) m/e 528 (M + H)$^+$ |
| 395 | N-(4-{1-[2-chloro-5-(trifluoromethyl)benzoyl]piperidin-4-yl}phenyl)-1-(pyridazin-3-yl)azetidine-3-carboxamide | (ESI(+)) m/e 544 (M + H)$^+$ |
| 397 | N-{4-[1-(cyclopentylacetyl)piperidin-4-yl]phenyl}-1-(pyridazin-3-yl)azetidine-3-carboxamide | (ESI(+)) m/e 448 (M + H)$^+$ |
| 398 | N-(4-{1-[(4-methylphenoxy)acetyl]piperidin-4-yl}phenyl)-1-(pyridazin-3-yl)azetidine-3-carboxamide | (ESI(+)) m/e 486 (M + H)$^+$ |
| 399 | N-(4-{1-[(2S)-2-phenylbutanoyl]piperidin-4-yl}phenyl)-1-(pyridazin-3-yl)azetidine-3-carboxamide | (ESI(+)) m/e 484 (M + H)$^+$ |
| 400 | N-{4-[1-(3,5-difluorobenzoyl)piperidin-4-yl]phenyl}-1-(pyridazin-3-yl)azetidine-3-carboxamide | (ESI(+)) m/e 478 (M + H)$^+$ |
| 401 | N-{4-[1-(4-chlorobenzoyl)piperidin-4-yl]phenyl}-1-(pyridazin-3-yl)azetidine-3-carboxamide | (ESI(+)) m/e 476 (M + H)$^+$ |
| 402 | N-{4-[1-(2,2-dimethylpropanoyl)piperidin-4-yl]phenyl}-1-(pyridazin-3-yl)azetidine-3-carboxamide | (ESI(+)) m/e 422 (M + H)$^+$ |
| 403 | 1-(pyridazin-3-yl)-N-[4-(1-{[3-(trifluoromethyl)phenyl]acetyl}piperidin-4-yl)phenyl]azetidine-3-carboxamide | (ESI(+)) m/e 524 (M + H)$^+$ |

TABLE 7-continued

The following Examples were prepared essentially as described in Example 1A, substituting N-(4-(piperidin-4-yl)phenyl)-1-(pyridazin-3-yl)azetidine-3-carboxamide for tert-butyl 4-(4-aminophenoxy)piperidine-1-carboxylate and the appropriate carboxylic acid for 1-(benzyloxycarbonyl)azetidine-3-carboxylic acid. Some products were purified by flash chromatography while others were purified by reverse-phase HPLC. Accordingly, some Examples were isolated as trifluoroacetic acid salts.

| Ex | Name | MS |
|---|---|---|
| 404 | N-(4-{1-[(3-chlorophenyl)acetyl]piperidin-4-yl}phenyl)-1-(pyridazin-3-yl)azetidine-3-carboxamide | (ESI(+)) m/e 490 (M + H)$^+$ |
| 405 | N-(4-{1-[(2,4-dichlorophenyl)acetyl]piperidin-4-yl}phenyl)-1-(pyridazin-3-yl)azetidine-3-carboxamide | (ESI(+)) m/e 524 (M + H)$^+$ |
| 406 | N-{4-[1-(naphthalen-1-ylcarbonyl)piperidin-4-yl]phenyl}-1-(pyridazin-3-yl)azetidine-3-carboxamide | (ESI(+)) m/e 492 (M + H)$^+$ |
| 407 | N-(4-{1-[(2R)-2-methoxy-2-phenylacetyl]piperidin-4-yl}phenyl)-1-(pyridazin-3-yl)azetidine-3-carboxamide | (ESI(+)) m/e 486 (M + H)$^+$ |
| 408 | N-(4-{1-[N-(furan-2-ylcarbonyl)glycyl]piperidin-4-yl}phenyl)-1-(pyridazin-3-yl)azetidine-3-carboxamide | (ESI(+)) m/e 489 (M + H)$^+$ |
| 409 | N-(4-{1-[(benzyloxy)acetyl]piperidin-4-yl}phenyl)-1-(pyridazin-3-yl)azetidine-3-carboxamide | (ESI(+)) m/e 486 (M + H)$^+$ |
| 410 | N-{4-[1-(naphthalen-1-ylacetyl)piperidin-4-yl]phenyl}-1-(pyridazin-3-yl)azetidine-3-carboxamide | (ESI(+)) m/e 506 (M + H)$^+$ |
| 411 | N-{4-[1-(cyclopropylcarbonyl)piperidin-4-yl]phenyl}-1-(pyridazin-3-yl)azetidine-3-carboxamide | (ESI(+)) m/e 406 (M + H)$^+$ |
| 412 | 1-(pyridazin-3-yl)-N-{4-[1-(tetrahydrofuran-2-ylcarbonyl)piperidin-4-yl]phenyl}azetidine-3-carboxamide | (ESI(+)) m/e 436 (M + H)$^+$ |
| 413 | N-{4-[1-(N-benzoylglycyl)piperidin-4-yl]phenyl}-1-(pyridazin-3-yl)azetidine-3-carboxamide | (ESI(+)) m/e 499 (M + H)$^+$ |
| 414 | 1-(pyridazin-3-yl)-N-{4-[1-(tetrahydrofuran-3-ylcarbonyl)piperidin-4-yl]phenyl}azetidine-3-carboxamide | (ESI(+)) m/e 436 (M + H)$^+$ |
| 415 | 1-(pyridazin-3-yl)-N-(4-{1-[4-(thiophen-2-yl)butanoyl]piperidin-4-yl}phenyl)azetidine-3-carboxamide | (ESI(+)) m/e 490 (M + H)$^+$ |
| 416 | N-{4-[1-(2,5-difluorobenzoyl)piperidin-4-yl]phenyl}-1-(pyridazin-3-yl)azetidine-3-carboxamide | (ESI(+)) m/e 478 (M + H)$^+$ |
| 417 | N-{4-[1-(cyclobutylcarbonyl)piperidin-4-yl]phenyl}-1-(pyridazin-3-yl)azetidine-3-carboxamide | (ESI(+)) m/e 420 (M + H)$^+$ |
| 418 | N-[4-(1-{N-[(4-methylphenyl)sulfonyl]glycyl}piperidin-4-yl)phenyl]-1-(pyridazin-3-yl)azetidine-3-carboxamide | (ESI(+)) m/e 549 (M + H)$^+$ |
| 419 | N-(4-{1-[(2,3-difluorophenyl)acetyl]piperidin-4-yl}phenyl)-1-(pyridazin-3-yl)azetidine-3-carboxamide | (ESI(+)) m/e 492 (M + H)$^+$ |
| 420 | N-(4-{1-[(2S)-2-methoxy-2-phenylacetyl]piperidin-4-yl}phenyl)-1-(pyridazin-3-yl)azetidine-3-carboxamide | (ESI(+)) m/e 486 (M + H)$^+$ |
| 421 | N-{4-[1-(naphthalen-2-ylacetyl)piperidin-4-yl]phenyl}-1-(pyridazin-3-yl)azetidine-3-carboxamide | (ESI(+)) m/e 506 (M + H)$^+$ |
| 422 | N-{4-[1-(3-phenylpropanoyl)piperidin-4-yl]phenyl}-1-(pyridazin-3-yl)azetidine-3-carboxamide | (ESI(+)) m/e 470 (M + H)$^+$ |
| 423 | N-(4-{1-[(2,6-dichlorophenyl)acetyl]piperidin-4-yl}phenyl)-1-(pyridazin-3-yl)azetidine-3-carboxamide | (ESI(+)) m/e 524 (M + H)$^+$ |
| 424 | N-(4-{1-[3-(phenylsulfonyl)propanoyl]piperidin-4-yl}phenyl)-1-(pyridazin-3-yl)azetidine-3-carboxamide | (ESI(+)) m/e 534 (M + H)$^+$ |
| 425 | 1-(pyridazin-3-yl)-N-{4-[1-(thiophen-3-ylcarbonyl)piperidin-4-yl]phenyl}azetidine-3-carboxamide | (ESI(+)) m/e 448 (M + H)$^+$ |
| 426 | N-(4-{1-[(2,5-dimethylfuran-3-yl)carbonyl]piperidin-4-yl}phenyl)-1-(pyridazin-3-yl)azetidine-3-carboxamide | (ESI(+)) m/e 460 (M + H)$^+$ |

TABLE 7-continued

The following Examples were prepared essentially as described in Example 1A, substituting N-(4-(piperidin-4-yl)phenyl)-1-(pyridazin-3-yl)azetidine-3-carboxamide for tert-butyl 4-(4-aminophenoxy)piperidine-1-carboxylate and the appropriate carboxylic acid for 1-(benzyloxycarbonyl)azetidine-3-carboxylic acid. Some products were purified by flash chromatography while others were purified by reverse-phase HPLC. Accordingly, some Examples were isolated as trifluoroacetic acid salts.

| Ex | Name | MS |
|---|---|---|
| 427 | N-{4-[1-(cyclopropylacetyl)piperidin-4-yl]phenyl}-1-(pyridazin-3-yl)azetidine-3-carboxamide | (ESI(+)) m/e 420 $(M + H)^+$ |
| 428 | N-{4-[1-(2-fluorobenzoyl)piperidin-4-yl]phenyl}-1-(pyridazin-3-yl)azetidine-3-carboxamide | (ESI(+)) m/e 460 $(M + H)^+$ |
| 429 | N-{4-[1-(2-methylbenzoyl)piperidin-4-yl]phenyl}-1-(pyridazin-3-yl)azetidine-3-carboxamide | (ESI(+)) m/e 456 $(M + H)^+$ |
| 430 | 1-(pyridazin-3-yl)-N-{4-[1-(1,3-thiazol-4-ylcarbonyl)piperidin-4-yl]phenyl}azetidine-3-carboxamide | (ESI(+)) m/e 449 $(M + H)^+$ |
| 431 | 1-(pyridazin-3-yl)-N-{4-[1-(1,3-thiazol-5-ylcarbonyl)piperidin-4-yl]phenyl}azetidine-3-carboxamide | (ESI(+)) m/e 449 $(M + H)^+$ |
| 432 | N-{4-[1-(ethoxyacetyl)piperidin-4-yl]phenyl}-1-(pyridazin-3-yl)azetidine-3-carboxamide | (ESI(+)) m/e 424 $(M + H)^+$ |
| 433 | 1-(pyridazin-3-yl)-N-{4-[1-(4,4,4-trifluorobutanoyl)piperidin-4-yl]phenyl}azetidine-3-carboxamide | (ESI(+)) m/e 462 $(M + H)^+$ |
| 434 | N-(4-{1-[(6-methylpyridin-3-yl)carbonyl]piperidin-4-yl}phenyl)-1-(pyridazin-3-yl)azetidine-3-carboxamide | (ESI(+)) m/e 457 $(M + H)^+$ |
| 435 | N-[4-(1-benzoylpiperidin-4-yl)phenyl]-1-(pyridazin-3-yl)azetidine-3-carboxamide | (ESI(+)) m/e 442 $(M + H)^+$ |
| 436 | N-{4-[1-(furan-2-ylcarbonyl)piperidin-4-yl]phenyl}-1-(pyridazin-3-yl)azetidine-3-carboxamide | (ESI(+)) m/e 432 $(M + H)^+$ |
| 437 | N-(4-{1-[(1-methylcyclohexyl)carbonyl]piperidin-4-yl}phenyl)-1-(pyridazin-3-yl)azetidine-3-carboxamide | (ESI(+)) m/e 462 $(M + H)^+$ |
| 438 | N-{4-[1-(2-oxopropanoyl)piperidin-4-yl]phenyl}-1-(pyridazin-3-yl)azetidine-3-carboxamide | (ESI(+)) m/e 408 $(M + H)^+$ |
| 439 | N-{4-[1-(cyclopentylcarbonyl)piperidin-4-yl]phenyl}-1-(pyridazin-3-yl)azetidine-3-carboxamide | (ESI(+)) m/e 434 $(M + H)^+$ |
| 440 | N-[4-(1-propanoylpiperidin-4-yl)phenyl]-1-(pyridazin-3-yl)azetidine-3-carboxamide | (ESI(+)) m/e 394 $(M + H)^+$ |
| 441 | N-{4-[1-(4-methylbenzoyl)piperidin-4-yl]phenyl}-1-(pyridazin-3-yl)azetidine-3-carboxamide | (ESI(+)) m/e 456 $(M + H)^+$ |

Example 148

N-{4-[1-(2-methylpropyl)-1H-pyrazol-4-yl]phenyl}-1-(pyridazin-4-yl)azetidine-3-carboxamide Example 148A 4-(1-isobutyl-1H-pyrazol-4-yl)aniline A suspension of 4-bromoaniline (406 mg, 2.362 mmol), 1-isobutyl-4-(4,4,5,5-tetramethyl-1,3,2-dioxaborolan-2-yl)-1H-pyrazole (650 mg, 2.60 mmol), PdCl$_2$(dppf)-dichloromethane adduct (57.9 mg, 0.071 mmol) and sodium carbonate (526 mg, 4.96 mmol) in a 6:2:1 mixture of tetrahydrofuran/methanol/water (12 ml) was taken through three vacuum/nitrogen purge cycles; and the reaction mixture was heated in an oil bath at 85° C. overnight. The mixture was diluted with ethyl acetate and water; the separated aqueous layer was extracted with ethyl acetate and the combined organic layers were washed with brine, dried with magnesium sulfate, filtered and concentrated. The residue was purified by normal phase chromatography to give the title compound.

Example 148B benzyl 3-((4-(1-isobutyl-1H-pyrazol-4-yl)phenyl) carbamoyl)azetidine-1-carboxylate The title compound was prepared as described in Example 1A, substituting 4-(1-isobutyl-1H-pyrazol-4-yl)aniline for tert-butyl 4-(4-aminophenoxy)piperidine-1-carboxylate.

Example 148C

N-(4-(1-isobutyl-1H-pyrazol-4-yl)phenyl)azetidine-3-carboxamide

The title compound was prepared as described in Example 1B, substituting benzyl 3-((4-(1-isobutyl-1H-pyrazol-4-yl)phenyl)carbamoyl)azetidine-1-carboxylate for tert-butyl 4-(4-(1-(benzyloxycarbonyl)azetidine-3-carboxamido)phenoxy)piperidine-1-carboxylate.

Example 148D

N-{4-[1-(2-methylpropyl)-1H-pyrazol-4-yl]phenyl}-1-(pyridazin-4-yl)azetidine-3-carboxamide The title compound was prepared as described in Example 1C, substituting 4-bromopyridazine for 3-bromopyridine and N-(4-(1-isobutyl-1H-pyrazol-4-yl)phenyl)azetidine-3-carboxamide for tert-butyl 4-(4-(azetidine-3-carboxamido)phenoxy)piperidine-1-carboxylate. $^1$H NMR (300 MHz, DMSO-$d_6$) δ ppm 10.10 (s, 1H), 8.61 (d, J=6.0 Hz, 1H), 8.51 (d, J=3.0 Hz, 1H), 8.08 (s, 1H), 7.81 (s, 1H), 7.64-7.56 (m, 2H), 7.55-7.48 (m, 2H), 6.55 (dd, J=6.0, 3.0 Hz, 1H), 4.31-3.96 (m, 4H), 3.91 (d, J=7.1 Hz, 2H), 3.74 (s, 1H), 2.12 (dd, J=13.3, 6.5 Hz, 1H), 0.86 (d, J=6.7 Hz, 6H); MS (ESI(+)) m/e 377 (M+H)$^+$.

Example 199

N-(4-{[1-(4-fluorobenzoyl)azetidin-3-yl]oxy}phenyl)-1-(pyridazin-4-yl)azetidine-3-carboxamide The title compound was prepared as described in Example 1, substituting tert-butyl 4-(4-aminophenoxy)azetidinyl-1-carboxylate for tert-butyl 4-(4-aminophenoxy)piperidine-1-carboxylate in Example 1A, 4-bromopyridazine for 3-bromopyridyl in Example 1C and 4-fluorobenzoic acid for 2-(tetrahydro-2H-pyran-4-yl)acetic acid in Example 1E. $^1$H NMR (300 MHz, DMSO-$d_6$) δ ppm 10.01 (s, 1H), 8.67-8.44 (m, 1H), 7.83-7.63 (m, 2H), 7.62-7.43 (m, 2H), 7.43-7.18 (m, 2H), 6.90-6.77 (m, 2H), 6.55 (dd, J=6.1, 3.1 Hz, 1H), 5.13-4.94 (m, 1H), 4.61 (d, J=52.0 Hz, 2H), 4.36-4.04 (m, 4H), 3.99 (s, 1H), 3.70 (ddt, J=33.0, 30.2, 15.0 Hz, 1H), 1.21 (t, J=15.0 Hz, 3H); MS (ESI(+)) m/e 448 (M+H)$^+$.

TABLE 8

The following Examples were prepared essentially as described in Example 1, substituting the appropriate amine for tert-butyl 4-(4-aminophenoxy)piperidine-1-carboxylate in Example 1A, 4-bromopyridazine for 3-bromopyridyl in Example 1C and the appropriate carboxylic acid for 2-(tetrahydro-2H-pyran-4-yl)acetic acid in Example 1E. Some products were purified by flash chromatography while others were purified by reverse-phase HPLC. Accordingly, some Examples were isolated as trifluoroacetic acid salts.

| Ex  | Name | MS |
| --- | --- | --- |
| 200 | N-(4-{[1-(2,4-difluorobenzoyl)azetidin-3-yl]oxy}phenyl)-1-(pyridazin-4-yl)azetidine-3-carboxamide | (ESI(+)) m/e 466 (M + H)$^+$ |
| 201 | N-[4-({1-[difluoro(phenyl)acetyl]azetidin-3-yl}oxy)phenyl]-1-(pyridazin-4-yl)azetidine-3-carboxamide | (ESI(+)) m/e 480 (M + H)$^+$ |
| 202 | N-[4-({1-[(4,4-difluorocyclohexyl)carbonyl]azetidin-3-yl}oxy)phenyl]-1-(pyridazin-4-yl)azetidine-3-carboxamide | (ESI(+)) m/e 472 (M + H)$^+$ |
| 203 | N-[4-({1-[(4-fluorophenyl)acetyl]azetidin-3-yl}oxy)phenyl]-1-(pyridazin-4-yl)azetidine-3-carboxamide | (ESI(+)) m/e 462 (M + H)$^+$ |
| 205 | 1-(pyridazin-4-yl)-N-[4-({1-[4-(trifluoromethyl)benzoyl]azetidin-3-yl}oxy)phenyl]azetidine-3-carboxamide | (ESI(+)) m/e 498 (M + H)$^+$ |
| 206 | N-{4-[(1-benzoylazetidin-3-yl)oxy]phenyl}-1-(pyridazin-4-yl)azetidine-3-carboxamide | (ESI(+)) m/e 430 (M + H)$^+$ |
| 207 | N-(4-{[1-(2-hydroxy-2-methylpropanoyl)azetidin-3-yl]oxy}phenyl)-1-(pyridazin-4-yl)azetidine-3-carboxamide | (ESI(+)) m/e 412 (M + H)$^+$ |
| 208 | 1-(pyridazin-4-yl)-N-(4-{[1-(tetrahydrofuran-3-ylcarbonyl)azetidin-3-yl]oxy}phenyl)azetidine-3-carboxamide | (ESI(+)) m/e 424 (M + H)$^+$ |
| 209 | N-(4-{[1-(furan-3-ylcarbonyl)azetidin-3-yl]oxy}phenyl)-1-(pyridazin-4-yl)azetidine-3-carboxamide | (ESI(+)) m/e 420 (M + H)$^+$ |
| 210 | N-{4-[(1-pentanoylazetidin-3-yl)oxy]phenyl}-1-(pyridazin-4-yl)azetidine-3-carboxamide | (ESI(+)) m/e 410 (M + H)$^+$ |
| 254 | N-(4-{[1-(3,3-dimethylbutanoyl)azetidin-3-yl]oxy}phenyl)-1-(pyridazin-4-yl)azetidine-3-carboxamide | (ESI(+)) m/e 424 (M + H)$^+$ |
| 255 | N-(4-{[1-(cyclohexylcarbonyl)azetidin-3-yl]oxy}phenyl)-1-(pyridazin-4-yl)azetidine-3-carboxamide | (ESI(+)) m/e 436 (M + H)$^+$ |
| 256 | 1-(pyridazin-4-yl)-N-(4-{[1-(tetrahydro-2H-pyran-4-ylacetyl)azetidin-3-yl]oxy}phenyl)azetidine-3-carboxamide | (ESI(+)) m/e 452 (M + H)$^+$ |

TABLE 8-continued

The following Examples were prepared essentially as described in Example 1, substituting the appropriate amine for tert-butyl 4-(4-aminophenoxy)piperidine-1-carboxylate in Example 1A, 4-bromopyridazine for 3-bromopyridyl in Example 1C and the appropriate carboxylic acid for 2-(tetrahydro-2H-pyran-4-yl)acetic acid in Example 1E. Some products were purified by flash chromatography while others were purified by reverse-phase HPLC. Accordingly, some Examples were isolated as trifluoroacetic acid salts.

| Ex | Name | MS |
|---|---|---|
| 257 | N-[4-({1-[(2-methylcyclopropyl)carbonyl]azetidin-3-yl}oxy)phenyl]-1-(pyridazin-4-yl)azetidine-3-carboxamide | (ESI(+)) m/e 408 (M + H)$^+$ |
| 258 | 1-(pyridazin-4-yl)-N-(4-{[1-(3,3,3-trifluoropropanoyl)azetidin-3-yl]oxy}phenyl)azetidine-3-carboxamide | (ESI(+)) m/e 436 (M + H)$^+$ |
| 259 | N-(4-{[1-(cyclopentylcarbonyl)azetidin-3-yl]oxy}phenyl)-1-(pyridazin-4-yl)azetidine-3-carboxamide | (ESI(+)) m/e 422 (M + H)$^+$ |
| 260 | N-(4-{[1-(3,3-dimethylbutanoyl)piperidin-4-yl]oxy}phenyl)-1-(pyridazin-4-yl)azetidine-3-carboxamide | (ESI(+)) m/e 452 (M + H)$^+$ |
| 261 | N-(4-{[1-(cyclobutylcarbonyl)azetidin-3-yl]oxy}phenyl)-1-(pyridazin-4-yl)azetidine-3-carboxamide | (ESI(+)) m/e 408 (M + H)$^+$ |
| 262 | 1-(pyridazin-4-yl)-N-(4-{[1-(tetrahydrofuran-2-ylcarbonyl)azetidin-3-yl]oxy}phenyl)azetidine-3-carboxamide | (ESI(+)) m/e 424 (M + H)$^+$ |
| 263 | N-(4-{[1-(4-methylpentanoyl)azetidin-3-yl]oxy}phenyl)-1-(pyridazin-4-yl)azetidine-3-carboxamide | (ESI(+)) m/e 424 (M + H)$^+$ |
| 264 | N-(4-{[1-(2-methylpropanoyl)azetidin-3-yl]oxy}phenyl)-1-(pyridazin-4-yl)azetidine-3-carboxamide | (ESI(+)) m/e 396 (M + H)$^+$ |
| 265 | N-[4-({1-[(2S)-2-methylbutanoyl]azetidin-3-yl}oxy)phenyl]-1-(pyridazin-4-yl)azetidine-3-carboxamide | (ESI(+)) m/e 410 (M + H)$^+$ |
| 266 | N-(4-{[1-(3-methylbutanoyl)piperidin-4-yl]oxy}phenyl)-1-(pyridazin-4-yl)azetidine-3-carboxamide | (ESI(+)) m/e 438 (M + H)$^+$ |
| 267 | N-(4-{[1-(methoxyacetyl)piperidin-4-yl]oxy}phenyl)-1-(pyridazin-4-yl)azetidine-3-carboxamide | (ESI(+)) m/e 426 (M + H)$^+$ |
| 268 | 1-(pyridazin-4-yl)-N-(4-{[1-(3,3,3-trifluoropropanoyl)piperidin-4-yl]oxy}phenyl)azetidine-3-carboxamide | (ESI(+)) m/e 464 (M + H)$^+$ |
| 269 | N-[4-({1-[difluoro(phenyl)acetyl]piperidin-4-yl}oxy)phenyl]-1-(pyridazin-4-yl)azetidine-3-carboxamide | (ESI(+)) m/e 508 (M + H)$^+$ |
| 270 | N-[4-({1-[(4,4-difluorocyclohexyl)carbonyl]piperidin-4-yl}oxy)phenyl]-1-(pyridazin-4-yl)azetidine-3-carboxamide | (ESI(+)) m/e 500 (M + H)$^+$ |
| 271 | N-(4-{[1-(4-fluorobenzoyl)piperidin-4-yl]oxy}phenyl)-1-(pyridazin-4-yl)azetidine-3-carboxamide | (ESI(+)) m/e 476 (M + H)$^+$ |
| 272 | 1-(pyridazin-4-yl)-N-(4-{[1-(1,3-thiazol-4-ylcarbonyl)piperidin-4-yl]oxy}phenyl)azetidine-3-carboxamide | (ESI(+)) m/e 465 (M + H)$^+$ |
| 273 | 1-(pyridazin-4-yl)-N-{4-[(1-{[4-(trifluoromethyl)phenyl]acetyl}piperidin-4-yl)oxy]phenyl}azetidine-3-carboxamide | (ESI(+)) m/e 540 (M + H)$^+$ |
| 274 | N-(4-{[1-(3,4-difluorobenzoyl)piperidin-4-yl]oxy}phenyl)-1-(pyridazin-4-yl)azetidine-3-carboxamide | (ESI(+)) m/e 494 (M + H)$^+$ |
| 275 | 1-(pyridazin-4-yl)-N-{4-[(1-{[4-(trifluoromethoxy)phenyl]acetyl}piperidin-4-yl)oxy]phenyl}azetidine-3-carboxamide | (ESI(+)) m/e 556 (M + H)$^+$ |
| 276 | N-[4-({1-[(4-fluorophenyl)acetyl]piperidin-4-yl}oxy)phenyl]-1-(pyridazin-4-yl)azetidine-3-carboxamide | (ESI(+)) m/e 490 (M + H)$^+$ |
| 277 | N-[4-({1-[(2,4-difluorophenyl)acetyl]piperidin-4-yl}oxy)phenyl]-1-(pyridazin-4-yl)azetidine-3-carboxamide | (ESI(+)) m/e 508 (M + H)$^+$ |
| 278 | 1-(pyridazin-4-yl)-N-(4-{[1-(thiophen-3-ylcarbonyl)piperidin-4-yl]oxy}phenyl)azetidine-3-carboxamide | (ESI(+)) m/e 464 (M + H)$^+$ |
| 279 | N-(4-{[1-(2-chlorobenzoyl)piperidin-4-yl]oxy}phenyl)-1-(pyridazin-4-yl)azetidine-3-carboxamide | (ESI(+)) m/e 492 (M + H)$^+$ |

TABLE 8-continued

The following Examples were prepared essentially as described in Example 1, substituting the appropriate amine for tert-butyl 4-(4-aminophenoxy)piperidine-1-carboxylate in Example 1A, 4-bromopyridazine for 3-bromopyridyl in Example 1C and the appropriate carboxylic acid for 2-(tetrahydro-2H-pyran-4-yl)acetic acid in Example 1E. Some products were purified by flash chromatography while others were purified by reverse-phase HPLC. Accordingly, some Examples were isolated as trifluoroacetic acid salts.

| Ex  | Name | MS |
|-----|------|----|
| 280 | N-(4-{[1-(2,2-dimethylpropanoyl)piperidin-4-yl]oxy}phenyl)-1-(pyridazin-4-yl)azetidine-3-carboxamide | (ESI(+)) m/e 438 (M + H)$^+$ |
| 281 | N-(4-{[1-(2-methyl-2-phenylpropanoyl)piperidin-4-yl]oxy}phenyl)-1-(pyridazin-4-yl)azetidine-3-carboxamide | (ESI(+)) m/e 500 (M + H)$^+$ |
| 282 | N-{4-[(1-acetylpiperidin-4-yl)oxy]phenyl}-1-(pyridazin-4-yl)azetidine-3-carboxamide | (ESI(+)) m/e 396 (M + H)$^+$ |
| 283 | 1-(pyridazin-4-yl)-N-(4-{[1-(1,3-thiazol-2-ylcarbonyl)piperidin-4-yl]oxy}phenyl)azetidine-3-carboxamide | (ESI(+)) m/e 465 (M + H)$^+$ |
| 284 | N-(4-{[1-(2,4-difluorobenzoyl)piperidin-4-yl]oxy}phenyl)-1-(pyridazin-4-yl)azetidine-3-carboxamide | (ESI(+)) m/e 494 (M + H)$^+$ |
| 285 | 1-(pyridazin-4-yl)-N-[4-({1-[3-(trifluoromethyl)benzoyl]piperidin-4-yl}oxy)phenyl]azetidine-3-carboxamide | (ESI(+)) m/e 526 (M + H)$^+$ |
| 286 | N-(4-{[1-(3-fluorobenzoyl)piperidin-4-yl]oxy}phenyl)-1-(pyridazin-4-yl)azetidine-3-carboxamide | (ESI(+)) m/e 476 (M + H)$^+$ |
| 287 | 1-(pyridazin-4-yl)-N-[4-({1-[4-(trifluoromethyl)benzoyl]piperidin-4-yl}oxy)phenyl]azetidine-3-carboxamide | (ESI(+)) m/e 526 (M + H)$^+$ |
| 288 | N-[4-({1-[(3-fluorophenyl)acetyl]piperidin-4-yl}oxy)phenyl]-1-(pyridazin-4-yl)azetidine-3-carboxamide | (ESI(+)) m/e 490 (M + H)$^+$ |
| 289 | N-(4-{[1-(2-fluorobenzoyl)piperidin-4-yl]oxy}phenyl)-1-(pyridazin-4-yl)azetidine-3-carboxamide | (ESI(+)) m/e 476 (M + H)$^+$ |
| 290 | 1-(pyridazin-4-yl)-N-[4-({1-[4-(trifluoromethoxy)benzoyl]piperidin-4-yl}oxy)phenyl]azetidine-3-carboxamide | (ESI(+)) m/e 542 (M + H)$^+$ |
| 291 | N-[4-({1-[(3,5-difluorophenyl)acetyl]piperidin-4-yl}oxy)phenyl]-1-(pyridazin-4-yl)azetidine-3-carboxamide | (ESI(+)) m/e 508 (M + H)$^+$ |
| 292 | 1-(pyridazin-4-yl)-N-[4-({1-[3-(trifluoromethoxy)benzoyl]piperidin-4-yl}oxy)phenyl]azetidine-3-carboxamide | (ESI(+)) m/e 542 (M + H)$^+$ |
| 293 | N-(4-{[1-(cyclopropylacetyl)piperidin-4-yl]oxy}phenyl)-1-(pyridazin-4-yl)azetidine-3-carboxamide | (ESI(+)) m/e 436 (M + H)$^+$ |
| 294 | N-(4-{[1-(2-methylpropanoyl)piperidin-4-yl]oxy}phenyl)-1-(pyridazin-4-yl)azetidine-3-carboxamide | (ESI(+)) m/e 424 (M + H)$^+$ |
| 295 | N-(4-{[1-(3-chlorobenzoyl)piperidin-4-yl]oxy}phenyl)-1-(pyridazin-4-yl)azetidine-3-carboxamide | (ESI(+)) m/e 492 (M + H)$^+$ |
| 296 | 1-(pyridazin-4-yl)-N-(4-{[1-(pyridin-2-ylcarbonyl)piperidin-4-yl]oxy}phenyl)azetidine-3-carboxamide | (ESI(+)) m/e 459 (M + H)$^+$ |
| 297 | N-(4-{[1-(4-chlorobenzoyl)piperidin-4-yl]oxy}phenyl)-1-(pyridazin-4-yl)azetidine-3-carboxamide | (ESI(+)) m/e 492 (M + H)$^+$ |
| 298 | 1-(pyridazin-4-yl)-N-(4-{[1-(tetrahydrofuran-3-ylcarbonyl)piperidin-4-yl]oxy}phenyl)azetidine-3-carboxamide | (ESI(+)) m/e 452 (M + H)$^+$ |
| 299 | N-(4-{[1-(3,5-difluorobenzoyl)piperidin-4-yl]oxy}phenyl)-1-(pyridazin-4-yl)azetidine-3-carboxamide | (ESI(+)) m/e 494 (M + H)$^+$ |
| 300 | N-(4-{[1-(2,2-dimethylbutanoyl)piperidin-4-yl]oxy}phenyl)-1-(pyridazin-4-yl)azetidine-3-carboxamide | (ESI(+)) m/e 452 (M + H)$^+$ |
| 301 | N-(4-{[1-(cyclopropylcarbonyl)piperidin-4-yl]oxy}phenyl)-1-(pyridazin-4-yl)azetidine-3-carboxamide | (ESI(+)) m/e 422 (M + H)$^+$ |
| 302 | 1-(pyridazin-4-yl)-N-(4-{[1-(tetrahydrofuran-2-ylcarbonyl)piperidin-4-yl]oxy}phenyl)azetidine-3-carboxamide | (ESI(+)) m/e 452 (M + H)$^+$ |

TABLE 8-continued

The following Examples were prepared essentially as described in Example 1, substituting the appropriate amine for tert-butyl 4-(4-aminophenoxy)piperidine-1-carboxylate in Example 1A, 4-bromopyridazine for 3-bromopyridyl in Example 1C and the appropriate carboxylic acid for 2-(tetrahydro-2H-pyran-4-yl)acetic acid in Example 1E. Some products were purified by flash chromatography while others were purified by reverse-phase HPLC. Accordingly, some Examples were isolated as trifluoroacetic acid salts.

| Ex | Name | MS |
|---|---|---|
| 303 | 1-(pyridazin-4-yl)-N-(4-{[1-(thiophen-2-ylcarbonyl)piperidin-4-yl]oxy}phenyl)azetidine-3-carboxamide | (ESI(+)) m/e 464 (M + H)$^+$ |
| 304 | N-[4-({1-[(5-methylthiophen-2-yl)carbonyl]piperidin-4-yl}oxy)phenyl]-1-(pyridazin-4-yl)azetidine-3-carboxamide | (ESI(+)) m/e 478 (M + H)$^+$ |
| 305 | 1-(pyridazin-4-yl)-N-{4-[(1-{[3-(trifluoromethyl)phenyl]acetyl}piperidin-4-yl)oxy]phenyl}azetidine-3-carboxamide | (ESI(+)) m/e 540 (M + H)$^+$ |
| 306 | 1-(pyridazin-4-yl)-N-(4-{[1-(tetrahydro-2H-pyran-4-ylcarbonyl)piperidin-4-yl]oxy}phenyl)azetidine-3-carboxamide | (ESI(+)) m/e 466 (M + H)$^+$ |
| 307 | N-[4-({1-[(2S)-2-methylbutanoyl]piperidin-4-yl}oxy)phenyl]-1-(pyridazin-4-yl)azetidine-3-carboxamide | (ESI(+)) m/e 438 (M + H)$^+$ |
| 308 | N-[4-({1-[(2-fluorophenyl)acetyl]piperidin-4-yl}oxy)phenyl]-1-(pyridazin-4-yl)azetidine-3-carboxamide | (ESI(+)) m/e 490 (M + H)$^+$ |
| 396 | N-(4-{[(3R)-1-(4-fluorobenzoyl)pyrrolidin-3-yl]oxy}phenyl)-1-(pyridazin-4-yl)azetidine-3-carboxamide | (ESI(+)) m/e 462 (M + H)$^+$ |
| 442 | N-(4-{[(3R)-1-(2-chlorobenzoyl)pyrrolidin-3-yl]oxy}phenyl)-1-(pyridazin-4-yl)azetidine-3-carboxamide | (ESI(+)) m/e 478 (M + H)$^+$ |
| 443 | 1-(pyridazin-4-yl)-N-(4-{[(3R)-1-(1,3-thiazol-2-ylcarbonyl)pyrrolidin-3-yl]oxy}phenyl)azetidine-3-carboxamide | (ESI(+)) m/e 451 (M + H)$^+$ |
| 444 | N-(4-{[(3R)-1-(cyclopropylacetyl)pyrrolidin-3-yl]oxy}phenyl)-1-(pyridazin-4-yl)azetidine-3-carboxamide | (ESI(+)) m/e 422 (M + H)$^+$ |
| 445 | N-[4-({(3R)-1-[(2S)-2-methylbutanoyl]pyrrolidin-3-yl}oxy)phenyl]-1-(pyridazin-4-yl)azetidine-3-carboxamide | (ESI(+)) m/e 424 (M + H)$^+$ |
| 446 | 1-(pyridazin-4-yl)-N-(4-{[(3R)-1-(tetrahydro-2H-pyran-4-ylcarbonyl)pyrrolidin-3-yl]oxy}phenyl)azetidine-3-carboxamide | (ESI(+)) m/e 452 (M + H)$^+$ |
| 447 | 1-(pyridazin-4-yl)-N-(4-{[(3R)-1-{[4-(trifluoromethoxy)phenyl]acetyl}pyrrolidin-3-yl]oxy}phenyl)azetidine-3-carboxamide | (ESI(+)) m/e 542 (M + H)$^+$ |
| 448 | 1-(pyridazin-4-yl)-N-(4-{[(3R)-1-(thiophen-3-ylcarbonyl)pyrrolidin-3-yl]oxy}phenyl)azetidine-3-carboxamide | (ESI(+)) m/e 450 (M + H)$^+$ |
| 449 | N-[4-({(3R)-1-[(4-fluorophenyl)acetyl]pyrrolidin-3-yl}oxy)phenyl]-1-(pyridazin-4-yl)azetidine-3-carboxamide | (ESI(+)) m/e 476 (M + H)$^+$ |
| 450 | N-[4-({(3R)-1-[(3,5-difluorophenyl)acetyl]pyrrolidin-3-yl}oxy)phenyl]-1-(pyridazin-4-yl)azetidine-3-carboxamide | (ESI(+)) m/e 494 (M + H)$^+$ |
| 451 | N-(4-{[(3R)-1-(3,4-difluorobenzoyl)pyrrolidin-3-yl]oxy}phenyl)-1-(pyridazin-4-yl)azetidine-3-carboxamide | (ESI(+)) m/e 480 (M + H)$^+$ |
| 452 | N-[4-({(3R)-1-[(3-fluorophenyl)acetyl]pyrrolidin-3-yl}oxy)phenyl]-1-(pyridazin-4-yl)azetidine-3-carboxamide | (ESI(+)) m/e 476 (M + H)$^+$ |
| 453 | 1-(pyridazin-4-yl)-N-[4-({(3R)-1-[3-(trifluoromethyl)benzoyl]pyrrolidin-3-yl}oxy)phenyl]azetidine-3-carboxamide | (ESI(+)) m/e 512 (M + H)$^+$ |
| 454 | N-[4-({(3R)-1-[(2,4-difluorophenyl)acetyl]pyrrolidin-3-yl}oxy)phenyl]-1-(pyridazin-4-yl)azetidine-3-carboxamide | (ESI(+)) m/e 494 (M + H)$^+$ |
| 455 | 1-(pyridazin-4-yl)-N-(4-{[(3R)-1-{[4-(trifluoromethyl)phenyl]acetyl}pyrrolidin-3-yl]oxy}phenyl)azetidine-3-carboxamide | (ESI(+)) m/e 526 (M + H)$^+$ |
| 456 | 1-(pyridazin-4-yl)-N-(4-{[(3R)-1-(1,3-thiazol-4-ylcarbonyl)pyrrolidin-3-yl]oxy}phenyl)azetidine-3-carboxamide | (ESI(+)) m/e 451 (M + H)$^+$ |
| 457 | 1-(pyridazin-4-yl)-N-(4-{[(3R)-1-(tetrahydrofuran-2-ylcarbonyl)pyrrolidin-3-yl]oxy}phenyl)azetidine-3-carboxamide | (ESI(+)) m/e 438 (M + H)$^+$ |

TABLE 8-continued

The following Examples were prepared essentially as described in Example 1, substituting the appropriate amine for tert-butyl 4-(4-aminophenoxy)piperidine-1-carboxylate in Example 1A, 4-bromopyridazine for 3-bromopyridyl in Example 1C and the appropriate carboxylic acid for 2-(tetrahydro-2H-pyran-4-yl)acetic acid in Example 1E. Some products were purified by flash chromatography while others were purified by reverse-phase HPLC. Accordingly, some Examples were isolated as trifluoroacetic acid salts.

| Ex | Name | MS |
|---|---|---|
| 458 | N-[4-({(3R)-1-[(5-methylthiophen-2-yl)carbonyl]pyrrolidin-3-yl}oxy)phenyl]-1-(pyridazin-4-yl)azetidine-3-carboxamide | (ESI(+)) m/e 464 (M + H)$^+$ |
| 459 | N-[4-({(3R)-1-[(2-fluorophenyl)acetyl]pyrrolidin-3-yl}oxy)phenyl]-1-(pyridazin-4-yl)azetidine-3-carboxamide | (ESI(+)) m/e 476 (M + H)$^+$ |
| 460 | N-(4-{[(3R)-1-(cyclopropylcarbonyl)pyrrolidin-3-yl]oxy}phenyl)-1-(pyridazin-4-yl)azetidine-3-carboxamide | (ESI(+)) m/e 408 (M + H)$^+$ |
| 461 | 1-(pyridazin-4-yl)-N-(4-{[(3R)-1-(tetrahydrofuran-3-ylcarbonyl)pyrrolidin-3-yl]oxy}phenyl)azetidine-3-carboxamide | (ESI(+)) m/e 438 (M + H)$^+$ |
| 462 | 1-(pyridazin-4-yl)-N-[4-({(3R)-1-[3-(trifluoromethoxy)benzoyl]pyrrolidin-3-yl}oxy)phenyl]azetidine-3-carboxamide | (ESI(+)) m/e 528 (M + H)$^+$ |
| 463 | 1-(pyridazin-4-yl)-N-(4-{[(3R)-1-(pyridin-2-ylcarbonyl)pyrrolidin-3-yl]oxy}phenyl)azetidine-3-carboxamide | (ESI(+)) m/e 445 (M + H)$^+$ |
| 464 | N-(4-{[(3R)-1-(3-chlorobenzoyl)pyrrolidin-3-yl]oxy}phenyl)-1-(pyridazin-4-yl)azetidine-3-carboxamide | (ESI(+)) m/e 478 (M + H)$^+$ |
| 465 | N-(4-{[(3R)-1-(4-chlorobenzoyl)pyrrolidin-3-yl]oxy}phenyl)-1-(pyridazin-4-yl)azetidine-3-carboxamide | (ESI(+)) m/e 478 (M + H)$^+$ |
| 466 | N-(4-{[(3R)-1-(2-methyl-2-phenylpropanoyl)pyrrolidin-3-yl]oxy}phenyl)-1-(pyridazin-4-yl)azetidine-3-carboxamide | (ESI(+)) m/e 486 (M + H)$^+$ |
| 467 | N-(4-{[(3R)-1-(2,4-difluorobenzoyl)pyrrolidin-3-yl]oxy}phenyl)-1-(pyridazin-4-yl)azetidine-3-carboxamide | (ESI(+)) m/e 480 (M + H)$^+$ |
| 468 | N-(4-{[(3R)-1-(methoxyacetyl)pyrrolidin-3-yl]oxy}phenyl)-1-(pyridazin-4-yl)azetidine-3-carboxamide | (ESI(+)) m/e 412 (M + H)$^+$ |
| 469 | 1-(pyridazin-4-yl)-N-(4-{[(3R)-1-(thiophen-2-ylcarbonyl)pyrrolidin-3-yl]oxy}phenyl)azetidine-3-carboxamide | (ESI(+)) m/e 450 (M + H)$^+$ |
| 470 | 1-(pyridazin-4-yl)-N-(4-{[(3R)-1-{[3-(trifluoromethyl)phenyl]acetyl}pyrrolidin-3-yl]oxy}phenyl)azetidine-3-carboxamide | (ESI(+)) m/e 526 (M + H)$^+$ |
| 471 | N-(4-{[(3R)-1-(2-methylpropanoyl)pyrrolidin-3-yl]oxy}phenyl)-1-(pyridazin-4-yl)azetidine-3-carboxamide | (ESI(+)) m/e 410 (M + H)$^+$ |
| 472 | N-(4-{[(3R)-1-(2-fluorobenzoyl)pyrrolidin-3-yl]oxy}phenyl)-1-(pyridazin-4-yl)azetidine-3-carboxamide | (ESI(+)) m/e 462 (M + H)$^+$ |
| 473 | N-(4-{[(3R)-1-(2,2-dimethylbutanoyl)pyrrolidin-3-yl]oxy}phenyl)-1-(pyridazin-4-yl)azetidine-3-carboxamide | (ESI(+)) m/e 438 (M + H)$^+$ |
| 474 | N-(4-{[(3R)-1-(3,5-difluorobenzoyl)pyrrolidin-3-yl]oxy}phenyl)-1-(pyridazin-4-yl)azetidine-3-carboxamide | (ESI(+)) m/e 480 (M + H)$^+$ |
| 475 | 1-(pyridazin-4-yl)-N-[4-({(3R)-1-[4-(trifluoromethyl)benzoyl]pyrrolidin-3-yl}oxy)phenyl]azetidine-3-carboxamide | (ESI(+)) m/e 512 (M + H)$^+$ |
| 476 | N-(4-{[(3R)-1-(3-fluorobenzoyl)pyrrolidin-3-yl]oxy}phenyl)-1-(pyridazin-4-yl)azetidine-3-carboxamide | (ESI(+)) m/e 462 (M + H)$^+$ |
| 477 | 1-(pyridazin-4-yl)-N-[4-({(3R)-1-[4-(trifluoromethoxy)benzoyl]pyrrolidin-3-yl}oxy)phenyl]azetidine-3-carboxamide | (ESI(+)) m/e 528 (M + H)$^+$ |
| 478 | N-(4-{[(3R)-1-(3-methylbutanoyl)pyrrolidin-3-yl]oxy}phenyl)-1-(pyridazin-4-yl)azetidine-3-carboxamide | (ESI(+)) m/e 424 (M + H)$^+$ |
| 479 | 1-(pyridazin-4-yl)-N-(4-{[(3R)-1-(3,3,3-trifluoropropanoyl)pyrrolidin-3-yl]oxy}phenyl)azetidine-3-carboxamide | (ESI(+)) m/e 450 (M + H)$^+$ |
| 480 | N-[4-({(3R)-1-[difluoro(phenyl)acetyl]pyrrolidin-3-yl}oxy)phenyl]-1-(pyridazin-4-yl)azetidine-3-carboxamide | (ESI(+)) m/e 494 (M + H)$^+$ |

TABLE 8-continued

The following Examples were prepared essentially as described in Example 1, substituting the appropriate amine for tert-butyl 4-(4-aminophenoxy)piperidine-1-carboxylate in Example 1A, 4-bromopyridazine for 3-bromopyridyl in Example 1C and the appropriate carboxylic acid for 2-(tetrahydro-2H-pyran-4-yl)acetic acid in Example 1E. Some products were purified by flash chromatography while others were purified by reverse-phase HPLC. Accordingly, some Examples were isolated as trifluoroacetic acid salts.

| Ex | Name | MS |
|---|---|---|
| 481 | N-(4-{[(3R)-1-(2,2-dimethylpropanoyl)pyrrolidin-3-yl]oxy}phenyl)-1-(pyridazin-4-yl)azetidine-3-carboxamide | (ESI(+)) m/e 424 (M + H)$^+$ |
| 482 | N-[4-({(3R)-1-[(4,4-difluorocyclohexyl)carbonyl]pyrrolidin-3-yl}oxy)phenyl]-1-(pyridazin-4-yl)azetidine-3-carboxamide | (ESI(+)) m/e 486 (M + H)$^+$ |

Example 204

(3S)—N-{4-[1-(cyclopentylacetyl)piperidin-4-yl]phenyl}-1-(pyridin-3-yl)pyrrolidine-3-carboxamide The title compound was prepared as described in Example 1, substituting (S)-1-((benzyloxy)carbonyl)pyrrolidine-3-carboxylic acid for 1-(benzyloxycarbonyl)azetidine-3-carboxylic acid and tert-butyl 4-(4-aminophenyl)piperidine-1-carboxylate for tert-butyl 4-(4-aminophenoxy)piperidine-1-carboxylate in Example 1A, and cyclopentylbenzoic acid for 2-(tetrahydro-2H-pyran-4-yl)acetic acid in Example 1E. $^1$H NMR (300 MHz, DMSO-d$_6$) δ ppm 10.03 (s, 1H), 7.95 (d, J=2.8 Hz, 1H), 7.85 (dd, J=4.6, 1.2 Hz, 1H), 7.55 (t, J=10.1 Hz, 2H), 7.16 (dd, J=8.3, 4.3 Hz, 3H), 6.92 (ddd, J=8.4, 2.9, 1.3 Hz, 1H), 4.54 (d, J=12.7 Hz, 1H), 3.98 (d, J=13.7 Hz, 1H), 3.64-3.48 (m, 1H), 3.48-3.38 (m, 1H), 3.22-2.87 (m, 2H), 2.68 (dd, J=24.3, 12.3 Hz, 1H), 2.41-2.01 (m, 6H), 1.77 (s, 4H), 1.68-1.04 (m, 9H); MS (ESI(+)) m/e 461 (M+H)$^+$.

Example 211

N-(4-{[1-(2-chlorobenzoyl)piperidin-4-yl]oxy}phenyl)-1-(pyridazin-3-yl)azetidine-3-carboxamide The title compound was prepared as described in Example 147, substituting tert-butyl 4-(4-(azetidine-3-carboxamido)phenoxy)piperidine-1-carboxylate for 4-(4-(azetidine-3-carboxamido)phenyl)piperidine-1-carboxylate in Example 147A and 2-chlorobenzoic acid for 2-methylpropanoic acid in Example 147D. $^1$H NMR (400 MHz, DMSO/D$_2$O) δ ppm 8.51 (dd, J=4.4, 1.2 Hz, 1H), 7.78-7.66 (m, 1H), 7.55-7.45 (m, 3H), 7.45-7.37 (m, 2H), 7.37-7.28 (m, 2H), 7.01-6.89 (m, 2H), 4.63-4.34 (m, 6H), 4.03-3.86 (m, 1H), 3.86-3.72 (m, 1H), 3.63-3.43 (m, 1H), 3.43-3.31 (m, 1H), 3.26-3.07 (m, 1H), 2.06-1.80 (m, 2H), 1.80-1.53 (m, 2H), 1.28-1.21 (m, 1H); MS (ESI(+)) m/e 492 (M+H)$^+$.

TABLE 9

The following Examples were prepared essentially as described in Example 147, substituting the appropriate amine in Example 147A and the appropriate carboxylic acid in Example 147D. Some products were purified by flash chromatography while others were purified by reverse-phase HPLC. Accordingly, some Examples were isolated as trifluoroacetic acid salts.

| Ex | Name | MS |
|---|---|---|
| 212 | N-[4-({1-[(2S)-2-methylbutanoyl]piperidin-4-yl}oxy)phenyl]-1-(pyridazin-3-yl)azetidine-3-carboxamide | (ESI(+)) m/e 438 (M + H)$^+$ |
| 213 | 1-(pyridazin-3-yl)-N-(4-{[1-(1,3-thiazol-2-ylcarbonyl)piperidin-4-yl]oxy}phenyl)azetidine-3-carboxamide | (ESI(+)) m/e 465 (M + H)$^+$ |
| 214 | 1-(pyridazin-3-yl)-N-(4-{[1-(tetrahydro-2H-pyran-4-ylcarbonyl)piperidin-4-yl]oxy}phenyl)azetidine-3-carboxamide | (ESI(+)) m/e 466 (M + H)$^+$ |
| 215 | N-[4-({1-[difluoro(phenyl)acetyl]piperidin-4-yl}oxy)phenyl]-1-(pyridazin-3-yl)azetidine-3-carboxamide | (ESI(+)) m/e 508 (M + H)$^+$ |
| 216 | N-[4-({1-[(4,4-difluorocyclohexyl)carbonyl]piperidin-4-yl}oxy)phenyl]-1-(pyridazin-3-yl)azetidine-3-carboxamide | (ESI(+)) m/e 500 (M + H)$^+$ |
| 217 | N-(4-{[1-(2-methyl-2-phenylpropanoyl)piperidin-4-yl]oxy}phenyl)-1-(pyridazin-3-yl)azetidine-3-carboxamide | (ESI(+)) m/e 500 (M + H)$^+$ |
| 218 | 1-(pyridazin-3-yl)-N-(4-{[1-(1,3-thiazol-4-ylcarbonyl)piperidin-4-yl]oxy}phenyl)azetidine-3-carboxamide | (ESI(+)) m/e 465 (M + H)$^+$ |
| 219 | N-[4-({1-[(5-methylthiophen-2-yl)carbonyl]piperidin-4-yl}oxy)phenyl]-1-(pyridazin-3-yl)azetidine-3-carboxamide | (ESI(+)) m/e 478 (M + H)$^+$ |

TABLE 9-continued

The following Examples were prepared essentially as described in Example 147, substituting the appropriate amine in Example 147A and the appropriate carboxylic acid in Example 147D. Some products were purified by flash chromatography while others were purified by reverse-phase HPLC. Accordingly, some Examples were isolated as trifluoroacetic acid salts.

| Ex | Name | MS |
|---|---|---|
| 220 | 1-(pyridazin-3-yl)-N-{4-[(1-{[4-(trifluoromethyl)phenyl]acetyl}piperidin-4-yl)oxy]phenyl}azetidine-3-carboxamide | (ESI(+)) m/e 540 (M + H)+ |
| 221 | 1-(pyridazin-3-yl)-N-(4-{[1-(tetrahydrofuran-2-ylcarbonyl)piperidin-4-yl]oxy}phenyl)azetidine-3-carboxamide | (ESI(+)) m/e 452 (M + H)+ |
| 222 | 1-(pyridazin-3-yl)-N-[4-({1-[3-(trifluoromethyl)benzoyl]piperidin-4-yl}oxy)phenyl]azetidine-3-carboxamide | (ESI(+)) m/e 526 (M + H)+ |
| 223 | 1-(pyridazin-3-yl)-N-(4-{[1-(thiophen-3-ylcarbonyl)piperidin-4-yl]oxy}phenyl)azetidine-3-carboxamide | (ESI(+)) m/e 464 (M + H)+ |
| 224 | 1-(pyridazin-3-yl)-N-[4-({1-[3-(trifluoromethoxy)benzoyl]piperidin-4-yl}oxy)phenyl]azetidine-3-carboxamide | (ESI(+)) m/e 542 (M + H)+ |
| 225 | N-(4-{[1-(3-methylbutanoyl)piperidin-4-yl]oxy}phenyl)-1-(pyridazin-3-yl)azetidine-3-carboxamide | (ESI(+)) m/e 438 (M + H)+ |
| 226 | 1-(pyridazin-3-yl)-N-(4-{[1-(tetrahydrofuran-3-ylcarbonyl)piperidin-4-yl]oxy}phenyl)azetidine-3-carboxamide | (ESI(+)) m/e 452 (M + H)+ |
| 227 | N-[4-({1-[(3-fluorophenyl)acetyl]piperidin-4-yl}oxy)phenyl]-1-(pyridazin-3-yl)azetidine-3-carboxamide | (ESI(+)) m/e 490 (M + H)+ |
| 228 | N-(4-{[1-(2-fluorobenzoyl)piperidin-4-yl]oxy}phenyl)-1-(pyridazin-3-yl)azetidine-3-carboxamide | (ESI(+)) m/e 476 (M + H)+ |
| 229 | N-(4-{[1-(2,4-difluorobenzoyl)piperidin-4-yl]oxy}phenyl)-1-(pyridazin-3-yl)azetidine-3-carboxamide | (ESI(+)) m/e 494 (M + H)+ |
| 230 | N-(4-{[1-(4-fluorobenzoyl)piperidin-4-yl]oxy}phenyl)-1-(pyridazin-3-yl)azetidine-3-carboxamide | (ESI(+)) m/e 476 (M + H)+ |
| 231 | N-(4-{[1-(3-fluorobenzoyl)piperidin-4-yl]oxy}phenyl)-1-(pyridazin-3-yl)azetidine-3-carboxamide | (ESI(+)) m/e 476 (M + H)+ |
| 232 | N-[4-({1-[(4-fluorophenyl)acetyl]piperidin-4-yl}oxy)phenyl]-1-(pyridazin-3-yl)azetidine-3-carboxamide | (ESI(+)) m/e 490 (M + H)+ |
| 233 | N-(4-{[1-(cyclopropylacetyl)piperidin-4-yl]oxy}phenyl)-1-(pyridazin-3-yl)azetidine-3-carboxamide | (ESI(+)) m/e 436 (M + H)+ |
| 234 | N-(4-{[1-(3,4-difluorobenzoyl)piperidin-4-yl]oxy}phenyl)-1-(pyridazin-3-yl)azetidine-3-carboxamide | (ESI(+)) m/e 494 (M + H)+ |
| 235 | 1-(pyridazin-3-yl)-N-[4-({1-[4-(trifluoromethoxy)benzoyl]piperidin-4-yl}oxy)phenyl]azetidine-3-carboxamide | (ESI(+)) m/e 542 (M + H)+ |
| 236 | N-[4-({1-[(2,4-difluorophenyl)acetyl]piperidin-4-yl}oxy)phenyl]-1-(pyridazin-3-yl)azetidine-3-carboxamide | (ESI(+)) m/e 508 (M + H)+ |
| 237 | 1-(pyridazin-3-yl)-N-[4-({1-[4-(trifluoromethyl)benzoyl]piperidin-4-yl}oxy)phenyl]azetidine-3-carboxamide | (ESI(+)) m/e 526 (M + H)+ |
| 238 | 1-(pyridazin-3-yl)-N-{4-[(1-{[4-(trifluoromethoxy)phenyl]acetyl}piperidin-4-yl)oxy]phenyl}azetidine-3-carboxamide | (ESI(+)) m/e 556 (M + H)+ |
| 239 | N-[4-({1-[(3,5-difluorophenyl)acetyl]piperidin-4-yl}oxy)phenyl]-1-(pyridazin-3-yl)azetidine-3-carboxamide | (ESI(+)) m/e 508 (M + H)+ |
| 240 | 1-(pyridazin-3-yl)-N-{4-[(1-{[3-(trifluoromethyl)phenyl]acetyl}piperidin-4-yl)oxy]phenyl}azetidine-3-carboxamide | (ESI(+)) m/e 540 (M + H)+ |
| 241 | N-(4-{[1-(2,2-dimethylpropanoyl)piperidin-4-yl]oxy}phenyl)-1-(pyridazin-3-yl)azetidine-3-carboxamide | (ESI(+)) m/e 438 (M + H)+ |
| 242 | 1-(pyridazin-3-yl)-N-(4-{[1-(pyridin-2-ylcarbonyl)piperidin-4-yl]oxy}phenyl)azetidine-3-carboxamide | (ESI(+)) m/e 459 (M + H)+ |
| 243 | N-(4-{[1-(3,5-difluorobenzoyl)piperidin-4-yl]oxy}phenyl)-1-(pyridazin-3-yl)azetidine-3-carboxamide | (ESI(+)) m/e 494 (M + H)+ |

TABLE 9-continued

The following Examples were prepared essentially as described in Example 147, substituting the appropriate amine in Example 147A and the appropriate carboxylic acid in Example 147D. Some products were purified by flash chromatography while others were purified by reverse-phase HPLC. Accordingly, some Examples were isolated as trifluoroacetic acid salts.

| Ex | Name | MS |
|---|---|---|
| 244 | -{4-[(1-acetylpiperidin-4-yl)oxy]phenyl}-1-(pyridazin-3-yl)azetidine-3-carboxamide | (ESI(+)) m/e 396 (M + H)$^+$ |
| 245 | N-(4-{[1-(4-chlorobenzoyl)piperidin-4-yl]oxy}phenyl)-1-(pyridazin-3-yl)azetidine-3-carboxamide | (ESI(+)) m/e 492 (M + H)$^+$ |
| 246 | N-(4-{[1-(methoxyacetyl)piperidin-4-yl]oxy}phenyl)-1-(pyridazin-3-yl)azetidine-3-carboxamide | (ESI(+)) m/e 426 (M + H)$^+$ |
| 247 | N-[4-({1-[(2-fluorophenyl)acetyl]piperidin-4-yl}oxy)phenyl]-1-(pyridazin-3-yl)azetidine-3-carboxamide | (ESI(+)) m/e 490 (M + H)$^+$ |
| 248 | N-(4-{[1-(2,2-dimethylbutanoyl)piperidin-4-yl]oxy}phenyl)-1-(pyridazin-3-yl)azetidine-3-carboxamide | (ESI(+)) m/e 452 (M + H)$^+$ |
| 249 | 1-(pyridazin-3-yl)-N-(4-{[1-(thiophen-2-ylcarbonyl)piperidin-4-yl]oxy}phenyl)azetidine-3-carboxamide | (ESI(+)) m/e 464 (M + H)$^+$ |
| 250 | N-(4-{[1-(3-chlorobenzoyl)piperidin-4-yl]oxy}phenyl)-1-(pyridazin-3-yl)azetidine-3-carboxamide | (ESI(+)) m/e 492 (M + H)$^+$ |
| 251 | N-(4-{[1-(cyclopropylcarbonyl)piperidin-4-yl]oxy}phenyl)-1-(pyridazin-3-yl)azetidine-3-carboxamide | (ESI(+)) m/e 422 (M + H)$^+$ |
| 252 | 1-(pyridazin-3-yl)-N-(4-{[1-(3,3,3-trifluoropropanoyl)piperidin-4-yl]oxy}phenyl)azetidine-3-carboxamide | (ESI(+)) m/e 464 (M + H)$^+$ |
| 253 | N-(4-{[1-(2-methylpropanoyl)piperidin-4-yl]oxy}phenyl)-1-(pyridazin-3-yl)azetidine-3-carboxamide | (ESI(+)) m/e 424 (M + H)$^+$ |
| 483 | N-(4-{[(3R)-1-(2-chlorobenzoyl)pyrrolidin-3-yl]oxy}phenyl)-1-(pyridazin-3-yl)azetidine-3-carboxamide | (ESI(+)) m/e 478 (M + H)$^+$ |
| 484 | 1-(pyridazin-3-yl)-N-(4-{[(3R)-1-(1,3-thiazol-2-ylcarbonyl)pyrrolidin-3-yl]oxy}phenyl)azetidine-3-carboxamide | (ESI(+)) m/e 451 (M + H)$^+$ |
| 485 | N-(4-{[(3R)-1-(cyclopropylacetyl)pyrrolidin-3-yl]oxy}phenyl)-1-(pyridazin-3-yl)azetidine-3-carboxamide | (ESI(+)) m/e 422 (M + H)$^+$ |
| 486 | N-[4-({(3R)-1-[(2S)-2-methylbutanoyl]pyrrolidin-3-yl}oxy)phenyl]-1-(pyridazin-3-yl)azetidine-3-carboxamide | (ESI(+)) m/e 424 (M + H)$^+$ |
| 487 | 1-(pyridazin-3-yl)-N-(4-{[(3R)-1-(tetrahydro-2H-pyran-4-ylcarbonyl)pyrrolidin-3-yl]oxy}phenyl)azetidine-3-carboxamide | (ESI(+)) m/e 452 (M + H)$^+$ |
| 488 | 1-(pyridazin-3-yl)-N-(4-{[(3R)-1-{[4-(trifluoromethoxy)phenyl]acetyl}pyrrolidin-3-yl]oxy}phenyl)azetidine-3-carboxamide | (ESI(+)) m/e 542 (M + H)$^+$ |
| 489 | N-(4-{[(3R)-1-(4-fluorobenzoyl)pyrrolidin-3-yl]oxy}phenyl)-1-(pyridazin-3-yl)azetidine-3-carboxamide | (ESI(+)) m/e 462 (M + H)$^+$ |
| 490 | 1-(pyridazin-3-yl)-N-(4-{[(3R)-1-(thiophen-3-ylcarbonyl)pyrrolidin-3-yl]oxy}phenyl)azetidine-3-carboxamide | (ESI(+)) m/e 450 (M + H)$^+$ |
| 491 | N-[4-({(3R)-1-[(4-fluorophenyl)acetyl]pyrrolidin-3-yl}oxy)phenyl]-1-(pyridazin-3-yl)azetidine-3-carboxamide | (ESI(+)) m/e 476 (M + H)$^+$ |
| 492 | N-[4-({(3R)-1-[(3,5-difluorophenyl)acetyl]pyrrolidin-3-yl}oxy)phenyl]-1-(pyridazin-3-yl)azetidine-3-carboxamide | (ESI(+)) m/e 494 (M + H)$^+$ |
| 493 | N-(4-{[(3R)-1-(3,4-difluorobenzoyl)pyrrolidin-3-yl]oxy}phenyl)-1-(pyridazin-3-yl)azetidine-3-carboxamide | (ESI(+)) m/e 480 (M + H)$^+$ |
| 494 | N-[4-({(3R)-1-[(3-fluorophenyl)acetyl]pyrrolidin-3-yl}oxy)phenyl]-1-(pyridazin-3-yl)azetidine-3-carboxamide | (ESI(+)) m/e 476 (M + H)$^+$ |
| 495 | 1-(pyridazin-3-yl)-N-[4-({(3R)-1-[3-(trifluoromethyl)benzoyl]pyrrolidin-3-yl}oxy)phenyl]azetidine-3-carboxamide | (ESI(+)) m/e 512 (M + H)$^+$ |
| 496 | N-[4-({(3R)-1-[(2,4-difluorophenyl)acetyl]pyrrolidin-3-yl}oxy)phenyl]-1-(pyridazin-3-yl)azetidine-3-carboxamide | (ESI(+)) m/e 494 (M + H)$^+$ |

TABLE 9-continued

The following Examples were prepared essentially as described in Example 147, substituting the appropriate amine in Example 147A and the appropriate carboxylic acid in Example 147D. Some products were purified by flash chromatography while others were purified by reverse-phase HPLC. Accordingly, some Examples were isolated as trifluoroacetic acid salts.

| Ex | Name | MS |
|---|---|---|
| 497 | 1-(pyridazin-3-yl)-N-(4-{[(3R)-1-{[4-(trifluoromethyl)phenyl]acetyl}pyrrolidin-3-yl]oxy}phenyl)azetidine-3-carboxamide | (ESI(+)) m/e 526 (M + H)$^+$ |
| 498 | 1-(pyridazin-3-yl)-N-(4-{[(3R)-1-(1,3-thiazol-4-ylcarbonyl)pyrrolidin-3-yl]oxy}phenyl)azetidine-3-carboxamide | (ESI(+)) m/e 451 (M + H)$^+$ |
| 499 | 1-(pyridazin-3-yl)-N-(4-{[(3R)-1-(tetrahydrofuran-2-ylcarbonyl)pyrrolidin-3-yl]oxy}phenyl)azetidine-3-carboxamide | (ESI(+)) m/e 438 (M + H)$^+$ |
| 500 | N-[4-({(3R)-1-[(5-methylthiophen-2-yl)carbonyl]pyrrolidin-3-yl}oxy)phenyl]-1-(pyridazin-3-yl)azetidine-3-carboxamide | (ESI(+)) m/e 464 (M + H)$^+$ |
| 501 | N-[4-({(3R)-1-[(2-fluorophenyl)acetyl]pyrrolidin-3-yl}oxy)phenyl]-1-(pyridazin-3-yl)azetidine-3-carboxamide | (ESI(+)) m/e 476 (M + H)$^+$ |
| 502 | N-(4-{[(3R)-1-(cyclopropylcarbonyl)pyrrolidin-3-yl]oxy}phenyl)-1-(pyridazin-3-yl)azetidine-3-carboxamide | (ESI(+)) m/e 408 (M + H)$^+$ |
| 503 | 1-(pyridazin-3-yl)-N-(4-{[(3R)-1-(tetrahydrofuran-3-ylcarbonyl)pyrrolidin-3-yl]oxy}phenyl)azetidine-3-carboxamide | (ESI(+)) m/e 438 (M + H)$^+$ |
| 504 | 1-(pyridazin-3-yl)-N-[4-({(3R)-1-[3-(trifluoromethoxy)benzoyl]pyrrolidin-3-yl}oxy)phenyl]azetidine-3-carboxamide | (ESI(+)) m/e 528 (M + H)$^+$ |
| 505 | 1-(pyridazin-3-yl)-N-(4-{[(3R)-1-(pyridin-2-ylcarbonyl)pyrrolidin-3-yl]oxy}phenyl)azetidine-3-carboxamide | (ESI(+)) m/e 445 (M + H)$^+$ |
| 506 | N-(4-{[(3R)-1-(3-chlorobenzoyl)pyrrolidin-3-yl]oxy}phenyl)-1-(pyridazin-3-yl)azetidine-3-carboxamide | (ESI(+)) m/e 478 (M + H)$^+$ |
| 507 | N-(4-{[(3R)-1-(4-chlorobenzoyl)pyrrolidin-3-yl]oxy}phenyl)-1-(pyridazin-3-yl)azetidine-3-carboxamide | (ESI(+)) m/e 478 (M + H)$^+$ |
| 508 | N-(4-{[(3R)-1-(2-methyl-2-phenylpropanoyl)pyrrolidin-3-yl]oxy}phenyl)-1-(pyridazin-3-yl)azetidine-3-carboxamide | (ESI(+)) m/e 486 (M + H)$^+$ |
| 509 | N-(4-{[(3R)-1-(2,4-difluorobenzoyl)pyrrolidin-3-yl]oxy}phenyl)-1-(pyridazin-3-yl)azetidine-3-carboxamide | (ESI(+)) m/e 480 (M + H)$^+$ |
| 510 | N-(4-{[(3R)-1-(methoxyacetyl)pyrrolidin-3-yl]oxy}phenyl)-1-(pyridazin-3-yl)azetidine-3-carboxamide | (ESI(+)) m/e 412 (M + H)$^+$ |
| 511 | 1-(pyridazin-3-yl)-N-(4-{[(3R)-1-(thiophen-2-ylcarbonyl)pyrrolidin-3-yl]oxy}phenyl)azetidine-3-carboxamide | (ESI(+)) m/e 450 (M + H)$^+$ |
| 512 | 1-(pyridazin-3-yl)-N-(4-{[(3R)-1-{[3-(trifluoromethyl)phenyl]acetyl}pyrrolidin-3-yl]oxy}phenyl)azetidine-3-carboxamide | (ESI(+)) m/e 526 (M + H)$^+$ |
| 513 | N-(4-{[(3R)-1-(2-methylpropanoyl)pyrrolidin-3-yl]oxy}phenyl)-1-(pyridazin-3-yl)azetidine-3-carboxamide | (ESI(+)) m/e 410 (M + H)$^+$ |
| 514 | N-(4-{[(3R)-1-(2-fluorobenzoyl)pyrrolidin-3-yl]oxy}phenyl)-1-(pyridazin-3-yl)azetidine-3-carboxamide | (ESI(+)) m/e 462 (M + H)$^+$ |
| 515 | N-(4-{[(3R)-1-(2,2-dimethylbutanoyl)pyrrolidin-3-yl]oxy}phenyl)-1-(pyridazin-3-yl)azetidine-3-carboxamide | (ESI(+)) m/e 438 (M + H)$^+$ |
| 516 | N-(4-{[(3R)-1-(3,5-difluorobenzoyl)pyrrolidin-3-yl]oxy}phenyl)-1-(pyridazin-3-yl)azetidine-3-carboxamide | (ESI(+)) m/e 480 (M + H)$^+$ |
| 517 | 1-(pyridazin-3-yl)-N-[4-({(3R)-1-[4-(trifluoromethyl)benzoyl]pyrrolidin-3-yl}oxy)phenyl]azetidine-3-carboxamide | (ESI(+)) m/e 512 (M + H)$^+$ |
| 518 | N-(4-{[(3R)-1-(3-fluorobenzoyl)pyrrolidin-3-yl]oxy}phenyl)-1-(pyridazin-3-yl)azetidine-3-carboxamide | (ESI(+)) m/e 462 (M + H)$^+$ |
| 519 | 1-(pyridazin-3-yl)-N-[4-({(3R)-1-[4-(trifluoromethoxy)benzoyl]pyrrolidin-3-yl}oxy)phenyl]azetidine-3-carboxamide | (ESI(+)) m/e 528 (M + H)$^+$ |
| 520 | N-(4-{[(3R)-1-(3-methylbutanoyl)pyrrolidin-3-yl]oxy}phenyl)-1-(pyridazin-3-yl)azetidine-3-carboxamide | (ESI(+)) m/e 424 (M + H)$^+$ |

TABLE 9-continued

The following Examples were prepared essentially as described in Example 147, substituting the appropriate amine in Example 147A and the appropriate carboxylic acid in Example 147D. Some products were purified by flash chromatography while others were purified by reverse-phase HPLC. Accordingly, some Examples were isolated as trifluoroacetic acid salts.

| Ex | Name | MS |
| --- | --- | --- |
| 521 | 1-(pyridazin-3-yl)-N-(4-{[(3R)-1-(3,3,3-trifluoropropanoyl)pyrrolidin-3-yl]oxy}phenyl)azetidine-3-carboxamide | (ESI(+)) m/e 450 (M + H)$^+$ |
| 522 | N-[4-({(3R)-1-[difluoro(phenyl)acetyl]pyrrolidin-3-yl}oxy)phenyl]-1-(pyridazin-3-yl)azetidine-3-carboxamide | (ESI(+)) m/e 494 (M + H)$^+$ |
| 523 | N-(4-{[(3R)-1-(2,2-dimethylpropanoyl)pyrrolidin-3-yl]oxy}phenyl)-1-(pyridazin-3-yl)azetidine-3-carboxamide | (ESI(+)) m/e 424 (M + H)$^+$ |
| 524 | N-[4-({(3R)-1-[(4,4-difluorocyclohexyl)carbonyl]pyrrolidin-3-yl}oxy)phenyl]-1-(pyridazin-3-yl)azetidine-3-carboxamide | (ESI(+)) m/e 486 (M + H)$^+$ |

Example 309

5-[1-(2-methylpropyl)-1H-pyrazol-4-yl]-N-[1-(pyridazin-3-yl)azetidin-3-yl]furan-2-carboxamide

Example 309A tert-butyl (1-(6-chloropyridazin-3-yl)azetidin-3-yl)carbamate tert-Butyl azetidin-3-ylcarbamate (500 mg, 2.90 mmol) and 3,6-dichloropyridazine (454 mg, 3.05 mmol) were combined in DMSO (5 mL) and N-ethyl-N-isopropylpropan-2-amine (563 mg, 4.35 mmol), and the mixture was heated overnight at 100° C. The mixture was cooled to room temperature and diluted with water. Filtration provided the title compound.

Example 309B tert-butyl (1-(pyridazin-3-yl)azetidin-3-yl)carbamate

A mixture of tert-butyl 1-(6-chloropyridizan-3-yl)azetidin-3-ylcarbamate (413 mg, 1.45 mmol), 1,4-cyclohexadiene (1.10 mL, 11.6 mmol) and triethylamine (0.61 mL, 1.45 mmol) was purged with nitrogen and 5% palladium on carbon (20 mg) was added. The reaction mixture was heated to 80° C. overnight, cooled to room temperature and filtered through diatomaceous earth, rinsing with methanol. Concentration provided the title compound.

Example 309C 1-(pyridazin-3-yl)azetidin-3-amine

Tert-butyl 1-(pyridazin-3-yl)azetidin-3-ylcarbamate.triethylamine hydrochloride (200 mg, 0.516 mmol) was dissolved in methanol (1.5 mL) and a 4N solution of HCl in dioxane (1.5 mL, 6.00 mmol) was added dropwise. The reaction mixture was stirred at room temperature for 1 hour then concentrated to dryness to give the title compound.

Example 309D 5-(1-isobutyl-1H-pyrazol-4-yl)furan-2-carboxylic acid

The title compound was prepared as described as described in Example 148A, substituting 5-bromofuran-2-carboxylic acid for 4-bromoaniline.

Example 309E

5-[1-(2-methylpropyl)-1H-pyrazol-4-yl]-N-[1-(pyridazin-3-yl)azetidin-3-yl]furan-2-carboxamide The title compound was prepared as described in Example 1A, substituting 1-(pyridazin-3-yl)azetidin-3-amine for tert-butyl 4-(4-aminophenoxy)piperidine-1-carboxylate and 5-(1-isobutyl-1H-pyrazol-4-yl)furan-2-carboxylic acid for 1-(benzyloxycarbonyl)azetidine-3-carboxylic acid. $^1$H NMR (300 MHz, DMSO-d$_6$) δ ppm 8.83 (d, J=7.5 Hz, 1H), 8.57 (dd, J=4.5, 1.3 Hz, 1H), 8.15 (d, J=0.7 Hz, 1H), 7.88 (d, J=0.7 Hz, 1H), 7.39 (dd, J=8.9, 4.5 Hz, 1H), 7.16 (d, J=3.5 Hz, 1H), 6.84 (dd, J=8.9, 1.4 Hz, 1H), 6.64 (d, J=3.5 Hz, 1H), 4.97-4.84 (m, 1H), 4.38 (t, J=8.1 Hz, 2H), 4.06 (dd, J=8.6, 5.7 Hz, 2H), 3.95 (d, J=7.2 Hz, 2H), 2.21-2.05 (m, 1H), 0.85 (d, J=6.7 Hz, 6H); MS (ESI(+)) m/e 367 (M+H)$^+$.

Example 310

(3S)—N-{4-[1-(2-methylpropanoyl)piperidin-4-yl]phenyl}-1-(pyridazin-3-yl)pyrrolidine-3-carboxamide The title compound was prepared as described in Example 147, substituting (S)-tert-butyl 4-(4-(pyrrolidine-3-carboxamido)phenyl)piperidine-1-carboxylate for tert-butyl 4-(4-(azetidine-3-carboxamido)phenyl)piperidine-1-carboxylate in Example 147A. $^1$H NMR (400 MHz, DMSO-d$_6$) δ ppm 10.06 (s, 1H), 8.48 (dd, J=4.4, 1.2 Hz, 1H), 7.54 (d, J=8.5 Hz, 2H), 7.43-7.25 (m, 1H), 7.18 (d, J=8.6 Hz, 2H), 6.87 (dd, J=9.2, 1.2 Hz, 1H), 4.64-4.48 (m, 1H), 4.15-3.97 (m, 1H), 3.76 (dd, J=10.4, 8.0 Hz, 1H), 3.69-3.54 (m, 2H), 3.54-3.38 (m, 1H), 3.20-3.03 (m, 1H), 3.02-2.83 (m, 2H), 2.79-2.64 (m, 1H), 2.64-2.52 (m, 1H), 2.37-2.13 (m, 2H), 1.90-1.68 (m, 2H), 1.59-1.29 (m, 2H), 0.99 (dt, J=14.5, 7.0 Hz, 6H); MS (ESI(+)) m/e 422 (M+H)$^+$.

Example 311

(3S)—N-[4-(1-benzoylpiperidin-4-yl)phenyl]-1-(pyridazin-3-yl)pyrrolidine-3-carboxamide The title compound was prepared as described in Example 147, substituting (S)-tert-butyl 4-(4-(pyrrolidine-3-carboxamido)phenyl)piperidine-1-carboxylate for tert-butyl 4-(4-(azetidine-3-carboxamido)phenyl)piperidine-1-carboxylate in Example 147A and benzoic acid for 2-methylpropanoic acid in Example 147D. $^1$H NMR (400 MHz, DMSO-$d_6$) δ ppm 10.06 (s, 1H), 8.48 (dd, J=4.4, 1.3 Hz, 1H), 7.55 (d, J=8.6 Hz, 1H), 7.51-7.39 (m, 5H), 7.34 (dd, J=9.1, 4.5 Hz, 1H), 7.25-7.19 (m, 2H), 6.87 (dd, J=9.1, 1.3 Hz, 1H), 4.65-4.48 (m, 1H), 3.84-3.53 (m, 4H), 3.48 (dt, J=10.2, 7.4 Hz, 1H), 3.22-2.69 (m, 3H), 2.36-2.13 (m, 2H), 1.98-1.48 (m, 4H); MS (ESI(+)) m/e 456 (M+H)$^+$.

Example 312

(3S)-1-(pyridazin-3-yl)-N-{4-[1-(tetrahydro-2H-pyran-4-ylacetyl)piperidin-4-yl]phenyl}pyrrolidine-3-carboxamide The title compound was prepared as described in Example 147, substituting (S)-tert-butyl 4-(4-(pyrrolidine-3-carboxamido)phenyl)piperidine-1-carboxylate for tert-butyl 4-(4-(azetidine-3-carboxamido)phenyl)piperidine-1-carboxylate in Example 147A and tetrahydro-2H-pyran-4-ylacetic acid for 2-methylpropanoic acid in Example 147D. $^1$H NMR (400 MHz, DMSO-$d_6$) δ ppm 10.06 (s, 1H), 8.48 (dd, J=4.4, 1.2 Hz, 1H), 7.54 (d, J=8.6 Hz, 2H), 7.39-7.27 (m, 1H), 7.17 (d, J=8.6 Hz, 2H), 6.87 (dd, J=9.2, 1.2 Hz, 1H), 4.65-4.45 (m, 1H), 4.07-3.92 (m, 1H), 3.89-3.68 (m, 3H), 3.68-3.54 (m, 2H), 3.54-3.39 (m, 1H), 3.22-2.93 (m, 2H), 2.80-2.65 (m, 1H), 2.64-2.52 (m, 1H), 2.38-2.13 (m, 4H), 2.00-1.84 (m, 1H), 1.80 (dt, J=27.7, 7.7 Hz, 2H), 1.68-1.14 (m, 7H); MS (ESI(+)) m/e 478 (M+H)$^+$.

Example 313

(3S)—N-{4-[1-(2,2-dimethylpropanoyl)piperidin-4-yl]phenyl}-1-(pyridazin-3-yl)pyrrolidine-3-carboxamide The title compound was prepared as described in Example 147, substituting (S)-tert-butyl 4-(4-(pyrrolidine-3-carboxamido)phenyl)piperidine-1-carboxylate for tert-butyl 4-(4-(azetidine-3-carboxamido)phenyl)piperidine-1-carboxylate in Example 147A and 2,2-dimethylpropanoic acid for 2-methylpropanoic acid in Example 147D. $^1$H NMR (400 MHz, DMSO-$d_6$) δ ppm 10.05 (s, 1H), 8.47 (dd, J=4.4, 1.0 Hz, 1H), 7.52 (d, J=8.5 Hz, 2H), 7.32 (dd, J=9.1, 4.5 Hz, 1H), 7.16 (d, J=8.5 Hz, 2H), 6.86 (dd, J=9.2, 1.0 Hz, 1H), 4.39 (d, J=13.2 Hz, 2H), 3.75 (dd, J=10.4, 8.0 Hz, 1H), 3.69-3.54 (m, 2H), 3.46 (dt, J=10.1, 7.5 Hz, 1H), 3.27 (dd, J=14.8, 7.4 Hz, 1H), 2.96 (dd, J=12.8, 7.0 Hz, 1H), 2.84 (dd, J=22.1, 9.6 Hz, 2H), 2.78-2.64 (m, 1H), 2.27 (dt, J=7.1, 5.0 Hz, 1H), 2.18 (ddd, J=14.3, 11.6, 7.3 Hz, 1H), 1.77 (d, J=11.3 Hz, 2H), 1.54-1.31 (m, 3H), 1.18 (d, J=16.8 Hz, 9H); MS (ESI(+)) m/e 436 (M+H)$^+$.

TABLE 10

The following Examples were essentially prepared as described in Example 313, substituting the appropriate carboxylic acid for 2,2-dimethylpropanoic acid.

| Ex | Name | MS |
|---|---|---|
| 630 | (3S)-1-(pyridazin-3-yl)-N-{4-[1-(1,3-thiazol-5-ylcarbonyl)piperidin-4-yl]phenyl}pyrrolidine-3-carboxamide | (ESI(+)) m/e 463 (M + H)$^+$ |
| 631 | (3S)-N-{4-[1-(4-methylbenzoyl)piperidin-4-yl]phenyl}-1-(pyridazin-3-yl)pyrrolidine-3-carboxamide | (ESI(+)) m/e 470 (M + H)$^+$ |
| 632 | (3S)-N-(4-{1-[(2S)-2-phenylbutanoyl]piperidin-4-yl}phenyl)-1-(pyridazin-3-yl)pyrrolidine-3-carboxamide | (ESI(+)) m/e 498 (M + H)$^+$ |
| 633 | (3S)-N-(4-{1-[(2S)-2-methoxy-2-phenylacetyl]piperidin-4-yl}phenyl)-1-(pyridazin-3-yl)pyrrolidine-3-carboxamide | (ESI(+)) m/e 500 (M + H)$^+$ |
| 634 | (3S)-N-(4-{1-[(2R)-2-methoxy-2-phenylacetyl]piperidin-4-yl}phenyl)-1-(pyridazin-3-yl)pyrrolidine-3-carboxamide | (ESI(+)) m/e 500 (M + H)$^+$ |
| 635 | (3S)-N-{4-[1-(ethoxyacetyl)piperidin-4-yl]phenyl}-1-(pyridazin-3-yl)pyrrolidine-3-carboxamide | (ESI(+)) m/e 438 (M + H)$^+$ |
| 636 | (3S)-N-(4-{1-[(4-methylphenoxy)acetyl]piperidin-4-yl}phenyl)-1-(pyridazin-3-yl)pyrrolidine-3-carboxamide | (ESI(+)) m/e 500 (M + H)$^+$ |
| 637 | (3S)-N-{4-[1-(2-fluorobenzoyl)piperidin-4-yl]phenyl}-1-(pyridazin-3-yl)pyrrolidine-3-carboxamide | (ESI(+)) m/e 474 (M + H)$^+$ |
| 638 | (3S)-1-(pyridazin-3-yl)-N-{4-[1-(tetrahydrofuran-3-ylcarbonyl)piperidin-4-yl]phenyl}pyrrolidine-3-carboxamide | (ESI(+)) m/e 450 (M + H)$^+$ |
| 639 | (3S)-N-{4-[1-(naphthalen-1-ylcarbonyl)piperidin-4-yl]phenyl}-1-(pyridazin-3-yl)pyrrolidine-3-carboxamide | (ESI(+)) m/e 506 (M + H)$^+$ |
| 640 | (3S)-N-(4-{1-[(2,6-dichlorophenyl)acetyl]piperidin-4-yl}phenyl)-1-(pyridazin-3-yl)pyrrolidine-3-carboxamide | (ESI(+)) m/e 538 (M + H)$^+$ |
| 641 | (3S)-N-{4-[1-(naphthalen-1-ylacetyl)piperidin-4-yl]phenyl}-1-(pyridazin-3-yl)pyrrolidine-3-carboxamide | (ESI(+)) m/e 520 (M + H)$^+$ |

TABLE 10-continued

The following Examples were essentially prepared as described in Example 313, substituting the appropriate carboxylic acid for 2,2-dimethylpropanoic acid.

| Ex | Name | MS |
|---|---|---|
| 642 | (3S)-1-(pyridazin-3-yl)-N-(4-{1-[4-(thiophen-2-yl)butanoyl]piperidin-4-yl}phenyl)pyrrolidine-3-carboxamide | (ESI(+)) m/e 504 (M + H)$^+$ |
| 643 | (3S)-N-{4-[1-(cyclopropylacetyl)piperidin-4-yl]phenyl}-1-(pyridazin-3-yl)pyrrolidine-3-carboxamide | (ESI(+)) m/e 434 (M + H)$^+$ |
| 644 | (3S)-N-{4-[1-(cyclopentylacetyl)piperidin-4-yl]phenyl}-1-(pyridazin-3-yl)pyrrolidine-3-carboxamide | (ESI(+)) m/e 462 (M + H)$^+$ |
| 645 | (3S)-N-{4-[1-(2,5-difluorobenzoyl)piperidin-4-yl]phenyl}-1-(pyridazin-3-yl)pyrrolidine-3-carboxamide | (ESI(+)) m/e 492 (M + H)$^+$ |
| 646 | (3S)-N-{4-[1-(naphthalen-2-ylacetyl)piperidin-4-yl]phenyl}-1-(pyridazin-3-yl)pyrrolidine-3-carboxamide | (ESI(+)) m/e 520 (M + H)$^+$ |
| 647 | (3S)-N-(4-{1-[3-(phenylsulfonyl)propanoyl]piperidin-4-yl}phenyl)-1-(pyridazin-3-yl)pyrrolidine-3-carboxamide | (ESI(+)) m/e 548 (M + H)$^+$ |
| 648 | (3S)-1-(pyridazin-3-yl)-N-[4-(1-{[3-(trifluoromethyl)phenyl]acetyl}piperidin-4-yl)phenyl]pyrrolidine-3-carboxamide | (ESI(+)) m/e 538 (M + H)$^+$ |
| 649 | (3S)-N-{4-[1-(furan-2-ylcarbonyl)piperidin-4-yl]phenyl}-1-(pyridazin-3-yl)pyrrolidine-3-carboxamide | (ESI(+)) m/e 446 (M + H)$^+$ |
| 650 | (3S)-N-{4-[1-(N-benzoylglycyl)piperidin-4-yl]phenyl}-1-(pyridazin-3-yl)pyrrolidine-3-carboxamide | (ESI(+)) m/e 513 (M + H)$^+$ |
| 651 | (3S)-N-(4-{1-[(2,4-dichlorophenyl)acetyl]piperidin-4-yl}phenyl)-1-(pyridazin-3-yl)pyrrolidine-3-carboxamide | (ESI(+)) m/e 538 (M + H)$^+$ |
| 652 | (3S)-N-{4-[1-(2-methylbenzoyl)piperidin-4-yl]phenyl}-1-(pyridazin-3-yl)pyrrolidine-3-carboxamide | (ESI(+)) m/e 470 (M + H)$^+$ |
| 653 | (3S)-1-(pyridazin-3-yl)-N-{4-[1-(4,4,4-trifluorobutanoyl)piperidin-4-yl]phenyl}pyrrolidine-3-carboxamide | (ESI(+)) m/e 476 (M + H)$^+$ |
| 654 | (3S)-N-(4-{1-[(1-methylcyclohexyl)carbonyl]piperidin-4-yl}phenyl)-1-(pyridazin-3-yl)pyrrolidine-3-carboxamide | (ESI(+)) m/e 476 (M + H)$^+$ |
| 655 | (3S)-1-(pyridazin-3-yl)-N-{4-[1-(thiophen-3-ylcarbonyl)piperidin-4-yl]phenyl}pyrrolidine-3-carboxamide | (ESI(+)) m/e 462 (M + H)$^+$ |
| 656 | (3S)-N-(4-{1-[(6-methylpyridin-3-yl)carbonyl]piperidin-4-yl}phenyl)-1-(pyridazin-3-yl)pyrrolidine-3-carboxamide | (ESI(+)) m/e 471 (M + H)$^+$ |
| 657 | (3S)-N-(4-{1-[(3-chlorophenyl)acetyl]piperidin-4-yl}phenyl)-1-(pyridazin-3-yl)pyrrolidine-3-carboxamide | (ESI(+)) m/e 504 (M + H)$^+$ |
| 658 | (3S)-N-[4-(1-propanoylpiperidin-4-yl)phenyl]-1-(pyridazin-3-yl)pyrrolidine-3-carboxamide | (ESI(+)) m/e 408 (M + H)$^+$ |
| 659 | (3S)-N-{4-[1-(3,5-difluorobenzoyl)piperidin-4-yl]phenyl}-1-(pyridazin-3-yl)pyrrolidine-3-carboxamide | (ESI(+)) m/e 492 (M + H)$^+$ |
| 660 | (3S)-N-{4-[1-(cyclopentylcarbonyl)piperidin-4-yl]phenyl}-1-(pyridazin-3-yl)pyrrolidine-3-carboxamide | (ESI(+)) m/e 448 (M + H)$^+$ |
| 661 | (3S)-1-(pyridazin-3-yl)-N-{4-[1-(tetrahydrofuran-2-ylcarbonyl)piperidin-4-yl]phenyl}pyrrolidine-3-carboxamide | (ESI(+)) m/e 450 (M + H)$^+$ |
| 662 | (3S)-N-{4-[1-(cyclopropylcarbonyl)piperidin-4-yl]phenyl}-1-(pyridazin-3-yl)pyrrolidine-3-carboxamide | (ESI(+)) m/e 420 (M + H)$^+$ |
| 663 | (3S)-N-{4-[1-(4-chlorobenzoyl)piperidin-4-yl]phenyl}-1-(pyridazin-3-yl)pyrrolidine-3-carboxamide | (ESI(+)) m/e 490 (M + H)$^+$ |
| 669 | (3S)-N-{4-[1-(2-chlorobenzoyl)piperidin-4-yl]phenyl}-1-(pyridazin-3-yl)pyrrolidine-3-carboxamide | (ESI(+)) m/e 490 (M + H)$^+$ |
| 670 | (3S)-N-{4-[1-(2-methylpentanoyl)piperidin-4-yl]phenyl}-1-(pyridazin-3-yl)pyrrolidine-3-carboxamide | (ESI(+)) m/e 450 (M + H)$^+$ |
| 671 | (3S)-N-{4-[1-(4-methylpentanoyl)piperidin-4-yl]phenyl}-1-(pyridazin-3-yl)pyrrolidine-3-carboxamide | (ESI(+)) m/e 450 (M + H)$^+$ |

TABLE 10-continued

The following Examples were essentially prepared as described in Example 313, substituting the appropriate carboxylic acid for 2,2-dimethylpropanoic acid.

| Ex | Name | MS |
|---|---|---|
| 672 | (3S)-N-{4-[1-(2,4-dimethylbenzoyl)piperidin-4-yl]phenyl}-1-(pyridazin-3-yl)pyrrolidine-3-carboxamide | (ESI(+)) m/e 484 (M + H)+ |
| 673 | (3S)-N-[4-(1-heptanoylpiperidin-4-yl)phenyl]-1-(pyridazin-3-yl)pyrrolidine-3-carboxamide | (ESI(+)) m/e 464 (M + H)+ |
| 674 | (3S)-N-{4-[1-(2,4-dichlorobenzoyl)piperidin-4-yl]phenyl}-1-(pyridazin-3-yl)pyrrolidine-3-carboxamide | (ESI(+)) m/e 524 (M + H)+ |
| 675 | (3S)-N-(4-{1-[(4-fluorophenyl)acetyl]piperidin-4-yl}phenyl)-1-(pyridazin-3-yl)pyrrolidine-3-carboxamide | (ESI(+)) m/e 488 (M + H)+ |
| 676 | (3S)-N-{4-[1-(2,3-difluorobenzoyl)piperidin-4-yl]phenyl}-1-(pyridazin-3-yl)pyrrolidine-3-carboxamide | (ESI(+)) m/e 492 (M + H)+ |
| 677 | (3S)-N-{4-[1-(3-methylbenzoyl)piperidin-4-yl]phenyl}-1-(pyridazin-3-yl)pyrrolidine-3-carboxamide | (ESI(+)) m/e 470 (M + H)+ |
| 678 | (3S)-N-[4-(1-hexanoylpiperidin-4-yl)phenyl]-1-(pyridazin-3-yl)pyrrolidine-3-carboxamide | (ESI(+)) m/e 450 (M + H)+ |
| 679 | (3S)-N-(4-{1-[(3-methylthiophen-2-yl)carbonyl]piperidin-4-yl}phenyl)-1-(pyridazin-3-yl)pyrrolidine-3-carboxamide | (ESI(+)) m/e 476 (M + H)+ |
| 680 | (3S)-N-{4-[1-(2,3-dimethylbutanoyl)piperidin-4-yl]phenyl}-1-(pyridazin-3-yl)pyrrolidine-3-carboxamide | (ESI(+)) m/e 450 (M + H)+ |
| 681 | (3S)-N-[4-(1-butanoylpiperidin-4-yl)phenyl]-1-(pyridazin-3-yl)pyrrolidine-3-carboxamide | (ESI(+)) m/e 422 (M + H)+ |
| 682 | (3S)-N-{4-[1-(3-methylpentanoyl)piperidin-4-yl]phenyl}-1-(pyridazin-3-yl)pyrrolidine-3-carboxamide | (ESI(+)) m/e 450 (M + H)+ |
| 683 | (3S)-N-(4-{1-[(3,5-dimethylphenyl)acetyl]piperidin-4-yl}phenyl)-1-(pyridazin-3-yl)pyrrolidine-3-carboxamide | (ESI(+)) m/e 498 (M + H)+ |
| 684 | (3S)-N-{4-[1-(3,5-dichlorobenzoyl)piperidin-4-yl]phenyl}-1-(pyridazin-3-yl)pyrrolidine-3-carboxamide | (ESI(+)) m/e 524 (M + H)+ |
| 685 | (3S)-N-{4-[1-(3-fluoro-2-methylbenzoyl)piperidin-4-yl]phenyl}-1-(pyridazin-3-yl)pyrrolidine-3-carboxamide | (ESI(+)) m/e 488 (M + H)+ |
| 686 | (3S)-N-(4-{1-[(4-chlorophenyl)acetyl]piperidin-4-yl}phenyl)-1-(pyridazin-3-yl)pyrrolidine-3-carboxamide | (ESI(+)) m/e 504 (M + H)+ |
| 687 | (3S)-N-{4-[1-(furan-3-ylcarbonyl)piperidin-4-yl]phenyl}-1-(pyridazin-3-yl)pyrrolidine-3-carboxamide | (ESI(+)) m/e 446 (M + H)+ |
| 688 | (3S)-N-{4-[1-(3,4-dimethylbenzoyl)piperidin-4-yl]phenyl}-1-(pyridazin-3-yl)pyrrolidine-3-carboxamide | (ESI(+)) m/e 484 (M + H)+ |
| 689 | (3S)-N-{4-[1-(4-fluorobenzoyl)piperidin-4-yl]phenyl}-1-(pyridazin-3-yl)pyrrolidine-3-carboxamide | (ESI(+)) m/e 474 (M + H)+ |
| 690 | (3S)-N-(4-{1-[2-chloro-5-(trifluoromethyl)benzoyl]piperidin-4-yl}phenyl)-1-(pyridazin-3-yl)pyrrolidine-3-carboxamide | (ESI(+)) m/e 558 (M + H)+ |
| 691 | (3S)-N-[4-(1-acetylpiperidin-4-yl)phenyl]-1-(pyridazin-3-yl)pyrrolidine-3-carboxamide | (ESI(+)) m/e 394 (M + H)+ |
| 692 | (3S)-N-{4-[1-(2,4-difluorobenzoyl)piperidin-4-yl]phenyl}-1-(pyridazin-3-yl)pyrrolidine-3-carboxamide | (ESI(+)) m/e 492 (M + H)+ |
| 693 | (3S)-N-{4-[1-(3,5-dimethylbenzoyl)piperidin-4-yl]phenyl}-1-(pyridazin-3-yl)pyrrolidine-3-carboxamide | (ESI(+)) m/e 484 (M + H)+ |
| 694 | (3S)-N-{4-[1-(3-ethoxypropanoyl)piperidin-4-yl]phenyl}-1-(pyridazin-3-yl)pyrrolidine-3-carboxamide | (ESI(+)) m/e 452 (M + H)+ |
| 695 | (3S)-N-{4-[1-(2,5-dichlorobenzoyl)piperidin-4-yl]phenyl}-1-(pyridazin-3-yl)pyrrolidine-3-carboxamide | (ESI(+)) m/e 524 (M + H)+ |
| 696 | (3S)-N-{4-[1-(2,5-dimethylbenzoyl)piperidin-4-yl]phenyl}-1-(pyridazin-3-yl)pyrrolidine-3-carboxamide | (ESI(+)) m/e 484 (M + H)+ |

TABLE 10-continued

The following Examples were essentially prepared as described in Example 313, substituting the appropriate carboxylic acid for 2,2-dimethylpropanoic acid.

| Ex | Name | MS |
|---|---|---|
| 697 | (3S)-N-{4-[1-(5-fluoro-2-methylbenzoyl)piperidin-4-yl]phenyl}-1-(pyridazin-3-yl)pyrrolidine-3-carboxamide | (ESI(+)) m/e 488 (M + H)$^+$ |
| 698 | (3S)-N-{4-[1-(diphenylacetyl)piperidin-4-yl]phenyl}-1-(pyridazin-3-yl)pyrrolidine-3-carboxamide | (ESI(+)) m/e 546 (M + H)$^+$ |
| 699 | (3S)-1-(pyridazin-3-yl)-N-(4-{1-[4-(trifluoromethyl)benzoyl]piperidin-4-yl}phenyl)pyrrolidine-3-carboxamide | (ESI(+)) m/e 524 (M + H)$^+$ |
| 700 | (3S)-N-{4-[1-(pent-4-enoyl)piperidin-4-yl]phenyl}-1-(pyridazin-3-yl)pyrrolidine-3-carboxamide | (ESI(+)) m/e 434 (M + H)$^+$ |
| 701 | (3S)-1-(pyridazin-3-yl)-N-(4-{1-[3-(trifluoromethoxy)benzoyl]piperidin-4-yl}phenyl)pyrrolidine-3-carboxamide | (ESI(+)) m/e 540 (M + H)$^+$ |
| 702 | (3S)-N-(4-{1-[(1-phenylcyclopropyl)carbonyl]piperidin-4-yl}phenyl)-1-(pyridazin-3-yl)pyrrolidine-3-carboxamide | (ESI(+)) m/e 496 (M + H)$^+$ |
| 703 | (3S)-N-(4-{1-[2-fluoro-5-(trifluoromethyl)benzoyl]piperidin-4-yl}phenyl)-1-(pyridazin-3-yl)pyrrolidine-3-carboxamide | (ESI(+)) m/e 542 (M + H)$^+$ |
| 704 | (3S)-N-{4-[1-(cyclohexylacetyl)piperidin-4-yl]phenyl}-1-(pyridazin-3-yl)pyrrolidine-3-carboxamide | (ESI(+)) m/e 476 (M + H)$^+$ |
| 705 | (3S)-N-{4-[1-(4-methoxybenzoyl)piperidin-4-yl]phenyl}-1-(pyridazin-3-yl)pyrrolidine-3-carboxamide | (ESI(+)) m/e 486 (M + H)$^+$ |
| 706 | (3S)-N-{4-[1-(2-methylbutanoyl)piperidin-4-yl]phenyl}-1-(pyridazin-3-yl)pyrrolidine-3-carboxamide | (ESI(+)) m/e 436 (M + H)$^+$ |
| 707 | (3S)-N-{4-[1-(2-ethylbutanoyl)piperidin-4-yl]phenyl}-1-(pyridazin-3-yl)pyrrolidine-3-carboxamide | (ESI(+)) m/e 450 (M + H)$^+$ |
| 708 | (3S)-N-{4-[1-(4-tert-butylbenzoyl)piperidin-4-yl]phenyl}-1-(pyridazin-3-yl)pyrrolidine-3-carboxamide | (ESI(+)) m/e 512 (M + H)$^+$ |
| 709 | (3S)-N-{4-[1-(3-chlorobenzoyl)piperidin-4-yl]phenyl}-1-(pyridazin-3-yl)pyrrolidine-3-carboxamide | (ESI(+)) m/e 490 (M + H)$^+$ |
| 710 | (3S)-N-(4-{1-[(2-fluorophenyl)acetyl]piperidin-4-yl}phenyl)-1-(pyridazin-3-yl)pyrrolidine-3-carboxamide | (ESI(+)) m/e 488 (M + H)$^+$ |
| 711 | (3S)-1-(pyridazin-3-yl)-N-(4-{1-[3-(trifluoromethyl)benzoyl]piperidin-4-yl}phenyl)pyrrolidine-3-carboxamide | (ESI(+)) m/e 524 (M + H)$^+$ |
| 712 | (3S)-N-(4-{1-[(1-methylcyclopropyl)carbonyl]piperidin-4-yl}phenyl)-1-(pyridazin-3-yl)pyrrolidine-3-carboxamide | (ESI(+)) m/e 434 (M + H)$^+$ |
| 713 | (3S)-N-{4-[1-(pent-4-ynoyl)piperidin-4-yl]phenyl}-1-(pyridazin-3-yl)pyrrolidine-3-carboxamide | (ESI(+)) m/e 432 (M + H)$^+$ |
| 714 | (3S)-N-(4-{1-[(3-fluorophenyl)acetyl]piperidin-4-yl}phenyl)-1-(pyridazin-3-yl)pyrrolidine-3-carboxamide | (ESI(+)) m/e 488 (M + H)$^+$ |
| 715 | (3S)-N-(4-{1-[3-(methylsulfanyl)propanoyl]piperidin-4-yl}phenyl)-1-(pyridazin-3-yl)pyrrolidine-3-carboxamide | (ESI(+)) m/e 454 (M + H)$^+$ |
| 716 | (3S)-N-(4-{1-[(1-acetylpiperidin-4-yl)carbonyl]piperidin-4-yl}phenyl)-1-(pyridazin-3-yl)pyrrolidine-3-carboxamide | (ESI(+)) m/e 505 (M + H)$^+$ |
| 717 | (3S)-N-{4-[1-(but-3-enoyl)piperidin-4-yl]phenyl}-1-(pyridazin-3-yl)pyrrolidine-3-carboxamide | (ESI(+)) m/e 420 (M + H)$^+$ |
| 718 | (3S)-N-{4-[1-(2,2-dimethylbutanoyl)piperidin-4-yl]phenyl}-1-(pyridazin-3-yl)pyrrolidine-3-carboxamide | (ESI(+)) m/e 450 (M + H)$^+$ |
| 719 | (3S)-N-{4-[1-(3-fluoro-4-methylbenzoyl)piperidin-4-yl]phenyl}-1-(pyridazin-3-yl)pyrrolidine-3-carboxamide | (ESI(+)) m/e 488 (M + H)$^+$ |

TABLE 10-continued

The following Examples were essentially prepared as described in Example 313, substituting the appropriate carboxylic acid for 2,2-dimethylpropanoic acid.

| Ex | Name | MS |
|---|---|---|
| 720 | (3S)-N-{4-[1-(3-methoxybenzoyl)piperidin-4-yl]phenyl}-1-(pyridazin-3-yl)pyrrolidine-3-carboxamide | (ESI(+)) m/e 486 (M + H)$^+$ |
| 721 | (3S)-N-(4-{1-[(2-chlorophenyl)acetyl]piperidin-4-yl}phenyl)-1-(pyridazin-3-yl)pyrrolidine-3-carboxamide | (ESI(+)) m/e 504 (M + H)$^+$ |
| 722 | (3S)-N-(4-{1-[(2-methoxyethoxy)acetyl]piperidin-4-yl}phenyl)-1-(pyridazin-3-yl)pyrrolidine-3-carboxamide | (ESI(+)) m/e 468 (M + H)$^+$ |
| 723 | (3S)-N-{4-[1-(3,3-dimethylbutanoyl)piperidin-4-yl]phenyl}-1-(pyridazin-3-yl)pyrrolidine-3-carboxamide | (ESI(+)) m/e 450 (M + H)$^+$ |
| 724 | (3S)-N-{4-[1-(N-acetyl-L-leucyl)piperidin-4-yl]phenyl}-1-(pyridazin-3-yl)pyrrolidine-3-carboxamide | (ESI(+)) m/e 507 (M + H)$^+$ |
| 725 | (3S)-N-{4-[1-(3-fluorobenzoyl)piperidin-4-yl]phenyl}-1-(pyridazin-3-yl)pyrrolidine-3-carboxamide | (ESI(+)) m/e 474 (M + H)$^+$ |
| 726 | (3S)-N-{4-[1-(4-cyanobenzoyl)piperidin-4-yl]phenyl}-1-(pyridazin-3-yl)pyrrolidine-3-carboxamide | (ESI(+)) m/e 481 (M + H)$^+$ |
| 727 | (3S)-N-{4-[1-(2-methoxybenzoyl)piperidin-4-yl]phenyl}-1-(pyridazin-3-yl)pyrrolidine-3-carboxamide | (ESI(+)) m/e 486 (M + H)$^+$ |
| 728 | (3S)-N-{4-[1-(2,3-dimethylbenzoyl)piperidin-4-yl]phenyl}-1-(pyridazin-3-yl)pyrrolidine-3-carboxamide | (ESI(+)) m/e 484 (M + H)$^+$ |
| 729 | (3S)-N-(4-{1-[4-(propan-2-yl)benzoyl]piperidin-4-yl}phenyl)-1-(pyridazin-3-yl)pyrrolidine-3-carboxamide | (ESI(+)) m/e 498 (M + H)$^+$ |
| 730 | (3S)-N-{4-[1-(cyclohexylcarbonyl)piperidin-4-yl]phenyl}-1-(pyridazin-3-yl)pyrrolidine-3-carboxamide | (ESI(+)) m/e 462 (M + H)$^+$ |
| 731 | (3S)-1-(pyridazin-3-yl)-N-{4-[1-(thiophen-2-ylcarbonyl)piperidin-4-yl]phenyl}pyrrolidine-3-carboxamide | (ESI(+)) m/e 462 (M + H)$^+$ |
| 732 | (3S)-N-{4-[1-(4-hydroxybenzoyl)piperidin-4-yl]phenyl}-1-(pyridazin-3-yl)pyrrolidine-3-carboxamide | (ESI(+)) m/e 472 (M + H)$^+$ |
| 733 | (3S)-N-{4-[1-(3-cyanobenzoyl)piperidin-4-yl]phenyl}-1-(pyridazin-3-yl)pyrrolidine-3-carboxamide | (ESI(+)) m/e 481 (M + H)$^+$ |
| 734 | (3S)-1-(pyridazin-3-yl)-N-{4-[1-(3,3,3-trifluoropropanoyl)piperidin-4-yl]phenyl}pyrrolidine-3-carboxamide | (ESI(+)) m/e 462 (M + H)$^+$ |
| 735 | (3S)-N-{4-[1-(methoxyacetyl)piperidin-4-yl]phenyl}-1-(pyridazin-3-yl)pyrrolidine-3-carboxamide | (ESI(+)) m/e 424 (M + H)$^+$ |
| 736 | (3S)-N-{4-[1-(3-methylbutanoyl)piperidin-4-yl]phenyl}-1-(pyridazin-3-yl)pyrrolidine-3-carboxamide | (ESI(+)) m/e 436 (M + H)$^+$ |

Example 314 tert-butyl 4-(4-{[1-(pyridazin-3-yl)azetidin-3-yl]carbamoyl}phenyl)piperidine-1-carboxylate The title compound was prepared as described in Example 1A, substituting 1-(pyridazin-3-yl)azetidin-3-amine for tert-butyl 4-(4-aminophenoxy)piperidine-1-carboxylate and 4-(1-(tert-butoxycarbonyl)piperidin-4-yl)benzoic acid for 1-(benzyloxycarbonyl)azetidine-3-carboxylic acid. $^1$H NMR (300 MHz, DMSO-$d_6$) δ 8.96 (d, J=7.0 Hz, 1H), 8.56 (dd, J=4.6, 1.3 Hz, 1H), 7.82 (d, J=8.3 Hz, 2H), 7.41-7.31 (m, 3H), 6.83 (dd, J=9.0, 1.3 Hz, 1H), 4.96-4.85 (m, 1H), 4.37 (t, J=8.1 Hz, 2H), 4.16-3.97 (m, 4H), 2.88-2.65 (m, 3H), 1.80-1.70 (m, 2H), 1.60-1.43 (m, 2H), 1.41 (s, 9H); MS (ESI(+)) m/e 438 (M+H)$^+$.

Example 315

5-[1-(2-methylpropyl)-1H-pyrazol-4-yl]-N-[1-(pyridazin-3-yl)azetidin-3-yl]thiophene-2-carboxamide

Example 315A 5-(1-isobutyl-1H-pyrazol-4-yl)thiophene-2-carboxylic acid

The title compound was prepared as described as described in Example 148A, substituting 5-bromothiophene-2-carboxylic acid for 4-bromoaniline.

Example 315B

5-[1-(2-methylpropyl)-1H-pyrazol-4-yl]-N-[1-(pyridazin-3-yl)azetidin-3-yl]thiophene-2-carboxamide The title compound was prepared as described in Example 1A, substituting 1-(pyridazin-3-yl)azetidin-3-amine for tert-butyl 4-(4-aminophenoxy)piperidine-1-carboxylate and 5-(1-isobutyl-1H-pyrazol-4-yl)thiophene-2-carboxylic acid for 1-(benzyloxycarbonyl)azetidine-3-carboxylic acid. $^1$H NMR (300 MHz, DMSO-$d_6$) δ ppm 8.99 (d, J=7.1 Hz, 1H), 8.57 (dd, J=4.5, 1.3 Hz, 1H), 8.14 (d, J=0.8 Hz, 1H), 7.81-7.79 (m, 1H), 7.72 (d, J=3.9 Hz, 1H), 7.39 (dd, J=8.9, 4.5 Hz, 1H), 7.21 (d, J=3.8 Hz, 1H), 6.84 (dd, J=9.0, 1.4 Hz, 1H), 4.92-4.81 (m, 1H), 4.37 (t, J=8.1 Hz, 2H), 4.03 (dd, J=8.6, 5.5 Hz, 2H), 3.92 (d, J=7.1 Hz, 2H), 2.19-2.04 (m, 1H), 0.85 (d, J=6.7 Hz, 6H); MS (ESI(+)) m/e 383 (M+H)$^+$.

Example 564

N-(4-{[1-(3-chlorobenzoyl)piperidin-4-yl]sulfonyl}phenyl)-1-(pyridazin-3-yl)azetidine-3-carboxamide

Example 564A tert-butyl 4-((4-(1-((benzyloxy)carbonyl)azetidine-3-carboxamido)phenyl)thio)piperidine-1-carboxylate The title compound was prepared as described in Example 1A, substituting tert-butyl 4-(4-aminophenylthio)piperidine-1-carboxylate for tert-butyl 4-(4-aminophenoxy)piperidine-1-carboxylate and 1-(benzyloxycarbonyl)azetidine-3-carboxylic acid for 1-(benzyloxycarbonyl)azetidine-3-carboxylic acid.

Example 564B tert-butyl 4-((4-(1-((benzyloxy)carbonyl)azetidine-3-carboxamido)phenyl)sulfonyl)piperidine-1-carboxylate To a 20 mL vial was added tert-butyl 4-((4-(1-((benzyloxy)carbonyl)azetidine-3-carboxamido)phenyl)thio)piperidine-1-carboxylate (8.3 g, 15.79 mmol) in dichloromethane (79 ml). The reaction mixture was cooled to ca −20° C. in a methanol/dry ice bath treated with m-chloroperbenzoic acid (8.17 g, 47 4 mmol) and was allowed to warm slowly to room temperature. When complete, the reaction mixture was treated with 1N aqueous sodium hydroxide and extracted with dichloromethane. The combined organics were dried with sodium sulfate, filtered and concentrated by rotary evaporation. The residue was purified by regular phase chromatography to give the title compound.

Example 564C tert-butyl 4-(4-(azetidine-3-carboxamido)phenylsulfonyl)piperidine-1-carboxylate tert-Butyl 4-(4-(1-(benzyloxycarbonyl)azetidine-3-carboxamido)phenylsulfonyl)piperidine-1-carboxylate (7.94 g, 14.24 mmol) and ethanol (160 ml) were added to 20% Pd(OH)$_2$/C, wet (1.5 g, 1.089 mmol) in a 250 mL SS pressure bottle and the mixture was stirred for 16 hours at 30 psi and room temperature. The mixture was filtered through a nylon membrane and concentrated to give the title compound.

Example 564D tert-butyl 4-((4-(1-(6-chloropyridazin-3-yl)azetidine-3-carboxamido)phenyl)sulfonyl)piperidine-1-carboxylate The title compound was prepared as described in Example 147A, substituting tert-butyl 4-(4-(azetidine-3-carboxamido)phenylsulfonyl)piperidine-1-carboxylate for tert-butyl 4-(4-(azetidine-3-carboxamido)phenyl)piperidine-1-carboxylate.

Example 564E tert-butyl 4-((4-(1-(pyridazin-3-yl)azetidine-3-carboxamido)phenyl)sulfonyl)piperidine-1-carboxylate The title compound was prepared as described in Example 147B, substituting tert-butyl 4-((4-(1-(6-chloropyridazin-3-yl)azetidine-3-carboxamido)phenyl)sulfonyl)piperidine-1-carboxylate for tert-butyl 4-(4-(1-(6-chloropyridazin-3-yl)azetidine-3-carboxamido)phenyl)piperidine-1-carboxylate.

Example 564F

N-(4-(piperidin-4-ylsulfonyl)phenyl)-1-(pyridazin-3-yl)azetidine-3-carboxamide

The title compound was prepared as described in Example 1D, substituting tert-butyl 4-((4-(1-(pyridazin-3-yl)azetidine-3-carboxamido)phenyl)sulfonyl)piperidine-1-carboxylate for tert-butyl 4-(4-(1-(pyridin-3-yl)azetidine-3-carboxamido)phenoxy)piperidine-1-carboxylate.

Example 564G

N-(4-{[1-(3-chlorobenzoyl)piperidin-4-yl]sulfonyl}phenyl)-1-(pyridazin-3-yl)azetidine-3-carboxamide The title compound was prepared as described in Example 1A, substituting N-(4-(piperidin-4-ylsulfonyl)phenyl)-1-(pyridazin-3-yl)azetidine-3-carboxamide for tert-butyl 4-(4-aminophenoxy)piperidine-1-carboxylate and 3-chlorobenzoic acid for 1-(benzyloxycarbonyl)azetidine-3-carboxylic acid. $^1$H NMR (400 MHz, DMSO/D$_2$O) δ ppm 8.53 (dd, J=4.4, 1.2 Hz, 1H), 7.93-7.84 (m, 2H), 7.84-7.77 (m, 2H), 7.72 (dd, J=9.3, 4.4 Hz, 1H), 7.58-7.38 (m, 2H), 7.40-7.21 (m, 3H), 4.58-4.37 (m, 5H), 4.02 (d, J=31.5 Hz, 3H), 3.88 (tt, J=8.8, 5.9 Hz, 1H), 3.48 (ddd, J=11.6, 7.7, 3.9 Hz, 1H), 2.99 (t, J=11.9 Hz, 2H), 1.92 (d, J=10.6 Hz, 2H), 1.53 (qd, J=12.2, 4.5 Hz, 3H); MS (ESI(+)) m/e 540 (M+H)$^+$.

TABLE 11

The following Examples were prepared essentially as described in Example 564, substituting the appropriate carboxylic acid in Example 564F. Some products were purified by flash chromatography while others were purified by reverse-phase HPLC. Accordingly, some Examples were isolated as trifluoroacetic acid salts.

| Ex | Name | MS |
| --- | --- | --- |
| 565 | N-(4-{[1-(4-tert-butylbenzoyl)piperidin-4-yl]sulfonyl}phenyl)-1-(pyridazin-3-yl)azetidine-3-carboxamide | (ESI(+)) m/e 562 (M + H)$^+$ |
| 566 | N-(4-{[1-(4-methoxybenzoyl)piperidin-4-yl]sulfonyl}phenyl)-1-(pyridazin-3-yl)azetidine-3-carboxamide | (ESI(+)) m/e 536 (M + H)$^+$ |
| 567 | N-(4-{[1-(4-methylbenzoyl)piperidin-4-yl]sulfonyl}phenyl)-1-(pyridazin-3-yl)azetidine-3-carboxamide | (ESI(+)) m/e 520 (M + H)$^+$ |
| 568 | N-(4-{[1-(cyclohexylcarbonyl)piperidin-4-yl]sulfonyl}phenyl)-1-(pyridazin-3-yl)azetidine-3-carboxamide | (ESI(+)) m/e 512 (M + H)$^+$ |
| 569 | N-(4-{[1-(cyclopropylacetyl)piperidin-4-yl]sulfonyl}phenyl)-1-(pyridazin-3-yl)azetidine-3-carboxamide | (ESI(+)) m/e 484 (M + H)$^+$ |
| 570 | N-(4-{[1-(2-methoxybenzoyl)piperidin-4-yl]sulfonyl}phenyl)-1-(pyridazin-3-yl)azetidine-3-carboxamide | (ESI(+)) m/e 536 (M + H)$^+$ |
| 571 | N-[4-({1-[(2S)-2-phenylbutanoyl]piperidin-4-yl}sulfonyl)phenyl]-1-(pyridazin-3-yl)azetidine-3-carboxamide | (ESI(+)) m/e 548 (M + H)$^+$ |
| 572 | N-[4-({1-[4-(propan-2-yl)benzoyl]piperidin-4-yl}sulfonyl)phenyl]-1-(pyridazin-3-yl)azetidine-3-carboxamide | (ESI(+)) m/e 548 (M + H)$^+$ |
| 573 | N-(4-{[1-(4-chlorobenzoyl)piperidin-4-yl]sulfonyl}phenyl)-1-(pyridazin-3-yl)azetidine-3-carboxamide | (ESI(+)) m/e 540 (M + H)$^+$ |
| 574 | N-{4-[(1-benzoylpiperidin-4-yl)sulfonyl]phenyl}-1-(pyridazin-3-yl)azetidine-3-carboxamide | (ESI(+)) m/e 506 (M + H)$^+$ |
| 575 | 1-(pyridazin-3-yl)-N-(4-{[1-(4,4,4-trifluorobutanoyl)piperidin-4-yl]sulfonyl}phenyl)azetidine-3-carboxamide | (ESI(+)) m/e 526 (M + H)$^+$ |
| 576 | N-(4-{[1-(2,5-difluorobenzoyl)piperidin-4-yl]sulfonyl}phenyl)-1-(pyridazin-3-yl)azetidine-3-carboxamide | (ESI(+)) m/e 542 (M + H)$^+$ |
| 577 | N-(4-{[1-(2-fluorobenzoyl)piperidin-4-yl]sulfonyl}phenyl)-1-(pyridazin-3-yl)azetidine-3-carboxamide | (ESI(+)) m/e 524 (M + H)$^+$ |
| 578 | N-(4-{[1-(2-methylbenzoyl)piperidin-4-yl]sulfonyl}phenyl)-1-(pyridazin-3-yl)azetidine-3-carboxamide | (ESI(+)) m/e 520 (M + H)$^+$ |
| 579 | N-[4-({1-[(4-fluorophenyl)acetyl]piperidin-4-yl}sulfonyl)phenyl]-1-(pyridazin-3-yl)azetidine-3-carboxamide | (ESI(+)) m/e 538 (M + H)$^+$ |
| 580 | N-(4-{[1-(3-methylbenzoyl)piperidin-4-yl]sulfonyl}phenyl)-1-(pyridazin-3-yl)azetidine-3-carboxamide | (ESI(+)) m/e 520 (M + H)$^+$ |
| 581 | N-(4-{[1-(2,3-dimethylbenzoyl)piperidin-4-yl]sulfonyl}phenyl)-1-(pyridazin-3-yl)azetidine-3-carboxamide | (ESI(+)) m/e 534 (M + H)$^+$ |
| 582 | N-[4-({1-[(3-fluorophenyl)acetyl]piperidin-4-yl}sulfonyl)phenyl]-1-(pyridazin-3-yl)azetidine-3-carboxamide | (ESI(+)) m/e 538 (M + H)$^+$ |
| 583 | N-(4-{[1-(3-fluorobenzoyl)piperidin-4-yl]sulfonyl}phenyl)-1-(pyridazin-3-yl)azetidine-3-carboxamide | (ESI(+)) m/e 524 (M + H)$^+$ |
| 584 | 1-(pyridazin-3-yl)-N-[4-({1-[3-(trifluoromethyl)benzoyl]piperidin-4-yl}sulfonyl)phenyl]azetidine-3-carboxamide | (ESI(+)) m/e 575 (M + H)$^+$ |

TABLE 11-continued

The following Examples were prepared essentially as described in Example 564, substituting the appropriate carboxylic acid in Example 564F. Some products were purified by flash chromatography while others were purified by reverse-phase HPLC. Accordingly, some Examples were isolated as trifluoroacetic acid salts.

| Ex | Name | MS |
|---|---|---|
| 585 | N-[4-({1-[(3,5-difluorophenyl)acetyl]piperidin-4-yl}sulfonyl)phenyl]-1-(pyridazin-3-yl)azetidine-3-carboxamide | (ESI(+)) m/e 556 (M + H)⁺ |
| 586 | N-(4-{[1-(2,4-difluorobenzoyl)piperidin-4-yl]sulfonyl}phenyl)-1-(pyridazin-3-yl)azetidine-3-carboxamide | (ESI(+)) m/e 542 (M + H)⁺ |
| 587 | 1-(pyridazin-3-yl)-N-[4-({1-[4-(trifluoromethyl)benzoyl]piperidin-4-yl}sulfonyl)phenyl]azetidine-3-carboxamide | (ESI(+)) m/e 574 (M + H)⁺ |
| 588 | N-(4-{[1-(4-fluorobenzoyl)piperidin-4-yl]sulfonyl}phenyl)-1-(pyridazin-3-yl)azetidine-3-carboxamide | (ESI(+)) m/e 524 (M + H)⁺ |
| 589 | N-(4-{[1-(2,3-difluorobenzoyl)piperidin-4-yl]sulfonyl}phenyl)-1-(pyridazin-3-yl)azetidine-3-carboxamide | (ESI(+)) m/e 542 (M + H)⁺ |
| 590 | N-(4-{[1-(2,4-dichlorobenzoyl)piperidin-4-yl]sulfonyl}phenyl)-1-(pyridazin-3-yl)azetidine-3-carboxamide | (ESI(+)) m/e 574 (M + H)⁺ |
| 591 | N-(4-{[1-(naphthalen-1-ylcarbonyl)piperidin-4-yl]sulfonyl}phenyl)-1-(pyridazin-3-yl)azetidine-3-carboxamide | (ESI(+)) m/e 556 (M + H)⁺ |
| 592 | N-(4-{[1-(cyclopropylcarbonyl)piperidin-4-yl]sulfonyl}phenyl)-1-(pyridazin-3-yl)azetidine-3-carboxamide | (ESI(+)) m/e 470 (M + H)⁺ |
| 593 | N-(4-{[1-(3,5-difluorobenzoyl)piperidin-4-yl]sulfonyl}phenyl)-1-(pyridazin-3-yl)azetidine-3-carboxamide | (ESI(+)) m/e 542 (M + H)⁺ |
| 594 | N-(4-{[1-(2,2-dimethylpropanoyl)piperidin-4-yl]sulfonyl}phenyl)-1-(pyridazin-3-yl)azetidine-3-carboxamide | (ESI(+)) m/e 486 (M + H)⁺ |
| 595 | N-(4-{[1-(3,3-dimethylbutanoyl)piperidin-4-yl]sulfonyl}phenyl)-1-(pyridazin-3-yl)azetidine-3-carboxamide | (ESI(+)) m/e 500 (M + H)⁺ |
| 596 | N-(4-{[1-(3-methoxybenzoyl)piperidin-4-yl]sulfonyl}phenyl)-1-(pyridazin-3-yl)azetidine-3-carboxamide | (ESI(+)) m/e 536 (M + H)⁺ |
| 597 | N-(4-{[1-(3-methylbutanoyl)piperidin-4-yl]sulfonyl}phenyl)-1-(pyridazin-3-yl)azetidine-3-carboxamide | (ESI(+)) m/e 486 (M + H)⁺ |
| 598 | N-(4-{[1-(2-methylpropanoyl)piperidin-4-yl]sulfonyl}phenyl)-1-(pyridazin-3-yl)azetidine-3-carboxamide | (ESI(+)) m/e 472 (M + H)⁺ |
| 599 | N-(4-{[1-(cyclopentylcarbonyl)piperidin-4-yl]sulfonyl}phenyl)-1-(pyridazin-3-yl)azetidine-3-carboxamide | (ESI(+)) m/e 498 (M + H)⁺ |
| 600 | N-(4-{[1-(phenylacetyl)piperidin-4-yl]sulfonyl}phenyl)-1-(pyridazin-3-yl)azetidine-3-carboxamide | (ESI(+)) m/e 520 (M + H)⁺ |
| 601 | N-[4-({1-[(1-phenylcyclopropyl)carbonyl]piperidin-4-yl}sulfonyl)phenyl]-1-(pyridazin-3-yl)azetidine-3-carboxamide | (ESI(+)) m/e 546 (M + H)⁺ |
| 611 | N-(4-{[1-(2-chlorobenzoyl)piperidin-4-yl]sulfonyl}phenyl)-1-(pyridazin-3-yl)azetidine-3-carboxamide | (ESI(+)) m/e 540 (M + H)⁺ |
| 612 | N-(4-{[1-(4-methylpentanoyl)piperidin-4-yl]sulfonyl}phenyl)-1-(pyridazin-3-yl)azetidine-3-carboxamide | (ESI(+)) m/e 500 (M + H)⁺ |
| 613 | N-[4-({1-[(2-fluorophenyl)acetyl]piperidin-4-yl}sulfonyl)phenyl]-1-(pyridazin-3-yl)azetidine-3-carboxamide | (ESI(+)) m/e 538 (M + H)⁺ |

Example 602

N-{4-[1-(2-methylalanyl)piperidin-4-yl]phenyl}-1-(pyridin-3-yl)azetidine-3-carboxamide The title compound was prepared as described in Example 1A, substituting N-(4-(piperidin-4-yl)phenyl)-1-(pyridin-3-yl)azetidine-3-carboxamide for tert-butyl 4-(4-aminophenoxy)piperidine-1-carboxylate and 2-methylalanine for 1-(benzyloxycarbonyl)azetidine-3-carboxylic acid. $^1$H NMR (400 MHz, DMSO-$d_6$) δ ppm 10.14 (s, 1H), 8.18-8.11 (m, 4H), 8.07 (d, J=2.5 Hz, 1H), 7.74 (dd, J=8.6, 5.4 Hz, 1H), 7.55 (d, J=8.5 Hz, 2H), 7.52 (dd, J=8.7, 2.3 Hz, 1H), 7.21 (d, J=8.5 Hz, 2H), 4.41-3.68 (m, 7H), 3.10-2.89 (m, 2H), 2.89-2.74 (m, 1H), 1.85 (d, J=12.3 Hz, 2H), 1.58 (s, 6H), 1.52-1.37 (m, 2H); MS (ESI(+)) m/e 422 (M+H)$^+$.

Example 603

5-[1-(2-methylpropyl)-1H-pyrazol-4-yl]-N-[(3R)-1-(pyridin-3-yl)pyrrolidin-3-yl]thiophene-2-carboxamide

Example 603A (R)-tert-butyl 3-(5-(1-isobutyl-1H-pyrazol-4-yl)thiophene-2-carboxamido)pyrrolidine-1-carboxylate The title compound was prepared as described in Example 1A, substituting (R)-tert-butyl 3-aminopyrrolidine-1-carboxylate for tert-butyl 4-(4-aminophenoxy)piperidine-1-carboxylate and 5-(1-isobutyl-1H-pyrazol-4-yl)thiophene-2-carboxylic acid for 1-(benzyloxycarbonyl)azetidine-3-carboxylic acid.

Example 603B (R)-5-(1-isobutyl-1H-pyrazol-4-yl)-N-(pyrrolidin-3-yl)thiophene-2-carboxamide The title compound was prepared as described in Example 1D, substituting (R)-tert-butyl 3-(5-(1-isobutyl-1H-pyrazol-4-yl)thiophene-2-carboxamido)pyrrolidine-1-carboxylate for tert-butyl 4-(4-(1-(pyridin-3-yl)azetidine-3-carboxamido)phenoxy)piperidine-1-carboxylate.

Example 603C

5-[1-(2-methylpropyl)-1H-pyrazol-4-yl]-N-[(3R)-1-(pyridin-3-yl)pyrrolidin-3-yl]thiophene-2-carboxamide The title compound was prepared as described in Example 1C, substituting (R)-5-(1-isobutyl-1H-pyrazol-4-yl)-N-(pyrrolidin-3-yl)thiophene-2-carboxamide for tert-butyl 4-(4-(azetidine-3-carboxamido)phenoxy)piperidine-1-carboxylate. $^1$H NMR (300 MHz, DMSO-$d_6$) δ ppm 0.85 (d, J=6.78 Hz, 6H) 1.90-2.38 (m, 3H) 3.16-3.66 (m, 4H) 3.92 (d, J=7.12 Hz, 2H) 4.59 (d, J=5.76 Hz, 1H) 6.92 (dd, J=8.48, 1.70 Hz, 1H) 7.08-7.27 (m, 2H) 7.72 (d, J=3.73 Hz, 1H) 7.79 (s, 1H) 7.85 (d, J=3.73 Hz, 1H) 7.95 (d, J=2.71 Hz, 1H) 8.13 (s, 1H) 8.54 (d, J=7.12 Hz, 1H); MS (ESI(+)) m/e 396 (M+H)$^+$.

Example 604

5-[1-(2-methylpropyl)-1H-pyrazol-4-yl]-N-[(3R)-1-(pyridazin-4-yl)pyrrolidin-3-yl]thiophene-2-carboxamide The title compound was prepared as described in Example 1C, substituting 4-bromopyridazine for 3-bromopyridine and (R)-5-(1-isobutyl-1H-pyrazol-4-yl)-N-(pyrrolidin-3-yl)thiophene-2-carboxamide for tert-butyl 4-(4-(azetidine-3-carboxamido)phenoxy)piperidine-1-carboxylate. $^1$H NMR (300 MHz, DMSO-$d_6$) δ ppm 0.85 (d, J=6.44 Hz, 6H) 1.90-2.39 (m, 3H) 3.38-3.75 (m, 4H) 3.92 (d, J=7.12 Hz, 2H) 4.43-4.71 (m, 1H) 6.62 (dd, J=6.44, 3.05 Hz, 1H) 7.19 (d, J=3.73 Hz, 1H) 7.71 (d, J=4.07 Hz, 1H) 7.79 (s, 1H) 8.13 (s, 1H) 8.55 (dd, J=8.99, 6.95 Hz, 2H) 8.64 (d, J=2.71 Hz, 1H); MS (ESI(+)) m/e 397 (M+H)$^+$.

Example 605

5-[1-(2-methylpropyl)-1H-pyrazol-4-yl]-N-[(3R)-1-(pyridazin-3-yl)pyrrolidin-3-yl]thiophene-2-carboxamide

Example 605A (R)—N-(1-(6-chloropyridazin-3-yl)pyrrolidin-3-yl)-5-(1-isobutyl-1H-pyrazol-4-yl)thiophene-2-carboxamide The title compound was prepared as described in Example 147A, substituting (R)-5-(1-isobutyl-1H-pyrazol-4-yl)-N-(pyrrolidin-3-yl)thiophene-2-carboxamide for tert-butyl 4-(4-(azetidine-3-carboxamido)phenyl)piperidine-1-carboxylate.

Example 605B

5-[1-(2-methylpropyl)-1H-pyrazol-4-yl]-N-[(3R)-1-(pyridazin-3-yl)pyrrolidin-3-yl]thiophene-2-carboxamide The title compound was prepared as described in Example 1B, substituting (R)—N-(1-(6-chloropyridazin-3-yl)pyrrolidin-3-yl)-5-(1-isobutyl-1H-pyrazol-4-yl)thiophene-2-carboxamide for tert-butyl 4-(4-(1-(benzyloxycarbonyl)azetidine-3-carboxamido)phenoxy)piperidine-1-carboxylate. $^1$H NMR (400 MHz, DMSO-$d_6$) δ ppm 0.85 (d, J=6.71 Hz, 6 H) 1.94-2.38 (m, 3 H) 3.39-3.84 (m, 4 H) 3.92 (d, J=7.32 Hz, 2 H) 4.45-4.66 (m, 1 H) 6.88 (d, J=8.24 Hz, 1 H) 7.19 (d, J=3.97 Hz, 1 H) 7.34 (dd, J=9.00, 4.43 Hz, 1 H) 7.73 (d, J=3.97 Hz, 1 H) 7.80 (s, 1 H) 8.14 (s, 1 H) 8.49 (d, J=3.66 Hz, 1 H) 8.56 (d, J=6.71 Hz, 1 H); MS (ESI(+)) m/e 397 (M+H)$^+$.

Example 606

5-[1-(2-methylpropyl)-1H-pyrazol-4-yl]-N-[(3S)-1-(pyridazin-3-yl)pyrrolidin-3-yl]thiophene-2-carboxamide

Example 606A (S)-tert-butyl 3-(5-(1-isobutyl-1H-pyrazol-4-yl)thiophene-2-carboxamido)pyrrolidine-1-carboxylate The title compound was prepared as described in Example 1A, substituting (S)-tert-butyl 3-aminopyrrolidine-1-carboxylate for tert-butyl 4-(4-aminophenoxy)piperidine-1-carboxylate and 5-(1-isobutyl-1H-pyrazol-4-yl)thiophene-2-carboxylic acid for 1-(benzyloxycarbonyl)azetidine-3-carboxylic acid.

Example 606B (S)-5-(1-isobutyl-1H-pyrazol-4-yl)-N-(pyrrolidin-3-yl)thiophene-2-carboxamide The title compound was prepared as described in Example 1D, substituting (S)-tert-butyl 3-(5-(1-isobutyl-1H-pyrazol-4-yl)thiophene-2-carboxamido)pyrrolidine-1-carboxylate for tert-butyl 4-(4-(1-(pyridin-3-yl)azetidine-3-carboxamido)phenoxy)piperidine-1-carboxylate.

Example 606C (S)—N-(1-(6-chloropyridazin-3-yl)pyrrolidin-3-yl)-5-(1-isobutyl-1H-pyrazol-4-yl)thiophene-2-carboxamide The title compound was prepared as described in Example 147A, substituting (S)-5-(1-isobutyl-1H-pyrazol-4-yl)-N-(pyrrolidin-3-yl)thiophene-2-carboxamide for tert-butyl 4-(4-(azetidine-3-carboxamido)phenyl)piperidine-1-carboxylate.

Example 606D

5-[1-(2-methylpropyl)-1H-pyrazol-4-yl]-N-[(3S)-1-(pyridazin-3-yl)pyrrolidin-3-yl]thiophene-2-carboxamide The title compound was prepared as described in Example 1B, substituting (S)—N-(1-(6-chloropyridazin-3-yl)pyrrolidin-3-yl)-5-(1-isobutyl-1H-pyrazol-4-yl)thiophene-2-carboxamide for tert-butyl 4-(4-(1-(benzyloxycarbonyl)azetidine-3-carboxamido)phenoxy)piperidine-1-carboxylate. $^1$H NMR (300 MHz, DMSO-$d_6$) δ ppm 0.85 (d, J=6.78 Hz, 6 H) 1.91-2.42 (m, 3 H) 3.49-3.88 (m, 4 H) 3.87-4.07 (m, 2 H) 4.30-4.81 (m, 1 H) 7.20 (d, J=3.73 Hz, 1 H) 7.68 (d, J=8.82 Hz, 1 H) 7.74-7.94 (m, 3 H) 8.14 (s, 1H) 8.58 (d, J=3.05 Hz, 1 H) 8.71 (d, J=6.44 Hz, 1 H); MS (ESI(+)) m/e 397 (M+H)$^+$.

Example 607

5-[1-(2-methylpropyl)-1H-pyrazol-4-yl]-N-[(3S)-1-(pyridazin-4-yl)pyrrolidin-3-yl]thiophene-2-carboxamide The title compound was prepared as described in Example 1C, substituting 4-bromopyridazine for 3-bromopyridine and (S)-5-(1-isobutyl-1H-pyrazol-4-yl)-N-(pyrrolidin-3-yl)thiophene-2-carboxamide for tert-butyl 4-(4-(azetidine-3-carboxamido)phenoxy)piperidine-1-carboxylate. $^1$H NMR (300 MHz, DMSO-$d_6$) δ ppm 0.75-0.98 (m, 6 H) 1.98-2.44 (m, 3 H) 3.67-4.18 (m, 6 H) 4.66 (s, 1 H) 7.15 (dd, J=7.12, 3.05 Hz, 1 H) 7.21 (d, J=3.73 Hz, 1 H) 7.54-7.91 (m, 2 H) 8.14 (s, 1 H) 8.56-8.95 (m, 3 H); MS (ESI(+)) m/e 397 (M+H)$^+$.

Example 608

5-[1-(2-methylpropyl)-1 H-pyrazol-4-yl]-N-[(3S)-1-(pyridin-3-yl)pyrrolidin-3-yl]thiophene-2-carboxamide The title compound was prepared as described in Example 1C, substituting (S)-5-(1-isobutyl-1 H-pyrazol-4-yl)-N-(pyr-rolidin-3-yl)thiophene-2-carboxamide for tert-butyl 4-(4-(azetidine-3-carboxamido)phenoxy)piperidine-1-carboxylate. $^1$H NMR (300 MHz, DMSO-$d_6$) δ ppm 0.85 (d, J=6.78 Hz, 6 H) 1.88-2.38 (m, 3 H) 3.11-3.67 (m, 4 H) 3.92 (d, J=7.46 Hz, 2 H) 4.45-4.76 (m, 1 H) 6.75-7.01 (m, 1 H) 7.03-7.25 (m, 2 H) 7.73 (d, J=4.07 Hz, 1 H) 7.79 (s, 1 H) 7.81-7.93 (m, 1 H) 7.95 (d, J=2.71 Hz, 1 H) 8.13 (s, 1 H) 8.54 (d, J=7.12 Hz, 1 H); MS (ESI(+)) m/e 396 (M+H)$^+$.

Example 609 tert-butyl 4-(2-methyl-1-oxo-1-{4-[4-({[1-(pyridin-3-yl)azetidin-3-yl]carbonyl}amino)phenyl]piperidin-1-yl}propan-2-yl)piperazine-1-carboxylate The title compound was prepared as described in Example 1A, substituting N-(4-(piperidin-4-yl)phenyl)-1-(pyridin-3-yl)azetidine-3-carboxamide for tert-butyl 4-(4-aminophenoxy)piperidine-1-carboxylate and 2-(4-(tert-butoxycarbonyl)piperazin-1-yl)-2-methylpropanoic acid for 1-(benzyloxycarbonyl)azetidine-3-carboxylic acid. $^1$H NMR (300 MHz, DMSO-$d_6$) δ ppm 10.00 (s, 1H), 7.93 (dd, J=4.6, 1.4 Hz, 1H), 7.85 (d, J=2.5 Hz, 1H), 7.53 (d, J=8.6 Hz, 2H), 7.23-7.13 (m, 3H), 6.86 (ddd, J=8.3, 2.9, 1.4 Hz, 1H), 5.43 (bs, 1H), 4.59 (bs, 1H), 4.15-4.03 (m, 2H), 4.02-3.90 (m, 2H), 3.71 (tt, J=8.3, 6.1 Hz, 1H), 3.42-3.32 (m, 4H), 3.04 (bs, 1H), 2.80-2.62 (m, 2H), 2.39 (bs, 4H), 1.78 (d, J=11.1 Hz, 2H), 1.57-1.42 (m, 2H), 1.39 (s, 9H), 1.17 (s, 6H); MS (ESI(+)) m/e 591 (M+H)$^+$.

Example 610

N-(4-{1-[2-methyl-2-(piperazin-1-yl)propanoyl]piperidin-4-yl}phenyl)-1-(pyridin-3-yl)azetidine-3-carboxamide The title compound was prepared as described in Example 1D, substituting tert-butyl 4-(2-methyl-1-oxo-1-{4-[4-({[1-(pyridin-3-yl)azetidin-3-yl]carbonyl}amino)phenyl]piperidin-1-yl}propan-2-yl)piperazine-1-carboxylate for tert-butyl 4-(4-(1-(pyridin-3-yl)azetidine-3-carboxamido)phenoxy)piperidine-1-carboxylate. $^1$H NMR (300 MHz, DMSO-$d_6$) δ ppm 10.08 (s, 1H), 8.52 (s, 1H), 8.14 (d, J=5.2 Hz, 1H), 8.07 (d, J=2.6 Hz, 1H), 7.76 (dd, J=8.7, 5.4 Hz, 1H), 7.54 (d, J=8.6 Hz, 2H), 7.20 (d, J=8.6 Hz, 2H), 4.88 (bs, 4H), 4.23 (t, J=8.4 Hz, 2H), 4.12 (dd, J=7.9, 5.9 Hz, 2H), 3.87-3.66 (m, 1H), 3.10 (bs, 4H), 2.85-2.54 (m, 5H), 1.79 (d, J=13.1 Hz, 2H), 1.61-1.32 (m, 2H), 1.21 (s, 6H); MS (ESI(+)) m/e 491 (M+H)$^+$.

Example 614

N-(4-{[1-(2-methylpropanoyl)piperidin-4-yl]sulfonyl}phenyl)-1-(pyridazin-4-yl)azetidine-3-carboxamide Example 614A tert-butyl 4-((4-(1-(5,6-dichloropyridazin-4-yl)azetidine-3-carboxamido)phenyl)sulfonyl)piperidine-1-carboxylate To 3,4,5-trichloropyridazine (1.624 g, 8.85 mmol) and N-ethyl-N-isopropylpropan-2-amine (2.289 g, 17.71 mmol) in 50 mL N,N-dimethylformamide at 0° C. was added tert-butyl 4-(4-(azetidine-3-carboxamido)phenylsulfonyl)piperidine-1-carboxylate (2.5 g, 5.90 mmol) in 10 ml N,N-dimethylformamide, dropwise. The reaction mixture was stirred from 0° C. to room temperature overnight, diluted with water and extracted with ethyl acetate. The organic layer was dried with magnesium sulfate, filtered, concentrated and purified by flash chromatography to give the title compound.

Example 614B tert-butyl 4-((4-(1-(pyridazin-4-yl)azetidine-3-carboxamido)phenyl)sulfonyl)piperidine-1-carboxylate The title compound was prepared as described in Example 1B, substituting tert-butyl 4-((4-(1-(5,6-dichloropyridazin-4-yl)azetidine-3 carboxamido)phenyl)sulfonyl)piperidine-1-carboxylate for tert-butyl 4-(4-(1-(benzyloxycarbonyl)azetidine-3-carboxamido)phenoxy)piperidine-1-carboxylate.

Example 614C

N-(4-(piperidin-4-ylsulfonyl)phenyl)-1-(pyridazin-4-yl)azetidine-3-carboxamide

The title compound was prepared as described in Example 1D, substituting tert-butyl 4-((4-(1-(pyridazin-4-yl)azetidine-3-carboxamido)phenyl)sulfonyl)piperidine-1-carboxylate for tert-butyl 4-(4-(1-(pyridin-3-yl)azetidine-3-carboxamido)phenoxy)piperidine-1-carboxylate.

Example 614D

N-(4-{[1-(2-methylpropanoyl)piperidin-4-yl]sulfonyl}phenyl)-1-(pyridazin-4-yl)azetidine-3-carboxamide The title compound was prepared as described in Example 1A, substituting N-(4-(piperidin-4-ylsulfonyl)phenyl)-1-(pyridazin-4-yl)azetidine-3-carboxamide for tert-butyl 4-(4-aminophenoxy)piperidine-1-carboxylate and isobutyric acid for 1-(benzyloxycarbonyl)azetidine-3-carboxylic acid. $^1$H NMR (300 MHz, DMSO-d$_6$) δ ppm 10.70 (s, 1H), 8.79 (d, J=7.2 Hz, 1H), 8.55 (d, J=3.1 Hz, 1H), 7.93-7.86 (m, 2H), 7.85-7.78 (m, 2H), 7.00 (dd, J=7.2, 3.1 Hz, 1H), 4.65-4.36 (m, 5H), 4.09-3.82 (m, 2H), 3.35-2.67 (m, 4H), 1.95-1.76 (m, 2H), 1.48-0.99 (m, 2H), 0.95 (d, J=6.7 Hz, 6H); MS (ESI(+)) m/e 472 (M+H)$^+$.

Example 615

N-{4-[(1-benzoylpiperidin-4-yl)sulfonyl]phenyl}-1-(pyridazin-4-yl)azetidine-3-carboxamide The title compound was prepared as described in Example 1A, substituting N-(4-(piperidin-4-ylsulfonyl)phenyl)-1-(pyridazin-4-yl)azetidine-3-carboxamide for tert-butyl 4-(4-aminophenoxy)piperidine-1-carboxylate and benzoic acid for 1-(benzyloxycarbonyl)azetidine-3-carboxylic acid. $^1$H NMR (300 MHz, DMSO-d$_6$) δ ppm 10.70 (s, 1H), 8.79 (d, J=7.2 Hz, 1H), 8.55 (d, J=3.3 Hz, 1H), 7.93-7.86 (m, 2H), 7.85-7.78 (m, 2H), 7.49-7.29 (m, 5H), 7.00 (dd, J=7.2, 3.1 Hz, 1H), 4.65-4.35 (m, 4H), 3.99-3.83 (m, 1H), 3.73-3.50 (m, 1H), 3.28-2.65 (m, 4H), 2.37-1.59 (m, 2H), 1.56-1.06 (m, 2H); MS (ESI(+)) m/e 506 (M+H)$^+$.

Example 616

N-(4-{[1-(4-fluorobenzoyl)piperidin-4-yl]sulfonyl}phenyl)-1-(pyridazin-4-yl)azetidine-3-carboxamide The title compound was prepared as described in Example 1A, substituting N-(4-(piperidin-4-ylsulfonyl)phenyl)-1-(pyridazin-4-yl)azetidine-3-carboxamide for tert-butyl 4-(4-aminophenoxy)piperidine-1-carboxylate and 4-fluorobenzoic acid for 1-(benzyloxycarbonyl)azetidine-3-carboxylic acid. $^1$H NMR (300 MHz, DMSO-d$_6$) δ ppm 10.70 (s, 1H), 8.79 (d, J=6.9 Hz, 1H), 8.55 (d, J=3.1 Hz, 1H), 7.93-7.86 (m, 2H), 7.85-7.78 (m, 2H), 7.52-7.38 (m, 2H), 7.31-7.20 (m, 2H), 7.00 (dd, J=7.2, 3.1 Hz, 1H), 4.63-4.19 (m, 4H), 3.99-3.83 (m, 1H), 3.73-3.46 (m, 2H), 3.23-2.65 (m, 3H), 2.37-1.60 (m, 2H), 1.56-1.06 (m, 2H); MS (ESI(+)) m/e 524 (M+H)$^+$.

Example 617

N-(4-{[1-(cyclopentylcarbonyl)piperidin-4-yl]sulfonyl}phenyl)-1-(pyridazin-4-yl)azetidine-3-carboxamide The title compound was prepared as described in Example 1A, substituting N-(4-(piperidin-4-ylsulfonyl)phenyl)-1-(pyridazin-4-yl)azetidine-3-carboxamide for tert-butyl 4-(4-aminophenoxy)piperidine-1-carboxylate and cyclopentanecarboxylic acid for 1-(benzyloxycarbonyl)azetidine-3-carboxylic acid. $^1$H NMR (300 MHz, DMSO-d$_6$) δ ppm 10.69 (s, 1H), 8.79 (d, J=7.2 Hz, 1H), 8.55 (d, J=3.1 Hz, 1H), 7.97-7.77 (m, 4H), 7.00 (dd, J=7.2, 3.1 Hz, 1H), 4.67-4.37 (m, 5H), 4.11-4.01 (m, 1H), 3.99-3.84 (m, 1H), 3.35-2.71 (m, 4H), 1.95-1.06 (m, 10H), 1.07-0.97 (m, 2H); MS (ESI(+)) m/e 498 (M+H)$^+$.

Example 618

N-[(3R)-1-(5,6-dichloropyridazin-4-yl)pyrrolidin-3-yl]-5-[1-(2-methylpropyl)-1H-pyrazol-4-yl]thiophene-2-carboxamide 3,4,5-Trichloropyridazine (269 mg, 1.464 mmol) was dissolved in 5 ml N,N-dimethylformamide and triethylamine (370 mg, 3.66 mmol) was added. The solution was cooled with an ice-bath when (R)-5-(1-isobutyl-1H-pyrazol-4-yl)-N-(pyrrolidin-3-yl)thiophene-2-carboxamide bistrifluoroacetate (400 mg, 0.732 mmol) in N,N-dimethylformamide was added dropwise. The reaction mixture was stirred from 0° C. to room temperature overnight, diluted with water and extracted with ethyl acetate. The organic layer was dried with magnesium sulfate, filtered, concentrated, and purified by flash chromatography to give the title compound. $^1$H NMR (300 MHz, DMSO-d$_6$) δ ppm 8.66 (s, 1H), 8.49 (d, J=6.5 Hz, 1H), 8.14 (s, 1H), 7.79 (s, 1H), 7.70 (d, J=3.9 Hz, 1H), 7.20 (d, J=3.8 Hz, 1H), 4.59-4.45 (m, 1H), 4.05 (dd, J=11.0, 6.4 Hz, 1H), 4.01-3.66 (m, 5H), 2.30-1.94 (m, 3H), 0.85 (d, J=6.7 Hz, 6H); MS (ESI(+)) m/e 465 (M+H)$^+$.

Example 619

N-[(3R)-1-(6-chloropyridazin-3-yl)pyrrolidin-3-yl]-5-[1-(2-methylpropyl)-1H-pyrazol-4-yl]thiophene-2-carboxamide The title compound was prepared as described in Example 147A, substituting (R)-5-(1-isobutyl-1H-pyrazol-4-yl)-N-(pyrrolidin-3-yl)thiophene-2-carboxamide for tert-butyl 4-(4-(azetidine-3-carboxamido)phenyl)piperidine-1-carboxylate. $^1$H NMR (400 MHz, DMSO-d$_6$) δ ppm 8.55 (d, J=6.6 Hz, 1H), 8.14 (s, 1H), 7.80 (s, 1H), 7.72 (d, J=3.9 Hz, 1H), 7.49 (d, J=9.4 Hz, 1H), 7.20 (d, J=3.8 Hz, 1H), 7.03 (d, J=9.4 Hz, 1H), 4.64-4.52 (m, 1H), 3.92 (d, J=7.2 Hz, 2H), 3.76 (dd, J=11.0, 6.6 Hz, 1H), 3.69-3.41 (m, 3H), 2.34-2.21 (m, 1H), 2.19-2.02 (m, 2H), 0.85 (d, J=6.7 Hz, 6H); MS (ESI(+)) m/e 431 (M+H)+.

Example 620

N-[(3S)-1-(5,6-dichloropyridazin-4-yl)pyrrolidin-3-yl]-5-[1-(2-methylpropyl)-1H-pyrazol-4-yl]thiophene-2-carboxamide The title compound was prepared as described in Example 618, substituting (S)-5-(1-isobutyl-1H-pyrazol-4-yl)-N-(pyrrolidin-3-yl)thiophene-2-carboxamide for (R)-5-(1-isobutyl-1H-pyrazol-4-yl)-N-(pyrrolidin-3-yl)thiophene-2-carboxamide. $^1$H NMR (400 MHz, DMSO-$d_6$) δ ppm 8.70 (s, 1H), 8.55 (d, J=6.5 Hz, 1H), 8.19 (s, 1H), 7.85 (s, 1H), 7.75 (d, J=3.9 Hz, 1H), 7.25 (d, J=3.8 Hz, 1H), 4.64-4.47 (m, 1H), 4.10 (dd, J=10.9, 6.4 Hz, 1H), 4.07-3.67 (m, 5H), 2.32-2.02 (m, 3H), 0.94-0.75 (m, 6H); MS (ESI(+)) m/e 465 (M+H)+.

Example 621

N-[(3S)-1-(6-chloropyridazin-3-yl)pyrrolidin-3-yl]-5-[1-(2-methylpropyl)-1H-pyrazol-4-yl]thiophene-2-carboxamide The title compound was prepared as described in Example 147A, substituting (S)-5-(1-isobutyl-1H-pyrazol-4-yl)-N-(pyrrolidin-3-yl)thiophene-2-carboxamide for tert-butyl 4-(4-(azetidine-3-carboxamido)phenyl)piperidine-1-carboxylate. $^1$H NMR (300 MHz, DMSO-$d_6$) δ ppm 8.54 (d, J=6.7 Hz, 1H), 8.13 (d, J=0.8 Hz, 1H), 7.79 (d, J=0.8 Hz, 1H), 7.72 (d, J=3.9 Hz, 1H), 7.49 (d, J=9.4 Hz, 1H), 7.19 (d, J=3.8 Hz, 1H), 7.03 (d, J=9.4 Hz, 1H), 4.63-4.53 (m, 1H), 3.92 (d, J=7.2 Hz, 2H), 3.76 (dd, J=11.0, 6.6 Hz, 1H), 3.71-3.39 (m, 3H), 2.37-2.00 (m, 3H), 0.85 (d, J=6.7 Hz, 6H); MS (ESI(+)) m/e 431 (M+H)+.

Example 622

N-[(3R)-1-(5,6-dichloropyridazin-4-yl)pyrrolidin-3-yl]-5-[1-(2-methylpropyl)-1H-pyrazol-4-yl]thiophene-3-carboxamide Example 622A 5-(1-isobutyl-1H-pyrazol-4-yl)thiophene-3-carboxylic acid The title compound was prepared as described as described in Example 148A, substituting 5-bromothiophene-3-carboxylic acid for 4-bromoaniline.

Example 622B (R)-tert-butyl 3-(5-(1-isobutyl-1H-pyrazol-4-yl)thiophene-3-carboxamido)pyrrolidine-1-carboxylate The title compound was prepared as described in Example 1A, substituting (R)-tert-butyl 3-aminopyrrolidine-1-carboxylate for tert-butyl 4-(4-aminophenoxy)piperidine-1-carboxylate and 5-(1-isobutyl-1H-pyrazol-4-yl)thiophene-3-carboxylic acid for 1-(benzyloxycarbonyl)azetidine-3-carboxylic acid.

Example 622B (R)-5-(1-isobutyl-1H-pyrazol-4-yl)-N-(pyrrolidin-3-yl)thiophene-3-carboxamide The title compound was prepared as described in Example 1D, substituting (R)-tert-butyl 3-(5-(1-isobutyl-1H-pyrazol-4-yl)thiophene-3-carboxamido)pyrrolidine-1-carboxylate for tert-butyl 4-(4-(1-(pyridin-3-yl)azetidine-3-carboxamido)phenoxy)piperidine-1-carboxylate.

Example 622C

N-[(3R)-1-(5,6-dichloropyridazin-4-yl)pyrrolidin-3-yl]-5-[1-(2-methylpropyl)-1H-pyrazol-4-yl]thiophene-3-carboxamide The title compound was prepared as described in Example 618, substituting (R)-5-(1-isobutyl-1H-pyrazol-4-yl)-N-(pyrrolidin-3-yl)thiophene-3-carboxamide for (R)-5-(1-isobutyl-1H-pyrazol-4-yl)-N-(pyrrolidin-3-yl)thiophene-2-carboxamide. $^1$H NMR (300 MHz, DMSO-$d_6$) δ ppm 8.66 (s, 1H), 8.37 (d, J=6.5 Hz, 1H), 8.08 (d, J=0.8 Hz, 1H), 7.94 (d, J=1.4 Hz, 1H), 7.74 (d, J=0.8 Hz, 1H), 7.51 (d, J=1.4 Hz, 1H), 4.53 (q, J=5.4 Hz, 1H), 4.06 (dd, J=10.9, 6.4 Hz, 1H), 3.98-3.66 (m, 5H), 2.30-1.96 (m, 3H), 0.85 (d, J=6.7 Hz, 6H); MS (ESI(+)) m/e 465 (M+H)+.

Example 623

5-[1-(2-methylpropyl)-1H-pyrazol-4-yl]-N-[(3R)-1-(pyridazin-3-yl)pyrrolidin-3-yl]thiophene-3-carboxamide Example 623A (R)—N-(1-(6-chloropyridazin-3-yl)pyrrolidin-3-yl)-5-(1-isobutyl-1H-pyrazol-4-yl)thiophene-3-carboxamide The title compound was prepared as described in Example 147A, substituting (R)-5-(1-isobutyl-1H-pyrazol-4-yl)-N-(pyrrolidin-3-yl)thiophene-3-carboxamide for tert-butyl 4-(4-(azetidine-3-carboxamido)phenyl)piperidine-1-carboxylate.

Example 623B

5-[1-(2-methylpropyl)-1H-pyrazol-4-yl]-N-[(3R)-1-(pyridazin-3-yl)pyrrolidin-3-yl]thiophene-3-carboxamide The title compound was prepared as described in Example 147B, substituting (R)—N-(1-(6-chloropyridazin-3-yl)pyrrolidin-3-yl)-5-(1-isobutyl-1H-pyrazol-4-yl)thiophene-3-carboxamide for 4-(4-(1-(6-chloropyridazin-3-yl)azetidine-3-carboxamido)phenyl)piperidine-1-carboxylate. $^1$H NMR (300 MHz, DMSO-$d_6$) δ ppm 8.49 (dd, J=4.5, 1.3 Hz, 1H), 8.41 (d, J=6.7 Hz, 1H), 8.08 (s, 1H), 7.96 (d, J=1.4 Hz, 1H), 7.73 (s, 1H), 7.54 (d, J=1.4 Hz, 1H), 7.37 (dd, J=9.1, 4.4 Hz, 1H), 6.92 (d, J=9.1 Hz, 1H), 4.67-4.55 (m, 1H), 3.92 (d, J=7.2

Hz, 2H), 3.78 (dd, J=10.9, 6.6 Hz, 1H), 3.72-3.41 (m, 3H), 2.40-1.98 (m, 3H), 0.85 (d, J=6.7 Hz, 6H); MS (ESI(+)) m/e 397 (M+H)+.

Example 624

5-[1-(2-methylpropyl)-1H-pyrazol-4-yl]-N-[(3R)-1-(pyridazin-4-yl)pyrrolidin-3-yl]thiophene-3-carboxamide The title compound was prepared as described in Example 1B, substituting N-[(3R)-1-(5,6-dichloropyridazin-4-yl)pyrrolidin-3-yl]-5-[1-(2-methylpropyl)-1H-pyrazol-4-yl]thiophene-3-carboxamide for tert-butyl 4-(4-(1-(benzyloxycarbonyl)azetidine-3-carboxamido)phenoxy)piperidine-1-carboxylate. $^1$H NMR (300 MHz, DMSO-$d_6$) δ ppm 8.86-8.69 (m, 2H), 8.58 (d, J=6.6 Hz, 1H), 8.08 (d, J=0.8 Hz, 1H), 8.01 (d, J=1.4 Hz, 1H), 7.74 (d, J=0.8 Hz, 1H), 7.55 (d, J=1.4 Hz, 1H), 7.15 (dd, J=7.3, 3.1 Hz, 1H), 4.72-4.59 (m, 1H), 4.08-3.47 (m, 6H), 2.37-1.97 (m, 3H), 0.85 (d, J=6.7 Hz, 6H); MS (ESI(+)) m/e 397 (M+H)+.

Example 625

N-{4-[1-(2,2-dimethylpropanoyl)piperidin-4-yl]phenyl}-1-(pyridazin-3-yl)piperidine-4-carboxamide Example 625A benzyl 4-((4-(1-(tert-butoxycarbonyl)piperidin-4-yl)phenyl)carbamoyl)piperidine-1-carboxylate The title compound was prepared as described in Example 1A, substituting tert-butyl 4-(4-aminophenyl)piperidine-1-carboxylate for tert-butyl 4-(4-aminophenoxy)piperidine-1-carboxylate and 1-(benzyloxycarbonyl)piperidine-4-carboxylic acid for 1-(benzyloxycarbonyl)azetidine-3-carboxylic acid.

Example 625B tert-butyl 4-(4-(piperidine-4-carboxamido)phenyl)piperidine-1-carboxylate The title compound was prepared as described in Example 1B, substituting benzyl 4-((4-(1-(tert-butoxycarbonyl)piperidin-4-yl)phenyl)carbamoyl)piperidine-1-carboxylate for tert-butyl 4-(4-(1-(benzyloxycarbonyl)azetidine-3-carboxamido)phenoxy)piperidine-1-carboxylate.

Example 625C tert-butyl 4-(4-(1-(6-chloropyridazin-3-yl)piperidine-4-carboxamido)phenyl)piperidine-1-carboxylate The title compound was prepared as described in Example 147A, substituting tert-butyl 4-(4-(piperidine-4-carboxamido)phenyl)piperidine-1-carboxylate for tert-butyl 4-(4-(azetidine-3-carboxamido)phenyl)piperidine-1-carboxylate.

Example 625D tert-butyl 4-(4-(1-(pyridazin-3-yl)piperidine-4-carboxamido)phenyl)piperidine-1-carboxylate The title compound was prepared as described in Example 147B, tert-butyl 4-(4-(1-(6-chloropyridazin-3-yl)piperidine-4-carboxamido)phenyl)piperidine-1-carboxylate for 4-(4-(1-(6-chloropyridazin-3-yl)azetidine-3-carboxamido)phenyl)piperidine-1-carboxylate.

Example 625E

N-(4-(piperidin-4-yl)phenyl)-1-(pyridazin-3-yl)piperidine-4-carboxamide

The title compound was prepared as described in Example 1D, substituting tert-butyl 4-(4-(1-(pyridazin-3-yl)piperidine-4-carboxamido)phenyl)piperidine-1-carboxylate for tert-butyl 4-(4-(1-(pyridin-3-yl)azetidine-3-carboxamido)phenoxy)piperidine-1-carboxylate.

Example 625F

N-{4-[1-(2,2-dimethylpropanoyl)piperidin-4-yl]phenyl}-1-(pyridazin-3-yl)piperidine-4-carboxamide The title compound was prepared as described in Example 1A, substituting N-(4-(piperidin-4-yl)phenyl)-1-(pyridazin-3-yl)piperidine-4-carboxamide for tert-butyl 4-(4-aminophenoxy)piperidine-1-carboxylate and 2,2-dimethylpropanoic acid for 1-(benzyloxycarbonyl)azetidine-3-carboxylic acid. $^1$H NMR (400 MHz, DMSO-$d_6$) δ ppm 9.86 (s, 1H), 8.51 (d, J=3.6 Hz, 1H), 7.53-7.47 (m, 2H), 7.43-7.31 (m, 1H), 7.26 (d, J=8.6 Hz, 1H), 7.17-7.11 (m, 2H), 4.45-4.34 (m, 4H), 2.94 (t, J=11.6 Hz, 1H), 2.82 (t, J=12.5 Hz, 1H), 2.66 (dddd, J=33.0, 15.2, 8.0, 3.6 Hz, 1H), 1.89-1.81 (m, 2H), 1.80-1.71 (m, 2H), 1.70-1.53 (m, 2H), 1.51-1.33 (m, 2H), 1.20 (s, 9H), MS (ESI(+)) m/e 450 (M+H)+.

Example 626

N-[4-(1-benzoylpiperidin-4-yl)phenyl]-1-(pyridazin-3-yl)piperidine-4-carboxamide The title compound was prepared as described in Example 1A, substituting N-(4-(piperidin-4-yl)phenyl)-1-(pyridazin-3-yl)piperidine-4-carboxamide for tert-butyl 4-(4-aminophenoxy)piperidine-1-carboxylate and benzoic acid for 1-(benzyloxycarbonyl)azetidine-3-carboxylic acid. $^1$H NMR (400 MHz, DMSO-$d_6$) δ ppm 9.87 (s, 1H), 8.51 (d, J=4.8 Hz, 1H), 7.54-7.48 (m, 2H), 7.47-7.36 (m, 5H), 7.35 (dd, J=9.3, 4.4 Hz, 1H), 7.26 (d, J=8.7 Hz, 1H), 7.21-7.15 (m, 2H), 4.60 (s, 1H), 4.46-4.37 (m, 2H), 3.63 (s, 1H), 3.24-2.56 (m, 6H), 1.89-1.80 (m, 2H), 1.80-1.46 (m, 5H), MS (ESI(+)) m/e 470 (M+H)+.

Example 627

N-{4-[1-(2-fluorobenzoyl)piperidin-4-yl]phenyl}-1-(pyridazin-3-yl)piperidine-4-carboxamide The title compound was prepared as described in Example 1A, substituting N-(4-(piperidin-4-yl)phenyl)-1-(pyridazin-3-yl)piperidine-4-carboxamide for tert-butyl 4-(4-aminophenoxy)piperidine-1-carboxylate and 2-fluorobenzoic acid for 1-(benzyloxycarbonyl)azetidine-3-carboxylic acid. $^1$H NMR (400 MHz, DMSO-$d_6$) δ ppm 9.87 (s, 1H), 8.51 (d, J=4.4 Hz, 1H), 7.56-7.38 (m, 4H), 7.35 (dd, J=9.3, 4.4 Hz, 1H), 7.32-7.21 (m, 3H), 7.16 (d, J=8.5 Hz, 2H), 4.64 (d, J=13.1 Hz, 1H), 4.41 (d, J=13.3 Hz, 2H), 3.15 (t, J=12.3 Hz, 1H), 2.93 (dd, J=18.0, 7.3 Hz, 2H), 2.70 (dddd, J=15.1, 11.4, 10.1, 7.0 Hz, 3H), 1.86 (t, J=13.8 Hz, 3H), 1.76-1.39 (m, 5H); MS (ESI(+)) m/e 488 (M+H)+.

Example 628

1-(pyridazin-3-yl)-N-{4-[1-(4,4,4-trifluorobutanoyl)piperidin-4-yl]phenyl}piperidine-4-carboxamide The title compound was prepared as described in Example 1A, substituting N-(4-(piperidin-4-yl)phenyl)-1-(pyridazin-3-yl)piperidine-4-carboxamide for tert-butyl 4-(4-aminophenoxy)piperidine-1-carboxylate and 4,4,4-trifluorobutanoic acid for 1-(benzyloxycarbonyl)azetidine-3-carboxylic acid. $^1$H NMR (400 MHz, DMSO-$d_6$) δ ppm 9.86 (s, 1H), 8.51 (d, J=4.3 Hz, 1H), 7.49 (t, J=8.9 Hz, 2H), 7.41-7.30 (m, 1H), 7.25 (d, J=9.3 Hz, 1H), 7.14 (d, J=8.5 Hz, 2H), 4.51 (d, J=13.0 Hz, 1H), 4.41 (d, J=13.3 Hz, 2H), 3.94 (d, J=13.4 Hz, 1H), 3.07 (t, J=12.0 Hz, 1H), 2.94 (dd, J=18.1, 7.3 Hz, 2H), 2.77-2.40 (m, 9H), 1.93-1.80 (m, 2H), 1.71 (d, J=25.3 Hz, 2H), 1.58 (dqd, J=29.0, 12.7, 4.0 Hz, 3H), 1.39 (qd, J=12.7, 4.1 Hz, 1H); MS (ESI(+)) m/e 490 (M+H)$^+$.

Example 629

N-[(3S)-1-(6-chloropyridazin-3-yl)pyrrolidin-3-yl]-5-[1-(2-methylpropyl)-1H-pyrazol-4-yl]thiophene-3-carboxamide The title compound was prepared as described in Example 147A, substituting (S)-5-(1-isobutyl-1H-pyrazol-4-yl)-N-(pyrrolidin-3-yl)thiophene-3-carboxamide for tert-butyl 4-(4-(azetidine-3-carboxamido)phenyl)piperidine-1-carboxylate. $^1$H NMR (500 MHz, DMSO-$d_6$) δ ppm 8.42 (d, J=6.7 Hz, 1H), 8.08 (s, 1H), 7.96 (d, J=1.3 Hz, 1H), 7.74 (d, J=0.5 Hz, 1H), 7.54 (d, J=1.3 Hz, 1H), 7.49 (d, J=9.5 Hz, 1H), 7.02 (d, J=9.5 Hz, 1H), 4.87-4.44 (m, 1H), 3.92 (d, 2H), 3.94-3.38 (m, 4H), 2.50-1.87 (m, 3H), 0.85 (d, J=6.7 Hz, 6H); MS (ESI(+)) m/e 431 (M+H)$^+$.

Example 664

5-[1-(2-methylpropyl)-1H-pyrazol-4-yl]-N-[(3S)-1-(pyridazin-3-yl)pyrrolidin-3-yl]thiophene-3-carboxamide The title compound was prepared as described in Example 147B, substituting N-[(3S)-1-(6-chloropyridazin-3-yl)pyrrolidin-3-yl]-5-[1-(2-methylpropyl)-1H-pyrazol-4-yl]thiophene-3-carboxamide for 4-(4-(1-(6-chloropyridazin-3-yl)azetidine-3-carboxamido)phenyl)piperidine-1-carboxylate. $^1$H NMR (300 MHz, DMSO-$d_6$) δ ppm 8.58 (dd, J=4.3, 1.2 Hz, 2H), 8.08 (d, J=0.8 Hz, 1H), 8.02 (d, J=1.4 Hz, 1H), 7.86 (dd, J=9.5, 4.3 Hz, 1H), 7.77-7.66 (m, 2H), 7.57 (d, J=1.4 Hz, 1H), 4.70-4.61 (m, 1H), 3.92 (d, J=7.2 Hz, 2H), 3.67-2.93 (m, 4H), 2.41-2.00 (m, 3H), 0.88-0.81 (m, 6H); MS (ESI(+)) m/e 397 (M+H)$^+$.

Example 665

N-[4-(1-benzoylpiperidin-4-yl)phenyl]-1-(6-fluoro-5-methylpyridin-3-yl)azetidine-3-carboxamide

Example 665A benzyl 3-((4-(piperidin-4-yl)phenyl)carbamoyl)azetidine-1-carboxylate The title compound was prepared as described in Example 1D, substituting tert-butyl 4-(4-(1-(benzyloxycarbonyl)azetidine-3-carboxamido)phenyl)piperidine-1-carboxylate for tert-butyl 4-(4-(1-(pyridin-3-yl)azetidine-3-carboxamido)phenoxy)piperidine-1-carboxylate.

Example 665B benzyl 3-((4-(1-benzoylpiperidin-4-yl)phenyl)carbamoyl)azetidine-1-carboxylate The title compound was prepared as described in Example 1A, substituting benzyl 3-((4-(piperidin-4-yl)phenyl)carbamoyl)azetidine-1-carboxylate for tert-butyl 4-(4-aminophenoxy)piperidine-1-carboxylate and benzoic acid for 1-(benzyloxycarbonyl)azetidine-3-carboxylic acid.

Example 665C

N-(4-(1-benzoylpiperidin-4-yl)phenyl)azetidine-3-carboxamide

The title compound was prepared as described in Example 1B, substituting benzyl 3-((4-(1-benzoylpiperidin-4-yl)phenyl)carbamoyl)azetidine-1-carboxylate for tert-butyl 4-(4-(1-(benzyloxycarbonyl)azetidine-3-carboxamido)phenoxy)piperidine-1-carboxylate.

Example 665D

N-[4-(1-benzoylpiperidin-4-yl)phenyl]-1-(6-fluoro-5-methylpyridin-3-yl)azetidine-3-carboxamide The title compound was prepared as described in Example 1C, substituting 3-bromo-6-fluoro-5-methylpyridine for 3-bromopyridine and N-(4-(1-benzoylpiperidin-4-yl)phenyl)azetidine-3-carboxamide for tert-butyl 4-(4-(azetidine-3-carboxamido)phenoxy)piperidine-1-carboxylate. $^1$H NMR (400 MHz, DMSO-$d_6$/$D_2$O) δ ppm 7.55-7.34 (m, 7H), 7.26-7.14 (m, 3H), 6.98-6.86 (m, 1H), 4.21-4.01 (m, 3H), 3.95 (dd, J=8.8, 4.6 Hz, 2H), 3.69 (ddd, J=8.5, 7.4, 4.3 Hz, 1H), 3.09-2.95 (m, 2H), 2.80 (d, J=0.6 Hz, 1H), 2.23-2.14 (m, 3H), 1.87-1.75 (m, 2H), 1.58 (tt, J=12.8, 6.1 Hz, 2H), 1.11-1.01 (m, 1H); MS (ESI(+)) m/e 473 (M+H)$^+$.

TABLE 12

The following Examples were essentially prepared as described in Example 665, substituting an appropriate bromoheterocycle in Example 665D.

| Ex | Name | MS |
|---|---|---|
| 666 | N-[4-(1-benzoylpiperidin-4-yl)phenyl]-1-(5-fluoropyridin-3-yl)azetidine-3-carboxamide | (ESI(+)) m/e 459 (M + H)$^+$ |
| 668 | N-[4-(1-benzoylpiperidin-4-yl)phenyl]-1-(2-fluoro-6-methylpyridin-3-yl)azetidine-3-carboxamide | (ESI(+)) m/e 473 (M + H)$^+$ |
| 737 | N-[4-(1-benzoylpiperidin-4-yl)phenyl]-1-(2-cyanopyridin-3-yl)azetidine-3-carboxamide | (ESI(+)) m/e 466 (M + H)$^+$ |
| 738 | N-[4-(1-benzoylpiperidin-4-yl)phenyl]-1-(4-cyanopyridin-3-yl)azetidine-3-carboxamide | (ESI(+)) m/e 466 (M + H)$^+$ |
| 739 | N-[4-(1-benzoylpiperidin-4-yl)phenyl]-1-(6-fluoro-4-methylpyridin-3-yl)azetidine-3-carboxamide | (ESI(+)) m/e 473 (M + H)$^+$ |
| 740 | N-[4-(1-benzoylpiperidin-4-yl)phenyl]-1-(5-cyanopyridin-3-yl)azetidine-3-carboxamide | (ESI(+)) m/e 466 (M + H)$^+$ |
| 741 | N-[4-(1-benzoylpiperidin-4-yl)phenyl]-1-(5-methylpyridin-3-yl)azetidine-3-carboxamide | (ESI(+)) m/e 455 (M + H)$^+$ |

Example 667

N-[4-(1-benzoylpiperidin-4-yl)phenyl]-1-(6-methylpyridazin-3-yl)azetidine-3-carboxamide

Example 667A tert-butyl 4-(4-(1-(6-methylpyridazin-3-yl)azetidine-3-carboxamido)phenyl)piperidine-1-carboxylate The title compound was prepared as described in Example 1C, substituting 3-bromo-6-methylpyridazine for 3-bromopyridine and tert-butyl 4-(4-(azetidine-3-carboxamido)phenyl)piperidine-1-carboxylate for tert-butyl 4-(4-(azetidine-3-carboxamido)phenoxy)piperidine-1-carboxylate.

Example 667B 1-(6-methylpyridazin-3-yl)-N-(4-(piperidin-4-yl)phenyl)azetidine-3-carboxamide The title compound was prepared as described in Example 1D, substituting tert-butyl 4-(4-(1-(6-methylpyridazin-3-yl)azetidine-3-carboxamido)phenyl)piperidine-1-carboxylate for tert-butyl 4-(4-(1-(pyridin-3-yl)azetidine-3-carboxamido)phenoxy)piperidine-1-carboxylate.

Example 667C

N-[4-(1-benzoylpiperidin-4-yl)phenyl]-1-(6-methylpyridazin-3-yl)azetidine-3-carboxamide The title compound was prepared as described in Example 1A, substituting 1-(6-methylpyridazin-3-yl)-N-(4-(piperidin-4-yl)phenyl)azetidine-3-carboxamide for tert-butyl 4-(4-aminophenoxy)piperidine-1-carboxylate and benzoic acid for 1-(benzyloxycarbonyl)azetidine-3-carboxylic acid. $^1$H NMR (300 MHz, DMSO-d6) δ 10.02 (s, 1H), 7.54 (d, J=8.5 Hz, 2H), 7.49-7.39 (m, 5H), 7.28 (d, J=9.1 Hz, 1H), 7.22 (d, J=8.5 Hz, 2H), 6.79 (d, J=9.0 Hz, 1H), 4.72-4.51 (m, 1H), 4.19 (t, J=8.2 Hz, 2H), 4.10 (dd, J=7.8, 6.2 Hz, 2H), 3.71 (tt, J=8.5, 6.1 Hz, 2H), 3.21-2.95 (m, 1H), 2.95-2.64 (m, 2H), 2.44 (s, 3H), 1.93-1.46 (m, 4H); (ESI(+)) m/e 456 (M+H)$^+$.

TABLE 13

The following Examples were essentially prepared as described in Example 667, substituting the appropriate carboxylic acid in Example 667C.

| Ex | Name | MS |
|---|---|---|
| 851 | N-{4-[1-(2-fluorobenzoyl)piperidin-4-yl]phenyl}-1-(6-methylpyridazin-3-yl)azetidine-3-carboxamide | (ESI(+)) m/e 474 (M + H)$^+$ |
| 852 | N-{4-[1-(2,2-dimethylpropanoyl)piperidin-4-yl]phenyl}-1-(6-methylpyridazin-3-yl)azetidine-3-carboxamide | (ESI(+)) m/e 436 (M + H)$^+$ |

Example 742

2-[1-(2-methylpropyl)-1H-pyrazol-4-yl]-N-[(3S)-1-(pyridazin-3-yl)pyrrolidin-3-yl]-1,3-thiazole-5-carboxamide

Example 742A 2-(1-isobutyl-1H-pyrazol-4-yl)thiazole-5-carboxylic acid

The title compound was prepared as described in Example 148A, substituting 2-bromothiazole-5-carboxylic acid for 4-bromoaniline.

Example 742B (S)-tert-butyl 3-(2-(1-isobutyl-1H-pyrazol-4-yl)thiazole-5-carboxamido)pyrrolidine-1-carboxylate The title compound was prepared as described in Example 1A, substituting (S)-tert-butyl 3-aminopyrrolidine-1-carboxylate for tert-butyl 4-(4-aminophenoxy)piperidine-1-carboxylate and 2-(1-isobutyl-1H-pyrazol-4-yl)thiazole-5-carboxylic acid for 1-(benzyloxycarbonyl)azetidine-3-carboxylic acid.

Example 742C (S)-2-(1-isobutyl-1H-pyrazol-4-yl)-N-(pyrrolidin-3-yl)thiazole-5-carboxamide The title compound was prepared as described in Example 1D, substituting (S)-tert-butyl 3-(2-(1-isobutyl-1H-pyrazol-4-yl)thiazole-5-carboxamido)pyrrolidine-1-carboxylate for tert-butyl 4-(4-(1-(pyridin-3-yl)azetidine-3-carboxamido)phenoxy)piperidine-1-carboxylate.

Example 742D (S)—N-(1-(6-chloropyridazin-3-yl)pyrrolidin-3-yl)-2-(1-isobutyl-1H-pyrazol-4-yl)thiazole-5-carboxamide The title compound was prepared as described in Example 147A, substituting (S)-2-(1-isobutyl-1H-pyrazol-4-yl)-N-(pyrrolidin-3-yl)thiazole-5-carboxamide for tert-butyl 4-(4-(azetidine-3-carboxamido)phenyl)piperidine-1-carboxylate.

Example 742E

2-[1-(2-methylpropyl)-1H-pyrazol-4-yl]-N-[(3S)-1-(pyridazin-3-yl)pyrrolidin-3-yl]-1,3-thiazole-5-carboxamide The title compound was prepared as described in Example 147B, substituting (S)—N-(1-(6-chloropyridazin-3-yl)pyrrolidin-3-yl)-2-(1-isobutyl-1H-pyrazol-4-yl)thiazole-5-carboxamide for 4-(4-(1-(6-chloropyridazin-3-yl)azetidine-3-carboxamido)phenyl)piperidine-1-carboxylate. $^1$H NMR (300 MHz, DMSO-d$_6$) δ ppm 8.80 (d, 1H), 8.41 (d, J=0.8 Hz, 1H), 8.30 (s, 1H), 8.28 (s, 1H), 7.90 (s, 1H), 7.34 (dd, J=9.1, 4.5 Hz, 1H), 6.88 (dd, J=9.1, 1.3 Hz, 1H), 4.67-4.52 (m, 1H), 4.03-3.93 (m, 2H), 3.90-3.40 (m, 4H), 2.36-2.02 (m, 3H), 0.89-0.82 (m, 6H); MS (ESI(+)) m/e 398 (M+H)$^+$.

Example 743

(3S)—N-[4-(1-benzoylpiperidin-4-yl)phenyl]-1-(2-methylpyridin-3-yl)pyrrolidine-3-carboxamide

Example 743A (S)-tert-butyl 4-(4-(1-((benzyloxy)carbonyl)pyrrolidine-3-carboxamido)phenyl)piperidine-1-carboxylate The title compound was prepared as described in Example 1A, substituting tert-butyl 4-(4-aminophenyl)piperidine-1-carboxylate for tert-butyl 4-(4-aminophenoxy)piperidine-1-carboxylate and (S)-1-((benzyloxy)carbonyl)pyrrolidine-3-carboxylic acid for 1-(benzyloxycarbonyl)azetidine-3-carboxylic acid.

Example 743B (S)-tert-butyl 4-(4-(pyrrolidine-3-carboxamido)phenyl)piperidine-1-carboxylate The title compound was prepared as described in Example 1B, substituting (S)-tert-butyl 4-(4-(1-((benzyloxy)carbonyl)pyrrolidine-3-carboxamido)phenyl)piperidine-1-carboxylate for tert-butyl 4-(4-(1-(benzyloxycarbonyl)azetidine-3-carboxamido)phenoxy)piperidine-1-carboxylate.

Example 743C (S)-tert-butyl 4-(4-(1-(2-methylpyridin-3-yl)pyrrolidine-3-carboxamido)phenyl)piperidine-1-carboxylate The title compound was prepared as described in Example 1C, substituting 3-bromo-2-methylpyridine for 3-bromopyridine and (S)-tert-butyl 4-(4-(pyrrolidine-3-carboxamido)phenyl)piperidine-1-carboxylate for tert-butyl 4-(4-(azetidine-3-carboxamido)phenoxy)piperidine-1-carboxylate.

Example 743D (S)-1-(2-methylpyridin-3-yl)-N-(4-(piperidin-4-yl)phenyl)pyrrolidine-3-carboxamide The title compound was prepared as described in Example 1D, substituting (S)-tert-butyl 4-(4-(1-(2-methylpyridin-3-yl)pyrrolidine-3-carboxamido)phenyl)piperidine-1-carboxylate for tert-butyl 4-(4-(1-(pyridin-3-yl)azetidine-3-carboxamido)phenoxy)piperidine-1-carboxylate.

Example 743E (3S)—N-[4-(1-benzoylpiperidin-4-yl)phenyl]-1-(2-methylpyridin-3-yl)pyrrolidine-3-carboxamide The title compound was prepared as described in Example 1A, substituting (S)-1-(2-methylpyridin-3-yl)-N-(4-(piperidin-4-yl)phenyl)pyrrolidine-3-carboxamide for tert-butyl 4-(4-aminophenoxy)piperidine-1-carboxylate and benzoic acid for 1-(benzyloxycarbonyl)azetidine-3-carboxylic acid. $^1$H NMR (400 MHz, DMSO-$d_6$) δ ppm 9.98 (s, 1H), 7.97 (ddd, J=5.1, 2.2, 1.3 Hz, 2H), 7.69 (dt, J=8.4, 0.9 Hz, 1H), 7.56-7.51 (m, 2H), 7.47-7.41 (m, 5H), 7.24-7.18 (m, 3H), 7.09 (dd, J=8.0, 4.7 Hz, 1H), 4.62 (s, 1H), 3.65 (s, 1H), 3.19 (ddd, J=14.2, 10.1, 6.4 Hz, 4H), 2.76 (t, J=11.9 Hz, 2H), 2.47 (s, 3H), 2.26-2.06 (m, 2H), 1.93-1.49 (m, 4H), 1.23 (s, 1H), MS (ESI(+)) m/e 469.3 (M+H)$^+$.

Example 744

(3S)—N-{4-[1-(2-fluorobenzoyl)piperidin-4-yl]phenyl}-1-(2-methylpyridin-3-yl)pyrrolidine-3-carboxamide The title compound was prepared as described in Example 1A, substituting (S)-1-(2-methylpyridin-3-yl)-N-(4-(piperidin-4-yl)phenyl)pyrrolidine-3-carboxamide for tert-butyl 4-(4-aminophenoxy)piperidine-1-carboxylate and 2-fluorobenzoic acid for 1-(benzyloxycarbonyl)azetidine-3-carboxylic acid. $^1$H NMR (400 MHz, DMSO-$d_6$) δ ppm 9.98 (s, 1H), 8.01-7.93 (m, 2H), 7.58-7.45 (m, 2H), 7.44-7.37 (m, 1H), 7.30 (tdd, J=6.6, 3.7, 2.8 Hz, 2H), 7.20 (dd, J=11.4, 4.7 Hz, 2H), 7.09 (dd, J=8.1, 4.6 Hz, 1H), 4.66 (d, J=13.1 Hz, 1H), 3.49-3.14 (m, 8H), 2.90-2.69 (m, 2H), 2.47 (s, 3H), 2.31-2.06 (m, 2H), 1.92-1.80 (m, 1H), 1.70 (s, 1H), 1.64-1.41 (m, 2H); MS (ESI(+)) m/e 487.3 (M+H)$^+$.

Example 745

(3S)-1-(2-methylpyridin-3-yl)-N-{4-[1-(4,4,4-trifluorobutanoyl)piperidin-4-yl]phenyl}pyrrolidine-3-carboxamide The title compound was prepared as described in Example 1A, substituting (S)-1-(2-methylpyridin-3-yl)-N-(4-(piperidin-4-yl)phenyl)pyrrolidine-3-carboxamide for tert-butyl 4-(4-aminophenoxy)piperidine-1-carboxylate and 4,4,4-trifluorobutanoic acid for 1-(benzyloxycarbonyl)azetidine-3-carboxylic acid. $^1$H NMR (400 MHz, DMSO-$d_6$) δ ppm 9.97 (s, 1H), 7.97 (dd, J=4.8, 3.6 Hz, 2H), 7.53 (d, J=8.3 Hz, 3H), 7.24-7.13 (m, 3H), 4.53 (d, J=12.9 Hz, 1H), 3.97 (d, J=13.3 Hz, 1H), 3.39 (d, J=7.5 Hz, 3H), 3.36-3.29 (m, 2H), 3.25-3.16 (m, 2H), 3.11 (dd, J=24.4, 11.8 Hz, 1H), 2.70 (ddd, J=15.1, 11.8, 8.3 Hz, 1H), 2.67-2.57 (m, 3H), 2.47 (s, 3H), 2.27-2.07 (m, 2H), 1.75 (s, 2H), 1.56 (dt, J=12.5, 8.7 Hz, 1H), 1.41 (qd, J=12.8, 4.3 Hz, 1H), MS (ESI(+)) m/e 489.3 (M+H)$^+$.

Example 746

N-[(3S)-1-(6-chloropyridazin-3-yl)pyrrolidin-3-yl]-5-[1-(2-methylpropyl)-1H-pyrazol-4-yl]furan-2-carboxamide

Example 746A 5-(1-isobutyl-1H-pyrazol-4-yl)furan-2-carboxylic acid

The title compound was prepared as described in Example 148A, substituting 5-bromofuran-2-carboxylic acid for 4-bromoaniline.

Example 746B (S)-tert-butyl 3-(5-(1-isobutyl-1H-pyrazol-4-yl)furan-2-carboxamido)pyrrolidine-1-carboxylate The title compound was prepared as described in Example 1A, substituting (S)-tert-butyl 3-aminopyrrolidine-1-carboxylate for tert-butyl 4-(4-aminophenoxy)piperidine-1-carboxylate and 5-(1-isobutyl-1H-pyrazol-4-yl)furan-2-carboxylic acid for 1-(benzyloxycarbonyl)azetidine-3-carboxylic acid.

Example 746C (S)-5-(1-isobutyl-1H-pyrazol-4-yl)-N-(pyrrolidin-3-yl)furan-2-carboxamide The title compound was prepared as described in Example 1D, substituting (S)-tert-butyl 3-(5-(1-isobutyl-1H-pyrazol-4-yl)furan-2-carboxamido)pyrrolidine-1-carboxylate for tert-butyl 4-(4-(1-(pyridin-3-yl)azetidine-3-carboxamido)phenoxy)piperidine-1-carboxylate.

Example 746D

N-[(3S)-1-(6-chloropyridazin-3-yl)pyrrolidin-3-yl]-5-[1-(2-methylpropyl)-1H-pyrazol-4-yl]furan-2-carboxamide The title compound was prepared as described in Example 147A, substituting (S)-5-(1-isobutyl-1H-pyrazol-4-yl)-N-(pyrrolidin-3-yl)furan-2-carboxamide for tert-butyl 4-(4-(azetidine-3-carboxamido)phenyl)piperidine-1-carboxylate. $^1$H NMR (300 MHz, DMSO-$d_6$) δ ppm 8.37 (d, J=6.9 Hz, 1H), 8.14 (s, 1H), 7.87 (s, 1H), 7.49 (d, J=9.4 Hz, 1H), 7.17 (d, J=3.5 Hz, 1H), 7.03 (d, J=9.4 Hz, 1H), 6.63 (d, J=3.5 Hz, 1H), 4.69-4.54 (m, 1H), 3.95 (d, J=7.2 Hz, 2H), 3.79 (dd, J=11.0, 6.8 Hz, 1H), 3.72-3.58 (m, 1H), 3.60-3.39 (m, 2H), 2.36-2.19 (m, 1H), 2.22-2.03 (m, 2H), 0.85 (d, J=6.7 Hz, 6H); MS (ESI(+)) m/e 415 (M+H)$^+$.

Example 747

5-[1-(2-methylpropyl)-1H-pyrazol-4-yl]-N-[(3S)-1-(pyridazin-3-yl)pyrrolidin-3-yl]furan-2-carboxamide The title compound was prepared as described in Example 147B, substituting N-[(3S)-1-(6-chloropyridazin-3-yl)pyrrolidin-3-yl]-5-[1-(2-methylpropyl)-1H-pyrazol-4-yl]furan-2-carboxamide for 4-(4-(1-(6-chloropyridazin-3-yl)azetidine-3-carboxamido)phenyl)piperidine-1-carboxylate. $^1$H NMR (300 MHz, DMSO-$d_6$) δ ppm 8.49 (dd, J=4.5, 1.2 Hz, 1H), 8.38 (d, J=7.0 Hz, 1H), 8.15 (s, 1H), 7.87 (s, 1H), 7.34 (d, J=9.1, 4.4 Hz, 1H), 7.17 (d, J=3.5 Hz, 1H), 6.88 (dd, J=9.1, 1.3 Hz, 1H), 6.63 (d, J=3.5 Hz, 1H), 4.70-4.54 (m, 1H), 3.95 (d, J=7.2 Hz, 2H), 3.79 (dd, J=10.8, 6.9 Hz, 1H), 3.75-3.61 (m, 1H), 3.61-3.39 (m, 2H), 2.37-2.01 (m, 3H), 0.85 (d, J=6.7 Hz, 6H); MS (ESI(+)) m/e 381 (M+H)$^+$.

Example 748

N-(4-{1-[(4-methyltetrahydro-2H-pyran-4-yl)methyl]-1H-pyrazol-4-yl}phenyl)-1-(pyridazin-3-yl)azetidine-3-carboxamide

Example 748A 1-(6-chloropyridazin-3-yl)azetidine-3-carboxylic acid

The title compound was prepared as described in Example 147A, substituting azetidine-3-carboxylic acid for tert-butyl 4-(4-(azetidine-3-carboxamido)phenyl)piperidine-1-carboxylate.

Example 748B 1-(pyridazin-3-yl)azetidine-3-carboxylic acid

The title compound was prepared as described in Example 147B, substituting 1-(6-chloropyridazin-3-yl)azetidine-3-carboxylic acid for 4-(4-(1-(6-chloropyridazin-3-yl)azetidine-3-carboxamido)phenyl)piperidine-1-carboxylate.

Example 748C

N-(4-bromophenyl)-1-(pyridazin-3-yl)azetidine-3-carboxamide

The title compound was prepared as described in Example 1A, substituting 4-bromoaniline for tert-butyl 4-(4-aminophenoxy)piperidine-1-carboxylate and 1-(pyridazin-3-yl)azetidine-3-carboxylic acid for 1-(benzyloxycarbonyl)azetidine-3-carboxylic acid.

Example 748D

N-(4-{1-[(4-methyltetrahydro-2H-pyran-4-yl)methyl]-1H-pyrazol-4-yl}phenyl)-1-(pyridazin-3-yl)azetidine-3-carboxamide The title compound was prepared as described in Example 148A, substituting 1-((4-methyltetrahydro-2H-pyran-4-yl)methyl)-4-(4,4,5,5-tetramethyl-1,3,2-dioxaborolan-2-O-1H-pyrazole for 1-isobutyl-4-(4,4,5,5-tetramethyl-1,3,2-dioxaborolan-2-yl)-1H-pyrazole and N-(4-bromophenyl)-1-(pyridazin-3-yl)azetidine-3-carboxamide for 4-bromoaniline. $^1$H NMR (300 MHz, DMSO-$d_6$) δ ppm 10.09 (s, 1H), 8.56 (dd, J=4.5, 1.2 Hz, 1H), 8.06 (s, 1H), 7.82 (s, 1H), 7.61 (d, J=8.7 Hz, 2H), 7.52 (d, J=8.6 Hz, 2H), 7.38 (dd, J=9.0, 4.5 Hz, 1H), 6.83 (dd, J=9.0, 1.2 Hz, 1H), 4.25 (t, J=8.3 Hz, 2H), 4.16 (dd, J=8.0, 6.0 Hz, 2H), 4.02 (s, 2H), 3.84-3.62 (m, 3H), 3.52 (ddd, J=11.8, 9.2, 3.0 Hz, 2H), 1.51 (ddd, J=13.3, 9.0, 4.2 Hz, 2H), 1.32-1.17 (m, 2H), 0.97 (s, 3H); MS (ESI(+)) m/e 433 (M+H)$^+$.

Example 749

N-[(3S)-1-(6-chloropyridazin-3-yl)pyrrolidin-3-yl]-4-[1-(2-methylpropanoyl)piperidin-4-yl]benzamide

Example 749A (S)-tert-butyl (1-(6-chloropyridazin-3-yl)pyrrolidin-3-yl)carbamate The title compound was prepared as described in Example 147A, substituting (S)-tert-butyl pyrrolidin-3-ylcarbamate for tert-butyl 4-(4-(azetidine-3-carboxamido)phenyl)piperidine-1-carboxylate.

Example 749B (S)-1-(6-chloropyridazin-3-yl)pyrrolidin-3-amine

The title compound was prepared as described in Example 1D, substituting (S)-tert-butyl (1-(6-chloropyridazin-3-yl)pyrrolidin-3-yl)carbamate for tert-butyl 4-(4-(1-(pyridin-3-yl)azetidine-3-carboxamido)phenoxy)piperidine-1-carboxylate.

Example 749C

N-[(3S)-1-(6-chloropyridazin-3-yl)pyrrolidin-3-yl]-4-[1-(2-methylpropanoyl)piperidin-4-yl]benzamide The title compound was prepared as described in Example 1A, substituting (S)-1-(6-chloropyridazin-3-yl)pyrrolidin-3-amine for tert-butyl 4-(4-aminophenoxy)piperidine-1-carboxylate and 4-(1-isobutyrylpiperidin-4-yl)benzoic acid for 1-(benzyloxycarbonyl)azetidine-3-carboxylic acid. $^1$H NMR (300 MHz, DMSO-d$_6$) δ ppm 8.53 (d, J=6.6 Hz, 1H), 7.83-7.76 (m, 2H), 7.48 (d, J=9.4 Hz, 1H), 7.37-7.30 (m, 2H), 7.01 (d, J=9.5 Hz, 1H), 4.68-4.49 (m, 2H), 4.12-4.00 (m, 1H), 3.77 (dd, J=11.0, 6.6 Hz, 1H), 3.68-3.39 (m, 3H), 3.19-3.00 (m, 1H), 3.02-2.50 (m, 3H), 2.35-2.19 (m, 1H), 2.08 (dq, J=12.5, 6.3 Hz, 1H), 1.91-1.70 (m, 2H), 1.65-1.07 (m, 2H). 1.05-0.88 (m, 6H); MS (ESI(+)) m/e 456 (M+H)$^+$.

Example 750

N-(4-{1-[2-(piperazin-1-yl)ethyl]-1H-pyrazol-4-yl}phenyl)-1-(pyridazin-3-yl)azetidine-3-carboxamide

Example 750A tert-butyl 4-(2-(4-(4-(1-(pyridazin-3-yl)azetidine-3-carboxamido)phenyl)-1H-pyrazol-1-yl)ethyl)piperazine-1-carboxylate The title compound was prepared as described in Example 148A, substituting tert-butyl 4-(2-(4-(4,4,5,5-tetramethyl-1,3,2-dioxaborolan-2-yl)-1H-pyrazol-1-yl)ethyl)piperazine-1-carboxylate for 1-isobutyl-4-(4,4,5,5-tetramethyl-1,3,2-dioxaborolan-2-yl)-1H-pyrazole and N-(4-bromophenyl)-1-(pyridazin-3-yl)azetidine-3-carboxamide for 4-bromoaniline.

Example 750B

N-(4-{1-[2-(piperazin-1-yl)ethyl]-1H-pyrazol-4-yl}phenyl)-1-(pyridazin-3-yl)azetidine-3-carboxamide The title compound was prepared as described in Example 1D, substituting tert-butyl 4-(2-(4-(4-(1-(pyridazin-3-yl)azetidine-3-carboxamido)phenyl)-1H-pyrazol-1-yl)ethyl)piperazine-1-carboxylate for tert-butyl 4-(4-(1-(pyridin-3-yl)azetidine-3-carboxamido)phenoxy)piperidine-1-carboxylate. $^1$H NMR (300 MHz, DMSO-d$_6$) δ ppm 10.20 (s, 1H), 8.71 (s, 2H), 8.57 (dd, J=4.3, 1.0 Hz, 1H), 8.14 (s, 1H), 7.86 (s, 1H), 7.80 (dd, J=9.4, 4.4 Hz, 1H), 7.66-7.58 (m, 2H), 7.57-7.49 (m, 2H), 7.45 (d, J=9.2 Hz, 1H), 4.56-4.36 (m, 4H), 4.31 (t, J=6.3 Hz, 2H), 3.91-3.73 (m, 1H), 3.25-3.09 (m, 4H), 3.04 (t, J=6.1 Hz, 2H), 2.83 (s, 4H); MS (ESI(+)) m/e 433 (M+H)$^+$.

Example 751

N-{4-[1-(2,2-dimethylpropyl)-1H-pyrazol-4-yl]phenyl}-1-(pyridazin-3-yl)azetidine-3-carboxamide The title compound was prepared as described in Example 148A, substituting 1-neopentyl-4-(4,4,5,5-tetramethyl-1,3,2-dioxaborolan-2-yl)-1H-pyrazole for 1-isobutyl-4-(4,4,5,5-tetramethyl-1,3,2-dioxaborolan-2-yl)-1H-pyrazole and N-(4-bromophenyl)-1-(pyridazin-3-yl)azetidine-3-carboxamide for 4-bromoaniline. $^1$H NMR (500 MHz, DMSO-d$_6$) δ ppm 10.14 (s, 1H), 8.57 (dd, J=4.5, 1.2 Hz, 1H), 8.05 (s, 1H), 7.82 (s, 1H), 7.66-7.58 (m, 2H), 7.55-7.51 (m, 2H), 7.48 (dd, J=9.1, 4.5 Hz, 1H), 6.98 (dd, J=9.1, 1.1 Hz, 1H), 4.30 (t, J=8.6 Hz, 2H), 4.22 (dd, J=8.4, 6.0 Hz, 2H), 3.90 (s, 2H), 3.77 (tt, J=8.6, 5.9 Hz, 1H), 0.92 (s, 9H); MS (ESI(+)) m/e 391 (M+H)$^+$.

Example 752

4-[1-(2-methylpropanoyl)piperidin-4-yl]-N-[(3S)-1-(pyridazin-3-yl)pyrrolidin-3-yl]benzamide The title compound was prepared as described in Example 147B, substituting N-[(3S)-1-(6-chloropyridazin-3-yl)pyrrolidin-3-yl]-4-[1-(2-methylpropanoyl)piperidin-4-yl]benzamide for 4-(4-(1-(6-chloropyridazin-3-yl)azetidine-3-carboxamido)phenyl)piperidine-1-carboxylate. $^1$H NMR (400 MHz, DMSO-d$_6$) δ ppm 8.69 (d, J=6.6 Hz, 1H), 8.57 (dd, J=4.3, 1.2 Hz, 1H), 8.16-7.75 (m, 3H), 7.69 (dd, J=9.5, 1.2 Hz, 1H), 7.37-7.31 (m, 2H), 4.90-4.41 (m, 2H), 4.33-3.60 (m, 5H), 3.20-2.50 (m, 4H), 2.37-2.14 (m, 2H), 1.87-1.74 (m, 2H), 1.63-1.20 (m, 2H), 1.02 (bs, J=7.4 Hz, 6H); MS (ESI(+)) m/e 422 (M+H)$^+$.

Example 753

N-{4-[1-(2-hydroxy-2-methylpropyl)-1H-pyrazol-4-yl]phenyl}-1-(pyridazin-3-yl)azetidine-3-carboxamide The title compound was prepared as described in Example 148A, substituting 2-methyl-1-(4-(4,4,5,5-tetramethyl-1,3,2-dioxaborolan-2-yl)-1H-pyrazol-1-yl)propan-2-ol for 1-isobutyl-4-(4,4,5,5-tetramethyl-1,3,2-dioxaborolan-2-yl)-1H-pyrazole and N-(4-bromophenyl)-1-(pyridazin-3-yl)azetidine-3-carboxamide for 4-bromoaniline. $^1$H NMR (300 MHz, DMSO-d$_6$) δ ppm 10.09 (s, 1H), 8.56 (dd, J=4.5, 1.3 Hz, 1H), 8.01 (s, 1H), 7.81 (s, 1H), 7.69-7.57 (m, 2H), 7.57-7.44 (m, 2H), 7.38 (dd, J=9.0, 4.5 Hz, 1H), 6.83 (dd, J=9.0, 1.3 Hz, 1H), 4.70 (s, 1H), 4.25 (t, J=8.4 Hz, 2H), 4.16 (dd, J=8.0, 6.0 Hz, 2H), 4.01 (s, 2H), 3.74 (tt, J=8.5, 6.0 Hz, 1H), 1.08 (s, 6H); MS (ESI(+)) m/e 393 (M+H)$^+$.

Example 754

5-[1-(3-fluorobenzoyl)piperidin-4-yl]-N-[(3S)-1-(pyridazin-3-yl)pyrrolidin-3-yl]thiophene-2-carboxamide

Example 754A (S)-tert-butyl (1-(pyridazin-3-yl)pyrrolidin-3-yl)carbamate

The title compound was prepared as described in Example 147B, substituting (S)-tert-butyl (1-(6-chloropyridazin-3-yl)pyrrolidin-3-yl)carbamate for 4-(4-(1-(6-chloropyridazin-3-yl)azetidine-3-carboxamido)phenyl)piperidine-1-carboxylate.

Example 754B (S)-1-(pyridazin-3-yl)pyrrolidin-3-amine

The title compound was prepared as described in Example 1D, substituting (S)-tert-butyl (1-(pyridazin-3-yl)pyrrolidin-3-yl)carbamate for tert-butyl 4-(4-(1-(pyridin-3-yl)azetidine-3-carboxamido)phenoxy)piperidine-1-carboxylate.

Example 754C 5-(1-(tert-butoxycarbonyl)-1,2,3,6-tetrahydropyridin-4-yl)thiophene-2-carboxylic acid The title compound was prepared as described in Example 148A, substituting tert-butyl 4-(4,4,5,5-tetramethyl-1,3,2-dioxaborolan-2-yl)-5,6-dihydropyridine-1(2H)-carboxylate for 1-isobutyl-4-(4,4,5,5-tetramethyl-1,3,2-dioxaborolan-2-yl)-1H-pyrazole and 5-bromothiophene-2-carboxylic acid for 4-bromoaniline.

Example 754D 5-(1-(tert-butoxycarbonyl)piperidin-4-yl)thiophene-2-carboxylic acid The title compound was prepared as described in Example 1B, substituting 5-(1-(tert-butoxycarbonyl)-1,2,3,6-tetrahydropyridin-4-yl)thiophene-2-carboxylic acid for tert-butyl 4-(4-(1-(benzyloxycarbonyl)azetidine-3-carboxamido)phenoxy)piperidine-1-carboxylate.

Example 754E (S)-tert-butyl 4-(5-((1-(pyridazin-3-yl)pyrrolidin-3-yl)carbamoyl)thiophen-2-yl)piperidine-1-carboxylate The title compound was prepared as described in Example 1A, substituting (S)-1-(pyridazin-3-yl)pyrrolidin-3-amine for tert-butyl 4-(4-aminophenoxy)piperidine-1-carboxylate and 5-(1-(tert-butoxycarbonyl)piperidin-4-yl)thiophene-2-carboxylic acid for 1-(benzyloxycarbonyl)azetidine-3-carboxylic acid.

Example 754F (S)-5-(piperidin-4-yl)-N-(1-(pyridazin-3-yl)pyrrolidin-3-yl)thiophene-2-carboxamide The title compound was prepared as described in Example 1D, substituting (S)-tert-butyl 4-(5-((1-(pyridazin-3-yl)pyrrolidin-3-yl)carbamoyl)thiophen-2-yl)piperidine-1-carboxylate for tert-butyl 4-(4-(1-(pyridin-3-yl)azetidine-3-carboxamido)phenoxy)piperidine-1-carboxylate.

Example 754G

5-[1-(3-fluorobenzoyl)piperidin-4-yl]-N-[(3S)-1-(pyridazin-3-yl)pyrrolidin-3-yl]thiophene-2-carboxamide The title compound was prepared as described in Example 1A, substituting (S)-5-(piperidin-4-yl)-N-(1-(pyridazin-3-yl)pyrrolidin-3-yl)thiophene-2-carboxamide for tert-butyl 4-(4-aminophenoxy)piperidine-1-carboxylate and 3-fluorobenzoic acid for 1-(benzyloxycarbonyl)azetidine-3-carboxylic acid. $^1$H NMR (300 MHz, DMSO-$d_6$) δ ppm 8.63-8.44 (m, 2H), 7.66 (d, J=3.8 Hz, 1H), 7.58-7.44 (m, 1H), 7.41-7.19 (m, 4H), 6.95 (d, J=3.8 Hz, 1H), 6.87 (dd, J=9.1, 1.4 Hz, 1H), 4.66-4.19 (m, 2H), 3.85-3.38 (m, 5H), 3.20-2.72 (m, 3H), 2.34-2.15 (m, 1H), 2.17-1.78 (m, 3H), 1.72-1.46 (m, 2H); MS (ESI(+)) m/e 480 (M+H)$^+$.

TABLE 14

The following Examples were essentially prepared as described in Example 754, substituting an appropriate carboxylic acid in Example 754G.

| Ex | Name | MS |
|---|---|---|
| 755 | 5-[1-(4-fluorobenzoyl)piperidin-4-yl]-N-[(3S)-1-(pyridazin-3-yl)pyrrolidin-3-yl]thiophene-2-carboxamide | (ESI(+)) m/e 480 (M + H)$^+$ |
| 758 | N-[(3S)-1-(pyridazin-3-yl)pyrrolidin-3-yl]-5-[1-(tetrahydro-2H-pyran-4-ylcarbonyl)piperidin-4-yl]thiophene-2-carboxamide | (ESI(+)) m/e 470 (M + H)$^+$ |
| 760 | 5-[1-(2-methylpropanoyl)piperidin-4-yl]-N-[(3S)-1-(pyridazin-3-yl)pyrrolidin-3-yl]thiophene-2-carboxamide | (ESI(+)) m/e 428 (M + H)$^+$ |
| 761 | 5-[1-(2,4-difluorobenzoyl)piperidin-4-yl]-N-[(3S)-1-(pyridazin-3-yl)pyrrolidin-3-yl]thiophene-2-carboxamide | (ESI(+)) m/e 498 (M + H)$^+$ |
| 762 | 5-{1-[(2-methylcyclopropyl)carbonyl]piperidin-4-yl}-N-[(3S)-1-(pyridazin-3-yl)pyrrolidin-3-yl]thiophene-2-carboxamide | (ESI(+)) m/e 440 (M + H)$^+$ |
| 763 | 5-[1-(2-fluorobenzoyl)piperidin-4-yl]-N-[(3S)-1-(pyridazin-3-yl)pyrrolidin-3-yl]thiophene-2-carboxamide | (ESI(+)) m/e 480 (M + H)$^+$ |
| 764 | 5-(1-benzoylpiperidin-4-yl)-N-[(3S)-1-(pyridazin-3-yl)pyrrolidin-3-yl]thiophene-2-carboxamide | (ESI(+)) m/e 462 (M + H)$^+$ |
| 765 | N-[(3S)-1-(pyridazin-3-yl)pyrrolidin-3-yl]-5-[1-(tetrahydrofuran-3-ylcarbonyl)piperidin-4-yl]thiophene-2-carboxamide | (ESI(+)) m/e 456 (M + H)$^+$ |
| 766 | N-[(3S)-1-(pyridazin-3-yl)pyrrolidin-3-yl]-5-{1-[(2R)-tetrahydrofuran-2-ylcarbonyl]piperidin-4-yl}thiophene-2-carboxamide | (ESI(+)) m/e 456 (M + H)$^+$ |
| 767 | 5-{1-[(1-methylpiperidin-4-yl)acetyl]piperidin-4-yl}-N-[(3S)-1-(pyridazin-3-yl)pyrrolidin-3-yl]thiophene-2-carboxamide | (ESI(+)) m/e 498 (M + H)$^+$ |
| 768 | N-[(3S)-1-(pyridazin-3-yl)pyrrolidin-3-yl]-5-[1-(1,3-thiazol-4-ylcarbonyl)piperidin-4-yl]thiophene-2-carboxamide | (ESI(+)) m/e 469 (M + H)$^+$ |
| 1013 | 5-[1-(2,2-dimethylpropanoyl)piperidin-4-yl]-N-[(3S)-1-(pyridazin-3-yl)pyrrolidin-3-yl]thiophene-2-carboxamide | (ESI(+)) m/e 442 (M + H)$^+$ |

TABLE 14-continued

The following Examples were essentially prepared as described in Example 754, substituting an appropriate carboxylic acid in Example 754G.

| Ex | Name | MS |
|---|---|---|
| 1014 | 5-[1-(3,3-dimethylbutanoyl)piperidin-4-yl]-N-[(3S)-1-(pyridazin-3-yl)pyrrolidin-3-yl]thiophene-2-carboxamide | (ESI(+)) m/e 456 (M + H)$^+$ |
| 1015 | 5-[1-(2,2-dimethylbutanoyl)piperidin-4-yl]-N-[(3S)-1-(pyridazin-3-yl)pyrrolidin-3-yl]thiophene-2-carboxamide | (ESI(+)) m/e 456 (M + H)$^+$ |
| 1016 | 5-{1-[(1-methylcyclopropyl)carbonyl]piperidin-4-yl}-N-[(3S)-1-(pyridazin-3-yl)pyrrolidin-3-yl]thiophene-2-carboxamide | (ESI(+)) m/e 440 (M + H)$^+$ |
| 1017 | N-[(3S)-1-(pyridazin-3-yl)pyrrolidin-3-yl]-5-[1-(3,3,3-trifluoropropanoyl)piperidin-4-yl]thiophene-2-carboxamide | (ESI(+)) m/e 468 (M + H)$^+$ |
| 1018 | 5-[1-(cyclopropylacetyl)piperidin-4-yl]-N-[(3S)-1-(pyridazin-3-yl)pyrrolidin-3-yl]thiophene-2-carboxamide | (ESI(+)) m/e 440 (M + H)$^+$ |
| 1019 | 5-[1-(bicyclo[2.2.1]hept-2-ylacetyl)piperidin-4-yl]-N-[(3S)-1-(pyridazin-3-yl)pyrrolidin-3-yl]thiophene-2-carboxamide | (ESI(+)) m/e 494 (M + H)$^+$ |

Example 756

(3S)—N-(4-{1-[(4-methyltetrahydro-2H-pyran-4-yl)methyl]-1H-pyrazol-4-yl}phenyl)-1-(pyridazin-3-yl)pyrrolidine-3-carboxamide

Example 756A (S)-1-(6-chloropyridazin-3-yl)pyrrolidine-3-carboxylic acid

The title compound was prepared as described in Example 147A, substituting (S)-pyrrolidine-3-carboxylic acid for tert-butyl 4-(4-(azetidine-3-carboxamido)phenyl)piperidine-1-carboxylate.

Example 756B (S)-1-(pyridazin-3-yl)pyrrolidine-3-carboxylic acid

The title compound was prepared as described in Example 147B, substituting (S)-1-(6-chloropyridazin-3-yl)pyrrolidine-3-carboxylic acid for 4-(4-(1-(6-chloropyridazin-3-yl)azetidine-3-carboxamido)phenyl)piperidine-1-carboxylate.

Example 756C (S)—N-(4-bromophenyl)-1-(pyridazin-3-yl)pyrrolidine-3-carboxamide The title compound was prepared as described in Example 1A, substituting 4-bromoaniline for tert-butyl 4-(4-aminophenoxy)piperidine-1-carboxylate and (S)-1-(pyridazin-3-yl)pyrrolidine-3-carboxylic acid for 1-(benzyloxycarbonyl)azetidine-3-carboxylic acid.

Example 756D (3S)—N-(4-{1-[(4-methyltetrahydro-2H-pyran-4-yl)methyl]-1H-pyrazol-4-yl}phenyl)-1-(pyridazin-3-yl)pyrrolidine-3-carboxamide The title compound was prepared as described in Example 148A, substituting 1-((4-methyltetrahydro-2H-pyran-4-yl)methyl)-4-(4,4,5,5-tetramethyl-1,3,2-dioxaborolan-2-yl)-1H-pyrazole for 1-isobutyl-4-(4,4,5,5-tetramethyl-1,3,2-dioxaborolan-2-yl)-1H-pyrazole and (S)—N-(4-bromophenyl)-1-(pyridazin-3-yl)pyrrolidine-3-carboxamide for 4-bromoaniline. $^1$H NMR (300 MHz, DMSO-d$_6$) δ ppm 10.11 (s, 1H), 8.48 (dd, J=4.5, 1.2 Hz, 1H), 8.07 (s, 1H), 7.82 (s, 1H), 7.64-7.58 (m, 2H), 7.54-7.49 (m, 2H), 7.34 (dd, J=9.1, 4.4 Hz, 1H), 6.88 (dd, J=9.2, 1.3 Hz, 1H), 4.02 (s, 2H), 3.78 (dd, J=10.5, 7.9 Hz, 1H), 3.72-3.58 (m, 4H), 3.56-3.45 (m, 3H), 3.37-3.32 (m, 1H), 2.42-2.09 (m, 2H), 1.51 (ddd, J=13.4, 9.1, 4.2 Hz, 2H), 1.32-1.12 (m, 2H), 0.97 (s, 3H); MS (ESI(+)) m/e 447 (M+H)$^+$.

TABLE 15

The following Examples were essentially prepared as described in Example 756, substituting an appropriate boronate in Example 756D.

| Ex | Name | MS |
|---|---|---|
| 757 | (3S)-N-{4-[1-(2-hydroxy-2-methylpropyl)-1H-pyrazol-4-yl]phenyl}-1-(pyridazin-3-yl)pyrrolidine-3-carboxamide | (ESI(+)) m/e 407 (M + H)$^+$ |
| 759 | (3S)-N-{4-[1-(2,2-dimethylpropyl)-1H-pyrazol-4-yl]phenyl}-1-(pyridazin-3-yl)pyrrolidine-3-carboxamide | (ESI(+)) m/e 405 (M + H)$^+$ |
| 769 | (3S)-N-{4-[1-(2-methylpropyl)-1H-pyrazol-4-yl]phenyl}-1-(pyridazin-3-yl)pyrrolidine-3-carboxamide | (ESI(+)) m/e 391 (M + H)$^+$ |

TABLE 15-continued

The following Examples were essentially prepared as described in Example 756, substituting an appropriate boronate in Example 756D.

| Ex | Name | MS |
|---|---|---|
| 770 | (3S)-N-{4-[1-(propan-2-yl)-1H-pyrazol-4-yl]phenyl}-1-(pyridazin-3-yl)pyrrolidine-3-carboxamide | (ESI(+)) m/e 377 (M + H)+ |
| 771 | (3S)-N-{4-[1-(cyclopropylmethyl)-1H-pyrazol-4-yl]phenyl}-1-(pyridazin-3-yl)pyrrolidine-3-carboxamide | (ESI(+)) m/e 389 (M + H)+ |
| 772 | (3S)-1-(pyridazin-3-yl)-N-{4-[1-(tetrahydro-2H-pyran-2-ylmethyl)-1H-pyrazol-4-yl]phenyl}pyrrolidine-3-carboxamide | (ESI(+)) m/e 433 (M + H)+ |
| 773 | (3S)-N-[4-(1-tert-butyl-1H-pyrazol-4-yl)phenyl]-1-(pyridazin-3-yl)pyrrolidine-3-carboxamide | (ESI(+)) m/e 391 (M + H)+ |

Example 774

(3S)—N-(4-{[(3R)-1-benzoylpyrrolidin-3-yl]oxy}phenyl)-1-(pyridazin-3-yl)pyrrolidine-3-carboxamide

Example 774A (R)-tert-butyl 3-(4-((S)-1-(pyridazin-3-yl)pyrrolidine-3-carboxamido)phenoxy)pyrrolidine-1-carboxylate The title compound was prepared as described in Example 1A, substituting (R)-tert-butyl 3-(4-aminophenoxy)pyrrolidine-1-carboxylate for tert-butyl 4-(4-aminophenoxy)piperidine-1-carboxylate and (S)-1-(pyridazin-3-yl)pyrrolidine-3-carboxylic acid for 1-(benzyloxycarbonyl)azetidine-3-carboxylic acid.

Example 774B (S)-1-(pyridazin-3-yl)-N-(4-((R)-pyrrolidin-3-yloxy)phenyl)pyrrolidine-3-carboxamide The title compound was prepared as described in Example 1D, substituting (R)-tert-butyl 3-(4-((S)-1-(pyridazin-3-yl)pyrrolidine-3-carboxamido)phenoxy)pyrrolidine-1-carboxylate for tert-butyl 4-(4-(1-(pyridin-3-yl)azetidine-3-carboxamido)phenoxy)piperidine-1-carboxylate.

Example 774C (3S)—N-(4-{[(3R)-1-benzoylpyrrolidin-3-yl]oxy}phenyl)-1-(pyridazin-3-yl)pyrrolidine-3-carboxamide The title compound was prepared as described in Example 1A, substituting (S)-1-(pyridazin-3-yl)-N-(4-((R)-pyrrolidin-3-yloxy)phenyl)pyrrolidine-3-carboxamide for tert-butyl 4-(4-aminophenoxy)piperidine-1-carboxylate and benzoic acid for 1-(benzyloxycarbonyl)azetidine-3-carboxylic acid. $^1$H NMR (400 MHz, DMSO-d$_6$) δ ppm 10.03 (d, J=18.3 Hz, 1H), 8.51 (d, J=4.2 Hz, 1H), 7.46 (tdt, J=21.9, 19.2, 10.8 Hz, 8H), 7.13-7.02 (m, 1H), 6.96 (d, J=8.9 Hz, 1H), 6.86 (d, J=8.9 Hz, 1H), 5.00 (d, J=34.1 Hz, 1H), 3.88-3.74 (m, 2H), 3.65 (dd, J=12.1, 7.4 Hz, 4H), 3.51 (d, J=7.3 Hz, 2H), 2.37-1.98 (m, 4H), MS (ESI(+)) m/e 458 (M+H)+.

TABLE 16

The following Examples were essentially prepared as described in Example 774, substituting an appropriate carboxylic acid in Example 774C.

| Ex | Name | MS |
|---|---|---|
| 775 | (3S)-N-(4-{[(3R)-1-(2-fluorobenzoyl)pyrrolidin-3-yl]oxy}phenyl)-1-(pyridazin-3-yl)pyrrolidine-3-carboxamide | (ESI(+)) m/e 476 (M + H)+ |
| 776 | (3S)-N-(4-{[(3R)-1-(3-fluorobenzoyl)pyrrolidin-3-yl]oxy}phenyl)-1-(pyridazin-3-yl)pyrrolidine-3-carboxamide | (ESI(+)) m/e 476 (M + H)+ |
| 777 | (3S)-N-(4-{[(3R)-1-(4-fluorobenzoyl)pyrrolidin-3-yl]oxy}phenyl)-1-(pyridazin-3-yl)pyrrolidine-3-carboxamide | (ESI(+)) m/e 476 (M + H)+ |
| 778 | (3S)-N-(4-{[(3R)-1-(3,5-difluorobenzoyl)pyrrolidin-3-yl]oxy}phenyl)-1-(pyridazin-3-yl)pyrrolidine-3-carboxamide | (ESI(+)) m/e 494 (M + H)+ |
| 779 | (3S)-N-(4-{[(3R)-1-(2-methylbenzoyl)pyrrolidin-3-yl]oxy}phenyl)-1-(pyridazin-3-yl)pyrrolidine-3-carboxamide | (ESI(+)) m/e 472 (M + H)+ |
| 780 | (3S)-N-(4-{[(3R)-1-(2,2-dimethylpropanoyl)pyrrolidin-3-yl]oxy}phenyl)-1-(pyridazin-3-yl)pyrrolidine-3-carboxamide | (ESI(+)) m/e 438 (M + H)+ |
| 781 | (3S)-N-[4-({(3R)-1-[(4,4-difluorocyclohexyl)carbonyl]pyrrolidin-3-yl}oxy)phenyl]-1-(pyridazin-3-yl)pyrrolidine-3-carboxamide | (ESI(+)) m/e 500 (M + H)+ |

TABLE 16-continued

The following Examples were essentially prepared as described in Example 774, substituting an appropriate carboxylic acid in Example 774C.

| Ex | Name | MS |
|---|---|---|
| 782 | (3S)-1-(pyridazin-3-yl)-N-(4-{[(3R)-1-(4,4,4-trifluorobutanoyl)pyrrolidin-3-yl]oxy}phenyl)pyrrolidine-3-carboxamide | (ESI(+)) m/e 478 (M + H)$^+$ |
| 783 | (3S)-N-(4-{[(3R)-1-(2,4-difluorobenzoyl)pyrrolidin-3-yl]oxy}phenyl)-1-(pyridazin-3-yl)pyrrolidine-3-carboxamide | (ESI(+)) m/e 494 (M + H)$^+$ |

Example 784

N-[4-(5-propyl-1,2,4-oxadiazol-3-yl)phenyl]-1-(pyridazin-3-yl)azetidine-3-carboxamide The title compound was prepared as described in Example 806, substituting butanoyl chloride for 3,3-dimethylbutanoyl chloride in Example 806A. $^1$H NMR (300 MHz, DMSO-d$_6$) δ ppm 10.39 (s, 1H), 8.57 (dd, J=4.5, 1.3 Hz, 1H), 8.04-7.89 (m, 2H), 7.89-7.74 (m, 2H), 7.38 (dd, J=9.0, 4.5 Hz, 1H), 6.84 (dd, J=8.9, 1.4 Hz, 1H), 4.26 (t, J=8.4 Hz, 2H), 4.18 (dd, J=8.2, 5.9 Hz, 2H), 3.79 (tt, J=8.6, 5.9 Hz, 1H), 2.96 (t, J=7.4 Hz, 2H), 1.81 (h, J=7.4 Hz, 2H), 0.99 (t, J=7.4 Hz, 3H); MS (ESI(+)) m/e 365 (M+H)$^+$.

Example 785

(3S)—N-{4-[1-(2-fluorobenzoyl)azetidin-3-yl]phenyl}-1-(pyridazin-3-yl)pyrrolidine-3-carboxamide

Example 785A

(S)-tert-butyl 3-(4-(1-(pyridazin-3-yl)pyrrolidine-3-carboxamido)phenyl)azetidine-1-carboxylate The title compound was prepared as described in Example 1A, substituting tert-butyl 3-(4-aminophenyl)azetidine-1-carboxylate for tert-butyl 4-(4-aminophenoxy)piperidine-1-carboxylate and substituting (S)-1-(pyridazin-3-yl)pyrrolidine-3-carboxylic acid for 1-(benzyloxycarbonyl)azetidine-3-carboxylic acid.

Example 785B

(S)—N-(4-(azetidin-3-yl)phenyl)-1-(pyridazin-3-yl)pyrrolidine-3-carboxamide The title compound was prepared as described in Example 1D, substituting (S)-tert-butyl 3-(4-(1-(pyridazin-3-yl)pyrrolidine-3-carboxamido)phenyl)azetidine-1-carboxylate for tert-butyl 4-(4-(1-(pyridin-3-yl)azetidine-3-carboxamido)phenoxy)piperidine-1-carboxylate.

Example 785C

(3S)—N-{4-[1-(2-fluorobenzoyl)azetidin-3-yl]phenyl}-1-(pyridazin-3-yl)pyrrolidine-3-carboxamide The title compound was prepared as described in Example 1A, substituting (S)—N-(4-(azetidin-3-yl)phenyl)-1-(pyridazin-3-yl)pyrrolidine-3-carboxamide for tert-butyl 4-(4-aminophenoxy)piperidine-1-carboxylate and 2-fluorobenzoic acid for 1-(benzyloxycarbonyl)azetidine-3-carboxylic acid. $^1$H NMR (500 MHz, DMSO-d$_6$) δ ppm 10.15 (bs, 1H), 8.51-8.46 (m, 1H), 7.67-7.40 (m, 4H), 7.40-7.24 (m, 5H), 6.90-6.85 (m, 1H), 4.50-4.42 (m, 1H), 4.41-4.34 (m, 1H), 4.02-3.96 (m, 2H), 3.93-3.83 (m, 1H), 3.81-3.73 (m, 1H), 3.67-3.58 (m, 2H), 3.53-3.44 (m, 1H), 3.40-3.30 (m, 1H), 2.43-2.12 (m, 2H); MS (ESI(+)) m/e 446 (M+H)$^+$.

TABLE 17

The following Examples were essentially prepared as described in Example 785, substituting an appropriate carboxylic acid in Example 785C.

| Ex | Name | MS |
|---|---|---|
| 786 | (3S)-N-{4-[1-(3-fluorobenzoyl)azetidin-3-yl]phenyl}-1-(pyridazin-3-yl)pyrrolidine-3-carboxamide | (ESI(+)) m/e 446 (M + H)$^+$ |
| 787 | (3S)-N-{4-[1-(4-fluorobenzoyl)azetidin-3-yl]phenyl}-1-(pyridazin-3-yl)pyrrolidine-3-carboxamide | (ESI(+)) m/e 446 (M + H)$^+$ |
| 788 | (3S)-N-[4-(1-benzoylazetidin-3-yl)phenyl]-1-(pyridazin-3-yl)pyrrolidine-3-carboxamide | (ESI(+)) m/e 428 (M + H)$^+$ |
| 789 | (3S)-N-{4-[1-(2,2-dimethylpropanoyl)azetidin-3-yl]phenyl}-1-(pyridazin-3-yl)pyrrolidine-3-carboxamide | (ESI(+)) m/e 408 (M + H)$^+$ |
| 790 | (3S)-N-{4-[1-(3,5-difluorobenzoyl)azetidin-3-yl]phenyl}-1-(pyridazin-3-yl)pyrrolidine-3-carboxamide | (ESI(+)) m/e 464 (M + H)$^+$ |
| 791 | 3S)-N-{4-[1-(2-methylbenzoyl)azetidin-3-yl]phenyl}-1-(pyridazin-3-yl)pyrrolidine-3-carboxamide | (ESI(+)) m/e 442 (M + H)$^+$ |

TABLE 17-continued

The following Examples were essentially prepared as described in Example 785, substituting an appropriate carboxylic acid in Example 785C.

| Ex | Name | MS |
|---|---|---|
| 792 | (3S)-N-{4-[1-(2,4-difluorobenzoyl)azetidin-3-yl]phenyl}-1-(pyridazin-3-yl)pyrrolidine-3-carboxamide | (ESI(+)) m/e 464 (M + H)+ |

Example 793

(3R)—N-[4-(1-benzoylpiperidin-4-yl)phenyl]-1-(pyridazin-3-yl)pyrrolidine-3-carboxamide

Example 793A (R)-1-(6-chloropyridazin-3-yl)pyrrolidine-3-carboxylic acid

The title compound was prepared as described in Example 147A, substituting (R)-pyrrolidine-3-carboxylic acid for tert-butyl 4-(4-(azetidine-3-carboxamido)phenyl)piperidine-1-carboxylate.

Example 793B (R)-1-(pyridazin-3-yl)pyrrolidine-3-carboxylic acid

The title compound was prepared as described in Example 147B, substituting (R)-1-(6-chloropyridazin-3-yl)pyrrolidine-3-carboxylic acid for 4-(4-(1-(6-chloropyridazin-3-yl)azetidine-3-carboxamido)phenyl)piperidine-1-carboxylate.

Example 793C (R)-tert-butyl 4-(4-(1-(pyridazin-3-yl)pyrrolidine-3-carboxamido)phenyl)piperidine-1-carboxylate The title compound was prepared as described in Example 1A, substituting tert-butyl 4-(4-aminophenyl)piperidine-1-carboxylate for tert-butyl 4-(4-aminophenoxy)piperidine-1-carboxylate and (R)-1-(pyridazin-3-yl)pyrrolidine-3-carboxylic acid for 1-(benzyloxycarbonyl)azetidine-3-carboxylic acid.

Example 793D (R)—N-(4-(piperidin-4-yl)phenyl)-1-(pyridazin-3-yl)pyrrolidine-3-carboxamide The title compound was prepared as described in Example 1D, substituting (R)-tert-butyl 4-(4-(1-(pyridazin-3-yl)pyrrolidine-3-carboxamido)phenyl)piperidine-1-carboxylate for tert-butyl 4-(4-(1-(pyridin-3-yl)azetidine-3-carboxamido)phenoxy)piperidine-1-carboxylate.

Example 793E (3R)—N-[4-(1-benzoylpiperidin-4-yl)phenyl]-1-(pyridazin-3-yl)pyrrolidine-3-carboxamide The title compound was prepared as described in Example 1A, substituting (R)—N-(4-(piperidin-4-yl)phenyl)-1-(pyridazin-3-yl)pyrrolidine-3-carboxamide for tert-butyl 4-(4-aminophenoxy)piperidine-1-carboxylate and benzoic acid for 1-(benzyloxycarbonyl)azetidine-3-carboxylic acid. $^1$H NMR (400 MHz, DMSO-d$_6$) δ ppm 10.06 (s, 1H), 8.48 (dd, J=4.4, 0.9 Hz, 1H), 7.54 (t, J=6.3 Hz, 2H), 7.47-7.40 (m, 5H), 7.35 (dd, J=9.1, 4.5 Hz, 1H), 7.22 (d, J=8.6 Hz, 2H), 6.89 (dd, J=9.2, 1.1 Hz, 1H), 4.62 (s, 1H), 3.75 (dt, J=25.9, 12.9 Hz, 1H), 3.62 (td, J=10.2, 5.8 Hz, 3H), 3.55-3.41 (m, 1H), 3.13 (s, 1H), 2.98-2.69 (m, 2H), 2.39-2.11 (m, 2H), 1.90-1.48 (m, 4H), MS (ESI(+)) m/e 456 (M+H)+.

Example 794

(3R)—N-{4-[1-(2-fluorobenzoyl)piperidin-4-yl]phenyl}-1-(pyridazin-3-yl)pyrrolidine-3-carboxamide The title compound was prepared as described in Example 1A, substituting (R)—N-(4-(piperidin-4-yl)phenyl)-1-(pyridazin-3-yl)pyrrolidine-3-carboxamide for tert-butyl 4-(4-aminophenoxy)piperidine-1-carboxylate and 2-fluorobenzoic acid for 1-(benzyloxycarbonyl)azetidine-3-carboxylic acid. $^1$H NMR (300 MHz, DMSO-d$_6$) δ ppm 10.06 (s, 1H), 8.48 (dd, J=4.5, 1.2 Hz, 1H), 7.59-7.40 (m, 4H), 7.41-7.23 (m, 3H), 7.19 (d, J=8.5 Hz, 2H), 6.89 (dd, J=9.2, 1.2 Hz, 1H), 4.66 (d, J=13.1 Hz, 1H), 3.77 (dd, J=10.5, 7.9 Hz, 1H), 3.73-3.56 (m, 2H), 3.48 (dt, J=10.2, 7.4 Hz, 2H), 3.17 (t, J=12.1 Hz, 1H), 2.82 (dt, J=24.1, 11.3 Hz, 2H), 2.38-2.09 (m, 2H), 1.97-1.79 (m, 1H), 1.69 (t, J=17.4 Hz, 1H), 1.52 (ddd, J=20.9, 12.0, 6.1 Hz, 2H), MS (ESI(+)) m/e 474 (M+H)+.

Example 795

(3R)—N-{4-[1-(2,2-dimethylpropanoyl)piperidin-4-yl]phenyl}-1-(pyridazin-3-yl)pyrrolidine-3-carboxamide The title compound was prepared as described in Example 1A, substituting (R)—N-(4-(piperidin-4-yl)phenyl)-1-(pyridazin-3-yl)pyrrolidine-3-carboxamide for tert-butyl 4-(4-aminophenoxy)piperidine-1-carboxylate and 2,2-dimethylpropanoic acid for 1-(benzyloxycarbonyl)azetidine-3-carboxylic acid. $^1$H NMR (300 MHz, DMSO-d$_6$) δ ppm 10.04 (s, 1H), 8.48 (dd, J=4.5, 1.3 Hz, 1H), 7.54 (t, J=6.4 Hz, 1H), 7.34 (dd, J=9.1, 4.5 Hz, 1H), 7.21-7.14 (m, 2H), 6.87 (dd, J=9.1, 1.3 Hz, 1H), 4.46-4.35 (m, 2H), 3.76 (dd, J=10.5, 7.9 Hz, 1H), 3.69-3.54 (m, 2H), 3.48 (dt, J=10.2, 7.4 Hz, 1H), 2.94-2.63 (m, 3H), 2.39-2.07 (m, 2H), 1.83-1.73 (m, 2H), 1.50 (s, 1H), 1.22 (s, 9H), MS (ESI(+)) m/e 436 (M+H)$^{-1}$.

Example 796

(3S)—N-(4-{[1-(cyclohexylcarbonyl)piperidin-4-yl]oxy}phenyl)-1-(pyridazin-3-yl)pyrrolidine-3-carboxamide

Example 796A (S)-tert-butyl 4-(4-(1-(pyridazin-3-yl)pyrrolidine-3-carboxamido)phenoxy)piperidine-1-carboxylate The title compound was prepared as described in Example 1A, substituting tert-butyl 4-(4-aminophenoxy)piperidine-1-carboxylate for tert-butyl 4-(4-aminophenoxy)piperidine-1- carboxylate and (S)-1-(pyridazin-3-yl)pyrrolidine-3-carboxylic acid for 1-(benzyloxycarbonyl)azetidine-3-carboxylic acid.

Example 796B (S)—N-(4-(piperidin-4-yloxy)phenyl)-1-(pyridazin-3-yl)pyrrolidine-3-carboxamide The title compound was prepared as described in Example 1D, substituting (S)-tert-butyl 4-(4-(1-(pyridazin-3-yl)pyrrolidine-3-carboxamido)phenoxy)piperidine-1-carboxylate for tert-butyl 4-(4-(1-(pyridin-3-yl)azetidine-3-carboxamido)phenoxy)piperidine-1-carboxylate.

Example 796C (3S)—N-(4-{[1-(cyclohexylcarbonyl)piperidin-4-yl]oxy}phenyl)-1-(pyridazin-3-yl)pyrrolidine-3-carboxamide The title compound was prepared as described in Example 1A, substituting (S)—N-(4-(piperidin-4-yloxy)phenyl)-1-(pyridazin-3-yl)pyrrolidine-3-carboxamide for tert-butyl 4-(4-aminophenoxy)piperidine-1-carboxylate and cyclohexanecarboxylic acid for 1-(benzyloxycarbonyl)azetidine-3-carboxylic acid. $^1$H NMR (300 MHz, DMSO-$d_6$) δ ppm 9.97 (s, 1H), 8.48 (dd, J=4.5, 1.3 Hz, 1H), 7.55-7.48 (m, 2H), 7.34 (dd, J=9.1, 4.4 Hz, 1H), 6.97-6.84 (m, 3H), 4.58-4.47 (m, 1H), 3.88-3.40 (m, 6H), 3.40-3.20 (m, 2H), 2.60-2.50 (m, 1H), 2.41-2.08 (m, 2H), 2.00-1.80 (m, 2H), 1.77-1.07 (m, 13H); MS (ESI(+)) m/e 478 (M+H)$^+$.

TABLE 18

The following Examples were essentially prepared as described in Example 796, substituting an appropriate carboxylic acid in Example 796C.

| Ex | Name | MS |
|---|---|---|
| 797 | (3S)-N-(4-{[1-(2-fluorobenzoyl)piperidin-4-yl]oxy}phenyl)-1-(pyridazin-3-yl)pyrrolidine-3-carboxamide | (ESI(+)) m/e 490 (M + H)$^+$ |
| 798 | (3S)-N-(4-{[1-(3-fluorobenzoyl)piperidin-4-yl]oxy}phenyl)-1-(pyridazin-3-yl)pyrrolidine-3-carboxamide | (ESI(+)) m/e 490 (M + H)$^+$ |
| 799 | (3S)-N-{4-[(1-benzoylpiperidin-4-yl)oxy]phenyl}-1-(pyridazin-3-yl)pyrrolidine-3-carboxamide | (ESI(+)) m/e 472 (M + H)$^+$ |
| 800 | (3S)-N-(4-{[1-(4-fluorobenzoyl)piperidin-4-yl]oxy}phenyl)-1-(pyridazin-3-yl)pyrrolidine-3-carboxamide | (ESI(+)) m/e 490 (M + H)$^+$ |
| 801 | (3S)-N-(4-{[1-(2,2-dimethylpropanoyl)piperidin-4-yl]oxy}phenyl)-1-(pyridazin-3-yl)pyrrolidine-3-carboxamide | (ESI(+)) m/e 452 (M + H)$^+$ |
| 802 | (3S)-N-[4-({1-[(2-methylcyclopropyl)carbonyl]piperidin-4-yl}oxy)phenyl]-1-(pyridazin-3-yl)pyrrolidine-3-carboxamide | (ESI(+)) m/e 450 (M + H)$^+$ |

Example 803

N-{4-[5-(2,2-dimethylpropyl)-1,3,4-oxadiazol-2-yl]phenyl}-1-(pyridazin-3-yl)azetidine-3-carboxamide

Example 803A

N'-(3,3-dimethylbutanoyl)-4-nitrobenzohydrazide

A suspension of 4-nitrobenzohydrazide (0.500 g, 2.76 mmol), and 4-methylmorpholine (0.455 ml, 4.14 mmol) were stirred in dichloromethane (20 ml). 3,3-Dimethylbutanoyl chloride (0.422 ml, 3.04 mmol) was added and the reaction mixture was stirred for 2 hours. Normal phase chromatography of the crude reaction mixture gave the title compound.

Example 803B 2-neopentyl-5-(4-nitrophenyl)-1,3,4-oxadiazole

A mixture of N'-(3,3-dimethylbutanoyl)-4-nitrobenzohydrazide (0.556 g, 1.991 mmol) and methyl N-(triethylammoniumsulfonyl)carbamate (0.572 g, 2.389 mmol) in tetrahydrofuran (10 ml) was heated to 120° C. in a microwave for 45 minutes. The crude reaction mixture was concentrated and purified by normal phase chromatography to give the title compound.

Example 803C 4-(5-neopentyl-1,3,4-oxadiazol-2-yl)aniline

The title compound was prepared as described in Example 1B, substituting 2-neopentyl-5-(4-nitrophenyl)-1,3,4-oxadiazole for tert-butyl 4-(4-(1-(benzyloxycarbonyl)azetidine-3-carboxamido)phenoxy)piperidine-1-carboxylate.

Example 803D

N-{4-[5-(2,2-dimethylpropyl)-1,3,4-oxadiazol-2-yl]phenyl}-1-(pyridazin-3-yl)azetidine-3-carboxamide The title compound was prepared as described in Example 1A, substituting 445-neopentyl-1,3,4-oxadiazol-2-yl)aniline for tert-butyl 4-(4-aminophenoxy)piperidine-1-carboxylate and 1-(pyridazin-3-yl)azetidine-3-carboxylic acid for 1-(benzyloxycarbonyl)azetidine-3-carboxylic acid. $^1$H NMR (300 MHz, DMSO-$d_6$) δ ppm 10.45 (s, 1H), 8.57 (dd, J=4.5, 1.3 Hz, 1H), 7.97-7.91 (m, 2H), 7.88-7.82 (m, 2H), 7.39 (dd, J=9.0, 4.5 Hz, 1H), 6.84 (dd, J=9.0, 1.4 Hz, 1H), 4.26 (t, J=8.4 Hz, 2H), 4.18 (dd, J=8.2, 5.9 Hz, 2H), 3.79 (tt, J=8.6, 5.9 Hz, 1H), 2.82 (s, 2H), 1.03 (s, 9H); MS (ESI(+)) m/e 393 (M+H)$^+$.

Example 804

N-{4-[1-(2,2-dimethylpropyl)-1H-imidazol-4-yl]phenyl}-1-(pyridazin-3-yl)azetidine-3-carboxamide

Example 804A 1-neopentyl-4-(4-nitrophenyl)-1H-imidazole

To a solution of 4-(4-nitrophenyl)-1H-imidazole (0.500 g, 2.64 mmol) in N,N-dimethylformamide (10 ml) was added cesium carbonate (1.292 g, 3.96 mmol) followed by 1-bromo-2,2-dimethylpropane (0.366 ml, 2.91 mmol). After heating at 85° overnight, the reaction mixture was cooled to room temperature, diluted with ethyl acetate, washed with water and brine, dried over magnesium sulfate, filtered and concentrated. Normal phase chromatography provided the title compound.

Example 804B 4-(1-neopentyl-1H-imidazol-4-yl)aniline

The title compound was prepared as described in Example 1B, substituting 1-neopentyl-4-(4-nitrophenyl)-1H-imidazole for tert-butyl 4-(4-(1-(benzyloxycarbonyl)azetidine-3-carboxamido)phenoxy)piperidine-1-carboxylate.

Example 804C

N-{4-[1-(2,2-dimethylpropyl)-1H-imidazol-4-yl]phenyl}-1-(pyridazin-3-yl)azetidine-3-carboxamide The title compound was prepared as described in Example 1A, substituting 4-(1-neopentyl-1H-imidazol-4-yl)aniline for tert-butyl 4-(4-aminophenoxy)piperidine-1-carboxylate and 1-(pyridazin-3-yl)azetidine-3-carboxylic acid for 1-(benzyloxycarbonyl)azetidine-3-carboxylic acid. $^1$H NMR (300 MHz, DMSO-$d_6$) δ ppm 10.08 (s, 1H), 8.56 (dd, J=4.6, 1.3 Hz, 1H), 7.73-7.66 (m, 2H), 7.64-7.58 (m, 2H), 7.57 (d, J=1.2 Hz, 1H), 7.49 (d, J=1.1 Hz, 1H), 7.38 (dd, J=9.0, 4.5 Hz, 1H), 6.83 (dd, J=9.0, 1.4 Hz, 1H), 4.25 (t, J=8.3 Hz, 2H), 4.16 (dd, J=8.1, 6.0 Hz, 2H), 3.77 (s, 2H), 3.77-3.69 (m, 1H), 0.91 (s, 9 H); MS (ESI(+)) m/e 391 (M+H)$^+$.

Example 805

N-[4-(3-cyclopropyl-1-methyl-1H-pyrazol-5-yl)phenyl]-1-(pyridazin-3-yl)azetidine-3-carboxamide

Example 805A 3-cyclopropyl-1-(4-nitrophenyl)prop-2-yn-1-one

A 250-mL round bottom flask was charged with bis(triphenylphosphine)palladium bischloride (151 mg, 0.216 mmol) and copper iodide (82 mg, 0.431 mmol), and the flask was degassed with nitrogen. Tetrahydrofuran (40 mL) was added through a septum, and nitrogen was bubbled through the mixture for 30 minutes. To this was added dropwise a nitrogen-degassed solution of 4-nitrobenzoyl chloride (2g, 10 8 mmol), ethynylcyclopropane (784 mg, 11.9 mmol) and triethylamine (1.31 g, 12.9 mmol) in tetrahydrofuran (15 mL). The reaction mixture was stirred at room temperature for 2 hours and then concentrated to dryness. The residue was purified by normal phase chromatography to give the title compound.

Example 805B 3-cyclopropyl-1-methyl-5-(4-nitrophenyl)-1H-pyrazole

3-Cyclopropyl-1-(4-nitrophenyl)prop-2-yn-1-one (500 mg, 2.323 mmol) was dissolved in N,N-dimethylformamide (7.75 mL), and the solution was chilled to 0° C. Methylhydrazine (118 mg, 2.56 mmol) was added dropwise. The mixture was stirred overnight at room temperature then diluted with water (25 mL) and stirred for 45 minutes. The resulting precipitate was collected by filtration to give the title compound.

Example 805C 4-(3-cyclopropyl-1-methyl-1H-pyrazol-5-yl)aniline

The title compound was prepared as described in Example 1B, substituting 3-cyclopropyl-1-methyl-5-(4-nitrophenyl)-1H-pyrazole for tert-butyl 4-(4-(1-(benzyloxycarbonyl)azetidine-3-carboxamido)phenoxy)piperidine-1-carboxylate.

Example 805D

N-[4-(3-cyclopropyl-1-methyl-1H-pyrazol-5-yl)phenyl]-1-(pyridazin-3-yl)azetidine-3-carboxamide The title compound was prepared as described in Example 1A, substituting 4-(3-cyclopropyl-1-methyl-1H-pyrazol-5-yl)aniline for tert-butyl 4-(4-aminophenoxy)piperidine-1-carboxylate and 1-(pyridazin-3-yl)azetidine-3-carboxylic acid for 1-(benzyloxycarbonyl)azetidine-3-carboxylic acid. $^1$H NMR (300 MHz, DMSO-$d_6$) δ 10.11 (s, 1 H), 8.56 (dd, J=4.5, 1.3 Hz, 1H), 7.69-7.58 (m, 4 H), 7.38 (dd, J=9.0, 4.5 Hz, 1H), 6.83 (dd, J=9.0, 1.3 Hz, 1H), 6.28 (s, 1H), 4.25 (t, J=8.3 Hz, 2H), 4.16 (dd, J=8.1, 6.0 Hz, 2H), 3.84 (s, 3 H), 3.75 (dq, J=8.3, 5.9 Hz, 1H), 1.95-1.82 (m, 1H), 1.02-0.92 (m, 2H), 0.71-0.62 (m, 2H); MS (ESI(+)) m/e 375 (M+H)$^+$.

Example 806

N-{4-[5-(2,2-dimethylpropyl)-1,2,4-oxadiazol-3-yl]phenyl}-1-(pyridazin-3-yl)azetidine-3-carboxamide

Example 806A 5-neopentyl-3-(4-nitrophenyl)-1,2,4-oxadiazole

To a suspension of (Z)—N'-hydroxy-4-nitrobenzimidamide (0.500 g, 2.76 mmol) in dichloromethane (6 ml) was added 4-methylmorpholine (0.455 ml, 4.14 mmol) followed by 3,3-dimethylbutanoyl chloride (0.422 ml, 3.04 mmol). After 1 hour, the crude reaction mixture was purified by normal phase chromatography and the collected intermediate was dissolved in dichloromethane (8 ml) and treated with tetrabutylammonium fluoride (1.0M in THF) (8.28 ml, 8.28 mmol). After 3 hours at room temperature, the mixture was diluted with ethyl acetate, washed with water, dried over magnesium sulfate, filtered, and concentrated. Normal phase chromatography provided the title compound.

Example 806B 4-(5-neopentyl-1,2,4-oxadiazol-3-yl)aniline

The title compound was prepared as described in Example 1B, substituting 5-neopentyl-3-(4-nitrophenyl)-1,2,4-oxadiazole for tert-butyl 4-(4-(1-(benzyloxycarbonyl)azetidine-3-carboxamido)phenoxy)piperidine-1-carboxylate.

Example 806C

N-{4-[5-(2,2-dimethylpropyl)-1,2,4-oxadiazol-3-yl]phenyl}-1-(pyridazin-3-yl)azetidine-3-carboxamide The title compound was prepared as described in Example 1A, substituting 445-neopentyl-1,2,4-oxadiazol-3-yl)aniline for tert-butyl 4-(4-aminophenoxy)piperidine-1-carboxylate and 1-(pyridazin-3-yl)azetidine-3-carboxylic acid for 1-(benzyloxycarbonyl)azetidine-3-carboxylic acid. $^1$H NMR (300 MHz, DMSO-$d_6$) δ ppm 10.40 (s, 1H), 8.57 (dd, J=4.6, 1.3 Hz, 1H), 8.05-7.89 (m, 2H), 7.89-7.75 (m, 2H), 7.38 (dd, J=9.0, 4.5 Hz, 1H), 6.84 (dd, J=9.0, 1.3 Hz, 1H), 4.26 (t, J=8.4 Hz, 2H), 4.18 (dd, J=8.1, 5.9 Hz, 2H), 3.79 (tt, J=8.5, 5.9 Hz, 1H), 2.90 (s, 2H), 1.04 (s, 9 H); MS (ESI(+)) m/e 393 (M+H)$^+$.

Example 807

N-{4-[3-cyclopropyl-1-(2-methoxyethyl)-1 H-pyrazol-5-yl]phenyl}-1-(pyridazin-3-yl)azetidine-3-carboxamide The title compound was prepared as described in Example 805, substituting (2-methoxyethyl)hydrazine for methylhydrazine in Example 805B. $^1$H NMR (400 MHz, DMSO-$d_6$) δ ppm 10.20 (s, 1H), 8.56 (d, J=4.5 Hz, 1H), 7.72-7.57 (m, 4H), 7.55-7.48 (m, 1H), 7.07-6.99 (m, 1 H), 6.28 (s, 1H), 4.38-4.18 (m, 6H), 3.83-3.69 (m, 3 H), 3.25 (s, 3 H), 1.98-1.87 (m, 1H), 1.00-0.91 (m, 2H), 0.67 (d, J=2.3 Hz, 2H); MS (ESI(+)) m/e 419 (M+H)$^+$.

Example 808 tert-butyl 4-(5-{[1-(pyridazin-3-yl)azetidin-3-yl]carbamoyl}thiophen-2-yl)piperidine-1-carboxylate

Example 808A tert-butyl (1-(6-chloropyridazin-3-yl)azetidin-3-yl)carbamate

The title compound was prepared as described in Example 147A, substituting tert-butyl azetidin-3-ylcarbamate for tert-butyl 4-(4-(azetidine-3-carboxamido)phenyl)piperidine-1-carboxylate.

Example 808B tert-butyl (1-(pyridazin-3-yl)azetidin-3-yl)carbamate

The title compound was prepared as described in Example 147B, substituting tert-butyl (1-(6-chloropyridazin-3-yl)azetidin-3-yl)carbamate for 4-(4-(1-(6-chloropyridazin-3-yl)azetidine-3-carboxamido)phenyl)piperidine-1-carboxylate.

Example 808C 1-(pyridazin-3-yl)azetidin-3-amine

The title compound was prepared as described in Example 1D, substituting tert-butyl (1-(pyridazin-3-yl)azetidin-3-yl)carbamate for tert-butyl 4-(4-(1-(pyridin-3-yl)azetidine-3-carboxamido)phenoxy)piperidine-1-carboxylate.

Example 808D tert-butyl 4-(5-{[1-(pyridazin-3-yl)azetidin-3-yl]carbamoyl}thiophen-2-yl)piperidine-1-carboxylate The title compound was prepared as described in Example 1A, substituting 1-(pyridazin-3-yl)azetidin-3-amine for tert-butyl 4-(4-aminophenoxy)piperidine-1-carboxylate and 5-(1-(tert-butoxycarbonyl)piperidin-4-yl)thiophene-2-carboxylic acid for 1-(benzyloxycarbonyl)azetidine-3-carboxylic acid. $^1$H NMR (300 MHz, DMSO-$d_6$) δ ppm 8.95 (d, J=7.2 Hz, 1H), 8.56 (dd, J=4.5, 1.3 Hz, 1H), 7.65 (d, J=3.8 Hz, 1H), 7.38 (dd, J=8.9, 4.5 Hz, 1H), 6.95 (dd, J=3.8, 0.8 Hz, 1H), 6.83 (dd, J=9.0, 1.4 Hz, 1H), 4.92-4.77 (m, 1H), 4.36 (t, J=8.1 Hz, 2H), 4.05-3.97 (m, 4 H), 3.09-2.66 (m, 3 H), 1.98-1.88 (m, 2H), 1.40 (s, 11H); MS (ESI(+)) m/e 444 (M+H)$^+$.

Example 809 tert-butyl 4-fluoro-4-[4-({[1-(pyridazin-3-yl)azetidin-3-yl]carbonyl}amino)phenyl]piperidine-1-carboxylate

Example 809A tert-butyl 4-(4-aminophenyl)-4-hydroxypiperidine-1-carboxylate

N-(4-Bromophenyl)-1,1,1-trimethyl-N-(trimethylsilyl)silanamine (7 g, 22.12 mmol) in tetrahydrofuran (100 mL) was treated with a solution of n-BuLi (1M, 22 mL) at −78° C. The reaction mixture was stirred an additional hour at −78° C. and then treated with a solution of tert-butyl 4-oxopiperidine-1-carboxylate (3.97 g, 19.91 mmol) in tetrahydrofuran (20 mL). The reaction mixture was stirred at −78° C. for 30 minutes and then warmed to room temperature. The reaction was quenched by addition of saturated ammonium chloride solution (100 mL) and then was extracted with ethyl acetate. The combined organics were washed with water, brine, dried with magnesium sulfate, filtered and concentrated. The crude tert-butyl 4-(4-(bis(trimethylsilyl)amino)phenyl)-4-hydroxypiperidine-1-carboxylate was treated with a solution of tetrabutylammonium fluoride (1M THF, 40 mL) at room temperature for 1 hour. The reaction mixture was diluted with water and extracted with ethyl acetate. The organics were washed with water and brine, dried with magnesium sulfate, filtered and concentrated. Purification by normal phase chromatography provided the title compound.

Example 809B tert-butyl 4-(4-(1-((benzyloxy)carbonyl)azetidine-3-carboxamido)phenyl)-4-hydroxypiperidine-1-carboxylate The title compound was prepared as described in Example 1A, substituting tert-butyl 4-(4-aminophenyl)-4-hydroxypiperidine-1-carboxylate for tert-butyl 4-(4-aminophenoxy)piperidine-1-carboxylate and 1-((benzyloxy)carbonyl)azetidine-3-carboxylic acid for 1-(benzyloxycarbonyl)azetidine-3-carboxylic acid.

Example 809C tert-butyl 4-(4-(1-((benzyloxy)carbonyl)azetidine-3-carboxamido)phenyl)-4-fluoropiperidine-1-carboxylate tert-Butyl 4-(4-(1-((benzyloxy)carbonyl)azetidine-3-carboxamido)phenyl)-4-hydroxypiperidine-1-carboxylate (2.5 g, 4.91 mmol) in 50 mL dichloromethane was cooled to −78° C. and diethylaminosulfur trifluoride was added dropwise via a syringe. The reaction solution was stirred at −78° C. for an additional 1 hour and then warmed to 0° C. The reaction was allowed to stir at 0° C. for 1 hour and was cooled back down to −78° C. The reaction mixture was diluted with 50 mL of dichloromethane followed by quenching with 10 mL methanol. The solution was washed with saturated sodium bicarbonate and brine, dried with magnesium sulfate and filtered. Concentration and normal phase chromatography provided the title compound.

Example 809D tert-butyl 4-(4-(azetidine-3-carboxamido)phenyl)-4-fluoropiperidine-1-carboxylate The title compound was prepared as described in Example 1B, substituting tert-butyl 4-(4-(1-((benzyloxy)carbonyl)azetidine-3-carboxamido)phenyl)-4-fluoropiperidine-1-carboxylate for tert-butyl 4-(4-(1-(benzyloxycarbonyl)azetidine-3-carboxamido)phenoxy)piperidine-1-carboxylate.

Example 809E tert-butyl 4-(4-(1-(6-chloropyridazin-3-yl)azetidine-3-carboxamido)phenyl)-4-fluoropiperidine-1-carboxylate The title compound was prepared as described in Example 147A, substituting tert-butyl 4-(4-(azetidine-3-carboxamido)phenyl)-4-fluoropiperidine-1-carboxylate for tert-butyl 4-(4-(azetidine-3-carboxamido)phenyl)piperidine-1-carboxylate.

Example 809F tert-butyl 4-fluoro-4-[4-({[1-(pyridazin-3-yl)azetidin-3-yl]carbonyl}amino)phenyl]piperidine-1-carboxylate The title compound was prepared as described in Example 147B, substituting tert-butyl 4-(4-(1-(6-chloropyridazin-3-yl)azetidine-3-carboxamido)phenyl)-4-fluoropiperidine-1-carboxylate for 4-(4-(1-(6-chloropyridazin-3-yl)azetidine-3-carboxamido)phenyl)piperidine-1-carboxylate. $^1$H NMR (400 MHz, DMSO-$d_6$) δ ppm 10.18-10.08 (m, 1H), 8.55 (dd, J=4.5, 1.4 Hz, 1H), 7.65-7.56 (m, 2H), 7.40-7.33 (m, 3 H), 6.82 (dd, J=8.9, 1.4 Hz, 1H), 4.23 (t, J=8.3 Hz, 2H), 4.14 (dd, J=8.2, 5.7 Hz, 2H), 4.08-3.91 (m, 2H), 3.81-3.68 (m, 1H), 3.17-2.70 (m, 2H), 2.07-1.82 (m, 3 H), 1.42-1.35 (s, 10 H); MS (ESI(+)) m/e 456 (M+H)$^+$.

Example 810

5-(1-benzoylpiperidin-4-yl)-N-[1-(pyridazin-3-yl)azetidin-3-yl]thiophene-2-carboxamide

Example 810A 5-(piperidin-4-yl)-N-(1-(pyridazin-3-yl)azetidin-3-yl)thiophene-2-carboxamide The title compound was prepared as described in Example 1D, substituting tert-butyl 4-(5-{[1-(pyridazin-3-yl)azetidin-3-yl]carbamoyl}thiophen-2-yl)piperidine-1-carboxylate for tert-butyl 4-(4-(1-(pyridin-3-yl)azetidine-3-carboxamido)phenoxy)piperidine-1-carboxylate.

Example 810B 5-(1-benzoylpiperidin-4-yl)-N-[1-(pyridazin-3-yl)azetidin-3-yl]thiophene-2-carboxamide The title compound was prepared as described in Example 1A, substituting 5-(piperidin-4-yl)-N-(1-(pyridazin-3-yl)azetidin-3-yl)thiophene-2-carboxamide for tert-butyl 4-(4-aminophenoxy)piperidine-1-carboxylate and benzoic acid for 1-(benzyloxycarbonyl)azetidine-3-carboxylic acid. $^1$H NMR (300 MHz, DMSO-$d_6$) δ ppm 8.96 (d, J=7.2 Hz, 1H), 8.56 (dd, J=4.5, 1.3 Hz, 1H), 7.66 (d, J=3.8 Hz, 1 H), 7.51-7.34 (m, 6 H), 6.98 (dd, J=3.8, 0.8 Hz, 1H), 6.84 (dd, J=9.0, 1.4 Hz, 1H), 4.92-4.77 (m, 1H), 4.6 (bs, 1H), 4.36 (t, J=8.1 Hz, 2H), 4.01 (dd, J=8.6, 5.6 Hz, 2H), 3.64 (bs, 1H), 3.23-2.83 (m, 3 H), 2.10-1.84 (m, 2H), 1.67-1.48 (m, 2H); MS (ESI(+)) m/e 448 (M+H)$^+$.

TABLE 19

The following Examples were essentially prepared as described in Example 810, substituting an appropriate carboxylic acid in Example 810B.

| Ex | Name | MS |
|---|---|---|
| 811 | 5-[1-(2-fluorobenzoyl)piperidin-4-yl]-N-[1-(pyridazin-3-yl)azetidin-3-yl]thiophene-2-carboxamide | (ESI(+)) m/e 466 (M + H)$^+$ |
| 812 | 5-[1-(2-methylbenzoyl)piperidin-4-yl]-N-[1-(pyridazin-3-yl)azetidin-3-yl]thiophene-2-carboxamide | (ESI(+)) m/e 462 (M + H)$^+$ |
| 813 | 5-[1-(2,4-difluorobenzoyl)piperidin-4-yl]-N-[1-(pyridazin-3-yl)azetidin-3-yl]thiophene-2-carboxamide | (ESI(+)) m/e 484 (M + H)$^+$ |
| 814 | 5-[1-(3-fluorobenzoyl)piperidin-4-yl]-N-[1-(pyridazin-3-yl)azetidin-3-yl]thiophene-2-carboxamide | (ESI(+)) m/e 466 (M + H)$^+$ |
| 815 | 5-[1-(4-fluorobenzoyl)piperidin-4-yl]-N-[1-(pyridazin-3-yl)azetidin-3-yl]thiophene-2-carboxamide | (ESI(+)) m/e 466 (M + H)$^+$ |

TABLE 19-continued

The following Examples were essentially prepared as described in Example 810, substituting an appropriate carboxylic acid in Example 810B.

| Ex | Name | MS |
|---|---|---|
| 816 | 5-[1-(3,5-difluorobenzoyl)piperidin-4-yl]-N-[1-(pyridazin-3-yl)azetidin-3-yl]thiophene-2-carboxamide | (ESI(+)) m/e 484 (M + H)$^+$ |
| 847 | 5-[1-(2,2-dimethylpropanoyl)piperidin-4-yl]-N-[1-(pyridazin-3-yl)azetidin-3-yl]thiophene-2-carboxamide | (ESI(+)) m/e 428 (M + H)$^+$ |
| 848 | 5-{1-[(1-methylcyclopropyl)carbonyl]piperidin-4-yl}-N-[1-(pyridazin-3-yl)azetidin-3-yl]thiophene-2-carboxamide | (ESI(+)) m/e 426 (M + H)$^+$ |
| 849 | N-[1-(pyridazin-3-yl)azetidin-3-yl]-5-[1-(3,3,3-trifluoropropanoyl)piperidin-4-yl]thiophene-2-carboxamide | (ESI(+)) m/e 454 (M + H)$^+$ |
| 850 | 5-[1-(2,2-dimethylbutanoyl)piperidin-4-yl]-N-[1-(pyridazin-3-yl)azetidin-3-yl]thiophene-2-carboxamide | (ESI(+)) m/e 442 (M + H)$^+$ |
| 855 | N-[1-(pyridazin-3-yl)azetidin-3-yl]-5-[1-(4,4,4-trifluorobutanoyl)piperidin-4-yl]thiophene-2-carboxamide | (ESI(+)) m/e 468 (M + H)$^+$ |
| 856 | 5-[1-(cyclopropylcarbonyl)piperidin-4-yl]-N-[1-(pyridazin-3-yl)azetidin-3-yl]thiophene-2-carboxamide | (ESI(+)) m/e 412 (M + H)$^+$ |

Example 817

N-{4-[3-cyclopropyl-1-(2-hydroxyethyl)-1H-pyrazol-5-yl]phenyl}-1-(pyridazin-3-yl)azetidine-3-carboxamide The title compound was prepared as described in Example 805, substituting 2-hydrazinylethanol for methylhydrazine in 805B. $^1$H NMR (300 MHz, DMSO-d$_6$) δ ppm 10.14 (s, 1H), 8.56 (dd, J=4.5, 1.3 Hz, 1H), 7.72-7.58 (m, 4 H), 7.38 (dd, J=9.0, 4.5 Hz, 1H), 6.83 (dd, J=9.0, 1.4 Hz, 1H), 6.27 (s, 1H), 4.90 (br s, 1H), 4.31-4.08 (m, 6 H), 3.84-3.69 (m, 3 H), 2.01-1.88 (m, 1H), 1.01-0.89 (m, 2H), 0.72-0.62 (m, 2H); MS (ESI(+)) m/e 405 (M+H)$^+$.

Example 818

N-[4-(1-benzoylpiperidin-4-yl)phenyl]-1-(6-fluoropyridazin-3-yl)azetidine-3-carboxamide Example 818A tert-butyl 4-(4-(1-((benzyloxy)carbonyl)azetidine-3-carboxamido)phenyl)piperidine-1-carboxylate The title compound was prepared as described in Example 1A, substituting tert-butyl 4-(4-aminophenyl)piperidine-1-carboxylate for tert-butyl 4-(4-aminophenoxy)piperidine-1-carboxylate and 1-((benzyloxy)carbonyl)azetidine-3-carboxylic acid for 1-(benzyloxycarbonyl)azetidine-3-carboxylic acid.

Example 818B tert-butyl 4-(4-(azetidine-3-carboxamido)phenyl)piperidine-1-carboxylate The title compound was prepared as described in Example 1B, substituting tert-butyl 4-(4-(1-((benzyloxy)carbonyl)azetidine-3-carboxamido)phenyl)piperidine-1-carboxylate for tert-butyl 4-(4-(1-(benzyloxycarbonyl)azetidine-3-carboxamido)phenoxy)piperidine-1-carboxylate.

Example 818C tert-butyl 4-(4-(1-(6-fluoropyridazin-3-yl)azetidine-3-carboxamido)phenyl)piperidine-1-carboxylate The title compound was prepared as described in Example 147A, substituting tert-butyl 4-(4-(azetidine-3-carboxamido)phenyl)piperidine-1-carboxylate for tert-butyl 4-(4-(azetidine-3-carboxamido)phenyl)piperidine-1-carboxylate and 3,6-difluoropyridazine for 3,6-dichloropyridazine.

Example 818D 1-(6-fluoropyridazin-3-yl)-N-(4-(piperidin-4-yl)phenyl)azetidine-3-carboxamide The title compound was prepared as described in Example 1D, substituting tert-butyl 4-(4-(1-(6-fluoropyridazin-3-yl)azetidine-3-carboxamido)phenyl)piperidine-1-carboxylate for tert-butyl 4-(4-(1-(pyridin-3-yl)azetidine-3-carboxamido)phenoxy)piperidine-1-carboxylate.

Example 818E

N-[4-(1-benzoylpiperidin-4-yl)phenyl]-1-(6-fluoropyridazin-3-yl)azetidine-3-carboxamide The title compound was prepared as described in Example 1A, substituting 1-(6-fluoropyridazin-3-yl)-N-(4-(piperidin-4-yl)phenyl)azetidine-3-carboxamide for tert-butyl 4-(4-aminophenoxy)piperidine-1-carboxylate and benzoic acid for 1-(benzyloxycarbonyl)azetidine-3-carboxylic acid. $^1$H NMR (300 MHz, DMSO-d$_6$) δ ppm 10.03 (s, 1H), 7.54 (d, J=8.6 Hz, 2H), 7.49-7.38 (m, 6 H), 7.22 (d, J=8.6 Hz, 2H), 7.12 (dd, J=9.5, 6.8 Hz, 1H), 4.23 (t, J=8.3 Hz, 2H), 4.14 (dd, J=8.0, 6.0 Hz, 2H), 3.71 (ddd, J=14.4, 8.4, 5.9 Hz, 2H), 2.86 (dd, J=67.9, 55.9 Hz, 3 H), 2.04-1.43 (m, 4 H); MS (ESI(+)) m/e 460 (M+H)$^+$.

Example 819

N-{4-[1-(2-fluorobenzoyl)piperidin-4-yl]phenyl}-1-(6-fluoropyridazin-3-yl)azetidine-3-carboxamide The title compound was prepared as described in Example 1A, substituting 1-(6-fluoropyridazin-3-yl)-N-(4-(piperidin-4-yl)phenyl)azetidine-3-carboxamide for tert-butyl 4-(4-aminophenoxy)piperidine-1-carboxylate and 2-fluorobenzoic acid for 1-(benzyloxycarbonyl)azetidine-3-carboxylic acid. $^1$H NMR (400 MHz, DMSO-$d_6$) δ ppm 10.04 (s, 1H), 7.58-7.34 (m, 5 H), 7.35-7.25 (m, 2 H), 7.23-7.17 (m, 2H), 7.12 (dd, J=9.4, 6.7 Hz, 1H), 4.70-4.61 (m, 1H), 4.23 (t, J=8.3 Hz, 2H), 4.14 (d, J=13.9 Hz, 2H), 3.77-3.66 (m, 1 H), 3.50-3.41 (m, 1H), 3.23-3.09 (m, 1 H), 2.95-2.72 (m, 2H), 1.91-1.82 (m, 1H), 1.79-1.42 (m, 3 H); MS (ESI(+)) m/e 478 (M+H)$^+$.

Example 820

N-{4-[1-(2,2-dimethylpropanoyl)piperidin-4-yl]phenyl}-1-(6-fluoropyridazin-3-yl)azetidine-3-carboxamide The title compound was prepared as described in Example 1A, substituting 1-(6-fluoropyridazin-3-yl)-N-(4-(piperidin-4-yl)phenyl)azetidine-3-carboxamide for tert-butyl 4-(4-aminophenoxy)piperidine-1-carboxylate and 2,2-dimethylpropanoic acid for 1-(benzyloxycarbonyl)azetidine-3-carboxylic acid. $^1$H NMR (400 MHz, DMSO-$d_6$) δ ppm 10.03 (s, 1H), 7.57-7.50 (m, 2H), 7.41 (dd, J=9.4, 1.9 Hz, 1H), 7.22-7.15 (m, 2H), 7.12 (dd, J=9.4, 6.7 Hz, 1H), 4.45-4.36 (m, 2 H), 4.23 (t, J=8.3 Hz, 2H), 4.14 (dd, J=8.0, 5.9 Hz, 2H), 3.77-3.66 (m, 1H), 2.93-2.66 (m, 3 H), 1.82-1.74 (m, 2H), 1.52-1.35 (m, 2H), 1.22 (s, 9 H); MS (ESI(+)) m/e 440 (M+H)$^+$.

Example 821

1-(6-fluoropyridazin-3-yl)-N-{4-[1-(2-methylpropanoyl)piperidin-4-yl]phenyl}azetidine-3-carboxamide The title compound was prepared as described in Example 1A, substituting 1-(6-fluoropyridazin-3-yl)-N-(4-(piperidin-4-yl)phenyl)azetidine-3-carboxamide for tert-butyl 4-(4-aminophenoxy)piperidine-1-carboxylate and isobutyric acid for 1-(benzyloxycarbonyl)azetidine-3-carboxylic acid. $^1$H NMR (400 MHz, DMSO-$d_6$) δ ppm 10.03 (s, 1H), 7.54 (d, J=8.5 Hz, 2H), 7.41 (dd, J=9.5, 1.9 Hz, 1H), 7.18 (d, J=8.5 Hz, 2H), 7.12 (dd, J=9.5, 6.8 Hz, 1H), 4.62-4.45 (m, 1H), 4.23 (t, J=8.3 Hz, 2H), 4.14 (dd, J=7.9, 6.1 Hz, 2H), 4.10-3.97 (m, 1H), 3.72 (ddd, J=8.4, 7.2, 4.2 Hz, 1H), 3.10 (s, 1H), 2.89 (dt, J=13.4, 6.7 Hz, 1H), 2.81-2.64 (m, 1H), 2.57 (s, 1H), 1.79 (ddd, J=16.4, 10.0, 2.9 Hz, 2H), 1.58-1.25 (m, 2H), 1.12-0.92 (m, 6 H); MS (ESI(+)) m/e 426 (M+H)$^+$.

Example 822

N-{4-[1-(2-ethylbutanoyl)piperidin-4-yl]phenyl}-1-(6-fluoropyridazin-3-yl)azetidine-3-carboxamide The title compound was prepared as described in Example 1A, substituting 1-(6-fluoropyridazin-3-yl)-N-(4-(piperidin-4-yl)phenyl)azetidine-3-carboxamide for tert-butyl 4-(4-aminophenoxy)piperidine-1-carboxylate and 2-ethylbutanoic acid for 1-(benzyloxycarbonyl)azetidine-3-carboxylic acid. $^1$H NMR (400 MHz, DMSO-$d_6$) δ ppm 10.03 (s, 1H), 7.57-7.51 (m, 2H), 7.41 (dd, J=9.4, 1.9 Hz, 1H), 7.21-7.08 (m, 3 H), 4.68-4.59 (m, 1H), 4.31-4.06 (m, 1H), 3.77-3.66 (m, 1H), 3.15-3.04 (m, 1H), 2.66 (ddt, J=25.3, 20.0, 12.2 Hz, 1H), 1.87-1.74 (m, 2H), 1.64-1.27 (m, 6 H), 0.87-0.76 (m, 6 H); MS (ESI(+)) m/e 454 (M+H)$^+$.

Example 823

N-{4-[1-(4-fluorobenzoyl)piperidin-4-yl]phenyl}-1-(6-fluoropyridazin-3-yl)azetidine-3-carboxamide The title compound was prepared as described in Example 1A, substituting 1-(6-fluoropyridazin-3-yl)-N-(4-(piperidin-4-yl)phenyl)azetidine-3-carboxamide for tert-butyl 4-(4-aminophenoxy)piperidine-1-carboxylate and 4-fluorobenzoic acid for 1-(benzyloxycarbonyl)azetidine-3-carboxylic acid. $^1$H NMR (400 MHz, DMSO-$d_6$) δ ppm 10.04 (s, 1H), 7.59-7.46 (m, 4 H), 7.41 (dd, J=9.4, 1.9 Hz, 1H), 7.32-7.17 (m, 4 H), 7.13 (dd, J=9.4, 6.7 Hz, 1H), 4.70-4.48 (m, 1H), 4.24 (t, J=8.3 Hz, 2H), 4.14 (dd, J=8.0, 5.9 Hz, 2H), 4.06-3.53 (m, 2H), 3.22-2.68 (m, 3 H), 2.04-1.50 (m, 4 H); MS (ESI(+)) m/e 478 (M+H)$^+$.

Example 824

(3S)—N-(4-{[(3S)-1-benzoylpyrrolidin-3-yl]oxy}phenyl)-1-(pyridazin-3-yl)pyrrolidine-3-carboxamide

Example 824A (S)-tert-butyl 3-(4-((S)-1-(pyridazin-3-yl)pyrrolidine-3-carboxamido)phenoxy)pyrrolidine-1-carboxylate The title compound was prepared as described in Example 1A, substituting (R)-tert-butyl 3-(4-aminophenoxy)pyrrolidine-1-carboxylate for tert-butyl 4-(4-aminophenoxy)piperidine-1-carboxylate and (S)-1-(pyridazin-3-yl)pyrrolidine-3-carboxylic acid for 1-(benzyloxycarbonyl)azetidine-3-carboxylic acid.

Example 824B (S)-1-(pyridazin-3-yl)-N-(4-((S)-pyrrolidin-3-yloxy)phenyl)pyrrolidine-3-carboxamide The title compound was prepared as described in Example 1D, substituting (S)-tert-butyl 3-(4-((S)-1-(pyridazin-3-yl)pyrrolidine-3-carboxamido)phenoxy)pyrrolidine-1-carboxylate for tert-butyl 4-(4-(1-(pyridin-3-yl)azetidine-3-carboxamido)phenoxy)piperidine-1-carboxylate.

Example 774C (3S)—N-(4-{[(3S)-1-benzoylpyrrolidin-3-yl]oxy}phenyl)-1-(pyridazin-3-yl)pyrrolidine-3-carboxamide The title compound was prepared as described in Example 1A, substituting (S)-1-(pyridazin-3-yl)-N-(4-((S)-pyrrolidin-3-yloxy)phenyl)pyrrolidine-3-carboxamide for tert-butyl 4-(4-aminophenoxy)piperidine-1-carboxylate and benzoic acid for 1-(benzyloxycarbonyl)azetidine-3-carboxylic acid. $^1$H NMR (400 MHz, DMSO-$d_6$) δ ppm 10.04-9.95 (m, 1H), 8.51-8.45 (m, 1H), 7.61-7.37 (m, 7 H), 7.37-7.30 (m, 1H), 6.99-6.92 (m, 1H), 6.90-6.83 (m, 2H), 5.07-4.92 (m, 1 H), 3.88-3.70 (m, 2H), 3.71-3.38 (m, 6 H), 2.37-1.97 (m, 4 H); MS (ESI(+)) m/e 458 (M+H)$^+$.

Example 825

(3S)—N-(4-{[(3S)-1-(2-fluorobenzoyl)pyrrolidin-3-yl]oxy}phenyl)-1-(pyridazin-3-yl)pyrrolidine-3-carboxamide The title compound was prepared as described in Example 1A, substituting (S)-1-(pyridazin-3-yl)-N-(4-((S)-pyrrolidin-3-yloxy)phenyl)pyrrolidine-3-carboxamide for tert-butyl 4-(4-aminophenoxy)piperidine-1-carboxylate and 2-fluorobenzoic acid for 1-(benzyloxycarbonyl)azetidine-3-carboxylic acid. $^1$H NMR (400 MHz, DMSO-$d_6$) δ ppm 10.04-9.96 (m, 1H), 8.48 (d, J=4.5 Hz, 1H), 7.59-7.37 (m, 4 H), 7.37-7.22 (m, 3 H), 6.94 (d, J=8.7 Hz, 1H), 6.87 (dd, J=8.9, 4.4 Hz, 2H), 3.86-3.52 (m, 5 H), 3.54-3.37 (m, 2H), 2.37-1.97 (m, 4 H); MS (ESI(+)) m/e 476(M+H)$^+$.

Example 826

(3S)—N-(4-{[(3S)-1-(3,5-difluorobenzoyl)pyrrolidin-3-yl]oxy}phenyl)-1-(pyridazin-3-yl)pyrrolidine-3-carboxamide The title compound was prepared as described in Example 1A, substituting (S)-1-(pyridazin-3-yl)-N-(4-((S)-pyrrolidin-3-yloxy)phenyl)pyrrolidine-3-carboxamide for tert-butyl 4-(4-aminophenoxy)piperidine-1-carboxylate and 2,4-fluorobenzoic acid for 1-(benzyloxycarbonyl)azetidine-3-carboxylic acid. $^1$H NMR (300 MHz, DMSO-$d_6$) δ ppm 10.07-9.93 (m, 1H), 8.47 (t, J=4.6 Hz, 1H), 7.54 (dt, J=12.8, 10.3 Hz, 2H), 7.44-7.18 (m, 4 H), 7.02-6.80 (m, 3 H), 5.16-4.85 (m, 1H), 3.91-3.70 (m, 2H), 3.70-3.35 (m, 7 H), 2.43-1.97 (m, 4 H); MS (ESI(+)) m/e 494 (M+H)$^+$.

Example 827

(3S)—N-(4-{[(3S)-1-(2,2-dimethylpropanoyl)pyrrolidin-3-yl]oxy}phenyl)-1-(pyridazin-3-yl)pyrrolidine-3-carboxamide The title compound was prepared as described in Example 1A, substituting (S)-1-(pyridazin-3-yl)-N-(4-((S)-pyrrolidin-3-yloxy)phenyl)pyrrolidine-3-carboxamide for tert-butyl 4-(4-aminophenoxy)piperidine-1-carboxylate and 2,2-dimethylpropanoic acid for 1-(benzyloxycarbonyl)azetidine-3-carboxylic acid. $^1$H NMR (300 MHz, DMSO-$d_6$) δ ppm 9.99 (s, 1H), 8.48 (dd, J=4.5, 1.3 Hz, 1H), 7.57-7.50 (m, 2 H), 7.33 (dd, J=9.1, 4.5 Hz, 1H), 6.95-6.83 (m, 4 H), 4.95 (bs, 1H), 3.86-3.39 (m, 8 H), 2.39-1.92 (m, 4 H), 1.15 (s, 9 H); MS (ESI(+)) m/e 438. (M+H)$^+$.

Example 828

N-{2-fluoro-4-[1-(2-fluorobenzoyl)piperidin-4-yl]phenyl}-1-(pyridazin-3-yl)azetidine-3-carboxamide

Example 828A tert-butyl 4-(4-amino-3-fluorophenyl)-5,6-dihydropyridine-1(2H)-carboxylate The title compound was prepared as described in Example 148A, substituting tert-butyl 4-(4,4,5,5-tetramethyl-1,3,2-dioxaborolan-2-yl)-5,6-dihydropyridine-1(2H)-carboxylate for 1-isobutyl-4-(4,4,5,5-tetramethyl-1,3,2-dioxaborolan-2-yl)-1 H-pyrazole and 4-bromo-2-fluoroaniline for 4-bromoaniline.

Example 828B tert-butyl 4-(4-amino-3-fluorophenyl)piperidine-1-carboxylate

The title compound was prepared as described in Example 1B, substituting tert-butyl 4-(4-amino-3-fluorophenyl)-5,6-dihydropyridine-1(2H)-carboxylate for tert-butyl 4-(4-(1-(benzyloxycarbonyl)azetidine-3-carboxamido)phenoxy)piperidine-1-carboxylate.

Example 828C tert-butyl 4-(4-(1-((benzyloxy)carbonyl)azetidine-3-carboxamido)-3-fluorophenyl)piperidine-1-carboxylate The title compound was prepared as described in Example 1A, substituting tert-butyl 4-(4-amino-3-fluorophenyl)piperidine-1-carboxylate for tert-butyl 4-(4-aminophenoxy)piperidine-1-carboxylate and 1-((benzyloxy)carbonyl)azetidine-3-carboxylic acid for 1-(benzyloxycarbonyl)azetidine-3-carboxylic acid.

Example 828D tert-butyl 4-(4-(azetidine-3-carboxamido)-3-fluorophenyl)piperidine-1-carboxylate The title compound was prepared as described in Example 1B, substituting tert-butyl 4-(4-(1-((benzyloxy)carbonyl)azetidine-3-carboxamido)-3-fluorophenyl)piperidine-1-carboxylate for tert-butyl 4-(4-(1-(benzyloxycarbonyl)azetidine-3-carboxamido)phenoxy)piperidine-1-carboxylate.

Example 828E tert-butyl 4-(4-(1-(6-chloropyridazin-3-yl)azetidine-3-carboxamido)-3-fluorophenyl)piperidine-1-carboxylate The title compound was prepared as described in Example 147A, substituting tert-butyl 4-(4-(azetidine-3-carboxamido)-3-fluorophenyl)piperidine-1-carboxylate for tert-butyl 4-(4-(azetidine-3-carboxamido)phenyl)piperidine-1-carboxylate.

Example 828F tert-butyl 4-(3-fluoro-4-(1-(pyridazin-3-yl)azetidine-3-carboxamido)phenyl)piperidine-1-carboxylate The title compound was prepared as described in Example 147B, substituting tert-butyl 4-(4-(1-(6-chloropyridazin-3-yl)azetidine-3-carboxamido)-3-fluorophenyl)piperidine-1-carboxylate for 4-(4-(1-(6-chloropyridazin-3-yl)azetidine-3-carboxamido)phenyl)piperidine-1-carboxylate.

Example 828G

N-(2-fluoro-4-(piperidin-4-yl)phenyl)-1-(pyridazin-3-yl)azetidine-3-carboxamide

The title compound was prepared as described in Example 1D, substituting tert-butyl 4-(3-fluoro-4-(1-(pyridazin-3-yl)azetidine-3-carboxamido)phenyl)piperidine-1-carboxylate for tert-butyl 4-(4-(1-(pyridin-3-yl)azetidine-3-carboxamido)phenoxy)piperidine-1-carboxylate.

Example 828 H

N-{2-fluoro-4-[1-(2-fluorobenzoyl)piperidin-4-yl]phenyl}-1-(pyridazin-3-yl)azetidine-3-carboxamide The title compound was prepared as described in Example 1A, substituting N-(2-fluoro-4-(piperidin-4-yl)phenyl)-1-

(pyridazin-3-yl)azetidine-3-carboxamide for tert-butyl 4-(4-aminophenoxy)piperidine-1-carboxylate and 2-fluorobenzoic acid for 1-(benzyloxycarbonyl)azetidine-3-carboxylic acid. $^1$H NMR (300 MHz, DMSO-d$_6$) δ ppm 9.86 (s, 1H), 8.56 (dd, J=4.5, 1.3 Hz, 1H), 7.79 (t, J=8.3 Hz, 1H), 7.58-7.41 (m, 2H), 7.42-7.25 (m, 3 H), 7.23-7.14 (m, 1H), 7.11-7.03 (m, 1H), 6.83 (dd, J=9.0, 1.4 Hz, 1H), 4.70-4.61 (m, 1H), 4.24 (t, J=8.3 Hz, 2H), 4.14 (dd, J=8.1, 5.8 Hz, 2H), 3.92-3.81 (m, 1H), 3.51-3.42 (m, 1H), 3.23-3.10 (m, 1H), 2.92-2.76 (m, 2H), 1.94-1.81 (m, 1H), 1.83-1.44 (m, 3 H); MS (ESI(+)) m/e 478 (M+H)$^+$.

TABLE 20

The following Examples were essentially prepared as described in Example 828, substituting the appropriate carboxylic acid in Example 828H.

| Ex | Name | MS |
|---|---|---|
| 829 | N-[4-(1-benzoylpiperidin-4-yl)-2-fluorophenyl]-1-(pyridazin-3-yl)azetidine-3-carboxamide | (ESI(+)) m/e 460 (M + H)$^+$ |
| 830 | N-{2-fluoro-4-[1-(3-fluorobenzoyl)piperidin-4-yl]phenyl}-1-(pyridazin-3-yl)azetidine-3-carboxamide | (ESI(+)) m/e 478 (M + H)$^+$ |
| 831 | N-{2-fluoro-4-[1-(2-methylbenzoyl)piperidin-4-yl]phenyl}-1-(pyridazin-3-yl)azetidine-3-carboxamide | (ESI(+)) m/e 474 (M + H)$^+$ |
| 832 | N-{2-fluoro-4-[1-(4-fluorobenzoyl)piperidin-4-yl]phenyl}-1-(pyridazin-3-yl)azetidine-3-carboxamide | (ESI(+)) m/e 478 (M + H)$^+$ |
| 833 | N-{4-[1-(2,4-difluorobenzoyl)piperidin-4-yl]-2-fluorophenyl}-1-(pyridazin-3-yl)azetidine-3-carboxamide | (ESI(+)) m/e 496 (M + H)$^+$ |
| 834 | N-{4-[1-(3,5-difluorobenzoyl)piperidin-4-yl]-2-fluorophenyl}-1-(pyridazin-3-yl)azetidine-3-carboxamide | (ESI(+)) m/e 460 (M + H)$^+$ |
| 835 | N-{4-[1-(3,3-dimethylbutanoyl)piperidin-4-yl]-2-fluorophenyl}-1-(pyridazin-3-yl)azetidine-3-carboxamide | (ESI(+)) m/e 454 (M + H)$^+$ |
| 858 | N-{2-fluoro-4-[1-(2-methylpropanoyl)piperidin-4-yl]phenyl}-1-(pyridazin-3-yl)azetidine-3-carboxamide | (ESI(+)) m/e 426 (M + H)$^+$ |
| 859 | N-{4-[1-(2,2-dimethylpropanoyl)piperidin-4-yl]-2-fluorophenyl}-1-(pyridazin-3-yl)azetidine-3-carboxamide | (ESI(+)) m/e 440 (M + H)$^+$ |
| 860 | N-{4-[1-(cyclopropylcarbonyl)piperidin-4-yl]-2-fluorophenyl}-1-(pyridazin-3-yl)azetidine-3-carboxamide | (ESI(+)) m/e 424 (M + H)$^+$ |
| 861 | N-(2-fluoro-4-{1-[(1-methylcyclopropyl)carbonyl]piperidin-4-yl}phenyl)-1-(pyridazin-3-yl)azetidine-3-carboxamide | (ESI(+)) m/e 438 (M + H)$^+$ |
| 862 | N-{4-[1-(cyclopropylacetyl)piperidin-4-yl]-2-fluorophenyl}-1-(pyridazin-3-yl)azetidine-3-carboxamide | (ESI(+)) m/e 438 (M + H)$^+$ |

Example 836

(3S)—N-(4-{[1-(2-fluorobenzoyl)piperidin-4-yl]oxy}phenyl)-1-(6-methylpyridazin-3-yl)pyrrolidine-3-carboxamide Example 836A (S)-tert-butyl 4-(4-(1-((benzyloxy)carbonyl)pyrrolidine-3-carboxamido)phenoxy)piperidine-1-carboxylate The title compound was prepared as described in Example 1A, substituting (S)-1-benzyl 3-tert-butyl pyrrolidine-1,3-dicarboxylate for tert-butyl 4-(4-aminophenoxy)piperidine-1-carboxylate and tert-butyl 4-(4-aminophenoxy)piperidine-1-carboxylate for 1-(benzyloxycarbonyl)azetidine-3-carboxylic acid.

Example 836B (S)-tert-butyl 4-(4-(pyrrolidine-3-carboxamido)phenoxy)piperidine-1-carboxylate The title compound was prepared as described in Example 1B, substituting (S)-tert-butyl 4-(4-(1-((benzyloxy)carbonyl)pyrrolidine-3-carboxamido)phenoxy)piperidine-1-carboxylate for tert-butyl 4-(4-(1-(benzyloxycarbonyl)azetidine-3-carboxamido)phenoxy)piperidine-1-carboxylate.

Example 836C (S)-tert-butyl 4-(4-(1-(6-methylpyridazin-3-yl)pyrrolidine-3-carboxamido)phenoxy)piperidine-1-carboxylate The title compound was prepared as described in Example 1C, substituting 3-bromo-6-methylpyridazine for 3-bromopyridine and (S)-tert-butyl 4-(4-(pyrrolidine-3-carboxamido)phenoxy)piperidine-1-carboxylate for tert-butyl 4-(4-(azetidine-3-carboxamido)phenoxy)piperidine-1-carboxylate.

Example 836D (S)-1-(6-methylpyridazin-3-yl)-N-(4-(piperidin-4-yloxy)phenyl)pyrrolidine-3-carboxamide The title compound was prepared as described in Example 1D, substituting (S)-tert-butyl 4-(4-(1-(6-methylpyridazin-3- yl)pyrrolidine-3-carboxamido)phenoxy)piperidine-1-carboxylate for tert-butyl 4-(4-(1-(pyridin-3-yl)azetidine-3-carboxamido)phenoxy)piperidine-1-carboxylate.

Example 836E (3S)—N-(4-{[1-(2-fluorobenzoyl)piperidin-4-yl]oxy}phenyl)-1-(6-methylpyridazin-3-yl)pyrrolidine-3-carboxamide The title compound was prepared as described in Example 1A, substituting (S)-1-(6-methylpyridazin-3-yl)-N-(4-(piperidin-4-yloxy)phenyl)pyrrolidine-3-carboxamide for tert-butyl 4-(4-aminophenoxy)piperidine-1-carboxylate and 2-fluorobenzoic acid for 1-(benzyloxycarbonyl)azetidine-3-carboxylic acid. $^1$H NMR (400 MHz, DMSO-$d_6$) δ ppm 9.98 (s, 1H), 7.57-7.45 (m, 3 H), 7.42 (td, J=7.2, 1.8 Hz, 1H), 7.35-7.20 (m, 3 H), 6.98-6.91 (m, 2H), 6.83 (d, J=9.1 Hz, 1H), 4.63-4.54 (m, 1H), 4.05-3.95 (m, 1H), 3.74 (dd, J=10.3, 7.9 Hz, 1H), 3.64-3.42 (m, 3H), 3.31-3.03 (m, 3 H), 2.40 (s, 3 H), 2.36-2.08 (m, 2H), 2.07-1.76 (m, 2H), 1.78-1.19 (m, 4 H); MS (ESI(+)) m/e 504 (M+H)$^+$.

Example 837

(3S)—N-{4-[(1-benzoylpiperidin-4-yl)oxy]phenyl}-1-(6-methylpyridazin-3-yl)pyrrolidine-3-carboxamide The title compound was prepared as described in Example 1A, substituting (S)-1-(6-methylpyridazin-3-yl)-N-(4-(piperidin-4-yloxy)phenyl)pyrrolidine-3-carboxamide for tert-butyl 4-(4-aminophenoxy)piperidine-1-carboxylate and benzoic acid for 1-(benzyloxycarbonyl)azetidine-3-carboxylic acid. $^1$H NMR (400 MHz, DMSO-$d_6$) δ ppm 9.98 (s, 1H), 7.55-7.48 (m, 2H), 7.48-7.37 (m, 5 H), 7.23 (d, J=9.1 Hz, 1H), 6.97-6.91 (m, 2H), 6.83 (d, J=9.1 Hz, 1H), 4.57 (dq, J=7.7, 3.8 Hz, 1H), 4.04-3.42 (m, 8 H), 3.26 (p, J=7.4 Hz, 1H), 2.41 (s, 3 H), 2.35-2.08 (m, 2H), 2.09-1.84 (m, 2H), 1.68-1.51 (m, 2H); MS (ESI(+)) m/e 486 (M+H)$^+$.

Example 838

(3S)—N-(4-{[1-(2,2-dimethylpropanoyl)piperidin-4-yl]oxy}phenyl)-1-(6-methylpyridazin-3-yl)pyrrolidine-3-carboxamide The title compound was prepared as described in Example 1A, substituting (S)-1-(6-methylpyridazin-3-yl)-N-(4-(piperidin-4-yloxy)phenyl)pyrrolidine-3-carboxamide for tert-butyl 4-(4-aminophenoxy)piperidine-1-carboxylate and 2,2-dimethylpropanoic acid for 1-(benzyloxycarbonyl)azetidine-3-carboxylic acid. $^1$H NMR (400 MHz, DMSO-$d_6$) δ ppm 9.98 (s, 1H), 7.55-7.48 (m, 2H), 7.24 (d, J=9.1 Hz, 1H), 6.96-6.90 (m, 2H), 6.83 (d, J=9.1 Hz, 1H), 4.59-4.50 (m, 1 H), 3.94-3.80 (m, 2H), 3.74 (dd, J=10.3, 7.9 Hz, 1 H), 3.65-3.52 (m, 2H), 3.32-3.18 (m, 4 H), 2.40 (s, 3 H), 2.34-2.08 (m, 2H), 1.97-1.83 (m, 2H), 1.58-1.43 (m, 2H), 1.20 (s, 9 H); MS (ESI(+)) m/e 466 (M+H)$^+$.

Example 839

(3S)—N-(4-{[1-(cyclohexylcarbonyl)piperidin-4-yl]oxy}phenyl)-1-(6-methylpyridazin-3-yl)pyrrolidine-3-carboxamide The title compound was prepared as described in Example 1A, substituting (S)-1-(6-methylpyridazin-3-yl)-N-(4-(piperidin-4-yloxy)phenyl)pyrrolidine-3-carboxamide for tert-butyl 4-(4-aminophenoxy)piperidine-1-carboxylate and cyclohexanecarboxylic acid for 1-(benzyloxycarbonyl)azetidine-3-carboxylic acid. $^1$H NMR (400 MHz, DMSO-$d_6$) δ ppm 9.98 (s, 1H), 7.55-7.48 (m, 2H), 7.24 (d, J=9.1 Hz, 1H), 6.97-6.90 (m, 2H), 6.83 (d, J=9.2 Hz, 1H), 4.52 (dq, J=7.8, 3.9 Hz, 1H), 3.89-3.66 (m, 3 H), 3.68-3.49 (m, 2H), 3.45-3.13 (m, 3 H), 2.61-2.55 (m, 1H), 2.40 (s, 3 H), 2.36-2.11 (m, 2H), 2.04-1.80 (m, 2H), 1.74-1.08 (m, 13 H); MS (ESI(+)) m/e 492 (M+H)$^+$.

Example 840

N-{4-[8-(2-methylpropanoyl)-8-azabicyclo[3.2.1]oct-3-yl]phenyl}-1-(pyridazin-3-yl)azetidine-3-carboxamide Example 840A tert-butyl 3-(4-nitrophenyl)-8-azabicyclo[3.2.1]oct-2-ene-8-carboxylate The title compound was prepared as described in Example 148A, substituting 2,2-dimethyl-1-(3-(4,4,5,5-tetramethyl-1,3,2-dioxaborolan-2-yl)-8-azabicyclo[3.2.1]oct-3-en-8-yl)propan-1-one for 1-isobutyl-4-(4,4,5,5-tetramethyl-1,3,2-dioxaborolan-2-yl)-1H-pyrazole and 1-bromo-4-nitrobenzene for 4-bromoaniline.

Example 840B tert-butyl 3-(4-aminophenyl)-8-azabicyclo[3.2.1]octane-8-carboxylate The title compound was prepared as described in Example 1B, substituting tert-butyl 3-(4-nitrophenyl)-8-azabicyclo[3.2.1]oct-2-ene-8-carboxylate for tert-butyl 4-(4-(1-(benzyloxycarbonyl)azetidine-3-carboxamido)phenoxy)piperidine-1-carboxylate.

Example 840C tert-butyl 3-(4-(1-((benzyloxy)carbonyl)azetidine-3-carboxamido)phenyl)-8-azabicyclo[3.2.1]octane-8-carboxylate The title compound was prepared as described in Example 1A, substituting tert-butyl 3-(4-aminophenyl)-8-azabicyclo[3.2.1]octane-8-carboxylate for tert-butyl 4-(4-aminophenoxy)piperidine-1-carboxylate and 1-((benzyloxy)carbonyl)azetidine-3-carboxylic acid for 1-(benzyloxycarbonyl)azetidine-3-carboxylic acid.

Example 840D tert-butyl 3-(4-(azetidine-3-carboxamido)phenyl)-8-azabicyclo[3.2.1]octane-8-carboxylate The title compound was prepared as described in Example 1B, substituting tert-butyl 3-(4-(1-((benzyloxy)carbonyl)azetidine-3-carboxamido)phenyl)-8-azabicyclo[3.2.1]octane-8-carboxylate for tert-butyl 4-(4-(1-(benzyloxycarbonyl)azetidine-3-carboxamido)phenoxy)piperidine-1-carboxylate.

Example 840F tert-butyl 3-(4-(1-(6-chloropyridazin-3-yl)azetidine-3-carboxamido)phenyl)-8-azabicyclo[3.2.1]octane-8-carboxylate The title compound was prepared as described in Example 147A, substituting tert-butyl 3-(4-(azetidine-3-carboxamido)phenyl)-8-azabicyclo[3.2.1]octane-8-carboxylate for tert-butyl 4-(4-(azetidine-3-carboxamido)phenyl)piperidine-1-carboxylate.

Example 840G tert-butyl 3-(4-(1-(pyridazin-3-yl)azetidine-3-carboxamido)phenyl)-8-azabicyclo[3.2.1]octane-8-carboxylate The title compound was prepared as described in Example 147B, substituting tert-butyl 3-(4-(1-(6-chloropyridazin-3-yl)azetidine-3-carboxamido)phenyl)-8-azabicyclo[3.2.1]octane-8-carboxylate for 4-(4-(1-(6-chloropyridazin-3-yl)azetidine-3-carboxamido)phenyl)piperidine-1-carboxylate.

Example 840 H

N-(4-(8-azabicyclo[3.2.1]octan-3-yl)phenyl)-1-(pyridazin-3-yl)azetidine-3-carboxamide The title compound was prepared as described in Example 1D, substituting tert-butyl 3-(4-(1-(pyridazin-3-yl)azetidine-3-carboxamido)phenyl)-8-azabicyclo[3.2.1]octane-8-carboxylate for tert-butyl 4-(4-(1-(pyridin-3-yl)azetidine-3-carboxamido)phenoxy)piperidine-1-carboxylate.

Example 840I

N-{4-[8-(2-methylpropanoyl)-8-azabicyclo[3.2.1]oct-3-yl]phenyl}-1-(pyridazin-3-yl)azetidine-3-carboxamide The title compound was prepared as described in Example 1A, substituting N-(4-(8-azabicyclo[3.2.1]octan-3-yl)phenyl)-1-(pyridazin-3-yl)azetidine-3-carboxamide for tert-butyl 4-(4-aminophenoxy)piperidine-1-carboxylate and isobutyric acid for 1-(benzyloxycarbonyl)azetidine-3-carboxylic acid. $^1$H NMR (300 MHz, DMSO-$d_6$) δ ppm 10.03 (s, 1H), 8.56 (dd, J=4.5, 1.3 Hz, 1H), 7.52 (dd, J=7.4, 3.4 Hz, 2H), 7.37 (dd, J=9.0, 4.5 Hz, 1H), 7.18 (dd, J=17.7, 8.6 Hz, 2H), 6.82 (dd, J=9.0, 1.3 Hz, 1H), 4.51 (ddd, J=15.0, 5.1, 4.4 Hz, 1H), 4.43-4.29 (m, 1H), 4.18 (dt, J=14.0, 8.1 Hz, 4 H), 3.72 (ddd, J=8.4, 5.9, 2.5 Hz, 1H), 2.77 (dt, J=13.4, 6.7 Hz, 1H), 2.48-2.14 (m, 3 H), 2.04-1.37 (m, 7 H), 1.15-0.94 (m, 6 H); MS (ESI(+)) m/e 434 (M+H)$^+$.

Example 841

1-(pyridazin-3-yl)-N-{4-[8-(4,4,4-trifluorobutanoyl)-8-azabicyclo[3.2.1]oct-3-yl]phenyl}azetidine-3-carboxamide The title compound was prepared as described in Example 1A, substituting N-(4-(8-azabicyclo[3.2.1]octan-3-yl)phenyl)-1-(pyridazin-3-yl)azetidine-3-carboxamide for tert-butyl 4-(4-aminophenoxy)piperidine-1-carboxylate and 4,4,4-trifluorobutanoic acid for 1-(benzyloxycarbonyl)azetidine-3-carboxylic acid. $^1$H NMR (400 MHz, DMSO-$d_6$) δ ppm 10.03 (d, J=3.6 Hz, 1H), 8.56 (dd, J=4.5, 1.1 Hz, 1H), 7.53 (dd, J=8.6, 2.7 Hz, 2H), 7.37 (dt, J=14.0, 7.0 Hz, 1 H), 7.21 (dd, J=23.0, 8.6 Hz, 2H), 6.80 (dd, J=19.3, 8.9 Hz, 1 H), 4.61-4.47 (m, 1H), 4.32 (dd, J=16.5, 8.6 Hz, 1H), 4.23 (t, J=8.3 Hz, 2H), 4.14 (t, J=7.0 Hz, 2H), 3.82-3.62 (m, 1H), 3.22-3.04 (m, 1H), 3.04-2.90 (m, 1H), 2.78-2.50 (m, 6 H), 2.41-2.12 (m, 1H), 2.05-1.38 (m, 8 H); MS (ESI(+)) m/e 488 (M+H)$^+$.

Example 842

N-[4-(8-benzoyl-8-azabicyclo[3.2.1]oct-3-yl)phenyl]-1-(pyridazin-3-yl)azetidine-3-carboxamide The title compound was prepared as described in Example 1A, substituting N-(4-(8-azabicyclo[3.2.1]octan-3-yl)phenyl)-1-(pyridazin-3-yl)azetidine-3-carboxamide for tert-butyl 4-(4-aminophenoxy)piperidine-1-carboxylate and benzoic acid for 1-(benzyloxycarbonyl)azetidine-3-carboxylic acid. $^1$H NMR (400 MHz, DMSO-$d_6$) δ ppm 10.04 (d, J=2.4 Hz, 1H), 8.56 (dt, J=9.1, 4.5 Hz, 1H), 7.63-7.42 (m, 7 H), 7.37 (dt, J=14.0, 7.0 Hz, 1H), 7.29 (d, J=8.5 Hz, 1H), 7.23 (d, J=8.5 Hz, 1H), 6.91-6.70 (m, 1H), 4.69 (d, J=6.1 Hz, 1H), 4.24 (t, J=8.3 Hz, 2H), 4.19-4.11 (m, 2H), 4.01 (d, J=14.9 Hz, 1H), 3.85-3.61 (m, 1H), 2.47-2.22 (m, 1H), 2.02-1.53 (m, 7 H); MS (ESI(+)) m/e 468 (M+H)$^+$.

Example 843

N-{4-[8-(2-fluorobenzoyl)-8-azabicyclo[3.2.1]oct-3-yl]phenyl}-1-(pyridazin-3-yl)azetidine-3-carboxamide The title compound was prepared as described in Example 1A, substituting N-(4-(8-azabicyclo[3.2.1]octan-3-yl)phenyl)-1-(pyridazin-3-yl)azetidine-3-carboxamide for tert-butyl 4-(4-aminophenoxy)piperidine-1-carboxylate and 2-fluorobenzoic acid for 1-(benzyloxycarbonyl)azetidine-3-carboxylic acid. $^1$H NMR (400 MHz, DMSO-$d_6$) δ ppm 10.04 (s, 1H), 8.56 (dd, J=4.5, 1.3 Hz, 1H), 7.59-7.44 (m, 4 H), 7.46-7.16 (m, 5 H), 6.82 (dd, J=9.0, 1.4 Hz, 1H), 4.73-4.65 (m, 1H), 4.24 (t, J=8.3 Hz, 2H), 4.14 (dd, J=8.0, 5.9 Hz, 2H), 3.81-3.67 (m, 2H), 2.10 (s, 1H), 2.05-1.35 (m, 8 H); MS (ESI(+)) m/e 486 (M+H)$^+$.

Example 844

N-{4-[8-(2,2-dimethylpropanoyl)-8-azabicyclo[3.2.1]oct-3-yl]phenyl}-1-(pyridazin-3-yl)azetidine-3-carboxamide The title compound was prepared as described in Example 1A, substituting N-(4-(8-azabicyclo[3.2.1]octan-3-yl)phenyl)-1-(pyridazin-3-yl)azetidine-3-carboxamide for tert-butyl 4-(4-aminophenoxy)piperidine-1-carboxylate and 2,2-dimethylpropanoic acid for 1-(benzyloxycarbonyl)azetidine-3-carboxylic acid. $^1$H NMR (300 MHz, DMSO-$d_6$) δ ppm 10.02 (s, 1H), 8.56 (dd, J=4.5, 1.3 Hz, 1H), 7.56-7.49 (m, 2H), 7.38 (dd, J=9.0, 4.5 Hz, 1H), 7.24-7.14 (m, 2H), 6.82 (dd, J=9.0, 1.4 Hz, 1H), 4.66-4.51 (m, 2H), 4.23 (t, J=8.3 Hz, 2H), 4.14 (dd, J=8.1, 5.9 Hz, 2H), 3.72 (tt, J=8.5, 5.9 Hz, 1H), 2.43-2.07 (m, 3 H), 1.92-1.39 (m, 8 H), 1.23-1.17 (m, 9 H); MS (ESI(+)) m/e 448 (M+H)$^+$.

Example 845

N-(4-{8-[(1-methylcyclopropyl)carbonyl]-8-azabicyclo[3.2.1]oct-3-yl}phenyl)-1-(pyridazin-3-yl)azetidine-3-carboxamide The title compound was prepared as described in Example 1A, substituting N-(4-(8-azabicyclo[3.2.1]octan-3-yl)phenyl)-1-(pyridazin-3-yl)azetidine-3-carboxamide for tert-butyl 4-(4-aminophenoxy)piperidine-1-carboxylate and 1-methylcyclopropylacetic acid for 1-(benzyloxycarbonyl)azetidine-3-carboxylic acid. $^1$H NMR (300 MHz, DMSO-$d_6$) δ ppm 10.03 (s, 1H), 8.56 (dd, J=4.5, 1.3 Hz, 1H), 7.56-7.49 (m, 2H), 7.38 (dd, J=8.9, 4.5 Hz, 1H), 7.26-7.15 (m, 2H), 6.82 (dd, J=8.9, 1.4 Hz, 1H), 4.62-4.38 (m, 2H), 4.23 (t, J=8.3 Hz, 2H), 4.14 (dd, J=8.1, 5.9 Hz, 2H), 3.72 (tt, J=8.5, 5.9 Hz, 1 H), 2.37-2.21 (m, 1H), 1.93-1.45 (m, 8 H), 1.28 (d, J=5.7 Hz, 3 H), 1.02-0.72 (m, 2H), 0.51 (dd, J=6.2, 2.1 Hz, 2H); MS (ESI(+)) m/e 446 (M+H)$^+$.

Example 846

N-{4-[1-(2-methoxyethyl)-3-(2-methylpropyl)-1H-pyrazol-5-yl]phenyl}-1-(pyridazin-3-yl)azetidine-3-carboxamide The title compound was prepared as described in Example 805, substituting 4-methylpent-1-yne for ethynylcyclopropane in Example 805A and (2-methoxyethyl)hydrazine for methylhydrazine in 805B. $^1$H NMR (300 MHz, DMSO-$d_6$) δ ppm 10.21 (s, 1H), 8.56 (dd, J=4.4, 1.2 Hz, 1H), 7.78-7.58 (m, 4 H), 7.24 (d, J=8.5 Hz, 1H), 6.42 (s, 1H), 4.45-4.25 (m, 3 H), 4.18 (t, J=5.5 Hz, 2H), 3.87-3.73 (m, 1H), 3.69 (t, J=5.5 Hz, 2H), 3.46-3.30 (m, 4 H), 3.22 (s, 3H), 2.01-1.84 (m, 1H), 0.95 (d, J=6.6 Hz, 6 H); MS (ESI(+)) m/e 435 (M+H)$^+$.

Example 853 benzyl 4-[4-({[1-(6-chloropyridazin-3-yl)azetidin-3-yl]carbonyl}amino)phenyl]-4-fluoropiperidine-1-carboxylate The title compound was prepared as described in Example 809C, substituting benzyl 4-[4-({[1-(6-chloropyridazin-3-yl)azetidin-3-yl]carbonyl}amino)phenyl]-4-hydroxypiperidine-1-carboxylate for tert-butyl 4-(4-(1-((benzyloxy)carbonyl)azetidine-3-carboxamido)phenoxy)-4-hydroxypiperidine-1-carboxylate. $^1$H NMR (300 MHz, DMSO-$d_6$) δ ppm 10.18-10.11 (m, 1H), 7.67-7.57 (m, 2H), 7.53 (d, J=9.3 Hz, 1H), 7.47-7.23 (m, 7 H), 6.96 (d, J=9.3 Hz, 1H), 5.14-5.08 (m, 2H), 4.26 (t, J=8.4 Hz, 2H), 4.17 (dd, J=8.3, 5.8 Hz, 2H), 4.09-3.98 (m, 2H). 3.80-3.60 (m, 2H), 3.30-3.20 (m, 2H), 2.2-1.8 (m, 3 H); MS (ESI(+)) m/e 524 (M+H)$^+$.

Example 854 benzyl 4-[4-({[1-(6-chloropyridazin-3-yl)azetidin-3-yl]carbonyl}amino)phenyl]-4-hydroxypiperidine-1-carboxylate

Example 854A benzyl 4-(4-aminophenyl)-4-hydroxypiperidine-1-carboxylate

The title compound was prepared as described in Example 809A, substituting benzyl 4-oxopiperidine-1-carboxylate for tert-butyl 4-oxopiperidine-1-carboxylate.

Example 854B benzyl 4-[4-({[1-(6-chloropyridazin-3-yl)azetidin-3-yl]carbonyl}amino)phenyl]-4-hydroxypiperidine-1-carboxylate The title compound was prepared as described in Example 1A, substituting benzyl 4-(4-aminophenyl)-4-hydroxypiperidine-1-carboxylate for tert-butyl 4-(4-aminophenoxy)piperidine-1-carboxylate and 1-(6-chloropyridazin-3-yl)azetidine-3-carboxylic acid for 1-(benzyloxycarbonyl)azetidine-3-carboxylic acid. $^1$H NMR (300 MHz, DMSO-$d_6$) δ ppm 10.06 (s, 1H), 7.59-7.49 (m, 3 H), 7.41-7.28 (m, 7 H), 6.96 (d, J=9.3 Hz, 1H), 5.09 (s, 2 H), 5.04 (s, 1H), 4.26 (t, J=8.4 Hz, 2H), 4.16 (dd, J=8.3, 5.8 Hz, 2H), 3.97-3.86 (m, 2H), 3.73 (tt, J=8.5, 5.8 Hz, 1H), 3.3-3.0 (m, 2H), 1.91-1.70 (m, 2H), 1.63-1.54 (m, 2H); MS (ESI(+)) m/e 522.0 (M+H)$^+$.

Example 857

N-{4-[4-fluoro-1-(2-fluorobenzoyl)piperidin-4-yl]phenyl}-1-(pyridazin-3-yl)azetidine-3-carboxamide

Example 857A

N-(4-(4-fluoropiperidin-4-yl)phenyl)-1-(pyridazin-3-yl)azetidine-3-carboxamide

The title compound was prepared as described in Example 1D, substituting tert-butyl 4-fluoro-4-[4-({[1-(pyridazin-3-yl)azetidin-3-yl]carbonyl}amino)phenyl]piperidine-1-carboxylate for tert-butyl 4-(4-(1-(pyridin-3-yl)azetidine-3-carboxamido)phenoxy)piperidine-1-carboxylate.

Example 857B

N-{4-[4-fluoro-1-(2-fluorobenzoyl)piperidin-4-yl]phenyl}-1-(pyridazin-3-yl)azetidine-3-carboxamide The title compound was prepared as described in Example 1A, substituting N-(4-(4-fluoropiperidin-4-yl)phenyl)-1-(pyridazin-3-yl)azetidine-3-carboxamide for tert-butyl 4-(4-aminophenoxy)piperidine-1-carboxylate and 2-fluorobenzoic acid for 1-(benzyloxycarbonyl)azetidine-3-carboxylic acid. $^1$H NMR (300 MHz, DMSO-$d_6$) δ ppm 10.06 (s, 1H), 7.59-7.49 (m, 3 H), 7.41-7.28 (m, 7 H), 6.96 (d, J=9.3 Hz, 1H), 5.09 (s, 2H), 5.04 (s, 1H), 4.26 (t, J=8.4 Hz, 2H), 4.16 (dd, J=8.3, 5.8 Hz, 2H), 3.97-3.86 (m, 2H), 3.73 (tt, J=8.5, 5.8 Hz, 1H), 3.3-3.0 (m, 2H), 1.91-1.70 (m, 2H), 1.63-1.54 (m, 2H); MS (ESI(+)) m/e 478 (M+H)$^+$.

Example 863

N-[4-(1-benzoyl-4-fluoropiperidin-4-yl)phenyl]-1-(pyridazin-3-yl)azetidine-3-carboxamide The title compound was prepared as described in Example 1A, substituting N-(4-(4-fluoropiperidin-4-yl)phenyl)-1-(pyridazin-3-yl)azetidine-3-carboxamide for tert-butyl 4-(4-aminophenoxy)piperidine-1-carboxylate and benzoic acid for 1-(benzyloxycarbonyl)azetidine-3-carboxylic acid. $^1$H NMR (400 MHz, DMSO-$d_6$) δ ppm 10.20-10.03 (m, 1H), 8.57 (d, J=4.5 Hz, 1H), 7.68-7.59 (m, 2H), 7.60-7.30 (m, 8H), 6.87-6.80 (m, 1H), 4.78-4.09 (m, 5 H), 4.10-3.44 (m, 3 H), 3.14-3.01 (m, 1H), 2.25-1.51 (m, 4 H); MS (ESI(+)) m/e 460 (M+H)$^+$.

Example 864

N-{4-[1-(2,2-dimethylpropanoyl)-4-fluoropiperidin-4-yl]phenyl}-1-(pyridazin-3-yl)azetidine-3-carboxamide The title compound was prepared as described in Example 1A, substituting N-(4-(4-fluoropiperidin-4-yl)phenyl)-1-(pyridazin-3-yl)azetidine-3-carboxamide for tert-butyl 4-(4-aminophenoxy)piperidine-1-carboxylate and 2,2-dimethypropanoic acid for 1-(benzyloxycarbonyl)azetidine-3-carboxylic acid. $^1$H NMR (400 MHz, DMSO-$d_6$) δ ppm 10.20-10.02 (m, 1H), 8.56 (dd, J=4.5, 1.3 Hz, 1H), 7.67-7.58 (m, 2H), 7.47-7.30 (m, 3 H), 6.83 (dd, J=8.9, 1.4 Hz, 1H), 4.48-4.10 (m, 6 H), 3.80-3.69 (m, 1H), 3.23-2.96 (m, 2H), 2.07-1.60 (m, 4 H), 1.23 (s, 9 H); MS (ESI(+)) m/e 440 (M+H)$^+$.

Example 865

N-{4-[3-tert-butyl-1-(2-methoxyethyl)-1H-pyrazol-5-yl]phenyl}-1-(pyridazin-3-yl)azetidine-3-carboxamide The title compound was prepared as described in Example 805, substituting 3,3-dimethylbut-1-yne for ethynylcyclopropane in Example 805A and (2-methoxyethyl)hydrazine for methylhydrazine in Example 805B. $^1$H NMR (400 MHz, DMSO-$d_6$) δ ppm 10.14 (s, 1H), 8.57 (dd, J=4.5, 1.3 Hz, 1H), 7.70 (d, J=8.7 Hz, 2H), 7.64 (d, J=8.7 Hz, 2H), 7.39 (dd, J=8.9, 4.5 Hz, 1H), 6.84 (d, J=8.9 Hz, 1H), 6.40 (s, 1 H), 4.31 (t, J=6.0 Hz, 2H), 4.25 (t, J=8.3 Hz, 2H), 4.17 (dd, J=8.0, 6.0 Hz, 2H), 3.83 (t, J=6.0 Hz, 2H), 3.75 (tt, J=8.7, 6.1 Hz, 1H), 3.25 (s, 3 H), 1.37 (s, 9 H); MS (ESI(+)) m/e 435 (M+H)$^+$.

Example 866

N-[4-(1-butyl-3-tert-butyl-1H-pyrazol-5-yl)phenyl]-1-(pyridazin-3-yl)azetidine-3-carboxamide The title compound was prepared as described in Example 805, substituting 3,3-dimethylbut-1-yne for ethynylcyclopropane in Example 805A and butylhydrazine for methylhydrazine in 805B. $^1$H NMR (400 MHz, DMSO-$d_6$) δ ppm 10.14 (s, 1H), 8.57 (dd, J=4.5, 1.3 Hz, 1H), 7.69 (d, J=8.7 Hz, 2H), 7.63 (d, J=8.8 Hz, 2H), 7.39 (dd, J=8.9, 4.5 Hz, 1H), 6.84 (dd, J=8.9, 1.3 Hz, 1H), 6.38 (s, 1H), 4.25 (t, J=8.3 Hz, 2H), 4.21-4.09 (m, 4 H), 3.81-3.70 (m, 1H), 1.92-1.77 (m, 2H), 1.46-1.37 (m, 2H), 1.36 (s, 9 H), 0.94 (t, J=7.3 Hz, 3 H); MS (ESI(+)) m/e 433 (M+H)$^+$.

Example 867

N-{4-[3-tert-butyl-1-(tetrahydro-2H-pyran-4-ylmethyl)-1H-pyrazol-5-yl]phenyl}-1-(pyridazin-3-yl)azetidine-3-carboxamide The title compound was prepared as described in Example 805, substituting 3,3-dimethylbut-1-yne for ethynylcyclopropane in Example 805A and (tetrahydro-2H-pyran-4-ylmethyl)hydrazine for methylhydrazine in Example 805B. $^1$H NMR (400 MHz, DMSO-$d_6$) δ ppm 10.14 (s, 1H), 8.57 (dd, J=4.5, 1.3 Hz, 1H), 7.70 (d, J=8.7 Hz, 2H), 7.63 (d, J=8.8 Hz, 2H), 7.39 (dd, J=8.9, 4.5 Hz, 1H), 6.83 (dd, J=8.9, 1.4 Hz, 1H), 6.41 (s, 1H), 4.25 (t, J=8.3 Hz, 2H), 4.16 (dd, J=8.1, 5.9 Hz, 2H), 4.03 (d, J=7.0 Hz, 2H), 3.85 (dd, J=11.3, 3.0 Hz, 2H), 3.80-3.71 (m, 1H), 3.32-3.22 (m, 2H), 2.39-2.25 (m, 1H), 1.55 (dd, J=12.8, 1.9 Hz, 2H), 1.37 (s, 9 H), 1.42-1.30 (m, 2H); MS (ESI(+)) m/e 475 (M+H)$^+$.

Example 868

N-{2-fluoro-4-[1-(2-fluorobenzoyl)piperidin-4-yl]phenyl}-1-(pyridazin-4-yl)azetidine-3-carboxamide

Example 868A tert-butyl 4-(4-(1-(5,6-dichloropyridazin-4-yl)azetidine-3-carboxamido)-3-fluorophenyl)piperidine-1-carboxylate The title compound was prepared as described in Example 618, substituting tert-butyl 4-(4-(azetidine-3-carboxamido)-3-fluorophenyl)piperidine-1-carboxylate for (R)-5-(1-isobutyl-1H-pyrazol-4-yl)-N-(pyrrolidin-3-yl)thiophene-2-carboxamide.

Example 868B tert-butyl 4-(3-fluoro-4-(1-(pyridazin-4-yl)azetidine-3-carboxamido)phenyl)piperidine-1-carboxylate The title compound was prepared as described in Example 147B, substituting tert-butyl 4-(4-(1-(5,6-dichloropyridazin-4-yl)azetidine-3-carboxamido)-3-fluorophenyl)piperidine-1-carboxylate for 4-(4-(1-(6-chloropyridazin-3-yl)azetidine-3-carboxamido)phenyl)piperidine-1-carboxylate.

Example 868C

N-(2-fluoro-4-(piperidin-4-yl)phenyl)-1-(pyridazin-4-yl)azetidine-3-carboxamide

The title compound was prepared as described in Example 1D, substituting tert-butyl 4-(3-fluoro-4-(1-(pyridazin-4-yl)azetidine-3-carboxamido)phenyl)piperidine-1-carboxylate for tert-butyl 4-(4-(1-(pyridin-3-yl)azetidine-3-carboxamido)phenoxy)piperidine-1-carboxylate.

Example 868D

N-{2-fluoro-4-[1-(2-fluorobenzoyl)piperidin-4-yl]phenyl}-1-(pyridazin-4-yl)azetidine-3-carboxamide The title compound was prepared as described in Example 1A, substituting N-(2-fluoro-4-(piperidin-4-yl)phenyl)-1-(pyridazin-4-yl)azetidine-3-carboxamide for tert-butyl 4-(4-aminophenoxy)piperidine-1-carboxylate and 2-fluorobenzoic acid for 1-(benzyloxycarbonyl)azetidine-3-carboxylic acid. $^1$H NMR (400 MHz, DMSO-$d_6$) δ ppm 10.39 (s, 1H), 8.66 (d, J=6.3 Hz, 1H), 8.52 (d, J=3.0 Hz, 1H), 7.66-7.37 (m, 4 H), 7.35-7.27 (m, 3 H), 6.68 (dd, J=6.3, 3.2 Hz, 1H), 4.71-4.62 (m, 1H), 4.37-3.92 (m, 4 H), 3.94-2.70 (m, 5 H), 1.88-12 (m, 4 H); MS (ESI(+)) m/e 478 (M+H)$^+$.

Example 869

N-[4-(1-benzoylpiperidin-4-yl)-2-fluorophenyl]-1-(pyridazin-4-yl)azetidine-3-carboxamide The title compound was prepared as described in Example 1A, substituting N-(2-fluoro-4-(piperidin-4-yl)phenyl)-1-(pyridazin-4-yl)azetidine-3-carboxamide for tert-butyl 4-(4-aminophenoxy)piperidine-1-carboxylate and benzoic acid for 1-(benzyloxycarbonyl)azetidine-3-carboxylic acid. $^1$H NMR (400 MHz, DMSO-d$_6$) δ ppm 10.27 (s, 1H), 8.61 (dd, J=6.0, 0.9 Hz, 1H), 8.51 (dd, J=3.0, 0.9 Hz, 1H), 7.57 (d, J=12.9, 2.0 Hz, 1H), 7.51-7.38 (m, 5 H), 7.34 (t, J=8.4 Hz, 1H), 7.28 (dd, J=8.4, 2.0 Hz, 1H), 6.55 (dd, J=6.0, 3.0 Hz, 1H), 4.71-4.51 (m, 1H), 4.22 (t, J=8.4 Hz, 2H), 4.12 (dd, J=8.2, 5.7 Hz, 2 H), 4.04-3.45 (m, 2H), 3.22-2.76 (m, 3 H), 2.08-1.33 (m, 4 H); MS (ESI(+)) m/e 460 (M+H)$^+$.

Example 870

N-{4-[1-(2,2-dimethylpropanoyl)piperidin-4-yl]-2-fluorophenyl}-1-(pyridazin-4-yl)azetidine-3-carboxamide The title compound was prepared as described in Example 1A, substituting N-(2-fluoro-4-(piperidin-4-yl)phenyl)-1-(pyridazin-4-yl)azetidine-3-carboxamide for tert-butyl 4-(4-aminophenoxy)piperidine-1-carboxylate and 2,2-dimethylpropanoic acid for 1-(benzyloxycarbonyl)azetidine-3-carboxylic acid. $^1$H NMR (500 MHz, DMSO-d$_6$) δ ppm 10.28 (s, 1H), 8.61 (dd, J=6.0, 0.9 Hz, 1H), 8.51 (d, J=3.4 Hz, 1H), 7.68-7.24 (m, 3 H), 6.57 (dd, J=6.1, 3.0 Hz, 1H), 4.5 (d, 2H), 4.30-4.13 (m, 4 H), 3.90-2.78 (m, 4 H), 1.79-1.71 (m, 2H), 1.72-1.44 (m, 2H), 1.21 (s, 9 H); MS (ESI(+)) m/e 440 (M+H)$^+$.

Example 871

N-{4-[1-(3,3-dimethylbutanoyl)piperidin-4-yl]-2-fluorophenyl}-1-(pyridazin-4-yl)azetidine-3-carboxamide The title compound was prepared as described in Example 1A, substituting N-(2-fluoro-4-(piperidin-4-yl)phenyl)-1-(pyridazin-4-yl)azetidine-3-carboxamide for tert-butyl 4-(4-aminophenoxy)piperidine-1-carboxylate and 3,3,-dimethylbutanoic acid for 1-(benzyloxycarbonyl)azetidine-3-carboxylic acid. $^1$H NMR (500 MHz, DMSO-d$_6$) δ ppm 10.28 (s, 1H), 8.62 (d, J=6.1 Hz, 1H), 8.51 (d, J=3.4 Hz, 1H), 7.60-7.23 (m, 3 H), 6.57 (dd, J=6.1, 3.0 Hz, 1H), 4.65-4.58 (m, 1H), 4.30-4.00 (m, 5 H), 3.85-2.83 (m, 3 H), 2.60-2.50 (m, 1H), 2.30 (d, J=14.0 Hz, 1H), 2.21 (d, J=14.0 Hz, 1H), 1.79-1.40 (m, 4 H), 1.00 (s, 9 H); MS (ESI(+)) m/e 454 (M+H)$^+$.

Example 872

N-{2-fluoro-4-[1-(4,4,4-trifluorobutanoyl)piperidin-4-yl]phenyl}-1-(pyridazin-4-yl)azetidine-3-carboxamide The title compound was prepared as described in Example 1A, substituting N-(2-fluoro-4-(piperidin-4-yl)phenyl)-1-(pyridazin-4-yl)azetidine-3-carboxamide for tert-butyl 4-(4-aminophenoxy)piperidine-1-carboxylate and 4,4,4-trifluorobutanoic acid for 1-(benzyloxycarbonyl)azetidine-3-carboxylic acid. $^1$H NMR (500 MHz, DMSO-d$_6$) δ ppm 10.3 (s, 1H), 8.70-8.50 (m, 2H), 7.90-7.20 (m, 3 H), 6.55-6.65 (m, 1H), 4.6 (, d, 1H), 4.30-3.90 (m, 5 H), 3.80-2.90 (m, 3 H), 2.80-2.50 (m, 5 H), 1.80-1.40 (m, 4 H); MS (ESI(+)) m/e 480 (M+H)$^+$.

Example 873

N-(4-{1-[(4-methylpiperidin-4-yl)methyl]-1H-pyrazol-4-yl}phenyl)-1-(pyridazin-3-yl)azetidine-3-carboxamide The title compound was prepared as described as described in Example 148A, substituting N-(4-bromophenyl)-1-(pyridazin-3-yl)azetidine-3-carboxamide for 4-bromoaniline and tert-butyl 4-methyl-4-44-(4,4,5,5-tetramethyl-1,3,2-dioxaborolan-2-yl)-1H-pyrazol-1-yl)methyl)piperidine-1-carboxylate for 1-isobutyl-4-(4,4,5,5-tetramethyl-1,3,2-dioxaborolan-2-yl)-1H-pyrazole followed by TFA deprotection as described in Example 1D to give the title compound as a TFA salt. $^1$H NMR (400 MHz, DMSO-d$_6$) δ ppm 10.24 (s, 1H), 8.57 (d, J=4.0 Hz, 1H), 8.52 (s, 1H), 8.40 (s, 1H), 8.11 (s, 1H), 7.87 (s, 1H), 7.80 (dd, J=9.3, 4.3 Hz, 1H), 7.63 (d, J=8.6 Hz, 2H), 7.55 (d, J=8.5 Hz, 2H), 7.45 (d, J=9.3 Hz, 1H), 4.47 (t, J=9.1 Hz, 2H), 4.43-4.34 (m, 2H), 4.08 (s, 2H), 3.81 (ddd, J=14.5, 8.7, 6.0 Hz, 1H), 3.27-3.13 (m, 2H), 3.13-2.97 (m, 2H), 1.73-1.58 (m, 2H), 1.57-1.42 (m, 2H), 0.98 (s, 3 H); MS (ESI(+)) m/e 432 (M+H)$^+$.

Example 874

N-{4-[1-methyl-3-(trifluoromethyl)-1H-pyrazol-5-yl]phenyl}-1-(pyridazin-3-yl)azetidine-3-carboxamide The title compound was prepared as described in Example 805, substituting 3,3,3-trifluoroprop-1-yne for ethynylcyclopropane in Example 805A. $^1$H NMR (500 MHz, DMSO-d$_6$) δ ppm 10.47 (s, 1H), 8.57 (d, J=3.8 Hz, 1H), 7.80 (d, J=8.4 Hz, 2H), 7.57 (d, J=8.4 Hz, 2H), 7.56-7.49 (m, 1H), 7.06 (d, J=8.6 Hz, 1H), 6.87 (s, 1H), 4.34 (t, J=8.4 Hz, 2H), 4.29-4.22 (m, 2H), 3.92 (s, 3H), 3.86-3.78 (m, 1H); MS (ESI(+)) m/e 403 (M+H)$^+$.

Example 875

1-(6-chloropyridazin-3-yl)-N-{4-[1-(2,2-dimethylpropyl)-1H-pyrazol-4-yl]phenyl}azetidine-3-carboxamide Example 875A 4-(1-neopentyl-1H-pyrazol-4-yl)aniline The title compound was prepared as described as described in Example 148A, substituting 1-neopentyl-4-(4,4,5,5-tetramethyl-1,3,2-dioxaborolan-2-yl)-1H-pyrazole for 1-isobutyl-4-(4,4,5,5-tetramethyl-1,3,2-dioxaborolan-2-yl)-1H-pyrazole.

Example 875B 1-(6-chloropyridazin-3-yl)-N-{4-[1-(2,2-dimethylpropyl)-1H-pyrazol-4-yl]phenyl}azetidine-3-carboxamide The title compound was prepared as described in Example 1A, substituting 4-(1-neopentyl-1H-pyrazol-4-yl)aniline for tert-butyl 4-(4-aminophenoxy)piperidine-1-carboxylate and 1-(6-chloropyridazin-3-yl)azetidine-3-carboxylic acid for 1-(benzyloxycarbonyl)azetidine-3-carboxylic acid. $^1$H NMR (400 MHz, DMSO-d$_6$) δ ppm 10.10 (s, 1H), 8.04 (s, 1H), 7.82 (s, 1H), 7.61 (d, J=8.7 Hz, 2H), 7.56-7.50 (m, 3 H), 6.98 (d, J=9.3 Hz, 1H), 4.27 (t, J=8.5 Hz, 2H), 4.19 (dd, J=8.3, 5.9 Hz, 2H), 3.90 (s, 2H), 3.74 (tt, J=8.6, 5.9 Hz, 1H), 0.92 (s, 9 H); MS (ESI(+)) m/e 425 (M+H)$^+$.

Example 876

N-[4-(1-benzoylpiperidin-4-yl)phenyl]-1-(6-methylpyridin-3-yl)azetidine-3-carboxamide

Example 876A tert-butyl 4-(4-(1-(6-methylpyridin-3-yl)azetidine-3-carboxamido)phenyl)piperidine-1-carboxylate The title compound was prepared as described in Example 1C, substituting 5-bromo-2-methylpyridine for 3-bromopyridine and tert-butyl 4-(4-(azetidine-3-carboxamido)phenyl)piperidine-1-carboxylate for tert-butyl 4-(4-(azetidine-3-carboxamido)phenoxy)piperidine-1-carboxylate.

Example 876B 1-(6-methylpyridin-3-yl)-N-(4-(piperidin-4-yl)phenyl)azetidine-3-carboxamide The title compound was prepared as described in Example 1D, substituting tert-butyl 4-(4-(1-(6-methylpyridin-3-yl)azetidine-3-carboxamido)phenyl)piperidine-1-carboxylate for tert-butyl 4-(4-(1-(pyridin-3-yl)azetidine-3-carboxamido)phenoxy)piperidine-1-carboxylate.

Example 876C

N-[4-(1-benzoylpiperidin-4-yl)phenyl]-1-(6-methylpyridin-3-yl)azetidine-3-carboxamide The title compound was prepared as described in Example 1A, substituting 1-(6-methylpyridin-3-yl)-N-(4-(piperidin-4-yl)phenyl)azetidine-3-carboxamide for tert-butyl 4-(4-aminophenoxy)piperidine-1-carboxylate and benzoic acid for 1-(benzyloxycarbonyl)azetidine-3-carboxylic acid. $^1$H NMR (400 MHz, DMSO-$d_6$) δ ppm 9.99 (s, 1H), 7.73 (d, J=2.8 Hz, 1H), 7.53 (d, J=8.5 Hz, 2H), 7.48-7.39 (m, 5 H), 7.22 (d, J=8.6 Hz, 2H), 7.04 (d, J=8.3 Hz, 1H), 6.80 (dd, J=8.3, 2.9 Hz, 1H), 4.62 (s, 1H), 4.05 (t, J=7.7 Hz, 2H), 3.90 (t, J=6.7 Hz, 2H), 3.69 (ddd, J=14.5, 8.1, 6.3 Hz, 2H), 3.13 (s, 1H), 2.99-2.69 (m, 2H), 2.34 (s, 3H), 1.89-1.47 (m, 4 H), MS (ESI(+)) m/e 455 (M+H)$^+$.

Example 877

N-(4-{1-[(4-methylpiperidin-4-yl)methyl]-1H-pyrazol-4-yl}phenyl)-1-(pyridin-3-yl)azetidine-3-carboxamide

Example 877A tert-butyl 1-(pyridin-3-yl)azetidine-3-carboxylate

The title compound was prepared as described in Example 1C, substituting tert-butyl azetidine-3-carboxylate for tert-butyl 4-(4-(azetidine-3-carboxamido)phenoxy)piperidine-1-carboxylate.

Example 877B 1-(pyridin-3-yl)azetidine-3-carboxylic acid

The title compound was prepared as described in Example 1D, substituting tert-butyl 1-(pyridin-3-yl)azetidine-3-carboxylate for tert-butyl 4-(4-(1-(pyridin-3-yl)azetidine-3-carboxamido)phenoxy)piperidine-1-carboxylate.

Example 877C

N-(4-bromophenyl)-1-(pyridin-3-yl)azetidine-3-carboxamide

The title compound was prepared as described in Example 1A, substituting 4-bromoaniline for tert-butyl 4-(4-aminophenoxy)piperidine-1-carboxylate and 1-(pyridin-3-yl)azetidine-3-carboxylic acid for 1-(benzyloxycarbonyl)azetidine-3-carboxylic acid.

Example 877D

N-(4-{1-[(4-methylpiperidin-4-yl)methyl]-1H-pyrazol-4-yl}phenyl)-1-(pyridin-3-yl)azetidine-3-carboxamide The title compound as described as described in Example 148A, substituting N-(4-bromophenyl)-1-(pyridin-3-yl)azetidine-3-carboxamide for 4-bromoaniline and tert-butyl 4-methyl-4-((4-(4,4,5,5-tetramethyl-1,3,2-dioxaborolan-2-yl)-1H-pyrazol-1-yl)methyl)piperidine-1-carboxylate for 1-isobutyl-4-(4,4,5,5-tetramethyl-1,3,2-dioxaborolan-2-yl)-1H-pyrazole followed by TFA deprotection as described in Example 1D to give the title compound as a TFA salt. $^1$H NMR (400 MHz, DMSO-$d_6$) δ ppm 10.21 (s, 1H), 8.58 (s, 1H), 8.45 (s, 1H), 8.15 (d, J=5.3 Hz, 1H), 8.10 (s, 1H), 8.08 (d, J=2.6 Hz, 1H), 7.86 (s, 1H), 7.77 (dd, J=8.6, 5.4 Hz, 1H), 7.62 (d, J=8.7 Hz, 2H), 7.58-7.51 (m, 3 H), 4.24 (t, J=8.3 Hz, 2 H), 4.15 (dd, J=7.9, 6.0 Hz, 2H), 4.08 (s, 2H), 3.79 (dq, J=8.6, 5.9 Hz, 1H), 3.28-3.12 (m, 2H), 3.12-2.95 (m, 2H), 1.65 (ddd, J=13.4, 9.3, 3.8 Hz, 2H), 1.56-1.40 (m, 2H), 0.97 (s, 3 H); MS (ESI(+)) m/e 431 (M+H)$^+$.

Example 878

N-{4-[1-(2,2-dimethylpropyl)-1H-pyrazol-4-yl]phenyl}-1-(6-methylpyridazin-3-yl)azetidine-3-carboxamide To 1-(6-chloropyridazin-3-yl)-N-(4-(1-neopentyl-1H-pyrazol-4-yl)phenyl)azetidine-3-carboxamide (0.076 g, 0.179 mmol) was added methylzinc(II) chloride (2.0M in THF) (0.179 ml, 0.358 mmol) and 5 mg of palladium catalyst. The reaction mixture was heated to 60° C. and a thick precipitate developed. N-methylpyrrolidine (0.2 ml) was added and the mixture was heated to 85° C. for 2 hours. The mixture was diluted with dichloromethane and purified by normal phase chromatography to give the title compound. $^1$H NMR (400 MHz, DMSO-$d_6$) δ ppm 10.11 (s, 1H), 8.04 (s, 1H), 7.82 (s, 1H), 7.61 (d, J=8.7 Hz, 2H), 7.53 (d, J=8.7 Hz, 2H), 7.43 (d, J=9.2 Hz, 1H), 6.99 (d, J=9.1 Hz, 1H), 4.27 (t, J=8.5 Hz, 2H), 4.19 (dd, J=8.2, 6.1 Hz, 2H), 3.90 (s, 2H), 3.75 (ddd, J=17.0, 8.5, 6.0 Hz, 1H), 2.45 (s, 3 H), 0.92 (s, 9 H); MS (ESI(+)) m/e 405 (M+H)$^+$.

Example 879

N-{3-fluoro-4-[1-(3-fluorobenzoyl)piperidin-4-yl]phenyl}-1-(pyridazin-3-yl)azetidine-3-carboxamide

Example 879A tert-butyl 4-(4-amino-2-fluorophenyl)-5,6-dihydropyridine-1(2H)-carboxylate The title compound was prepared as described as described in Example 148A, substituting 4-bromo-3-fluoroaniline for 4-bromoaniline and tert-butyl 4-(4,4,5,5-tetramethyl-1,3,2-dioxaborolan-2-yl)-5,6-dihydropyridine-1(2H)-carboxylate for 1-isobutyl-4-(4,4,5,5-tetramethyl-1,3,2-dioxaborolan-2-yl)-1H-pyrazole.

Example 879B tert-butyl 4-(4-amino-2-fluorophenyl)piperidine-1-carboxylate

The title compound was prepared as described in Example 1B, substituting tert-butyl 4-(4-amino-2-fluorophenyl)-5,6-dihydropyridine-1(2H)-carboxylate for tert-butyl 4-(4-(1-(benzyloxycarbonyl)azetidine-3-carboxamido)phenoxy)piperidine-1-carboxylate.

Example 879C tert-butyl 4-(2-fluoro-4-(1-(pyridazin-3-yl)azetidine-3-carboxamido)phenyl)piperidine-1-carboxylate The title compound was prepared as described in Example 1A, substituting tert-butyl 4-(4-amino-2-fluorophenyl)piperidine-1-carboxylate for tert-butyl 4-(4-aminophenoxy)piperidine-1-carboxylate and 1-(pyridazin-3-yl)azetidine-3-carboxylic acid for 1-(benzyloxycarbonyl)azetidine-3-carboxylic acid.

Example 879D

N-(3-fluoro-4-(piperidin-4-yl)phenyl)-1-(pyridazin-3-yl)azetidine-3-carboxamide

The title compound was prepared as described in Example 1D, substituting tert-butyl 4-(2-fluoro-4-(1-(pyridazin-3-yl)azetidine-3-carboxamido)phenyl)piperidine-1-carboxylate for tert-butyl 4-(4-(1-(pyridin-3-yl)azetidine-3-carboxamido)phenoxy)piperidine-1-carboxylate.

Example 879E

N-{3-fluoro-4-[1-(3-fluorobenzoyl)piperidin-4-yl]phenyl}-1-(pyridazin-3-yl)azetidine-3-carboxamide The title compound was prepared as described in Example 1A, substituting N-(3-fluoro-4-(piperidin-4-yl)phenyl)-1-(pyridazin-3-yl)azetidine-3-carboxamide for tert-butyl 4-(4-aminophenoxy)piperidine-1-carboxylate and 3-fluorobenzoic acid for 1-(benzyloxycarbonyl)azetidine-3-carboxylic acid. $^1$H NMR (400 MHz, DMSO-$d_6$) δ ppm 9.86 (s, 1H), 8.56 (dd, J=4.5, 1.1 Hz, 1H), 7.79 (t, J=8.3 Hz, 1H), 7.56-7.45 (m, 1H), 7.38 (dd, J=9.0, 4.5 Hz, 1H), 7.25 (ddd, J=20.2, 14.3, 8.7 Hz, 4 H), 7.10 (d, J=8.2 Hz, 1H), 6.83 (dd, J=8.9, 1.0 Hz, 1H), 4.60 (s, 1H), 4.19 (dt, J=14.0, 8.2 Hz, 4 H), 3.99-3.74 (m, 1H), 3.59 (s, 1H), 3.07 (d, J=59.7 Hz, 1H), 2.85 (dd, J=39.3, 27.7 Hz, 2H), 2.08-1.43 (m, 4 H); MS (ESI(+)) m/e 478.3 (M+H)$^+$.

TABLE 21

The following Examples were essentially prepared as described in Example 879, substituting an appropriate carboxylic acid in Example 879E.

| Ex | Name | MS |
|---|---|---|
| 880 | N-{3-fluoro-4-[1-(2-methylpropanoyl)piperidin-4-yl]phenyl}-1-(pyridazin-3-yl)azetidine-3-carboxamide | (ESI(+)) m/e 426 (M + H)$^+$ |
| 881 | N-{3-fluoro-4-[1-(3,3,3-trifluoropropanoyl)piperidin-4-yl]phenyl}-1-(pyridazin-3-yl)azetidine-3-carboxamide | (ESI(+)) m/e 466 (M + H)$^+$ |
| 882 | N-{4-[1-(3,3-dimethylbutanoyl)piperidin-4-yl]-3-fluorophenyl}-1-(pyridazin-3-yl)azetidine-3-carboxamide | (ESI(+)) m/e 454 (M + H)$^+$ |
| 883 | N-{3-fluoro-4-[1-(4,4,4-trifluorobutanoyl)piperidin-4-yl]phenyl}-1-(pyridazin-3-yl)azetidine-3-carboxamide | (ESI(+)) m/e 480 (M + H)$^+$ |
| 884 | N-[4-(1-benzoylpiperidin-4-yl)-3-fluorophenyl]-1-(pyridazin-3-yl)azetidine-3-carboxamide | (ESI(+)) m/e 460 (M + H)$^+$ |
| 885 | N-{3-fluoro-4-[1-(2-fluorobenzoyl)piperidin-4-yl]phenyl}-1-(pyridazin-3-yl)azetidine-3-carboxamide | (ESI(+)) m/e 478 (M + H)$^+$ |
| 886 | N-{4-[1-(2,2-dimethylpropanoyl)piperidin-4-yl]-3-fluorophenyl}-1-(pyridazin-3-yl)azetidine-3-carboxamide | (ESI(+)) m/e 440 (M + H)$^+$ |
| 887 | N-{3-fluoro-4-[1-(3-methylbutanoyl)piperidin-4-yl]phenyl}-1-(pyridazin-3-yl)azetidine-3-carboxamide | (ESI(+)) m/e 440 (M + H)$^+$ |
| 888 | N-{4-[1-(cyclopropylacetyl)piperidin-4-yl]-3-fluorophenyl}-1-(pyridazin-3-yl)azetidine-3-carboxamide | (ESI(+)) m/e 438 (M + H)$^+$ |

Example 889

N-{4-[1-(2-fluorobenzoyl)-4-hydroxypiperidin-4-yl]phenyl}-1-(pyridazin-3-yl)azetidine-3-carboxamide

Example 889A benzyl 4-(4-(1-(6-chloropyridazin-3-yl)azetidine-3-carboxamido)phenyl)-4-hydroxypiperidine-1-carboxylate The title compound was prepared as described in Example 1A, substituting benzyl 4-(4-aminophenyl)-4-hydroxypiperidine-1-carboxylate for tert-butyl 4-(4-aminophenoxy)piperidine-1-carboxylate and 1-(6-chloropyridazin-3-yl)azetidine-3-carboxylic acid for 1-(benzyloxycarbonyl)azetidine-3-carboxylic acid.

Example 889B

N-(4-(4-hydroxypiperidin-4-yl)phenyl)-1-(pyridazin-3-yl)azetidine-3-carboxamide

The title compound was prepared as described in Example 1B, substituting benzyl 4-(4-(1-(6-chloropyridazin-3-yl)azetidine-3-carboxamido)phenyl)-4-hydroxypiperidine-1-carboxylate for tert-butyl 4-(4-(1-(benzyloxycarbonyl)azetidine-3-carboxamido)phenoxy)piperidine-1-carboxylate.

Example 889C

N-{4-[1-(2-fluorobenzoyl)-4-hydroxypiperidin-4-yl]phenyl}-1-(pyridazin-3-yl)azetidine-3-carboxamide The title compound was prepared as described in Example 1A, substituting N-(4-(4-hydroxypiperidin-4-yl)phenyl)-1-(pyridazin-3-yl)azetidine-3-carboxamide for tert-butyl 4-(4-aminophenoxy)piperidine-1-carboxylate and 2-fluorobenzoic acid for 1-(benzyloxycarbonyl)azetidine-3-carboxylic acid. $^1$H NMR (400 MHz, DMSO-$d_6$) δ ppm 10.08 (s, 1H), 8.56 (dd, J=4.5, 1.3 Hz, 1H), 7.61-7.54 (m, 2H), 7.55-7.33 (m, 5 H), 7.35-7.22 (m, 2H), 6.83 (dd, J=8.9, 1.3 Hz, 1H), 5.16 (s, 1H), 4.50-4.42 (m, 1H), 4.24 (t, J=8.3 Hz, 2H), 4.15 (dd, J=8.1, 5.9 Hz, 2H), 3.79-3.68 (m, 1H), 3.52-3.41 (m, 1H), 3.27-3.13 (m, 2H), 2.07-1.65 (m, 3 H), 1.66-1.40 (m, 1H); MS (ESI(+)) m/e 476.1 (M+H)$^+$.

Example 890

N-{4-[1-(2,2-dimethylpropanoyl)-4-hydroxypiperidin-4-yl]phenyl}-1-(pyridazin-3-yl)azetidine-3-carboxamide The title compound was prepared as described in Example 1A, substituting N-(4-(4-hydroxypiperidin-4-yl)phenyl)-1-(pyridazin-3-yl)azetidine-3-carboxamide for tert-butyl 4-(4-aminophenoxy)piperidine-1-carboxylate and 2,2-dimethylpropanoic acid for 1-(benzyloxycarbonyl)azetidine-3-carboxylic acid. $^1$H NMR (400 MHz, DMSO-$d_6$) δ ppm 10.06 (s, 1H), 8.56 (dd, J=4.5, 1.3 Hz, 1H), 7.59-7.53 (m, 2H), 7.46-7.33 (m, 3 H), 6.83 (dd, J=8.9, 1.3 Hz, 1H), 5.06 (s, 1H), 4.30-4.08 (m, 6 H), 3.79-3.68 (m, 1H), 3.25-3.13 (m, 2H), 1.83-1.68 (m, 2H), 1.66-1.58 (m, 2H), 1.22 (s, 9 H); MS (ESI(+)) m/e 438.2 (M+H)$^+$.

Example 891

1-(6-methylpyridazin-3-yl)-N-(4-{1-[(4-methyltetrahydro-2H-pyran-4-yl)methyl]-1H-pyrazol-4-yl}phenyl)azetidine-3-carboxamide

Example 891A tert-butyl 1-(6-methylpyridazin-3-yl)azetidine-3-carboxylate

The title compound was prepared as described in Example 1C, substituting 3-chloro-6-methylpyridazine for 3-bromopyridine and tert-butyl azetidine-3-carboxylate for tert-butyl 4-(4-(azetidine-3-carboxamido)phenoxy)piperidine-1-carboxylate.

Example 891B 1-(6-methylpyridazin-3-yl)azetidine-3-carboxylic acid

The title compound was prepared as described in Example 1D, substituting tert-butyl 1-(6-methylpyridazin-3-yl)azetidine-3-carboxylate for tert-butyl 4-(4-(1-(pyridin-3-yl)azetidine-3-carboxamido)phenoxy)piperidine-1-carboxylate.

Example 891C

N-(4-bromophenyl)-1-(6-methylpyridazin-3-yl)azetidine-3-carboxamide

The title compound was prepared as described in Example 1A, substituting 4-bromoaniline for tert-butyl 4-(4-aminophenoxy)piperidine-1-carboxylate and 1-(6-methylpyridazin-3-yl)azetidine-3-carboxylic acid for 1-(benzyloxycarbonyl)azetidine-3-carboxylic acid.

Example 891D 1-(6-methylpyridazin-3-yl)-N-(4-{1-[(4-methyltetrahydro-2H-pyran-4-yl)methyl]-1H-pyrazol-4-yl}phenyl)azetidine-3-carboxamide The title compound was prepared as described as described in Example 148A, substituting N-(4-bromophenyl)-1-(6-methylpyridazin-3-yl)azetidine-3-carboxamide for 4-bromoaniline and 1-((4-methyltetrahydro-2H-pyran-4-yl)methyl)-4-(4,4,5,5-tetramethyl-1,3,2-dioxaborolan-2-yl)-1H-pyrazole for 1-isobutyl-4-(4,4,5,5-tetramethyl-1,3,2-dioxaborolan-2-yl)-1H-pyrazole. $^1$H NMR (400 MHz, DMSO-$d_6$) δ ppm 10.08 (s, 1H), 8.06 (s, 1H), 7.82 (s, 1H), 7.61 (d, J=8.7 Hz, 2H), 7.52 (d, J=8.6 Hz, 2H), 7.29 (d, J=9.1 Hz, 1H), 6.79 (d, J=9.0 Hz, 1H), 4.20 (t, J=8.2 Hz, 2 H), 4.12 (dd, J=7.8, 6.2 Hz, 2H), 4.02 (s, 2H), 3.78-3.64 (m, 3 H), 3.52 (ddd, J=11.8, 9.3, 2.9 Hz, 2H), 2.44 (s, 3 H), 1.51 (ddd, J=13.3, 9.1, 4.1 Hz, 2H), 1.30-1.19 (m, 2H), 0.97 (s, 3 H); MS (ESI(+)) m/e 447 (M+H)$^+$.

Example 892

(3S)—N-{4-[1-(2-fluorobenzoyl)piperidin-4-yl]phenyl}-1-(6-methylpyridazin-3-yl)pyrrolidine-3-carboxamide

Example 892A (S)-tert-butyl 4-(4-(1-(6-methylpyridazin-3-yl)pyrrolidine-3-carboxamido)phenyl)piperidine-1-carboxylate The title compound was prepared as described in Example 1C, substituting 3-bromo-6-methylpyridazine for 3-bromopyridine and (S)-tert-butyl 4-(4-(pyrrolidine-3-carboxamido)phenyl)piperidine-1-carboxylate for tert-butyl 4-(4-(azetidine-3-carboxamido)phenoxy)piperidine-1-carboxylate.

Example 892B (S)-1-(6-methylpyridazin-3-yl)-N-(4-(piperidin-4-yl)phenyl)pyrrolidine-3-carboxamide The title compound was prepared as described in Example 1D, substituting (S)-tert-butyl 4-(4-(1-(6-methylpyridazin-3-yl)pyrrolidine-3-carboxamido)phenyl)piperidine-1-carboxylate for tert-butyl 4-(4-(1-(pyridin-3-yl)azetidine-3-carboxamido)phenoxy)piperidine-1-carboxylate.

Example 892C (3S)—N-{4-[1-(2-fluorobenzoyl)piperidin-4-yl]phenyl}-1-(6-methylpyridazin-3-yl)pyrrolidine-3-carboxamide The title compound was prepared as described in Example 1A, substituting (S)-1-(6-methylpyridazin-3-yl)-N-(4-(piperidin-4-yl)phenyl)pyrrolidine-3-carboxamide for tert-butyl 4-(4-aminophenoxy)piperidine-1-carboxylate and 2-fluorobenzoic acid for 1-(benzyloxycarbonyl)azetidine-3-carboxylic acid. $^1$H NMR (400 MHz, DMSO-$d_6$) δ ppm 10.25-9.59 (m, 1H), 7.63-7.39 (m, 4 H), 7.38-7.11 (m, 5 H), 6.84 (dd, J=10.8, 7.3 Hz, 1H), 4.79-4.47 (m, 1H), 3.85-3.39 (m, 6 H), 3.25-3.07 (m, 1H), 3.00-2.68 (m, 2H), 2.42 (s, 3 H), 2.37-2.09 (m, 2H), 1.97-1.37 (m, 4 H); MS (ESI(+)) m/e 488.3 (M+H)$^+$.

(S)-tert-butyl 4-(4-(pyrrolidine-3-carboxamido)phenyl)piperidine-1-carboxylate

Example 893

(3S)—N-[4-(1-benzoylpiperidin-4-yl)phenyl]-1-(6-methylpyridazin-3-yl)pyrrolidine-3-carboxamide The title compound was prepared as described in Example 1A, substituting (S)-1-(6-methylpyridazin-3-yl)-N-(4-(piperidin-4-yl)phenyl)pyrrolidine-3-carboxamide for tert-butyl 4-(4-aminophenoxy)piperidine-1-carboxylate and benzoic acid for 1-(benzyloxycarbonyl)azetidine-3-carboxylic acid. $^1$H NMR (400 MHz, DMSO-$d_6$) δ ppm 10.25-9.84 (m, 1H), 7.62-7.51 (m, 2H), 7.50-7.36 (m, 5 H), 7.31-7.12 (m, 3 H), 6.91-6.76 (m, 1H), 4.77-4.30 (m, 1H), 3.98-3.37 (m, 7 H), 3.02-2.62 (m, 2H), 2.42 (s, 3 H), 2.38-2.01 (m, 2H), 1.97-1.43 (m, 4 H); MS (ESI(+)) m/e 470.2 (M+H)$^+$.

Example 894

(3S)—N-{4-[1-(2,2-dimethylpropanoyl)piperidin-4-yl]phenyl}-1-(6-methylpyridazin-3-yl)pyrrolidine-3-carboxamide The title compound was prepared as described in Example 1A, substituting (S)-1-(6-methylpyridazin-3-yl)-N-(4-(piperidin-4-yl)phenyl)pyrrolidine-3-carboxamide for tert-butyl 4-(4-aminophenoxy)piperidine-1-carboxylate and 2,2-dimethylpropanoic acid for 1-(benzyloxycarbonyl)azetidine-3-carboxylic acid. $^1$H NMR (400 MHz, DMSO-$d_6$) δ ppm 10.04 (s, 1H), 7.56-7.50 (m, 2H), 7.23 (d, J=9.1 Hz, 1H), 7.21-7.14 (m, 2H), 6.83 (d, J=9.1 Hz, 1H), 4.45-4.36 (m, 2H), 3.74 (dd, J=10.3, 7.9 Hz, 1H), 3.64-3.52 (m, 2H), 3.50-3.39 (m, 1H), 3.35-3.25 (m, 1H), 2.93-2.66 (m, 3 H), 2.40 (s, 3 H), 2.37-2.11 (m, 2H), 1.82-1.74 (m, 2H), 1.53-1.35 (m, 2H), 1.22 (s, 9 H); MS (ESI(+)) m/e 450.3 (M+H)$^+$.

Example 895

N-{4[(1-benzoylpiperidin-4-yl)methyl]phenyl}-1-(pyridazin-3-yl)azetidine-3-carboxamide

Example 895A 4-(pyridin-4-ylmethyl)aniline

The title compound was prepared as described in Example 1B, substituting 4-(4-nitrobenzyl)pyridine for tert-butyl 4-(4-(1-(benzyloxycarbonyl)azetidine-3-carboxamido)phenoxy)piperidine-1-carboxylate.

Example 348B 2,2,2-trifluoro-N-(4-(pyridin-4-ylmethyl)phenyl)acetamide

A solution of 4-(pyridin-4-ylmethyl)aniline (21.6 g, 117 mmol) and triethylamine (19.61 ml, 141 mmol) in dichloromethane (586 ml) was cooled to 0° C. Trifluoroacetic anhydride (19.87 ml, 141 mmol) was added dropwise via additional funnel over a period of 20 minutes. The mixture was stirred at 0° C. for 1 hour and then at room temperature for 2 hours. The reaction mixture was then concentrated in vacuo and the resulting residue was purified by regular phase column chromatography to give the title compound.

Example 895C 2,2,2-trifluoro-N-(4-(piperidin-4-ylmethyl)phenyl)acetamide 2,2,2-Trifluoro-N-(4-(pyridin-4-ylmethyl)phenyl)acetamide (28.5 g, 102 mmol) and acetic acid (205 ml) were added to platinum(IV) oxide (3.42 g, 15.06 mmol) in a 500 mL stainless steel pressure bottle and the mixture was stirred for 16 hours at 40 psi. The mixture was filtered through a nylon membrane and concentrated in vacuo; and the resulting residue was taken up in methanol (100 mL) and poured into diethyl ether (600 mL). The precipitate was filtered, washed with ether and dried with sodium sulfate to afford the title compound.

Example 895D tert-butyl 4-(4-aminobenzyl)piperidine-1-carboxylate

A solution of 2,2,2-trifluoro-N-(4-(piperidin-4-ylmethyl)phenyl)acetamide (26.4 g, 92 mmol) in dichloromethane (369 ml) was cooled to 0° C. and triethylamine (19.28 ml, 138 mmol) was added slowly. To the resulting solution was added di-tert-butyl dicarbonate (22.14 g, 101 mmol) in dichloromethane (75 ml) via addition funnel over 10 minutes. The 0° C. mixture was stirred for 2 hours and warmed slowly overnight. The reaction mixture was recooled to 0° C., treated with 1 N aqueous sodium hydroxide (100 ml), warmed to room temperature and stirred for 1 hour. The bilayer was separated and the organics were washed with water and brine, dried with magnesium sulfate, filtered and concentrated in vacuo. The residue was purified by normal phase chromatography to give the title compound.

Example 895E tert-butyl 4-(4-(1-(pyridazin-3-yl)azetidine-3-carboxamido)benzyl)piperidine-1-carboxylate The title compound was prepared as described in Example 1A, substituting tert-butyl 4-(4-aminobenzyl)piperidine-1-carboxylate for tert-butyl 4-(4-aminophenoxy)piperidine-1-carboxylate and 1-(pyridazin-3-yl)azetidine-3-carboxylic acid for 1-(benzyloxycarbonyl)azetidine-3-carboxylic acid.

Example 895F

N-(4-(piperidin-4-ylmethyl)phenyl)-1-(pyridazin-3-yl)azetidine-3-carboxamide

The title compound was prepared as described in Example 1D, substituting tert-butyl 4-(4-(1-(pyridazin-3-yl)azetidine-3-carboxamido)benzyl)piperidine-1-carboxylate for tert-butyl 4-(4-(1-(pyridin-3-yl)azetidine-3-carboxamido)phenoxy)piperidine-1-carboxylate.

Example 895G

The title compound was prepared as described in Example 1A, substituting N-(4-(piperidin-4-ylmethyl)phenyl)-1-(pyridazin-3-yl)azetidine-3-carboxamide for tert-butyl 4-(4-aminophenoxy)piperidine-1-carboxylate and benzoic acid for 1-(benzyloxycarbonyl)azetidine-3-carboxylic acid. $^1$H NMR (400 MHz, DMSO-$d_6$) δ ppm 10.03 (s, 1H), 8.56 (dd, J=4.5, 1.3 Hz, 1H), 7.52 (d, J=8.5 Hz, 2H), 7.47-7.28 (m, 6H), 7.11 (d, J=8.5 Hz, 2H), 6.83 (dd, J=9.0, 1.3 Hz, 1H), 4.58-4.34 (m, 1H), 4.23 (t, J=8.3 Hz, 2H), 4.14 (dd, J=8.1, 6.0 Hz, 2H), 3.72 (tt, J=8.6, 6.0 Hz, 1H), 3.66-3.47 (m, 1H), 3.08-2.83 (m, 1H), 2.83-2.59 (m, 1H), 1.87-1.69 (m, 1H), 1.69-1.57 (m, 1H), 1.57-1.41 (m, 1H), 1.31-0.90 (m, 2H); MS (ESI(+)) m/e 456 (M+H)$^+$.

TABLE 22

The following Examples were essentially prepared as described in Example 895, substituting an appropriate carboxylic acid in Example 895G. Some products were purified by flash chromatography while others were purified by reverse-phase HPLC. Accordingly, some Examples were isolated as trifluoroacetic acid salts.

| Ex | Name | MS |
| --- | --- | --- |
| 896 | N-(4-{[1-(2-fluorobenzoyl)piperidin-4-yl]methyl}phenyl)-1-(pyridazin-3-yl)azetidine-3-carboxamide | (ESI(+)) m/e 474 (M + H)$^+$ |
| 897 | N-(4-{[1-(2,2-dimethylpropanoyl)piperidin-4-yl]methyl}phenyl)-1-(pyridazin-3-yl)azetidine-3-carboxamide | (ESI(+)) m/e 436 (M + H)$^+$ |
| 898 | N-(4-{[1-(3,3-dimethylbutanoyl)piperidin-4-yl]methyl}phenyl)-1-(pyridazin-3-yl)azetidine-3-carboxamide | (ESI(+)) m/e 450 (M + H)$^+$ |
| 899 | N-(4-{[1-(2-ethylbutanoyl)piperidin-4-yl]methyl}phenyl)-1-(pyridazin-3-yl)azetidine-3-carboxamide | (ESI(+)) m/e 450 (M + H)$^+$ |
| 900 | 1-(pyridazin-3-yl)-N-(4-{[1-(4,4,4-trifluorobutanoyl)piperidin-4-yl]methyl}phenyl)azetidine-3-carboxamide | (ESI(+)) m/e 476 (M + H)$^+$ |
| 901 | N-(4-{[1-(2-methylpropanoyl)piperidin-4-yl]methyl}phenyl)-1-(pyridazin-3-yl)azetidine-3-carboxamide | (ESI(+)) m/e 422 (M + H)$^+$ |
| 902 | N-{4-[(1-acetylpiperidin-4-yl)methyl]phenyl}-1-(pyridazin-3-yl)azetidine-3-carboxamide | (ESI(+)) m/e 394 (M + H)$^+$ |
| 903 | N-[4-({1-[(2S)-2-methylbutanoyl]piperidin-4-yl}methyl)phenyl]-1-(pyridazin-3-yl)azetidine-3-carboxamide | (ESI(+)) m/e 436 (M + H)$^+$ |
| 904 | N-[4-({1-[(1-methylcyclopropyl)carbonyl]piperidin-4-yl}methyl)phenyl]-1-(pyridazin-3-yl)azetidine-3-carboxamide | (ESI(+)) m/e 434 (M + H)$^+$ |
| 927 | 1-(pyridazin-3-yl)-N-(4-{[1-(1,3-thiazol-5-ylcarbonyl)piperidin-4-yl]methyl}phenyl)azetidine-3-carboxamide | (ESI(+)) m/e 463 (M + H)$^+$ |
| 928 | N-(4-{[1-(cyclopentylcarbonyl)piperidin-4-yl]methyl}phenyl)-1-(pyridazin-3-yl)azetidine-3-carboxamide | (ESI(+)) m/e 448 (M + H)$^+$ |
| 929 | N-(4-{[1-(1H-pyrazol-4-ylcarbonyl)piperidin-4-yl]methyl}phenyl)-1-(pyridazin-3-yl)azetidine-3-carboxamide | (ESI(+)) m/e 446 (M + H)$^+$ |
| 930 | N-(4-{[1-(2,2-dimethylbutanoyl)piperidin-4-yl]methyl}phenyl)-1-(pyridazin-3-yl)azetidine-3-carboxamide | (ESI(+)) m/e 450 (M + H)$^+$ |

TABLE 22-continued

The following Examples were essentially prepared as described in Example 895, substituting an appropriate carboxylic acid in Example 895G. Some products were purified by flash chromatography while others were purified by reverse-phase HPLC. Accordingly, some Examples were isolated as trifluoroacetic acid salts.

| Ex | Name | MS |
|---|---|---|
| 931 | N-[4-({1-[(2-methylcyclopropyl)carbonyl]piperidin-4-yl}methyl)phenyl]-1-(pyridazin-3-yl)azetidine-3-carboxamide | (ESI(+)) m/e 434 (M + H)+ |
| 932 | N-(4-({1-[(methylsulfanyl)acetyl]piperidin-4-yl}methyl)phenyl]-1-(pyridazin-3-yl)azetidine-3-carboxamide | (ESI(+)) m/e 440 (M + H)+ |
| 933 | N-[4-({1-[(1S,4R)-bicyclo[2.2.1]hept-2-ylacetyl]piperidin-4-yl}methyl)phenyl]-1-(pyridazin-3-yl)azetidine-3-carboxamide | (ESI(+)) m/e 488 (M + H)+ |
| 934 | N-(4-{[1-(2-methylpentanoyl)piperidin-4-yl]methyl}phenyl)-1-(pyridazin-3-yl)azetidine-3-carboxamide | (ESI(+)) m/e 450 (M + H)+ |
| 935 | N-(4-{[1-(4-methylpentanoyl)piperidin-4-yl]methyl}phenyl)-1-(pyridazin-3-yl)azetidine-3-carboxamide | (ESI(+)) m/e 450 (M + H)+ |
| 936 | N-[4-({1-[3-(methylsulfanyl)propanoyl]piperidin-4-yl}methyl)phenyl]-1-(pyridazin-3-yl)azetidine-3-carboxamide | (ESI(+)) m/e 454 (M + H)+ |
| 937 | 1-(pyridazin-3-yl)-N-(4-{[1-(1,3-thiazol-4-ylcarbonyl)piperidin-4-yl]methyl}phenyl)azetidine-3-carboxamide | (ESI(+)) m/e 463 (M + H)+ |
| 938 | N-(4-{[1-(1H-pyrazol-5-ylcarbonyl)piperidin-4-yl]methyl}phenyl)-1-(pyridazin-3-yl)azetidine-3-carboxamide | (ESI(+)) m/e 446 (M + H)+ |
| 939 | N-[4-({1-[(6-methylpyridin-3-yl)carbonyl]piperidin-4-yl}methyl)phenyl]-1-(pyridazin-3-yl)azetidine-3-carboxamide | (ESI(+)) m/e 471 (M + H)+ |
| 940 | N-[4-({1-[(3-methylthiophen-2-yl)carbonyl]piperidin-4-yl}methyl)phenyl]-1-(pyridazin-3-yl)azetidine-3-carboxamide | (ESI(+)) m/e 476 (M + H)+ |
| 941 | N-(4-{[1-(pent-4-ynoyl)piperidin-4-yl]methyl}phenyl)-1-(pyridazin-3-yl)azetidine-3-carboxamide | (ESI(+)) m/e 432 (M + H)+ |
| 942 | 1-(pyridazin-3-yl)-N-(4-{[1-(thiophen-3-ylcarbonyl)piperidin-4-yl]methyl}phenyl)azetidine-3-carboxamide | (ESI(+)) m/e 462 (M + H)+ |
| 943 | N-(4-{[1-(methoxyacetyl)piperidin-4-yl]methyl}phenyl)-1-(pyridazin-3-yl)azetidine-3-carboxamide | (ESI(+)) m/e XXX (M + H)+ |
| 944 | 1-(pyridazin-3-yl)-N-(4-{[1-(tetrahydrofuran-2-ylcarbonyl)piperidin-4-yl]methyl}phenyl)azetidine-3-carboxamide | (ESI(+)) m/e 424 (M + H)+ |
| 945 | N-[4-({1-[(2-methoxyethoxy)acetyl]piperidin-4-yl}methyl)phenyl]-1-(pyridazin-3-yl)azetidine-3-carboxamide | (ESI(+)) m/e 468 (M + H)+ |
| 946 | N-(4-{[1-(ethoxyacetyl)piperidin-4-yl]methyl}phenyl)-1-(pyridazin-3-yl)azetidine-3-carboxamide | (ESI(+)) m/e 438 (M + H)+ |
| 947 | 1-(pyridazin-3-yl)-N-(4-{[1-(thiophen-2-ylcarbonyl)piperidin-4-yl]methyl}phenyl)azetidine-3-carboxamide | (ESI(+)) m/e 462 (M + H)+ |
| 948 | N-{4-[(1-hexanoylpiperidin-4-yl)methyl]phenyl}-1-(pyridazin-3-yl)azetidine-3-carboxamide | (ESI(+)) m/e 450 (M + H)+ |
| 949 | N-[4-({1-[(1-methyl-1H-pyrrol-2-yl)carbonyl]piperidin-4-yl}methyl)phenyl]-1-(pyridazin-3-yl)azetidine-3-carboxamide | (ESI(+)) m/e 459 (M + H)+ |
| 950 | N-(4-{[1-(but-3-enoyl)piperidin-4-yl]methyl}phenyl)-1-(pyridazin-3-yl)azetidine-3-carboxamide | (ESI(+)) m/e 420 (M + H)+ |
| 951 | 1-(pyridazin-3-yl)-N-(4-{[1-(1,3-thiazol-2-ylcarbonyl)piperidin-4-yl]methyl}phenyl)azetidine-3-carboxamide | (ESI(+)) m/e 463 (M + H)+ |
| 952 | N-(4-{[1-(furan-2-ylcarbonyl)piperidin-4-yl]methyl}phenyl)-1-(pyridazin-3-yl)azetidine-3-carboxamide | (ESI(+)) m/e 446 (M + H)+ |
| 953 | N-(4-{[1-(1,2-oxazol-5-ylcarbonyl)piperidin-4-yl]methyl}phenyl)-1-(pyridazin-3-yl)azetidine-3-carboxamide | (ESI(+)) m/e 447 (M + H)+ |
| 954 | 1-(pyridazin-3-yl)-N-(4-{[1-(pyridin-2-ylcarbonyl)piperidin-4-yl]methyl}phenyl)azetidine-3-carboxamide | (ESI(+)) m/e 457 (M + H)+ |

TABLE 22-continued

The following Examples were essentially prepared as described in Example 895, substituting an appropriate carboxylic acid in Example 895G. Some products were purified by flash chromatography while others were purified by reverse-phase HPLC. Accordingly, some Examples were isolated as trifluoroacetic acid salts.

| Ex | Name | MS |
|---|---|---|
| 955 | N-(4-{[1-(furan-3-ylcarbonyl)piperidin-4-yl]methyl}phenyl)-1-(pyridazin-3-yl)azetidine-3-carboxamide | (ESI(+)) m/e 446 (M + H)+ |
| 956 | N-(4-{[1-(cyclopropylacetyl)piperidin-4-yl]methyl}phenyl)-1-(pyridazin-3-yl)azetidine-3-carboxamide | (ESI(+)) m/e 434 (M + H)+ |
| 957 | N-(4-{[1-(2-methylbutanoyl)piperidin-4-yl]methyl}phenyl)-1-(pyridazin-3-yl)azetidine-3-carboxamide | (ESI(+)) m/e 436 (M + H)+ |
| 958 | N-{4-[(1-propanoylpiperidin-4-yl)methyl]phenyl}-1-(pyridazin-3-yl)azetidine-3-carboxamide | (ESI(+)) m/e 408 (M + H)+ |
| 959 | N-{4-[(1-butanoylpiperidin-4-yl)methyl]phenyl}-1-(pyridazin-3-yl)azetidine-3-carboxamide | (ESI(+)) m/e 422 (M + H)+ |
| 960 | N-(4-{[1-(cyclobutylcarbonyl)piperidin-4-yl]methyl}phenyl)-1-(pyridazin-3-yl)azetidine-3-carboxamide | (ESI(+)) m/e 434 (M + H)+ |
| 961 | N-{4-[(1-pentanoylpiperidin-4-yl)methyl]phenyl}-1-(pyridazin-3-yl)azetidine-3-carboxamide | (ESI(+)) m/e 436 (M + H)+ |
| 962 | N-(4-{[1-(cyclopentylacetyl)piperidin-4-yl]methyl}phenyl)-1-(pyridazin-3-yl)azetidine-3-carboxamide | (ESI(+)) m/e 462 (M + H)+ |
| 963 | N-(4-{[1-(2-methylbenzoyl)piperidin-4-yl]methyl}phenyl)-1-(pyridazin-3-yl)azetidine-3-carboxamide | (ESI(+)) m/e 470 (M + H)+ |
| 964 | N-(4-{[1-(3-methylpentanoyl)piperidin-4-yl]methyl}phenyl)-1-(pyridazin-3-yl)azetidine-3-carboxamide | (ESI(+)) m/e 450 (M + H)+ |
| 965 | N-(4-{[1-(cyclohexylcarbonyl)piperidin-4-yl]methyl}phenyl)-1-(pyridazin-3-yl)azetidine-3-carboxamide | (ESI(+)) m/e 462 (M + H)+ |
| 966 | N-(4-{[1-(3-methylbutanoyl)piperidin-4-yl]methyl}phenyl)-1-(pyridazin-3-yl)azetidine-3-carboxamide | (ESI(+)) m/e 436 (M + H)+ |
| 967 | N-(4-{[1-(cyclopropylcarbonyl)piperidin-4-yl]methyl}phenyl)-1-(pyridazin-3-yl)azetidine-3-carboxamide | (ESI(+)) m/e 420 (M + H)+ |
| 968 | 1-(pyridazin-3-yl)-N-(4-{[1-(3,3,3-trifluoropropanoyl)piperidin-4-yl]methyl}phenyl)azetidine-3-carboxamide | (ESI(+)) m/e 462 (M + H)+ |

Example 905

N-[4-(1-{[4-methyl-1-(oxetan-3-yl)piperidin-4-yl]methyl}-1H-pyrazol-4-yl)phenyl]-1-(6-methylpyridazin-3-yl)azetidine-3-carboxamide

Example 905A tert-butyl 4-methyl-4-((4-(4-(1-(6-methylpyridazin-3-yl)azetidine-3-carboxamido)phenyl)-1H-pyrazol-1-yl)methyl)piperidine-1-carboxylate The title compound was prepared as described as described in Example 148A, substituting N-(4-bromophenyl)-1-(6-methylpyridazin-3-yl)azetidine-3-carboxamide for 4-bromoaniline and tert-butyl 4-methyl-4-((4-(4,4,5,5-tetramethyl-1,3,2-dioxaborolan-2-O-1H-pyrazol-1-yl)methyl)piperidine-1-carboxylate for 1-isobutyl-4-(4,4,5,5-tetramethyl-1,3,2-dioxaborolan-2-O-1H-pyrazole.

Example 905B

N-(4-(1((4-methylpiperidin-4-yl)methyl)-1H-pyrazol-4-yl)phenyl)-1-(6-methylpyridazin-3-yl)azetidine-3-carboxamide The title compound was prepared as described in Example 1D, substituting tert-butyl 4-methyl-4-((4-(4-(1-(6-methylpyridazin-3-yl)azetidine-3-carboxamido)phenyl)-1H-pyrazol-1-yl)methyl)piperidine-1-carboxylate for tert-butyl 4-(4-(1-(pyridin-3-yl)azetidine-3-carboxamido)phenoxy)piperidine-1-carboxylate.

Example 905C

N-[4-(1-{[4-methyl-1-(oxetan-3-yl)piperidin-4-yl]methyl}-1H-pyrazol-4-yl)phenyl]-1-(6-methylpyridazin-3-yl)azetidine-3-carboxamide N-(4-(1-((4-Methylpiperidin-4-yl)methyl)-1H-pyrazol-4-yl)phenyl)-1-(6-methylpyridazin-3-yl)azetidine-3-carboxamide was dissolved in methanol (3 ml) and treated with oxetan-3-one (0.022 ml, 0.338 mmol) and sodium cyanoborohydride (0.021 g, 0.338 mmol) and stirred overnight. The mixture was concentrated, purified by normal phase chromatography, triturated with ether and concentrated to give the title compound. $^1$H NMR (400 MHz, DMSO-$d_6$) δ ppm 10.09 (s, 1H), 8.05 (s, 1H), 7.82 (s, 1H), 7.64-7.58 (m, 2H), 7.56-7.49 (m, 2H), 7.29 (d, J=9.1 Hz, 1H), 6.80 (d, J=9.0 Hz, 1H), 4.51 (t, J=6.4 Hz, 2H), 4.40 (t, J=5.8 Hz, 2H), 4.20 (t, J=8.3 Hz, 2 H), 4.12 (dd, J=7.9, 6.1 Hz, 2H), 3.98 (s, 2H), 3.73 (tt, J=8.5, 6.1 Hz, 1H), 3.48-3.39 (m, 1H), 2.44 (s, 3 H), 2.42-2.33 (m, 2H), 2.16-1.99 (m, 2H), 1.58-1.46 (m, 2H), 1.30 (d, J=12.6 Hz, 2H), 0.89 (s, 3 H); MS (ESI(+)) m/e 502 (M+H)$^+$.

Example 906

N-[4-(1-benzoylpiperidin-4-yl)phenyl]-1-(4-methylpyridazin-3-yl)azetidine-3-carboxamide Example 906A tert-butyl 4-(4-(1-(4-methylpyridazin-3-yl)azetidine-3-carboxamido)phenyl)piperidine-1-carboxylate The title compound was prepared as described in Example 1C, substituting 3-chloro-4-methylpyridazine for 3-bromopyridine and tert-butyl 4-(4-(azetidine-3-carboxamido)phenyl)piperidine-1-carboxylate for tert-butyl 4-(4-(azetidine-3-carboxamido)phenoxy)piperidine-1-carboxylate.

Example 906B 1-(4-methylpyridazin-3-yl)-N-(4-(piperidin-4-yl)phenyl)azetidine-3-carboxamide The title compound was prepared as described in Example 1D, substituting tert-butyl 4-(4-(1-(4-methylpyridazin-3-yl)azetidine-3-carboxamido)phenyl)piperidine-1-carboxylate for tert-butyl 4-(4-(1-(pyridin-3-yl)azetidine-3-carboxamido)phenoxy)piperidine-1-carboxylate.

Example 906C

N-[4-(1-benzoylpiperidin-4-yl)phenyl]-1-(4-methylpyridazin-3-yl)azetidine-3-carboxamide The title compound was prepared as described in Example 1A, substituting 1-(4-methylpyridazin-3-yl)-N-(4-(piperidin-4-yl)phenyl)azetidine-3-carboxamide for tert-butyl 4-(4-aminophenoxy)piperidine-1-carboxylate and benzoic acid for 1-(benzyloxycarbonyl)azetidine-3-carboxylic acid. $^1$H NMR (400 MHz, DMSO-$d_6$) δ ppm 10.03 (s, 1H), 8.49 (d, J=4.6 Hz, 1H), 7.58-7.52 (m, 2H), 7.53-7.37 (m, 5 H), 7.25-7.17 (m, 3 H), 4.81-4.37 (m, 1H), 4.39-4.25 (m, 4 H), 4.26-3.38 (m, 2H), 3.24-2.58 (m, 3 H), 2.19 (s, 3 H), 2.10-1.11 (m, 4 H); MS (ESI(+)) m/e 456.2 (M+H)$^+$ Example 907

5-[1-(2-fluorobenzoyl)piperidin-4-yl]-N-[(3S)-1-(pyridazin-3-yl)pyrrolidin-3-yl]furan-2-carboxamide Example 907A 5-(1-(tert-butoxycarbonyl)-1,2,3,6-tetrahydropyridin-4-yl)furan-2-carboxylic acid The title compound was prepared as described as described in Example 148A, substituting 5-bromofuran-2-carboxylic acid for 4-bromoaniline and tert-butyl 4-(4,4,5,5-tetramethyl-1,3,2-dioxaborolan-2-yl)-5,6-dihydropyridine-1(2H)-carboxylate for 1-isobutyl-4-(4,4,5,5-tetramethyl-1,3,2-dioxaborolan-2-yl)-1H-pyrazole.

Example 907B 5-(1-(tert-butoxycarbonyl)piperidin-4-yl)furan-2-carboxylic acid

The title compound was prepared as described in Example 1B, substituting 5-(1-(tert-butoxycarbonyl)-1,2,3,6-tetrahydropyridin-4-yl)furan-2-carboxylic acid for tert-butyl 4-(4-(1-(benzyloxycarbonyl)azetidine-3-carboxamido)phenoxy)piperidine-1-carboxylate.

Example 907C (S)-1-(6-chloropyridazin-3-yl)pyrrolidin-3-amine

The title compound was prepared as described in Example 1C, substituting 3,6-dichloropyridazine for 3-bromopyridine and (S)-tert-butyl pyrrolidin-3-ylcarbamate for tert-butyl 4-(4-(azetidine-3-carboxamido)phenoxy)piperidine-1-carboxylate followed by TFA deprotection as described in Example 1D.

Example 907D (S)-tert-butyl 4-(5-((1-(6-chloropyridazin-3-yl)pyrrolidin-3-yl)carbamoyl)furan-2-yl)piperidine-1-carboxylate The title compound was prepared as described in Example 1A, substituting (S)-1-(6-chloropyridazin-3-yl)pyrrolidin-3-amine for tert-butyl 4-(4-aminophenoxy)piperidine-1-carboxylate and 5-(1-(tert-butoxycarbonyl)piperidin-4-yl)furan-2-carboxylic acid for 1-(benzyloxycarbonyl)azetidine-3-carboxylic acid.

Example 907E (S)-tert-butyl 4-(5-((1-(pyridazin-3-yl)pyrrolidin-3-yl)carbamoyl)furan-2-yl)piperidine-1-carboxylate The title compound was prepared as described in Example 1B, substituting (S)-tert-butyl 4-(5-((1-(6-chloropyridazin-3-yl)pyrrolidin-3-yl)carbamoyl)furan-2-yl)piperidine-1-carboxylate for tert-butyl 4-(4-(1-(benzyloxycarbonyl)azetidine-3-carboxamido)phenoxy)piperidine-1-carboxylate.

Example 907F (S)-5-(piperidin-4-yl)-N-(1-(pyridazin-3-yl)pyrrolidin-3-yl)furan-2-carboxamide The title compound was prepared as described in Example 1D, substituting (S)-tert-butyl 4-(5-((1-(pyridazin-3-yl)pyrrolidin-3-yl)carbamoyl)furan-2-yl)piperidine-1-carboxylate for tert-butyl 4-(4-(1-(pyridin-3-yl)azetidine-3-carboxamido)phenoxy)piperidine-1-carboxylate.

Example 907G

5-[1-(2-fluorobenzoyl)piperidin-4-yl]-N-[(3S)-1-(pyridazin-3-yl)pyrrolidin-3-yl]furan-2-carboxamide The title compound was prepared as described in Example 1A, substituting (S)-5-(piperidin-4-yl)-N-(1-(pyridazin-3-yl)

pyrrolidin-3-yl)furan-2-carboxamide for tert-butyl 4-(4-aminophenoxy)piperidine-1-carboxylate and 2-fluorobenzoic acid for 1-(benzyloxycarbonyl)azetidine-3-carboxylic acid. $^1$H NMR (400 MHz, DMSO-$d_6$) δ ppm 8.48 (dd, J=4.4, 0.9 Hz, 1H), 8.40 (d, J=7.0 Hz, 1H), 7.55-7.46 (m, 1H), 7.41 (t, J=6.9 Hz, 1H), 7.37-7.24 (m, 3H), 7.06 (d, J=3.4 Hz, 1H), 6.86 (dd, J=9.1, 0.8 Hz, 1H), 6.31 (d, J=3.4 Hz, 1H), 4.67-4.47 (m, 2H), 3.76 (dd, J=10.8, 6.9 Hz, 1H), 3.70-3.59 (m, 1H), 3.59-3.48 (m, 1H), 3.48-3.39 (m, 2H), 3.19 (t, J=12.1 Hz, 1H), 3.08-2.89 (m, 2H), 2.33-2.19 (m, 1H), 2.13-2.02 (m, 2H), 1.99-1.88 (m, 1H), 1.67-1.41 (m, 2H); MS (ESI(+)) m/e 464 (M+H)$^+$.

Example 908

N-[4-(1-benzoylpiperidin-4-yl)phenyl]-1-(3-methylpyridazin-4-yl)azetidine-3-carboxamide Example 908A tert-butyl 4-(4-(1-(3-methylpyridazin-4-yl)azetidine-3-carboxamido)phenyl)piperidine-1-carboxylate The title compound was prepared as described in Example 1C, substituting 4-chloro-3-methylpyridazine for 3-bromopyridine and tert-butyl 4-(4-(azetidine-3-carboxamido)phenyl)piperidine-1-carboxylate for tert-butyl 4-(4-(azetidine-3-carboxamido)phenoxy)piperidine-1-carboxylate.

Example 908B 1-(3-methylpyridazin-4-yl)-N-(4-(piperidin-4-yl)phenyl)azetidine-3-carboxamide The title compound was prepared as described in Example 1D, substituting tert-butyl 4-(4-(1-(3-methylpyridazin-4-yl)azetidine-3-carboxamido)phenyl)piperidine-1-carboxylate for tert-butyl 4-(4-(1-(pyridin-3-yl)azetidine-3-carboxamido)phenoxy)piperidine-1-carboxylate.

Example 908C

N-[4-(1-benzoylpiperidin-4-yl)phenyl]-1-(3-methylpyridazin-4-yl)azetidine-3-carboxamide The title compound was prepared as described in Example 1A, substituting 1-(3-methylpyridazin-4-yl)-N-(4-(piperidin-4-yl)phenyl)azetidine-3-carboxamide for tert-butyl 4-(4-aminophenoxy)piperidine-1-carboxylate and benzoic acid for 1-(benzyloxycarbonyl)azetidine-3-carboxylic acid. $^1$H NMR (400 MHz, DMSO-$d_6$) δ ppm 10.05 (s, 1H), 8.55 (d, J=5.8 Hz, 1H), 7.57-7.51 (m, 2H), 7.49-7.33 (m, 5H), 7.26-7.19 (m, 2H), 6.45 (d, J=5.8 Hz, 1H), 4.62 (s, 1H), 4.31 (t, J=8.4 Hz, 2H), 4.24 (dd, J=20.4, 14.1 Hz, 3H), 3.66 (ddd, J=14.6, 8.5, 6.1 Hz, 2H), 2.76 (t, J=11.9 Hz, 2H), 2.52 (s, 3H), 2.13-1.45 (m, 5H); MS (ESI(+)) m/e 456.3 (M+H)$^+$.

Example 909

N-{4-[1-(2-fluorobenzoyl)piperidin-4-yl]phenyl}-1-(3-methylpyridazin-4-yl)azetidine-3-carboxamide The title compound was prepared as described in Example 1A, substituting 1-(3-methylpyridazin-4-yl)-N-(4-(piperidin-4-yl)phenyl)azetidine-3-carboxamide for tert-butyl 4-(4-aminophenoxy)piperidine-1-carboxylate and 2-fluorobenzoic acid for 1-(benzyloxycarbonyl)azetidine-3-carboxylic acid. $^1$H NMR (400 MHz, DMSO-$d_6$) δ ppm 10.08 (s, 1H), 8.55 (d, J=5.8 Hz, 1H), 7.76-7.24 (m, 8H), 6.45 (d, J=5.8 Hz, 1H), 4.50-4.45 (m, 1H), 4.32 (t, J=8.3 Hz, 2H), 4.23 (d, J=13.9 Hz, 2H), 3.73-3.62 (m, 1H), 3.50-3.41 (m, 1H), 3.26-3.07 (m, 2H), 2.94-2.56 (m, 3H), 2.45-1.03 (m, 5H),; MS (ESI(+)) m/e 474.2 (M+H)$^+$.

Example 910

N-(4-{1-[(2-aminopyridin-3-yl)carbonyl]piperidin-4-yl}phenyl)-1-(pyridazin-3-yl)azetidine-3-carboxamide The title compound was prepared as described in Example 1A, substituting N-(4-(piperidin-4-yl)phenyl)-1-(pyridazin-3-yl)azetidine-3-carboxamide for tert-butyl 4-(4-aminophenoxy)piperidine-1-carboxylate and 2-aminonicotinic acid for 1-(benzyloxycarbonyl)azetidine-3-carboxylic acid. $^1$H NMR (400 MHz, DMSO-$d_6$) δ ppm 10.04 (s, 1H), 8.56 (dd, J=4.5, 1.1 Hz, 1H), 8.00 (dd, J=4.9, 1.8 Hz, 1H), 7.54 (d, J=8.5 Hz, 2H), 7.46-7.32 (m, 2H), 7.21 (d, J=8.5 Hz, 2H), 6.83 (dd, J=9.0, 1.2 Hz, 1H), 6.59 (dd, J=7.3, 4.9 Hz, 1H), 5.92 (s, 2H), 4.24 (t, J=8.3 Hz, 2H), 4.14 (dd, J=8.0, 6.0 Hz, 2H), 4.09-3.84 (m, 2H), 3.73 (tt, J=8.5, 6.0 Hz, 1H), 2.99 (bs, 2H), 2.74 (tt, J=11.7, 3.2 Hz, 1H), 1.76 (d, J=11.8 Hz, 2H), 1.70-1.52 (m, 2H); MS (ESI(+)) m/e 458 (M+H)$^+$.

Example 911

1-methyl-5-[4-({[1-(pyridazin-3-yl)azetidin-3-yl]carbonyl}amino)phenyl]-1H-pyrazole-3-carboxylic acid Ethyl 1-methyl-5-(4-(1-(pyridazin-3-yl)azetidine-3-carboxamido)phenyl)-1H-pyrazole-3-carboxylate (368 mg, 0.905 mmol) was taken up in tetrahydrofuran (3.38 mL), and methanol (3.38 mL) then 1N aqueous lithium hydroxide (1.35 mL, 1.350 mmol) was added. The mixture was heated at 60° C. for 2 hours. The mixture was concentrated to dryness, suspended in water and treated with 1N aqueous HCl to pH 2. The solution was extracted with ethyl acetate and the organic layers were dried with sodium sulfate, filtered, and concentrated to give a colorless syrup that solidified upon standing. This solid was triturated with ether and collected by filtration to give the title compound. $^1$H NMR (400 MHz, DMSO-$d_6$) δ ppm 12.67 (s, 1H), 10.32 (bs, 1H), 8.60-8.55 (m, 1H), 7.77 (d, J=8.4 Hz, 2H), 7.54 (d, J=8.4 Hz, 2H), 7.42 (dd, J=9.0, 4.5 Hz, 1H), 6.89 (d, J=8.9 Hz, 1H), 6.80 (s, 1H), 4.34-4.13 (m, 4H), 3.91 (s, 3H), 3.83-3.74 (m, 1H); MS (ESI(+)) m/e 379 (M+H)$^+$.

Example 912 ethyl 1-methyl-5-[4-({[1-(pyridazin-3-yl)azetidin-3-yl]carbonyl}amino)phenyl]-1H-pyrazole-3-carboxylate Example 912A ethyl 4-(4-nitrophenyl)-2,4-dioxobutanoate 1-(4-Nitrophenyl)ethanone (2 g, 12.11 mmol) was dissolved in tetrahydrofuran (20 mL) and chilled to 0° C. Sodium ethanolate (21% in ethanol) (7.85 g, 24.22 mmol) was added dropwise and the resulting solution was stirred for 15 minutes at 0° C. Diethyl oxylate (1.947 g, 13.32 mmol) was added dropwise and the ice bath was removed. The mixture was stirred at room temperature for 3 hours and diluted with 1N aqueous HCl (125 mL). The resulting suspension was stirred for 30 minutes and collected by filtration to give the title compound.

Example 912B ethyl 1-methyl-5-(4-nitrophenyl)-1H-pyrazole-3-carboxylate

Ethyl 4-(4-nitrophenyl)-2,4-dioxobutanoate (500 mg, 1.885 mmol) was dissolved in hexafluoroisopropanol (4 ml) and methylhydrazine (87 mg, 1.885 mmol) was added dropwise. The reaction mixture was stirred at room temperature for 3 hours, concentrated to dryness, triturated with ether; and filtered to provide the title compound.

Example 912C ethyl 5-(4-aminophenyl)-1-methyl-1H-pyrazole-3-carboxylate

The title compound was prepared as described in Example 1B, substituting ethyl 1-methyl-5-(4-nitrophenyl)-1H-pyrazole-3-carboxylate for tert-butyl 4-(4-(1-(benzyloxycarbonyl)azetidine-3-carboxamido)phenoxy)piperidine-1-carboxylate.

Example 912D ethyl 1-methyl-5-[4-({[1-(pyridazin-3-yl)azetidin-3-yl]carbonyl}amino)phenyl]-1H-pyrazole-3-carboxylate The title compound was prepared as described in Example 1A, substituting ethyl 5-(4-aminophenyl)-1-methyl-1H-pyrazole-3-carboxylate for tert-butyl 4-(4-aminophenoxy)piperidine-1-carboxylate and 1-(pyridazin-3-yl)azetidine-3-carboxylic acid for 1-(benzyloxycarbonyl)azetidine-3-carboxylic acid. $^1$H NMR (400 MHz, DMSO-$d_6$) δ ppm 10.31 (s, 1H), 8.57 (dd, J=4.5, 1.3 Hz, 1H), 7.77 (d, J=8.7 Hz, 2H), 7.54 (d, J=8.6 Hz, 2H), 7.39 (dd, J=8.9, 4.5 Hz, 1H), 6.84 (s, 1H), 6.84 (dd, J=9.0, 1.4 Hz, 1H), 4.32-4.22 (m, 4 H), 4.18 (dd, J=8.1, 5.8 Hz, 2H), 3.92 (s, 3 H), 3.84-3.72 (m, 1H), 1.30 (t, J=7.1 Hz, 3 H); MS (ESI(+)) m/e 407 (M+H)$^+$.

Example 913 ethyl 1-phenyl-5-[4-({[1-(pyridazin-3-yl)azetidin-3-yl]carbonyl}amino)phenyl]-1H-pyrazole-3-carboxylate The title compound was prepared as described in Example 912, substituting phenylhydrazine for methylhydrazine in Example 912B. $^1$H NMR (500 MHz, DMSO-$d_6$) δ ppm 10.24 (s, 1H), 8.56 (dd, J=4.5, 1.3 Hz, 1H), 7.60 (d, J=8.7 Hz, 2H), 7.51-7.41 (m, 3 H), 7.38 (dd, J=9.0, 4.5 Hz, 1H), 7.34-7.30 (m, 2H), 7.20 (d, J=8.7 Hz, 2H), 7.08 (s, 1H), 6.82 (dd, J=9.0, 1.3 Hz, 1H), 4.33 (q, J=7.1 Hz, 2H), 4.24 (t, J=8.4 Hz, 2H), 4.14 (dd, J=8.0, 6.0 Hz, 2H), 3.77-3.69 (m, 1H), 1.32 (t, J=7.1 Hz, 3 H); MS (ESI(+)) m/e 469 (M+H)$^+$.

Example 914

N-{6-[1-(2-fluorobenzoyl)piperidin-4-yl]pyridin-3-yl}-1-(pyridazin-3-yl)azetidine-3-carboxamide Example 914A tert-butyl 4-(5-(1-(pyridazin-3-yl)azetidine-3-carboxamido)pyridin-2-yl)piperidine-1-carboxylate The title compound was prepared as described in Example 1A, substituting tert-butyl 4-(5-aminopyridin-2-yl)piperidine-1-carboxylate for tert-butyl 4-(4-aminophenoxy)piperidine-1-carboxylate and 1-(pyridazin-3-yl)azetidine-3-carboxylic acid for 1-(benzyloxycarbonyl)azetidine-3-carboxylic acid.

Example 914B

N-(6-(piperidin-4-yl)pyridin-3-yl)-1-(pyridazin-3-yl)azetidine-3-carboxamide

The title compound was prepared as described in Example 1D, substituting tert-butyl 4-(5-(1-(pyridazin-3-yl)azetidine-3-carboxamido)pyridin-2-yl)piperidine-1-carboxylate for tert-butyl 4-(4-(1-(pyridazin-3-yl)azetidine-3-carboxamido)phenoxy)piperidine-1-carboxylate.

Example 914C

N-{6-[1-(2-fluorobenzoyl)piperidin-4-yl]pyridin-3-yl}-1-(pyridazin-3-yl)azetidine-3-carboxamide The title compound was prepared as described in Example 1A, substituting N-(6-(piperidin-4-yl)pyridin-3-yl)-1-(pyridazin-3-yl)azetidine-3-carboxamide for tert-butyl 4-(4-aminophenoxy)piperidine-1-carboxylate and 2-fluorobenzoic acid for 1-(benzyloxycarbonyl)azetidine-3-carboxylic acid. $^1$H NMR (400 MHz, DMSO-$d_6$) δ ppm 10.27 (s, 1H), 8.67 (d, J=2.5 Hz, 1H), 8.57 (dd, J=4.5, 1.2 Hz, 1H), 8.01 (dd, J=8.5, 2.5 Hz, 1H), 7.56-7.46 (m, 1H), 7.46-7.35 (m, 2H), 7.35-7.23 (m, 3 H), 6.83 (dd, J=9.0, 1.2 Hz, 1H), 4.64 (d, J=13.0 Hz, 1H), 4.26 (t, J=8.4 Hz, 2H), 4.16 (dd, J=8.0, 6.0 Hz, 2H), 3.76 (tt, J=8.5, 5.9 Hz, 1H), 3.47 (d, J=12.6 Hz, 1H), 3.19 (t, J=12.3 Hz, 1H), 3.01-2.85 (m, 2H), 1.94 (d, J=13.0 Hz, 1H), 1.79 (d, J=12.1 Hz, 1H), 1.73-1.53 (m, 2H); MS (ESI(+)) m/e 461 (M+H)$^+$.

Example 915

N-(4-{[(3R)-1-(3-methylbutanoyl)pyrrolidin-3-yl]oxy}phenyl)-1-(6-methylpyridazin-3-yl)azetidine-3-carboxamide Example 915A (R)-tert-butyl 3-(4-(1-(6-methylpyridazin-3-yl)azetidine-3-carboxamido)phenoxy)pyrrolidine-1-carboxylate The title compound was prepared as described in Example 1A, substituting (R)-tert-butyl 3-(4-aminophenoxy)pyrrolidine-1-carboxylate for tert-butyl 4-(4-aminophenoxy)piperidine-1-carboxylate and 1-(6-methylpyridazin-3-yl)azetidine-3-carboxylic acid for 1-(benzyloxycarbonyl)azetidine-3-carboxylic acid.

Example 915B (R)-1-(6-methylpyridazin-3-yl)-N-(4-(pyrrolidin-3-yloxy)phenyl)azetidine-3-carboxamide The title compound was prepared as described in Example 1D, substituting (R)-tert-butyl 3-(4-(1-(6-methylpyridazin-3-yl)azetidine-3-carboxamido)phenoxy)pyrrolidine-1-carboxylate for tert-butyl 4-(4-(1-(pyridin-3-yl)azetidine-3-carboxamido)phenoxy)piperidine-1-carboxylate.

Example 915C

N-(4-{[(3R)-1-(3-methylbutanoyl)pyrrolidin-3-yl]oxy}phenyl)-1-(6-methylpyridazin-3-yl)azetidine-3-carboxamide The title compound was prepared as described in Example 1A, substituting (R)-1-(6-methylpyridazin-3-yl)-N-(4-(pyrrolidin-3-yloxy)phenyl)azetidine-3-carboxamide for tert-butyl 4-(4-aminophenoxy)piperidine-1-carboxylate and 3-methylbutanoic acid for 1-(benzyloxycarbonyl)azetidine-3-carboxylic acid. $^1$H NMR (400 MHz, DMSO-$d_6$, T=90° C.) δ ppm 9.63 (s, 1H), 7.49 (d, J=8.9 Hz, 2H), 7.21 (d, J=9.0 Hz, 1H), 6.88 (d, J=8.7 Hz, 2H), 6.71 (d, J=9.0 Hz, 1H), 5.03-4.85 (m, 1H), 4.16 (dt, J=14.0, 8.0 Hz, 4 H), 3.69 (tt, J=8.5, 6.1 Hz, 1H), 3.62-3.34 (m, 3 H), 2.43 (s, 3 H), 2.23-1.98 (m, 6 H), 0.91 (d, J=6.2 Hz, 6 H); MS (ESI(+)) m/e 438 (M+H)$^+$.

Example 916

N-(4-{[(3R)-1-(2-methylpropanoyl)pyrrolidin-3-yl]oxy}phenyl)-1-(6-methylpyridazin-3-yl)azetidine-3-carboxamide The title compound was prepared as described in Example 1A, substituting (R)-1-(6-methylpyridazin-3-yl)-N-(4-(pyrrolidin-3-yloxy)phenyl)azetidine-3-carboxamide for tert-butyl 4-(4-aminophenoxy)piperidine-1-carboxylate and isobutyric acid for 1-(benzyloxycarbonyl)azetidine-3-carboxylic acid. $^1$H NMR (400 MHz, DMSO-$d_6$, T=90° C.) δ ppm 9.63 (s, 1H), 7.50 (d, J=9.0 Hz, 2H), 7.21 (d, J=9.0 Hz, 1H), 6.88 (d, J=8.9 Hz, 2H), 6.71 (d, J=9.0 Hz, 1H), 5.01-4.86 (m, 1H), 4.23-4.10 (m, 4 H), 3.74-3.64 (m, 1H), 3.64-3.40 (m, 4 H), 2.72-2.58 (m, 1H), 2.43 (s, 3 H), 2.26-1.98 (m, 2H), 1.03 (dd, J=9.7, 4.0 Hz, 6 H); MS (ESI(+)) m/e 424 (M+H)$^+$.

Example 917

N-(4-{[(3R)-1-(2,4-difluorobenzoyl)pyrrolidin-3-yl]oxy}phenyl)-1-(6-methylpyridazin-3-yl)azetidine-3-carboxamide The title compound was prepared as described in Example 1A, substituting (R)-1-(6-methylpyridazin-3-yl)-N-(4-(pyrrolidin-3-yloxy)phenyl)azetidine-3-carboxamide for tert-butyl 4-(4-aminophenoxy)piperidine-1-carboxylate and 2,4-difluorobenzoic acid for 1-(benzyloxycarbonyl)azetidine-3-carboxylic acid. $^1$H NMR (400 MHz, DMSO-$d_6$, T=90° C.) δ ppm 9.63 (bs, 1H), 7.53-7.44 (m, 3 H), 7.25-7.18 (m, 2H), 7.14-7.03 (m, 1H), 6.95-6.80 (m, 2H), 6.71 (d, J=8.9 Hz, 1H), 5.05-4.92 (m, 1H), 4.19 (t, J=8.2 Hz, 2H), 4.13 (t, J=7.0 Hz, 2H), 3.68 (tdd, J=10.3, 5.0, 1.7 Hz, 1H), 3.82-3.22 (m, 4 H), 2.43 (s, 3 H), 2.32-2.05 (m, 2H); MS (ESI(+)) m/e 494 (M+H)$^+$.

Example 918

1-(6-methylpyridazin-3-yl)-N-(4-{[(3R)-1-(1,3-thiazol-4-ylcarbonyl)pyrrolidin-3-yl]oxy}phenyl)azetidine-3-carboxamide The title compound was prepared as described in Example 1A, substituting (R)-1-(6-methylpyridazin-3-yl)-N-(4-(pyrrolidin-3-yloxy)phenyl)azetidine-3-carboxamide for tert-butyl 4-(4-aminophenoxy)piperidine-1-carboxylate and thiazole-4-carboxylic acid for 1-(benzyloxycarbonyl)azetidine-3-carboxylic acid. $^1$H NMR (400 MHz, DMSO-$d_6$, T=90° C.) δ ppm 9.63 (s, 1H), 9.09 (d, J=1.6 Hz, 1H), 8.19 (d, J=2.0 Hz, 1H), 7.49 (d, J=8.7 Hz, 2H), 7.21 (d, J=9.0 Hz, 1H), 6.89 (d, J=8.6 Hz, 2H), 6.71 (d, J=9.0 Hz, 1H), 5.00 (dt, J=4.5, 2.2 Hz, 1H), 4.16 (dt, J=14.0, 8.0 Hz, 4 H), 4.09-3.57 (m, 4 H), 3.69 (tt, J=8.4, 6.1 Hz, 1H), 2.43 (s, 3 H), 2.20 (dd, J=33.6, 24.3 Hz, 2H); MS (ESI(+)) m/e 465.2 (M+H)$^+$.

Example 919

1-(pyridazin-3-yl)-N-{6-[1-(4,4,4-trifluorobutanoyl)piperidin-4-yl]pyridin-3-yl}azetidine-3-carboxamide The title compound was prepared as described in Example 1A, substituting N-(6-(piperidin-4-yl)pyridin-3-yl)-1-(pyridazin-3-yl)azetidine-3-carboxamide for tert-butyl 4-(4-aminophenoxy)piperidine-1-carboxylate and 4,4,4-trifluorobutanoic acid for 1-(benzyloxycarbonyl)azetidine-3-carboxylic acid. $^1$H NMR (400 MHz, DMSO-$d_6$) δ ppm 10.27 (s, 1H), 8.67 (d, J=2.6 Hz, 1H), 8.57 (dd, J=4.5, 1.3 Hz, 1H), 8.00 (dd, J=8.5, 2.6 Hz, 1H), 7.40 (dd, J=9.0, 4.5 Hz, 1H), 7.26 (d, J=8.5 Hz, 1H), 6.86 (dd, J=9.0, 1.3 Hz, 1H), 4.50 (d, J=13.0 Hz, 1H), 4.26 (t, J=8.4 Hz, 2H), 4.17 (dd, J=8.2, 5.9 Hz, 2H), 3.97 (d, J=13.6 Hz, 1H), 3.76 (tt, J=8.6, 5.9 Hz, 1H), 3.11 (dd, J=18.5, 7.6 Hz, 1H), 2.90 (tt, J=11.7, 3.6 Hz, 1H), 2.76-2.59 (m, 2H), 2.59-2.43 (m, 2H), 1.91-1.77 (m, 2H), 1.66 (qd, J=12.6, 4.0 Hz, 1H), 1.51 (qd, J=12.7, 4.1 Hz, 1H); MS (ESI(+)) m/e 463 (M+H)$^+$.

Example 920

N-{6-[1-(3,3-dimethylbutanoyl)piperidin-4-yl]pyridin-3-yl}-1-(pyridazin-3-yl)azetidine-3-carboxamide The title compound was prepared as described in Example 1A, substituting N-(6-(piperidin-4-yl)pyridin-3-yl)-1-(pyridazin-3-yl)azetidine-3-carboxamide for tert-butyl 4-(4-aminophenoxy)piperidine-1-carboxylate and 3,3-dimethylbutanoic acid for 1-(benzyloxycarbonyl)azetidine-3-carboxylic acid. $^1$H NMR (400 MHz, DMSO-$d_6$) δ ppm 10.26 (s, 1H), 8.66 (d, J=2.5 Hz, 1H), 8.57 (dd, J=4.5, 1.1 Hz, 1H), 8.00 (dd, J=8.5, 2.6 Hz, 1H), 7.38 (dd, J=9.0, 4.5 Hz, 1H), 7.25 (d, J=8.5 Hz, 1H), 6.83 (dd, J=9.0, 1.2 Hz, 1H), 4.58 (d, J=12.9 Hz, 1H), 4.26 (t, J=8.4 Hz, 2 H), 4.16 (dd, J=8.0, 6.0 Hz, 2H), 4.07 (d, J=13.4 Hz, 1H), 3.76 (tt, J=8.5, 5.9 Hz, 1H), 3.10 (t, J=12.1 Hz, 1H), 2.88 (tt, J=11.7, 3.6 Hz, 1H), 2.59 (t, J=11.8 Hz, 1H), 2.29 (d, J=14.0 Hz, 1H), 2.22 (d, J=14.0 Hz, 1H), 1.84 (t, J=10.8 Hz, 2H), 1.60 (qd, J=12.7, 3.8 Hz, 1H), 1.48 (qd, J=12.7, 4.0 Hz, 1H), 1.00 (s, 9 H); MS (ESI(+)) m/e 437 (M+H)$^+$.

Example 921

(3S)—N-[4-(1-benzoylpiperidin-4-yl)phenyl]-1-(4-methylpyridazin-3-yl)pyrrolidine-3-carboxamide

Example 921A (S)-tert-butyl 4-(4-(1-(4-methylpyridazin-3-yl)pyrrolidine-3-carboxamido)phenyl)piperidine-1-carboxylate The title compound was prepared as described in Example 1C, substituting 3-chloro-4-methylpyridazine for 3-bromopyridine and (S)-tert-butyl 4-(4-(pyrrolidine-3-carboxamido)phenyl)piperidine-1-carboxylate for tert-butyl 4-(4-(azetidine-3-carboxamido)phenoxy)piperidine-1-carboxylate.

Example 921B (S)-1-(4-methylpyridazin-3-yl)-N-(4-(piperidin-4-yl)phenyl)pyrrolidine-3-carboxamide The title compound was prepared as described in Example 1D, substituting (S)-tert-butyl 4-(4-(1-(4-methylpyridazin-3-yl)pyrrolidine-3-carboxamido)phenyl)piperidine-1-carboxylate for tert-butyl 4-(4-(1-(pyridin-3-yl)azetidine-3-carboxamido)phenoxy)piperidine-1-carboxylate.

Example 921C (3S)—N-[4-(1-benzoylpiperidin-4-yl)phenyl]-1-(4-methylpyridazin-3-yl)pyrrolidine-3-carboxamide The title compound was prepared as described in Example 1A, substituting (S)-1-(4-methylpyridazin-3-yl)-N-(4-(piperidin-4-yl)phenyl)pyrrolidine-3-carboxamide for tert-butyl 4-(4-aminophenoxy)piperidine-1-carboxylate and benzoic acid for 1-(benzyloxycarbonyl)azetidine-3-carboxylic acid. $^1$H NMR (400 MHz, DMSO-d$_6$) δ ppm 10.03 (s, 1H), 8.46 (d, J=4.6 Hz, 1H), 7.58-7.52 (m, 2H), 7.50-7.37 (m, 5H), 7.28-7.15 (m, 3H), 4.71-4.55 (m, 1H), 3.89-3.38 (m, 5H), 3.28-2.58 (m, 4H), 2.34 (s, 3H), 2.32-1.98 (m, 2H), 2.00-1.49 (m, 4H); MS (ESI(+)) m/e 470.2 (M+H)$^+$.

Example 922

(3S)—N-{4-[1-(2,2-dimethylpropanoyl)piperidin-4-yl]phenyl}-1-(4-methylpyridazin-3-yl)pyrrolidine-3-carboxamide The title compound was prepared as described in Example 1A, substituting (S)-1-(4-methylpyridazin-3-yl)-N-(4-(piperidin-4-yl)phenyl)pyrrolidine-3-carboxamide for tert-butyl 4-(4-aminophenoxy)piperidine-1-carboxylate and 2,2-dimethylpropanoic acid for 1-(benzyloxycarbonyl)azetidine-3-carboxylic acid. $^1$H NMR (400 MHz, DMSO-d$_6$) δ ppm 10.02 (s, 1H), 8.46 (d, J=4.6 Hz, 1H), 7.57-7.51 (m, 2H), 7.22-7.13 (m, 3H), 4.45-4.36 (m, 2H), 3.85-3.72 (m, 2H), 3.68 (dd, J=7.9, 5.7 Hz, 2H), 3.21 (p, J=7.7 Hz, 1H), 2.93-2.66 (m, 3H), 2.34 (s, 3H), 2.31-2.05 (m, 2H), 1.82-1.74 (m, 2H), 1.53-1.34 (m, 2H), 1.22 (s, 9H); MS (ESI(+)) m/e 450.3 (M+H)$^+$.

Example 923

N-{4-[1-phenyl-3-(trifluoromethyl)-1H-pyrazol-5-yl]phenyl}-1-(pyridazin-3-yl)azetidine-3-carboxamide The title compound was prepared as described in Example 805, substituting 3,3,3-trifluoroprop-1-yne for ethynylcyclopropane in Example 805A and phenylhydrazine for methylhydrazine in Example 805B. $^1$H NMR (400 MHz, DMSO-d$_6$) δ ppm 10.26 (s, 1H), 8.56 (dd, J=4.5, 1.3 Hz, 1H), 7.61 (d, J=8.7 Hz, 2H), 7.50-7.44 (m, 3H), 7.41-7.31 (m, 3H), 7.23 (d, J=8.7 Hz, 2H), 7.14 (s, 1H), 6.83 (dd, J=8.9, 1.4 Hz, 1H), 4.24 (t, J=8.3 Hz, 2H), 4.14 (dd, J=8.1, 5.8 Hz, 2H), 3.74 (tt, J=8.5, 5.8 Hz, 1H); MS (ESI(+)) m/e 465.1 (M+H)$^+$.

Example 924

N-{6-[1-(2,2-dimethylpropyl)-1H-pyrazol-4-yl]pyridin-3-yl}-1-(pyridazin-3-yl)azetidine-3-carboxamide

Example 924A

N-(6-chloropyridin-3-yl)-1-(pyridazin-3-yl)azetidine-3-carboxamide

The title compound was prepared as described in Example 1A, substituting 6-chloropyridin-3-amine for tert-butyl 4-(4-aminophenoxy)piperidine-1-carboxylate and 1-(pyridazin-3-yl)azetidine-3-carboxylic acid for 1-(benzyloxycarbonyl)azetidine-3-carboxylic acid.

Example 924B

N-{6-[1-(2,2-dimethylpropyl)-1H-pyrazol-4-yl]pyridin-3-yl}-1-(pyridazin-3-yl)azetidine-3-carboxamide The title compound was prepared as described as described in Example 148A, substituting N-(6-chloropyridin-3-yl)-1-(pyridazin-3-yl)azetidine-3-carboxamide for 4-bromoaniline and 1-neopentyl-4-(4,4,5,5-tetramethyl-1,3,2-dioxaborolan-2-yl)-1H-pyrazole for 1-isobutyl-4-(4,4,5,5-tetramethyl-1,3,2-dioxaborolan-2-yl)-1H-pyrazole. $^1$H NMR (400 MHz, DMSO-d$_6$) δ ppm 10.31 (s, 1H), 8.69 (d, J=2.6 Hz, 1H), 8.57 (dd, J=4.5, 1.3 Hz, 1H), 8.18 (s, 1H), 8.06 (dd, J=8.6, 2.6 Hz, 1H), 7.95 (d, J=0.4 Hz, 1H), 7.63 (dd, J=8.6, 0.4 Hz, 1H), 7.39 (dd, J=8.9, 4.5 Hz, 1H), 6.84 (dd, J=9.0, 1.4 Hz, 1H), 4.27 (t, J=8.4 Hz, 2H), 4.18 (dd, J=8.2, 5.9 Hz, 2H), 3.94 (s, 2H), 3.78 (tt, J=8.6, 5.9 Hz, 1H), 0.93 (s, 9H); MS (ESI(+)) m/e 392 (M+H)$^+$.

Example 925 tert-butyl 4-[4-({[1-(pyridazin-3-yl)azetidin-3-yl]carbonyl}amino)-1H-pyrazol-1-yl]piperidine-1-carboxylate The title compound was prepared as described in Example 1A, substituting tert-butyl 4-(4-amino-1H-pyrazol-1-yl)piperidine-1-carboxylate for tert-butyl 4-(4-aminophenoxy)piperidine-1-carboxylate and 1-(pyridazin-3-yl)azetidine-3-carboxylic acid for 1-(benzyloxycarbonyl)azetidine-3-carboxylic acid. $^1$H NMR (400 MHz, DMSO-d$_6$) δ ppm 10.15 (s, 1H), 8.56 (dd, J=4.5, 1.3 Hz, 1H), 7.98-7.90 (m, 1H), 7.47 (d, J=0.5 Hz, 1H), 7.38 (dd, J=9.0, 4.5 Hz, 1H), 6.82 (dd, J=9.0, 1.4 Hz, 1H), 4.31 (tt, J=11.3, 3.9 Hz, 1H), 4.22 (t, J=8.3 Hz, 2H), 4.12 (dd, J=8.1, 6.0 Hz, 2H), 4.02 (d, J=12.3 Hz, 2H), 3.67 (tt, J=8.6, 6.0 Hz, 1H), 2.88 (bs, 2H), 1.95 (dd, J=12.4, 2.4 Hz, 2H), 1.74 (qd, J=12.4, 4.4 Hz, 2H), 1.41 (s, 9H); MS (ESI(+)) m/e 428 (M+H)$^+$.

Example 926

N-(6-{1-[(4-methylpiperidin-4-yl)methyl]-1H-pyrazol-4-yl}pyridin-3-yl)-1-(pyridazin-3-yl)azetidine-3-carboxamide The title compound was prepared as described as described in Example 148A, substituting N-(6-chloropyridin-3-yl)-1-(pyridazin-3-yl)azetidine-3-carboxamide for 4-bromoaniline and tert-butyl 4-methyl-4-((4-(4,4,5,5-tetramethyl-1,3,2-dioxaborolan-2-yl)-1H-pyrazol-1-yl)methyl)piperidine-1-carboxylate for 1-isobutyl-4-(4,4,5,5-tetramethyl-1,3,2-dioxaborolan-2-yl)-1H-pyrazole followed by TFA deprotection as described in Example 1D to give the title compound as a TFA salt. $^1$H NMR (400 MHz, DMSO-$d_6$) δ ppm 10.63 (s, 1H), 8.79 (d, J=2.5 Hz, 1H), 8.67-8.54 (m, 2H), 8.52-8.39 (m, 1H), 8.31 (s, 1H), 8.13 (dd, J=8.7, 2.5 Hz, 1H), 8.05 (s, 1H), 7.84 (dd, J=9.4, 4.4 Hz, 1H), 7.76 (d, J=8.7 Hz, 1H), 7.51 (dd, J=9.4, 0.9 Hz, 1H), 4.51 (t, J=9.3 Hz, 2H), 4.44 (dd, J=9.5, 5.9 Hz, 2H), 4.14 (s, 2H), 3.87 (tt, J=8.8, 5.9 Hz, 1H), 3.29-3.14 (m, 2H), 3.14-2.96 (m, 2H), 1.74-1.58 (m, 2H), 1.56-1.42 (m, 2H), 0.98 (s, 3 H); MS (ESI(+)) m/e 433 (M+H)$^+$.

Example 969

N-{4-[1-(3,3-dimethylbutanoyl)piperidin-4-yl]phenyl}-1-(4-methylpyridazin-3-yl)azetidine-3-carboxamide The title compound was prepared as described in Example 1A, substituting 1-(4-methylpyridazin-3-yl)-N-(4-(piperidin-4-yl)phenyl)azetidine-3-carboxamide for tert-butyl 4-(4-aminophenoxy)piperidine-1-carboxylate and 3,3-dimethylbutanoic acid for 1-(benzyloxycarbonyl)azetidine-3-carboxylic acid. $^1$H NMR (400 MHz, DMSO-$d_6$) δ ppm 10.02 (s, 1H), 8.49 (d, J=4.6 Hz, 1H), 7.57-7.51 (m, 2H), 7.22-7.14 (m, 3 H), 4.65-4.57 (m, 1H), 4.39-4.24 (m, 4 H), 4.12-4.03 (m, 1H), 3.68 (p, J=7.4 Hz, 1H), 3.07 (t, J=12.0 Hz, 1H), 2.77-2.64 (m, 1H), 2.34-2.26 (m, 1H), 2.25-2.16 (m, 4 H), 2.12-1.56 (m, 2H), 1.58-1.07 (m, 3 H), 1.09-0.87 (m, 9 H); MS (ESI(+)) m/e 450.3 (M+H)$^+$.

Example 970

N-{1-[1-(3,3-dimethylbutanoyl)piperidin-4-yl]-1H-pyrazol-4-yl}-1-(pyridazin-3-yl)azetidine-3-carboxamide

Example 970A

N-(1-(piperidin-4-yl)-1H-pyrazol-4-yl)-1-(pyridazin-3-yl)azetidine-3-carboxamide The title compound was prepared as described in Example 1D, substituting tert-butyl 4-[4-({[1-(pyridazin-3-yl)azetidin-3-yl]carbonyl}amino)-1H-pyrazol-1-yl]piperidine-1-carboxylate for tert-butyl 4-(4-(1-(pyridazin-3-yl)azetidine-3-carboxamido)phenoxy)piperidine-1-carboxylate.

Example 970B

N-{1-[1-(3,3-dimethylbutanoyl)piperidin-4-yl]-1H-pyrazol-4-yl}-1-(pyridazin-3-yl)azetidine-3-carboxamide The title compound was prepared as described in Example 1A, substituting N-(1-(piperidin-4-yl)-1H-pyrazol-4-yl)-1-(pyridazin-3-yl)azetidine-3-carboxamide for tert-butyl 4-(4-aminophenoxy)piperidine-1-carboxylate and 3,3-dimethylbutanoic acid for 1-(benzyloxycarbonyl)azetidine-3-carboxylic acid. $^1$H NMR (500 MHz, DMSO-$d_6$) δ ppm 10.16 (s, 1H), 8.56 (dd, J=4.5, 1.1 Hz, 1H), 7.95 (s, 1H), 7.46 (s, 1H), 7.38 (dd, J=9.0, 4.5 Hz, 1H), 6.83 (dd, J=9.0, 1.2 Hz, 1H), 4.53 (d, J=13.3 Hz, 1H), 4.38 (tt, J=11.3, 4.0 Hz, 1H), 4.23 (t, J=8.3 Hz, 2H), 4.12 (dd, J=8.0, 6.1 Hz, 2H), 4.07 (d, J=13.6 Hz, 1H), 3.67 (tt, J=8.5, 6.0 Hz, 1H), 3.15 (t, J=12.1 Hz, 1H), 2.66 (t, J=11.9 Hz, 1H), 2.30 (d, J=14.1 Hz, 1H), 2.23 (d, J=14.1 Hz, 1H), 1.98 (t, J=10.7 Hz, 2H), 1.80 (qd, J=12.3, 4.1 Hz, 1H), 1.68 (qd, J=12.3, 4.2 Hz, 1H), 1.00 (s, 9 H); MS (ESI(+)) m/e 426 (M+H)$^+$.

Example 971

N-{1-[1-(2-fluorobenzoyl)piperidin-4-yl]-1H-pyrazol-4-yl}-1-(pyridazin-3-yl)azetidine-3-carboxamide The title compound was prepared as described in Example 1A, substituting N-(1-(piperidin-4-yl)-1H-pyrazol-4-yl)-1-(pyridazin-3-yl)azetidine-3-carboxamide for tert-butyl 4-(4-aminophenoxy)piperidine-1-carboxylate and 2-fluorobenzoic acid for 1-(benzyloxycarbonyl)azetidine-3-carboxylic acid. $^1$H NMR (400 MHz, DMSO-$d_6$) δ ppm 10.15 (s, 1H), 8.56 (dd, J=4.5, 1.3 Hz, 1H), 7.98 (s, 1H), 7.54-7.42 (m, 3 H), 7.38 (dd, J=9.0, 4.5 Hz, 1H), 7.34-7.26 (m, 2H), 6.82 (dd, J=9.0, 1.3 Hz, 1H), 4.59 (d, J=13.3 Hz, 1H), 4.45 (tt, J=11.2, 3.9 Hz, 1H), 4.23 (t, J=8.3 Hz, 2 H), 4.12 (dd, J=8.0, 6.0 Hz, 2H), 3.67 (tt, J=8.5, 6.0 Hz, 1H), 3.47 (d, J=13.3 Hz, 1H), 3.22 (t, J=12.2 Hz, 1H), 2.98 (td, J=13.0, 2.7 Hz, 1H), 2.09 (d, J=11.2 Hz, 1H), 2.00-1.91 (m, 1H), 1.90-1.74 (m, 2H); MS (ESI(+)) m/e 450 (M+H)$^+$.

Example 972

N-[4-(phenylcarbamoyl)phenyl]-1-(pyridazin-3-yl)azetidine-3-carboxamide

Example 972A methyl 4-(1-(pyridazin-3-yl)azetidine-3-carboxamido)benzoate

The title compound was prepared as described in Example 1A, substituting methyl 4-aminobenzoate for tert-butyl 4-(4-aminophenoxy)piperidine-1-carboxylate and 1-(pyridazin-3-yl)azetidine-3-carboxylic acid for 1-(benzyloxycarbonyl)azetidine-3-carboxylic acid.

Example 972B 4-(1-(pyridazin-3-yl)azetidine-3-carboxamido)benzoic acid

The procedure was followed as described in Example 911, substituting methyl 4-(1-(pyridazin-3-yl)azetidine-3-carboxamido)benzoate for ethyl 1-methyl-5-(4-(1-(pyridazin-3-yl)azetidine-3-carboxamido)phenyl)-1H-pyrazole-3-carboxylate.

Example 972C

N-[4-(phenylcarbamoyl)phenyl]-1-(pyridazin-3-yl)azetidine-3-carboxamide

The title compound was prepared as described in Example 1A, substituting aniline for tert-butyl 4-(4-aminophenoxy)piperidine-1-carboxylate and 4-(1-(pyridazin-3-yl)azetidine- 3-carboxamido)benzoic acid for 1-(benzyloxycarbonyl)azetidine-3-carboxylic acid. $^1$H NMR (400 MHz, DMSO-d$_6$/D$_2$O) δ ppm 8.53 (dd, J=4.4, 1.3 Hz, 1H), 7.98-7.92 (m, 2H), 7.77-7.65 (m, 5 H), 7.38-7.24 (m, 3 H), 7.15-7.07 (m, 1H), 4.49 (t, J=9.0 Hz, 2H), 4.46-4.38 (m, 2H), 4.00-3.81 (m, 1H); MS (ESI(+)) m/e 374 (M+H)$^+$.

TABLE 23

The following Examples were essentially prepared as described in Example 972, substituting an appropriate amine in Example 972C. Some products were purified by flash chromatography while others were purified by reverse-phase HPLC. Accordingly, some Examples were isolated as trifluoroacetic acid salts.

| Ex | Name | MS |
|---|---|---|
| 973 | N-{4-[(2,2-dimethylpropyl)carbamoyl]phenyl}-1-(pyridazin-3-yl)azetidine-3-carboxamide | (ESI(+)) m/e 368 (M + H)$^+$ |
| 974 | N-{4-[(3-methoxy-2,2-dimethylpropyl)carbamoyl]phenyl}-1-(pyridazin-3-yl)azetidine-3-carboxamide | (ESI(+)) m/e 398 (M + H)$^+$ |
| 975 | N-{4-[(2-cyclopropylethyl)carbamoyl]phenyl}-1-(pyridazin-3-yl)azetidine-3-carboxamide | (ESI(+)) m/e XXX (M + H)$^+$ |
| 976 | N-(4-{[2-(2-ethylpiperidin-1-yl)ethyl]carbamoyl}phenyl)-1-(pyridazin-3-yl)azetidine-3-carboxamide | (ESI(+)) m/e 366 (M + H)$^+$ |
| 977 | N-{4-[(cyclobutylmethyl)carbamoyl]phenyl}-1-(pyridazin-3-yl)azetidine-3-carboxamide | (ESI(+)) m/e 366 (M + H)$^+$ |
| 978 | N-{4-[(2S)-butan-2-ylcarbamoyl]phenyl}-1-(pyridazin-3-yl)azetidine-3-carboxamide | (ESI(+)) m/e 354 (M + H)$^+$ |
| 979 | N-[4-(butylcarbamoyl)phenyl]-1-(pyridazin-3-yl)azetidine-3-carboxamide | (ESI(+)) m/e 354 (M + H)$^+$ |
| 980 | N-{4-[(2,2-dimethyltetrahydro-2H-pyran-4-yl)carbamoyl]phenyl}-1-(pyridazin-3-yl)azetidine-3-carboxamide | (ESI(+)) m/e 410 (M + H)$^+$ |
| 981 | N-(4-{[(1S)-1-cyclopropylethyl]carbamoyl}phenyl)-1-(pyridazin-3-yl)azetidine-3-carboxamide | (ESI(+)) m/e 366 (M + H)$^+$ |
| 982 | N-[4-({2-[methyl(phenyl)amino]ethyl}carbamoyl)phenyl]-1-(pyridazin-3-yl)azetidine-3-carboxamide | (ESI(+)) m/e 430 (M + H)$^+$ |
| 983 | N-{4-[1,1'-bi(cyclopropyl)-1-ylcarbamoyl]phenyl}-1-(pyridazin-3-yl)azetidine-3-carboxamide | (ESI(+)) m/e 378 (M + H)$^+$ |
| 984 | 1-(pyridazin-3-yl)-N-[4-(thiophen-3-ylcarbamoyl)phenyl]azetidine-3-carboxamide | (ESI(+)) m/e 366 (M + H)$^+$ |
| 985 | N-(4-{[(1R)-1-cyclopropylethyl]carbamoyl}phenyl)-1-(pyridazin-3-yl)azetidine-3-carboxamide | (ESI(+)) m/e 366 (M + H)$^+$ |
| 986 | N-{4-[(1-methylpiperidin-4-yl)carbamoyl]phenyl}-1-(pyridazin-3-yl)azetidine-3-carboxamide | (ESI(+)) m/e 395 (M + H)$^+$ |
| 987 | N-{4-[(2R)-butan-2-ylcarbamoyl]phenyl}-1-(pyridazin-3-yl)azetidine-3-carboxamide | (ESI(+)) m/e 354 (M + H)$^+$ |
| 988 | N-[4-(1-azabicyclo[2.2.2]oct-3-ylcarbamoyl)phenyl]-1-(pyridazin-3-yl)azetidine-3-carboxamide | (ESI(+)) m/e 407 (M + H)$^+$ |
| 989 | 1-(pyridazin-3-yl)-N-{4-[(tetrahydrofuran-3-ylmethyl)carbamoyl]phenyl}azetidine-3-carboxamide | (ESI(+)) m/e 382 (M + H)$^+$ |
| 990 | N-{4-[(oxetan-3-ylmethyl)carbamoyl]phenyl}-1-(pyridazin-3-yl)azetidine-3-carboxamide | (ESI(+)) m/e 368 (M + H)$^+$ |
| 991 | N-{4-[(2-methylcyclopropyl)carbamoyl]phenyl}-1-(pyridazin-3-yl)azetidine-3-carboxamide | (ESI(+)) m/e 352 (M + H)$^+$ |
| 992 | N-[4-(cyclobutylcarbamoyl)phenyl]-1-(pyridazin-3-yl)azetidine-3-carboxamide | (ESI(+)) m/e 352 (M + H)$^+$ |
| 993 | N-{4-[(1-methylcyclopropyl)carbamoyl]phenyl}-1-(pyridazin-3-yl)azetidine-3-carboxamide | (ESI(+)) m/e 352 (M + H)$^+$ |
| 994 | N-{4-[(2-methoxy-2-methylpropyl)carbamoyl]phenyl}-1-(pyridazin-3-yl)azetidine-3-carboxamide | (ESI(+)) m/e 384 (M + H)$^+$ |

TABLE 23-continued

The following Examples were essentially prepared as described in Example 972, substituting an appropriate amine in Example 972C. Some products were purified by flash chromatography while others were purified by reverse-phase HPLC. Accordingly, some Examples were isolated as trifluoroacetic acid salts.

| Ex | Name | MS |
|---|---|---|
| 995 | N-{4-[(cyclopropylmethyl)carbamoyl]phenyl}-1-(pyridazin-3-yl)azetidine-3-carboxamide | (ESI(+)) m/e 352 (M + H)⁺ |
| 996 | 1-(pyridazin-3-yl)-N-(4-{[(2R)-tetrahydrofuran-2-ylmethyl]carbamoyl}phenyl)azetidine-3-carboxamide | (ESI(+)) m/e 382 (M + H)⁺ |
| 997 | 1-(pyridazin-3-yl)-N-{4-[(3,3,3-trifluoropropyl)carbamoyl]phenyl}azetidine-3-carboxamide | (ESI(+)) m/e 394 (M + H)⁺ |
| 998 | N-{4-[(1-methylpiperidin-3-yl)carbamoyl]phenyl}-1-(pyridazin-3-yl)azetidine-3-carboxamide | (ESI(+)) m/e 395 (M + H)⁺ |
| 999 | N-(4-{[(3-methyloxetan-3-yl)methyl]carbamoyl}phenyl)-1-(pyridazin-3-yl)azetidine-3-carboxamide | (ESI(+)) m/e 382 (M + H)⁺ |
| 1000 | 1-(pyridazin-3-yl)-N-(4-{[(2S)-tetrahydrofuran-2-ylmethyl]carbamoyl}phenyl)azetidine-3-carboxamide | (ESI(+)) m/e 382 (M + H)⁺ |
| 1001 | 1-(pyridazin-3-yl)-N-{4-[(tetrahydro-2H-pyran-4-ylmethyl)carbamoyl]phenyl}azetidine-3-carboxamide | (ESI(+)) m/e 396 (M + H)⁺ |
| 1002 | 1-(pyridazin-3-yl)-N-[4-(tetrahydro-2H-pyran-4-ylcarbamoyl)phenyl]azetidine-3-carboxamide | (ESI(+)) m/e 382 (M + H)⁺ |
| 1003 | N-(4-{[(1-methylpiperidin-3-yl)methyl]carbamoyl}phenyl)-1-(pyridazin-3-yl)azetidine-3-carboxamide | (ESI(+)) m/e 409 (M + H)⁺ |
| 1004 | N-[4-(cyclopropylcarbamoyl)phenyl]-1-(pyridazin-3-yl)azetidine-3-carboxamide | (ESI(+)) m/e 338 (M + H)⁺ |
| 1005 | N-[4-(cyclopentylcarbamoyl)phenyl]-1-(pyridazin-3-yl)azetidine-3-carboxamide | (ESI(+)) m/e 366 (M + H)⁺ |
| 1006 | N-[4-(benzylcarbamoyl)phenyl]-1-(pyridazin-3-yl)azetidine-3-carboxamide | (ESI(+)) m/e 388 (M + H)⁺ |
| 1007 | N-{4-[(3-fluorophenyl)carbamoyl]phenyl}-1-(pyridazin-3-yl)azetidine-3-carboxamide | (ESI(+)) m/e 392 (M + H)⁺ |
| 1008 | N-[4-(propylcarbamoyl)phenyl]-1-(pyridazin-3-yl)azetidine-3-carboxamide | (ESI(+)) m/e 340 (M + H)⁺ |
| 1009 | N-{4-[(4-fluorophenyl)carbamoyl]phenyl}-1-(pyridazin-3-yl)azetidine-3-carboxamide | (ESI(+)) m/e 392 (M + H)⁺ |
| 1010 | N-{4-[(2-fluorophenyl)carbamoyl]phenyl}-1-(pyridazin-3-yl)azetidine-3-carboxamide | (ESI(+)) m/e 392 (M + H)⁺ |
| 1011 | N-{4-[(1-methylcyclobutyl)carbamoyl]phenyl}-1-(pyridazin-3-yl)azetidine-3-carboxamide | (ESI(+)) m/e 366 (M + H)⁺ |
| 1012 | N-[4-(prop-2-en-1-ylcarbamoyl)phenyl]-1-(pyridazin-3-yl)azetidine-3-carboxamide | (ESI(+)) m/e 338 (M + H)⁺ |
| 1020 | 1-(pyridazin-3-yl)-N-{4-[(3S)-tetrahydrofuran-3-ylcarbamoyl]phenyl}azetidine-3-carboxamide | (ESI(+)) m/e 368 (M + H)⁺ |
| 1021 | N-[4-({4-[2-(dimethylamino)ethyl]phenyl}carbamoyl)phenyl]-1-(pyridazin-3-yl)azetidine-3-carboxamide | (ESI(+)) m/e 445 (M + H)⁺ |
| 1022 | 1-(pyridazin-3-yl)-N-{4-[(3R)-tetrahydrofuran-3-ylcarbamoyl]phenyl}azetidine-3-carboxamide | (ESI(+)) m/e 368 (M + H)⁺ |
| 1023 | N-{4-[(2-methoxyethyl)carbamoyl]phenyl}-1-(pyridazin-3-yl)azetidine-3-carboxamide | (ESI(+)) m/e 356 (M + H)⁺ |

Example 1024

N-{4-[1-(3-amino-2,2-dimethylpropyl)-1H-pyrazol-4-yl]phenyl}-1-(pyridazin-3-yl)azetidine-3-carboxamide

Example 1024A tert-butyl (2,2-dimethyl-3-(4-(4,4,5,5-tetramethyl-1,3,2-dioxaborolan-2-yl)-1H-pyrazol-1-yl)propyl)carbamate A solution of tert-butyl (3-hydroxy-2,2-dimethylpropyl)carbamate (1.000 g, 4.92 mmol), 4-(4,4,5,5-tetramethyl-1,3,2-dioxaborolan-2-yl)-1H-pyrazole (1.145 g, 5.90 mmol) and 2-(tributylphosphoranylidene)acetonitrile (1.425 g, 5.90 mmol) were stirred together in toluene (20 ml) at 90° C. overnight. The reaction mixture was concentrated and purified by normal phase chromatography to give the title compound.

Example 1024B tert-butyl (2,2-dimethyl-3-(4-(4-(1-(pyridazin-3-yl)azetidine-3-carboxamido)phenyl)-1H-pyrazol-1-yl)propyl)carbamate The title compound was prepared as described as described in Example 148A, substituting N-(4-bromophenyl)-1-(pyridazin-3-yl)azetidine-3-carboxamide for 4-bromoaniline and tert-butyl (2,2-dimethyl-3-(4-(4,4,5,5-tetramethyl-1,3,2-dioxaborolan-2-yl)-1H-pyrazol-1-yl)propyl)carbamate for 1-isobutyl-4-(4,4,5,5-tetramethyl-1,3,2-dioxaborolan-2-yl)-1H-pyrazole.

Example 1024C

N-{4-[1-(3-amino-2,2-dimethylpropyl)-1H-pyrazol-4-yl]phenyl}-1-(pyridazin-3-yl)azetidine-3-carboxamide The title compound was prepared as described in Example 1D, substituting tert-butyl (2,2-dimethyl-3-(4-(4-(1-(pyridazin-3-yl)azetidine-3-carboxamido)phenyl)-1H-pyrazol-1-yl)propyl)carbamate for tert-butyl 4-(4-(1-(pyridin-3-yl)azetidine-3-carboxamido)phenoxy)piperidine-1-carboxylate to give the title compound as a TFA salt. $^1$H NMR (500 MHz, DMSO-$d_6$) δ ppm 10.26 (s, 1H), 8.57 (dd, J=4.4, 1.1 Hz, 1H), 8.12 (s, 1H), 7.95 (bs, 3 H), 7.92 (s, 1H), 7.74 (dd, J=9.3, 4.4 Hz, 1H), 7.64 (d, J=8.7 Hz, 2H), 7.55 (d, J=8.6 Hz, 2H), 7.36 (d, J=9.2 Hz, 1H), 4.44 (t, J=9.1 Hz, 2H), 4.37 (dd, J=9.2, 5.9 Hz, 2 H), 4.10 (s, 2H), 3.81 (tt, J=8.8, 5.9 Hz, 1H), 2.83-2.70 (m, 2H), 0.96 (s, 6 H); MS (ESI(+)) m/e 406 (M+H)$^+$.

Example 1025

N-(4-{1-[2,2-dimethyl-3-(piperazin-1-yl)propyl]-1H-pyrazol-4-yl}phenyl)-1-(pyridazin-3-yl)azetidine-3-carboxamide

Example 1025A tert-butyl 4-(2,2-dimethyl-3-(4-(4,4,5,5-tetramethyl-1,3,2-dioxaborolan-2-yl)-1H-pyrazol-1-yl)propyl)piperidine-1-carboxylate The title compound was prepared as described in Example 1024A, substituting tert-butyl 4-(3-hydroxy-2,2-dimethylpropyl)piperidine-1-carboxylate for tert-butyl (3-hydroxy-2,2-dimethylpropyl)carbamate.

Example 1025B tert-butyl 4-(2,2-dimethyl-3-(4-(4-(1-(pyridazin-3-yl)azetidine-3-carboxamido)phenyl)-1H-pyrazol-1-yl)propyl)piperazine-1-carboxylate The title compound was prepared as described as described in Example 148A, substituting N-(4-bromophenyl)-1-(pyridazin-3-yl)azetidine-3-carboxamide for 4-bromoaniline and tert-butyl 4-(2,2-dimethyl-3-(4-(4,4,5,5-tetramethyl-1,3,2-dioxaborolan-2-yl)-1H-pyrazol-1-yl)propyl)piperidine-1-carboxylate for 1-isobutyl-4-(4,4,5,5-tetramethyl-1,3,2-dioxaborolan-2-yl)-1H-pyrazole.

Example 1025C

N-(4-{1-[2,2-dimethyl-3-(piperazin-1-yl)propyl]-1H-pyrazol-4-yl}phenyl)-1-(pyridazin-3-yl)azetidine-3-carboxamide The title compound was prepared as described in Example 1D, substituting tert-butyl 4-(2,2-dimethyl-3-(4-(4-(1-(pyridazin-3-yl)azetidine-3-carboxamido)phenyl)-1H-pyrazol-1-yl)propyl)piperazine-1-carboxylate for tert-butyl 4-(4-(1-(pyridin-3-yl)azetidine-3-carboxamido)phenoxy)piperidine-1-carboxylate to give the title compound as a TFA salt. $^1$H NMR (500 MHz, DMSO-$d_6$) δ ppm 10.25 (s, 1H), 8.81 (s, 2H), 8.57 (dd, J=4.3, 1.0 Hz, 1H), 8.07 (s, 1H), 7.86 (s, 1H), 7.80 (dd, J=9.3, 4.4 Hz, 1 H), 7.62 (d, J=8.7 Hz, 2H), 7.54 (d, J=8.6 Hz, 2H), 7.45 (d, J=8.9 Hz, 1H), 4.47 (t, J=9.2 Hz, 2H), 4.40 (dd, J=9.3, 5.9 Hz, H), 4.03 (s, 2H), 3.87-3.74 (m, 1H), 3.19 (s, 4 H), 2.92 (s, 4 H), 2.45 (s, 2H), 0.89 (s, 6 H); MS (ESI(+)) m/e 475 (M+H)$^+$.

Example 1026

N-(4-{1-[2-methyl-2-(piperazin-1-yl)propanoyl]piperidin-4-yl}phenyl)-1-(pyridazin-3-yl)azetidine-3-carboxamide The title compound was prepared as described in Example 1A, substituting N-(4-(piperidin-4-yl)phenyl)-1-(pyridazin-3-yl)azetidine-3-carboxamide for tert-butyl 4-(4-aminophenoxy)piperidine-1-carboxylate and 2-(4-(tert-butoxycarbonyl)piperazin-1-yl)-2-methylpropanoic acid for 1-(benzyloxycarbonyl)azetidine-3-carboxylic acid, followed by TFA deprotection as described in Example 1D to give the title compound as a TFA salt. $^1$ H NMR (400 MHz, DMSO-$d_6$) δ ppm 10.17 (s, 1H), 8.67 (s, 2H), 8.56 (d, J=4.3 Hz, 1H), 7.77 (dd, J=9.3, 4.4 Hz, 1H), 7.55 (d, J=8.4 Hz, 2H), 7.42 (d, J=9.3 Hz, 1H), 7.21 (d, J=8.5 Hz, 2H), 5.27 (s, 1H), 4.59 (s, 1H), 4.45 (t, J=9.1 Hz, 2H), 4.37 (dd, J=9.2, 5.9 Hz, 2H), 3.91-3.71 (m, 1H), 3.11 (s, 5 H), 2.81-2.53 (m, 6 H), 1.80 (d, J=12.0 Hz, 2H), 1.45 (td, J=12.3, 9.1 Hz, 2H), 1.21 (s, 6 H); MS (ESI(+)) m/e 492 (M+H)$^+$.

What is claimed is:

1. A compound of formula (IC), or a therapeutically acceptable salt thereof,

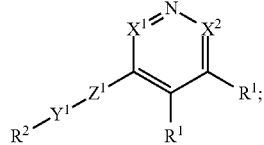

Formula (IC)

$X^1$ is N and $X^2$ is $CR^1$;
$Y^1$ is C(O)NH, or NHC(O);
$Z^1$ is

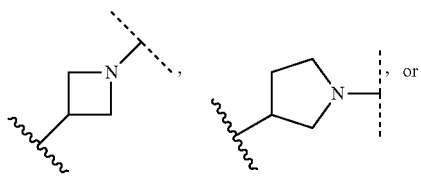

or wherein ⌇ indicates the point of attachment to $Y^1$ and ⌇ indicates the point of attachment to the nitrogen containing heteroaryl;

$R^1$, at each occurrence, is independently selected from the group consisting of hydrogen, alkyl, alkenyl, alkynyl, haloalkyl, hydoxyalkyl, alkoxy, OH, $NH_2$, CN, $NO_2$, F, Cl, Br and I;

$R^2$ is independently selected from the group consisting of $C_4$-$C_6$-alkyl, $C_4$-$C_6$-alkenyl, $C_4$-$C_6$-alkynyl, aryl, and 5-6 membered heteroaryl; wherein each $R^2$ $C_4$-$C_6$-alkyl, $C_4$-$C_6$-alkenyl, and $C_4$-$C_6$-alkynyl is substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(N)NH_2$, $C(N)NHR^3$, $C(N)N(R^3)_2$, CNOH, $CNOCH_3$, OH, (O), CN, $N_3$, $NO_2$, F, Cl, Br and I; wherein each $R^2$ aryl and 5-6 membered heteroaryl is optionally substituted with one or more substituents independently selected from the group consisting of $R^4$, $OR^4$, $SR^4$, $S(O)R^4$, $SO_2R^4$, $C(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, and I;

$R^3$, at each occurrence, is independently selected from the group consisting of alkyl, alkenyl, alkynyl, aryl, cycloalkyl, cycloalkenyl, and heterocyclyl; wherein each $R^3$ alkyl, alkenyl, and alkynyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, CNOH, $CNOCH_3$, OH, (O), CN, $N_3$, $NO_2$, F, Cl, Br and I; wherein each $R^3$ aryl, cycloalkyl, cycloalkenyl, and heterocyclyl is optionally substituted with one or more substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $C(N)NH_2$, $C(N)NHR^6$, $C(N)N(R^6)_2$, CNOH, $CNOCH_3$, OH, CN, $N_3$, $NO_2$, F, Cl, Br and I;

$R^4$, at each occurrence, is independently selected from the group consisting of alkyl, alkenyl, alkynyl, aryl, heterocyclyl, cycloalkyl, and cycloalkenyl; wherein each $R^4$ alkyl, alkenyl, and alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, CNOH, $CNOCH_3$, OH, (O), CN, $N_3$, $NO_2$, F, Cl, Br and I;

$R^5$, at each occurrence, is independently selected from the group consisting of alkyl, alkenyl, alkynyl, aryl, heterocyclyl, cycloalkyl, and cycloalkenyl; wherein each $R^5$ alkyl, alkenyl, and alkynyl is optionally substituted with one or more substituents independently selected from the group consisting of $R^8$, $OR^8$, $SR^8$, $S(O)R^8$, $SO_2R^8$, $NHR^8$, $N(R^8)_2$, $C(O)R^8$, $C(O)NH_2$, $C(O)NHR^8$, $C(O)N(R^8)_2$, $NHC(O)R^8$, $NR^8C(O)R^8$, $NHSO_2R^8$, $NHC(O)OR^8$, $SO_2NH_2$, $SO_2NHR^8$, $SO_2N(R^8)_2$, $NHC(O)NH_2$, $NHC(O)NHR^8$, OH, (O), $C(O)OH$, $N_3$, CN, $NH_2$, F, Cl, Br and I;

$R^6$, at each occurrence, is independently selected from the group consisting of alkyl, alkenyl, alkynyl, aryl, heterocyclyl, cycloalkyl, and cycloalkenyl; wherein each $R^6$ alkyl, alkenyl, and alkynyl is optionally substituted with one or more substituents independently selected from the group consisting of $R^9$, $OR^9$, $SR^9$, $S(O)R^9$, $SO_2R^9$, $NHR^9$, $N(R^9)_2$, $C(O)R^9$, $C(O)NH_2$, $C(O)NHR^9$, $C(O)N(R^9)_2$, $NHC(O)R^9$, $NR^9C(O)R^9$, $NHSO_2R^9$, $NHC(O)OR^9$, $SO_2NH_2$, $SO_2NHR^9$, $SO_2N(R^9)_2$, $NHC(O)NH_2$, $NHC(O)NHR^9$, OH, (O), $C(O)OH$, $N_3$, CN, $NH_2$, $CF_3$, $CF_2CF_3$, F, Cl, Br and I;

$R^7$, at each occurrence, is independently selected from the group consisting of alkyl, alkenyl, alkynyl, aryl, heterocyclyl, cycloalkyl, and cycloalkenyl;

$R^8$, at each occurrence, is independently selected from the group consisting of alkyl, alkenyl, alkynyl, aryl, heterocyclyl, cycloalkyl, and cycloalkenyl;

R⁹, at each occurrence, is independently selected from the group consisting of alkyl, alkenyl, alkynyl, aryl, heterocyclyl, cycloalkyl, and cycloalkenyl;

wherein the cyclic moieties represented by R⁴, R⁵, R⁶, R⁷, R⁸, and R⁹ are independently optionally substituted with one or more substituents independently selected from the group consisting of R¹⁰, OR¹⁰, SR¹⁰, S(O)R¹⁰, SO₂R¹⁰, C(O)R¹⁰, CO(O)R¹⁰, OC(O)R¹⁰, OC(O)OR¹⁰, C(O)C(O)R¹⁰, NH₂, NHR¹⁰, N(R¹⁰)₂, NHC(O)R¹⁰, NR¹⁰C(O)R¹⁰, NHS(O)₂R¹⁰, NR¹⁰S(O)₂R¹⁰, NHC(O)OR¹⁰, NR¹⁰C(O)OR¹⁰, NHC(O)NH₂, NHC(O)NHR¹⁰, NHC(O)N(R¹⁰)₂, NR¹⁰C(O)NHR¹⁰, NR¹⁰C(O)N(R¹⁰)₂, C(O)NH₂, C(O)NHR¹⁰, C(O)N(R¹⁰)₂, C(O)NHOH, C(O)NHOR¹⁰, C(O)NHSO₂R¹⁰, C(O)NR¹⁰SO₂R¹⁰, SO₂NH₂, SO₂NHR¹⁰, SO₂N(R¹⁰)₂, C(O)H, C(O)OH, C(N)NH₂, C(N)NHR¹⁰, C(N)N(R¹⁰)₂, CNOH, CNOCH₃, OH, CN, N₃, NO₂, F, Cl, Br and I;

R¹⁰, at each occurrence, is independently selected from the group consisting of alkyl, alkenyl, alkynyl, aryl, heterocyclyl, cycloalkyl, and cycloalkenyl; wherein each R¹⁰ alkyl, alkenyl, and alkynyl is optionally substituted with one or more substituents independently selected from the group consisting of R¹¹, OR¹¹, SR¹¹, S(O)R¹¹, SO₂R¹¹, C(O)R¹¹, CO(O)R¹¹, OC(O)R¹¹, OC(O)OR¹¹, NH₂, NHR¹¹, N(R¹¹)₂, NHC(O)R¹¹, NR¹¹C(O)R¹¹, NHS(O)₂R¹¹, NR¹¹S(O)₂R¹¹, NHC(O)OR¹¹, NR¹¹C(O)OR¹¹, NHC(O)NH₂, NHC(O)NHR¹¹, NHC(O)N(R¹¹)₂, NR¹¹C(O)NHR¹¹, NR¹¹C(O)N(R¹¹)₂, C(O)NH₂, C(O)NHR¹¹, C(O)N(R¹¹)₂, C(O)NHOH, C(O)NHOR¹¹, C(O)NHSO₂R¹¹, C(O)NR¹¹SO₂R¹¹, SO₂NH₂, SO₂NHR¹¹, SO₂N(R¹¹)₂, C(O)H, C(O)OH, C(N)NH₂, C(N)NHR¹¹, C(N)N(R¹¹)₂, CNOH, CNOCH₃, OH, (O), CN, N₃, NO₂, F, Cl, Br and I; wherein each R¹⁰ aryl, heterocyclyl, cycloalkyl, and cycloalkenyl is optionally substituted with one or more substituents independently selected from the group consisting of R¹², OR¹², SR¹², S(O)R¹², SO₂R¹², C(O)R¹², CO(O)R¹², OC(O)R¹², OC(O)OR¹², NH₂, NHR¹², N(R¹²)₂, NHC(O)R¹², NR¹²C(O)R¹², NHS(O)₂R¹², NR¹²S(O)₂R¹², NHC(O)OR¹², NR¹²C(O)OR¹², NHC(O)NH₂, NHC(O)NHR¹², NHC(O)N(R¹²)₂, NR¹²C(O)NHR¹², NR¹²C(O)N(R¹²)₂, C(O)NH₂, C(O)NHR¹², C(O)N(R¹²)₂, C(O)NHOH, C(O)NHOR¹², C(O)NHSO₂R¹², C(O)NR¹²SO₂R¹², SO₂NH₂, SO₂NHR¹², SO₂N(R¹²)₂, C(O)H, C(O)OH, C(N)NH₂, C(N)NHR¹², C(N)N(R¹²)₂, CNOH, CNOCH₃, OH, CN, N₃, NO₂, CF₃, OCF₃, F, Cl, Br and I;

R¹¹, at each occurrence, is independently selected from the group consisting of alkyl, alkenyl, alkynyl, aryl, heterocyclyl, cycloalkyl, and cycloalkenyl; wherein each R¹¹ alkyl, alkenyl, and alkynyl is optionally substituted with alkoxy or aryl; wherein each R¹¹ aryl, heterocyclyl, cycloalkyl, and cycloalkenyl is optionally substituted with one or more substituents independently selected from the group consisting of R¹³, OR¹³, C(O)OR¹³, OCF₃, CF₃, F, Cl, Br and I;

R¹², at each occurrence, is independently selected from the group consisting of alkyl, alkenyl, alkynyl, aryl, heterocyclyl, cycloalkyl, and cycloalkenyl; and R¹³, at each occurrence, is independently selected from the group consisting of alkyl, haloalkyl, alkenyl, alkynyl, aryl, heterocyclyl, cycloalkyl, and cycloalkenyl.

2. The compound of claim 1, or a therapeutically acceptable salt thereof, wherein Z¹ is

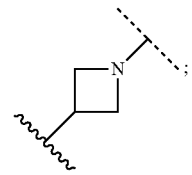

wherein ⁓ indicates the point of attachment to Y¹ and ⁓ indicates the point of attachment to the nitrogen containing heteroaryl.

3. The compound of claim 1, or a therapeutically acceptable salt thereof, wherein Z¹ is

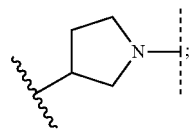

wherein ⁓ indicates the point of attachment to Y¹ and ⁓ indicates the point of attachment to the nitrogen containing heteroaryl.

4. The compound of claim 2, or a therapeutically acceptable salt thereof, wherein Y¹ is C(O)NH.

5. The compound of claim 3, or a therapeutically acceptable salt thereof, wherein Y¹ is C(O)NH.

6. The compound of claim 4, or a therapeutically acceptable salt thereof, wherein R² is phenyl; wherein each R² phenyl is substituted with one substituent independently selected from the group consisting of R⁴, OR⁴, and SO₂R⁴.

7. The compound of claim 5, or a therapeutically acceptable salt thereof, wherein R² is phenyl; wherein each R² phenyl is substituted with one substituent independently selected from the group consisting of R⁴, OR⁴, and SO₂R⁴.

8. The compound of claim 6, or a therapeutically acceptable salt thereof, wherein R¹, at each occurrence, is hydrogen.

9. The compound of claim 7, or a therapeutically acceptable salt thereof, wherein R¹, at each occurrence, is hydrogen.

10. The compound of claim 8, or a therapeutically acceptable salt thereof, wherein R⁴, at each occurrence, is heterocyclyl.

11. The compound of claim 9, or a therapeutically acceptable salt thereof, wherein R⁴, at each occurrence, is heterocyclyl.

12. The compound of claim 1, selected from the group consisting of
  N-{4-[1-(2-methylpropanoyl)piperidin-4-yl]phenyl})-1-(pyridazin-3-yl)azetidine-3-carboxamide;
  N-(4-{[1-(2-chlorobenzoyl)piperidin-4-yl]oxy}phenyl)-1-(pyridazin-3-yl)azetidine-3-carboxamide;
  N-[4-({1-[(2S)-2-methylbutanoyl]piperidin-4-yl}oxy)phenyl]-1-(pyridazin-3-yl)azetidine-3-carboxamide;
  1-(pyridazin-3-yl)-N-(4-{[1-(1,3-thiazol-2-ylcarbonyl)piperidin-4-yl]oxy}phenyl)azetidine-3-carboxamide;
  1-(pyridazin-3-yl)-N-(4-{[1-(tetrahydro-2H-pyran-4-ylcarbonyl)piperidin-4-yl]oxy}phenyl)azetidine-3-carboxamide;

N-[4-({1-[difluoro(phenyl)acetyl]piperidin-4-yl}oxy)phenyl]-1-(pyridazin-3-yl)azetidine-3-carboxamide;
N-[4-({1-[(4,4-difluorocyclohexyl)carbonyl]piperidin-4-yl}oxy)phenyl]-1-(pyridazin-3-yl)azetidine-3-carboxamide;
N-(4-{[1-(2-methyl-2-phenylpropanoyl)piperidin-4-yl]oxy}phenyl)-1-(pyridazin-3-yl)azetidine-3-carboxamide;
1-(pyridazin-3-yl)-N-(4-{[1-(1,3-thiazol-4-ylcarbonyl)piperidin-4-yl]oxy}phenyl)azetidine-3-carboxamide;
N-[4-({1-[(5-methylthiophen-2-yl)carbonyl]piperidin-4-yl}oxy)phenyl]-1-(pyridazin-3-yl)azetidine-3-carboxamide;
1-(pyridazin-3-yl)-N-{4-[(1-{[4-(trifluoromethyl)phenyl]acetyl}piperidin-4-yl)oxy]phenyl}azetidine-3-carboxamide;
1-(pyridazin-3-yl)-N-(4-{[1-(tetrahydrofuran-2-ylcarbonyl)piperidin-4-yl]oxy}phenyl)azetidine-3-carboxamide;
1-(pyridazin-3-yl)-N-[4-({1-[3-(trifluoromethyl)benzoyl]piperidin-4-yl}oxy)phenyl]azetidine-3-carboxamide;
1-(pyridazin-3-yl)-N-(4-{[1-(thiophen-3-ylcarbonyl)piperidin-4-yl]oxy}phenyl)azetidine-3-carboxamide;
1-(pyridazin-3-yl)-N-[4-({1-[3-(trifluoromethoxy)benzoyl]piperidin-4-yl}oxy)phenyl]azetidine-3-carboxamide;
N-(4-{[1-(3-methylbutanoyl)piperidin-4-yl]oxy}phenyl)-1-(pyridazin-3-yl)azetidine-3-carboxamide;
1-(pyridazin-3-yl)-N-(4-{[1-(tetrahydrofuran-3-ylcarbonyl)piperidin-4-yl]oxy}phenyl)azetidine-3-carboxamide;
N-[4-({1-[(3-fluorophenyl)acetyl]piperidin-4-yl}oxy)phenyl]-1-(pyridazin-3-yl)azetidine-3-carboxamide;
N-(4-{[1-(2-fluorobenzoyl)piperidin-4-yl]oxy}phenyl)-1-(pyridazin-3-yl)azetidine-3-carboxamide;
N-(4-{[1-(2,4-difluorobenzoyl)piperidin-4-yl]oxy}phenyl)-1-(pyridazin-3-yl)azetidine-3-carboxamide;
N-(4-{[1-(4-fluorobenzoyl)piperidin-4-yl]oxy}phenyl)-1-(pyridazin-3-yl)azetidine-3-carboxamide;
N-(4-{[1-(3-fluorobenzoyl)piperidin-4-yl]oxy}phenyl)-1-(pyridazin-3-yl)azetidine-3-carboxamide;
N-[4-({1-[(4-fluorophenyl)acetyl]piperidin-4-yl}oxy)phenyl]1-(pyridazin-3-yl)azetidine-3-carboxamide;
N-(4-{[1-(cyclopropylacetyl)piperidin-4-yl]oxy}phenyl)-1-(pyridazin-3-yl)azetidine-3-carboxamide;
N-(4-{[1-(3,4-difluorobenzoyl)piperidin-4-yl]oxy}phenyl)-1-(pyridazin-3-yl)azetidine-3-carboxamide;
1-(pyridazin-3-yl)-N-[4({1-[4-(trifluoromethoxy)benzoyl]piperidin-4-yl}oxy)phenyl]azetidine-3-carboxamide;
N-[4-({1-[(2,4-difluorophenyl)acetyl]piperidin-4-yl}oxy)phenyl]-1-(pyridazin-3-yl)azetidine-3-carboxamide;
1-(pyridazin-3-yl)-N-[4-({1-[4-(trifluoromethyl)benzoyl]piperidin-4-yl}oxy)phenyl]azetidine-3-carboxamide;
1-(pyridazin-3-yl)-N-{4-[(1-{[4-(trifluoromethoxy)phenyl]acetyl}piperidin-4-yl)oxy]phenyl}azetidine-3-carboxamide;
N-[4-({1-[(3,5-difluorophenyl)acetyl]piperidin-4-yl}oxy)phenyl]-1-(pyridazin-3-yl)azetidine-3-carboxamide;
1-(pyridazin-3-yl)-N-{4-[(1-{[3-(trifluoromethyl)phenyl]acetyl}piperidin-4-yl)oxy]phenyl}azetidine-3-carboxamide;
N-(4-{[1-(2,2-dimethylpropanoyl)piperidin-4-yl]oxy}phenyl)-1-(pyridazin-3-yl)azetidine-3-carboxamide;
1-(pyridazin-3-yl)-N-(4-{[1-(pyridin-2-ylcarbonyl)piperidin-4-yl]oxy}phenyl)azetidine-3-carboxamide;
N-(4-{[1-(3,5-difluorobenzoyl)piperidin-4-yl]oxy}phenyl)-1-(pyridazin-3-yl)azetidine-3-carboxamide;
N-{4-[(1-acetylpiperidin-4-yl)oxy]phenyl}-1-(pyridazin-3-yl)azetidine-3-carboxamide;
N-(4-{[1-(4-chlorobenzoyl)piperidin-4-yl]oxy}phenyl)-1-(pyridazin-3-yl)azetidine-3-carboxamide;
N-(4-{[1-(methoxyacetyl)piperidin-4-yl]oxy}phenyl)-1-(pyridazin-3-yl)azetidine-3-carboxamide;
N-[4-({1-[(2-fluorophenyl)acetyl]piperidin-4-yl}oxy)phenyl]-1-(pyridazin-3-yl)azetidine-3-carboxamide;
N-(4-{[1-(2,2-dimethylbutanoyl)piperidin-4-yl]oxy}phenyl)-1-(pyridazin-3-yl)azetidine-3-carboxamide;
1-(pyridazin-3-yl)-N-(4-{[1-(thiophen-2-ylcarbonyl)piperidin-4-yl]oxy}phenyl)azetidine-3-carboxamide;
N-(4-{[1-(3-chlorobenzoyl)piperidin-4-yl]oxy}phenyl)-1-(pyridazin-3-yl)azetidine-3-carboxamide;
N-(4-{[1-(cyclopropylcarbonyl)piperidin-4-yl]oxy}phenyl)-1-(pyridazin-3-yl)azetidine-3-carboxamide;
1-(pyridazin-3-yl)-N-(4-{[1-(3,3,3-trifluoropropanoyl)piperidin-4-yl]oxy}phenyl)azetidine-3-carboxamide;
N-(4-{[1-(2-methylpropanoyl)piperidin-4-yl]oxy}phenyl)-1-(pyridazin-3-yl)azetidine-3-carboxamide;
5-[1-(2-methylpropyl)-1H-pyrazol-4-yl]-N-[1-(pyridazin-3-yl)azetidin-3-yl]furan-2-carboxamide;
(3S)-N-{4-[1-(2-methylpropanoyl)piperidin-4-yl]phenyl}-1-(pyridazin-3-yl)pyrrolidine-3-carboxamide;
(3S)-N-[4-(1-benzoylpiperidin-4-yl)phenyl]-1-(pyridazin-3-yl)pyrrolidine-3-carboxamide;
(3S)-1-(pyridazin-3-yl)-N-{4-[1-(tetrahydro-2H-pyran-4-ylacetyl)piperidin-4-yl]phenyl}pyrrolidine-3-carboxamide;
(3S)-N-{4-[1-(2,2-dimethylpropanoyl)piperidin-4-yl]phenyl}-1-(pyridazin-3-yl)pyrrolidine-3-carboxamide;
tert-butyl 4-(4-{[1-(pyridazin-3-yl)azetidin-3-yl]carbamoyl}phenyl)piperidine-1-carboxylate;
5-[1-(2-methylpropyl)-1H-pyrazol-4-yl]-N-[1-(pyridazin-3-yl)azetidin-3-yl]thiophene-2-carboxamide;
N-[4-(1-acetylpiperidin-4-yl)phenyl]-1-(pyridazin-3-yl)azetidine-3-carboxamide;
N-[4-(1-butanoylpiperidin-4-yl)phenyl]-1-(pyridazin-3-yl)azetidine-3-carboxamide;
N-[4-(1-pentanoylpiperidin-4-yl)phenyl]-1-(pyridazin-3-yl)azetidine-3-carboxamide;
N-{4-[1-(2-methylbutanoyl)piperidin-4-yl]phenyl}-1-(pyridazin-3-yl)azetidine-3-carboxamide;
N-{4-[1-(3-methylbutanoyl)piperidin-4-yl]phenyl}-1-(pyridazin-3-yl)azetidine-3-carboxamide;
N-[4-(1-hexanoylpiperidin-4-yl)phenyl]-1-(pyridazin-3-yl)azetidine-3-carboxamide;
N-{4-[1-(2-methylpentanoyl)piperidin-4-yl]phenyl}-1-(pyridazin-3-yl)azetidine-3-carboxamide;
N-{4-[1-(3-methylpentanoyl)piperidin-4-yl]phenyl}-1-(pyridazin-3-yl)azetidine-3-carboxamide;
N-{4-[1-(4-methylpentanoyl)piperidin-4-yl]phenyl}-1-(pyridazin-3-yl)azetidine-3-carboxamide;
N-{4-[1-(2,2-dimethylbutanoyl)piperidin-4-yl]phenyl}-1-(pyridazin-3-yl)azetidine-3-carboxamide;
N-{4-[1-(2,3-dimethylbutanoyl)piperidin-4-yl]phenyl}-1-(pyridazin-3-yl)azetidine-3-carboxamide;
N-{4-[1-(3,3-dimethylbutanoyl)piperidin-4-yl]phenyl}-1-(pyridazin-3-yl)azetidine-3-carboxamide;

N-{4-[1-(2-ethylbutanoyl)piperidin-4-yl]phenyl}-1-(pyridazin-3-yl)azetidine-3-carboxamide;
N-[4-(1-heptanoylpiperidin-4-yl)phenyl]-1-(pyridazin-3-yl)azetidine-3-carboxamide;
N-{4-[1-(but-3-enoyl)piperidin-4-yl]phenyl}-1-(pyridazin-3-yl)azetidine-3-carboxamide;
N-{4-[1-(pent-4-enoyl)piperidin-4-yl]phenyl}-1-(pyridazin-3-yl)azetidine-3-carboxamide;
1-(pyridazin-3-yl)-N-{4-[1-(3,3,3-trifluoropropanoyl)piperidin-4-yl]phenyl}azetidine-3-carboxamide;
N-{4-[1-(methoxyacetyl)piperidin-4-yl]phenyl}-1-(pyridazin-3-yl)azetidine-3-carboxamide;
N-(4-{1-[(methylsulfanyl)acetyl]piperidin-4-yl}phenyl)-1-(pyridazin-3-yl)azetidine-3-carboxamide;
N-(4-{1-[(2-methoxyethoxy)acetyl]piperidin-4-yl}phenyl)-1-(pyridazin-3-yl)azetidine-3-carboxamide;
N-{4-[1-(3-nitropropanoyl)piperidin-4-yl]phenyl}-1-(pyridazin-3-yl)azetidine-3-carboxamide;
N-(4-{1-[3-(methylsulfanyl)propanoyl]piperidin-4-yl}phenyl)-1-(pyridazin-3-yl)azetidine-3-carboxamide;
N-{4-[1-(pent-4-ynoyl)piperidin-4-yl]phenyl}-1-(pyridazin-3-yl)azetidine-3-carboxamide;
N-{4-[1-(cyclohexylcarbonyl)piperidin-4-yl]phenyl}-1-(pyridazin-3-yl)azetidine-3-carboxamide;
N-{4-[1-(cyclohexylacetyl)piperidin-4-yl]phenyl}-1-(pyridazin-3-yl)azetidine-3-carboxamide;
N-{4-[1-(3-methylbenzoyl)piperidin-4-yl]phenyl}-1-(pyridazin-3-yl)azetidine-3-carboxamide;
N-{4-[1-(2-hydroxybenzoyl)piperidin-4-yl]phenyl}-1-(pyridazin-3-yl)azetidine-3-carboxamide;
N-{4-[1-(3-hydroxybenzoyl)piperidin-4-yl]phenyl}-1-(pyridazin-3-yl)azetidine-3-carboxamide;
N-{4-[1-(4-hydroxybenzoyl)piperidin-4-yl]phenyl}-1-(pyridazin-3-yl)azetidine-3-carboxamide;
N-{4-[1-(2-methoxybenzoyl)piperidin-4-yl]phenyl}-1-(pyridazin-3-yl)azetidine-3-carboxamide;
N-{4-[1-(3-methoxybenzoyl)piperidin-4-yl]phenyl}-1-(pyridazin-3-yl)azetidine-3-carboxamide;
N-{4-[1-(4-methoxybenzoyl)piperidin-4-yl]phenyl}-1-(pyridazin-3-yl)azetidine-3-carboxamide;
N-{4-[1-(3-fluorobenzoyl)piperidin-4-yl]phenyl}-1-(pyridazin-3-yl)azetidine-3-carboxamide;
N-{4-[1-(4-fluorobenzoyl)piperidin-4-yl]phenyl}-1-(pyridazin-3-yl)azetidine-3-carboxamide;
N-{4-[1-(2-chlorobenzoyl)piperidin-4-yl]phenyl}-1-(pyridazin-3-yl)azetidine-3-carboxamide;
N-{4-[1-(3-chlorobenzoyl)piperidin-4-yl]phenyl}-1-(pyridazin-3-yl)azetidine-3-carboxamide;
N-{4-[1-(3-cyanobenzoyl)piperidin-4-yl]phenyl}-1-(pyridazin-3-yl)azetidine-3-carboxamide;
N-{4-[1-(4-cyanobenzoyl)piperidin-4-yl]phenyl}-1-(pyridazin-3-yl)azetidine-3-carboxamide;
1-(pyridazin-3-yl)-N-(4-{1-[3-(trifluoromethyl)benzoyl]piperidin-4-yl}phenyl)azetidine-3-carboxamide;
1-(pyridazin-3-yl)-N-(4-{1-[4-(trifluoromethyl)benzoyl]piperidin-4-yl}phenyl)azetidine-3-carboxamide;
1-(pyridazin-3-yl)-N-(4-{1-[3-(trifluoromethoxy)benzoyl]piperidin-4-yl}phenyl)azetidine-3-carboxamide;
N-{4-[1-(2,3-dimethylbenzoyl)piperidin-4-yl]phenyl}-1-(pyridazin-3-yl)azetidine-3-carboxamide;
N-{4-[1-(2,4-dimethylbenzoyl)piperidin-4-yl]phenyl}-1-(pyridazin-3-yl)azetidine-3-carboxamide;
N-{4-[1-(2,5-dimethylbenzoyl)piperidin-4-yl]phenyl}-1-(pyridazin-3-yl)azetidine-3-carboxamide;
N-{4-[1-(3,4-dimethylbenzoyl)piperidin-4-yl]phenyl}-1-(pyridazin-3-yl)azetidine-3-carboxamide;
N-{4-[1-(3,5-dimethylbenzoyl)piperidin-4-yl]phenyl}-1-(pyridazin-3-yl)azetidine-3-carboxamide;
N-{4-[1-(2,4-dichlorobenzoyl)piperidin-4-yl]phenyl}-1-(pyridazin-3-yl)azetidine-3-carboxamide;
N-{4-[1-(2,5-dichlorobenzoyl)piperidin-4-yl]phenyl}-1-(pyridazin-3-yl)azetidine-3-carboxamide;
N-{4-[1-(3,4-dichlorobenzoyl)piperidin-4-yl]phenyl}-1-(pyridazin-3-yl)azetidine-3-carboxamide;
N-{4-[1-(3,5-dichlorobenzoyl)piperidin-4-yl]phenyl}-1-(pyridazin-3-yl)azetidine-3-carboxamide;
N-(4-{1-[(2-fluorophenyl)acetyl]piperidin-4-yl}phenyl)-1-(pyridazin-3-yl)azetidine-3-carboxamide;
N-(4-{1-[(3-fluorophenyl)acetyl]piperidin-4-yl}phenyl)-1-(pyridazin-3-yl)azetidine-3-carboxamide;
N-(4-{1-[(4-fluorophenyl)acetyl]piperidin-4-yl}phenyl)-1-(pyridazin-3-yl)azetidine-3-carboxamide;
N-(4-{1-[(2-chlorophenyl)acetyl]piperidin-4-yl}phenyl)-1-(pyridazin-3-yl)azetidine-3-carboxamide;
N-(4-{1-[(4-chlorophenyl)acetyl]piperidin-4-yl}phenyl)-1-(pyridazin-3-yl)azetidine-3-carboxamide;
1-(pyridazin-3-yl)-N-[4-(1-{[4-(trifluoromethyl)phenyl]acetyl}piperidin-4-yl)phenyl]azetidine-3-carboxamide;
N-(4-{1-[(3,5-dimethylphenyl)acetyl]piperidin-4-yl}phenyl)-1-(pyridazin-3-yl)azetidine-3-carboxamide;
N-(4-{1-[(2,5-difluorophenyl)acetyl]piperidin-4-yl}phenyl)-1-(pyridazin-3-yl)azetidine-3-carboxamide;
N-(4-{1-[(3,4-dichlorophenyl)acetyl]piperidin-4-yl}phenyl)-1-(pyridazin-3-yl)azetidine-3-carboxamide;
N-{4-[1-(furan-3-ylcarbonyl)piperidin-4-yl]phenyl}-1-(pyridazin-3-yl)azetidine-3-carboxamide;
1-(pyridazin-3-yl)-N-{4-[1-(thiophen-2-ylcarbonyl)piperidin-4-yl]phenyl}azetidine-3-carboxamide;
N-(4-{1-[(5-methylthiophen-2-yl)carbonyl]piperidin-4-yl}phenyl)-1-(pyridazin-3-yl)azetidine-3-carboxamide;
N-(4-{1-[(5-methylpyrazin-2-yl)carbonyl]piperidin-4-yl}phenyl)-1-(pyridazin-3-yl)azetidine-3-carboxamide;
N-(4-{1-[(1-methylcyclopropyl)carbonyl]piperidin-4-yl}phenyl)-1-(pyridazin-3-yl)azetidine-3-carboxamide;
N-{4-[1-(3-ethoxypropanoyl)piperidin-4-yl]phenyl}-1-(pyridazin-3-yl)azetidine-3-carboxamide;
N-(4-{1-[(1-phenylcyclopropyl)carbonyl]piperidin-4-yl}phenyl)-1-(pyridazin-3-yl)azetidine-3-carboxamide;
1-(pyridazin-3-yl)-N-(4-{1-[(pyrimidin-2-ylsulfanyl)acetyl]piperidin-4-yl}phenyl)azetidine-3-carboxamide;
N-(4-{1-[(1-acetylpiperidin-4-yl)carbonyl]piperidin-4-yl}phenyl)-1-(pyridazin-3-yl)azetidine-3-carboxamide;
N-(4-{1-[(3,5-difluorophenyl)acetyl]piperidin-4-yl}phenyl)-1-(pyridazin-3-yl)azetidine-3-carboxamide;
N-{4-[1-(N-acetyl-L-leucyl)piperidin-4-yl]phenyl}-1-(pyridazin-3-yl)azetidine-3-carboxamide;
N-{4-[1-(diphenylacetyl)piperidin-4-yl]phenyl}-1-(pyridazin-3-yl)azetidine-3-carboxamide;
N-{4-[1-(3-fluoro-2-methylbenzoyl)piperidin-4-yl]phenyl}-1-(pyridazin-3-yl)azetidine-3-carboxamide;

N-{4-[1-(5-fluoro-2-methylbenzoyl)piperidin-4-yl]phenyl}-1-(pyridazin-3-yl)azetidine-3-carboxamide;
N-{4-[1-(3-fluoro-4-methylbenzoyl)piperidin-4-yl]phenyl}-1-(pyridazin-3-yl)azetidine-3-carboxamide;
N-{4-[1-(2,3-difluorobenzoyl)piperidin-4-yl]phenyl}-1-(pyridazin-3-yl)azetidine-3-carboxamide;
N-{4-[1-(2,4-difluorobenzoyl)piperidin-4-yl]phenyl}-1-(pyridazin-3-yl)azetidine-3-carboxamide;
N-(4-{1-[4-(propan-2-yl)benzoyl]piperidin-4-yl}phenyl)-1-(pyridazin-3-yl)azetidine-3-carboxamide;
N-{4-[1-(4-tert-butylbenzoyl)piperidin-4-yl]phenyl}-1-(pyridazin-3-yl)azetidine-3-carboxamide;
N-(4-{1-[2-fluoro-5-(trifluoromethyl)benzoyl]piperidin-4-yl}phenyl)-1-(pyridazin-3-yl)azetidine-3-carboxamide;
N-(4-{1-[2-chloro-5-(trifluoromethyl)benzoyl]piperidin-4-yl}phenyl)-1-(pyridazin-3-yl)azetidine-3-carboxamide;
N-{4-[1-(cyclopentylacetyl)piperidin-4-yl]phenyl}-1-(pyridazin-3-yl)azetidine-3-carboxamide;
N-(4-{1-[(4-methylphenoxy)acetyl]piperidin-4-yl}phenyl)-1-(pyridazin-3-yl)azetidine-3-carboxamide;
N-(4-{1-[(2S)-2-phenylbutanoyl]piperidin-4-yl}phenyl)-1-(pyridazin-3-yl)azetidine-3-carboxamide;
N-{4-[1-(3,5-difluorobenzoyl)piperidin-4-yl]phenyl}-1-(pyridazin-3-yl)azetidine-3-carboxamide;
N-{4-[1-(4-chlorobenzoyl)piperidin-4-yl]phenyl}-1-(pyridazin-3-yl)azetidine-3-carboxamide;
N-{4-[1-(2,2-dimethylpropanoyl)piperidin-4-yl]phenyl}-1-(pyridazin-3-yl)azetidine-3-carboxamide;
1-(pyridazin-3-yl)-N-[4-(1-{[3-(trifluoromethyl)phenyl]acetyl}piperidin-4-yl)phenyl]azetidine-3-carboxamide;
N-(4-{1-[(3-chlorophenyl)acetyl]piperidin-4-yl}phenyl)-1-(pyridazin-3-yl)azetidine-3-carboxamide;
N-(4-{1-[(2,4-dichlorophenyl)acetyl]piperidin-4-yl}phenyl)-1-(pyridazin-3-yl)azetidine-3-carboxamide;
N-{4-[1-(naphthalen-1-ylcarbonyl)piperidin-4-yl]phenyl}-1-(pyridazin-3-yl)azetidine-3-carboxamide;
N-(4-{1-[(2R)-2-methoxy-2-phenylacetyl]piperidin-4-yl}phenyl)-1-(pyridazin-3-yl)azetidine-3-carboxamide;
N-(4-{1-[N-(furan-2-ylcarbonyl)glycyl]piperidin-4-yl}phenyl)-1-(pyridazin-3-yl)azetidine-3-carboxamide;
N-(4-{1-[(benzyloxy)acetyl]piperidin-4-yl}phenyl)-1-(pyridazin-3-yl)azetidine-3-carboxamide;
N-{4-[1-(naphthalen-1-ylacetyl)piperidin-4-yl]phenyl}-1-(pyridazin-3-yl)azetidine-3-carboxamide;
N-{4-[1-(cyclopropylcarbonyl)piperidin-4-yl]phenyl}-1-(pyridazin-3-yl)azetidine-3-carboxamide;
1-(pyridazin-3-yl)-N-{4-[1-(tetrahydrofuran-2-ylcarbonyl)piperidin-4-yl]phenyl}azetidine-3-carboxamide;
N-{4-[1-(N-benzoylglycyl)piperidin-4-yl]phenyl}-1-(pyridazin-3-yl)azetidine-3-carboxamide;
1-(pyridazin-3-yl)-N-{4-[1-(tetrahydrofuran-3-ylcarbonyl)piperidin-4-yl]phenyl}azetidine-3-carboxamide;
1-(pyridazin-3-yl)-N-(4-{1-[4-(thiophen-2-yl)butanoyl]piperidin-4-yl}phenyl)azetidine-3-carboxamide;
N-{4-[1-(2,5-difluorobenzoyl)piperidin-4-yl]phenyl}-1-(pyridazin-3-yl)azetidine-3-carboxamide;
N-{4-[1-(cyclobutylcarbonyl)piperidin-4-yl]phenyl}-1-(pyridazin-3-yl)azetidine-3-carboxamide;
N-[4-(1-{N-[(4-methylphenyl)sulfonyl]glycyl}piperidin-4-yl)phenyl]-1-(pyridazin-3-yl)azetidine-3-carboxamide;
N-(4-{1-[(2,3-difluorophenyl)acetyl]piperidin-4-yl}phenyl)-1-(pyridazin-3-yl)azetidine-3-carboxamide;
N-(4-{1-[(2S)-2-methoxy-2-phenylacetyl]piperidin-4-yl}phenyl)-1-(pyridazin-3-yl)azetidine-3-carboxamide;
N-{4-[1-(naphthalen-2-ylacetyl)piperidin-4-yl]phenyl}-1-(pyridazin-3-yl)azetidine-3-carboxamide;
N-{4-[1-(3-phenylpropanoyl)piperidin-4-yl]phenyl}-1-(pyridazin-3-yl)azetidine-3-carboxamide;
N-(4-{1-[(2,6-dichlorophenyl)acetyl]piperidin-4-yl}phenyl)-1-(pyridazin-3-yl)azetidine-3-carboxamide;
N-(4-{1-[3-(phenylsulfonyl)propanoyl]piperidin-4-yl}phenyl) -1-(pyridazin-3-yl)azetidine-3-carboxamide;
1-(pyridazin-3-yl)-N-{4-[1-(thiophen-3-ylcarbonyl)piperidin-4-yl]phenyl}azetidine-3-carboxamide;
N-(4-{1-[(2,5-dimethylfuran-3-yl)carbonyl]piperidin-4-yl}phenyl) -1-(pyridazin-3-yl)azetidine-3-carboxamide;
N-{4-[1-(cyclopropylacetyl)piperidin-4-yl]phenyl}-1-(pyridazin-3-yl)azetidine-3-carboxamide;
N-{4-[1-(2-fluorobenzoyl)piperidin-4-yl]phenyl}-1-(pyridazin-3-yl)azetidine-3-carboxamide;
N-{4-[1-(2-methylbenzoyl)piperidin-4-yl]phenyl}-1-(pyridazin-3-yl)azetidine-3-carboxamide;
1-(pyridazin-3-yl)-N-{4-[1-(1,3-thiazol-4-ylcarbonyl)piperidin-4-yl]phenyl}azetidine-3-carboxamide;
1-(pyridazin-3-yl)-N-{4-[1-(1,3-thiazol-5-ylcarbonyl)piperidin-4-yl]phenyl}azetidine-3-carboxamide;
N-{4-[1-(ethoxyacetyl)piperidin-4-yl]phenyl}-1-(pyridazin-3-yl)azetidine-3-carboxamide;
1-(pyridazin-3-yl)-N-{4-[1-(4,4,4-trifluorobutanoyl)piperidin-4-yl]phenyl}azetidine-3-carboxamide;
N-(4-{1-[(6-methylpyridin-3-yl)carbonyl]piperidin-4-yl}phenyl)-1-(pyridazin-3-yl)azetidine-3-carboxamide;
N-[4-(1-benzoylpiperidin-4-yl)phenyl]-1-(pyridazin-3-yl)azetidine-3-carboxamide;
N-{4-[1-(furan-2-ylcarbonyl)piperidin-4-yl]phenyl}-1-(pyridazin-3-yl)azetidine-3-carboxamide;
N-(4-{1-[(1-methylcyclohexyl)carbonyl]piperidin-4-yl}phenyl)-1-(pyridazin-3-yl)azetidine-3-carboxamide;
N-{4-[1-(2-oxopropanoyl)piperidin-4-yl]phenyl}-1-(pyridazin-3-yl)azetidine-3-carboxamide;
N-{4-[1-(cyclopentylcarbonyl)piperidin-4-yl]phenyl}-1-(pyridazin-3-yl)azetidine-3-carboxamide;
N-[4-(1-propanoylpiperidin-4-yl)phenyl]-1-(pyridazin-3-yl)azetidine-3-carboxamide;
N-{4-[1-(4-methylbenzoyl)piperidin-4-yl]phenyl}-1-(pyridazin-3-yl)azetidine-3-carboxamide;
N-(4-{[(3R)-1-(2-chlorobenzoyl)pyrrolidin-3-yl]oxy}phenyl)-1-(pyridazin-3-yl)azetidine-3-carboxamide;
1-(pyridazin-3-yl)-N-(4-{[(3R)-1-(1,3-thiazol-2-ylcarbonyl)pyrrolidin-3-yl]oxy}phenyl)azetidine-3-carboxamide;
N-(4-{[(3R)-1-(cyclopropylacetyl)pyrrolidin-3-yl]oxy}phenyl)-1-(pyridazin-3-yl)azetidine-3-carboxamide;

N-[4-({(3R)-1-[(2S)-2-methylbutanoyl]pyrrolidin-3-yl}oxy)phenyl]-1-(pyridazin-3-yl)azetidine-3-carboxamide;

1-(pyridazin-3-yl)-N-(4-{[(3R)-1-(tetrahydro-2H-pyran-4-ylcarbonyl)pyrrolidin-3-yl]oxy}phenyl)azetidine-3-carboxamide;

1-(pyridazin-3-yl)-N-(4-{[(3R)-1-{[4-(trifluoromethoxy)phenyl]acetyl}pyrrolidin-3-yl]oxy}phenyl)azetidine-3-carboxamide;

N-(4-{[(3R)-1-(4-fluorobenzoyl)pyrrolidin-3-yl]oxy}phenyl)-1-(pyridazin-3-yl)azetidine-3-carboxamide;

1-(pyridazin-3-yl)-N-(4-{[(3R)-1-(thiophen-3-ylcarbonyl)pyrrolidin-3-yl]oxy}phenyl)azetidine-3-carboxamide;

N-[4-({(3R)-1-[(4-fluorophenyl)acetyl]pyrrolidin-3-yl}oxy)phenyl]-1-(pyridazin-3-yl)azetidine-3-carboxamide;

N-[4-({(3R)-1-[(3,5-difluorophenyl)acetyl]pyrrolidin-3-yl}oxy)phenyl]-1-(pyridazin-3-yl)azetidine-3-carboxamide;

N-(4-{[(3R)-1-(3,4-difluorobenzoyl)pyrrolidin-3-yl]oxy}phenyl)-1-(pyridazin-3-yl)azetidine-3-carboxamide;

N-[4-({(3R)-1-[(3-fluorophenyl)acetyl]pyrrolidin-3-yl}oxy)phenyl]-1-(pyridazin-3-yl)azetidine-3-carboxamide;

1-(pyridazin-3-yl)-N-[4-({(3R)-1-[3-(trifluoromethyl)benzoyl]pyrrolidin-3-yl}oxy)phenyl]azetidine-3-carboxamide;

N-[4-({(3R)-1-[(2,4-difluorophenyl)acetyl]pyrrolidin-3-yl}oxy)phenyl]-1-(pyridazin-3-yl)azetidine-3-carboxamide;

1-(pyridazin-3-yl)-N-(4-{[(3R)-1-{[4-(trifluoromethyl)phenyl]acetyl}pyrrolidin-3-yl]oxy}phenyl)azetidine-3-carboxamide;

1-(pyridazin-3-yl)-N-(4-{[(3R)-1-(1,3-thiazol-4-ylcarbonyl)pyrrolidin-3-yl]oxy}phenyl)azetidine-3-carboxamide;

1-(pyridazin-3-yl)-N-(4-{[(3R)-1-(tetrahydrofuran-2-ylcarbonyl)pyrrolidin-3-yl]oxy}phenyl)azetidine-3-carboxamide;

N-[4-({(3R)-1-[(5-methylthiophen-2-yl)carbonyl]pyrrolidin-3-yl}oxy)phenyl]-1-(pyridazin-3-yl)azetidine-3-carboxamide;

N-[4-({(3R)-1-[(2-fluorophenyl)acetyl]pyrrolidin-3-yl}oxy)phenyl]-1-(pyridazin-3-yl)azetidine-3-carboxamide;

N-(4-{[(3R)-1-(cyclopropylcarbonyl)pyrrolidin-3-yl]oxy}phenyl)-1-(pyridazin-3-yl)azetidine-3-carboxamide;

1-(pyridazin-3-yl)-N-(4-{[(3R)-1-(tetrahydrofuran-3-ylcarbonyl)pyrrolidin-3-yl]oxy}phenyl)azetidine-3-carboxamide;

1-(pyridazin-3-yl)-N-[4-({(3R)-1-[3-(trifluoromethoxy)benzoyl]pyrrolidin-3-yl}oxy)phenyl]azetidine-3-carboxamide;

1-(pyridazin-3-yl)-N-(4-{[(3R)-1-(pyridin-2-ylcarbonyl)pyrrolidin-3-yl]oxy}phenyl)azetidine-3-carboxamide;

N-(4-{[(3R)-1-(3-chlorobenzoyl)pyrrolidin-3-yl]oxy}phenyl)-1-(pyridazin-3-yl)azetidine-3-carboxamide;

N-(4-{[(3R)-1-(4-chlorobenzoyl)pyrrolidin-3-yl]oxy}phenyl)-1-(pyridazin-3-yl)azetidine-3-carboxamide;

N-(4-{[(3R)-1-(2-methyl-2-phenylpropanoyl)pyrrolidin-3-yl]oxy}phenyl)-1-(pyridazin-3-yl)azetidine-3-carboxamide;

N-(4-{[(3R)-1-(2,4-difluorobenzoyl)pyrrolidin-3-yl]oxy}phenyl)-1-(pyridazin-3-yl)azetidine-3-carboxamide;

N-(4-{[(3R)-1-(methoxyacetyl)pyrrolidin-3-yl]oxy}phenyl)-1-(pyridazin-3-yl)azetidine-3-carboxamide;

1-(pyridazin-3-yl)-N-(4-{[(3R)-1-(thiophen-2-ylcarbonyl)pyrrolidin-3-yl]oxy}phenyl)azetidine-3-carboxamide;

1-(pyridazin-3-yl)-N-(4-{[(3R)-1-{[3-(trifluoromethyl)phenyl]acetyl}pyrrolidin-3-yl]oxy}phenyl)azetidine-3-carboxamide;

N-(4-{[(3R)-1-(2-methylpropanoyl)pyrrolidin-3-yl]oxy}phenyl)-1-(pyridazin-3-yl)azetidine-3-carboxamide;

N-(4-{[(3R)-1-(2-fluorobenzoyl)pyrrolidin-3-yl]oxy}phenyl)-1-(pyridazin-3-yl)azetidine-3-carboxamide;

N-(4-{[(3R)-1-(2,2-dimethylbutanoyOpyrrolidin-3-yl]oxy}phenyl)-1-(pyridazin-3-yl)azetidine-3-carboxamide;

N-(4-{[(3R)-1-(3,5-difluorobenzoyl)pyrrolidin-3-yl]oxy}phenyl)-1-(pyridazin-3-yl)azetidine-3-carboxamide;

1-(pyridazin-3-yl)-N-[4-({(3R)-1-[4-(trifluoromethyl)benzoyl]pyrrolidin-3-yl}oxy)phenyl]azetidine-3-carboxamide;

N-(4-{[(3R)-1-(3-fluorobenzoyl)pyrrolidin-3-yl]oxy}phenyl)-1-(pyridazin-3-yl)azetidine-3-carboxamide;

1-(pyridazin-3-yl)-N-[4-({(3R)-1-[4-(trifluoromethoxy)benzoyl]pyrrolidin-3-yl}oxy)phenyl]azetidine-3-carboxamide;

N-(4-{[(3R)-1-(3-methylbutanoyl)pyrrolidin-3-yl]oxy}phenyl)-1-(pyridazin-3-yl)azetidine-3-carboxamide;

1-(pyridazin-3-yl)-N-(4-{[(3R)-1-(3,3,3-trifluoropropanoyOpyrrolidin-3-yl]oxy}phenyl)azetidine-3-carboxamide;

N-[4-({(3R)-1-[difluoro(phenyl)acetyl]pyrrolidin-3-yl}oxy)phenyl]-1-(pyridazin-3-yl)azetidine-3-carboxamide;

N-(4-{[(3R)-1-(2,2-dimethylpropanoyl)pyrrolidin-3-yl]oxy}phenyl)-1-(pyridazin-3-yl)azetidine-3-carboxamide;

N-[4-({(3R)-1-[(4,4-difluorocyclohexyl)carbonyl]pyrrolidin-3-yl}oxy)phenyl]-1-(pyridazin-3-yl)azetidine-3-carboxamide;

N-(4-{[1-(3-chlorobenzoyl)piperidin-4-yl]sulfonyl}phenyl)-1-(pyridazin-3-yl)azetidine-3-carboxamide;

N-(4-{[1-(4-tert-butylbenzoyl)piperidin-4-yl]sulfonyl}phenyl)-1-(pyridazin-3-yl)azetidine-3-carboxamide;

N-(4-{[1-(4-methoxybenzoyl)piperidin-4-yl]sulfonyl}phenyl)-1-(pyridazin-3-yl)azetidine-3-carboxamide;

N-(4-{[1-(4-methylbenzoyl)piperidin-4-yl]sulfonyl}phenyl)-1-(pyridazin-3-yl)azetidine-3-carboxamide;

N-(4-{[1-(cyclohexylcarbonyl)piperidin-4-yl]sulfonyl}phenyl)-1-(pyridazin-3-yl)azetidine-3-carboxamide;

N-(4-{[1-(cyclopropylacetyl)piperidin-4-yl]
sulfonyl}phenyl)-1-(pyridazin-3-yl)azetidine-3-carboxamide;
N-(4-{[1-(2-methoxybenzoyl)piperidin-4-yl]
sulfonyl}phenyl)-1-(pyridazin-3-yl)azetidine-3-carboxamide;
N-[4-({1-[(2S)-2-phenylbutanoyl]piperidin-4-yl}sulfonyl)phenyl]-1-(pyridazin-3-yl)azetidine-3-carboxamide;
N-[4-({1-[4-(propan-2-yl)benzoyl]piperidin-4-yl}sulfonyl)phenyl]-1-(pyridazin-3-yl)azetidine-3-carboxamide;
N-(4-{[1-(4-chlorobenzoyl)piperidin-4-yl]
sulfonyl}phenyl)-1-(pyridazin-3-yl)azetidine-3-carboxamide;
N-{4-[(1-benzoylpiperidin-4-yl)sulfonyl]phenyl}-1-(pyridazin-3-yl)azetidine-3-carboxamide;
1-(pyridazin-3-yl)-N-(4-{[1-(4,4,4-trifluorobutanoyl)piperidin-4-yl]sulfonyl}phenyl)azetidine-3-carboxamide;
N-(4-{[1-(2,5-difluorobenzoyl)piperidin-4-yl]
sulfonyl}phenyl)-1-(pyridazin-3-yl)azetidine-3-carboxamide;
N-(4-{[1-(2-fluorobenzoyl)piperidin-4-yl]
sulfonyl}phenyl) -1-(pyridazin-3-yl)azetidine-3-carboxamide;
N-(4-{[1-(2-methylbenzoyl)piperidin-4-yl]
sulfonyl}phenyl)-1-(pyridazin-3-yl)azetidine-3-carboxamide;
N-[4-({1-[(4-fluorophenyl)acetyl]piperidin-4-yl}sulfonyl)phenyl]-1-(pyridazin-3-yl)azetidine-3-carboxamide;
N-(4-{[1-(3-methylbenzoyl)piperidin-4-yl]
sulfonyl}phenyl)-1-(pyridazin-3-yl)azetidine-3-carboxamide;
N-(4-{[1-(2,3-dimethylbenzoyl)piperidin-4-yl]
sulfonyl}phenyl)-1-(pyridazin-3-yl)azetidine-3-carboxamide;
N-[4-({1-[(3-fluorophenyl)acetyl]piperidin-4-yl}sulfonyl)phenyl]-1-(pyridazin-3-yl)azetidine-3-carboxamide;
N-(4-{[1-(3-fluorobenzoyl)piperidin-4-yl]
sulfonyl}phenyl) -1-(pyridazin-3-yl)azetidine-3-carboxamide;
1-(pyridazin-3-yl)-N-[4-({1-[3-(trifluoromethyl)benzoyl]piperidin-4-yl}sulfonyl)phenyl]azetidine-3-carboxamide;
N-[4-({1-[(3,5-difluorophenyl)acetyl]piperidin-4-yl}sulfonyl)phenyl]-1-(pyridazin-3-yl)azetidine-3-carboxamide;
N-(4-{[1-(2,4-difluorobenzoyl)piperidin-4-yl]
sulfonyl}phenyl)-1-(pyridazin-3-yl)azetidine-3-carboxamide;
1-(pyridazin-3-yl)-N-[4-({1-[4-(trifluoromethyl)benzoyl]piperidin-4-yl}sulfonyl)phenyl]azetidine-3-carboxamide;
N-(4-{[1-(4-fluorobenzoyl)piperidin-4-yl]
sulfonyl}phenyl)-1-(pyridazin-3-yl)azetidine-3-carboxamide;
N-(4-{[1-(2,3-difluorobenzoyl)piperidin-4-yl]
sulfonyl}phenyl)-1-(pyridazin-3-yl)azetidine-3-carboxamide;
N-(4-{[1-(2,4-dichlorobenzoyl)piperidin-4-yl]
sulfonyl}phenyl)-1-(pyridazin-3-yl)azetidine-3-carboxamide;
N-(4-{[1-(naphthalen-1-ylcarbonyl)piperidin-4-yl]
sulfonyl}phenyl)-1-(pyridazin-3-yl)azetidine-3-carboxamide;
N-(4-{[1-(cyclopropylcarbonyl)piperidin-4-yl]
sulfonyl}phenyl)-1-(pyridazin-3-yl)azetidine-3-carboxamide;
N-(4-{[1-(3,5-difluorobenzoyl)piperidin-4-yl]
sulfonyl}phenyl)-1-(pyridazin-3-yl)azetidine-3-carboxamide;
N-(4-{[1-(2,2-dimethylpropanoyl)piperidin-4-yl]
sulfonyl}phenyl)-1-(pyridazin-3-yl)azetidine-3-carboxamide;
N-(4-{[1-(3,3-dimethylbutanoyl)piperidin-4-yl]
sulfonyl}phenyl)-1-(pyridazin-3-yl)azetidine-3-carboxamide;
N-(4-{[1-(3-methoxybenzoyl)piperidin-4-yl]
sulfonyl}phenyl)-1-(pyridazin-3-yl)azetidine-3-carboxamide;
N-(4-{[1-(3-methylbutanoyl)piperidin-4-yl]
sulfonyl}phenyl)-1-(pyridazin-3-yl)azetidine-3-carboxamide;
N-(4-{[1-(2-methylpropanoyl)piperidin-4-yl]
sulfonyl}phenyl)-1-(pyridazin-3-yl)azetidine-3-carboxamide;
N-(4-{[1-(cyclopentylcarbonyl)piperidin-4-yl]
sulfonyl}phenyl)-1-(pyridazin-3-yl)azetidine-3-carboxamide;
N-(4-{[1-(phenylacetyl)piperidin-4-yl]sulfonyl}phenyl)-1-(pyridazin-3-yl)azetidine-3-carboxamide;
N-[4-({1-[(1-phenylcyclopropyl)carbonyl]piperidin-4-yl}sulfonyl)phenyl]-1-(pyridazin-3-yl)azetidine-3-carboxamide;
5-[1-(2-methylpropyl)-1H-pyrazol-4-yl]-N-[(3R)-1-(pyridazin-3-yl)pyrrolidin-3-yl]thiophene-2-carboxamide;
5-[1-(2-methylpropyl)-1H-pyrazol-4-yl]-N-[(3S)-1-(pyridazin-3-yl)pyrrolidin-3-yl]thiophene-2-carboxamide;
N-(4-{[1-(2-chlorobenzoyl)piperidin-4-yl]
sulfonyl}phenyl)-1-(pyridazin-3-yl)azetidine-3-carboxamide;
N-(4-{[1-(4-methylpentanoyl)piperidin-4-yl]
sulfonyl}phenyl)-1-(pyridazin-3-yl)azetidine-3-carboxamide;
N-[4-({1-[(2-fluorophenyl)acetyl]piperidin-4-yl}sulfonyl)phenyl]-1-(pyridazin-3-yl)azetidine-3-carboxamide;
N-[(3R)-1-(6-chloropyridazin-3-yl)pyrrolidin-3-yl]-5-[1-(2-methylpropyl)-1H-pyrazol-4-yl]thiophene-2-carboxamide;
N-[(3S)-1-(6-chloropyridazin-3-yl)pyrrolidin-3-yl]-5-[1-(2-methylpropyl)-1H-pyrazol-4-yl]thiophene-2-carboxamide;
5-[1-(2-methylpropyl)-1H-pyrazol-4-yl]-N-[(3R)-1-(pyridazin-3-yl)pyrrolidin-3-yl]thiophene-3-carboxamide;
N-[(3S)-1-(6-chloropyridazin-3-yl)pyrrolidin-3-yl]-5-[1-(2-methylpropyl)-1H-pyrazol-4-yl]thiophene-3-carboxamide;
(3S)-1-(pyridazin-3-yl)-N-{4-[1-(1,3-thiazol-5-ylcarbonyl)piperidin-4-yl]phenyl}pyrrolidine-3-carboxamide;
(3S)-N-{4-[1-(4-methylbenzoyl)piperidin-4-yl]phenyl}-1-(pyridazin-3-yl)pyrrolidine-3-carboxamide;
(3S)-N-(4-{1-[(2S)-2-phenylbutanoyl]piperidin-4-yl}phenyl)-1-(pyridazin-3-yl)pyrrolidine-3-carboxamide;
(3S)-N-(4-{1-[(2S)-2-methoxy-2-phenylacetyl]piperidin-4-yl}phenyl)-1-(pyridazin-3-yl)pyrrolidine-3-carboxamide;
(3S)-N-(4-{1-[(2R)-2-methoxy-2-phenylacetyl]piperidin-4-yl}phenyl)-1-(pyridazin-3-yl)pyrrolidine-3-carboxamide;

(3S)-N-{4-[1-(ethoxyacetyl)piperidin-4-yl]phenyl}-1-(pyridazin-3-yl)pyrrolidine-3-carboxamide;
(3S)-N-(4-{1-[(4-methylphenoxy)acetyl]piperidin-4-yl}phenyl)-1-(pyridazin-3-yl)pyrrolidine-3-carboxamide;
(3S)-N-{4-[1-(2-fluorobenzoyl)piperidin-4-yl]phenyl}-1-(pyridazin-3-yl)pyrrolidine-3-carboxamide;
(3S)-1-(pyridazin-3-yl)-N-{4-[1-(tetrahydrofuran-3-ylcarbonyl)piperidin-4-yl]phenyl}pyrrolidine-3-carboxamide;
(3S)-N-{4-[1-(naphthalen-1-ylcarbonyl)piperidin-4-yl]phenyl}-1-(pyridazin-3-yl)pyrrolidine-3-carboxamide;
(3S)-N-(4-{1-[(2,6-dichlorophenyl)acetyl]piperidin-4-yl}phenyl)-1-(pyridazin-3-yl)pyrrolidine-3-carboxamide;
(3S)-N-{4-[1-(naphthalen-1-ylacetyl)piperidin-4-yl]phenyl}-1-(pyridazin-3-yl)pyrrolidine-3-carboxamide;
(3S)-1-(pyridazin-3-yl)-N-(4-{1-[4-(thiophen-2-yl)butanoyl]piperidin-4-yl}phenyl)pyrrolidine-3-carboxamide;
(3S)-N-{4-[1-(cyclopropylacetyl)piperidin-4-yl]phenyl}-1-(pyridazin-3-yl)pyrrolidine-3-carboxamide;
(3S)-N-{4-[1-(cyclopentylacetyl)piperidin-4-yl]phenyl}-1-(pyridazin-3-yl)pyrrolidine-3-carboxamide;
(3S)-N-{4-[1-(2,5-difluorobenzoyl)piperidin-4-yl]phenyl}-1-(pyridazin-3-yl)pyrrolidine-3-carboxamide;
(3S)-N-{4-[1-(naphthalen-2-ylacetyl)piperidin-4-yl]phenyl}-1-(pyridazin-3-yl)pyrrolidine-3-carboxamide;
(3S)-N-(4-{1-[3-(phenylsulfonyl)propanoyl]piperidin-4-yl}phenyl)-1-(pyridazin-3-yl)pyrrolidine-3-carboxamide;
(3S)-1-(pyridazin-3-yl)-N-[4-(1-{[3-(trifluoromethyl)phenyl]acetyl}piperidin-4-yl)phenyl]pyrrolidine-3-carboxamide;
(3S)-N-{4-[1-(furan-2-ylcarbonyl)piperidin-4-yl]phenyl}-1-(pyridazin-3-yl)pyrrolidine-3-carboxamide;
(3S)-N-{4-[1-(N-benzoylglycyl)piperidin-4-yl]phenyl}-1-(pyridazin-3-yl)pyrrolidine-3-carboxamide;
(3S)-N-(4-{1-[(2,4-dichlorophenyl)acetyl]piperidin-4-yl}phenyl)-1-(pyridazin-3-yl)pyrrolidine-3-carboxamide;
(3S)-N-{4-[1-(2-methylbenzoyl)piperidin-4-yl]phenyl}-1-(pyridazin-3-yl)pyrrolidine-3-carboxamide;
(3S)-1-(pyridazin-3-yl)-N-{4-[1-(4,4,4-trifluorobutanoyl)piperidin-4-yl]phenyl}pyrrolidine-3-carboxamide;
(3S)-N-(4-{1-[(1-methylcyclohexyl)carbonyl]piperidin-4-yl}phenyl)-1-(pyridazin-3-yl)pyrrolidine-3-carboxamide;
(3S)-1-(pyridazin-3-yl)-N-{4-[1-(thiophen-3-ylcarbonyl)piperidin-4-yl]phenyl}pyrrolidine-3-carboxamide;
(3S)-N-(4-{1-[(6-methylpyridin-3-yl)carbonyl]piperidin-4-yl}phenyl)-1-(pyridazin-3-yl)pyrrolidine-3-carboxamide;
(3S)-N-(4-{1-[(3-chlorophenyl)acetyl]piperidin-4-yl}phenyl)-1-(pyridazin-3-yl)pyrrolidine-3-carboxamide;
(3S)-N-[4-(1-propanoylpiperidin-4-yl)phenyl]-1-(pyridazin-3-yl)pyrrolidine-3-carboxamide;
(3S)-N-{4-[1-(3,5-difluorobenzoyl)piperidin-4-yl]phenyl}-1-(pyridazin-3-yl)pyrrolidine-3-carboxamide;
(3S)-N-{4-[1-(cyclopentylcarbonyl)piperidin-4-yl]phenyl}-1-(pyridazin-3-yl)pyrrolidine-3-carboxamide;
(3S)-1-(pyridazin-3-yl)-N-{4-[1-(tetrahydrofuran-2-ylcarbonyl)piperidin-4-yl]phenyl}pyrrolidine-3-carboxamide;
(3S)-N-{4-[1-(cyclopropylcarbonyl)piperidin-4-yl]phenyl}-1-(pyridazin-3-yl)pyrrolidine-3-carboxamide;
(3S)-N-{4-[1-(4-chlorobenzoyl)piperidin-4-yl]phenyl}-1-(pyridazin-3-yl)pyrrolidine-3-carboxamide;
5-[1-(2-methylpropyl)-1H-pyrazol-4-yl]-N-[(3S)-1-(pyridazin-3-yl)pyrrolidin-3-yl]thiophene-3-carboxamide;
N-[4-(1-benzolpiperidin-4-yl)phenyl]-1-(6-pyridazin-3-yl azetidine-3-carboxamide;
(3S)-N-{4-[1-(2-chlorobenzoyl)piperidin-4-yl]phenyl}-1-(pyridazin-3-yl)pyrrolidine-3-carboxamide;
(3S)-N-{4-[1-(2-methylpentanoyl)piperidin-4-yl]phenyl}-1-(pyridazin-3-yl)pyrrolidine-3-carboxamide;
(3S)-N-{4-[1-(4-methylpentanoyl)piperidin-4-yl]phenyl}-1-(pyridazin-3-yl)pyrrolidine-3-carboxamide;
(3S)-N-{4-[1-(2,4-dimethylbenzoyl)piperidin-4-yl]phenyl}-1-(pyridazin-3-yl)pyrrolidine-3-carboxamide;
(3S)-N-[4-(1-heptanoylpiperidin-4-yl)phenyl]-1-(pyridazin-3-yl)pyrrolidine-3-carboxamide;
(3S)-N-{4-[1-(2,4-dichlorobenzoyl)piperidin-4-yl]phenyl}-1-(pyridazin-3-yl)pyrrolidine-3-carboxamide;
(3S)-N-(4-{1-[(4-fluorophenyl)acetyl]piperidin-4-yl}phenyl)-1-(pyridazin-3-yl)pyrrolidine-3-carboxamide;
(3S)-N-{4-[1-(2,3-difluorobenzoyl)piperidin-4-yl]phenyl}-1-(pyridazin-3-yl)pyrrolidine-3-carboxamide;
(3S)-N-{4-[1-(3-methylbenzoyl)piperidin-4-yl]phenyl}-1-(pyridazin-3-yl)pyrrolidine-3-carboxamide;
(3S)-N-[4-(1-hexanoylpiperidin-4-yl)phenyl]-1-(pyridazin-3-yl)pyrrolidine-3-carboxamide;
(3S)-N-(4-{1-[(3-methylthiophen-2-yl)carbonyl]piperidin-4-yl}phenyl)-1-(pyridazin-3-yl)pyrrolidine-3-carboxamide;
(3S)-N-{4-[1-(2,3-dimethylbutanoyl)piperidin-4-yl]phenyl}-1-(pyridazin-3-yl)pyrrolidine-3-carboxamide;
(3S)-N-[4-(1-butanoylpiperidin-4-yl)phenyl]-1-(pyridazin-3-yl)pyrrolidine-3-carboxamide;
(3S)-N-{4-[1-(3-methylpentanoyl)piperidin-4-yl]phenyl}-1-(pyridazin-3-yl)pyrrolidine-3-carboxamide;
(3S)-N-(4-{1-[(3,5-dimethylphenyl)acetyl]piperidin-4-yl}phenyl)-1-(pyridazin-3-yl)pyrrolidine-3-carboxamide;
(3S)-N-{4-[1-(3,5-dichlorobenzoyl)piperidin-4-yl]phenyl}-1-(pyridazin-3-yl)pyrrolidine-3-carboxamide;
(3S)-N-{4-[1-(3-fluoro-2-methylbenzoyl)piperidin-4-yl]phenyl}-1-(pyridazin-3-yl)pyrrolidine-3-carboxamide;
(3S)-N-(4-{1-[(4-chlorophenyl)acetyl]piperidin-4-yl}phenyl)-1-(pyridazin-3-yl)pyrrolidine-3-carboxamide;
(3S)-N-{4-[1-(furan-3-ylcarbonyl)piperidin-4-yl]phenyl}-1-(pyridazin-3-yl)pyrrolidine-3-carboxamide;
(3S)-N-{4-[1-(3,4-dimethylbenzoyl)piperidin-4-yl]phenyl}-1-(pyridazin-3-yl)pyrrolidine-3-carboxamide;
(3S)-N-{4-[1-(4-fluorobenzoyl)piperidin-4-yl]phenyl}-1-(pyridazin-3-yl)pyrrolidine-3-carboxamide;
(3S)-N-(4-{1-[2-chloro-5-(trifluoromethyl)benzoyl]piperidin-4-yl}phenyl)-1-(pyridazin-3-yl)pyrrolidine-3-carboxamide;
(3S)-N-[4-(1-acetylpiperidin-4-yl)phenyl]-1-(pyridazin-3-yl)pyrrolidine-3-carboxamide;
(3S)-N-{4-[1-(2,4-difluorobenzoyl)piperidin-4-yl]phenyl}-1-(pyridazin-3-yl)pyrrolidine-3-carboxamide;
(3S)-N-{4-[1-(3,5-dimethylbenzoyl)piperidin-4-yl]phenyl}-1-(pyridazin-3-yl)pyrrolidine-3-carboxamide;
(3S)-N-{4-[1-(3-ethoxypropanoyl)piperidin-4-yl]phenyl}-1-(pyridazin-3-yl)pyrrolidine-3-carboxamide;
(3S)-N-{4-[1-(2,5-dichlorobenzoyl)piperidin-4-yl]phenyl}-1-(pyridazin-3-yl)pyrrolidine-3-carboxamide;
(3S)-N-{4-[1-(2,5-dimethylbenzoyl)piperidin-4-yl]phenyl}-1-(pyridazin-3-yl)pyrrolidine-3-carboxamide;

(3S)-N-{4-[1-(5-fluoro-2-methylbenzoyl)piperidin-4-yl]
phenyl}-1-(pyridazin-3-yl)pyrrolidine-3-carboxamide;
(3S)-N-{4-[1-(diphenylacetyl)piperidin-4-yl]phenyl}-1-
(pyridazin-3-yl)pyrrolidine-3-carboxamide;
(3S)-1-(pyridazin-3-yl)-N-(4-{1-[4-(trifluoromethyl)benzoyl]piperidin-4-yl}phenyl)pyrrolidine-3-carboxamide;
(3S)-N-{4-[1-(pent-4-enoyl)piperidin-4-yl]phenyl}-1-
(pyridazin-3-yl)pyrrolidine-3-carboxamide;
(3S)-1-(pyridazin-3-yl)-N-(4-{1-[3-(trifluoromethoxy)
benzoyl]piperidin-4-yl}phenyl)pyrrolidine-3-carboxamide;
(3S)-N-(4-{1-[(1-phenylcyclopropyl)carbonyl]piperidin-4-yl}phenyl)-1-(pyridazin-3-yl)pyrrolidine-3-carboxamide;
(3S)-N-(4-{1-[2-fluoro-5-(trifluoromethyl)benzoyl]piperidin-4-yl}phenyl)-1-(pyridazin-3-yl)pyrrolidine-3-carboxamide;
(3S)-N-{4-[1-(cyclohexylacetyl)piperidin-4-yl]phenyl}-
1-(pyridazin-3-yl)pyrrolidine-3-carboxamide;
(3S)-N-{4-[1-(4-methoxybenzoyl)piperidin-4-yl]phenyl}-1-(pyridazin-3-yl)pyrrolidine-3-carboxamide;
(3S)-N-{4-[1-(2-methylbutanoyl)piperidin-4-yl]phenyl}-
1-(pyridazin-3-yl)pyrrolidine-3-carboxamide;
(3S)-N-{4-[1-(2-ethylbutanoyl)piperidin-4-yl]phenyl}-1-
(pyridazin-3-yl)pyrrolidine-3-carboxamide;
(3S)-N-{4-[1-(4-tert-butylbenzoyl)piperidin-4-yl]phenyl}-1-(pyridazin-3-yl)pyrrolidine-3-carboxamide;
(3S)-N-{4-[1-(3-chlorobenzoyl)piperidin-4-yl]phenyl}-
1-(pyridazin-3-yl)pyrrolidine-3-carboxamide;
(3S)-N-(4-{1-[(2-fluorophenyl)acetyl]piperidin-4-
yl}phenyl)-1-(pyridazin-3-yl)pyrrolidine-3-carboxamide;
(3S)-1-(pyridazin-3-yl)-N-(4-{1-[3-(trifluoromethyl)benzoyl]piperidin-4-yl}phenyl)pyrrolidine-3-carboxamide;
(3S)-N-(4-{1-[(1-methylcyclopropyl)carbonyl]piperidin-4-yl}phenyl)-1-(pyridazin-3-yl)pyrrolidine-3-carboxamide;
(3S)-N-{4-[1-(pent-4-ynoyl)piperidin-4-yl]phenyl}-1-
(pyridazin-3-yl)pyrrolidine-3-carboxamide;
(3S)-N-(4-{1-[(3-fluorophenyl)acetyl]piperidin-4-
yl}phenyl)-1-(pyridazin-3-yl)pyrrolidine-3-carboxamide;
(3S)-N-(4-{1-[3-(methylsulfanyl)propanoyl]piperidin-4-
yl}phenyl)-1-(pyridazin-3-yl)pyrrolidine-3-carboxamide;
(3S)-N-(4-{1-[(1-acetylpiperidin-4-yl)carbonyl]piperidin-4-yl}phenyl)-1-(pyridazin-3-yl)pyrrolidine-3-carboxamide;
(3S)-N-{4-[1-(but-3-enoyl)piperidin-4-yl]phenyl}-1-(pyridazin-3-yl)pyrrolidine-3-carboxamide;
(3S)-N-{4-[1-(2,2-dimethylbutanoyl)piperidin-4-yl]phenyl}-1-(pyridazin-3-yl)pyrrolidine-3-carboxamide;
(3S)-N-{4-[1-(3-fluoro-4-methylbenzoyl)piperidin-4-yl]
phenyl}-1-(pyridazin-3-yl)pyrrolidine-3-carboxamide;
(3S)-N-{4-[1-(3-methoxybenzoyl)piperidin-4-yl]phenyl}-1-(pyridazin-3-yl)pyrrolidine-3-carboxamide;
(3S)-N-(4-{1-[(2-chlorophenyl)acetyl]piperidin-4-
yl}phenyl)-1-(pyridazin-3-yl)pyrrolidine-3-carboxamide;
(3S)-N-(4-{1-[(2-methoxyethoxy)acetyl]piperidin-4-
yl}phenyl)-1-(pyridazin-3-yl)pyrrolidine-3-carboxamide;
(3S)-N-{4-[1-(3,3-dimethylbutanoyl)piperidin-4-yl]phenyl}-1-(pyridazin-3-yl)pyrrolidine-3-carboxamide;
(3S)-N-{4-[1-(N-acetyl-L-leucyl)piperidin-4-yl]phenyl}-
1-(pyridazin-3-yl)pyrrolidine-3-carboxamide;
(3S)-N-{4-[1-(3-fluorobenzoyl)piperidin-4-yl]phenyl}-1-
(pyridazin-3-yl)pyrrolidine-3-carboxamide;
(3S)-N-{4-[1-(4-cyanobenzoyl)piperidin-4-yl]phenyl}-1-
(pyridazin-3-yl)pyrrolidine-3-carboxamide;
(3S)-N-{4-[1-(2-methoxybenzoyl)piperidin-4-yl]phenyl}-1-(pyridazin-3-yl)pyrrolidine-3-carboxamide;
(3S)-N-{4-[1-(2,3-dimethylbenzoyl)piperidin-4-yl]phenyl}-1-(pyridazin-3-yl)pyrrolidine-3-carboxamide;
(3S)-N-(4-{1-[4-(propan-2-yl)benzoyl]piperidin-4-
yl}phenyl)-1-(pyridazin-3-yl)pyrrolidine-3-carboxamide;
(3S)-N-{4-[1-(cyclohexylcarbonyl)piperidin-4-yl]phenyl}-1-(pyridazin-3-yl)pyrrolidine-3-carboxamide;
(3S)-1-(pyridazin-3-yl)-N-{4-[1-(thiophen-2-ylcarbonyl)
piperidin-4-yl]phenyl}pyrrolidine-3-carboxamide;
(3S)-N-{4-[1-(4-hydroxybenzoyl)piperidin-4-yl]phenyl}-
1-(pyridazin-3-yl)pyrrolidine-3-carboxamide;
(3S)-N-{4-[1-(3-cyanobenzoyl)piperidin-4-yl]phenyl}-1-
(pyridazin-3-yl)pyrrolidine-3-carboxamide;
(3S)-1-(pyridazin-3-yl)-N-{4-[1-(3,3,3-trifluoropropanoyl)piperidin-4-yl]phenyl}pyrrolidine-3-carboxamide;
(3S)-N-{4-[1-(methoxyacetyl)piperidin-4-yl]phenyl}-1-
(pyridazin-3-yl)pyrrolidine-3-carboxamide;
(3S)-N-{4-[1-(3-methylbutanoyl)piperidin-4-yl]phenyl}-
1-(pyridazin-3-yl)pyrrolidine-3-carboxamide;
2-[1-(2-methylpropyl)-1H-pyrazol-4-yl]-N-[(3S)-1-(pyridazin-3-yl)pyrrolidin-3-yl]-1,3-thiazole-5-carboxamide;
N-[(3S)-1-(6-chloropyridazin-3-yl)pyrrolidin-3-yl]-5-[1-
(2-methylpropyl)-1H-pyrazol 1-4-yl]furan-2-carboxamide;
5-[1-(2-methylpropyl)-1H-pyrazol-4-yl]-N-[(3S)-1-(pyridazin-3-yl)pyrrolidin-3-yl]furan-2-carboxamide;
N-(4-{1-[(4-methyltetrahydro-2H-pyran-4-yl)methyl]-
1H-pyrazol-4-yl}phenyl)-1-(pyridazin-3-yl)azetidine-
3-carboxamide;
N-[(3S)-1-(6-chloropyridazin-3-yl)pyrrolidin-3-yl]-4-[1-
(2-methylpropanoyl)piperidin-4-yl]benzamide;
N-(4-{1-[2-(piperazin-1-yl)ethyl]-1H-pyrazol-4-
yl}phenyl)-1-(pyridazin-3-yl)azetidine-3-carboxamide;
N-{4-[1-(2,2-dimethylpropyl)-1H-pyrazol-4-yl]phenyl}-
1-(pyridazin-3-yl)azetidine-3-carboxamide;
4-[1-(2-methylpropanoyfl)piperidin-4-yl]-N-[(3S)-1-(pyridazin-3-yl)pyrrolidin-3-yl]benzamide;
N-{4-[1-(2-hydroxy-2-methylpropyl)-1H-pyrazol-4-yl]
phenyl}-1-(pyridazin-3-yl)azetidine-3-carboxamide;
5-[1-(3-fluorobenzoyl)piperidin-4-yl]-N-[(3S)-1-(pyridazin-3-yflpyrrolidin-3-yl]thiophene-2-carboxamide;
5-[1-(4-fluorobenzoyl)piperidin-4-yl]-N-[(3S)-1-(pyridazin-3-yflpyrrolidin-3-yl]thiophene-2-carboxamide;
(3S)-N-(4-{1-[(4-methyltetrahydro-2H-pyran-4-yl)methyl]-1H-pyrazol-4-yl}phenyl)-1-(pyridazin-3-yl)pyrrolidine-3-carboxamide;
(3S)-N-{4-[1-(2-hydroxy-2-methylpropyl)-1H-pyrazol-4-yl]phenyl}-1-(pyridazin-3-yl)pyrrolidine-3-carboxamide;
N-[(3S)-1-(pyridazin-3-yl)pyrrolidin-3-yl]-5-[1-(tetrahydro-2H-pyran-4-ylcarbonyl)piperidin-4-yl]thiophene-
2-carboxamide;
(3S)-N-{4-[1-(2,2-dimethylpropyl)-1H-pyrazol-4-yl]phenyl}-1-(pyridazin-3-yl)pyrrolidine-3-carboxamide;
5-[1-(2-methylpropanoyl)piperidin-4-yl]-N-[(3S)-1-(pyridazin-3-yl)pyrrolidin-3-yl]thiophene-2-carboxamide;

5-[1-(2,4-difluorobenzoyl)piperidin-4-yl]-N-[(3S)-1-(pyridazin-3-yl)pyrrolidin-3-yl]thiophene-2-carboxamide;
5-{1-[(2-methylcyclopropyl)carbonyl]piperidin-4-yl}-N-[(3S)-1-(pyridazin-3-yl)pyrrolidin-3-yl]thiophene-2-carboxamide;
5-[1-(2-fluorobenzoyl)piperidin-4-yl]-N-[(3S)-1-(pyridazin-3-yl)pyrrolidin-3-yl]thiophene-2-carboxamide;
5-(1-benzoylpiperidin-4-yl)-N-[(3S)-1-(pyridazin-3-yl)pyrrolidin-3-yl]thiophene-2-carboxamide;
N-[(3S)-1-(pyridazin-3-yl)pyrrolidin-3-yl]-5-[1-(tetrahydrofuran-3-ylcarbonyl)piperidin-4-yl]thiophene-2-carboxamide;
N-[(3S)-1-(pyridazin-3-yl)pyrrolidin-3-yl]-5-{1-[(2R)-tetrahydrofuran-2-ylcarbonyl]piperidin-4-yl}thiophene-2-carboxamide;
5-{1-[(1-methylpiperidin-4-yl)acetyl]piperidin-4-yl}-N-[(3S)-1-(pyridazin-3-yl)pyrrolidin-3-yl]thiophene-2-carboxamide;
N-[(3S)-1-(pyridazin-3-yl)pyrrolidin-3-yl]-5-[1-(1,3-thiazol-4-ylcarbonyl)piperidin-4-yl]thiophene-2-carboxamide;
(3S)-N-{4-[1-(2-methylpropyl)-1H-pyrazol-4-yl]phenyl}-1-(pyridazin-3-yl)pyrrolidine-3-carboxamide;
(3S)-N-{4-[1-(propan-2-yl)-1H-pyrazol-4-yl]phenyl}-1-(pyridazin-3-yl)pyrrolidine-3-carboxamide;
(3S)-N-{4-[1-(cyclopropylmethyl)-1H-pyrazol-4-yl]phenyl}-1-(pyridazin-3-yl)pyrrolidine-3-carboxamide;
(3S)-1-(pyridazin-3-yl)-N-{4-[1-(tetrahydro-2H-pyran-2-ylmethyl)-1H-pyrazol-4-yl]phenyl}pyrrolidine-3-carboxamide;
(3S)-N-[4-(1-tert-butyl-1H-pyrazol-4-yl)phenyl]-1-(pyridazin-3-yl)pyrrolidine-3-carboxamide;
(3S)-N-(4-{[(3R)-1-benzoylpyrrolidin-3-yl]oxy}phenyl)-1-(pyridazin-3-yl)pyrrolidine-3-carboxamide;
(3S)-N-(4-{[(3R)-1-(2-fluorobenzoyl)pyrrolidin-3-yl]oxy}phenyl)-1-(pyridazin-3-yl)pyrrolidine-3-carboxamide;
(3S)-N-(4-{[(3R)-1-(3-fluorobenzoyl)pyrrolidin-3-yl]oxy}phenyl)-1-(pyridazin-3-yl)pyrrolidine-3-carboxamide;
(3S)-N-(4-{[(3R)-1-(4-fluorobenzoyl)pyrrolidin-3-yl]oxy}phenyl)-1-(pyridazin-3-yl)pyrrolidine-3-carboxamide;
(3S)-N-(4-{[(3R)-1-(3,5-difluorobenzoyl)pyrrolidin-3-yl]oxy}phenyl)-1-(pyridazin-3-yl)pyrrolidine-3-carboxamide;
(3S)-N-(4-{[(3R)-1-(2-methylbenzoyl)pyrrolidin-3-yl]oxy}phenyl)-1-(pyridazin-3-yl)pyrrolidine-3-carboxamide;
(3S)-N-(4-{[(3R)-1-(2,2-dimethylpropanoyl)pyrrolidin-3-yl]oxy}phenyl)-1-(pyridazin-3-yl)pyrrolidine-3-carboxamide;
(3S)-N-[4-({(3R)-1-[(4,4-difluorocyclohexyl)carbonyl]pyrrolidin-3-yl}oxy)phenyl]-1-(pyridazin-3-yl)pyrrolidine-3-carboxamide;
(3S)-1-(pyridazin-3-yl)-N-(4-{[(3R)-1-(4,4,4-trifluorobutanoyl)pyrrolidin-3-yl]oxy}phenyl)pyrrolidine-3-carboxamide;
(3S)-N-(4-{[(3R)-1-(2,4-difluorobenzoyl)pyrrolidin-3-yl]oxy}phenyl)-1-(pyridazin-3-yl)pyrrolidine-3-carboxamide;
N-[4-(5-propyl-1,2,4-oxadiazol-3-yl)phenyl]-1-(pyridazin-3-yl)azetidine-3-carboxamide;
(3S)-N-{4-[1-(2-fluorobenzoyl)azetidin-3-yl]phenyl}-1-(pyridazin-3-yl)pyrrolidine-3-carboxamide;
(3S)-N-{4-[1-(3-fluorobenzoyl)azetidin-3-yl]phenyl}-1-(pyridazin-3-yl)pyrrolidine-3-carboxamide;
(3S)-N-{4-[1-(4-fluorobenzoyl)azetidin-3-yl]phenyl}-1-(pyridazin-3-yl)pyrrolidine-3-carboxamide;
(3S)-N-[4-(1-benzoylazetidin-3-yl)phenyl]-1-(pyridazin-3-yl)pyrrolidine-3-carboxamide;
(3S)-N-{4-[1-(2,2-dimethylpropanoyl)azetidin-3-yl]phenyl}-1-(pyridazin-3-yl)pyrrolidine-3-carboxamide;
(3S)-N-{4-[1-(3,5-difluorobenzoyl)azetidin-3-yl]phenyl}-1-(pyridazin-3-yl)pyrrolidine-3-carboxamide;
(3S)-N-{4-[1-(2-methylbenzoyl)azetidin-3-yl]phenyl}-1-(pyridazin-3-yl)pyrrolidine-3-carboxamide;
(3S)-N-{4-[1-(2,4-difluorobenzoyl)azetidin-3-yl]phenyl}-1-(pyridazin-3-yl)pyrrolidine-3-carboxamide;
(3R)-N-[4-(1-benzoylpiperidin-4-yl)phenyl]-1-(pyridazin-3-yl)pyrrolidine-3-carboxamide;
(3R)-N-{4-[1-(2-fluorobenzoyl)piperidin-4-yl]phenyl}-1-(pyridazin-3-yl)pyrrolidine-3-carboxamide;
(3R)-N-{4-[1-(2,2-dimethylpropanoyl)piperidin-4-yl]phenyl}-1-(pyridazin-3-yl)pyrrolidine-3-carboxamide;
(3S)-N-(4-{[1-(cyclohexylcarbonyl)piperidin-4-yl]oxy}phenyl)-1-(pyridazin-3-yl)pyrrolidine-3-carboxamide;
(3S)-N-(4-{[1-(2-fluorobenzoyl)piperidin-4-yl]oxy}phenyl)-1-(pyridazin-3-yl)pyrrolidine-3-carboxamide;
(3S)-N-(4-{[1-(3-fluorobenzoyl)piperidin-4-yl]oxy}phenyl)-1-(pyridazin-3-yl)pyrrolidine-3-carboxamide;
(3S)-N-{4-[(1-benzoylpiperidin-4-yl)oxy]phenyl}-1-(pyridazin-3-yl)pyrrolidine-3-carboxamide;
(3S)-N-(4-{[1-(4-fluorobenzoyl)piperidin-4-yl]oxy}phenyl)-1-(pyridazin-3-yl)pyrrolidine-3-carboxamide;
(3S)-N-(4-{[1-(2,2-dimethylpropanoyl)piperidin-4-yl]oxy}phenyl)-1-(pyridazin-3-yl)pyrrolidine-3-carboxamide;
(3S)-N-[4-({1-[(2-methylcyclopropyl)carbonyl]piperidin-4-yl}oxy)phenyl]-1-(pyridazin-3-yl)pyrrolidine-3-carboxamide;
N-{4-[5 2,2-dimethylpropyl)-1,3,4-oxadiazol-2-yl]phenyl}-1-(pyridazin-3-yl)azetidine-3-carboxamide;
N-{4-[1-(2,2-dimethylpropyl)-1H-imidazol-4-yl]phenyl}-1-(pyridazin-3-yl)azetidine-3-carboxamide;
N-[4-(3-cyclopropyl-1-methyl-1H-pyrazol-5-yl)phenyl]-1-(pyridazin-3-yl)azetidine-3-carboxamide;
N-{4-[5 2,2-dimethylpropyl)-1,2,4-oxadiazol-3-yl]phenyl}-1-(pyridazin-3-yl)azetidine-3-carboxamide;
N-{4-[3-cyclopropyl-1-(2-methoxyethyl)-1H-pyrazol-5-yl]phenyl}-1-(pyridazin-3-yl)azetidine-3-carboxamide;
tert-butyl 4-(5-{[1-(pyridazin-3-yl)azetidin-3-yl]carbamoyl}thiophen-2-yl)piperidine-1-carboxylate;
tert-butyl 4-fluoro-4-[4-({[1-(pyridazin-3-yl)azetidin-3-yl]carbonyl}amino)phenyl]piperidine-1-carboxylate;
5-(1-benzoylpiperidin-4-yl)-N-[1-(pyridazin-3-yl)azetidin-3-yl]thiophene-2-carboxamide;
5-[1-(2-fluorobenzoyl)piperidin-4-yl]-N-[1-(pyridazin-3-yl)azetidin-3-yl]thiophene-2-carboxamide;
5-[1-(2-methylbenzoyl)piperidin-4-yl]-N-[1-(pyridazin-3-yl)azetidin-3-yl]thiophene-2-carboxamide;
5-[1-(2,4-difluorobenzoyl)piperidin-4-yl]-N-[1-(pyridazin-3-yl)azetidin-3-yl]thiophene-2-carboxamide;
5-[1-(3-fluorobenzoyl)piperidin-4-yl]-N-[1-(pyridazin-3-yl)azetidin-3-yl]thiophene-2-carboxamide;
5-[1-(4-fluorobenzoyl)piperidin-4-yl]-N-[1-(pyridazin-3-yl)azetidin-3-yl]thiophene-2-carboxamide;
5-[1-(3,5-difluorobenzoyl)piperidin-4-yl]-N-[1-(pyridazin-3-yl)azetidin-3-yl]thiophene-2-carboxamide;

N-{4-[3-cycopropyl-1-(2-hydroxyethyl)-1H-pyrazol-5-yl]phenyl}-1-(pyridazin-3-yl)azetidine-3-carboxamide;
N-[4-(1-benzoylpiperidin-4-yl)phenyl]-1-(6-fluoropyridazin-3-yl)azetidine-3-carboxamide;
N-{4-[1-(2-fluorobenzoyl)piperidin-4-yl]phenyl}-1-(6-fluoropyridazin-3-yl)azetidine-3-carboxamide;
N-{4-[1-(2,2-dimethylpropanoyl)piperidin-4-yl]phenyl}-1-(6-fluoropyridazin-3-yl)azetidine-3-carboxamide;
1-(6-fluoropyridazin-3-yl)-N-{4-[1-(2-methylpropanoyl)piperidin-4-yl]phenyl}azetidine-3-carboxamide;
N-{4-[1-(2-ethylbutanoyl)piperidin-4-yl]phenyl}-1-(6-fluoropyridazin-3-yl)azetidine-3-carboxamide;
N-{4-[1-(4-fluorobenzoyl)piperidin-4-yl]phenyl}-1-(6-fluoropyridazin-3-yl)azetidine-3-carboxamide;
(3S)-N-(4-{[(3S)-1-benzoylpyrrolidin-3-yl]oxy}phenyl)-1-(pyridazin-3-yl)pyrrolidine-3-carboxamide;
(3S)-N-(4-{[(3S)-1-(2-fluorobenzoyl)pyrrolidin-3-yl]oxy}phenyl)-1-(pyridazin-3-yl)pyrrolidine-3-carboxamide;
(3S)-N-(4-{[(3S)-1-(3,5-difluorobenzoyl)pyrrolidin-3-yl]oxy}phenyl)-1-(pyridazin-3-yl)pyrrolidine-3-carboxamide;
(3S)-N-(4-{[(3S)-1-(2,2-dimethylpropanoyl)pyrrolidin-3-yl]oxy}phenyl)-1-(pyridazin-3-yl)pyrrolidine-3-carboxamide;
N-{2-fluoro-4-[1-(2-fluorobenzoyl)piperidin-4-yl]phenyl}-1-(pyridazin-3-yl)azetidine-3-carboxamide;
N-[4-(1-benzoylpiperidin-4-yl)-2-fluorophenyl]-1-(pyridazin-3-yl)azetidine-3-carboxamide;
N-{2-fluoro-4-[1-(3-fluorobenzoyl)piperidin-4-yl]phenyl}-1-(pyridazin-3-yl)azetidine-3-carboxamide;
N-{2-fluoro-4-[1-(2-methylbenzoyl)piperidin-4-yl]phenyl}-1-(pyridazin-3-yl)azetidine-3-carboxamide;
N-{2-fluoro-4-[1-(4-fluorobenzoyl)piperidin-4-yl]phenyl}-1-(pyridazin-3-yl)azetidine-3-carboxamide;
N-{4-[1-(2,4-difluorobenzoyl)piperidin-4-yl]-2-fluorophenyl}-1-(pyridazin-3-yl)azetidine-3-carboxamide;
N-{4-[1-(3,5-difluorobenzoyl)piperidin-4-yl]-2-fluorophenyl}-1-(pyridazin-3-yl)azetidine-3-carboxamide;
N-{4-[1-(3,3-dimethylbutanoyl)piperidin-4-yl]-2-fluorophenyl}-1-(pyridazin-3-yl)azetidine-3-carboxamide;
(3S)-N-(4-{[1-(2-fluorobenzoyl)piperidin-4-yl]oxy}phenyl)-1-(6-methylpyridazin-3-yl)pyrrolidine-3-carboxamide;
(3S)-N-{4-[(1-benzoylpiperidin-4-yl)oxy]phenyl}-1-(6-methylpyridazin-3-yl)pyrrolidine-3-carboxamide;
(3S)-N-(4-{[1-(2,2-dimethylpropanoyl)piperidin-4-yl]oxy}phenyl)-1-(6-methylpyridazin-3-yl)pyrrolidine-3-carboxamide;
(3S)-N-(4-{[1-(cyclohexylcarbonyl)piperidin-4-yl]oxy}phenyl)-1-(6-methylpyridazin-3-yl)pyrrolidine-3-carboxamide;
N-{4-[8-(2-methylpropanoyl)-8-azabicyclo[3.2.1]oct-3-yl]phenyl}-1-(pyridazin-3-yl)azetidine-3-carboxamide;
1-(pyridazin-3-yl)-N-{4-[8-(4,4,4-trifluorobutanoyl)-8-azabicyclo[3.2.1]oct-3-yl]phenyl}azetidine-3-carboxamide;
N-[4-(8-benzoyl-8-azabicyclo[3.2.1]oct-3-yl)phenyl]-1-(pyridazin-3-yl)azetidine-3-carboxamide;
N-{4-[8-(2-fluorobenzoyl)-8-azabicyclo[3.2.1]oct-3-yl]phenyl}-1-(pyridazin-3-yl)azetidine-3-carboxamide;
N-{4-[8-(2,2-dimethylpropanoyl)-8-azabicyclo[3.2.1]oct-3-yl]phenyl}-1-(pyridazin-3-yl)azetidine-3-carboxamide;
N-(4-{8-[(1-methylcyclopropyl)carbonyl]-8-azabicyclo[3.2.1]oct-3-yl}phenyl)-1-(pyridazin-3-yl)azetidine-3-carboxamide;
N-{4-[1-(2-methoxyethyl)-3-(2-methylpropyl)-1H-pyrazol-5-yl]phenyl}-1-(pyridazin-3-yl)azetidine-3-carboxamide;
5-[1-(2,2-dimethylpropanoyl)piperidin-4-yl]-N-[1-(pyridazin-3-yl)azetidin-3-yl]thiophene-2-carboxamide;
5-{1-[(1-methylcyclopropyl)carbonyl]piperidin-4-yl}-N-[1-(pyridazin-3-yl)azetidin-3-yl]thiophene-2-carboxamide;
N-[1-(pyridazin-3-yl)azetidin-3-yl]-5-[1-(3,3,3-trifluoropropanoyl)piperidin-4-yl]thiophene-2-carboxamide;
5-[1-(2,2-dimethylbutanoyl)piperidin-4-yl]-N-[1-(pyridazin-3-yl)azetidin-3-yl]thiophene-2-carboxamide;
N-{4-[1-(2-fluorobenzoyl)piperidin-4-yl]phenyl}-1-(6-methylpyridazin-3-yl)azetidine-3-carboxamide;
N-{4-[1-(2,2-dimethylpropanoyl)piperidin-4-yl]phenyl}-1-(6-methylpyridazin-3-yl)azetidine-3-carboxamide;
benzyl 4-[4-({[1-(6-chloropyridazin-3-yl)azetidin-3-yl]carbonyl}amino)phenyl]-4-fluoropiperidine-1-carboxylate;
benzyl 4-[4-({[1-(6-chloropyridazin-3-yl)azetidin-3-yl]carbonyl}amino)phenyl]-4-hydroxypiperidine-1-carboxylate;
N-[1-(pyridazin-3-yl)azetidin-3-yl]-5-[1-(4,4,4-trifluorobutanoyl)piperidin-4-yl]thiophene-2-carboxamide;
5-[1-(cyclopropylcarbonyl)piperidin-4-yl]-N-[1-(pyridazin-3-yl)azetidin-3-yl]thiophene-2-carboxamide;
N-{4-[4-fluoro-1-(2-fluorobenzoyl)piperidin-4-yl]phenyl}-1-(pyridazin-3-yl)azetidine-3-carboxamide;
N-{2-fluoro-4-[1-(2-methylpropanoyl)piperidin-4-yl]phenyl}-1-(pyridazin-3-yl)azetidine-3-carboxamide;
N-{4-[1-(2,2-dimethylpropanoyl)piperidin-4-yl]-2-fluorophenyl}-1-(pyridazin-3-yl)azetidine-3-carboxamide;
N-{4-[1-(cyclopropylcarbonyl)piperidin-4-yl]-2-fluorophenyl}-1-(pyridazin-3-yl)azetidine-3-carboxamide;
N-(2-fluoro-4-{1-[(1-methylcyclopropyl)carbonyl]piperidin-4-yl}phenyl)-1-(pyridazin-3-yl)azetidine-3-carboxamide;
N-{4-[1-(cyclopropylacetyl)piperidin-4-yl]-2-fluorophenyl}-1-(pyridazin-3-yl)azetidine-3-carboxamide;
N-[4-(1-benzoyl-4-fluoropiperidin-4-yl)phenyl]-1-(pyridazin-3-yl)azetidine-3-carboxamide;
N-{4-[1-(2,2-dimethylpropanoyl)-4-fluoropiperidin-4-yl]phenyl}-1-(pyridazin-3-yl)azetidine-3-carboxamide;
N-{4-[3-tert-butyl-1-(2-methoxyethyl)-1H-pyrazol-5-yl]phenyl}-1-(pyridazin-3-yl)azetidine-3-carboxamide;
N-[4-(1-butyl-3-tert-butyl-1H-pyrazol-5-yl)phenyl]-1-(pyridazin-3-yl)azetidine-3-carboxamide;
N-{4-[3-tert-butyl-1-(tetrahydro-2H-pyran-4-ylmethyl)-1H-pyrazol-5-yl]phenyl}-1-(pyridazin-3-yl)azetidine-3-carboxamide;
N-(4-{1-[(4-methylpiperidin-4-yl)methyl]-1H-pyrazol-4-yl}phenyl)-1-(pyridazin-3-yl)azetidine-3-carboxamide;
N-{4-[1-methyl-3-(trifluoromethyl)-1H-pyrazol-5-yl]phenyl}-1-(pyridazin-3-yl)azetidine-3-carboxamide;
1-(6-chloropyridazin-3-yl)-N-{4-[1-(2,2-dimethylpropyl)-1H-pyrazol-4-yl]phenyl}azetidine-3-carboxamide;
N-{4-[1-(2,2-dimethylpropyl)-1H-pyrazol-4-yl]phenyl}-1-(6-methylpyridazin-3-yl)azetidine-3-carboxamide;
N-{3-fluoro-4-[1-(3-fluorobenzoyl)piperidin-4-yl]phenyl}-1-(pyridazin-3-yl)azetidine-3-carboxamide;
N-{3-fluoro-4-[1-(2-methylpropanoyl)piperidin-4-yl]phenyl}-1-(pyridazin-3-yl)azetidine-3-carboxamide;

N-{3-fluoro-4-[1-(3,3,3-trifluoropropanoyl)piperidin-4-yl]phenyl}-1-(pyridazin-3-yl)azetidine-3-carboxamide;
N-{4-[1-(3,3-dimethylbutanoyl)piperidin-4-yl]-3-fluorophenyl}-1-(pyridazin-3-yl)azetidine-3-carboxamide;
N-{3-fluoro-4-[1-(4,4,4-trifluorobutanoyl)piperidin-4-yl]phenyl}-1-(pyridazin-3-yl)azetidine-3-carboxamide;
N-[4-(1-benzoylpiperidin-4-yl)-3-fluorophenyl]-1-(pyridazin-3-yl)azetidine-3-carboxamide;
N-{3-fluoro-4-[1-(2-fluorobenzoyl)piperidin-4-yl]phenyl}-1-(pyridazin-3-yl)azetidine-3-carboxamide;
N-{4-[1-(2,2-dimethylpropanoyl)piperidin-4-yl]-3-fluorophenyl}-1-(pyridazin-3-yl)azetidine-3-carboxamide;
N-{3-fluoro-4-[1-(3-methylbutanoyl)piperidin-4-yl]phenyl}-1-(pyridazin-3-yl)azetidine-3-carboxamide;
N-{4-[1-(cyclopropylacetyl)piperidin-4-yl]-3-fluorophenyl}-1-(pyridazin-3-yl)azetidine-3-carboxamide;
N-{4-[1-(2-fluorobenzoyl)-4-hydroxypiperidin-4-yl]phenyl}-1-(pyridazin-3-yl)azetidine-3-carboxamide;
N-{4-[1-(2,2-dimethylpropanoyl)-4-hydroxypiperidin-4-yl]phenyl}-1-(pyridazin-3-yl)azetidine-3-carboxamide;
1-(6-methylpyridazin-3-yl)-N-(4-{1-[(4-methyltetrahydro-2H-pyran-4-yl)methyl]-1H-pyrazol-4-yl}phenyl)azetidine-3-carboxamide;
(3S)-N-{4-[1-(2-fluorobenzoyl)piperidin-4-yl]phenyl}-1-(6-methylpyridazin-3-yl)pyrrolidine-3-carboxamide;
(3S)-N-[4-(1-benzoylpiperidin-4-yl)phenyl]-1-(6-methylpyridazin-3-yl)pyrrolidine-3-carboxamide;
(3S)-N-{4-[1-(2,2-dimethylpropanoyl)piperidin-4-yl]phenyl}-1-(6-methylpyridazin-3-yl)pyrrolidine-3-carboxamide;
N-{4-[(1-benzoylpiperidin-4-yl)methyl]phenyl}-1-(pyridazin-3-yl)azetidine-3-carboxamide;
N-(4-{[1-(2-fluorobenzoyl)piperidin-4-yl]methyl}phenyl)-1-(pyridazin-3-yl)azetidine-3-carboxamide;
N-(4-{[1-(2,2-dimethylpropanoyl)piperidin-4-yl]methyl}phenyl)-1-(pyridazin-3-yl)azetidine-3-carboxamide;
N-(4-{[1-(3,3-dimethylbutanoyl)piperidin-4-yl]methyl}phenyl)-1-(pyridazin-3-yl)azetidine-3-carboxamide;
N-(4-{[1-(2-ethylbutanoyl)piperidin-4-yl]methyl}phenyl)-1-(pyridazin-3-yl)azetidine-3-carboxamide;
1-(pyridazin-3-yl)-N-(4-{[1-(4,4,4-trifluorobutanoyl)piperidin-4-yl]methyl}phenyl)azetidine-3-carboxamide;
N-(4-{[1-(2-methylpropanoyl)piperidin-4-yl]methyl}phenyl)-1-(pyridazin-3-yl)azetidine-3-carboxamide;
N-{4-[(1-acetylpiperidin-4-yl)methyl]phenyl}-1-(pyridazin-3-yl)azetidine-3-carboxamide;
N-[4-({1-[(2S)-2-methylbutanoyl]piperidin-4-yl}methyl)phenyl]-1-(pyridazin-3-yl)azetidine-3-carboxamide;
N-[4-({1-[(1-methylcyclopropyl)carbonyl]piperidin-4-yl}methyl)phenyl]-1-(pyridazin-3-yl)azetidine-3-carboxamide;
N-[4-(1-{[4-methyl-1-(oxetan-3-yl)piperidin-4-yl]methyl}-1H-pyrazol-4-yl)phenyl]-1-(6-methylpyridazin-3-yl)azetidine-3-carboxamide;
N-[4-(1-benzoylpiperidin-4-yl)phenyl]-1-(4-methylpyridazin-3-yl)azetidine-3-carboxamide;
5-[1-(2-fluorobenzoyl)piperidin-4-yl]-N-[(3S)-1-(pyridazin-3-yl)pyrrolidin-3-yl]furan-2-carboxamide;
N-(4-{1-[(2-aminopyridin-3-yl)carbonyl]piperidin-4-yl}phenyl)-1-(pyridazin-3-yl)azetidine-3-carboxamide;
1-methyl-5-[4-({[1-(pyridazin-3-yl)azetidin-3-yl]carbonyl}amino)phenyl]-1H-pyrazole-3-carboxylic acid;
ethyl 1-methyl-5-[4-({[1-(pyridazin-3-yl)azetidin-3-yl]carbonyl}amino)phenyl]-1H-pyrazole-3-carboxylate;
ethyl 1-phenyl-5-[4-({[1-(pyridazin-3-yl)azetidin-3-yl]carbonyl}amino)phenyl]-1H-pyrazole-3-carboxylate;
N-{6-[1-(2-fluorobenzoyl)piperidin-4-yl]pyridin-3-yl}-1-(pyridazin-3-yl)azetidine-3-carboxamide;
N-(4-{[(3R)-1-(3-methylbutanoyl)pyrrolidin-3-yl]oxy}phenyl)-1-(6-methylpyridazin-3-yl)azetidine-3-carboxamide;
N-(4-{[(3R)-1-(2-methylpropanoyl)pyrrolidin-3-yl]oxy}phenyl)-1-(6-methylpyridazin-3-yl)azetidine-3-carboxamide;
N-(4-{[(3R)-1-(2,4-difluorobenzoyl)pyrrolidin-3-yl]oxy}phenyl)-1-(6-methylpyridazin-3-yl)azetidine-3-carboxamide;
1-(6-methylpyridazin-3-yl)-N-(4-{[(3R)-1-(1,3-thiazol-4-ylcarbonyl)pyrrolidin-3-yl]oxy}phenyl)azetidine-3-carboxamide;
1-(pyridazin-3-yl)-N-{6-[1-(4,4,4-trifluorobutanoyl)piperidin-4-yl]pyridin-3-yl}azetidine-3-carboxamide;
N-{6-[1-(3,3-dimethylbutanoyl)piperidin-4-yl]pyridin-3-yl}-1-(pyridazin-3-yl)azetidine-3-carboxamide;
(3S)-N-[4-(1-benzoylpiperidin-4-yl)phenyl]-1-(4-methylpyridazin-3-yl)pyrrolidine-3-carboxamide;
(3S)-N-{4-[1-(2,2-dimethylpropanoyl)piperidin-4-yl]phenyl}-1-(4-methylpyridazin-3-yl)pyrrolidine-3-carboxamide;
N-{4-[1-phenyl-3-(trifluoromethyl)-1H-pyrazol-5-yl]phenyl}-1-(pyridazin-3-yl)azetidine-3-carboxamide;
N-{6-[1-(2,2-dimethylpropyl)-1H-pyrazol-4-yl]pyridin-3-yl}-1-(pyridazin-3-yl)azetidine-3-carboxamide;
tert-butyl 4-[4-({[1-(pyridazin-3-yl)azetidin-3-yl]carbonyl}amino)-1H-pyrazol-1-yl]piperidine-1-carboxylate;
N-(6-{1-[(4-methylpiperidin-4-yl)methyl]-1H-pyrazol-4-yl}pyridin-3-yl)-1-(pyridazin-3-yl)azetidine-3-carboxamide;
1-(pyridazin-3-yl)-N-(4-{[1-(1,3-thiazol-5-ylcarbonyl)piperidin-4-yl]methyl}phenyl)azetidine-3-carboxamide;
N-(4-{[1-(cyclopentylcarbonyl)piperidin-4-yl]methyl}phenyl)-1-(pyridazin-3-yl)azetidine-3-carboxamide;
N-(4-{[1-(1H-pyrazol-4-ylcarbonyl)piperidin-4-yl]methyl}phenyl)-1-(pyridazin-3-yl)azetidine-3-carboxamide;
N-(4-{[1-(2,2-dimethylbutanoyl)piperidin-4-yl]methyl}phenyl)-1-(pyridazin-3-yl)azetidine-3-carboxamide;
N-[4-({1-[(2-methylcyclopropyl)carbonyl]piperidin-4-yl}methyl)phenyl]-1-(pyridazin-3-yl)azetidine-3-carboxamide;
N-[4-({1-[(methylsulfanyl)acetyl]piperidin-4-yl}methyl)phenyl]-1-(pyridazin-3-yl)azetidine-3-carboxamide;
N-[4-({1-[(1S,4R)-bicyclo[2.2.1]hept-2-ylacetyl]piperidin-4-yl}methyl)phenyl]-1-(pyridazin-3-yl)azetidine-3-carboxamide;
N-(4-{[1-(2-methylpentanoyl)piperidin-4-yl]methyl}phenyl)-1-(pyridazin-3-yl)azetidine-3-carboxamide;

N-(4-{[1-(4-methylpentanoyl)piperidin-4-yl]methyl}phenyl)-1-(pyridazin-3-yl)azetidine-3-carboxamide;
N-[4-({1-[3-(methylsulfanyl)propanoyl]piperidin-4-yl}methyl)phenyl]-1-(pyridazin-3-yl)azetidine-3-carboxamide;
1-(pyridazin-3-yl)-N-(4-{[1-(1,3-thiazol-4-ylcarbonyl)piperidin-4-yl]methyl}phenyl)azetidine-3-carboxamide;
N-(4-{[1-(1H-pyrazol-5-ylcarbonyl)piperidin-4-yl]methyl}phenyl)-1-(pyridazin-3-yl)azetidine-3-carboxamide;
N-[4-({1-[(6-methylpyridin-3-yl)carbonyl]piperidin-4-yl}methyl)phenyl]-1-(pyridazin-3-yl)azetidine-3-carboxamide;
N-[4-({1-[(3-methylthiophen-2-yl)carbonyl]piperidin-4-yl}methyl)phenyl]-1-(pyridazin-3-yl)azetidine-3-carboxamide;
N-(4-{[1-(pent-4-ynoyl)piperidin-4-yl]methyl}phenyl)-1-(pyridazin-3-yl)azetidine-3-carboxamide;
1-(pyridazin-3-yl)-N-(4-{[1-(thiophen-3-ylcarbonyl)piperidin-4-yl]methyl}phenyl)azetidine-3-carboxamide;
N-(4-{[1-(methoxyacetyl)piperidin-4-yl]methyl}phenyl)-1-(pyridazin-3-yl)azetidine-3-carboxamide;
1-(pyridazin-3-yl)-N-(4-{[1-(tetrahydrofuran-2-ylcarbonyl)piperidin-4-yl]methyl}phenyl)azetidine-3-carboxamide;
N-[4-({1-[(2-methoxyethoxy)acetyl]piperidin-4-yl}methyl)phenyl]-1-(pyridazin-3-yl)azetidine-3-carboxamide;
N-(4-{[1-(ethoxyacetyl)piperidin-4-yl]methyl}phenyl)-1-(pyridazin-3-yl)azetidine-3-carboxamide;
1-(pyridazin-3-yl)-N-(4-{[1-(thiophen-2-ylcarbonyl)piperidin-4-yl]methyl}phenyl)azetidine-3-carboxamide;
N-{4-[(1-hexanoylpiperidin-4-yl)methyl]phenyl}-1-(pyridazin-3-yl)azetidine-3-carboxamide;
N-(4-({1-[(1-methyl-1H-pyrrol-2-yl)carbonyl]piperidin-4-yl}methyl)phenyl)-1-(pyridazin-3-yl)azetidine-3-carboxamide;
N-(4-{[1-(but-3-enoyl)piperidin-4-yl]methyl}phenyl)-1-(pyridazin-3-yl)azetidine-3-carboxamide;
1-(pyridazin-3-yl)-N-(4-{[1-(1,3-thiazol-2-ylcarbonyl)piperidin-4-yl]methyl}phenyl)azetidine-3-carboxamide;
N-(4-{[1-(furan-2-ylcarbonyl)piperidin-4-yl]methyl}phenyl)-1-(pyridazin-3-yl)azetidine-3-carboxamide;
N-(4-{[1-(1,2-oxazol-5-ylcarbonyl)piperidin-4-yl]methyl}phenyl)-1-(pyridazin-3-yl)azetidine-3-carboxamide;
1-(pyridazin-3-yl)-N-(4-{[1-(pyridin-2-ylcarbonyl)piperidin-4-yl]methyl}phenyl)azetidine-3-carboxamide;
N-(4-{[1-(furan-3-ylcarbonyl)piperidin-4-yl]methyl}phenyl)-1-(pyridazin-3-yl)azetidine-3-carboxamide;
N-(4-{[1-(cyclopropylacetyl)piperidin-4-yl]methyl}phenyl)-1-(pyridazin-3-yl)azetidine-3-carboxamide;
N-(4-{[1-(2-methylbutanoyl)piperidin-4-yl]methyl}phenyl)-1-(pyridazin-3-yl)azetidine-3-carboxamide;
N-{4-[(1-propanoylpiperidin-4-yl)methyl]phenyl}-1-(pyridazin-3-yl)azetidine-3-carboxamide;
N-{4-[(1-butanoylpiperidin-4-yl)methyl]phenyl}-1-(pyridazin-3-yl)azetidine-3-carboxamide;
N-(4-{[1-(cyclobutylcarbonyl)piperidin-4-yl]methyl}phenyl)-1-(pyridazin-3-yl)azetidine-3-carboxamide;
N-{4-[(1-pentanoylpiperidin-4-yl)methyl]phenyl}-1-(pyridazin-3-yl)azetidine-3-carboxamide;
N-(4-{[1-(cyclopentylacetyl)piperidin-4-yl]methyl}phenyl)-1-(pyridazin-3-yl)azetidine-3-carboxamide;
N-(4-{[1-(2-methylbenzoyl)piperidin-4-yl]methyl}phenyl)-1-(pyridazin-3-yl)azetidine-3-carboxamide;
N-(4-{[1-(3-methylpentanoyl)piperidin-4-yl]methyl}phenyl)-1-(pyridazin-3-yl)azetidine-3-carboxamide;
N-(4-{[1-(cyclohexylcarbonyl)piperidin-4-yl]methyl}phenyl)-1-(pyridazin-3-yl)azetidine-3-carboxamide;
N-(4-{[1-(3-methylbutanoyl)piperidin-4-yl]methyl}phenyl)-1-(pyridazin-3-yl)azetidine-3-carboxamide;
N-(4-{[1-(cyclopropylcarbonyl)piperidin-4-yl]methyl}phenyl)-1-(pyridazin-3-yl)azetidine-3-carboxamide;
1-(pyridazin-3-yl)-N-(4-{[1-(3,3,3-trifluoropropanoyl)piperidin-4-yl]methyl}phenyl)azetidine-3-carboxamide;
N-{4-[1-(3,3-dimethylbutanoyl)piperidin-4-yl]phenyl}-1-(4-methylpyridazin-3-yl)azetidine-3-carboxamide;
N-{1-[1-(3,3-dimethylbutanoyl)piperidin-4-yl]-1H-pyrazol-4-yl}-1-(pyridazin-3-yl)azetidine-3-carboxamide;
N-{1-[1-(2-fluorobenzoyl)piperidin-4-yl]-1H-pyrazol-4-yl}-1-(pyridazin-3-yl)azetidine-3-carboxamide;
N-[4-(phenylcarbamoyl)phenyl]-1-(pyridazin-3-yl)azetidine-3-carboxamide;
N-{4-[(2,2-dimethylpropyl)carbamoyl]phenyl}-1-(pyridazin-3-yl)azetidine-3-carboxamide;
N-{4-[(3-methoxy-2,2-dimethylpropyl)carbamoyl]phenyl}-1-(pyridazin-3-yl)azetidine-3-carboxamide;
N-{4-[(2-cyclopropylethyl)carbamoyl]phenyl}-1-(pyridazin-3-yl)azetidine-3-carboxamide;
N-(4-{[2-(2-ethylpiperidin-1-yl)ethyl]carbamoyl}phenyl)-1-(pyridazin-3-yl)azetidine-3-carboxamide;
N-{4-[(cyclobutylmethyl)carbamoyl]phenyl}-1-(pyridazin-3-yl)azetidine-3-carboxamide;
N-{4-[(2S)-butan-2-ylcarbamoyl]phenyl}-1-(pyridazin-3-yl)azetidine-3-carboxamide;
N-[4-(butylcarbamoyl)phenyl]-1-(pyridazin-3-yl)azetidine-3-carboxamide;
N-{4-[(2,2-dimethyltetrahydro-2H-pyran-4-yl)carbamoyl]phenyl}-1-(pyridazin-3-yl)azetidine-3-carboxamide;
N-(4-{[(1S)-1-cyclopropylethyl]carbamoyl}phenyl)-1-(pyridazin-3-yl)azetidine-3-carboxamide;
N-[4-({2-[methyl(phenyl)amino]ethyl}carbamoyl)phenyl]-1-(pyridazin-3-yl)azetidine-3-carboxamide;
N-{4-[1,1'-bi(cyclopropyl)-1-ylcarbamoyl]phenyl}-1-(pyridazin-3-yl)azetidine-3-carboxamide;
1-(pyridazin-3-yl)-N-[4-(thiophen-3-ylcarbamoyl)phenyl]azetidine-3-carboxamide;
N-(4-{[(1R)-1-cyclopropylethyl]carbamoyl}phenyl)-1-(pyridazin-3-yl)azetidine-3-carboxamide;
N-{4-[(1-methylpiperidin-4-yl)carbamoyl]phenyl}-1-(pyridazin-3-yl)azetidine-3-carboxamide;
N-{4-[(2R)-butan-2-ylcarbamoyl]phenyl}-1-(pyridazin-3-yl)azetidine-3-carboxamide;
N-[4-(1-azabicyclo[2.2.2]oct-3-ylcarbamoyl)phenyl]-1-(pyridazin-3-yl)azetidine-3-carboxamide;
1-(pyridazin-3-yl)-N-{4-[(tetrahydrofuran-3-ylmethyl)carbamoyl]phenyl}azetidine-3-carboxamide;

N-{4-[(oxetan-3-ylmethyl)carbamoyl]phenyl}-1-(pyridazin-3-yl)azetidine-3-carboxamide;
N-{4-[(2-methylcyclopropyl)carbamoyl]phenyl}-1-(pyridazin-3-yl)azetidine-3-carboxamide;
N-[4-(cyclobutylcarbamoyl)phenyl]-1-(pyridazin-3-yl)azetidine-3-carboxamide;
N-{4-[(1-methylcyclopropyl)carbamoyl]phenyl}-1-(pyridazin-3-yl)azetidine-3-carboxamide;
N-{4-[(2-methoxy-2-methylpropyl)carbamoyl]phenyl}-1-(pyridazin-3-yl)azetidine-3-carboxamide;
N-{4-[(cyclopropylmethyl)carbamoyl]phenyl}-1-(pyridazin-3-yl)azetidine-3-carboxamide;
1-(pyridazin-3-yl)-N-(4-{[(2R)-tetrahydrofuran-2-ylmethyl]carbamoyl}phenyl)azetidine-3-carboxamide;
1-(pyridazin-3-yl)-N-{4-[(3,3,3-trifluoropropyl)carbamoyl]phenyl}azetidine-3-carboxamide;
N-{4-[(1-methylpiperidin-3-yl)carbamoyl]phenyl}-1-(pyridazin-3-yl)azetidine-3-carboxamide;
N-(4-{[(3-methyloxetan-3-yl)methyl]carbamoyl}phenyl)-1-(pyridazin-3-yl)azetidine-3-carboxamide;
1-(pyridazin-3-yl)-N-(4-{[(2S)-tetrahydrofuran-2-ylmethyl]carbamoyl}phenyl)azetidine-3-carboxamide;
1-(pyridazin-3-yl)-N-{4-[(tetrahydro-2H-pyran-4-ylmethyl)carbamoyl]phenyl}azetidine-3-carboxamide;
1-(pyridazin-3-yl)-N-[4-(tetrahydro-2H-pyran-4-ylcarbamoyl)phenyl]azetidine-3-carboxamide;
N-(4-{[(1-methylpiperidin-3-yl)methyl]carbamoyl}phenyl)-1-(pyridazin-3-yl)azetidine-3-carboxamide;
N-[4-(cyclopropyl carbamoyl)phenyl]-1-(pyridazin-3-yl)azetidine-3-carboxamide;
N-[4-(cyclopentyl carbamoyl)phenyl]-1-(pyridazin-3-yl)azetidine-3-carboxamide;
N-[4-(benzylcarbamoyl)phenyl]-1-(pyridazin-3-yl)azetidine-3-carboxamide;
N-{4-[(3-fluorophenyl)carbamoyl]phenyl}-1-(pyridazin-3-yl)azetidine-3-carboxamide;
N-[4-(propylcarbamoyl)phenyl]-1-(pyridazin-3-yl)azetidine-3-carboxamide;
N-{4-[(4-fluorophenyl)carbamoyl]phenyl}-1-(pyridazin-3-yl)azetidine-3-carboxamide;
N-{4-[(2-fluorophenyl)carbamoyl]phenyl}-1-(pyridazin-3-yl)azetidine-3-carboxamide;
N-{4-[(1-methylcyclobutyl)carbamoyl]phenyl}-1-(pyridazin-3-yl)azetidine-3-carboxamide;
N-[4-(prop-2-en-1-ylcarbamoyl)phenyl]-1-(pyridazin-3-yl)azetidine-3-carboxamide;
5-[1-(2,2-dimethylpropanoyl)piperidin-4-yl]-N-[(3S)-1-(pyridazin-3-yl)pyrrolidin-3-yl]thiophene-2-carboxamide;
5-[1-(3,3-dimethylbutanoyl)piperidin-4-yl]-N-[(3S)-1-(pyridazin-3-yl)pyrrolidin-3-yl]thiophene-2-carboxamide;
5-[1-(2,2-dimethylbutanoyl)piperidin-4-yl]-N-[(3S)-1-(pyridazin-3-yl)pyrrolidin-3-yl]thiophene-2-carboxamide;
5-{1-[(1-methylcyclopropyl)carbonyl]piperidin-4-yl}-N-[(3S)-1-(pyridazin-3-yl)pyrrolidin-3-yl]thiophene-2-carboxamide;
N-[(3S)-1-(pyridazin-3-yl)pyrrolidin-3-yl]-5-[1-(3,3,3-trifluoropropanoyl)piperidin-4-yl]thiophene-2-carboxamide;
5-[1-(cyclopropylacetyl)piperidin-4-yl]-N-[(3S)-1-(pyridazin-3-yl)pyrrolidin-3-yl]thiophene-2-carboxamide;
5-[1-(bicyclo [2.2.1]hept-2-ylacetyl)piperidin-4-yl]-N-[(3S)-1-(pyridazin-3-yl)pyrrolidin-3-yl]thiophene-2-carboxamide;
1-(pyridazin-3-yl)-N-{4-[(3S)-tetrahydrofuran-3-ylcarbamoyl]phenyl}azetidine-3-carboxamide;
N-[4-({4-[2-(dimethylamino)ethyl]phenyl}carbamoyl)phenyl]-1-(pyridazin-3-yl)azetidine-3-carboxamide;
1-(pyridazin-3-yl)-N-{4-[(3R)-tetrahydrofuran-3-ylcarbamoyl]phenyl}azetidine-3-carboxamide;
N-{4-[(2-methoxyethyl)carbamoyl]phenyl}-1-(pyridazin-3-yl)azetidine-3-carboxamide;
N-{4-[1-(3-amino-2,2-dimethylpropyl)-1H-pyrazol-4-yl]phenyl}-1-(pyridazin-3-yl)azetidine-3-carboxamide;
N-(4-{1-[2,2-dimethyl-3-(piperazin-1-yl)propyl]-1H-pyrazol-4-yl}phenyl)-1-(pyridazin-3-yl)azetidine-3-carboxamide;
N-(4-{1-[2-methyl-2-(piperazin-1-yl)propanoyl]piperidin-4-yl}phenyl)-1-(pyridazin-3-yl)azetidine-3-carboxamide; and pharmaceutically acceptable salts thereof.

13. The compound of claim 1, selected from the group consisting of
N-{4-[1-(2-methylpropanoyl)piperidin-4-yl]phenyl}-1-(pyridazin-3-yl)azetidine-3-carboxamide;
(3S)-N-{4-[1-(2-methylpropanoyl)piperidin-4-yl]phenyl}-1-(pyridazin-3-yl)pyrrolidine-3-carboxamide;
(3S)-N-{4-[1-(2,2-dimethylpropanoyl)piperidin-4-yl]phenyl}-1-(pyridazin-3-yl)pyrrolidine-3-carboxamide;
N-[4-(1-acetylpiperidin-4-yl)phenyl]-1-(pyridazin-3-yl)azetidine-3-carboxamide;
N-[4-(1-butanoylpiperidin-4-yl)phenyl]-1-(pyridazin-3-yl)azetidine-3-carboxamide;
N-{4-[1-(3-methylbutanoyl)piperidin-4-yl]phenyl}-1-(pyridazin-3-yl)azetidine-3-carboxamide;
1-(pyridazin-3-yl)-N-{4-[1-(3,3,3-trifluoropropanoyl)piperidin-4-yl]phenyl}azetidine-3-carboxamide;
N-{4-[1-(methoxyacetyl)piperidin-4-yl]phenyl}-1-(pyridazin-3-yl)azetidine-3-carboxamide;
N-(4-{1-[(methylsulfanyl)acetyl]piperidin-4-yl}phenyl)-1-(pyridazin-3-yl)azetidine-3-carboxamide;
N-{4-[1-(2,2-dimethylpropanoyl)piperidin-4-yl]phenyl}-1-(pyridazin-3-yl)azetidine-3-carboxamide;
1-(pyridazin-3-yl)-N-{4-[1-(4,4,4-trifluorobutanoyl)piperidin-4-yl]phenyl}azetidine-3-carboxamide;
N-[4-(1-propanoylpiperidin-4-yl)phenyl]-1-(pyridazin-3-yl)azetidine-3-carboxamide;
(3S)-N-[4-(1-propanoylpiperidin-4-yl)phenyl]-1-(pyridazin-3-yl)pyrrolidine-3-carboxamide;
(3S)-N-[4-(1-butanoylpiperidin-4-yl)phenyl]-1-(pyridazin-3-yl)pyrrolidine-3-carboxamide;
(3S)-N-[4-(1-acetylpiperidin-4-yl)phenyl]-1-(pyridazin-3-yl)pyrrolidine-3-carboxamide;
(3S)-N-{4-[1-(2-methylbutanoyl)piperidin-4-yl]phenyl}-1-(pyridazin-3-yl)pyrrolidine-3-carboxamide;
(3S)-N-{4-[1-(2-ethylbutanoyl)piperidin-4-yl]phenyl}-1-(pyridazin-3-yl)pyrrolidine-3-carboxamide;
(3S)-N-{4-[1-(3,3-dimethylbutanoyl)piperidin-4-yl]phenyl}-1-(pyridazin-3-yl)pyrrolidine-3-carboxamide;
(3S)-N-{4-[1-(3-methylbutanoyl)piperidin-4-yl]phenyl}-1-(pyridazin-3-yl)pyrrolidine-3-carboxamide;
(3R)-N-{4-[1-(2,2-dimethylpropanoyl)piperidin-4-yl]phenyl}-1-(pyridazin-3-yl)pyrrolidine-3-carboxamide; and pharmaceutically acceptable salts thereof.

* * * * *